(12) United States Patent
Chenard et al.

(10) Patent No.: US 9,969,736 B2
(45) Date of Patent: *May 15, 2018

(54) SUBSTITUTED XANTHINES AND METHODS OF USE THEREOF

(71) Applicant: Hydra Biosciences, Inc., Cambridge, MA (US)

(72) Inventors: Bertrand L. Chenard, Waterford, CT (US); Randall J. Gallaschun, Lebanon, CT (US)

(73) Assignee: Hydra Biosciences, Inc., Cambridge, MA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/622,838

(22) Filed: Jun. 14, 2017

(65) Prior Publication Data

US 2017/0305910 A1  Oct. 26, 2017

Related U.S. Application Data

(63) Continuation of application No. 15/137,327, filed on Apr. 25, 2016, which is a continuation of application No. 14/210,781, filed on Mar. 14, 2014, now Pat. No. 9,359,359.

(60) Provisional application No. 61/789,724, filed on Mar. 15, 2013.

(51) Int. Cl.
| C07D 473/04 | (2006.01) |
| C07D 487/04 | (2006.01) |
| C07D 487/12 | (2006.01) |
| C07D 473/06 | (2006.01) |

(52) U.S. Cl.
CPC ......... *C07D 473/04* (2013.01); *C07D 473/06* (2013.01); *C07D 487/04* (2013.01); *C07D 487/12* (2013.01)

(58) Field of Classification Search
None
See application file for complete search history.

(56) References Cited

U.S. PATENT DOCUMENTS

| 6,187,780 | B1 | 2/2001 | Blech et al. |
| 6,825,223 | B2 | 11/2004 | Shibuya et al. |
| 6,878,715 | B1 | 4/2005 | Klein et al. |
| 6,919,339 | B2 | 7/2005 | Campbell et al. |
| 7,393,827 | B2 | 7/2008 | Nadler |
| 9,359,359 | B2 | 6/2016 | Chenard et al. |
| 2004/0077645 | A1 | 4/2004 | Himmelsbach et al. |
| 2005/0182011 | A1 | 8/2005 | Olson et al. |
| 2006/0160736 | A1 | 7/2006 | Nadler |
| 2007/0232673 | A1 | 10/2007 | Roth et al. |
| 2009/0018148 | A1 | 1/2009 | Moureau et al. |
| 2009/0269313 | A1 | 10/2009 | Nadler |
| 2012/0148604 | A1 | 6/2012 | Ostertag et al. |

FOREIGN PATENT DOCUMENTS

| CA | 2115737 A1 | 8/1994 |
| CA | 2411864 A1 | 1/2002 |
| CN | 1771250 A1 | 12/2004 |
| CN | 1585769 A | 2/2005 |
| CN | 103121970 A | 5/2013 |
| WO | 2006089168 A2 | 8/2006 |
| WO | 2007065595 A2 | 6/2007 |
| WO | 2007101213 A2 | 9/2007 |
| WO | 2008011518 A2 | 1/2008 |
| WO | 2009157938 A1 | 12/2009 |
| WO | 2011114184 A1 | 9/2011 |
| WO | 2012050641 A2 | 4/2012 |

OTHER PUBLICATIONS

Bahnasi et al., "Modulation of TRPC5 cation channels by halothane, chloroform, and propofol", Briti. J. Pharmacol., 2008, vol. 153, No. 7, pp. 1505-1512.
Evseyeva L. V., "Synthesis and study of antioxidant activity of 8-R-thio-7-p-chlorobenzyltheophyllines", VISNIK FARMATSII, 2009, vol. 3, pp. 3-6.
Jiang et al. "Effect of non-steroidal anti-inflammatory drugs and new fenamate analogueson TRPC4 and TRPC5 channels" Biochem Pharmacol. 2012, vol. 83, Iss. 7, pp. 923-931.
Kim et al. "Molecular determinant of sensing extracellular pH in classical; transient receptor potential channel 5", Biochem. Biophys. Res. 2007, vol. 365, Iss. 2,; pp. 239-245.
Miller et al. "Identification of ML204, a Novel Potent Antagonist That Selectively Modulates Native TRPC4/C5 Ion Channels", J. Biol. Chem., 2011, vol. 286, Iss. 38, pp. 33436-33446.
Mizota et al., "Endocrine Disrupting Chemical Atrazine Causes Degranulation through Gq/11 Protein-Coupled Neurosteroid Receptor in Mast Cells", Toxicol. Sci., 2006, vol. 90, Iss. 2, pp. 362-368.
Naylor et al., "TRPC5 Channel Sensitivities to Antioxidants and Hydroxylated Stilbenes.", J. Biol. Chem., 2011, vol. 286, Iss. 7, pp. 5078-5086.
Riccio et al., "Essential role for TRPC5 in amygdala function and fear-related behavior", Cell, 2009, vol. 137, Iss. 4, pp. 761-772.
Riccio A. et al., "Decreased Anxiety-Like Behavior and Gaq/11-Dependent Responses in the Amygdala of Mice Lacking TRPC4 channels", J. Neurosci., 2014, vol. 34, Iss. 10, pp. 3653-3667.
Richter JM et al., "Riluzole activates TRPC5 channels independently of phospholipase C activity", J. Diabetes Investig., 2010, vol. 1, Iss. 5, pp. 208-211.
Richter JM et al., "Clemizole Hydrochloride is a Novel and Potent Inhibitor of Transient Receptor Potential Channel TRPC5", Mol. Pharmacol., 2014, vol. 86, Iss. 5, pp. 514-521.
Segura-Cabrera A. et al., "Structure-based prediction of *Mycobacterium tuberculosis*; shikimate kinase inhibitors by high-throughput virtual screening", Bioorg. Med. Chem. Lett., 2008, vol. 18, Iss. 11, pp. 3152-3157.

(Continued)

*Primary Examiner* — Deepak R Rao
*Assistant Examiner* — Laura M Daniel
(74) *Attorney, Agent, or Firm* — Wolf, Greenfield & Sacks, P.C.

(57) ABSTRACT

Compounds, compositions and methods are described for inhibiting the TRPC5 ion channel and disorders related to TRPC5.

2 Claims, No Drawings

(56) References Cited

OTHER PUBLICATIONS

Singh et al., "The transient receptor potential channel antagonist SKF96365 is a potent blocker of low-voltage-ictivated T-type calcium channels", Brit. J. Pharmacol., 2010, vol. 160, pp. 1464-1475.

Westlund et al., "A rat knockout model implicates TRPC4 in visceral pain sensation", Neuroscience, 2014, vol. 262, pp. 165-175.

Yoshida J. et al., "Capacitative Ca<2+> entries and mRNA expression for TRPC1 and; TRPC5 channels in human epidermoid carcinoma A431 cells", Eur. J. Pharmacol., 2005, vol. 510, Iss. 3, pp. 217-222.

Non-Final Office Action dated Feb. 12, 2015 from U.S. Appl. No. 14/210,666.

Final Office Action dated Sep. 1, 2015 from U.S. Appl. No. 14/210,666.

Amendment and Response to Non-Final Office Action dated Jun. 12, 2015 from U.S. Appl. No. 14/210,666.

Fischer et al. "Characterization of "Mini-Nucleotides" as P2X Receptor Agonists in Rat Cardiomyocyte Cultures" J. Med. Chem. 42:2685-2696, 1999.

Romanenko, N.I. Ukrainskil Khimicheskii Zhumal (Russian Edition), 53(9):983-6, 1987.

WebMd. Parkinson's Disease Health Center: Prevention (2014) ,http://www.webmd.com/parkinsons-disease/guide/Parkinson-disease-prevention.

NIH, Preventing Alzheimer's Disease: What do we know? (2012) <https://www.nia.nih.gov/alzheimers/publication/preventing-alzheimers-disease/introduction>.

WebMd. Understanding depression-Prevention (2015) 1-2, <http://www.webmd.com/depression/guide/understanding-depression-prevention>.

MayoClinic. Generalized Anxiety Disorder: Prevention (2014 <http://www.mayoclinic.org/diseases-conditions/generalized-anxiety-disorder/basics/prevention/con-20024562>.

MedicineNet.com. Definition of Cancer (2004) <http://www.medterms.com>.

MedicineNet.com Pain management (2015) <http://www.medicinenet.com/pain_management/page2.htm>.

Jiang L.H. Current Drug Targets (2011) vol. 12 No. 5, 724-736.

International Search Report and Written Opinion dated Sep. 12, 2014 in connection with PCT/US2014/027920.

STN Registry File. Registry No. 301329-33-9, entered Nov. 6, 2000, 1 page.

U.S. Appl. No. 15/137,327, filed Apr. 25, 2016, Chenard et al.

PCT/US2014/027920, Sep. 12, 2014, International Search Report and Written Opinion.

SUBSTITUTED XANTHINES AND METHODS OF USE THEREOF

CLAIM OF PRIORITY

This application is a Continuation of U.S. patent application Ser. No. 15/137,327, filed Apr. 25, 2016, which is a Continuation of, and claims priority to, U.S. patent application Ser. No. 14/210,781, filed Mar. 14, 2014, now U.S. Pat. No. 9,359,359, issued Jun. 7, 2016, which claims priority to U.S. Provisional Application No. 61/789,724 filed Mar. 15, 2013, the contents of which are incorporated herein by reference in its entirety.

BACKGROUND

A variety of ion channel proteins exist to mediate ion flux across cellular membranes. The proper expression and function of ion channel proteins is essential for the maintenance of cell function, intracellular communication, and the like. Numerous diseases are the result of misregulation of membrane potential or aberrant calcium handling. Given the central importance of ion channels in modulating membrane potential and ion flux in cells, identification of agents that can promote or inhibit particular ion channels are of great interest as research tools and as possible therapeutic agents.

SUMMARY OF THE INVENTION

The present invention provides methods of treating a TRPC5 mediated disorder in a subject, comprising administering to the subject a compound of Formula I:

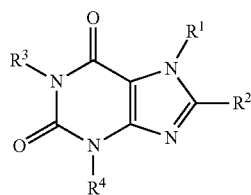

Formula I or a pharmaceutically acceptable salt thereof, wherein constituent members are provided herein.

The present invention further provides compounds of Formula I(a):

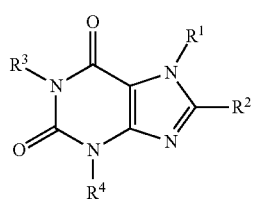

Formula I(a)

or a pharmaceutically acceptable salt thereof, wherein constituent members are provided herein.

The present invention further provides compounds of Formula II:

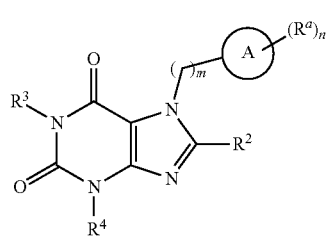

Formula II or a pharmaceutically acceptable salt thereof, wherein constituent members are provided herein.

The present invention further provides compounds of Formula III:

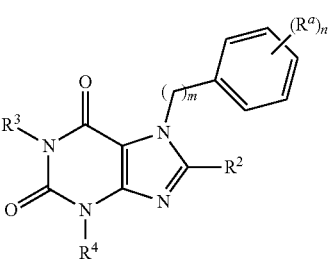

Formula III or a pharmaceutically acceptable salt thereof, wherein constituent members are provided herein.

The present invention further provides compositions comprising a compound of Formula I(a), II or III, and a pharmaceutically acceptable carrier.

The present invention further provides methods of treating a TRPC5 mediated disorder in a subject, e.g. a human, comprising administering to the subject a compound or composition of a compound of Formula I(a), II or Formula III, or a pharmaceutically acceptable salt thereof.

The present invention provides methods, compounds and compositions for treating conditions such as a neuropsychiatric disorder, a neurodegenerative disorder, nephropathy, and seizure disorder by modulating the activity of the transient receptor potential cation channel subfamily C, member 5 (TRPC5), which can exist in homomultimeric form as well as heteromultimeric form with other ion channels such as TRPC1 or TRPC3 (i.e., TRPC5-TRPC1 and TRPC1-TRPC3-TRPC5). The compounds described herein modulate the function of TRPC5 by inhibiting a TRPC5-mediated ion flux or by inhibiting the inward current, the outward current, or both currents mediated by TRPC5. The inhibition of a particular current is the ability to inhibit or reduce such current (e.g., inward and/or outward) in an in vitro or an in vivo assay. The activation of a particular current is the ability to activate or increase such current (e.g., inward and/or outward) in an in vitro or an in vivo assay.

In one aspect, the invention relates to a method for treating a condition for which reduced TRPC5 activity can reduce the severity of the condition, by administering a TRPC5 antagonist, such as a compound as described herein that inhibits TRPC5-mediated current and/or TRPC5-mediated ion flux. Described herein are compounds, which are TRPC5 antagonists that have a measured $IC_{50}$ for inhibition of TRPC5 of 10 nanomolar or less. In certain embodiments, the compounds described herein, which are TRPC5 antagonists inhibit one or both of inward and outward TRPC5-mediated currents with an $IC_{50}$ 10 nanomolar or less. In certain embodiments, the compounds described herein inhibit at least 95% of TRPC5-mediated current or TRPC5-mediated ion flux when administered at 1 micromolar or less.

In another aspect, the compounds described herein, which are TRPC5 antagonists can be used to inhibit a function of TRPC5, for example a TRPC5-mediated current and/or a TRPC5-mediated ion flux. In some embodiments, the compounds described herein can be used to inhibit a TRPC5 mediated current in vitro, for example in cells in culture. In other embodiments, the compounds described herein can be used to inhibit a TRPC5 mediated current in vivo. In certain embodiments, the compounds described herein inhibit both an inward and an outward TRPC5-mediated current.

Another aspect of the invention features a pharmaceutical preparation suitable for use in a human patient, or for veterinary use, comprising an effective amount of a compound described herein (or a salt thereof, or a solvate, hydrate, oxidative metabolite or prodrug of the compound or its salt), and one or more pharmaceutically acceptable excipients. The invention further contemplates the use of the compounds described herein in the manufacture of a medicament or pharmaceutical preparation to treat or reduce the symptoms of any of the diseases or conditions provided in the specification. The compounds described herein can be used for treating a particular disease or condition can be formulated for administration via a route appropriate for the particular disease or condition.

The compounds described herein can be administered alone or in combination with another therapeutic agent. For instance, the compounds described herein can be administered conjointly with one or more of an anti-inflammatory agent, anti-acne agent, anti-wrinkle agent, anti-scarring agent, anti-psoriatic agent, anti-proliferative agent, anti-fungal agent, anti-viral agent, anti-septic agent, anti-migraine agent, keratolytic agent, or a hair growth inhibitor.

The compounds described herein can be administered topically, orally, transdermally, rectally, vaginally, parentally, intranasally, intrapulmonary, intraocularly, intravenously, intramuscularly, intraarterially, intrathecally, intracapsularly, intraorbitally, intracardiacly, intradermally, intraperitoneally, transtracheally, subcutaneously, subcuticularly, intraarticularly, subcapsularly, subarachnoidly, intraspinally, intrasternally, sublingually, or by inhalation.

In some embodiments, the compounds described herein can be administered topically.

In some embodiments, the compounds described herein can be administered orally.

In some embodiments, the compounds described herein can be administered parentally.

DETAILED DESCRIPTION OF THE INVENTION

Cation channels such as TRPC5 modulate the flux of calcium and sodium ions across cellular membranes. Sodium and calcium influx leads to a depolarization of the cell. This increases the probability that voltage-gated ion channels will reach the threshold required for activation. As a result, activation of non-selective cation channels can increase electrical excitability and increase the frequency of voltage-dependent events. Voltage-dependent events include, but are not limited to, neuronal action potentials, cardiac action potentials, smooth muscle contraction, cardiac muscle contraction, and skeletal muscle contraction.

Calcium influx caused by the activation of non-selective cation channels such as TRPC5 also alters the intracellular free calcium concentration. Calcium is a ubiquitous second messenger molecule within the cell and the alterations in intracellular calcium levels have profound effects on signal transduction and gene expression. Thus, activation of non-selective cation channels such as TRPC5 can lead to changes in gene expression and cellular phenotype. Gene expression events include, but are not limited to, production of mRNAs encoding cell surface receptors, ion channels, and kinases. These changes in gene expression can lead to hyperexcitability in that cell.

Transient receptor potential (TRP) homomeric TRPC5 ion channels are signal transduction gated, $Ca^{2+}$-permeable channels predominantly expressed in the neurons. TRPC5 forms homomultimeric structures such as tetramers (i.e., TRPC5 homomultimers) and heteromultimeric structures such as tetramers (i.e., TRPC5-TRPC1 heteromultimers). Unless expressly stated otherwise, when the term TRPC5 is used herein, for example, when identifying a modulator of TRPC5 such as a TRPC5 antagonist, the term TRPC5 is used generically so as to include either or both of a TRPC5 homomultimer or a heteromultimer (e.g., TRPC5-TPRC1 or TRPC5-TRPC4 heteromultimer). Examples of TRPC5 in the literature include the following: Nature. 2008 Jan. 3; 451 (7174):69-72; Mol Pharmacol. 2008 January; 73 (1):42-9; J Biol Chem. 2007 Nov. 16; 282 (46):33868-78; Biochem Biophys Res Commun. 2008 Jan. 11; 365 (2):239-45; J Biol Chem. 2006 Nov. 3; 281 (44):33487-96; Eur J Pharmacol. 2005 Mar. 14; 510 (3):217-22; J Biol Chem. 2006 Feb. 24; 281 (8):4977-82; Biochem Soc Trans. 2007 February; 35 (Pt 1):101-4; Handb Exp Pharmacol. 2007; (179):109-23; J Biol Chem. 2005 Mar. 25; 280 (12):10997-1006; J Physiol. 2006 Jan. 15; 570 (Pt 2):219-35; and Nat Neurosci. (2003) 6: 837-45.

Modulating the function of TRPC5 proteins provides a means of modulating calcium homeostasis, sodium homeostasis, membrane polarization, and/or intracellular calcium levels, and compounds that can modulate TRPC5 function are useful in many aspects, including, but not limited to, maintaining calcium homeostasis, modulating intracellular calcium levels, modulating membrane polarization, and treating or preventing diseases, disorders, or conditions associated with calcium and/or sodium homeostasis or dyshomeostasis.

In one aspect, the invention provides methods of treating a TRPC5 mediated disorder in a subject comprising administering to the subject a compound of Formula I:

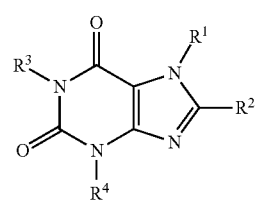

Formula I or a pharmaceutically acceptable salt thereof, wherein:
$R^1$ is $C_1$-$C_6$ alkyl, $C_2$-$C_6$ alkenyl or $C_2$-$C_6$ alkynyl, each of which is optionally substituted with 1-4 $R^5$;
$R^2$ is $C_1$-$C_6$ alkyl, $C_1$-$C_6$ heteroalkyl, $C_2$-$C_6$ alkenyl, $C_2$-$C_6$ alkynyl, $C_1$-$C_6$ haloalkyl, halo, $C_1$-$C_6$ haloalkoxy, hydroxyl, $C_1$-$C_6$ alkoxy, $C_3$-$C_7$ cycloalkyloxy, $C_6$-$C_{10}$ aryl, $C_6$-$C_{10}$ aryloxy, $C_7$-$C_{16}$ arylalkoxy, amino, $C_1$-$C_6$ akylamino, $C_2$-$C_{12}$ dialkylamino, —S—, —S—$C_1$-$C_6$ alkyl, —S(O)—, —S(O)$_2$—, heterocycloalkyl, heteroaryl, heteroaryloxy, sulfonamidyl, amido, urea, sulfonylurea, acyl, nitro, cyano, wherein each of $C_1$-$C_6$ alkyl, $C_1$-$C_6$ heteroalkyl, $C_2$-$C_6$ alkenyl, $C_2$-$C_6$ alkynyl, $C_1$-$C_6$ haloalkyl, $C_1$-$C_6$ haloalkoxy, hydroxyl, $C_1$-$C_6$ alkoxy, $C_3$-$C_7$ cycloalkyloxy, $C_6$-$C_{10}$ aryl, $C_6$-$C_{10}$ aryloxy, $C_7$-$C_{16}$ arylalkoxy, amino, $C_1$-$C_6$ akylamino, $C_2$-$C_{12}$ dialkylamino, —S—, —S—$C_1$-$C_6$ alkyl, —S(O)—, —S(O)$_2$—, heterocycloalkyl, heteroaryl, heteroaryloxy, sulfonamidyl, amido, urea, sulfonylurea, acyl, is optionally substituted with 1-3 $R^6$;

$R^3$ is $C_1$-$C_6$ alkyl, $C_1$-$C_6$ heteroalkyl, $C_3$-$C_7$ cycloalkyl, $C_2$-$C_6$ alkenyl, $C_2$-$C_6$ alkynyl, $C_2$-$C_6$ hydroxyalkyl, or $C_1$-$C_6$ alkoxy, each of which is optionally substituted with 1-4 $R^7$;

$R^4$ is $C_1$-$C_6$ alkyl, $C_1$-$C_6$ heteroalkyl, $C_2$-$C_6$ alkenyl or $C_2$-$C_6$ alkynyl, each of which is optionally substituted with 1-4 $R^8$;

$R^5$, $R^6$, $R^7$, and $R^8$ are each independently $C_1$-$C_6$ alkyl, $C_1$-$C_6$ heteroalkyl, halo, $C_1$-$C_6$ haloalkyl, $C_1$-$C_6$ haloalkoxy, hydroxyl, $C_1$-$C_6$ alkoxy, amino, $C_1$-$C_6$ alkylamino, $C_2$-$C_{12}$ dialkylamino, cyano, nitro, amido, $C_1$-$C_6$ alkylamido, $C_2$-$C_{12}$ dialkylamido, —S—, —S(O)$_2$—, —C(O)O—, —C(O)—, —C(O)O—$C_1$-$C_6$ alkyl, $C_3$-$C_7$ cycloalkyl, $C_6$-$C_{10}$ aryl, heterocycloalkyl, or heteroaryl, wherein each of $C_1$-$C_6$ alkyl, $C_1$-$C_6$ heteroalkyl, $C_1$-$C_6$ haloalkyl, $C_1$-$C_6$ haloalkoxy, hydroxyl, $C_1$-$C_6$ alkoxy, amino, $C_1$-$C_6$ alkylamino, $C_2$-$C_{12}$ dialkylamino, amido, $C_1$-$C_6$ alkylamido, $C_2$-$C_{12}$ dialkylamido, —S—, —S(O)$_2$—, —C(O)O—, —C(O)—, —C(O)O—$C_1$-$C_6$ alkyl, $C_3$-$C_7$ cycloalkyl, $C_6$-$C_{10}$ aryl, heterocycloalkyl, or heteroaryl is optionally substituted with 1-3 $R^9$; and each $R^9$ is independently $C_1$-$C_6$ alkyl, $C_1$-$C_6$ heteroalkyl, $C_1$-$C_6$ haloalkyl, $C_1$-$C_6$ haloalkoxy, heterocycloalkyl, $C_6$-$C_{10}$ aryl, heteroaryl, $C_4$-$C_{10}$ cycloalkylalkyl, heterocycloalkyl-$C_1$-$C_6$ alkyl, $C_7$-$C_{16}$ arylalkyl, heteroaryl-$C_1$-$C_6$ alkyl, halo, hydroxyl, $C_1$-$C_6$ alkoxy, $C_6$-$C_{10}$ aryloxy, $C_7$-$C_{16}$ arylalkoxy, $C_2$-$C_8$ alkoxyalkoxyl, amino, $C_1$-$C_6$ akylamino, $C_2$-$C_{12}$ dialkylamino, $C_1$-$C_6$ akyl-amino-$C_1$-$C_6$ akyl, $C_1$-$C_6$ akyl-amino-$C_2$-$C_{12}$ dialkyl, —S—, —S—$C_1$-$C_6$ alkyl, —S(O)$_2$—$C_1$-$C_6$ alkyl, sulfonamidyl, amido, urea, sulfonylurea, acyl, —C(O)—$C_6$-$C_{10}$ aryl, —NHC(O)—$C_6$-$C_{10}$ aryl, —C(O)NH—$C_6$-$C_{10}$ aryl, —C(O)OH, —C(O)O—$C_1$-$C_6$ alkyl, —C(O)—$C_1$-$C_6$ alkyl acyl, nitro, or cyano; to thereby treat the subject.

In some embodiments, the TRPC5 mediated disorder is selected from the group consisting of: a neuropsychiatric disorder, a neurodegenerative disorder, nephropathy, and seizure disorder.

In some embodiments, $R^1$ is $C_1$-$C_6$ alkyl.

In some embodiments, $R^1$ is $C_1$-$C_6$ alkyl and $R^5$ is independently $C_6$-$C_{10}$ aryl or heteroaryl.

In some embodiments, $R^2$ is $C_6$-$C_{10}$ aryl, $C_6$-$C_{10}$ aryloxy or heteroaryloxy.

In some embodiments, $R^2$ is $C_6$-$C_{10}$ aryloxy.

In some embodiments, $R^2$ is $C_1$-$C_6$ alkoxy.

In some embodiments, $R^2$ is $C_1$-$C_6$ alkyl.

In some embodiments, $R^2$ is or $C_1$-$C_6$ akylamino.

In some embodiments, $R^2$ is —S(O)— or —S(O)$_2$—.

In some embodiments, $R^3$ is $C_1$-$C_6$ alkyl, $C_2$-$C_6$ hydroxyalkyl, or $C_1$-$C_6$ alkoxy.

In some embodiments, $R^3$ is $C_2$-$C_6$ hydroxyalkyl, e.g., hydroxypropyl.

In some embodiments, $R^3$ is hydroxypropyl.

In some embodiments, $R^4$ is $C_1$-$C_6$ alkyl.

In some embodiments, $R^5$ is independently $C_6$-$C_{10}$ aryl, heteroaryl, $C_3$-$C_7$ cycloalkyl, or heterocycloalkyl.

In some embodiments, $R^5$ is phenyl, pyridyl, thiazolyl, pyrimidinyl, or oxazolyl.

In some embodiments, $R^5$ is phenyl.

In some embodiments, $R^5$ is pyridyl.

In some embodiments, $R^5$ is thiazolyl.

In some embodiments, $R^9$ is independently $C_1$-$C_6$ alkyl, $C_1$-$C_6$ alkoxy, halo, $C_1$-$C_6$ haloalkyl, $C_1$-$C_6$ haloalkoxy, or heterocycloalkyl.

In some embodiments, $R^2$ is $C_6$-$C_{10}$ aryl or $C_6$-$C_{10}$ aryloxy, and $R^6$ is independently $C_1$-$C_6$ alkyl, $C_1$-$C_6$ haloalkyl, $C_1$-$C_6$ or haloalkoxy.

In some embodiments, $R^2$ is $C_6$-$C_{10}$ aryloxy and $R^6$ is independently $C_1$-$C_6$ haloalkyl or $C_1$-$C_6$ or haloalkoxy.

In some embodiments, $R^2$ is $C_6$-$C_{10}$ aryloxy and $R^6$ is —$CF_3$ or —$OCF_3$.

In another aspect, the invention provides compounds of Formula I(a):

Formula I(a)

or a pharmaceutically acceptable salt thereof, wherein:

$R^1$ is $C_1$-$C_6$ alkyl, $C_2$-$C_6$ alkenyl or $C_2$-$C_6$ alkynyl, each of which is optionally substituted with 1-4 $R^5$;

$R^2$ is $C_1$-$C_6$ alkyl, $C_1$-$C_6$ heteroalkyl, $C_2$-$C_6$ alkenyl, $C_2$-$C_6$ alkynyl, $C_1$-$C_6$ haloalkyl, halo, $C_1$-$C_6$ haloalkoxy, hydroxyl, $C_1$-$C_6$ alkoxy, $C_3$-$C_7$ cycloalkyloxy, $C_6$-$C_{10}$ aryl, $C_6$-$C_{10}$ aryloxy, $C_7$-$C_{16}$ arylalkoxy, amino, $C_1$-$C_6$ akylamino, $C_2$-$C_{12}$ dialkylamino, —S—, —S—$C_1$-$C_6$ alkyl, —S(O)—, —S(O)$_2$—, heterocycloalkyl, heteroaryl, heteroaryloxy, sulfonamidyl, amido, urea, sulfonylurea, acyl, nitro, cyano, wherein each of $C_1$-$C_6$ alkyl, $C_1$-$C_6$ heteroalkyl, $C_2$-$C_6$ alkenyl, $C_2$-$C_6$ alkynyl, $C_1$-$C_6$ haloalkyl, $C_1$-$C_6$ haloalkoxy, hydroxyl, $C_1$-$C_6$ alkoxy, $C_3$-$C_7$ cycloalkyloxy, $C_6$-$C_{10}$ aryl, $C_6$-$C_{10}$ aryloxy, $C_7$-$C_{16}$ arylalkoxy, amino, $C_1$-$C_6$ akylamino, $C_2$-$C_{12}$ dialkylamino, —S—, —S—$C_1$-$C_6$ alkyl, —S(O)—, —S(O)$_2$—, heterocycloalkyl, heteroaryl, heteroaryloxy, sulfonamidyl, amido, urea, sulfonylurea, acyl, is optionally substituted with 1-3 $R^6$;

$R^3$ is $C_2$-$C_6$ hydroxyalkyl or $C_1$-$C_6$ heteroalkyl;

$R^4$ is $C_1$-$C_6$ alkyl, $C_1$-$C_6$ heteroalkyl, $C_2$-$C_6$ alkenyl or $C_2$-$C_6$ alkynyl, each of which is optionally substituted with 1-4 $R^8$;

$R^5$, $R^6$, and $R^8$ are each independently $C_1$-$C_6$ alkyl, $C_1$-$C_6$ heteroalkyl, halo, $C_1$-$C_6$ haloalkyl, $C_1$-$C_6$ haloalkoxy, hydroxyl, $C_1$-$C_6$ alkoxy, amino, $C_1$-$C_6$ alkylamino, $C_2$-$C_{12}$ dialkylamino, cyano, nitro, amido, $C_1$-$C_6$ alkylamido, $C_2$-$C_{12}$ dialkylamido, —S—, —S(O)$_2$—, —C(O)O—, —C(O)—, —C(O)O—$C_1$-$C_6$ alkyl, $C_3$-$C_7$ cycloalkyl, $C_6$-$C_{10}$ aryl, heterocycloalkyl, or heteroaryl, each of $C_1$-$C_6$ alkyl, $C_1$-$C_6$ heteroalkyl, $C_1$-$C_6$ haloalkyl, $C_1$-$C_6$ haloalkoxy, hydroxyl, $C_1$-$C_6$ alkoxy, amino, $C_1$-$C_6$ alkylamino, $C_2$-$C_{12}$ dialkylamino, amido, $C_1$-$C_6$ alkylamido, $C_2$-$C_{12}$ dialkylamido, —S—, —S(O)$_2$—, —C(O)O—, —C(O)—, —C(O)O—$C_1$-$C_6$ alkyl, $C_3$-$C_7$ cycloalkyl, $C_6$-$C_{10}$ aryl, heterocycloalkyl, or heteroaryl is optionally substituted with 1-3 $R^9$; and each $R^9$ is independently $C_1$-$C_6$ alkyl, $C_1$-$C_6$ heteroalkyl, $C_1$-$C_6$ haloalkyl, $C_1$-$C_6$ haloalkoxy, heterocycloalkyl, $C_6$-$C_{10}$ aryl, heteroaryl, $C_4$-$C_{10}$ cycloalkylalkyl, heterocycloalkyl-$C_1$-$C_6$ alkyl, $C_7$-$C_{16}$ arylalkyl, heteroaryl-$C_1$-$C_6$ alkyl, halo, hydroxyl, $C_1$-$C_6$ alkoxy, $C_6$-$C_{10}$ aryloxy, $C_7$-$C_{16}$ arylalkoxy, $C_2$-$C_8$ alkoxyalkoxyl, amino, $C_1$-$C_6$ akylamino, $C_2$-$C_{12}$ dialkylamino, $C_1$-$C_6$ akyl-amino-$C_1$-$C_6$ akyl, $C_1$-$C_6$ akyl-amino-$C_2$-$C_{12}$ dialkyl, —S—, —S—$C_1$-$C_6$ alkyl, —S(O)$_2$—$C_1$-$C_6$ alkyl, sulfonamidyl, amido, urea, sulfonylurea, acyl, —C(O)—$C_6$-$C_{10}$ aryl, —NHC(O)—$C_6$-$C_{10}$ aryl, —C(O)NH—$C_6$-$C_{10}$ aryl, —C(O)OH, —C(O)O—$C_1$-$C_6$ alkyl, —C(O)—$C_1$-$C_6$ alkyl acyl, nitro, or cyano.

In some embodiments, $R^1$ is $C_1$-$C_6$ alkyl and $R^5$ is phenyl, pyridyl, thiazolyl, pyrimidinyl, or oxazolyl, e.g., phenyl, pyridinyl, or thiazolyl.

In some embodiments, $R^2$ is $C_6$-$C_{10}$ aryl or $C_6$-$C_{10}$ aryloxy, and $R^6$ is independently $C_1$-$C_6$ alkyl, $C_1$-$C_6$ haloalkyl, $C_1$-$C_6$ or haloalkoxy.

In some embodiments, $R^3$ is $C_2$-$C_6$ hydroxyalkyl, e.g., hydroxypropyl.

In another aspect, the invention provides compounds of Formula II:

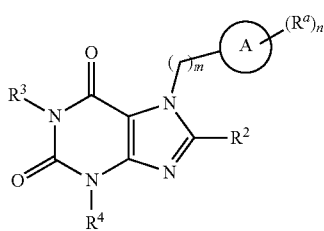

Formula II or a pharmaceutically acceptable salt thereof, wherein:
Ring A is phenyl, thiazolyl, pyrimidinyl, or oxazolyl;
$R^2$ is $C_1$-$C_6$ alkyl, $C_1$-$C_6$ heteroalkyl, $C_2$-$C_6$ alkenyl, $C_2$-$C_6$ alkynyl, $C_1$-$C_6$ haloalkyl, halo, $C_1$-$C_6$ haloalkoxy, hydroxyl, $C_1$-$C_6$ alkoxy, $C_3$-$C_7$ cycloalkyloxy, $C_6$-$C_{10}$ aryl, $C_6$-$C_{10}$ aryloxy, $C_7$-$C_{16}$ arylalkoxy, amino, $C_1$-$C_6$ akylamino, $C_2$-$C_{12}$ dialkylamino, —S—, —S—$C_1$-$C_6$ alkyl, —S(O)—, —S(O)$_2$—, heterocycloalkyl, heteroaryl, heteroaryloxy, sulfonamidyl, amido, urea, sulfonylurea, acyl, nitro, cyano, wherein each of $C_1$-$C_6$ alkyl, $C_1$-$C_6$ heteroalkyl, $C_2$-$C_6$ alkenyl, $C_2$-$C_6$ alkynyl, $C_1$-$C_6$ haloalkyl, $C_1$-$C_6$ haloalkoxy, hydroxyl, $C_1$-$C_6$ alkoxy, $C_3$-$C_7$ cycloalkyloxy, $C_6$-$C_{10}$ aryl, $C_6$-$C_{10}$ aryloxy, $C_7$-$C_{16}$ arylalkoxy, amino, $C_1$-$C_6$ akylamino, $C_2$-$C_{12}$ dialkylamino, —S—, —S—$C_1$-$C_6$ alkyl, —S(O)—, —S(O)$_2$—, heterocycloalkyl, heteroaryl, heteroaryloxy, sulfonamidyl, amido, urea, sulfonylurea, acyl, is optionally substituted with 1-3 $R^6$;
$R^3$ is $C_1$-$C_6$ alkyl, $C_1$-$C_6$ heteroalkyl, $C_2$-$C_6$ alkenyl, $C_2$-$C_6$ alkynyl, $C_2$-$C_6$ hydroxyalkyl, or $C_1$-$C_6$ alkoxy, each of which is optionally substituted with 1-4 $R^7$;
$R^4$ is $C_1$-$C_6$ alkyl, $C_1$-$C_6$ heteroalkyl, $C_2$-$C_6$ alkenyl or $C_2$-$C_6$ alkynyl, each of which is optionally substituted with 1-4 $R^8$;
$R^6$, $R^7$, and $R^8$ are each independently $C_1$-$C_6$ alkyl, $C_1$-$C_6$ heteroalkyl, halo, $C_1$-$C_6$ haloalkyl, $C_1$-$C_6$ haloalkoxy, hydroxyl, $C_1$-$C_6$ alkoxy, amino, $C_1$-$C_6$ alkylamino, $C_2$-$C_{12}$ dialkylamino, cyano, nitro, amido, $C_1$-$C_6$ alkylamido, $C_2$-$C_{12}$ dialkylamido, —S—, —S(O)$_2$—, —C(O)O—, —C(O)—, —C(O)O—$C_1$-$C_6$ alkyl, $C_3$-$C_7$ cycloalkyl, $C_6$-$C_{10}$ aryl, heterocycloalkyl, or heteroaryl, wherein each of $C_1$-$C_6$ alkyl, $C_1$-$C_6$ heteroalkyl, $C_1$-$C_6$ haloalkyl, $C_1$-$C_6$ haloalkoxy, hydroxyl, $C_1$-$C_6$ alkoxy, amino, $C_1$-$C_6$ alkylamino, $C_2$-$C_{12}$ dialkylamino, amido, $C_1$-$C_6$ alkylamido, $C_2$-$C_{12}$ dialkylamido, —S—, —S(O)$_2$—, —C(O)O—, —C(O)—, —C(O)O—$C_1$-$C_6$ alkyl, $C_3$-$C_7$ cycloalkyl, $C_6$-$C_{10}$ aryl, heterocycloalkyl, or heteroaryl is optionally substituted with 1-3 $R^9$;

each $R^9$ is independently $C_1$-$C_6$ alkyl, $C_1$-$C_6$ heteroalkyl, $C_1$-$C_6$ haloalkyl, $C_1$-$C_6$ haloalkoxy, heterocycloalkyl, $C_6$-$C_{10}$ aryl, heteroaryl, $C_4$-$C_{10}$ cycloalkylalkyl, heterocycloalkyl-$C_1$-$C_6$ alkyl, $C_7$-$C_{16}$ arylalkyl, heteroaryl-$C_1$-$C_6$ alkyl, halo, hydroxyl, $C_1$-$C_6$ alkoxy, $C_6$-$C_{10}$ aryloxy, $C_7$-$C_{16}$ arylalkoxy, $C_2$-$C_8$ alkoxyalkoxyl, amino, $C_1$-$C_6$ akylamino, $C_2$-$C_{12}$ dialkylamino, $C_1$-$C_6$ akyl-amino-$C_1$-$C_6$ akyl, $C_1$-$C_6$ akyl-amino-$C_2$-$C_{12}$ dialkyl, —S—, —S—$C_1$-$C_6$ alkyl, —S(O)$_2$—$C_1$-$C_6$ alkyl, sulfonamidyl, amido, urea, sulfonylurea, acyl, —C(O)—$C_6$-$C_{10}$ aryl, —NHC(O)—$C_6$-$C_{10}$ aryl, —C(O)NH—$C_6$-$C_{10}$ aryl, —C(O)OH, —C(O)O—$C_1$-$C_6$ alkyl, —C(O)—$C_1$-$C_6$ alkyl acyl, nitro, or cyano;
each $R^a$ is $C_1$-$C_6$ alkyl, $C_1$-$C_6$ haloalkyl, halo;
n is 1 or 2; and
m is 1, 2, or 3.

In some embodiments, Ring A is phenyl or thiazolyl.

In some embodiments, $R^3$ is hydroxypropyl.

In another aspect, the invention provides compound of Formula III:

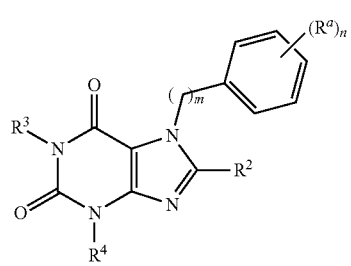

Formula III or a pharmaceutically acceptable salt thereof, wherein:
$R^2$ is $C_1$-$C_6$ alkoxy or $C_6$-$C_{10}$ aryloxy substituted with 1-3 $R^6$;
$R^3$ is $C_1$-$C_6$ heteroalkyl or $C_2$-$C_6$ hydroxyalkyl;
$R^4$ is $C_1$-$C_6$ alkyl;
$R^6$ is independently $C_1$-$C_6$ alkyl, halo, $C_1$-$C_6$ haloalkyl, $C_1$-$C_6$ haloalkoxy, or $C_1$-$C_6$ alkoxy;
each $R^a$ is $C_1$-$C_6$ alkyl, $C_1$-$C_6$ haloalkyl, halo;
n is 1 or 2; and
m is 1, 2, or 3.

In some embodiments, $R^3$ is hydroxypropyl.

In some embodiments, $R^a$ is independently chloro, fluoro, or methyl.

In another aspect, the invention provides methods of treating a TRPC5 mediated disorder in a subject, the method comprising administering to the subject a compound or composition of any one of claims 23 to 33, to thereby treat the subject.

In some embodiments, the TRPC5 mediated disorder is selected from the group consisting of: a neuropsychiatric disorder, a neurodegenerative disorder, nephropathy, and seizure disorder.

In certain embodiments, exemplary compounds of the invention include the compounds described in Table A and in the Examples.

TABLE A
| Compound Number | Structure |
| --- | --- |
| 1 | 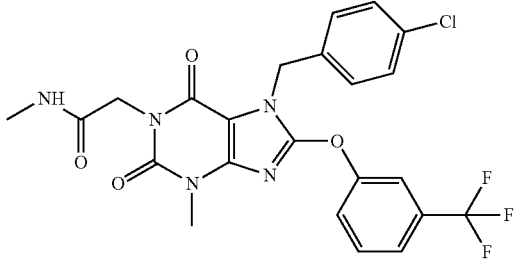 [SMILES: CNC(=O)Cn1c(=O)c2c(nc(Oc3cccc(C(F)(F)F)c3)n2Cc2ccc(Cl)cc2)n(C)c1=O] |
| 2 | 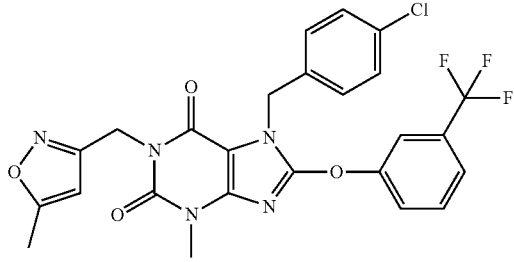 [SMILES: Cc1cc(Cn2c(=O)c3c(nc(Oc4cccc(C(F)(F)F)c4)n3Cc3ccc(Cl)cc3)n(C)c2=O)no1] |
| 3 | 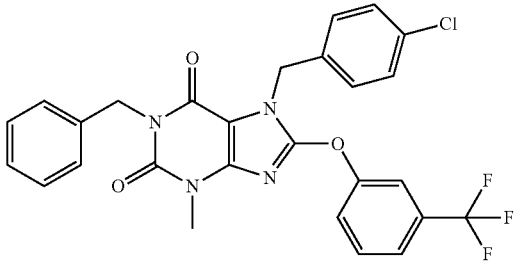 [SMILES: Cn1c(=O)n(Cc2ccccc2)c(=O)c2c1nc(Oc1cccc(C(F)(F)F)c1)n2Cc1ccc(Cl)cc1] |
| 4 | 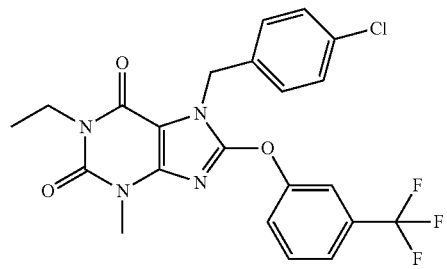 [SMILES: CCn1c(=O)c2c(nc(Oc3cccc(C(F)(F)F)c3)n2Cc2ccc(Cl)cc2)n(C)c1=O] |
| 5 | 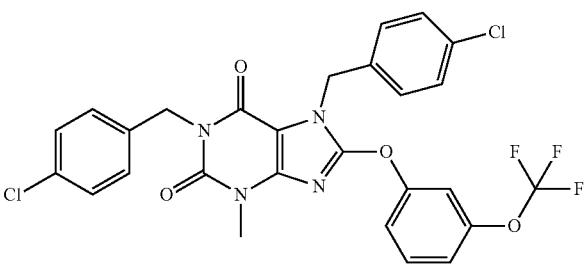 [SMILES: Cn1c(=O)n(Cc2ccc(Cl)cc2)c(=O)c2c1nc(Oc1cccc(OC(F)(F)F)c1)n2Cc1ccc(Cl)cc1] |

TABLE A-continued

| Compound Number | Structure |
|---|---|
| 6 | 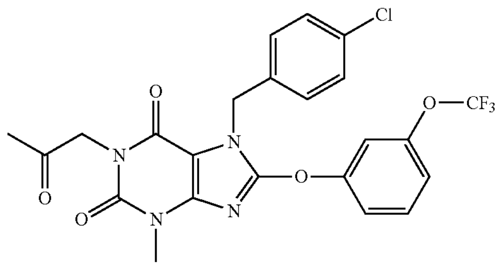 [SMILES: CC(=O)Cn1c(=O)c2c(nc(Oc3cccc(OC(F)(F)F)c3)n2Cc2ccc(Cl)cc2)n(C)c1=O] |
| 7 | 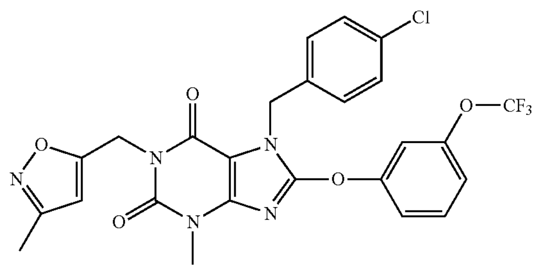 [SMILES: Cc1cc(Cn2c(=O)c3c(nc(Oc4cccc(OC(F)(F)F)c4)n3Cc3ccc(Cl)cc3)n(C)c2=O)on1] |
| 8 | 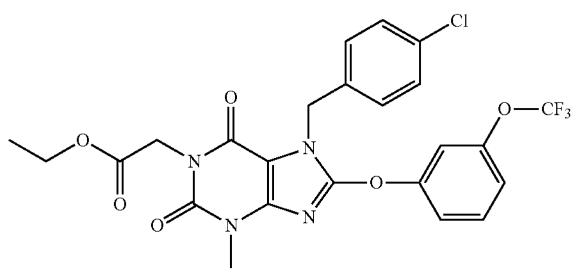 [SMILES: CCOC(=O)Cn1c(=O)c2c(nc(Oc3cccc(OC(F)(F)F)c3)n2Cc2ccc(Cl)cc2)n(C)c1=O] |
| 9 | 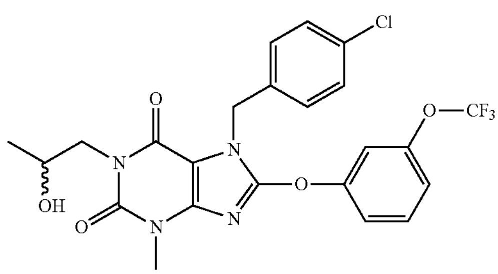 |
| 10 | 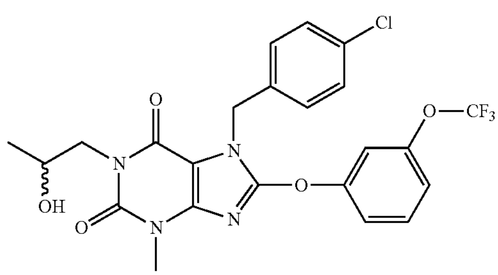 [SMILES: CC(O)Cn1c(=O)c2c(nc(Oc3cccc(OC(F)(F)F)c3)n2Cc2ccc(Cl)cc2)n(C)c1=O] |

TABLE A-continued

| Compound Number | Structure |
|---|---|
| 11 | 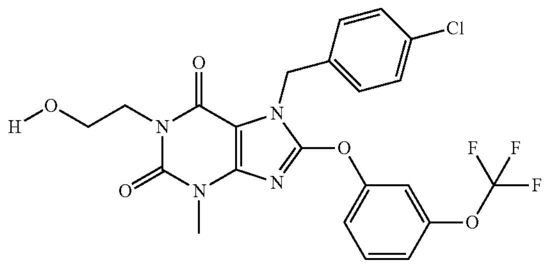 |
| 12 | 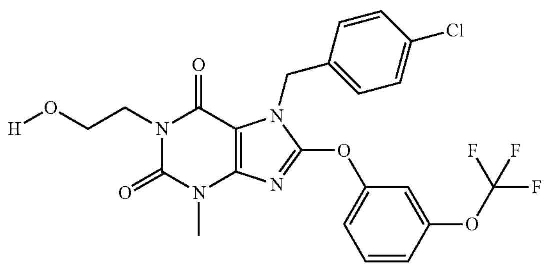 [SMILES: Cn1c(=O)n(CCO)c(=O)c2c1nc(Oc1cccc(OC(F)(F)F)c1)n2Cc1ccc(Cl)cc1] |
| 13 | 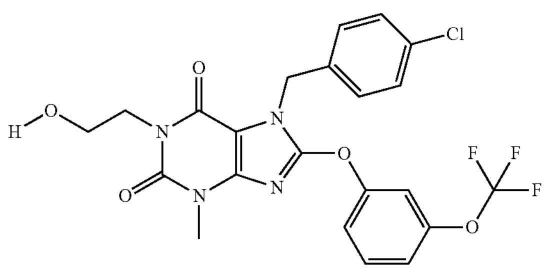 [SMILES: Cn1c(=O)n(CCO)c(=O)c2c1nc(Oc1cccc(OC(F)(F)F)c1)n2Cc1ccc(Cl)cc1] |
| 14 | 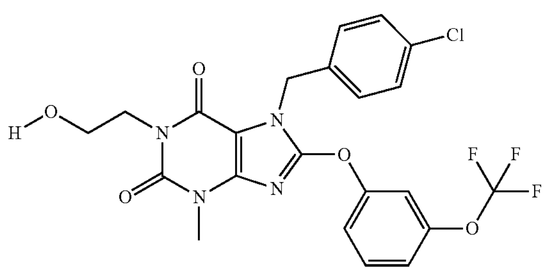 [SMILES: Cn1c(=O)n(CCO)c(=O)c2c1nc(Oc1cccc(OC(F)(F)F)c1)n2Cc1ccc(Cl)cc1] |
| 15 | 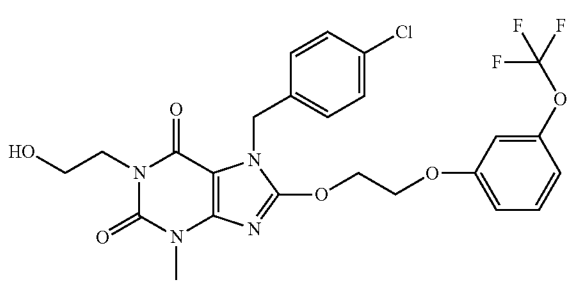 [SMILES: Cn1c(=O)n(CCO)c(=O)c2c1nc(OCCOc1cccc(OC(F)(F)F)c1)n2Cc1ccc(Cl)cc1] |

TABLE A-continued
| Compound Number | Structure |
|---|---|
| 16 | 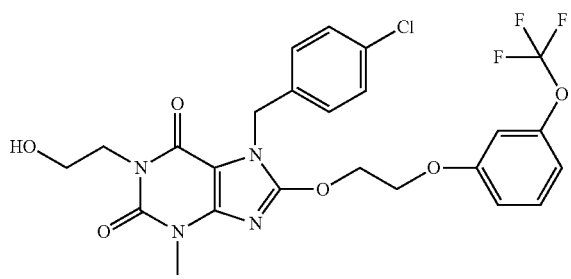 [SMILES: Cn1c(=O)n(CCO)c(=O)c2c1nc(OCCOc1cccc(OC(F)(F)F)c1)n2Cc1ccc(Cl)cc1] |
| 17 | 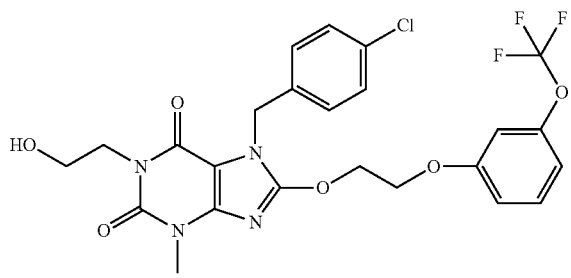 [SMILES: Cn1c(=O)n(CCO)c(=O)c2c1nc(OCCOc1cccc(OC(F)(F)F)c1)n2Cc1ccc(Cl)cc1] |
| 18 | 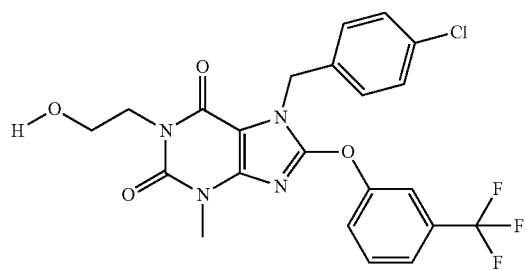 [SMILES: Cn1c(=O)n(CCO)c(=O)c2c1nc(Oc1cccc(C(F)(F)F)c1)n2Cc1ccc(Cl)cc1] |
| 19 | 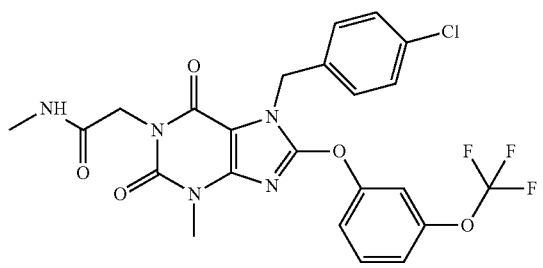 [SMILES: CNC(=O)Cn1c(=O)c2c(nc(Oc3cccc(OC(F)(F)F)c3)n2Cc2ccc(Cl)cc2)n(C)c1=O] |
| 20 | 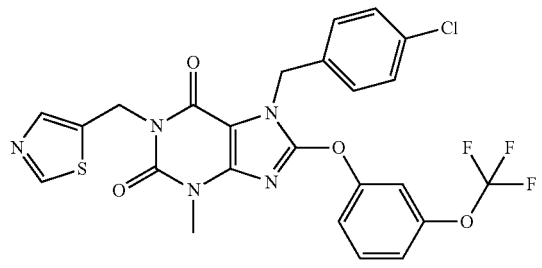 [SMILES: Cn1c(=O)n(Cc2cncs2)c(=O)c2c1nc(Oc1cccc(OC(F)(F)F)c1)n2Cc1ccc(Cl)cc1] |

TABLE A-continued
| Compound Number | Structure |
|---|---|
| 21 | 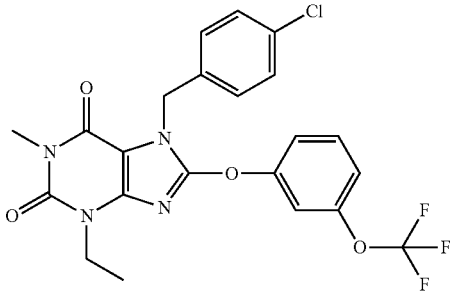 [SMILES: CCn1c(=O)n(C)c(=O)c2c1nc(Oc1cccc(OC(F)(F)F)c1)n2Cc1ccc(Cl)cc1] |
| 22 | 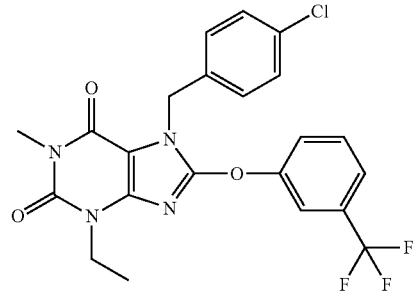 [SMILES: CCn1c(=O)n(C)c(=O)c2c1nc(Oc1cccc(C(F)(F)F)c1)n2Cc1ccc(Cl)cc1] |
| 23 | 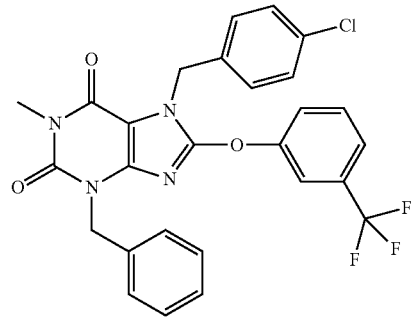 [SMILES: Cn1c(=O)c2c(nc(Oc3cccc(C(F)(F)F)c3)n2Cc2ccc(Cl)cc2)n(Cc2ccccc2)c1=O] |
| 24 | 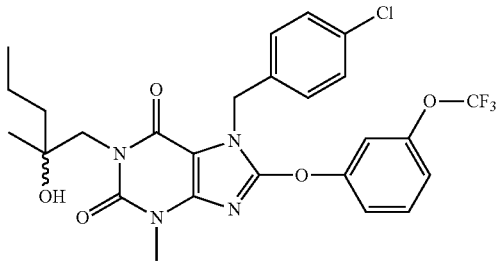 [SMILES: CCCC(C)(O)Cn1c(=O)c2c(nc(Oc3cccc(OC(F)(F)F)c3)n2Cc2ccc(Cl)cc2)n(C)c1=O] |
| 25 | 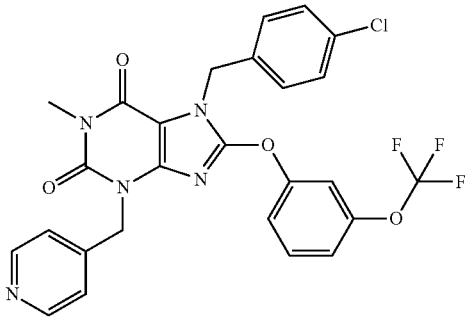 [SMILES: Cn1c(=O)c2c(nc(Oc3cccc(OC(F)(F)F)c3)n2Cc2ccc(Cl)cc2)n(Cc2ccncc2)c1=O] |

TABLE A-continued
| Compound Number | Structure |
|---|---|
| 26 | 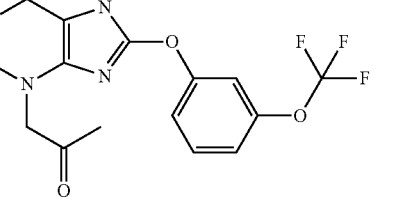 |
| 27 | 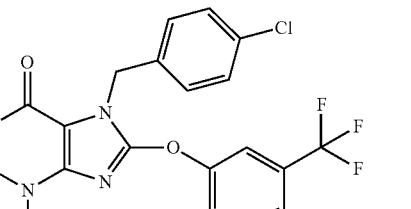 |
| 28 | 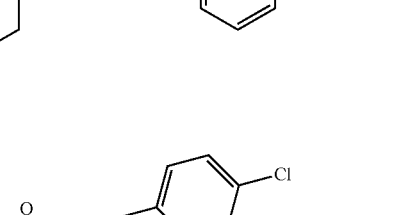 |
| 29 | 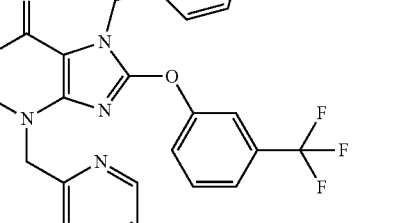 |
| 30 | 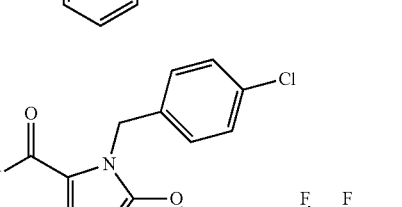 |

TABLE A-continued
| Compound Number | Structure |
|---|---|
| 31 | 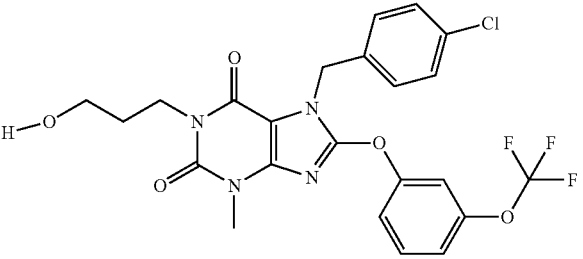 [SMILES: Cn1c(=O)n(CCCO)c(=O)c2c1nc(Oc1cccc(OC(F)(F)F)c1)n2Cc1ccc(Cl)cc1] |
| 32 | 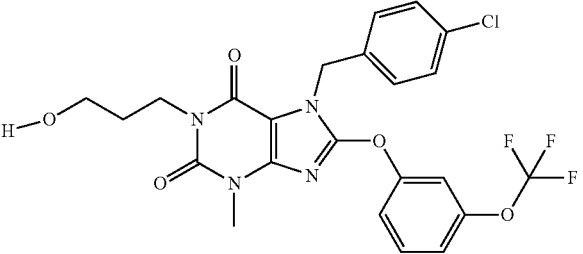 [SMILES: Cn1c(=O)n(CCCO)c(=O)c2c1nc(Oc1cccc(OC(F)(F)F)c1)n2Cc1ccc(Cl)cc1] |
| 33 | 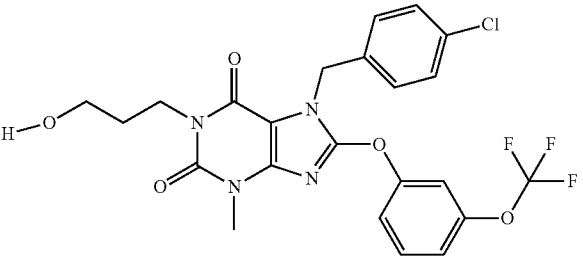 [SMILES: Cn1c(=O)n(CCCO)c(=O)c2c1nc(Oc1cccc(OC(F)(F)F)c1)n2Cc1ccc(Cl)cc1] |
| 34 | 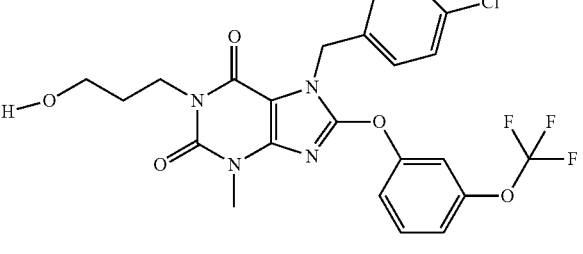 |
| 35 | 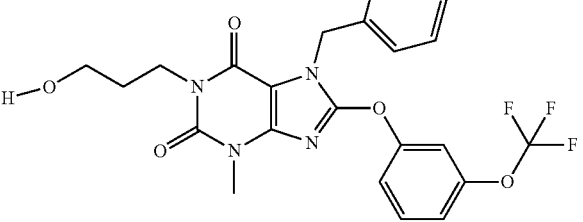 |

TABLE A-continued

| Compound Number | Structure |
|---|---|
| 36 | 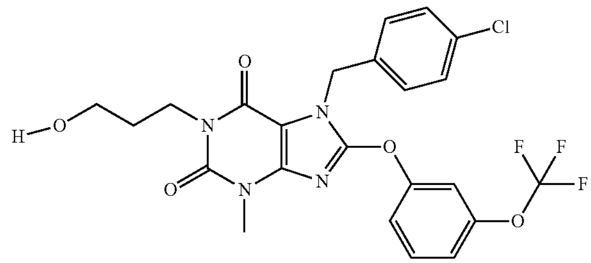 [SMILES: Cn1c(=O)n(CCCO)c(=O)c2c1nc(Oc1cccc(OC(F)(F)F)c1)n2Cc1ccc(Cl)cc1] |
| 37 | 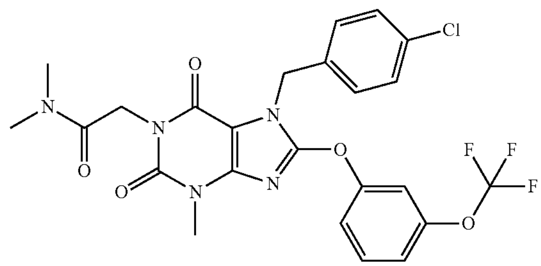 [SMILES: CN(C)C(=O)Cn1c(=O)c2c(nc(Oc3cccc(OC(F)(F)F)c3)n2Cc2ccc(Cl)cc2)n(C)c1=O] |
| 38 | 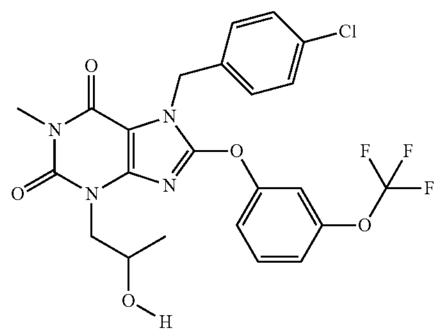 [SMILES: CC(O)Cn1c(=O)n(C)c(=O)c2c1nc(Oc1cccc(OC(F)(F)F)c1)n2Cc1ccc(Cl)cc1] |
| 39 | 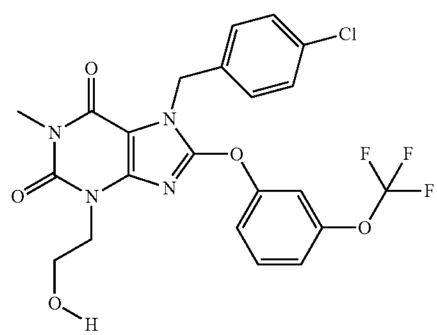 [SMILES: Cn1c(=O)c2c(nc(Oc3cccc(OC(F)(F)F)c3)n2Cc2ccc(Cl)cc2)n(CCO)c1=O] |
| 40 | 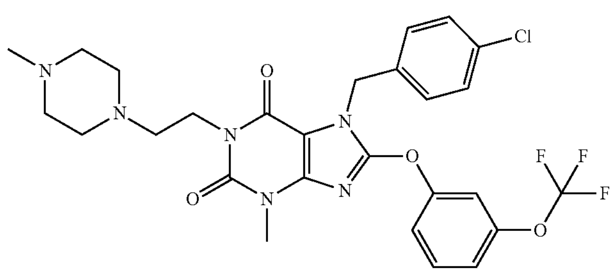 [SMILES: CN1CCN(CCn2c(=O)c3c(nc(Oc4cccc(OC(F)(F)F)c4)n3Cc3ccc(Cl)cc3)n(C)c2=O)CC1] |

TABLE A-continued
| Compound Number | Structure |
|---|---|
| 41 | 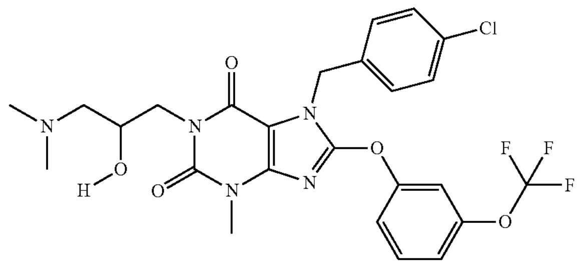 [SMILES: CN(C)CC(O)Cn1c(=O)c2c(nc(Oc3cccc(OC(F)(F)F)c3)n2Cc2ccc(Cl)cc2)n(C)c1=O] |
| 42 | 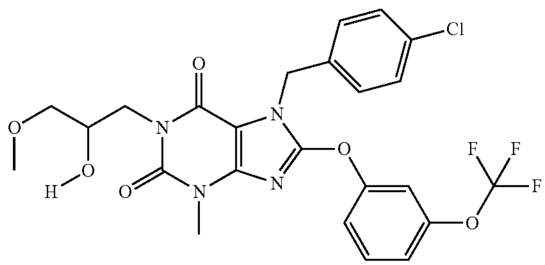 [SMILES: COCC(O)Cn1c(=O)c2c(nc(Oc3cccc(OC(F)(F)F)c3)n2Cc2ccc(Cl)cc2)n(C)c1=O] |
| 43 | 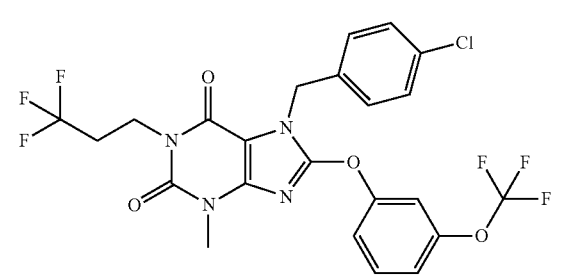 [SMILES: Cn1c(=O)n(CCC(F)(F)F)c(=O)c2c1nc(Oc1cccc(OC(F)(F)F)c1)n2Cc1ccc(Cl)cc1] |
| 44 | 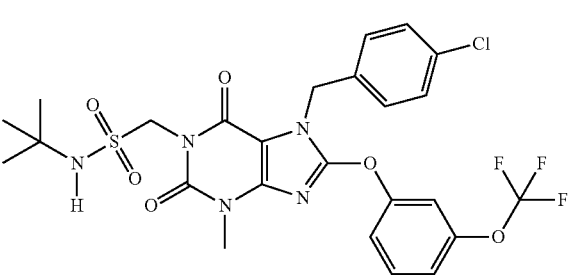 [SMILES: Cn1c(=O)n(CS(=O)(=O)NC(C)(C)C)c(=O)c2c1nc(Oc1cccc(OC(F)(F)F)c1)n2Cc1ccc(Cl)cc1] |
| 45 | 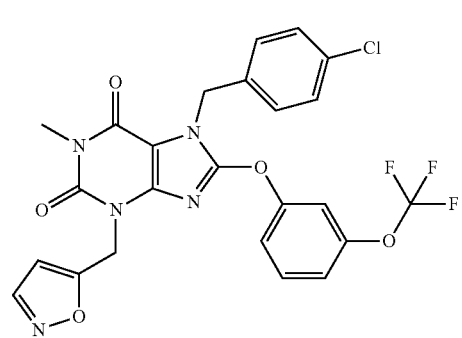 [SMILES: Cn1c(=O)c2c(nc(Oc3cccc(OC(F)(F)F)c3)n2Cc2ccc(Cl)cc2)n(Cc2ccno2)c1=O] |

TABLE A-continued
| Compound Number | Structure |
|---|---|
| 46 | 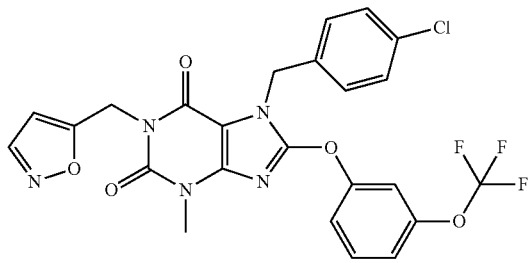 [SMILES: Cn1c(=O)n(Cc2ccno2)c(=O)c2c1nc(Oc1cccc(OC(F)(F)F)c1)n2Cc1ccc(Cl)cc1] |
| 47 | 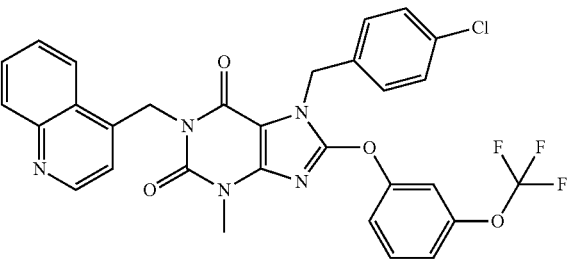 [SMILES: Cn1c(=O)n(Cc2ccnc3ccccc23)c(=O)c2c1nc(Oc1cccc(OC(F)(F)F)c1)n2Cc1ccc(Cl)cc1] |
| 48 | 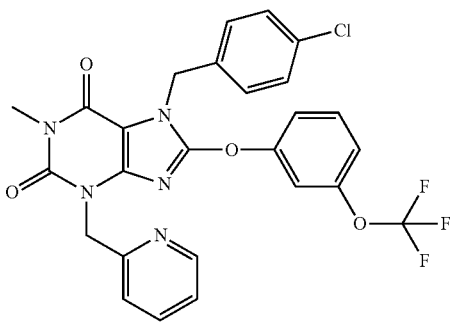 [SMILES: Cn1c(=O)c2c(nc(Oc3cccc(OC(F)(F)F)c3)n2Cc2ccc(Cl)cc2)n(Cc2ccccn2)c1=O] |
| 49 | 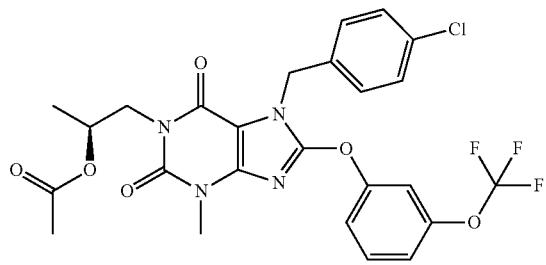 [SMILES: CC(=O)O[C@@H](C)Cn1c(=O)c2c(nc(Oc3cccc(OC(F)(F)F)c3)n2Cc2ccc(Cl)cc2)n(C)c1=O] |
| 50 | 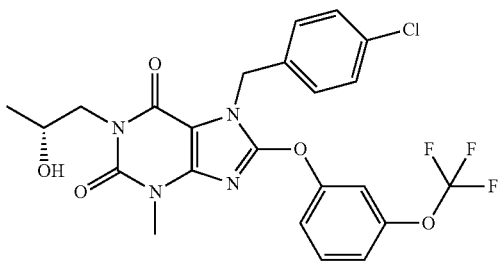 [SMILES: C[C@@H](O)Cn1c(=O)c2c(nc(Oc3cccc(OC(F)(F)F)c3)n2Cc2ccc(Cl)cc2)n(C)c1=O] |

TABLE A-continued
| Compound Number | Structure |
|---|---|
| 51 | 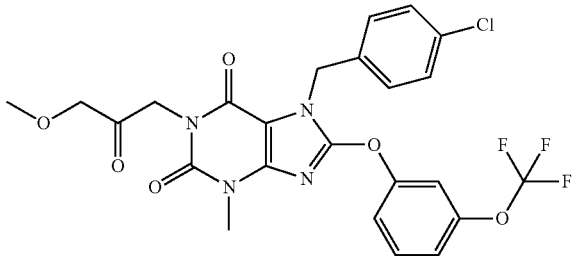 [SMILES: COCC(=O)Cn1c(=O)c2c(nc(Oc3cccc(OC(F)(F)F)c3)n2Cc2ccc(Cl)cc2)n(C)c1=O] |
| 52 | 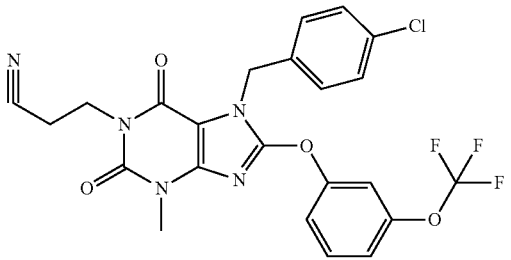 [SMILES: Cn1c(=O)n(CCC#N)c(=O)c2c1nc(Oc1cccc(OC(F)(F)F)c1)n2Cc1ccc(Cl)cc1] |
| 53 | 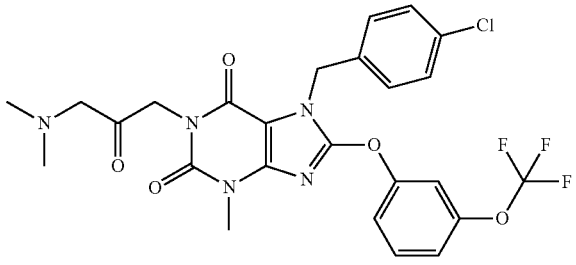 [SMILES: CN(C)CC(=O)Cn1c(=O)c2c(nc(Oc3cccc(OC(F)(F)F)c3)n2Cc2ccc(Cl)cc2)n(C)c1=O] |
| 54 | 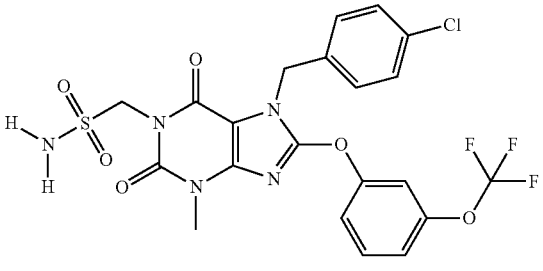 [SMILES: Cn1c(=O)n(CS(N)(=O)=O)c(=O)c2c1nc(Oc1cccc(OC(F)(F)F)c1)n2Cc1ccc(Cl)cc1] |
| 55 | 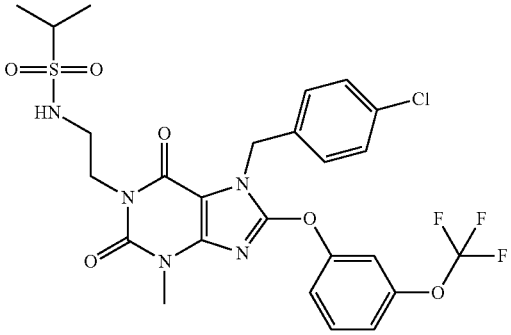 [SMILES: CC(C)S(=O)(=O)NCCn1c(=O)c2c(nc(Oc3cccc(OC(F)(F)F)c3)n2Cc2ccc(Cl)cc2)n(C)c1=O] |

TABLE A-continued

| Compound Number | Structure |
|---|---|
| 56 | 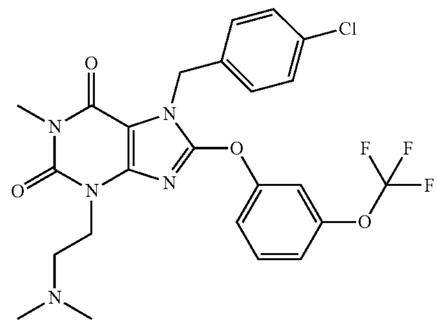 [SMILES: CN(C)CCn1c(=O)n(C)c(=O)c2c1nc(Oc1cccc(OC(F)(F)F)c1)n2Cc1ccc(Cl)cc1] |
| 57 | 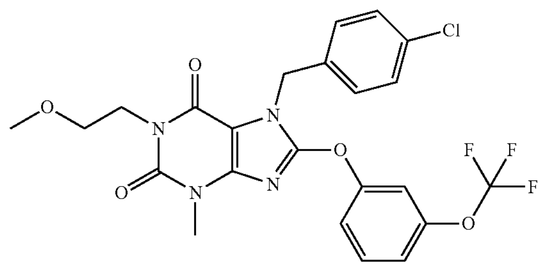 [SMILES: COCCn1c(=O)c2c(nc(Oc3cccc(OC(F)(F)F)c3)n2Cc2ccc(Cl)cc2)n(C)c1=O] |
| 58 | 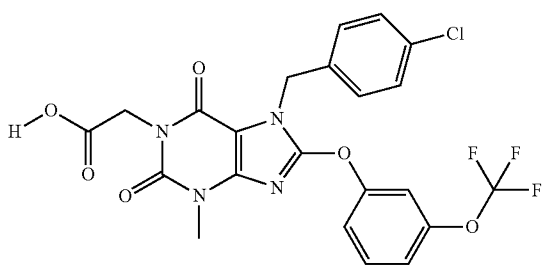 [SMILES: Cn1c(=O)n(CC(=O)O)c(=O)c2c1nc(Oc1cccc(OC(F)(F)F)c1)n2Cc1ccc(Cl)cc1] |
| 59 | 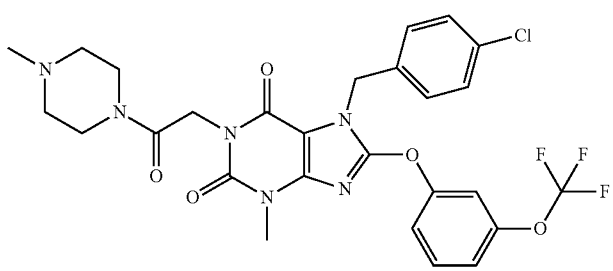 [SMILES: CN1CCN(C(=O)Cn2c(=O)c3c(nc(Oc4cccc(OC(F)(F)F)c4)n3Cc3ccc(Cl)cc3)n(C)c2=O)CC1] |
| 60 | 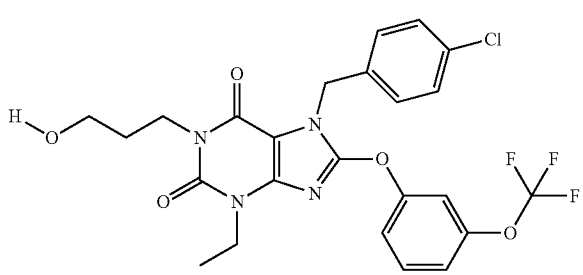 [SMILES: CCn1c(=O)n(CCCO)c(=O)c2c1nc(Oc1cccc(OC(F)(F)F)c1)n2Cc1ccc(Cl)cc1] |

TABLE A-continued

| Compound Number | Structure |
|---|---|
| 61 | 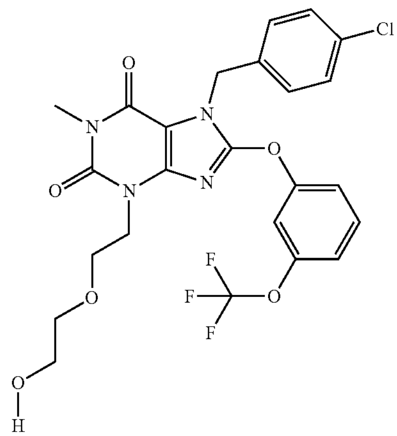 [SMILES: Cn1c(=O)c2c(nc(Oc3cccc(OC(F)(F)F)c3)n2Cc2ccc(Cl)cc2)n(CCOCCO)c1=O] |
| 62 | 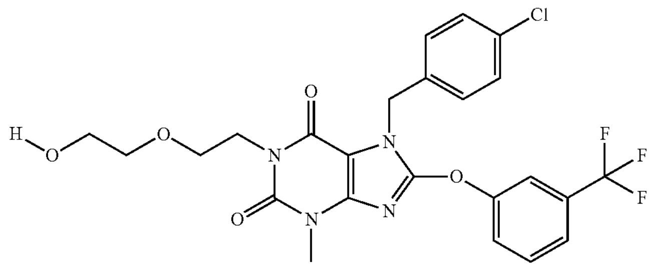 [SMILES: Cn1c(=O)n(CCOCCO)c(=O)c2c1nc(Oc1cccc(C(F)(F)F)c1)n2Cc1ccc(Cl)cc1] |
| 63 | 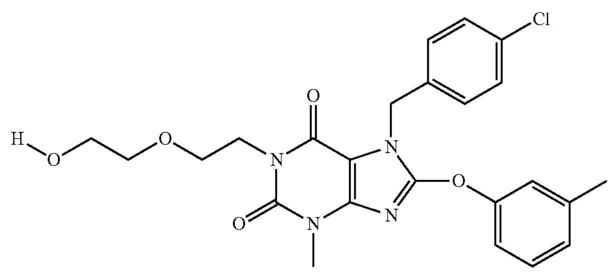 [SMILES: Cc1cccc(Oc2nc3c(c(=O)n(CCOCCO)c(=O)n3C)n2Cc2ccc(Cl)cc2)c1] |
| 64 | 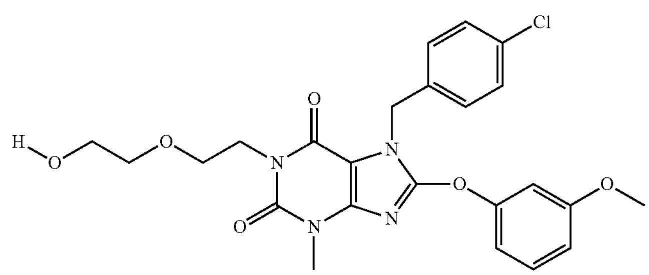 [SMILES: COc1cccc(Oc2nc3c(c(=O)n(CCOCCO)c(=O)n3C)n2Cc2ccc(Cl)cc2)c1] |
| 65 | 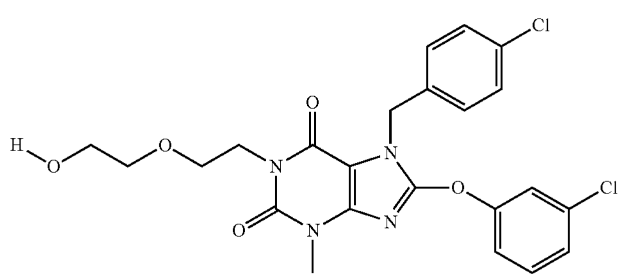 [SMILES: Cn1c(=O)n(CCOCCO)c(=O)c2c1nc(Oc1cccc(Cl)c1)n2Cc1ccc(Cl)cc1] |

TABLE A-continued

| Compound Number | Structure |
|---|---|
| 66 | 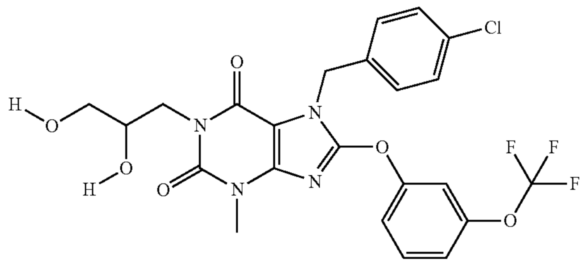 [SMILES: Cn1c(=O)n(CC(O)CO)c(=O)c2c1nc(Oc1cccc(OC(F)(F)F)c1)n2Cc1ccc(Cl)cc1] |
| 67 | 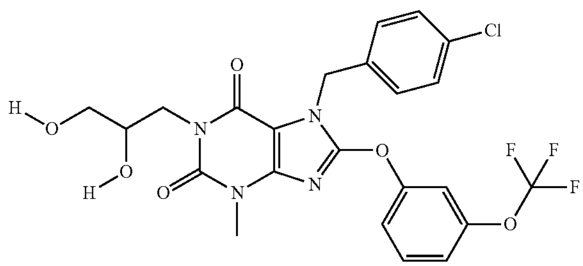 [SMILES: Cn1c(=O)n(CC(O)CO)c(=O)c2c1nc(Oc1cccc(OC(F)(F)F)c1)n2Cc1ccc(Cl)cc1] |
| 68 | 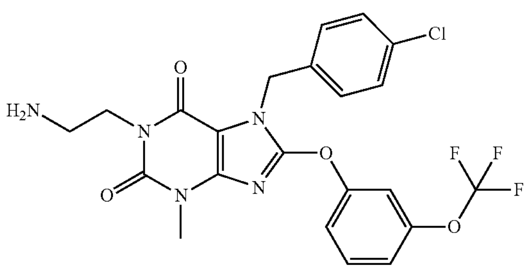 [SMILES: Cn1c(=O)n(CCN)c(=O)c2c1nc(Oc1cccc(OC(F)(F)F)c1)n2Cc1ccc(Cl)cc1] |
| 69 | 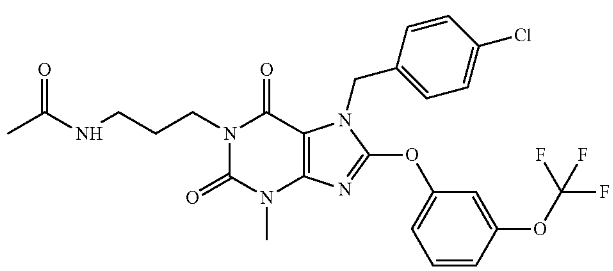 [SMILES: CC(=O)NCCCn1c(=O)c2c(nc(Oc3cccc(OC(F)(F)F)c3)n2Cc2ccc(Cl)cc2)n(C)c1=O] |
| 70 | 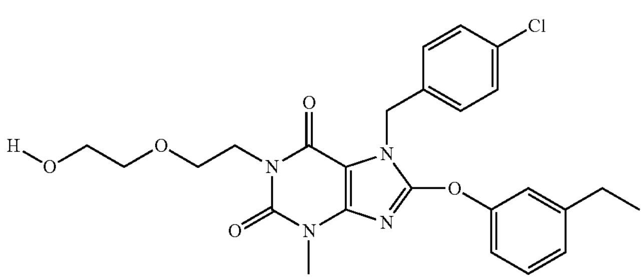 |

TABLE A-continued
| Compound Number | Structure |
|---|---|
| 71 | 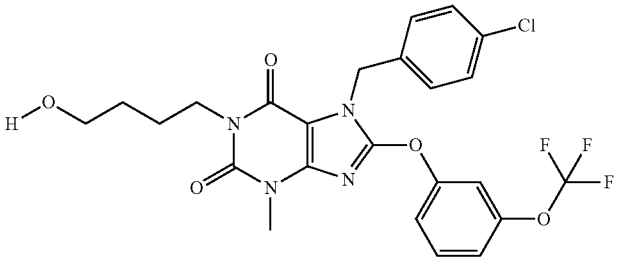 [SMILES: Cn1c(=O)n(CCCCO)c(=O)c2c1nc(Oc1cccc(OC(F)(F)F)c1)n2Cc1ccc(Cl)cc1] |
| 72 | 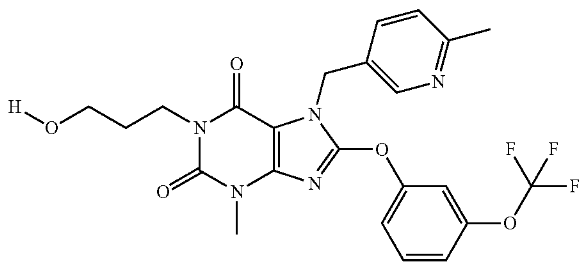 [SMILES: Cc1ccc(Cn2c(Oc3cccc(OC(F)(F)F)c3)nc3c2c(=O)n(CCCO)c(=O)n3C)cn1] |
| 73 | 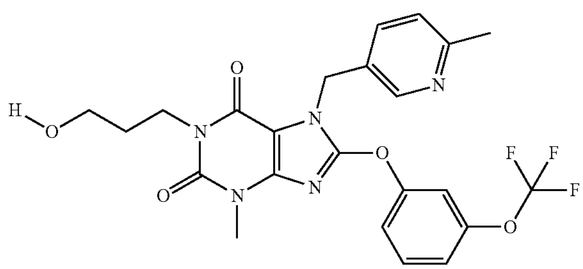 [SMILES: Cc1ccc(Cn2c(Oc3cccc(OC(F)(F)F)c3)nc3c2c(=O)n(CCCO)c(=O)n3C)cn1] |
| 74 | 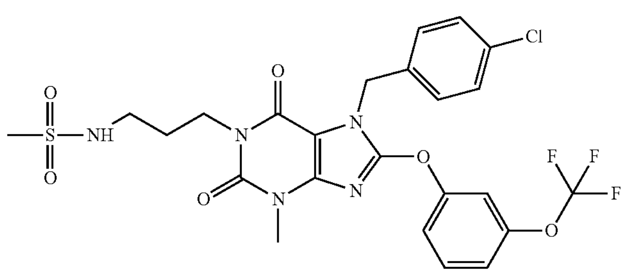 [SMILES: Cn1c(=O)n(CCCNS(C)(=O)=O)c(=O)c2c1nc(Oc1cccc(OC(F)(F)F)c1)n2Cc1ccc(Cl)cc1] |
| 75 | 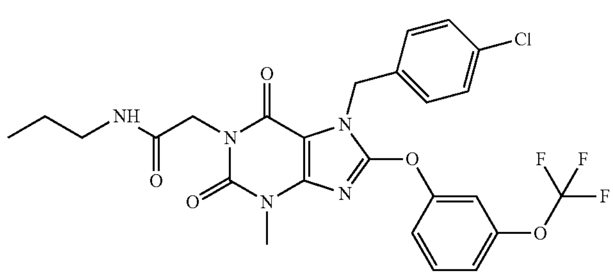 [SMILES: CCCNC(=O)Cn1c(=O)c2c(nc(Oc3cccc(OC(F)(F)F)c3)n2Cc2ccc(Cl)cc2)n(C)c1=O] |

TABLE A-continued

| Compound Number | Structure |
|---|---|
| 76 | (structure) |
| 77 | (structure) |
| 78 | (structure) |
| 79 | (structure) |
| 80 | (structure) |
| 81 | (structure) |

TABLE A-continued

| Compound Number | Structure |
| --- | --- |
| 82 | 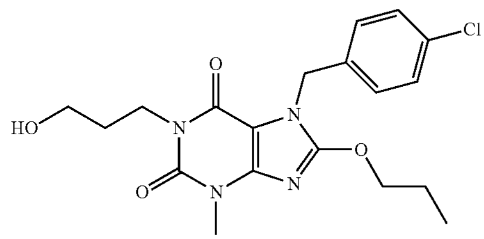 [SMILES: CCCOc1nc2c(c(=O)n(CCCO)c(=O)n2C)n1Cc1ccc(Cl)cc1] |
| 83 | 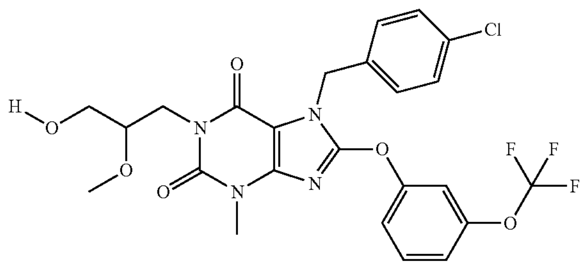 [SMILES: COC(CO)Cn1c(=O)c2c(nc(Oc3cccc(OC(F)(F)F)c3)n2Cc2ccc(Cl)cc2)n(C)c1=O] |
| 84 | 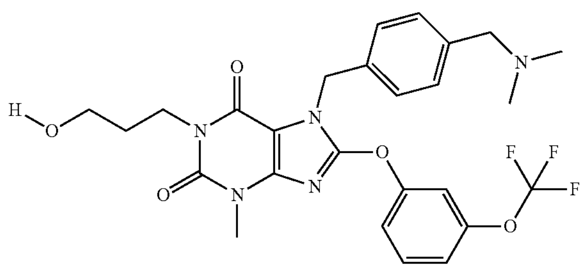 [SMILES: CN(C)Cc1ccc(Cn2c(Oc3cccc(OC(F)(F)F)c3)nc3c2c(=O)n(CCCO)c(=O)n3C)cc1] |
| 85 | 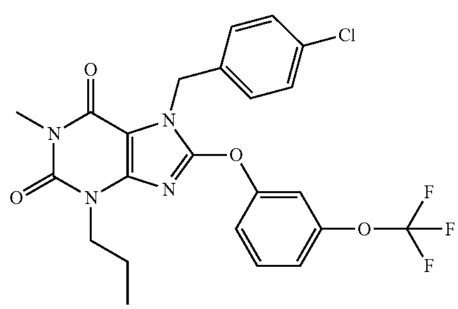 [SMILES: CCCn1c(=O)n(C)c(=O)c2c1nc(Oc1cccc(OC(F)(F)F)c1)n2Cc1ccc(Cl)cc1] |
| 86 | 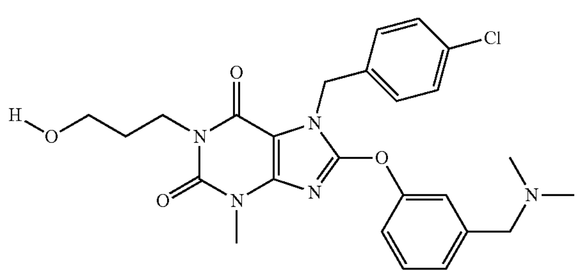 [SMILES: CN(C)Cc1cccc(Oc2nc3c(c(=O)n(CCCO)c(=O)n3C)n2Cc2ccc(Cl)cc2)c1] |

TABLE A-continued

| Compound Number | Structure |
|---|---|
| 87 | 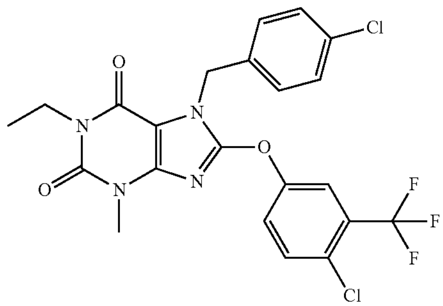 [SMILES: CCn1c(=O)c2c(nc(Oc3ccc(Cl)c(C(F)(F)F)c3)n2Cc2ccc(Cl)cc2)n(C)c1=O] |
| 88 | 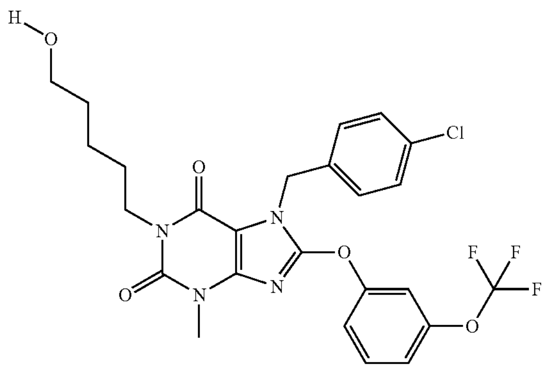 [SMILES: Cn1c(=O)n(CCCCCO)c(=O)c2c1nc(Oc1cccc(OC(F)(F)F)c1)n2Cc1ccc(Cl)cc1] |
| 89 | 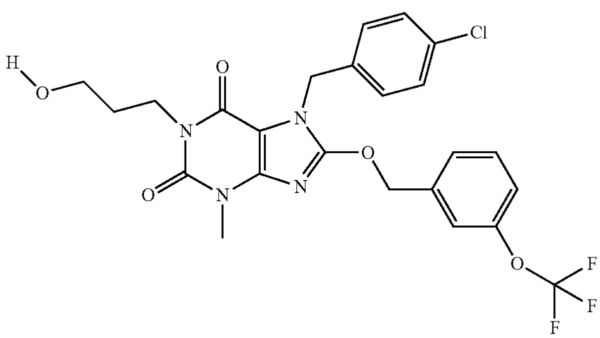 [SMILES: Cn1c(=O)n(CCCO)c(=O)c2c1nc(OCc1cccc(OC(F)(F)F)c1)n2Cc1ccc(Cl)cc1] |
| 90 | 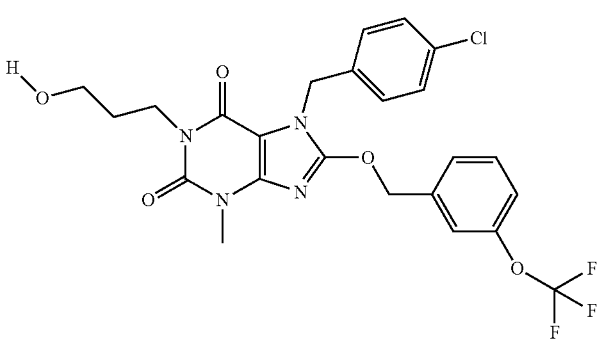 [SMILES: Cn1c(=O)n(CCCO)c(=O)c2c1nc(OCc1cccc(OC(F)(F)F)c1)n2Cc1ccc(Cl)cc1] |

TABLE A-continued

| Compound Number | Structure |
|---|---|
| 91 | 1-(2-(2-hydroxyethoxy)ethyl)-7-(4-chlorobenzyl)-3-methyl-8-(3-(morpholinomethyl)phenoxy)-3,7-dihydro-1H-purine-2,6-dione |
| 92 | 1-(2-(2-hydroxyethoxy)ethyl)-7-(4-chlorobenzyl)-3-methyl-8-(4-chloro-3-(trifluoromethyl)phenoxy)-3,7-dihydro-1H-purine-2,6-dione |
| 93 | 1-(2-(2-hydroxyethoxy)ethyl)-7-(4-chlorobenzyl)-3-methyl-8-(3,5-bis(trifluoromethyl)phenoxy)-3,7-dihydro-1H-purine-2,6-dione |
| 94 | 1-(2-(2-hydroxyethoxy)ethyl)-7-(4-methoxybenzyl)-3-methyl-8-(3-(trifluoromethoxy)phenoxy)-3,7-dihydro-1H-purine-2,6-dione |
| 95 | 1-(2-(2-hydroxyethoxy)ethyl)-7-(4-methoxybenzyl)-3-methyl-8-(3-(trifluoromethoxy)phenoxy)-3,7-dihydro-1H-purine-2,6-dione |

TABLE A-continued
| Compound Number | Structure |
|---|---|
| 96 | 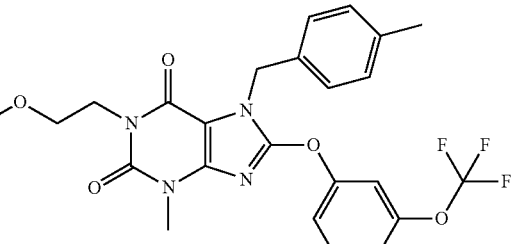 |
| 97 | 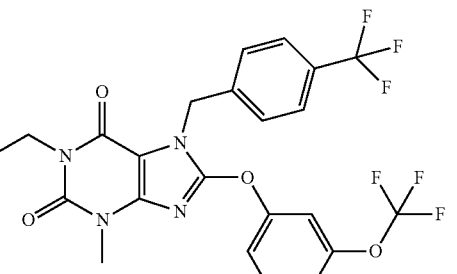 |
| 98 | 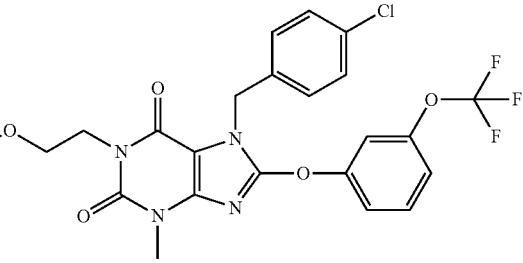 |
| 99 | 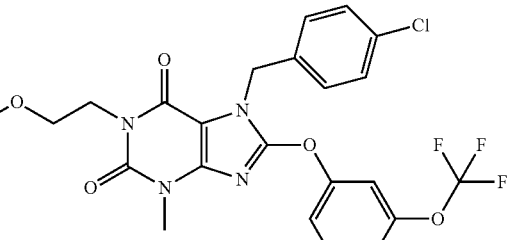 |
| 100 | 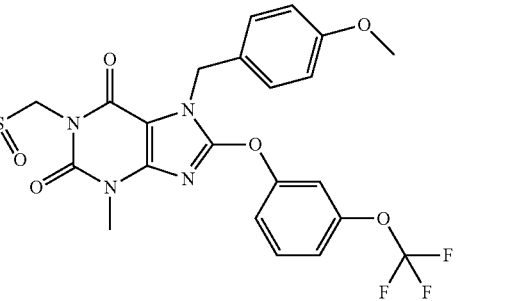 |

TABLE A-continued

| Compound Number | Structure |
|---|---|
| 101 | 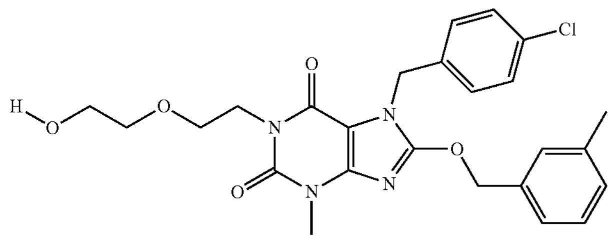 [SMILES: Cc1cccc(COc2nc3c(c(=O)n(CCOCCO)c(=O)n3C)n2Cc2ccc(Cl)cc2)c1] |
| 102 | 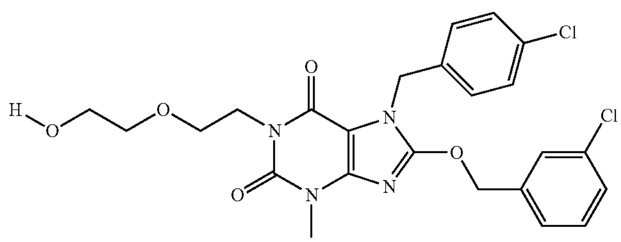 [SMILES: Cn1c(=O)n(CCOCCO)c(=O)c2c1nc(OCc1cccc(Cl)c1)n2Cc1ccc(Cl)cc1] |
| 103 | 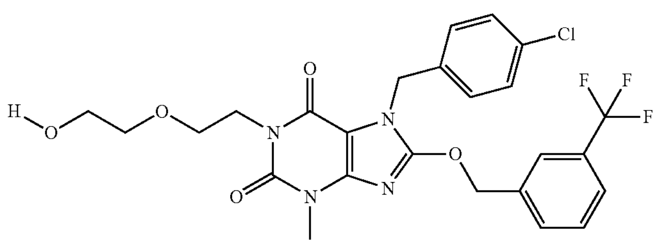 [SMILES: Cn1c(=O)n(CCOCCO)c(=O)c2c1nc(OCc1cccc(C(F)(F)F)c1)n2Cc1ccc(Cl)cc1] |
| 104 | 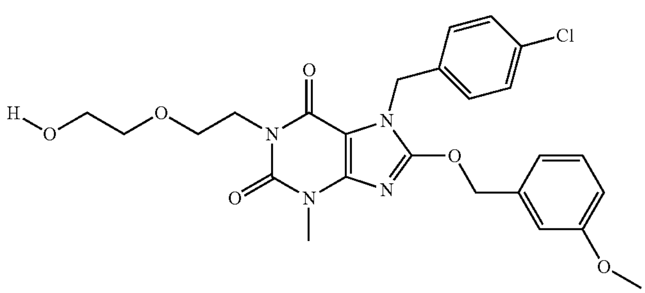 [SMILES: COc1cccc(COc2nc3c(c(=O)n(CCOCCO)c(=O)n3C)n2Cc2ccc(Cl)cc2)c1] |
| 105 | 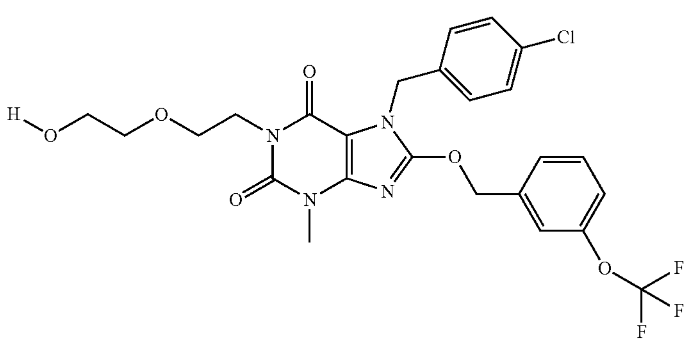 [SMILES: Cn1c(=O)n(CCOCCO)c(=O)c2c1nc(OCc1cccc(OC(F)(F)F)c1)n2Cc1ccc(Cl)cc1] |

TABLE A-continued
| Compound Number | Structure |
|---|---|
| 106 | 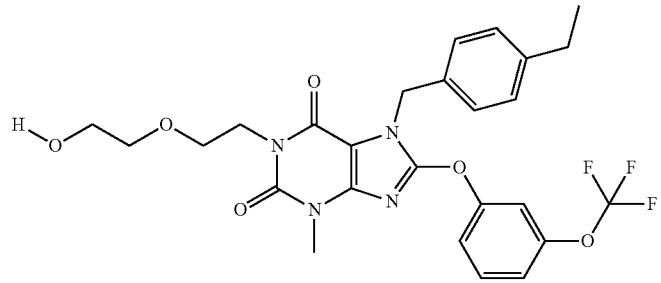 [SMILES: CCc1ccc(Cn2c(Oc3cccc(OC(F)(F)F)c3)nc3c2c(=O)n(CCOCCO)c(=O)n3C)cc1] |
| 107 | 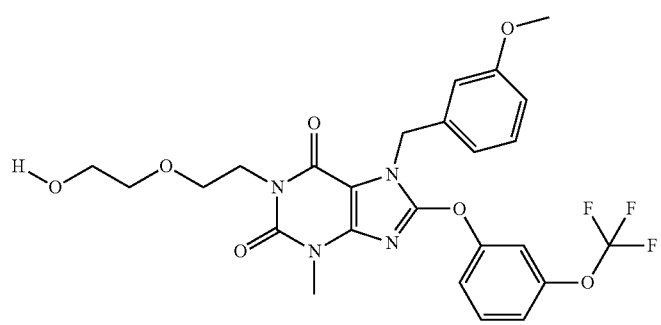 [SMILES: COc1cccc(Cn2c(Oc3cccc(OC(F)(F)F)c3)nc3c2c(=O)n(CCOCCO)c(=O)n3C)c1] |
| 108 | 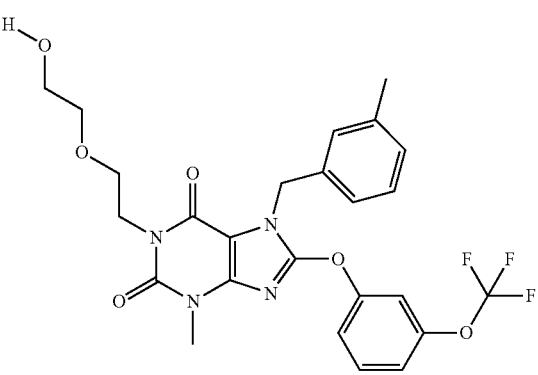 [SMILES: Cc1cccc(Cn2c(Oc3cccc(OC(F)(F)F)c3)nc3c2c(=O)n(CCOCCO)c(=O)n3C)c1] |
| 109 | 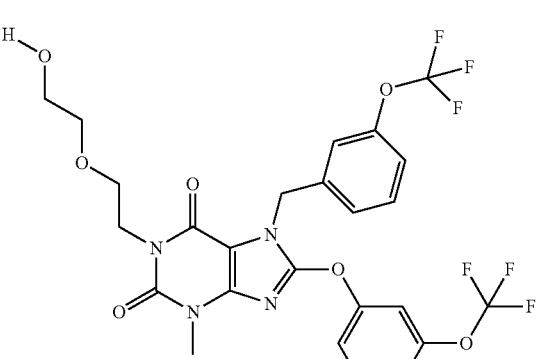 |

TABLE A-continued
| Compound Number | Structure |
|---|---|
| 110 | 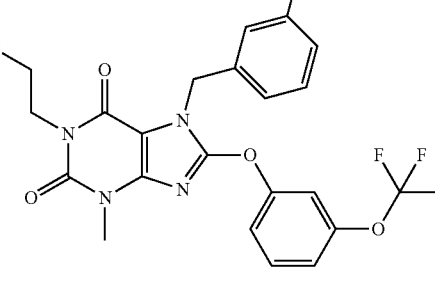 |
| 111 | 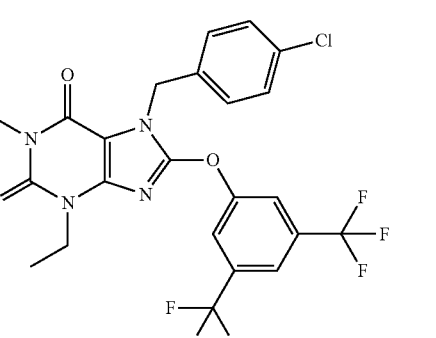 |
| 112 | 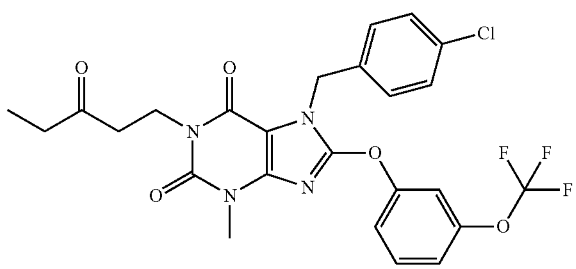 [SMILES: CCC(=O)CCn1c(=O)c2c(nc(Oc3cccc(OC(F)(F)F)c3)n2Cc2ccc(Cl)cc2)n(C)c1=O] |
| 113 | 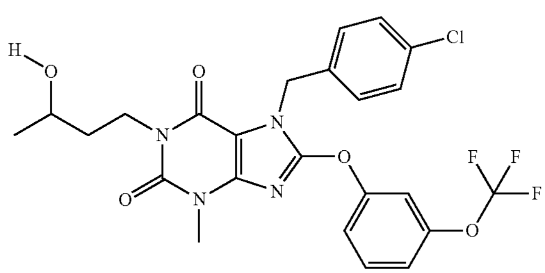 [SMILES: CC(O)CCn1c(=O)c2c(nc(Oc3cccc(OC(F)(F)F)c3)n2Cc2ccc(Cl)cc2)n(C)c1=O] |
| 114 | 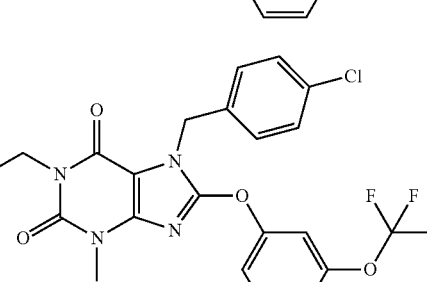 |

TABLE A-continued

| Compound Number | Structure |
|---|---|
| 115 | 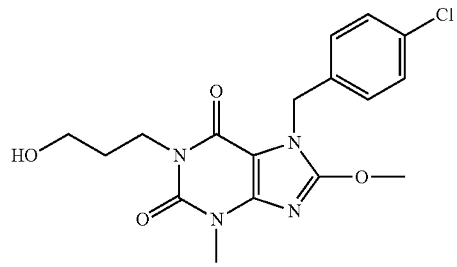 [SMILES: COc1nc2c(c(=O)n(CCCO)c(=O)n2C)n1Cc1ccc(Cl)cc1] |
| 116 | 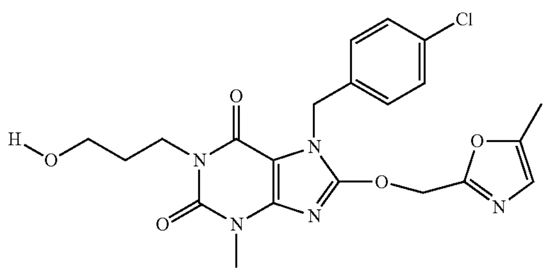 [SMILES: Cc1cnc(COc2nc3c(c(=O)n(CCCO)c(=O)n3C)n2Cc2ccc(Cl)cc2)o1] |
| 117 | 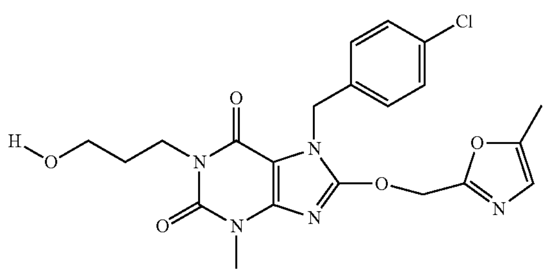 [SMILES: Cc1cnc(COc2nc3c(c(=O)n(CCCO)c(=O)n3C)n2Cc2ccc(Cl)cc2)o1] |
| 118 | 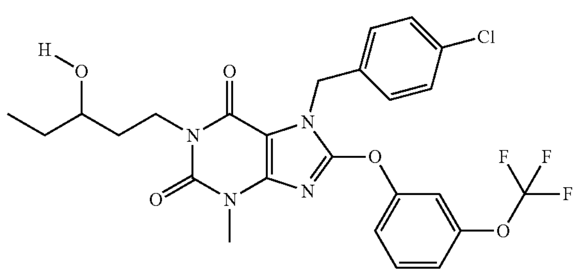 [SMILES: CCC(O)CCn1c(=O)c2c(nc(Oc3cccc(OC(F)(F)F)c3)n2Cc2ccc(Cl)cc2)n(C)c1=O] |
| 119 | 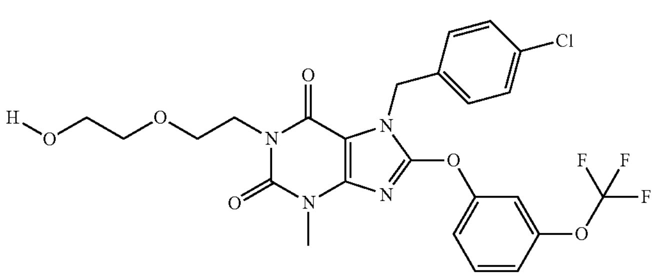 [SMILES: Cn1c(=O)n(CCOCCO)c(=O)c2c1nc(Oc1cccc(OC(F)(F)F)c1)n2Cc1ccc(Cl)cc1] |

TABLE A-continued
| Compound Number | Structure |
|---|---|
| 120 | 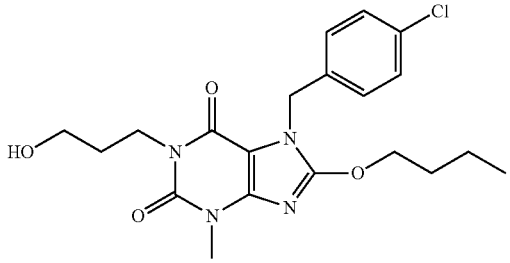 [SMILES: CCCCOc1nc2c(c(=O)n(CCCO)c(=O)n2C)n1Cc1ccc(Cl)cc1] |
| 121 | 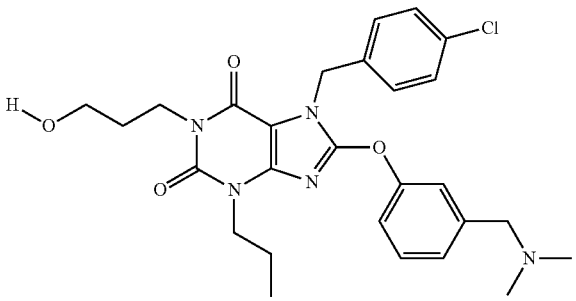 [SMILES: CCCn1c(=O)n(CCCO)c(=O)c2c1nc(Oc1cccc(CN(C)C)c1)n2Cc1ccc(Cl)cc1] |
| 122 | 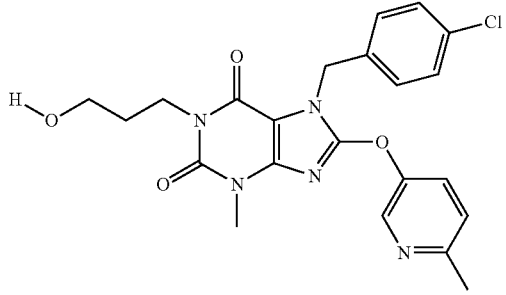 [SMILES: Cc1ccc(Oc2nc3c(c(=O)n(CCCO)c(=O)n3C)n2Cc2ccc(Cl)cc2)cn1] |
| 123 | 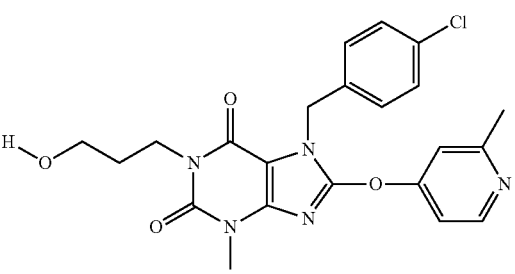 [SMILES: Cc1cc(Oc2nc3c(c(=O)n(CCCO)c(=O)n3C)n2Cc2ccc(Cl)cc2)ccn1] |
| 124 | 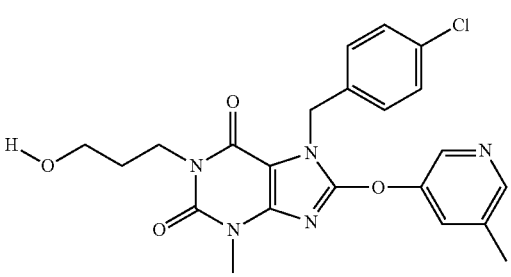 [SMILES: Cc1cncc(Oc2nc3c(c(=O)n(CCCO)c(=O)n3C)n2Cc2ccc(Cl)cc2)c1] |

TABLE A-continued
| Compound Number | Structure |
|---|---|
| 125 | 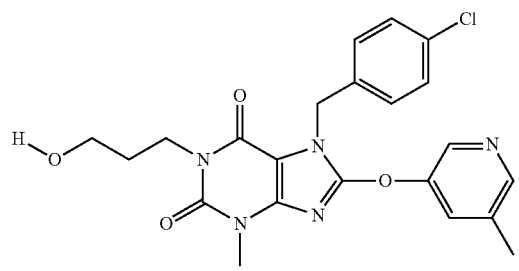 [SMILES: Cc1cncc(Oc2nc3c(c(=O)n(CCCO)c(=O)n3C)n2Cc2ccc(Cl)cc2)c1] |
| 126 | 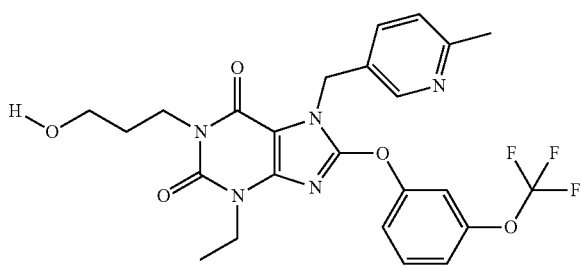 [SMILES: CCn1c(=O)n(CCCO)c(=O)c2c1nc(Oc1cccc(OC(F)(F)F)c1)n2Cc1ccc(C)nc1] |
| 127 | 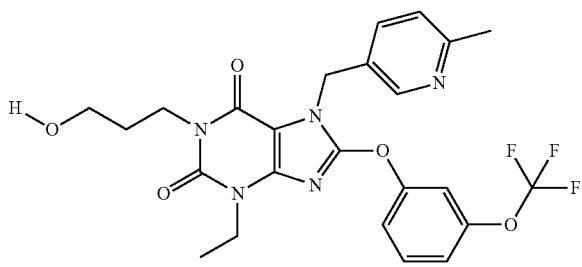 [SMILES: CCn1c(=O)n(CCCO)c(=O)c2c1nc(Oc1cccc(OC(F)(F)F)c1)n2Cc1ccc(C)nc1] |
| 128 | 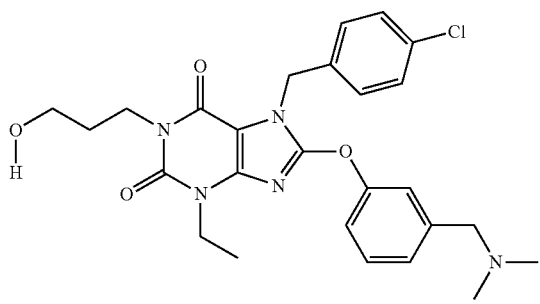 [SMILES: CCn1c(=O)n(CCCO)c(=O)c2c1nc(Oc1cccc(CN(C)C)c1)n2Cc1ccc(Cl)cc1] |
| 129 | 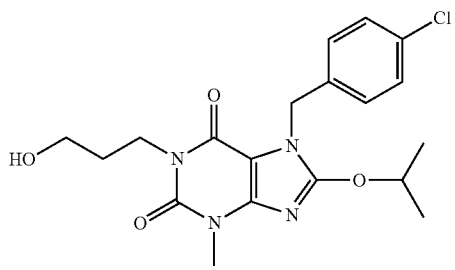 |

TABLE A-continued
| Compound Number | Structure |
|---|---|
| 130 | 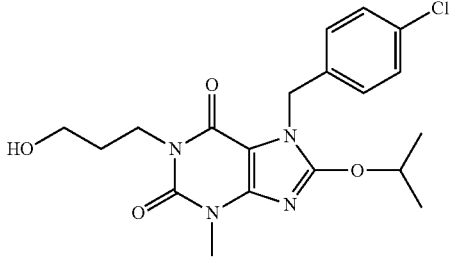 [SMILES: CC(C)Oc1nc2c(c(=O)n(CCCO)c(=O)n2C)n1Cc1ccc(Cl)cc1] |
| 131 | 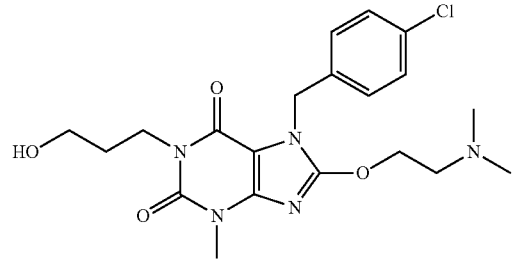 |
| 132 | 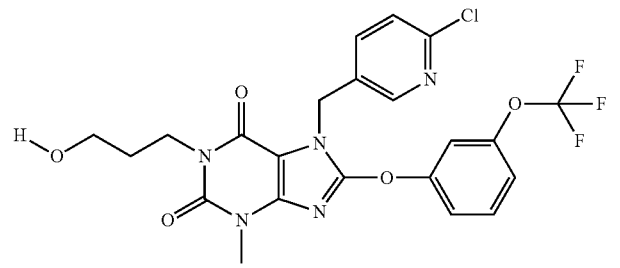 |
| 133 | 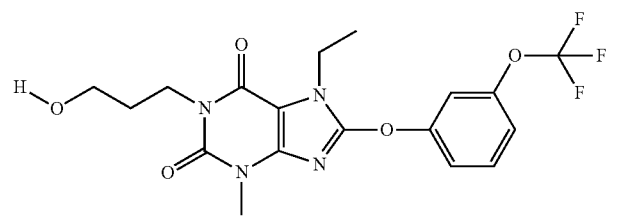 [SMILES: CCn1c(Oc2cccc(OC(F)(F)F)c2)nc2c1c(=O)n(CCCO)c(=O)n2C] |
| 134 | 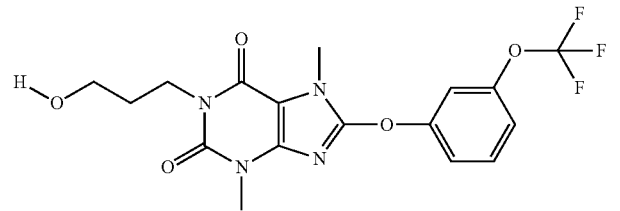 [SMILES: Cn1c(Oc2cccc(OC(F)(F)F)c2)nc2c1c(=O)n(CCCO)c(=O)n2C] |
| 135 | 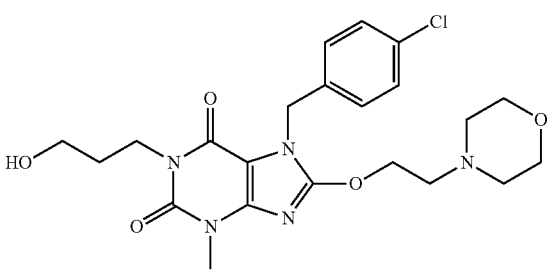 [SMILES: Cn1c(=O)n(CCCO)c(=O)c2c1nc(OCCN1CCOCC1)n2Cc1ccc(Cl)cc1] |

TABLE A-continued
| Compound Number | Structure |
|---|---|
| 136 | 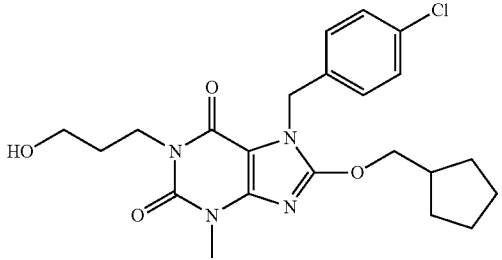 [SMILES: Cn1c(=O)n(CCCO)c(=O)c2c1nc(OCC1CCCC1)n2Cc1ccc(Cl)cc1] |
| 137 | 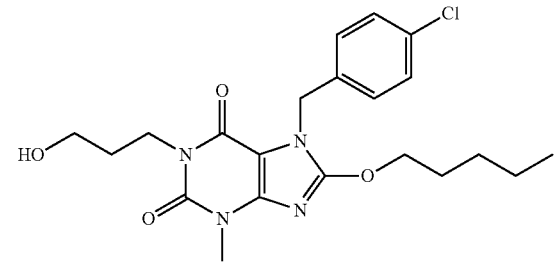 [SMILES: CCCCCOc1nc2c(c(=O)n(CCCO)c(=O)n2C)n1Cc1ccc(Cl)cc1] |
| 138 | 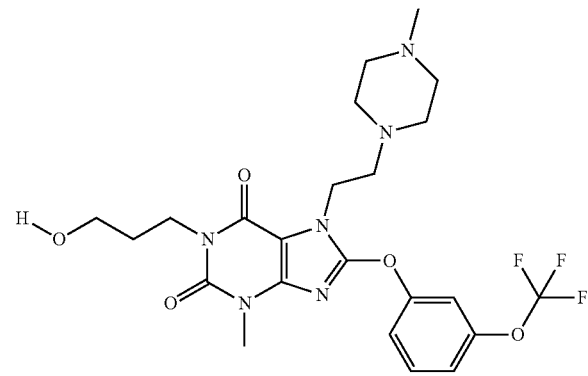 [SMILES: CN1CCN(CCn2c(Oc3cccc(OC(F)(F)F)c3)nc3c2c(=O)n(CCCO)c(=O)n3C)CC1] |
| 139 | 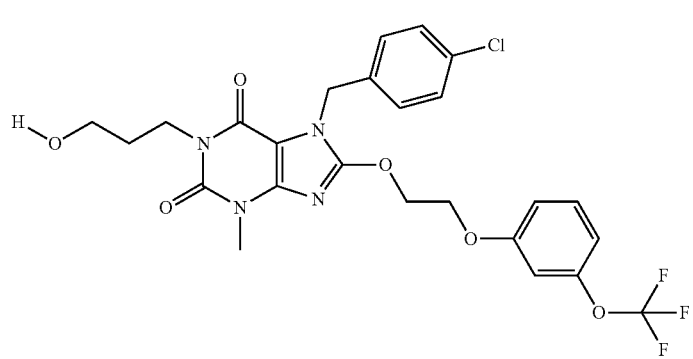 [SMILES: Cn1c(=O)n(CCCO)c(=O)c2c1nc(OCCOc1cccc(OC(F)(F)F)c1)n2Cc1ccc(Cl)cc1] |

TABLE A-continued

| Compound Number | Structure |
|---|---|
| 140 | 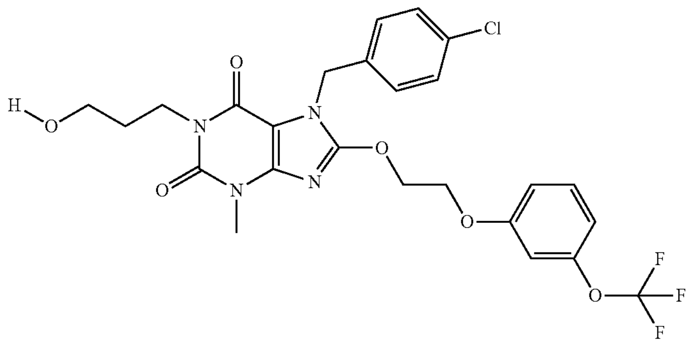 [SMILES: Cn1c(=O)n(CCCO)c(=O)c2c1nc(OCCOc1cccc(OC(F)(F)F)c1)n2Cc1ccc(Cl)cc1] |
| 141 | 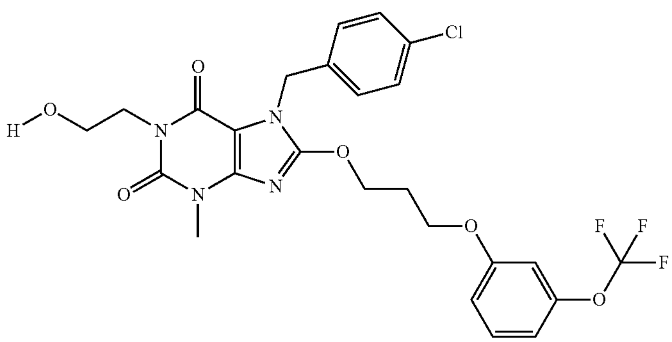 [SMILES: Cn1c(=O)n(CCO)c(=O)c2c1nc(OCCCOc1cccc(OC(F)(F)F)c1)n2Cc1ccc(Cl)cc1] |
| 142 | 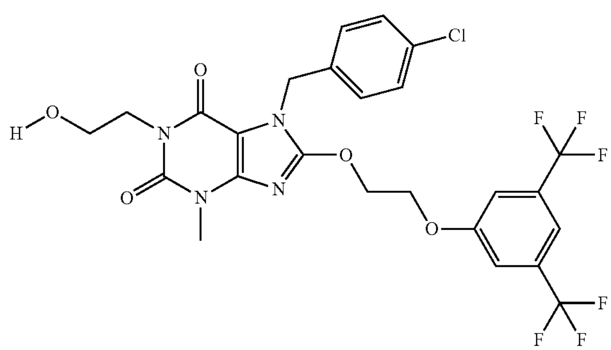 [SMILES: Cn1c(=O)n(CCO)c(=O)c2c1nc(OCCOc1cc(C(F)(F)F)cc(C(F)(F)F)c1)n2Cc1ccc(Cl)cc1] |
| 143 | 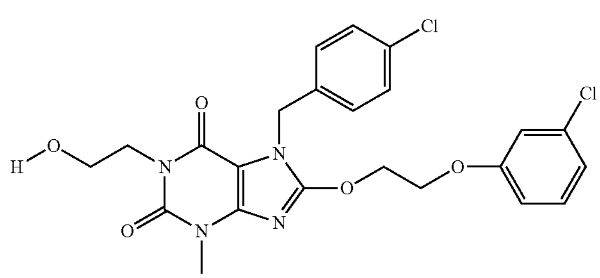 [SMILES: Cn1c(=O)n(CCO)c(=O)c2c1nc(OCCOc1cccc(Cl)c1)n2Cc1ccc(Cl)cc1] |
| 144 | 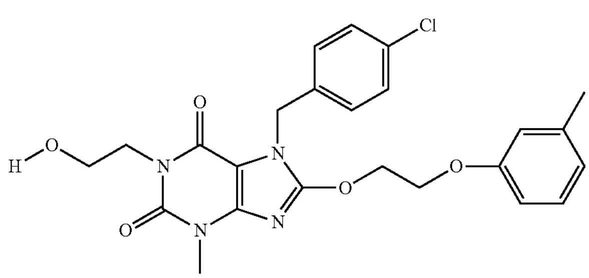 [SMILES: Cc1cccc(OCCOc2nc3c(c(=O)n(CCO)c(=O)n3C)n2Cc2ccc(Cl)cc2)c1] |

TABLE A-continued
| Compound Number | Structure |
|---|---|
| 145 | 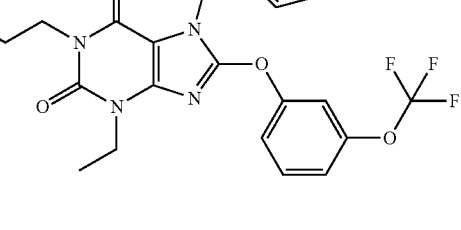 |
| 146 | 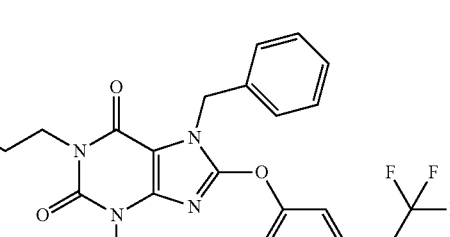 |
| 147 | 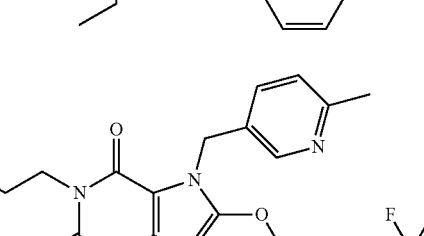 |
| 148 | 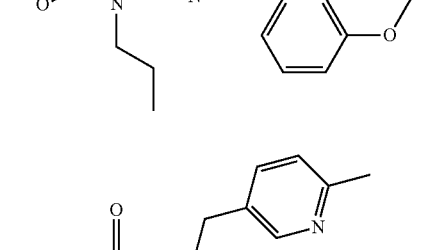 |
| 149 | 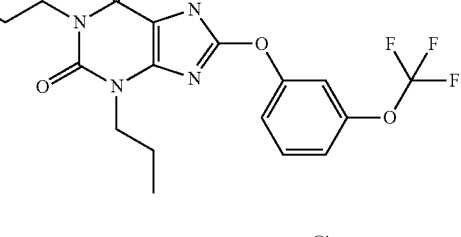 |

TABLE A-continued
| Compound Number | Structure |
|---|---|
| 150 | 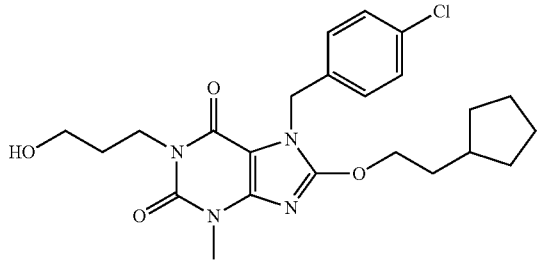 [SMILES: Cn1c(=O)n(CCCO)c(=O)c2c1nc(OCCC1CCCC1)n2Cc1ccc(Cl)cc1] |
| 151 | 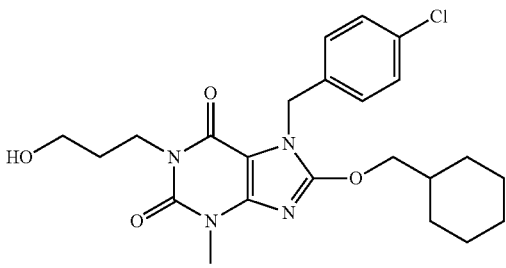 [SMILES: Cn1c(=O)n(CCCO)c(=O)c2c1nc(OCC1CCCCC1)n2Cc1ccc(Cl)cc1] |
| 152 | 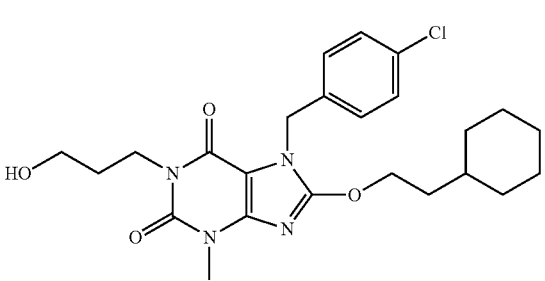 [SMILES: Cn1c(=O)n(CCCO)c(=O)c2c1nc(OCCC1CCCCC1)n2Cc1ccc(Cl)cc1] |
| 153 | 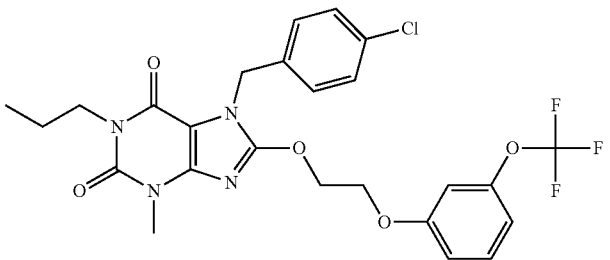 [SMILES: CCCn1c(=O)c2c(nc(OCCOc3cccc(OC(F)(F)F)c3)n2Cc2ccc(Cl)cc2)n(C)c1=O] |
| 154 | 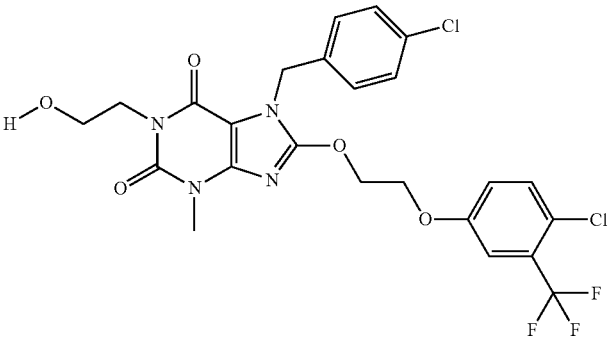 [SMILES: Cn1c(=O)n(CCO)c(=O)c2c1nc(OCCOc1ccc(Cl)c(C(F)(F)F)c1)n2Cc1ccc(Cl)cc1] |

TABLE A-continued

| Compound Number | Structure |
|---|---|
| 155 | 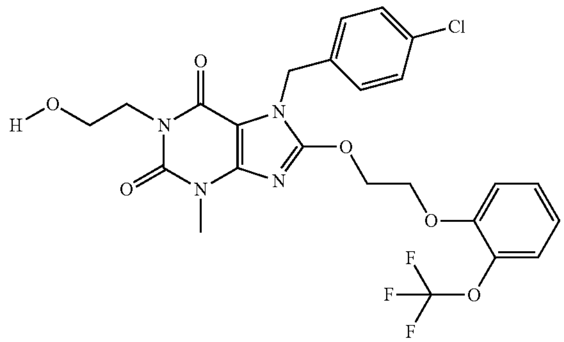 [SMILES: Cn1c(=O)n(CCO)c(=O)c2c1nc(OCCOc1ccccc1OC(F)(F)F)n2Cc1ccc(Cl)cc1] |
| 156 | 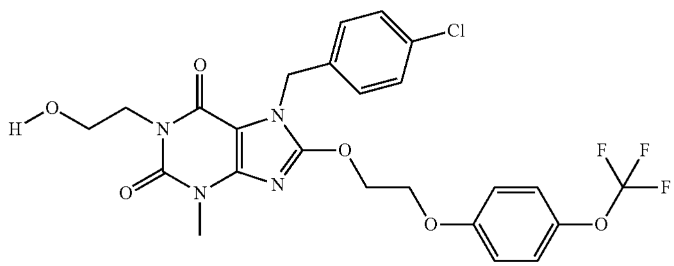 [SMILES: Cn1c(=O)n(CCO)c(=O)c2c1nc(OCCOc1ccc(OC(F)(F)F)cc1)n2Cc1ccc(Cl)cc1] |
| 157 | 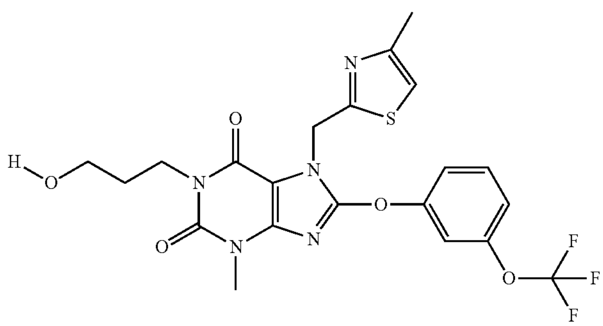 [SMILES: Cc1csc(Cn2c(Oc3cccc(OC(F)(F)F)c3)nc3c2c(=O)n(CCCO)c(=O)n3C)n1] |
| 158 | 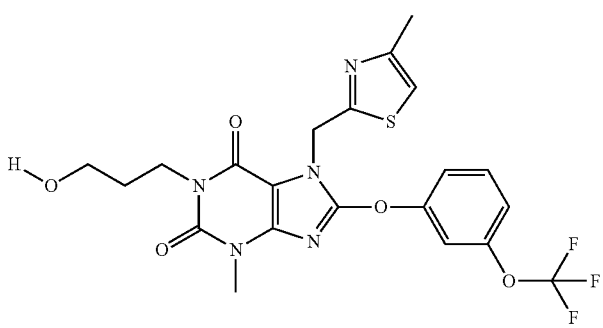 [SMILES: Cc1csc(Cn2c(Oc3cccc(OC(F)(F)F)c3)nc3c2c(=O)n(CCCO)c(=O)n3C)n1] |
| 159 | 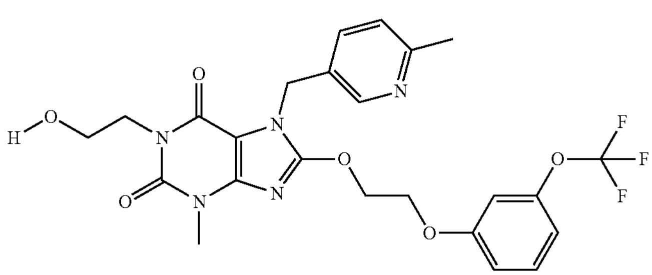 [SMILES: Cc1ccc(Cn2c(OCCOc3cccc(OC(F)(F)F)c3)nc3c2c(=O)n(CCO)c(=O)n3C)cn1] |

TABLE A-continued

| Compound Number | Structure |
|---|---|
| 160 | 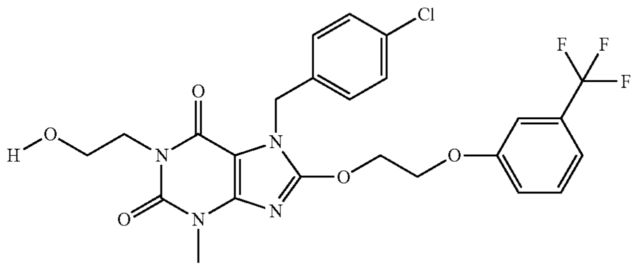 [SMILES: Cn1c(=O)n(CCO)c(=O)c2c1nc(OCCOc1cccc(C(F)(F)F)c1)n2Cc1ccc(Cl)cc1] |
| 161 | 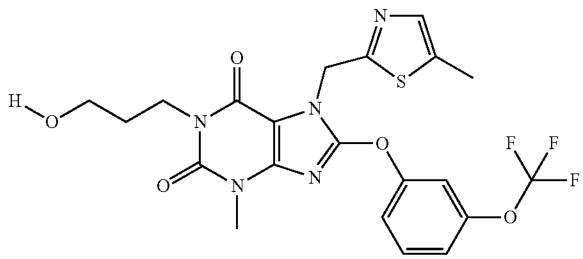 [SMILES: Cc1cnc(Cn2c(Oc3cccc(OC(F)(F)F)c3)nc3c2c(=O)n(CCCO)c(=O)n3C)s1] |
| 162 | 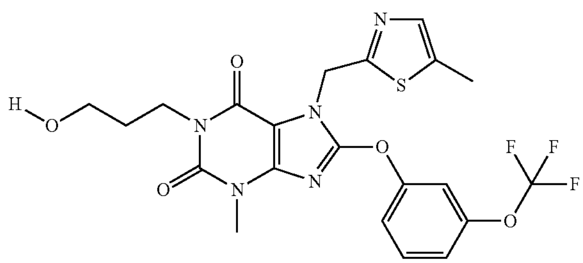 |
| 163 | 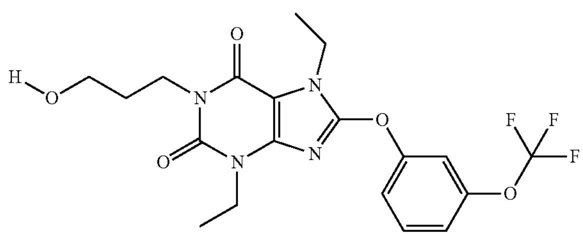 [SMILES: CCn1c(Oc2cccc(OC(F)(F)F)c2)nc2c1c(=O)n(CCCO)c(=O)n2CC] |
| 164 | 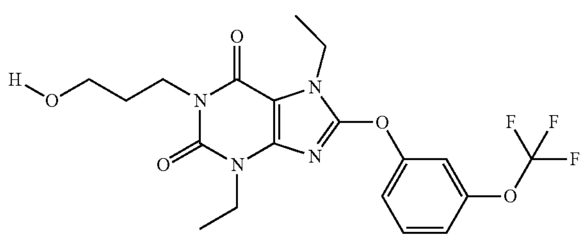 [SMILES: CCn1c(Oc2cccc(OC(F)(F)F)c2)nc2c1c(=O)n(CCCO)c(=O)n2CC] |
| 165 | 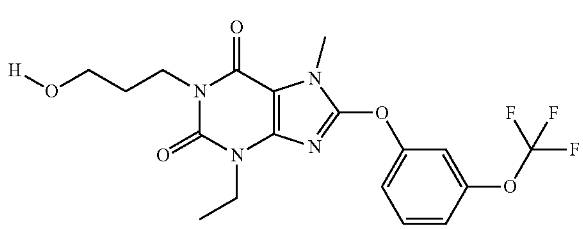 [SMILES: CCn1c(=O)n(CCCO)c(=O)c2c1nc(Oc1cccc(OC(F)(F)F)c1)n2C] |

TABLE A-continued
| Compound Number | Structure |
|---|---|
| 166 | 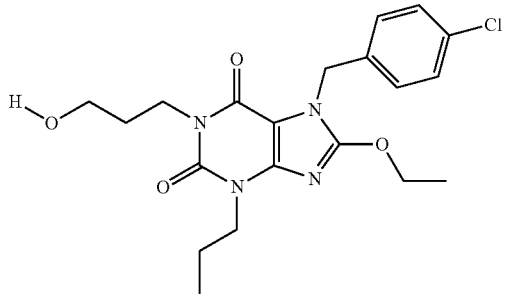 [SMILES: CCCn1c(=O)n(CCCO)c(=O)c2c1nc(OCC)n2Cc1ccc(Cl)cc1] |
| 167 | 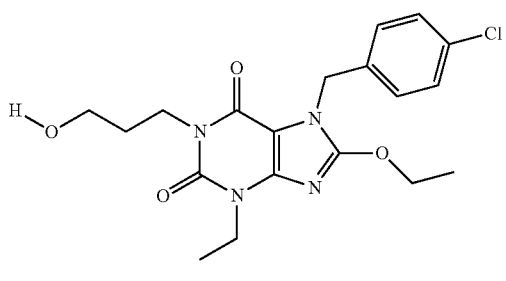 [SMILES: CCOc1nc2c(c(=O)n(CCCO)c(=O)n2CC)n1Cc1ccc(Cl)cc1] |
| 168 | 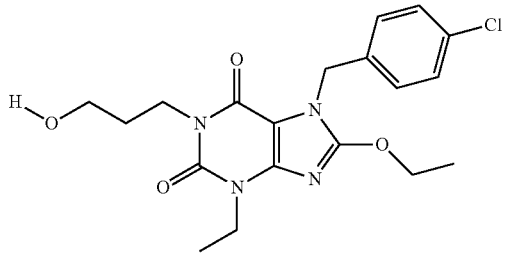 [SMILES: CCOc1nc2c(c(=O)n(CCCO)c(=O)n2CC)n1Cc1ccc(Cl)cc1] |
| 169 | 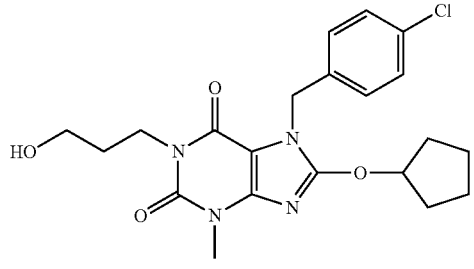 [SMILES: Cn1c(=O)n(CCCO)c(=O)c2c1nc(OC1CCCC1)n2Cc1ccc(Cl)cc1] |
| 170 | 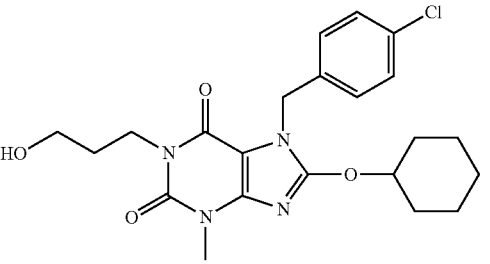 [SMILES: Cn1c(=O)n(CCCO)c(=O)c2c1nc(OC1CCCCC1)n2Cc1ccc(Cl)cc1] |

TABLE A-continued
| Compound Number | Structure |
|---|---|
| 171 | 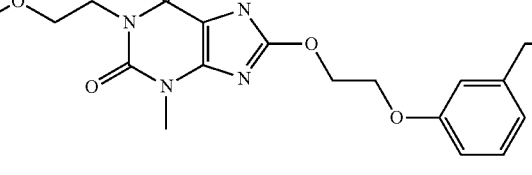 |
| 172 | 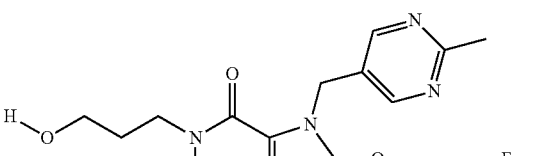 |
| 173 | 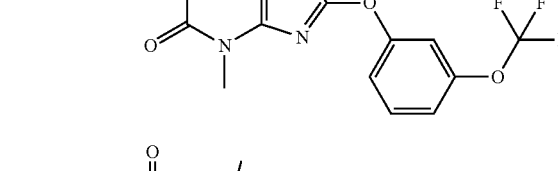 |
| 174 | 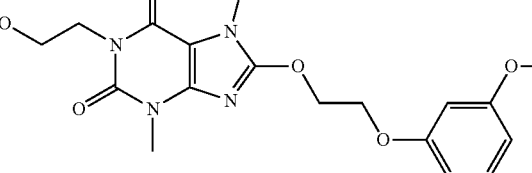 |
| 175 | 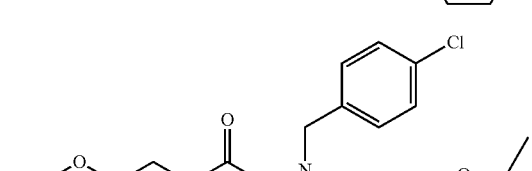 |
| 176 | 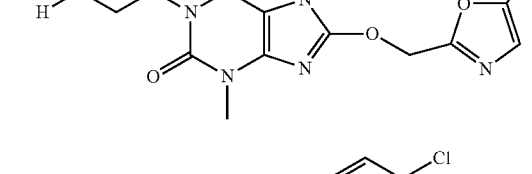 |

TABLE A-continued

| Compound Number | Structure |
|---|---|
| 177 | 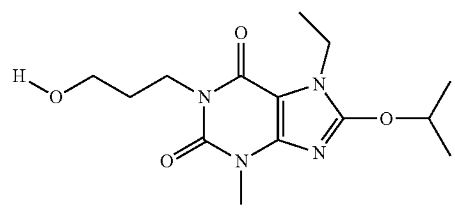 [SMILES: CCn1c(OC(C)C)nc2c1c(=O)n(CCCO)c(=O)n2C] |
| 178 | 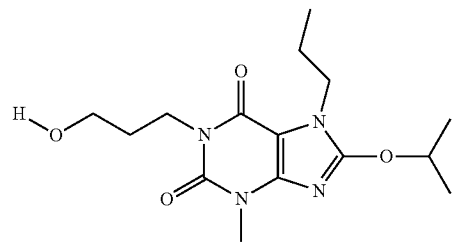 [SMILES: CCCn1c(OC(C)C)nc2c1c(=O)n(CCCO)c(=O)n2C] |
| 179 | 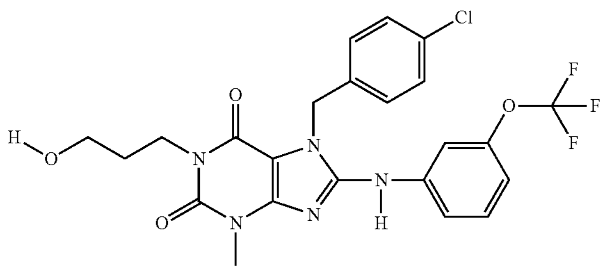 [SMILES: Cn1c(=O)n(CCCO)c(=O)c2c1nc(Nc1cccc(OC(F)(F)F)c1)n2Cc1ccc(Cl)cc1] |
| 180 | 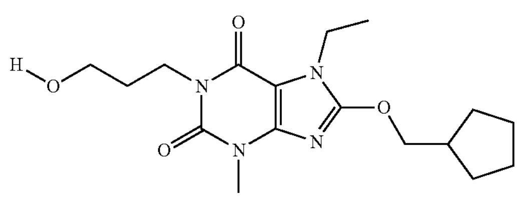 [SMILES: CCn1c(OCC2CCCC2)nc2c1c(=O)n(CCCO)c(=O)n2C] |
| 181 | 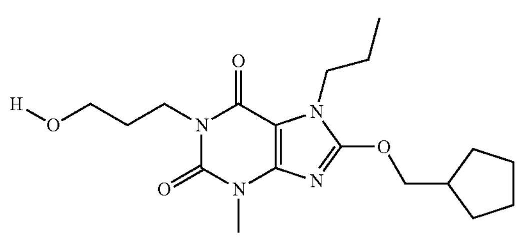 [SMILES: CCCn1c(OCC2CCCC2)nc2c1c(=O)n(CCCO)c(=O)n2C] |
| 182 | 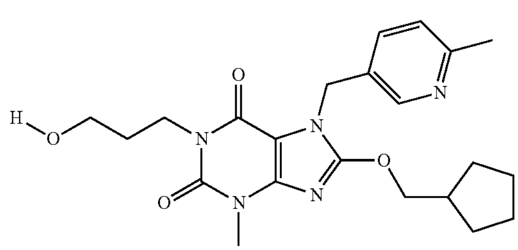 [SMILES: Cc1ccc(Cn2c(OCC3CCCC3)nc3c2c(=O)n(CCCO)c(=O)n3C)cn1] |

TABLE A-continued
| Compound Number | Structure |
|---|---|
| 183 | 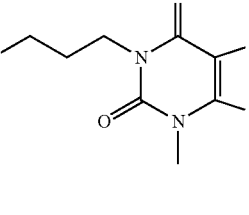 |
| 184 | 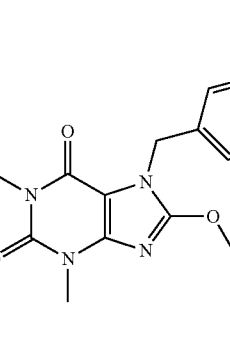 |
| 185 | 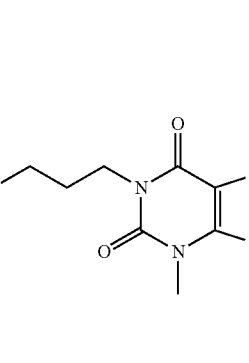 |
| 186 | 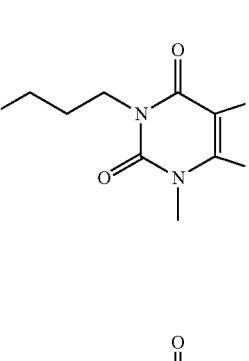 |
| 187 | 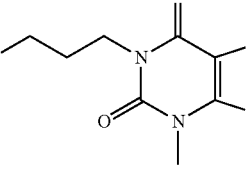 |

TABLE A-continued

| Compound Number | Structure |
|---|---|
| 188 | 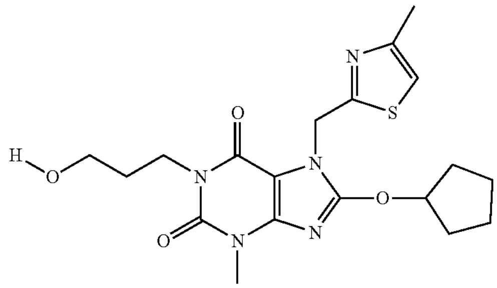 [SMILES: Cc1csc(Cn2c(OC3CCCC3)nc3c2c(=O)n(CCCO)c(=O)n3C)n1] |
| 189 | 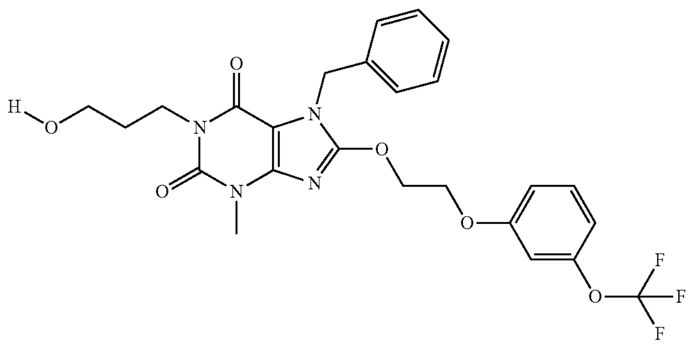 [SMILES: Cn1c(=O)n(CCCO)c(=O)c2c1nc(OCCOc1cccc(OC(F)(F)F)c1)n2Cc1ccccc1] |
| 190 | 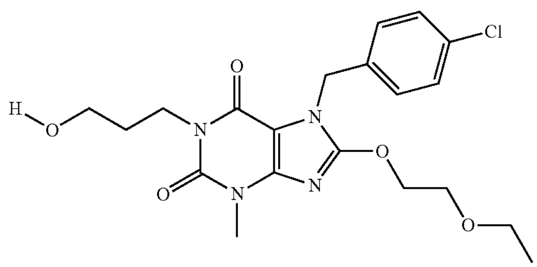 |
| 191 | 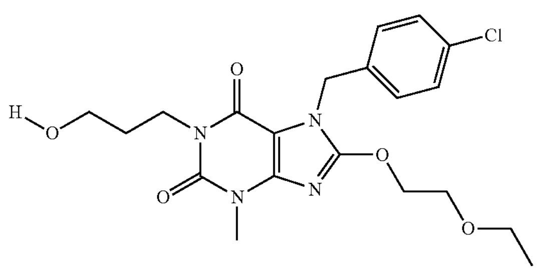 |
| 192 | 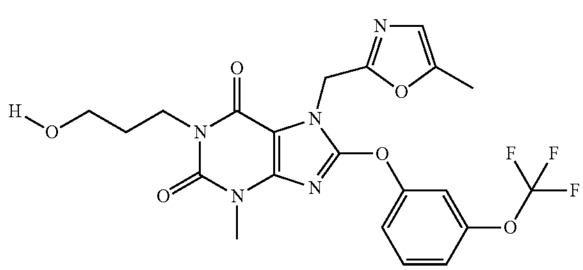 |

TABLE A-continued
| Compound Number | Structure |
|---|---|
| 193 | 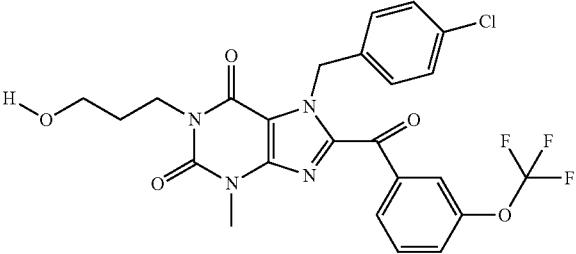 [SMILES: Cn1c(=O)n(CCCO)c(=O)c2c1nc(C(=O)c1cccc(OC(F)(F)F)c1)n2Cc1ccc(Cl)cc1] |
| 194 | 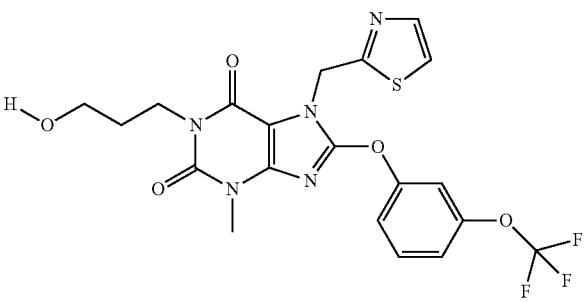 [SMILES: Cn1c(=O)n(CCCO)c(=O)c2c1nc(Oc1cccc(OC(F)(F)F)c1)n2Cc1nccs1] |
| 195 | 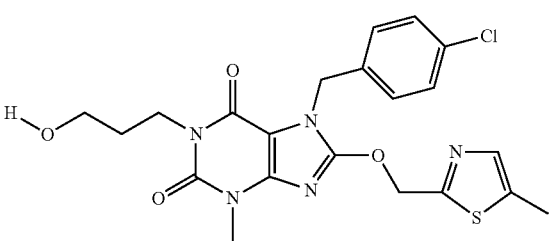 [SMILES: Cc1cnc(COc2nc3c(c(=O)n(CCCO)c(=O)n3C)n2Cc2ccc(Cl)cc2)s1] |
| 196 | 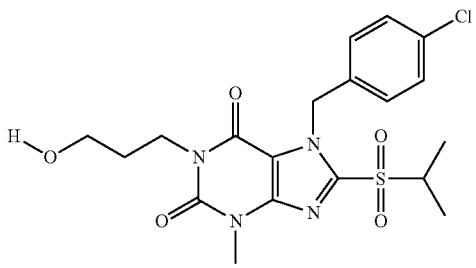 [SMILES: CC(C)S(=O)(=O)c1nc2c(c(=O)n(CCCO)c(=O)n2C)n1Cc1ccc(Cl)cc1] |
| 197 | 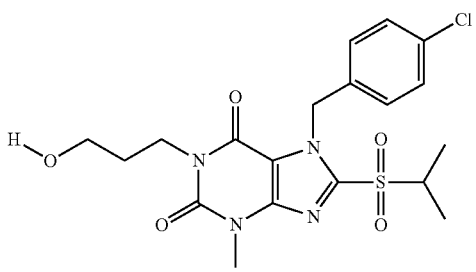 [SMILES: CC(C)S(=O)(=O)c1nc2c(c(=O)n(CCCO)c(=O)n2C)n1Cc1ccc(Cl)cc1] |

TABLE A-continued
| Compound Number | Structure |
|---|---|
| 198 | 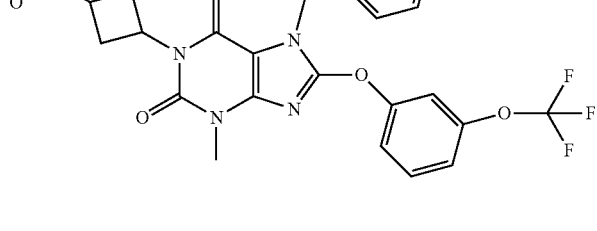 |
| 199 | 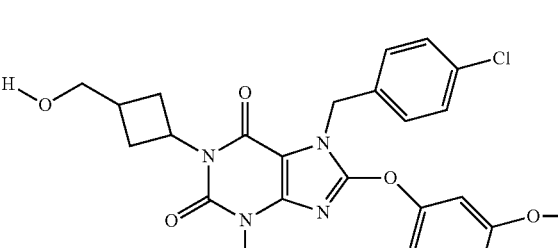 |
| 200 | 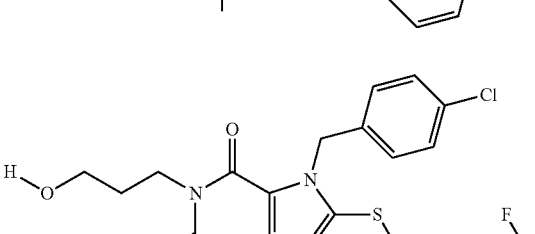 |
| 201 | 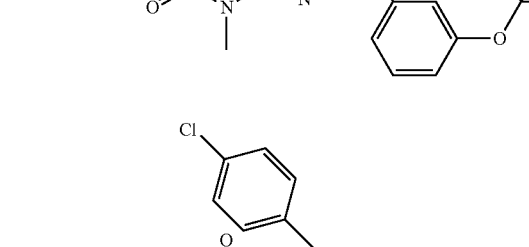 |
| 202 | 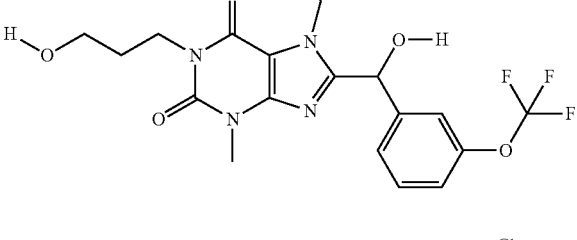 |

TABLE A-continued

| Compound Number | Structure |
|---|---|
| 203 | 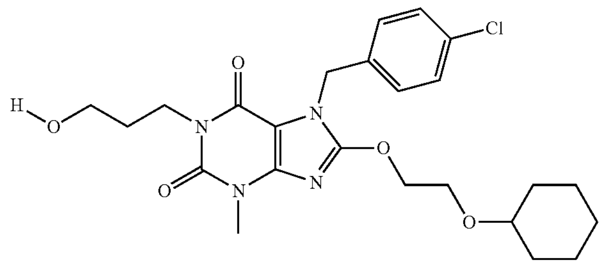 [SMILES: Cn1c(=O)n(CCCO)c(=O)c2c1nc(OCCOC1CCCCC1)n2Cc1ccc(Cl)cc1] |
| 204 | 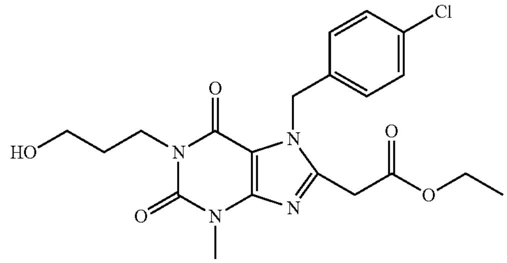 [SMILES: CCOC(=O)Cc1nc2c(c(=O)n(CCCO)c(=O)n2C)n1Cc1ccc(Cl)cc1] |
| 205 | 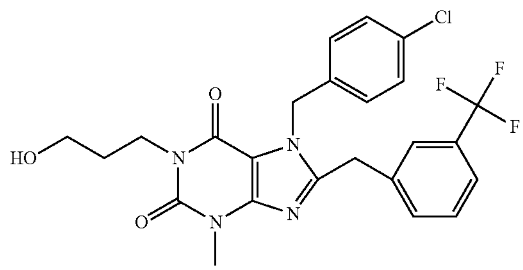 [SMILES: Cn1c(=O)n(CCCO)c(=O)c2c1nc(Cc1cccc(C(F)(F)F)c1)n2Cc1ccc(Cl)cc1] |
| 206 | 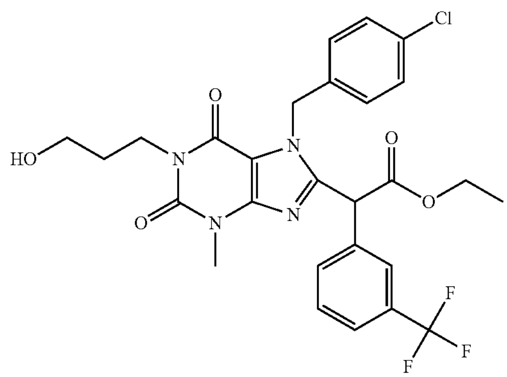 [SMILES: CCOC(=O)C(c1cccc(C(F)(F)F)c1)c1nc2c(c(=O)n(CCCO)c(=O)n2C)n1Cc1ccc(Cl)cc1] |
| 207 | 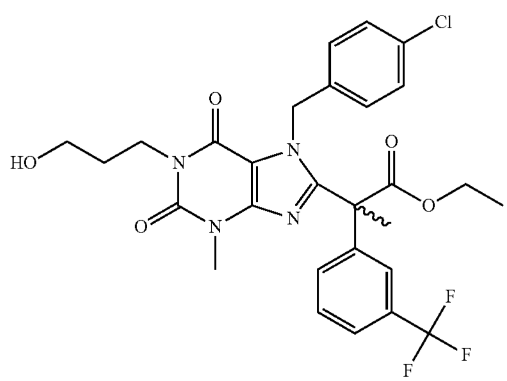 [SMILES: CCOC(=O)C(C)(c1cccc(C(F)(F)F)c1)c1nc2c(c(=O)n(CCCO)c(=O)n2C)n1Cc1ccc(Cl)cc1] |

TABLE A-continued
| Compound Number | Structure |
|---|---|
| 208 | 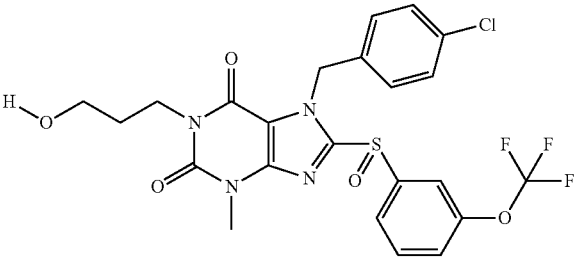 [SMILES: Cn1c(=O)n(CCCO)c(=O)c2c1nc(S(=O)c1cccc(OC(F)(F)F)c1)n2Cc1ccc(Cl)cc1] |
| 209 | 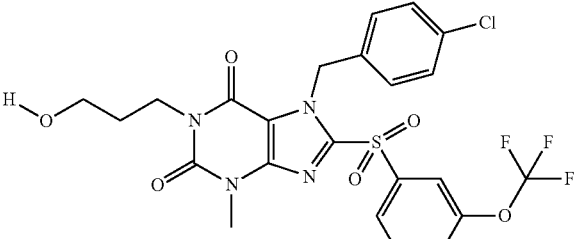 |
| 210 | 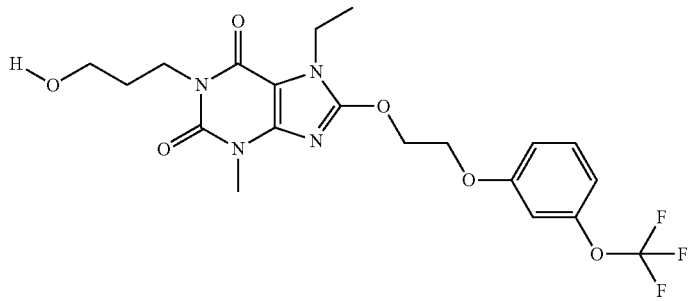 [SMILES: CCn1c(OCCOc2cccc(OC(F)(F)F)c2)nc2c1c(=O)n(CCCO)c(=O)n2C] |
| 211 | 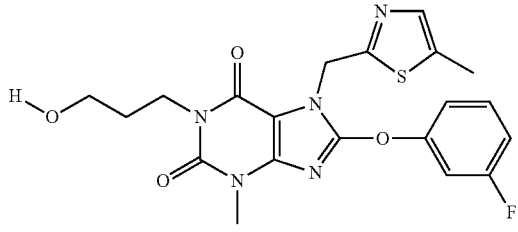 [SMILES: Cc1cnc(Cn2c(Oc3cccc(F)c3)nc3c2c(=O)n(CCCO)c(=O)n3C)s1] |
| 212 | 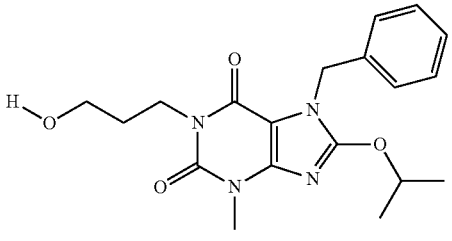 [SMILES: CC(C)Oc1nc2c(c(=O)n(CCCO)c(=O)n2C)n1Cc1ccccc1] |
| 213 | 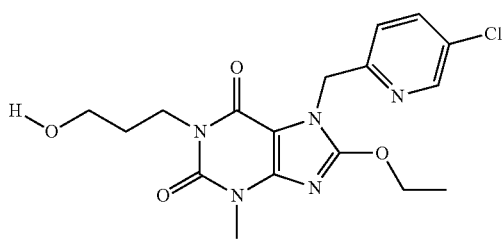 [SMILES: CCOc1nc2c(c(=O)n(CCCO)c(=O)n2C)n1Cc1ccc(Cl)cn1] |

TABLE A-continued

| Compound Number | Structure |
|---|---|
| 214 | 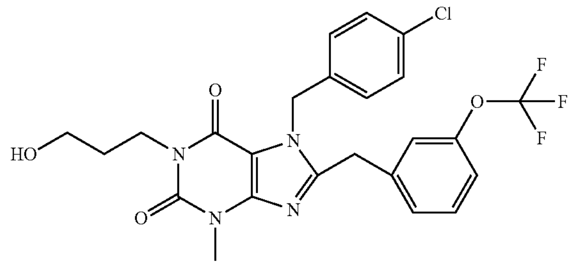 [SMILES: Cn1c(=O)n(CCCO)c(=O)c2c1nc(Cc1cccc(OC(F)(F)F)c1)n2Cc1ccc(Cl)cc1] |
| 215 | 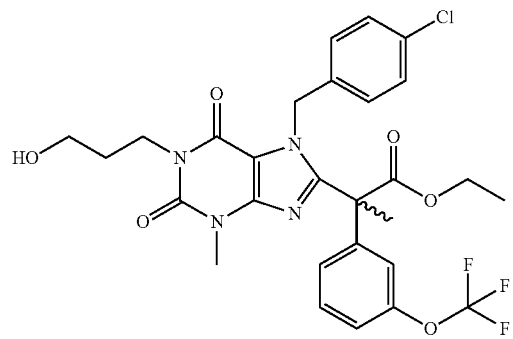 [SMILES: CCOC(=O)C(C)(c1cccc(OC(F)(F)F)c1)c1nc2c(c(=O)n(CCCO)c(=O)n2C)n1Cc1ccc(Cl)cc1] |
| 216 | 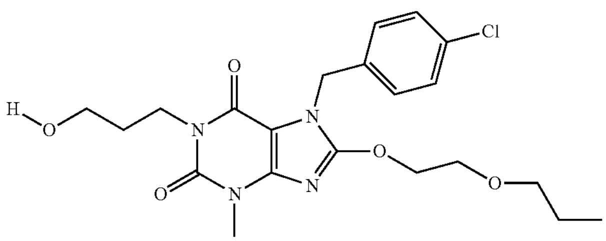 [SMILES: CCCOCCOc1nc2c(c(=O)n(CCCO)c(=O)n2C)n1Cc1ccc(Cl)cc1] |
| 217 | 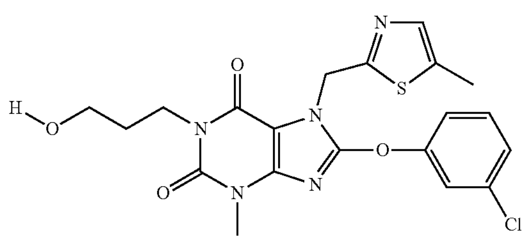 [SMILES: Cc1cnc(Cn2c(Oc3cccc(Cl)c3)nc3c2c(=O)n(CCCO)c(=O)n3C)s1] |
| 218 | 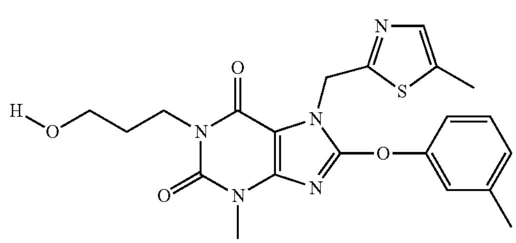 [SMILES: Cc1cccc(Oc2nc3c(c(=O)n(CCCO)c(=O)n3C)n2Cc2ncc(C)s2)c1] |
| 219 | 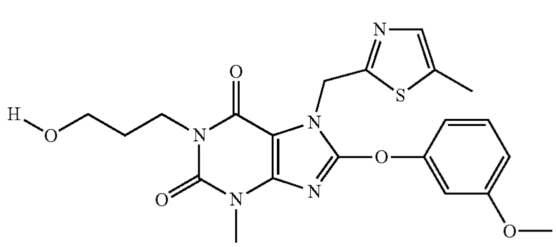 [SMILES: COc1cccc(Oc2nc3c(c(=O)n(CCCO)c(=O)n3C)n2Cc2ncc(C)s2)c1] |

TABLE A-continued
| Compound Number | Structure |
|---|---|
| 220 | 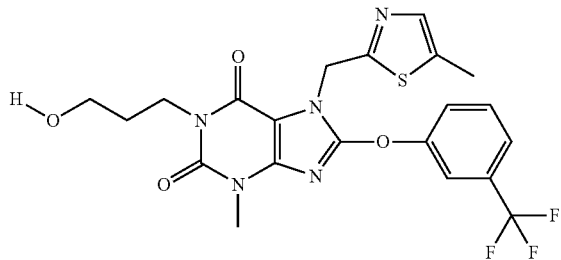 [SMILES: Cc1cnc(Cn2c(Oc3cccc(C(F)(F)F)c3)nc3c2c(=O)n(CCCO)c(=O)n3C)s1] |
| 221 | 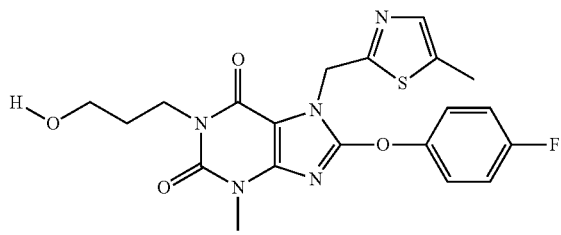 [SMILES: Cc1cnc(Cn2c(Oc3ccc(F)cc3)nc3c2c(=O)n(CCCO)c(=O)n3C)s1] |
| 222 | 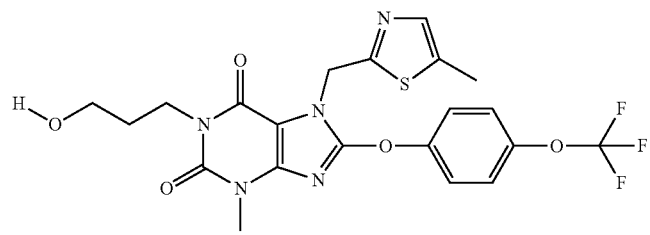 [SMILES: Cc1cnc(Cn2c(Oc3ccc(OC(F)(F)F)cc3)nc3c2c(=O)n(CCCO)c(=O)n3C)s1] |
| 223 | 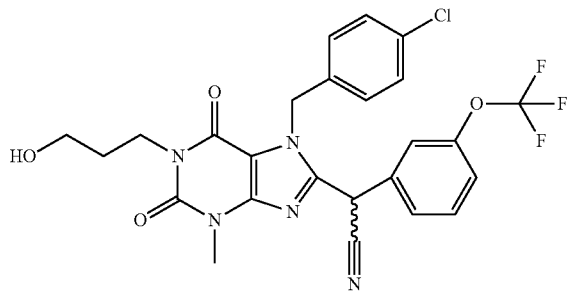 [SMILES: Cn1c(=O)n(CCCO)c(=O)c2c1nc(C(C#N)c1cccc(OC(F)(F)F)c1)n2Cc1ccc(Cl)cc1] |
| 224 | 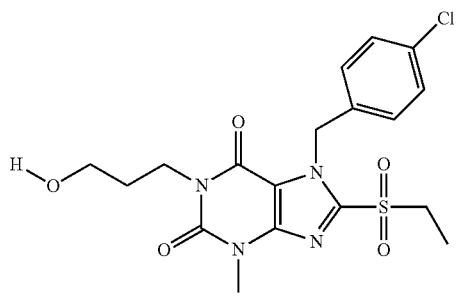 [SMILES: CCS(=O)(=O)c1nc2c(c(=O)n(CCCO)c(=O)n2C)n1Cc1ccc(Cl)cc1] |

TABLE A-continued
| Compound Number | Structure |
|---|---|
| 225 | 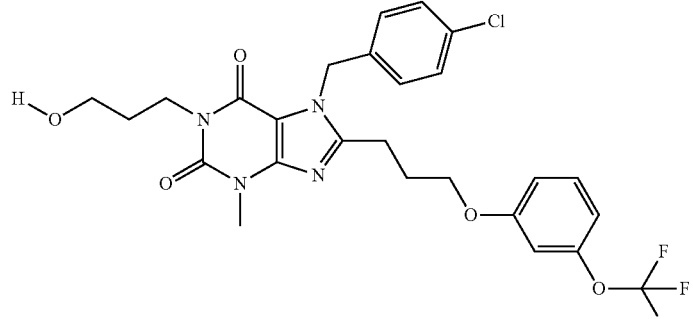 |
| 226 | 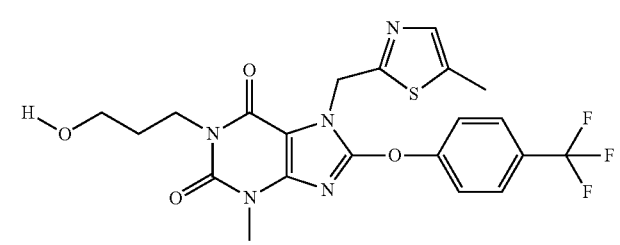 [SMILES: Cc1cnc(Cn2c(Oc3ccc(C(F)(F)F)cc3)nc3c2c(=O)n(CCCO)c(=O)n3C)s1] |
| 227 | 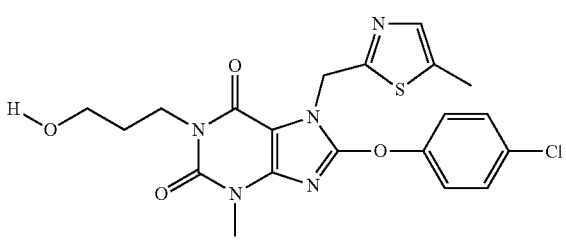 [SMILES: Cc1cnc(Cn2c(Oc3ccc(Cl)cc3)nc3c2c(=O)n(CCCO)c(=O)n3C)s1] |
| 228 | 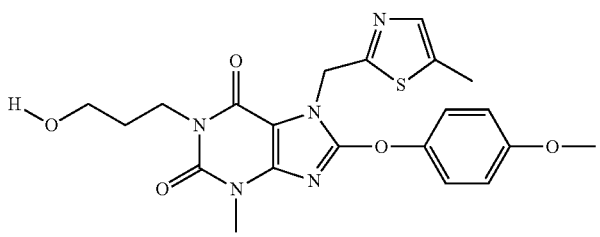 [SMILES: COc1ccc(Oc2nc3c(c(=O)n(CCCO)c(=O)n3C)n2Cc2ncc(C)s2)cc1] |
| 229 | 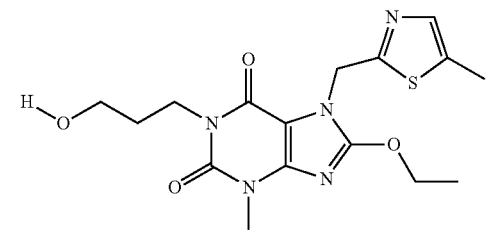 [SMILES: CCOc1nc2c(c(=O)n(CCCO)c(=O)n2C)n1Cc1ncc(C)s1] |
| 230 | 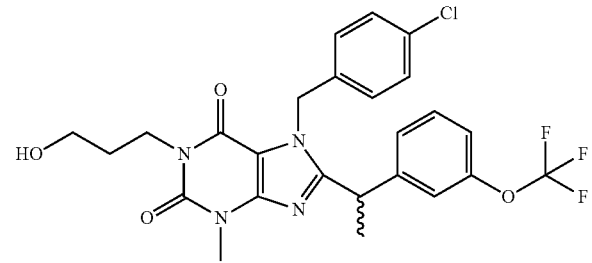 [SMILES: CC(c1cccc(OC(F)(F)F)c1)c1nc2c(c(=O)n(CCCO)c(=O)n2C)n1Cc1ccc(Cl)cc1] |

TABLE A-continued

| Compound Number | Structure |
|---|---|
| 231 | *(chemical structure: 1-(3-hydroxypropyl)-3-methyl-7-(4-chlorobenzyl)-8-[hydroxy(3-(trifluoromethoxy)phenyl)methyl]xanthine)* |
| 232 | *(chemical structure: 1-(3-hydroxypropyl)-3-methyl-7-(4-chlorobenzyl)-8-(1-hydroxyethyl)xanthine)* |
| 233 | *(chemical structure: 1-(3-hydroxypropyl)-3-methyl-7-(4-chlorobenzyl)-8-(methylsulfonyl)xanthine)* |
| 234 | *(chemical structure: 1-(3-hydroxypropyl)-3-methyl-7-(4-chlorobenzyl)-8-(2-isopropoxyethoxy)xanthine)* |
| 235 | *(chemical structure: 1-(3-hydroxypropyl)-3-methyl-7-(4-chlorobenzyl)-8-(propylsulfonyl)xanthine)* |

TABLE A-continued
| Compound Number | Structure |
|---|---|
| 236 | 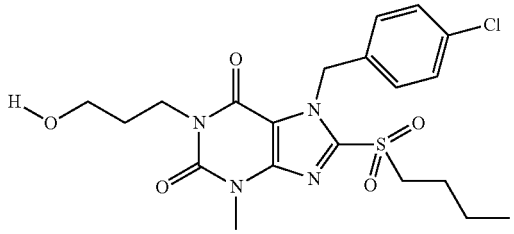 [SMILES: CCCCS(=O)(=O)c1nc2c(c(=O)n(CCCO)c(=O)n2C)n1Cc1ccc(Cl)cc1] |
| 237 | 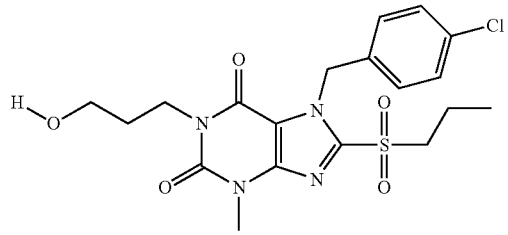 [SMILES: CCCS(=O)(=O)c1nc2c(c(=O)n(CCCO)c(=O)n2C)n1Cc1ccc(Cl)cc1] |
| 238 | 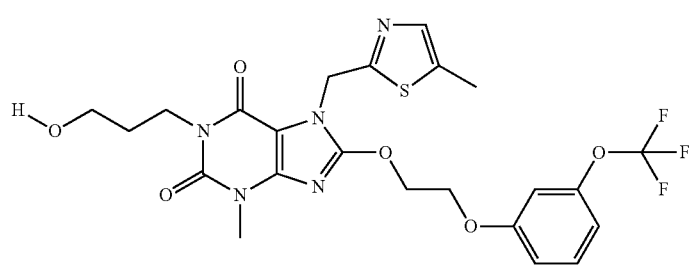 [SMILES: Cc1cnc(Cn2c(OCCOc3cccc(OC(F)(F)F)c3)nc3c2c(=O)n(CCCO)c(=O)n3C)s1] |
| 239 | 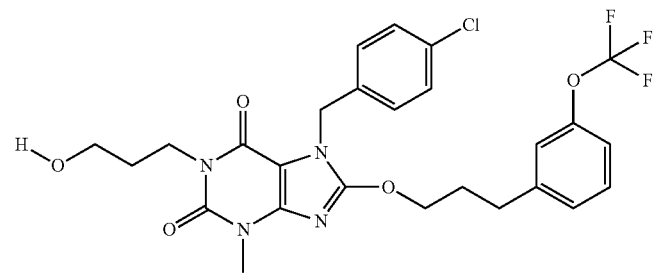 [SMILES: Cn1c(=O)n(CCCO)c(=O)c2c1nc(OCCCc1cccc(OC(F)(F)F)c1)n2Cc1ccc(Cl)cc1] |
| 240 | 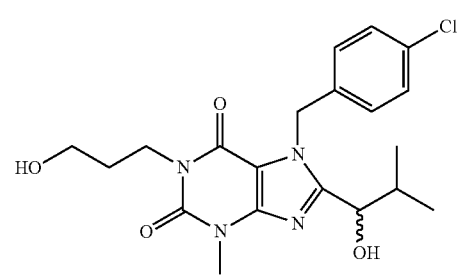 [SMILES: CC(C)C(O)c1nc2c(c(=O)n(CCCO)c(=O)n2C)n1Cc1ccc(Cl)cc1] |

TABLE A-continued
| Compound Number | Structure |
|---|---|
| 241 | 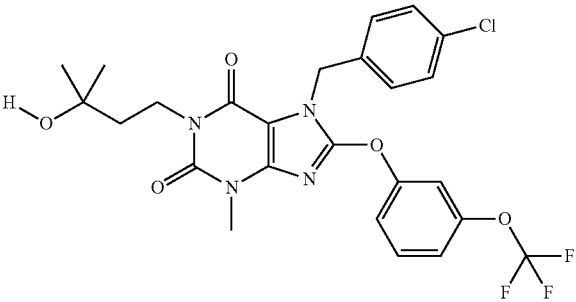 [SMILES: Cn1c(=O)n(CCC(C)(C)O)c(=O)c2c1nc(Oc1cccc(OC(F)(F)F)c1)n2Cc1ccc(Cl)cc1] |
| 242 | 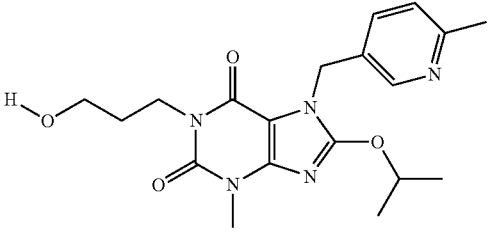 [SMILES: Cc1ccc(Cn2c(OC(C)C)nc3c2c(=O)n(CCCO)c(=O)n3C)cn1] |
| 243 | 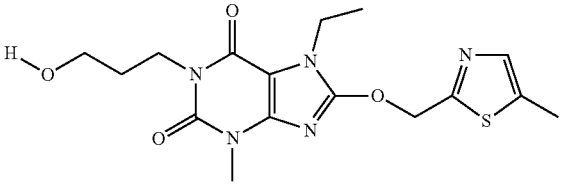 [SMILES: CCn1c(OCc2ncc(C)s2)nc2c1c(=O)n(CCCO)c(=O)n2C] |
| 244 | 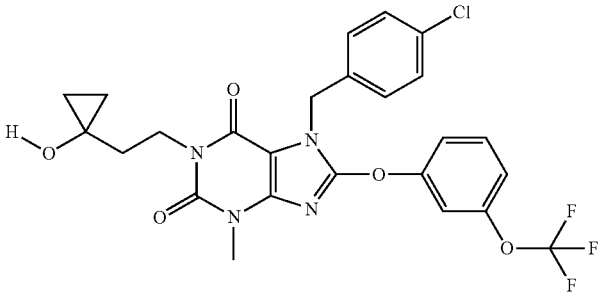 [SMILES: Cn1c(=O)n(CCC2(O)CC2)c(=O)c2c1nc(Oc1cccc(OC(F)(F)F)c1)n2Cc1ccc(Cl)cc1] |
| 245 | 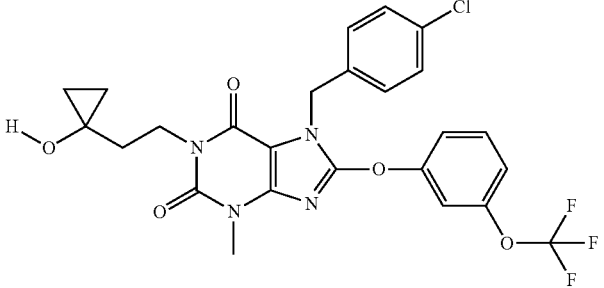 [SMILES: Cn1c(=O)n(CCC2(O)CC2)c(=O)c2c1nc(Oc1cccc(OC(F)(F)F)c1)n2Cc1ccc(Cl)cc1] |

TABLE A-continued
| Compound Number | Structure |
|---|---|
| 246 | 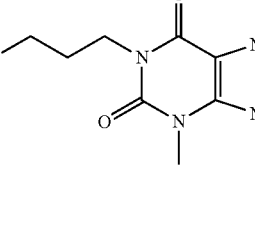 |
| 247 | 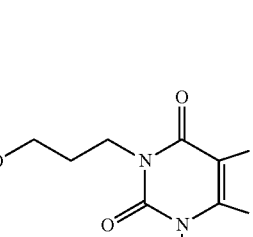 |
| 248 | 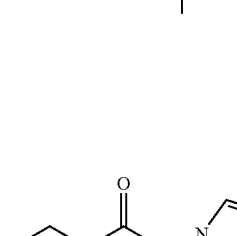 |
| 249 | 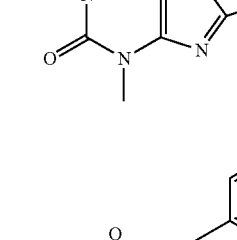 |
| 250 | 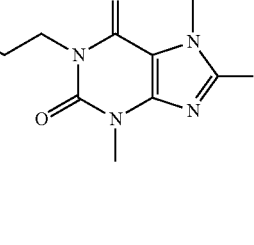 |

TABLE A-continued
| Compound Number | Structure |
|---|---|
| 251 | 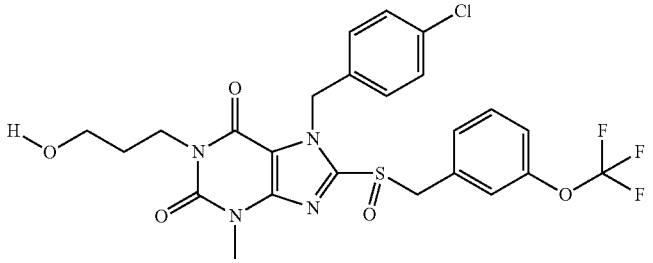 [SMILES: Cn1c(=O)n(CCCO)c(=O)c2c1nc(S(=O)Cc1cccc(OC(F)(F)F)c1)n2Cc1ccc(Cl)cc1] |
| 252 | 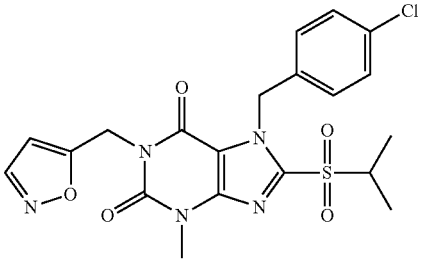 [SMILES: CC(C)S(=O)(=O)c1nc2c(c(=O)n(Cc3ccno3)c(=O)n2C)n1Cc1ccc(Cl)cc1] |
| 253 | 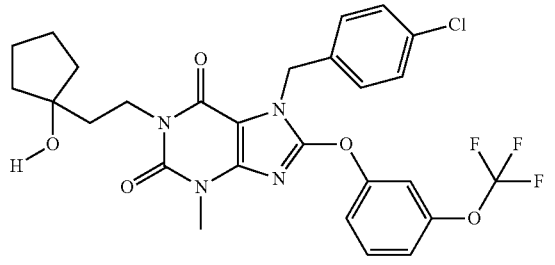 [SMILES: Cn1c(=O)n(CCC2(O)CCCC2)c(=O)c2c1nc(Oc1cccc(OC(F)(F)F)c1)n2Cc1ccc(Cl)cc1] |
| 254 | 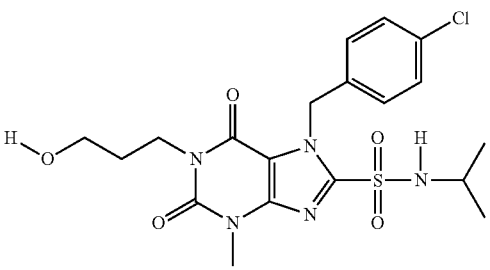 [SMILES: CC(C)NS(=O)(=O)c1nc2c(c(=O)n(CCCO)c(=O)n2C)n1Cc1ccc(Cl)cc1] |
| 255 | 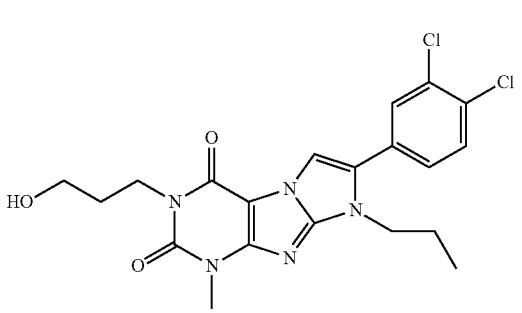 [SMILES: CCCn1c(-c2ccc(Cl)c(Cl)c2)cn2c3c(=O)n(CCCO)c(=O)n(C)c3nc12] |

TABLE A-continued
| Compound Number | Structure |
|---|---|
| 256 | 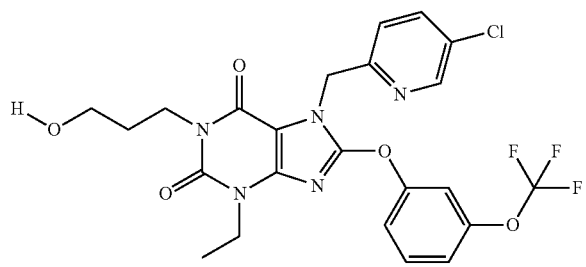 [SMILES: CCn1c(=O)n(CCCO)c(=O)c2c1nc(Oc1cccc(OC(F)(F)F)c1)n2Cc1ccc(Cl)cn1] |
| 257 | 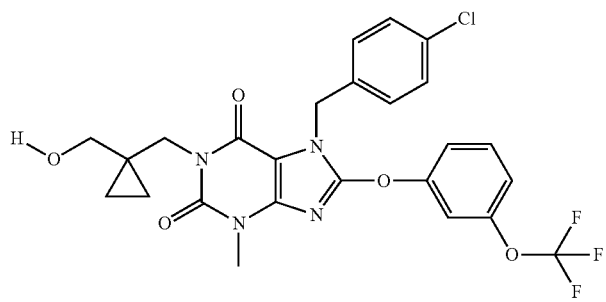 [SMILES: Cn1c(=O)n(CC2(CO)CC2)c(=O)c2c1nc(Oc1cccc(OC(F)(F)F)c1)n2Cc1ccc(Cl)cc1] |
| 258 | 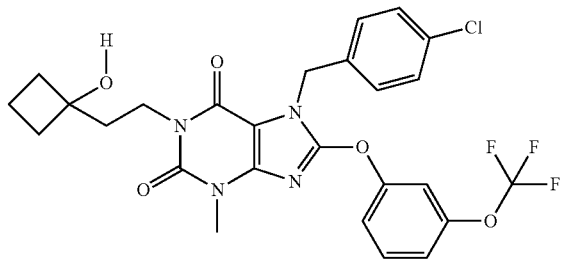 [SMILES: Cn1c(=O)n(CCC2(O)CCC2)c(=O)c2c1nc(Oc1cccc(OC(F)(F)F)c1)n2Cc1ccc(Cl)cc1] |
| 259 | 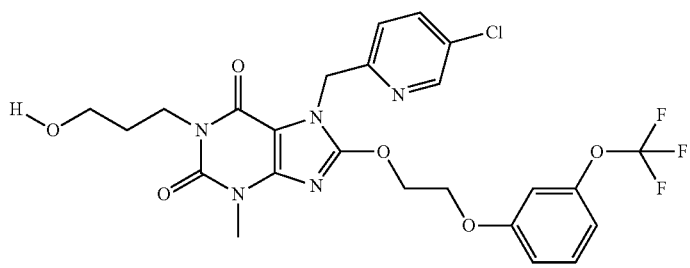 [SMILES: Cn1c(=O)n(CCCO)c(=O)c2c1nc(OCCOc1cccc(OC(F)(F)F)c1)n2Cc1ccc(Cl)cn1] |
| 260 | 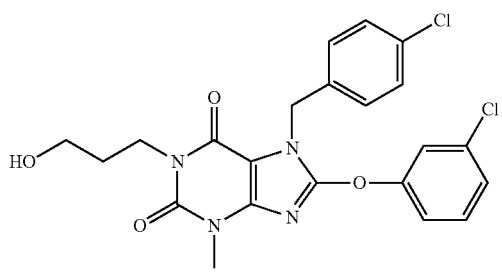 [SMILES: Cn1c(=O)n(CCCO)c(=O)c2c1nc(Oc1cccc(Cl)c1)n2Cc1ccc(Cl)cc1] |

TABLE A-continued

| Compound Number | Structure |
|---|---|
| 261 | 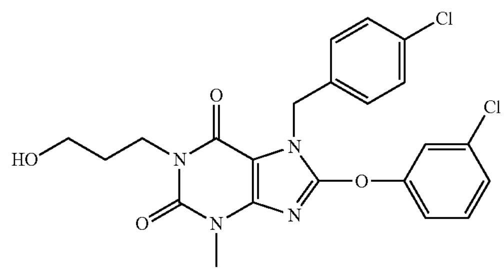 [SMILES: Cn1c(=O)n(CCCO)c(=O)c2c1nc(Oc1cccc(Cl)c1)n2Cc1ccc(Cl)cc1] |
| 262 | 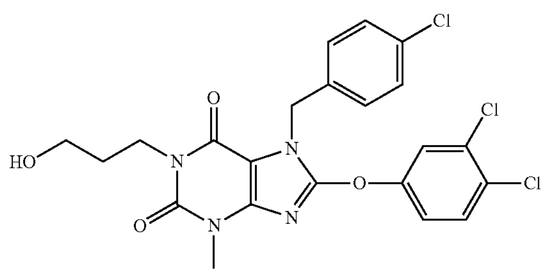 |
| 263 | 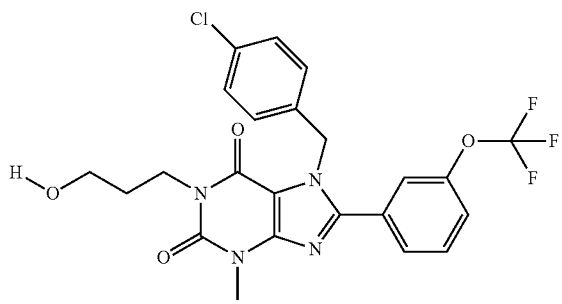 [SMILES: Cn1c(=O)n(CCCO)c(=O)c2c1nc(-c1cccc(OC(F)(F)F)c1)n2Cc1ccc(Cl)cc1] |
| 264 | 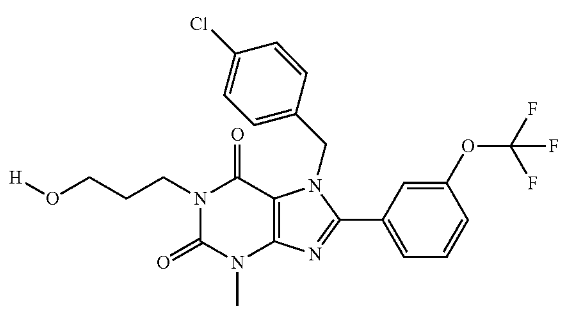 [SMILES: Cn1c(=O)n(CCCO)c(=O)c2c1nc(-c1cccc(OC(F)(F)F)c1)n2Cc1ccc(Cl)cc1] |
| 265 | 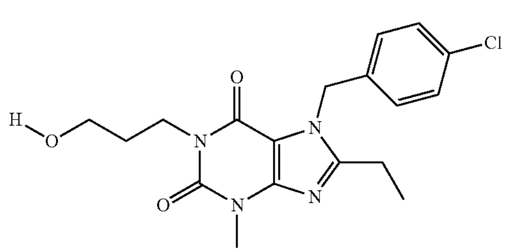 [SMILES: CCc1nc2c(c(=O)n(CCCO)c(=O)n2C)n1Cc1ccc(Cl)cc1] |

TABLE A-continued
| Compound Number | Structure |
|---|---|
| 266 | 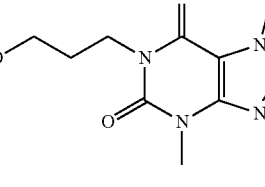 |
| 267 | 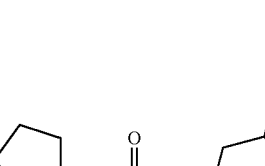 |
| 268 | 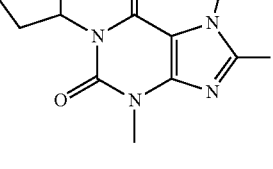 |
| 269 | 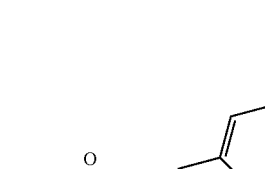 |
| 270 | 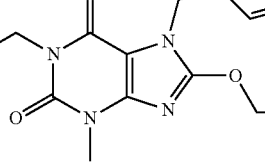 |

TABLE A-continued
| Compound Number | Structure |
|---|---|
| 271 | 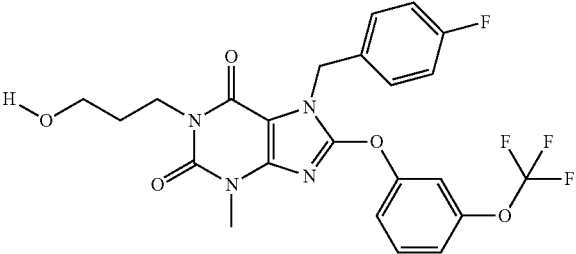 [SMILES: Cn1c(=O)n(CCCO)c(=O)c2c1nc(Oc1cccc(OC(F)(F)F)c1)n2Cc1ccc(F)cc1] |
| 272 | 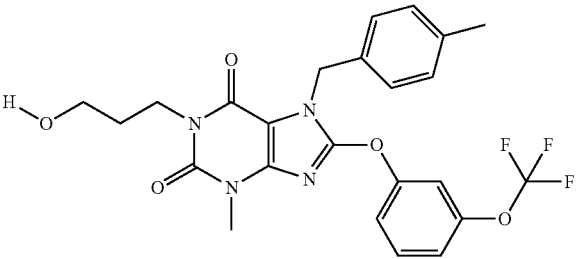 [SMILES: Cc1ccc(Cn2c(Oc3cccc(OC(F)(F)F)c3)nc3c2c(=O)n(CCCO)c(=O)n3C)cc1] |
| 273 | 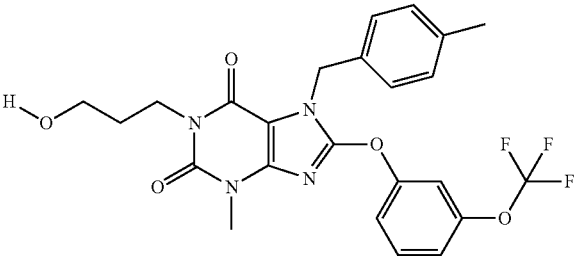 |
| 274 | 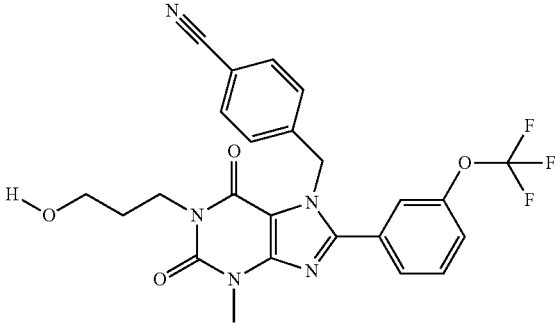 [SMILES: Cn1c(=O)n(CCCO)c(=O)c2c1nc(-c1cccc(OC(F)(F)F)c1)n2Cc1ccc(C#N)cc1] |
| 275 | 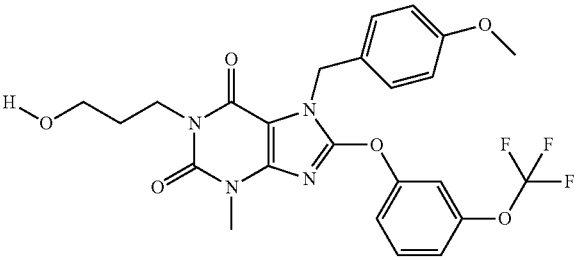 [SMILES: COc1ccc(Cn2c(Oc3cccc(OC(F)(F)F)c3)nc3c2c(=O)n(CCCO)c(=O)n3C)cc1] |

TABLE A-continued

| Compound Number | Structure |
|---|---|
| 276 | 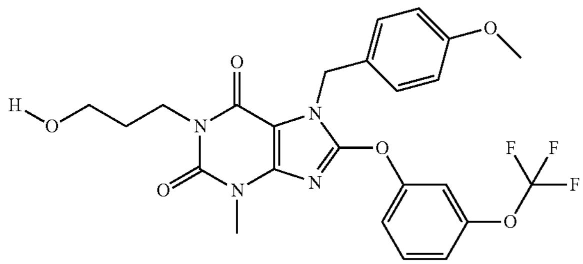 [SMILES: COc1ccc(Cn2c(Oc3cccc(OC(F)(F)F)c3)nc3c2c(=O)n(CCCO)c(=O)n3C)cc1] |
| 277 | 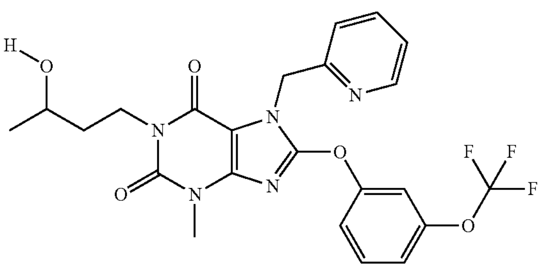 [SMILES: CC(O)CCn1c(=O)c2c(nc(Oc3cccc(OC(F)(F)F)c3)n2Cc2ccccn2)n(C)c1=O] |
| 278 | 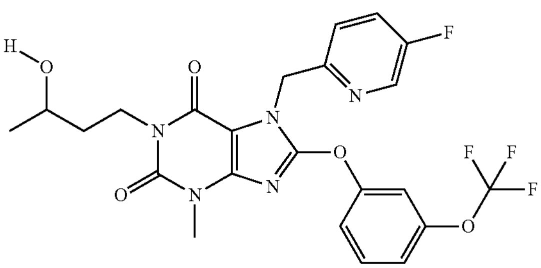 [SMILES: CC(O)CCn1c(=O)c2c(nc(Oc3cccc(OC(F)(F)F)c3)n2Cc2ccc(F)cn2)n(C)c1=O] |
| 279 | 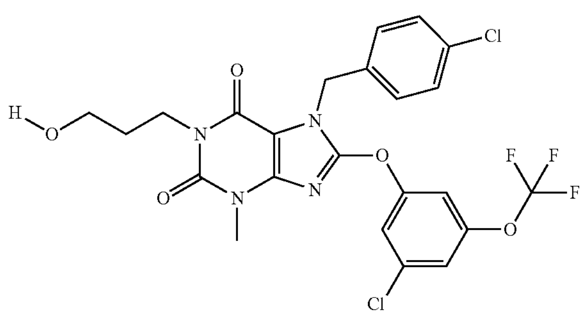 [SMILES: Cn1c(=O)n(CCCO)c(=O)c2c1nc(Oc1cc(Cl)cc(OC(F)(F)F)c1)n2Cc1ccc(Cl)cc1] |
| 280 | 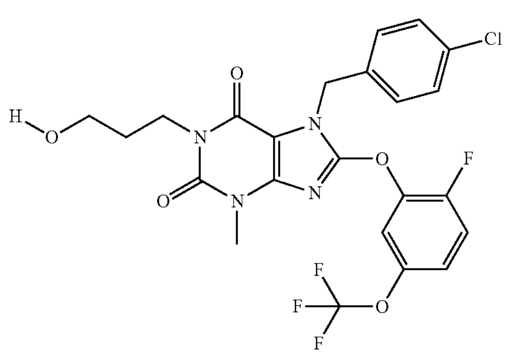 [SMILES: Cn1c(=O)n(CCCO)c(=O)c2c1nc(Oc1cc(OC(F)(F)F)ccc1F)n2Cc1ccc(Cl)cc1] |

TABLE A-continued
| Compound Number | Structure |
|---|---|
| 281 | 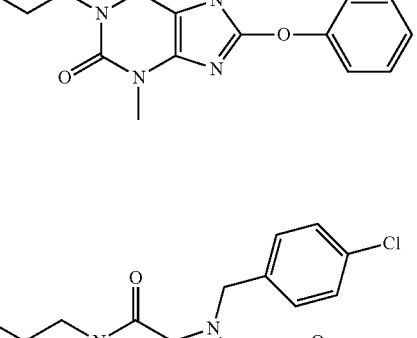 |
| 282 | 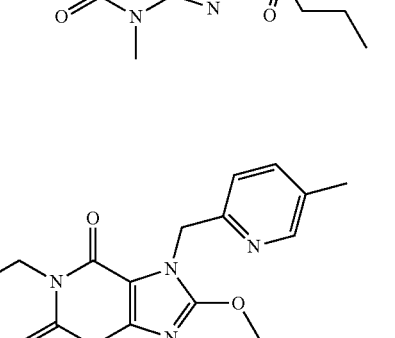 |
| 283 | 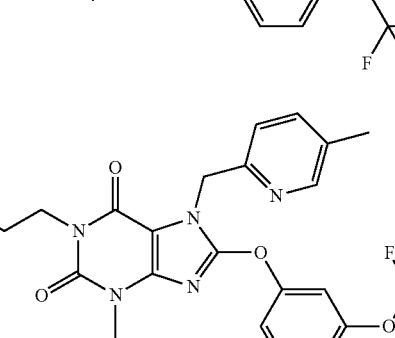 |
| 284 | 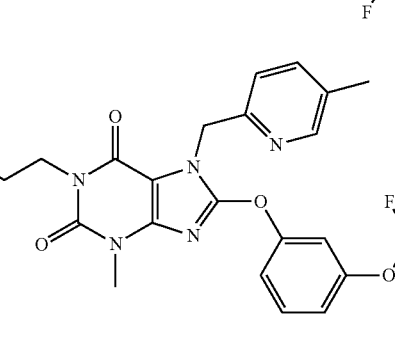 |
| 285 | 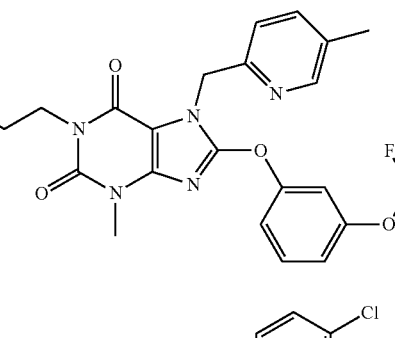 |

TABLE A-continued

| Compound Number | Structure |
|---|---|
| 286 | 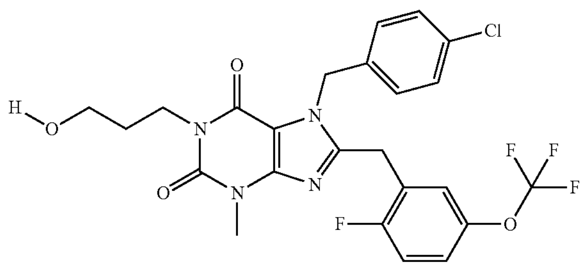 [SMILES: Cn1c(=O)n(CCCO)c(=O)c2c1nc(Cc1cc(OC(F)(F)F)ccc1F)n2Cc1ccc(Cl)cc1] |
| 287 | 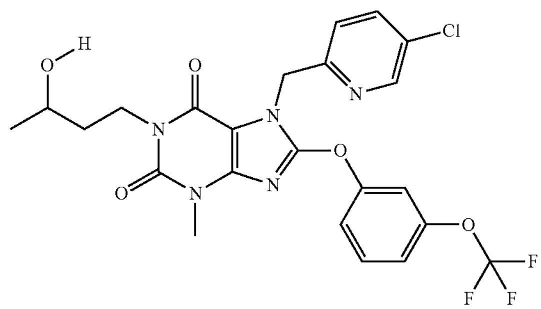 [SMILES: CC(O)CCn1c(=O)c2c(nc(Oc3cccc(OC(F)(F)F)c3)n2Cc2ccc(Cl)cn2)n(C)c1=O] |
| 288 | 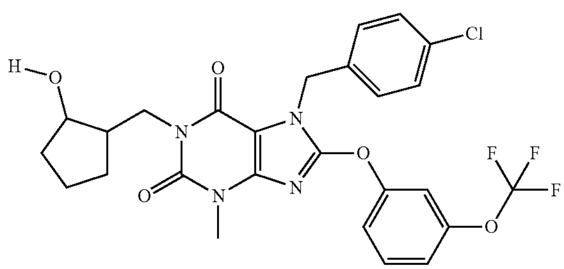 [SMILES: Cn1c(=O)n(CC2CCCC2O)c(=O)c2c1nc(Oc1cccc(OC(F)(F)F)c1)n2Cc1ccc(Cl)cc1] |
| 289 | 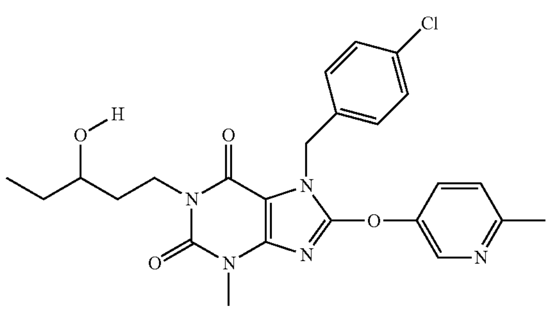 [SMILES: CCC(O)CCn1c(=O)c2c(nc(Oc3ccc(C)nc3)n2Cc2ccc(Cl)cc2)n(C)c1=O] |
| 290 | 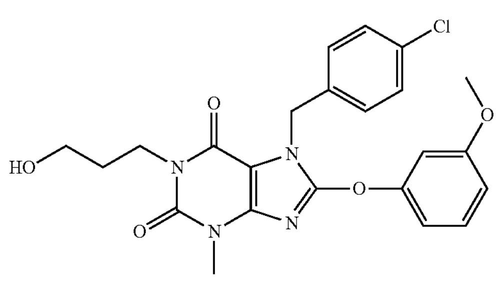 [SMILES: COc1cccc(Oc2nc3c(c(=O)n(CCCO)c(=O)n3C)n2Cc2ccc(Cl)cc2)c1] |

TABLE A-continued
| Compound Number | Structure |
|---|---|
| 291 | 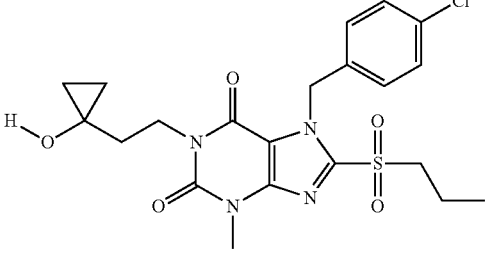 |
| 292 | 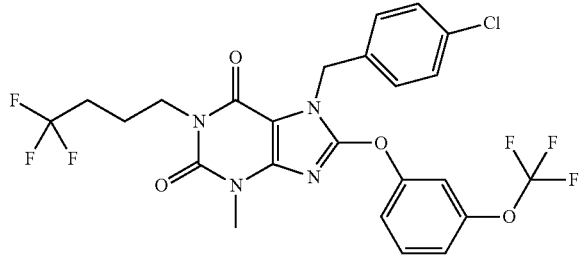 [SMILES: Cn1c(=O)n(CCCC(F)(F)F)c(=O)c2c1nc(Oc1cccc(OC(F)(F)F)c1)n2Cc1ccc(Cl)cc1] |
| 293 | 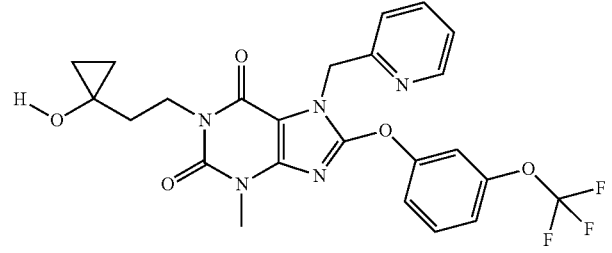 [SMILES: Cn1c(=O)n(CCC2(O)CC2)c(=O)c2c1nc(Oc1cccc(OC(F)(F)F)c1)n2Cc1ccccn1] |
| 294 | 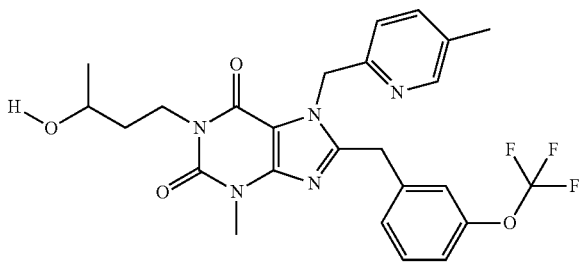 [SMILES: Cc1ccc(Cn2c(Cc3cccc(OC(F)(F)F)c3)nc3c2c(=O)n(CCC(C)O)c(=O)n3C)nc1] |
| 295 | 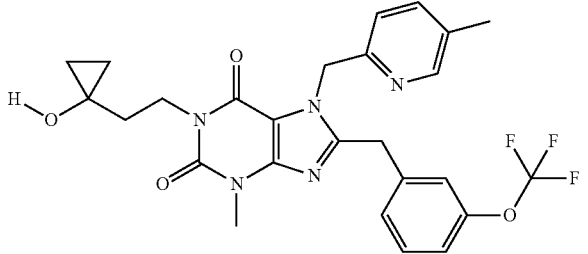 [SMILES: Cc1ccc(Cn2c(Cc3cccc(OC(F)(F)F)c3)nc3c2c(=O)n(CCC2(O)CC2)c(=O)n3C)nc1] |

TABLE A-continued
| Compound Number | Structure |
|---|---|
| 296 | 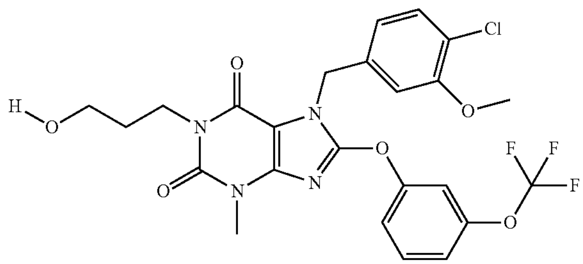 [SMILES: COc1cc(Cn2c(Oc3cccc(OC(F)(F)F)c3)nc3c2c(=O)n(CCCO)c(=O)n3C)ccc1Cl] |
| 297 | 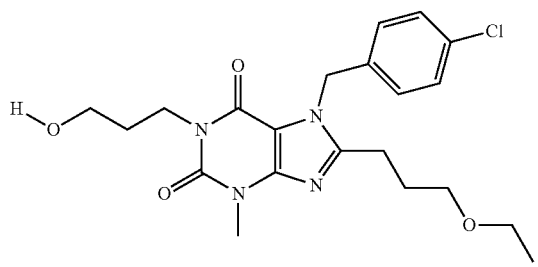 [SMILES: CCOCCCc1nc2c(c(=O)n(CCCO)c(=O)n2C)n1Cc1ccc(Cl)cc1] |
| 298 | 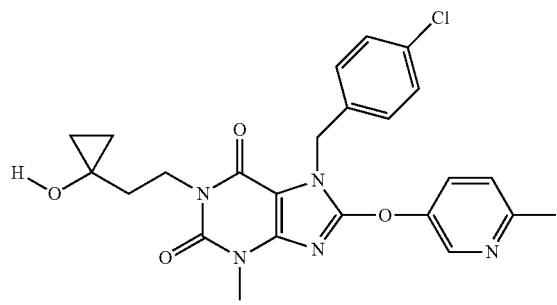 [SMILES: Cc1ccc(Oc2nc3c(c(=O)n(CCC4(O)CC4)c(=O)n3C)n2Cc2ccc(Cl)cc2)cn1] |
| 299 | 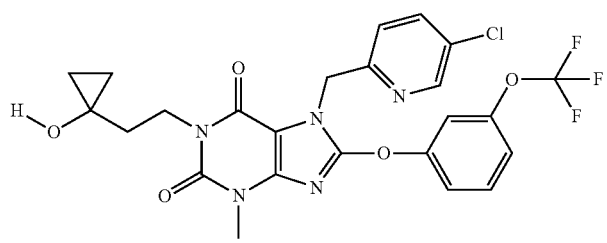 [SMILES: Cn1c(=O)n(CCC2(O)CC2)c(=O)c2c1nc(Oc1cccc(OC(F)(F)F)c1)n2Cc1ccc(Cl)cn1] |
| 300 | 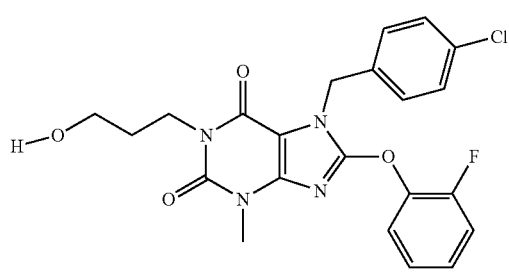 [SMILES: Cn1c(=O)n(CCCO)c(=O)c2c1nc(Oc1ccccc1F)n2Cc1ccc(Cl)cc1] |

TABLE A-continued
| Compound Number | Structure |
|---|---|
| 301 | 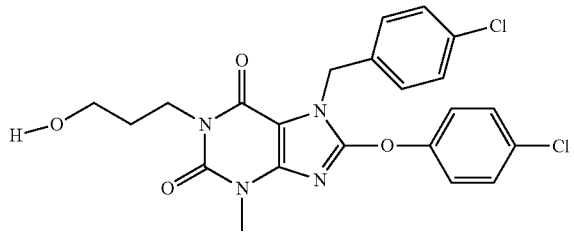 [SMILES: Cn1c(=O)n(CCCO)c(=O)c2c1nc(Oc1ccc(Cl)cc1)n2Cc1ccc(Cl)cc1] |
| 302 | 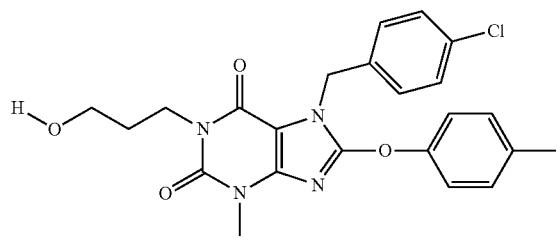 [SMILES: Cc1ccc(Oc2nc3c(c(=O)n(CCCO)c(=O)n3C)n2Cc2ccc(Cl)cc2)cc1] |
| 303 | 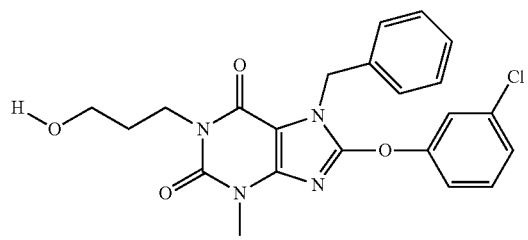 [SMILES: Cn1c(=O)n(CCCO)c(=O)c2c1nc(Oc1cccc(Cl)c1)n2Cc1ccccc1] |
| 304 | 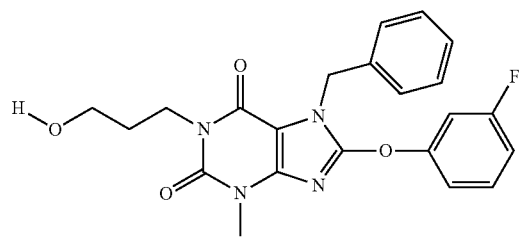 [SMILES: Cn1c(=O)n(CCCO)c(=O)c2c1nc(Oc1cccc(F)c1)n2Cc1ccccc1] |
| 305 | 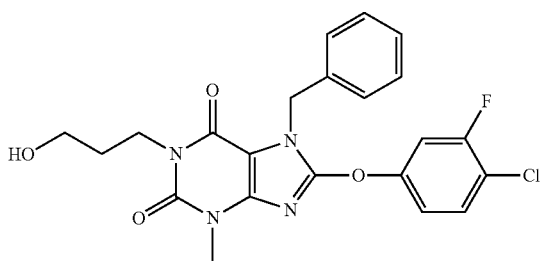 [SMILES: Cn1c(=O)n(CCCO)c(=O)c2c1nc(Oc1ccc(Cl)c(F)c1)n2Cc1ccccc1] |
| 306 | 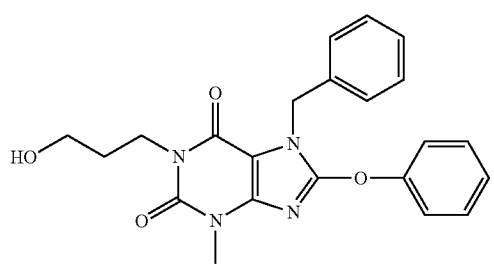 [SMILES: Cn1c(=O)n(CCCO)c(=O)c2c1nc(Oc1ccccc1)n2Cc1ccccc1] |

TABLE A-continued

| Compound Number | Structure |
|---|---|
| 307 | 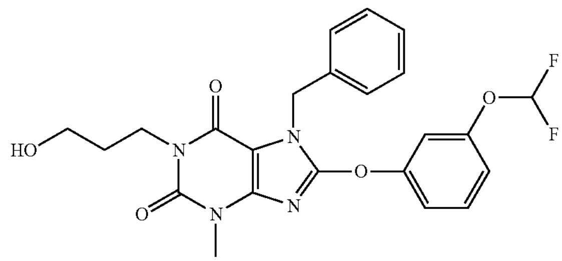 [SMILES: Cn1c(=O)n(CCCO)c(=O)c2c1nc(Oc1cccc(OC(F)F)c1)n2Cc1ccccc1] |
| 308 | 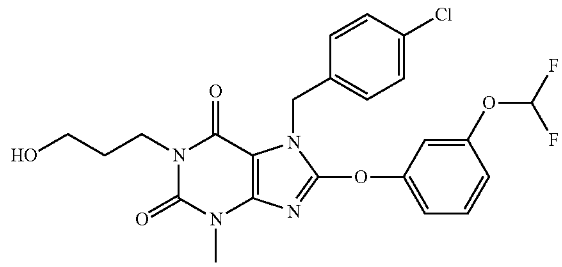 [SMILES: Cn1c(=O)n(CCCO)c(=O)c2c1nc(Oc1cccc(OC(F)F)c1)n2Cc1ccc(Cl)cc1] |
| 309 | 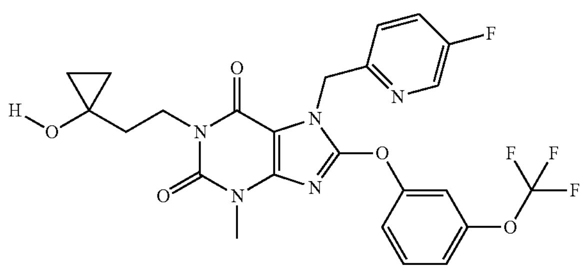 |
| 310 | 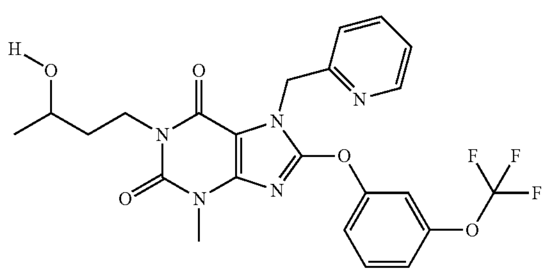 [SMILES: CC(O)CCn1c(=O)c2c(nc(Oc3cccc(OC(F)(F)F)c3)n2Cc2ccccn2)n(C)c1=O] |
| 311 | 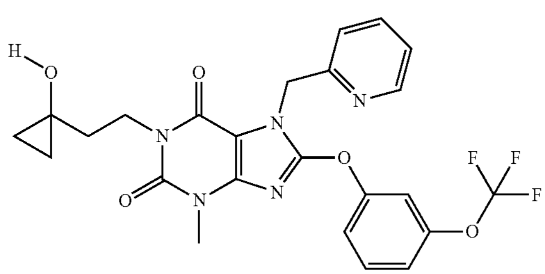 [SMILES: Cn1c(=O)n(CCC2(O)CC2)c(=O)c2c1nc(Oc1cccc(OC(F)(F)F)c1)n2Cc1ccccn1] |

TABLE A-continued
| Compound Number | Structure |
|---|---|
| 312 | 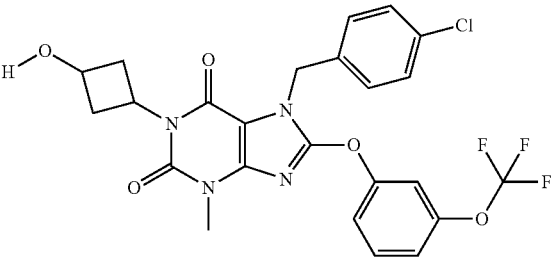 [SMILES: Cn1c(=O)n(C2CC(O)C2)c(=O)c2c1nc(Oc1cccc(OC(F)(F)F)c1)n2Cc1ccc(Cl)cc1] |
| 313 | 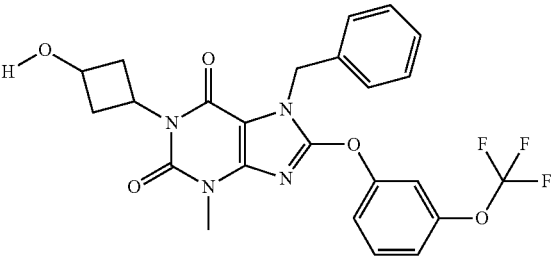 [SMILES: Cn1c(=O)n(C2CC(O)C2)c(=O)c2c1nc(Oc1cccc(OC(F)(F)F)c1)n2Cc1ccccc1] |
| 314 | 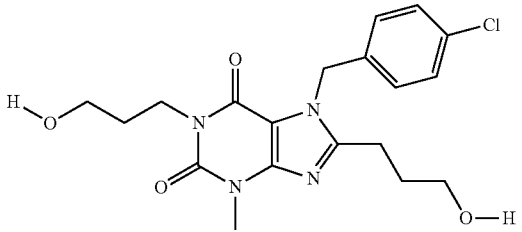 [SMILES: Cn1c(=O)n(CCCO)c(=O)c2c1nc(CCCO)n2Cc1ccc(Cl)cc1] |
| 315 | 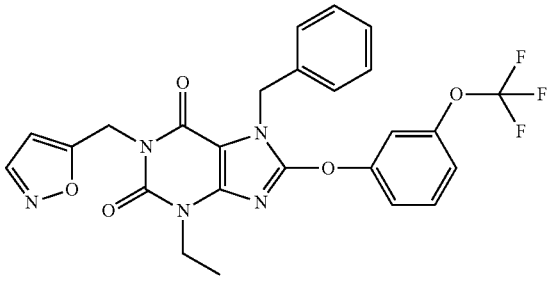 [SMILES: CCn1c(=O)n(Cc2ccno2)c(=O)c2c1nc(Oc1cccc(OC(F)(F)F)c1)n2Cc1ccccc1] |
| 316 | 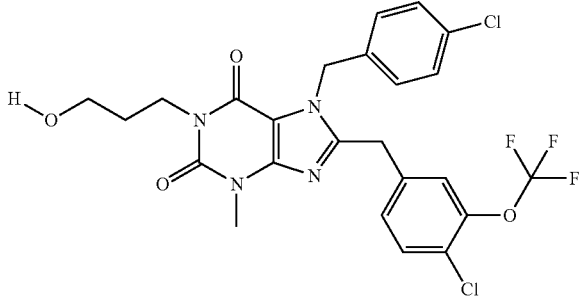 [SMILES: Cn1c(=O)n(CCCO)c(=O)c2c1nc(Oc1ccc(Cl)c(OC(F)(F)F)c1)n2Cc1ccc(Cl)cc1] |

TABLE A-continued

| Compound Number | Structure |
|---|---|
| 317 | 7-benzyl-3-methyl-8-(3-(trifluoromethoxy)phenoxy)-1-(3,3,3-trifluoropropyl)-3,7-dihydro-1H-purine-2,6-dione |
| 318 | 7-((5-chloropyridin-2-yl)methyl)-3-methyl-8-(3-(trifluoromethoxy)phenoxy)-1-(3,3,3-trifluoropropyl)-3,7-dihydro-1H-purine-2,6-dione |
| 319 | 8-(4-chloro-3-(trifluoromethoxy)phenoxy)-7-(4-chlorobenzyl)-1-(3-hydroxypropyl)-3-methyl-3,7-dihydro-1H-purine-2,6-dione |
| 320 | 7-(4-chlorobenzyl)-1-(3-hydroxypropyl)-3-methyl-8-phenoxy-3,7-dihydro-1H-purine-2,6-dione |
| 321 | 3-((7-(4-chlorobenzyl)-1-(3-hydroxypropyl)-3-methyl-2,6-dioxo-2,3,6,7-tetrahydro-1H-purin-8-yl)oxy)benzonitrile |

TABLE A-continued

| Compound Number | Structure |
|---|---|
| 322 | 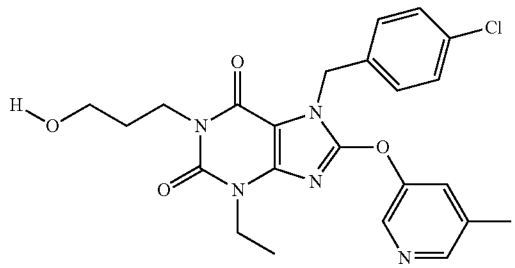 [SMILES: CCn1c(=O)n(CCCO)c(=O)c2c1nc(Oc1cncc(C)c1)n2Cc1ccc(Cl)cc1] |
| 323 | 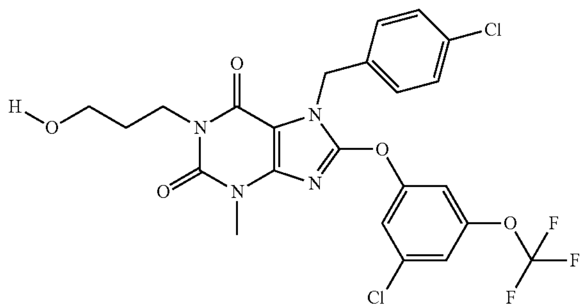 [SMILES: Cn1c(=O)n(CCCO)c(=O)c2c1nc(Oc1cc(Cl)cc(OC(F)(F)F)c1)n2Cc1ccc(Cl)cc1] |
| 324 | 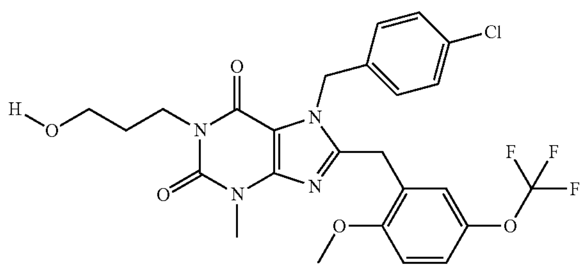 [SMILES: COc1ccc(OC(F)(F)F)cc1Cc1nc2c(c(=O)n(CCCO)c(=O)n2C)n1Cc1ccc(Cl)cc1] |
| 325 | 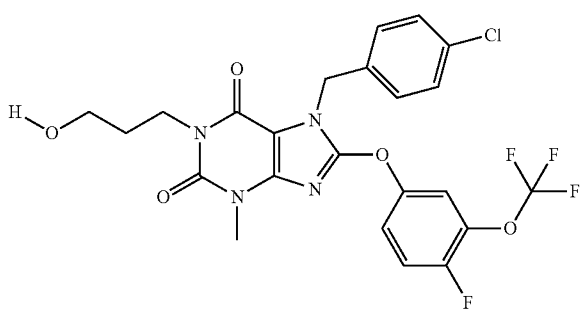 [SMILES: Cn1c(=O)n(CCCO)c(=O)c2c1nc(Oc1ccc(F)c(OC(F)(F)F)c1)n2Cc1ccc(Cl)cc1] |
| 326 | 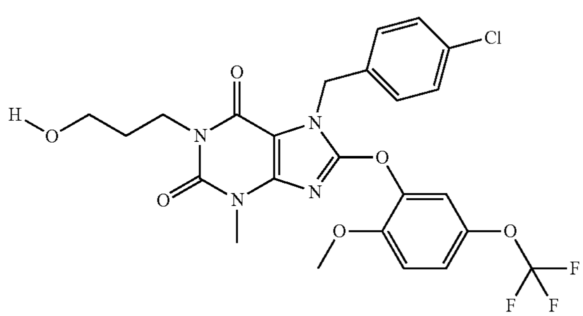 [SMILES: COc1ccc(OC(F)(F)F)cc1Oc1nc2c(c(=O)n(CCCO)c(=O)n2C)n1Cc1ccc(Cl)cc1] |

TABLE A-continued
| Compound Number | Structure |
|---|---|
| 327 | 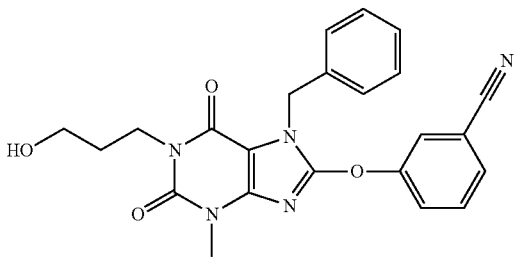 [SMILES: Cn1c(=O)n(CCCO)c(=O)c2c1nc(Oc1cccc(C#N)c1)n2Cc1ccccc1] |
| 328 | 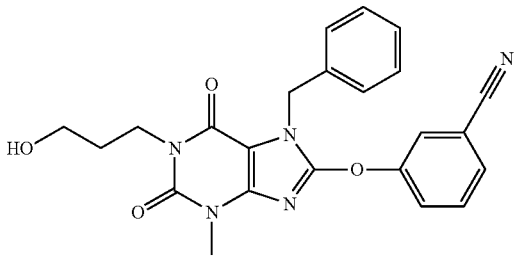 [SMILES: Cn1c(=O)n(CCCO)c(=O)c2c1nc(Oc1cccc(C#N)c1)n2Cc1ccccc1] |
| 329 | 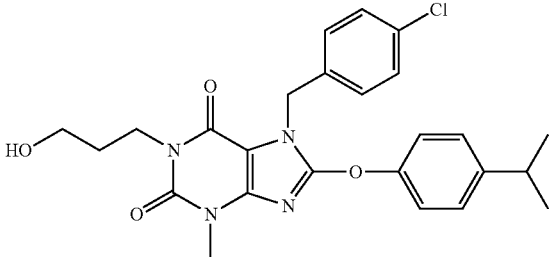 [SMILES: CC(C)c1ccc(Oc2nc3c(c(=O)n(CCCO)c(=O)n3C)n2Cc2ccc(Cl)cc2)cc1] |
| 330 | 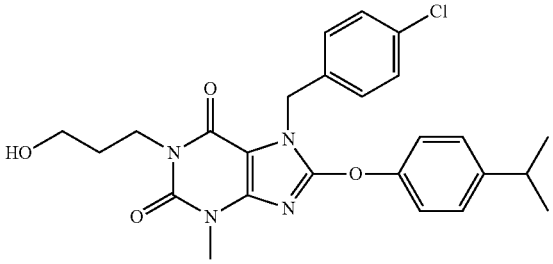 [SMILES: CC(C)c1ccc(Oc2nc3c(c(=O)n(CCCO)c(=O)n3C)n2Cc2ccc(Cl)cc2)cc1] |
| 331 | 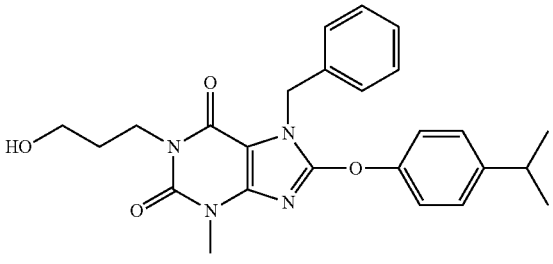 [SMILES: CC(C)c1ccc(Oc2nc3c(c(=O)n(CCCO)c(=O)n3C)n2Cc2ccccc2)cc1] |

TABLE A-continued
| Compound Number | Structure |
|---|---|
| 332 | 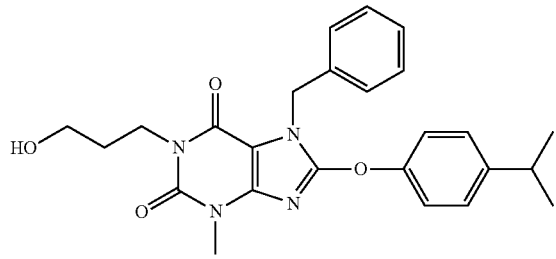 [SMILES: CC(C)c1ccc(Oc2nc3c(c(=O)n(CCCO)c(=O)n3C)n2Cc2ccccc2)cc1] |
| 333 | 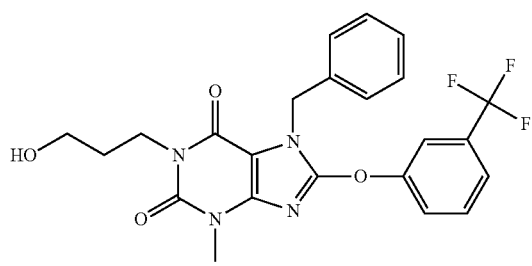 [SMILES: Cn1c(=O)n(CCCO)c(=O)c2c1nc(Oc1cccc(C(F)(F)F)c1)n2Cc1ccccc1] |
| 334 | 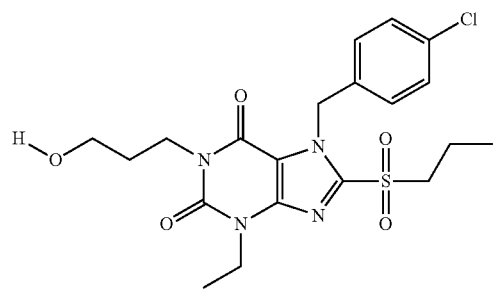 [SMILES: CCCS(=O)(=O)c1nc2c(c(=O)n(CCCO)c(=O)n2CC)n1Cc1ccc(Cl)cc1] |
| 335 | 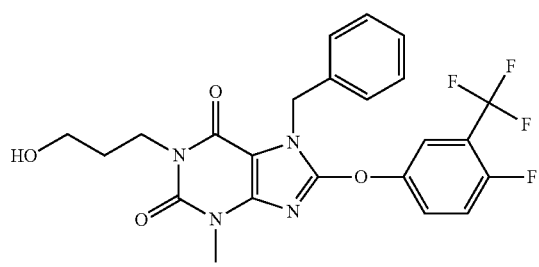 [SMILES: Cn1c(=O)n(CCCO)c(=O)c2c1nc(Oc1ccc(F)c(C(F)(F)F)c1)n2Cc1ccccc1] |
| 336 | 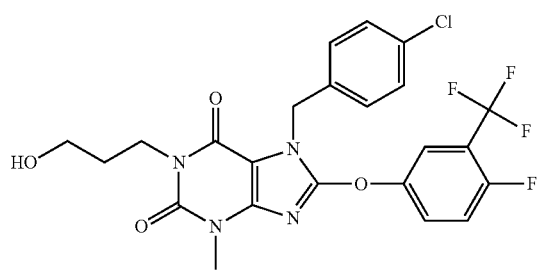 [SMILES: Cn1c(=O)n(CCCO)c(=O)c2c1nc(Oc1ccc(F)c(C(F)(F)F)c1)n2Cc1ccc(Cl)cc1] |

TABLE A-continued

| Compound Number | Structure |
|---|---|
| 337 | 7-(4-chlorobenzyl)-8-(4-chloro-3-fluorophenoxy)-1-(3-hydroxypropyl)-3-methyl-3,7-dihydro-1H-purine-2,6-dione |
| 338 | 7-benzyl-8-(4-chloro-3-(trifluoromethyl)phenyl)-1-(3-hydroxypropyl)-3-methyl-3,7-dihydro-1H-purine-2,6-dione |
| 339 | 4-((7-(4-chlorobenzyl)-1-(3-hydroxypropyl)-3-methyl-2,6-dioxo-2,3,6,7-tetrahydro-1H-purin-8-yl)oxy)benzonitrile |
| 340 | 7-(4-chlorobenzyl)-8-(3,4-difluorophenoxy)-1-(3-hydroxypropyl)-3-methyl-3,7-dihydro-1H-purine-2,6-dione |
| 341 | 7-(4-chlorobenzyl)-1-(3-hydroxypropyl)-3-methyl-8-(2-(trifluoromethyl)phenoxy)-3,7-dihydro-1H-purine-2,6-dione |

TABLE A-continued
| Compound Number | Structure |
|---|---|
| 342 | 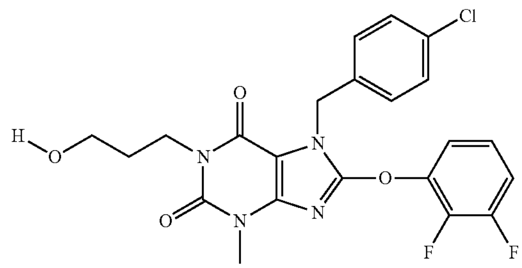 [SMILES: Cn1c(=O)n(CCCO)c(=O)c2c1nc(Oc1cccc(F)c1F)n2Cc1ccc(Cl)cc1] |
| 343 | 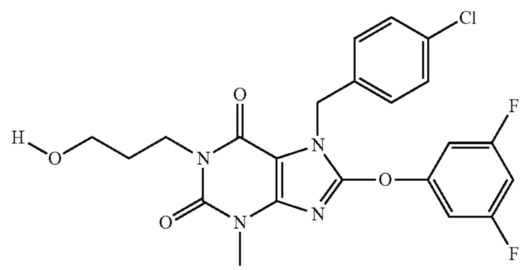 |
| 344 | 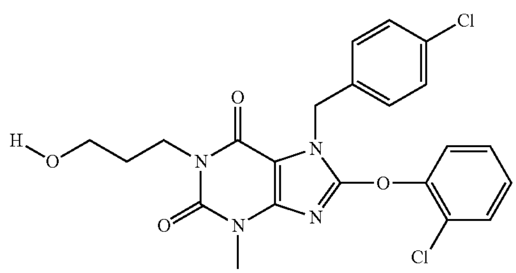 [SMILES: Cn1c(=O)n(CCCO)c(=O)c2c1nc(Oc1ccccc1Cl)n2Cc1ccc(Cl)cc1] |
| 345 | 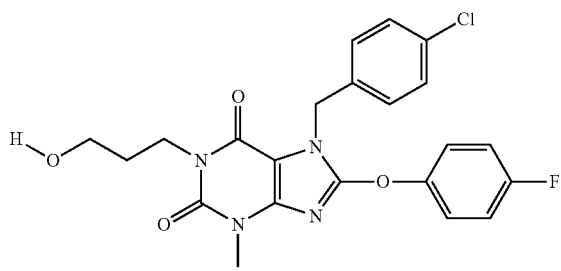 [SMILES: Cn1c(=O)n(CCCO)c(=O)c2c1nc(Oc1ccc(F)cc1)n2Cc1ccc(Cl)cc1] |
| 346 | 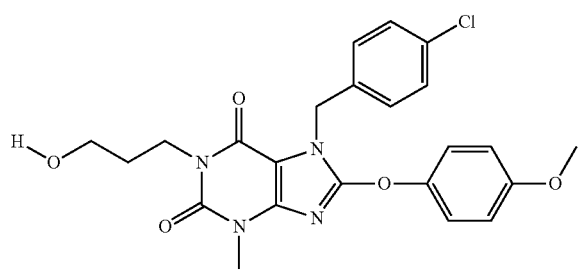 [SMILES: COc1ccc(Oc2nc3c(c(=O)n(CCCO)c(=O)n3C)n2Cc2ccc(Cl)cc2)cc1] |

TABLE A-continued
| Compound Number | Structure |
|---|---|
| 347 | 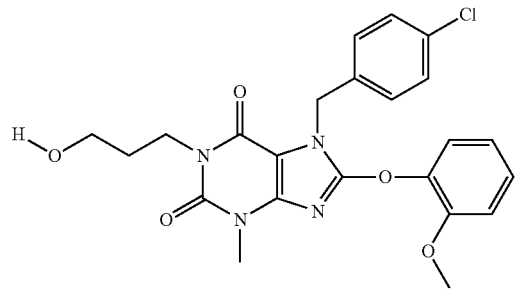 [SMILES: COc1ccccc1Oc1nc2c(c(=O)n(CCCO)c(=O)n2C)n1Cc1ccc(Cl)cc1] |
| 348 | 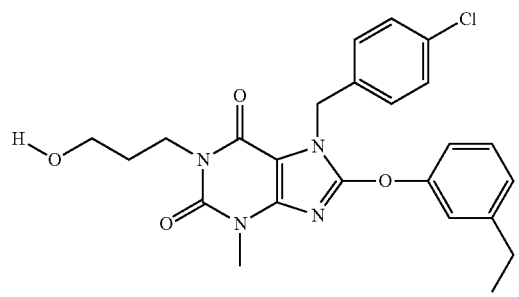 [SMILES: CCc1cccc(Oc2nc3c(c(=O)n(CCCO)c(=O)n3C)n2Cc2ccc(Cl)cc2)c1] |
| 349 | 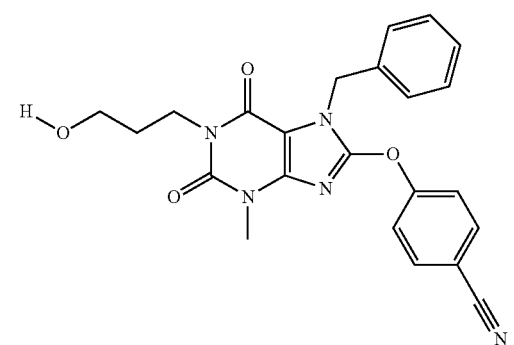 [SMILES: Cn1c(=O)n(CCCO)c(=O)c2c1nc(Oc1ccc(C#N)cc1)n2Cc1ccccc1] |
| 350 | 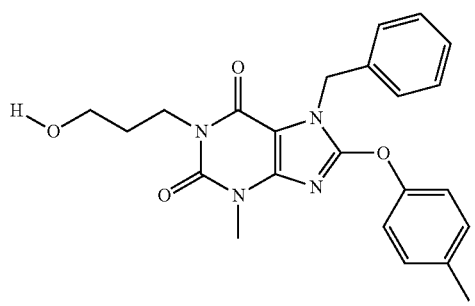 [SMILES: Cc1ccc(Oc2nc3c(c(=O)n(CCCO)c(=O)n3C)n2Cc2ccccc2)cc1] |
| 351 | 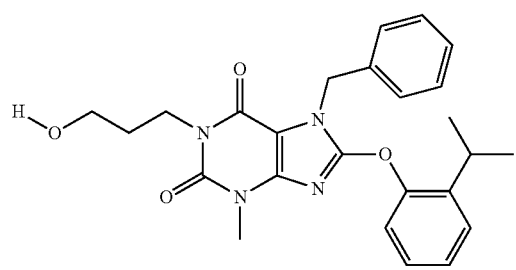 [SMILES: CC(C)c1ccccc1Oc1nc2c(c(=O)n(CCCO)c(=O)n2C)n1Cc1ccccc1] |

TABLE A-continued

| Compound Number | Structure |
|---|---|
| 352 | 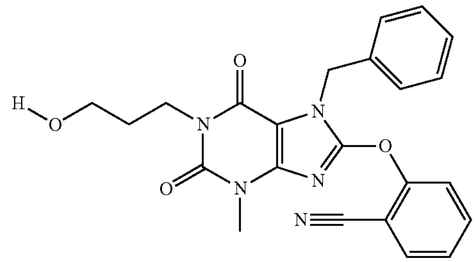 [SMILES: Cn1c(=O)n(CCCO)c(=O)c2c1nc(Oc1ccccc1C#N)n2Cc1ccccc1] |
| 353 | 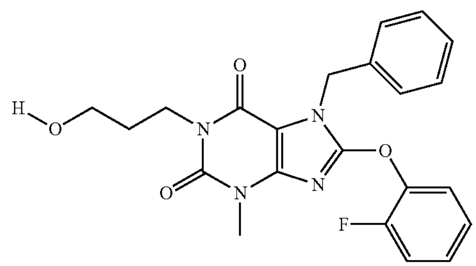 [SMILES: Cn1c(=O)n(CCCO)c(=O)c2c1nc(Oc1ccccc1F)n2Cc1ccccc1] |
| 354 | 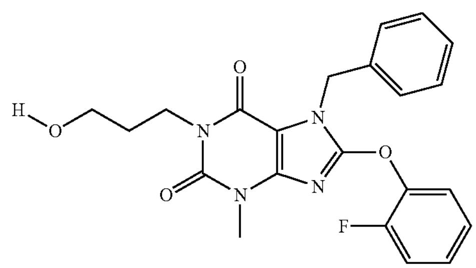 [SMILES: Cn1c(=O)n(CCCO)c(=O)c2c1nc(Oc1ccccc1F)n2Cc1ccccc1] |
| 355 | 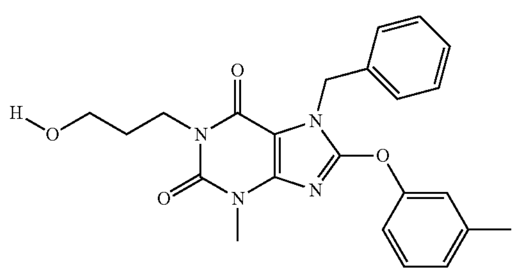 [SMILES: Cc1cccc(Oc2nc3c(c(=O)n(CCCO)c(=O)n3C)n2Cc2ccccc2)c1] |
| 356 | 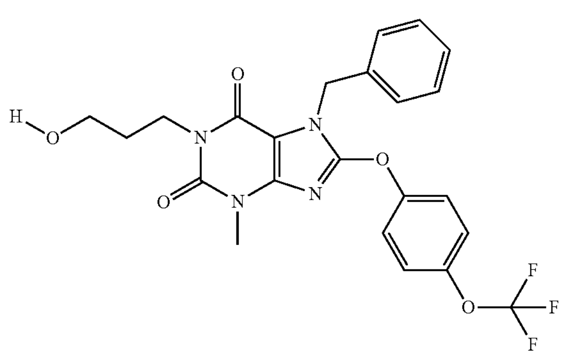 [SMILES: Cn1c(=O)n(CCCO)c(=O)c2c1nc(Oc1ccc(OC(F)(F)F)cc1)n2Cc1ccccc1] |

TABLE A-continued
| Compound Number | Structure |
|---|---|
| 357 | 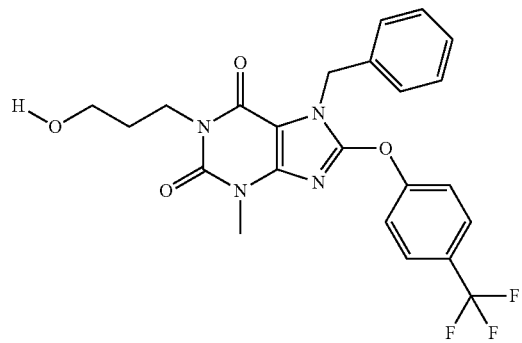 [SMILES: Cn1c(=O)n(CCCO)c(=O)c2c1nc(Oc1ccc(C(F)(F)F)cc1)n2Cc1ccccc1] |
| 358 | 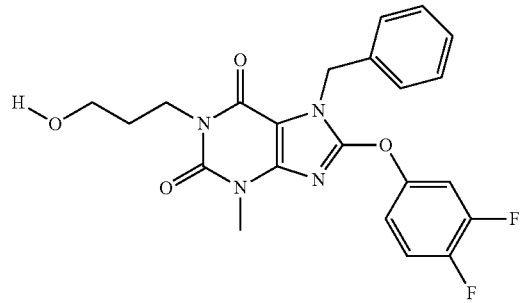 [SMILES: Cn1c(=O)n(CCCO)c(=O)c2c1nc(Oc1ccc(F)c(F)c1)n2Cc1ccccc1] |
| 359 | 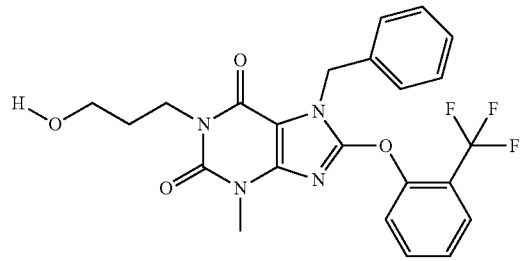 [SMILES: Cn1c(=O)n(CCCO)c(=O)c2c1nc(Oc1ccccc1C(F)(F)F)n2Cc1ccccc1] |
| 360 | 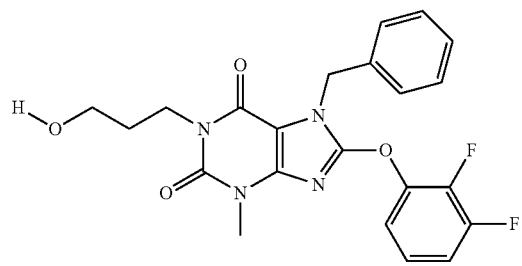 [SMILES: Cn1c(=O)n(CCCO)c(=O)c2c1nc(Oc1cccc(F)c1F)n2Cc1ccccc1] |
| 361 | 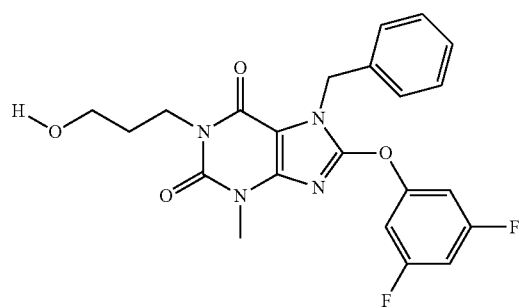 [SMILES: Cn1c(=O)n(CCCO)c(=O)c2c1nc(Oc1cc(F)cc(F)c1)n2Cc1ccccc1] |

TABLE A-continued

| Compound Number | Structure |
|---|---|
| 362 | 1-(3-hydroxypropyl)-3-methyl-7-benzyl-8-(4-fluorophenoxy)xanthine |
| 363 | 1-(3-hydroxypropyl)-3-methyl-7-benzyl-8-(4-fluorophenoxy)xanthine |
| 364 | 1-(3-hydroxypropyl)-3-methyl-7-benzyl-8-(4-chlorophenoxy)xanthine |
| 365 | 1-(3-hydroxypropyl)-3-methyl-7-benzyl-8-(4-methoxyphenoxy)xanthine |
| 366 | 1-(3-hydroxypropyl)-3-methyl-7-benzyl-8-(2-methoxyphenoxy)xanthine |

TABLE A-continued

| Compound Number | Structure |
|---|---|
| 367 | 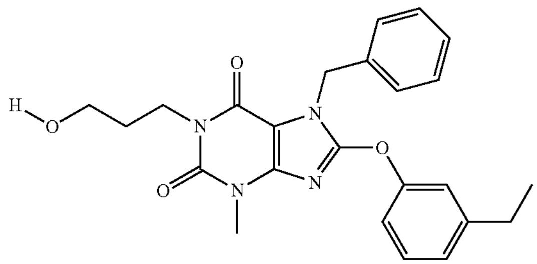 [SMILES: CCc1cccc(Oc2nc3c(c(=O)n(CCCO)c(=O)n3C)n2Cc2ccccc2)c1] |
| 368 | 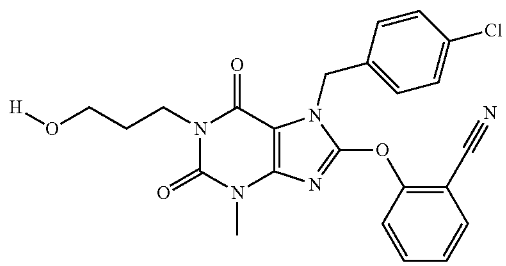 [SMILES: Cn1c(=O)n(CCCO)c(=O)c2c1nc(Oc1ccccc1C#N)n2Cc1ccc(Cl)cc1] |
| 369 | 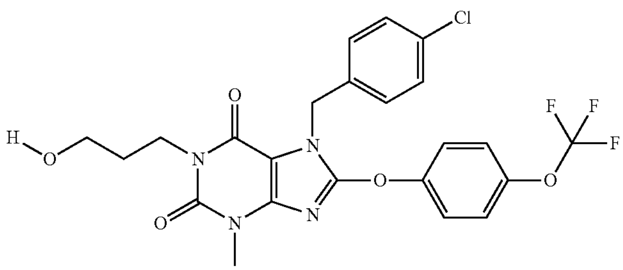 [SMILES: Cn1c(=O)n(CCCO)c(=O)c2c1nc(Oc1ccc(OC(F)(F)F)cc1)n2Cc1ccc(Cl)cc1] |
| 370 | 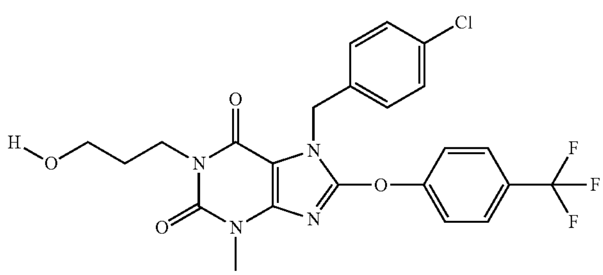 [SMILES: Cn1c(=O)n(CCCO)c(=O)c2c1nc(Oc1ccc(C(F)(F)F)cc1)n2Cc1ccc(Cl)cc1] |
| 371 | 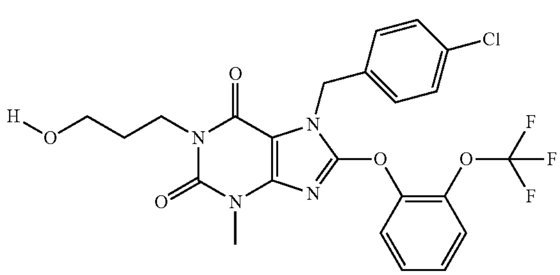 [SMILES: Cn1c(=O)n(CCCO)c(=O)c2c1nc(Oc1ccccc1OC(F)(F)F)n2Cc1ccc(Cl)cc1] |

TABLE A-continued

| Compound Number | Structure |
|---|---|
| 372 | 1-(3-hydroxypropyl)-3-methyl-7-(4-chlorobenzyl)-8-(2-methylphenoxy)xanthine |
| 373 | 1-(3-hydroxypropyl)-3-methyl-7-(4-fluorobenzyl)-8-(3,4-difluorophenoxy)xanthine |
| 374 | 1-(3-hydroxypropyl)-3-methyl-7-(4-fluorobenzyl)-8-(2-trifluoromethylphenoxy)xanthine |
| 375 | 1-(3-hydroxypropyl)-3-methyl-7-(4-fluorobenzyl)-8-(2,3-difluorophenoxy)xanthine |
| 376 | 1-(3-hydroxypropyl)-3-methyl-7-(4-fluorobenzyl)-8-(3,5-difluorophenoxy)xanthine |

TABLE A-continued
| Compound Number | Structure |
|---|---|
| 377 | 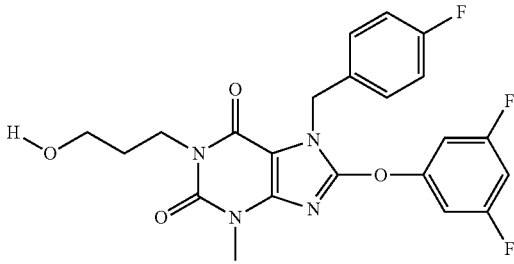 [SMILES: Cn1c(=O)n(CCCO)c(=O)c2c1nc(Oc1cc(F)cc(F)c1)n2Cc1ccc(F)cc1] |
| 378 | 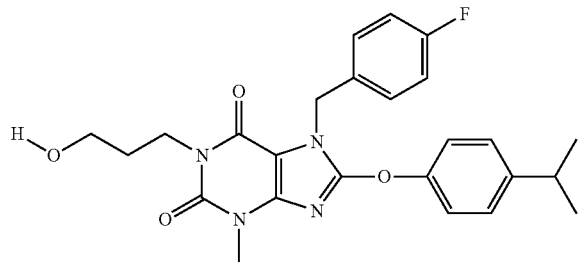 [SMILES: CC(C)c1ccc(Oc2nc3c(c(=O)n(CCCO)c(=O)n3C)n2Cc2ccc(F)cc2)cc1] |
| 379 | 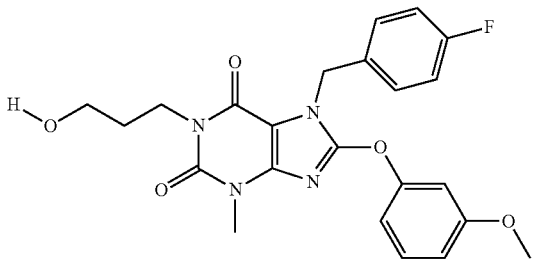 [SMILES: COc1cccc(Oc2nc3c(c(=O)n(CCCO)c(=O)n3C)n2Cc2ccc(F)cc2)c1] |
| 380 | 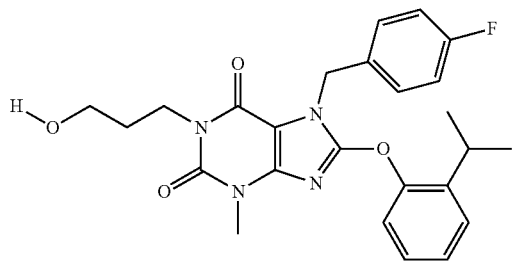 [SMILES: CC(C)c1ccccc1Oc1nc2c(c(=O)n(CCCO)c(=O)n2C)n1Cc1ccc(F)cc1] |
| 381 | 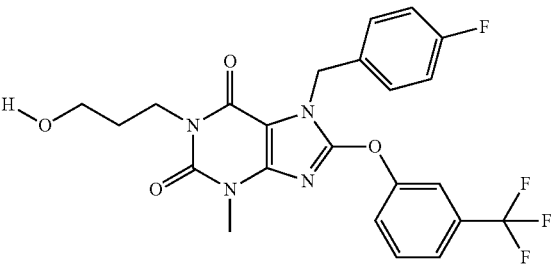 |

TABLE A-continued
| Compound Number | Structure |
|---|---|
| 382 | 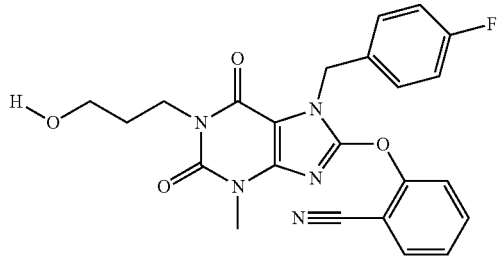 [SMILES: Cn1c(=O)n(CCCO)c(=O)c2c1nc(Oc1ccccc1C#N)n2Cc1ccc(F)cc1] |
| 383 | 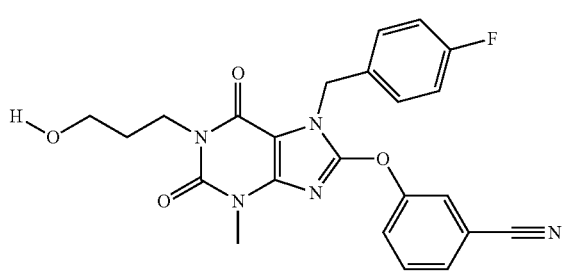 [SMILES: Cn1c(=O)n(CCCO)c(=O)c2c1nc(Oc1cccc(C#N)c1)n2Cc1ccc(F)cc1] |
| 384 | 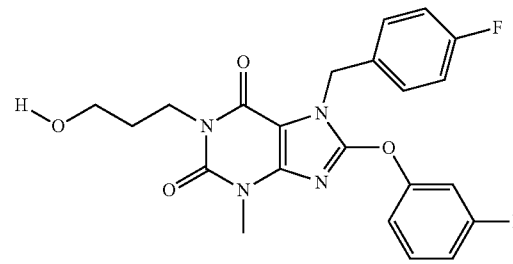 |
| 385 | 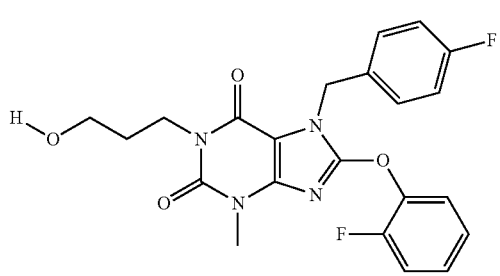 [SMILES: Cn1c(=O)n(CCCO)c(=O)c2c1nc(Oc1ccccc1F)n2Cc1ccc(F)cc1] |
| 386 | 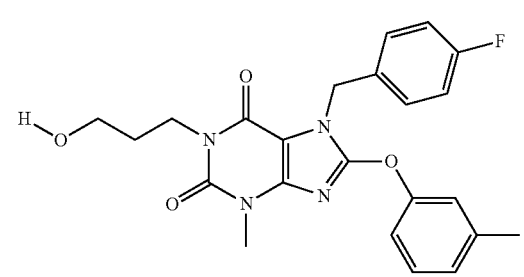 [SMILES: Cc1cccc(Oc2nc3c(c(=O)n(CCCO)c(=O)n3C)n2Cc2ccc(F)cc2)c1] |

TABLE A-continued
| Compound Number | Structure |
|---|---|
| 387 | 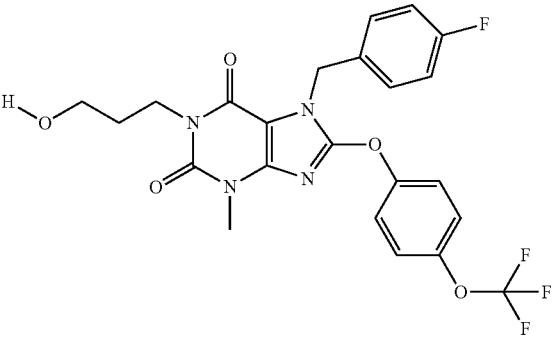 [SMILES: Cn1c(=O)n(CCCO)c(=O)c2c1nc(Oc1ccc(OC(F)(F)F)cc1)n2Cc1ccc(F)cc1] |
| 388 | 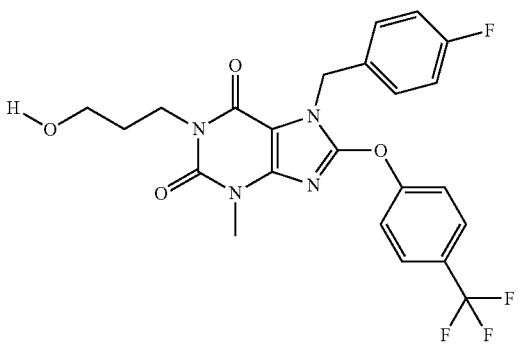 [SMILES: Cn1c(=O)n(CCCO)c(=O)c2c1nc(Oc1ccc(C(F)(F)F)cc1)n2Cc1ccc(F)cc1] |
| 389 | 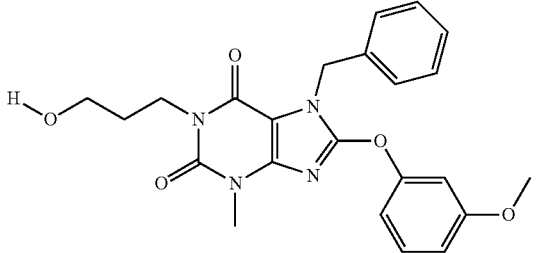 |
| 390 | 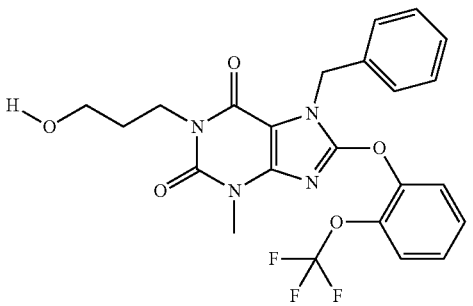 [SMILES: Cn1c(=O)n(CCCO)c(=O)c2c1nc(Oc1ccccc1OC(F)(F)F)n2Cc1ccccc1] |
| 391 | 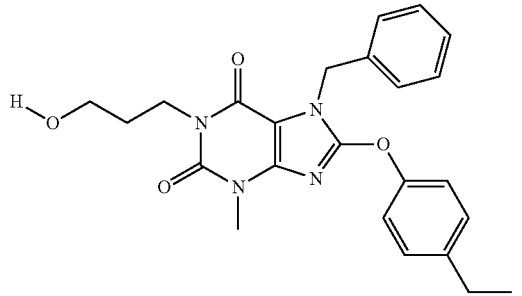 [SMILES: CCc1ccc(Oc2nc3c(c(=O)n(CCCO)c(=O)n3C)n2Cc2ccccc2)cc1] |

TABLE A-continued

| Compound Number | Structure |
|---|---|
| 392 | 1-(3-hydroxypropyl)-3-methyl-7-benzyl-8-(2,3-dichlorophenoxy)xanthine |
| 393 | 1-(3-hydroxypropyl)-3-methyl-7-(4-fluorobenzyl)-8-(4-cyanophenoxy)xanthine |
| 394 | 1-(3-hydroxypropyl)-3-methyl-7-(4-fluorobenzyl)-8-phenoxyxanthine |
| 395 | 1-(3-hydroxypropyl)-3-methyl-7-(4-fluorobenzyl)-8-(2-chlorophenoxy)xanthine |
| 396 | 1-(3-hydroxypropyl)-3-methyl-7-benzyl-8-(2-chlorophenoxy)xanthine |

TABLE A-continued
| Compound Number | Structure |
|---|---|
| 397 | 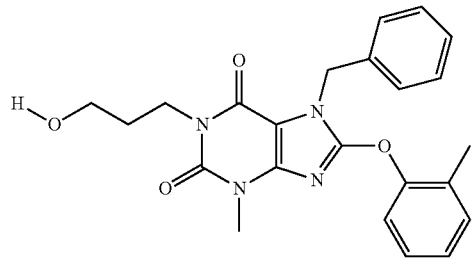 [SMILES: Cc1ccccc1Oc1nc2c(c(=O)n(CCCO)c(=O)n2C)n1Cc1ccccc1] |
| 398 | 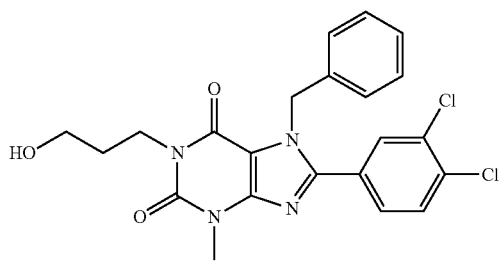 |
| 399 | 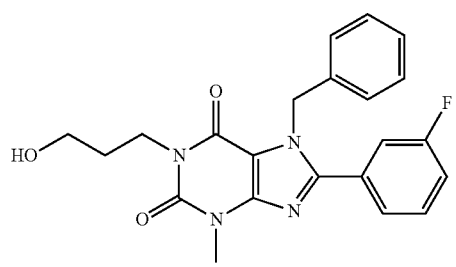 [SMILES: Cn1c(=O)n(CCCO)c(=O)c2c1nc(-c1cccc(F)c1)n2Cc1ccccc1] |
| 400 | 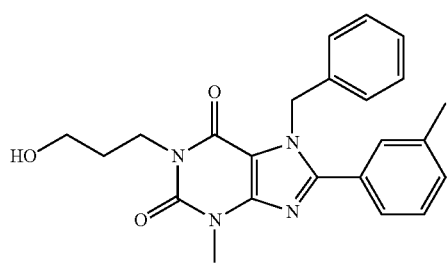 |
| 401 | 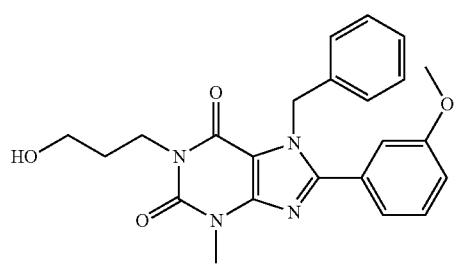 [SMILES: COc1cccc(-c2nc3c(c(=O)n(CCCO)c(=O)n3C)n2Cc2ccccc2)c1] |

TABLE A-continued

| Compound Number | Structure |
|---|---|
| 402 | 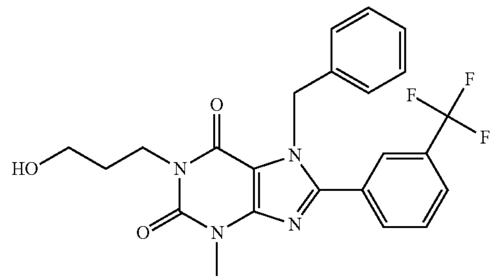 [SMILES: Cn1c(=O)n(CCCO)c(=O)c2c1nc(-c1cccc(C(F)(F)F)c1)n2Cc1ccccc1] |
| 403 | 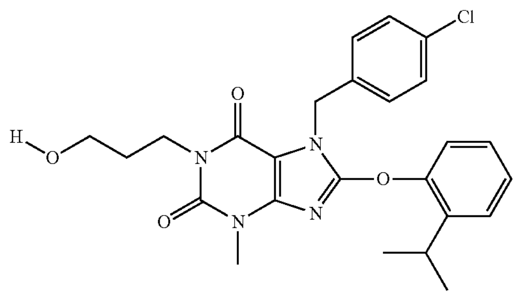 [SMILES: CC(C)c1ccccc1Oc1nc2c(c(=O)n(CCCO)c(=O)n2C)n1Cc1ccc(Cl)cc1] |
| 404 | 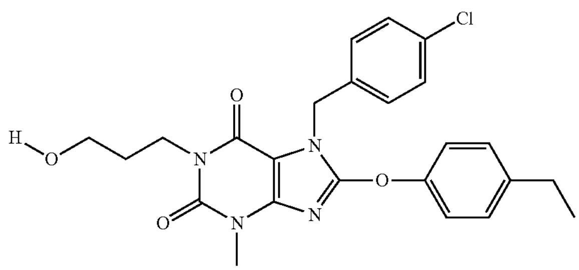 [SMILES: CCc1ccc(Oc2nc3c(c(=O)n(CCCO)c(=O)n3C)n2Cc2ccc(F)cc2)cc1] |
| 405 | 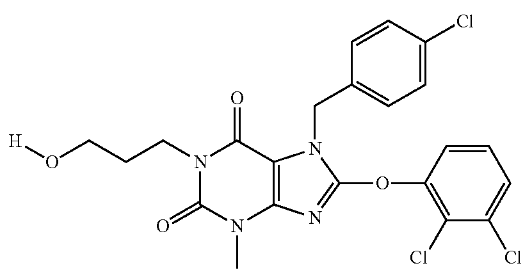 [SMILES: Cn1c(=O)n(CCCO)c(=O)c2c1nc(Oc1cccc(Cl)c1Cl)n2Cc1ccc(F)cc1] |
| 406 | 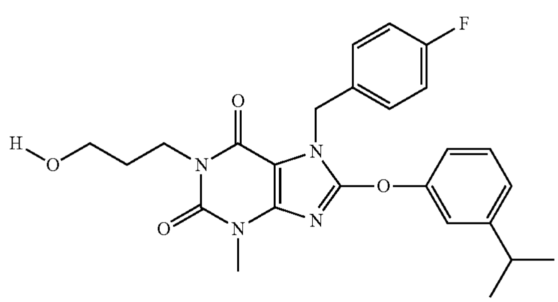 |

TABLE A-continued

| Compound Number | Structure |
|---|---|
| 407 | 1-(3-hydroxypropyl)-7-(4-fluorobenzyl)-3-methyl-8-(2-(trifluoromethoxy)phenoxy)-xanthine |
| 408 | 1-(3-hydroxypropyl)-7-(4-fluorobenzyl)-3-methyl-8-(3-(difluoromethoxy)phenoxy)-xanthine |
| 409 | 1-(3-hydroxypropyl)-7-(4-fluorobenzyl)-3-methyl-8-(4-ethylphenoxy)-xanthine |
| 410 | 1-(3-hydroxypropyl)-7-(4-fluorobenzyl)-3-methyl-8-(2,3-dichlorophenoxy)-xanthine |
| 411 | 1-(3-hydroxypropyl)-7-((5-chloropyridin-2-yl)methyl)-3-methyl-8-(3,4-difluorophenoxy)-xanthine |

TABLE A-continued
| Compound Number | Structure |
|---|---|
| 412 | 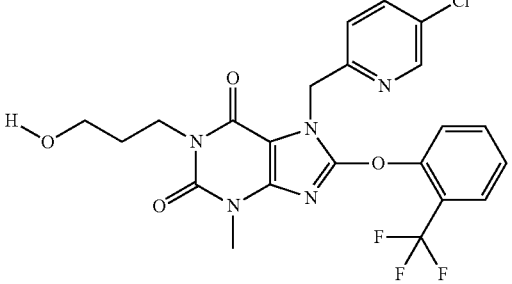 |
| 413 | 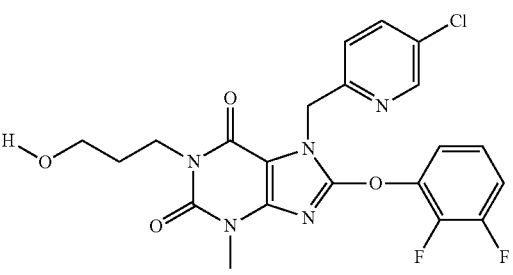 [SMILES: Cn1c(=O)n(CCCO)c(=O)c2c1nc(Oc1cccc(F)c1F)n2Cc1ccc(Cl)cn1] |
| 414 | 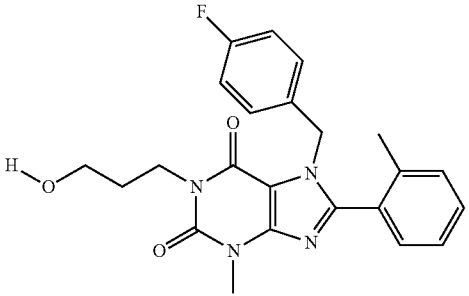 [SMILES: Cc1ccccc1-c1nc2c(c(=O)n(CCCO)c(=O)n2C)n1Cc1ccc(F)cc1] |
| 415 | 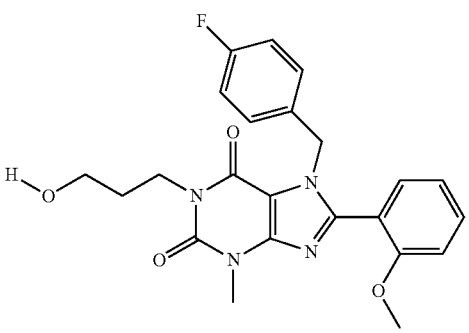 |
| 416 | 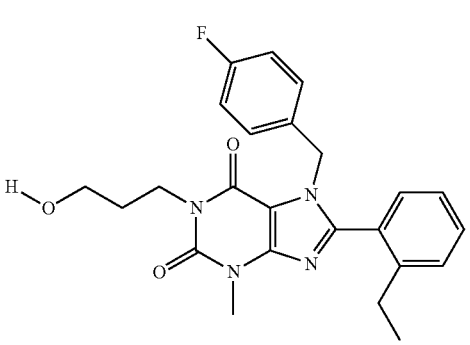 [SMILES: COc1ccccc1-c1nc2c(c(=O)n(CCCO)c(=O)n2C)n1Cc1ccc(F)cc1] |

TABLE A-continued

| Compound Number | Structure |
|---|---|
| 417 | 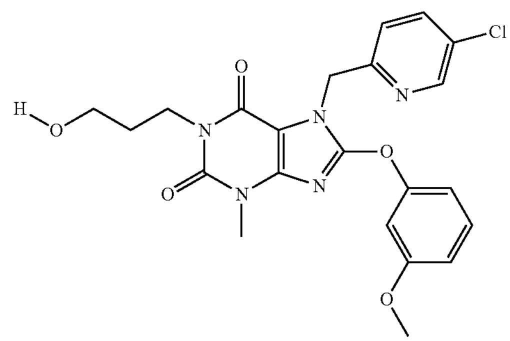 [SMILES: COc1cccc(Oc2nc3c(c(=O)n(CCCO)c(=O)n3C)n2Cc2ccc(Cl)cn2)c1] |
| 418 | 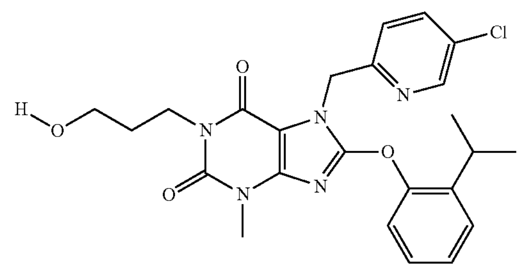 [SMILES: CC(C)c1ccccc1Oc1nc2c(c(=O)n(CCCO)c(=O)n2C)n1Cc1ccc(Cl)cn1] |
| 419 | 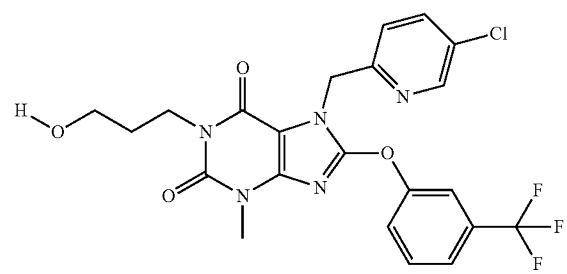 [SMILES: Cn1c(=O)n(CCCO)c(=O)c2c1nc(Oc1cccc(C(F)(F)F)c1)n2Cc1ccc(Cl)cn1] |
| 420 | 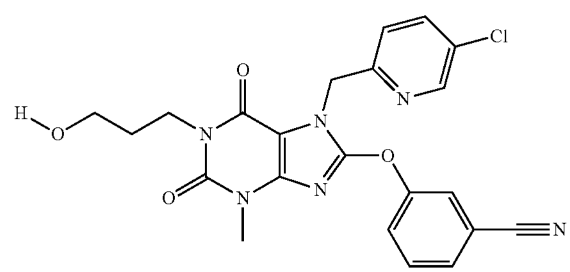 [SMILES: Cn1c(=O)n(CCCO)c(=O)c2c1nc(Oc1cccc(C#N)c1)n2Cc1ccc(Cl)cn1] |
| 421 | 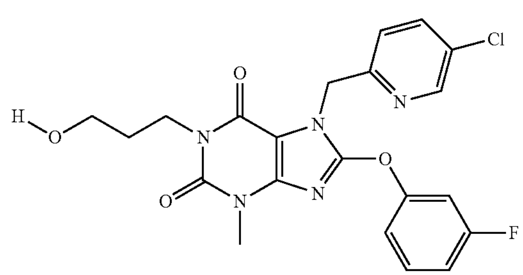 |

TABLE A-continued
| Compound Number | Structure |
|---|---|
| 422 | 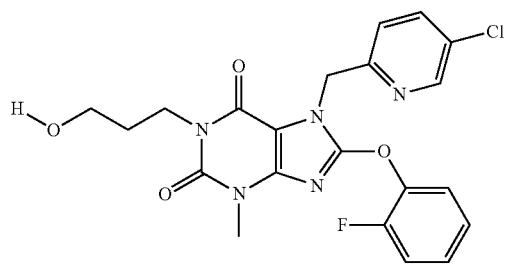 [SMILES: Cn1c(=O)n(CCCO)c(=O)c2c1nc(Oc1ccccc1F)n2Cc1ccc(Cl)cn1] |
| 423 | 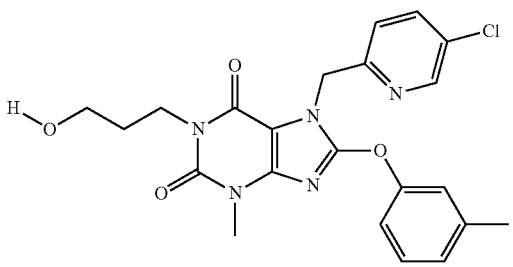 [SMILES: Cc1cccc(Oc2nc3c(c(=O)n(CCCO)c(=O)n3C)n2Cc2ccc(Cl)cn2)c1] |
| 424 | 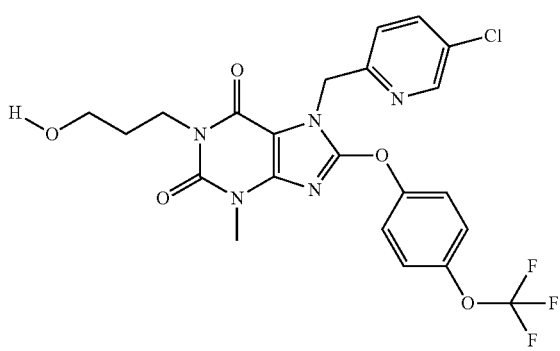 [SMILES: Cn1c(=O)n(CCCO)c(=O)c2c1nc(Oc1ccc(OC(F)(F)F)cc1)n2Cc1ccc(Cl)cn1] |
| 425 | 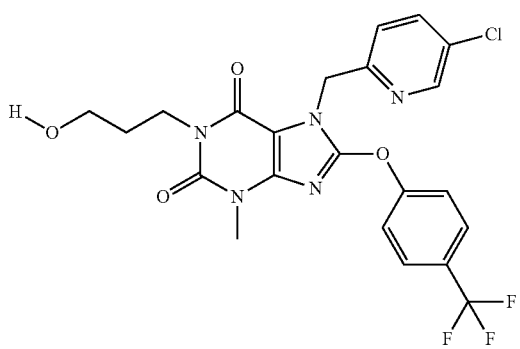 [SMILES: Cn1c(=O)n(CCCO)c(=O)c2c1nc(Oc1ccc(C(F)(F)F)cc1)n2Cc1ccc(Cl)cn1] |
| 426 | 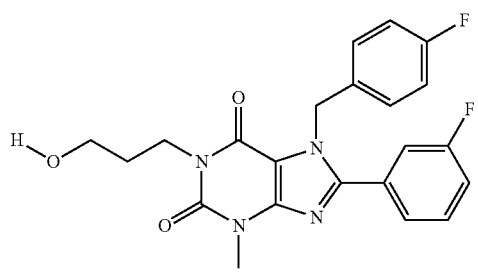 [SMILES: Cn1c(=O)n(CCCO)c(=O)c2c1nc(-c1cccc(F)c1)n2Cc1ccc(F)cc1] |

US 9,969,736 B2
TABLE A-continued
| Compound Number | Structure |
|---|---|
| 427 | 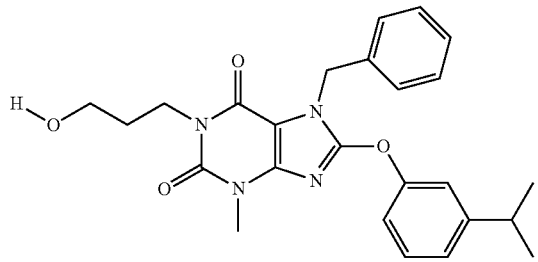 [SMILES: CC(C)c1cccc(Oc2nc3c(c(=O)n(CCCO)c(=O)n3C)n2Cc2ccccc2)c1] |
| 428 | 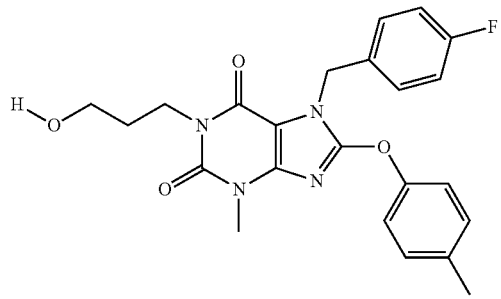 [SMILES: Cc1ccc(Oc2nc3c(c(=O)n(CCCO)c(=O)n3C)n2Cc2ccc(F)cc2)cc1] |
| 429 | 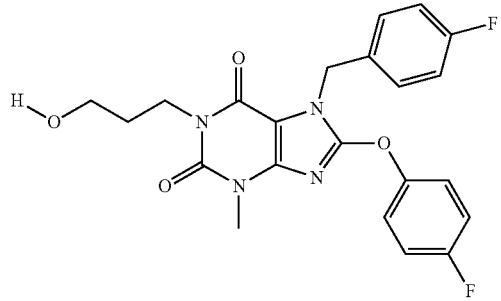 [SMILES: Cn1c(=O)n(CCCO)c(=O)c2c1nc(Oc1ccc(Cl)cc1)n2Cc1ccc(F)cc1] |
| 430 | 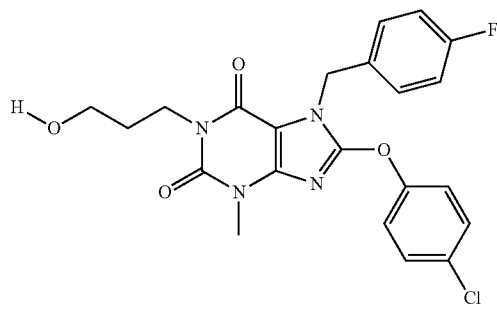 |
| 431 | 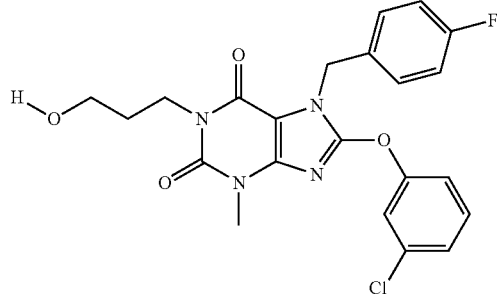 [SMILES: Cn1c(=O)n(CCCO)c(=O)c2c1nc(Oc1cccc(Cl)c1)n2Cc1ccc(F)cc1] |

TABLE A-continued

| Compound Number | Structure |
|---|---|
| 432 | 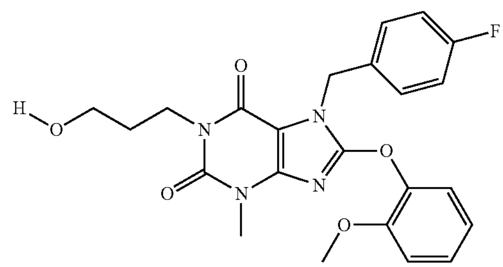 [SMILES: COc1ccccc1Oc1nc2c(c(=O)n(CCCO)c(=O)n2C)n1Cc1ccc(F)cc1] |
| 433 | 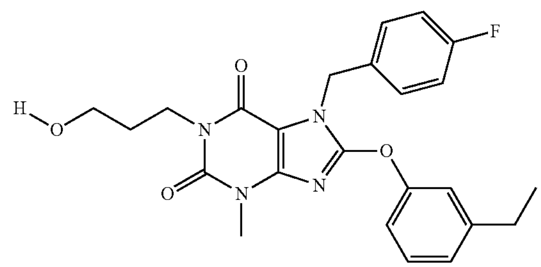 [SMILES: CCc1cccc(Oc2nc3c(c(=O)n(CCCO)c(=O)n3C)n2Cc2ccc(F)cc2)c1] |
| 434 | 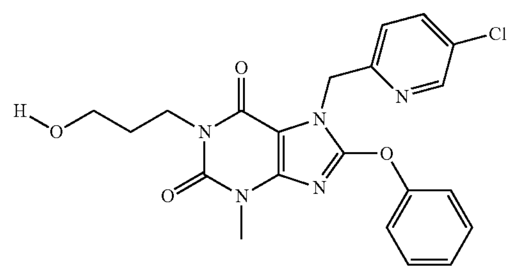 [SMILES: Cn1c(=O)n(CCCO)c(=O)c2c1nc(Oc1ccccc1)n2Cc1ccc(Cl)cn1] |
| 435 | 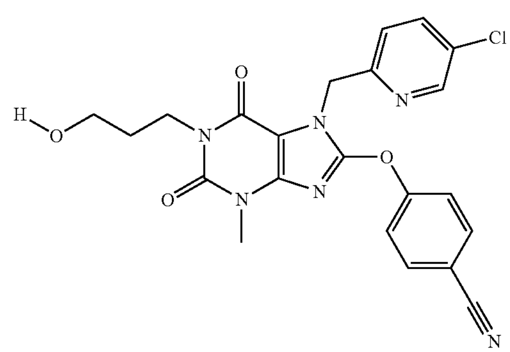 [SMILES: Cn1c(=O)n(CCCO)c(=O)c2c1nc(Oc1ccc(C#N)cc1)n2Cc1ccc(Cl)cn1] |
| 436 | 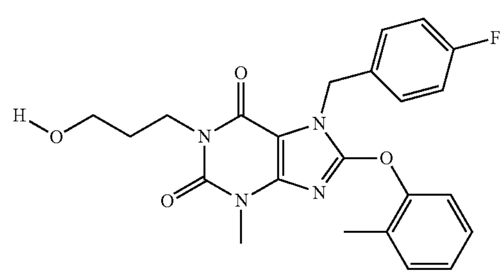 [SMILES: Cc1ccccc1Oc1nc2c(c(=O)n(CCCO)c(=O)n2C)n1Cc1ccc(F)cc1] |

TABLE A-continued

| Compound Number | Structure |
|---|---|
| 437 | 1-(3-hydroxypropyl)-7-(4-fluorobenzyl)-8-(4-methoxyphenoxy)-3-methylxanthine |
| 438 | 7-benzyl-8-(4-chlorophenyl)-1-(3-hydroxypropyl)-3-methylxanthine |
| 439 | 7-benzyl-8-(4-fluorophenyl)-1-(3-hydroxypropyl)-3-methylxanthine |
| 440 | 7-benzyl-1-(3-hydroxypropyl)-3-methyl-8-(4-methylphenyl)xanthine |
| 441 | 7-benzyl-1-(3-hydroxypropyl)-8-(4-methoxyphenyl)-3-methylxanthine |

TABLE A-continued
| Compound Number | Structure |
|---|---|
| 442 | 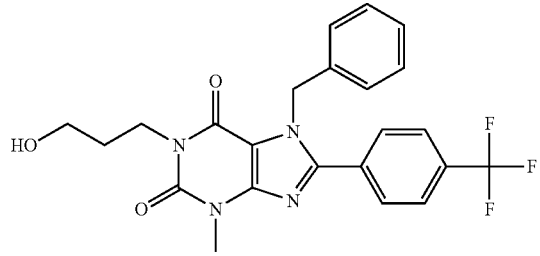 [SMILES: Cn1c(=O)n(CCCO)c(=O)c2c1nc(-c1ccc(C(F)(F)F)cc1)n2Cc1ccccc1] |
| 443 | 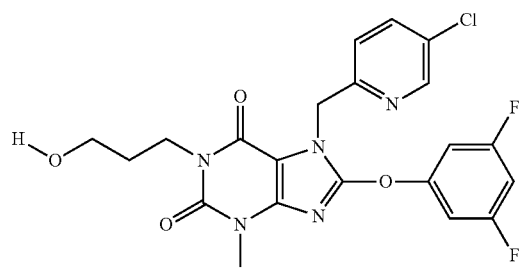 |
| 444 | 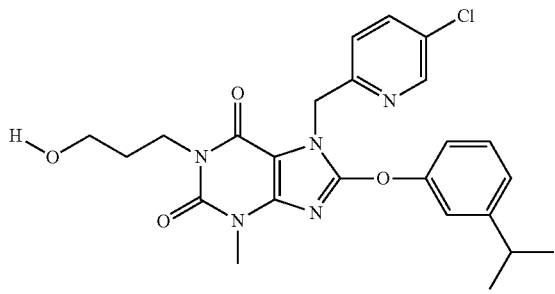 [SMILES: CC(C)c1cccc(Oc2nc3c(c(=O)n(CCCO)c(=O)n3C)n2Cc2ccc(Cl)cn2)c1] |
| 445 | 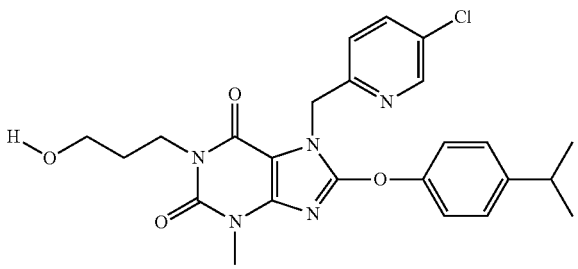 |
| 446 | 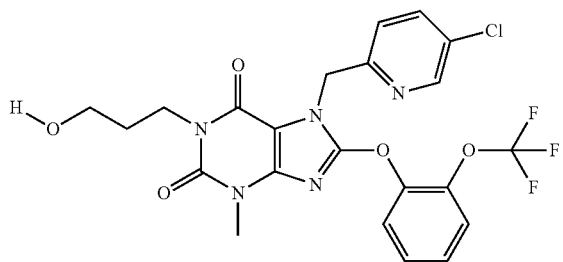 [SMILES: Cn1c(=O)n(CCCO)c(=O)c2c1nc(Oc1ccccc1OC(F)(F)F)n2Cc1ccc(Cl)cn1] |

TABLE A-continued
| Compound Number | Structure |
|---|---|
| 447 | 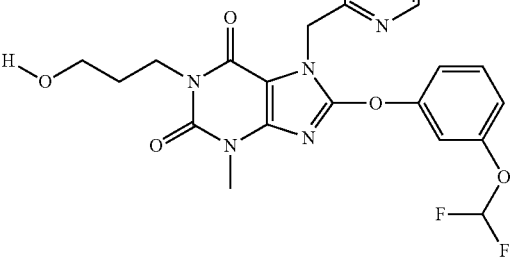 |
| 448 | 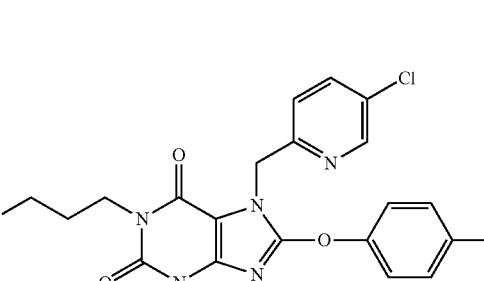 |
| 449 | 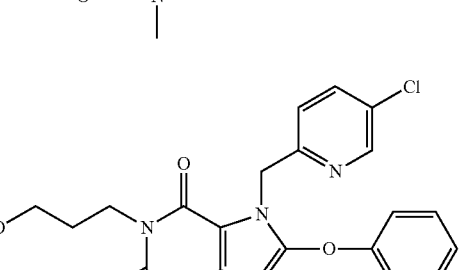 |
| 450 | 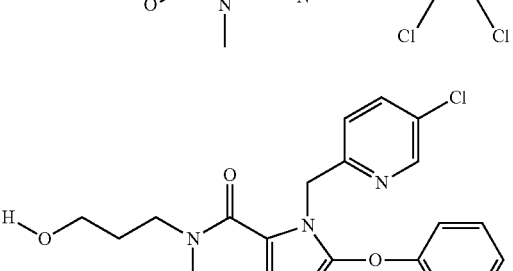 |
| 451 | 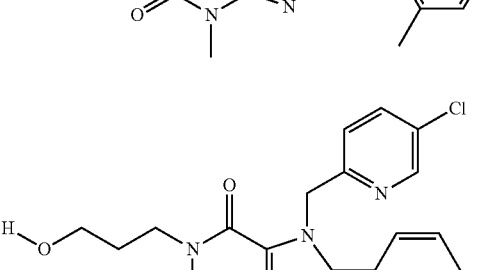 |

TABLE A-continued

| Compound Number | Structure |
| --- | --- |
| 452 | 7-[(5-chloropyridin-2-yl)methyl]-1-(3-hydroxypropyl)-8-(3-methoxyphenyl)-3-methyl-3,7-dihydro-1H-purine-2,6-dione |
| 453 | 7-[(5-chloropyridin-2-yl)methyl]-1-(3-hydroxypropyl)-3-methyl-8-[3-(trifluoromethyl)phenyl]-3,7-dihydro-1H-purine-2,6-dione |
| 454 | 8-(biphenyl-3-yl)-7-[(5-chloropyridin-2-yl)methyl]-1-(3-hydroxypropyl)-3-methyl-3,7-dihydro-1H-purine-2,6-dione |
| 455 | 7-(4-fluorobenzyl)-1-(3-hydroxypropyl)-3-methyl-8-(4-methylphenyl)-3,7-dihydro-1H-purine-2,6-dione |
| 456 | 7-(4-fluorobenzyl)-1-(3-hydroxypropyl)-3-methyl-8-[4-(trifluoromethyl)phenyl]-3,7-dihydro-1H-purine-2,6-dione |

TABLE A-continued
| Compound Number | Structure |
|---|---|
| 457 | 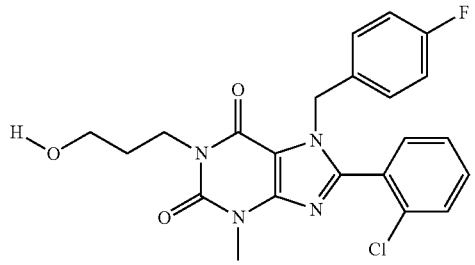 |
| 458 | 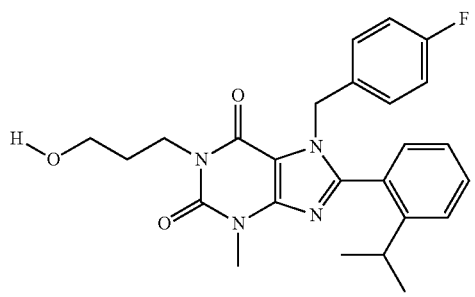 [SMILES: CC(C)c1ccccc1-c1nc2c(c(=O)n(CCCO)c(=O)n2C)n1Cc1ccc(F)cc1] |
| 459 | 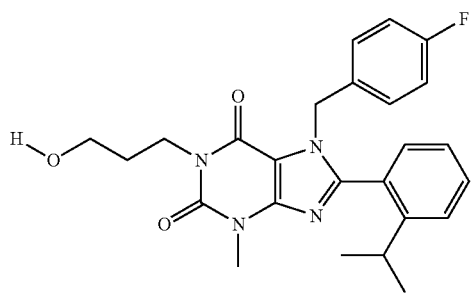 [SMILES: CC(C)c1ccccc1-c1nc2c(c(=O)n(CCCO)c(=O)n2C)n1Cc1ccc(F)cc1] |
| 460 | 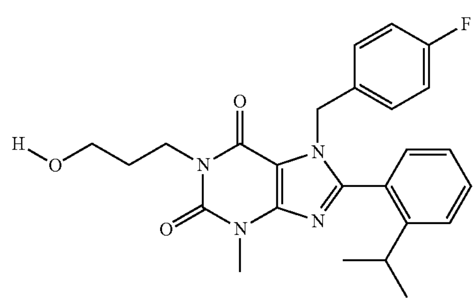 [SMILES: CC(C)c1ccccc1-c1nc2c(c(=O)n(CCCO)c(=O)n2C)n1Cc1ccc(F)cc1] |
| 461 | 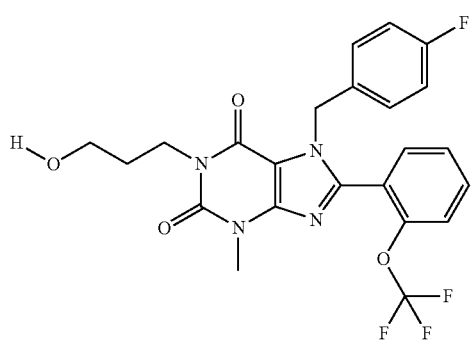 [SMILES: Cn1c(=O)n(CCCO)c(=O)c2c1nc(-c1ccccc1OC(F)(F)F)n2Cc1ccc(F)cc1] |

TABLE A-continued
| Compound Number | Structure |
|---|---|
| 462 | 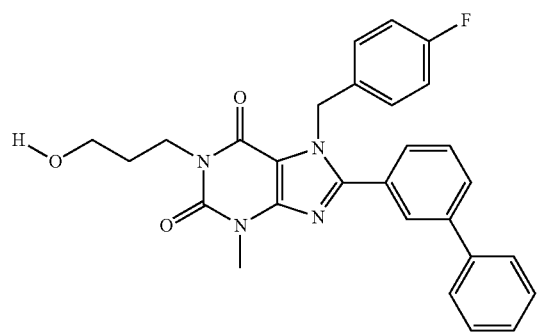 [SMILES: Cn1c(=O)n(CCCO)c(=O)c2c1nc(-c1cccc(-c3ccccc3)c1)n2Cc1ccc(F)cc1] |
| 463 | 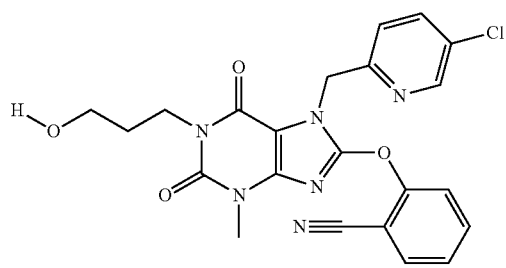 [SMILES: Cn1c(=O)n(CCCO)c(=O)c2c1nc(Oc1ccccc1C#N)n2Cc1ccc(Cl)cn1] |
| 464 | 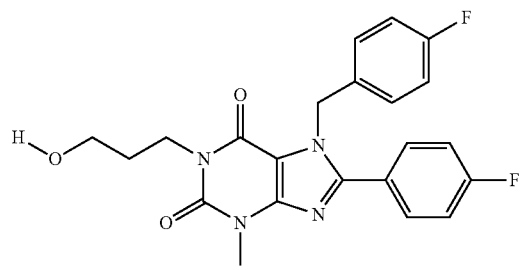 [SMILES: Cn1c(=O)n(CCCO)c(=O)c2c1nc(-c1ccc(F)cc1)n2Cc1ccc(F)cc1] |
| 465 | 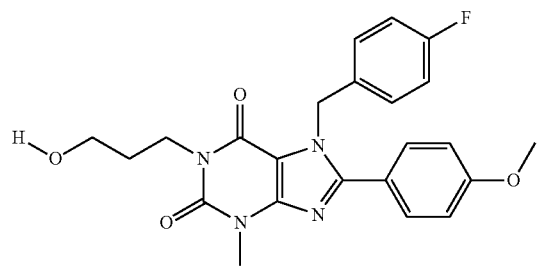 [SMILES: COc1ccc(-c2nc3c(c(=O)n(CCCO)c(=O)n3C)n2Cc2ccc(F)cc2)cc1] |
| 466 | 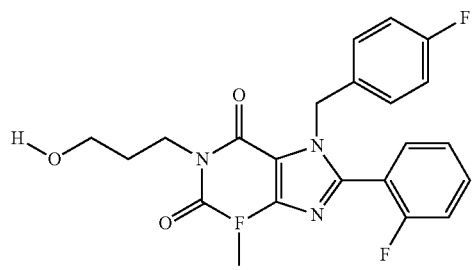 |

TABLE A-continued
| Compound Number | Structure |
|---|---|
| 467 | 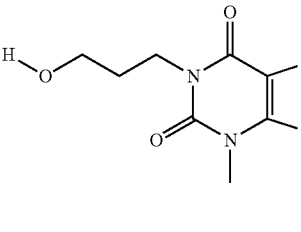 |
| 468 | 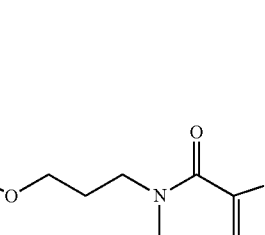 |
| 469 | 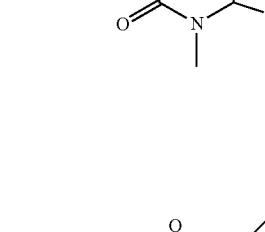 |
| 470 | 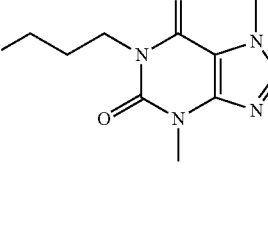 |
| 471 | 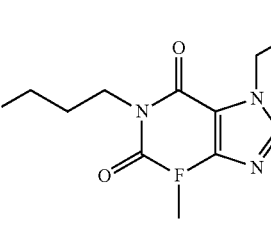 |

TABLE A-continued

| Compound Number | Structure |
|---|---|
| 472 | 1-(3-hydroxypropyl)-7-[(5-chloropyridin-2-yl)methyl]-8-(2-chlorophenoxy)-3-methyl-xanthine |
| 473 | 1-(3-hydroxypropyl)-7-[(5-chloropyridin-2-yl)methyl]-8-(4-fluorophenoxy)-3-methyl-xanthine |
| 474 | 1-(3-hydroxypropyl)-7-[(5-chloropyridin-2-yl)methyl]-8-(4-chlorophenoxy)-3-methyl-xanthine |
| 475 | 1-(3-hydroxypropyl)-7-[(5-chloropyridin-2-yl)methyl]-8-(4-methoxyphenoxy)-3-methyl-xanthine |
| 476 | 1-(3-hydroxypropyl)-7-[(5-chloropyridin-2-yl)methyl]-8-(3-chlorophenoxy)-3-methyl-xanthine |

TABLE A-continued
| Compound Number | Structure |
|---|---|
| 477 | 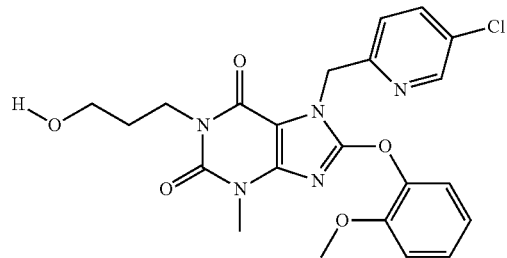 [SMILES: COc1ccccc1Oc1nc2c(c(=O)n(CCCO)c(=O)n2C)n1Cc1ccc(Cl)cn1] |
| 478 | 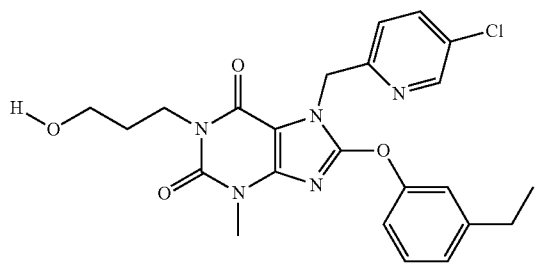 [SMILES: CCc1cccc(Oc2nc3c(c(=O)n(CCCO)c(=O)n3C)n2Cc2ccc(Cl)cn2)c1] |
| 479 | 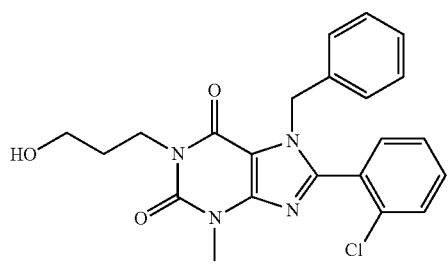 |
| 480 | 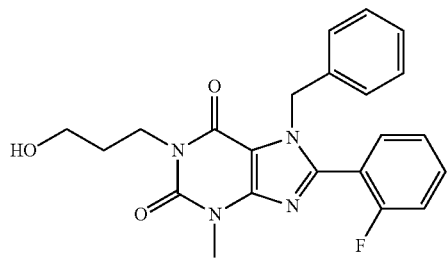 |
| 481 | 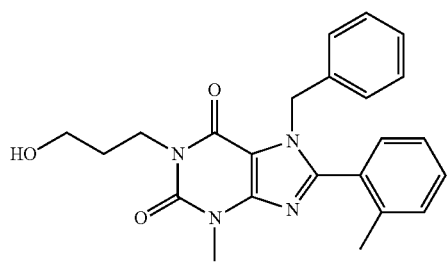 [SMILES: Cc1ccccc1-c1nc2c(c(=O)n(CCCO)c(=O)n2C)n1Cc1ccccc1] |

TABLE A-continued
| Compound Number | Structure |
|---|---|
| 482 | 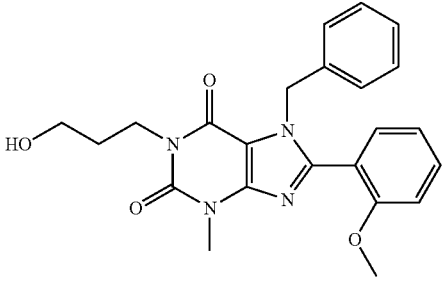 [SMILES: COc1ccccc1-c1nc2c(c(=O)n(CCCO)c(=O)n2C)n1Cc1ccccc1] |
| 483 | 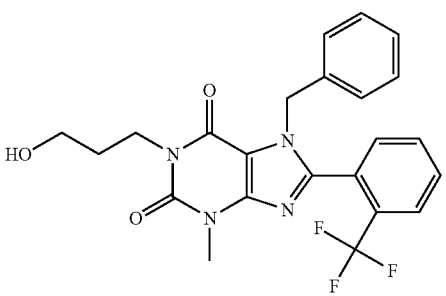 [SMILES: Cn1c(=O)n(CCCO)c(=O)c2c1nc(-c1ccccc1C(F)(F)F)n2Cc1ccccc1] |
| 484 | 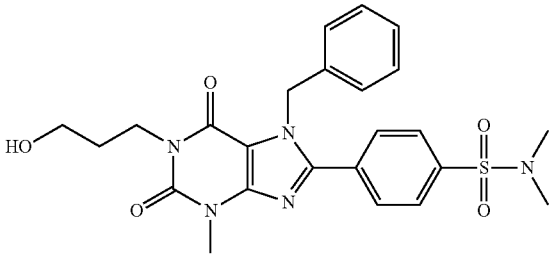 |
| 485 | 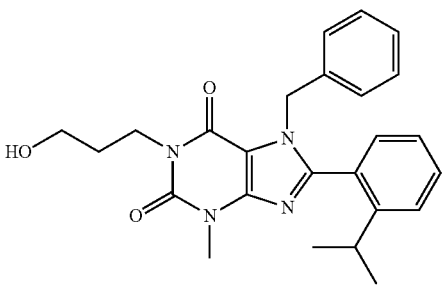 [SMILES: CC(C)c1ccccc1-c1nc2c(c(=O)n(CCCO)c(=O)n2C)n1Cc1ccccc1] |
| 486 | 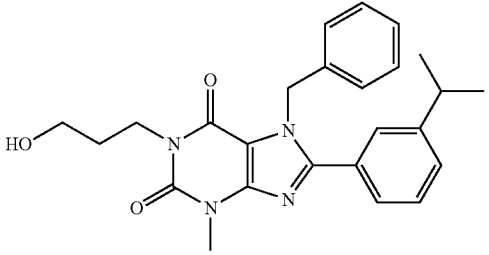 [SMILES: CC(C)c1cccc(-c2nc3c(c(=O)n(CCCO)c(=O)n3C)n2Cc2ccccc2)c1] |

TABLE A-continued

| Compound Number | Structure |
|---|---|
| 487 | 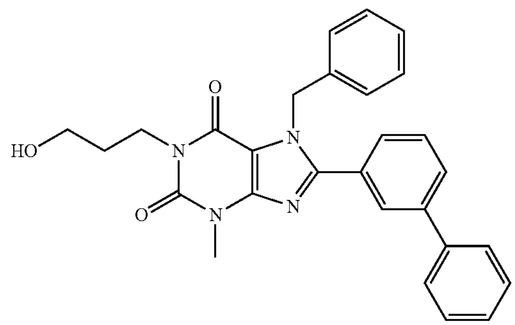 [SMILES: Cn1c(=O)n(CCCO)c(=O)c2c1nc(-c1cccc(-c3ccccc3)c1)n2Cc1ccccc1] |
| 488 | 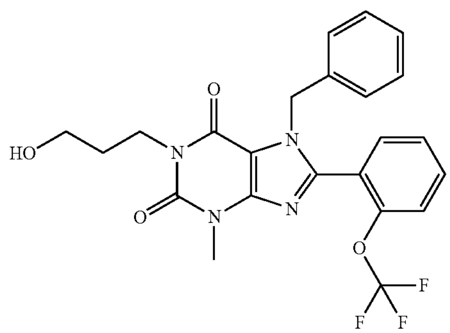 [SMILES: Cn1c(=O)n(CCCO)c(=O)c2c1nc(-c1ccccc1OC(F)(F)F)n2Cc1ccccc1] |
| 489 | 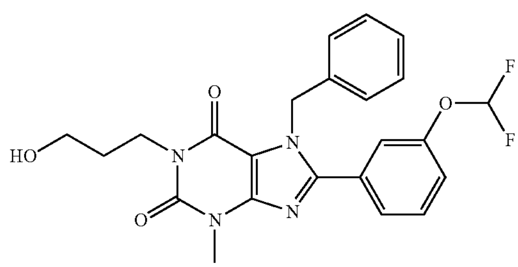 [SMILES: Cn1c(=O)n(CCCO)c(=O)c2c1nc(-c1cccc(OC(F)F)c1)n2Cc1ccccc1] |
| 490 | 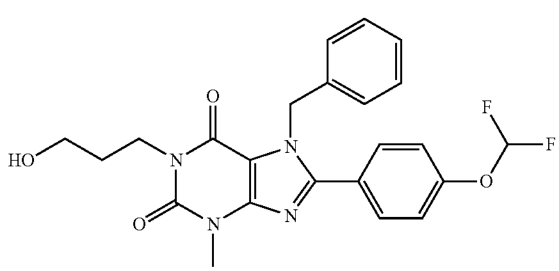 [SMILES: Cn1c(=O)n(CCCO)c(=O)c2c1nc(-c1ccc(OC(F)F)cc1)n2Cc1ccccc1] |
| 491 | 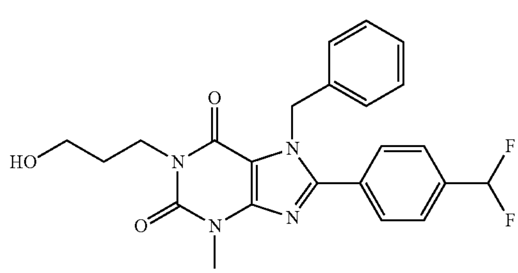 [SMILES: Cn1c(=O)n(CCCO)c(=O)c2c1nc(-c1ccc(C(F)F)cc1)n2Cc1ccccc1] |

TABLE A-continued

| Compound Number | Structure |
|---|---|
| 492 | 1-(3-hydroxypropyl)-7-((5-chloropyridin-2-yl)methyl)-8-(3-isopropylphenoxy)-3-methyl-xanthine |
| 493 | 1-(3-hydroxypropyl)-7-((5-chloropyridin-2-yl)methyl)-8-(4-fluorophenyl)-3-methyl-xanthine |
| 494 | 1-(3-hydroxypropyl)-7-((5-chloropyridin-2-yl)methyl)-8-(3-isopropylphenyl)-3-methyl-xanthine |
| 495 | 1-(3-hydroxypropyl)-7-((5-chloropyridin-2-yl)methyl)-3-methyl-8-(3-(trifluoromethoxy)phenyl)-xanthine |
| 496 | 1-(3-hydroxypropyl)-7-((5-chloropyridin-2-yl)methyl)-8-(4-chlorophenyl)-3-methyl-xanthine |

TABLE A-continued
| Compound Number | Structure |
|---|---|
| 497 | 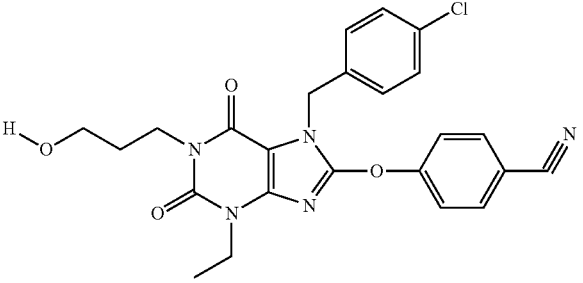 [SMILES: CCn1c(=O)n(CCCO)c(=O)c2c1nc(Oc1ccc(C#N)cc1)n2Cc1ccc(Cl)cc1] |
| 498 | 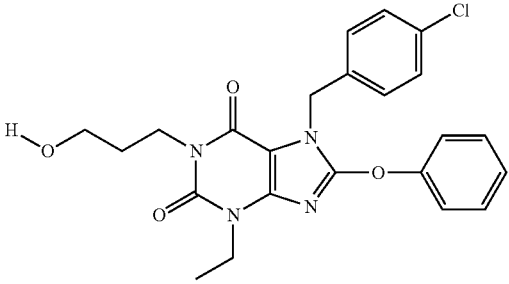 [SMILES: CCn1c(=O)n(CCCO)c(=O)c2c1nc(Oc1ccccc1)n2Cc1ccc(Cl)cc1] |
| 499 | 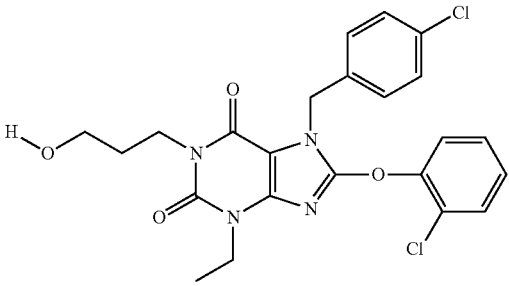 [SMILES: CCn1c(=O)n(CCCO)c(=O)c2c1nc(Oc1ccccc1Cl)n2Cc1ccc(Cl)cc1] |
| 500 | 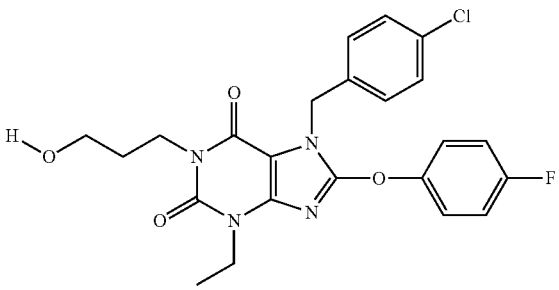 [SMILES: CCn1c(=O)n(CCCO)c(=O)c2c1nc(Oc1ccc(F)cc1)n2Cc1ccc(Cl)cc1] |
| 501 | 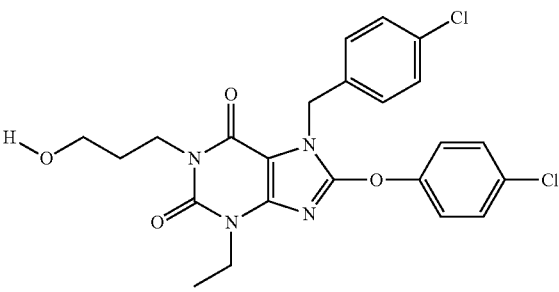 [SMILES: CCn1c(=O)n(CCCO)c(=O)c2c1nc(Oc1ccc(Cl)cc1)n2Cc1ccc(Cl)cc1] |

TABLE A-continued
| Compound Number | Structure |
|---|---|
| 502 | 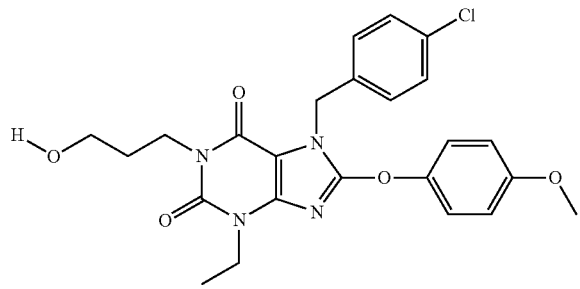 [SMILES: CCn1c(=O)n(CCCO)c(=O)c2c1nc(Oc1ccc(OC)cc1)n2Cc1ccc(Cl)cc1] |
| 503 | 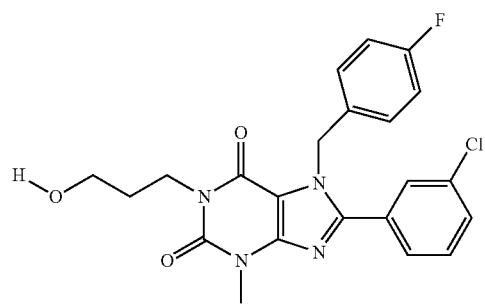 [SMILES: Cn1c(=O)n(CCCO)c(=O)c2c1nc(-c1cccc(Cl)c1)n2Cc1ccc(F)cc1] |
| 504 | 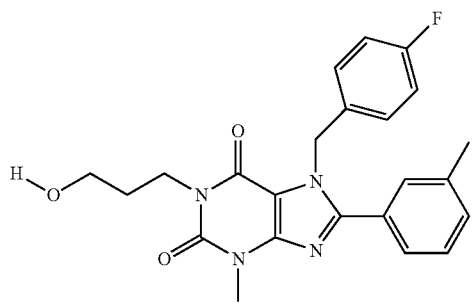 |
| 505 | 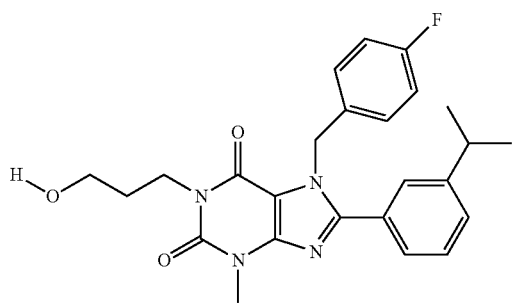 [SMILES: CC(C)c1cccc(-c2nc3c(c(=O)n(CCCO)c(=O)n3C)n2Cc2ccc(F)cc2)c1] |
| 506 | 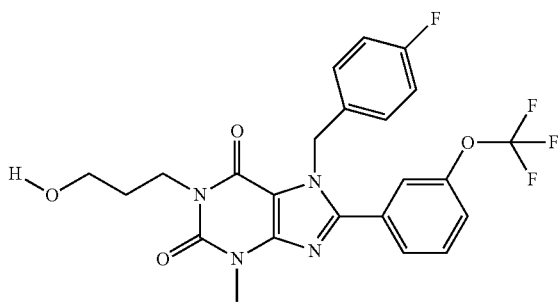 [SMILES: Cn1c(=O)n(CCCO)c(=O)c2c1nc(-c1cccc(OC(F)(F)F)c1)n2Cc1ccc(F)cc1] |

TABLE A-continued

| Compound Number | Structure |
|---|---|
| 507 | 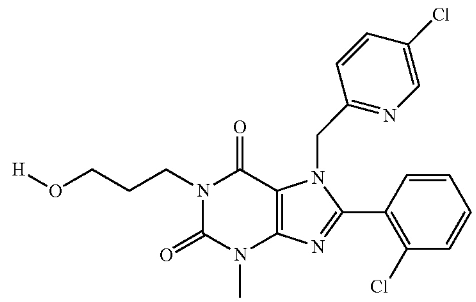 [SMILES: Cn1c(=O)n(CCCO)c(=O)c2c1nc(-c1ccccc1Cl)n2Cc1ccc(Cl)cn1] |
| 508 | 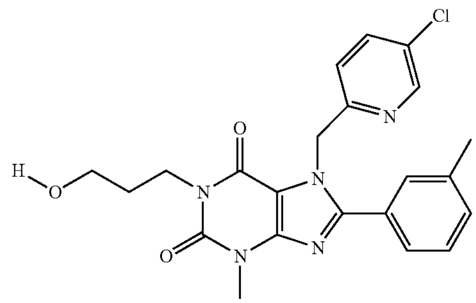 [SMILES: Cc1cccc(-c2nc3c(c(=O)n(CCCO)c(=O)n3C)n2Cc2ccc(Cl)cn2)c1] |
| 509 | 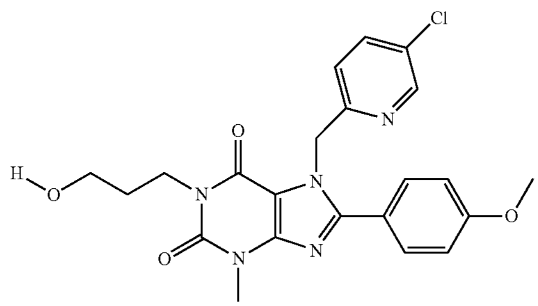 [SMILES: COc1ccc(-c2nc3c(c(=O)n(CCCO)c(=O)n3C)n2Cc2ccc(Cl)cn2)cc1] |
| 510 | 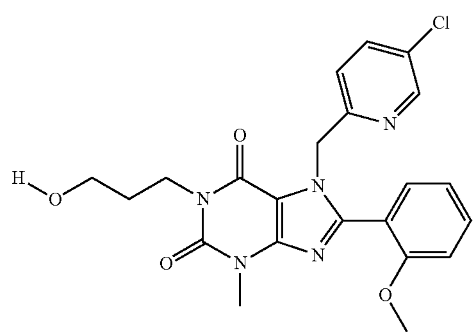 |
| 511 | 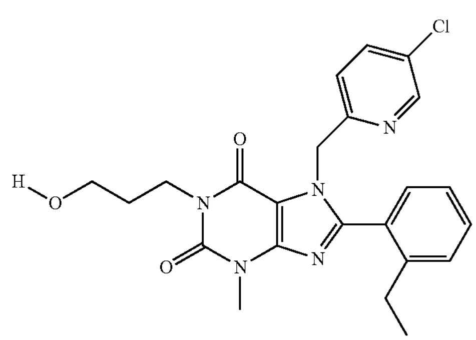 [SMILES: COc1ccccc1-c1nc2c(c(=O)n(CCCO)c(=O)n2C)n1Cc1ccc(Cl)cn1] |

TABLE A-continued
| Compound Number | Structure |
|---|---|
| 512 | 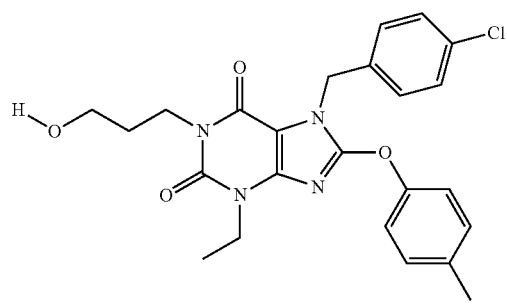 [SMILES: CCn1c(=O)n(CCCO)c(=O)c2c1nc(Oc1ccc(C)cc1)n2Cc1ccc(Cl)cc1] |
| 513 | 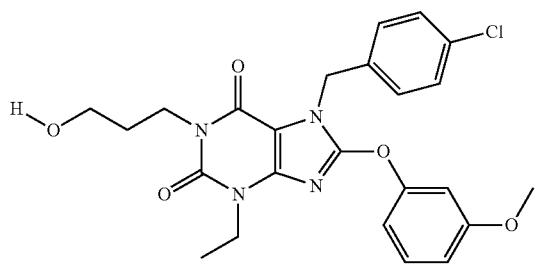 |
| 514 | 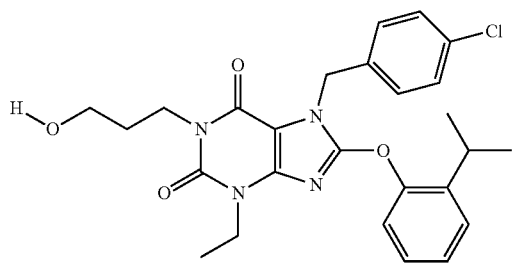 [SMILES: CCn1c(=O)n(CCCO)c(=O)c2c1nc(Oc1ccccc1C(C)C)n2Cc1ccc(Cl)cc1] |
| 515 | 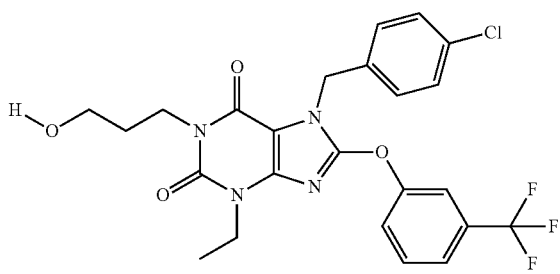 [SMILES: CCn1c(=O)n(CCCO)c(=O)c2c1nc(Oc1cccc(C(F)(F)F)c1)n2Cc1ccc(Cl)cc1] |
| 516 | 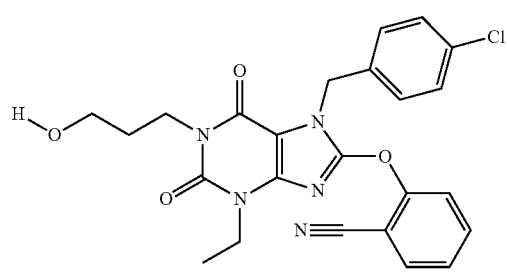 [SMILES: CCn1c(=O)n(CCCO)c(=O)c2c1nc(Oc1ccccc1C#N)n2Cc1ccc(Cl)cc1] |

TABLE A-continued
| Compound Number | Structure |
|---|---|
| 517 | 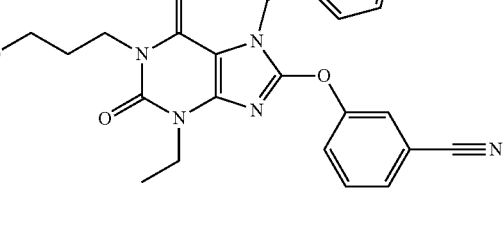 |
| 518 | 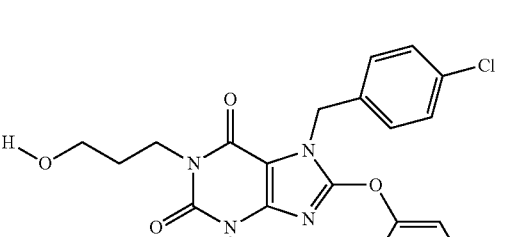 |
| 519 | 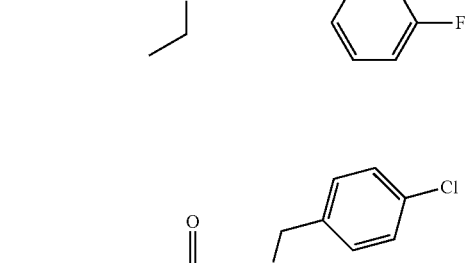 |
| 520 | 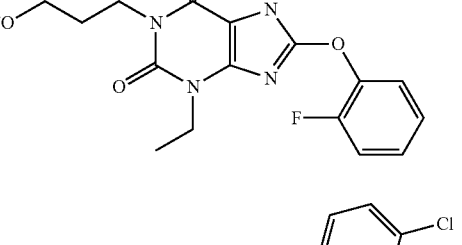 |
| 521 | 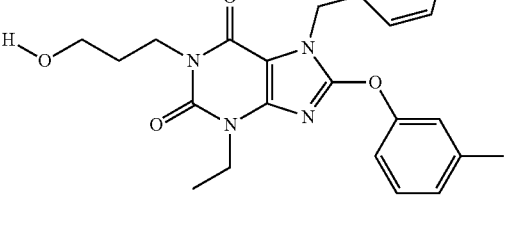 |

TABLE A-continued

| Compound Number | Structure |
|---|---|
| 522 | 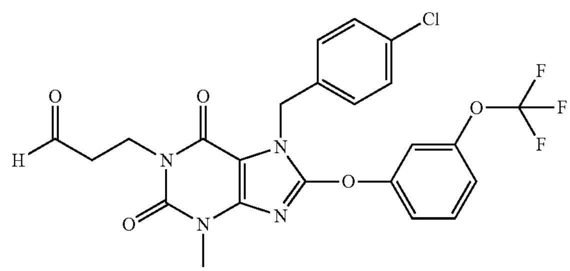 [SMILES: Cn1c(=O)n(CCC=O)c(=O)c2c1nc(Oc1cccc(OC(F)(F)F)c1)n2Cc1ccc(Cl)cc1] |
| 523 | 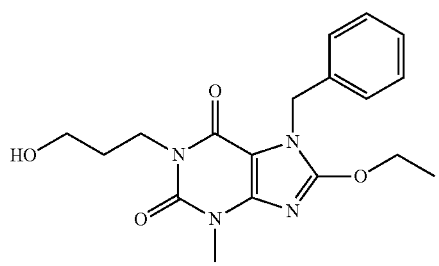 [SMILES: CCOc1nc2c(c(=O)n(CCCO)c(=O)n2C)n1Cc1ccccc1] |
| 524 | 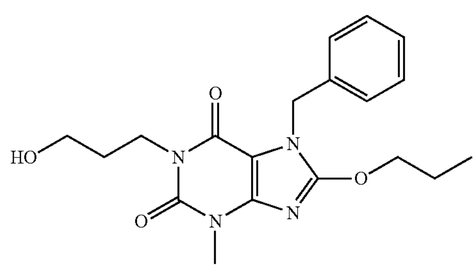 [SMILES: CCCOc1nc2c(c(=O)n(CCCO)c(=O)n2C)n1Cc1ccccc1] |
| 525 | 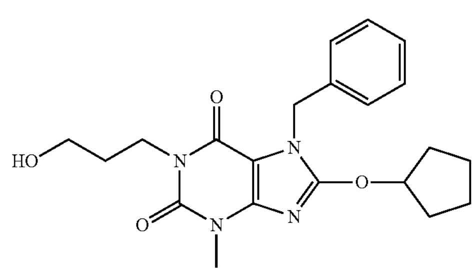 [SMILES: Cn1c(=O)n(CCCO)c(=O)c2c1nc(OC1CCCC1)n2Cc1ccccc1] |
| 526 | 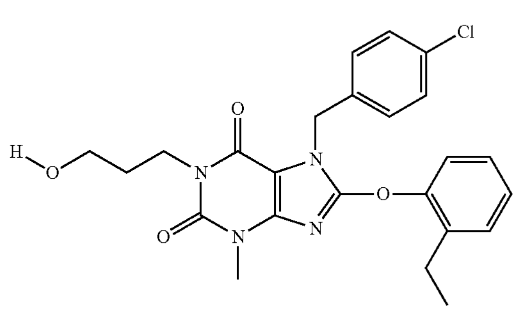 [SMILES: CCc1ccccc1Oc1nc2c(c(=O)n(CCCO)c(=O)n2C)n1Cc1ccc(F)cc1] |

TABLE A-continued
| Compound Number | Structure |
|---|---|
| 527 | 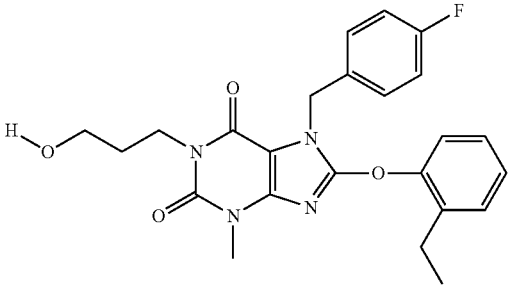 [SMILES: CCc1ccccc1Oc1nc2c(c(=O)n(CCCO)c(=O)n2C)n1Cc1ccc(F)cc1] |
| 528 | 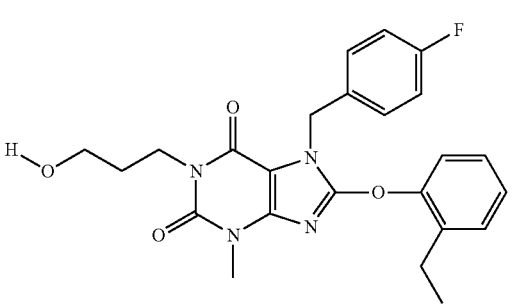 |
| 529 | 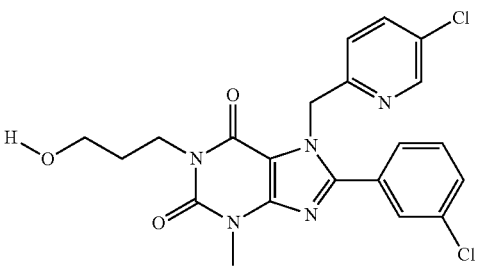 [SMILES: Cn1c(=O)n(CCCO)c(=O)c2c1nc(-c1cccc(Cl)c1)n2Cc1ccc(Cl)cn1] |
| 530 | 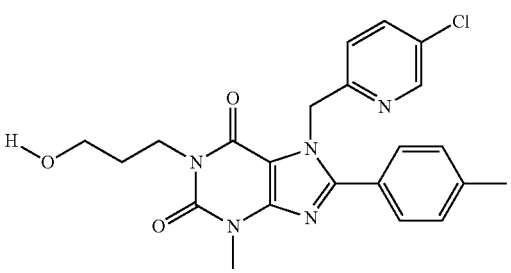 |
| 531 | 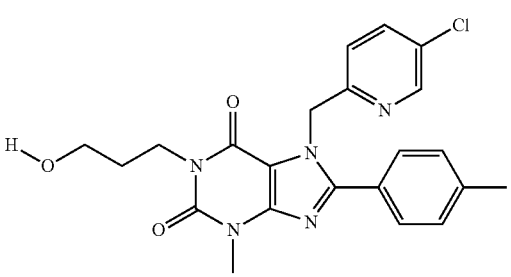 [SMILES: Cc1ccc(-c2nc3c(c(=O)n(CCCO)c(=O)n3C)n2Cc2ccc(Cl)cn2)cc1] |

TABLE A-continued
| Compound Number | Structure |
|---|---|
| 532 | 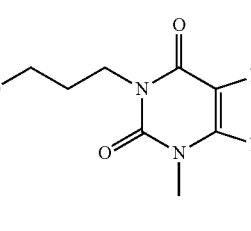 |
| 533 | 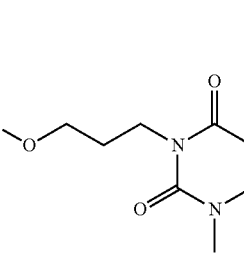 |
| 534 | 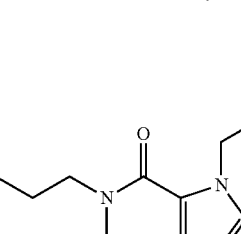 |
| 535 | 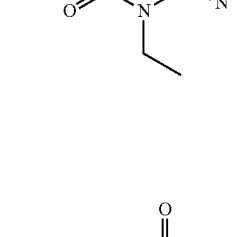 |
| 536 | 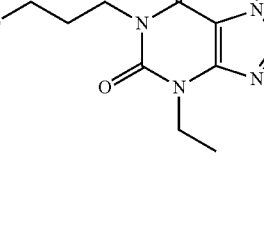 |

TABLE A-continued
| Compound Number | Structure |
|---|---|
| 537 | 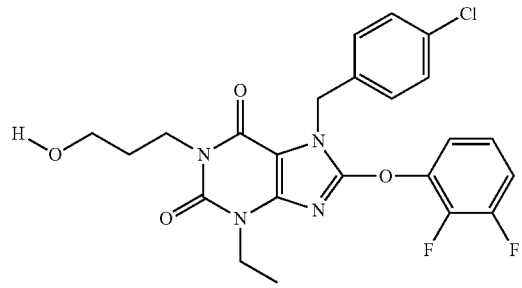 [SMILES: CCn1c(=O)n(CCCO)c(=O)c2c1nc(Oc1cccc(F)c1F)n2Cc1ccc(Cl)cc1] |
| 538 | 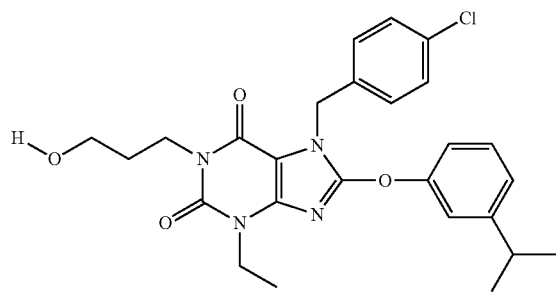 [SMILES: CCn1c(=O)n(CCCO)c(=O)c2c1nc(Oc1cccc(C(C)C)c1)n2Cc1ccc(Cl)cc1] |
| 539 | 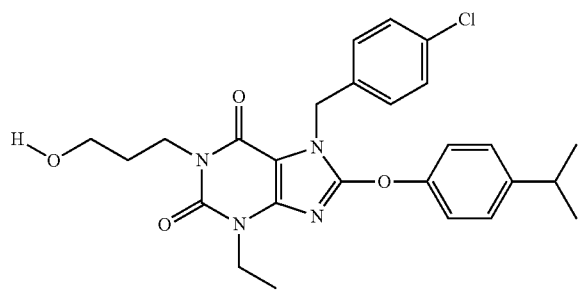 [SMILES: CCn1c(=O)n(CCCO)c(=O)c2c1nc(Oc1ccc(C(C)C)cc1)n2Cc1ccc(Cl)cc1] |
| 540 | 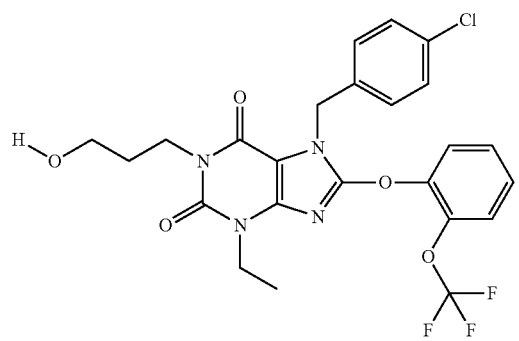 [SMILES: CCn1c(=O)n(CCCO)c(=O)c2c1nc(Oc1ccccc1OC(F)(F)F)n2Cc1ccc(Cl)cc1] |
| 541 | 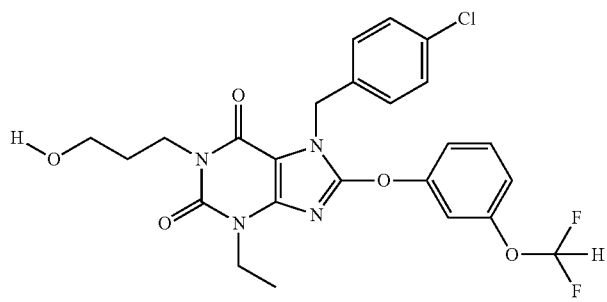 [SMILES: CCn1c(=O)n(CCCO)c(=O)c2c1nc(Oc1cccc(OC(F)F)c1)n2Cc1ccc(Cl)cc1] |

TABLE A-continued
| Compound Number | Structure |
|---|---|
| 542 | 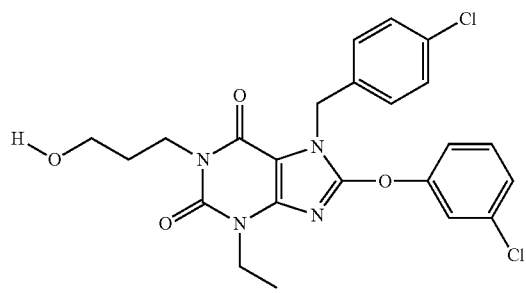 [SMILES: CCn1c(=O)n(CCCO)c(=O)c2c1nc(Oc1cccc(Cl)c1)n2Cc1ccc(Cl)cc1] |
| 543 | 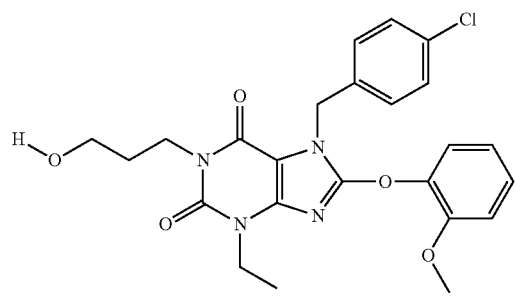 [SMILES: CCn1c(=O)n(CCCO)c(=O)c2c1nc(Oc1ccccc1OC)n2Cc1ccc(Cl)cc1] |
| 544 | 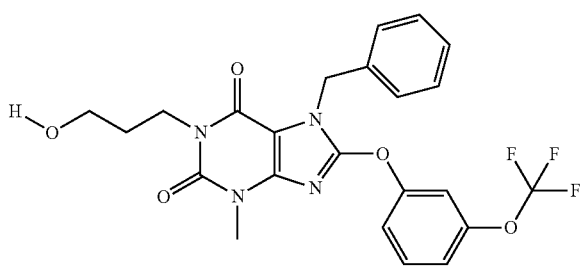 [SMILES: Cn1c(=O)n(CCCO)c(=O)c2c1nc(Oc1cccc(OC(F)(F)F)c1)n2Cc1ccccc1] |
| 545 | 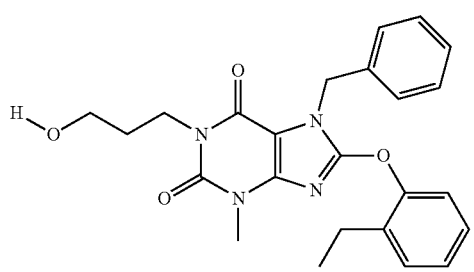 [SMILES: CCc1ccccc1Oc1nc2c(c(=O)n(CCCO)c(=O)n2C)n1Cc1ccccc1] |
| 546 | 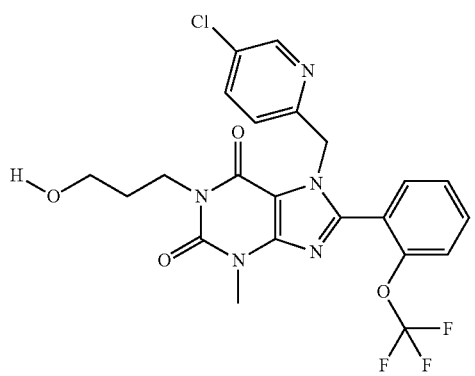 [SMILES: Cn1c(=O)n(CCCO)c(=O)c2c1nc(-c1ccccc1OC(F)(F)F)n2Cc1ccc(Cl)cn1] |

TABLE A-continued
| Compound Number | Structure |
|---|---|
| 547 | 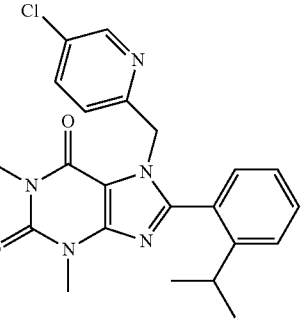 |
| 548 | 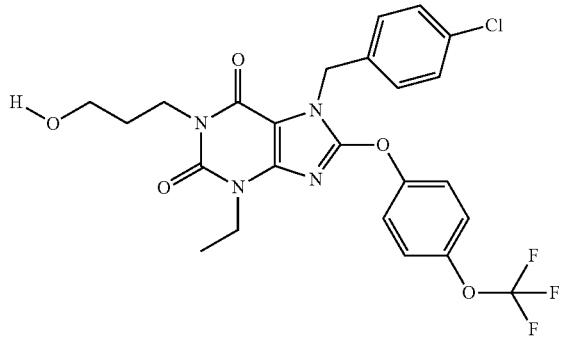 [SMILES: CCn1c(=O)n(CCCO)c(=O)c2c1nc(Oc1ccc(OC(F)(F)F)cc1)n2Cc1ccc(Cl)cc1] |
| 549 | 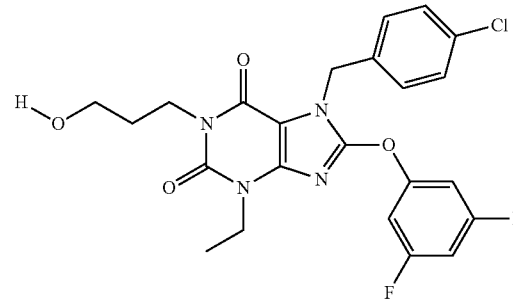 |
| 550 | 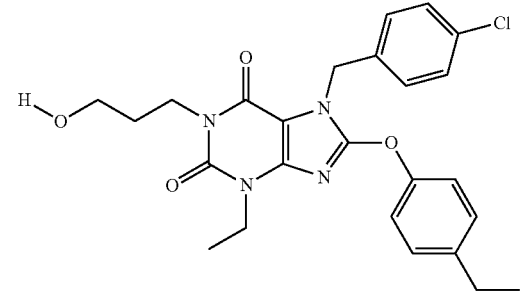 [SMILES: CCc1ccc(Oc2nc3c(c(=O)n(CCCO)c(=O)n3CC)n2Cc2ccc(Cl)cc2)cc1] |

TABLE A-continued
| Compound Number | Structure |
|---|---|
| 551 | 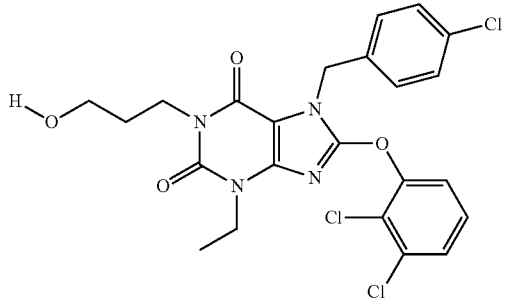 [SMILES: CCn1c(=O)n(CCCO)c(=O)c2c1nc(Oc1cccc(Cl)c1Cl)n2Cc1ccc(Cl)cc1] |
| 552 | 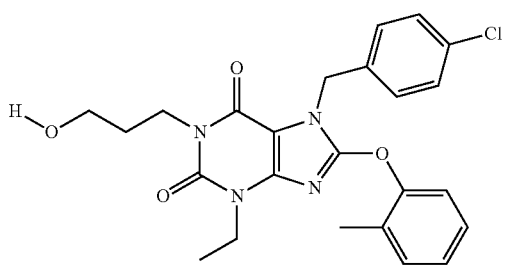 [SMILES: CCn1c(=O)n(CCCO)c(=O)c2c1nc(Oc1ccccc1C)n2Cc1ccc(Cl)cc1] |
| 553 | 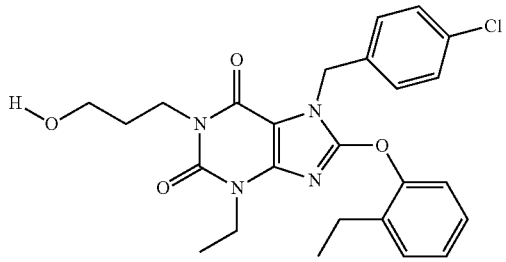 [SMILES: CCc1ccccc1Oc1nc2c(c(=O)n(CCCO)c(=O)n2CC)n1Cc1ccc(Cl)cc1] |
| 554 | 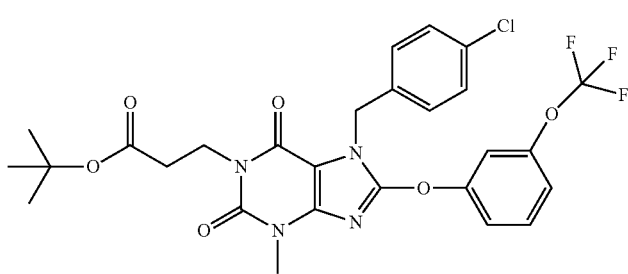 [SMILES: Cn1c(=O)n(CCC(=O)OC(C)(C)C)c(=O)c2c1nc(Oc1cccc(OC(F)(F)F)c1)n2Cc1ccc(Cl)cc1] |
| 555 | 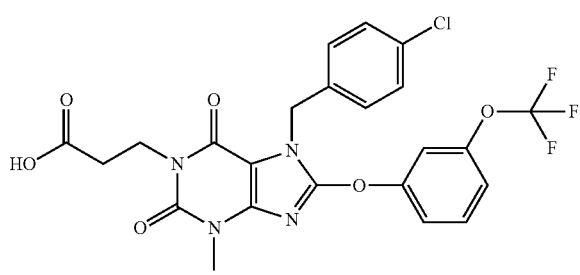 [SMILES: Cn1c(=O)n(CCC(=O)O)c(=O)c2c1nc(Oc1cccc(OC(F)(F)F)c1)n2Cc1ccc(Cl)cc1] |

TABLE A-continued
| Compound Number | Structure |
|---|---|
| 556 | 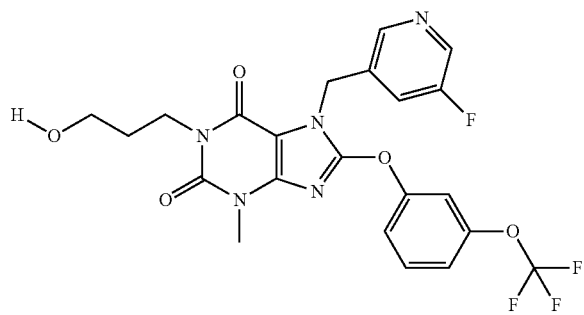 [SMILES: Cn1c(=O)n(CCCO)c(=O)c2c1nc(Oc1cccc(OC(F)(F)F)c1)n2Cc1cncc(F)c1] |
| 557 | 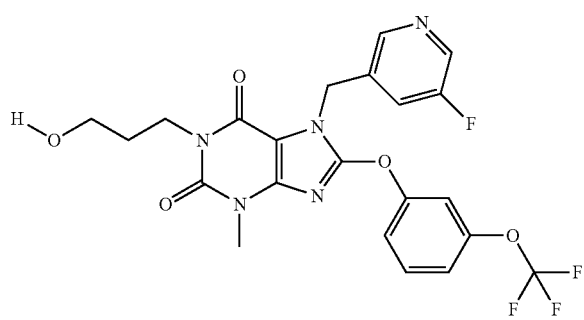 [SMILES: Cn1c(=O)n(CCCO)c(=O)c2c1nc(Oc1cccc(OC(F)(F)F)c1)n2Cc1cncc(F)c1] |
| 558 | 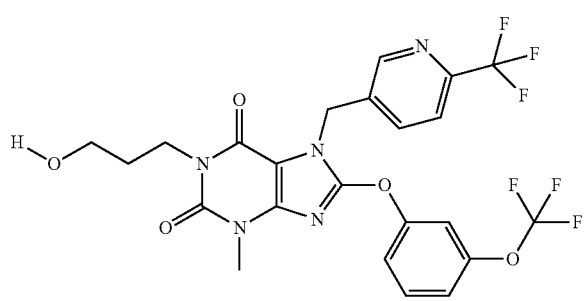 [SMILES: Cn1c(=O)n(CCCO)c(=O)c2c1nc(Oc1cccc(OC(F)(F)F)c1)n2Cc1ccc(C(F)(F)F)nc1] |
| 559 | 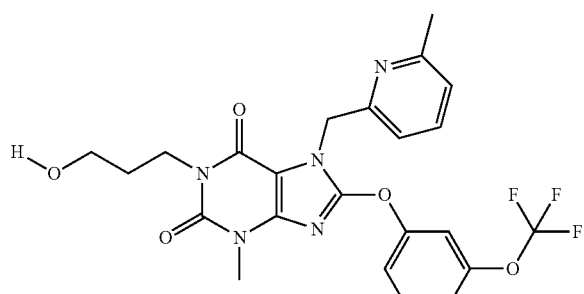 |
| 560 | 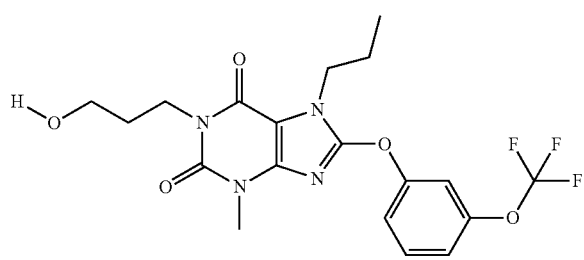 [SMILES: CCCn1c(Oc2cccc(OC(F)(F)F)c2)nc2c1c(=O)n(CCCO)c(=O)n2C] |

TABLE A-continued
| Compound Number | Structure |
|---|---|
| 561 | 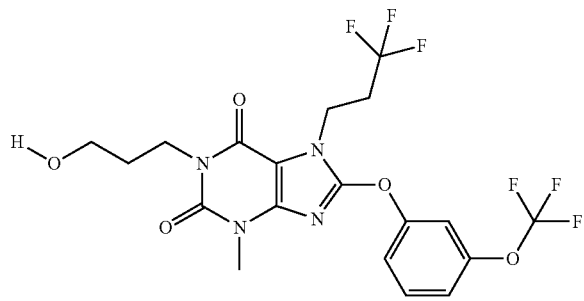 [SMILES: Cn1c(=O)n(CCCO)c(=O)c2c1nc(Oc1cccc(OC(F)(F)F)c1)n2CCC(F)(F)F] |
| 562 | 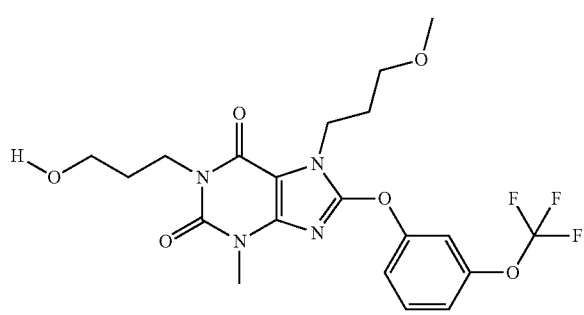 [SMILES: COCCCn1c(Oc2cccc(OC(F)(F)F)c2)nc2c1c(=O)n(CCCO)c(=O)n2C] |
| 563 | 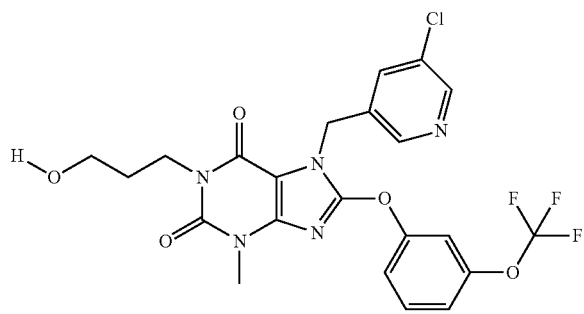 [SMILES: Cn1c(=O)n(CCCO)c(=O)c2c1nc(Oc1cccc(OC(F)(F)F)c1)n2Cc1cncc(Cl)c1] |
| 564 | 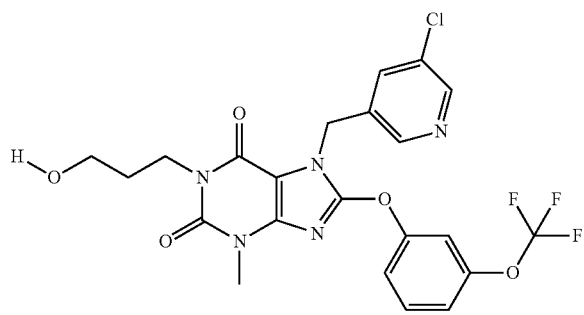 [SMILES: Cn1c(=O)n(CCCO)c(=O)c2c1nc(Oc1cccc(OC(F)(F)F)c1)n2Cc1cncc(Cl)c1] |
| 565 | 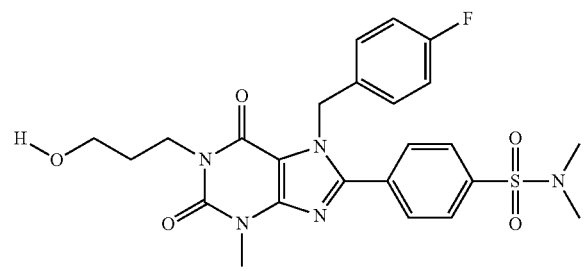 [SMILES: CN(C)S(=O)(=O)c1ccc(-c2nc3c(c(=O)n(CCCO)c(=O)n3C)n2Cc2ccc(F)cc2)cc1] |

TABLE A-continued

| Compound Number | Structure |
|---|---|
| 566 | 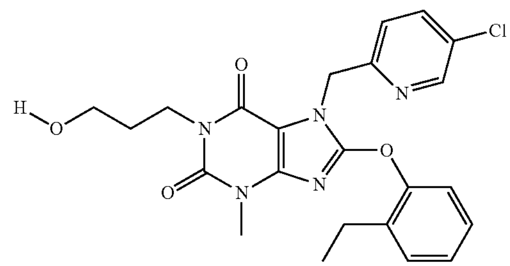 [SMILES: CCc1ccccc1Oc1nc2c(c(=O)n(CCCO)c(=O)n2C)n1Cc1ccc(Cl)cn1] |
| 567 | 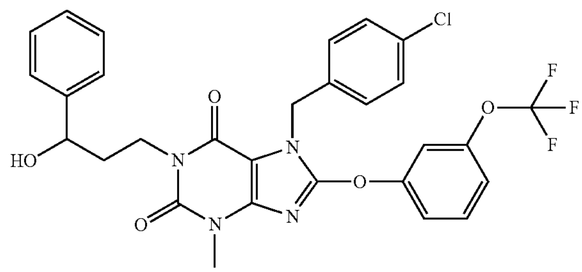 [SMILES: Cn1c(=O)n(CCC(O)c2ccccc2)c(=O)c2c1nc(Oc1cccc(OC(F)(F)F)c1)n2Cc1ccc(Cl)cc1] |
| 568 | 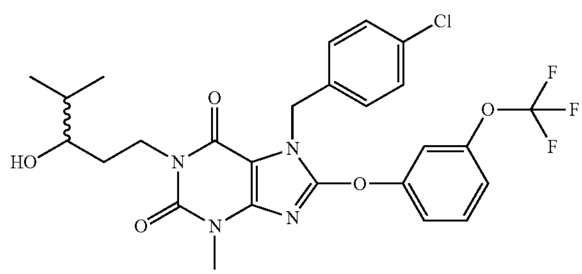 [SMILES: CC(C)C(O)CCn1c(=O)c2c(nc(Oc3cccc(OC(F)(F)F)c3)n2Cc2ccc(Cl)cc2)n(C)c1=O] |
| 569 | 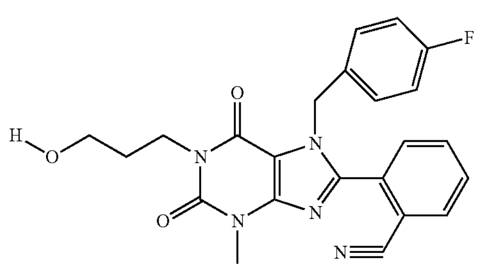 [SMILES: Cn1c(=O)n(CCCO)c(=O)c2c1nc(-c1ccccc1C#N)n2Cc1ccc(F)cc1] |
| 570 | 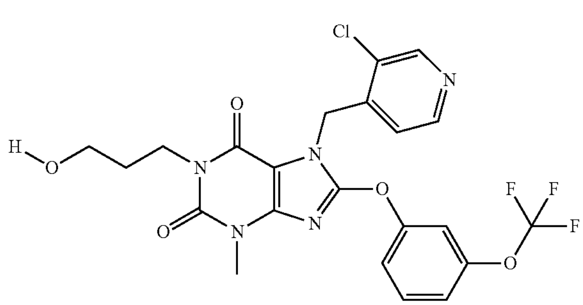 [SMILES: Cn1c(=O)n(CCCO)c(=O)c2c1nc(Oc1cccc(OC(F)(F)F)c1)n2Cc1ccncc1Cl] |

TABLE A-continued

| Compound Number | Structure |
|---|---|
| 571 | (structure) |
| 572 | (structure) |
| 573 | (structure) |
| 574 | (structure) |
| 575 | (structure) |
| 576 | (structure) |

TABLE A-continued
| Compound Number | Structure |
|---|---|
| 577 | 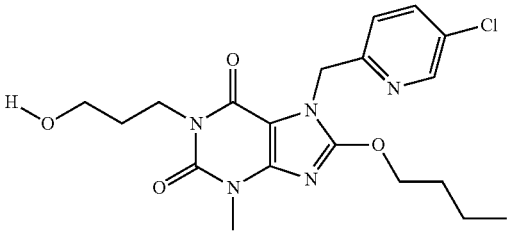 [SMILES: CCCCOc1nc2c(c(=O)n(CCCO)c(=O)n2C)n1Cc1ccc(Cl)cn1] |
| 578 | 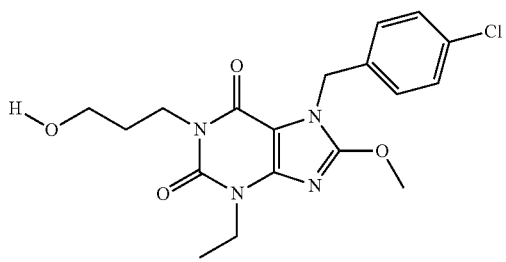 [SMILES: CCn1c(=O)n(CCCO)c(=O)c2c1nc(OC)n2Cc1ccc(Cl)cc1] |
| 579 | 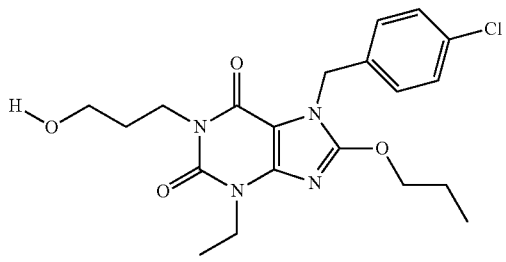 [SMILES: CCCOc1nc2c(c(=O)n(CCCO)c(=O)n2CC)n1Cc1ccc(Cl)cc1] |
| 580 | 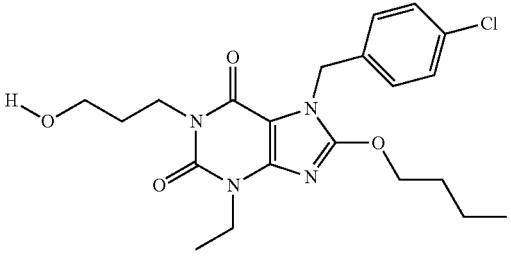 [SMILES: CCCCOc1nc2c(c(=O)n(CCCO)c(=O)n2CC)n1Cc1ccc(Cl)cc1] |
| 581 | 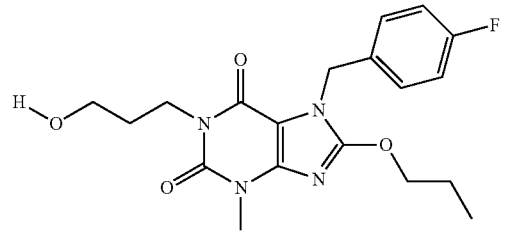 |
| 582 | 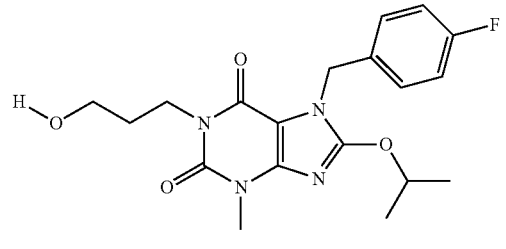 [SMILES: CC(C)Oc1nc2c(c(=O)n(CCCO)c(=O)n2C)n1Cc1ccc(F)cc1] |

TABLE A-continued

| Compound Number | Structure |
|---|---|
| 583 | 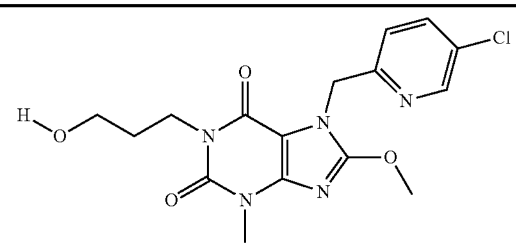 |
| 584 | 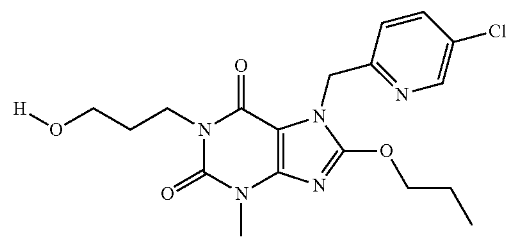 [SMILES: CCCOc1nc2c(c(=O)n(CCCO)c(=O)n2C)n1Cc1ccc(Cl)cn1] |
| 585 | 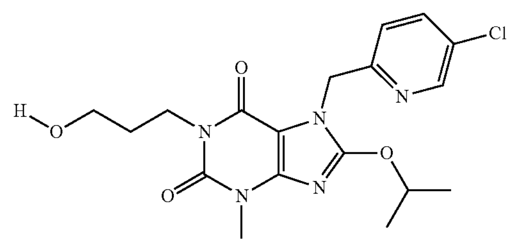 [SMILES: CC(C)Oc1nc2c(c(=O)n(CCCO)c(=O)n2C)n1Cc1ccc(Cl)cn1] |
| 586 | 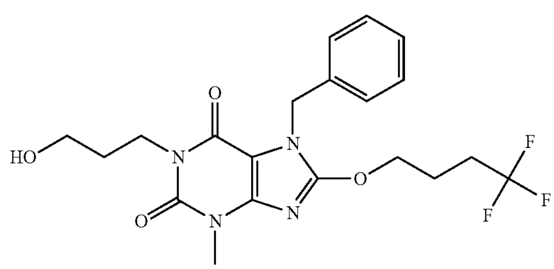 [SMILES: Cn1c(=O)n(CCCO)c(=O)c2c1nc(OCCCC(F)(F)F)n2Cc1ccccc1] |
| 587 | 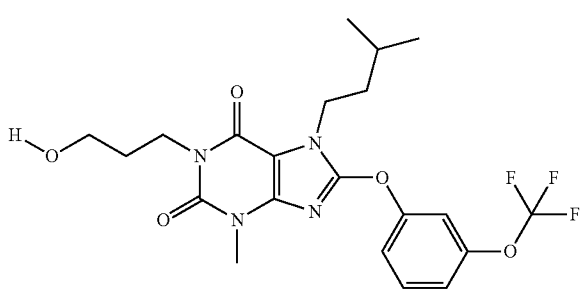 [SMILES: CC(C)CCn1c(Oc2cccc(OC(F)(F)F)c2)nc2c1c(=O)n(CCCO)c(=O)n2C] |
| 588 | 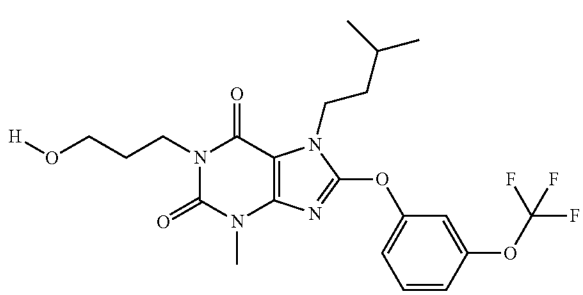 [SMILES: CC(C)CCn1c(Oc2cccc(OC(F)(F)F)c2)nc2c1c(=O)n(CCCO)c(=O)n2C] |

TABLE A-continued

| Compound Number | Structure |
|---|---|
| 589 | 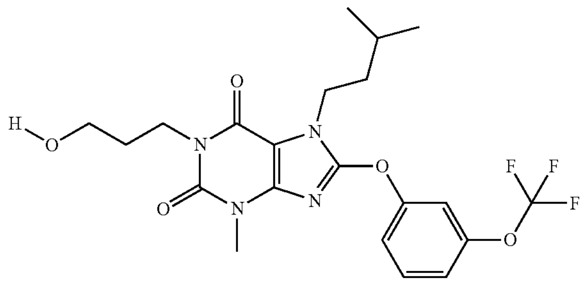 [SMILES: CC(C)CCn1c(Oc2cccc(OC(F)(F)F)c2)nc2c1c(=O)n(CCCO)c(=O)n2C] |
| 590 | 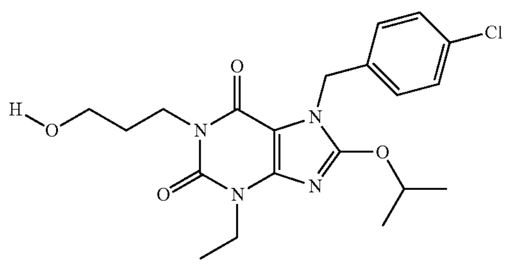 [SMILES: CCn1c(=O)n(CCCO)c(=O)c2c1nc(OC(C)C)n2Cc1ccc(Cl)cc1] |
| 591 | 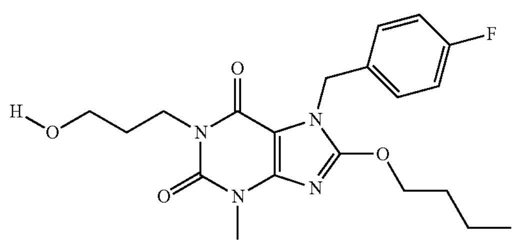 [SMILES: CCCCOc1nc2c(c(=O)n(CCCO)c(=O)n2C)n1Cc1ccc(F)cc1] |
| 592 | 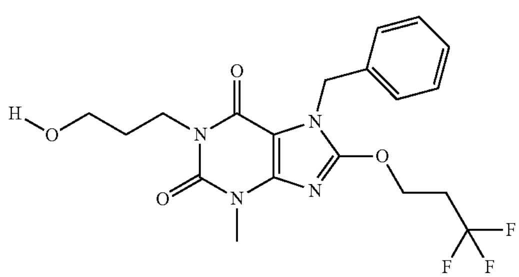 [SMILES: Cn1c(=O)n(CCCO)c(=O)c2c1nc(OCCC(F)(F)F)n2Cc1ccccc1] |
| 593 | 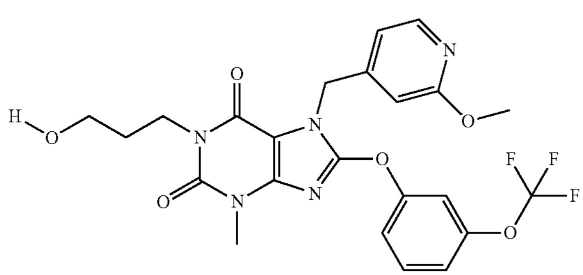 [SMILES: COc1cc(Cn2c(Oc3cccc(OC(F)(F)F)c3)nc3c2c(=O)n(CCCO)c(=O)n3C)ccn1] |

TABLE A-continued

| Compound Number | Structure |
|---|---|
| 594 | (structure) |
| 595 | (structure) |
| 596 | (structure) |
| 597 | (structure) |
| 598 | (structure) |
| 599 | (structure) |

TABLE A-continued
| Compound Number | Structure |
|---|---|
| 600 | 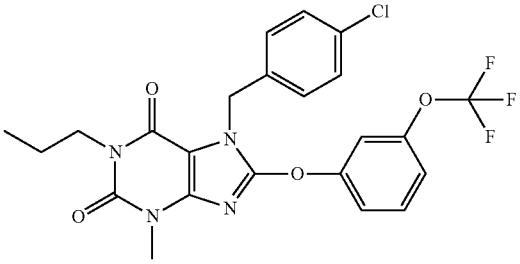 [SMILES: CCCn1c(=O)c2c(nc(Oc3cccc(OC(F)(F)F)c3)n2Cc2ccc(Cl)cc2)n(C)c1=O] |
| 601 | 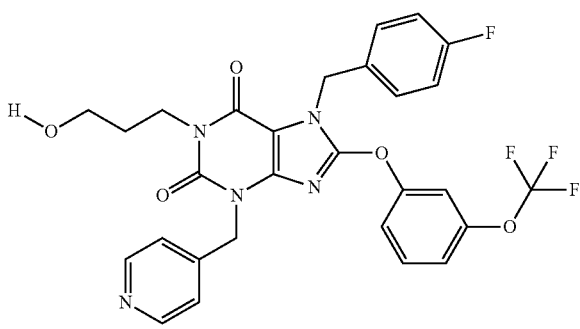 [SMILES: O=c1c2c(nc(Oc3cccc(OC(F)(F)F)c3)n2Cc2ccc(F)cc2)n(Cc2ccncc2)c(=O)n1CCCO] |
| 602 | 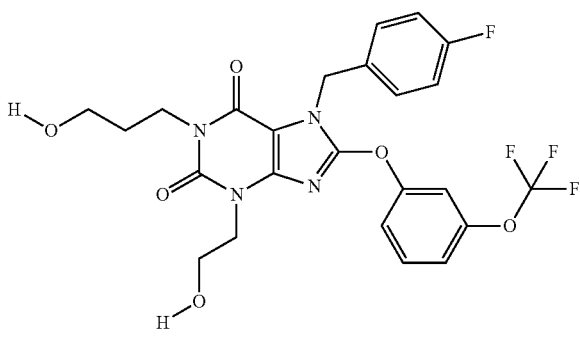 [SMILES: O=c1c2c(nc(Oc3cccc(OC(F)(F)F)c3)n2Cc2ccc(F)cc2)n(CCO)c(=O)n1CCCO] |
| 603 | 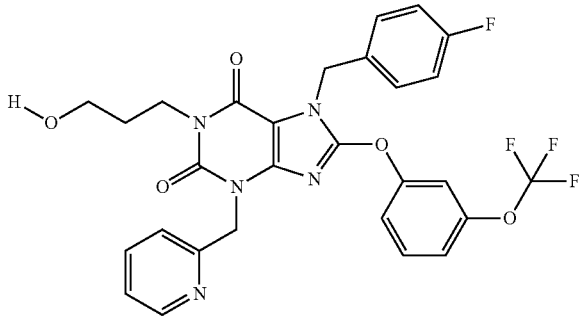 |
| 604 | 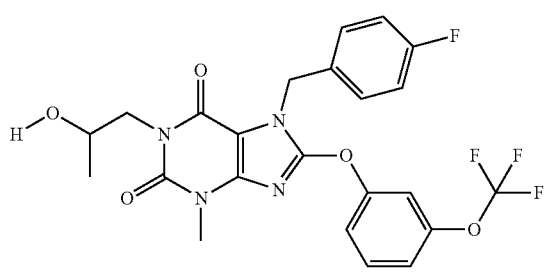 [SMILES: CC(O)Cn1c(=O)c2c(nc(Oc3cccc(OC(F)(F)F)c3)n2Cc2ccc(F)cc2)n(C)c1=O] |

247
TABLE A-continued
| Compound Number | Structure |
|---|---|
| 605 | 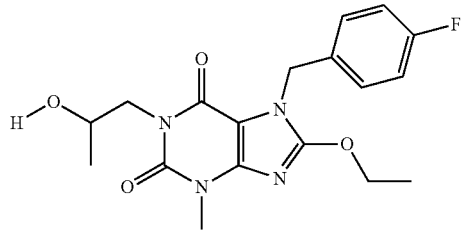 [SMILES: CCOc1nc2c(c(=O)n(CC(C)O)c(=O)n2C)n1Cc1ccc(F)cc1] |
| 606 | 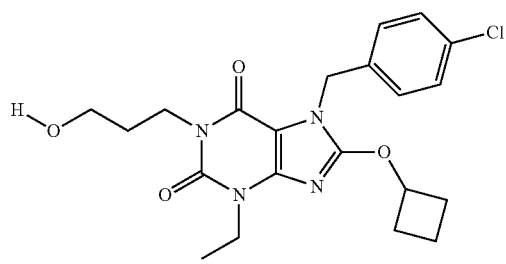 [SMILES: CCn1c(=O)n(CCCO)c(=O)c2c1nc(OC1CCC1)n2Cc1ccc(Cl)cc1] |
| 607 | 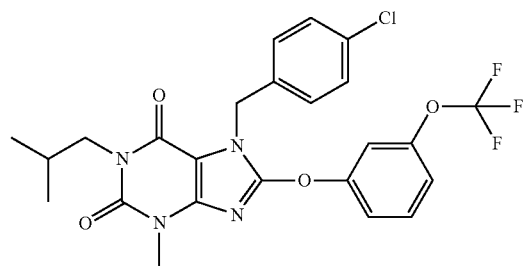 [SMILES: CC(C)Cn1c(=O)c2c(nc(Oc3cccc(OC(F)(F)F)c3)n2Cc2ccc(Cl)cc2)n(C)c1=O] |
| 608 | 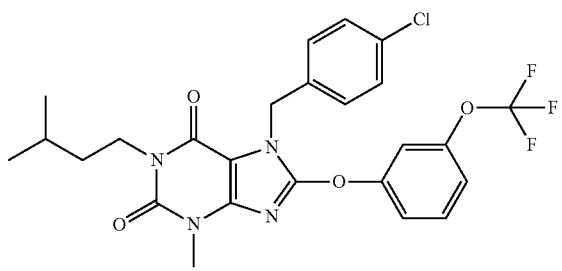 [SMILES: CC(C)CCn1c(=O)c2c(nc(Oc3cccc(OC(F)(F)F)c3)n2Cc2ccc(Cl)cc2)n(C)c1=O] |
| 609 | 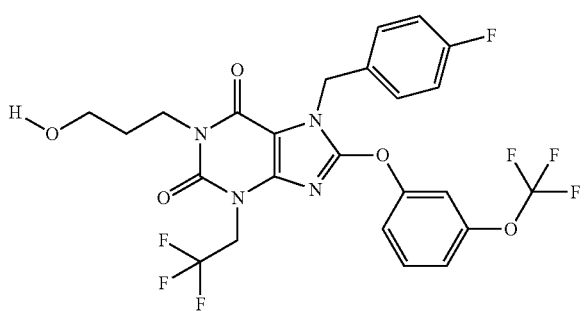 [SMILES: O=c1c2c(nc(Oc3cccc(OC(F)(F)F)c3)n2Cc2ccc(F)cc2)n(CC(F)(F)F)c(=O)n1CCCO] |

TABLE A-continued
| Compound Number | Structure |
|---|---|
| 610 | 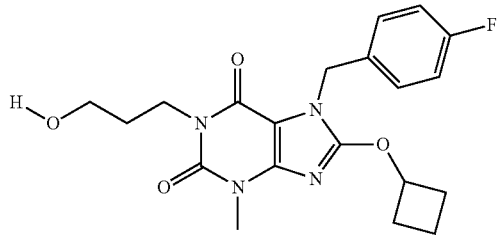 [SMILES: Cn1c(=O)n(CCCO)c(=O)c2c1nc(OC1CCC1)n2Cc1ccc(F)cc1] |
| 611 | 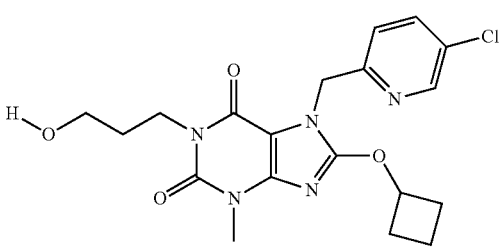 [SMILES: Cn1c(=O)n(CCCO)c(=O)c2c1nc(OC1CCC1)n2Cc1ccc(Cl)cn1] |
| 612 | 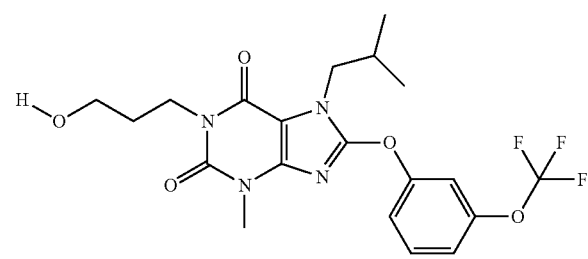 [SMILES: CC(C)Cn1c(Oc2cccc(OC(F)(F)F)c2)nc2c1c(=O)n(CCCO)c(=O)n2C] |
| 613 | 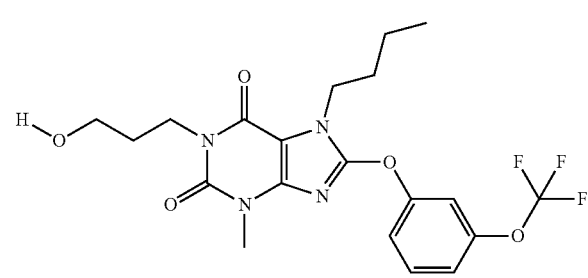 |
| 614 | 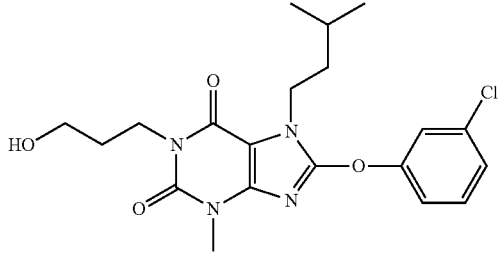 [SMILES: CC(C)CCn1c(Oc2cccc(Cl)c2)nc2c1c(=O)n(CCCO)c(=O)n2C] |

TABLE A-continued

| Compound Number | Structure |
|---|---|
| 615 | 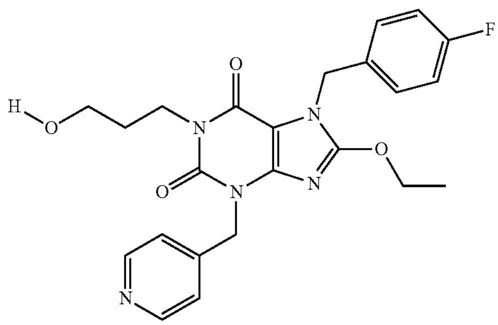 [SMILES: CCOc1nc2c(c(=O)n(CCCO)c(=O)n2Cc2ccncc2)n1Cc1ccc(F)cc1] |
| 616 | 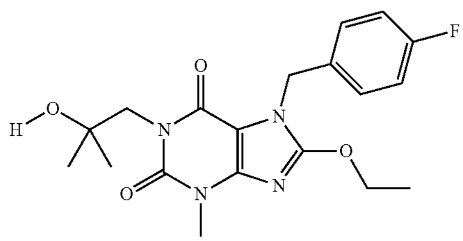 [SMILES: CCOc1nc2c(c(=O)n(CC(C)(C)O)c(=O)n2C)n1Cc1ccc(F)cc1] |
| 617 | 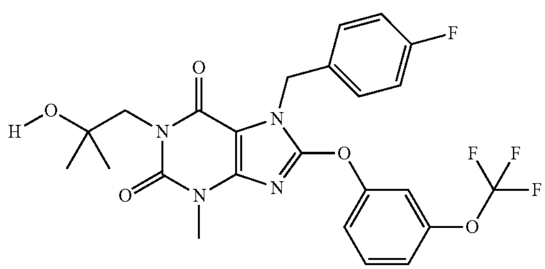 [SMILES: Cn1c(=O)n(CC(C)(C)O)c(=O)c2c1nc(Oc1cccc(OC(F)(F)F)c1)n2Cc1ccc(F)cc1] |
| 618 | 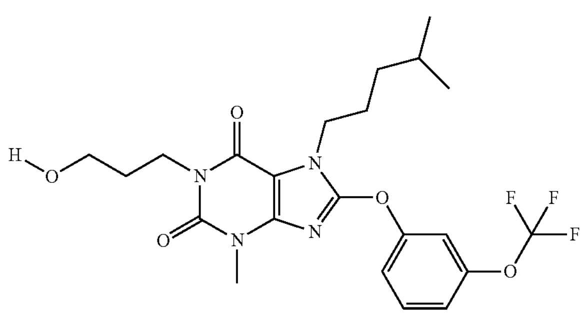 [SMILES: CC(C)CCCn1c(Oc2cccc(OC(F)(F)F)c2)nc2c1c(=O)n(CCCO)c(=O)n2C] |
| 619 | 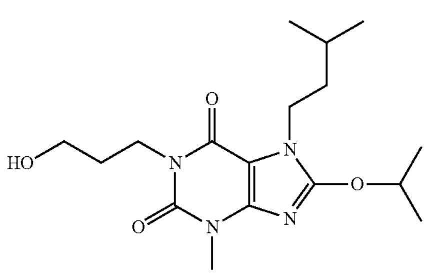 [SMILES: CC(C)CCn1c(OC(C)C)nc2c1c(=O)n(CCCO)c(=O)n2C] |

TABLE A-continued
| Compound Number | Structure |
|---|---|
| 620 | 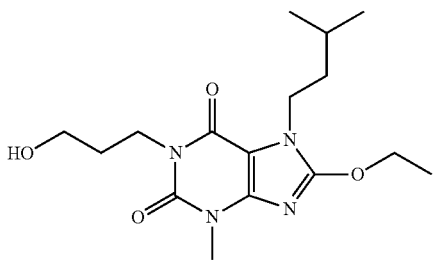 [SMILES: CCOc1nc2c(c(=O)n(CCCO)c(=O)n2C)n1CCC(C)C] |
| 621 | 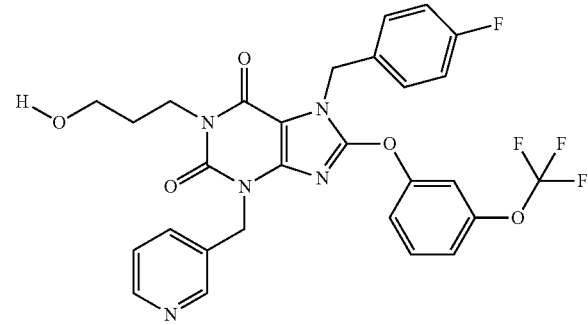 [SMILES: O=c1c2c(nc(Oc3cccc(OC(F)(F)F)c3)n2Cc2ccc(F)cc2)n(Cc2cccnc2)c(=O)n1CCCO] |
| 622 | 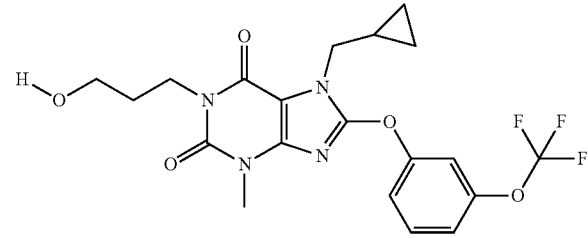 [SMILES: Cn1c(=O)n(CCCO)c(=O)c2c1nc(Oc1cccc(OC(F)(F)F)c1)n2CC1CC1] |
| 623 | 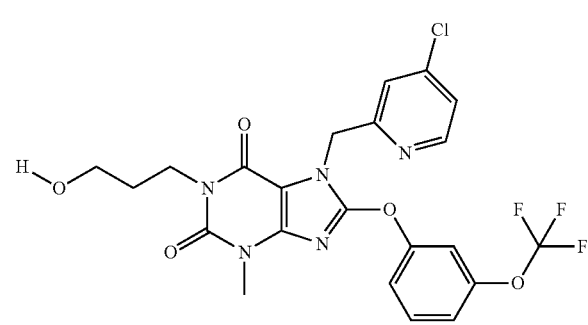 [SMILES: Cn1c(=O)n(CCCO)c(=O)c2c1nc(Oc1cccc(OC(F)(F)F)c1)n2Cc1cc(Cl)ccn1] |
| 624 | 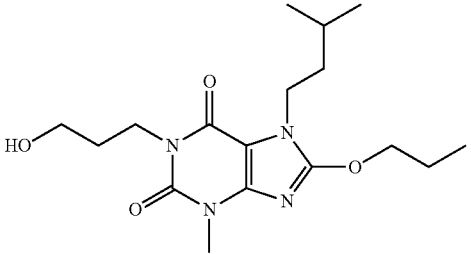 [SMILES: CCCOc1nc2c(c(=O)n(CCCO)c(=O)n2C)n1CCC(C)C] |

TABLE A-continued
| Compound Number | Structure |
|---|---|
| 625 | 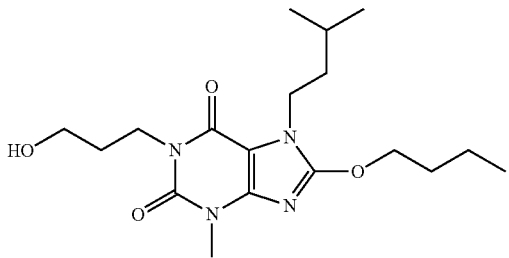 [SMILES: CCCCOc1nc2c(c(=O)n(CCCO)c(=O)n2C)n1CCC(C)C] |
| 626 | 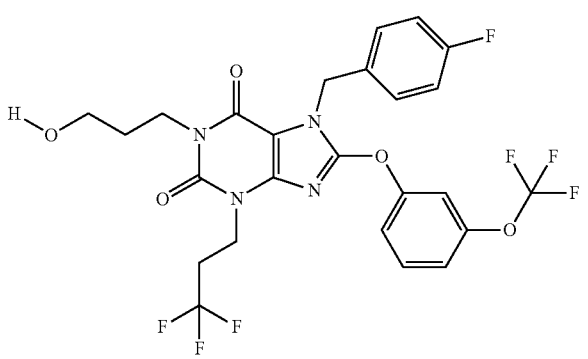 [SMILES: O=c1c2c(nc(Oc3cccc(OC(F)(F)F)c3)n2Cc2ccc(F)cc2)n(CCC(F)(F)F)c(=O)n1CCCO] |
| 627 | 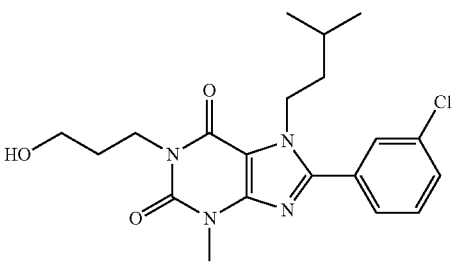 [SMILES: CC(C)CCn1c(-c2cccc(Cl)c2)nc2c1c(=O)n(CCCO)c(=O)n2C] |
| 628 | 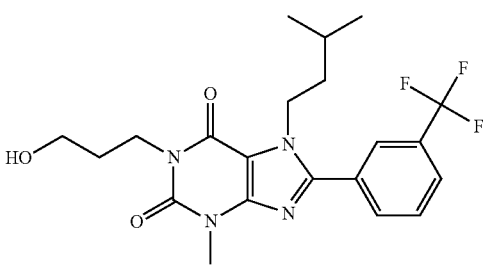 [SMILES: CC(C)CCn1c(-c2cccc(C(F)(F)F)c2)nc2c1c(=O)n(CCCO)c(=O)n2C] |
| 629 | 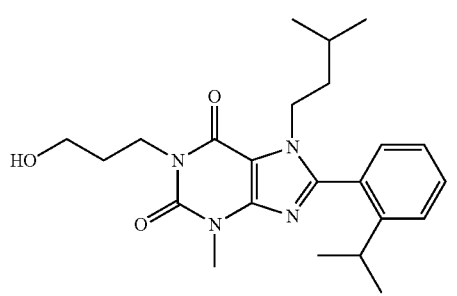 |

TABLE A-continued
| Compound Number | Structure |
|---|---|
| 630 | 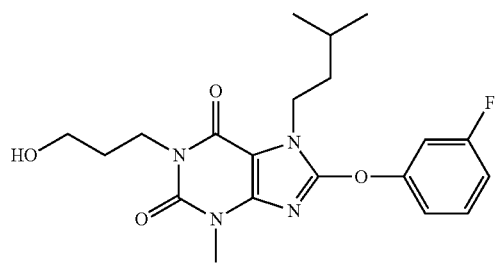 |
| 631 | 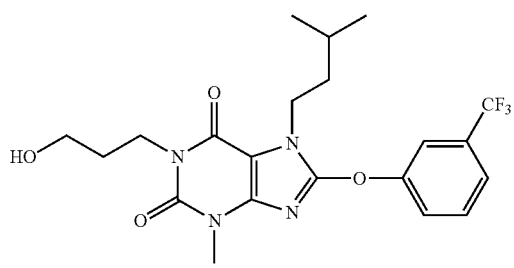 [SMILES: CC(C)CCn1c(Oc2cccc(C(F)(F)F)c2)nc2c1c(=O)n(CCCO)c(=O)n2C] |
| 632 | 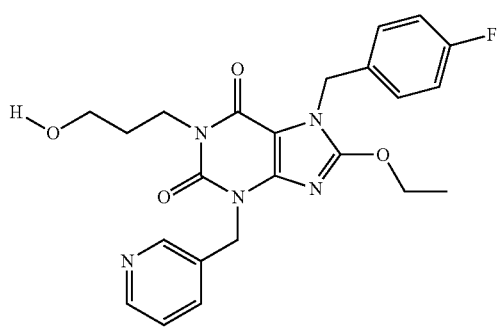 [SMILES: CCOc1nc2c(c(=O)n(CCCO)c(=O)n2Cc2cccnc2)n1Cc1ccc(F)cc1] |
| 633 | 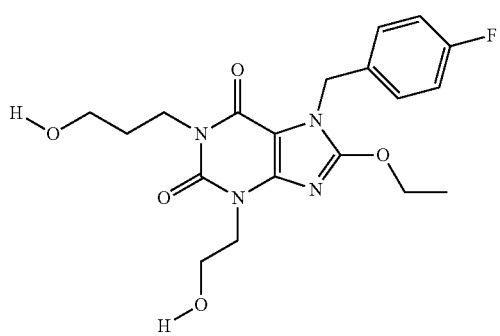 [SMILES: CCOc1nc2c(c(=O)n(CCCO)c(=O)n2CCO)n1Cc1ccc(F)cc1] |
| 634 | 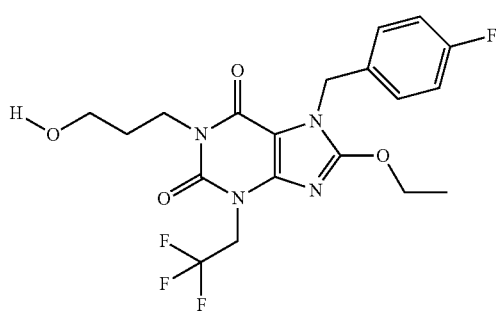 [SMILES: CCOc1nc2c(c(=O)n(CCCO)c(=O)n2CC(F)(F)F)n1Cc1ccc(F)cc1] |

TABLE A-continued

| Compound Number | Structure |
|---|---|
| 635 | 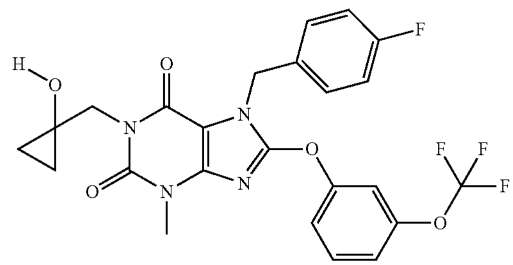 [SMILES: Cn1c(=O)n(CC2(O)CC2)c(=O)c2c1nc(Oc1cccc(OC(F)(F)F)c1)n2Cc1ccc(F)cc1] |
| 636 | 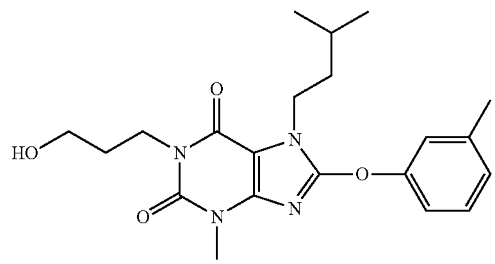 [SMILES: Cc1cccc(Oc2nc3c(c(=O)n(CCCO)c(=O)n3C)n2CCC(C)C)c1] |
| 637 | 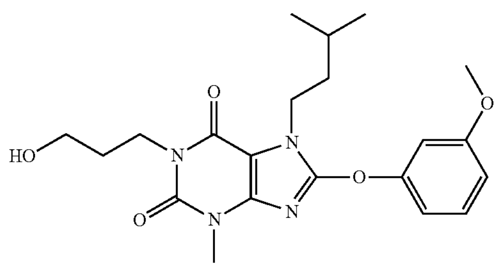 [SMILES: COc1cccc(Oc2nc3c(c(=O)n(CCCO)c(=O)n3C)n2CCC(C)C)c1] |
| 638 | 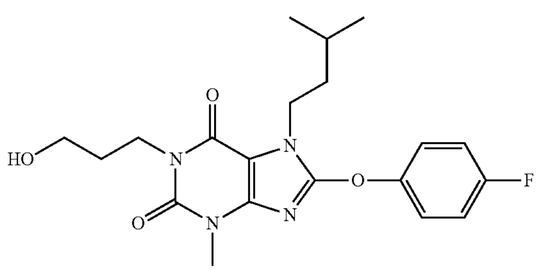 [SMILES: CC(C)CCn1c(Oc2ccc(F)cc2)nc2c1c(=O)n(CCCO)c(=O)n2C] |
| 639 | 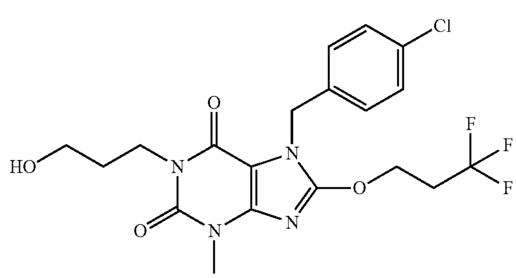 [SMILES: Cn1c(=O)n(CCCO)c(=O)c2c1nc(OCCC(F)(F)F)n2Cc1ccc(Cl)cc1] |

TABLE A-continued
| Compound Number | Structure |
|---|---|
| 640 | 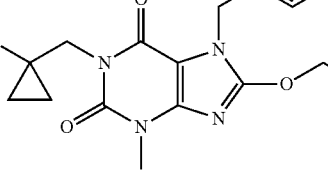 |
| 641 | 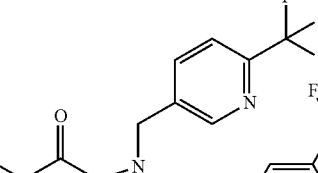 |
| 642 | 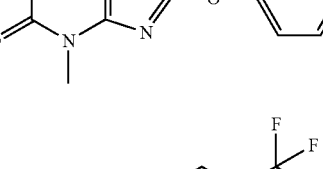 |
| 643 | 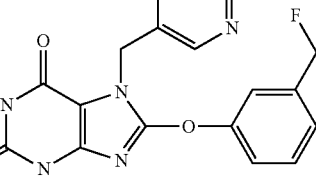 |
| 644 | 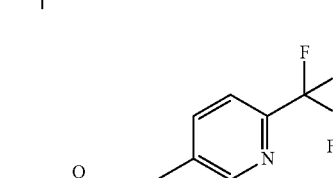 |

TABLE A-continued

| Compound Number | Structure |
|---|---|
| 645 | (structure) |
| 646 | (structure) |
| 647 | (structure) |
| 648 | (structure) |

Definitions

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

For compounds of the invention in which a variable appears more than once, each variable can be a different moiety selected from the Markush group defining the variable. For example, where a structure is described having two R groups that are simultaneously present on the same compound; the two R groups can represent different moieties selected from the Markush group defined for R.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, "acyl" refers to the group ($C_1$-$C_6$ alkyl)-C(O)—.

As used herein, "alkyl," by itself or as part of another substituent, means, unless otherwise stated, a straight or branched chain, and can have a number of carbon atoms optionally designated (i.e., $C_1$-$C_6$ means one to six carbons). Examples of saturated hydrocarbon groups include, but are not limited to, groups such as methyl, ethyl, n-propyl, isopropyl, n-butyl, t-butyl, isobutyl, sec-butyl, n-pentyl, isopentyl, homologs and isomers of, for example, n-pentyl, n-hexyl, and the like.

As used herein, "alkenyl" can be a straight or branched hydrocarbon chain, containing at least one double bond, and having from two to six carbon atoms (i.e. $C_2$-$C_6$ alkenyl). Examples of alkenyl groups, include, but are not limited to, groups such as ethenyl (i.e., vinyl), prop-1-enyl (i.e., allyl), but-1-enyl, pent-1-enyl, penta-1,4-dienyl, and the like.

As used herein, "alkoxy" can be a straight chain or branched alkoxy group having from one to six carbon atoms (i.e., $C_1$-$C_6$ alkoxy). Examples of alkoxy groups, include, but are not limited to, groups such as methoxy, ethoxy, propyloxy, isopropyloxy, butyloxy, isobutyloxy, tert-butyloxy, pentyloxy, or hexyloxy, and the like.

As used herein, "alkynyl" can be a straight or branched hydrocarbon chain, containing at least one triple bond, having from two to six carbon atoms (i.e. $C_2$-$C_6$ alkynyl). Examples of alkynyl groups, include, but are not limited to, groups such as ethynyl, propynyl, butynyl, pentynyl, hexynyl, and the like.

As used herein, "amide" or "amido" refers to a chemical moiety with the formula —C(O)NR$^a$— or —NR$^a$C(O)— wherein R$^a$ is H or $C_1$-$C_6$ alkyl.

As used herein, "amino" or "amine" refers to a —NH$_2$ radical group.

As used herein, "alkylamino" refers to a group of formula —NH(alkyl), wherein the alkyl group each has 1 to 6 carbons.

As used herein, the term "dialkylamino" refers to a group of formula —N(alkyl)$_2$, wherein the two alkyl groups each independently has, 1 to 6 carbons.

As used herein, "aryl" refers to a polyunsaturated, aromatic, hydrocarbon moiety which can be a single ring or multiple rings (e.g., 1 to 2 rings) which are fused together or linked covalently, having from six to twelve carbon atoms (i.e. $C_6$-$C_{12}$ aryl). Non-limiting examples of aryl groups include phenyl, 1-naphthyl, 2-naphthyl, and 4-biphenyl.

As used herein, "arylalkyl" refers to an (aryl)alkyl- radical wherein aryl and alkyl moieties are as disclosed herein.

As used herein, "aryloxy" refers to —O-(aryl), wherein the heteroaryl moiety is as defined herein.

As used herein, "arylalkoxy" refers to —O-(arylalkyl), wherein the heteroaryl moiety is as defined herein.

As used herein, "carboxyl" refers to a —(C=O)OH radical.

As used herein, "cyano" refers to a —CN radical.

As used herein, "cycloalkyl" refers to a monocyclic or polycyclic radical that contains only carbon and hydrogen, and may be saturated, or partially unsaturated. Cycloalkyl groups include groups having from 3 to 10 ring atoms (i.e. $C_3$-$C_{10}$ cycloalkyl). Examples of cycloalkyl groups include, but are not limited to, groups such as cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like.

As used herein, "$C_3$-$C_7$ cycloalkyloxy" refers to —O—($C_3$-$C_7$ cycloalkyl), wherein the $C_3$-$C_7$cycloalkyl moiety is as defined herein.

As used herein, "halo" or "halogen," independently or as part of another substituent, mean, unless otherwise stated, a fluorine, chlorine, bromine, or iodine atom. The term "halide" by itself or as part of another substituent, refers to a fluoride, chloride, bromide, or iodide atom.

As used herein, "haloalkyl" and "haloalkoxy" can include alkyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

As used herein, "heteroalkyl" can include an optionally substituted alkyl, which has one or more skeletal chain atoms selected from an atom other than carbon, e.g., oxygen, nitrogen, sulfur, phosphorus or combinations thereof. A numerical range may be given, e.g. $C_1$-$C_6$ heteroalkyl which refers to the number of carbons in the chain, which in this example includes 1 to 6 carbon atoms. For example, a —CH$_2$OCH$_2$CH$_3$ radical is referred to as a "$C_3$" heteroalkyl. Connection to the rest of the molecule may be through either a heteroatom or a carbon in the heteroalkyl chain.

As used herein, "heteroaryl" refers to a 5- to 14-membered aromatic radical (e.g., $C_2$-$C_{13}$ heteroaryl) that includes one or more ring heteroatoms selected from nitrogen, oxygen and sulfur, and which may be a monocyclic or bicyclic ring system. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. An N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryl groups include without limitation, pyridyl, pyrimidinyl, pyrazinyl, pyridazinyl, triazinyl, furyl (furanyl), quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like.

As used herein, "heteroaryloxy" refers to —O-(heteroaryl), wherein the heteroaryl moiety is as defined herein.

As used herein, "heterocycloalkyl" can be a stable 3- to 18-membered non-aromatic ring radical that comprises two to twelve carbon atoms and from one to six heteroatoms selected from nitrogen, oxygen and sulfur. Examples of heterocycloalkyl groups include, but are not limited to, groups such as dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, and the like.

As used herein, "hydroxy" or "hydroxyl" refers to —OH.

As used herein, "hydroxyalkyl" refers to an alkyl group having 1 to 6 carbon atoms, which is substituted with a hydroxyl group, e.g., hydroxypropyl.

As used herein, "cyano" refers to —CN.

As used herein, "nitro" refers to —NO$_2$.

As used herein, "urea" refers to —NR$^a$—C(O)—NR$^a{}_2$ or —NR$^a$—C(O)NR$^a$—, wherein R$^a$ is H or C$_1$-C$_6$ alkyl.

As used herein, "sulfonylurea" refers to —S(O)$_2$—NR$^a$—C(O)—NR$^a$— or —NR$^a$—C(O)—NR$^a$—SO$_2$—, wherein R$^a$ is H or C$_1$-C$_6$ alkyl.

As used herein, "sulfonamidyl" refers to —S(O)$_2$—NR$^a$— or —NR$^a$—S(O)$_2$—, wherein R$^a$ is H or C$_1$-C$_6$ alkyl.

The terms "antagonist" and "inhibitor" are used interchangeably to refer to an agent that decreases or suppresses a biological activity, such as to repress an activity of an ion channel, such as TRPC5. TRPC5 ion channels as described herein include homomultimeric and heteromultimeric structures (e.g., homomultimeric TRPC5 and heteromeric TRPC5-TRPC1 or TRPC5-TRPC4). TRPC5 antagonists include inhibitors having any combination of the structural and/or functional properties disclosed herein.

An "effective amount" of, e.g., a TRPC5 antagonist, with respect to the subject methods of inhibition or treatment, refers to an amount of the antagonist in a preparation which, when applied as part of a desired dosage regimen brings about a desired clinical or functional result. Without being bound by theory, an effective amount of a TRPC5 antagonist for use in the methods of the present invention includes an amount of a TRPC5 antagonist effective to decrease one or more in vitro or in vivo function of a TRPC5 channel. Exemplary functions include, but are not limited to, membrane polarization (e.g., an antagonist may promote hyperpolarization of a cell), ion flux, ion concentration in a cell, outward current, and inward current. Compounds that antagonize TRPC5 function include compounds that antagonize an in vitro or in vivo functional activity of TRPC5. When a particular functional activity is only readily observable in an in vitro assay, the ability of a compound to inhibit TRPC5 function in that in vitro assay serves as a reasonable proxy for the activity of that compound. In certain embodiments, an effective amount is an amount sufficient to inhibit a TRPC5-mediated current and/or the amount sufficient to inhibit TRPC5 mediated ion flux.

The TRPC5 antagonists for use in the methods of the present invention may be characterized according to their activity, or lack of activity, against one or more other ion channels. When other ion channels are referred to, inhibition of a function of such other ion channels is defined similarly. For example, inhibition of an ion channel or an activity of an ion channel means the antagonist inhibits one or more functional activities of the other ion channel. Such functions include the current mediated by the particular ion channel, ion flux, or membrane polarization.

The term "preventing" is art-recognized, and when used in relation to a condition, such as a local recurrence, a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "prodrug" is intended to encompass compounds that, under physiological conditions, are converted into the therapeutically active agents of the present invention. A common method for making a prodrug is to include selected moieties that are hydrolyzed under physiological conditions to reveal the desired molecule. In other embodiments, the prodrug is converted by an enzymatic activity of the host animal.

The term "small molecule" refers to a compound having a molecular weight less than about 2500 amu, preferably less than about 2000 amu, even more preferably less than about 1500 amu, still more preferably less than about 1000 amu, or most preferably less than about 750 amu.

The terms "TRPC5", "TRPC5 protein", and "TRPC5 channel" are used interchangeably throughout the application. Unless expressly stated, the term TRPC5 includes homomultimeric structures (e.g., homomultimeric TRPC5) and heteromultimeric structures (e.g., heteromultimeric TRPC5-TRPC1).

The term "oxidative metabolite" is intended to encompass compounds that are produced by metabolism of the parent compound under normal physiological conditions. Specifically, an oxidative metabolite is formed by oxidation of the parent compound during metabolism. For example, a thio-ether group may be oxidized to the corresponding sulfoxide or sulfone.

The term "solvate" as used herein, refers to a compound formed by solvation (e.g., a compound formed by the combination of solvent molecules with molecules or ions of the solute).

The term "hydrate" as used herein, refers to a compound formed by the union of water with the parent compound.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The terms "compound" and "agent" are used interchangeably to refer to the inhibitors/antagonists of the invention. In certain embodiments, the compounds are small organic or inorganic molecules, e.g., with molecular weights less than 7500 amu, preferably less than 5000 amu, and even more preferably less than 2000, 1500, 1000, or 600 amu. Such compounds can bind to and inhibit a function of TRPC5. In certain other embodiments, the compounds are nucleic acids, for example, TRPC5 antisense oligonucleotides or TRPC5 RNAi constructs. Such compounds can inhibit the expression of TRPC5, thereby inhibiting the activity of TRPC5. Other exemplary compounds that may act as inhibitors include ribozymes and peptide fragments.

Contemplated equivalents of the compounds described above include compounds which otherwise correspond thereto, and which have the same general properties thereof (e.g., the ability to antagonize TRPC5 activity), wherein one or more simple variations of substituents are made which do not adversely affect the efficacy of the compound. In general, the compound of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art. Compounds of the invention also include tautomeric forms, such as keto-enol tautomers.

Compounds of the invention can also include all isotopes of atoms occurring in the intermediates or final compounds. For example, the compound of the invention may be radio-labeled with radioactive isotopes, such as for example tritium ($^3H$) or carbon-14 ($^{14}C$). All isotopic variations, whether radioactive or not, are intended to be encompassed within the scope of the present invention.

Compounds of the invention can exist in unsolvated forms as well as solvated forms, including hydrated forms. In general, the solvated forms are equivalent to unsolvated forms and are encompassed within the scope of the present invention. A compound of formula (I) may exist in multiple crystalline or amorphous forms. In general, all physical forms are equivalent for the uses contemplated by the present invention and are intended to be within the scope of the present invention.

The term "pharmaceutically acceptable salts" includes salts of a compound of the invention which are prepared with relatively nontoxic acids or bases. Base addition salts can be obtained by contacting the neutral form of a compound of the invention with a sufficient amount of the desired base, either neat or in a suitable inert solvent. Examples of pharmaceutically acceptable base addition salts include sodium, potassium, calcium, ammonium, organic amino, or magnesium salt, or a similar salt. Acid addition salts can be obtained by contacting the neutral form of compound of the invention with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, trifluoroacetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are the salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19).

The neutral forms of compound of the invention is preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The term "low enough pyrogen activity", with reference to a pharmaceutical preparation, refers to a preparation that does not contain a pyrogen in an amount that would lead to an adverse effect (e.g., irritation, fever, inflammation, diarrhea, respiratory distress, endotoxic shock, etc.) in a subject to which the preparation has been administered. For example, the term is meant to encompass preparations that are free of, or substantially free of, an endotoxin such as, for example, a lipopolysaccharide (LPS).

Diseases, Disorders, or Conditions Related to TRPC5 Function

In certain embodiments, the invention provides methods and compositions for antagonizing a function of a TRPC5 channel in vitro or in vivo. Exemplary functions include, but are not limited to, TRPC5-mediated current. In certain embodiments, the invention provides methods for treating a disease or disorder or condition by administering compound of the invention. In other embodiments, the compound of formula (I) selectively inhibits the expression level and/or activity of a TRPC5 protein. In other words, in certain embodiment, the compound of the invention inhibits the activity of a TRPC5 protein preferentially in comparison to the activity of one or more other ion channels.

Treatment of Anxiety and Fear-Related Disorders

In certain embodiments, the compound of the invention can be used for preventing or treating anxiety and fear-related disorders (see, e.g., Riccio et al. (2009) Cell 137: 761-72). Examples of such disorders include post-traumatic stress disorder, panic disorder, agoraphobia, social phobias, generalized anxiety disorder, panic disorder, social anxiety disorder, obsessive-compulsive disorder, and separation anxiety.

Memory, Motion and Mood Disorders

A compound of the invention is also useful for the treatment of Parkinson's disease, epilepsy, memory disorders, stroke, seizure, and mood disorders. Mood disorders include depression (e.g., major depression, psychiatric depression, dysthymia, and postpartum depression) and bipolar disorder (e.g., bipolar I, bipolar II, and cyclothymia). Memory disorders are conditions associated with any memory loss and may result from Alzheimer's disease, amnesia, aphasia, atherosclerosis, brain injury or disorder, brain tumor, chronic fatigue syndrome, Creutzfedt-Jacob disease, dissociative amnesia, depression, fuge amnesia, Huntington's disease, learning disorders, sleeping disorders, multiple personality disorder, pain, post-traumatic stress disorder, schizophrenia, sports injuries, stroke, and Wernicke-Korsakoff syndrome.

Treatment of Pain, Sensitivity to Pain and Touch, or Pain-Related Diseases or Disorders In certain embodiments, a compound of the invention is used to treat or ameliorate pain. Exemplary classes of pain that can be treated using a compound of formula (I) include, but are not limited to nociceptive pain, inflammatory pain, and neuropathic pain. The pain can be chronic or acute.

A compound of the invention may be particularly useful in the treatment of pain associated with cancer, osteoarthritis, rheumatoid arthritis, post-herpetic neuralgia, burns, and other indications detailed above. To further illustrate, additional exemplary indications for which a compound of the invention can be used include oral pain, pelvic pain, Fabry's disease, complex regional pain syndrome, pancreatitis, and fibromyalgia syndrome.

A compound of the invention may also be used in connection with prevention or treatment of sensitivity to pain and touch. Pain or sensitivity to pain and touch may be indicated in a variety of diseases, disorders or conditions, including, but not limited to, diabetic neuropathy, breast pain, psoriasis, eczema, dermatitis, burn, post-herpetic neuralgia (shingles), nociceptive pain, peripheral neuropathic and central neuropathic pain, chronic pain, cancer and tumor pain, spinal cord injury, crush injury and trauma induced pain, migraine, cerebrovascular and vascular pain, sickle cell disease pain, rheumatoid arthritis pain, musculoskeletal pain including treating signs and symptoms of osteoarthritis and rheumatoid arthritis, orofacial and facial pain, including dental, temperomandibular disorder, and cancer related, lower back or pelvic pain, surgical incision related pain, inflammatory and non-inflammatory pain, visceral pain, psychogenic pain and soft tissue inflammatory pain, fibromyalgia-related pain, and reflex sympathetic dystrophy, and pain resulting from kidney stones or urinary tract infection.

The foregoing are merely exemplary of diseases and conditions that cause or lead to inflammation, lesions, ulcers, or other sources of oral pain. In other embodiments, the oral pain is due to an injury to the mouth, jaw, lips, gums, or teeth. In other embodiments, the oral pain is due to oral surgery, for example, surgery for cancer, tooth extraction, or jaw remodeling. Other conditions that may lead to oral ulcers, and thus oral pain, include, but are not limited to chickpox, herpes zoster, infectious mononucleosis, syphilis, tuberculosis, acute necrotizing gingivitis, and burning mouth syndrome.

Fibromyalgia (FMS; fibromyalgia syndrome) is a widespread musculoskeletal pain and fatigue disorder. Fibromyalgia is characterized by pain in the muscles, ligaments, and tendons. The condition affects more women than men, and occurs in people of all ages. Overall, FMS is estimated to afflict 3-6% of the population. Patients have described the pain associated with fibromyalgia as deep muscular aching, throbbing, shooting, and stabbing. The pain sometimes includes an intense burning sensation. The pain and stiffness are often worse in the morning or after repetitive use of a particular muscle group.

Additionally, varying levels of fatigue ranging from mild to incapacitating are often associated with fibromyalgia. Other symptoms of fibromyalgia include gastrointestinal symptoms. Irritable bowel syndrome and IBS-like symptoms such as constipation, diarrhea, frequent abdominal pain, abdominal gas, and nausea occur in roughly 40 to 70% of FMS patients. Acid reflux or gastroesophogeal reflux disease (GERD) occurs at a similar frequency.

Complex Regional Pain Syndrome (CRPS; also known as chronic regional pain syndrome) is a chronic pain condition. CRPS was formerly known as reflex sympathetic dystrophy (RSD). CRPS is a chronic, painful, and progressive neurological condition that affects skin, muscles, joints, and bones. The syndrome usually develops in an injured limb, such as a broken leg or following surgery. However, many cases involve only a minor injury, such as a sprain, and sometimes no precipitating injurious event can be identified. CRPS involves continuous, intense pain that is disproportionate to the severity of the injury. The pain worsens, rather than improves, over time.

Although CRPS can affect a variety of regions of the body, it most often affects the arms, legs, hands, or feet. Often the pain begins in one portion of a limb, but spreads over time to include the entire limb or even to include a different limb. Typical features include dramatic changes in the color and temperature of the skin over the affected limb or body part, accompanied by intense burning pain, skin sensitivity, sweating, and swelling.

The compounds disclosed herein can also be used to treat endometriosis and the pain associated therewith.

Neurological or Neurodegenerative Diseases and Disorders

Neurodegenerative diseases and disorders include but are not limited to Alzheimer's disease (AD), Parkinson's disease, Huntington's disease, amyotrophic lateral sclerosis (ALS), and other brain disorders caused by trauma or other insults including aging.

Mechanisms associated with calcium signaling may be altered in many neurodegenerative diseases and in disorders resulting from brain injury. For example, fibroblasts or T-lymphocytes from patients with AD have consistently displayed an increase in $Ca^{2+}$ release from intracellular stores compared to controls (Ito et al. (1994) Proc. Natl. Acad. Sci. U.S.A. 91:534-538; Gibson et al. (1996) Biochem. Biophys. ACTA 1316:71-77; Etchenberrigaray et al. (1998) Neurobiology of Disease, 5:37-45). Consistent with these observations, mutations in presenilin genes (PS1 or PS2) associated with familial AD (FAD) have been shown to increase InsP3-mediated $Ca^{2+}$ release from internal stores (Guo et al. (1996) Neuro Report, 8:379-383; Leissring et al. (1999) J. Neurochemistry, 72:1061-1068; Leissring et al. (1999) J. Biol. Chem. 274 (46):32535-32538; Leissring et al. (2000) J. Cell Biol. 149 (4):793-797; Leissring et al. (2000) Proc. Natl. Acad. Sci. U.S.A. 97 (15):8590-8593). Furthermore, mutations in PS1 or PS2 associated with an increase in amyloidogenic amyloid β peptide generation in AD are reported to be associated with a decrease in intracellular calcium level (Yoo et al. (2000) Neuron, 27 (3):561-572).

Experimental traumatic brain injury has been shown to initiate massive disturbances in $Ca^{2+}$ concentrations in the brain that may contribute to further neuronal damage. Intracellular $Ca^{2+}$ may be elevated by many different ion channels. It has been further shown that channel blockers may be beneficial in the treatment of neurological motor dysfunction when administered in the acute posttraumatic period (Cheney et al. (2000) J. Neurotrauma, 17 (1):83-91).

Seizure

Excitotoxicity of a variety of origins leads to seizures. Commonly excess neuronal firing can drive seizure activity. Compounds that reduce the hyperexcitability of relevant neuronal populations have significant potential in reducing seizure activity. Compounds of the invention that inhibit TRPC5 may reduce hyperexcitability and thus reduce seizure activity.

Proteinuric Kidney Disease

TRPC5 is also expressed in the podocyte of the kidney. It has been proposed that there is an antagonistic regulation of actin dynamics and cell in the podocytes by TRPC5 and TRPC6 (Tian et al., (2010) Science Signaling). Thus, inhibiting TRPC5 may impact the reaction of the podocyte to injury.

Combination Therapy

The present invention provides compounds of the invention for use in vitro and in vivo. The present invention also provides compositions and pharmaceutical compositions comprising a compound of formula (I) that inhibits TRPC5 activity. In certain embodiments, the compound of the invention is selective. In other words, in certain embodiments, the compound of the invention inhibits TRPC5 activity preferentially over the activity of other ion channels. In certain embodiments, the compound of formula (I) inhibits TRPC5 activity preferentially over TRPV1, TRPV2, TRPV3, TRPV4, TRPC3, TRPC6, TRPC7, TRPA1, and/or TRPM8 activity. For example, in certain embodiments, the compound of formula (I) inhibits the activity of TRPC5 and also inhibits the activity of one or more of TRPC4, TRPV1, TRPV2, TRPV3, TRPV4, TRPC3, TRPC6, TRPC7, TRPA1, and TRPM8.

A compound of the invention can be used alone or in combination with other pharmaceutically active agents. Examples of such other pharmaceutically active agents include, but are not limited to, anti-depressants, anti-anxiety agents, anti-epileptic agents, anti-inflammatory agents (e.g., NSAIDS, bradykinin receptor antagonists, hormones and autacoids such as corticosteroids), or anti-migraine agents. Certain active agents belong to more than one category.

In certain embodiments, a compound of the invention is conjointly administered with an analgesic. Suitable analgesics include, but are not limited to, opioids, glucocorticosteroids, non-steroidal anti-inflammatories, naphthylalkanones, oxicams, para-aminophenol derivatives, propionic acids, propionic acid derivatives, salicylates, fenamates, fenamate derivatives, pyrozoles, and pyrozole derivatives. Examples of such analgesic compounds include, but are not limited to, codeine, hydrocodone, hydromorphone, levorpharnol, morphine, oxycodone, oxymorphone, butorphanol, dezocine, nalbuphine, pentazocine, etodolac, indomethacin, sulindac, tolmetin, nabumetone, piroxicam, acetaminophen, fenoprofen, flurbiprofen, ibuprofen, ketoprofen, naproxen, diclofenac, oxaprozin, aspirin, diflunisal, meclofenamic acid, mefenamic acid, prednisolone, and dexamethasone. Preferred analgesics are non-steroidal anti-inflammatories and opioids (preferably morphine).

In some embodiments, a compound of the invention can be administered in conjunction with a therapeutic whose administration causes pain. For example, a compound of the invention can be administered in conjunction with an anesthetic, to reduce the pain caused by the administration of the anaesthetic. A compound of the invention can also be administered in conjunction with a chemotherapeutic agent, to reduce the pain caused by administration of the chemotherapeutic agent.

In certain embodiments, a compound of the invention is conjointly administered with a non-steroidal anti-inflammatory. Suitable non-steroidal anti-inflammatory compounds include, but are not limited to, piroxicam, diclofenac, etodolac, indomethacin, ketoralac, oxaprozin, tolmetin, naproxen, flubiprofen, fenoprofen, ketoprofen, ibuprofen, mefenamic acid, sulindac, apazone, phenylbutazone, aspirin, celecoxib and rofecoxib.

Pharmaceutical Compositions

While it is possible for a compound of the invention to be administered alone, it is preferable to administer the compound as a pharmaceutical formulation, where the compound is combined with one or more pharmaceutically acceptable excipients or carriers. The compound of the invention may be formulated for administration in any convenient way for use in human or veterinary medicine. In certain embodiments, the compound of the invention may be a prodrug, e.g., capable of being converted to an active compound in a physiological setting.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Examples of pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) cyclodextrins such as Captisol®; and (22) other non-toxic compatible substances employed in pharmaceutical formulations.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Solid dosage forms (e.g., capsules, tablets, pills, dragees, powders, granules and the like) can include one or more pharmaceutically acceptable carriers, such as sodium citrate or dicalcium phosphate, and/or any of the following: (1)

fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents.

Liquid dosage forms can include pharmaceutically acceptable emulsions, microemulsions, solutions, suspensions, syrups and elixirs. In addition to the compound of the invention, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the compound of the invention, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Ointments, pastes, creams and gels may contain, in addition to the compound of the invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compound of the invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The formulations may conveniently be presented in unit dosage form and may be prepared by any methods well known in the art of pharmacy. The amount of a compound of the invention which can be combined with a carrier material to produce a single dosage form will vary depending upon the host being treated, the particular mode of administration. The amount of a compound of the invention that can be combined with a carrier material to produce a single dosage form will generally be that amount of the compound which produces a therapeutic effect. Generally, out of one hundred percent, this amount will range from about 1 percent to about ninety-nine percent of a compound of the invention, preferably from about 5 percent to about 70 percent, most preferably from about 10 percent to about 30 percent.

The tablets, and other solid dosage forms of the pharmaceutical compositions disclosed herein, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain pacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Dosage forms for the topical or transdermal administration of a compound of the invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The formulations disclosed herein can be delivered via a device. Exemplary devices include, but are not limited to, a catheter, wire, stent, or other intraluminal device. Further exemplary delivery devices also include a patch, bandage, mouthguard, or dental apparatus. Transdermal patches have the added advantage of providing controlled delivery of a compound of the invention to the body. Such dosage forms can be made by dissolving or dispersing the compound of the invention in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, drops, solutions and the like, are also contemplated as being within the scope of this invention.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

When a compound of the invention is administered as a pharmaceutical, to humans and animals, it can be given per se or as a pharmaceutical composition containing, for example, 0.1 to 99.5% (more preferably, 0.5 to 90%) of the compound of the invention in combination with a pharmaceutically acceptable carrier.

The formulations can be administered topically, orally, transdermally, rectally, vaginally, parentally, intranasally, intrapulmonary, intraocularly, intravenously, intramuscularly, intraarterially, intrathecally, intracapsularly, intraorbitally, intracardiacly, intradermally, intraperitoneally, transtracheally, subcutaneously, subcuticularly, intraarticularly, subcapsularly, subarachnoidly, intraspinally, intrasternally, sublingually, or by inhalation.

Dosages

Actual dosage levels of the compound of the invention in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the compound of the invention disclosed herein employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compound of the invention in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous, intracerebroventricular and subcutaneous doses of the compounds of the invention for a patient will range from about 0.0001 to about 100 mg per kilogram of body weight per day. For example, the dose can be 0.1-50, 0.1-25, 0.5-10, 1-10, or 5-10 mg/kg.

If desired, the effective daily dose of the compound of the invention may be administered as two, three, four, five, six or more sub-doses administered separately at appropriate intervals throughout the day, optionally, in unit dosage forms.

Disease and Injury Models

A compound of the invention which antagonizes TRPC5 function may be useful in the prophylaxis and treatment of any of the foregoing injuries, diseases, disorders, or conditions. In addition to in vitro assays of the activity of the compound of the invention, its efficacy can be readily tested in one or more animal models. By way of example, numerous well known animal models exist. One or more suitable animal models (e.g., suitable in light of the particular indication) can be selected.

Fear-related behaviors can be measured as described, e.g., in Riccio et al. Pain behaviors can be studied using various agents or procedures to simulate pain resulting from injuries, diseases, or other conditions. Blackburn-Munro (2004) Trends in Pharmacological Sciences 25: 299-305 (see, for example, Table 1). Behavioral characteristics of challenged animals can then be observed. Compounds or procedures that may reduce pain in the animals can be readily tested by observing behavioral characteristics of challenged animals in the presence versus the absence of the test compound(s) or procedure.

Exemplary behavioral tests used to study chronic pain include tests of spontaneous pain, allodynia, and hyperalgesia. Id. To assess spontaneous pain, posture, gait, nocifensive signs (e.g., paw licking, excessive grooming, excessive exploratory behavior, guarding of the injured body part, and self-mutilation) can be observed. To measure evoked pain, behavioral responses can be examined following exposure to heat (e.g., thermal injury model).

Exemplary animal models of pain include, but are not limited to, the Chung model, the carageenan induced hyperalgesia model, the Freund's complete adjuvant induced hyperalgesia model, the thermal injury model, the formalin model and the Bennett Model. The Chung model of neuropathic pain (without inflammation) involves ligating one or more spinal nerves. Chung et al. (2004) Methods Mol Med 99: 35-45; Kim and Chung (1992) Pain 50: 355-363. Ligation of the spinal nerves results in a variety of behavioral changes in the animals including heat hyperalgesia, cold allodynia, and ongoing pain. Compounds that antagonize TRPC5 can be administered to ligated animals to assess whether they diminish these ligation-induced behavioral changes in comparison to that observed in the absence of compound.

Useful anxiety and depression models include the maternal separation model, the elevated plus-maze model, the forced swim test, the tail suspension test, the light/dark preference model, the light-enhanced startle model, and the ultrasonic vocalization model.

Useful seizure models include but are not limited to maximal electric shock (MES), acoustic startle in susceptible animals (eg DBA mice), and chemical induced seizure (with proconvulsant compounds such as pilocarpine, pentalene tetrazole, kainic acid, N-methyl-D-aspartic acid).

Useful models of kidney function include the LPS-induced proteinuria (waiting for a reference for others).

EXAMPLES

Example 1: Patch Clamp Experiments

Patch clamp experiments permit the detection of currents through the TRPC5 channel in the cell line described above. In normal whole-cell patch clamp recordings, a glass electrode is brought into contact with a single cell and a high-resistance (gigaohm) seal is established with the cell membrane. The membrane is then ruptured to achieve the whole-cell configuration, permitting control of the voltage of the cell membrane and measurement of currents flowing across the membrane using the amplifier attached to the electrode and resulting in the replacement of cytoplasm with the pipette solution. A perfusion system permits control of the extracellular solution, including the addition of blockers and activators of the current. The current can be activated by including 1.4 µM free $Ca^{2+}$ in the pipette (intracellular) solution, and 80 µM $LaCl_3$ in the extracellular solution.

TRPC5 cells were induced 20-48 hours, removed from growth plates, and replated at low density (to attain good single-cell physical separation) on glass coverslips for measurement. In some cases, cells were grown in low density overnight on glass coverslips. Patch clamp recordings were made in the whole-cell mode with a holding potential of −40 mV. Every 5 seconds, a voltage ramp was applied from −120 to +100 mV, 400 ms in duration. Currents elicited were quantified at −80 mV and +80 mV. The internal solution consisted of 140 mM cesium aspartate, 10 mM HEDTA, 2 mM $CaCl_2$, 2.27 mM $MgCl_2$ and 10 mM HEPES, pH 7.2, with 1,400 nM calculated free $Ca^{2+}$. The external solution consisted of 150 mM NaCl, 4.5 mM KCl, 1 mM $MgCl_2$, 2 mM $CaCl_2$, 10 mM HEPES, 10 mM glucose, 1 mM EGTA, pH 7.4. Upon addition of $LaCl_3$, TRPC5 current was induced only in TRPC5-expressing cells and not in parental HEK293 TREx cells. Removal of the $LaCl_3$ stimulus causes most of the current to go away. Potential blockers were tested for ability to block both inward and outward currents in the continued presence of $LaCl_3$.

$IC_{50}$ of a compound of the invention was estimated by testing the compound at 5 μM and 500 nM. When 5 μM of a compound showed no block, $IC_{50}$ was estimated as >10 μM. When 5 μM of a compound showed 50% or less block, a rough estimate of $IC_{50}$ in the range of 5-10 μM could be made. $IC_{50}$ for a compound of Formula I or Formula II between 500 nM and 5 μM was similarly estimated.

A compound described herein may be tested for its ability to block both inward and outward currents through the TRPC5 channel, e.g., by an assay as described in Example 1. For example, $IC_{50}$ of a compound of the invention was estimated by testing the compound at 5 μM and 500 nM. When 5 μM of a compound showed no block, $IC_{50}$ was estimated as >10 μM. When 5 μM of a compound showed 50% or less block, a rough estimate of $IC_{50}$ in the range of 5-10 μM could be made. $IC_{50}$ for a compound of the invention between 500 nM and 5 μM was similarly estimated. Exemplary compounds are shown in Table B below. As shown in Table B, "A" refers to an $IC_{50}$<100 nM. "B" refers to an $IC_{50}$ between 100 nM and 500 nM. "C" refers to an $IC_{50}$ between 500 nM and 1000 nM. "D" refers to an $IC_{50}$ between 1 μM and 2 μM. "E" refers to an $IC_{50}$ between 2 μM and 10 μM. "F" refers to agonist compounds. "ND" refers to compounds wherein the $IC_{50}$ was not determined.

TABLE B

| Compound Number | Structure | hTRPC4 Patch Inwd (nM) (All Batches) |
|---|---|---|
| 11 | | A |
| 15 | | F |
| 30 | | A |
| 77 | | ND |

TABLE B-continued
| Compound Number | | hTRPC4 Patch Inwd (nM) (All Batches) |
|---|---|---|
| 82 | 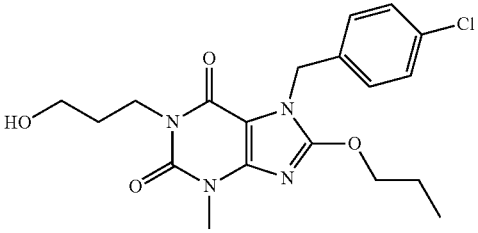 [SMILES: CCCOc1nc2c(c(=O)n(CCCO)c(=O)n2C)n1Cc1ccc(Cl)cc1] | A |
| 115 | 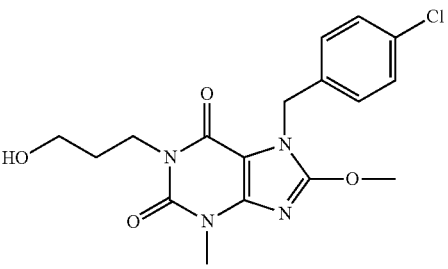 [SMILES: COc1nc2c(c(=O)n(CCCO)c(=O)n2C)n1Cc1ccc(Cl)cc1] | F |
| 129 | 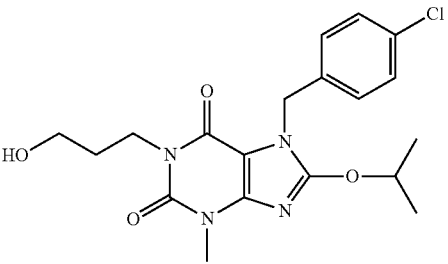 | ND |
| 139 | 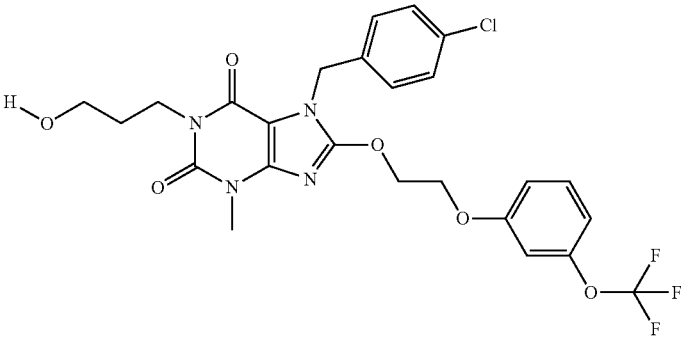 [SMILES: Cn1c(=O)n(CCCO)c(=O)c2c1nc(OCCOc1cccc(OC(F)(F)F)c1)n2Cc1ccc(Cl)cc1] | F |
| 145 | 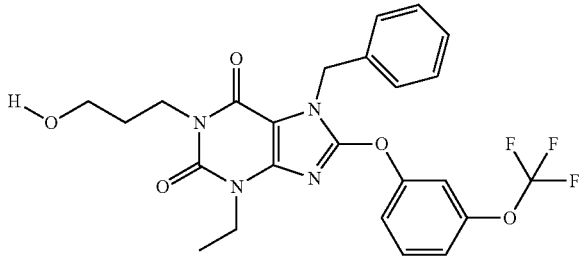 [SMILES: CCn1c(=O)n(CCCO)c(=O)c2c1nc(Oc1cccc(OC(F)(F)F)c1)n2Cc1ccccc1] | A |

TABLE B-continued

| Compound Number | | hTRPC4 Patch Inwd (nM) (All Batches) |
|---|---|---|
| 161 | [structure] | A |
| 166 | [structure] | F |
| 168 | [structure] | F |
| 198 | [structure] | F |
| 255 | [structure] | B |

TABLE B-continued

| Compound Number | Structure | hTRPC4 Patch Inwd (nM) (All Batches) |
|---|---|---|
| 260 | | A |
| 263 | | ND |
| 415 | | F |
| 485 | | A |
| 587 | | A |

Example 2

General Procedures

All reagents were purchased from commercial suppliers and used without further purification unless otherwise stated. THF was continuously refluxed and freshly distilled from sodium and benzophenone under nitrogen, DCM was continuously refluxed and freshly distilled from $CaH_2$ under nitrogen.

Reactions were monitored via TLC on silica gel plates (either 60 HSGF254 percolated plates (0.15-0.2 mm $SiO_2$) or Baker-flex IB2-F TLC plates), and visualized using UV light (254 nm or 365 nm) and/or staining with a solution of DNP (12 g, 2,4-dinitrofenylhydrazin, 60 mL concentrated $H_2SO_4$, 80 ml $H_2O$, 200 mL ethanol) and subsequent heating or monitored via LCMS.

Microwave reactions were carried out with a Biotage Smith Synthesizer.

LCMS were performed on a SHIMADZU LCMS-2010EV instrument using one of two sets of conditions. LCMS conditions one: (Chromolith SpeedROD, RP-18e column, 50×4.6 mm, mobile phase: Solvent A: $CH_3CN/H_2O/HCOOH=10/90/0.05$, Solvent B: $CH_3CN/H_2O/HCOOH=90/10/0.05$, 0.8 min@ 10% B, 2.7 min gradient (10-95% B), then 0.8 min@95% B, Flow rate: 3 mL/min, temperature: 40° C.). LCMS conditions two: (Zorbax, 3.5 micron, 2.1×50 mm C18 column. Mobile phase: Solvent A: 0.1% formic acid/acetonitrile Solvent B: 0.1% formic acid/water. Gradient: 5% to 95% B using a 5 min or 8 min runtime).

Preparative HPLC were performed either on a SHIMADZU LC-8A instrument. (Column: YMC Pack ODS-A (150*30 mm, 10 μm)) or LC-6AD (Column: Shim=Pack PREP-ODS-H (250*20 mm, 10 μm)) with UV detection which were controlled by LC solution Chemstation software. $H_2O$ (0.1% HCOOH) and methanol (MeCN) as mobile phase at the indicated flow rate.

Analytical HPLC were performed on a SHIMADZU LC-2010A instrument. (Chromolith SpeedROD, RP-18e, 50×4.6 mm, mobile phase: Solvent A: $CH_3CN/H_2O/HCOOH=10/90/0.05$, Solvent B: $CH_3CN/H_2O/HCOOH=90/10/0.05$, 0.8 min@ 10% B, 2.7 min gradient (10-95% B), then 0.8 min@95% B, Flow rate: 3 mL/min, temperature: 40° C.).

$^1$H-NMR spectra were recorded on either a Bruker Avance II 400 MHz or a Varian Unity Inova 400 MHz instrument. Chemical shifts (δ) are reported in ppm relative to tetramethylsilane (δ=0.000 ppm) and the spectra were calibrated to the residual solvent signal of chloroform (δ=7.26), Dimethyl sulfoxide (δ=2.50), methanol (δ=3.30). Data for $^1$H-NMR spectra are reported as follows: chemical shift (multiplicity, number of hydrogens). Abbreviations are as follows: s (singlet), d (doublet), t (triplet), q (quartet), quint (quintet), m (multiplet), br (broad).

List of Abbreviations and Terms

BPO benzoyl peroxide
CDI carbonyldiimidazole
Chromatography compound purification using silica gel
Concentrated [or concentrated at reduced pressure] solvent removal with the aid of a rotary evaporation device
DCM dichloromethane
DBU 1,8-diazabicyclo[5.4.0]undec-7-ene
Dess Martin [or Dess Martin periodinane] 1,1,1-triacetoxy-1,1-dihydro-1,2-benziodoxol-3(1H)-one
Dilute HCl 1N hydrochloric acid
DMF N,N-dimethylformamide
DMAP 4-dimethylaminopyridine
Dried, referring to removal of residual water from organic solutions implies the use of an inorganic drying agent such as sodium sulfate
Dried in vacuo [or dried under vacuum] residual solvent removal with the aid of a vacuum pump
DMSO dimethyl sulfoxide
Eaton's reagent 7.7 wt % phosphorus pentoxide in methanesulfonic acid
EDCI 1-ethyl-3-(3-dimethylaminopropyl)carbodiimide)
Evaporated solvent removal with the aid of a rotary evaporation device
h hour
HMDS hexamethyldisilazane
LAH lithium aluminum hydride
MCPBA 3-chloroperoxybenzoic acid
min minutes
n-BuLi n-Butyllithium
NBS N-bromosuccinimide
NCS N-chlorosuccinimide
NMP N-methylpyrolidinone
Oxone potassium peroxomonosulfate
Pd/C palladium on activated carbon
Pd-dppf 1,1'-Bis(diphenylphosphino)ferrocene-palladium (II)dichloride dichloromethane complex
PMB 4-methoxybenzyl
PPTS pyridinium p-toluenesulfonate
Preparative TLC preparative thin layer chromatography
SEM (trimethylsilyl)ethoxy)methyl
TBAI tetrabutylammonium iodide
TBAF tetrabutylammonium fluoride
TBAH tetrabutylammonium hydroxide
TEA triethylamine
TFA trifluoroacetic acid
THF tetrahydrofuran
tlc thin layer chromatography on silica gel
X-phos 2-(dicyclohexylphosphino)-2',4',6'-triisopropylbiphenyl
Purine Numbering

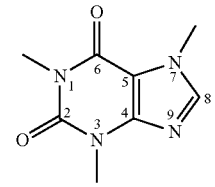

Preparation of Intermediates

Intermediate 1
2-(2-(2-chloroethoxy)ethoxy)tetrahydro-2H-pyran

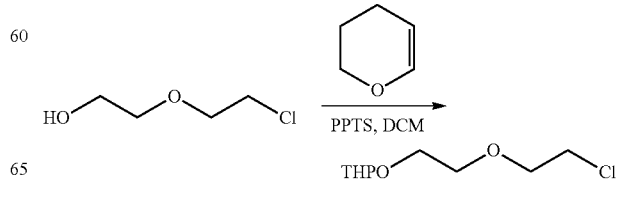

To a solution of 2-(2-chloroethoxy)ethanol (10 g, 0.071 mol) in DCM (150 mL) was added PPTS (891 mg, 3.6 mmol), then dihydropyran (10.2 g, 0.107 mol) was added dropwise at 0° C. The mixture was stirred at room temperature for 16 h. It was partitioned between DCM and water. The organic phase was washed with brine, dried over sodium sulfate, filtered and concentrated to give a crude product which was purified by silica gel chromatography eluted with petroleum ether to give 2-(2-bromoethoxy)tetrahydro-2H-pyran (11.9 g, 79.8% yield) as light yellow oil. $^1$H-NMR (CDCl$_3$) δ 4.65-4.67 (t, 1H), 3.86-3.92 (m, 2H), 3.78-0.381 (m, 2H), 3.71-3.73 (t, 2H), 3.64-3.67 (t, 2H), 1.77-1.87 (m, 2H), 1.51-1.64 (m, 6H).

Intermediate 2
2-(2-bromoethoxy)tetrahydro-2H-pyran

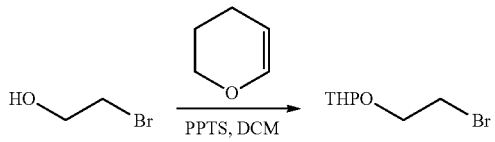

To a solution of 2-bromoethanol (15 g, 0.12 mol) in DCM (150 mL) was added PPTS (891 mg, 3.6 mmol), then dihydropyran (10.6 g, 0.126 mol) was added dropwise at 0° C. The mixture was stirred at room temperature for 4 h. It was partitioned between DCM and water. The organic phase was washed with brine, dried over sodium sulfate, filtered and concentrated to give a crude product which was purified by column chromatography eluting with petroleum ether/ethyl acetate (50:1) to give 2-(2-bromoethoxy)tetrahydro-2H-pyran (18.0 g, 72.0% yield) as a light yellow oil.

Intermediate 3
2-(3-bromopropoxy)tetrahydro-2H-pyran

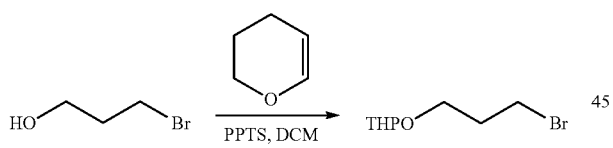

To a solution of 3-bromopropan-1-ol (8 g, 57.9 mmol) in DCM (100 mL) was added PPTS (891 mg, 3.6 mmol), then dihydropyran (7.3 g, 86.9 mmol) was added dropwise at 0° C. The mixture was stirred at room temperature overnight. It was partitioned between DCM and water. The organic phase was washed with brine, dried over sodium sulfate, filtered and concentrated to give a crude product which was purified by column chromatography eluting with petroleum ether/ethyl acetate (50:1) to give 2-(3-bromopropoxy)tetrahydro-2H-pyran (8.9 g, 69.0% yield) as a light yellow oil.

Intermediate 4 2-(chloromethyl)-5-methylthiazole

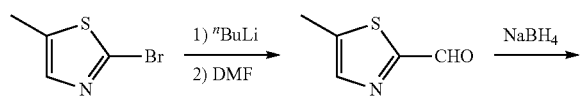

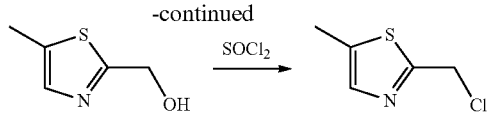

Step 1 (5-methylthiazol-2-yl)methanol

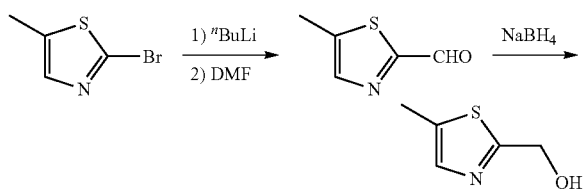

To a solution of n-BuLi (8.4 ml, 13.48 mmol) in THF (30 mL) was added 2-bromo-5-methylthiazole (2.0 g, 11.23 mmol) dropwise under a nitrogen atmosphere at −70° C.; then it was stirred at this temperature for 1.5 h. DMF (1.3 ml, 16.85 mmol) was added dropwise under nitrogen atmosphere at −70° C. The resulting mixture was stirred at this temperature for 1 h. Then the mixture was quenched with aqueous saturated ammonium chloride (5 mL), the mixture was partitioned between ethyl acetate and water. The organic layers were combined, dried over sodium sulfate, filtered and concentrated to give a yellow oil. The yellow oil was dissolved in methanol (15 ml), sodium borohydride (512 mg, 13.48 mmol) was added portionwise under a nitrogen atmosphere at −60° C. The mixture was stirred at this temperature for 1 h. The reaction mixture was quenched with acetone and concentrated. The residue was partitioned between ethyl acetate and water. The organic layers were dried over sodium sulfate, filtered and concentrated, then purified by silica gel chromatography eluting with petroleum/ethyl acetate=3:1 to give thiazol-2-ylmethanol (1.3 g, 90.3%) as brown oil. LCMS retention time 0.366 min; LCMS MH$^+$ 130.

Step 2 2-(chloromethyl)-5-methylthiazole

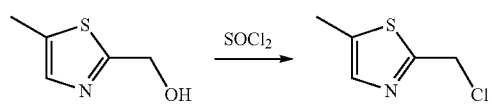

To a solution of (5-methylthiazol-2-yl)methanol (0.5 g, 3.87 mmol) in DCM (5 mL) was added thionyl chloride (0.19 ml, 2.6 mmol) at 0° C., then the mixture was stirred at room temperature for 2 h. The solvent was concentrated to give 2-(chloromethyl)-5-methylthiazole (570 mg) as a yellow oil which was used without purification. LCMS retention time 0.912 min; LCMS MH$^+$ 148.

Intermediate 5
2-(3-(trifluoromethoxy)phenoxy)ethanol

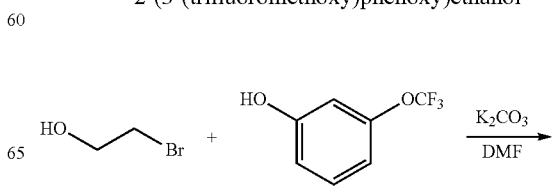

291

-continued

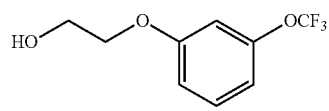

To a solution of 3-(trifluoromethoxy)phenol (3 g, 16.8 mmol) in DMF (30 mL) was added 2-bromoethanol (3.16 g, 25.3 mmol), potassium carbonate (4.65 g, 33.7 mmol). The mixture was heated at 80° C. overnight. The mixture was cooled, partitioned between ethyl acetate and water. The organic layers were combined, dried over sodium sulfate, filtered and concentrated to give a crude product which was purified by a column chromatography eluting with petroleum ether and ethyl acetate (10:1) to give 2-(3-(trifluoromethoxy)phenoxy)ethanol (3.5 g, 94.5% yield) as a yellow oil. $^1$H-NMR (DMSO-d$_6$) δ 7.28-7.30 (t, 1H), 6.81-6.86 (m, 2H), 6.78 (s, 1H), 4.07-4.09 (t, 2H), 3.95-3.99 (m, 2H), 2.58 (t, 1H).

Intermediate 6 8-bromo-7-ethyl-3-methyl-1-(3-(tetrahydro-2H-pyran-2-yloxy)propyl)-1H-purine-2,6(3H,7H)-dione

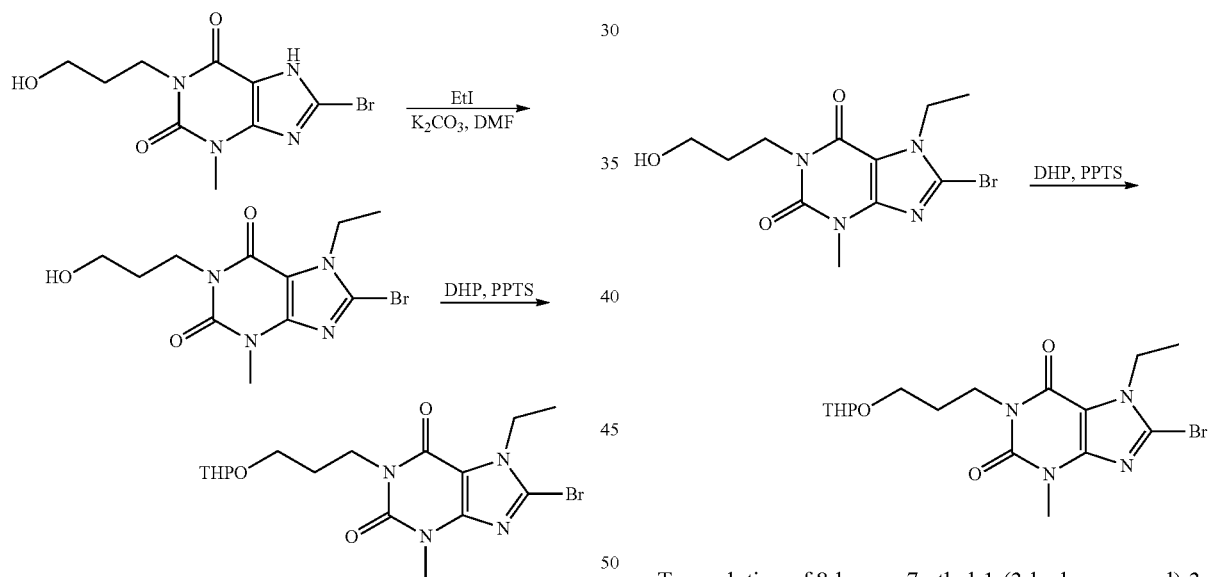

Step 1 8-bromo-7-ethyl-1-(3-hydroxypropyl)-3-methyl-1H-purine-2,6(3H,7H)-dione

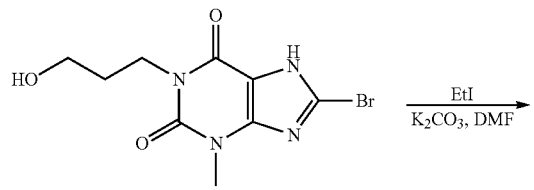

292

-continued

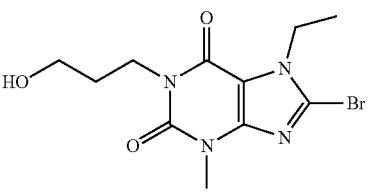

To a solution of 8-bromo-1-(3-hydroxypropyl)-3-methyl-1H-purine-2,6(3H,7H)-dione (0.4 g, 1.32 mmol, product of intermediate 16 step 2) in DMF (10 mL) was added iodoethane (0.25 g, 1.58 mmol) and potassium carbonate (0.27 g, 1.98 mmol). The reaction was heated at 50° C. for 2 h. The mixture was cooled and partitioned between ethyl acetate and water. The combined organic layer was dried over sodium sulfate, filtered and concentrated to give 8-bromo-7-ethyl-1-(3-hydroxypropyl)-3-methyl-1H-purine-2,6(3H, 7H)-dione (0.4 g, 91.7% yield) as white solid. LCMS retention time 1.674 min; LCMS MH$^+$ 331.

Step 2 8-bromo-7-ethyl-3-methyl-1-(3-(tetrahydro-2H-pyran-2-yloxy)propyl)-1H-purine-2,6(3H,7H)-dione To a solution of 8-bromo-7-ethyl-1-(3-hydroxypropyl)-3-methyl-1H-purine-2,6(3H,7H)-dione (0.4 g, 1.2 mmol) in DCM (10 mL) was added PPTS (27 mg, 0.1 mmol); then dihydropyran (0.15 g, 1.8 mmol) was added dropwise at 0° C. The mixture was stirred at room temperature overnight. The mixture was partitioned between DCM and water. The organic phase was washed with brine, dried over sodium sulfate, filtered and concentrated to give a crude product which was purified by a column chromatography eluting with petroleum ether/ethyl acetate (3:1) to give 8-bromo-7-ethyl-3-methyl-1-(3-(tetrahydro-2H-pyran-2-yloxy)propyl)-1H-purine-2,6(3H,7H)-dione (0.38 g, 76.9% yield) as white solid. LCMS retention time 1.871 min; LCMS MH$^+$-THP 331.

293

Intermediate 7 7-(4-chlorobenzyl)-8-mercapto-3-methyl-1-(3-(tetrahydro-2H-pyran-2-yloxy)propyl)-1H-purine-2,6(3H,7H)-dione

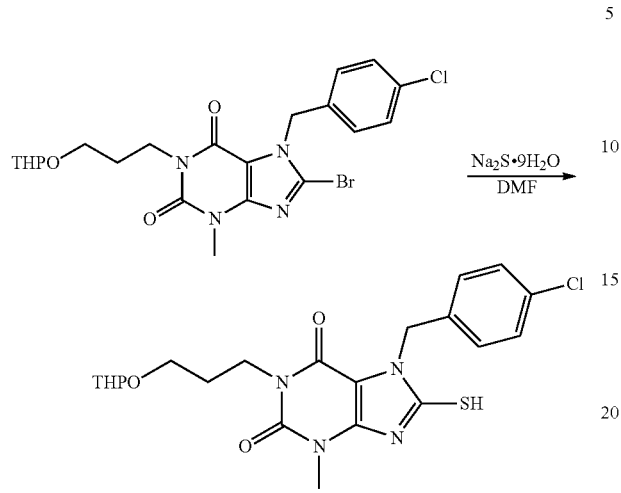

To a solution of 8-bromo-7-(4-chlorobenzyl)-3-methyl-1-(3-(tetrahydro-2H-pyran-2-yloxy)propyl)-1H-purine-2,6(3H,7H)-dione (400 mg, 0.781 mmol, intermediate 14) in DMF (10 mL) was added sodium sulfide nonahydrate (375 mg, 1.563 mmol). The reaction was stirred at 85° C. for 16 h. The mixture was cooled, diluted with ethyl acetate and water, and the phases were separated. The organic phase was washed with brine, dried over sodium sulfate, filtered and concentrated to give 7-(4-chlorobenzyl)-8-mercapto-3-methyl-1-(3-(tetrahydro-2H-pyran-2-yloxy)propyl)-1H-purine-2,6(3H,7H)-dione (230 mg, 63.4%) as orange oil. LCMS retention time 1.517 min; LCMS MH$^+$-THP 381.

Intermediate 8 8-bromo-7-(4-chlorobenzyl)-3-methyl-1H-purine-2,6(3H,7H)-dione

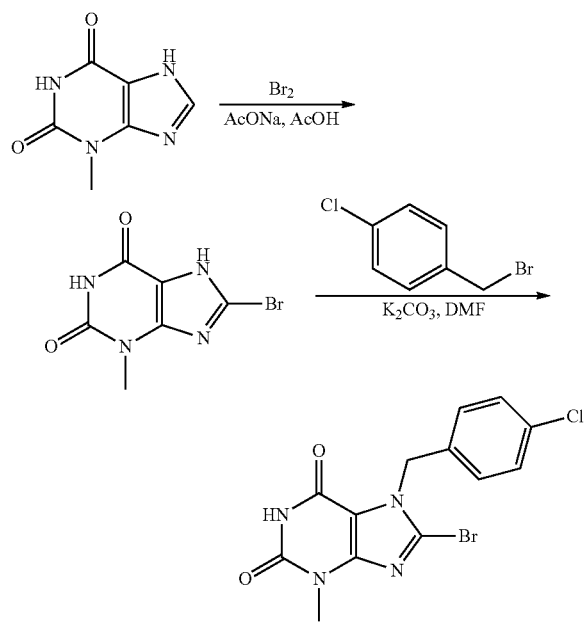

294

Step 1
8-bromo-3-methyl-1H-purine-2,6(3H,7H)-dione

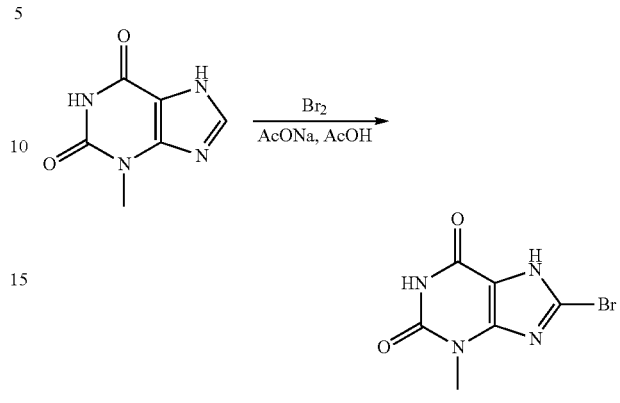

To a solution of 3-methyl-1H-purine-2,6(3H,7H)-dione (11.3 g, 6.8 mmol) in acetic acid (300 mL) was added sodium acetate (8.37 g, 13.6 mmol) followed by drop-wise addition of bromine (13.04 g, 8.2 mmol) at 50° C. After addition, the mixture was stirred at 65° C. for 3 h. The mixture was cooled and poured into ice-water (500 g), and the product precipitated. The slurry was filtered and the filter cake was washed with water twice and dried under vacuum to give 8-bromo-3-methyl-1H-purine-2,6(3H,7H)-dione (16.1 g, 96.6% yield) as light yellow solid. LCMS retention time 0.541 min; LCMS MH$^+$ 245.

Step 2 8-bromo-7-(4-chlorobenzyl)-3-methyl-1H-purine-2,6(3H,7H)-dione

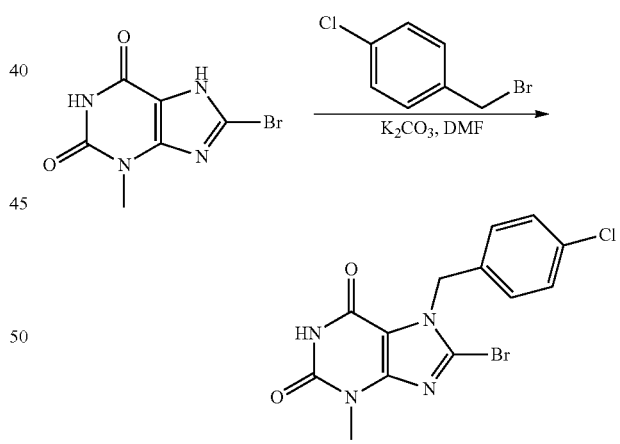

To a solution of 8-bromo-3-methyl-1H-purine-2,6(3H,7H)-dione (10.8 g, 4.42 mmol) in DMF (200 mL) was added 1-(bromomethyl)-4-chlorobenzene (10 g, 4.86 mmol) followed by potassium carbonate (9.16 g, 6.63 mmol). The resulting mixture was stirred at 45° C. for 2 h. The mixture was diluted with ethyl acetate (300 mL) and washed with brine (200 mL). The layers were separated and the organic slurry was filtered and the filter cake was washed with ice cold ethanol, dried under vacuum to give 8-bromo-7-(4-chlorobenzyl)-3-methyl-1H-purine-2,6(3H,7H)-dione (10.6 g, 64.9% yield) as white solid. LCMS retention time 1.637 min; LCMS MH$^+$ 369.

Intermediate 9 7-(4-chlorobenzyl)-3-methyl-8-(3-(trifluoromethoxy)phenoxy)-1H-purine-2,6(3H,7H)-dione

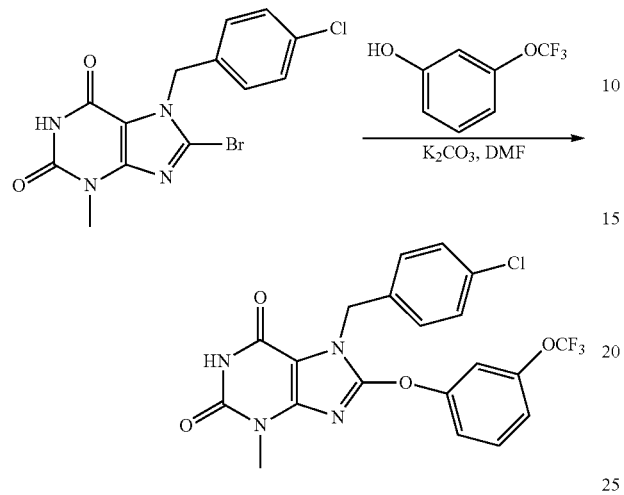

The title compound was prepared using the method of intermediate 12, step 2 to give 7-(4-chlorobenzyl)-3-methyl-8-(3-(trifluoromethoxy)phenoxy)-1H-purine-2,6(3H,7H)-dione (1.97 g, 80.1% yield) as white solid. LCMS retention time 1.724 min, LCMS MH+ 467.

Intermediate 10 8-chloro-7-(4-chlorobenzyl)-1-methyl-1H-purine-2,6(3H,7H)-dione

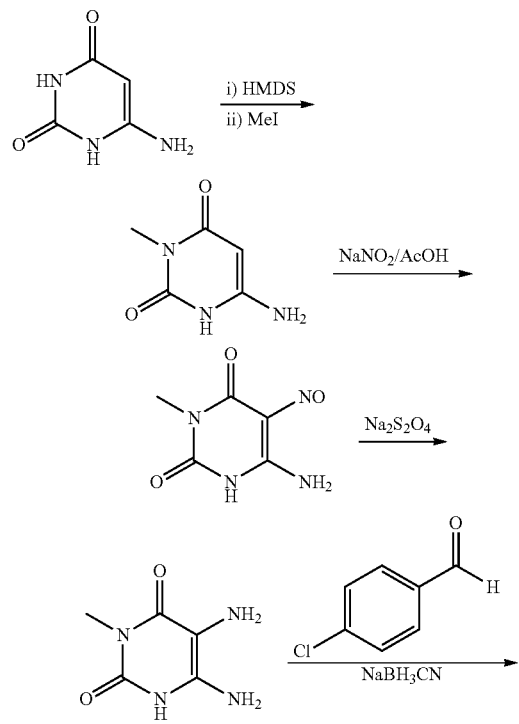

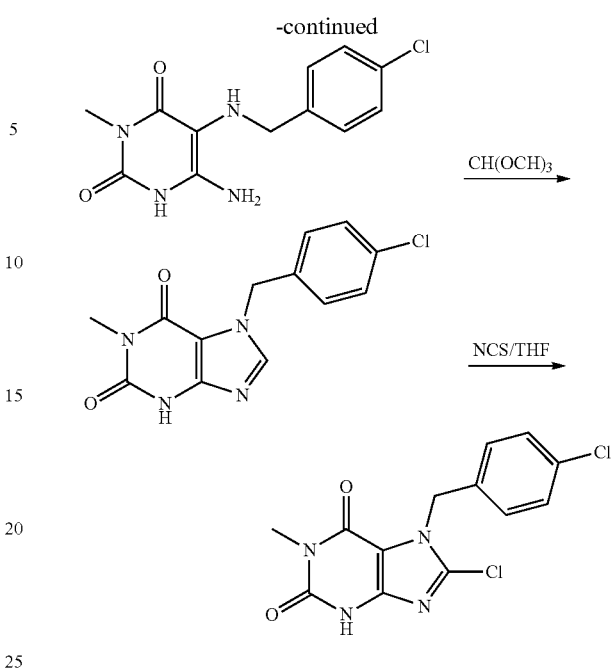

Step 1 6-amino-3-methylpyrimidine-2,4(1H,3H)-dione

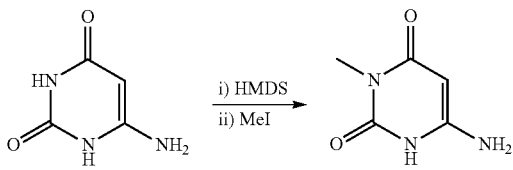

To a solution of the 6-aminopyrimidine-2,4(1H,3H)-dione (15 g, 118 mmol) in 1,1,1,3,3,3-hexamethyldisilazane (50 mL) was added ammonium sulfate (0.671 g, 5 mmol), then the resulting mixture was heated to reflux with stirring for 6 h. The mixture was concentrated to give a light-yellow solid. This solid was combined with acetonitrile (50 mL) and iodomethane (15 mL, 250 mmol) was added. The resulting mixture was stirred at 40° C. for 16 h. Then the mixture was concentrated, neutralized with saturated sodium bicarbonate to pH=7, filtered, and the filter cake was washed with brine and ethanol, dried under vacuum to give 6-amino-3-methylpyrimidine-2,4 (1H,3H)-dione (7.1 g, 42.6% yield) as yellow solid. LCMS MH+ 142.

Step 2 6-amino-3-methyl-5-nitrosopyrimidine-2,4(1H,3H)-dione

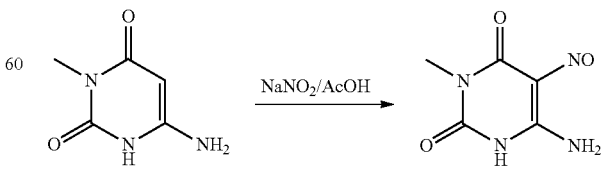

To a solution of 6-amino-3-methylpyrimidine-2,4(1H,3H)-dione (6 g, 42.6 mmol) in acetic acid (50 mL) was added a solution of sodium nitrite (6.8 g, 98.6 mmol) in water (20 mL) dropwise, then the mixture was stirred at room temperature for 1 h. The mixture was filtered, the filter cake was washed with water and ethanol and dried under vacuum to give 6-amino-3-methyl-5-nitrosopyrimidine-2,4 (1H,3H)-dione as violet solid, which was used directly in the next step.

Step 3
5,6-diamino-3-methylpyrimidine-2,4(1H,3H)-dione

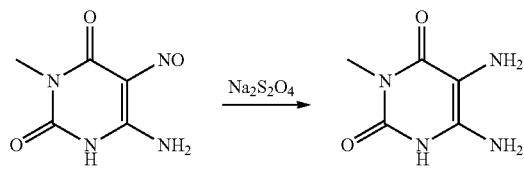

To a solution of 6-amino-3-methyl-5-nitrosopyrimidine-2,4(1H,3H)-dione in ammonium hydroxide (100 mL) was added sodium hydrosulfite (6.8 g, 39.1 mmol) in small portions at 70° C., the mixture was stirred at 70° C. for 1 h. The mixture was concentrated and ice-water was added. The slurry was filtered and the filter cake was washed with water and ethanol and dried under vacuum to give 5,6-diamino-3-methylpyrimidine-2,4(1H,3H)-dione (2.0 g, 30.1% yield over two steps) as yellow solid. LCMS MH+ 157.

Step 4 6-amino-5-(4-chlorobenzylamino)-3-methyl-pyrimidine-2,4(1H,3H)-dione

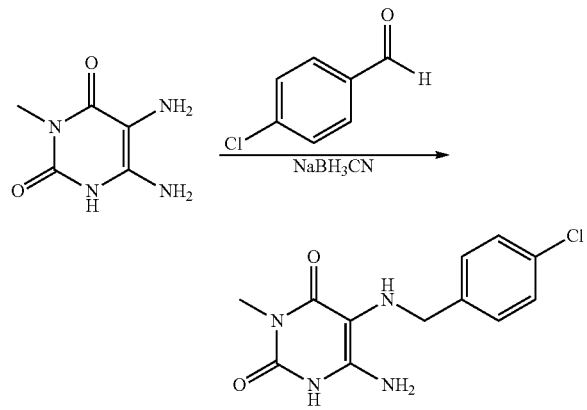

To a solution of 5,6-diamino-3-methylpyrimidine-2,4(1H, 3H)-dione (0.8 g, 5.13 mmol) in water (10 mL) and acetic acid (0.5 mL) was added 4-chlorobenzaldehyde (0.72 g, 5.14 mmol), the mixture was stirred at room temperature for 5 h. The mixture was cooled to 0° C., sodium cyanoborohydride (0.3 g, 4.76 mmol) was added and the resulting mixture was stirred at room temperature overnight. The mixture was concentrated and filtered, and the filter cake was washed with methanol, dried in vacuo to give 6-amino-5-(4-chlorobenzylamino)-3-methylpyrimidine-2,4(1H,3H)-dione (0.6 g, 42.9% yield) as yellow solid. LCMS MH+ 281.

Step 5 6-amino-5-(4-chlorobenzylamino)-3-methyl-pyrimidine-2,4(1H,3H)-dione

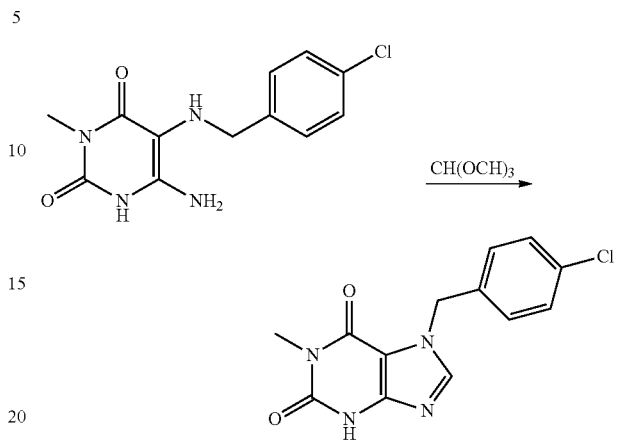

To a solution of 6-amino-5-(4-chlorobenzylamino)-3-methylpyrimidine-2,4(1H,3H)-dione (0.56 g, 2.0 mmol) in toluene (10 mL) was added trimethyl orthoformate (20 mL, 183 mmol), the mixture was stirred at 110° C. for 5 h. Then the mixture was concentrated and filtered, the filter cake was washed with diethyl ether and dried under vacuum to give 6-amino-5-(4-chlorobenzylamino)-3-methylpyrimidine-2,4 (1H,3H)-dione (0.5 g, 86.2% yield) as light-yellow solid. Mass spec: 291 (M+H).

Step 6 8-chloro-7-(4-chlorobenzyl)-1-methyl-1H-purine-2,6(3H,7H)-dione

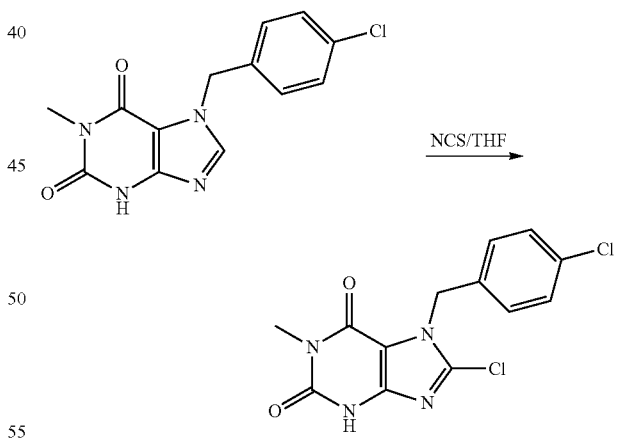

To a solution of 6-amino-5-(4-chlorobenzylamino)-3-methylpyrimidine-2,4(1H,3H)-dione (0.5 g, 1.72 mmol) in THF (20 ml) was added NCS (0.3 g, 2.26 mmol), the mixture was stirred at room temperature for 16 h. Then the mixture was concentrated, diluted with ethyl acetate and water, and the phases were separated. The organic phase was washed with brine, dried over sodium sulfate, filtered and concentrated to give product 8-chloro-7-(4-chlorobenzyl)-1-methyl-1H-purine-2,6(3H,7H)-dione (500 mg, 89.3% yield) as light yellow solid. LCMS MH+ 325.

Intermediate 11 8-bromo-7-(4-chlorobenzyl)-3-methyl-1-(2-(2-(tetrahydro-2H-pyran-2-yloxy)ethoxy)ethyl)-1H-purine-2,6(3H,7H)-dione

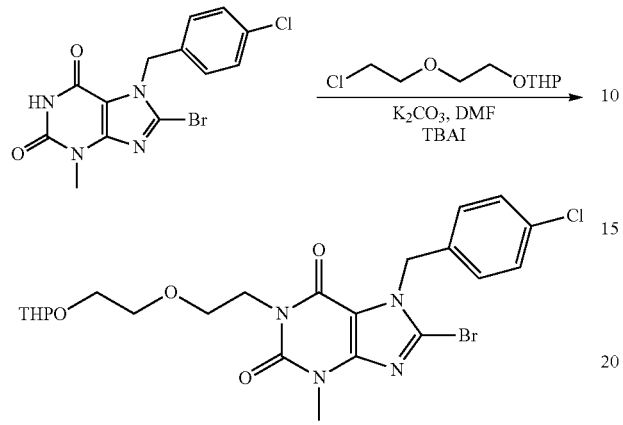

To a solution of 8-bromo-7-(4-chlorobenzyl)-3-methyl-1H-purine-2,6(3H,7H)-dione (0.2 g, 0.54 mmol, intermediate 8) in DMF (3 mL) were added 2-(2-bromoethoxy)tetrahydro-2H-pyran (169 mg, 0.81 mmol, intermediate 1), potassium carbonate (150 mg, 1.08 mmol) and a catalytic amount of TBAI. The mixture was stirred at 50° C. overnight. It was partitioned between ethyl acetate and water. The organic phase was washed with brine, dried over sodium sulfate, filtered and concentrated to give crude product, which was washed with ethanol and dried under vacuum to give 8-bromo-7-(4-chlorobenzyl)-3-methyl-1-(2-(tetrahydro-2H-pyran-2-yloxy)ethyl)-1H-purine-2,6(3H,7H)-dione (260 mg, 88.8%) as white solid. LCMS retention time 1.712 min, LCMS MH⁺-THP 459.

Intermediate 12 1-(2-(2-hydroxyethoxy)ethyl)-3-methyl-8-(3-(trifluoromethoxy)phenoxy)-1H-purine-2,6(3H,7H)-dione

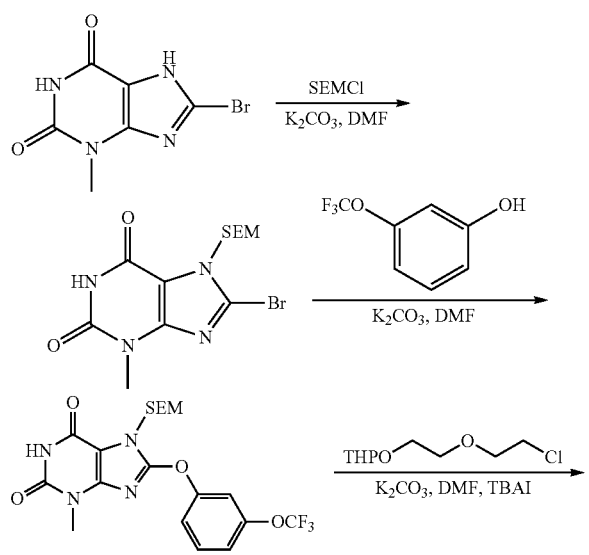

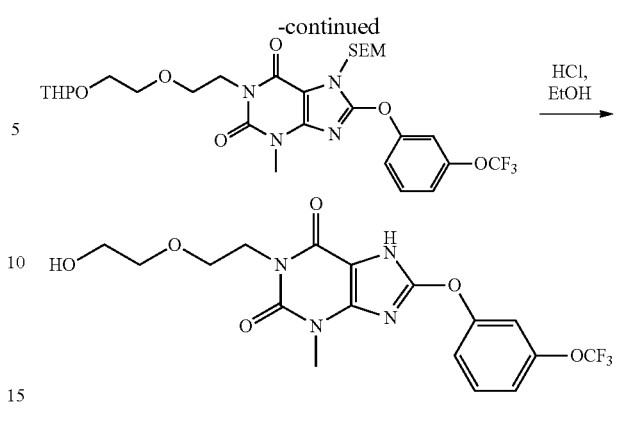

Step 1 8-bromo-3-methyl-7-((2-(trimethylsilyl)ethoxy)methyl)-1H-purine-2,6(3H,7H)-dione

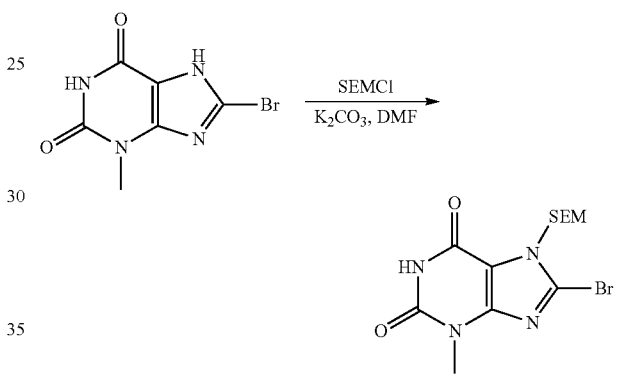

To a solution of 8-bromo-3-methyl-1H-purine-2,6(3H,7H)-dione (3.5 g, 14.3 mmol, intermediate 8 step 1) in DMF (30 mL) was added potassium carbonate (3.9 g, 28.6 mmol). Then 2-(trimethylsilyl)ethoxymethyl chloride (2.37 g, 14.3 mmol) was added dropwise 0° C., it was stirred room temperature for 3 h. The mixture was partitioned between ethyl acetate and water. The organic layers were combined, dried over sodium sulfate, filtered and concentrated to give a crude product which was washed with ethanol and dried in vacuo to give 8-bromo-3-methyl-7-((2-(trimethylsilyl)ethoxy)methyl)-1H-purine-2,6(3H,7H)-dione (4.0 g, 74.9%) as a white solid. LCMS retention time 1.458 min, LCMS MH⁺ 377.

Step 2 3-methyl-8-(3-(trifluoromethoxy)phenoxy)-7-((2-(trimethylsilyl)ethoxy)methyl)-1H-purine-2,6(3H,7H)-dione

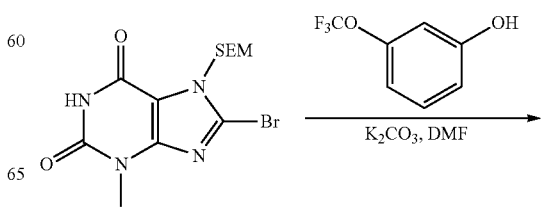

301

-continued

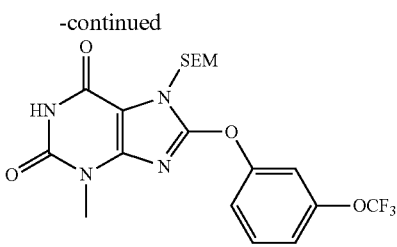

To a solution of 8-bromo-3-methyl-7-((2-(trimethylsilyl)ethoxy)methyl)-1H-purine-2,6(3H,7H)-dione (2.5 g, 6.65 mmol) in DMF (30 mL) were added 3-(trifluoromethoxy)phenol (1.78 g, 9.97 mmol) and potassium carbonate (3.9 g, 28.6 mmol). It was heated at 80° C. overnight. The mixture was cooled, partitioned between ethyl acetate and water. The organic layers were combined, dried over sodium sulfate, filtered and concentrated to give a crude product which was washed with ethanol and dried in vacuo to give 3-methyl-8-(3-(trifluoromethoxy)phenoxy)-7-((2-(trimethylsilyl)ethoxy)methyl)-1H-purine-2,6(3H,7H)-dione (1.7 g, 54.3%) as a white solid. LCMS retention time 1.850 min, LCMS MH+ 473.

Step 3 3-methyl-1-(2-(2-(tetrahydro-2H-pyran-2-yloxy)ethoxy)ethyl)-8-(3-(trifluoromethoxy)phenoxy)-7-((2-(trimethylsilyl)ethoxy)methyl)-1H-purine-2,6(3H,7H)-dione

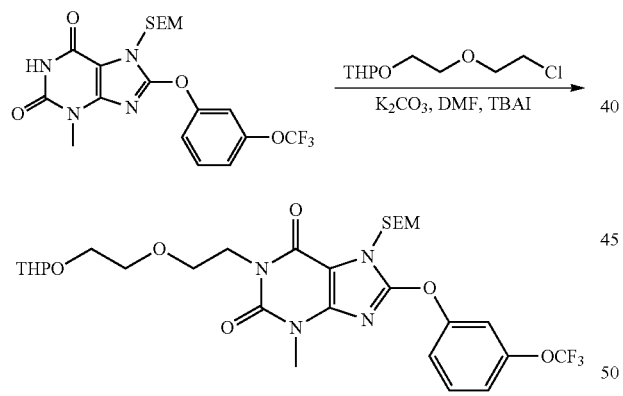

To a solution of 3-methyl-8-(3-(trifluoromethoxy)phenoxy)-7-((2-(trimethylsilyl)ethoxy)methyl)-1H-purine-2,6(3H,7H)-dione (1.2 g, 2.54 mmol) in DMF (15 mL) were added 2-(2-(2-chloroethoxy)ethoxy)tetrahydro-2H-pyran (0.79 g, 3.82 mmol, intermediate 1), potassium carbonate (0.7 g, 5.08 mmol), TBAI (2 mg, 0.02 mmol). It was heated at 80° C. overnight. The mixture was cooled, partitioned between ethyl acetate and water. The organic layers were combined, dried over sodium sulfate, filtered and concentrated to give a crude product (1.6 g, 98.1%) as a yellow oil which was used without purification. LCMS retention time 2.179 min, LCMS MH+-THP 561.

302

Step 4 1-(2-(2-hydroxyethoxy)ethyl)-3-methyl-8-(3-(trifluoromethoxy)phenoxy)-1H-purine-2,6(3H,7H)-dione

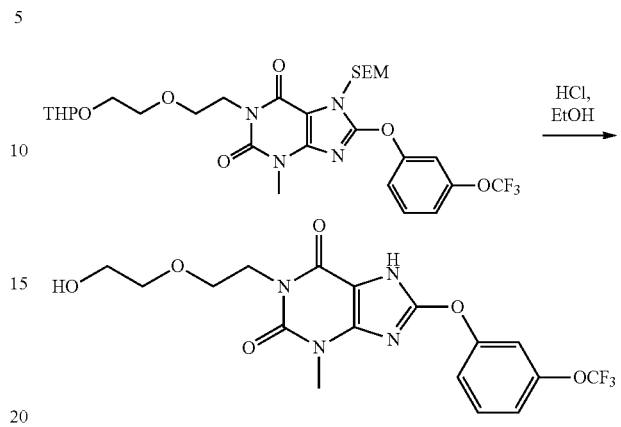

To a solution of 3-methyl-1-(2-(2-(tetrahydro-2H-pyran-2-yloxy)ethoxy)ethyl)-8-(3-(trifluoromethoxy)phenoxy)-7-((2-(trimethylsilyl)ethoxy)methyl)-1H-purine-2,6(3H,7H)-dione (0.64 g, 1.16 mmol) in ethanol (15 mL) was added HCl (3 mL); then it was refluxed overnight. The solvent was concentrated to give a crude product which was purified by a column chromatography to give 1-(2-(2-hydroxyethoxy)ethyl)-3-methyl-8-(3-(trifluoromethoxy)phenoxy)-1H-purine-2,6(3H,7H)-dione (420 mg, 84% yield) as a white solid. LCMS retention time 1.209 min, LCMS MH+ 431.

Intermediate 13 8-bromo-7-(4-chlorobenzyl)-3-methyl-1-(2-(tetrahydro-2H-pyran-2-yloxy)ethyl)-1H-purine-2,6(3H,7H)-dione

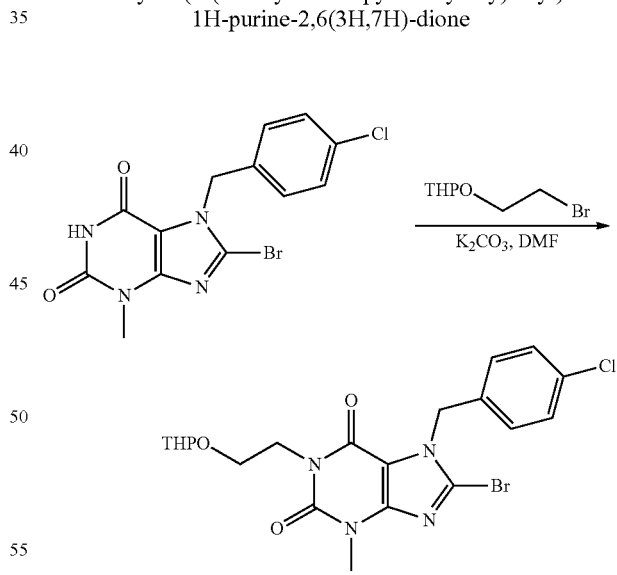

To a solution of 8-bromo-7-(4-chlorobenzyl)-3-methyl-1H-purine-2,6(3H,7H)-dione (2.0 g, 5.4 mmol, intermediate 8) in DMF (10 mL) was added 2-(2-bromoethoxy)tetrahydro-2H-pyran (1.35 g, 6.5 mmol, intermediate 2), potassium carbonate (1.49 g, 10.8 mmol). The mixture was stirred at 50° C. overnight. It was partitioned between ethyl acetate and water. The organic phase was washed with brine, dried over sodium sulfate, filtered and concentrated to give a crude product which was washed with ethanol and dried under vacuum to give 8-bromo-7-(4-chlorobenzyl)-3-methyl-1-(2-

(tetrahydro-2H-pyran-2-yloxy)ethyl)-1H-purine-2,6(3H,7H)-dione (2.10 g, 74.4%) as a white solid. LCMS retention time 1.669 min LCMS MH+-THP 415.

Intermediate 14 8-bromo-7-(4-chlorobenzyl)-3-methyl-1-(3-(tetrahydro-2H-pyran-2-yloxy)propyl)-1H-purine-2,6(3H,7H)-dione

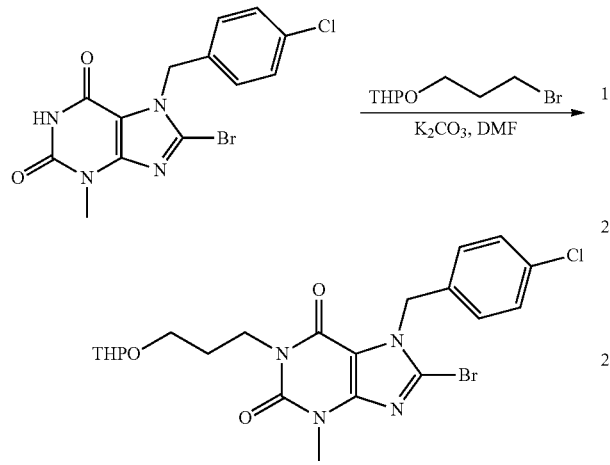

To a solution of 8-bromo-7-(4-chlorobenzyl)-3-methyl-1H-purine-2,6(3H,7H)-dione (0.5 g, 1.35 mmol, intermediate 8) in DMF (5 mL) was added 2-(3-bromopropoxy)tetrahydro-2H-pyran (0.45 g, 2.03 mmol, intermediate 3), potassium carbonate (0.37 g, 2.7 mmol). The mixture was stirred at 50° C. for 3 h; then it was partitioned between ethyl acetate and water. The organic phase was washed with brine, dried over sodium sulfate, filtered and concentrated to give a crude product which was washed with ethanol and dried under vacuum to give 8-bromo-7-(4-chlorobenzyl)-3-methyl-1-(3-(tetrahydro-2H-pyran-2-yloxy)propyl)-1H-purine-2,6(3H,7H)-dione (0.5 g, 72.2%) as a white solid. LCMS retention time 1.732 min, LCMS MH+-THP 429.

Intermediate 15 1-(3-hydroxypropyl)-3-methyl-8-(3-(trifluoromethoxy)phenoxy)-1H-purine-2,6(3H,7H)-dione

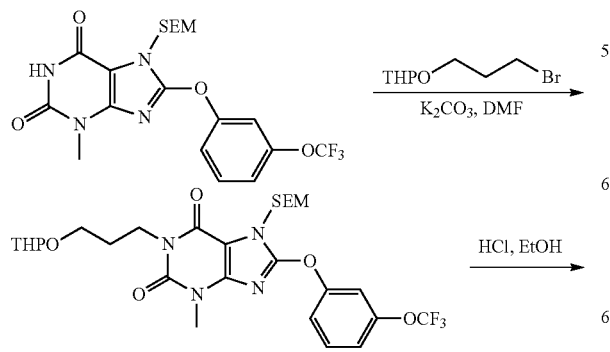

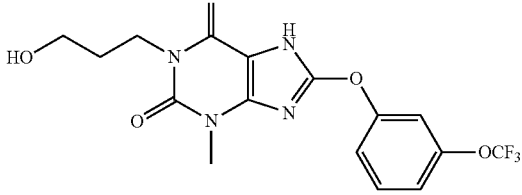

Step 1 3-methyl-1-(3-(tetrahydro-2H-pyran-2-yloxy)propyl)-8-(3-(trifluoromethoxy)phenoxy)-7-((2-(trimethylsilyl)ethoxy)methyl)-1H-purine-2,6(3H,7H)-dione

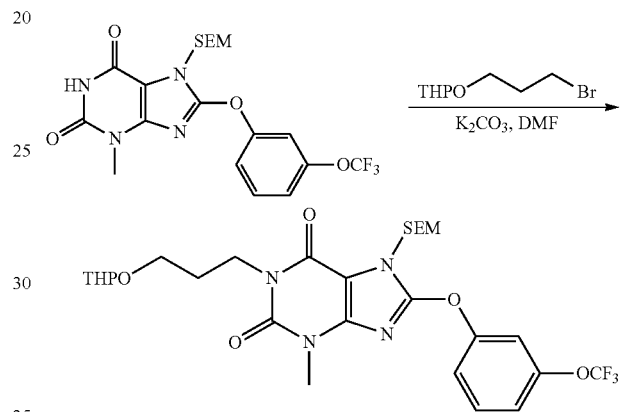

To a solution of 3-methyl-8-(3-(trifluoromethoxy)phenoxy)-7-((2-(trimethylsilyl)ethoxy)methyl)-1H-purine-2,6(3H,7H)-dione (1.0 g, 2.12 mmol, intermediate 12, step 2) in DMF (10 mL) was added 2-(3-bromopropoxy)tetrahydro-2H-pyran (0.57 g, 2.54 mmol, intermediate 3) and potassium carbonate (0.88 g, 6.36 mmol). The reaction was heated at 50° C. for 3 h. The mixture was cooled, partitioned between ethyl acetate and water. The organic layers were combined, dried over sodium sulfate, filtered and concentrated to give a crude product which was purified by column chromatography eluting with petroleum ether/ethyl acetate (1:3) to give 3-methyl-1-(3-(tetrahydro-2H-pyran-2-yloxy)propyl)-8-(3-(trifluoromethoxy)phenoxy)-7-((2-(trimethylsilyl)ethoxy)methyl)-1H-purine-2,6(3H,7H)-dione (0.9 g, 70.0% yield) as a white solid. LCMS retention time 2.270 min, LCMS MH+-THP 531.

Step 2 1-(3-hydroxypropyl)-3-methyl-8-(3-(trifluoromethoxy)phenoxy)-1H-purine-2,6(3H,7H)-dione

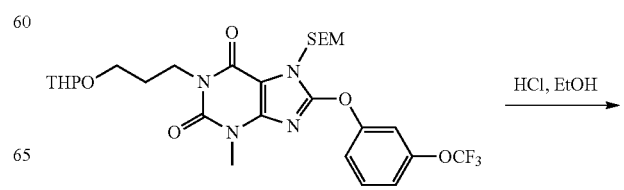

-continued

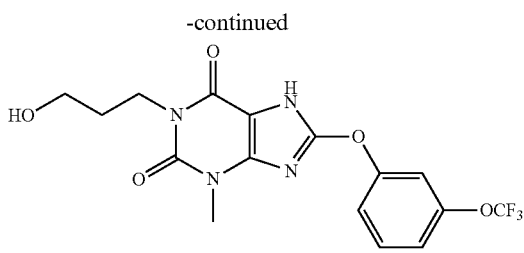

To a solution of 3-methyl-1-(3-(tetrahydro-2H-pyran-2-yloxy)propyl)-8-(3-(trifluoromethoxy)phenoxy)-7-((2-(trimethylsilyl)ethoxy)methyl)-1H-purine-2,6(3H,7H)-dione (0.9 g, 1.5 mmol) in ethanol (10 mL) was added HCl (2 mL), then it was refluxed overnight. The solvent was concentrated to give a crude product which was collected, washed with ethanol and dried in vacuo to give 1-(3-hydroxypropyl)-3-methyl-8-(3-(trifluoromethoxy)phenoxy)-1H-purine-2,6(3H,7H)-dione (0.5 g, 80% yield) as a white solid. $^1$H-NMR (DMSO-d6) δ 13.52 (br, 1H), 7.55-7.59 (t, 1H), 7.47 (s, 1H), 7.36-7.38 (d, 1H), 7.28-7.30 (d, 1H), 4.45 (br, 1H), 3.89-3.93 (t, 2H), 3.39-3.43 (t, 2H), 3.42 (s, 3H), 1.66-1.69 (m, 2H). LCMS retention time 1.308 min, LCMS MH$^+$ 401.

Intermediate 16 8-bromo-1-(3-hydroxypropyl)-3-methyl-7-((5-methylthiazol-2-yl)methyl)-1H-purine-2,6(3H,7H)-dione

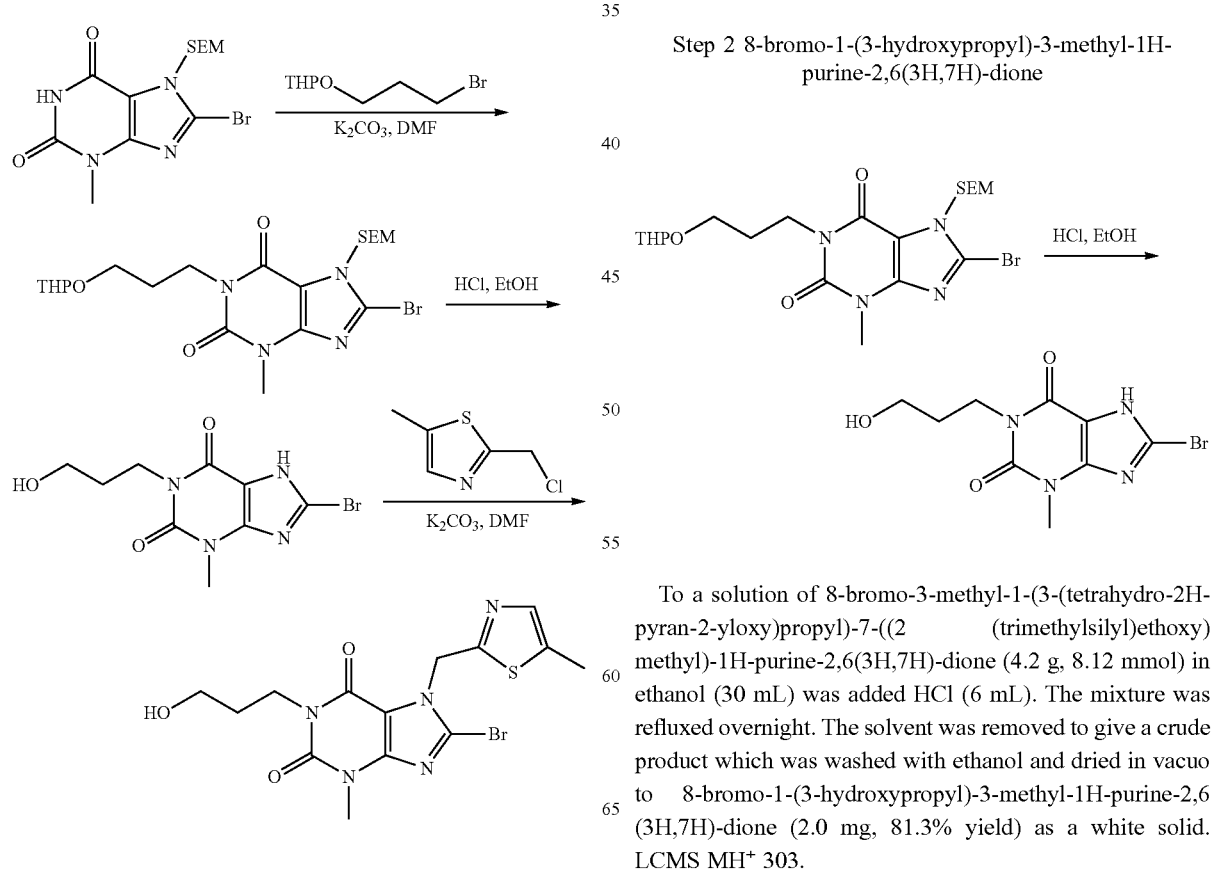

Step 1 8-bromo-3-methyl-1-(3-(tetrahydro-2H-pyran-2-yloxy)propyl)-7-((2 (trimethylsilyl)ethoxy)methyl)-1H-purine-2,6(3H,7H)-dione

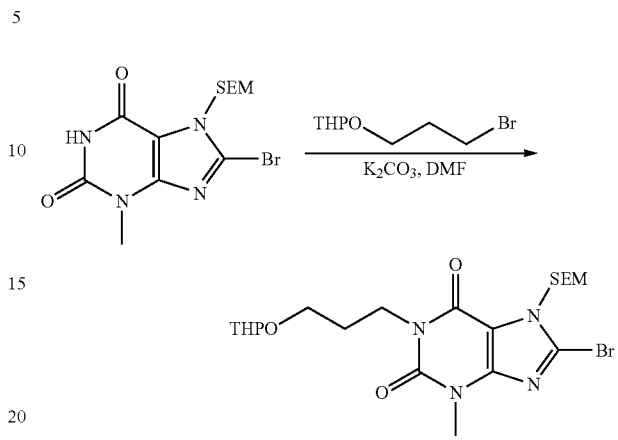

To a solution of 8-bromo-3-methyl-7-((2-(trimethylsilyl)ethoxy)methyl)-1H-purine-2,6(3H,7H)-dione (4.0 g, 10.6 mmol, intermediate 12 step 1) in DMF (50 mL) was added 2-(3-bromopropoxy)tetrahydro-2H-pyran (2.6 g, 11.6 mmol, intermediate 3), potassium carbonate (2.4 g, 17.4 mmol). It was heated at 60° C. overnight. The mixture was cooled, partitioned between ethyl acetate and water. The organic layers were combined, dried over sodium sulfate, filtered and concentrated to give a crude product (5.2 g, 94.5%) as a yellow oil which was used directly for the next step had LCMS MH$^+$ 518.

Step 2 8-bromo-1-(3-hydroxypropyl)-3-methyl-1H-purine-2,6(3H,7H)-dione

To a solution of 8-bromo-3-methyl-1-(3-(tetrahydro-2H-pyran-2-yloxy)propyl)-7-((2 (trimethylsilyl)ethoxy)methyl)-1H-purine-2,6(3H,7H)-dione (4.2 g, 8.12 mmol) in ethanol (30 mL) was added HCl (6 mL). The mixture was refluxed overnight. The solvent was removed to give a crude product which was washed with ethanol and dried in vacuo to 8-bromo-1-(3-hydroxypropyl)-3-methyl-1H-purine-2,6(3H,7H)-dione (2.0 mg, 81.3% yield) as a white solid. LCMS MH$^+$ 303.

307

Step 3 8-bromo-1-(3-hydroxypropyl)-3-methyl-7-((5-methylthiazol-2-yl)methyl)-1H-purine-2,6(3H,7H)-dione

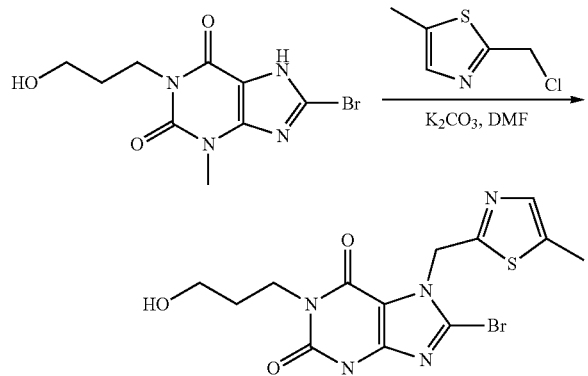

308

To a solution of 8-bromo-1-(3-hydroxypropyl)-3-methyl-1H-purine-2,6(3H,7H)-dione (0.5 g, 1.65 mmol) in DMF (50 mL) was added 2-(chloromethyl)-5-methylthiazole (0.27 g, 1.81 mmol, intermediate 4), potassium carbonate (0.34 g, 2.48 mmol) and TBAI (2 mg, 0.02 mmol). The mixture was heated at 60° C. for 3 h. The mixture was cooled; then partitioned between ethyl acetate and water. The organic layers were combined, dried over sodium sulfate, filtered and concentrated. The residue was purified by a column chromatography eluting with DCM/methanol (60:1 to 30:1) to give 8-bromo-1-(3-hydroxypropyl)-3-methyl-7-((5-methylthiazol-2-yl)methyl)-1H-purine-2,6(3H,7H)-dione (0.4 g, 58.4%) as a yellow oil which was used without further purification. LCMS MH+ 416.

Intermediate 17 3-methyl-1-(3-(tetrahydro-2H-pyran-2-yloxy)propyl)-8-(2-(3-(trifluoromethoxy)phenoxy)ethoxy)-1H-purine-2,6(3H,7H)-dione

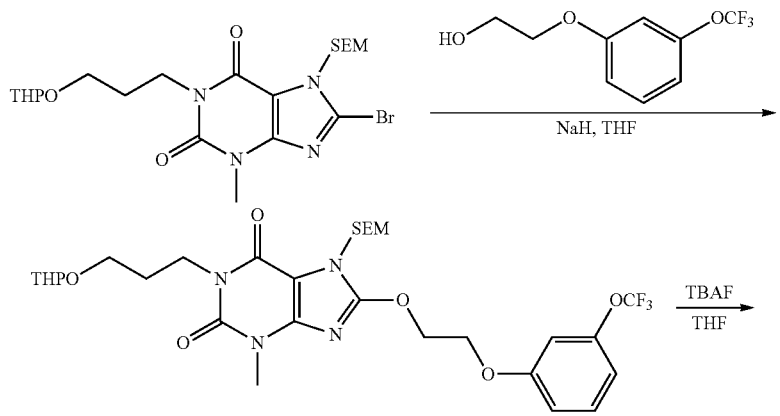

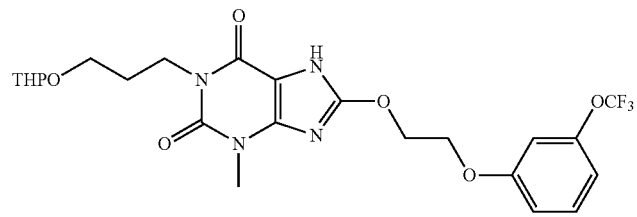

Step 1 3-methyl-1-(3-(tetrahydro-2H-pyran-2-yloxy)propyl)-8-(2-(3-(trifluoromethoxy)phenoxy)ethoxy)-7-((2-(trimethylsilyl)ethoxy)methyl)-1H-purine-2,6(3H,7H)-dione

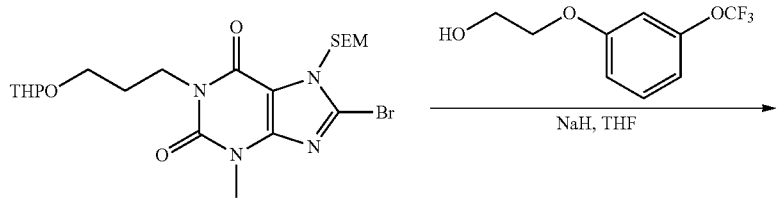

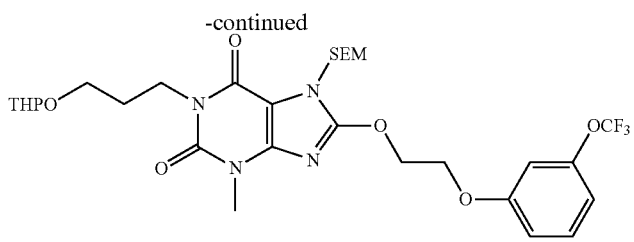

To a solution of 2-(3-(trifluoromethoxy)phenoxy)ethanol (0.64 g, 2.9 mmol, intermediate 5) in THF (15 mL) was added sodium hydride (0.23 g, 9.67 mmol) at 0° C. it was stirred at 0° C. for 30 min, then 8-bromo-3-methyl-1-(3-(tetrahydro-2H-pyran-2-yloxy)propyl)-7-((2-(trimethylsilyl)ethoxy)methyl)-1H-purine-2,6(3H,7H)-dione (1.0 g, 1.93 mmol, intermediate 16 step 1) was added. The mixture was stirred 16 h. The reaction was quenched with aq. ammonium chloride (2 mL) at 0° C.; then it was partitioned between ethyl acetate and water. The organic phases were combined, dried over sodium sulfate, filtered and concentrated to give a crude product which was used without purification. LCMS retention time 2.144; LCMS MH⁺-THP 575.

Step 2 3-methyl-1-(3-(tetrahydro-2H-pyran-2-yloxy)propyl)-8-(2-(3-(trifluoromethoxy)phenoxy)ethoxy)-1H-purine-2,6(3H,7H)-dione

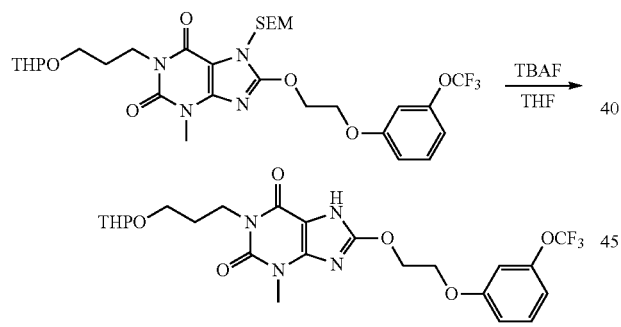

To a solution of 3-methyl-1-(3-(tetrahydro-2H-pyran-2-yloxy)propyl)-8-(2-(3-(trifluoromethoxy)phenoxy)ethoxy)-7-((2-(trimethylsilyl)ethoxy)methyl)-1H-purine-2,6(3H,7H)-dione (1.2 g, 1.82 mmol) in THF (15 mL) was added TBAF (3.7 mL, 3.64 mmol). The mixture was stirred at 80° C. overnight. Then it was cooled, partitioned between ethyl acetate and water. The organic layers were combined, washed with water, dried over sodium sulfate, filtered and concentrated to give a crude product which was purified by column chromatography eluting with petroleum ether and ethyl acetate (2:1) to give 3-methyl-1-(3-(tetrahydro-2H-pyran-2-yloxy)propyl)-8-(2-(3-(trifluoromethoxy)phenoxy)ethoxy)-1H-purine-2,6(3H,7H)-dione (900 mg, 93.7% yield) as a white solid. LCMS retention time 1.613; LCMS MH⁺-THP 445.

Intermediate 18 7-benzyl-8-chloro-1-(3-(tetrahydro-2H-pyran-2-yloxy)propyl)-3-((2-(trimethylsilyl)ethoxy)methyl)-1H-purine-2,6(3H,7H)-dione

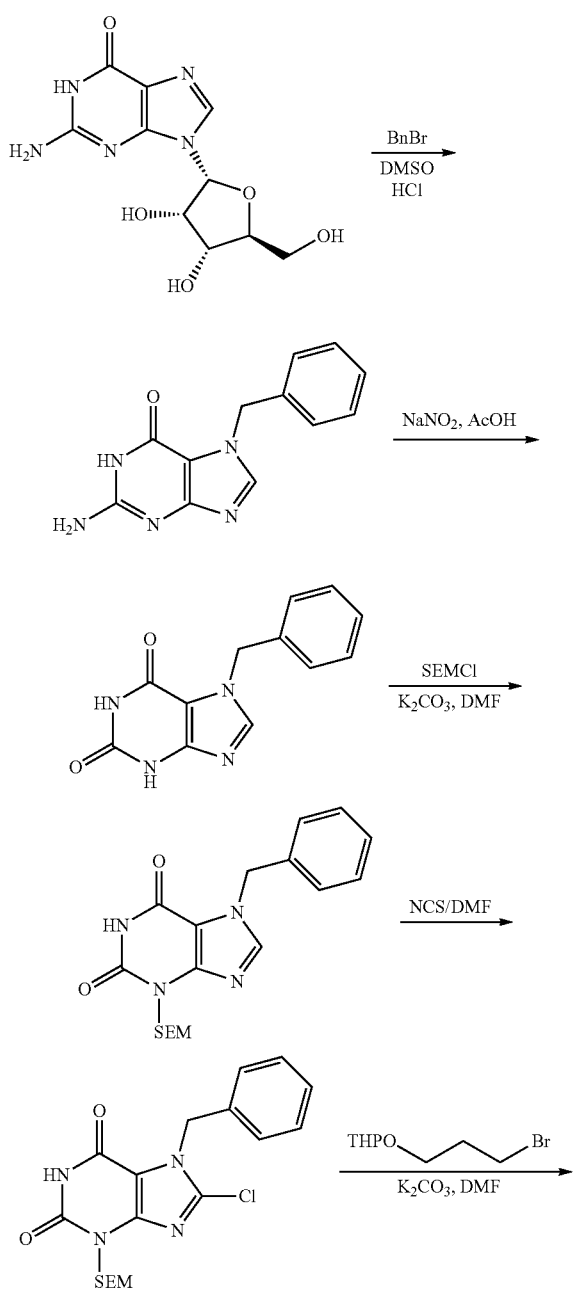

-continued

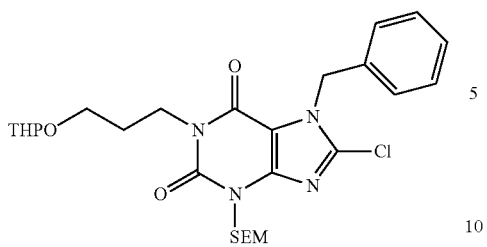

Step 1 2-amino-7-benzyl-1H-purin-6(7H)-one

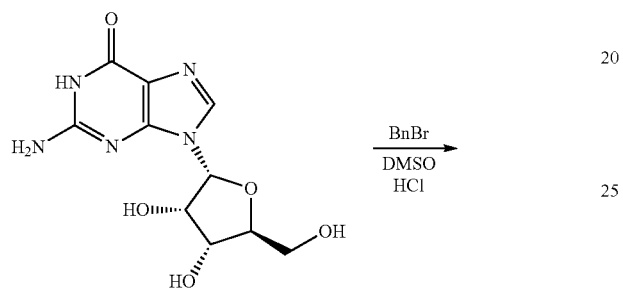

To a solution of 2-amino-9-((2R,3S,4R,5S)-3,4-dihydroxy-5-(hydroxymethyl)tetrahydrofuran-2-yl)-1H-purin-6(9H)-one (14 g, 49.47 mmol) in DMSO (50 mL) was added (bromomethyl)benzene (10 g, 59.36 mmol). The mixture was stirred at 50° C. overnight. Then the mixture was cooled to room temperature and HCl (50 mL, 10% w·w) was added and the mixture was stirred at 70° C. for 2 h. The reaction was cooled to room temperature, filtered and the filter cake was washed with water and ethanol and dried under vacuum to give 2-amino-7-benzyl-1H-purin-6(7H)-one (10 g, 74.2% yield) as grey solid. LCMS retention time 0.529 min; LCMS MH⁺ 242.

Step 2 2-amino-7-benzyl-1H-purin-6(7H)-one

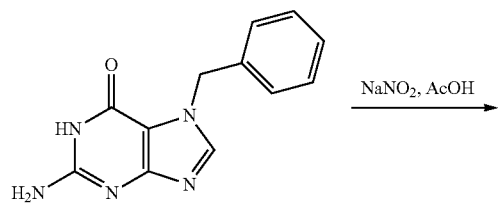

-continued

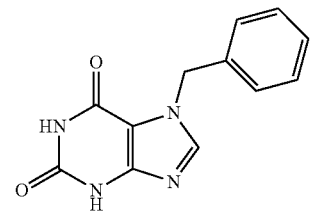

To a solution of 2-amino-7-benzyl-1H-purin-6(7H)-one (6.8 g, 28.33 mmol) in acetic acid (80 mL) and water (10 mL) was added a solution of sodium nitrite (1.95 g, 28.26 mmol) in water (10 mL) at 50° C. dropwise, the mixture was stirred at 50° C. for 1 h. Then the mixture was cooled to room temperature and stirred for another 1.5 h. The mixture was filtered; then the filter cake was washed with water and ethanol, dried in vacuo to give 2-amino-7-benzyl-1H-purin-6(7H)-one (6.5 g, 94.9% yield) as yellow solid. LCMS retention time 0.502 min; LCMS MH⁺ 243.

Step 3 7-benzyl-3-((2-(trimethylsilyl)ethoxy)methyl)-1H-purine-2,6(3H,7H)-dione

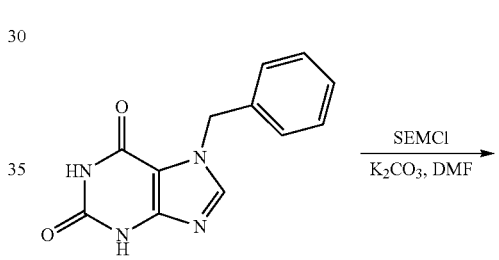

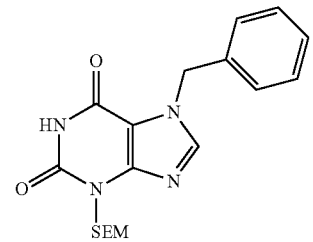

To a solution of 2-amino-7-benzyl-1H-purin-6(7H)-one (6.5 g, 26.86 mmol) in DMF (50 mL) was added potassium carbonate (5.6 g, 40.58 mmol), followed by 2-(trimethylsilyl)ethoxymethyl chloride (4.45 g, 27.08 mmol) at 0° C. The resulting mixture was stirred at 60° C. for 16 h. The mixture was diluted with water and filtered. The filter cake was washed with water twice, dried in vacuo to give 7-benzyl-3-((2-(trimethylsilyl)ethoxy)methyl)-1H-purine-2,6(3H,7H)-dione (10.8 g, 100% yield) as yellow oil. LCMS retention time 1.523 min; LCMS MH⁺-58 315.

Step 4 7-benzyl-8-chloro-3-((2-(trimethylsilyl)ethoxy)methyl)-1H-purine-2,6(3H,7H)-dione

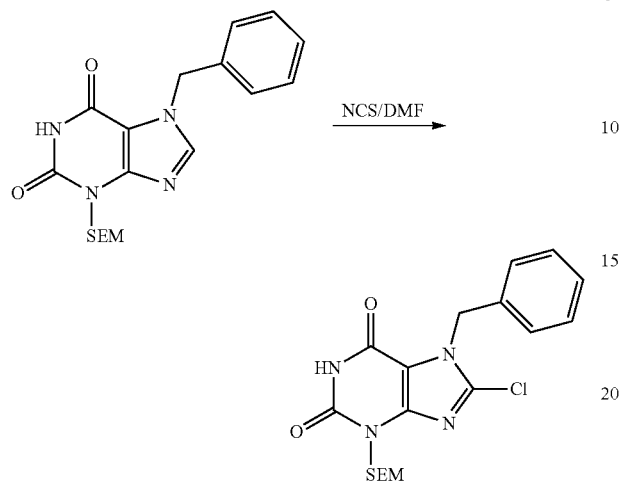

To a solution of 7-benzyl-3-((2-(trimethylsilyl)methyl)-1H-purine-2,6(3H,7H)-dione (6.0 g, 16.13 mmol) in DMF (50 mL) was added NCS (3.23 g, 24.19 mmol) and the resulting mixture was stirred at room temperature for 8 h. The mixture was diluted with ethyl acetate and water, and the phases were separated. The organic phase was washed with brine, dried over sodium sulfate, filtered and concentrated to give 7-benzyl-8-chloro-3-((2-(trimethylsilyl)ethoxy)methyl)-1H-purine-2,6(3H,7H)-dione (5.1 g, 77.9% yield) as light yellow oil. Product tlc [petroleum ether/ethyl acetate (15:1) iodine detection, Rf 0.6)

Step 5 7-benzyl-8-chloro-1-(3-(tetrahydro-2H-pyran-2-yloxy)propyl)-3-((2-(trimethylsilyl)ethoxy)methyl)-1H-purine-2,6(3H,7H)-dione

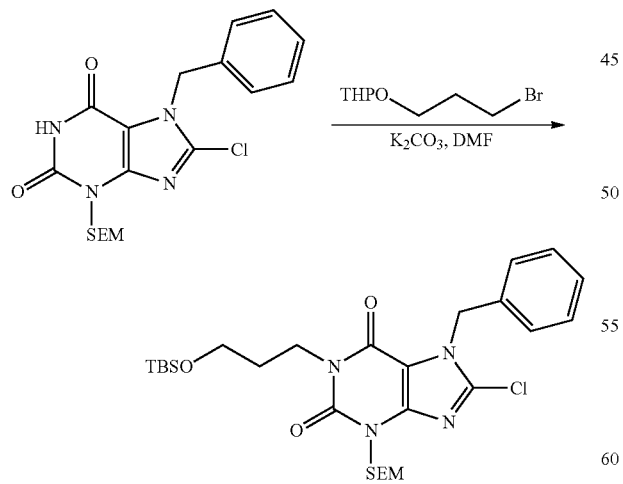

To a solution of 7-benzyl-8-chloro-3-((2-(trimethylsilyl)ethoxy)methyl)-1H-purine-2,6(3H,7H)-dione (5 g, 12.32 mmol) in DMF (30 mL) was added 2-(3-bromopropoxy)tetrahydro-2H-pyran (3.60 g, 16.22 mmol, intermediate 14 step 1), followed by potassium carbonate (3.4 g, 24.64 mmol). The mixture was stirred at 65° C. overnight. The mixture was diluted with ethyl acetate and water, and the phases were separated. The organic phase was washed with brine, dried over sodium sulfate, filtered and concentrated to give 7-benzyl-8-chloro-1-(3-(tetrahydro-2H-pyran-2-yloxy)propyl)-3-((2-(trimethylsilyl)ethoxy)methyl)-1H-purine-2,6(3H,7H)-dione (6.3 g, 93.3% yield) as yellow oil. LCMS retention time 3.574 min; LCMS MNa+ 571.

Intermediate 19
1-(4-(bromomethyl)phenyl)ethanone

To a solution of 1-p-tolylethanone (600 mg, 4.47 mmol) in carbon tetrachloride (15 mL) was added N-bromosuccinimide (955 mg, 5.37 mmol) and BPO (31 mg, 0.13 mmol). The mixture was refluxed for 3 h; then it was cooled, and filtered. The filtrate was concentrated to give 1-(4-(bromomethyl)phenyl)ethanone (683 mg, 71%) as a brown oil. LCMS MH+ 213.

Intermediate 20
2-(3-(4-methyloxazol-2-yl)phenyl)acetic acid

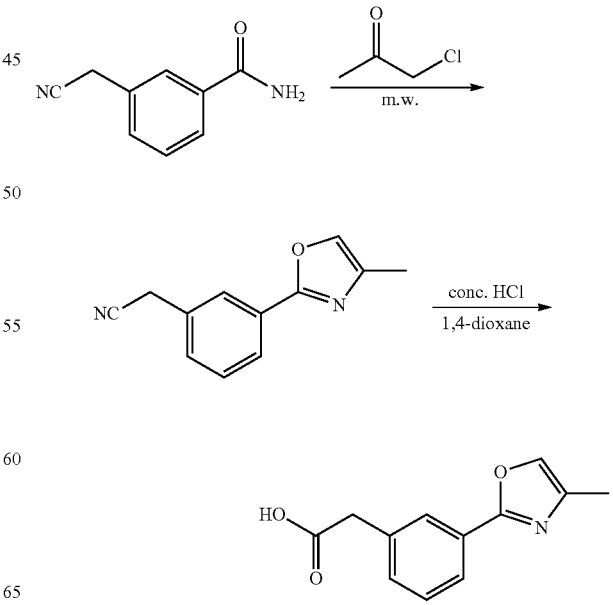

Step 1
2-(3-(4-methyloxazol-2-yl)phenyl)acetonitrile

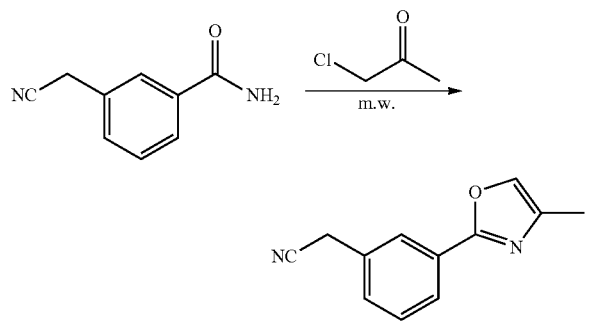

A solution of 3-(cyanomethyl)benzamide (200 mg, 1.25 mmol) in 1-chloropropan-2-one (2 mL) was microwave irradiated at 120 □ for 20 min in a sealed tube. The mixture was concentrated to give crude product (110 mg), which was directly used to the next reaction without purification. LCMS MH⁺ 199.

Step 2 2-(3-(4-methyloxazol-2-yl)phenyl)acetic acid

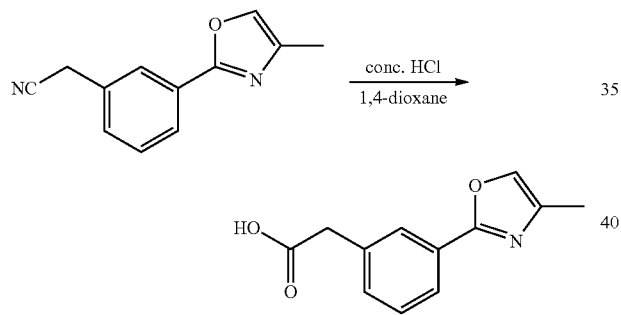

To a solution of 2-(3-(4-methyloxazol-2-yl)phenyl)acetonitrile (110 mg, 0.555 mmol) in 1,4-dioxane (3 mL) was added 6N HCl (1 mL). Then the mixture was stirred at 80° C. for 2 h. The mixture was concentrated and purified via silica gel chromatography eluted with DCM/methanol (20:1) to give 2-(3-(4-methyloxazol-2-yl)phenyl)acetic acid (85 mg, 70.5%) as yellow syrup. LCMS retention time 0.920 min, LCMS MH⁺ 218.

Intermediate 21 1-(4-chlorophenyl)ethyl methanesulfonate

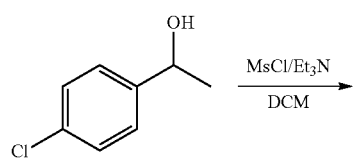

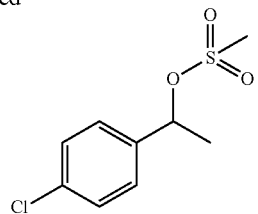

The title compound was prepared using the method of intermediate 34 to give 1-(4-chlorophenyl)ethyl methanesulfonate (258 mg, 23.6% yield) as yellow oil, which was directly used to the next reaction without purification.

Intermediate 22 2-(bromomethyl)-5-methylthiazole

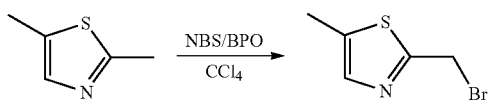

To a solution of 2,5-dimethylthiazole (200 mg, 1.77 mmol) in carbon tetrachloride (5 mL) was added NBS (377 mg, 2.12 mmol), followed by BPO (20 mg, 0.083 mmol). Then the mixture was heated to reflux for 4 h with stirring. The mixture was cooled to room temperature and filtered, the filtrate was concentrated to give crude product 2-(bromomethyl)-5-methylthiazole (260 mg, 76.9%) as yellow oil, which was used without purification.

Intermediate 23 2-(chloromethyl)thiazole

Step 1 thiazol-2-ylmethanol

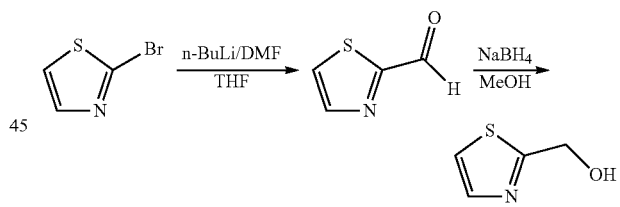

To a solution of n-BuLi (8.4 ml, 1.6 mol/1, 13.4 mmol) in THF (30 mL) was added 2-bromothiazole (377 mg, 2.12 mmol) dropwise under nitrogen atmosphere at −70° C., and the mixture was stirred at the temperature for 1 h. Then DMF (1.4 ml, 18.3 mmol) was added into the solution dropwise under nitrogen atmosphere at −70° C. The resulting mixture was stirred at the temperature for 1 h. Then the mixture was quenched with aqueous saturated ammonium chloride, diluted with ethyl acetate and water, and the phases were separated. The organic phase was washed with brine, dried over sodium sulfate, filtered and concentrated to give yellow oil. The yellow oil was dissolved in methanol (15 ml), cooled to −60° C., and sodium borohydride (463 mg, 12.2 mmol) was added portionwise under nitrogen atmosphere. The mixture was stirred at the temperature for 1 h. The reaction was quenched with acetone and concentrated. The residue was diluted with ethyl acetate and water, and the phases were separated. The organic layer was dried over sodium sulfate, filtered and concentrated, then purified by silica gel chromatography eluting with petroleum/ethyl acetate=3:1 to give thiazol-2-ylmethanol (230 mg, 16.4% yield) as brown oil. LCMS MH+ 116.

Step 2 2-(chloromethyl)thiazole

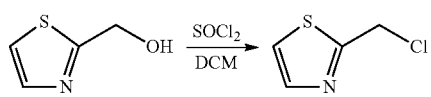

To a solution of thiazol-2-ylmethanol (230 mg, 2.0 mmol) in DCM (5 mL) was added thionyl chloride (0.19 ml, 2.6 mmol) at 0° C. and the mixture was stirred at room temperature for 1 h. The mixture was diluted with DCM and water, and the phases were separated. The organic layer was dried over sodium sulfate, filtered and concentrated to give 2-(chloromethyl)thiazole (240 mg, crude), which was used without purification.

Intermediate 24
5-(chloromethyl)-2-methylpyrimidine

Step 1 (2-methylpyrimidin-5-yl)methanol

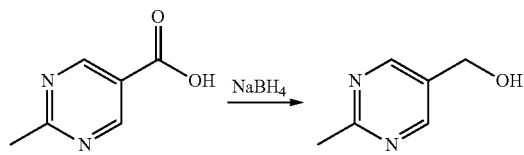

To a solution of 2-methylpyrimidine-5-carboxylic acid (150 mg, 1.23 mm01) in ethanol (5 mL) was added sodium borohydride (93 mg, 2.46 mmol). The mixture was stirred at room temperature for 3 h. It was quenched with aqueous HCl (2 N, 2 mL), extracted with DCM, dried over sodium sulfate, filtered and concentrated give the yellow oil product (2-methylpyrimidin-5-yl)methanol (95 mg, 62.6%). LCMS MH+ 125.

Step 2 5-(chloromethyl)-2-methylpyrimidine

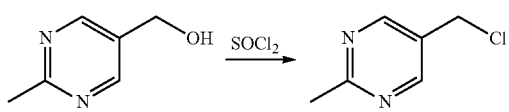

A solution of (2-methylpyrimidin-5-yl)methanol (95 mg, 0.77 mmol) in thionyl chloride (1 mL) was stirred at room temperature for 1 h. The mixture was concentrated to dryness and used without purification. LCMS MH+ 143.

Intermediate 25 3-(4-methyloxazol-2-yl)phenol

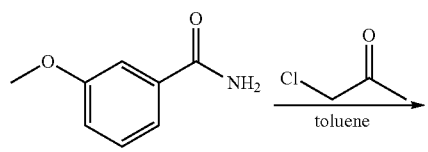

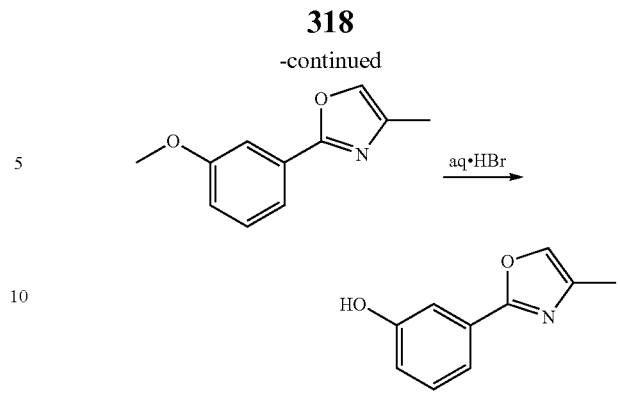

Step 1 2-(3-methoxyphenyl)-4-methyloxazole

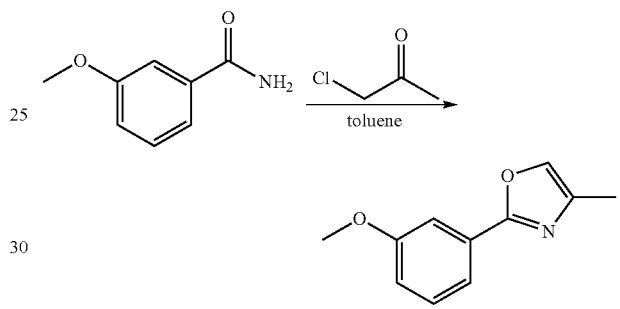

To a solution of 3-methoxybenzamide (1.5 g, 9.9 mmol) in toluene (15 mL) was added 1-chloropropan-2-one (1.37 g, 14.9 mmol), and the mixture was stirred at reflux for 16 h. The mixture was cooled and concentrated to give crude product, which was purified via silica gel chromatography eluted with ethyl acetate/petroleum ether (1:5) to give 2-(3-methoxyphenyl)-4-methyloxazole (1.21 g, 64.6% yield) as yellow syrup. LCMS MH+ 190.

Step 2 3-(4-methyloxazol-2-yl)phenol

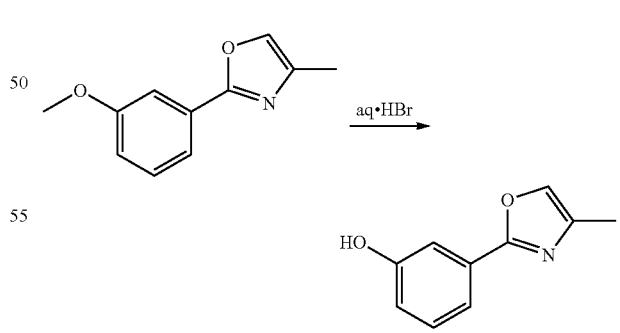

A solution of 2-(3-methoxyphenyl)-4-methyloxazole (1.1 g, 5.79 mmol) in aqueous hydrogen bromide (10 mL, 48% w/w) was heated to 100° C. for 16 h. The mixture was concentrated to give 3-(4-methyloxazol-2-yl)phenol (0.97 g, crude), which was used without purification. LCMS MH+ 176.

Intermediate 26 8-ethoxy-3-ethyl-1-(3-hydroxypropyl)-1H-purine-2,6(3H,7H)-dione

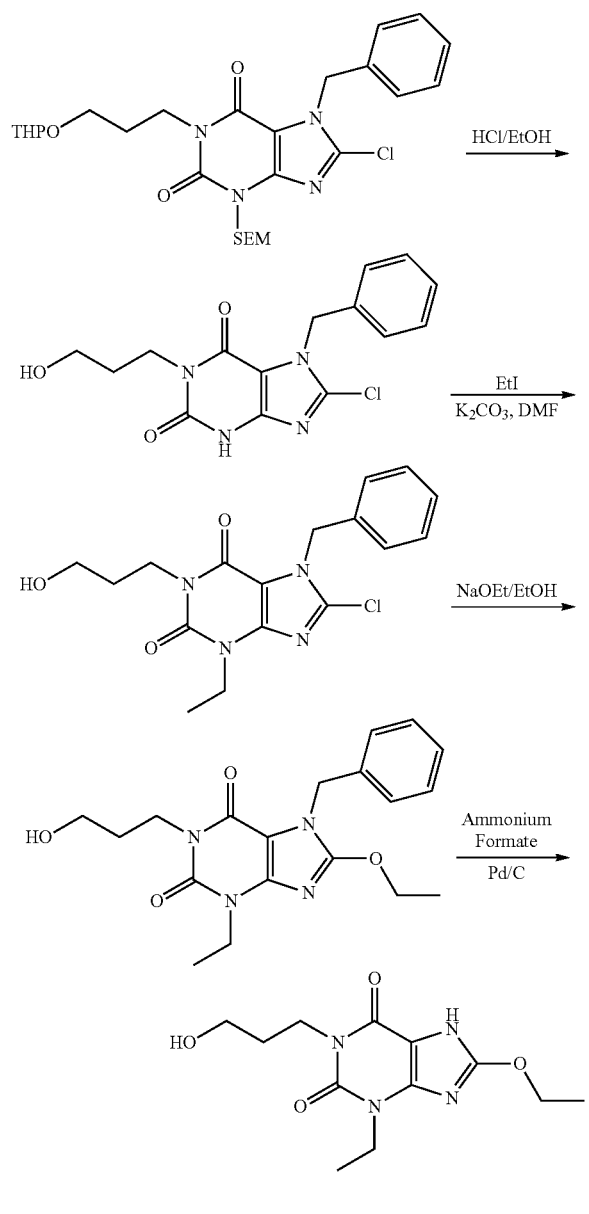

Step 1 7-benzyl-8-chloro-1-(3-hydroxypropyl)-1H-purine-2,6(3H,7H)-dione

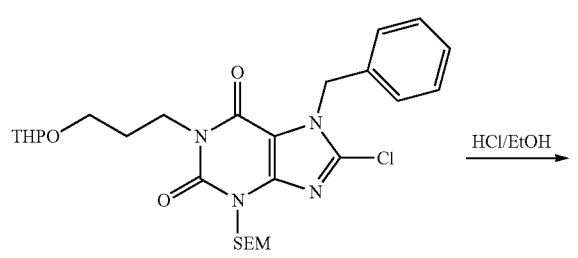

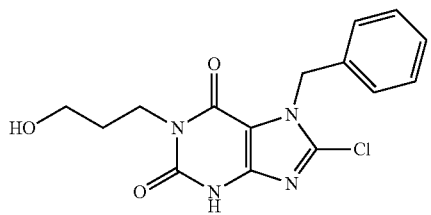

To a solution of 7-benzyl-8-chloro-1-(3-(tetrahydro-2H-pyran-2-yloxy)propyl)-3-((2-(trimethylsilyl)ethoxy)methyl)-1H-purine-2,6(3H,7H)-dione (500 mg, 0.912 mmol, intermediate 18) in ethyl alcohol (20 mL) was added concentrated HCl (5 mL). The mixture was stirred at 80° C. overnight. Then the mixture was concentrated, neutralized with saturated sodium bicarbonate and extracted with ethyl acetate. The organic phase was washed with brine, dried over sodium sulfate, filtered and concentrated to give 7-benzyl-8-chloro-1-(3-hydroxypropyl)-1H-purine-2,6(3H,7H)-dione (280 mg, 91.9% yield) as yellow oil. LCMS retention time 1.710 min; LCMS MH+ 335.

Step 2 7-benzyl-8-chloro-3-ethyl-1-(3-hydroxypropyl)-1H-purine-2,6(3H,7H)-dione

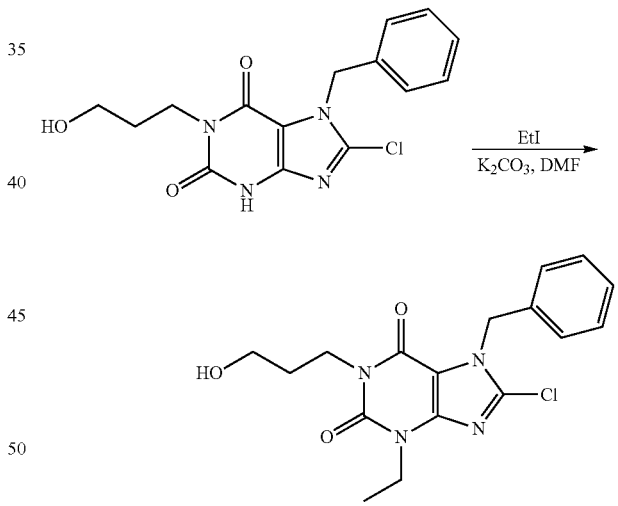

To a solution of 7-benzyl-8-chloro-1-(3-hydroxypropyl)-1H-purine-2,6(3H,7H)-dione (150 mg, 0.449 mmol) in DMF (5 mL) was added iodoethane (0.16 g, 0.13 mmol), followed by potassium carbonate (0.4 g, 2.90 mmol). The mixture was stirred at 40° C. for 4 h. The reaction was cooled and diluted with ethyl acetate. The organic phase was washed with water and brine; then it was dried over sodium sulfate, filtered and concentrated to give 7-benzyl-8-chloro-3-ethyl-1-(3-hydroxypropyl)-1H-purine-2,6(3H,7H)-dione (0.15 g, 92.3% yield) as yellow oil. LCMS retention time 1.296 min; LCMS MH+ 363.

Step 3 7-benzyl-8-ethoxy-3-ethyl-1-(3-hydroxypropyl)-1H-purine-2,6(3H,7H)-dione

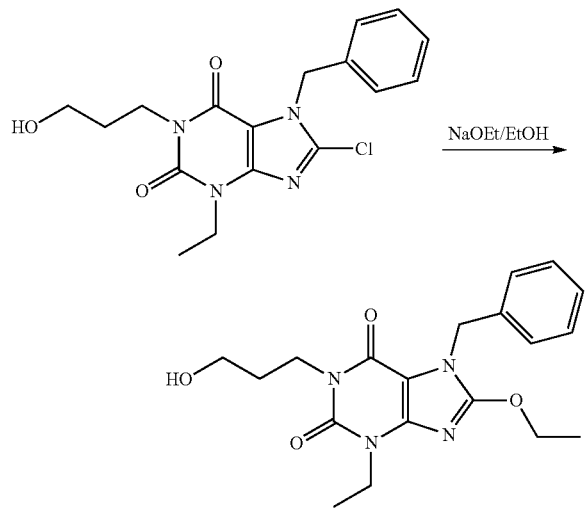

A solution of sodium (50 mg, 2.17 mmol) in ethyl alcohol (10 mL) was stirred at 40° C. under nitrogen until the sodium was consumed. Then 7-benzyl-8-chloro-3-ethyl-1-(3-hydroxypropyl)-1H-purine-2,6(3H,7H)-dione (150 mg, 0.414 mmol) was added at 0° C. and the mixture was stirred at 40° C. for 4 h. The mixture was quenched with ice-water (15 mL) and concentrated. The aqueous residue was extracted with ethyl acetate. The organic phase was dried over sodium sulfate, filtered and concentrated to give 7-benzyl-8-ethoxy-3-ethyl-1-(3-hydroxypropyl)-1H-purine-2,6 (3H,7H)-dione (120 mg, 77.9% yield) as yellow solid. LCMS retention time 1.488 min; LCMS MH+ 373.

Step 4 8-ethoxy-3-ethyl-1-(3-hydroxypropyl)-1H-purine-2,6(3H,7H)-dione

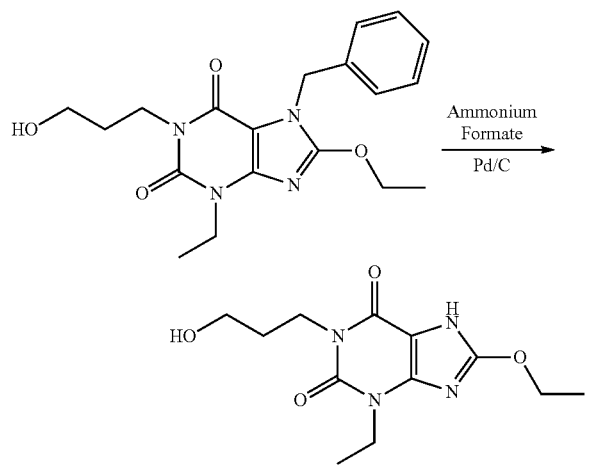

7-benzyl-8-ethoxy-3-ethyl-1-(3-hydroxypropyl)-1H-purine-2,6(3H,7H)-dione (0.12 g, 0.323 mmol) was dissolved in ethanol (20 mL) and the mixture was degassed and refilled with nitrogen three times. Ammonium formate (0.5 g, 7.94 mmol) and 10% Pd/C (30 mg) were added. The mixture was again degassed and refilled with nitrogen three times; then it was warmed to 80° C. and stirred overnight. The mixture was cooled and filtered, and the filter cake was washed with methanol. The filtrate was concentrated to give 8-ethoxy-3-ethyl-1-(3-hydroxypropyl)-1H-purine-2,6(3H,7H)-dione (70 mg, 77.1% yield) as white solid. LCMS retention time 0.413 min; LCMS MH+ 283.

Intermediate 27 3-(morpholinomethyl)phenol

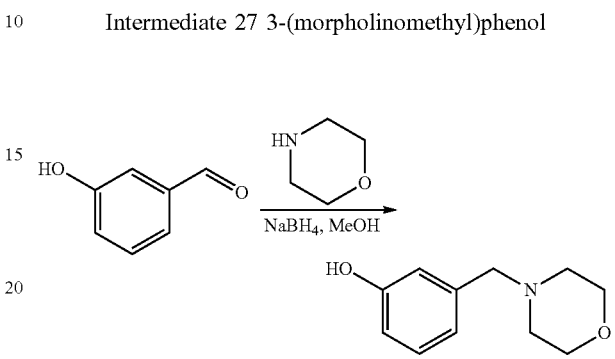

To a solution of 3-hydroxybenzaldehyde (1 g, 8.19 mmol) in methanol (15 mL) was added morpholine (1.42 g, 16.4 mmol). Then the mixture was stirred at room temperature for 1 h. The mixture was cooled to −5° C., and sodium borohydride (403 mg, 10.6 mmol) was added in small portions. The resulting mixture was stirred at room temperature for 4 h. The mixture was quenched with diluted hydrochloride acid and concentrated. The aqueous solution was washed with ethyl acetate and then made basic by addition of ammonium hydroxide. The basic aqueous slurry was extracted with ethyl acetate and this organic layer was dried and concentrated to give 3-(morpholinomethyl)phenol (0.76 g, 48.2%) as white solid. LCMS retention time 0.871 min, LCMS MH+ 194.

Intermediate 28a and 28b 2-chloro-5-hydroxybenzaldehyde (28a) and 4-chloro-3-hydroxybenzaldehyde (28b)

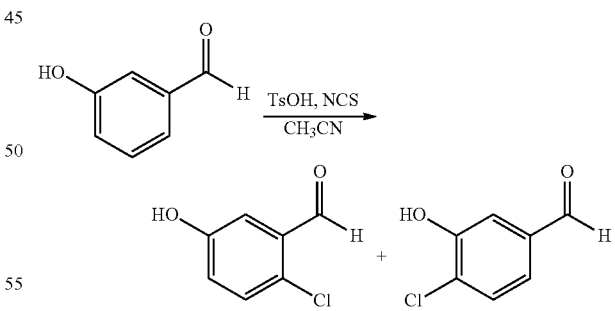

To a solution of 3-hydroxybenzaldehyde (1 g, 10 mmol) in acetonitrile (50 mL) was added p-toluenesulfonic acid (3.4 g, 20 mmol) portionwise. The mixture was stirred at room temperature for 5 min, and NCS (1.33 g, 10 mmol) was added and the resulting mixture was stirred at room temperature for 2 h. The mixture was quenched with aqueous sodium thiosulfate, and diluted with ethyl acetate and brine. The organic layer was separated, dried, and concentrated to give the crude products which were purified by silica gel chromatography eluting with petroleum ether/ethyl acetate (10:1 to 5:1) to give 2-chloro-5-hydroxybenzaldehyde (340 mg, 21.7% yield intermediate 28a) as yellow solid; $^1$H-NMR (CDCl$_3$) δ 10.43 (s, 1H), 7.54-7.56 (d, 1H), 7.30-7.37 (m, 2H) and 4-chloro-3-hydroxybenzaldehyde (310 mg, 19.7% yield, intermediate 28b) as yellow solid. $^1$H-NMR (CDCl$_3$) δ 10.43 (s, 1H), 7.40 (d, 1H), 7.33 (d, 1H), 7.06-7.09 (dd, 1H).

Intermediate 29
4-chloro-3-(morpholinomethyl)phenol

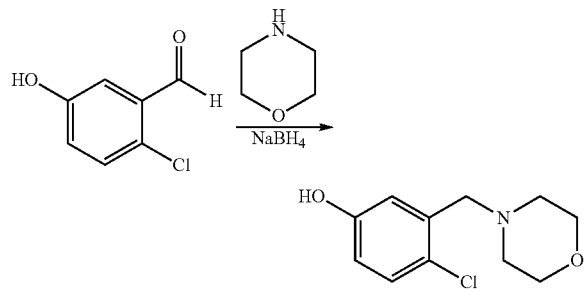

To a mixture of 2-chloro-5-hydroxybenzaldehyde (200 mg, 1.27 mmol, intermediate 28a) and morpholine (280 mg, 3.21 mmol) in methanol (10 mL) was added 2 drops of acetic acid and the mixture was stirred at room temperature for 2 h. To the mixture, sodium borohydride (97 mg, 2.56 mmol) was added and the resulting mixture was stirred at room temperature for 4 h. The mixture was quenched with dilute hydrochloride acid and concentrated to give crude product. This crude material was purified by silica gel chromatography eluting with petroleum ether/ethyl acetate (5:1 to 1:1) to give 4-chloro-3-(morpholinomethyl)phenol (150 mg, 51.8% yield) as white solid. LCMS retention time 0.378; LCMS MH$^+$ 228.

Intermediate 30
4-chloro-3-(morpholinomethyl)phenol

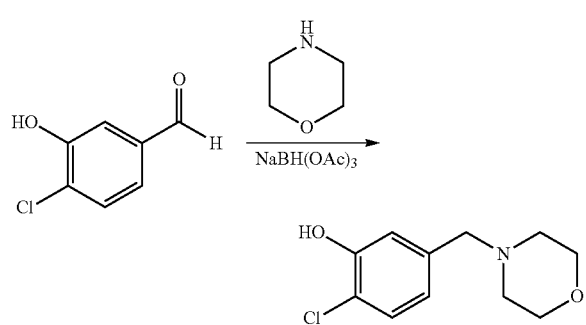

The title compound was prepared using the method of intermediate 29 starting with intermediate 28b but using sodium triacetoxyborohydride as the reducing agent to give 4-chloro-3-(morpholinomethyl)phenol (190 mg, 68.1% yield) as yellow solid. LCMS retention time 0.347; LCMS MH$^+$ 228.

Intermediate 31 3-(chloromethyl)-5-methylisoxazole

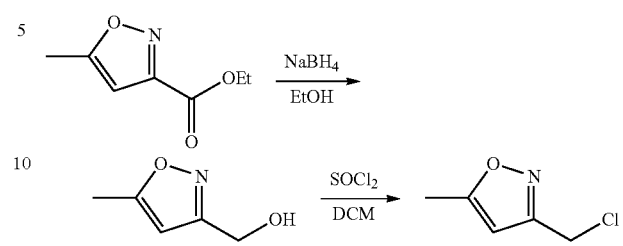

Step 1 (5-methylisoxazol-3-yl)methanol

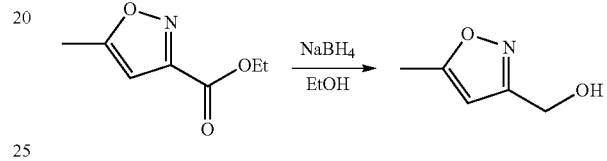

To a solution of ethyl 5-methylisoxazole-3-carboxylate (500 mg, 3.22 mmol) in ethanol (8 mL) was added sodium borohydride (244 mg, 6.44 mmol) in portions at 0° C. After addition, the mixture was stirred at room temperature for 16 h. The mixture was quenched with diluted hydrochloride acid. The mixture was extracted with ethyl acetate. The organic phase was washed with brine, dried and concentrated to give (5-methylisoxazol-3-yl)methanol (370 mg, 100% yield) as yellow oil, which was used directly in the next reaction without purification. LCMS retention time 0.391 min; LCMS MH$^+$ 114.

Step 2 3-(chloromethyl)-5-methylisoxazole

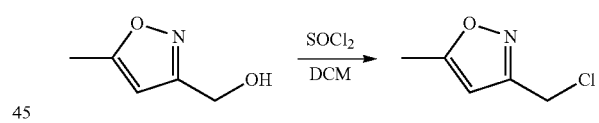

To a solution of (5-methylisoxazol-3-yl)methanol (370 mg, 3.27 mmol) in DCM (5 mL) was added thionyl chloride (5 mL) dropwise. The resulting mixture was stirred at room temperature for 16 h. The mixture was concentrated to give 3-(chloromethyl)-5-methylisoxazole (350 mg, crude) as brown oil, which was used without purification. LCMS retention time 0.768 min; LCMS MH$^+$ 132.

Intermediate 32 2-(2-ethyl-1,3-dioxolan-2-yl)ethyl methanesulfonate

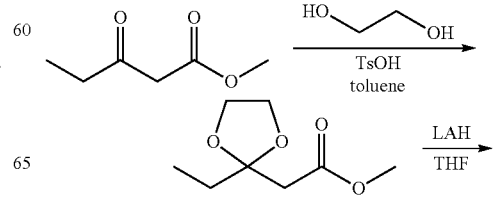

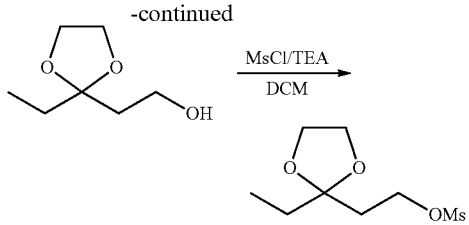

Step 1 methyl 2-(2-ethyl-1,3-dioxolan-2-yl)acetate

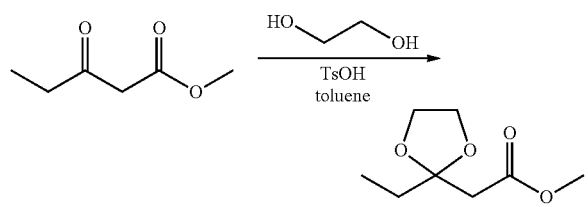

To a solution of methyl 3-oxopentanoate (3 g, 23.1 mmol) in toluene (30 mL) was added ethane-1,2-diol (3 mL, 70.2 mmol) and p-toluenesulfonic acid (500 mg, 2.91 mmol), the resulting mixture was stirred at 120° C. overnight. Then the mixture was concentrated and partitioned between ethyl acetate and aqueous saturated sodium bicarbonate solution. The phases were separated and the aqueous layer was extracted with ethyl acetate. The combined organic phase was washed with brine and dried over sodium sulfate; then it was filtered and concentrated to give methyl 2-(2-ethyl-1,3-dioxolan-2-yl)acetate (1.7 g, 42.5%) as yellow oil which was used without purification. Product tlc [petroleum ether/ethyl acetate (15:1) developed with iodine, Rf 0.6]

Step 2 2-(2-ethyl-1,3-dioxolan-2-yl)ethanol

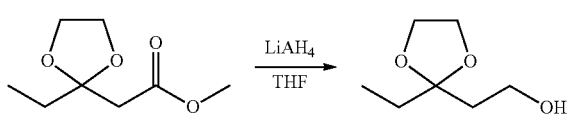

To a solution of methyl 2-(2-ethyl-1,3-dioxolan-2-yl)acetate (1 g, 5.75 mmol) in anhydrous THF (40 mL) was added LAH (900 mg, 23.7 mmol) at 0° C. under nitrogen atmosphere, the resulting mixture was stirred at 90° C. overnight. The mixture was cooled to room temperature, and ethyl acetate was added to the mixture. The resulting slurry was filtered and the filtrate was concentrated to dryness. The crude product was purified by silica gel chromatography eluting with DCM/methanol (100:1 to 20:1) to give 2-(2-ethyl-1,3-dioxolan-2-yl)ethanol (233 mg, 27.4%) as yellow oil that was used without purification.

Step 3 2-(2-ethyl-1,3-dioxolan-2-yl)ethyl methanesulfonate

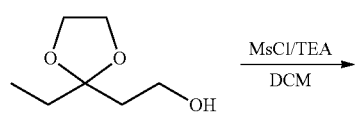

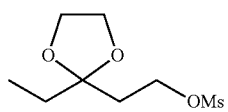

To a solution of 2-(2-ethyl-1,3-dioxolan-2-yl)ethanol (233 mg, 1.59 mmol) and TEA (327 mg, 3.2 mmol) in DCM (10 mL) was added methanesulfonyl chloride (0.23 ml, 2.92 mmol) at 0° C. The resulting mixture was stirred at room temperature for 3 h. The mixture was diluted with DCM and water, and the phases were separated. The organic phase was washed with brine, dried over sodium sulfate, filtered and concentrated to give 2-(2-ethyl-1,3-dioxolan-2-yl)ethyl methanesulfonate (500 mg, 100%) as yellow oil that was used without purification. Product tlc [DCM/methanol (100:1) developed with potassium permanganate, Rf 0.6]

Intermediate 33 3-hydroxybutyl 4-methylbenzenesulfonate

To a solution of butane-1,3-diol (1 g, 11.1 mmol), TEA (4.6 mL, 33.2 mmol) and DMAP (30 mg, 0.25 mmol) in DCM (20 mL) was added p-toluenesulfonyl chloride (2.75 g, 14.4 mmol) at 0° C. The resulting mixture was stirred at room temperature for 16 h. The mixture was diluted with DCM and water, and the phases were separated. The organic phase was washed with brine, dried over sodium sulfate, filtered and concentrated to give 3-hydroxybutyl 4-methylbenzenesulfonate (3 g, 100% yield) as yellow oil, which was used without purification. Product tlc [DCM/methanol (100:1) developed with potassium permanganate, Rf 0.4]

Intermediate 34 2-(2-methoxyethoxy)ethyl methanesulfonate

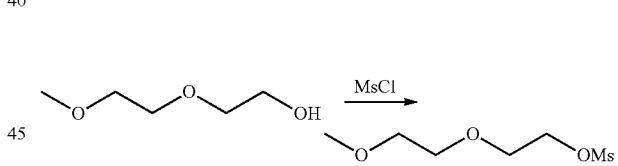

To a solution of 2-(2-methoxyethoxy)ethanol (300 mg, 2.5 mmol) in DCM (5 mL) was added methanesulfonyl chloride (370 mg, 2.6 mmol) dropwise at 0° C. After stirred at this temperature for 5 min, TEA (505 mg, 5.0 mmol) was added. It was stirred at room temperature overnight. The mixture was partitioned between DCM and water. The organic layers were combined, dried over sodium sulfate, filtered and concentrated to give a crude oil product, which was used without purification. Product tlc [petroleum ether/ethyl acetate [1:1] developed with iodine, Rf 0.5]

Intermediate 35 3-(3-(trifluoromethoxy)phenoxy)propan-1-ol

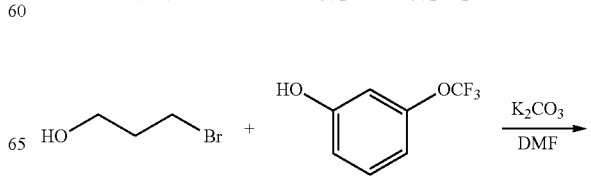

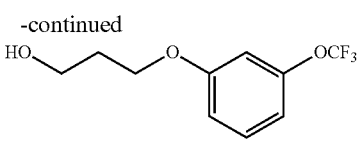

To a solution of 3-(trifluoromethoxy)phenol (0.3 g, 1.68 mmol) in DMF (10 mL) was added 3-bromopropan-1-ol (0.47 g, 3.37 mmol) and potassium carbonate (0.47 g, 3.37 mmol). The reaction was heated at 80° C. overnight. The mixture was cooled and partitioned between ethyl acetate and water. The organic layer was dried over sodium sulfate, filtered and concentrated to give a crude product which was purified by column chromatography eluting with petroleum ether and ethyl acetate (10:1) to give 3-(3-(trifluoromethoxy)phenoxy)propan-1-ol (0.32 g, 80.6% yield) as yellow oil.

Intermediate 36 3-(2-hydroxyethoxy)benzaldehyde

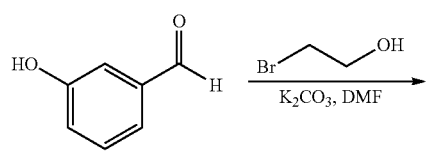

The title compound was prepared using the method of intermediate 5 except the reaction was carried out at 140° C. to give 3-(2-hydroxyethoxy)benzaldehyde (1.1 g, 73.4% yield) as yellow oil which was used without purification. $^1$H-NMR (DMSO-d$_6$) δ 9.98 (s, 1H), 7.53-7.51 (m, 2H), 7.44-7.43 (m, 1H), 7.30-7.29 (m, 1H), 4.95-4.93 (t, 1H), 4.08-4.06 (t, 2H), 3.77-3.73 (q, 2H)

Intermediate 37
3-(3-(trifluoromethoxy)phenyl)propan-1-ol

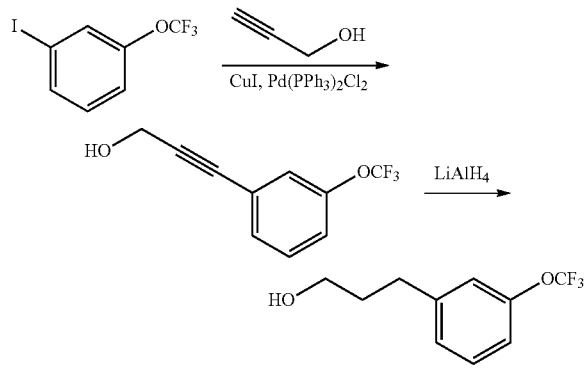

Step 1
3-(3-(trifluoromethoxy)phenyl)prop-2-yn-1-ol

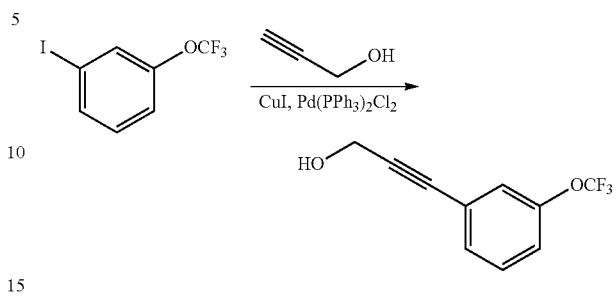

To a solution of 1-iodo-3-(trifluoromethoxy)benzene (0.5 g, 1.73 mmol) in toluene (10 mL) was added prop-2-yn-1-ol (0.15 g, 2.62 mmol) and morpholine (0.5 mL). Then cuprous iodide (4 mg, 0.02 mmol) and bis(triphenylphosphine)palladium(II) chloride (14 mg, 0.02 mmol) were added to the mixture under nitrogen. The reaction was heated at 80° C. overnight. The mixture was cooled and partitioned between ethyl acetate and water. The combined organic layer was dried over sodium sulfate, filtered and concentrated to give a crude product which was purified by column chromatography eluting with ethyl acetate/petroleum ether (1:6 to 1:3) to give 3-(3-(trifluoromethoxy)phenyl)prop-2-yn-1-ol (0.3 g, 80.2%) as a yellow oil. LCMS retention time 1.552 min.

Step 2 3-(3-(trifluoromethoxy)phenyl)propan-1-ol

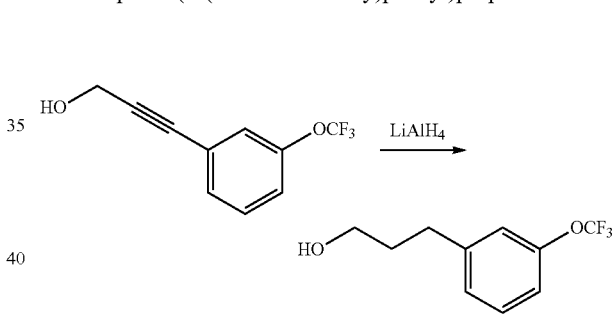

To a solution of 3-(3-(trifluoromethoxy)phenyl)prop-2-yn-1-ol (0.3 g, 1.39 mmol) in THF (10 mL) was added LAH (63 mg, 1.68 mmol) portionwise at 0° C. The reaction was stirred at 0° C. for 3 h. The reaction was carefully quenched by dropwise addition of ethyl acetate at 0° C. and the mixture was partitioned between ethyl acetate and water. The combined organic layer was dried over sodium sulfate, filtered and concentrated to give a crude product which was purified by column chromatography eluting with ethyl acetate/petroleum ether (1:4 to 1:1) to give 3-(3-(trifluoromethoxy)phenyl)propan-1-ol (0.26 g, 85.2%) as a yellow oil which was used without purification. $^1$H-NMR (CD$_3$OD) δ 7.37-7.39 (d, 1H), 7.31-7.35 (m, 1H), 7.15-7.17 (d, 1H), 4.07-4.11 (t, 2H), 2.72-2.76 (t, 2H), 1.83-1.90 (m, 2H).

Intermediate 38 2-(cyclohexyloxy)ethanol

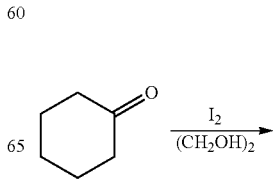

-continued

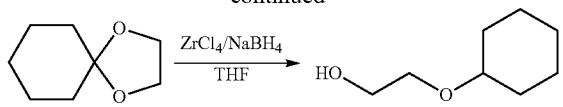

Step 1 1,4-dioxaspiro[4.5]decane (JF-000357-022)

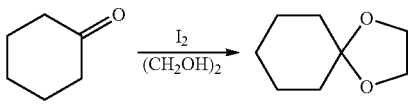

To a solution of cyclohexanone (10 g, 0.102 mol) in ethylene glycol (50 mL) was added iodine (3.88 g, 15.3 mmol) and the resulting mixture was stirred at room temperature overnight. The mixture was diluted with ethyl acetate and extracted with saturated aqueous sodium thiosulfate. The organic phase was dried and concentrated to give a crude product, which was purified via silica gel chromatography eluting with ethyl acetate/petroleum ether (1:8) to give 1,4-dioxaspiro[4.5]decane (6.8 g, 46.9% yield) as light oil. $^1$H-NMR (CDCl$_3$) δ 3.93 (s, 4H), 1.58-1.59 (d, 8H), 1.39-1.41 (m, 2H).

Step 2 2-(cyclohexyloxy)ethanol

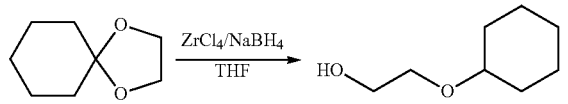 [SMILES: C1CCC2(CC1)OCCO2 ; OCCOC1CCCCC1 ; "THF"]

To the slurry of zirconium tetrachloride (10.65 g, 45.7 mmol) in THF (100 mL) was added sodium borohydride (4.3 g, 114.3 mmol) in small portions at room temperature. A solution of 1,4-dioxaspiro[4.5]decane (6.5 g, 45.7 mmol) in THF (20 mL) was added dropwise and the resulting mixture was stirred at room temperature overnight. The reaction was carefully quenched with 1N HCl and extracted with ethyl acetate. The organic phase was washed with brine, dried and concentrated to give a crude product, which was purified via silica gel chromatography eluting with petroleum ether/ethyl acetate (3:2) to give 2-(cyclohexyloxy)ethanol (3.9 g, 59.2% yield) as light yellow oil. $^1$H-NMR (CDCl$_3$) δ 3.68-3.70 (t, 2H), 3.53-3.56 (m, 2H), 3.27-3.29 (m, 1H), 2.54 (br, 1H), 1.89-1.93 (m, 2H), 1.70-1.73 (m, 2H), 1.51-1.54 (m, 1H), 1.17-1.28 (m, 5H).

Intermediate 39 7-(4-chlorobenzyl)-8-(2-fluoro-5-(trifluoromethoxy)benzyl)-3-methyl-1H-purine-2,6(3H,7H)-dione

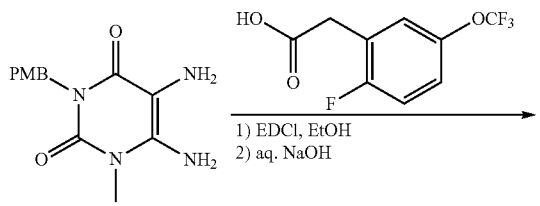

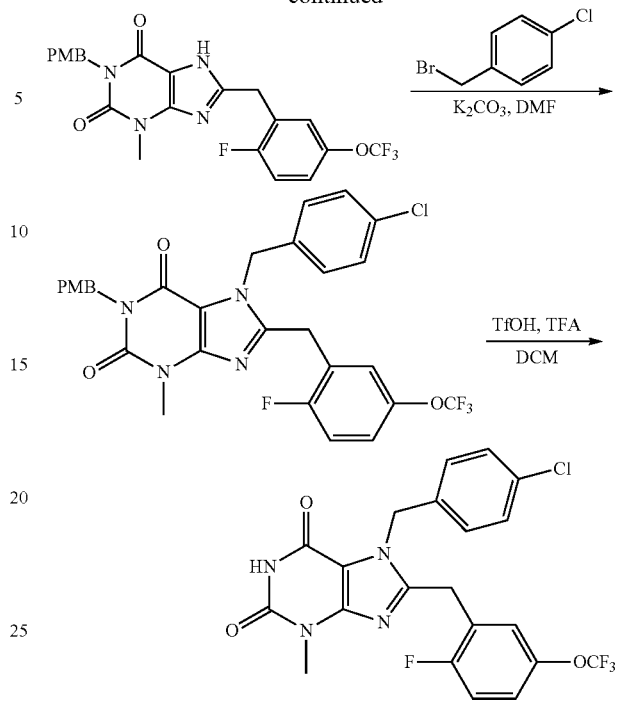

Step 1 8-(2-fluoro-5-(trifluoromethoxy)benzyl)-1-(4-methoxybenzyl)-3-methyl-1H-purine-2,6(3H,7H)-dione

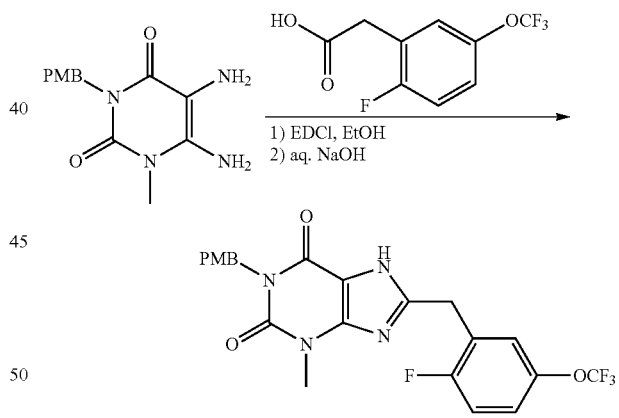

To a solution of 5,6-diamino-3-(4-methoxybenzyl)-1-methylpyrimidine-2,4(1H,3H)-dione (80 mg, 0.289 mmol, intermediate 59) in ethanol (2 mL) was added 2-(2-fluoro-5-(trifluoromethoxy)phenyl)acetic acid (68.8 mg, 0.289 mmol) followed by EDCI (66.5 mg, 0.347 mmol) and the mixture was stirred at room temperature for 2 h. The reaction was partitioned between ethyl acetate and brine. The organic phase was dried and concentrated. The residue was dissolved in ethanol (3 mL) and 1 mM sodium hydroxide (1 mL) was added. The resulting mixture was stirred at reflux for 3 h. The reaction was concentrated and residue was partitioned between ethyl acetate and brine. The organic layer was dried and concentrated to give a crude solid product, which was triturated with ethanol, collected and dried to afford 8-(2-fluoro-5-(trifluoromethoxy)benzyl)-1-(4-methoxybenzyl)-3-methyl-1H-purine-2,6(3H,7H)-dione (67 mg, 48.4% yield) as a light yellow solid. LCMS retention time 1.611 min; LCMS MH+ 479.

Step 2 7-(4-chlorobenzyl)-8-(2-fluoro-5-(trifluoromethoxy)benzyl)-1-(4-methoxybenzyl)-3-methyl-1H-purine-2,6(3H,7H)-dione

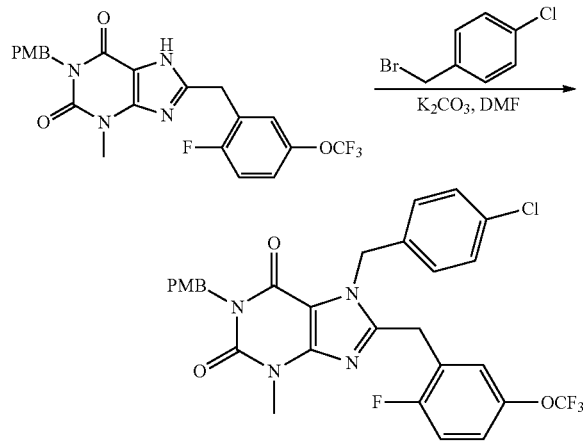

To a solution of 8-(2-fluoro-5-(trifluoromethoxy)benzyl)-1-(4-methoxybenzyl)-3-methyl-1H-purine-2,6(3H,7H)-dione (67 mg, 0.14 mmol) in DMF (3 mL) was added 1-(bromomethyl)-4-chlorobenzene (43.2 mg, 0.21 mmol) followed by potassium carbonate (38.7 mg, 0.28 mmol). The reaction was heated to 60° C. for 3 h. The reaction was partitioned between ethyl acetate and brine. The organic phase was dried and concentrated to give a crude product, which was purified by silica gel chromatography eluting with DCM/methanol (60:1) to give 7-(4-chlorobenzyl)-8-(2-fluoro-5-(trifluoromethoxy)benzyl)-1-(4-methoxybenzyl)-3-methyl-1H-purine-2,6(3H,7H)-dione (71.2 mg, 84.3% yield) as a white solid. LCMS retention time 2.375 min; LCMS MH+ 603.

Step 3 7-(4-chlorobenzyl)-8-(2-fluoro-5-(trifluoromethoxy)benzyl)-3-methyl-1H-purine-2,6(3H,7H)-dione

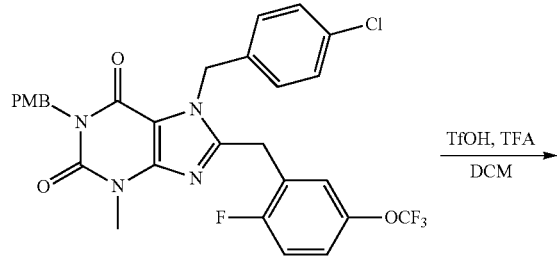

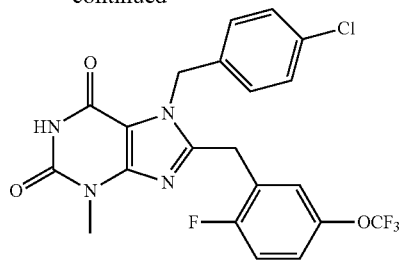

To a solution of 7-(4-chlorobenzyl)-8-(2-fluoro-5-(trifluoromethoxy)benzyl)-1-(4-methoxybenzyl)-3-methyl-1H-purine-2,6(3H,7H)-dione (71 mg, 0.118 mmol) in DCM (1 mL) was added TFA (0.3 mL) and trifluoromethanesulfonic acid (0.2 mL). The reaction was stirred at room temperature for 16 h. The mixture was concentrated and the residue was partitioned between DCM and aqueous sodium bicarbonate. The organic layer was dried and concentrated to give 7-(4-chlorobenzyl)-8-(2-fluoro-5-(trifluoromethoxy)benzyl)-3-methyl-1H-purine-2,6(3H,7H)-dione (39 mg, 68.4% yield) as a yellow syrup, which was directly without purification. LCMS retention time 1.686 min; LCMS MH+ 483.

Intermediate 40 (5-methyloxazol-2-yl)methanol

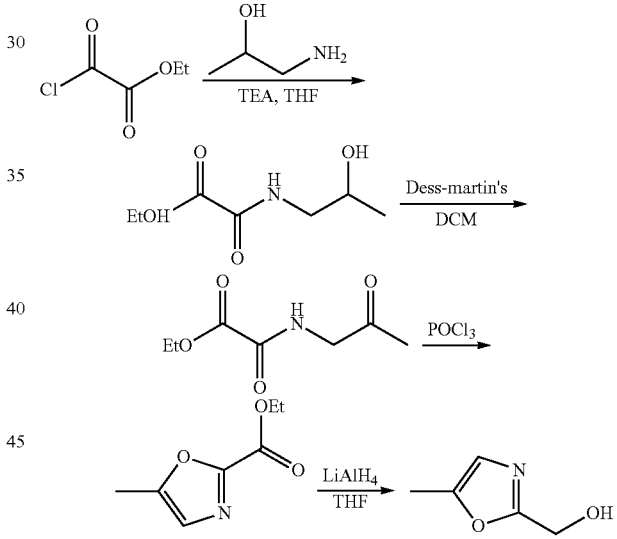

Step 1 ethyl 2-(2-hydroxypropylamino)-2-oxoacetate

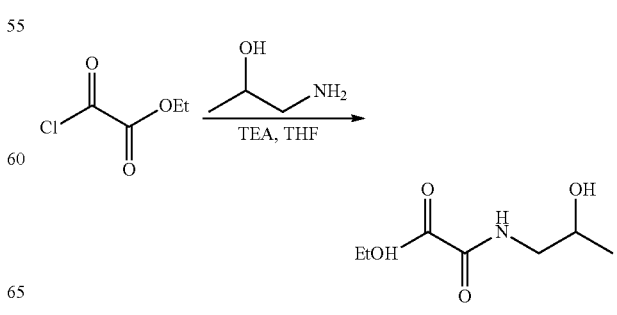

To a mixture of 1-aminopropan-2-ol (2 g, 26.6 mmol) and TEA (4.03 g, 39.9 mmol) in DCM (50 mL) was added ethyl 2-chloro-2-oxoacetate (4.36 g, 31.95 mmol) dropwise at 0° C. The mixture was stirred at room temperature for 16 h. The mixture was diluted with DCM and extracted with brine. The organic layer was dried and concentrated to give a crude product which was purified by silica gel chromatography eluting with petroleum ether/ethyl acetate (2:1) to give ethyl 2-(2-hydroxypropylamino)-2-oxoacetate (2.19 g, 51% yield) as yellow syrup. LCMS retention time 0.348 min, LCMS MH+ 176.

Step 2 ethyl 2-oxo-2-(2-oxopropylamino)acetate

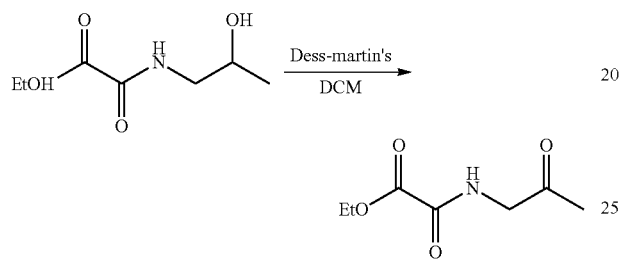

To a solution of ethyl 2-(2-hydroxypropylamino)-2-oxoacetate (2.1 g, 13 mmol) in DCM (30 mL) was added Dess-Martin periodinane (6.2 g, 14.6 mmol) in portions at 0° C. and the resulting mixture was stirred at room temperature for 16 h. The reaction was diluted with DCM and extracted with saturated aqueous sodium bicarbonate solution and brine. The organic layer was dried and concentrated to give crude product, which was purified via silica gel chromatography eluting with DCM/methanol (60:1) to give ethyl 2-oxo-2-(2-oxopropylamino)acetate (1.7 g, 81.2% yield) as yellow syrup. LCMS retention time 0.392 min, LCMS MH+ 174.

Step 3 ethyl 5-methyloxazole-2-carboxylate

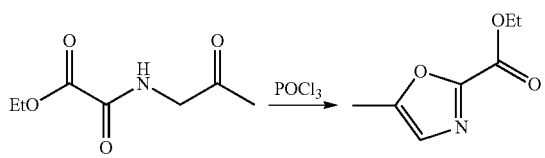

To a solution of ethyl 2-oxo-2-(2-oxopropylamino)acetate (1.7 g, 9.8 mmol) in toluene (10 mL) was added phosphorus oxychloride (2 mL). The mixture was heated to reflux for 3 h. The reaction was concentrated to dryness and the residue was taken up in ethyl acetate (20 mL). This organic phase was washed with saturated aqueous sodium bicarbonate solution and brine, dried and concentrated to give a crude product which was purified via silica gel chromatography eluting with petroleum ether/ethyl acetate (4:1) to give ethyl 5-methyloxazole-2-carboxylate (0.68 g, 44.1% yield) as yellow syrup. $^1$H-NMR (CDCl$_3$) δ 6.97 (s, 1H), 4.44-4.49 (q, 2H), 2.43 (s, 3H), 1.42-1.46 (t, 2H). LCMS retention time 0.643 min; LCMS MH+ 156.

Step 4 (5-methyloxazol-2-yl)methanol

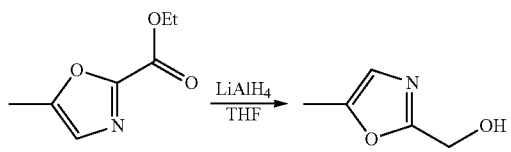

To a solution of ethyl 5-methyloxazole-2-carboxylate (0.68 g, 4.38 mmol) in anhydrous THF (10 mL) was added LAH (250 mg, 6.59 mmol) in portions at 0° C. The resulting mixture was stirred at room temperature for 16 h. The mixture was quenched with ethyl acetate and filtered. The filter cake was washed several times with ethyl acetate and the combined filtrate was concentrated to give crude product which was purified via silica gel chromatography eluting with DCM/methanol (65:1) to give (5-methyloxazol-2-yl)methanol (0.33 g, 66.6% yield) as yellow syrup. LCMS retention time 0.328 min; LCMS MH+ 114.

Intermediate 41 5-(chloromethyl)isoxazole

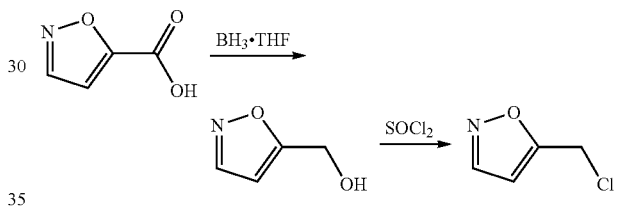

To a solution of isoxazole-5-carboxylic acid (1.0 g, 8.8 mmol) in THF (10 mL) was added borane-THF complex (26.4 mL, 26.4 mmol) at 0° C. The reaction was stirred at room temperature until the substrate was consumed. The reaction was quenched with ethanol (5 mL) at 0° C. The reaction mixture was partitioned between ethyl acetate and water. The combined organic phase was dried over sodium sulfate, filtered and concentrated to give a crude product which was purified by column chromatography eluting with petroleum ether/ethyl acetate (2:1 to give isoxazol-5-yl-methanol (670 mg, 77.0% yield) as a light yellow oil. LCMS retention time 0.329 min; LCMS MH+ 100.

Isoxazol-5-ylmethanol (50 mg, 0.5 mmol) was dissolved in thionyl chloride (1 mL) at 0° C. The reaction was stirred at room temperature until the substrate was consumed. The reaction was concentrated to give 5-(chloromethyl)isoxazole as a brown solid which was used without purification. LCMS retention time 0.349 min; LCMS MH+ 118.

Intermediate 42 (1-(hydroxymethyl)cyclopropyl)methyl methanesulfonate

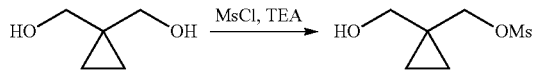 [SMILES: OCC1(CO)CC1 ; CS(=O)(=O)OCC1(CO)CC1]

To a solution of cyclopropane-1,1-diyldimethanol (0.1 g, 0.98 mmol) in DCM (5 mL) was added TEA (0.15 g, 1.44 mmol). Methanesulfonyl chloride (0.11 g, 0.98 mmol) was added dropwise at 0° C. The reaction was stirred at room temperature for 2 h. The mixture was partitioned between DCM and water. The combined organic layer was dried over sodium sulfate, filtered and concentrated to give a crude product which was used without purification.

Intermediate 43 2-(1-hydroxycyclopentyl)ethyl methanesulfonate

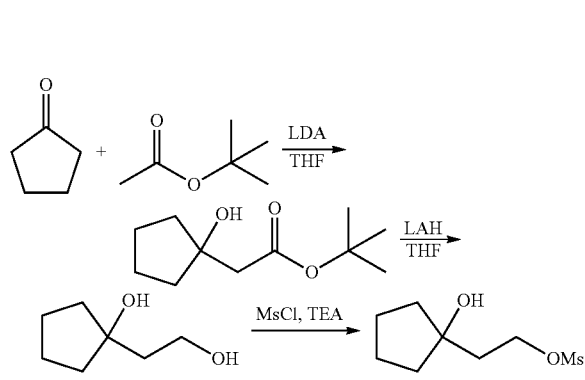

Step 1 tert-butyl 2-(1-hydroxycyclopentyl)acetate

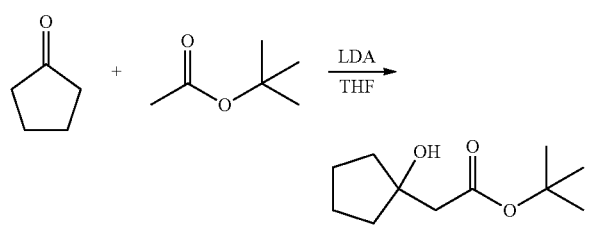

To a solution of tert-butyl acetate (5.0 g, 42.8 mmol) in THF (20 mL) was added lithium diisopropylamide (21.4 mL, 42.8 mmol) at −60° C. After stirred at −60° C. for 30 min, cyclopentanone (3.0 g, 35.7 mmol) was added at −60° C. The reaction was stirred 1 h; then it was quenched with aqueous ammonium chloride (5 mL) at −60° C. and the mixture was warmed to room temperature. The reaction was partitioned between ethyl acetate and water. The combined organic layer was dried over sodium sulfate, filtered and concentrated to give a crude product which was purified by column chromatography eluting with petroleum ether/ethyl acetate (3:1) to give tert-butyl 2-(1-hydroxycyclopentyl) acetate (5.0 g, 70.1% yield) as a yellow oil.

Step 2 1-(2-hydroxyethyl)cyclopentanol

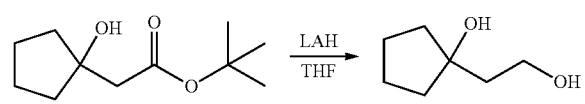

To a solution of tert-butyl 2-(1-hydroxycyclopentyl)acetate (0.5 g, 2.5 mmol) in THF (10 mL) was added lithium aluminium hydride (0.28 g, 7.5 mmol) portionwise at 0° C. The reaction was stirred at 0° C. overnight. The mixture was partitioned between ethyl acetate and water. The combined organic layer was dried over sodium sulfate, filtered and concentrated to give a crude product which was purified by column chromatography eluting with petroleum ether/ethyl acetate (1:1) to give 1-(2-hydroxyethyl)cyclopentanol (0.33 g, 100%) as a yellow oil.

Step 3 2-(1-hydroxycyclopentyl)ethyl methanesulfonate

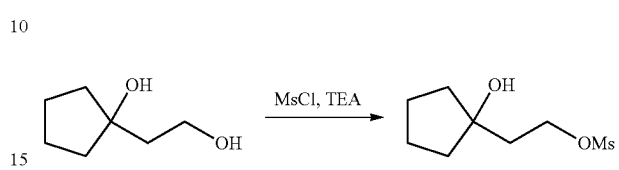

To a solution of 1-(2-hydroxyethyl)cyclopentanol (19 0 mg, 1.46 mmol) in dry dichloromethane (2 mL) was added methanesulfonyl chloride (200.3 mg, 1.75 mmol) dropwise at 0° C., followed by TEA (295 mg, 2.92 mmol). Then the mixture was stirred at room temperature 1 h. The mixture was partitioned between ethyl acetate and water. The organic phase was washed with brine, dried over sodium sulfate, filtered and concentrated to give crude product (50 mg, 31.1% yield), which was used without purification.

Intermediate 44 2-(1-hydroxycyclobutyl)ethyl methanesulfonate

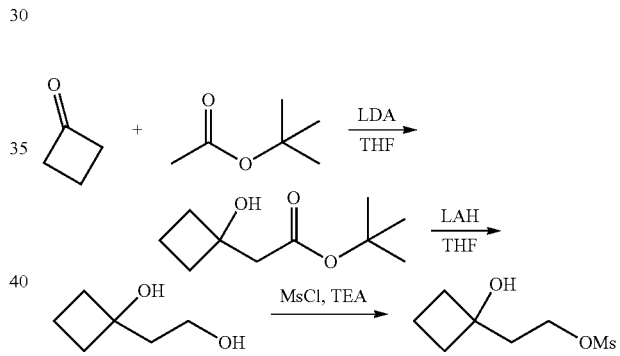

The title product was prepared using the method of intermediate 43.

Intermediate 45 4-bromo-2-methylbutan-2-ol

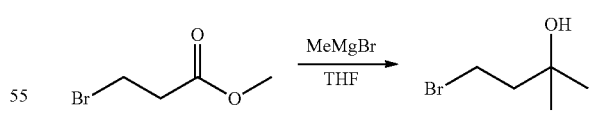

To a solution of methyl 3-bromopropanoate (0.2 g, 1.2 mmol) in THF (5 mL) was added methyl magnesium bromide (2.4 mL, 2.4 mmol) at 0° C. The mixture was stirred at this temperature until the substrate was consumed based on tlc [petroleum ether/ethyl acetate (3:1); product Rf 0.3]. The reaction was quenched with ammonium chloride (2 mL) at 0° C. The mixture was partitioned between ethyl acetate and water. The combined organic layer was dried over sodium sulfate, filtered and concentrated to give a crude product which was purified by a column chromatography eluting with petroleum ether/ethyl acetate (3:1) to give 4-bromo-2-methylbutan-2-ol (0.15 g, 75.1% yield) as a yellow oil.

Intermediate 46 1-(2-bromoethyl)cyclopropanol

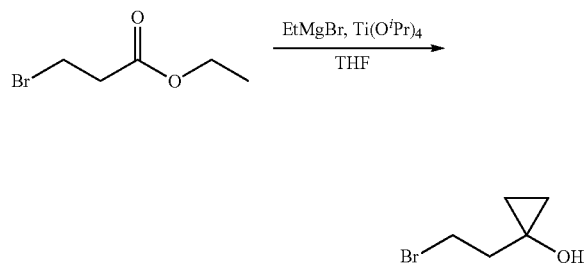

To a solution of ethyl 3-bromopropanoate (0.5 g, 2.76 mmol) in THF (5 mL) was added titanium tetra-isopropanolate (0.8 mL, 0.27 mmol) at 0° C. Ethyl magnesium bromide (8.27 mL, 8.27 mmol) was added to the mixture at 0° C. The reaction was stirred at this temperature 2 h. The reaction was quenched with aqueous ammonium chloride (2 mL) at 0° C. The mixture was partitioned between ethyl acetate and water. The combined organic layer was dried over sodium sulfate, filtered and concentrated to give a crude product which was purified by column chromatography eluting with petroleum ether/ethyl acetate (5:1) to give 1-(2-bromoethyl)cyclopropanol (0.35 g, 77.7% yield) as a yellow oil.

Intermediate 47 7-benzyl-3-ethyl-8-(3-(trifluoromethoxy)phenoxy)-1H-purine-2,6(3H,7H)-dione

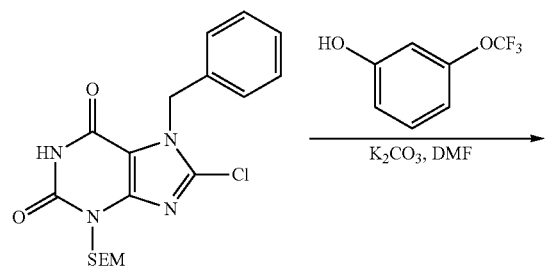

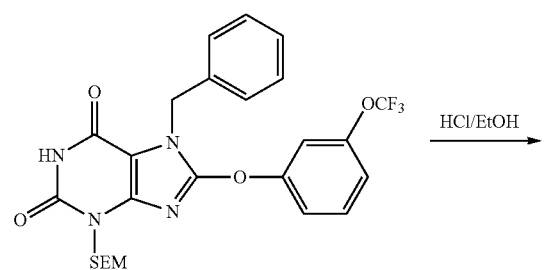

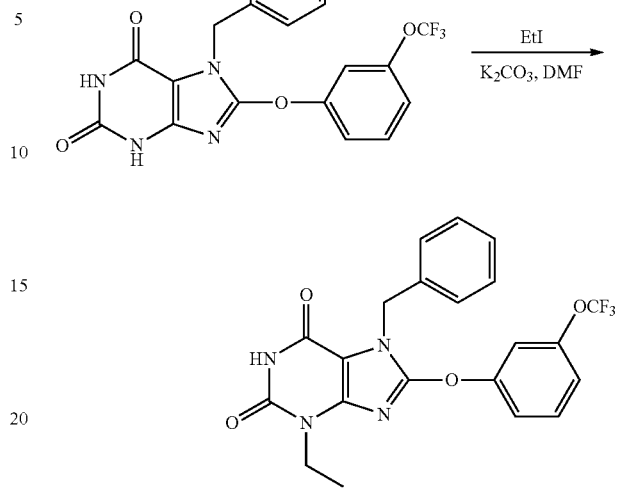

Step 1 7-benzyl-8-(3-(trifluoromethoxy)phenoxy)-3-((2-(trimethylsilyl)ethoxy)methyl)-1H-purine-2,6(3H,7H)-dione

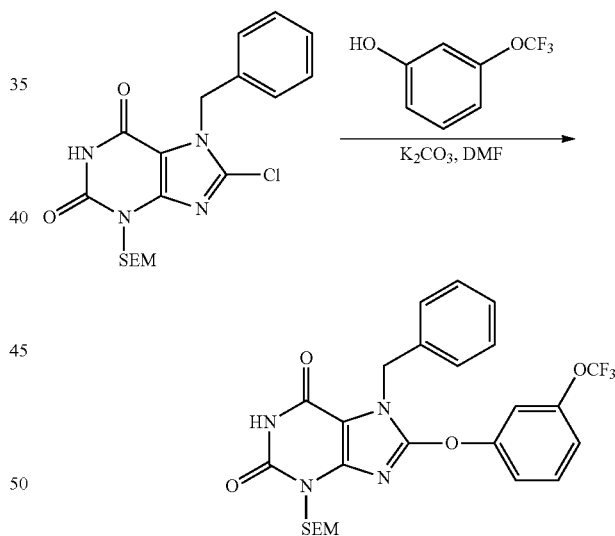

To a solution of 7-benzyl-8-chloro-3-((2-(trimethylsilyl)ethoxy)methyl)-1H-purine-2,6(3H,7H)-dione (500 mg, 1.232 mmol, product of intermediate 18, step 4) in DMF (3 mL) was added 3-(trifluoromethoxy)phenol (280 mg, 1.55 mmol), followed by potassium carbonate (400 mg, 2.90 mmol). The mixture was stirred at 80° C. overnight. The reaction was cooled and partitioned between ethyl acetate and water. The organic phase was washed with brine, dried over sodium sulfate, and concentrated to give 7-benzyl-8-(3-(trifluoromethoxy)phenoxy)-3-((2-(trimethylsilyl)ethoxy)methyl)-1H-purine-2,6(3H,7H)-dione (0.59 g, 87.3% yield) as brown oil. LCMS retention time 2.157 min; LCMS MH+ 549.

Step 2 7-benzyl-8-(3-(trifluoromethoxy)phenoxy)-1H-purine-2,6(3H,7H)-dione

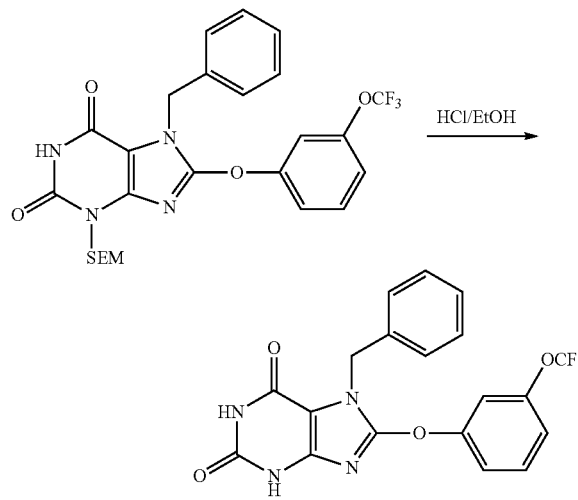

To a solution of 7-benzyl-8-(3-(trifluoromethoxy)phenoxy)-3-((2-(trimethylsilyl)ethoxy)methyl)-1H-purine-2,6(3H,7H)-dione (0.59 g, 1.07 mmol) in ethanol (20 mL) was added concentrated HCl (2 mL). The reaction was stirred at 80° C. for 16 h. The reaction was concentrated and partitioned between ethyl acetate and saturated sodium bicarbonate. The organic phase was washed with brine, dried over sodium sulfate, and concentrated to give 7-benzyl-8-(3-(trifluoromethoxy)phenoxy)-1H-purine-2,6(3H,7H)-dione (390 mg, 87.1% yield) as yellow oil. LCMS retention time 1.543 min; LCMS MH+ 419.

Step 3 7-benzyl-3-ethyl-8-(3-(trifluoromethoxy)phenoxy)-1H-purine-2,6(3H,7H)-dione

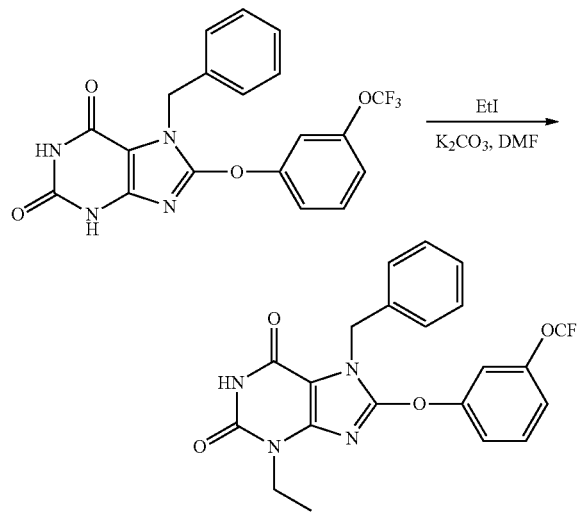

To a solution of 7-benzyl-8-(3-(trifluoromethoxy)phenoxy)-1H-purine-2,6(3H,7H)-dione (390 mg, 0.93 mmol) in DMF (3 mL) was added iodoethane (150 mg, 0.962 mmol), followed by potassium carbonate (350 mg, 2.54 mmol). The reaction was stirred at 40° C. for 2 h. The mixture was cooled and partitioned between ethyl acetate and water. The organic phase was washed with brine, dried over sodium sulfate, and concentrated to give 7-benzyl-3-ethyl-8-(3-(trifluoromethoxy)phenoxy)-1H-purine-2,6(3H,7H)-dione (271 mg, 65.2% yield) as yellow solid. LCMS retention time 1.765 min; LCMS MH+ 447.

Step 4 8-ethoxy-3-ethyl-1-(3-hydroxypropyl)-1H-purine-2,6(3H,7H)-dione

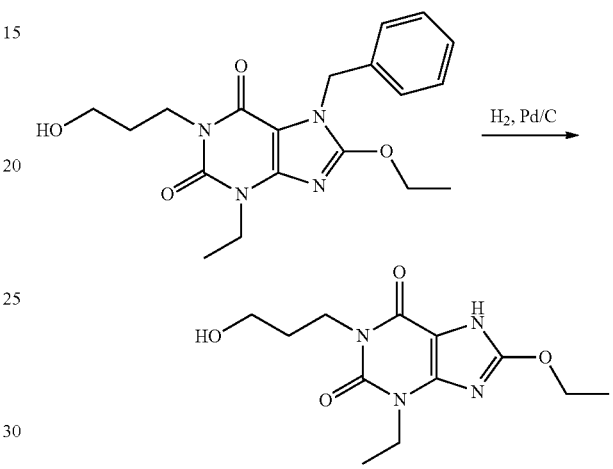

7-benzyl-8-ethoxy-3-ethyl-1-(3-hydroxypropyl)-1H-purine-2,6(3H,7H)-dione (0.12 g, 0.323 mmol) was dissolved in ethanol (20 mL) and degassed and refilled with nitrogen three times. Ammonium formate (0.5 g, 7.94 mmol) and 10% Pd/C (30 mg) were added and the mixture was again degassed and refilled with nitrogen three times. The reaction was stirred at 80° C. overnight. Then the mixture was cooled, filtered and the filter cake was washed with methanol. The filtrate was concentrated to give 8-ethoxy-3-ethyl-1-(3-hydroxypropyl)-1H-purine-2,6(3H,7H)-dione (70 mg, 77.1% yield) as white solid. LCMS retention time 0.413 min; LCMS MH+ 283.

Intermediate 48 1-(4-methoxybenzyl)-3-methyl-8-(3-(trifluoromethoxy)benzyl)-1H-purine-2,6(3H,7H)-dione

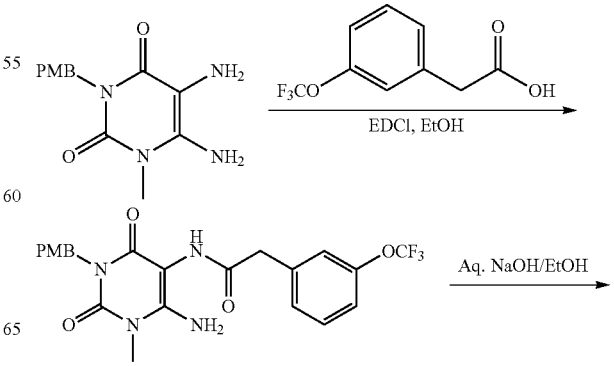

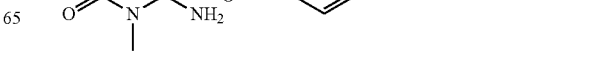

-continued

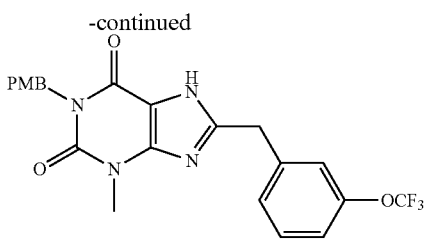

Step 1 N-(6-amino-3-(4-methoxybenzyl)-1-methyl-2,4-dioxo-1,2,3,4-tetrahydropyrimidin-5-yl)-2-(3-(trifluoromethoxy)phenyl)acetamide

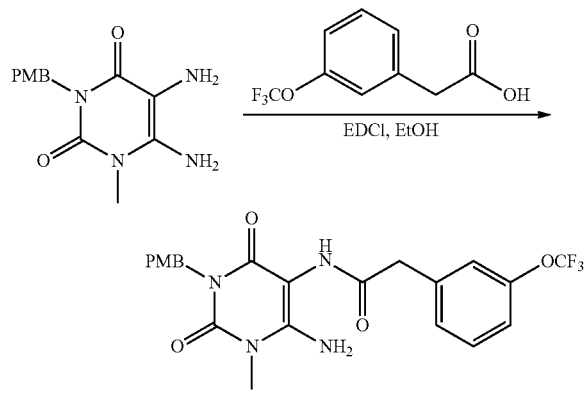

To a solution of 5,6-diamino-3-(4-methoxybenzyl)-1-methylpyrimidine-2,4(1H,3H)-dione (50 mg, 0.181 mmol, intermediate 59) in ethanol (3 ml) was added 2-(3-(trifluoromethoxy)phenyl)acetic acid (40 mg, 0.181 mmol) and EDCI (52 mg, 0.271 mmol) The mixture was stirred at room temperature for 2 h. The reaction was diluted with water, filtered and the solids were rinsed with water. The solid residue was dissolved in ethyl acetate, dried over sodium sulfate, filtered and concentrated to give N-(6-amino-3-(4-methoxybenzyl)-1-methyl-2,4-dioxo-1,2,3,4-tetrahydropyrimidin-5-yl)-2-(3-(trifluoromethoxy)phenyl)acetamide (70 mg, 80.1%) as light gray solid. LCMS retention time 1.239 min; LCMS MH⁺ 479.

Step 2 1-(4-methoxybenzyl)-3-methyl-8-(3-(trifluoromethoxy)benzyl)-1H-purine-2,6(3H,7H)-dione

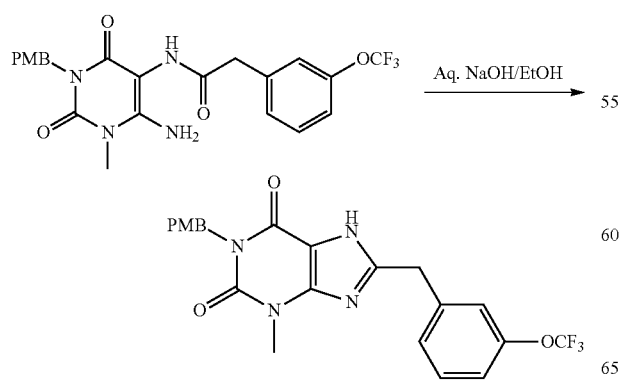

To a solution of N-(6-amino-3-(4-methoxybenzyl)-1-methyl-2,4-dioxo-1,2,3,4-tetrahydropyrimidin-5-yl)-2-(3-(trifluoromethoxy)phenyl)acetamide (70 mg, 0.146 mmol) in ethanol (7 ml) was added 2N sodium hydroxide (1 ml). The reaction was stirred at 80° C. for 3 h. The reaction was neutralized with aqueous ammonium chloride, filtered and the solids were rinsed with water. The solid residue was dissolved in ethyl acetate, dried over sodium sulfate, filtered and concentrated to give 1-(4-methoxybenzyl)-3-methyl-8-(3-(trifluoromethoxy)benzyl)-1H-purine-2,6(3H,7H)-dione (60 mg, 89.1%) as light yellow solid. LCMS retention time 1.499 min; LCMS MH⁺ 461.

Intermediate 49 3-(5-methylthiazol-2-yl)propanoic acid

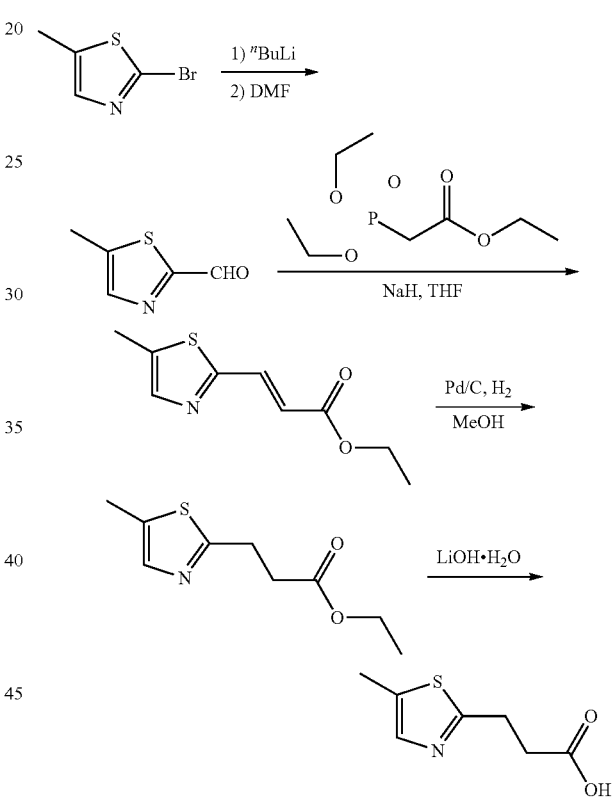

Step 1 (E)-ethyl 3-(5-methylthiazol-2-yl)acrylate

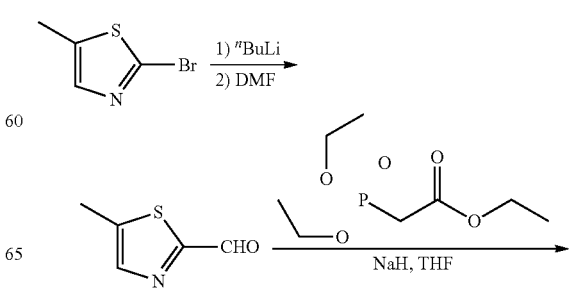

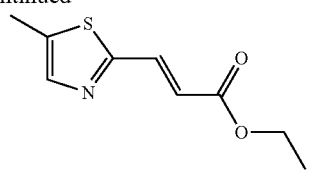

To a solution of n-BuLi (4.2 ml, 6.74 mmol) in THF (15 mL) was added 2-bromo-5-methylthiazole (1.0 g, 5.65 mmol) dropwise under nitrogen at −70° C. The reaction was stirred at this temperature for 1.5 h. DMF (0.65 ml, 8.43 mmol) was added dropwise at −70° C. The reaction was maintained at this temperature 1 h. The reaction was quenched with aqueous saturated ammonium chloride (5 mL) and warmed to room temperature. The mixture was partitioned between ethyl acetate and water. The combined organic layer was dried over sodium sulfate, filtered and concentrated to give the aldehyde intermediate as a yellow oil which was used without purification.

To a suspension of sodium hydride (0.27 g, 6.78 mmol) in THF (10 mL) was added ethyl 2-(diethoxyphosphoryl)acetate (1.52 g, 6.78 mmol) dropwise at 0° C. After the reaction was stirred 30 min, a solution of the aldehyde in THF (3 mL) was added dropwise at 0° C. The reaction was stirred at room temperature overnight. The mixture was quenched with aqueous saturated ammonium chloride (5 mL) and partitioned between ethyl acetate and water. The combined organic layer was dried over sodium sulfate, filtered and concentrated to give a yellow oil which was purified by column chromatography eluting with petroleum ether/ethyl acetate (4:1) to give (E)-ethyl 3-(5-methylthiazol-2-yl)acrylate (600 mg, 54.1% yield) as a light yellow oil. LCMS retention time 1.410 min; LCMS MH+ 198.

Step 2 ethyl 3-(5-methylthiazol-2-yl)propanoate

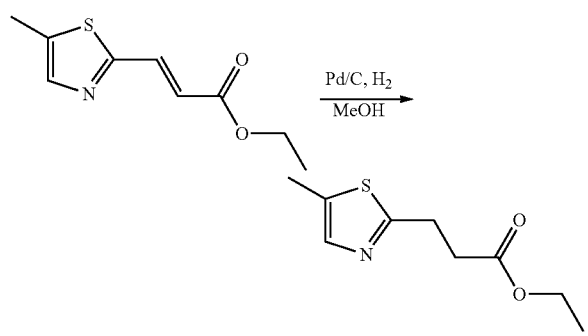

To a solution of (E)-ethyl 3-(5-methylthiazol-2-yl)acrylate (200 mg, 1.01 mmol) in methanol (5 mL) was added 5% Pd/C (20 mg). The reaction was purged with nitrogen and then hydrogen and then was stirred under a hydrogen atmosphere (balloon). The reaction was filtered. The filtrate was concentrated to give ethyl 3-(5-methylthiazol-2-yl)propanoate (200 mg, 99% yield) as a light yellow oil. LCMS retention time 1.33 min; LCMS MH+ 200.

Step 3 3-(5-methylthiazol-2-yl)propanoic acid

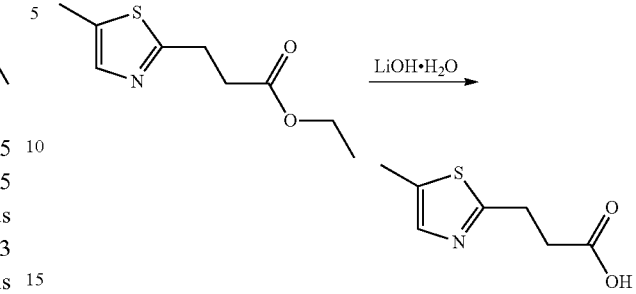

To a solution of ethyl 3-(5-methylthiazol-2-yl)propanoate (0.2 g, 1 mmol) in THF/water (3 mL/3 mL) was added lithium hydroxide (61 mg, 1.5 mmol) portionwise at room temperature. The resulting mixture was stirred for 3 h. The solvent was evaporated and the residue was acidified with conc. HCl to adjust the pH to 1-2. The mixture was partitioned between ethyl acetate and water. The combined organic layer was dried over sodium sulfate and concentrated to afford 3-(5-methylthiazol-2-yl)propanoic acid (0.17 g, 87.7% yield) as a colorless oil. LCMS retention time 0.436 min; LCMS MH+ 172.

Intermediate 50 2-(chloromethyl)-5-methylpyridine hydrochloride

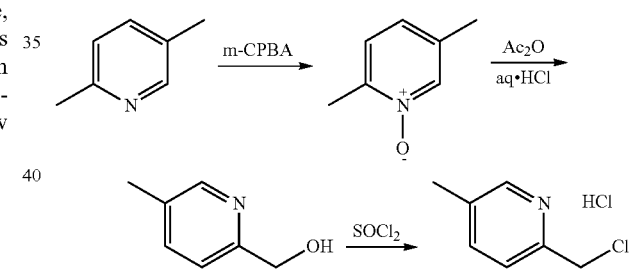

Step 1 2,5-dimethylpyridine 1-oxide

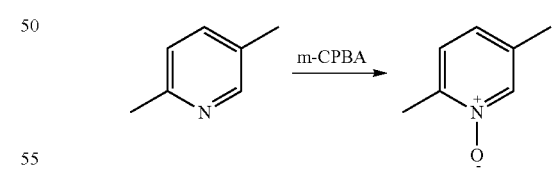

To a solution of 2,5-dimethylpyridine (2.24 g, 21 mmol) in CHCl3 (20 mL) was added MCPBA (4.31 g, 25 mmol) in portions over 30 min. The mixture was stirred at room temperature overnight. Calcium hydroxide (4 g, 54 mmol) was added to quench the reaction and the mixture was stirred vigorously for 3 h. The mixture was filtered through a Celite pad. The filtrate was concentrated and dried under vacuum to give 2, 5-dimethylpyridine 1-oxide (2.5 g, 97.1% yield) as white solid, which was used without purification. CMS retention time 0.442 min; LCMS MH+ 124.

345

Step 2 (5-methylpyridin-2-yl)methanol

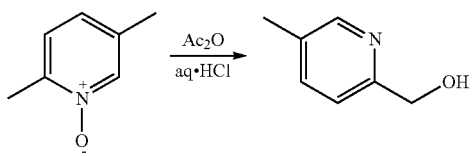

2,5-Dimethylpyridine 1-oxide (2.5 g, 20.3 mmol) was added to acetic anhydride (8.2 mL) at 100° C. over a period of 30 min. Then the mixture was refluxed 1 h. The mixture was cooled to room temperature and carefully quenched with ethanol (11 mL). The reaction mixture was concentrated. The residue was treated with 1N HCl (6 mL) and refluxed 1 h. The reaction was concentrated and the residue was partitioned between ethyl acetate and water. The organic phase was dried over sodium sulfate, filtered and concentrated to give (5-methylpyridin-2-yl) methanol (2 g, 80.0% yield) as a light yellow oil. LCMS MH+ 124.

Step 3 2-(chloromethyl)-5-methylpyridine hydrochloride

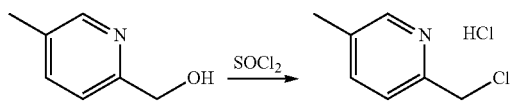

A solution of (5-methylpyridin-2-yl)methanol in SOCl$_2$ (10 mL) was refluxed 30 min. The mixture was concentrated and dried in vacuo to give 2-(chloromethyl)-5-methylpyridine hydrochloride (2.1 g, 91.3% yield) as white solid. LCMS MH+ 142.

Intermediate 51 3-methyl-7-((5-methylpyridin-2-yl)methyl)-8-(3-(trifluoromethoxy)benzyl)-1H-purine-2,6(3H,7H)-dione

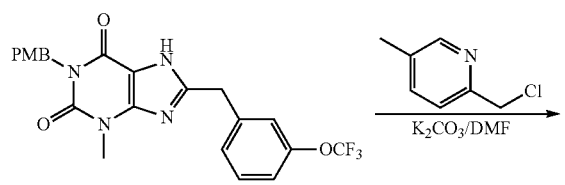

346

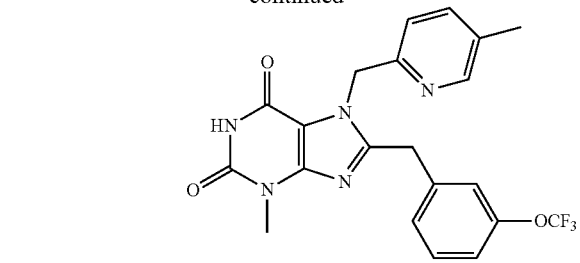

Step 1 1-(4-methoxybenzyl)-3-methyl-7-((5-methylpyridin-2-yl)methyl)-8-(3-(trifluoromethoxy)benzyl)-1H-purine-2,6(3H,7H)-dione

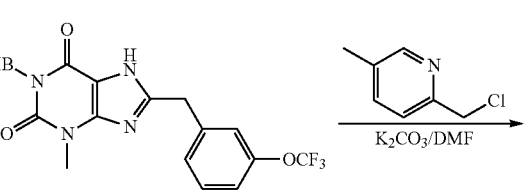

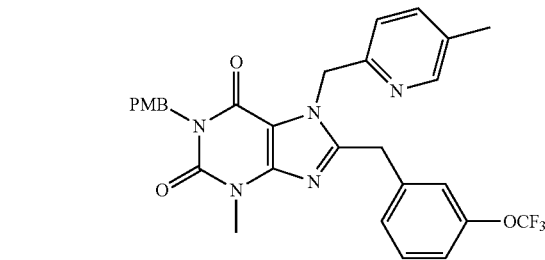

To a solution of 1-(4-methoxybenzyl)-3-methyl-8-(3-(trifluoromethoxy)benzyl)-1H-purine-2,6(3H,7H)-dione (110 mg, 0.238 mmol, intermediate 48) in DMF (4 mL) was added 2-(chloromethyl)-5-methylpyridine (33.8 mg, 0.238 mmol, intermediate 50), followed by potassium carbonate (49.5 mg, 0.358 mmol). The reaction was stirred at 55° C. for 2 h. The mixture was partitioned between ethyl acetate and water. The organic phase was washed with brine, dried over sodium sulfate, filtered and concentrated to give a white solid product (120 mg, 88.8% yield) which was used without purification. LCMS MH+ 566.

Step 2 3-methyl-7-((5-methylpyridin-2-yl)methyl)-8-(3-(trifluoromethoxy)benzyl)-1H-purine-2,6(3H,7H)-dione

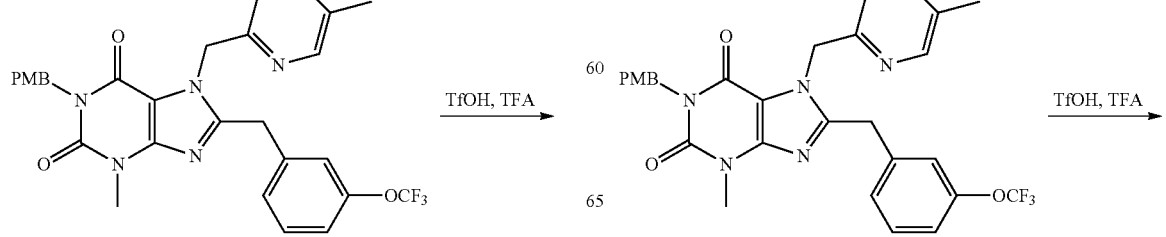

-continued

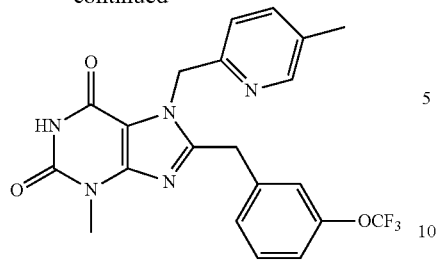

To a solution of 1-(4-methoxybenzyl)-3-methyl-7-((5-methylpyridin-2-yl)methyl)-8-(3-(trifluoromethoxy) benzyl)-1H-purine-2,6(3H,7H)-dione (120 mg, 0.212 mmol) in DCM (1.4 mL) was added triflic acid (0.7 mL) and TFA (0.7 mL). The reaction was stirred at room temperature overnight. The mixture was partitioned between ethyl acetate and water. The organic phase was washed with saturated NaHCO$_3$ and brine, dried over sodium sulfate, filtered and concentrated to give crude product, which was purified by silica gel chromatography eluting with petroleum/ethyl acetate (10:1 to 1:1) to give 3-methyl-7-((5-methylpyridin-2-yl)methyl)-8-(3-(trifluoromethoxy)benzyl)-1H-purine-2,6(3H,7H)-dione (60 mg, 63.5% yield) as white solid. LCMS MH$^+$ 446.

Intermediate 52 4,4,4-trifluorobutyl methanesulfonate

To a solution of 4,4,4-trifluorobutan-1-ol (100 mg, 83 mmol) in dry DCM (2 mL) was added methanesulfonyl chloride (107.3 mg, 72 mmol) and then by TEA (158 mg, 216 mmol) at 0° C. The reaction was stirred at room temperature for 1 h. The reaction was partitioned between ethyl acetate and water. The organic phase was washed with brine, dried over sodium sulfate, filtered and concentrated to give a yellow oil product (50 mg, 31.1% yield), which was used without purification. Product tlc [petroleum ether/ethyl acetate (3:1) Rf 0.4]

Intermediate 53 8-amino-7-(4-chlorobenzyl)-3-methyl-1-(3-(tetrahydro-2H-pyran-2-yloxy)propyl)-1H-purine-2,6(3H,7H)-dione

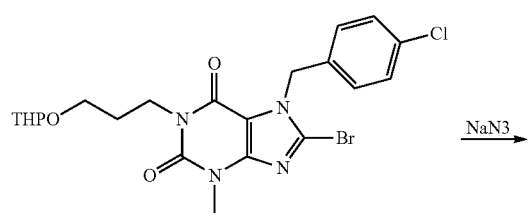

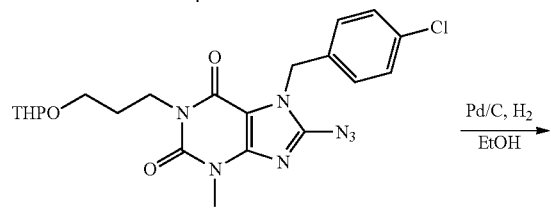

Step 1 8-azido-7-(4-chlorobenzyl)-3-methyl-1-(3-(tetrahydro-2H-pyran-2-yloxy)propyl)-1H-purine-2,6(3H,7H)-dione

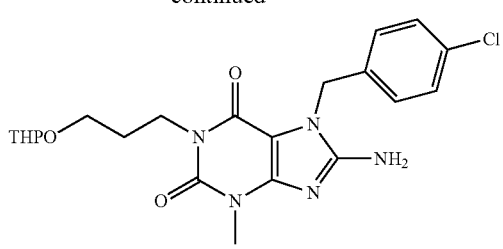

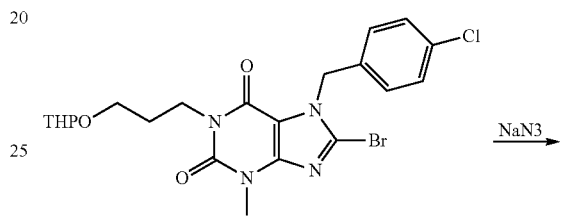

To a solution of 8-bromo-7-(4-chlorobenzyl)-3-methyl-1-(3-(tetrahydro-2H-pyran-2-yloxy)propyl)-1H-purine-2,6(3H,7H)-dione (0.28 g, 0.4 mmol, intermediate 14) in DMSO (10 mL) was added sodium azide (65 mg, 1 mmol). The reaction was heated at 65° C. for 2.5 h. The mixture was cooled and partitioned between ethyl acetate and water. The combined organic layer was dried over sodium sulfate, filtered and concentrated to give a crude product which was used without purification. LCMS retention time 1.800 min; LCMS MH$^+$-THP 390.

Step 2 8-amino-7-(4-chlorobenzyl)-3-methyl-1-(3-(tetrahydro-2H-pyran-2-yloxy)propyl)-1H-purine-2,6(3H,7H)-dione

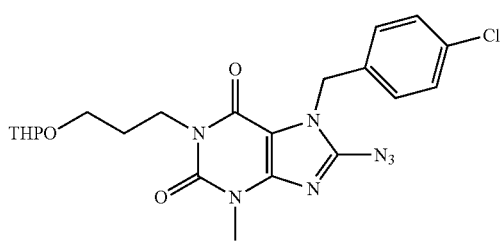

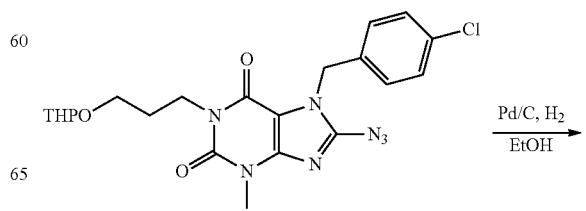

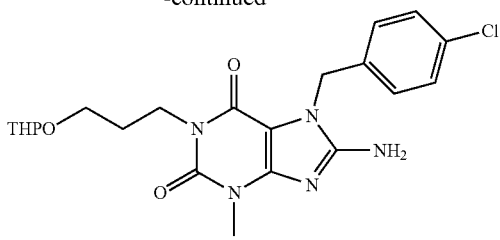

8-azido-7-(4-chlorobenzyl)-3-methyl-1-(3-(tetrahydro-2H-pyran-2-yloxy)propyl)-1H-purine-2,6(3H,7H)-dione (0.19 g, 0.4 mmol) was dissolved in THF (5 mL) and 10% Pd/C (20 mg) was added. The reaction was blanketed in a hydrogen atmosphere (balloon) and stirred overnight at room temperature. The mixture was filtered through celite, the filter cake was washed with methanol. The filtrate was concentrated in vacuo to give a 8-amino-7-(4-chlorobenzyl)-3-methyl-1-(3-(tetrahydro-2H-pyran-2-yloxy)propyl)-1H-purine-2,6(3H,7H)-dione (0.2 g, 100% yield) as a white solid. LCMS retention time 1.324 min; LCMS MH$^+$-THP 364

Intermediate 54 Synthesis of 2-(chloromethyl)-4-methylthiazole

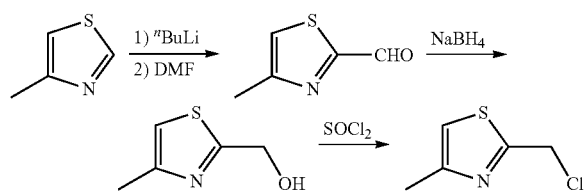

Step 1 Synthesis of (4-methylthiazol-2-yl)methanol

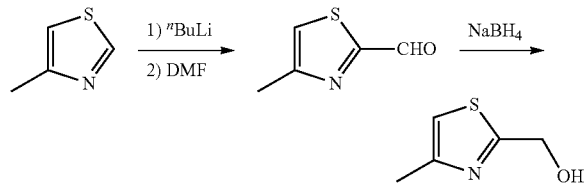

To a solution of 4-methylthiazole (1.0 g, 10.1 mmol) in THF (30 mL) was added n-BuLi (7.56 mL, 13.48 mmol) dropwise under a nitrogen atmosphere at −60° C. The reaction was stirred for 1 h; then DMF (1.4 ml, 18.2 mmol) was added dropwise while maintaining −60° C. The resulting mixture was stirred at this temperature for 30 min. The reaction was quenched with aqueous saturated ammonium chloride (5 mL) and partitioned between ethyl acetate and water. The combined organic layer was dried over sodium sulfate, filtered and concentrated to give a yellow oil. This oil was dissolved in methanol (15 ml) and sodium borohydride (460 mg, 12.1 mmol) was added portionwise under nitrogen atmosphere at −60° C. The mixture was stirred at this temperature for 1 h. The reaction mixture was quenched with acetone, warmed to room temperature, and concentrated. The residue was partitioned between ethyl acetate and water. The combined organic layer was dried over sodium sulfate, filtered and concentrated. The residue was purified by silica gel chromatography eluting with petroleum ether/ethyl acetate (3:1) to give (4-methylthiazol-2-yl)methanol (1.3 g, 90.3%) as brown oil. LCMS retention time 0.375 min; LCMS MH$^+$ 130.

Step 2 Synthesis of 2-(chloromethyl)-4-methylthiazole

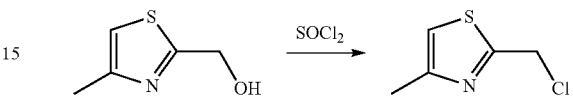

To a solution of (4-methylthiazol-2-yl)methanol (0.5 g, 3.87 mmol) in DCM (5 mL) was added thionyl chloride (0.19 ml, 2.6 mmol) at 0° C. The mixture was stirred at room temperature for 2 hour. The reaction was concentrated to give 2-(chloromethyl)-4-methylthiazole (570 mg, crude) as yellow oil, which was used without purification. LCMS retention time 0.895 min; LCMS MH$^+$ 148

Intermediate 55 2-(chloromethyl)-5-methylpyrazine

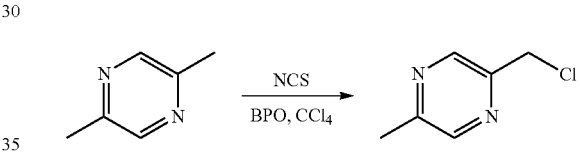

To a solution of 2,5-dimethylpyrazine (500 mg, 4.62 mmol) in carbon tetrachloride (7 mL) was added NCS (679 mg, 5.09 mmol) followed by BPO (20 mg) and the mixture was heated to 80° C. for 6 hours. The mixture was diluted with DCM and extracted with saturated aqueous sodium sulfite solution and brine. The organic layer was dried and concentrated to give a crude product which was purified via silica gel chromatography eluting with petroleum ether/ethyl acetate (1:0 to 15:1) to give 2-(chloromethyl)-5-methylpyrazine (133 mg, 20.19% yield) as yellow oil. LCMS retention time 0.557 min; LCMS MH$^+$ 143.

Intermediate 56 8-bromo-7-(4-chlorobenzyl)-1-(2-(1-hydroxycyclopropyl)ethyl)-3-methyl-1H-purine-2,6(3H,7H)-dione

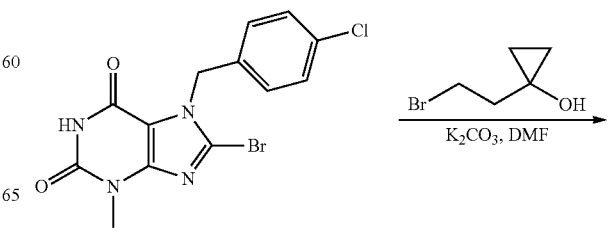

-continued

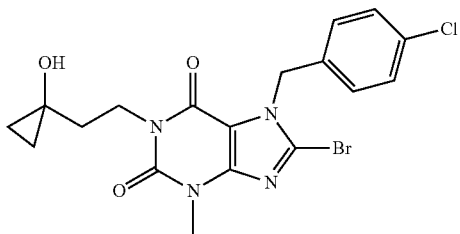

To a solution of 8-bromo-7-(4-chlorobenzyl)-3-methyl-1H-purine-2,6(3H,7H)-dione (150 mg, 0.405 mmol, intermediate 8) in DMF (5 mL) was added 1-(2-bromoethyl) cyclopropanol (94 mg, 0.568 mmol) followed by potassium carbonate (84 mg, 0.609 mmol) and TBAI (catalytic amount). The resulting mixture was stirred at 50° C. overnight. The reaction was diluted with ethyl acetated and washed with brine. The organic phase was dried and concentrated to give crude product which was purified via silica gel chromatography eluting with petroleum ether/ethyl acetate (5:1 to 2:1) to give 8-bromo-7-(4-chlorobenzyl)-1-(2-(1-hydroxycyclopropyl)ethyl)-3-methyl-1H-purine-2,6(3H,7H)-dione (150 mg, 81.6% yield) as light yellow solid. LCMS retention time 1.523 min; LCMS MH+ 455.

Intermediate 57 1-(3-hydroxybutyl)-3-methyl-8-(3-(trifluoromethoxy)phenoxy)-1H-purine-2,6(3H,7H)-dione

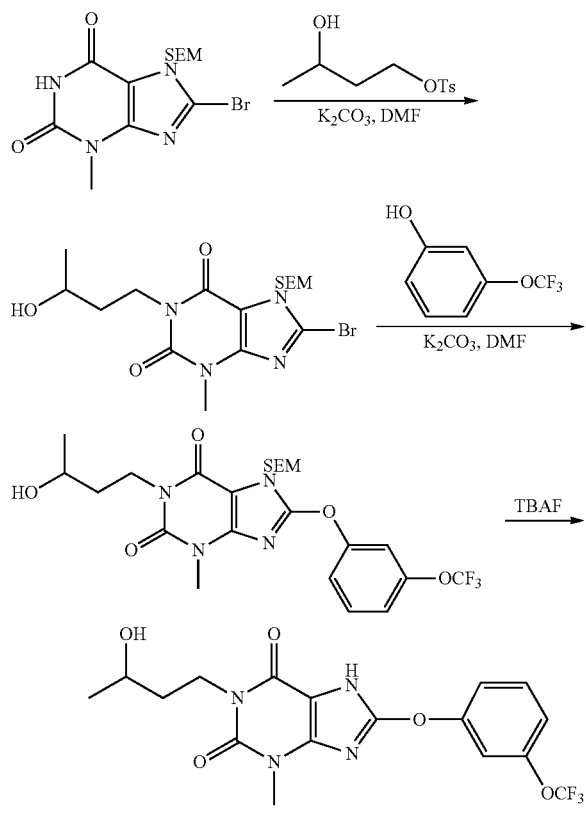

Step 1 8-bromo-1-(3-hydroxybutyl)-3-methyl-7-((2-(trimethylsilyl)ethoxy)methyl)-1H-purine-2,6(3H,7H)-dione

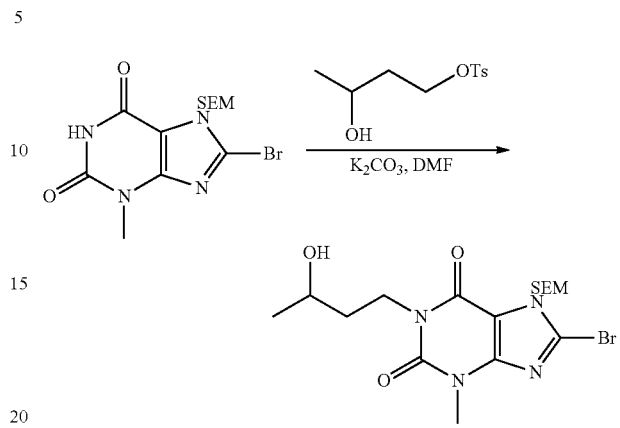

To a solution of 8-bromo-3-methyl-7-((2-(trimethylsilyl)ethoxy)methyl)-1H-purine-2,6(3H,7H)-dione (3 g, 8 mmol, product of intermediate 12, step 1) in DMF (15 mL) was added 3-hydroxybutyl 4-methylbenzenesulfonate (2.3 g, 8.8 mmol, intermediate 33) followed by potassium carbonate (2.2 g, 16 mmol) and TBAI (catalytic amount). The resulting mixture was stirred at 80° C. for 4 h. The reaction was diluted with ethyl acetated and washed with brine. The organic phase was dried and concentrated to give 8-bromo-1-(3-hydroxybutyl)-3-methyl-7-((2-(trimethylsilyl)ethoxy)methyl)-1H-purine-2,6(3H,7H)-dione (3.5 g, 97.9% yield) as yellow solid. LCMS retention time 1.428 min; LCMS MH+ 448.

Step 3 1-(3-hydroxybutyl)-3-methyl-8-(3-(trifluoromethoxy)phenoxy)-7-((2-(trimethylsilyl)ethoxy)methyl)-1H-purine-2,6(3H,7H)-dione

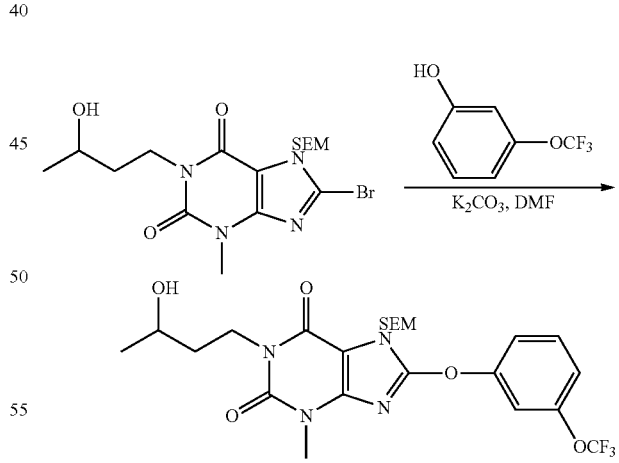

To a solution of 8-bromo-1-(3-hydroxybutyl)-3-methyl-7-((2-(trimethylsilyl)ethoxy)methyl)-1H-purine-2,6(3H, 7H)-dione (1 g, 2.2 mmol) in DNF (10 mL) was added 3-(trifluoromethoxy)phenol (0.6 g, 3 mmol) followed by potassium carbonate (0.6 g, 4.4 mmol). The reaction was stirred at 80° C. for 4 h. The mixture was diluted with ethyl acetate and washed with brine. The organic phase was dried and concentrated to give 1-(3-hydroxybutyl)-3-methyl-8-(3-(trifluoromethoxy)phenoxy)-7-((2-(trimethylsilyl)ethoxy)

methyl)-1H-purine-2,6(3H,7H)-dione (1.1 g, 91.8% yield) as yellow syrup. LCMS retention time 2.036 min; LCMS MH+ 545.

Step 3 Synthesis of 1-(3-hydroxybutyl)-3-methyl-8-(3-(trifluoromethoxy)phenoxy)-1H-purine-2,6(3H, 7H)-dione

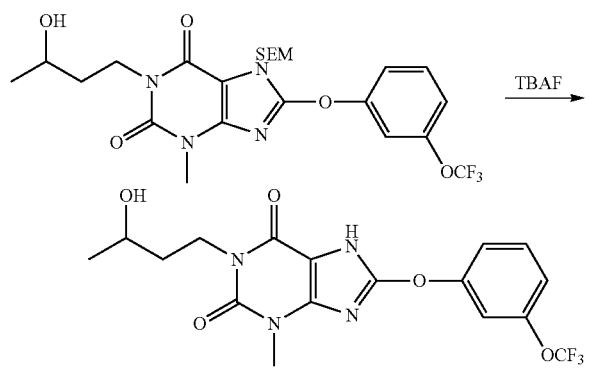

To a solution of 1-(3-hydroxybutyl)-3-methyl-8-(3-(trifluoromethoxy)phenoxy)-7-((2-(trimethylsilyl)ethoxy)methyl)-1H-purine-2,6(3H,7H)-dione (1.1 g, 2.02 mmol) in THF (5 mL) was added TBAF (5 mL, 1 mmol/L in THF) and the mixture was heated at reflux for 16 h. The mixture was cooled and diluted with ethyl acetate. The organic phase was washed with brine and saturated aqueous ammonium chloride; then it was dried and concentrated to give a crude product which was purified by silica gel chromatography eluting with DCM/methanol (45:1) to give (701 mg, 83.8% yield) as white solid. LCMS retention time 1.372 min; LCMS MH+ 415.

Intermediate 58 1-(2-(1-hydroxycyclopropyl)ethyl)-3-methyl-8-(3-(trifluoromethoxy)phenoxy)-1H-purine-2,6(3H,7H)-dione

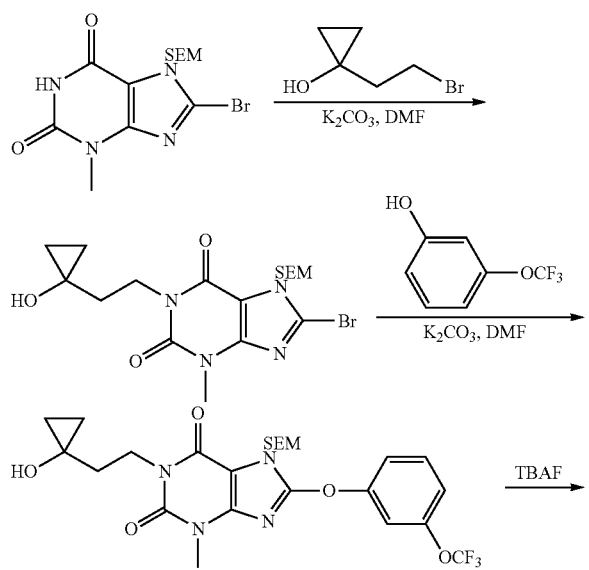

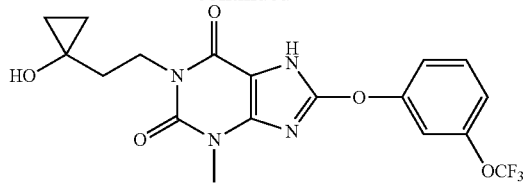

The title compound was prepared using the method of intermediate 57 and purified by silica gel chromatography eluting with petroleum ether/ethyl acetate (1:1) to give 1-(2-(1-hydroxycyclopropyl)ethyl)-3-methyl-8-(3-(trifluoromethoxy)phenoxy)-1H-purine-2,6(3H,7H)-dione (400 mg, 87.0% yield) as white solid. LCMS retention time 1.457 min; LCMS MH+ 427.

Intermediate 59 5,6-diamino-3-(4-methoxybenzyl)-1-methylpyrimidine-2,4(1H,3H)-dione

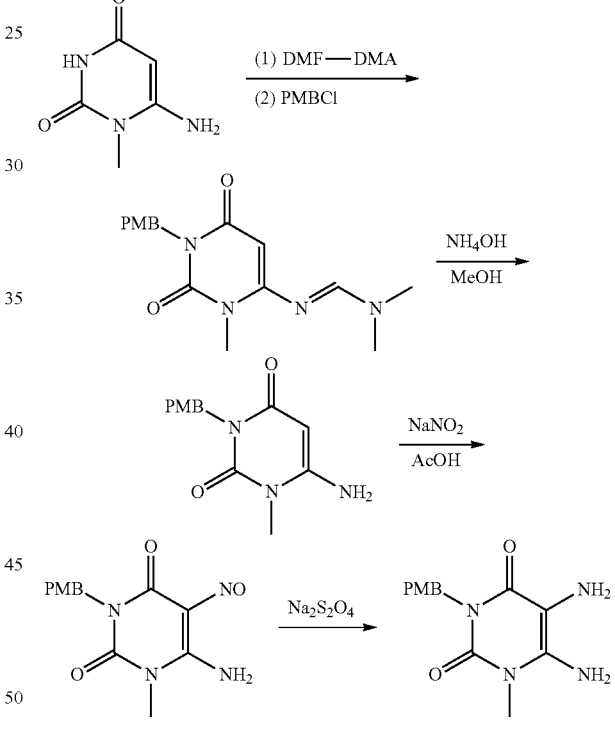

Step 1 (E)-N'-(1-(4-methoxybenzyl)-3-methyl-2,6-dioxo-1,2,3,6-tetrahydropyrimidin-4-yl)-N,N-dimethylformimidamide

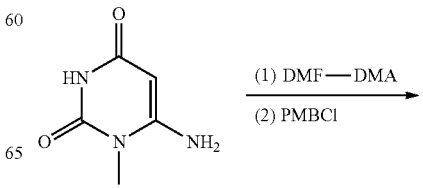

Step 3 6-amino-3-(4-methoxybenzyl)-1-methyl-5-nitrosopyrimidine-2,4(1H,3H)-dione

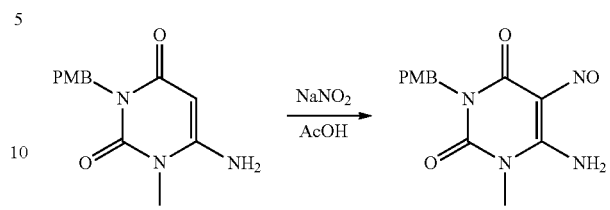

To a solution of 6-amino-3-(4-methoxybenzyl)-1-methylpyrimidine-2,4(1H,3H)-dione (4.3 g, 16.45 mmol) in water (20 mL) and acetic acid (20 mL) was added sodium nitrite (3.4 g, 49.4 mmol) in small portions at 70° C. After addition, the mixture was stirred at 70° C. for 4 h. The reaction was cooled and concentrated. The solids were collected, washed with water and dried under vacuum to give 6-amino-3-(4-methoxybenzyl)-1-methyl-5-nitrosopyrimidine-2,4(1H,3H)-dione (4.1 g, 85.9% yield) as purple solid. LCMS retention time 0.885 min; LCMS MH$^+$ 291.

Step 4 5,6-diamino-3-(4-methoxybenzyl)-1-methyl-pyrimidine-2,4(1H,3H)-dione

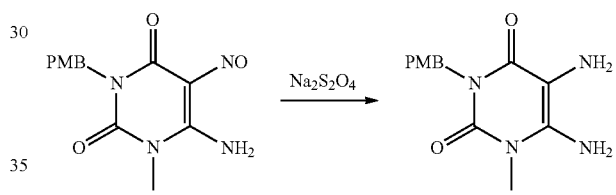

To a solution of 6-amino-3-(4-methoxybenzyl)-1-methyl-5-nitrosopyrimidine-2,4(1H,3H)-dione (4.1 g, 14.1 mmol) in ammonium hydroxide (100 mL, 14% wt/wt) was added sodium dithionite (4.9 g, 28.2 mmol) in small portions at 60° C., and the mixture was stirred at this temperature for 4 h. The reaction was cooled and was diluted with water. The solids were collected, rinsed with water and dried under vacuum to give 5,6-diamino-3-(4-methoxybenzyl)-1-methylpyrimidine-2,4(1H,3H)-dione (3.5 g, 89.8% yield) as a light yellow solid. LCMS retention time 0.404 min; LCMS MH$^+$ 277.

Intermediate 60 1-(4-methoxybenzyl)-3-methyl-8-(3-(3-(trifluoromethoxy)phenoxy)propyl)-1H-purine-2,6(3H,7H)-dione

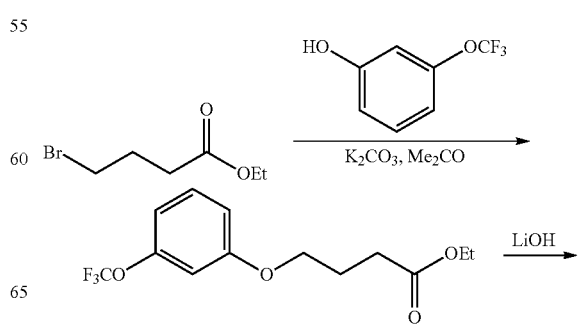

---

-continued

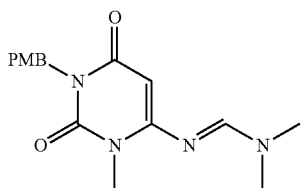

To a solution of 6-amino-1-methylpyrimidine-2,4(1H,3H)-dione (13.1 g, 92.9 mmol) in DMF (200 mL) was added 1,1-dimethoxy-N,N-dimethylmethanamine (13 mL, 97.9 mmol) and the mixture was stirred at 40° C. for 3 h. Then 1-(chloromethyl)-4-methoxybenzene (15.05 mL, 111.5 mmol) was added followed by potassium carbonate (25.64 g, 0.186 mmol) and DMF (100 mL), the resulting mixture was stirred at 80° C. for 48 h. The reaction was cooled and diluted with ethyl acetate. The organic phase was washed with brine, dried and concentrated to give a crude product which was purified by silica gel chromatography eluting with methanol/DCM (1:80 to 1:20) to give (E)-N'-(1-(4-methoxybenzyl)-3-methyl-2,6-dioxo-1,2,3,6-tetrahydropyrimidin-4-yl)-N,N-dimethylformimidamide (7.8 g, 26.5% yield) as yellow solid. LCMS retention time 1.023 min; LCMS MH$^+$ 317.

Step 2 6-amino-3-(4-methoxybenzyl)-1-methylpyrimidine-2,4(1H,3H)-dione

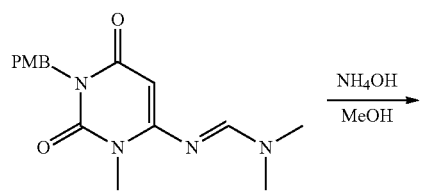

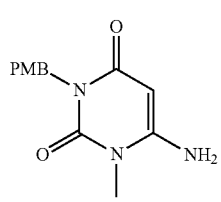

To a solution of (E)-N'-(1-(4-methoxybenzyl)-3-methyl-2,6-dioxo-1,2,3,6-tetrahydropyrimidin-4-yl)-N,N-dimethylformimidamide (7.8 g, 24.7 mmol) in methanol (90 mL) was added ammonium hydroxide (155 mL, 28% wt/wt) and the mixture was stirred at room temperature for 48 h. The reaction was concentrated to give crude product which was purified by silica gel chromatography eluting with methanol/DCM (1:15) to give 6-amino-3-(4-methoxybenzyl)-1-methylpyrimidine-2,4(1H,3H)-dione (4.3 g, 66.6%) as yellow solid. LCMS retention time 0.445 min; LCMS MH$^+$ 262.

-continued

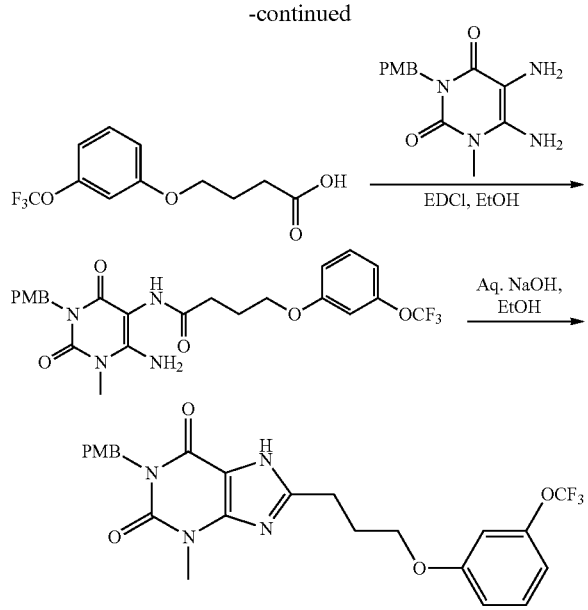

Step 1 ethyl 3-(3-(trifluoromethoxy)phenoxy)propanoate

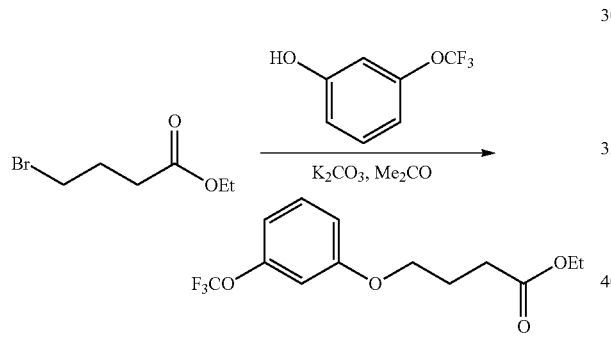

To a solution of ethyl 4-bromobutanoate (2 g, 10.26 mmol) in acetone (20 mL) was added 3-(trifluoromethoxy)phenol (1.52 g, 8.54 mmol), followed by potassium carbonate (3.5 g, 25.36 mmol). The reaction was stirred at room temperature overnight. The mixture was partitioned between DCM and water. The organic phase was washed with brine, dried over sodium sulfate, and concentrated to give a crude product which was purified by silica gel chromatography eluting with petroleum/ethyl acetate (10:1 to 5:1) to give ethyl 3-(3-(trifluoromethoxy)phenoxy)propanoate (2.3 g, 92.1% yield) as a colorless oil.

Step 2 3-(3-(trifluoromethoxy)phenoxy)propanoic acid

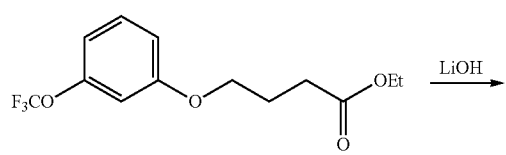

-continued

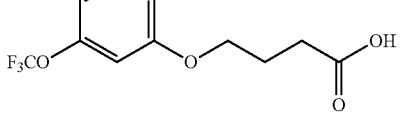

To a solution of ethyl 3-(3-(trifluoromethoxy)phenoxy)propanoate (1.0 g, 3.42 mmol) in THF (8 mL) was added a solution of lithium hydroxide (164 mg, 6.83 mmol) in water (4 mL). The reaction was stirred at room temperature overnight. The reaction was neutralized with diluted HCl and extracted with ethyl acetate. The organic phase was washed with brine, dried over sodium sulfate, and concentrated to give 3-(3-(trifluoromethoxy)phenoxy)propanoic acid (0.9 g, 99.1% yield) as colorless oil which was used without purification.

Step 3 N-(6-amino-3-(4-methoxybenzyl)-1-methyl-2,4-dioxo-1,2,3,4-tetrahydropyrimidin-5-yl)-4-(3-(trifluoromethoxy)phenoxy)butanamide

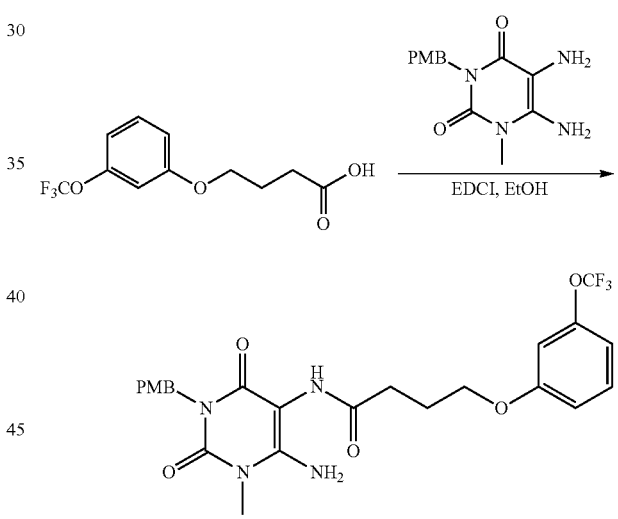

To a solution of 5,6-diamino-3-(4-methoxybenzyl)-1-methylpyrimidine-2,4(1H,3H)-dione (100 mg, 0.362 mmol, Intermediate 59) in ethanol (3 mL) was added 3-(3-(trifluoromethoxy)phenoxy)propanoic acid (96 mg, 0.364 mmol) and EDCI (105 mg, 0.546 mmol). The reaction was stirred at room temperature for 3 h. Then the mixture was diluted with water and the precipitate was collected by filtration and rinsed with water. The solids were then dissolved in ethyl acetate. This organic solution was dried over sodium sulfate and concentrated to give N-(6-amino-3-(4-methoxybenzyl)-1-methyl-2,4-dioxo-1,2,3,4-tetrahydropyrimidin-5-yl)-4-(3-(trifluoromethoxy)phenoxy)butanamide (150 mg, 79.3%) as a yellow solid. LCMS retention time 1.422 min; LCMS MH$^+$ 523.

Step 4 1-(4-methoxybenzyl)-3-methyl-8-(3-(trifluoromethoxy)phenoxy)propyl)-1H-purine-2,6(3H,7H)-dione

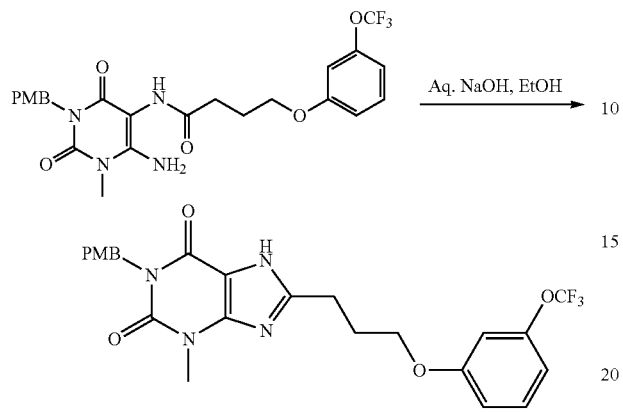

To a solution of N-(6-amino-3-(4-methoxybenzyl)-1-methyl-2,4-dioxo-1,2,3,4-tetrahydropyrimidin-5-yl)-4-(3-(trifluoromethoxy)phenoxy)butanamide (150 mg, 0.287 mmol) in ethanol (7 mL) was added 2N NaOH (1 mL). The mixture was stirred at 80° C. for 3 h. The reaction was neutralized with saturated ammonium chloride and the product precipitated. The solids were collected and washed with water. The solids were dissolved in ethyl acetate, dried over sodium sulfate and concentrated to give 1-(4-methoxybenzyl)-3-methyl-8-(3-(3-(trifluoromethoxy)phenoxy)propyl)-1H-purine-2,6(3H,7H)-dione (130 mg, 89.7%) as a light yellow solid. LCMS retention time 1.635 min; LCMS MH+ 505.

Intermediate 61 8-chloro-7-(4-chlorobenzyl)-1-(3-hydroxypropyl)-1H-purine-2,6(3H,7H)-dione

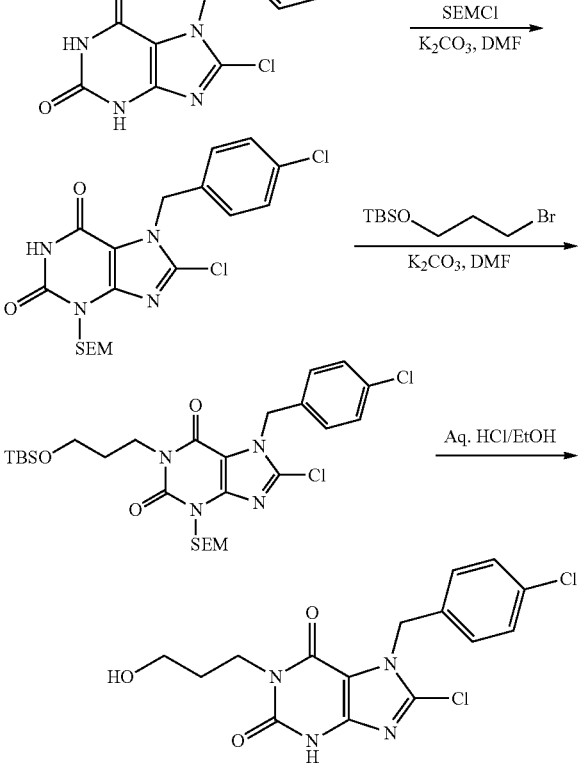

Step 1 2-amino-7-(4-chlorobenzyl)-1H-purin-6(7H)-one

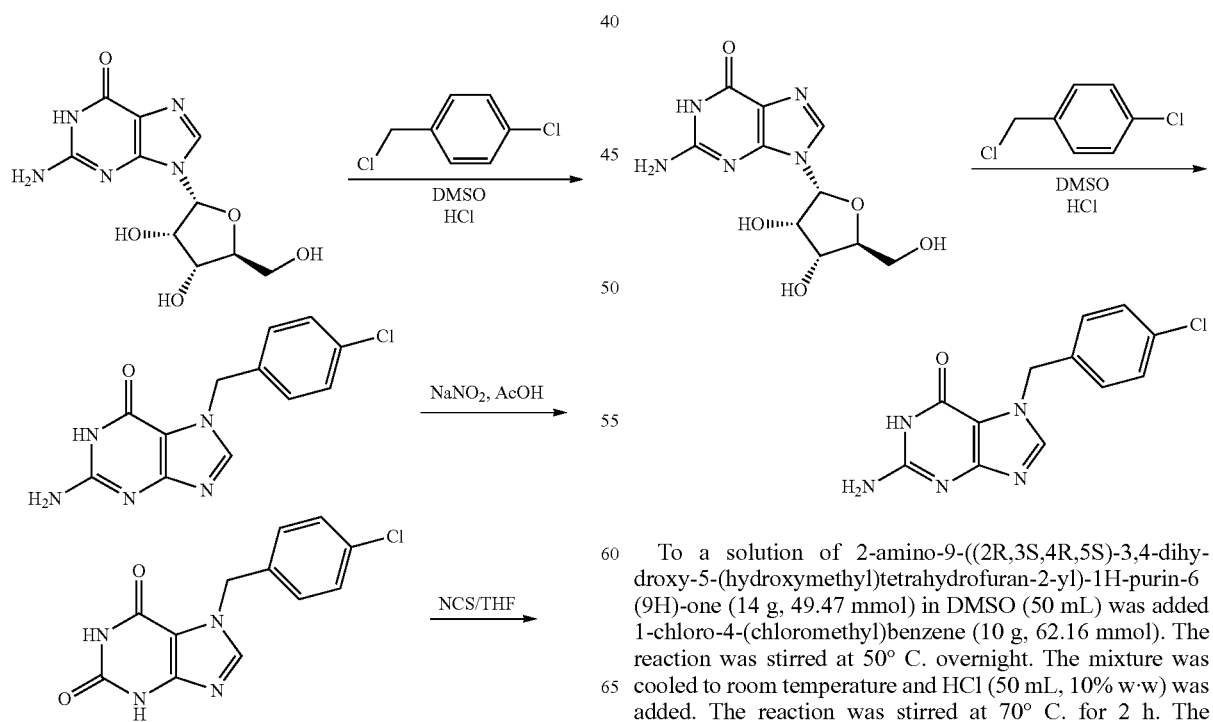

To a solution of 2-amino-9-((2R,3S,4R,5S)-3,4-dihydroxy-5-(hydroxymethyl)tetrahydrofuran-2-yl)-1H-purin-6(9H)-one (14 g, 49.47 mmol) in DMSO (50 mL) was added 1-chloro-4-(chloromethyl)benzene (10 g, 62.16 mmol). The reaction was stirred at 50° C. overnight. The mixture was cooled to room temperature and HCl (50 mL, 10% w·w) was added. The reaction was stirred at 70° C. for 2 h. The reaction was cooled and the precipitate was collected and washed with water and ethanol. The product was dried under vacuum to give 2-amino-7-(4-chlorobenzyl)-1H-purin-6(7H)-one (10 g, 74.1% yield) as grey solid. LCMS retention time 0.529 min; LCMS MH+ 276.

Step 2
7-(4-chlorobenzyl)-1H-purine-2,6(3H,7H)-dione

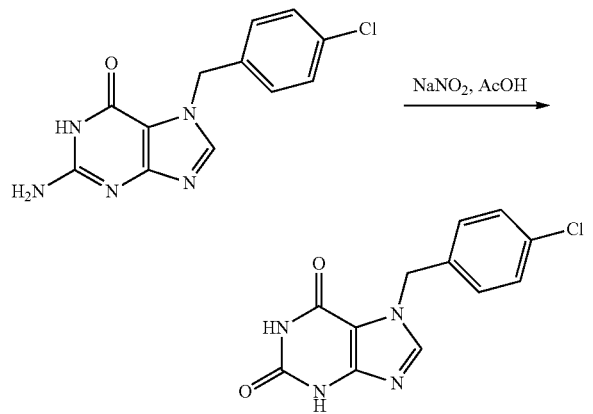

To a solution of 2-amino-7-(4-chlorobenzyl)-1H-purin-6(7H)-one (6.8 g, 24.7 mmol) in acetic acid (80 mL) and water (10 mL) was added a solution of sodium nitrite (3.4 g, 24.7 mmol) in water (10 mL) dropwise at 50° C. The reaction was stirred at 50° C. for 1 h. The mixture was cooled to room temperature and stirred for another 1.5 h. The precipitate was collected, washed with water and ethanol, and dried in vacuo to give 7-(4-chlorobenzyl)-1H-purine-2,6(3H,7H)-dione (6.5 g, 95.3% yield) as yellow solid. LCMS retention time 0.635 min; LCMS MH+ 277.

Step 3 8-chloro-7-(4-chlorobenzyl)-1H-purine-2,6(3H,7H)-dione

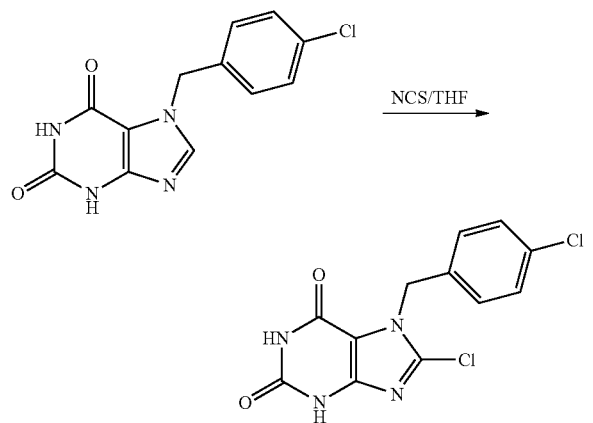

To a solution of 7-(4-chlorobenzyl)-1H-purine-2,6(3H,7H)-dione (2.2 g, 7.97 mmol) in THF (30 mL) was added NCS (1.1 g, 8.27 mmol) at 0° C. in portions. Then the resulting mixture was stirred at room temperature until it became a clear solution. The reaction was immediately quenched with ice-water and concentrated. The residue was extracted with ethyl acetate. The organic phase was washed with saturated sodium bicarbonate and brine, dried over sodium sulfate, and concentrated to give a crude product. This material was purified by silica gel chromatography eluting with DCM/methanol (50:1 to 20:1) to give 8-chloro-7-(4-chlorobenzyl)-1H-purine-2,6(3H,7H)-dione (450 mg, 18.2% yield) as white solid. LCMS retention time 1.071; LCMS MH+-58 311.

Step 4 8-chloro-7-(4-chlorobenzyl)-3-((2-(trimethylsilyl)ethoxy)methyl)-1H-purine-2,6(3H,7H)-dione

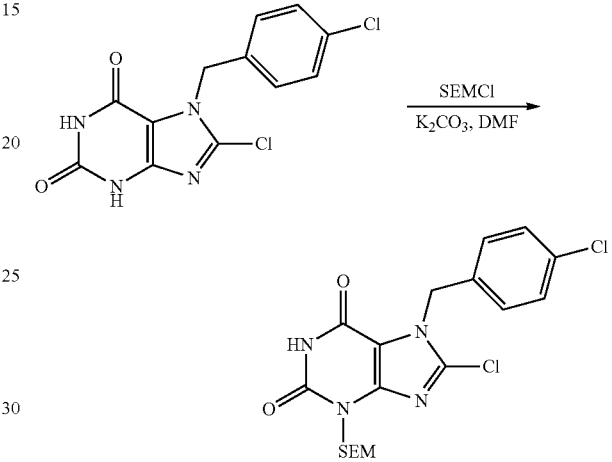

To a solution of 8-chloro-7-(4-chlorobenzyl)-1H-purine-2,6(3H,7H)-dione (450 mg, 1.45 mmol) in DMF (20 mL) was added potassium carbonate (0.4 g, 2.90 mmol), followed by 2-(trimethylsilyl)ethoxymethyl chloride (0.7 mL, 3.96 mmol) at 0° C. The resulting mixture was stirred at 60° C. for 16 h. The mixture was partitioned between ethyl acetate and water. The combined organic phase was washed with brine, dried over sodium sulfate, and concentrated to give crude product. This material was purified by silica gel chromatography eluting with petroleum/ethyl acetate (3:1 to 1:1) to give 8-chloro-7-(4-chlorobenzyl)-3-((2-(trimethylsilyl)ethoxy)methyl)-1H-purine-2,6(3H,7H)-dione (250 mg, 39.2% yield) as yellow oil. LCMS retention time 1.886; LCMS MH+-28 413.

Step 5 7-benzyl-1-(3-(tert-butyldimethylsilyloxy)propyl)-8-chloro-3-((2-(trimethylsilyl)ethoxy)methyl)-1H-purine-2,6(3H,7H)-dione

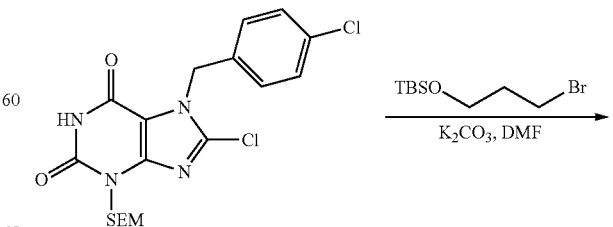

-continued

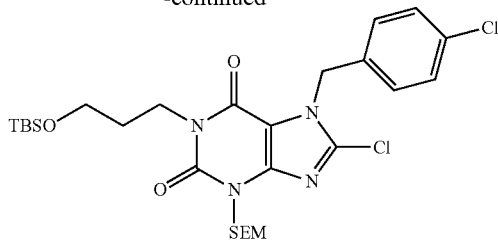

To a solution of 8-chloro-7-(4-chlorobenzyl)-3-((2-(trimethylsilyl)ethoxy)methyl)-1H-purine-2,6(3H,7H)-dione (250 mg, 0.568 mmol) in DMF (30 mL) was added (3-bromopropoxy)(tert-butyl)dimethylsilane (0.2 g, 0.794 mmol), followed by potassium carbonate (160 mg, 1.13 mmol). The mixture was stirred at 70° C. overnight. The reaction was cooled and partitioned between ethyl acetate and water. The combined organic phase was washed with brine, dried over sodium sulfate, and concentrated to give 7-benzyl-1-(3-(tert-butyldimethylsilyloxy)propyl)-8-chloro-3-((2-(trimethylsilyl)ethoxy)methyl)-1H-purine-2,6(3H,7H)-dione (340 mg, 97.4% yield) as colorless oil. LCMS retention time 4.675 min; LCMS MH+ 613.

Step 6 8-chloro-7-(4-chlorobenzyl)-1-(3-hydroxypropyl)-1H-purine-2,6(3H,7H)-dione

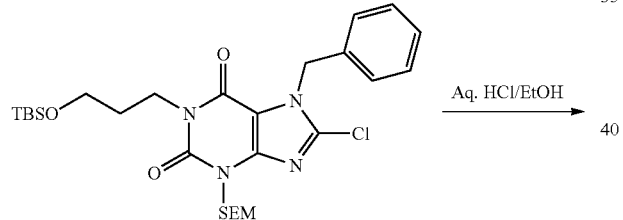

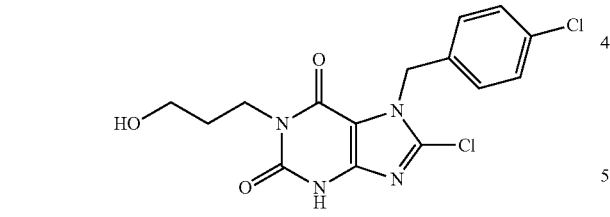

To a solution of 7-benzyl-1-(3-(tert-butyldimethylsilyloxy)propyl)-8-chloro-3-((2-(trimethylsilyl)ethoxy)methyl)-1H-purine-2,6(3H,7H)-dione (340 mg, 0.56 mmol) in ethyl alcohol (20 mL) was added concentrated HCl (2 mL). The mixture was stirred at 80° C. overnight. The reaction was concentrated, neutralized with saturated sodium bicarbonate, extracted with ethyl acetate. The organic phase was washed with brine, dried over sodium sulfate, and concentrated to give 8-chloro-7-(4-chlorobenzyl)-1-(3-hydroxypropyl)-1H-purine-2,6(3H,7H)-dione (180 mg, 87.5% yield) as colorless oil. LCMS retention time 1.990 min; LCMS MH+ 369.

Intermediate 62 8-bromo-7-(4-fluorobenzyl)-3-methyl-1-(3-hydroxypropyl)-1H-purine-2,6(3H,7H)-dione

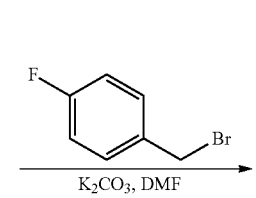

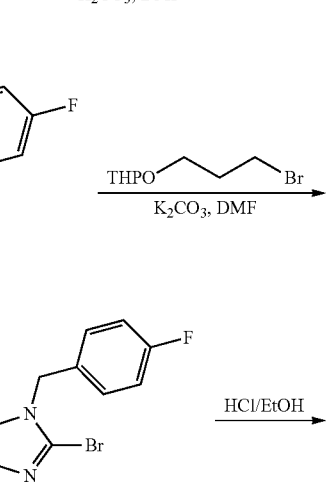

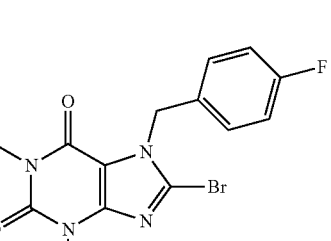

Steps 1 and 2 8-bromo-7-(4-fluorobenzyl)-3-methyl-1-(3-(tetrahydro-2H-pyran-2-yloxy)propyl)-1H-purine-2,6(3H,7H)-dione

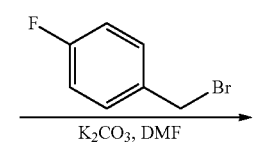

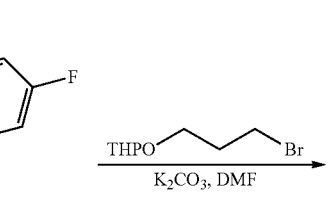

365
-continued

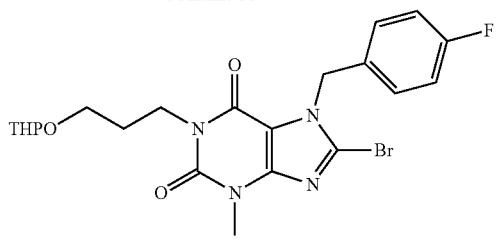

The title compound was prepared using the methods of intermediate 8, step 2 and intermediate 14 to give 8-bromo-7-(4-fluorobenzyl)-3-methyl-1-(3-(tetrahydro-2H-pyran-2-yloxy)propyl)-1H-purine-2,6(3H,7H)-dione (26 g, 64.3% yield) as white solid. LCMS retention time 1.694 min; LCMS MH$^+$-THP 411.

Step 3 8-bromo-7-(4-fluorobenzyl)-1-(3-hydroxypropyl)-3-methyl-1H-purine-2,6(3H,7H)-dione

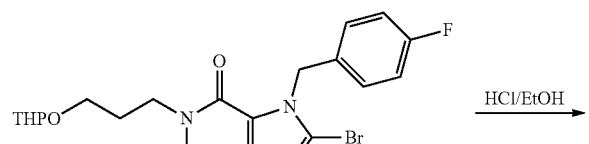

To a solution of 8-bromo-7-(4-fluorobenzyl)-3-methyl-1-(3-(tetrahydro-2H-pyran-2-yloxy)propyl)-1H-purine-2,6(3H,7H)-dione (26 g, 52.5 mmol) in ethanol (500 mL) was added concentrated HCl (50 mL) and the mixture was stirred at room temperature for 1 h. The mixture was concentrated to half its volume and the product precipitated. The solids were collected and washed with water and ethanol; then dried under vacuum to give 8-bromo-7-(4-fluorobenzyl)-1-(3-hydroxypropyl)-3-methyl-1H-purine-2,6(3H,7H)-dione (18.1 g, 83.9% yield) as white solid. LCMS retention time 1.243 min; LCMS MH$^+$ 411.

366

Intermediate 63 8-bromo-7-(4-chlorobenzyl)-1-(3-hydroxypropyl)-3-methyl-1H-purine-2,6(3H,7H)-dione

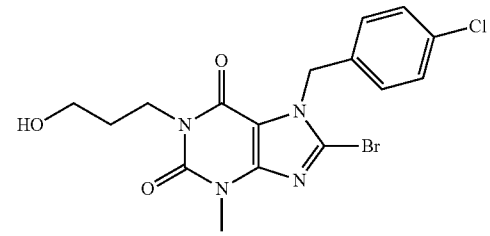 [SMILES: Cn1c(=O)n(CCCO)c(=O)c2c1nc(Br)n2Cc1ccc(Cl)cc1]

The title compound was prepared using the method of intermediate 62 to give 8-bromo-7-(4-chlorobenzyl)-1-(3-hydroxypropyl)-3-methyl-1H-purine-2,6(3H,7H)-dione (21 g, 93.1% yield) as white solid. LCMS retention time 1.375 min; LCMS MH$^+$ 429.

Intermediate 64 7-(4-chlorobenzyl)-3-methyl-2,6-dioxo-2,3,6,7-tetrahydro-1H-purine-8-sulfonyl chloride

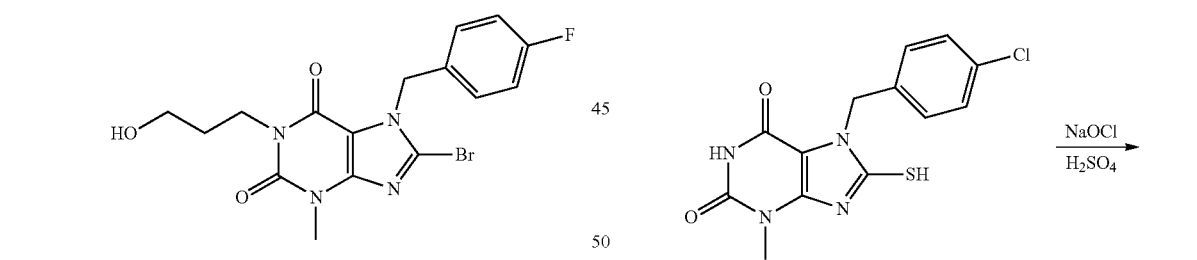

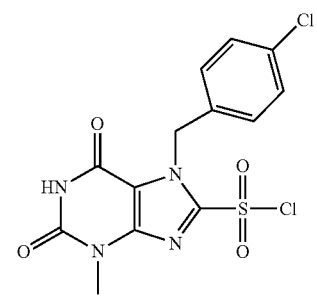

Step 1 7-(4-chlorobenzyl)-8-mercapto-3-methyl-1H-purine-2,6(3H,7H)-dione

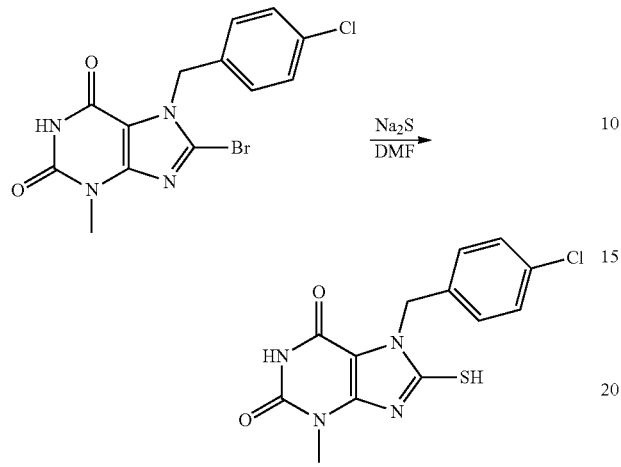

The title compound was prepared using the method of intermediate 7 to give 7-(4-chlorobenzyl)-8-mercapto-3-methyl-1H-purine-2,6(3H,7H)-dione (710 mg, 81.5% yield) as yellow solid. LCMS retention time 0.973 min; LCMS MH+ 323.

Step 2 7-(4-chlorobenzyl)-3-methyl-2,6-dioxo-2,3,6,7-tetrahydro-1H-purine-8-sulfonyl chloride

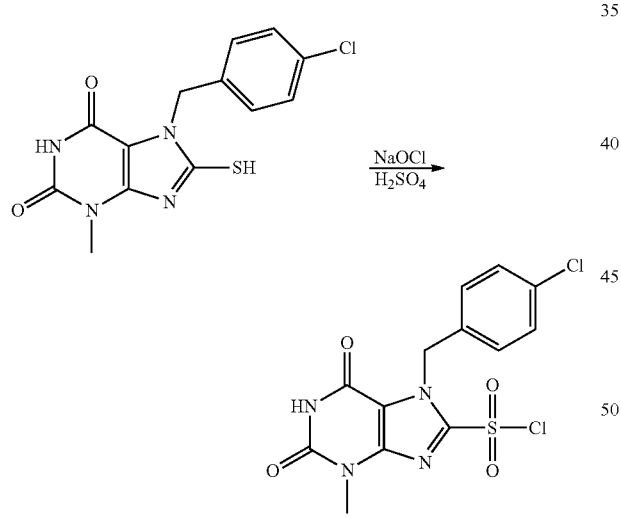

To a solution of 7-(4-chlorobenzyl)-8-mercapto-3-methyl-1H-purine-2,6(3H,7H)-dione (400 mg, 1.24 mmol) in concentrated sulfuric acid (5 mL) was added aqueous sodium hypochlorite solution (5 mL, 5% active chlorine) dropwise at 0° C. and the mixture was stirred at room temperature for 15 min. The mixture was poured into ice-water and extracted with ethyl acetate. The organic layer was washed with brine, dried and concentrated to give 7-(4-chlorobenzyl)-3-methyl-2,6-dioxo-2,3,6,7-tetrahydro-1H-purine-8-sulfonyl chloride (230 mg, 47.6% yield) as brown solid, which was directly used immediately without purification.

The following intermediates 65-71 were prepared using the method of intermediate 5,

Intermediate 65
2-(3,5-bis(trifluoromethyl)phenoxy)ethanol

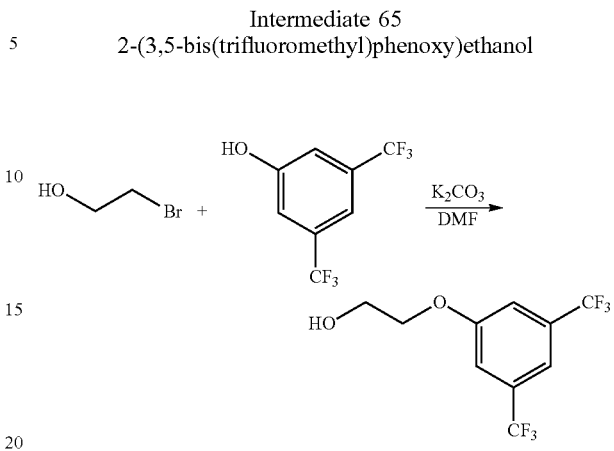

Light yellow oil, mg, 87.6% yield. TLC petroleum ether/ethyl acetate (1:2), UV detection, Rf=0.4

Intermediate 66 2-(3-chlorophenoxy)ethanol


Light yellow oil, 350 mg, 89.1% yield. TLC petroleum ether/ethyl acetate (1:2), UV detection, Rf=0.4

Intermediate 67 2-(m-tolyloxy)ethanol

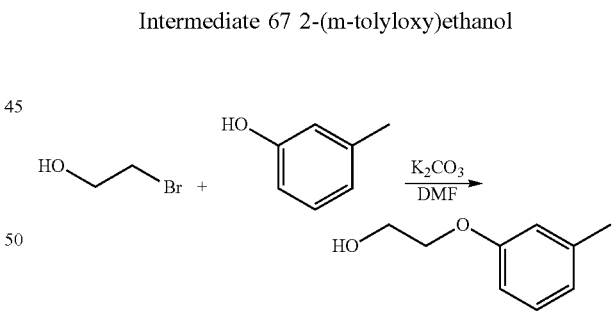

Light yellow oil, 357 mg, 91% yield. TLC petroleum ether/ethyl acetate (1:2), UV detection, Rf=0.35

Intermediate 68
2-(3-(trifluoromethyl)phenoxy)ethanol

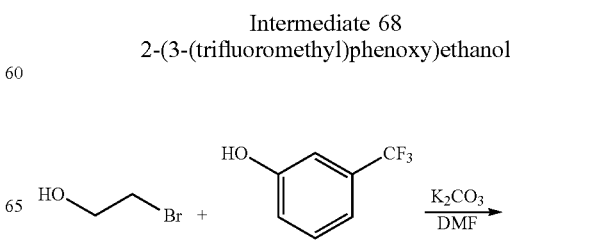

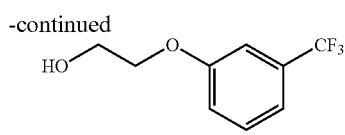

Light yellow oil, 332 mg, 81.9% yield. TLC petroleum ether/ethyl acetate (1:2), UV detection, Rf=0.4

Intermediate 69
2-(4-(trifluoromethoxy)phenoxy)ethanol

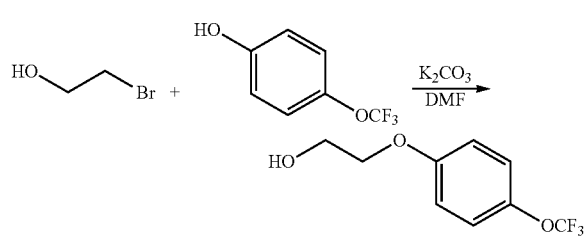

Light yellow oil, 100 mg, 78.9% yield. TLC petroleum ether/ethyl acetate (1:2), UV detection, Rf=0.4

Intermediate 70
2-(2-(trifluoromethoxy)phenoxy)ethanol

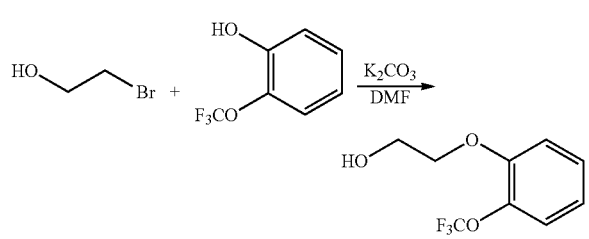

Light yellow oil, 105 mg, 85% yield. TLC petroleum ether/ethyl acetate (1:2), UV detection, Rf=0.4

Intermediate 71
2-(4-chloro-3-(trifluoromethyl)phenoxy)ethanol

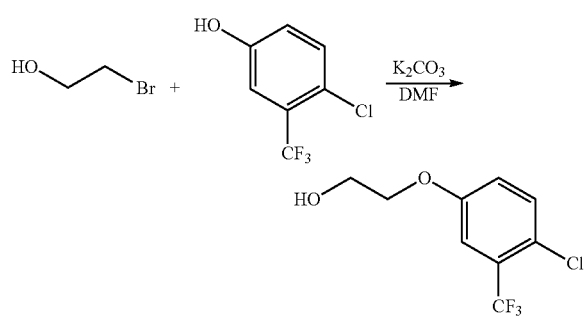

Light yellow oil, 100 mg, 81% yield. TLC petroleum ether/ethyl acetate (1:2), UV detection, Rf=0.4

Intermediate 72 (2-hydroxycyclopentyl)methyl methanesulfonate

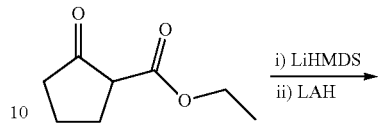

Step 1 2-(hydroxymethyl)cyclopentanol

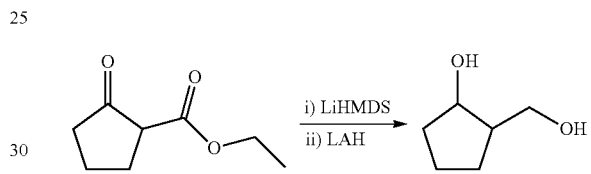

To a solution of ethyl 2-oxocyclopentanecarboxylate (1 g, 6.41 mmol) in anhydrous THF (40 mL) was added lithium bis(trimethylsilyl)amide (6.41 mL, 6.41 mmol, 1 mmol/L in THF) at 0° C. under nitrogen. The reaction was stirred at 0° C. for 40 min. Then LAH (500 mg, 13.2 mmol) was added in portions into the above solution at 0° C. The reaction was stirred at 0° C. for 1 h. The mixture was quenched with ice-water, filtered and the filter cake washed with ethyl acetate. The filtrate was washed with brine, dried over sodium sulfate, and concentrated to give a crude product, which was purified by silica gel chromatography eluting with DCM/methanol (30:1 to 10:1) to give 2-(hydroxymethyl)cyclopentanol (40 mg, 5.4%) as yellow oil. $^1$H-NMR (CDCl$_3$) δ 4.03-4.05 (m, 1H), 3.76-3.80 (q, 1H), 3.54-3.59 (t, 1H), 1.57-2.01 (m, 7H).

Step 2 (2-hydroxycyclopentyl)methyl methanesulfonate

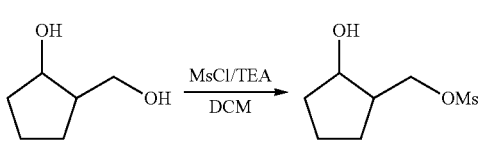 [SMILES: OCC1CCCC1O ; CS(=O)(=O)OCC1CCCC1O]

The title compound was prepared using the method of intermediate 42 to give (2-hydroxycyclopentyl)methyl methanesulfonate (50 mg, 73.5% yield) as yellow oil.

371

Intermediate 73 1-(3-(benzyloxy)cyclobutyl)-8-chloro-7-(4-chlorobenzyl)-3-methyl-1H-purine-2,6(3H,7H)-dione

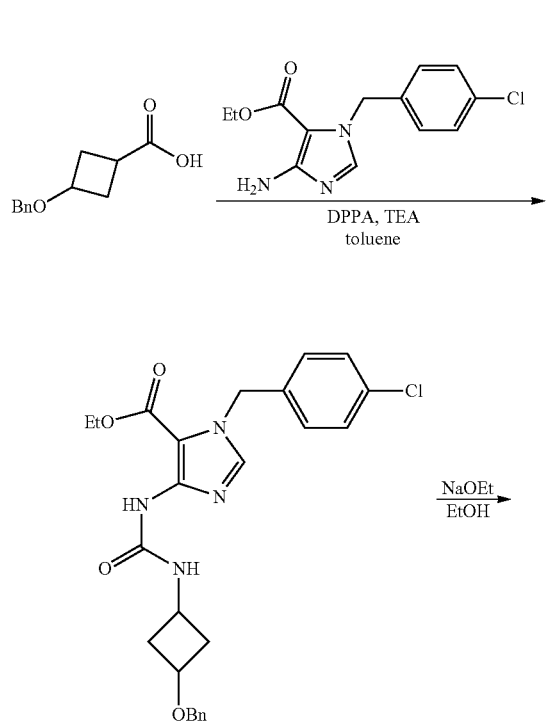

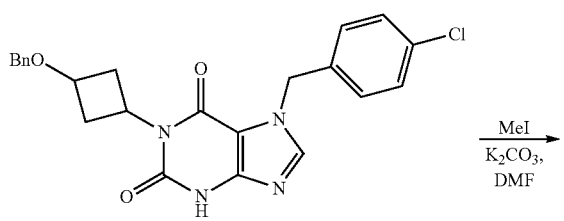

372

Step 1 ethyl 4-(3-(3-(benzyloxy)cyclobutyl)ureido)-1-(4-chlorobenzyl)-1H-imidazole-5-carboxylate

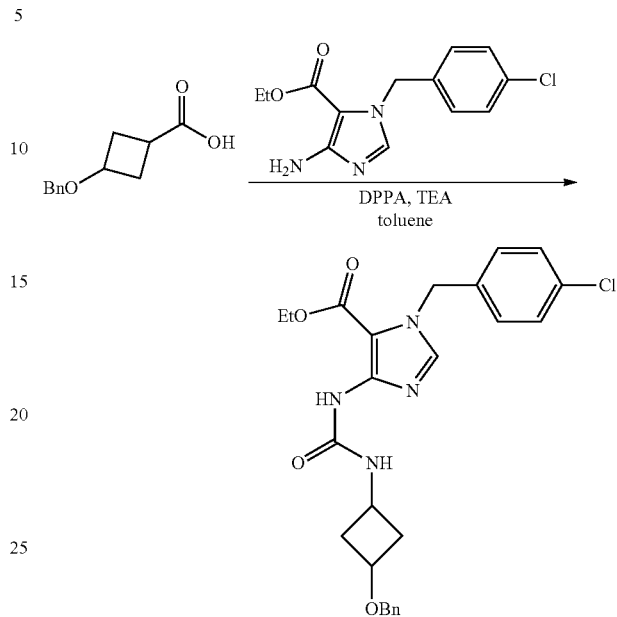

To a solution of 3-(benzyloxy)cyclobutanecarboxylic acid (442 mg, 2.14 mmol) in toluene (10 mL) was added diphenylphosphoryl azide (589 mg, 2.14 mmol) followed by TEA (216 mg, 2.14 mmol). The reaction was stirred at room temperature for 30 min. Ethyl 4-amino-1-(4-chlorobenzyl)-1H-imidazole-5-carboxylate (300 mg, 1.07 mmol) was added to the mixture and the resulting mixture was stirred at 110° C. for 6 h. The reaction was partitioned between ethyl acetate and brine. The organic phase was dried and concentrated to give a crude product, which was purified by silica gel chromatography eluting with DCM/methanol (50:1) to give ethyl 4-(3-(3-(benzyloxy)cyclobutyl)ureido)-1-(4-chlorobenzyl)-1H-imidazole-5-carboxylate (310 mg, 59.9 yield) as yellow solid. LCMS retention time 1.909 min; LCMS MH+ 483.

Step 2 1-(3-(benzyloxy)cyclobutyl)-7-(4-chlorobenzyl)-1H-purine-2,6(3H,7H)-dione

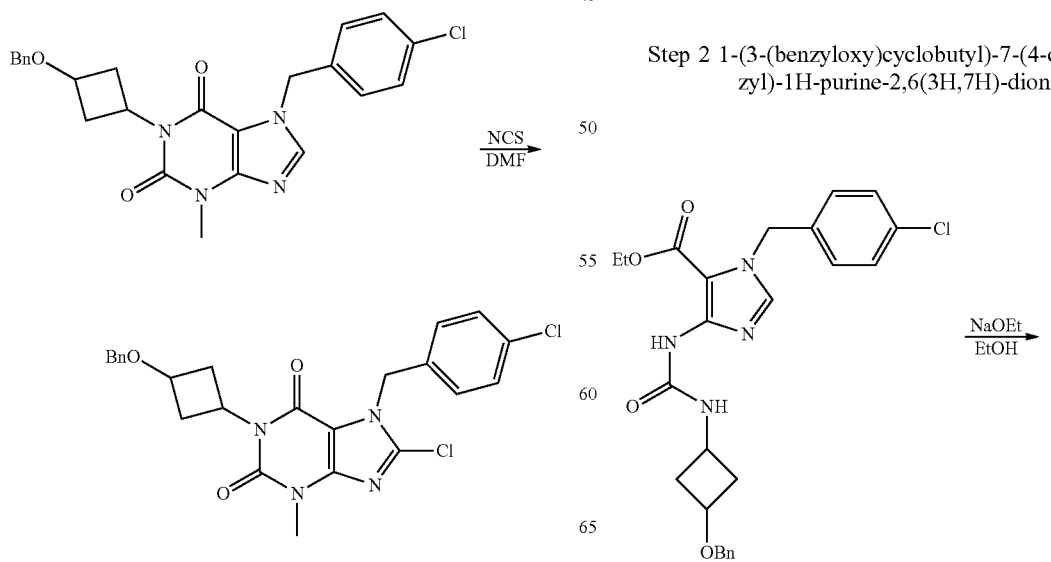

-continued

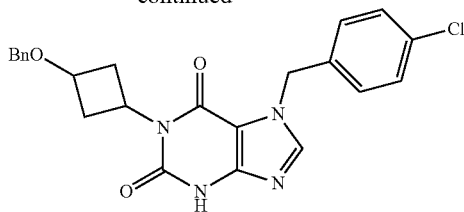

To a solution of ethyl 4-(3-(3-(benzyloxy)cyclobutyl)ureido)-1-(4-chlorobenzyl)-1H-imidazole-5-carboxylate (310 mg, 0.64 mmol) in ethanol (50 mL) was added freshly prepared sodium ethoxide (87.4 mg, 1.28 mmol) and the reaction was heated at reflux for 4 h. The reaction was cooled and concentrated. The residue was partitioned between ethyl acetate and brine. The organic layer was dried and concentrated to give 1-(3-(benzyloxy)cyclobutyl)-7-(4-chlorobenzyl)-1H-purine-2,6(3H,7H)-dione (240 mg, 85.5% yield) as a yellow solid. LCMS retention time 1.764 min; LCMS MH$^+$ 437.

Step 3 1-(3-(benzyloxy)cyclobutyl)-7-(4-chlorobenzyl)-1H-purine-2,6(3H,7H)-dione

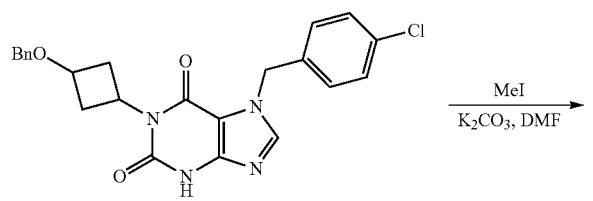

To a solution of 1-(3-(benzyloxy)cyclobutyl)-7-(4-chlorobenzyl)-1H-purine-2,6(3H,7H)-dione (240 mg, 0.62 mmol) in DMF (5 mL) was added iodomethane (105.3 mg, 0.74 mmol) followed by potassium carbonate (128 mg, 0.93 mmol) and the reaction was stirred at room temperature for 16 h. The reaction was partitioned between ethyl acetate and brine. The organic phase was dried and concentrated to give 1-(3-(benzyloxy)cyclobutyl)-7-(4-chlorobenzyl)-3-methyl-1H-purine-2,6(3H,7H)-dione (220 mg, 78.9% yield) as a yellow solid. LCMS retention time 1.914 min; LCMS MH$^+$ 451.

Step 4 1-(3-(benzyloxy)cyclobutyl)-8-chloro-7-(4-chlorobenzyl)-3-methyl-1H-purine-2,6(3H,7H)-dione

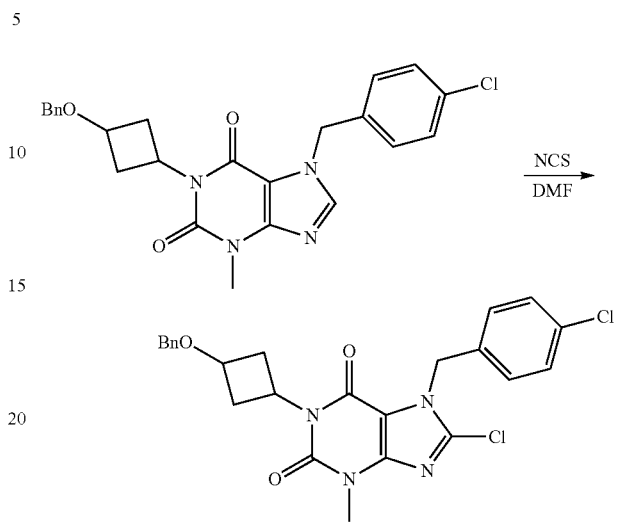

To a solution of 1-(3-(benzyloxy)cyclobutyl)-7-(4-chlorobenzyl)-3-methyl-1H-purine-2,6(3H,7H)-dione (220 mg, 0.49 mmol) in DMF (3 mL) was added NCS (71.7 mg, 0.54 mmol) in portions at 0° C. The reaction was stirred at room temperature for 4 h. The reaction was partitioned between ethyl acetate and saturated aqueous sodium bicarbonate. The organic phase was washed with brine, dried and concentrated to give a crude product, which was purified by silica gel chromatography eluting with DCM/methanol (60:1) to give 1-(3-(benzyloxy)cyclobutyl)-8-chloro-7-(4-chlorobenzyl)-3-methyl-1H-purine-2,6(3H,7H)-dione (170 mg, 71.8% yield) as yellow solid. LCMS retention time 2.079 min; LCMS MH$^+$ 485.

Intermediate 74 3-hydroxycyclopentyl methanesulfonate

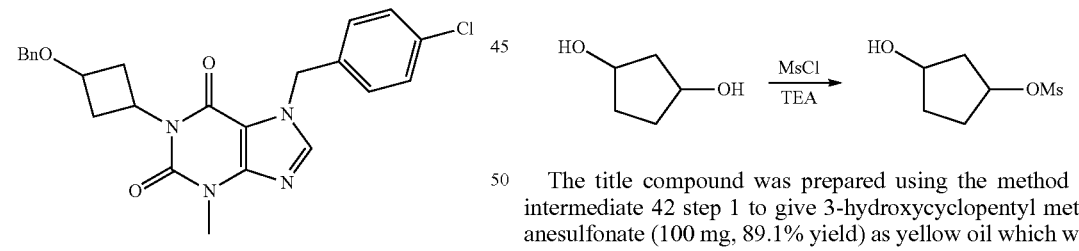

The title compound was prepared using the method of intermediate 42 step 1 to give 3-hydroxycyclopentyl methanesulfonate (100 mg, 89.1% yield) as yellow oil which was used without characterization.

Intermediate 75 benzyl 3-(methylsulfonyloxy)cyclobutanecarboxylate

The title compound was prepared using the method of intermediate 42 to give benzyl 3-(methylsulfonyloxy)cyclobutanecarboxylate (0.71 g, 79.8% yield) as yellow solid which was used without characterization.

Intermediate 76 3-(chloromethyl)-5-fluoropyridine

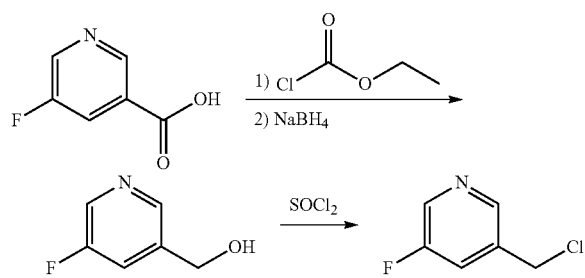

Step 1 (5-fluoropyridin-3-yl)methanol

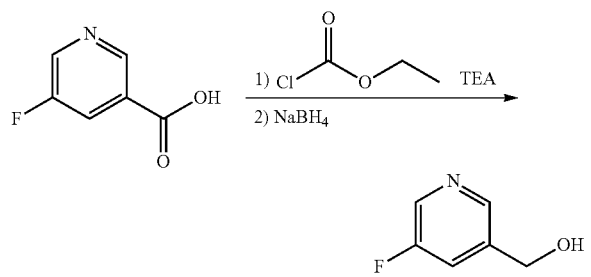

To a solution of 5-fluoronicotinic acid (1.0 g, 7.09 mmol) in THF (10 mL) was added TEA (0.9 mL, 7.73 mmol), followed by ethyl chloroformate (0.6 mL, 7.73 mmol) at 0° C. The reaction was stirred at room temperature 2 h; then it was filtered. The residue was washed with a small amount of THF. The filtrate was chilled to 0° C. and sodium borohydride (0.67 g, 17.73 mmol) was added, followed by dropwise addition of water (5 mL). The reaction was stirred at room temperature overnight. The reaction was partitioned between ethyl acetate and water. The organic layers were combined, dried over sodium sulfate, and concentrated to give a crude product which was used purified by a silica gel chromatography to give (5-fluoropyridin-3-yl)methanol (197 mg, 21.8% yield) as a colorless oil. LCMS retention time 0.375 min; LCMS MH+ 128.

Step 2 3-(chloromethyl)-5-fluoropyridine

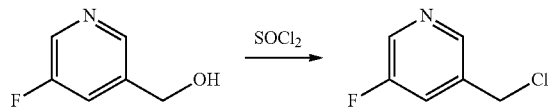 [SMILES: OCc1cncc(F)c1 ; "SOCl2" ; Fc1cncc(CCl)c1]

To a solution of (5-fluoropyridin-3-yl)methanol (0.19 g, 1.50 mmol) in DCM (5 mL) was added thionyl chloride (0.19 ml, 2.6 mmol) at 0° C. The reaction was stirred at room temperature for 2 h. The reaction was concentrated and the residue was dried in vacuo to yield 3-(chloromethyl)-5-fluoropyridine (166 mg) which was used without characterization.

Intermediate 77 8-Bromo-1-(3-((tert-butyldimethyl-silyl)oxy)propyl)-7-(4-chlorobenzyl)-3-methyl-1H-purine-2,6(3H,7H)-dione

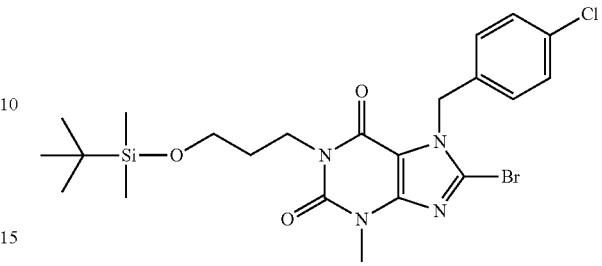

8-Bromo-7-(4-chlorobenzyl)-3-methyl-1H-purine-2,6 (3H,7H)-dione (33.4 g, 90.4 mmol, intermediate 8), potassium carbonate (25.0 g, 180.8 mmol) and TBAI (0.225 g) were combined in DMF (460 mL). To the mixture was added (3-bromopropoxy)(tert-butyl)dimethylsilane (25.17 g, 99.4 mmol) and the reaction was heated at 100° C. for 4 h. The reaction was cooled to room temperature, diluted with water (1.2 L) and extracted with ethyl acetate (3×400 mL). The combined organic extracts were washed with 1N lithium chloride (2×500 mL), dried with magnesium sulfate, filtered and the solvent removed under reduced pressure to give a light golden oil. The oil was purified using 2×120 g silica gel columns eluted with 10% ethyl acetate/hexanes to yield 8-bromo-1-(3-((tert-butyldimethylsilyl)oxy)propyl)-7-(4-chlorobenzyl)-3-methyl-1H-purine-2,6(3H,7H)-dione (38.3 g, 78% yield) as an off-white solid. LCMS retention time=5.083 min and 99% purity, LCMS MH+ 543. $^1$H NMR (CDCl$_3$) δ 7.29-7.34 (m, 4H), 5.50 (s, 2H), 4.08 (t, 2H, J=8 Hz), 3.70 (t, 2H, J=8 Hz), 3.53 (s, 3H), 1.83-1.90 (m, 2H), 0.86 (s, 9H), 0.02 (s, 6H).

Intermediate 78 8-chloro-7-(4-chlorobenzyl)-3-ethyl-1-(3-hydroxypropyl)-1H-purine-2,6(3H,7H)-dione

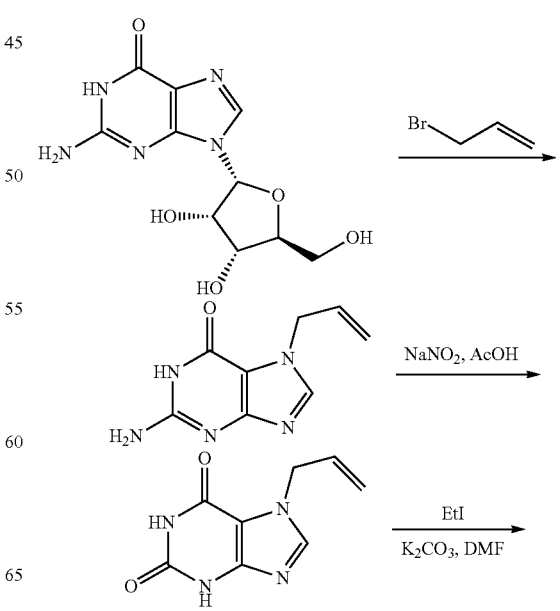

377
-continued

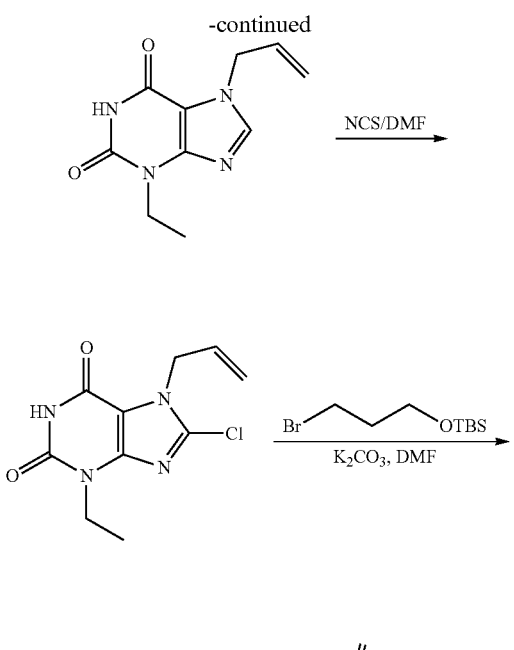

378

Step 1 7-allyl-2-amino-1H-purin-6(7H)-one

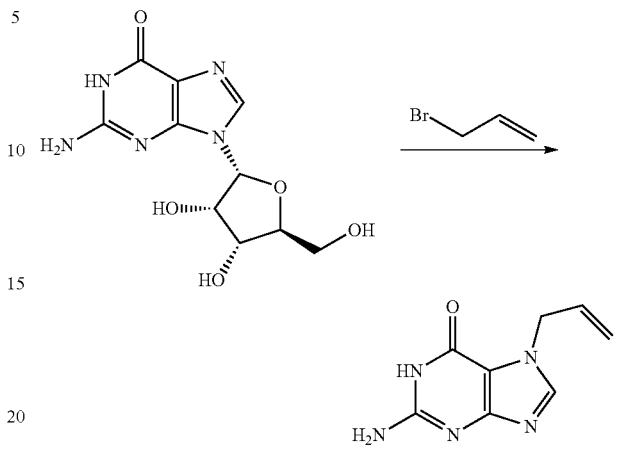

To a solution of 2-amino-9-((2R,3S,4R,5S)-3,4-dihydroxy-5-(hydroxymethyl)tetrahydrofuran-2-yl)-1H-purin-6(9H)-one (50 g, 176.7 mmol) in DMSO (150 mL) was added allyl bromide (36 mL, 420 mmol), the mixture was stirred at room temperature overnight under nitrogen atmosphere. The reaction was chilled to 0° C. concentrated HCl (100 mL) was added and the reaction was stirred at 70° C. for 4 h. The reaction was cooled to room temperature, poured into water (800 mL), and neutralized with 6N sodium hydroxide to pH 7-8. The solids that formed were collected and the filter cake was washed with water and ethanol, then dried under vacuum to give 7-allyl-2-amino-1H-purin-6(7H)-one (20 g, 59.2% yield) as yellow solid. LCMS retention time 0.330 min; LCMS MH+ 192.

Step 2 7-allyl-1H-purine-2,6(3H,7H)-dione

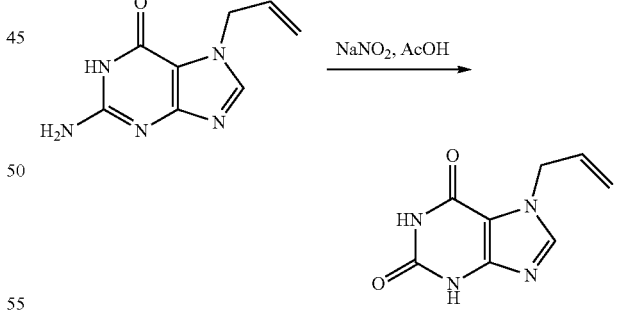

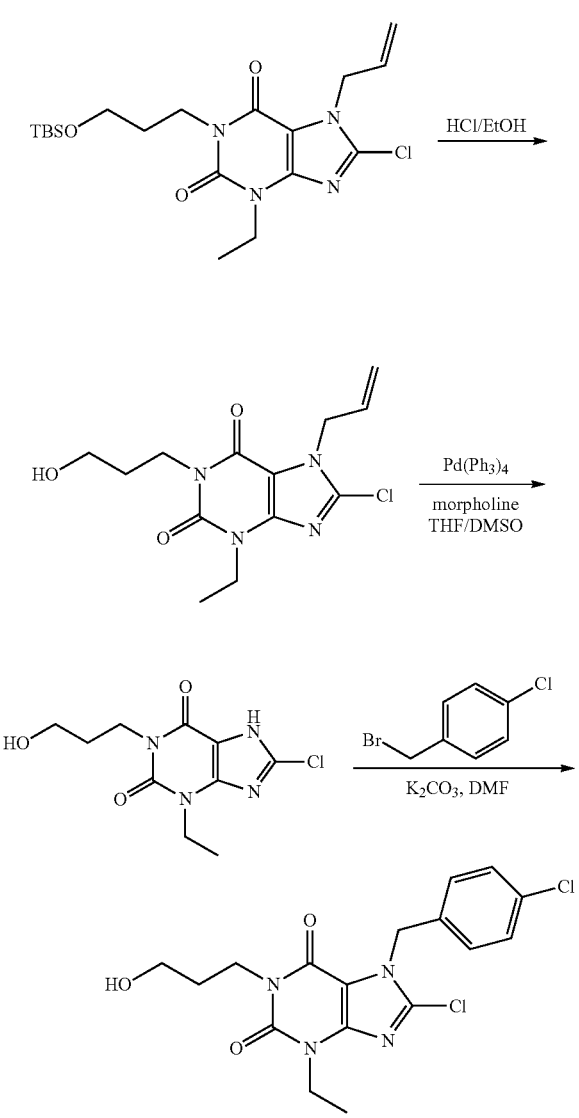

To a solution of 7-allyl-2-amino-1H-purin-6(7H)-one (20 g, 104.7 mmol) in acetic acid (500 mL) and water (70 mL) was added a solution of sodium nitrite (30 g, 434.8 mmol) in water (70 mL) dropwise at 50° C. The reaction was stirred at 50° C. for 1 h. The reaction was concentrated and poured into ice-water. The solids that formed were filtered and the filter cake was washed with water and ethanol, then dried under vacuum to give 7-allyl-1H-purine-2,6(3H,7H)-dione (15 g, 74.4% yield) as yellow solid. LCMS retention time 0.555 min; LCMS MH+ 193.

Step 3 7-allyl-3-ethyl-1H-purine-2,6(3H,7H)-dione

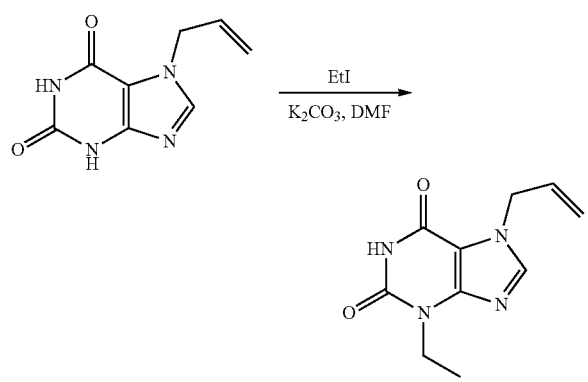

To a solution of 7-allyl-1H-purine-2,6(3H,7H)-dione (15 g, 78.13 mmol) in DMF (200 mL) was added potassium carbonate (23.7 g, 171.74 mmol), followed by dropwise addition of iodoethane (3.6 mL, 44.54 mmol). The reaction was stirred at room temperature overnight. The reaction was concentrated and partitioned between ethyl acetate and water. The organic phase was washed with brine and dried over sodium sulfate, and concentrated to give a crude product which was purified by silica gel chromatography eluting with petroleum/ethyl acetate (6:1 to 3:1) to give 7-allyl-3-ethyl-1H-purine-2,6(3H,7H)-dione (7 g, 40.7% yield) as yellow solid. LCMS retention time 0.402 min; LCMS MH+ 221.

Step 4 7-allyl-8-chloro-3-ethyl-1H-purine-2,6(3H,7H)-dione

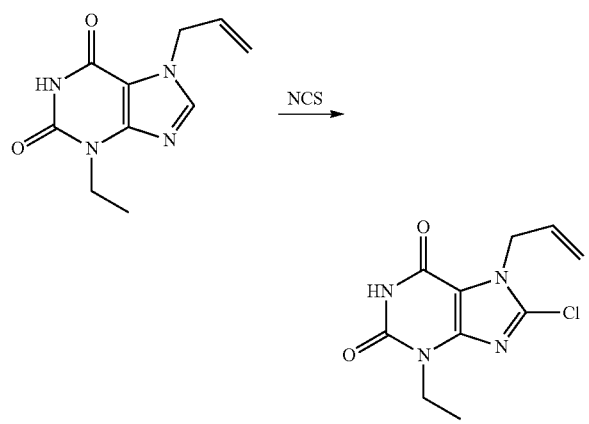

To a solution of 7-allyl-3-ethyl-1H-purine-2,6(3H,7H)-dione (7 g, 31.82 mmol) in DMF (50 mL) was added NCS (5 g, 37.45 mmol) in portions at 0° C. The resulting mixture was stirred at room temperature for 5 h under nitrogen. The reaction was partitioned between ethyl acetate and water. The organic phase was washed with brine, dried over sodium sulfate, and concentrated to give 7-allyl-8-chloro-3-ethyl-1H-purine-2,6(3H,7H)-dione (11.8 g, ~50% pure) as light yellow oil. LCMS retention time 0.764 min; LCMS MH+ 255.

Step 5 7-allyl-1-(3-(tert-butyldimethylsilyloxy)propyl)-8-chloro-3-ethyl-1H-purine-2,6(3H,7H)-dione

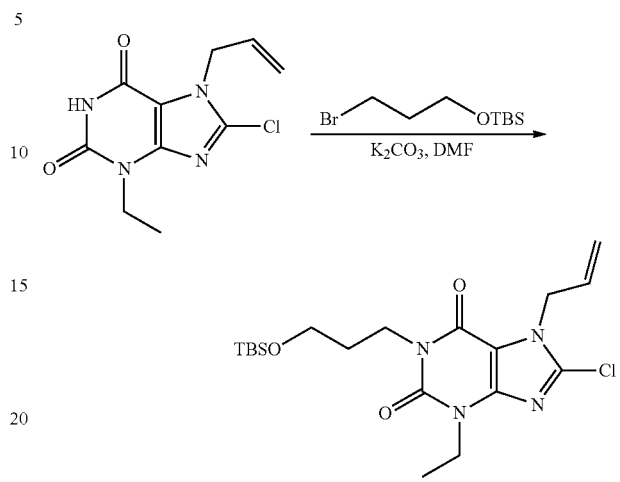

To a solution of 7-allyl-8-chloro-3-ethyl-1H-purine-2,6(3H,7H)-dione (6.8 g, 26.77 mmol) in DMF (50 mL) was added (3-bromopropoxy)(tert-butyl)dimethylsilane (8 g, 31.75 mmol), followed by potassium carbonate (5 g, 36.23 mmol) and TBAI (5 mg, 0.014 mmol). The reaction was stirred at 60° C. overnight. The reaction was cooled to room temperature and partitioned between ethyl acetate and water. The organic phase was washed with brine, dried over sodium sulfate, and concentrated to give a crude product which was purified by silica gel chromatography eluting with petroleum/ethyl acetate (15:1 to 1:1) to give 7-allyl-1-(3-(tert-butyldimethylsilyloxy)propyl)-8-chloro-3-ethyl-1H-purine-2,6(3H,7H)-dione (5.88 g, 51.6% yield) as a colorless oil. LCMS retention time 2.224 min; LCMS MH+ 427.

Step 6 7-allyl-8-chloro-3-ethyl-1-(3-hydroxypropyl)-1H-purine-2,6(3H,7H)-dione

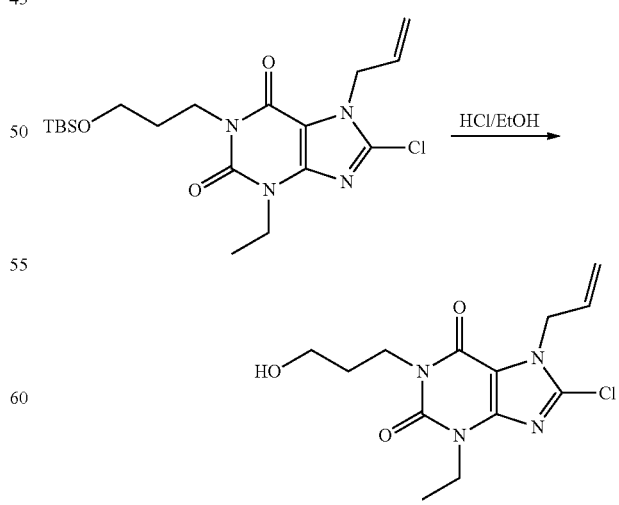

To a solution of 7-allyl-1-(3-(tert-butyldimethylsilyloxy)propyl)-8-chloro-3-ethyl-1H-purine-2,6(3H,7H)-dione (3.8 g, 8.92 mmol) in ethanol (20 mL) was added concentrated HCl (2 mL). The mixture was stirred at room temperature for 0.5 h. The mixture was concentrated and partitioned between ethyl acetate and saturated sodium bicarbonate. The organic phase was washed with brine and dried over sodium sulfate, and concentrated to give 7-allyl-8-chloro-3-ethyl-1-(3-hydroxypropyl)-1H-purine-2,6(3H,7H)-dione (3.8 g) as yellow oil, which was used without purification. LCMS retention time 0.999 min; LCMS MH+ 313.

Step 7 8-chloro-3-ethyl-1-(3-hydroxypropyl)-1H-purine-2,6(3H,7H)-dione

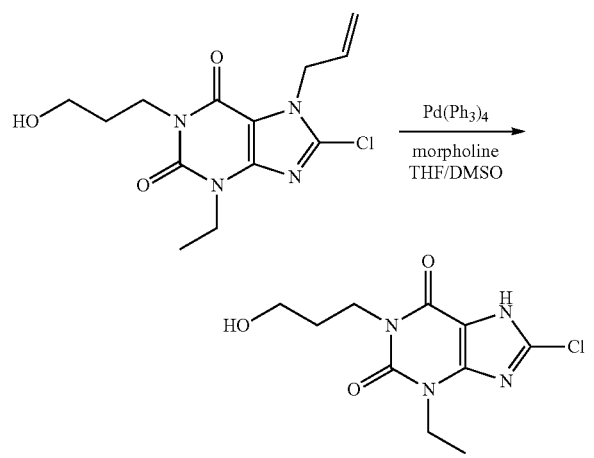

To a solution of 7-allyl-8-chloro-3-ethyl-1-(3-hydroxypropyl)-1H-purine-2,6(3H,7H)-dione (3.8 g, 12.18 mmol) in THF (40 mL) and DMSO (10 mL) was added tetrakis(triphenylphosphine)palladium(0) (800 mg, 0.693 mmol) and morpholine (5.4 mL, 62.07 mmol). The reaction was degassed and refilled with nitrogen 3 times. The reaction was stirred at room temperature overnight. The mixture was poured into water (20 mL) and ethyl acetate (100 mL). The solid precipitate was collected, washed with ethyl acetate, and dried under vacuum to give 8-chloro-3-ethyl-1-(3-hydroxypropyl)-1H-purine-2,6(3H,7H)-dione (2.2 g, 66.4% yield) as grey solid. LCMS retention time 0.404 min; LCMS MH+ 273.

Step 8 8-chloro-7-(4-chlorobenzyl)-3-ethyl-1-(3-hydroxypropyl)-1H-purine-2,6(3H,7H)-dione

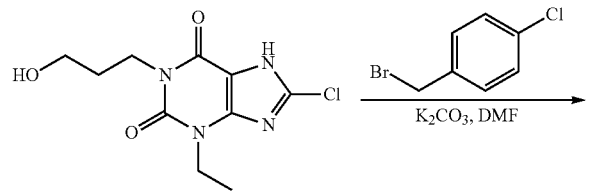

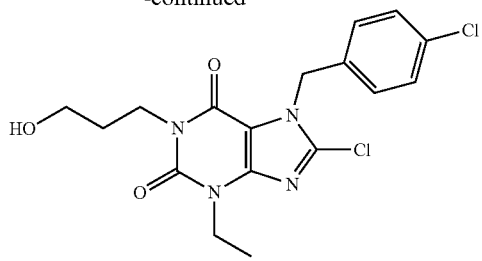

To a solution of 8-chloro-3-ethyl-1-(3-hydroxypropyl)-1H-purine-2,6(3H,7H)-dione (2.2 g, 8.09 mmol) in DMF (10 mL) was added 1-(bromomethyl)-4-chlorobenzene (2.47 g, 12.11 mmol), followed by potassium carbonate (2.23 g, 16.18 mmol) and TBAI (15 mg, 0.042 mmol). The reaction was stirred at 50° C. for 2 h. The reaction was cooled to room temperature and partitioned between ethyl acetate and water. The organic phase was washed with brine and dried over sodium sulfate, and concentrated to give a crude product which was purified by silica gel chromatography eluting with petroleum/ethyl acetate (5:1 to 1:2) to give 8-chloro-7-(4-chlorobenzyl)-3-ethyl-1-(3-hydroxypropyl)-1H-purine-2,6(3H,7H)-dione (2.3 g, 71.8% yield) as white solid. LCMS retention time 1.485 min; LCMS MH+ 397.

Intermediate 79 3,3,3-trifluoropropyl methanesulfonate

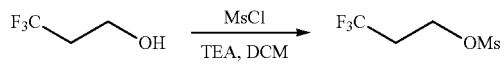

To a solution of 3,3,3-trifluoropropan-1-ol (500 mg, 4.38 mmol) in DCM (10 mL) was added TEA (1.22 mL, 8.77 mmol) followed by dropwise addition of methanesulfonyl chloride (0.51 mL, 6.58 mmol) at 0° C. The resulting mixture was stirred at room temperature for 2 h. The reaction was diluted with DCM and the organic phase washed with brine, dried and concentrated to give crude product which was purified via silica gel chromatography eluting with petroleum ether/ethyl acetate (5:1) to give 3,3,3-trifluoropropyl methanesulfonate (490 mg, 58.2% yield) as light yellow oil. TLC (petroleum ether/ethyl acetate=3:1), Rf=0.6.

Intermediate 80 3-methyl-8-(3-(trifluoromethoxy)phenoxy)-1-(3,3,3-trifluoropropyl)-1H-purine-2,6(3H,7H)-dione

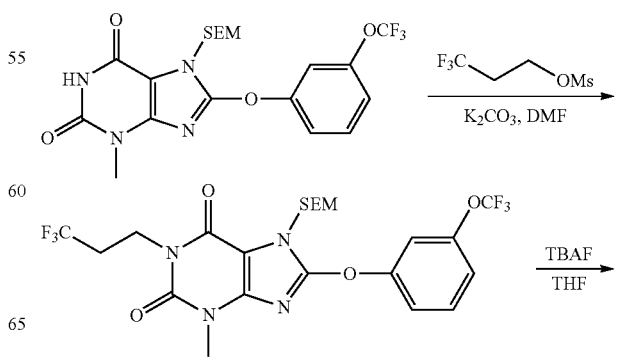

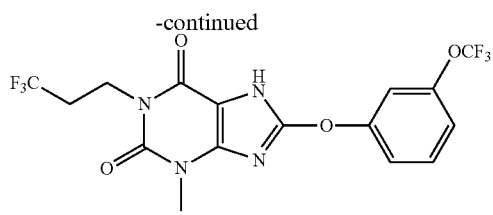

Step 1 3-methyl-8-(3-(trifluoromethoxy)phenoxy)-1-(3,3,3-trifluoropropyl)-7-((2-(trimethylsilyl)ethoxy)methyl)-1H-purine-2,6(3H,7H)-dione

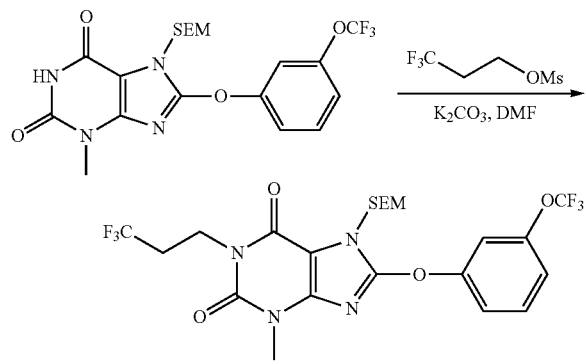

To a solution of 3-methyl-8-(3-(trifluoromethoxy)phenoxy)-7-((2-(trimethylsilyl)ethoxy)methyl)-1H-purine-2,6(3H,7H)-dione (500 mg, 1.06 mmol, intermediate 12, step 2) in DMF (6 mL) was added 3,3,3-trifluoropropyl methanesulfonate (305 mg, 1.59 mmol) followed by potassium carbonate (439 mg, 3.17 mmol). The reaction was stirred at 60° C. overnight. The mixture was diluted with ethyl acetate and extracted with brine. The organic phase was dried and concentrated to give 3-methyl-8-(3-(trifluoromethoxy)phenoxy)-1-(3,3,3-trifluoropropyl)-7-((2-(trimethylsilyl)ethoxy)methyl)-1H-purine-2,6(3H,7H)-dione (510 mg, 84.6% yield) as yellow syrup. LCMS retention time 2.275 min; LCMS MH+ 569.

Step 2 3-methyl-8-(3-(trifluoromethoxy)phenoxy)-1-(3,3,3-trifluoropropyl)-1H-purine-2,6(3H,7H)-dione

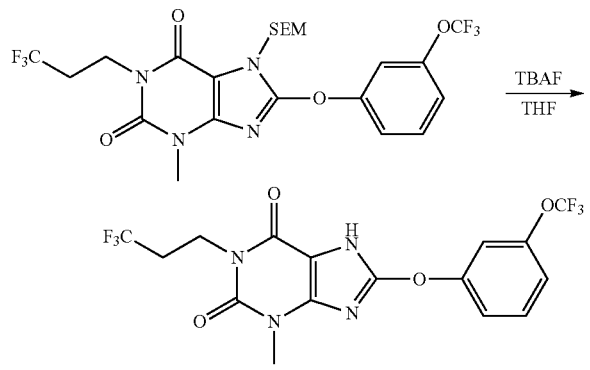

The title compound was prepared as intermediate 17, step 2 to give 3-methyl-8-(3-(trifluoromethoxy)phenoxy)-1-(3,3,3-trifluoropropyl)-1H-purine-2,6(3H,7H)-dione (228 mg, 56.3% yield) as white solid. LCMS retention time 1.626 min; LCMS MH+ 439.

Intermediate 81 8-Bromo-7-isopentyl-3-methyl-1H-purine-2,6(3H,7H)-dione

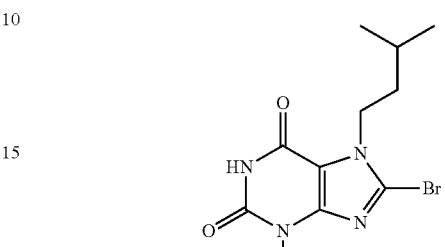

8-Bromo-3-methyl-1H-purine-2,6(3H,7H)-dione (2.0 g, 8.16 mmol), diisopropylethylamine (2.13 mL, 12.24 mmol) and 1-bromo-3-methylbutane (0.98 mL, 8.16 mmol) were combined in DMF (20 mL) and stirred at room temperature for 15 h. The reaction was diluted with water (200 mL) and extracted with ethyl acetate (3×100 mL). The combined extracts were washed with 1 N LiCl (2×100 mL), dried with magnesium sulfate, filtered and evaporated under reduced pressure to give 8-bromo-7-isopentyl-3-methyl-1H-purine-2,6(3H,7H)-dione (2.2 g, 78% yield) as a white solid. LCMS retention time=2.654 min and 98% purity, LCMS MH+ 315.

Intermediate 82 8-Bromo-1-(3-((tert-butyldimethylsilyl)oxy)propyl-7-isopentyl-3-methyl-1H-purine-2,6(3H,7H)-dione

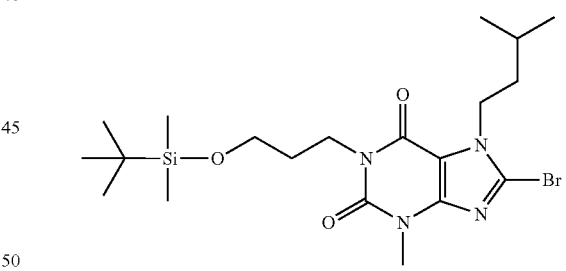

8-Bromo-7-isopentyl-3-methyl-1H-purine-2,6(3H,7H)-dione (2.0 g, 6.35 mmol), (3-bromopropoxy)(tert-butyl)dimethylsilane (1.77 g, 6.98 mmol intermediate 81), potassium carbonate (1.76 g, 12.70 mmoL) and TBAI (0.020 g) were combined in DMF (45 mL) and stirred at room temperature for 6 h. The reaction was diluted with water (200 mL) and extracted with ethyl acetate (3×100 mL). The combined extracts were washed with 1 N LiCl (2×100 mL), dried with magnesium sulfate, filtered and evaporated under reduced pressure to leave a golden oil. The oil was purified using a 40 g silica gel flash column eluted with 10% ethyl acetate/hexanes to give 8-bromo-1-(3-((tert-butyldimethylsilyl)oxy)propyl-7-isopentyl-3-methyl-1H-purine-2,6(3H, 7H)-dione (2.73 g, 88% yield) as a clear oil: LCMS retention time=5.271 minutes and 92% purity, LCMS MH+=489.

385

Intermediate 83 7-Benzyl-8-bromo-1-(3-((tert-butyldimethylsilyl)oxy)propyl)-3-methyl-1H-purine-2,6(3H,7H)-dione

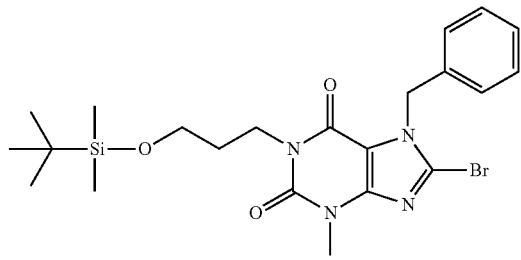 [SMILES: Cn1c(=O)n(CCCO[Si](C)(C)C(C)(C)C)c(=O)c2c1nc(Br)n2Cc1ccccc1]

The title compound was prepared using the methods of intermediates 81 and 82. Light golden oil, 15.5 g, 100% yield: LCMS retention time=4.872 minutes and 96% purity, LCMS MH$^+$=509.

EXAMPLES

Example 1 7-(4-chlorobenzyl)-3-methyl-8-(3-(trifluoromethyl)phenoxy)-1H-purine-2,6(3H,7H)-dione

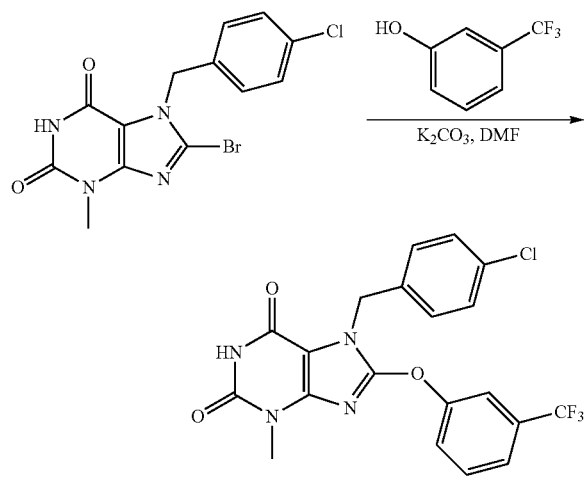

To a solution of 8-bromo-7-(4-chlorobenzyl)-3-methyl-1H-purine-2,6(3H,7H)-dione (240 mg, 0.649 mmol, intermediate 8) in dimethyl formamide (5 mL) was added 3-(trifluoromethyl)phenol (105 mg, 0.649 mmol) followed by potassium carbonate (107 mg, 0.779 mmol). The resulting mixture was stirred at 80° C. for 6 h. The mixture was diluted with ethyl acetate (15 mL) and extracted with brine and saturated aqueous ammonium chloride solution. Then the organic phase was dried and concentrated to give a crude solid product which was collected and washed with ethanol to give 7-(4-chlorobenzyl)-3-methyl-8-(3-(trifluoromethyl)phenoxy)-1H-purine-2,6(3H,7H)-dione (237 mg, 81.1% yield) as white solid. $^1$H-NMR (DMSO-d$_6$) δ 11.24 (s, 1H), 7.77 (s, 1H), 7.69-7.71 (m, 3H), 7.43 (s, 4H), 5.42 (s, 2H), 3.22 (s, 3H). LCMS retention time 2.306 min; LCMS MH$^+$ 451.

386

Example 2 7-(4-chlorobenzyl)-1-ethyl-3-methyl-8-(3-(trifluoromethyl)phenoxy)-1H-purine-2,6(3H,7H)-dione

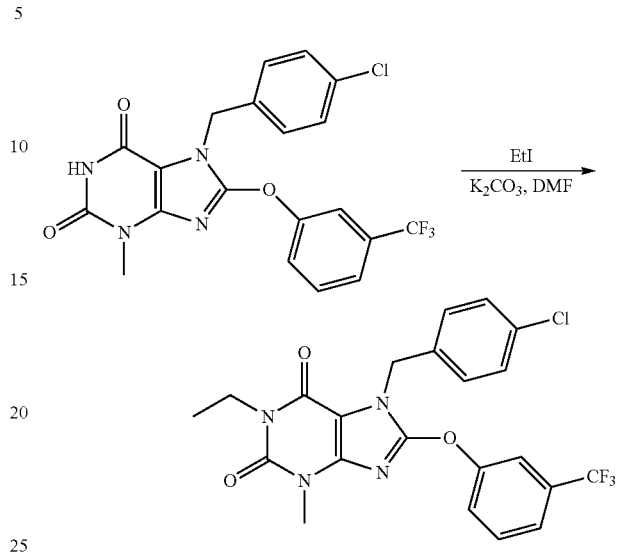

To a solution of 7-(4-chlorobenzyl)-3-methyl-8-(3-(trifluoromethyl)phenoxy)-1H-purine-2,6(3H,7H)-dione (50 mg, 0.11 mmol, example 1) in DMF (1 mL) was added iodoethane (18.7 mg, 0.12 mmol) followed by potassium carbonate (23 mg, 0.16 mmol). Then the mixture was stirred at 50° C. for 3 h. The mixture was diluted with ethyl acetate and extracted with brine and saturated aqueous ammonium chloride solution. The organic phase was dried and concentrated to give crude solid product which was collected and washed with ethanol to give 7-(4-chlorobenzyl)-1-ethyl-3-methyl-8-(3-(trifluoromethyl)phenoxy)-1H-purine-2,6(3H,7H)-dione (15 mg, 26.7% yield) as white solid. $^1$H-NMR (DMSO-d$_6$) δ 7.77 (s, 1H), 7.69-7.73 (m, 3H), 7.43 (s, 4H), 5.46 (s, 2H), 3.91-3.93 (q, 2H), 3.29 (s, 3H), 1.11-1.14 (t, 3H). LCMS retention time 3.109 min; LCMS MH$^+$ 479.

Example 3 2-(7-(4-chlorobenzyl)-3-methyl-2,6-dioxo-8-(3-(trifluoromethyl)phenoxy)-2,3,6,7-tetrahydro-1H-purin-1-yl)-N-methylacetamide

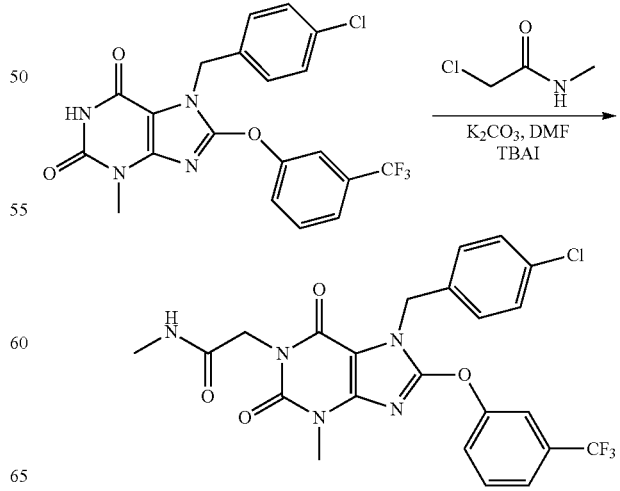

387

The title compound was prepared using the method of example 2 except a catalytic amount of TBAI was added to give 2-(7-(4-chlorobenzyl)-3-methyl-2,6-dioxo-8-(3-(trifluoromethyl)phenoxy)-2,3,6,7-tetrahydro-1H-purin-1-yl)-N-methylacetamide (36 mg, 62.1% yield) as white solid. $^1$H-NMR (DMSO-d$_6$) δ 7.97-7.98 (m, 1H), 7.79 (s, 1H), 7.69-7.74 (m, 3H), 7.44 (s, 4H), 5.45 (s, 2H), 4.43 (s, 2H), 3.91-3.93 (q, 2H), 3.29 (s, 3H), 2.58-2.59 (d, 3H). LCMS retention time 2.547 min; LCMS MH$^+$ 522.

Example 4 7-(4-chlorobenzyl)-3-methyl-1-((5-methylisoxazol-3-yl)methyl)-8-(3-(trifluoromethyl)phenoxy)-1H-purine-2,6(3H,7H)-dione

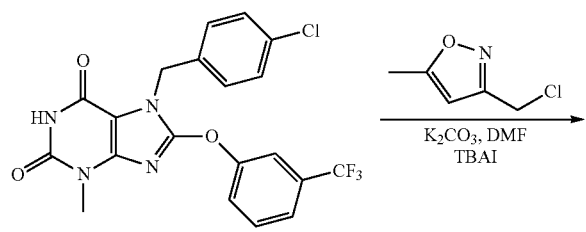

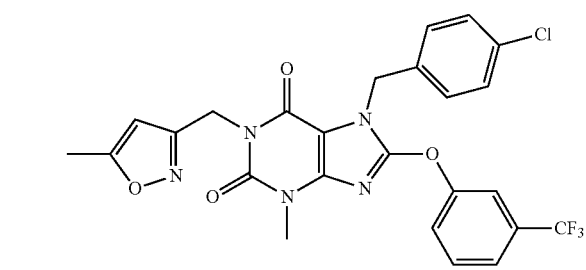

The title compound was prepared using the method of example 2 except a catalytic amount of TBAI was added to give 7-(4-chlorobenzyl)-3-methyl-1-((5-methylisoxazol-3-yl)methyl)-8-(3-(trifluoromethyl)phenoxy)-1H-purine-2,6(3H,7H)-dione (29 mg, 39.9% yield) as white solid. $^1$H-NMR (DMSO-d$_6$) δ 7.79 (s, 1H), 7.69-7.73 (m, 3H), 7.44 (s, 4H), 6.12 (s, 1H), 5.45 (s, 2H), 5.07 (s, 1H), 3.30 (s, 3H), 2.35 (S, 3H). LCMS retention time 2.920 min; LCMS MH$^+$ 546.

Example 5 7-(4-chlorobenzyl)-1-(2-hydroxyethyl)-3-methyl-8-(3-(trifluoromethyl)phenoxy)-1H-purine-2,6(3H,7H)-dione

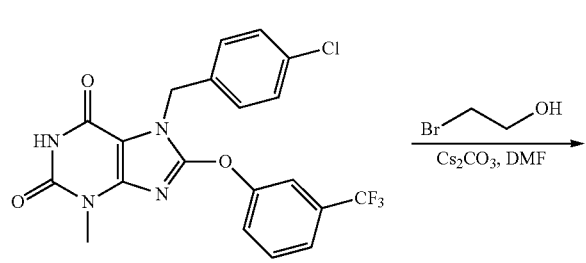

388

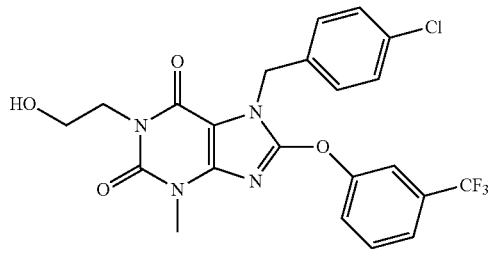

To a solution of 7-(4-chlorobenzyl)-3-methyl-8-(3-(trifluoromethyl)phenoxy)-1H-purine-2,6(3H,7H)-dione (60 mg, 0.133 mmol, example 1) in DMF (1 mL) was added 2-bromoethanol (16.5 mg, 0.133 mmol) and cesium carbonate (86.6 mg, 0.266 mmol). The resulting mixture was subjected to microwave irradiation at 120 □ for 20 min in a sealed tube. The mixture was diluted with ethyl acetate (5 mL) and extracted with saturated aqueous ammonium chloride solution. The organic phase was dried and concentrated to give crude product which was purified preparative HPLC to give 7-(4-chlorobenzyl)-1-(2-hydroxyethyl)-3-methyl-8-(3-(trifluoromethyl)phenoxy)-1H-purine-2,6(3H,7H)-dione (19 mg, 28.8% yield) as white solid. $^1$H-NMR (DMSO-d$_6$) δ 7.76 (s, 1H), 7.69-7.71 (m, 3H), 7.43 (s, 4H), 5.45 (s, 2H), 4.77-4.78 (d, 1H), 3.95-3.98 (t, 2H), 3.51-3.54 (t, 2H), 3.28 (s, 3H). LCMS retention time 2.608 min; LCMS MH$^+$ 495.

Example 6 7-(4-chlorobenzyl)-1-(2-(dimethylamino)ethyl)-3-methyl-8-(3-(trifluoromethoxy)phenoxy)-1H-purine-2,6(3H,7H)-dione hydrochloride

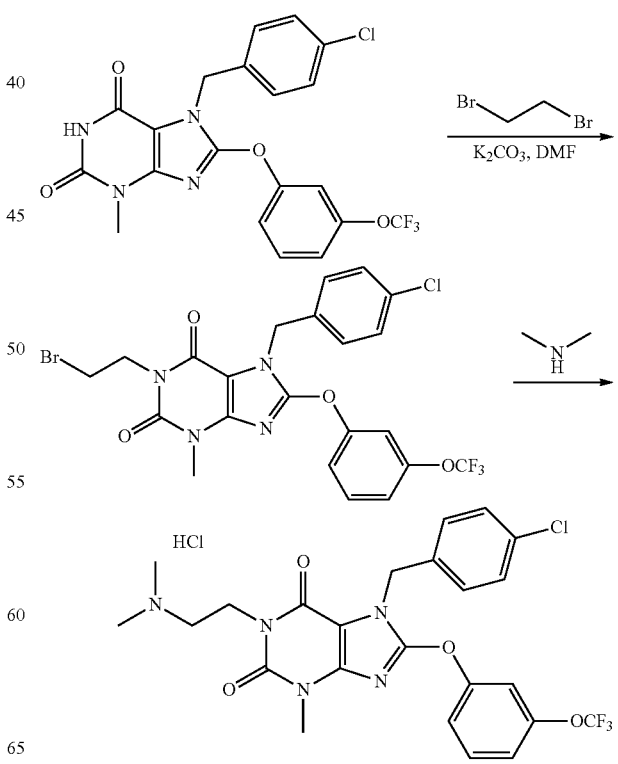

Step 1 1-(2-bromoethyl)-7-(4-chlorobenzyl)-3-methyl-8-(3-(trifluoromethoxy)phenoxy)-1H-purine-2,6(3H,7H)-dione

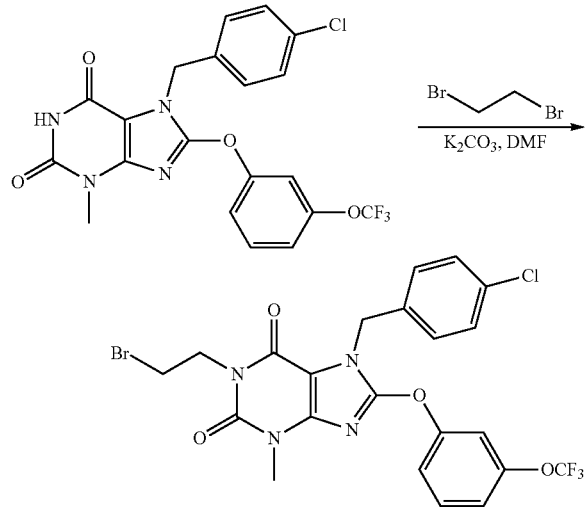

To a solution of 7-(4-chlorobenzyl)-3-methyl-8-(3-(trifluoromethoxy)phenoxy)-1H-purine-2,6(3H,7H)-dione (100 mg, 0.215 mmol, Intermediate 9) in DMF (3 mL) was added 1,2-dibromoethane (100 mg, 0.532 mmol), followed by potassium carbonate (60 mg, 0.429 mmol). The mixture was stirred at 80° C. overnight. The mixture was diluted with ethyl acetate and water, and the phases were separated. The organic phase was washed with brine, dried over sodium sulfate, filtered and concentrated to give crude product, which was purified by recrystallization from ethanol to give 1-(2-bromoethyl)-7-(4-chlorobenzyl)-3-methyl-8-(3-(trifluoromethoxy)phenoxy)-1H-purine-2,6(3H,7H)-dione (120 mg, 97.6% yield) as white solid. LCMS retention time 2.103 min; LCMS MH+ 573.

Step 2 7-(4-chlorobenzyl)-1-(2-(dimethylamino)ethyl)-3-methyl-8-(3-(trifluoromethoxy)phenoxy)-1H-purine-2,6(3H,7H)-dione hydrochloride

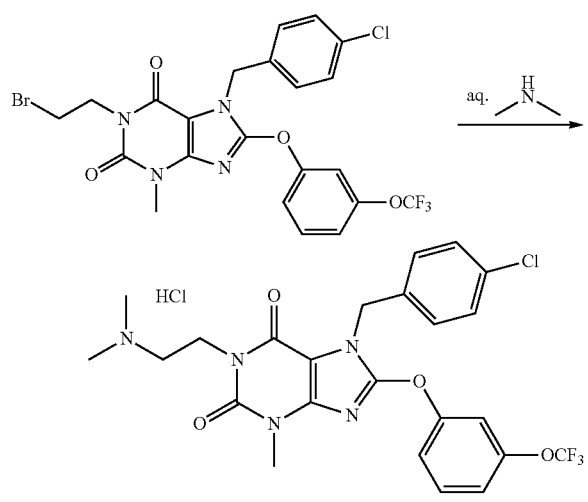

1-(2-bromoethyl)-7-(4-chlorobenzyl)-3-methyl-8-(3-(trifluoromethoxy)phenoxy)-1H-purine-2,6(3H,7H)-dione (120 mg, 0.0.210 mmol) was dissolved in aqueous dimethylamine (3 mL), then the mixture was heated to 100° C. in a sealed tube with stirring overnight. The mixture was diluted with ethyl acetate and water, and the phases were separated. The organic phase was washed with brine, dried over sodium sulfate, filtered and concentrated to give crude product, which was purified by preparative HPLC and lyophilized to give 7-(4-chlorobenzyl)-1-(2-(dimethylamino)ethyl)-3-methyl-8-(3-(trifluoromethoxy)phenoxy)-1H-purine-2,6(3H,7H)-dione hydrochloride (29 mg, 25.6% yield) as white solid. $^1$H-NMR (DMSO-$d_6$) δ 9.67 (s, 1H), 7.64-7.60 (t, 1H), 7.47-7.41 (m, 6H), 7.36-7.34 (m, 1H), 5.46 (s, 2H), 4.23-4.21 (m, 2H), 3.37-3.34 (m, 2H), 3.31 (s, 3H), 2.87-2.86 (d, 6H). LCMS retention time 2.174 min; LCMS MH+ 538.

The following examples 7a through 7k were prepared using the method of example 6, step 1.

Example 7a 7-(4-chlorobenzyl)-1-(3-hydroxypropyl)-3-methyl-8-(3-(trifluoromethoxy)phenoxy)-1H-purine-2,6(3H,7H)-dione

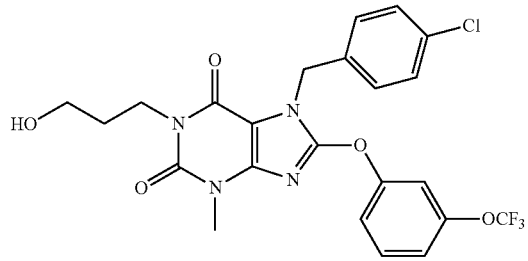 [SMILES: Cn1c(=O)n(CCCO)c(=O)c2c1nc(Oc1cccc(OC(F)(F)F)c1)n2Cc1ccc(Cl)cc1]

The title compound was prepared using the method of example 6, step 1 and purified via preparative HPLC to give 7-(4-chlorobenzyl)-1-(3-hydroxypropyl)-3-methyl-8-(3-(trifluoromethoxy)phenoxy)-1H-purine-2,6(3H,7H)-dione (10 mg, 17.3% yield) as white solid. $^1$H-NMR (CD$_3$OD) δ 7.57-7.53 (t, 1H), 7.46-7.44 (d, 2H), 7.37-7.33 (m, 4H), 7.26-7.24 (d, 1H), 5.49 (s, 2H), 4.13-4.09 (t, 1H), 3.64-3.60 (t, 2H), 3.42 (s, 3H), 1.89-1.86 (m, 2H). LCMS retention time 3.059 min; LCMS MH+ 525.

Example 7b 2-(7-(4-chlorobenzyl)-3-methyl-2,6-dioxo-8-(3-(trifluoromethoxy)phenoxy)-2,3,6,7-tetrahydro-1H-purin-1-yl)-N,N-dimethylacetamide

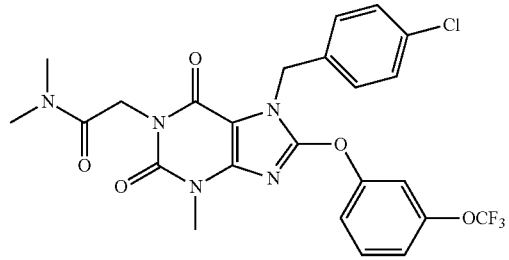 [SMILES: CN(C)C(=O)Cn1c(=O)c2c(nc(Oc3cccc(OC(F)(F)F)c3)n2Cc2ccc(Cl)cc2)n(C)c1=O]

The title compound was prepared with 2-chloro-N,N-dimethylacetamide and purified via preparative HPLC to give 2-(7-(4-chlorobenzyl)-3-methyl-2,6-dioxo-8-(3-(trifluoromethoxy)phenoxy)-2,3,6,7-tetrahydro-1H-purin-1-yl)-N,N-dimethylacetamide (20 mg, 17.2% yield) as white solid. $^1$H-NMR (400 Hz, DMSO-$d_6$) δ=7.64-7.59 (t, 1H), 7.55 (s, 1H), 7.48-7.40 (m, 5H), 7.35-7.33 (d, 1H), 5.42 (s, 2H), 4.69 (s, 2H), 3.30 (s, 3H), 3.07 (s, 3H), 2.84 (s, 3H). LCMS retention time 3.079 min; LCMS MH$^+$ 552.

Example 7c 7-(4-chlorobenzyl)-3-methyl-8-(3-(trifluoromethoxy)phenoxy)-1-(3,3,3-trifluoropropyl)-1H-purine-2,6(3H,7H)-dione

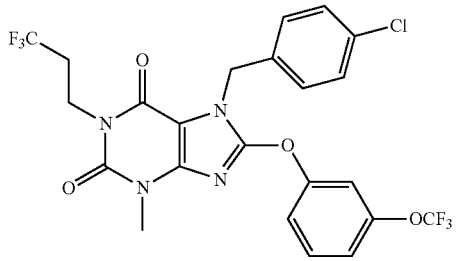 [SMILES: Cn1c(=O)n(CCC(F)(F)F)c(=O)c2c1nc(Oc1cccc(OC(F)(F)F)c1)n2Cc1ccc(Cl)cc1]

The title compound was prepared with 1,1,1-trifluoro-3-iodopropane to give 7-(4-chlorobenzyl)-3-methyl-8-(3-(trifluoromethoxy)phenoxy)-1-(3,3,3-trifluoropropyl)-1H-purine-2,6(3H,7H)-dione (30 mg, 35.6% yield) as white solid. $^1$H-NMR (DMSO-$d_6$) δ 7.64-7.59 (t, 1H), 7.50 (s, 1H), 7.45-7.41 (m, 5H), 7.35-7.33 (d, 1H), 5.44 (s, 2H), 4.15-4.12 (t, 2H), 3.22 (s, 3H), 2.63-2.55 (m, 2H). LCMS retention time 3.575 min; LCMS MH$^+$ 563.

Example 7d 7-(4-chlorobenzyl)-1-(4-hydroxybutyl)-3-methyl-8-(3-(trifluoromethoxy)phenoxy)-1H-purine-2,6(3H,7H)-dione

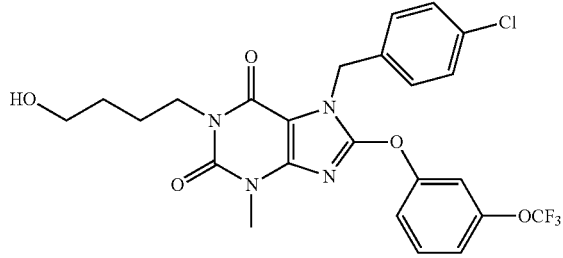 [SMILES: Cn1c(=O)n(CCCCO)c(=O)c2c1nc(Oc1cccc(OC(F)(F)F)c1)n2Cc1ccc(Cl)cc1]

The title compound was prepared using the method of example 58, step 1 except the reaction was facilitated by microwave irradiation at 120° C. for 45 min to give 7-(4-chlorobenzyl)-1-(4-hydroxybutyl)-3-methyl-8-(3-(trifluoromethoxy)phenoxy)-1H-purine-2,6(3H,7H)-dione (10 mg, 8.9% yield) as white solid. $^1$H-NMR (DMSO-$d_6$) δ 7.63-7.58 (t, 1H), 7.49 (s, 1H), 7.44-7.42 (m, 5H), 7.38-7.32 (d, 1H), 5.44 (s, 2H), 4.41 (s, 1H), 3.89-3.86 (t, 2H), 3.39-3.34 (m, 2H), 3.29 (s, 3H), 1.61-1.54 (m, 2H), 1.45-1.38 (m, 2H). LCMS retention time 3.053 min; LCMS MH$^+$ 539.

Example 7e 7-(4-chlorobenzyl)-1-(5-hydroxypentyl)-3-methyl-8-(3-(trifluoromethoxy)phenoxy)-1H-purine-2,6(3H,7H)-dione

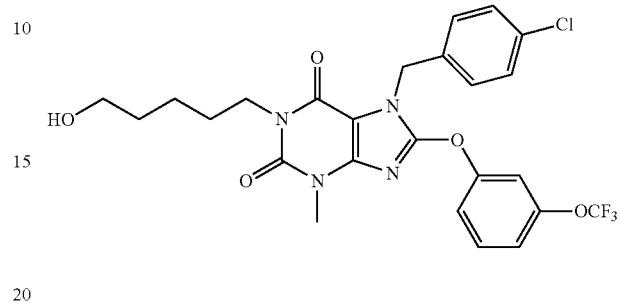

The title compound was prepared with 5-bromopentan-1-ol to give 7-(4-chlorobenzyl)-1-(5-hydroxypentyl)-3-methyl-8-(3-(trifluoromethoxy)phenoxy)-1H-purine-2,6(3H,7H)-dione (30 mg, 20.9% yield) as white solid. $^1$H-NMR (DMSO-$d_6$) δ 7.63-7.58 (t, 1H), 7.49 (s, 1H), 7.44-7.42 (m, 5H), 7.34-7.32 (d, 1H), 5.44 (s, 2H), 4.40-3.78 (t, 1H), 3.88-3.84 (t, 2H), 3.40-3.36 (m, H), 3.29 (s, 3H), 1.56-1.52 (m, 2H), 1.46-1.42 (m, 2H), 1.31-1.27 (m, 2H). LCMS retention time 3.057 min; LCMS MH$^+$ 553.

Example 7f 7-(4-chlorobenzyl)-1-(2-hydroxy-3-methoxypropyl)-3-methyl-8-(3-(trifluoromethoxy)phenoxy)-1H-purine-2,6(3H,7H)-dione

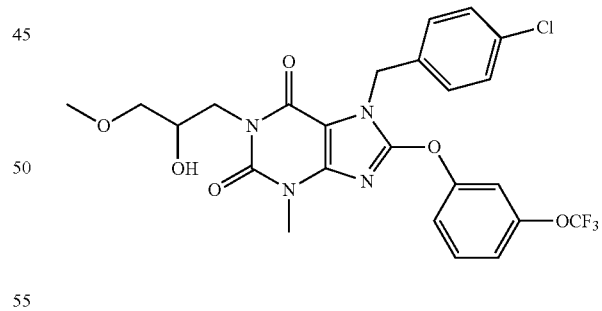

The title compound was prepared with 1-chloro-3-methoxypropan-2-ol and with heating to 130° C. White solid, 70 mg, 58.8% yield: $^1$H-NMR (400 Hz, CD$_3$OD) δ 7.57-7.53 (t, 1H), 7.47-7.44 (d, 2H), 7.37-7.33 (m, 4H), 7.26-7.24 (d, 1H), 5.49 (s, 2H), 4.24-4.19 (m, 1H), 4.12-4.11 (m, 1H), 4.04-3.99 (m, 1H), 3.45-3.42 (m, 5H), 3.36-3.30 (d, 3H). LCMS retention time 3.044 min; LCMS MH$^+$ 555.

Example 7g 7-(4-chlorobenzyl)-1-(2-methoxyethyl)-3-methyl-8-(3-(trifluoromethoxy)phenoxy)-1H-purine-2,6(3H,7H)-dione

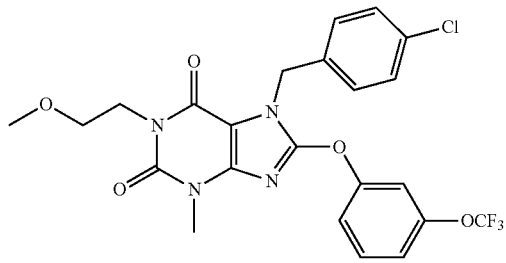 [SMILES: COCCn1c(=O)c2c(nc(Oc3cccc(OC(F)(F)F)c3)n2Cc2ccc(Cl)cc2)n(C)c1=O]

The title compound was prepared with 1-bromo-2-methoxyethane and purified via preparative HPLC. White solid, 40 mg, 50.9% yield: $^1$H-NMR (DMSO-$d_6$) δ 7.63-7.59 (t, 1H), 7.50 (s, 1H), 7.45-7.43 (m, 5H), 7.34-7.32 (d, 1H), 5.44 (s, 2H), 4.08-4.05 (t, 2H), 3.88-3.84 (t, 2H), 3.52-3.49 (t, 2H), 3.29 (s, 3H), 3.24 (s, 3H). LCMS retention time 3.322 min; LCMS MH$^+$ 525.

Example 7h 7-(4-chlorobenzyl)-1-(isoxazol-5-ylmethyl)-3-methyl-8-(3-(trifluoromethoxy)phenoxy)-1H-purine-2,6(3H,7H)-dione

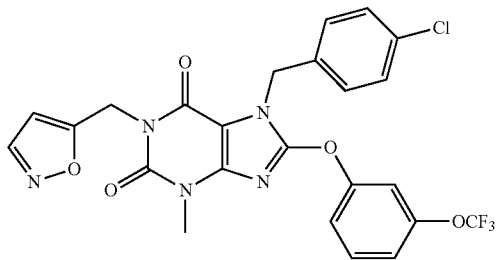 [SMILES: Cn1c(=O)n(Cc2ccno2)c(=O)c2c1nc(Oc1cccc(OC(F)(F)F)c1)n2Cc1ccc(Cl)cc1]

The title compound was prepared with 5-(chloromethyl) isoxazole and the reaction was catalyzed with TBAI. The crude product was purified by preparative HPLC to give 7-(4-chlorobenzyl)-1-(isoxazol-5-ylmethyl)-3-methyl-8-(3-(trifluoromethoxy)phenoxy)-1H-purine-2,6(3H,7H)-dione (21 mg, 8.9% yield) as white solid. $^1$H-NMR (DMSO-$d_6$) δ 8.50-8.49 (d, 1H), 7.64-7.59 (t, 1H), 7.51 (s, 1H), 7.46-7.43 (m, 5H), 7.36-7.33 (d, 1H), 6.39-6.38 (d, 1H), 5.44 (s, 2H), 5.22 (s, 2H), 3.32 (s, 3H). LCMS retention time 3.269 min; LCMS MH$^+$ 548.

Example 7i N-tert-butyl-1-(7-(4-chlorobenzyl)-3-methyl-2,6-dioxo-8-(3-(trifluoromethoxy)phenoxy)-2,3,6,7-tetrahydro-1H-purin-1-yl)methanesulfonamide

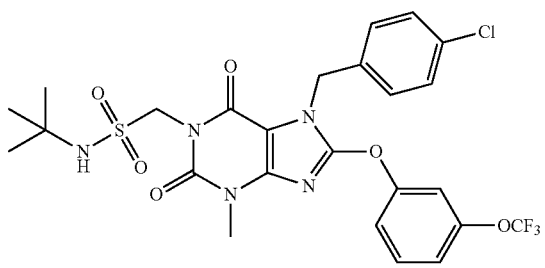 [SMILES: Cn1c(=O)n(CS(=O)(=O)NC(C)(C)C)c(=O)c2c1nc(Oc1cccc(OC(F)(F)F)c1)n2Cc1ccc(Cl)cc1]

The title compound was prepared with N-tert-butyl-1-chloromethanesulfonamide. White solid, 180 mg, 68.3% yield: $^1$H-NMR (DMSO-$d_6$) δ 7.64-7.59 (t, 1H), 7.49 (s, 1H), 7.45-7.39 (m, 6H), 7.35-7.33 (d, 1H), 7.14 (s, 1H), 5.45 (s, 2H), 5.21 (s, 2H), 3.31 (s, 3H), 1.28 (s, 9H). LCMS retention time 3.426 min; LCMS MH$^+$ 616.

Example 7j 7-(4-chlorobenzyl)-1-(2-hydroxyethyl)-3-methyl-8-(3-(trifluoromethoxy)phenoxy)-1H-purine-2,6(3H,7H)-dione

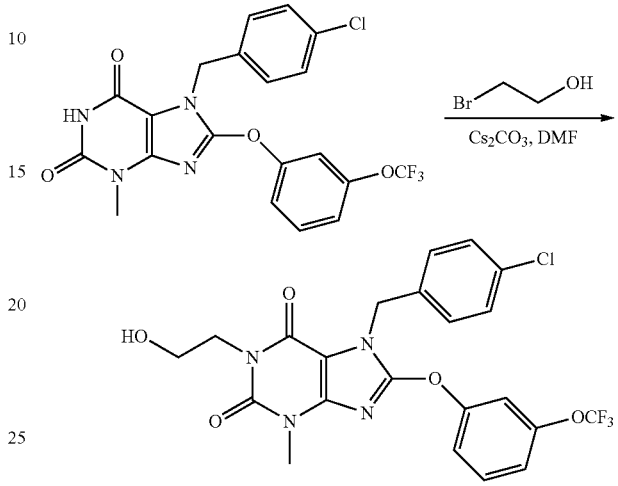

The title compounds prepared with 2-bromoethanol. White solid, 11 mg, 16.7% yield: $^1$H-NMR (DMSO-$d_6$) δ 7.58-7.62 (m, 1H), 7.49 (s, 1H), 7.41-7.43 (m, 5H), 7.31-7.32 (d, 1H), 5.44 (s, 2H), 4.76-4.79 (t, 1H), 3.95-3.98 (t, 2H), 3.50-3.54 (t, 2H), 3.28 (s, 3H). LCMS retention time 2.690 min; LCMS MH$^+$ 511.

Example 7k 7-(4-chlorobenzyl)-1-(3-hydroxybutyl)-3-methyl-8-(3-(trifluoromethoxy)phenoxy)-1H-purine-2,6(3H,7H)-dione

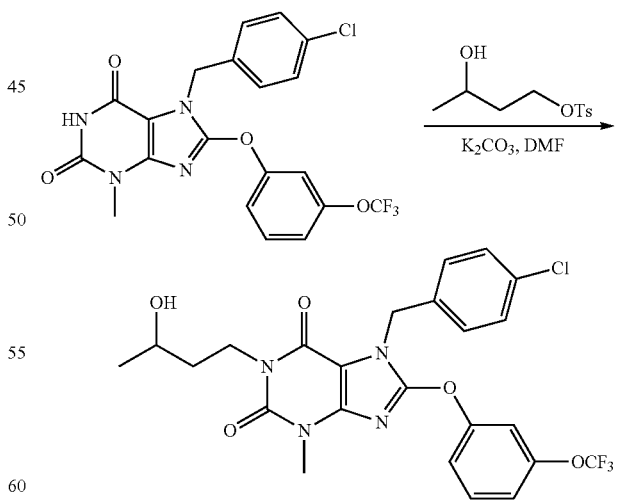

The title compound was prepared with 3-hydroxybutyl-4-methylbenzenesulfonate (intermediate 33). White solid, 70 mg, 61.9% yield: $^1$H-NMR (DMSO-$d_6$) δ 7.59-7.55 (t, 1H), 7.46-7.39 (d, 6H), 7.30-7.28 (d, 1H), 5.41 (s, 2H), 4.49-4.48 (d, 1H), 4.02-3.97 (m, 1H), 3.84-3.79 (m, 1H), 3.64-3.61 (m, 1H), 3.26 (s, 3H), 1.59-1.52 (m, 2H), 1.06-1.05 (d, 3H). LCMS retention time 3.159 min; LCMS MH+ 539.

Example 8 3-(7-(4-chlorobenzyl)-3-methyl-2,6-dioxo-8-(3-(trifluoromethoxy)phenoxy)-2,3,6,7-tetrahydro-1H-purin-1-yl)propanenitrile

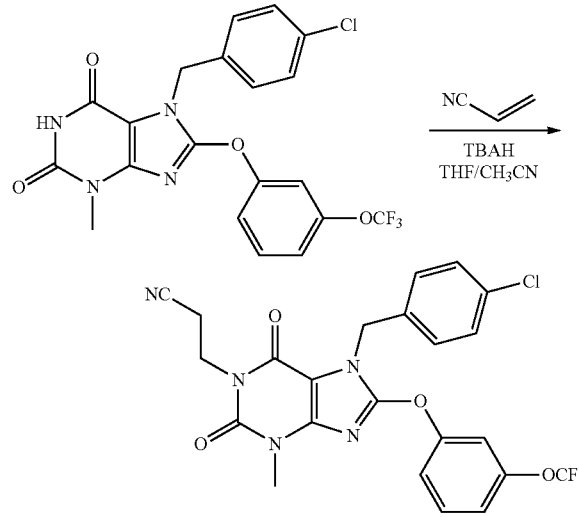

To a solution of 7-(4-chlorobenzyl)-3-methyl-8-(3-(trifluoromethoxy)phenoxy)-1H-purine-2,6(3H,7H)-dione (100 mg, 0.215 mmol, Intermediate 9) in a mixed solution of THF (3 mL) and acetonitrile (5 mL) was added TBAH (0.05 ml, 0.193 mmol) and acrylonitrile (40 mg, 0.642 mmol). The mixture was stirred at 60° C. overnight. Then the mixture was diluted with DCM and water, and the phases were separated. The organic phase was washed with brine, dried over sodium sulfate, filtered and concentrated to give crude product. This crude material was purified by silica gel chromatography eluting with petroleum/ethyl acetate (3:1 to 1:1) to give 3-(7-(4-chlorobenzyl)-3-methyl-2,6-dioxo-8-(3-(trifluoromethoxy)phenoxy)-2,3,6,7-tetrahydro-1H-purin-1-yl)propanenitrile (75 mg, 68.8%) as white solid. $^1$H-NMR (DMSO-d$_6$) δ 7.63-7.59 (t, 1H), 7.50 (s, 1H), 7.45-7.40 (m, 5H), 7.35-7.33 (d, 1H), 5.45 (s, 2H), 4.16-4.13 (t, 2H), 3.31 (s, 3H), 2.89-2.86 (t, 2H). LCMS retention time 3.248 min; LCMS MH+ 520.

Example 9 2-(7-(4-chlorobenzyl)-3-methyl-2,6-dioxo-8-(3-(trifluoromethoxy)phenoxy)-2,3,6,7-tetrahydro-1H-purin-1-yl)acetic acid

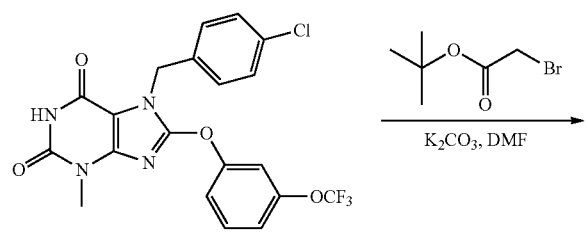

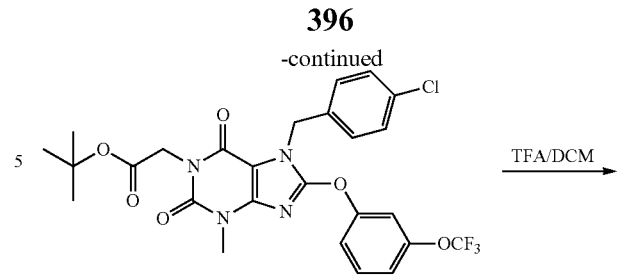

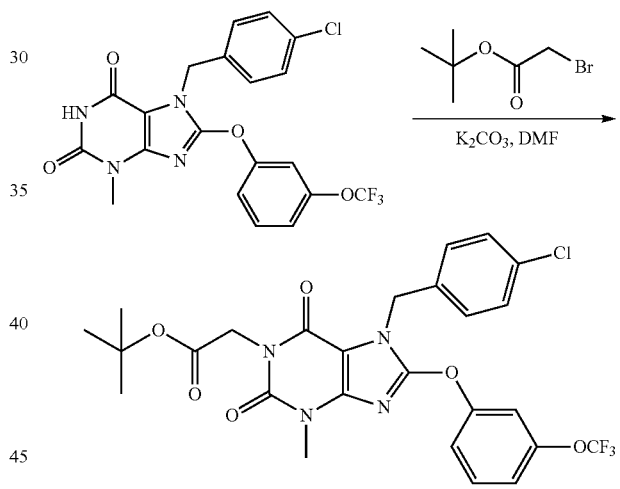

Step 1 tert-butyl 2-(7-(4-chlorobenzyl)-3-methyl-2,6-dioxo-8-(3-(trifluoromethoxy)phenoxy)-2,3,6,7-tetrahydro-1H-purin-1-yl)acetate The title compound was prepared using the method of example 6, step 1 to give 200 mg (100% yield) as yellow oil which was used without purification. LCMS M-$^t$Bu+H 525.

Step 2 2-(7-(4-chlorobenzyl)-3-methyl-2,6-dioxo-8-(3-(trifluoromethoxy)phenoxy)-2,3,6,7-tetrahydro-1H-purin-1-yl)acetic acid

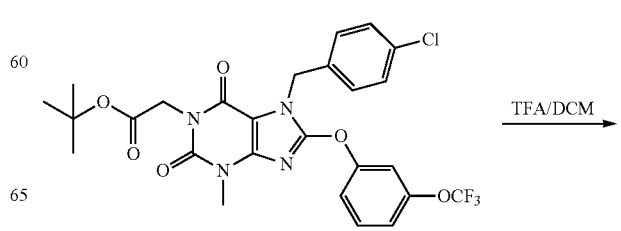

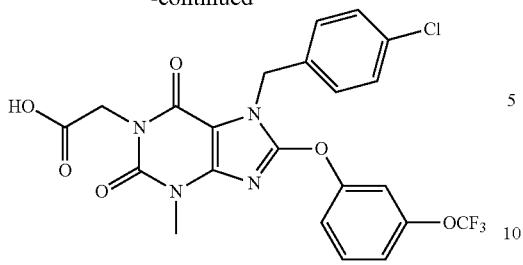

To a solution of tert-butyl 2-(7-(4-chlorobenzyl)-3-methyl-2,6-dioxo-8-(3-(trifluoromethoxy)phenoxy)-2,3,6,7-tetrahydro-1H-purin-1-yl)acetate (200 mg, 0.342 mmol) in DCM (5 ml) was added trifluoroacetic acid (2 ml, 26.9 mmol) at 0° C. The mixture was stirred at 0° C. to room temperature for 3 h. Then the mixture was concentrated, diluted with DCM and water. The phases were separated and the organic phase was washed with brine, dried over sodium sulfate, filtered and concentrated to give 2-(7-(4-chlorobenzyl)-3-methyl-2,6-dioxo-8-(3-(trifluoromethoxy)phenoxy)-2,3,6,7-tetrahydro-1H-purin-1-yl)acetic acid (180 mg, 99.9% yield) as white solid. $^1$H-NMR (DMSO-$d_6$) δ 13.06 (s, 1H), 7.64-7.59 (t, 1H), 7.55 (s, 1H), 7.48-7.43 (m, 5H), 7.36-7.34 (d, 1H), 5.43 (s, 2H), 4.53 (s, 2H), 3.37 (s, 3H). LCMS retention time 2.994 min; LCMS MH$^+$ 525.

Example 10 7-(4-chlorobenzyl)-3-methyl-1-(2-(4-methylpiperazin-1-yl)-2-oxoethyl)-8-(3-(trifluoromethoxy)phenoxy)-1H-purine-2,6(3H,7H)-dione

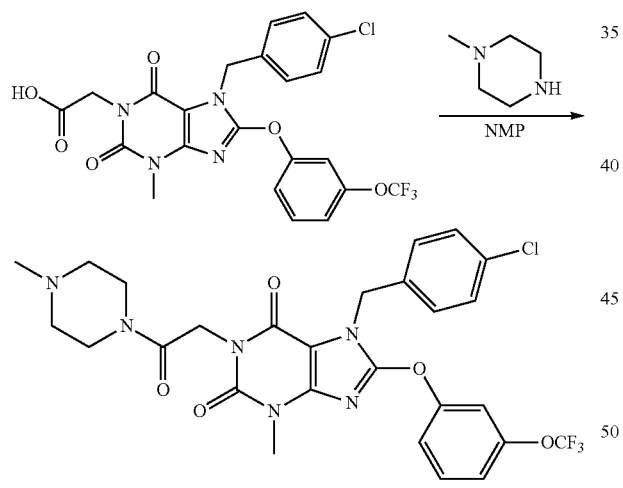

To a solution of 2-(7-(4-chlorobenzyl)-3-methyl-2,6-dioxo-8-(3-(trifluoromethoxy)phenoxy)-2,3,6,7-tetrahydro-1H-purin-1-yl)acetic acid (80 mg, 0.152 mmol, example 9) in NMP (2 mL) was added TEA (0.1 mL, 0.614 mmol), 1-methylpiperazine (0.07 mL, 0.614 mmol) and O-(7-aza-1H-benzotriazol-1-yl)-N,N,N',N'-tetramethyluronium hexafluorophosphate (87 mg, 0.231 mmol); then the mixture was stirred at 60° C. for 16 h. Then the mixture was diluted with ethyl acetate and water, the phases were separated. The organic phase was washed with brine, dried over sodium sulfate, filtered and concentrated to give crude product. This crude material was purified by recrystallization from methanol to give 7-(4-chlorobenzyl)-3-methyl-1-(2-(4-methylpiperazin-1-yl)-2-oxoethyl)-8-(3-(trifluoromethoxy)phenoxy)-1H-purine-2,6(3H,7H)-dione (25 mg, 27.5% yield) as white solid. $^1$H-NMR (DMSO-$d_6$) δ 7.62-7.59 (t, 1H), 7.55 (s, 1H), 7.49-7.39 (m, 5H), 7.36-7.34 (d, 1H), 5.43 (s, 2H), 4.71 (s, 2H), 3.55-3.48 (m, 4H), 3.30 (s, 3H), 2.46-2.36 (m, 4H), 2.21 (s, 3H). LCMS retention time 2.298 min; LCMS MH$^+$ 607.

Example 11 7-(4-chlorobenzyl)-1-(3-(dimethylamino)-2-oxopropyl)-3-methyl-8-(3-(trifluoromethoxy)phenoxy)-1H-purine-2,6(3H,7H)-dione hydrochloride

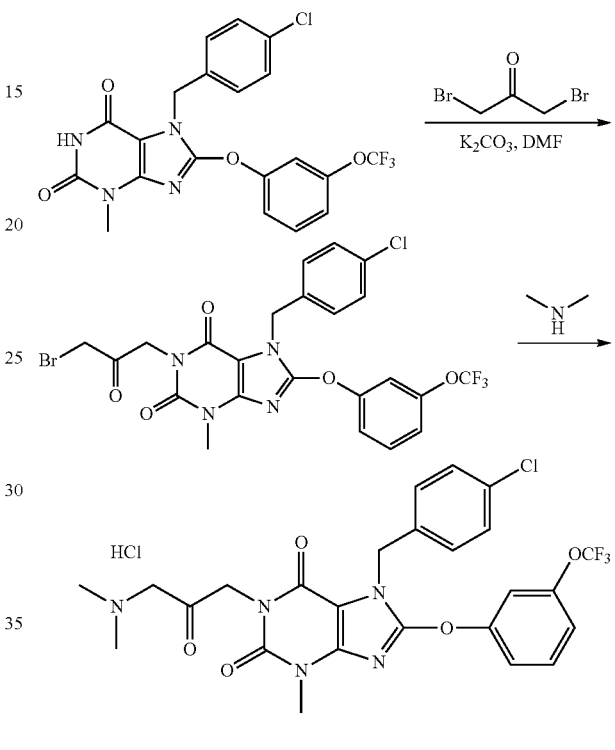

The title compound was prepared using the 2 step method of example 6 to give 7-(4-chlorobenzyl)-1-(3-(dimethylamino)-2-oxopropyl)-3-methyl-8-(3-(trifluoromethoxy)phenoxy)-1H-purine-2,6(3H,7H)-dione hydrochloride (20 mg, 25.6% yield) as white solid. $^1$H-NMR (DMSO-$d_6$) δ 10.05 (s, 1H), 7.65-7.61 (t, 1H), 7.54 (s, 1H), 7.48-7.40 (m, 5H), 7.37-7.35 (d, 1H), 5.43 (s, 2H), 4.85 (s, 2H), 4.52 (s, 2H), 3.32 (s, 3H), 2.80 (s, 6H). LCMS retention time 2.352 min; LCMS MH$^+$ 566.

Example 12 7-(4-chlorobenzyl)-3-methyl-1-(2-(4-methylpiperazin-1-yl)ethyl)-8-(3-(trifluoromethoxy)phenoxy)-1H-purine-2,6(3H,7H)-dione

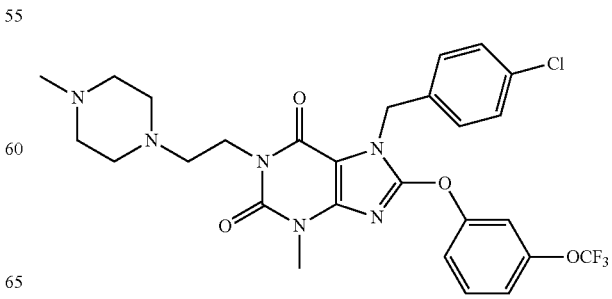

The title compound was prepared using the 2 step method of example 6 with 1-methylpiperazine to give 7-(4-chlorobenzyl)-3-methyl-1-(2-(4-methylpiperazin-1-yl)ethyl)-8-(3-(trifluoromethoxy)phenoxy)-1H-purine-2,6(3H,7H)-dione (40 mg, 38.7% yield) as white solid. $^1$H-NMR (CD$_3$OD) δ 7.59-7.55 (t, 1H), 7.46-7.34 (m, 6H), 7.27-7.25 (d, 2H), 5.51 (s, 2H), 4.19-4.16 (t, 2H), 3.43 (s, 3H), 3.33-3.32 (m, 4H), 3.03-3.93 (bs, 4H), 2.82-2.73 (t, 2H), 2.69 (s, 3H). LCMS retention time 2.310 min; LCMS MH$^+$ 593.

Example 13 7-(4-chlorobenzyl)-1-(2,3-dihydroxypropyl)-3-methyl-8-(3-(trifluoromethyl)phenoxy)-1H-purine-2,6(3H,7H)-dione

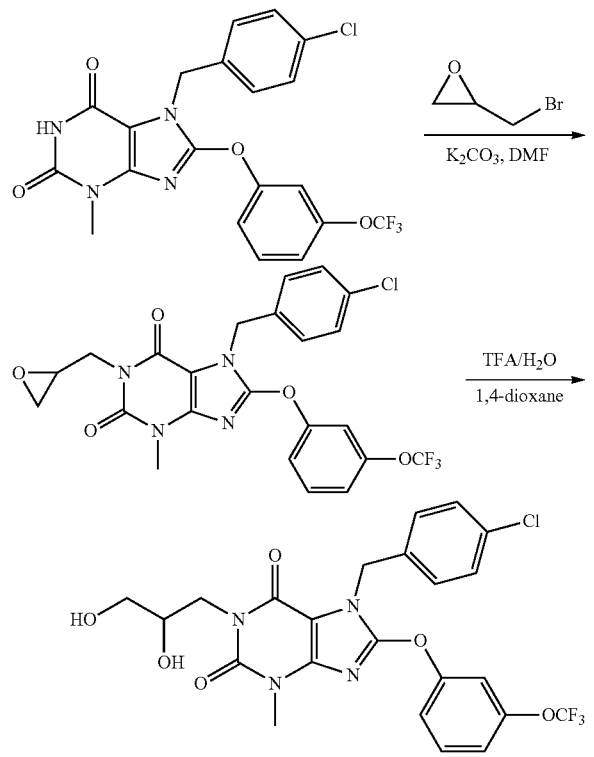

Step 1 7-(4-chlorobenzyl)-3-methyl-1-(oxiran-2-ylmethyl)-8-(3-(trifluoromethoxy)phenoxy)-1H-purine-2,6(3H,7H)-dione The title compound was prepared using the method of example 6, step 1 to give 7-(4-chlorobenzyl)-3-methyl-1-(oxiran-2-ylmethyl)-8-(3-(trifluoromethoxy)phenoxy)-1H-purine-2,6(3H,7H)-dione (220 mg, 100% yield) as yellow solid which was used without purification. LCMS MH$^+$ 523.

Step 2 7-(4-chlorobenzyl)-1-(2,3-dihydroxypropyl)-3-methyl-8-(3-(trifluoromethyl)phenoxy)-1H-purine-2,6(3H,7H)-dione

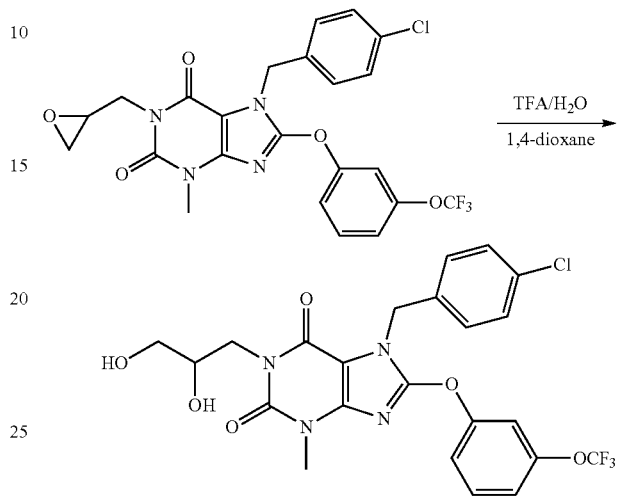

To a solution of 7-(4-chlorobenzyl)-3-methyl-1-(oxiran-2-ylmethyl)-8-(3-(trifluoromethoxy)phenoxy)-1H-purine-2,6(3H,7H)-dione (140 mg, 0.268 mmol) in 1,4-dioxane (10 mL) was added TFA (0.11 mL, 1.48 mmol) and water (2 mL); then the mixture was stirred at 80° C. for 2 h. The mixture was concentrated; then purified by silica gel chromatography eluting with DCM/methanol (50:1 to 20:1) to give 7-(4-chlorobenzyl)-1-(2,3-dihydroxypropyl)-3-methyl-8-(3-(trifluoromethyl)phenoxy)-1H-purine-2,6(3H,7H)-dione (70 mg, 48.4% yield) as white solid. $^1$H-NMR (DMSO-d$_6$) δ 7.63-7.58 (t, 1H), 7.48 (s, 1H), 7.44-7.41 (m, 5H), 7.34-7.31 (d, 1H), 5.44 (s, 2H), 4.68-4.67 (d, 1H), 4.55-4.52 (m, 1H), 4.01-3.98 (m, 1H), 3.84-3.80 (m, 2H), 3.33 (s, 2H), 3.29 (s, 3H). LCMS retention time 2.811 min; LCMS MH$^+$ 541.

Example 14 7-(4-chlorobenzyl)-1-(3-hydroxy-2-methoxypropyl)-3-methyl-8-(3-(trifluoromethoxy)phenoxy)-1H-purine-2,6(3H,7H)-dione

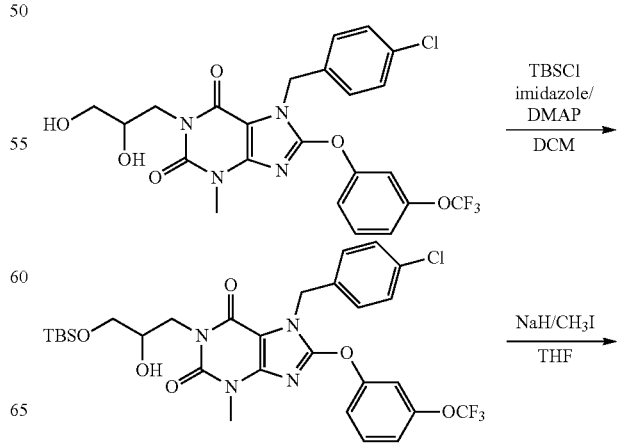

401

-continued

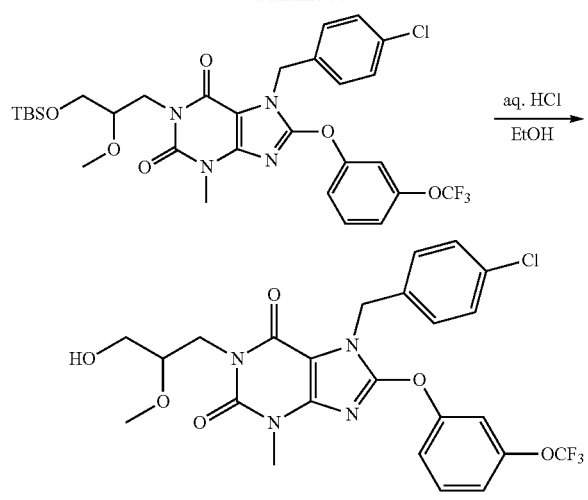

Step 1 1-(3-(tert-butyldimethylsilyloxy)-2-hydroxy-propyl)-7-(4-chlorobenzyl)-3-methyl-8-(3-(trifluoromethoxy)phenoxy)-1H-purine-2,6(3H,7H)-dione

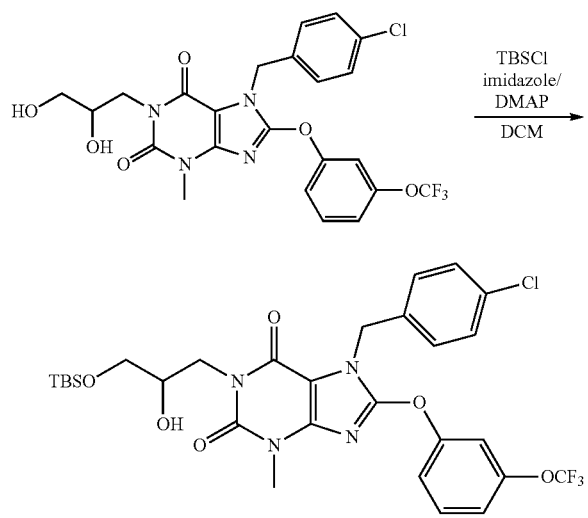

To a solution of 7-(4-chlorobenzyl)-1-(2,3-dihydroxypropyl)-3-methyl-8-(3-(trifluoromethyl)phenoxy)-1H-purine-2,6(3H,7H)-dione (100 mg, 0.185 mmol, product of example 13) in DCM (10 mL) was added imidazole (11 mg, 0.16 mmol) and DMAP (10 mg, 0.08 mmol) at 0° C., then tert-butylchlorodimethylsilane (40 mg, 0.27 mmol) was added in one portion. The mixture was stirred at room temperature overnight. The mixture was diluted with DCM and water, and the phases were separated. The organic phase was washed with brine, dried over sodium sulfate, filtered and concentrated to give crude 1-(3-(tert-butyldimethylsilyloxy)-2-hydroxypropyl)-7-(4-chlorobenzyl)-3-methyl-8-(3-(trifluoromethoxy)phenoxy)-1H-purine-2,6(3H,7H)-dione (180 mg, 100% yield) as white solid. LCMS MH+ 655.

402

Step 2 1-(3-(tert-butyldimethylsilyloxy)-2-methoxypropyl)-7-(4-chlorobenzyl)-3-methyl-8-(3-(trifluoromethoxy)phenoxy)-1H-purine-2,6(3H,7H)-dione

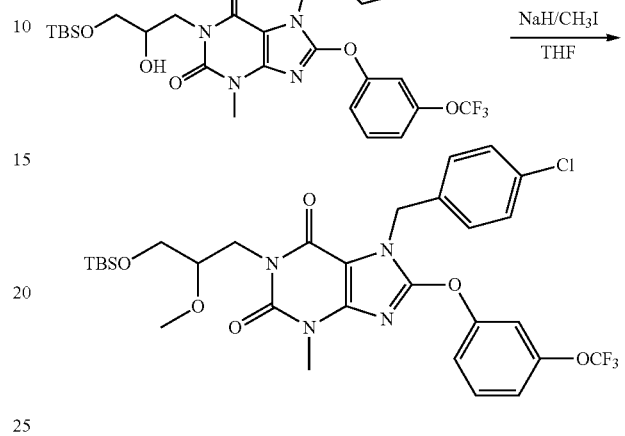

To a slurry of sodium hydride (240 mg, 9.6 mmol) in anhydrous THF (10 ml) was added dropwise a solution of 1-(3-(tert-butyldimethylsilyloxy)-2-hydroxypropyl)-7-(4-chlorobenzyl)-3-methyl-8-(3-(trifluoromethoxy)phenoxy)-1H-purine-2,6(3H,7H)-dione (124 mg, 0.19 mmol) in THF (3 mL) at 0° C. under nitrogen. The reaction was stirred at 0° C. for 10 minutes. Then iodomethane (1.2 ml, 19.4 mmol) was added dropwise and the resulting mixture was allowed to warm from 0° C. to room temperature over 2 h. The mixture was quenched with ice-water (5 mL). The mixture was concentrated, diluted with ethyl acetate and water, and the organic layer was separated. The organic layer was dried over sodium sulfate, filtered and concentrated to give crude product (150 mg, 100% yield) as yellow oil. LCMS MH+ 669.

Step 3 7-(4-chlorobenzyl)-1-(3-hydroxy-2-methoxypropyl)-3-methyl-8-(3-(trifluoromethoxy)phenoxy)-1H-purine-2,6(3H,7H)-dione

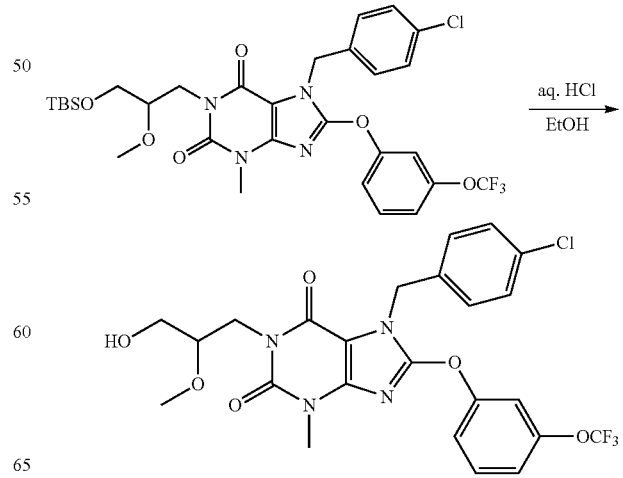

To a solution of 1-(3-(tert-butyldimethylsilyloxy)-2-methoxypropyl)-7-(4-chlorobenzyl)-3-methyl-8-(3-(trifluoromethoxy)phenoxy)-1H-purine-2,6(3H,7H)-dione (150 mg, 0.22 mmol) in ethyl alcohol (5 mL) was added concentrated HCl (0.1 mL). The reaction was stirred for 10 minutes. Then it was concentrated and purified by preparative HPLC to give 7-(4-chlorobenzyl)-1-(3-hydroxy-2-methoxypropyl)-3-methyl-8-(3-(trifluoromethoxy)phenoxy)-1H-purine-2,6(3H,7H)-dione (18 mg, 16.2% yield) as white solid. $^1$H-NMR (DMSO-$d_6$) δ 7.63-7.59 (t, 1H), 7.50 (s, 1H), 7.45-7.43 (m, 5H), 7.34-7.32 (d, 1H), 5.44 (s, 2H), 4.65-4.62 (t, 1H), 4.12-4.08 (q, 1H), 3.84-3.79 (q, 1H), 3.53-3.41 (m, 2H), 3.29-3.28 (d, 6H). LCMS retention time 3.089 min; LCMS MH$^+$ 555.

Example 15 7-(4-chlorobenzyl)-1-(3-(dimethylamino)-2-hydroxypropyl)-3-methyl-8-(3-(trifluoromethoxy)phenoxy)-1H-purine-2,6(3H,7H)-dione

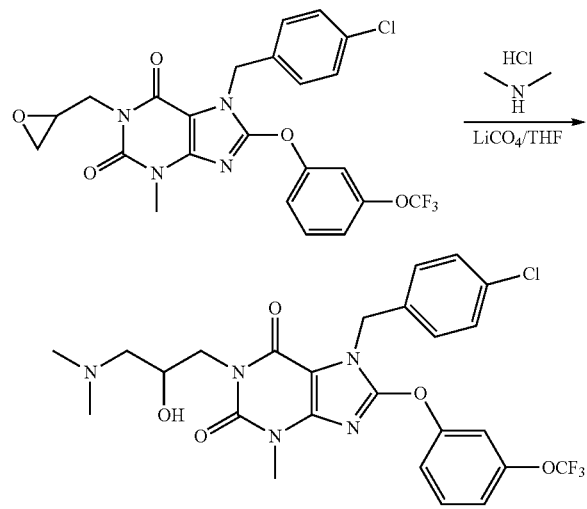

To a solution of 7-(4-chlorobenzyl)-3-methyl-1-(oxiran-2-ylmethyl)-8-(3-(trifluoromethoxy)phenoxy)-1H-purine-2,6(3H,7H)-dione (100 mg, 0.192 mmol, example 13, step 1) in THF (10 mL) was added dimethylamine hydrochloride (160 mg, 1.98 mmol) and lithium perchlorate (20 mg, 0.189 mmol). The mixture was stirred at 25° C. in a sealed tube for 2 h. The mixture was diluted with ethyl acetate and water. The phases were separated and the organic phase was washed with brine, dried over sodium sulfate, filtered and concentrated to give crude product. This crude material was purified via preparative HPLC to give 7-(4-chlorobenzyl)-1-(3-(dimethylamino)-2-hydroxypropyl)-3-methyl-8-(3-(trifluoromethoxy)phenoxy)-1H-purine-2,6(3H,7H)-dione (50 mg, 46.2% yield) as white solid. $^1$H-NMR (CD$_3$OD) δ 8.48 (s, 1H), 7.59-7.54 (t, 1H), 7.47-7.45 (d, 2H), 7.38-7.34 (m, 4H), 7.27-7.25 (d, 1H), 5.51 (s, 2H), 4.34-4.31 (m, 1H), 4.23-4.18 (m, 1H), 4.07-4.02 (m, 1H), 3.44 (s, 1H), 3.22-3.21 (d, 2H), 2.90 (s, 6H). LCMS retention time 2.227 min; LCMS MH$^+$ 568.

Example 16 7-(4-chlorobenzyl)-1-(3-methoxy-2-oxopropyl)-3-methyl-8-(3-(trifluoromethoxy)phenoxy)-1H-purine-2,6(3H,7H)-dione

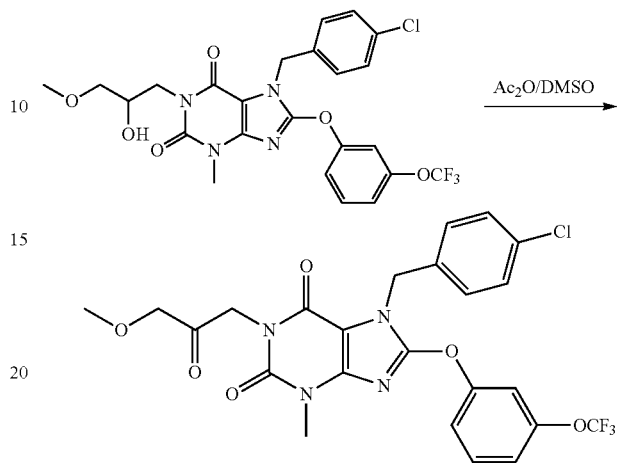

To a solution of 7-(4-chlorobenzyl)-1-(2-hydroxy-3-methoxypropyl)-3-methyl-8-(3-(trifluoromethoxy)phenoxy)-1H-purine-2,6(3H,7H)-dione (40 mg, 0.072 mmol, example 70 in methyl sulfoxide (4 mL) was added acetic anhydride (37 mg, 0.363 mmol) dropwise. Then the mixture was stirred at 25° C. for 16 h. The mixture was partitioned between ethyl acetate and water and the organic phase was washed with brine, dried over sodium sulfate, filtered and was concentrated to give crude product. This crude material was further purified preparative HPLC to give 7-(4-chlorobenzyl)-1-(3-methoxy-2-oxopropyl)-3-methyl-8-(3-(trifluoromethoxy)phenoxy)-1H-purine-2,6(3H,7H)-dione (12 mg, 30.2%) as white solid. $^1$H-NMR (CD$_3$OD) δ 7.56-7.52 (t, 1H), 7.42-7.39 (d, 2H), 7.36-7.31 (m, 4H), 7.24-7.22 (d, 1H), 5.45 (s, 2H), 4.92 (s, 2H), 4.24 (s, 2H), 3.46 (s, 3H), 3.39 (s, 3H). LCMS retention time 3.210 min; LCMS MH$^+$ 553.

Example 17 N-(2-(7-(4-chlorobenzyl)-3-methyl-2,6-dioxo-8-(3-(trifluoromethoxy)phenoxy)-2,3,6,7-tetrahydro-1H-purin-1-yl)ethyl)propane-2-sulfonamide

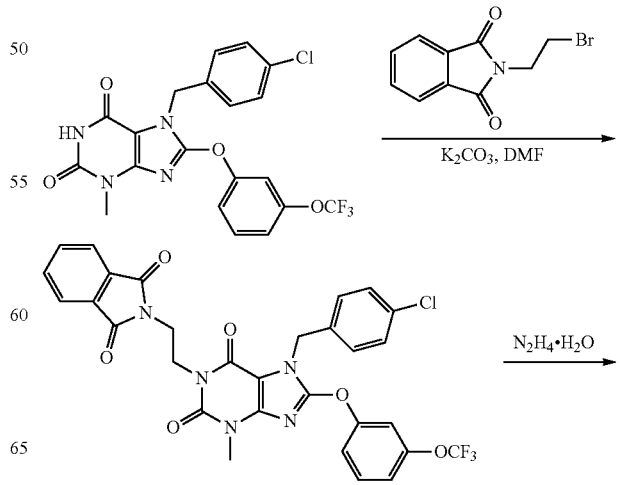

405

-continued

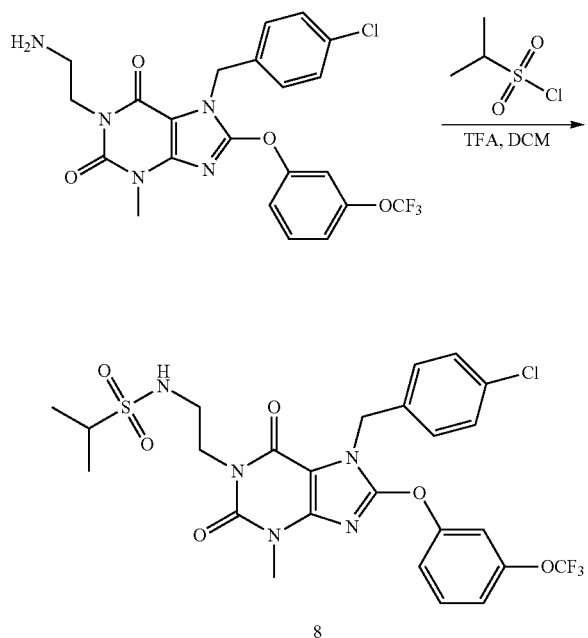

Step 1 7-(4-chlorobenzyl)-1-(2-(1,3-dioxoisoindolin-2-yl)ethyl)-3-methyl-8-(3-(trifluoromethoxy)phenoxy)-1H-purine-2,6(3H,7H)-dione

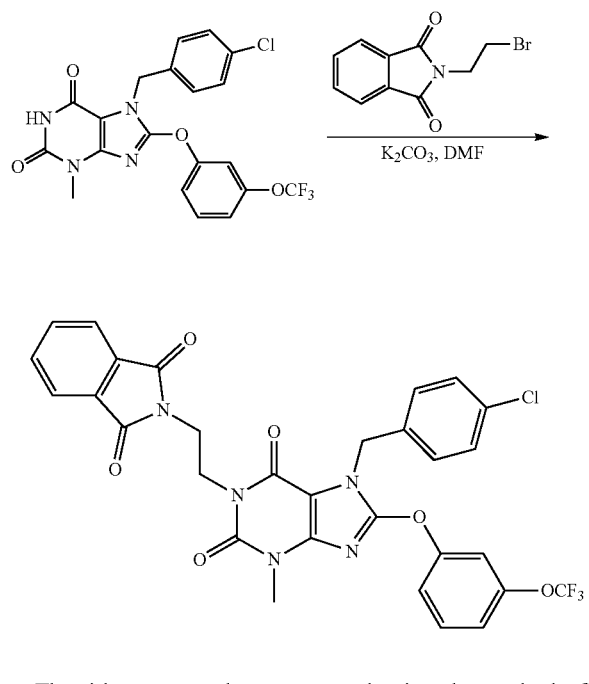

The title compound was prepared using the method of example 6, step 1 with 2-(2-bromoethyl)isoindoline-1,3-dione to give 7-(4-chlorobenzyl)-1-(2-(1,3-dioxoisoindolin-2-yl)ethyl)-3-methyl-8-(3-(trifluoromethoxy)phenoxy)-1H-purine-2,6(3H,7H)-dione (150 mg, 72.9% yield) as a white solid. LCMS retention time 2.045 min; LCMS MH+ 640.

406

Step 2 1-(2-aminoethyl)-7-(4-chlorobenzyl)-3-methyl-8-(3-(trifluoromethoxy)phenoxy)-1H-purine-2,6(3H,7H)-dione

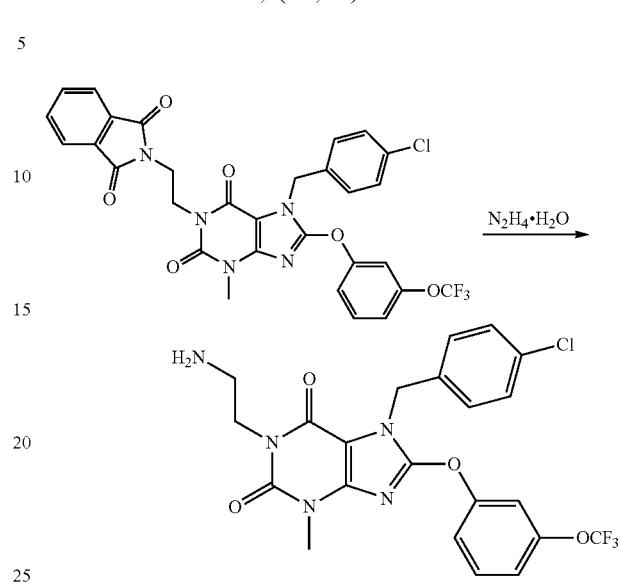

To a solution of 7-(4-chlorobenzyl)-1-(2-(1,3-dioxoisoindolin-2-yl)ethyl)-3-methyl-8-(3-(trifluoromethoxy)phenoxy)-1H-purine-2,6(3H,7H)-dione (100 mg, 0.157 mmol) in ethanol (10 mL) was added hydrazine hydrate (2 ml) dropwise, then the mixture was stirred at 80° C. for 2 h. The mixture was concentrated to give 1-(2-aminoethyl)-7-(4-chlorobenzyl)-3-methyl-8-(3-(trifluoromethoxy)phenoxy)-1H-purine-2,6(3H,7H)-dione (100 mg, 100%) as yellow oil. LCMS MH+ 510.

Step 3 N-(2-(7-(4-chlorobenzyl)-3-methyl-2,6-dioxo-8-(3-(trifluoromethoxy)phenoxy)-2,3,6,7-tetrahydro-1H-purin-1-yl)ethyl)propane-2-sulfonamide

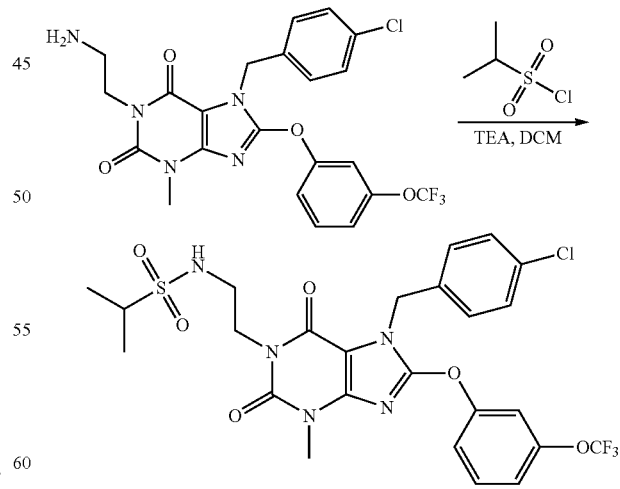

To a solution of 1-(2-aminoethyl)-7-(4-chlorobenzyl)-3-methyl-8-(3-(trifluoromethoxy)phenoxy)-1H-purine-2,6 (3H,7H)-dione (100 mg, 0.197 mmol) and TEA (40 mg, 0.393 mmol) in DCM (10 mL) was added propane-2-sulfonyl chloride (42 mg, 0.295 mmol) dropwise at 0° C.

The resulting mixture was stirred at 40° C. for 16 h. The mixture was diluted with DCM and water, and the phases were separated. The organic phase was washed with brine, dried over sodium sulfate, filtered and concentrated to give crude product. This crude material was recrystallized from ethanol to give N-(2-(7-(4-chlorobenzyl)-3-methyl-2,6-dioxo-8-(3-(trifluoromethoxy)phenoxy)-2,3,6,7-tetrahydro-1H-purin-1-yl)ethyl)propane-2-sulfonamide (20 mg, 16.5% yield) as white solid. $^1$H-NMR (DMSO-d$_6$) δ 7.63-7.59 (t, 1H), 7.48 (s, 1H), 7.45-7.41 (m, 5H), 7.35-7.33 (d, 1H), 7.26-7.18 (m, 1H), 5.45 (s, 2H), 4.01-3.97 (t, 1H), 3.29 (s, 6H). LCMS retention time 3.195 min; LCMS MH$^+$ 616.

Example 18 (7-(4-chlorobenzyl)-3-methyl-2,6-dioxo-8-(3-(trifluoromethoxy)phenoxy)-2,3,6,7-tetrahydro-1H-purin-1-yl)methanesulfonamide

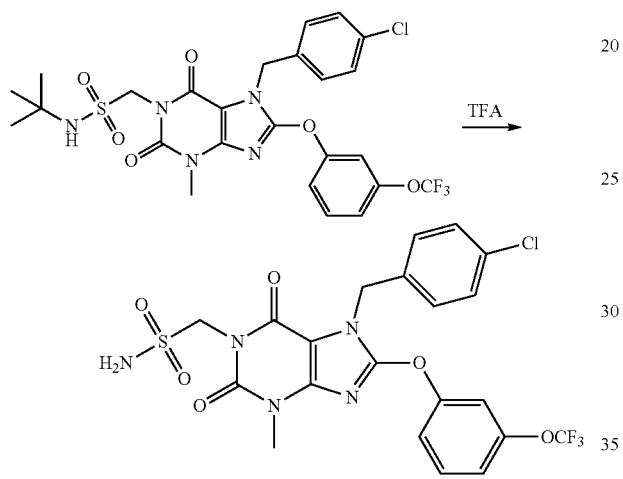

A solution of N-tert-butyl-1-(7-(4-chlorobenzyl)-3-methyl-2,6-dioxo-8-(3-(trifluoromethoxy)phenoxy)-2,3,6,7-tetrahydro-1H-purin-1-yl)methanesulfonamide (120 mg, 0.195 mmol, example 7i) in TFA (2 ml, 26.9 mmol) was stirred at 50° C. for 16 h. The mixture was concentrated and then purified by silica gel chromatography eluting with DCM/methanol (40:1) to give (7-(4-chlorobenzyl)-3-methyl-2,6-dioxo-8-(3-(trifluoromethoxy)phenoxy)-2,3,6,7-tetrahydro-1H-purin-1-yl)methanesulfonamide (79 mg, 72.4% yield) as white solid. $^1$H-NMR (DMSO-d$_6$) δ 7.65-7.61 (t, 1H), 7.49 (s, 1H), 7.47-7.41 (m, 6H), 7.36-7.35 (d, 1H), 7.05 (s, 2H), 5.45 (s, 2H), 5.23 (s, 2H), 3.31 (s, 3H). LCMS retention time 3.004 min; LCMS MH$^+$ 560.

Example 19 1-(7-(4-chlorobenzyl)-3-methyl-2,6-dioxo-8-(3-(trifluoromethoxy)phenoxy)-2,3,6,7-tetrahydro-1H-purin-1-yl)-N-methylmethanesulfonamide

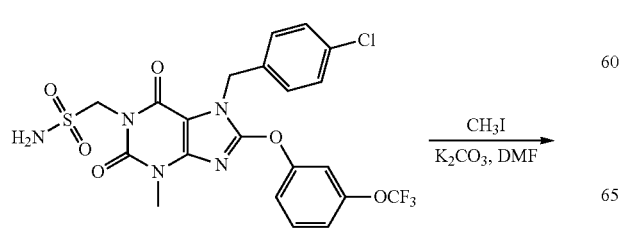

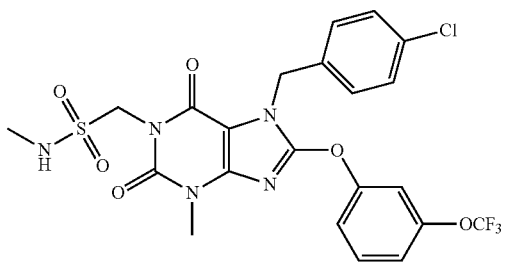

To a solution of 7-(4-chlorobenzyl)-3-methyl-2,6-dioxo-8-(3-(trifluoromethoxy)phenoxy)-2,3,6,7-tetrahydro-1H-purin-1-yl)methanesulfonamide (0.1 g, 0.18 mmol, example 18) in DMF (3 mL) was added iodomethane (16 mg, 0.18 mmol) and potassium carbonate (36 mg, 0.26 mmol). The reaction was stirred at room temperature overnight. The mixture was partitioned between ethyl acetate and water. The organic layers were combined, dried over sodium sulfate, filtered and concentrated. The crude product was purified by preparative-HPLC to give 1-(7-(4-chlorobenzyl)-3-methyl-2,6-dioxo-8 (3-(trifluoromethoxy)-phenoxy)-2,3,6,7-tetrahydro-1H-purin-1-yl)-N-methylmethanesulfonamide (23 mg, 22.3% yield) as a white solid. $^1$H-NMR (DMSO-d$_6$) δ 7.63 (t, 1H), 7.50 (d, 1H), 7.41-7.46 (m, 4H), 7.34-7.37 (m, 1H), 7.19-7.23 (m, 1H), 5.45 (s, 2H), 5.20 (s, 2H), 3.31 (s, 3H), 2.60 (d, 3H). LCMS retention time 3.097 min; LCMS MH$^+$ 574

Example 20 8-(3,5-bis(trifluoromethyl)phenoxy)-7-(4-chlorobenzyl)-3-ethyl-1-methyl-1H-purine-2,6 (3H,7H)-dione

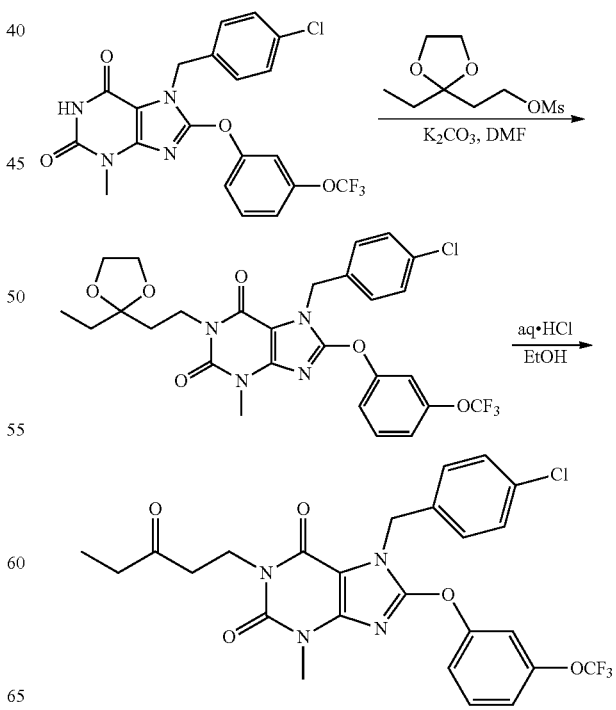

Step 1 7-(4-chlorobenzyl)-1-(2-(2-ethyl-1,3-dioxolan-2-yl)ethyl)-3-methyl-8-(3-(trifluoromethoxy)phenoxy)-1H-purine-2,6(3H,7H)-dione

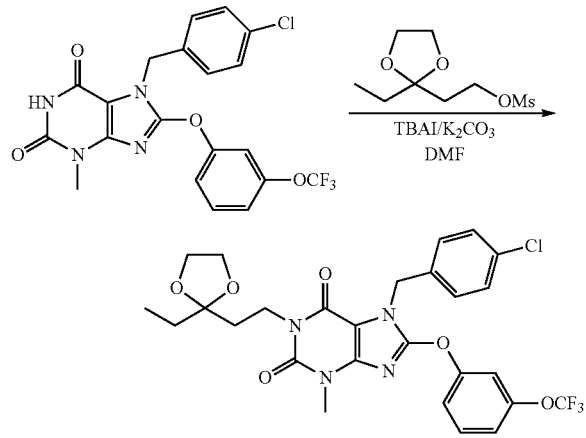

The title compound was prepared using the method of example 6, step 1 with intermediate 32 to give 7-(4-chlorobenzyl)-1-(2-(2-ethyl-1,3-dioxolan-2-yl)ethyl)-3-methyl-8-(3-(trifluoromethoxy)phenoxy)-1H-purine-2,6(3H,7H)-dione (360 mg, 100% yield) as white solid. LCMS MH+ 595.

Step 2 7-(4-chlorobenzyl)-3-methyl-1-(3-oxopentyl)-8-(3-(trifluoromethoxy)phenoxy)-1H-purine-2,6(3H,7H)-dione

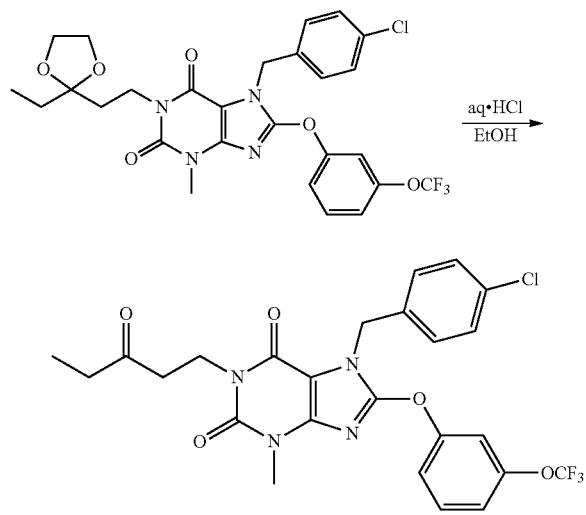

The title compound was prepared using the method of example 14, step 3 to give 7-(4-chlorobenzyl)-3-methyl-1-(3-oxopentyl)-8-(3-(trifluoromethoxy)phenoxy)-1H-purine-2,6(3H,7H)-dione (60 mg, 64.2% yield) as white solid. $^1$H-NMR (DMSO-d$_6$) δ 7.59-7.55 (t, 1H), 7.46-7.39 (d, 6H), 7.31-7.29 (d, 1H), 5.39 (s, 2H), 4.06-4.03 (m, 2H), 3.26 (s, 3H), 2.69-2.65 (t, 2H), 2.48-2.42 (t, 2H), 0.91-0.87 (t, 3H). LCMS retention time 3.384 min; LCMS MH+ 551.

Example 21 7-(4-chlorobenzyl)-1-(3-hydroxypentyl)-3-methyl-8-(3-(trifluoromethoxy)phenoxy)-1H-purine-2,6(3H,7H)-dione

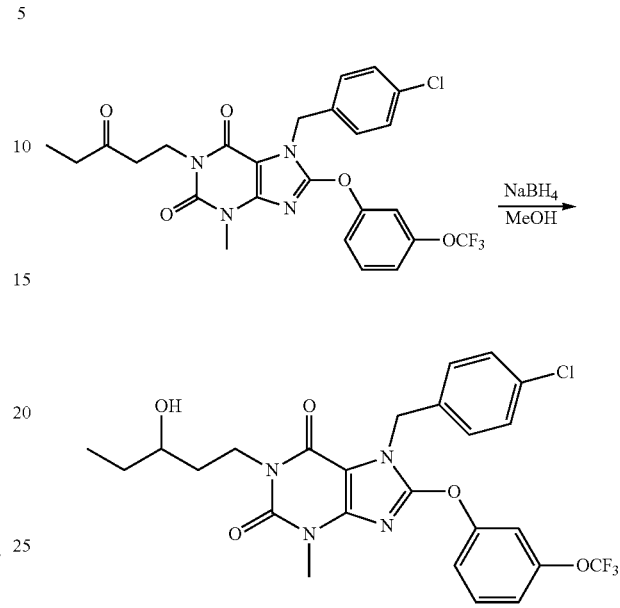

To a solution of 7-(4-chlorobenzyl)-3-methyl-1-(3-oxopentyl)-8-(3-(trifluoromethoxy)phenoxy)-1H-purine-2,6(3H,7H)-dione (150 mg, 0.273 mmol, example 20) in methanol (20 mL) was added sodium borohydride (40 mg, 1.05 mmol) at 0° C. under nitrogen. The mixture was stirred at 0° C. for 2 h. The mixture was diluted with ethyl acetate and water, and the phases were separated. The organic phase was washed with brine, dried over sodium sulfate, filtered and concentrated. The crude product was purified by preparative HPLC to give 7-(4-chlorobenzyl)-1-(3-hydroxypentyl)-3-methyl-8-(3-(trifluoromethoxy)phenoxy)-1H-purine-2,6(3H,7H)-dione (50 mg, 33.5% yield) as white solid. $^1$H-NMR (DMSO-d$_6$) δ 7.63-7.58 (t, 1H), 7.49 (s, 1H), 7.44-7.42 (m, 5H), 7.34-7.31 (d, 1H), 5.44 (s, 2H), 4.48-4.46 (d, 1H), 4.08-4.01 (m, 1H), 3.89-3.83 (m, 1H), 3.42-3.37 (m, 1H), 3.29 (s, 3H), 1.63-1.55 (m, 2H), 1.44-1.31 (m, 2H), 0.87-0.84 (t, 3H). LCMS retention time 3.372 min; LCMS MH+ 553.

Example 22 7-(4-chlorobenzyl)-1-(3-hydroxybutyl)-3-methyl-8-(6-methylpyridin-3-yloxy)-1H-purine-2,6(3H,7H)-dione

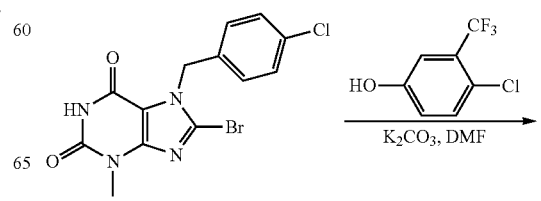

411
-continued

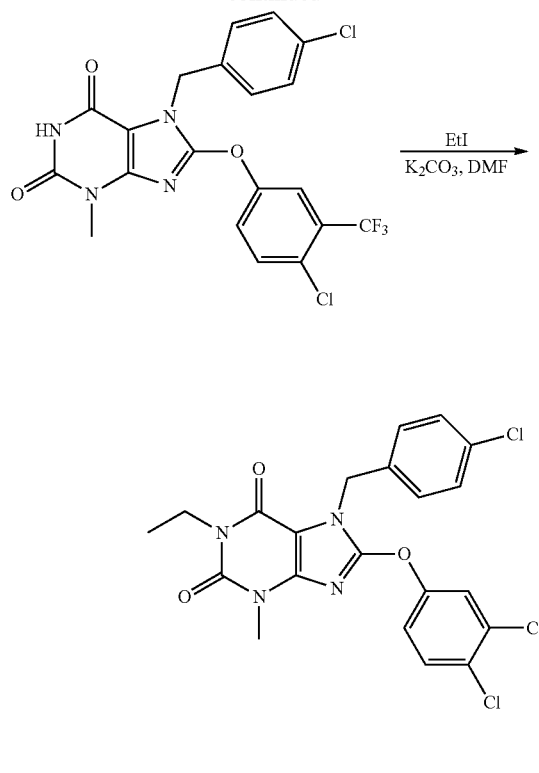

Step 1 8-(4-chloro-3-(trifluoromethyl)phenoxy)-7-(4-chlorobenzyl)-3-methyl-1H-purine-2,6(3H,7H)-dione

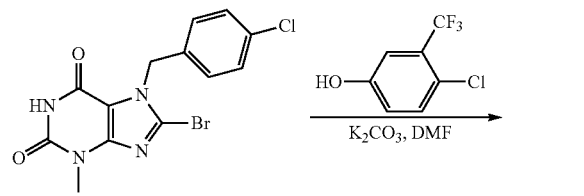

The title compound was prepared from intermediate 8 using the method of intermediate 12, step 2 to give 8-(4-chloro-3-(trifluoromethyl)phenoxy)-7-(4-chlorobenzyl)-3-methyl-1H-purine-2,6(3H,7H)-dione (77 mg, 39.5% yield) as white solid. LCMS retention time 1.809 min; LCMS MH+ 485

412

Step 2 7-(4-chlorobenzyl)-1-(3-hydroxybutyl)-3-methyl-8-(6-methylpyridin-3-yloxy)-1H-purine-2,6(3H,7H)-dione The title compound was prepared using the method of example 6, step 1 to give 7-(4-chlorobenzyl)-1-(3-hydroxybutyl)-3-methyl-8-(6-methylpyridin-3-yloxy)-1H-purine-2,6(3H,7H)-dione (20 mg, 24.4% yield) as white solid. $^1$H-NMR (DMSO-$d_6$) δ 7.94-7.93 (d, 1H), 7.86-7.84 (d, 1H), 7.79-7.77 (m, 1H), 7.46 (s, 4H), 5.44 (s, 2H), 3.94-3.89 (m, 2H), 3.29 (s, 3H), 1.14-1.10 (t, 3H). LCMS retention time 3.400 min; LCMS MH+ 513

Example 23 3-benzyl-7-(4-chlorobenzyl)-1-methyl-8-(3-(trifluoromethyl)phenoxy)-1H-purine-2,6(3H,7H)-dione

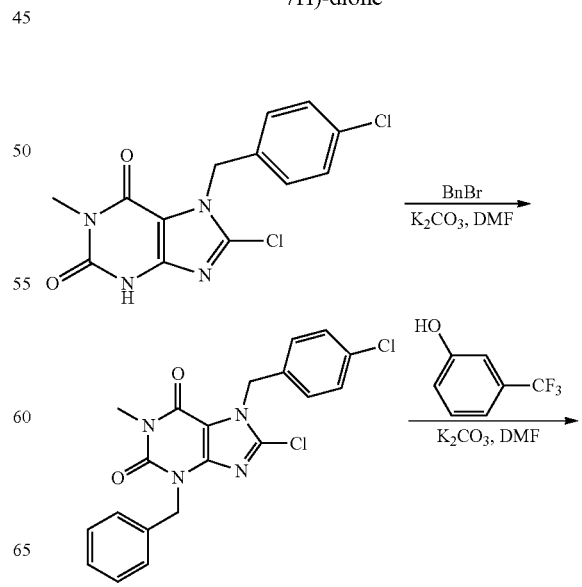

413
-continued

414
Step 2 3-benzyl-7-(4-chlorobenzyl)-1-methyl-8-(3-(trifluoromethyl)phenoxy)-1H-purine-2,6(3H,7H)-dione

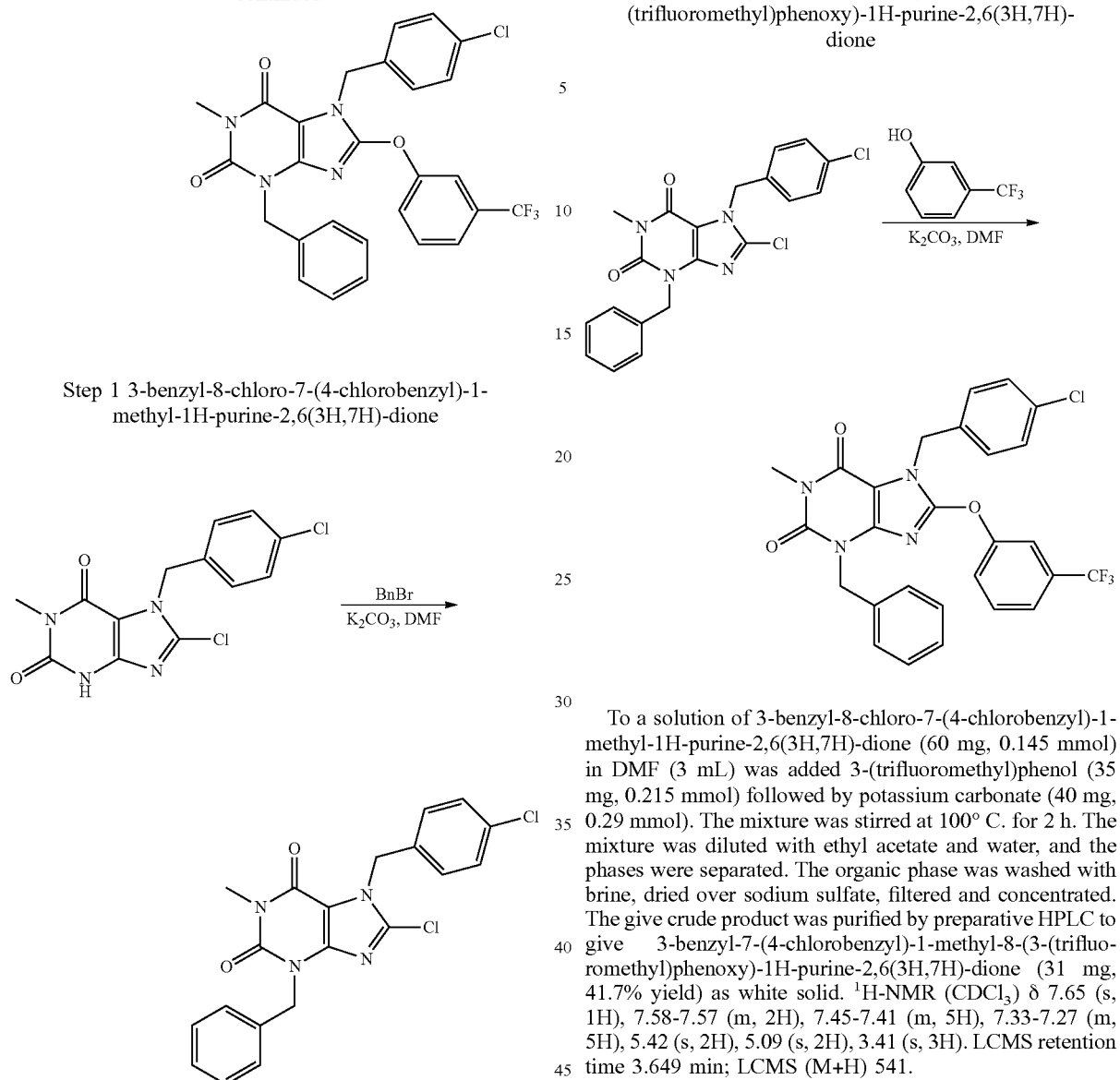

Step 1 3-benzyl-8-chloro-7-(4-chlorobenzyl)-1-methyl-1H-purine-2,6(3H,7H)-dione

To a solution of 8-chloro-7-(4-chlorobenzyl)-1-methyl-1H-purine-2,6(3H,7H)-dione (50 mg, 0.154 mmol, intermediate 10) in DMF (3 mL) was added (bromomethyl)benzene (50 mg, 0.29 mmol) followed by potassium carbonate (40 mg, 0.29 mmol). The mixture was stirred at 40° C. overnight. The mixture was diluted with ethyl acetate and water, and the phases were separated. The organic phase was washed with brine, dried over sodium sulfate, filtered and concentrated. The crude product was purified by silica gel chromatography eluting with petroleum/ethyl acetate (5:1 to 3:1) to give 3-benzyl-8-chloro-7-(4-chlorobenzyl)-1-methyl-1H-purine-2,6(3H,7H)-dione (60 mg, 93.6% yield) as white solid. LCMS retention time 1.893 min; LCMS MH+ 415.

To a solution of 3-benzyl-8-chloro-7-(4-chlorobenzyl)-1-methyl-1H-purine-2,6(3H,7H)-dione (60 mg, 0.145 mmol) in DMF (3 mL) was added 3-(trifluoromethyl)phenol (35 mg, 0.215 mmol) followed by potassium carbonate (40 mg, 0.29 mmol). The mixture was stirred at 100° C. for 2 h. The mixture was diluted with ethyl acetate and water, and the phases were separated. The organic phase was washed with brine, dried over sodium sulfate, filtered and concentrated. The give crude product was purified by preparative HPLC to give 3-benzyl-7-(4-chlorobenzyl)-1-methyl-8-(3-(trifluoromethyl)phenoxy)-1H-purine-2,6(3H,7H)-dione (31 mg, 41.7% yield) as white solid. $^1$H-NMR (CDCl$_3$) δ 7.65 (s, 1H), 7.58-7.57 (m, 2H), 7.45-7.41 (m, 5H), 7.33-7.27 (m, 5H), 5.42 (s, 2H), 5.09 (s, 2H), 3.41 (s, 3H). LCMS retention time 3.649 min; LCMS (M+H) 541.

The following examples 24a through 24m were prepared using the 2 step method of example 23.

Example 24a 7-(4-chlorobenzyl)-3-(2-hydroxyethyl)-1-methyl-8-(3-(trifluoromethyl)phenoxy)-1H-purine-2,6(3H,7H)-dione

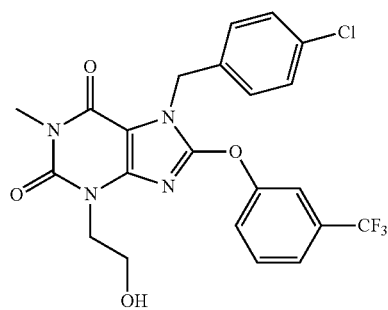 [SMILES: Cn1c(=O)c2c(nc(Oc3cccc(C(F)(F)F)c3)n2Cc2ccc(Cl)cc2)n(CCO)c1=O]

White solid, 7 mg, 10.1% yield: $^1$H-NMR (CDCl$_3$) δ 7.57-7.51 (m, 3H), 7.44-7.42 (m, 3H), 7.34-7.32 (m, 2H), 5.44 (s, 2H), 4.21-4.18 (m, 2H), 3.88-3.84 (m, 2H), 3.42 (s, 3H). LCMS retention time 3.045 min; LCMS MH$^+$ 495.

Example 24b 7-(4-chlorobenzyl)-1-methyl-3-(pyridin-2-ylmethyl)-8-(3-(trifluoromethyl)phenoxy)-1H-purine-2,6(3H,7H)-dione

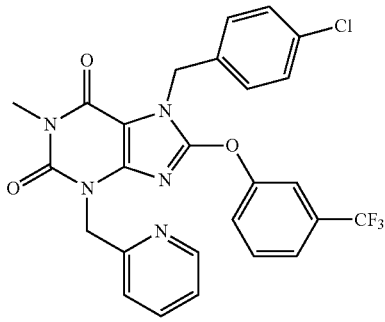 [SMILES: Cn1c(=O)c2c(nc(Oc3cccc(C(F)(F)F)c3)n2Cc2ccc(Cl)cc2)n(Cc2ccccn2)c1=O]

White solid, 30 mg, 50.4% yield: $^1$H-NMR (DMSO-d$_6$) δ 8.43-8.41 (d, 1H), 7.71-7.63 (m, 5H), 7.49-7.44 (m, 4H), 7.28-7.23 (m, 2H), 5.46 (s, 2H), 5.14 (s, 2H), 3.26 (s, 3H). LCMS retention time 3.279 min; LCMS MH$^+$ 542.

Example 24c 3-benzyl-7-(4-chlorobenzyl)-1-methyl-8-(3-(trifluoromethoxy)phenoxy)-1H-purine-2,6(3H,7H)-dione

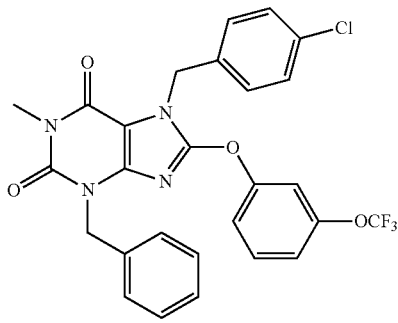 [SMILES: Cn1c(=O)c2c(nc(Oc3cccc(OC(F)(F)F)c3)n2Cc2ccc(Cl)cc2)n(Cc2ccccc2)c1=O]

White solid, 15 mg, 10.8% yield: $^1$H-NMR (DMSO-d$_6$) δ 7.61-7.56 (m, 1H), 7.49 (bs, 1H), 7.41-7.39 (m, 5H), 7.31-7.24 (m, 6H), 5.41 (s, 2H), 4.99 (s, 2H), 3.22 (s, 3H). LCMS retention time 3.705 min; LCMS MH$^+$ 557.

Example 24d 7-(4-chlorobenzyl)-3-(2-hydroxyethyl)-1-methyl-8-(3-(trifluoromethoxy)phenoxy)-1H-purine-2,6(3H,7H)-dione

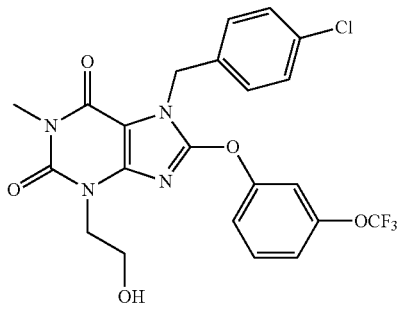 [SMILES: Cn1c(=O)c2c(nc(Oc3cccc(OC(F)(F)F)c3)n2Cc2ccc(Cl)cc2)n(CCO)c1=O]

White solid, 58 mg, 18.9% yield: $^1$H-NMR (DMSO-d$_6$) δ 7.63-7.59 (m, 1H), 7.49-7.42 (m, 6H), 7.34-7.31 (m, 1H), 5.44 (s, 2H), 4.81-4.78 (t, 1H), 3.94-3.90 (m, 2H), 3.60-3.37 (m, 2H), 3.24 (s, 3H). LCMS retention time 3.002 min; LCMS MH$^+$ 511.

Example 24e 7-(4-chlorobenzyl)-1-methyl-3-(pyridin-2-ylmethyl)-8-(3-(trifluoromethoxy)phenoxy)-1H-purine-2,6(3H,7H)-dione

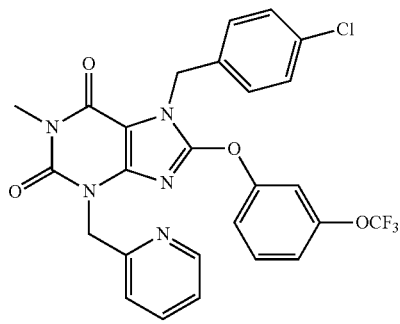 [SMILES: Cn1c(=O)c2c(nc(Oc3cccc(OC(F)(F)F)c3)n2Cc2ccc(Cl)cc2)n(Cc2ccccn2)c1=O]

White solid, 38 mg, 62.0% yield: $^1$H-NMR (DMSO-d$_6$) δ 8.43-8.42 (d, 1H), 7.73-7.69 (m, 1H), 7.56-7.52 (t, 1H), 7.48-7.43 (m, 4H), 7.38-7.34 (m, 2H), 7.29-7.23 (m, 3H), 5.45 (s, 2H), 5.15 (s, 2H), 3.26 (s, 3H). LCMS retention time 3.266 min; LCMS MH$^+$ 558.

Example 24f 8-(3,5-bis(trifluoromethyl)phenoxy)-7-(4-chlorobenzyl)-3-ethyl-1-methyl-1H-purine-2,6(3H,7H)-dione

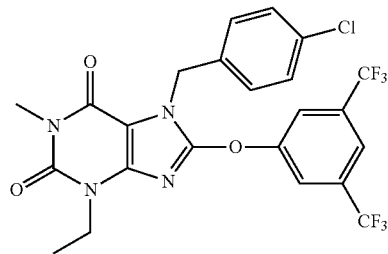 [SMILES: CCn1c(=O)n(C)c(=O)c2c1nc(Oc1cc(C(F)(F)F)cc(C(F)(F)F)c1)n2Cc1ccc(Cl)cc1]

White solid, 10 mg, 26.2% yield: $^1$H-NMR (DMSO-d$_6$) δ 8.23 (s, 2H), 8.05 (s, 1H), 7.48-7.39 (dd, 4H), 5.42 (s, 2H), 3.86-3.84 (m, 2H), 3.22 (s, 3H), 1.14-1.11 (t, 3H). LCMS retention time 3.591 min; LCMS MH$^+$ 547.

Example 24g 7-(4-chlorobenzyl)-3-ethyl-1-methyl-8-(3-(trifluoromethoxy)phenoxy)-1H-purine-2,6(3H,7H)-dione

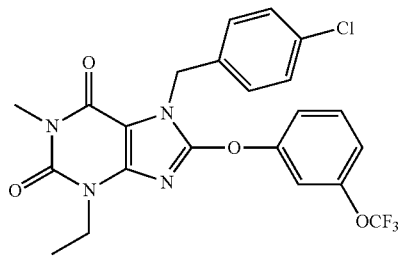 [SMILES: CCn1c(=O)n(C)c(=O)c2c1nc(Oc1cccc(OC(F)(F)F)c1)n2Cc1ccc(Cl)cc1]

White solid, 20 mg, 20.4% yield: $^1$H-NMR (DMSO-d$_6$) δ 7.61-7.59 (t, 1H), 7.52 (s, 1H), 7.43 (s, 5H), 7.33-7.32 (d, 1H), 5.44 (s, 2H), 3.89-3.88 (m, 2H), 3.24 (s, 3H), 1.17-1.13 (t, 3H). LCMS retention time 3.561 min; LCMS MH$^+$ 495.

Example 24h 7-(4-chlorobenzyl)-3-ethyl-1-methyl-8-(3-(trifluoromethyl)phenoxy)-1H-purine-2,6(3H,7H)-dione

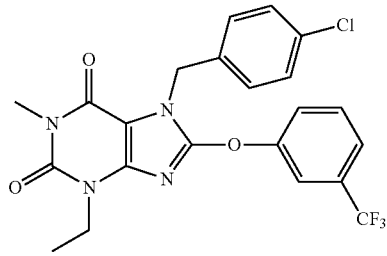 [SMILES: CCn1c(=O)n(C)c(=O)c2c1nc(Oc1cccc(C(F)(F)F)c1)n2Cc1ccc(Cl)cc1]

White solid, 20 mg, 24.5% yield: $^1$H-NMR (DMSO-d$_6$) δ 7.79 (s, 1H), 7.73-7.67 (m, 3H), 7.47-7.42 (m, 4H), 5.45 (s, 2H), 3.90-3.85 (q, 2H), 3.30 (s, 3H), 1.24-1.13 (t, 3H). LCMS retention time 3.511 min; LCMS MH$^+$ 479.

Example 24i 7-(4-chlorobenzyl)-1-methyl-3-(pyridin-4-ylmethyl)-8-(3-(trifluoromethoxy)phenoxy)-1H-purine-2,6(3H,7H)-dione

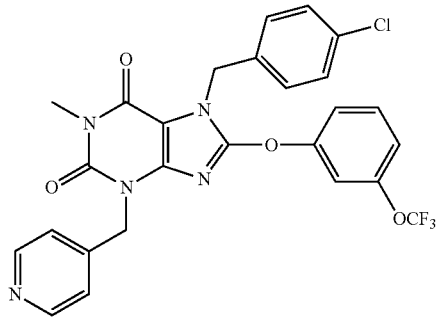 [SMILES: Cn1c(=O)c2c(nc(Oc3cccc(OC(F)(F)F)c3)n2Cc2ccc(Cl)cc2)n(Cc2ccncc2)c1=O]

White solid, 10 mg, 6.21% yield: $^1$H-NMR (DMSO-d$_6$) δ 8.48-8.46 (d, 2H), 7.59-7.55 (t, 1H), 7.47-7.45 (m, 5H), 7.43-7.39 (d, 1H), 7.38-7.37 (d, 1H), 7.31-7.24 (m, 2H), 5.45 (s, 2H), 5.05 (s, 2H), 3.25 (s, 3H). LCMS retention time 2.856 min; LCMS MH$^+$ 558.

Example 24j 7-(4-chlorobenzyl)-1-methyl-3-(2-oxopropyl)-8-(3-(trifluoromethoxy)phenoxy)-1H-purine-2,6(3H,7H)-dione

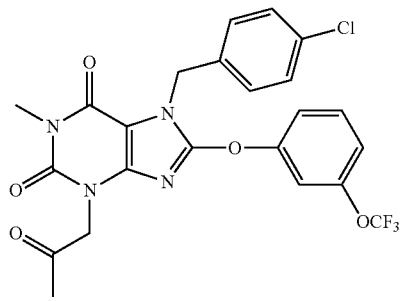 [SMILES: CC(=O)Cn1c(=O)n(C)c(=O)c2c1nc(Oc1cccc(OC(F)(F)F)c1)n2Cc1ccc(Cl)cc1]

White solid, 11 mg, 9.93% yield: $^1$H-NMR (DMSO-d$_6$) δ 7.61-7.59 (t, 1H), 7.44-7.38 (m, 6H), 7.32-7.30 (d, 1H), 5.44 (s, 2H), 4.74 (s, 2H), 3.24 (s, 3H), 2.16 (s, 3H). LCMS retention time 3.210 min; LCMS MH$^+$ 523.

Example 24k 7-(4-chlorobenzyl)-3-(2-(2-hydroxyethoxy)ethyl)-1-methyl-8-(3-(trifluoromethoxy)phenoxy)-1H-purine-2,6(3H,7H)-dione

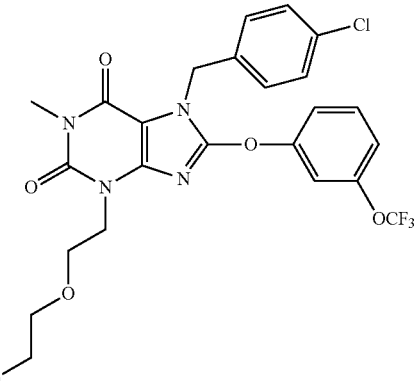

White solid, 31 mg, 45.3% yield: $^1$H-NMR (DMSO-d$_6$) δ 7.59-7.56 (t, 1H), 7.44-7.37 (m, 6H), 7.31-7.29 (d, 1H), 5.42 (s, 2H), 4.01-3.98 (t, 2H), 3.35 (s, 4H), 3.22 (s, 3H). LCMS retention time 2.969 min; LCMS MH$^+$ 555.

Example 24l 7-(4-chlorobenzyl)-1-methyl-3-propyl-8-(3-(trifluoromethoxy)phenoxy)-1H-purine-2,6(3H,7H)-dione

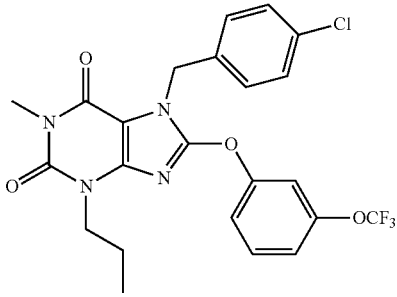 [SMILES: CCCn1c(=O)n(C)c(=O)c2c1nc(Oc1cccc(OC(F)(F)F)c1)n2Cc1ccc(Cl)cc1]

White solid, 15 mg, 26.8% yield: $^1$H-NMR (CDCl$_3$) δ 7.49-7.43 (m, 3H), 7.35-7.31 (m, 3H), 7.24-7.15 (m, 2H), 5.44 (s, 2H), 3.97-3.93 (t, 2H), 3.43 (s, 3H), 1.76-1.70 (m, 2H), 0.94-0.90 (t, 3H). LCMS retention time 3.526 min; LCMS MH$^+$ 509.

Example 24m 7-(4-chlorobenzyl)-3-(isoxazol-5-ylmethyl)-1-methyl-8-(3-(trifluoromethoxy)phenoxy)-1H-purine-2,6(3H,7H)-dione

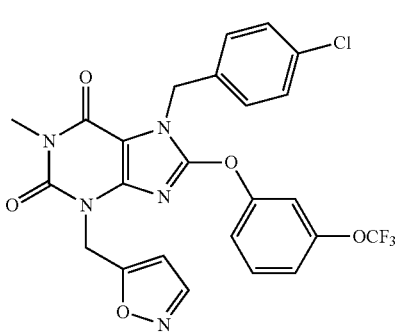 [SMILES: Cn1c(=O)c2c(nc(Oc3cccc(OC(F)(F)F)c3)n2Cc2ccc(Cl)cc2)n(Cc2ccno2)c1=O]

White solid, 16 mg, 16.3% yield: $^1$H-NMR (DMSO-d$_6$) δ 8.33-8.31 (d, 2H), 7.61-7.57 (t, 1H), 7.45-7.41 (m, 6H), 7.32-7.29 (d, 1H), 5.44 (s, 2H), 4.34 (bs, 2H), 3.26 (s, 3H). LCMS retention time 3.114 min; LCMS MH$^+$ 548.

Example 25 7-(4-chlorobenzyl)-3-(2-(dimethylamino)ethyl)-1-methyl-8-(3-(trifluoromethoxy)phenoxyl-1H-purine-2,6(3H,7H)-dione

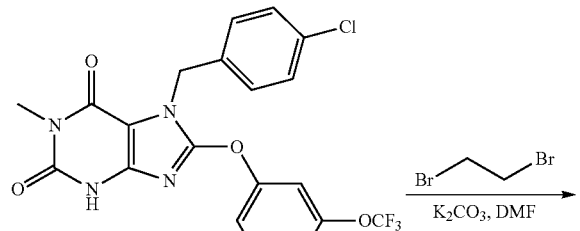

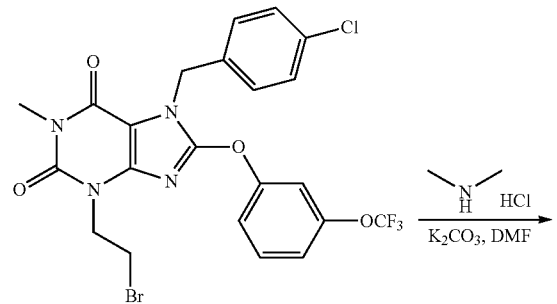

Step 1 3-(2-bromoethyl)-7-(4-chlorobenzyl)-1-methyl-8-(3-(trifluoromethoxy)phenoxy)-1H-purine-2,6(3H,7H)-dione

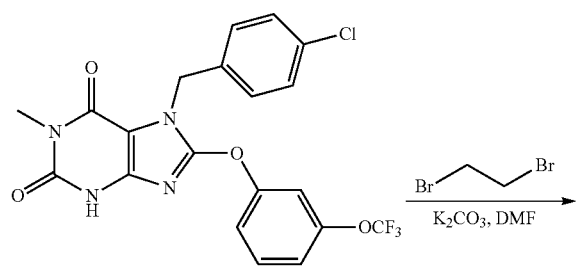

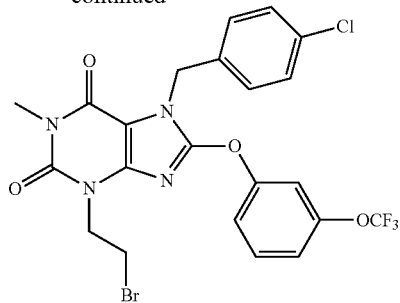

To a solution of 7-(4-chlorobenzyl)-1-methyl-8-(3-(trifluoromethoxy)phenoxy)-1H-purine-2,6(3H,7H)-dione (100 mg, 0.215 mmol) in DMF (3 mL) was added 1,2-dibromoethane (0.2 mL, 2.32 mmol), followed by potassium carbonate (60 mg, 0.435 mmol). The mixture was stirred at 50° C. for 16 h. The reaction was partitioned between ethyl acetate and water. The organic phase was washed with brine and dried over sodium sulfate, filtered and concentrated to give the crude product (110 mg, 91.6% yield) as white solid. LCMS retention time 2.099 min; LCMS MH$^+$ 573.

Step 2 7-(4-chlorobenzyl)-3-(2-(dimethylamino)ethyl)-1-methyl-8-(3-(trifluoromethoxy)phenoxy)-1H-purine-2,6(3H,7H)-dione

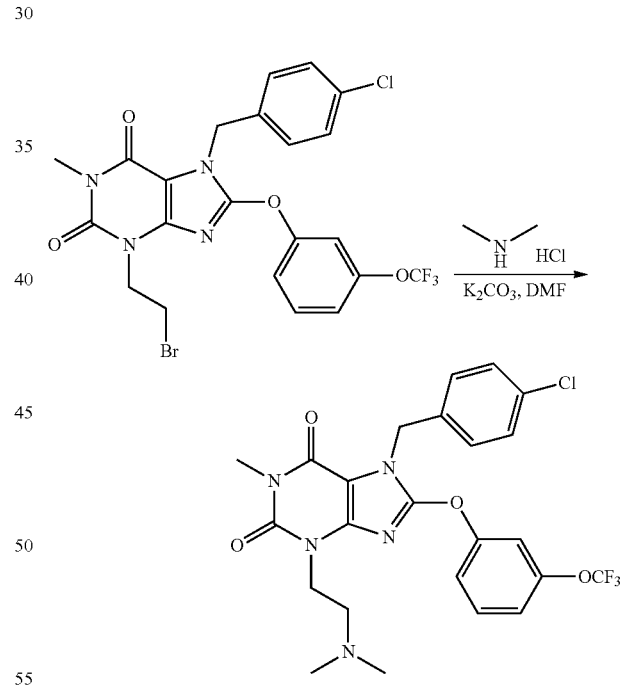

To a solution of 3-(2-bromoethyl)-7-(4-chlorobenzyl)-1-methyl-8-(3-(trifluoromethoxy)phenoxy)-1H-purine-2,6(3H,7H)-dione (110 mg, 0.192 mmol) in DMF (3 mL) was added dimethylamine hydrochloride (150 mg, 1.84 mmol), followed by potassium carbonate (100 mg, 0.725 mmol). The mixture was stirred at 40° C. for 16 h; then it was diluted with ethyl acetate and water. The phases were separated and the organic phase was washed with brine, dried over sodium sulfate, filtered and concentrated. The residue was purified by preparative HPLC to give 7-(4-chlorobenzyl)-3-(2-(dimethylamino)ethyl)-1-methyl-8-(3-(trifluoromethoxy)phenoxy)-1H-purine-2,6(3H,7H)-dione (15 mg, 13.3% yield) as white solid. ¹H-NMR (DMSO-d₆) δ 9.69 (s, 1H), 7.64-7.60 (t, 1H), 7.54 (s, 1H), 7.49-7.43 (m, 5H), 7.35-7.33 (d, 1H), 5.47 (s, 2H), 4.21-4.18 (t, 2H), 3.39 (m, 2H), 3.26 (s, 3H), 2.79-2.78 (d, 6H). LCMS retention time 3.266 min; LCMS MH⁺ 558.

Example 26 7-(4-chlorobenzyl)-1-methyl-3-(2-oxo-propyl)-8-(3-(trifluoromethoxy)phenoxy)-1H-purine-2,6(3H,7H)-dione

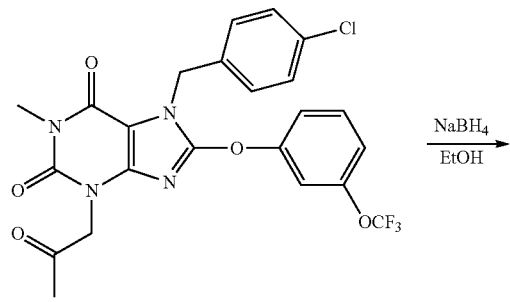

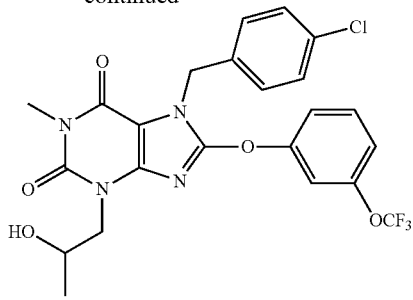

To a solution of 7-(4-chlorobenzyl)-1-methyl-3-(2-oxo-propyl)-8-(3-(trifluoromethoxy)phenoxy)-1H-purine-2,6 (3H,7H)-dione (80 mg, 0.153 mmol, example 24j) in ethanol (3 mL) was added sodium borohydride (12 mg, 0.317 mmol) at 0° C. The resulting mixture was stirred at 0° C. overnight. The mixture was concentrated and the residue was purified by preparative HPLC to give the title product (6 mg, 7.47% yield) as white solid. ¹H-NMR (DMSO-d₆) δ 7.63-7.58 (t, 1H), 7.50 (s, 1H), 7.43-7.41 (m, 5H), 7.33-7.31 (d, 1H), 5.44 (s, 2H), 4.80-4.79 (d, 1H), 4.02-3.99 (bs, 1H), 3.89-3.84 (m, 1H), 3.69-3.65 (dd, 1H), 3.24 (s, 3H), 1.01-0.99 (d, 3H). LCMS retention time 3.095 min; LCMS MH⁺ 525.

Example 27 8-(4-chloro-3-(trifluoromethyl)phenoxy)-7-(4-chlorobenzyl)-1-(2-(2-hydroxyethoxy) ethyl)-3-methyl-1H-purine-2,6(3H,7H)-dione

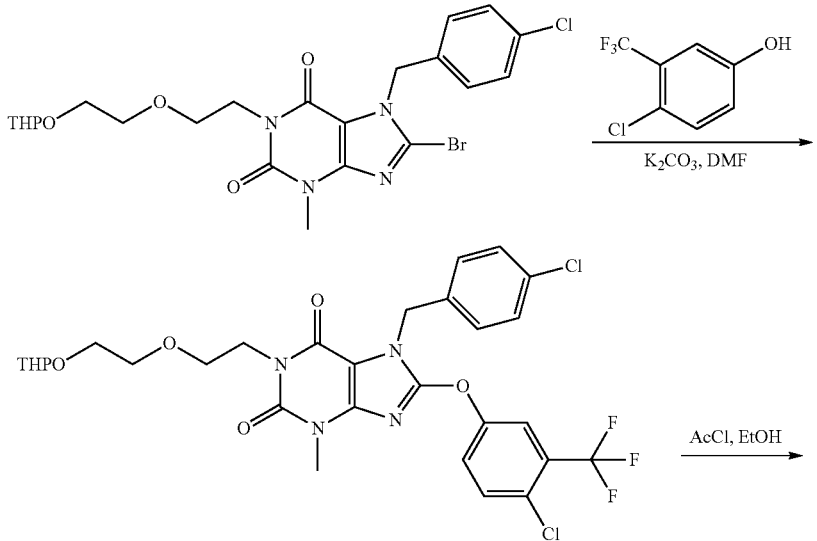

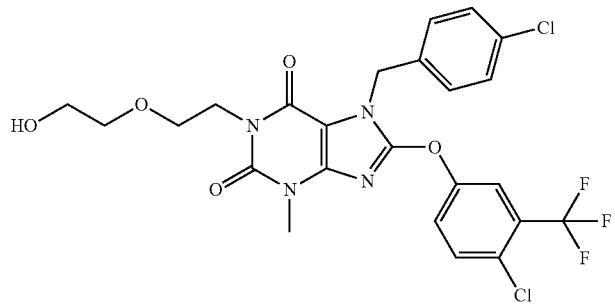

Step 1 8-(4-chloro-3-(trifluoromethyl)phenoxy)-7-(4-chlorobenzyl)-3-methyl-1-(2-(2-(tetrahydro-2H-pyran-2-yloxy)ethoxy)ethyl)-1H-purine-2,6(3H,7H)-dione

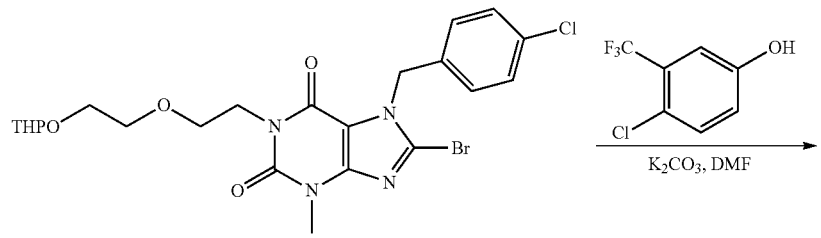

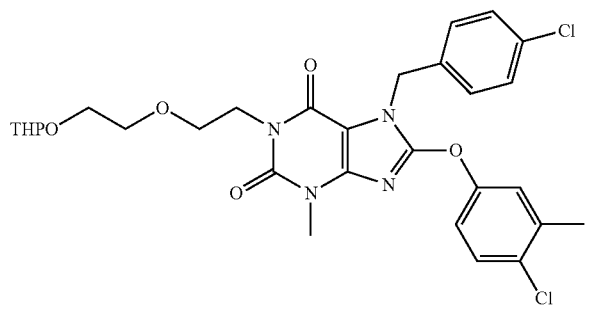

To a solution of 8-bromo-7-(4-chlorobenzyl)-3-methyl-1-(2-(2-(tetrahydro-2H-pyran-2-yloxy)ethoxy)ethyl)-1H-purine-2,6(3H,7H)-dione (150 mg, 0.28 mmol, intermediate 11) in DMF (5 mL) was added 4-chloro-3-(trifluoromethyl) phenol (81 mg, 0.45 mmol) and potassium carbonate (76 mg, 0.55 mmol). The mixture was stirred at 80° C. overnight. The mixture was partitioned between ethyl acetate and water. The organic phase was washed with brine, dried over sodium sulfate, filtered and concentrated to give a crude product which was used without purification. LCMS retention time 2.112 min; LCMS MH$^+$-THP 573.

Step 2 8-(4-chloro-3-(trifluoromethyl)phenoxy)-7-(4-chlorobenzyl)-1-(2-(2-hydroxyethoxy)ethyl)-3-methyl-1H-purine-2,6(3H,7H)-dione

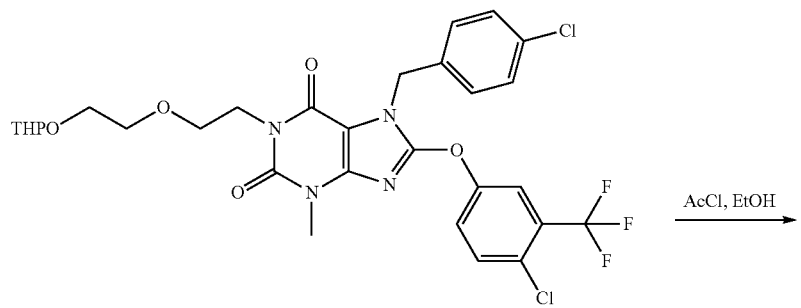

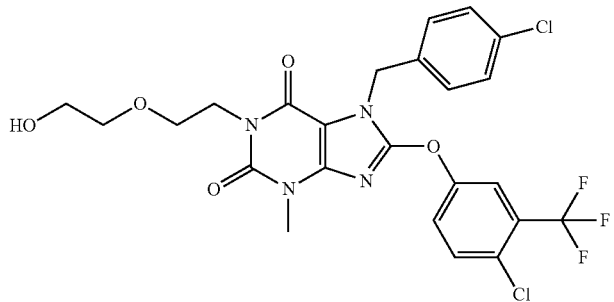

To a solution of 8-(4-chloro-3-(trifluoromethyl)phenoxy)-7-(4-chlorobenzyl)-3-methyl-1-(2-(2-(tetrahydro-2H-pyran-2-yloxy)ethoxy)ethyl)-1H-purine-2,6(3H,7H)-dione (100 mg, 0.15 mmol) in ethanol (5 mL) was added acetyl chloride (0.2 mL) at 0° C. The mixture was stirred at room temperature for 1 h. The mixture was partitioned between ethyl acetate and water. The organic phase was dried over sodium sulfate, filtered and concentrated to give a crude product, which was purified via preparative HPLC to give 8-(4-chloro-3-(trifluoromethyl)phenoxy)-7-(4-chlorobenzyl)-1-(2-(2-hydroxyethoxy)ethyl)-3-methyl-1H-purine-2,6(3H,7H)-dione (37 mg, 43.1% yield) as white solid. $^1$H-NMR (DMSO-$d_6$) δ 7.95 (d, 1H), 7.85 (d, 1H), 7.77-7.80 (m, 1H), 7.44 (s, 4H), 5.44 (s, 2H), 4.58-4.61 (m, 1H), 4.06 (t, 2H), 3.59 (t, 2H), 3.43-3.46 (m, 4H), 3.29 (s, 3). LCMS retention time 3.070 min; LCMS MH$^+$ 573.

The following examples 28a through 28g were prepared using the method of example 27.

Example 28a 8-(3,5-bis(trifluoromethyl)phenoxy)-7-(4-chlorobenzyl)-1-(2-(2-hydroxyethoxy)ethyl)-3-methyl-1H-purine-2,6(3H,7H)-dione

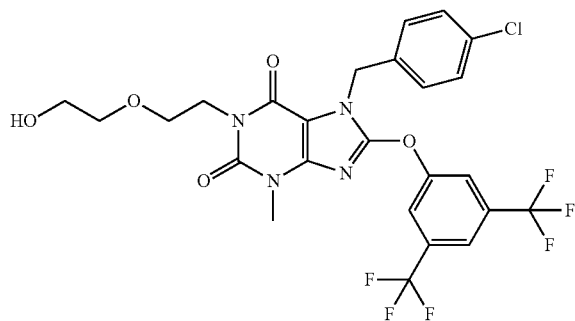 [SMILES: Cn1c(=O)n(CCOCCO)c(=O)c2c1nc(Oc1cc(C(F)(F)F)cc(C(F)(F)F)c1)n2Cc1ccc(Cl)cc1]

White solid, 27 mg, 30.1% yield: $^1$H-NMR (DMSO-$d_6$) δ 8.25 (s, 1H), 8.09 (s, 1H), 7.48 (d, 2H), 7.42 (d, 2H), 5.46 (s, 2H), 4.59 (s, 1H), 4.07 (t, 2H), 3.57 (t, 2H), 3.40-3.46 (m, 4H), 3.29 (s, 3H). LCMS retention time 3.150 min; LCMS MH$^+$ 607.

Example 28b 7-(4-chlorobenzyl)-1-(2-(2-hydroxyethoxy)ethyl)-3-methyl-8-(3-(trifluoromethyl)phenoxy)-1H-purine-2,6(3H,7H)-dione

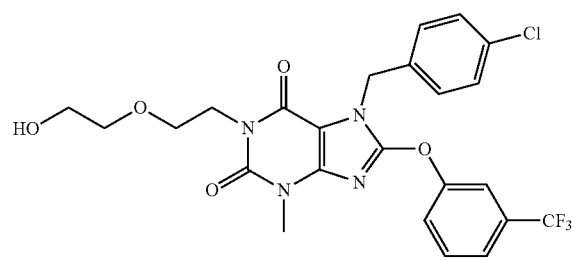 [SMILES: Cn1c(=O)n(CCOCCO)c(=O)c2c1nc(Oc1cccc(C(F)(F)F)c1)n2Cc1ccc(Cl)cc1]

White solid, 30 mg, 40.5% yield: $^1$H-NMR (DMSO-$d_6$) δ 7.78 (s, 1H), 7.70-7.73 (m, 3H), 7.44 (s, 4H), 5.45 (s, 2H), 4.59 (t, 1H), 4.06 (t, 2H), 3.60 (t, 2H), 3.44 (s, 4H), 3.32 (s, 3H). LCMS retention time 2.923 min; LCMS MH$^+$ 539.

Example 28c 7-(4-chlorobenzyl)-1-(2-(2-hydroxyethoxy)ethyl)-3-methyl-8-(m-tolyloxy)-1H-purine-2,6(3H,7H)-dione

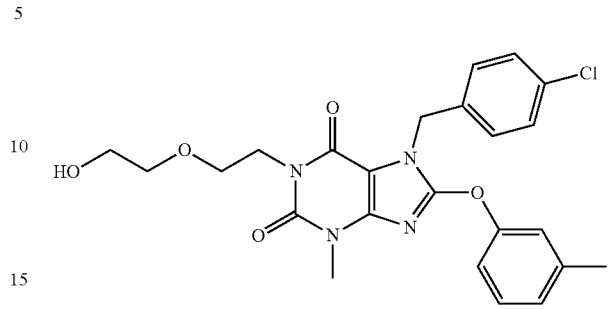

White solid, 21 mg, 29.8% yield: $^1$H-NMR (DMSO-$d_6$) δ 7.37-7.46 (m, 4H), 7.33 (t, 1H), 7.09-7.12 (m, 3H), 5.42 (s, 2H), 4.58 (t, 1H), 4.06 (t, 2H), 3.56 (t, 2H), 3.45 (t, 4H), 3.32 (s, 3H), 2.32 (d, 3H). LCMS retention time 2.801 min; LCMS MH$^+$ 485.

Example 28d 7-(4-chlorobenzyl)-1-(2-(2-hydroxyethoxy)ethyl)-8-(3-methoxyphenoxy)-3-methyl-1H-purine-2,6(3H,7H)-dione

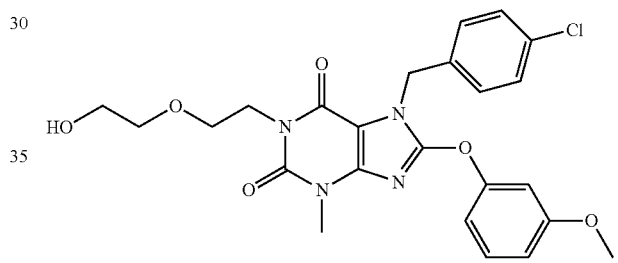

White solid, 26 mg, 37.7% yield: $^1$H-NMR (DMSO-$d_6$) δ 7.38-7.47 (m, 4H), 7.36 (t, 1H), 6.88-6.90 (m, 3H), 5.42 (s, 2H), 4.59 (t, 1H), 4.06 (t, 2H), 3.76 (s, 3H), 3.56 (t, 2H), 3.45 (s, 4H), 3.29 (s, 3H). LCMS retention time 2.631 min; LCMS MH$^+$ 501.

Example 28e 7-(4-chlorobenzyl)-8-(3-chlorophenoxy)-1-(2-(2-hydroxyethoxy)ethyl)-3-methyl-1H-purine-2,6(3H,7H)-dione

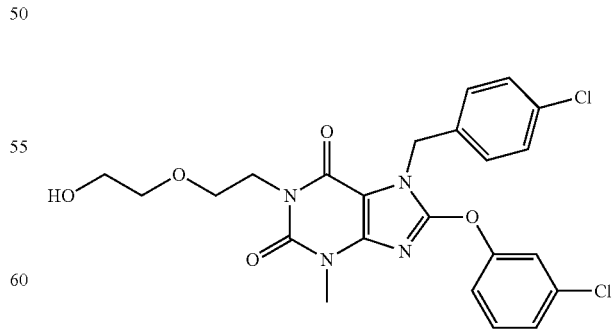

White solid, 33 mg, 36.8% yield: $^1$H-NMR (DMSO-$d_6$) δ 7.48-7.52 (m, 2H), 7.35-7.42 (m, 6H), 5.43 (s, 2H), 4.59 (t, 1H), 4.06 (t, 2H), 3.58 (t, 2H), 3.45 (s, 4H), 3.30 (s, 3H). LCMS retention time 2.856 min; LCMS MH$^+$ 505.

Example 28f 7-(4-chlorobenzyl)-8-(3-ethylphenoxy)-1-(2-(2-hydroxyethoxy)ethyl)-3-methyl-1H-purine-2,6(3H,7H)-dione

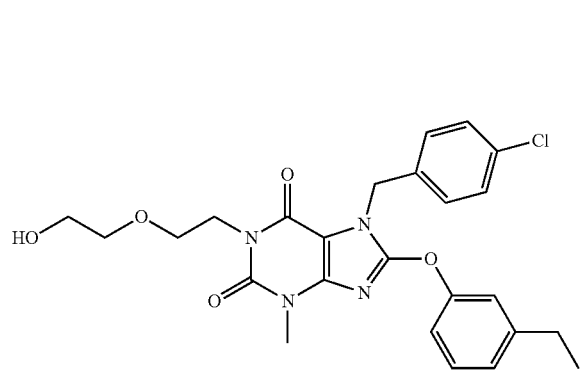 [SMILES: CCc1cccc(Oc2nc3c(c(=O)n(CCOCCO)c(=O)n3C)n2Cc2ccc(Cl)cc2)c1]

White solid, 27 mg, 36.8% yield: $^1$H-NMR (DMSO-$d_6$) δ 7.36-7.46 (m, 5H), 7.11-7.15 (m, 3H), 5.43 (s, 2H), 4.61 (t, 1H), 4.06 (t, 2H), 3.56 (t, 2H), 3.43-3.47 (m, 4H), 3.28 (s, 3H), 2.62 (q, 2H), 1.17 (t, 3H). LCMS retention time 2.909 min; LCMS MH$^+$ 499.

Example 28g 7-(4-chlorobenzyl)-1-(2-(2-hydroxyethoxy)ethyl)-3-methyl-8-(3-(morpholinomethyl)phenoxy)-1H-purine-2,6(3H,7H)-dione

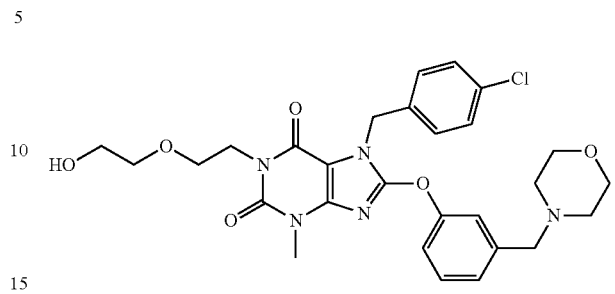

White solid, 41 mg, 41.1% yield: $^1$H-NMR (DMSO-$d_6$) δ 7.77 (s, 1H), 7.51-7.58 (m, 2H), 7.43-7.46 (m, 5H), 5.43 (s, 2H), 4.32-4.37 (m, 2H), 4.03-4.06 (m, 2H), 3.85-3.90 (m, 4H), 3.54-3.57 (t, 2H), 3.44 (m, 4H), 3.27 (s, 3H), 3.00-3.09 (m, 4H). LCMS retention time 1.699 min; LCMS MH$^+$ 570.

Example 29 7-(4-chlorobenzyl)-1-(2-(2-hydroxyethoxy)ethyl)-3-methyl-8-(3-methylbenzyloxy)-1H-purine-2,6(3H,7H)-dione

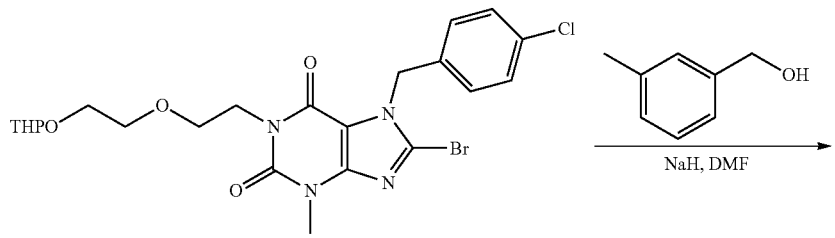

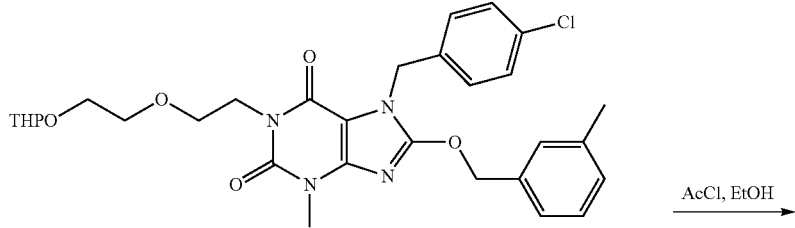

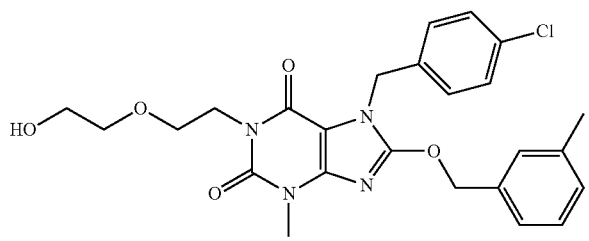

Step 1 7-(4-chlorobenzyl)-3-methyl-8-(3-methylbenzyloxy)-1-(2-(2-(tetrahydro-2H-pyran-2-yloxy)ethoxy)ethyl)-1H-purine-2,6(3H,7H)-dione

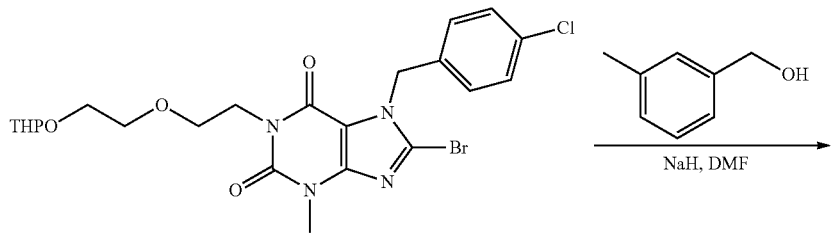

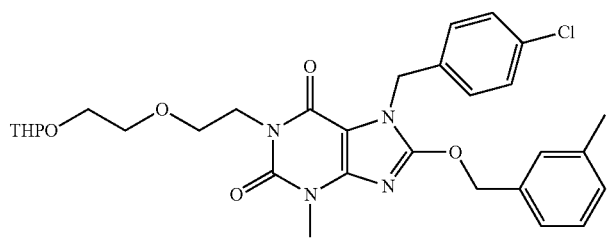

To a solution of m-tolylmethanol (37 mg, 0.3 mmol) in DMF (2 mL) was added sodium hydride (18 mg, 0.45 mmol) at 0° C. After stirring at 0° C. for 30 min, 8-bromo-7-(4-chlorobenzyl)-3-methyl-1-(2-(2-(tetrahydro-2H-pyran-2-yloxy)ethoxy)ethyl)-1H-purine-2,6(3H,7H)-dione (80 mg, 0.15 mmol, intermediate 11) was added. The mixture was stirred at 0° C. for 15 min, then aqueous ammonium chloride solution (2 mL) was added at 0° C. The mixture was partitioned between ethyl acetate and water. The organic layers were combined, dried over sodium sulfate, filtered and concentrated to give a crude product which was used without purification. LCMS retention time 1.967 min; LCMS MH$^+$-THP 499.

Step 2 7-(4-chlorobenzyl)-1-(2-(2-hydroxyethoxy)ethyl)-3-methyl-8-(3-methylbenzyloxy)-1H-purine-2,6(3H,7H)-dione

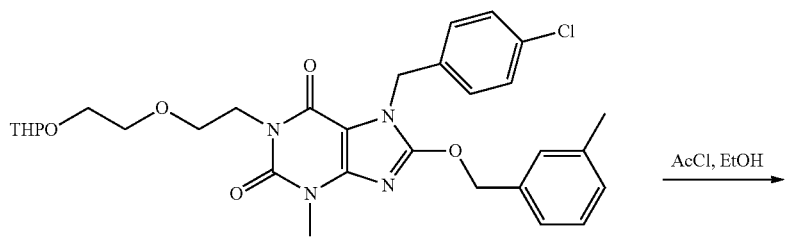

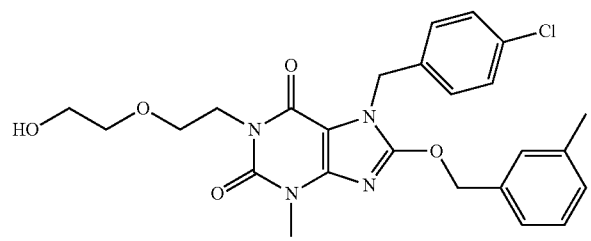

The title product was prepared using the method of example 27, step 2. White solid, 12 mg, 16.2% yield: $^1$H-NMR (DMSO-d$_6$) δ 7.39 (d, 2H), 7.25-7.28 (m, 3H), 7.15-7.21 (m, 3H), 5.49 (s, 2H), 5.25 (s, 2H), 4.57 (d, 1H), 4.03 (t, 2H), 3.54 (t, 2H), 3.44 (t, 4H), 3.41 (s, 3H). LCMS retention time 2.888 min; LCMS MH$^+$ 499.

The following examples 30a through 30d were prepared using the 2 step method of example 29.

Example 30a 7-(4-chlorobenzyl)-8-(3-chlorobenzyloxy)-1-(2-(2-hydroxyethoxy)ethyl)-3-methyl-1H-purine-2,6(3H,7H)-dione

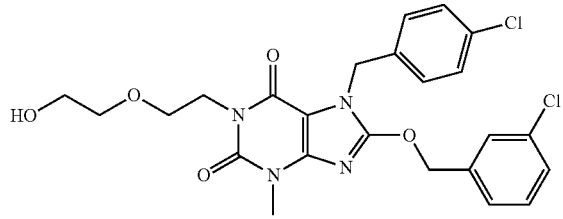 [SMILES: Cn1c(=O)n(CCOCCO)c(=O)c2c1nc(OCc1cccc(Cl)c1)n2Cc1ccc(Cl)cc1]

White solid, 15 mg, 19.4% yield: $^1$H-NMR (DMSO-d$_6$) δ 7.37-7.44 (m, 6H), 7.28 (d, 2H), 5.53 (s, 2H), 5.28 (s, 2H), 4.58 (t, 1H), 4.03 (t, 2H), 3.56 (t, 2H), 3.45 (t, 4H), 3.39 (s, 3H). LCMS retention time 2.894 min; LCMS MH$^+$ 519.

Example 30b 7-(4-chlorobenzyl)-1-(2-(2-hydroxyethoxy)ethyl)-3-methyl-8-(3-(trifluoromethyl)benzyloxy)-1H-purine-2,6(3H,7H)-dione

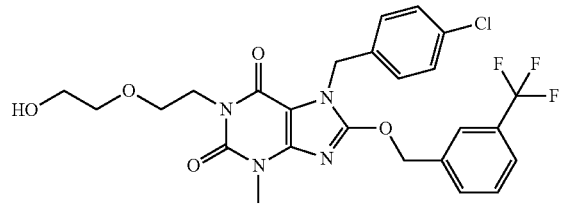 [SMILES: Cn1c(=O)n(CCOCCO)c(=O)c2c1nc(OCc1cccc(C(F)(F)F)c1)n2Cc1ccc(Cl)cc1]

White solid, 18 mg, 21.6% yield: $^1$H-NMR (DMSO-d$_6$) δ 7.79 (s, 1H), 7.74 (d, 2H), 7.63 (t, 1H), 7.37 (d, 2H), 7.28 (d, 2H), 5.62 (s, 2H), 5.28 (s, 2H), 4.58 (t, 1H), 4.04 (t, 2H), 3.55 (t, 2H), 3.44-3.45 (m, 4H), 3.42 (s, 3H). LCMS retention time 2.921 min; LCMS MH$^+$ 553.

Example 30c 7-(4-chlorobenzyl)-1-(2-(2-hydroxyethoxy)ethyl)-8-(3-methoxybenzyloxy)-3-methyl-1H-purine-2,6(3H,7H)-dione

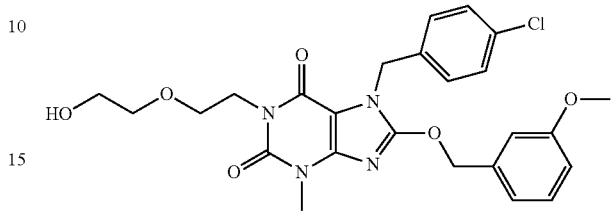

White solid, 17 mg, 22.1% yield: $^1$H-NMR (DMSO-d$_6$) δ 7.36-7.38 (m, 2H), 7.25-7.32 (m, 3H), 6.91-6.99 (m, 3H), 5.50 (s, 2H), 5.25 (s, 2H), 4.60 (t, 1H), 4.03 (t, 2H), 3.73 (s, 3H), 3.54 (t, 2H), 3.42-3.47 (m, 7H). LCMS retention time 2.718 min; LCMS MH$^+$ 515.

Example 30d 7-(4-chlorobenzyl)-1-(2-(2-hydroxyethoxy)ethyl)-3-methyl-8-(3-(trifluoromethoxy)benzyloxy)-1H-purine-2,6(3H,7H)-dione

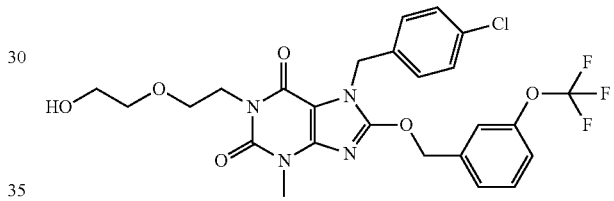

White solid, 31 mg, 22.1% yield: $^1$H-NMR (DMSO-d$_6$) δ 7.53 (t, 1H), 7.37-7.47 (m, 5H), 7.28 (d, 2H), 5.58 (s, 2H), 5.28 (s, 2H), 4.58 (t, 1H), 4.04 (t, 2H), 3.54 (t, 2H), 3.44 (t, 4H), 3.42 (s, 3H). LCMS retention time 2.984 min; LCMS MH$^+$ 569.

Example 31 1-(2-(2-hydroxyethoxy)ethyl)-7-(4-methoxybenzyl)-3-methyl-8-(3-(trifluoromethoxy)phenoxy)-1H-purine-2,6(3H,7H)-dione

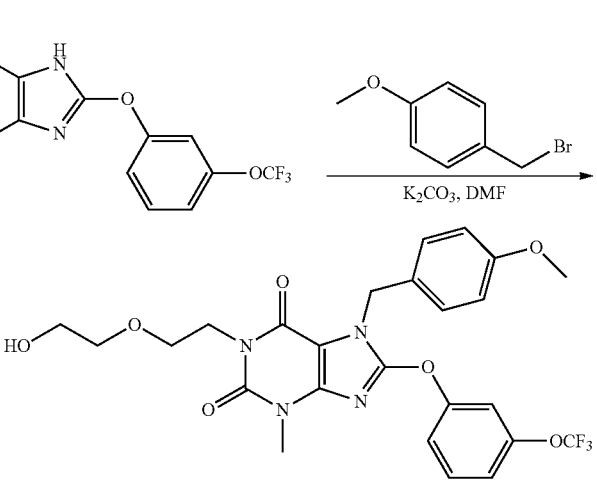

433

To a solution of 1-(2-(2-hydroxyethoxy)ethyl)-3-methyl-8-(3-(trifluoromethoxy)phenoxy)-1H-purine-2,6(3H,7H)-dione (50 mg, 0.116 mmol, intermediate 12) in DMF (3 mL) was added 1-(bromomethyl)-4-methoxybenzene (35 mg, 0.174 mmol) and potassium carbonate (32 g, 0.232 mmol). The reaction was heated at 50° C. for 3 h. The mixture was cooled and partitioned between ethyl acetate and water. The organic layers were combined, dried over sodium sulfate, filtered and concentrated to give a crude product which was purified by preparative HPLC to give 1-(2-(2-hydroxyethoxy)ethyl)-7-(4-methoxybenzyl)-3-methyl-8-(3-(trifluoromethoxy)phenoxy)-1H-purine-2,6(3H,7H)-dione (14 mg, 22.2% yield) as white solid. $^1$H-NMR (DMSO-$d_6$) δ 7.61 (t, 1H), 7.48 (s, 1H), 7.32-7.44 (m, 4H), 6.91 (d, 2H), 5.37 (s, 2H), 4.60 (t, 1H), 4.08 (t, 2H), 3.73 (s, 3H), 3.58 (t, 2H), 3.46 (s, 4H), 3.29 (s, 3H). LCMS retention time 2.581 min; LCMS MH$^+$ 551.

The following products 32a through 32h were prepared using the method of example 31.

Example 32a 7-(3-chlorobenzyl)-1-(2-(2-hydroxyethoxy)ethyl)-3-methyl-8-(3-(trifluoromethoxy)phenoxy)-1H-purine-2,6(3H,7H)-dione

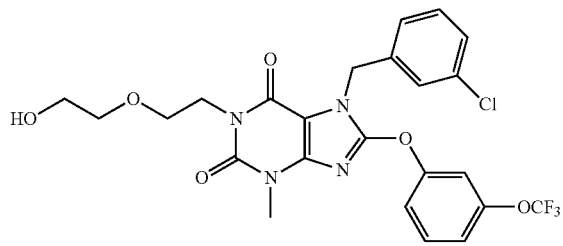 [SMILES: Cn1c(=O)n(CCOCCO)c(=O)c2c1nc(Oc1cccc(OC(F)(F)F)c1)n2Cc1cccc(Cl)c1]

White solid, 16 mg, 25.0% yield: $^1$H-NMR (400 MHz, DMSO-$d_6$) δ=7.61 (t, 1H), 7.49 (d, 2H), 7.34-7.44 (m, 3H), 7.33 (d, 2H), 5.45 (s, 2H), 4.59 (t, 1H), 4.07 (t, 2H), 3.57 (t, 2H), 3.45 (s, 4H), 3.30 (s, 3H). LCMS retention time 2.876 min; LCMS MH$^+$ 555.

Example 32b 1-(2-(2-hydroxyethoxy)ethyl)-3-methyl-7-(4-methylbenzyl)-8-(3-(trifluoromethoxy)phenoxy)-1H-purine-2,6(3H,7H)-dione

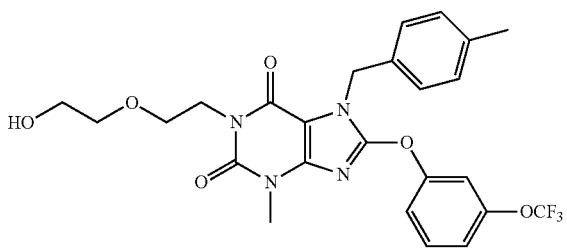

White solid, 23 mg, 25.0% yield: $^1$H-NMR (DMSO-$d_6$) δ 7.61 (t, 1H), 7.47 (d, 1H), 7.42 (dd, 1H), 7.29-7.34 (m, 3H), 7.16 (d, 2H), 5.77 (s, 2H), 4.60 (t, 1H), 4.07 (t, 2H), 3.57 (t, 2H), 3.44-3.47 (m, 4H), 3.30 (s, 3H), 2.27 (s, 3H). LCMS retention time 2.750 min; LCMS MH$^+$ 535.

434

Example 32c 1-(2-(2-hydroxyethoxy)ethyl)-3-methyl-8-(3-(trifluoromethoxy)phenoxy)-7-(4-(trifluoromethyl)benzyl)-1H-purine-2,6(3H,7H)-dione

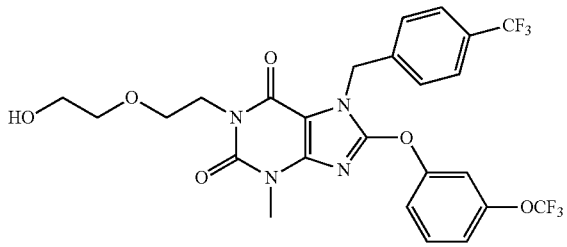

White solid, 19 mg, 27.9% yield: $^1$H-NMR (DMSO-$d_6$) δ 7.74 (d, 2H), 7.61 (t, 3H), 7.44-7.48 (m, 2H), 7.33 (d, 1H) 5.55 (s, 2H), 4.58 (q, 1H), 4.09 (t, 2H), 3.56 (t, 2H), 3.45 (s, 4H), 3.31 (s, 3H). LCMS retention time 2.831 min; LCMS MH$^+$ 589.

Example 32d 7-(4-ethylbenzyl)-1-(2-(2-hydroxyethoxy)ethyl)-3-methyl-8-(3-(trifluoromethoxy)phenoxy)-1H-purine-2,6(3H,7H)-dione

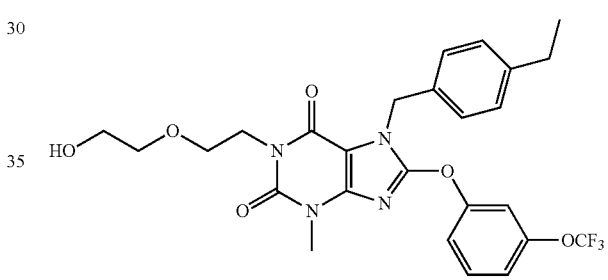

White solid, 16 mg, 25.4% yield: $^1$H-NMR (DMSO-$d_6$) δ 7.61 (t, 1H), 7.46 (s, 1H), 7.42 (d, 1H), 7.31-7.34 (m, 3H), 7.19 (d, 2H), 5.40 (s, 2H), 4.60 (t, 1H), 4.07 (t, 2H), 3.57 (t, 2H), 3.47 (s, 4H), 3.29 (s, 3H), 2.57 (q, 2H), 1.14 (t, 3H). LCMS retention time 2.897 min; LCMS MH$^+$ 549.

Example 32e 1-(2-(2-hydroxyethoxy)ethyl)-7-(3-methoxybenzyl)-3-methyl-8-(3-(trifluoromethoxy)phenoxy)-1H-purine-2,6(3H,7H)-dione

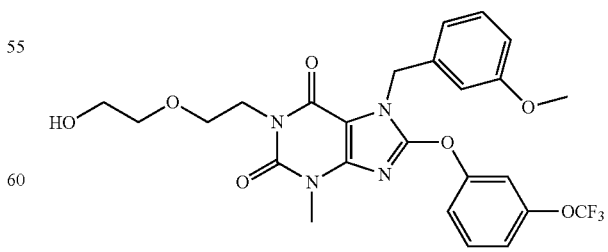

White solid, 10 mg, 25.0% yield: $^1$H-NMR (DMSO-$d_6$) δ 7.61 (t, 1H), 7.48 (s, 1H), 7.40-7.43 (m, 1H), 7.26-7.34 (m, 2H), 6.87-6.98 (m, 3H), 5.41 (s, 2H), 4.60 (t, 1H), 4.07 (t, 2H), 3.71 (s, 3H), 3.57 (t, 2H), 3.46 (s, 4H), 3.30 (s, 3H). LCMS retention time 2.644 min; LCMS MH+ 551.

Example 32f 1-(2-(2-hydroxyethoxy)ethyl)-3-methyl-7-(3-methylbenzyl)-8-(3-(trifluoromethoxy)phenoxy).1H-purine-2,6(3H,7H)-dione

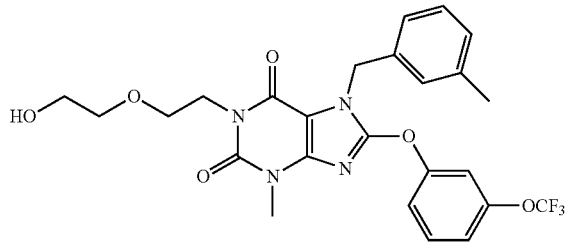 [SMILES: Cc1cccc(Cn2c(Oc3cccc(OC(F)(F)F)c3)nc3c2c(=O)n(CCOCCO)c(=O)n3C)c1]

White solid, 12 mg, 19.6% yield: ¹H-NMR (DMSO-d₆) δ 7.61 (t, 1H), 7.46 (s, 1H), 7.40 (dd, 1H), 7.33 (d, 1H), 7.24 (d, 1H), 7.11-7.19 (m, 3H), 5.41 (s, 2H), 4.59 (t, 1H), 4.07 (t, 2H), 3.57 (t, 2H), 3.47 (s, 4H), 3.30 (s, 3H), 2.27 (s, 3H). LCMS retention time 2.726 min; LCMS MH+ 535.

Example 32g 1-(2-(2-hydroxyethoxy)ethyl)-3-methyl-7-(3-(trifluoromethoxy)benzyl)-8-(3-(trifluoromethoxy)phenoxy)-1H-purine-2,6(3H,7H)-dione

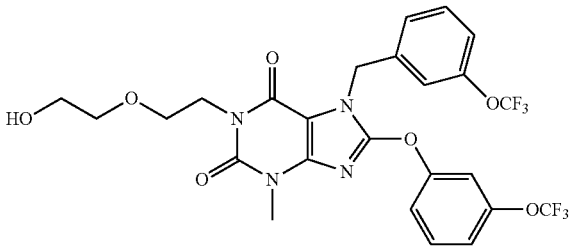 [SMILES: Cn1c(=O)n(CCOCCO)c(=O)c2c1nc(Oc1cccc(OC(F)(F)F)c1)n2Cc1cccc(OC(F)(F)F)c1]

White solid, 22 mg, 31.4% yield: ¹H-NMR (DMSO-d₆) δ 7.61 (t, 1H), 7.53 (t, 1H), 7.41-7.49 (m, 4H), 7.33 (d, 2H), 5.50 (s, 2H), 4.59 (t, 1H), 4.07 (t, 2H), 3.56 (t, 2H), 3.46 (s, 4H), 3.30 (s, 3H). LCMS retention time 2.865 min; LCMS MH+ 605.

Example 32h 1-(2-(2-hydroxyethoxy)ethyl)-3-methyl-8-(3-(trifluoromethoxy)phenoxy)-7-(3-(trifluoromethyl)benzyl)-1H-purine-2,6(3H,7H)-dione

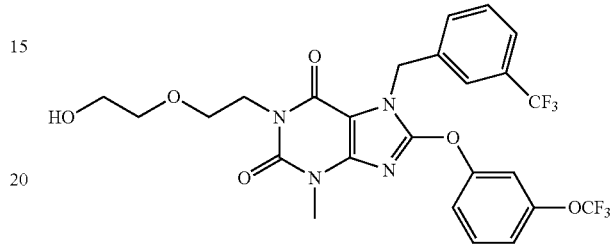

White solid, 10 mg, 31.4% yield: ¹H-NMR (DMSO-d₆) δ 7.81 (s, 1H), 7.58-7.71 (m, 4H), 7.41-7.46 (m, 2H), 7.33 (d, 2H), 5.55 (s, 2H), 4.59 (t, 1H), 4.07 (t, 2H), 3.57 (t, 2H), 3.47 (s, 4H), 3.30 (s, 3H). LCMS retention time 2.795 min; LCMS MH+ 589.

Example 33 1-(2-(2-aminoethoxy)ethyl)-7-(4-chlorobenzyl)-3-methyl-8-(3-(trifluoromethoxy)phenoxy)-1H-purine-2,6(3H,7H)-dione

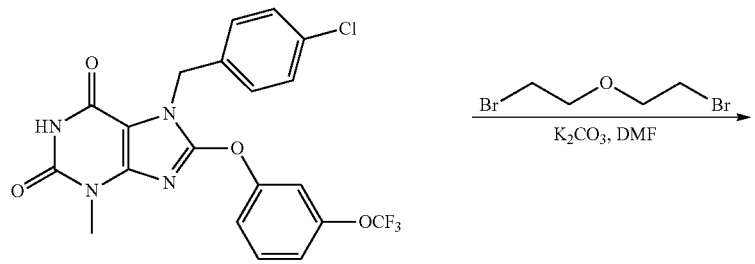

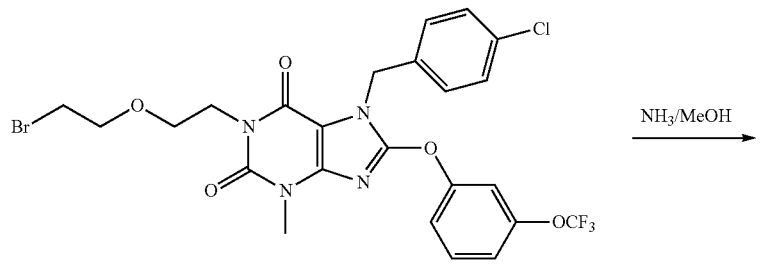

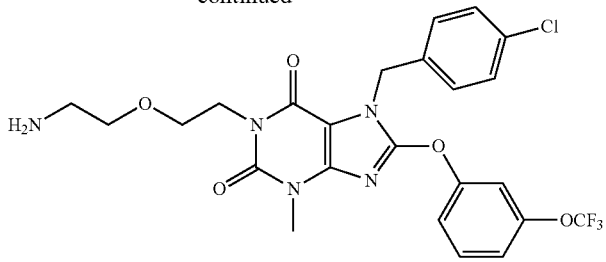

Step 1 1-(2-(2-bromoethoxy)ethyl)-7-(4-chlorobenzyl)-3-methyl-8-(3-(trifluoromethoxy)phenoxy)-1H-purine-2,6(3H,7H)-dione

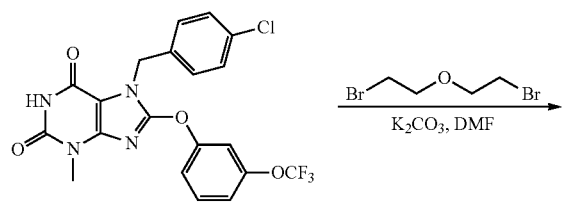

mg, 0.26 mmol, intermediate 9) in DMF (3 mL) was added 1-bromo-2-(2-bromoethoxy)ethane (77 mg, 0.33 mmol), potassium carbonate (71 mg, 0.51 mmol). The reaction was heated at 60° C. overnight. The mixture was cooled and partitioned between ethyl acetate and water. The organic layers were combined, dried over sodium sulfate, filtered and concentrated to give crude product (100 mg, 70% of purity by HPLC), which was used without purification. LCMS retention time 2.054 min; LCMS MH$^+$ 617

Step 2 1-(2-(2-aminoethoxy)ethyl)-7-(4-chlorobenzyl)-3-methyl-8-(3-(trifluoromethoxy)phenoxy)-1H-purine-2,6(3H,7H)-dione

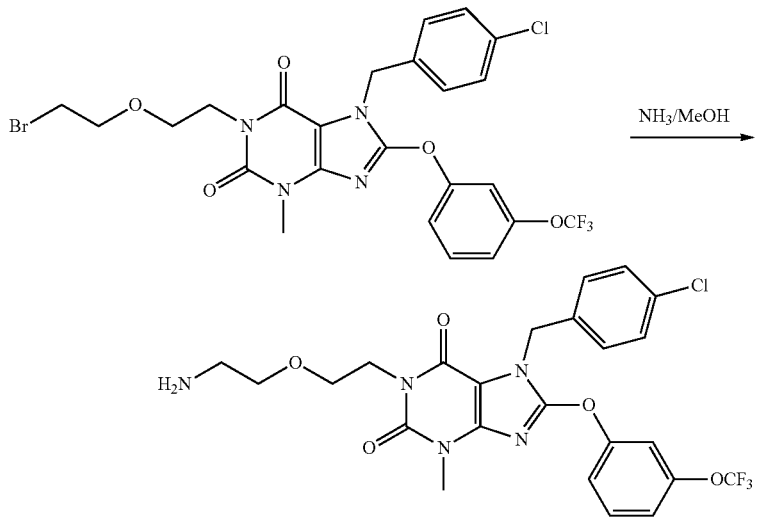

-continued

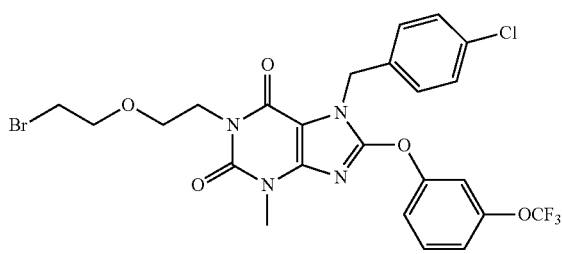

To a solution of 7-(4-chlorobenzyl)-3-methyl-8-(3-(trifluoromethoxy)phenoxy)-1H-purine-2,6(3H,7H)-dione (120

1-(2-(2-bromoethoxy)ethyl)-7-(4-chlorobenzyl)-3-methyl-8-(3-(trifluoromethoxy)phenoxy)-1H-purine-2,6(3H,7H)-dione (100 mg, 0.16 mmol) was dissolved in a preformed solution of ammonia in methanol (15 mL). The reaction was heated at 60° C. overnight in a sealed tube. The reaction was cooled to room temperature and the solvent was evaporated. The residue was purified by preparative HPLC to give 1-(2-(2-aminoethoxy)ethyl)-7-(4-chlorobenzyl)-3-methyl-8-(3-(trifluoromethoxy)phenoxy)-1H-purine-2,6(3H,7H)-dione (35 mg, 39% yield) as white solid. $^1$H-NMR (CD$_3$OD) δ 7.94 (s, 3H), 7.62 (t, 1H), 7.41-7.49 (m, 6H), 7.34 (d, 1H), 5.45 (s, 2H), 4.10 (t, 2H), 3.65-3.67 (m, 4H), 3.30 (s, 3H), 2.94 (q, 2H). LCMS retention time 2.323 min; LCMS MH$^+$ 554.

Example 34 7-(4-chlorobenzyl)-1-(2-(2-methoxyethoxy)ethyl)-3-methyl-8-(3-(trifluoromethoxy)phenoxy)-1H-purine-2,6(3H,7H)-dione

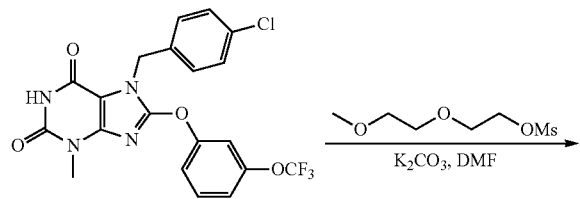

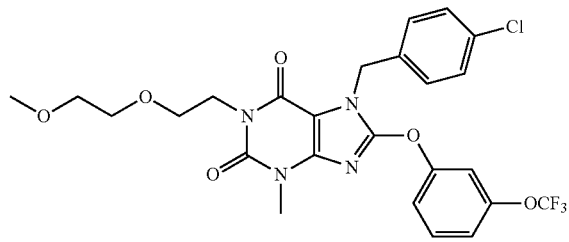

The title product was prepared using the method of example 33, step 1 with 2-(2-methoxyethoxy)ethyl methanesulfonate (51 mg, 0.26 mmol, intermediate 34) as the alkylating agent. White solid, 44 mg, 45% yield: $^1$H-NMR (CD$_3$OD) δ 7.61 (t, 1H), 7.50 (s, 1H), 7.40-7.45 (m, 5H), 7.33 (d, 1H), 5.44 (s, 2H), 4.05 (t, 2H), 3.51-3.57 (m, 4H), 3.36 (s, 2H), 3.29 (s, 3H), 3.20 (s, 3H). LCMS retention time 3.161 min; LCMS MH$^+$ 569.

Example 35 7-(4-chlorobenzyl)-1-(2-hydroxyethyl)-3-methyl-8-(2-(3-(trifluoromethoxy)phenoxy)ethoxy)-1H-purine-2,6(3H,7H)-dione

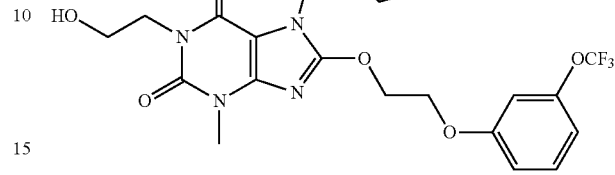

To a solution of 7-(4-chlorobenzyl)-3-methyl-8-(3-(trifluoromethoxy)phenoxy)-1H-purine-2,6(3H,7H)-dione (120 mg, 0.257 mmol) in DMF (5 mL) was added 2-bromoethanol (128.9 mg, 1.028 mmol) followed by cesium carbonate (167 mg, 0.515 mmol). The resulting mixture was microwave irradiated at 120° C. for 30 min. The reaction was partitioned between ethyl acetate and brine. The combined organic phase was dried and concentrated to give a residue, which was purified via preparative HPLC to give 7-(4-chlorobenzyl)-1-(2-hydroxyethyl)-3-methyl-8-(2-(3-(trifluoromethoxy)phenoxy)ethoxy)-1H-purine-2,6(3H,7H)-dione (17 mg, 34.7% yield) as white solid. $^1$H-NMR (DMSO-d$_6$) δ 7.43 (t, 1H), 7.27-7.32 (m, 4H), 6.95-7.03 (m, 3H), 5.20 (s, 2H), 4.81 (t, 2H), 4.75 (t, 1H), 4.41 (t, 2H), 3.92-3.95 (m, 2H), 3.47-3.52 (m, 2H), 3.31 (s, 3H). LCMS retention time 2.731 min; LCMS MH$^+$ 555.

Example 36 7-(4-chlorobenzyl)-1-(2-hydroxyethyl)-3-methyl-8-(2-(3-(trifluoromethoxy)phenoxy)ethoxy)-1H-purine-2,6(3H,7H)-dione

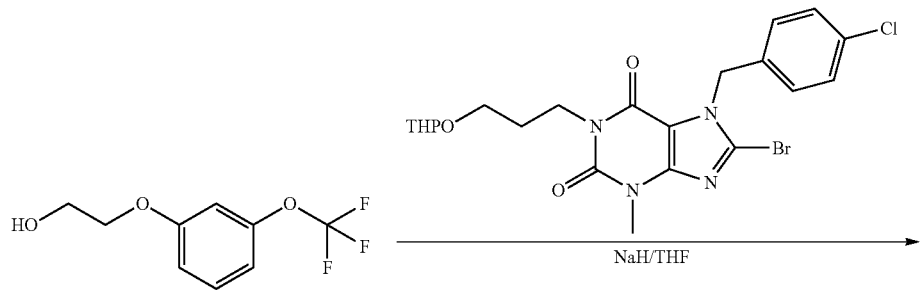

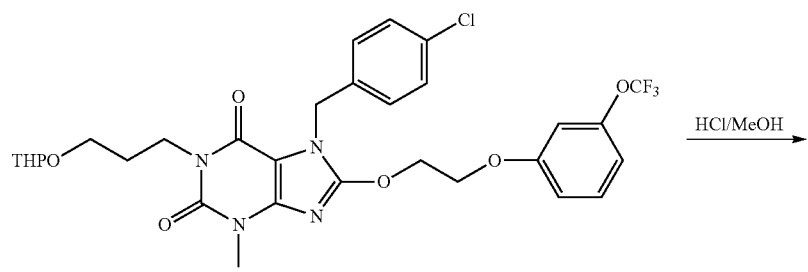

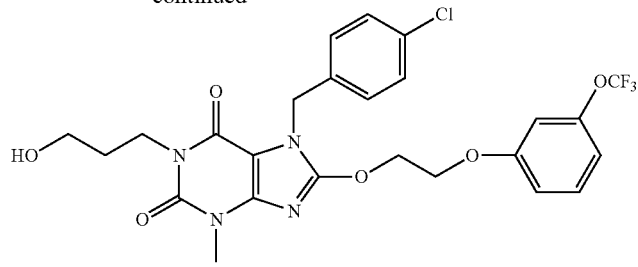

Step 1 7-(4-chlorobenzyl)-3-methyl-1-(2-(tetra-hydro-2H-pyran-2-yloxy)ethyl)-8-(2-(3-(trifluo-romethoxy)phenoxy)ethoxy)-1H-purine-2,6(3H,7H)-dione

15

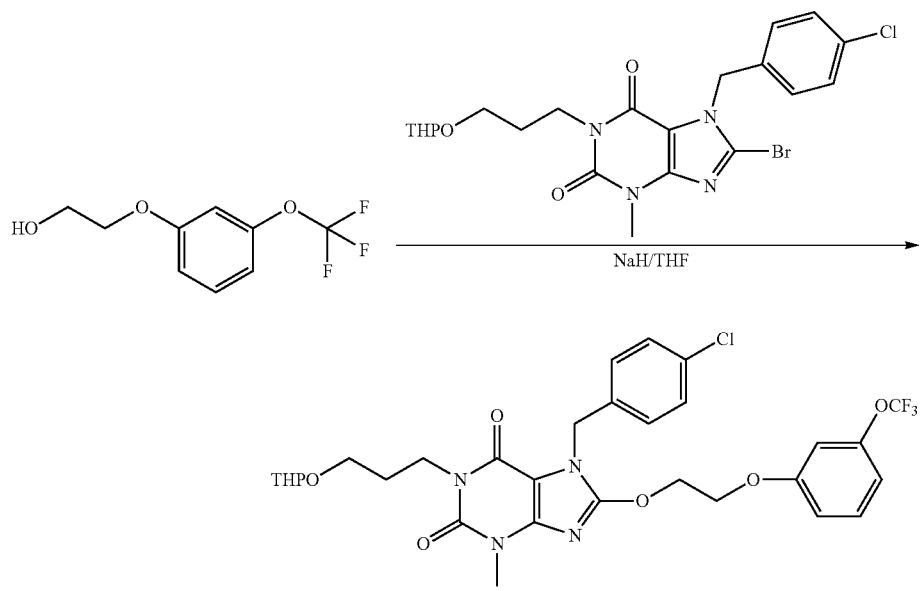

To a solution of 2-(3-(trifluoromethoxy)phenoxy)ethanol (61 mg, 0.275 mmol, intermediate 5) in anhydrous THF (10 mL) was added sodium hydride (66 mg, 2.75 mmol) at 0° C. under a nitrogen atmosphere. The mixture was stirred at 0° C. for 20 min; then a solution of 8-bromo-7-(4-chlorobenzyl)-3-methyl-1-(3-(tetrahydro-2H-pyran-2-yloxy)propyl)-1H-purine-2,6(3H,7H)-dione (70 mg, 0.137 mmol, intermediate 14) in THF (3 mL) was added dropwise, and the resulting mixture was stirred at 0° C. to room temperature for 16 h under nitrogen atmosphere. The mixture was quenched with ice-water and partitioned between ethyl acetate and brine. The organic layer was dried over sodium sulfate, filtered and concentrated to give a crude product which was purified via silica gel chromatography eluting with petroleum ether/ethyl acetate (1:0 to 2:1) to give 7-(4-chlorobenzyl)-3-methyl-1-(2-(tetrahydro-2H-pyran-2-yloxy)ethyl)-8-(2-(3-(trifluoromethoxy)phenoxy)ethoxy)-1H-purine-2,6(3H,7H)-dione (70 mg, 78.2%) as yellow oil. LCMS MH$^+$-THP 569.

Step 2 7-(4-chlorobenzyl)-1-(2-hydroxyethyl)-3-methyl-8-(2-(3-(trifluoromethoxy)phenoxy)ethoxy)-1H-purine-2,6(3H,7H)-dione

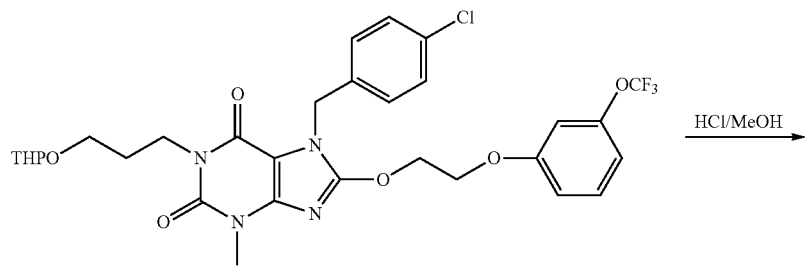

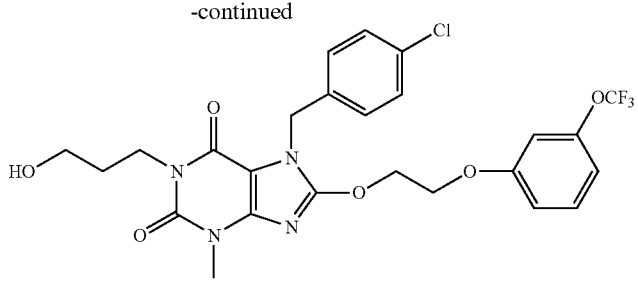

To a solution of 7-(4-chlorobenzyl)-3-methyl-1-(2-(tetrahydro-2H-pyran-2-yloxy)ethyl)-8-(2-(3-(trifluoromethoxy)phenoxy)ethoxy)-1H-purine-2,6(3H,7H)-dione (70 mg, 0.107 mmol) in methanol (3 mL) was added concentrated HCl (4 drops). The mixture was stirred for 1 h at room temperature. The mixture was neutralized with saturated sodium bicarbonate, and extracted with ethyl acetate. The organic phase was dried over sodium sulfate, filtered and concentrated to give a crude product which was recrystallized from ethanol to give 7-(4-chlorobenzyl)-1-(2-hydroxyethyl)-3-methyl-8-(2-(3-(trifluoromethoxy)phenoxy)ethoxy)-1H-purine-2,6(3H,7H)-dione (16 mg, 25.6% yield) as white solid. $^1$H-NMR (DMSO-$d_6$) δ 7.45-7.41 (t, 1H), 7.32-7.27 (m, 4H), 7.03-6.95 (m, 3H), 5.19 (s, 2H), 4.81 (s, 2H), 4.49-4.46 (t, 1H), 4.41-4.40 (d, 2H), 3.91-3.88 (t, 2H), 3.44-3.40 (m, 5H), 1.69-1.65 (t, 2H). LCMS retention time 3.142 min; LCMS MH$^+$ 569.

Example 37 7-(4-chlorobenzyl)-1-(2-hydroxyethyl)-3-methyl-8-(3-(3-(trifluoromethoxy)phenoxy)propoxy)-1H-purine-2,6(3H,7H)-dione

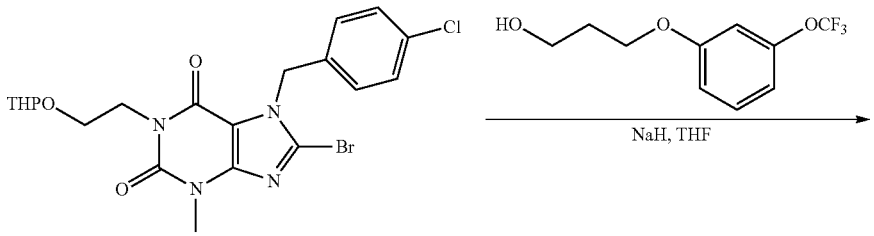

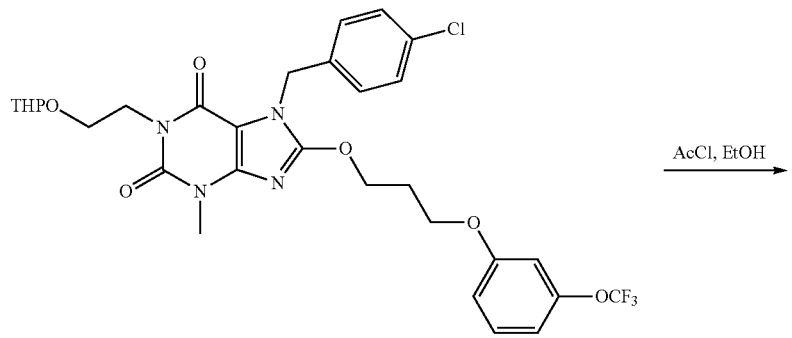

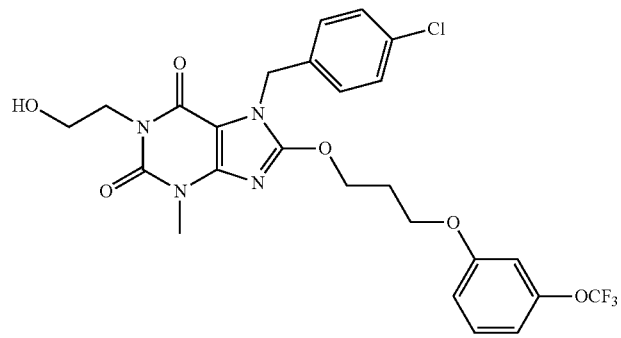

Step 1 7-(4-chlorobenzyl)-3-methyl-1-(2-(tetrahydro-2H-pyran-2-yloxy)ethyl)-8-(3-(3-(trifluoromethoxy)phenoxy)propoxy)-1H-purine-2,6(3H,7H)-dione

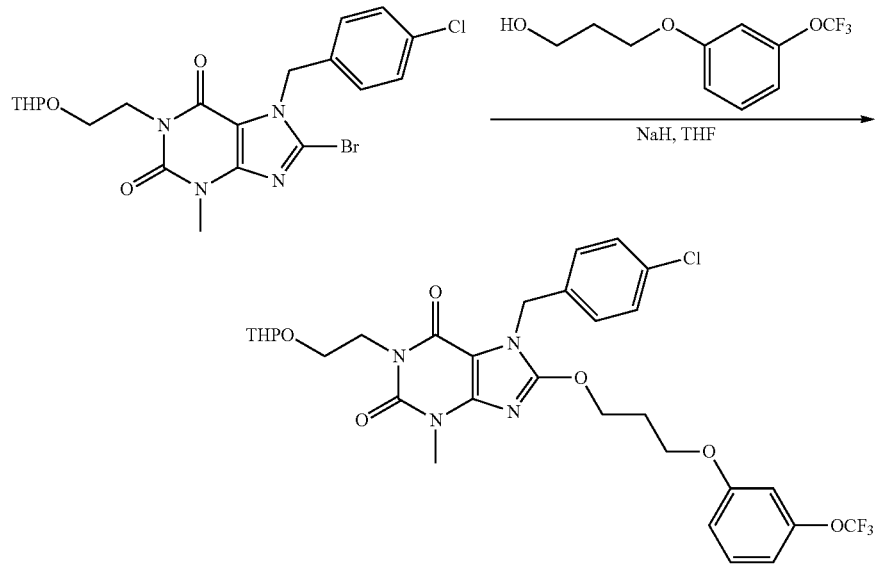

To a solution of 3-(3-(trifluoromethoxy)phenoxy)propan-1-ol (95 mg, 0.4 mmol, intermediate 35) in THF (5 mL) was added sodium hydride (19 mg, 0.40 mmol) at 0° C. After stirred at 0° C. for 30 min, 8-bromo-7-(4-chlorobenzyl)-3-methyl-1-(2-(tetrahydro-2H-pyran-2-yloxy)ethyl)-1H-purine-2,6(3H,7H)-dione (0.1 g, 0.20 mmol, intermediate 13) was added. The mixture was allowed to warm to room temperature and stirred for 16 h. Then the reaction was chilled to 0° C. and aqueous ammonium chloride solution (2 mL) was added. The mixture was partitioned between ethyl acetate and water. The organic layer was dried over sodium sulfate, filtered and concentrated to give crude product which was used without purification. LCMS MH$^+$-THP 569.

Step 2 7-(4-chlorobenzyl)-1-(2-hydroxyethyl)-3-methyl-8-(3-(3-(trifluoromethoxy) phenoxy) propoxy)1H-purine-2,6(3H,7H)-dione

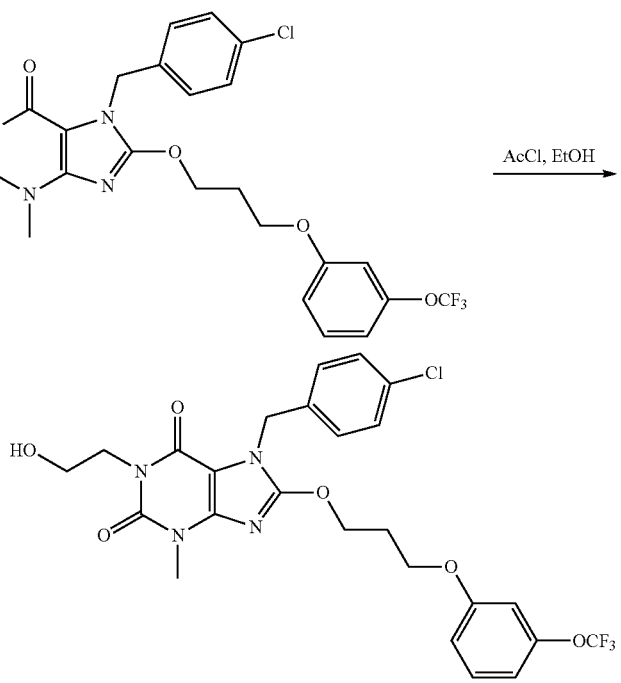

To a solution of 7-(4-chlorobenzyl)-3-methyl-1-(2-(tetrahydro-2H-pyran-2-yloxy)ethyl)-8-(3-(3-(trifluoromethoxy)phenoxy)propoxy)-1H-purine-2,6(3H,7H)-dione (50 mg, 0.09 mmol) in ethanol (5 mL) was added acetyl chloride (0.2 mL) at 0° C. The mixture was stirred at room temperature for 1 h; then it was partitioned between ethyl acetate and water. The organic phase was separated and dried over sodium sulfate. This organic layer was then filtered and concentrated to give a crude product which was purified by preparative HPLC to give 7-(4-chlorobenzyl)-1-(2-hydroxyethyl)-3-methyl-8-(3-(3-(trifluoromethoxy) phenoxy)propoxy)1H-purine-2,6(3H,7H)-dione (20 mg, 39.2% yield) as a white solid. $^1$H-NMR (DMSO-$d_6$) δ 7.40 (t, 1H), 7.28-7.33 (m, 4H), 6.92 (dd, 2H), 6.85 (s, 1H), 5.23 (s, 2H), 4.76 (t, 1H), 4.62 (t, 2H), 4.08 (t, 2H), 3.93 (t, 2H), 3.49 (q, 2H), 3.33 (s, 3H), 2.18-2.24 (m, 2H). LCMS retention time 3.058 min; LCMS MH$^+$ 569.

The following examples 38a through 38l were prepared using the methods of examples 36 and/or 37.

Example 38a 8-(2-(3,5-bis(trifluoromethyl)phenoxy)ethoxy)-7-(4-chlorobenzyl)-1-(2-hydroxyethyl)-3-methyl-1H-purine-2,6(3H,7H)-dione

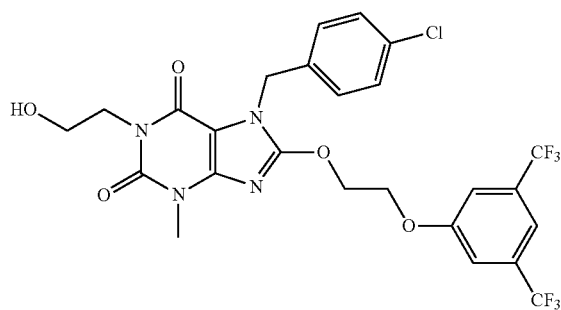 [SMILES: Cn1c(=O)n(CCO)c(=O)c2c1nc(OCCOc1cc(C(F)(F)F)cc(C(F)(F)F)c1)n2Cc1ccc(Cl)cc1]

The title product was prepared using intermediate 65. White solid, 49 mg, 44.6% yield: $^1$H-NMR (DMSO-$d_6$) δ 7.66 (s, 1H), 7.60 (s, 2H), 7.23-7.29 (m, 4H), 5.20 (s, 2H), 4.85 (t, 2H), 4.84 (t, 1H), 4.55-4.57 (m, 2H), 3.94 (t, 2H), 3.49 (q, 2H), 3.33 (s, 3H). LCMS retention time 3.229 min; LCMS MH$^+$ 607.

Example 38b 7-(4-chlorobenzyl)-8-(2-(3-chlorophenoxy)ethoxy)-1-(2-hydroxyethyl)-3-methyl-1H-purine-2,6(3H,7H)-dione

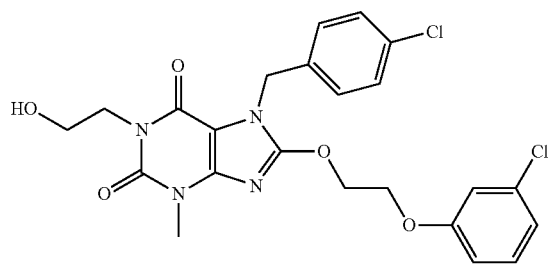 [SMILES: Cn1c(=O)n(CCO)c(=O)c2c1nc(OCCOc1cccc(Cl)c1)n2Cc1ccc(Cl)cc1]

The title product was prepared using intermediate 66. White solid, 10 mg, 22.2% yield: $^1$H-NMR (DMSO-$d_6$) δ 7.30-7.34 (m, 5H), 7.01-7.04 (m, 2H), 6.92-6.94 (m, 1H), 5.19 (s, 2H), 4.74-4.80 (m, 3H), 4.37-4.40 (m, 2H), 3.93 (t, 2H), 3.49 (q, 2H), 3.34 (s, 3H). LCMS retention time 2.837 min; LCMS MH$^+$ 505.

Example 38c 7-(4-chlorobenzyl)-1-(2-hydroxyethyl)-3-methyl-8-(2-(m-tolyloxy)ethoxy)-1H-purine-2,6(3H,7H)-dione

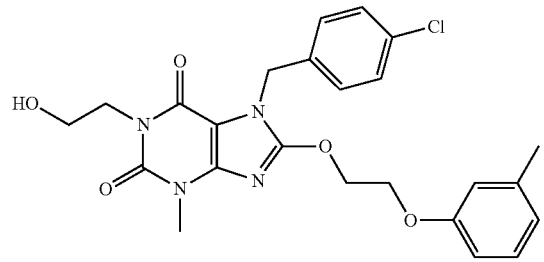 [SMILES: Cc1cccc(OCCOc2nc3c(c(=O)n(CCO)c(=O)n3C)n2Cc2ccc(Cl)cc2)c1]

The title product was prepared using intermediate 67. White solid, 12 mg, 27.9% yield: $^1$H-NMR (DMSO-$d_6$) δ 7.27-7.32 (m, 4H), 7.15-7.19 (m, 1H), 6.74-6.79 (m, 3H), 5.19 (s, 2H), 4.74-4.80 (m, 3H), 4.32-4.34 (m, 2H), 3.94 (t, 2H), 3.49 (q, 2H), 3.35 (s, 3H), 2.27 (s, 3H). LCMS retention time 2.676 min; LCMS MH$^+$ 485.

Example 38d 7-(4-chlorobenzyl)-1-(2-hydroxyethyl)-3-methyl-8-(2-(3-(trifluoromethyl)phenoxy)ethoxy)-1H-purine-2,6(3H,7H)-dione

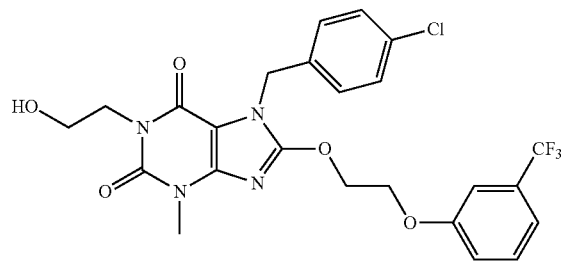 [SMILES: Cn1c(=O)n(CCO)c(=O)c2c1nc(OCCOc1cccc(C(F)(F)F)c1)n2Cc1ccc(Cl)cc1]

The title product was prepared using intermediate 68. White solid, 10 mg, 20.8% yield: $^1$H-NMR (DMSO-$d_6$) δ 7.54 (t, 1H), 7.24-7.33 (m, 7H), 6.74-6.79 (m, 3H), 5.19 (s, 2H), 4.81-4.83 (m, 2H), 4.75 (t, 1H), 4.45-4.46 (m, 2H), 3.94 (t, 2H), 3.49 (q, 2H), 3.35 (s, 3H). LCMS retention time 2.857 min; LCMS MH$^+$ 539.

Example 38e 8-(2-(4-chloro-3-(trifluoromethyl)phenoxy)ethoxy)-7-(4-chlorobenzyl)-1-(2-hydroxyethyl)-3-methyl-1H-purine-2,6(3H,7H)-dione

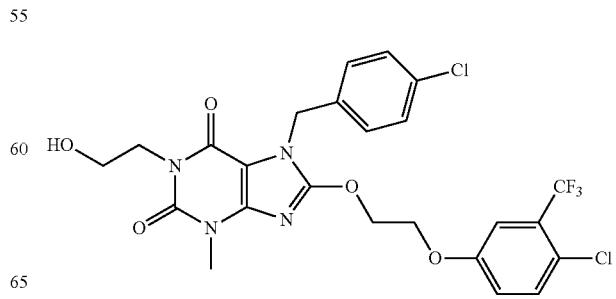

The title product was prepared using intermediate 71. White solid, 30 mg, 49.2% yield: ¹H-NMR (DMSO-d$_6$) δ 7.64-7.62 (d, 1H), 7.31-7.26 (m, 6H), 5.20 (s, 2H), 4.83-4.80 (m, 2H), 4.76-4.73 (t, 1H), 4.46-4.44 (m, 2H), 3.95-3.92 (t, 2H), 3.52-3.49 (m, 2H), 3.47 (s, 3H). LCMS retention time 2.973 min; LCMS MH⁺ 573

Example 38f 7-(4-chlorobenzyl)-1-(2-hydroxy-ethyl)-3-methyl-8-(2-(2-(trifluoromethoxy)phenoxy)ethoxy)-1H-purine-2,6(3H,7H)-dione

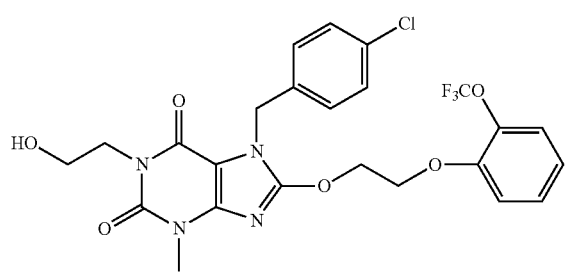 [SMILES: Cn1c(=O)n(CCO)c(=O)c2c1nc(OCCOc1ccccc1OC(F)(F)F)n2Cc1ccc(Cl)cc1]

The title product was prepared using intermediate 70. White solid, 18 mg, 29.7% yield: ¹H-NMR (DMSO-d$_6$) δ 7.36-7.34 (d, 2H), 7.29-7.24 (m, 5H), 7.07-7.03 (t, 1H), 5.17 (s, 2H), 4.85-4.83 (m, 2H), 4.77-4.74 (t, 1H), 4.46-4.44 (m, 2H), 3.95-3.92 (t, 2H), 3.51-3.48 (m, 2H), 3.47 (s, 3H). LCMS retention time 2.828 min; LCMS MH⁺ 555.

Example 38g 7-(4-chlorobenzyl)-1-(2-hydroxy-ethyl)-3-methyl-8-(2-(4-(trifluoromethoxy)phenoxy)ethoxy)-1H-purine-2,6(3H,7H)-dione

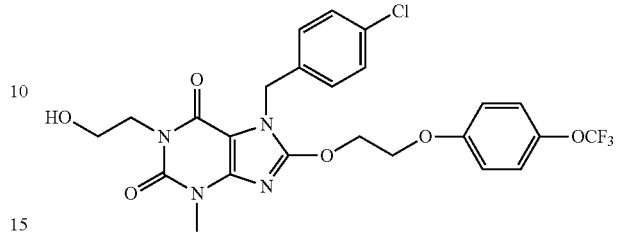

The title product was prepared using intermediate 69. White solid, 30 mg, 49.4% yield: ¹H-NMR (DMSO-d$_6$) δ 7.32-7.26 (m, 6H), 7.06-7.03 (m, 2H), 5.19 (s, 2H), 4.82-4.80 (m, 2H), 4.76-4.73 (t, 1H), 4.38-4.36 (m, 2H), 3.95-3.92 (t, 2H), 3.52-3.47 (m, 2H), 3.39 (s, 3H). LCMS retention time 2.908 min; LCMS MH⁺ 555.

Example 38h 7-(4-chlorobenzyl)-1-(3-hydroxypropyl)-3-methyl-8-(3-(3-(trifluoromethoxy)phenyl)propoxy)-1H-purine-2,6(3H,7H)-dione

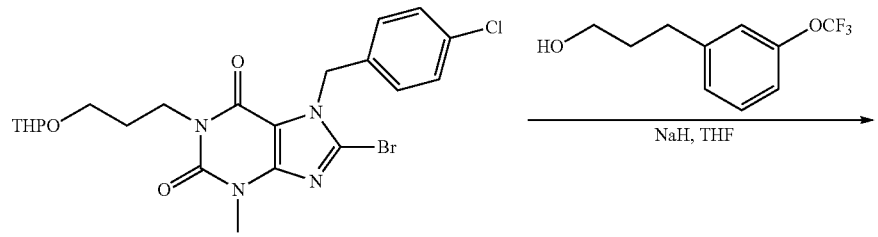

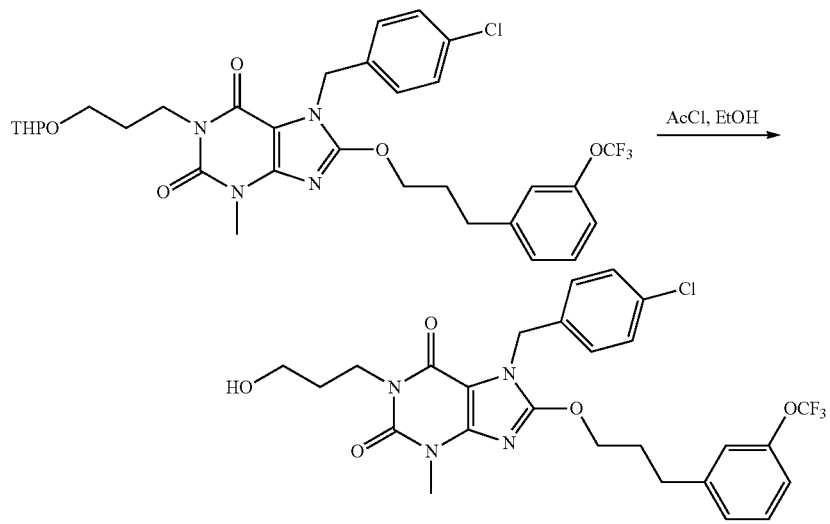

The title product was prepared using the methods of examples 36 and 37, and using intermediate 37 in the first step. White solid, 12 mg, 21.4% yield: ¹H-NMR (CD$_3$OD) δ 7.35-7.49 (m, 5H), 7.07-7.17 (m, 3H), 5.28 (s, 2H), 4.54 (t, 2H), 4.10 (t, 2H), 3.67 (t, 2H), 3.45 (s, 2H), 2.75 (t, 2H), 2.11-2.18 (m, 2H), 1.83-1.91 (m, 2H). LCMS retention time 3.125 min; LCMS MH⁺ 567.

Example 38i 7-(4-chlorobenzyl)-1-(3-hydroxypropyl)-3-methyl-8-(3-(trifluoromethoxy)benzyloxy)-1H-purine-2,6(3H,7H)-dione

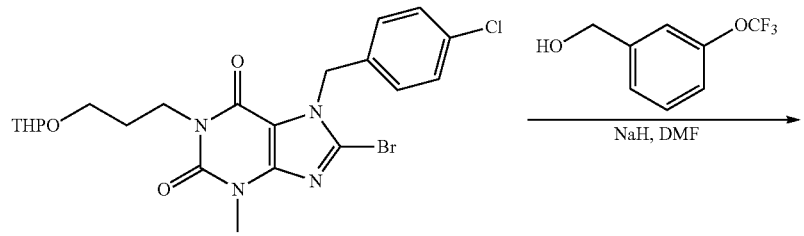

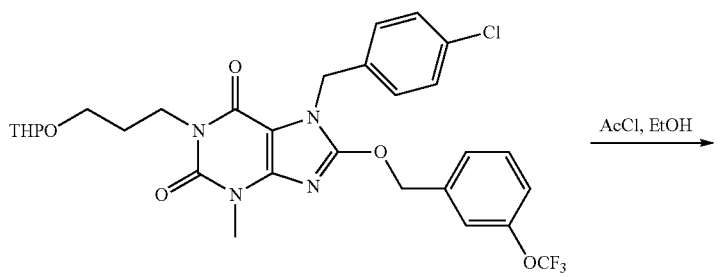

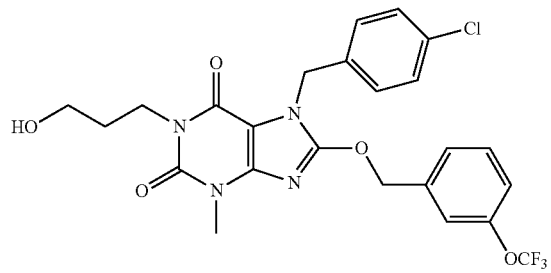

The title product was prepared using the methods of examples 36 and 37, and using 3-trifluoromethoxy-benzyl alcohol in the first step. White solid, 12 mg, 16.0% yield): $^1$H-NMR (DMSO-d$_6$) δ 7.27-7.55 (m, 8H), 5.57 (s, 2H), 5.28 (s, 2H), 4.47 (t, 1H), 3.90 (t, 2H), 3.56-3.45 (m, 5H), 1.65-1.90 (m, 2H). LCMS retention time 2.870 min; LCMS MH$^+$ 539.

Example 38j 7-(4-chlorobenzyl)-1-(3-hydroxypropyl)-3-methyl-8-((5-methylthiazol-2-yl)methoxy)-1H-purine-2,6(3H,7H)-dione

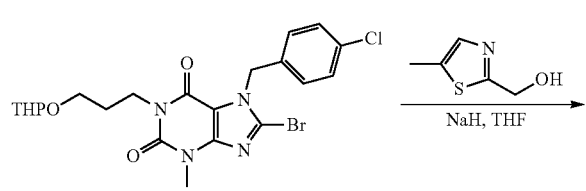

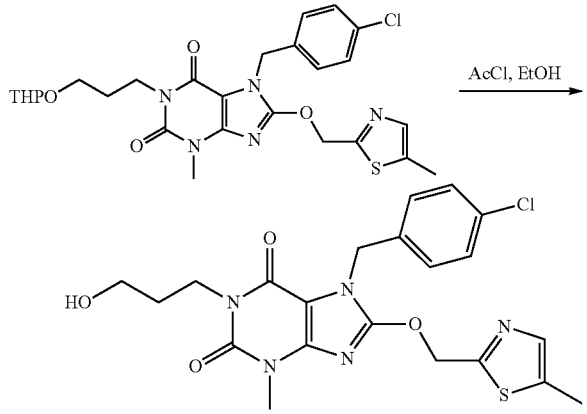

The title compound was prepared using the methods of examples 36 and 37, and using (5-methylthiazol-2-yl)methanol (intermediate 4, step 1) in the first step. White solid, 46 mg, 54.1% yield: $^1$H-NMR (CDCl$_3$) δ 7.50 (d, 1H), 7.33-7.32 (m, 2H), 7.26-7.28 (m, 2H), 5.74 (s, 2H), 5.27 (s, 2H), 4.19 (t, 2H), 3.61 (t, 1H), 3.51-3.55 (m, 5H), 2.51 (d, 3H), 1.88-1.92 (m, 2H). LCMS retention time 2.366 min; LCMS MH$^+$ 476.

Example 38k 7-(4-chlorobenzyl)-1-(3-hydroxypropyl)-3-methyl-8-((5-methyloxazol-2-yl)methoxy)-1H-purine-2,6(3H,7H)-dione

Example 38l 7-(4-chlorobenzyl)-1-(3-hydroxypropyl)-3-methyl-8-((5-methylthiazol-2-yl)methoxy)-1H-purine-2,6(3H,7H)-dione

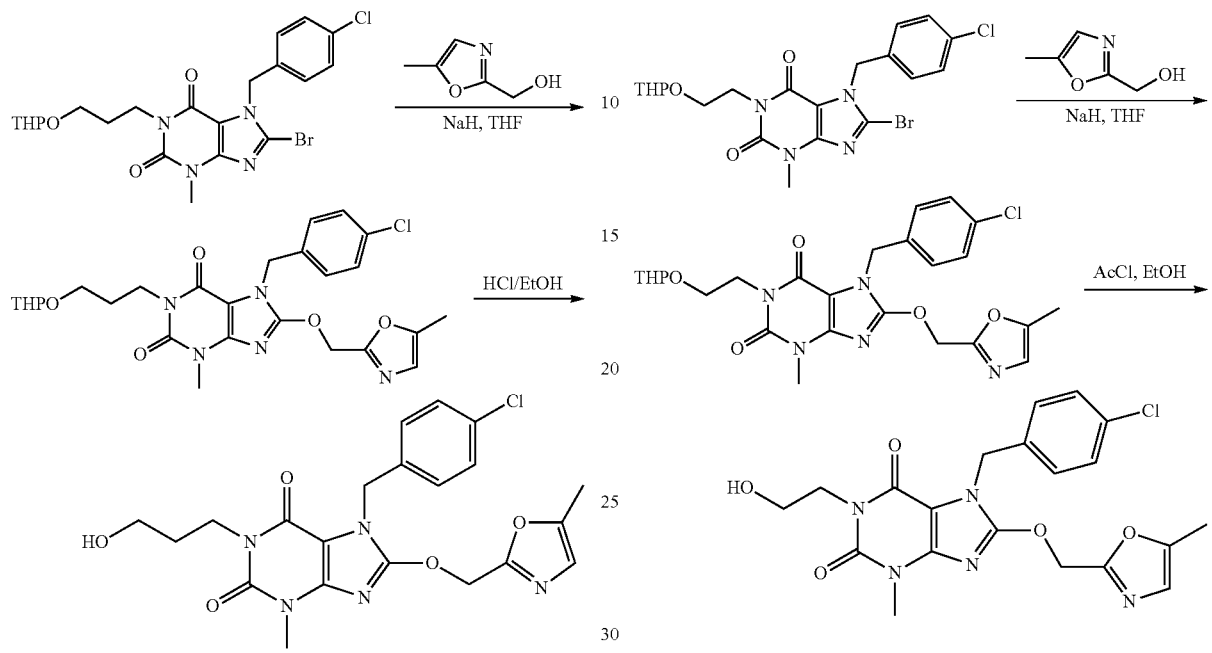

The title compound was prepared using the methods of examples 36 and 37 and with (5-methyloxazol-2-yl)methanol (intermediate 40). The crude product was purified via preparative HPLC to give 7-(4-chlorobenzyl)-1-(3-hydroxypropyl)-3-methyl-8-((5-methyloxazol-2-yl)methoxy)-1H-purine-2,6(3H,7H)-dione (17 mg, 40.9%) as white solid. $^1$H-NMR (DMSO-d$_6$) δ 7.38-7.40 (d, 2H), 7.26-7.28 (d, 2H), 6.90 (s, 1H), 5.58 (s, 2H), 5.23 (s, 2H), 4.45-4.48 (t, 1H), 3.87-3.91 (t, 2H), 3.39-3.44 (t, 2H), 2.28 (s, 3H), 1.65-1.68 (m, 2H). LCMS retention time 2.284 min; LCMS MH$^+$ 460.

The title compound was prepared using the methods of examples 36 and 37 and with (5-methyloxazol-2-yl)methanol (intermediate 40). White solid, 46 mg, 54.1% yield: $^1$H-NMR (DMSO-d$_6$) δ 7.37-7.39 (d, 2H), 7.26-7.28 (d, 2H), 6.90 (s, 1H), 5.58 (s, 2H), 5.23 (s, 2H), 4.73-4.76 (t, 1H), 3.93-3.95 (t, 2H), 3.47-3.51 (m, 2H), 3.43 (s, 3H), 2.28 (s, 3H). LCMS retention time 2.194 min; LCMS MH$^+$ 446.

Example 39 7-(4-chlorobenzyl)-8-(2-(3-((dimethylamino)methyl)phenoxy)ethoxy)-1-(2-hydroxyethyl)-3-methyl-1H-purine-2,6(3H,7H)-dione hydrochloride

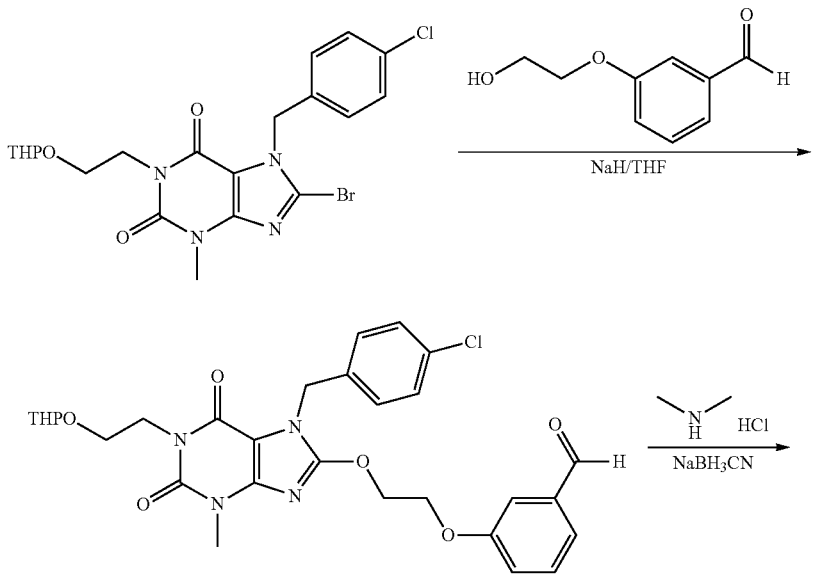

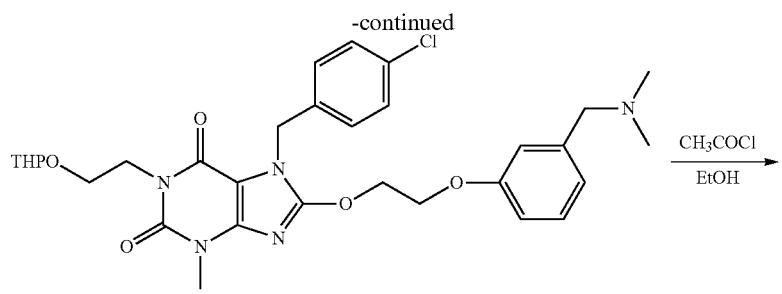

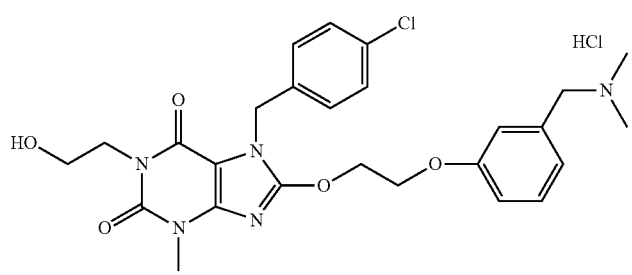

Step 1 3-(2-(7-(4-chlorobenzyl)-3-methyl-2,6-dioxo-1-(2-(tetrahydro-2H-pyran-2-yloxy)ethyl)-2,3,6,7-tetrahydro-1H-purin-8-yloxy)ethoxy)benzaldehyde

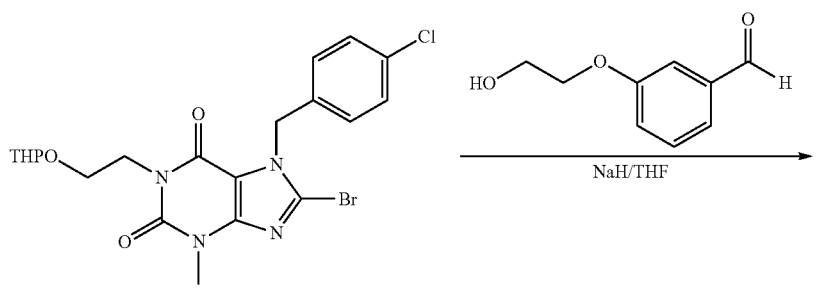

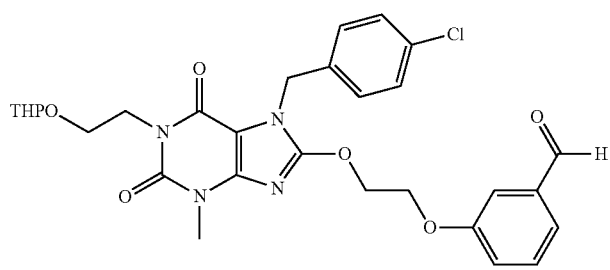

The title compound was prepared using the method of example 36, step 1 and using intermediate 36. The product was purified by silica gel chromatography eluting with petroleum/ethyl acetate (3:1 to 1:1) to give 3-(2-(7-(4-chlorobenzyl)-3-methyl-2,6-dioxo-1-(2-(tetrahydro-2H-pyran-2-yloxy)ethyl)-2,3,6,7-tetrahydro-1H-purin-8-yloxy)ethoxy)benzaldehyde (64 mg, 36.4% yield) as yellow syrup. LCMS MH$^+$-THP 499.

Step 2 7-(4-chlorobenzyl)-8-(2-(3-((dimethylamino)methyl)phenoxy)ethoxy)-3-methyl-1-(2-(tetrahydro-2H-pyran-2-yloxy)ethyl)-1H-purine-2,6(3H,7H)-dione

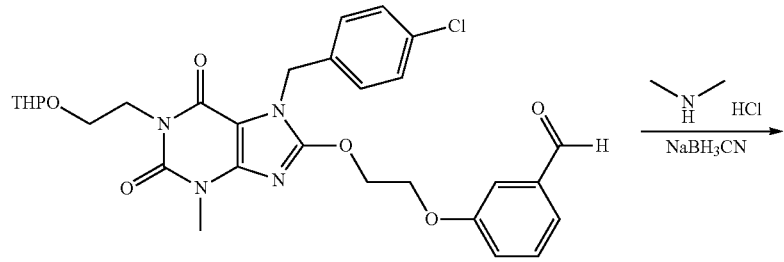

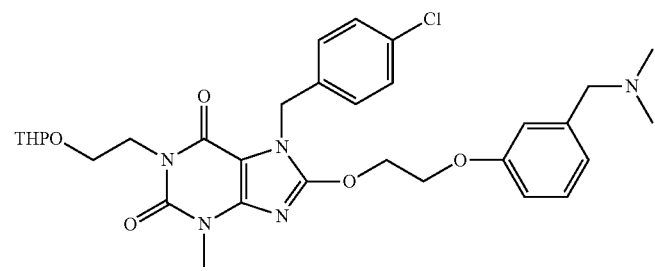

To a solution of 3-(2-(7-(4-chlorobenzyl)-3-methyl-2,6-dioxo-1-(2-(tetrahydro-2H-pyran-2-yloxy)ethyl)-2,3,6,7-tetrahydro-1H-purin-8-yloxy)ethoxy)benzaldehyde (100 mg, 0.171 mmol) in methanol (3 mL) and THF (3 mL) was added acetic acid (0.2 ml, 3.49 mmol) and dimethylamine hydrochloride (90 mg, 1.10 mmol). The mixture was stirred at room temperature for 1 h. Then the mixture was cooled to 0° C., sodium cyanoborohydride (16.1 mg, 0.256 mmol) was added under a nitrogen atmosphere. The resulting mixture was stirred and allowed to warm to room temperature overnight. The mixture was concentrated and purified via silica gel chromatography eluting with DCM/methanol (60:1) to give 7-(4-chlorobenzyl)-8-(2-(3-((dimethylamino)methyl)phenoxy)ethoxy)-3-methyl-1-(2-(tetrahydro-2H-pyran-2-yloxy)ethyl)-1H-purine-2,6(3H,7H)-dione (26.1 mg, 24.9%) as white solid. LCMS MH$^+$ 613.

Step 3 7-(4-chlorobenzyl)-8-(2-(3-((dimethylamino)methyl)phenoxy)ethoxy)-1-(2-hydroxyethyl)-3-methyl-1H-purine-2,6(3H,7H)-dione hydrochloride

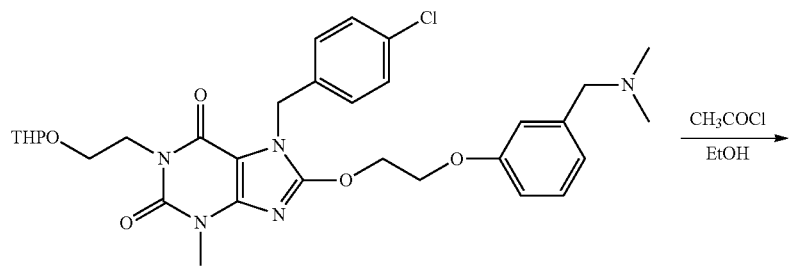

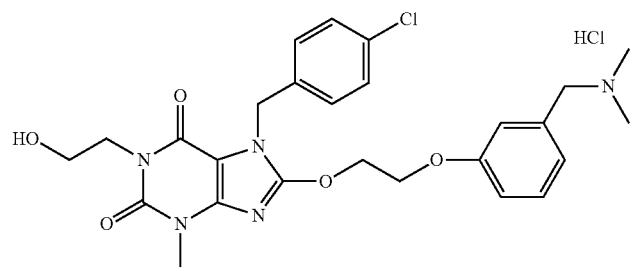

The title compound was prepared using the method of example 37, step 2 to give 7-(4-chlorobenzyl)-8-(2-(3-((dimethylamino)methyl)phenoxy)ethoxy)-1-(2-hydroxyethyl)-3-methyl-1H-purine-2,6(3H,7H)-dione hydrochloride (13.6 mg, 65.2% yield) as white solid. $^1$H-NMR (DMSO-$d_6$) δ 10.11 (bs, 1H), 7.42-7.38 (t, 1H), 7.33-7.28 (m, 4H), 7.18 (s, 1H), 7.11-7.09 (d, 1H), 7.06-7.04 (m, 1H), 5.20 (s, 2H), 4.85-4.83 (m, 2H), 4.76-4.73 (t, 1H), 4.39-4.37 (m, 2H), 4.22 (s, 2H), 3.96-3.92 (t, 2H), 3.52-3.46 (m, 2H), 3.29 (s, 3H), 2.69 (s, 6H). LCMS retention time 1.678 min; LCMS MH$^+$ 553.

Example 40 7-(4-chlorobenzyl)-1-(2-(dimethylamino)ethyl)-3-methyl-8-(2-(3-(trifluoromethoxy)phenoxy)ethoxy)-1H-purine-2,6(3H,7H)-dione Step 1 8-bromo-7-(4-chlorobenzyl)-1-(2-(dimethylamino)ethyl)-3-methyl-1H-purine-2,6(3H,7H)-dione

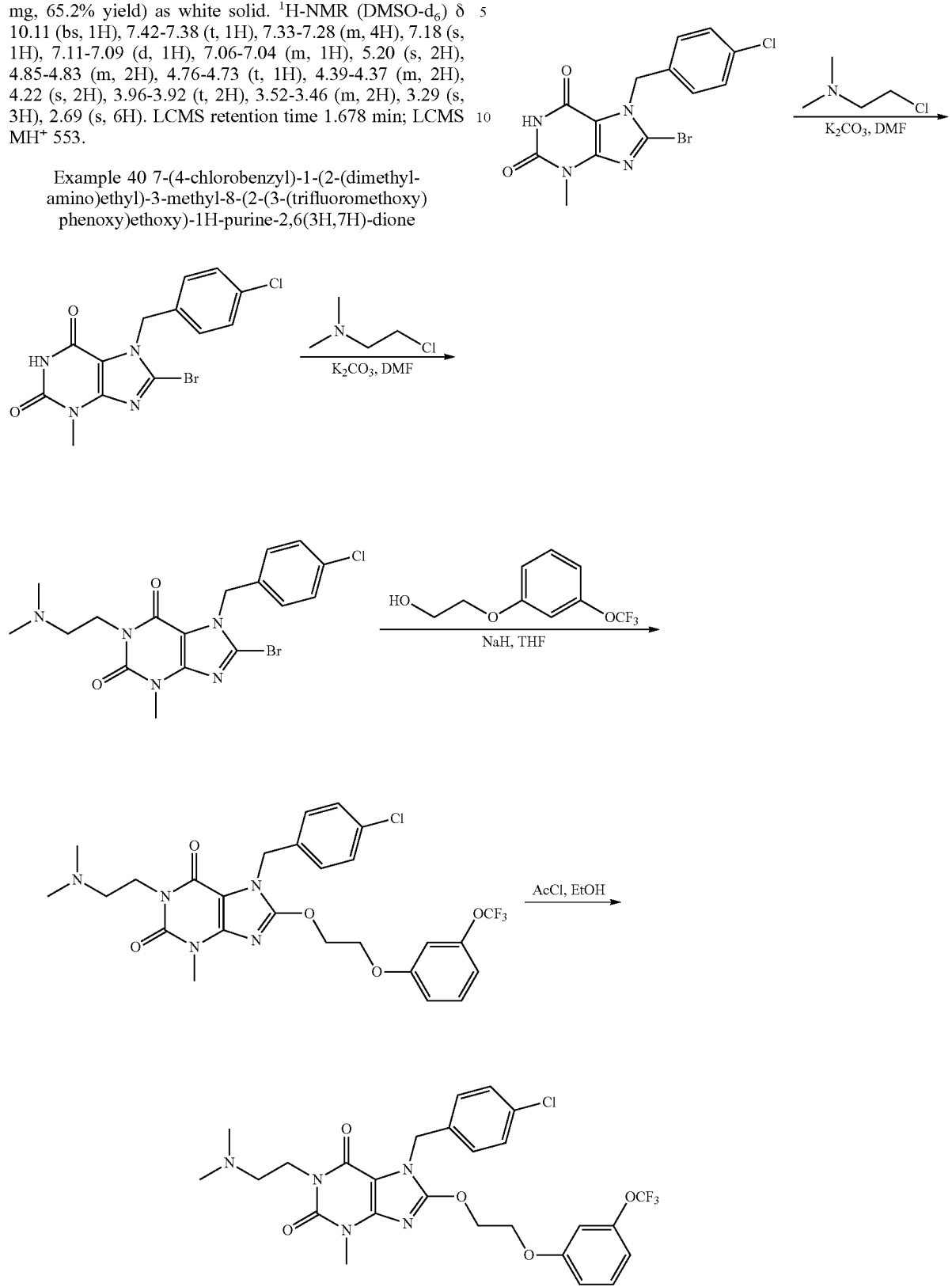

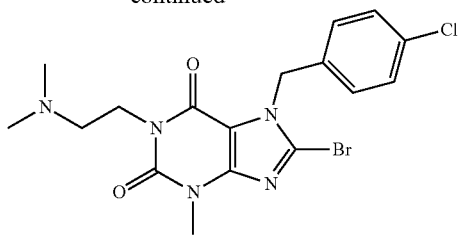

To a solution of 8-bromo-7-(4-chlorobenzyl)-3-methyl-1H-purine-2,6(3H,7H)-dione (0.2 g, 0.54 mmol, intermediate 8) in DMF (5 mL) was added 2-chloro-N,N-dimethylethanamine (0.87 mg, 0.83 mmol), potassium carbonate (0.15 g, 1.08 mmol), and TBAI (2 mg, 0.02 mmol). The reaction was heated at 80° C. overnight. The mixture was cooled and partitioned between ethyl acetate and water. The combined organic layer was dried over sodium sulfate, filtered and concentrated to give a crude product (0.2 g, 84%) as yellow oil, which was used without purification. LCMS MH$^+$ 442.

Step 2 7-(4-chlorobenzyl)-1-(2-(dimethylamino)ethyl)-3-methyl-8-(2-(3-(trifluoromethoxy)phenoxy)ethoxy)-1H-purine-2,6(3H,7H)-dione

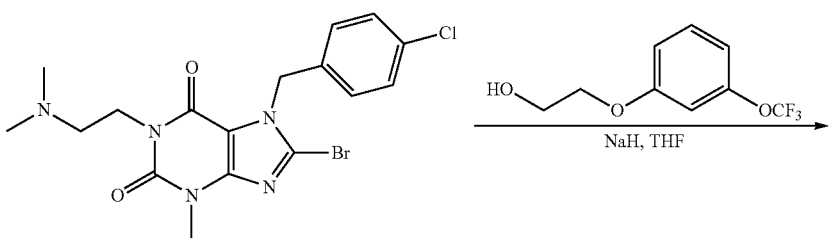

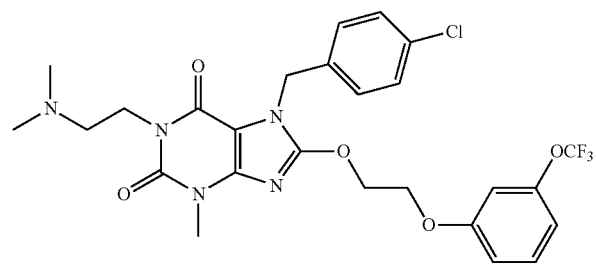

The title compound was prepared using the method of example 36, step 1 and purified by preparative HPLC to give 7-(4-chlorobenzyl)-1-(2-(dimethylamino)ethyl)-3-methyl-8-(2-(3-(trifluoromethoxy)phenoxy)ethoxy)-1H-purine-2,6(3H,7H)-dione (20 mg, 16.4% yield) as white solid. $^1$H-NMR (DMSO-d$_6$) δ 8.18 (s, 1H), 7.43 (t, 1H), 7.26-7.32 (m, 4H), 6.93-7.02 (m, 3H), 5.20 (s, 2H), 4.80-4.82 (m, 2H), 4.39-4.41 (m, 2H), 3.99 (t, 2H), 3.67 (s, 3H), 2.58 (t, 2H), 2.30 (s, 6H). LCMS retention time 2.352 min; LCMS MH$^+$ 582

Example 41 7-(4-chlorobenzyl)-3-methyl-1-propyl-8-(2-(3-(trifluoromethoxy)phenoxy)ethoxy)-1H-purine-2,6(3H,7H)-dione

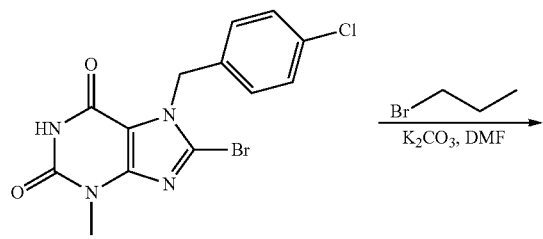

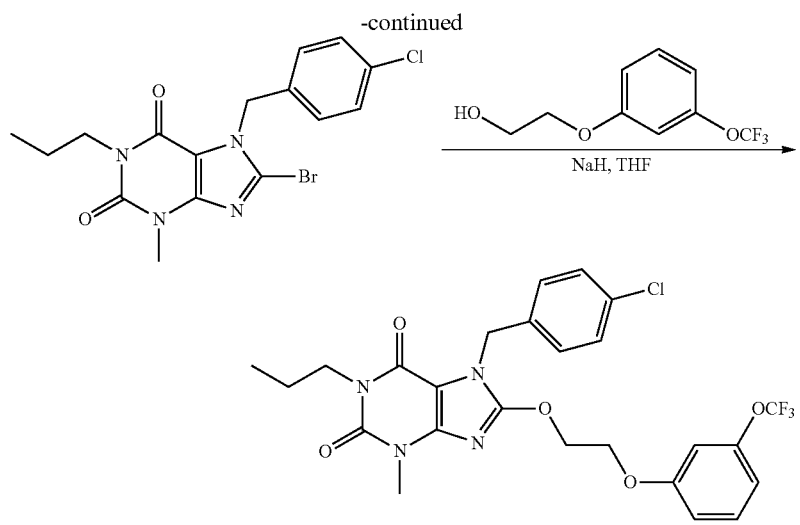

The title compound was prepared using the 2 step method of example 40 and purified via preparative HPLC to give 7-(4-chlorobenzyl)-3-methyl-1-propyl-8-(2-(3-(trifluoromethoxy)phenoxy)ethoxy)-1H-purine-2,6(3H,7H)-dione (80 mg, 29.7% yield) as white solid. $^1$H-NMR (DMSO-d$_6$) δ 7.45-7.41 (t, 1H), 7.32-7.26 (m, 4H), 7.02-6.94 (m, 3H), 5.19 (s, 2H), 4.82-4.79 (m, 2H), 4.41-4.39 (m, 2H), 3.81-3.78 (t, 2H), 1.58-1.49 (m, 2H), 0.86-0.83 (t, 3H). LCMS retention time 3.571 min; LCMS MH$^+$ 553

Example 42 7-((5-chloropyridin-2-yl)methyl)-1-(3-hydroxypropyl)-3-methyl-8-(2-(3-(trifluoromethoxy)phenoxy)ethoxy)-1H-purine-2,6(3H,7H)-dione

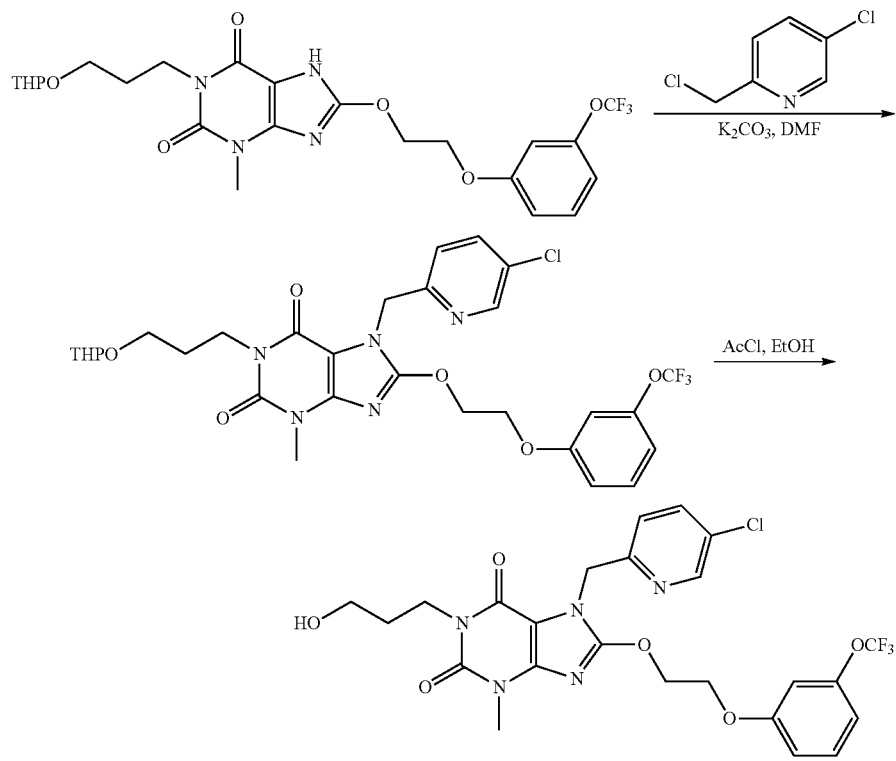

Step 1 7-((5-chloropyridin-2-yl)methyl)-3-methyl-1-(3-(tetrahydro-2H-pyran-2-yloxy)propyl)-8-(2-(3-(trifluoromethoxy)phenoxy)ethoxy)-1H-purine-2,6(3H,7H)-dione

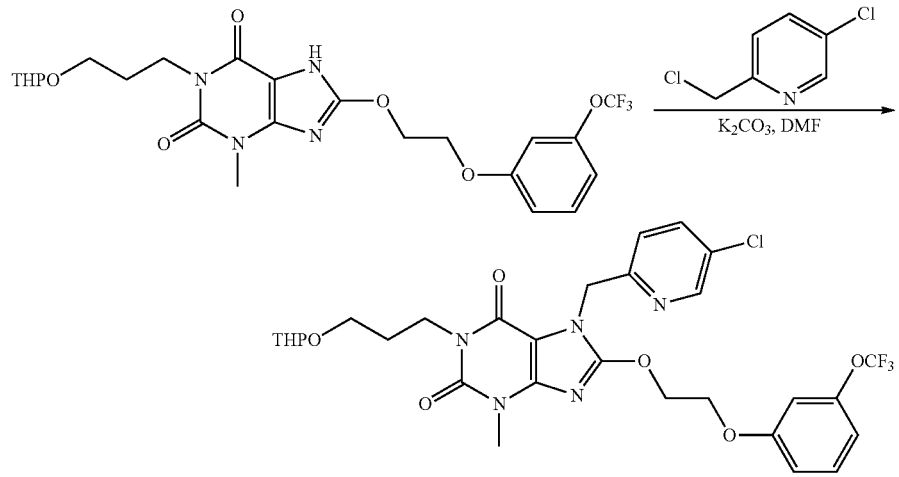

To a solution of 3-methyl-1-(3-(tetrahydro-2H-pyran-2-yloxy)propyl)-8-(2-(3-(trifluoromethoxy)phenoxy)ethoxy)-1H-purine-2,6(3H,7H)-dione (60 mg, 0.14 mmol, intermediate 17) in DMF (5 mL) was added 5-chloro-2-(chloromethyl)pyridine (33 mg, 0.20 mmol), potassium carbonate (37 mg, 0.27 mmol) and TBAI (2 mg, 0.02 mmol). The reaction was heated at 50° C. for 8 h. The mixture was cooled and partitioned between ethyl acetate and water. The combined organic layer was dried over sodium sulfate, filtered and concentrated to give crude product, which was used without purification. LCMS MH$^+$-THP 570.

Step 2 7-((5-chloropyridin-2-yl)methyl)-1-(3-hydroxypropyl)-3-methyl-8-(2-(3-(trifluoromethoxy)phenoxy)ethoxy)-1H-purine-2,6(3H,7H)-dione

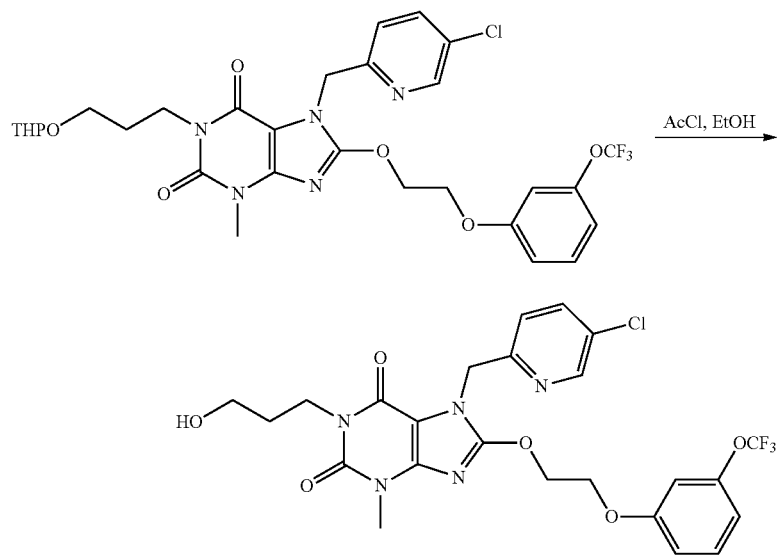

To a solution of 7-((5-chloropyridin-2-yl)methyl)-3-methyl-1-(3-(tetrahydro-2H-pyran-2-yloxy)propyl)-8-(2-(3-(trifluoromethoxy)phenoxy)ethoxy)-1H-purine-2,6(3H,7H)-dione (80 mg, 0.14 mmol) in ethanol (5 mL) was added acetyl chloride (0.2 mL) at 0° C. The mixture was stirred at room temperature for 1 h. The mixture was partitioned between ethyl acetate and water. The organic phase was dried over sodium sulfate, filtered and concentrated to give crude product which was purified by preparative HPLC to give 7-((5-chloropyridin-2-yl)methyl)-1-(3-hydroxypropyl)-3-methyl-8-(2-(3-(trifluoromethoxy)phenoxy)ethoxy)-1H-purine-2,6(3H,7H)-dione (15 mg, 19.0% yield) as white solid. $^1$H-NMR (CD$_3$OD) δ 8.33 (d, 1H), 7.70 (dd, 1H), 7.35 (t, 1H), 7.26 (d, 1H), 6.87 (dd, 1H), 6.76 (s, 1H), 5.43 (s, 2H), 4.86-4.87 (m, 2H), 4.33-4.35 (m, 2H), 4.04 (t, 2H), 3.56 (t, 2H), 3.54 (s, 3H), 1.80-1.85 (m, 2H). LCMS retention time 2.606 min; LCMS MH$^+$ 570.

The following examples 43a through 43e were prepared using the method of example 42.

Example 43a 1-(3-hydroxypropyl)-3-methyl-7-((6-methylpyridin-3-yl)methyl)-8-(2-(3-(trifluoromethoxy)phenoxy)ethoxy)-1H-purine-2,6(3H,7H)-dione

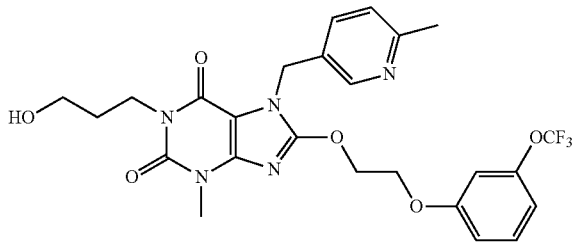 [SMILES: Cc1ccc(Cn2c(OCCOc3cccc(OC(F)(F)F)c3)nc3c2c(=O)n(CCCO)c(=O)n3C)cn1]

White solid, 20 mg, 26.3% yield: $^1$H-NMR (CD$_3$OD) δ 8.55 (s, 1H), 7.95 (d, 1H), 7.39 (dd, 2H), 6.96 (dd, 1H), 6.90 (d, 1H), 6.81 (s, 1H), 5.37 (s, 2H), 4.93-4.95 (m, 2H), 4.43-4.45 (m, 2H), 4.07 (t, 2H), 3.61 (t, 2H), 3.50 (s, 3H), 2.55 (s, 3H), 1.84-1.88 (m, 2H). LCMS retention time 2.022 min; LCMS MH$^+$ 550.

Example 43b 7-benzyl-1-(3-hydroxypropyl)-3-methyl-8-(2-(3-(trifluoromethoxy)phenoxy)ethoxy)-1H-purine-2,6(3H,7H)-dione

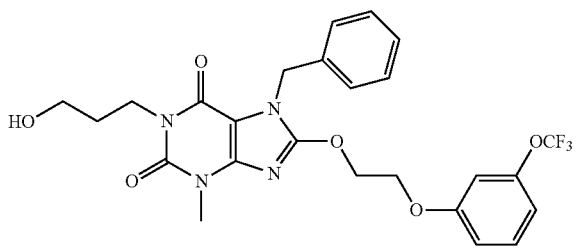 [SMILES: Cn1c(=O)n(CCCO)c(=O)c2c1nc(OCCOc1cccc(OC(F)(F)F)c1)n2Cc1ccccc1]

White solid, 17 mg, 23.0% yield: $^1$H-NMR (DMSO-d$_6$) δ 7.43 (t, 1H), 7.23-7.32 (m, 5H), 6.95-7.04 (m, 3H), 5.20 (s, 2H), 4.80-4.82 (m, 2H), 4.70 (t, 1H), 4.40-4.43 (m, 2H), 3.90 (t, 2H), 3.33-3.44 (m, 5H), 1.65-1.70 (m, 2H). LCMS retention time 2.897 min; LCMS MH$^+$ 535.

Example 43c 1-(3-hydroxypropyl)-3-methyl-7-((5-methylthiazol-2-yl)methyl)-8-(2-(3-(trifluoromethoxy)phenoxy)ethoxy)-1H-purine-2,6(3H,7H)-dione

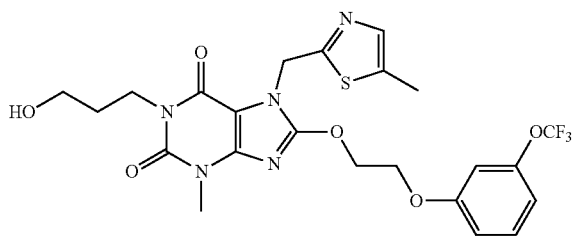 [SMILES: Cc1cnc(Cn2c(OCCOc3cccc(OC(F)(F)F)c3)nc3c2c(=O)n(CCCO)c(=O)n3C)s1]

White solid, 20 mg, 43.2% yield: $^1$H-NMR (CD$_3$OD) δ 7.39-7.35 (t, 1H), 7.28 (s, 1H), 6.93-6.80 (m, 2H), 6.79 (s, 1H), 5.56 (s, 2H), 4.89 (s, 2H), 4.39-4.36 (dd, 2H), 4.10-4.06 (t, 2H), 3.61-3.58 (t, 2H), 3.53 (s, 3H), 2.35 (s, 3H), 1.90-1.85 (m, 2H). LCMS retention time 2.536 min; LCMS MH$^+$ 556.

Example 43d 7-ethyl-1-(3-hydroxypropyl)-3-methyl-8-(2-(3-(trifluoromethoxy)phenoxy)ethoxy)-1H-purine-2,6(3H,7H)-dione

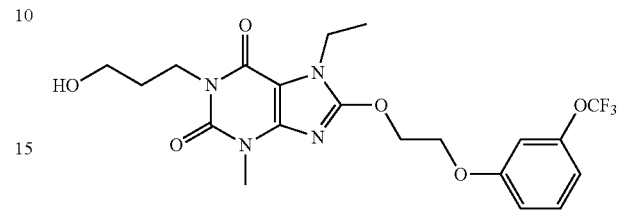

White solid, 33 mg, 37.1% yield: $^1$H-NMR (CD$_3$OD) δ 7.39 (t, 1H), 7.01 (dd, 1H), 6.88-6.90 (m, 2H), 4.87-4.88 (m, 2H), 4.44-4.46 (m, 2H), 4.08-4.16 (m, 4H), 3.61 (t, 2H), 3.51 (s, 3H), 1.80-1.90 (m, 2H), 1.32 (t, 3H). LCMS retention time 1.526 min; LCMS MH$^+$ 473.

Example 43e 1-(2-hydroxyethyl)-3,7-dimethyl-8-(2-(3-(trifluoromethoxy)phenoxy)ethoxy)-1H-purine-2,6(3H,7H)-dione

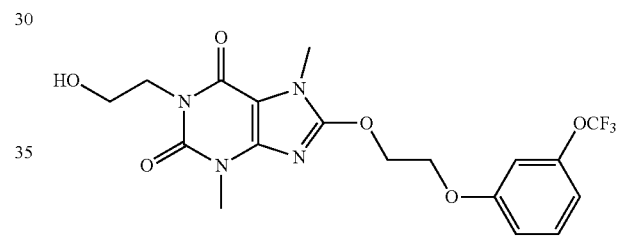

White solid, 16 mg, 50.1% yield: $^1$H-NMR (DMSO-d$_6$) δ 7.41-7.45 (t, 1H), 7.04-7.06 (dd, 1H), 6.97-7.00 (m, 2H), 4.75-4.79 (m, 4H), 4.42-4.44 (t, 2H), 3.92-3.95 (t, 2H), 3.57 (s, 3H), 3.50-3.52 (t, 2H), 3.47 (s, 3H). LCMS retention time 2.411 min; LCMS MH$^+$ 445.

Example 44 1-(3-hydroxypropyl)-3-methyl-7-((4-methylthiazol-2-yl)methyl)-8-(3-(trifluoromethoxy)phenoxy)-1H-purine-2,6(3H,7H)-dione

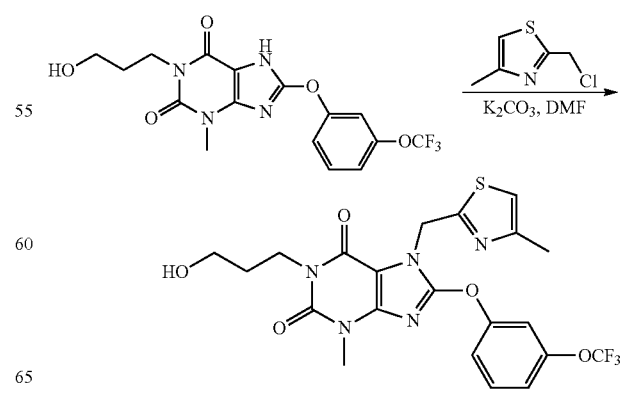

To a solution of 1-(3-hydroxypropyl)-3-methyl-8-(3-(trifluoromethoxy)phenoxy)-1H-purine-2,6(3H,7H)-dione (100 mg, 0.25 mmol, intermediate 13) in DMF (5 mL) was added 2-(chloromethyl)-4-methylthiazole (47.9 mg, 0.32 mmol, intermediate 54) followed by potassium carbonate (51.6 mg, 0.37 mmol) and a catalytic amount of TBAI. The mixture was stirred at 60° C. for 4 h. The mixture was diluted with ethyl acetate and extracted with brine and saturated aqueous ammonium chloride solution. Then the organic phase was dried and concentrated to give a crude product which was purified by preparative HPLC to give 1-(3-hydroxypropyl)-3-methyl-7-((4-methylthiazol-2-yl)methyl)-8-(3-(trifluoromethoxy)phenoxy)-1H-purine-2,6(3H,7H)-dione (29 mg, 22.7% yield) as white solid. $^1$H-NMR (DMSO-$d_6$) δ 7.62 (t, 1H), 7.41-7.46 (m, 2H), 7.33 (dd, 1H), 7.26 (d, 1H), 5.73 (s, 2H), 4.49 (t, 1H), 3.91 (t, 2H), 3.35 (t, 2H), 3.31 (s, 3H), 2.29 (d, 3H), 1.67-1.71 (m, 2H). LCMS retention time 2.681 min; LCMS MH$^+$ 512.

The following examples 45a through 45m were prepared using the method of example 44.

Example 45a 1-(3-hydroxypropyl)-3-methyl-7-(thiazol-2-ylmethyl)-8-(3-(trifluoromethoxy)phenoxy)-1H-purine-2,6(3H,7H)-dione

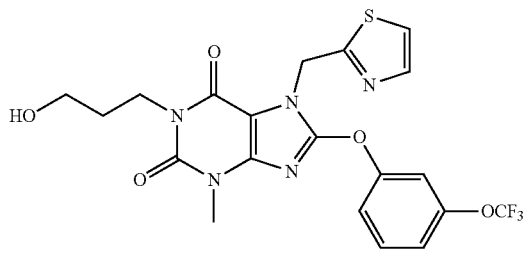 [SMILES: Cn1c(=O)n(CCCO)c(=O)c2c1nc(Oc1cccc(OC(F)(F)F)c1)n2Cc1nccs1]

White solid, 42 mg, 38.1% yield: $^1$H-NMR (DMSO-$d_6$) δ 7.74-7.77 (m, 2H) 7.62 (t, 1H), 7.41-7.49 (m, 2H), 7.33 (d, 1H), 5.80 (s, 2H), 4.47 (t, 1H), 3.91 (t, 2H), 3.43 (t, 2H), 3.31 (s, 3H), 2.29 (d, 3H), 1.65-1.70 (m, 2H). LCMS retention time 2.378 min; LCMS MH$^+$ 498.

Example 45b 1-(3-hydroxypropyl)-3-methyl-7-((5-methylthiazol-2-yl)methyl)-8-(3-(trifluoromethoxy)phenoxy)-1H-purine-2,6(3H,7H)-dione

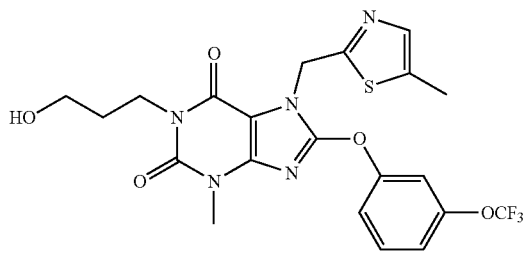 [SMILES: Cc1cnc(Cn2c(Oc3cccc(OC(F)(F)F)c3)nc3c2c(=O)n(CCCO)c(=O)n3C)s1]

White solid, 22 mg, 28.9% yield: $^1$H-NMR (DMSO-$d_6$) δ 7.70 (s, 1H), 7.63 (t, 1H), 7.56 (s, 1H), 7.47-7.50 (m, 1H), 7.34-7.37 (m, 1H), 5.60 (s, 2H), 4.50 (t, 1H), 3.95 (t, 2H), 3.46 (t, 2H), 3.30 (s, 3H), 2.59 (s, 3H), 1.67-1.74 (m, 2H). LCMS retention time 2.419 min; LCMS MH$^+$ 512.

Example 45c 7-(4-fluorobenzyl)-1-(3-hydroxypropyl)-3-methyl-8-(3-(trifluoromethoxy)phenoxy)-1H-purine-2,6(3H,7H)-dione

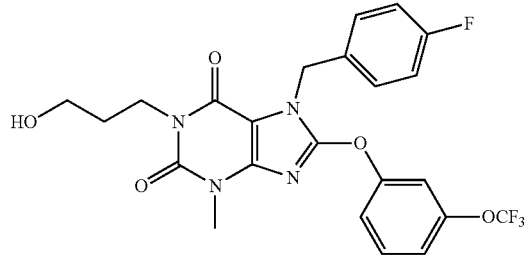 [SMILES: Cn1c(=O)n(CCCO)c(=O)c2c1nc(Oc1cccc(OC(F)(F)F)c1)n2Cc1ccc(F)cc1]

White solid, 23 mg, 30.2% yield: $^1$H-NMR (CD$_3$OD) δ 7.46-7.55 (m, 3H), 7.30 (d, 2H), 7.22 (d, 1H), 7.07 (t, 2H), 5.48 (s, 2H), 4.10 (t, 1H), 3.60 (t, 2H), 3.40 (s, 3H), 1.84-1.90 (m, 2H). LCMS retention time 2.944 min; LCMS MH$^+$ 509.

Example 45d 1-(3-hydroxypropyl)-3-methyl-7-(4-methylbenzyl)-8-(3-(trifluoromethoxy)phenoxy)-1H-purine-2,6(3H,7H)-dione

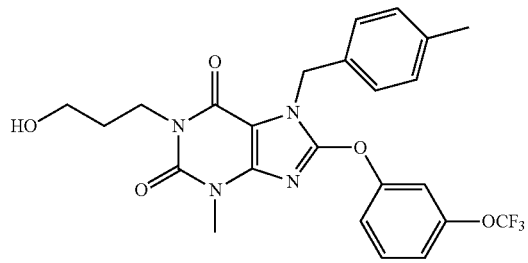 [SMILES: Cc1ccc(Cn2c(Oc3cccc(OC(F)(F)F)c3)nc3c2c(=O)n(CCCO)c(=O)n3C)cc1]

White solid, 28 mg, 37.3% yield: $^1$H-NMR (CD$_3$OD) δ 7.51 (t, 1H), 7.19-7.31 (m, 4H), 7.14 (d, 2H), 5.44 (s, 2H), 4.10 (t, 1H), 3.60 (t, 2H), 3.40 (s, 3H), 2.28 (s, 3H), 1.83-1.90 (m, 2H). LCMS retention time 3.075 min; LCMS MH$^+$ 505.

Example 45e 4-((1-(3-hydroxypropyl)-3-methyl-2,6-dioxo-8-(3-(trifluoromethoxy)phenoxy)-2,3-dihydro-1H-purin-7(6H)-yl)methyl)benzonitrile

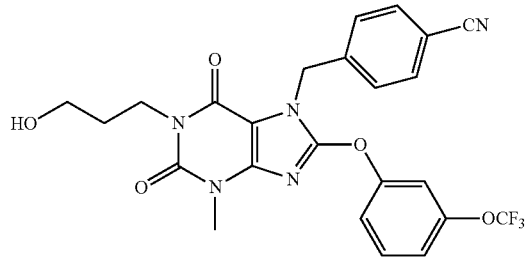 [SMILES: Cn1c(=O)n(CCCO)c(=O)c2c1nc(Oc1cccc(OC(F)(F)F)c1)n2Cc1ccc(C#N)cc1]

White solid, 16 mg, 20.7% yield: $^1$H-NMR (CD$_3$OD) δ 7.72 (d, 2H), 7.51-7.59 (m, 3H), 7.32 (d, 2H), 7.22 (d, 1H), 5.58 (s, 2H), 4.08 (t, 1H), 3.59 (t, 2H), 3.41 (s, 3H), 1.82-1.87 (m, 2H). LCMS retention time 2.750 min; LCMS MH+ 516.

Example 45f 1-(3-hydroxypropyl)-7-(4-methoxybenzyl)-3-methyl-8-(3-(trifluoromethoxy)phenoxy)-1H-purine-2,6(3H,7H)-dione

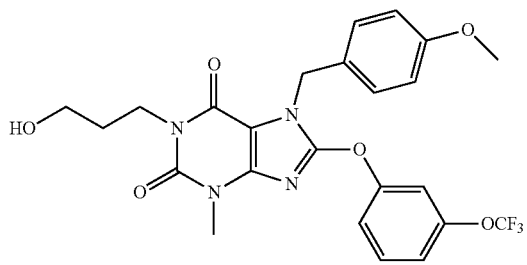 [SMILES: COc1ccc(Cn2c(Oc3cccc(OC(F)(F)F)c3)nc3c2c(=O)n(CCCO)c(=O)n3C)cc1]

White solid, 22 mg, 28.2% yield: ¹H-NMR (CD₃OD) δ 7.52 (t, 2H), 7.38 (d, 2H), 7.20-7.30 (m, 3H), 6.87 (d, 2H), 5.41 (s, 2H), 4.10 (t, 1H), 3.75 (s, 3H), 3.60 (t, 2H), 3.40 (s, 3H), 1.83-1.89 (m, 2H). LCMS retention time 2.899 min; LCMS MH+ 521.

Example 45g 1-(3-hydroxypropyl)-3-methyl-7-((6-methylpyridin-3-yl)methyl)-8-(3-(trifluoromethoxy)phenoxy)-1H-purine-2,6(3H,7H)-dione

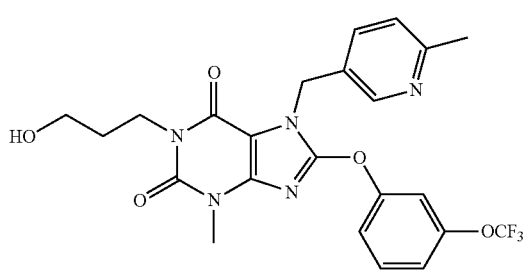 [SMILES: Cc1ccc(Cn2c(Oc3cccc(OC(F)(F)F)c3)nc3c2c(=O)n(CCCO)c(=O)n3C)cn1]

White solid, 45 mg, 29.7% yield: ¹H-NMR (DMSO-d₆) δ 8.53-8.52 (d, 1H), 7.71-7.69 (dd, 1H), 7.63-7.59 (t, 1H), 7.52 (s, 1H), 7.46-7.44 (dd, 1H), 7.34-7.32 (d, 1H), 7.25-7.23 (d, 1H), 5.43 (s, 2H), 4.53 (bs, 1H), 3.95-3.91 (t, 2H), 3.46-3.43 (t, 2H), 3.28 (s, 3H), 2.43 (s, 3H), 1.71-1.68 (m, 2H). LCMS retention time 1.923 min; LCMS MH+ 506.

Example 45h 7-((5-chloropyridin-2-yl)methyl)-1-(3-hydroxypropyl)-3-methyl-8-(3-(trifluoromethoxy)phenoxy)-1H-purine-2,6(3H,7H)-dione

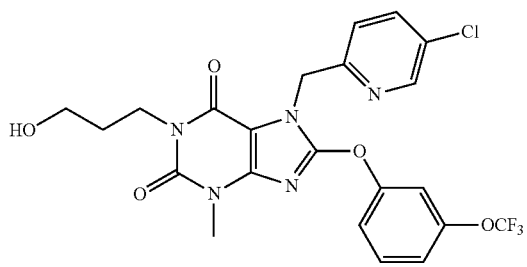

White solid, 49 mg, 37.3% yield: ¹H-NMR (DMSO-d₆) δ 8.54 (s, 1H), 7.94-7.97 (dd, 1H), 7.57-7.61 (t, 1H), 7.49-7.51 (d, 1H), 7.38-7.43 (m, 2H), 7.30-7.32 (d, 1H), 5.58 (s, 2H), 4.44-4.47 (t, 1H), 3.85-3.89 (t, 2H), 3.40-3.42 (t, 2H), 3.30 (s, 3H), 1.63-1.66 (m, 2H). LCMS retention time 2.710 min; LCMS MH+ 526.

Example 45i 7-((6-chloropyridin-3-yl)methyl)-1-(3-hydroxypropyl)-3-methyl-8-(3-(trifluoromethoxy)phenoxy)-1H-purine-2,6(3H,7H)-dione

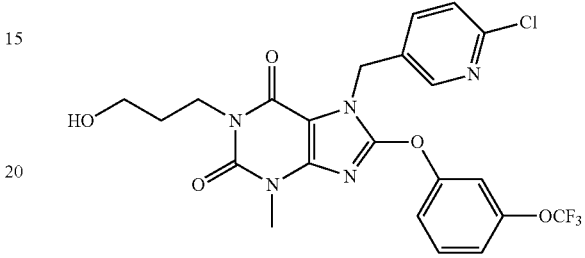

White solid, 20 mg, 22.4% yield: ¹H-NMR (DMSO-d₆) δ 8.50-8.49 (d, 1H), 7.90-7.87 (dd, 1H), 7.63-7.58 (t, 1H), 7.54-7.45 (m, 3H), 7.33-7.31 (d, 1H), 5.48 (s, 2H), 3.94-3.90 (t, 2H), 3.62-3.59 (t, 2H), 3.28 (s, 3H), 1.71-1.67 (t, 2H). LCMS retention time 2.625 min; LCMS MH+ 526.

Example 45j 7-ethyl-1-(3-hydroxypropyl)-3-methyl-8-(3-(trifluoromethoxy)phenoxy)-1H-purine-2,6(3H,7H)-dione

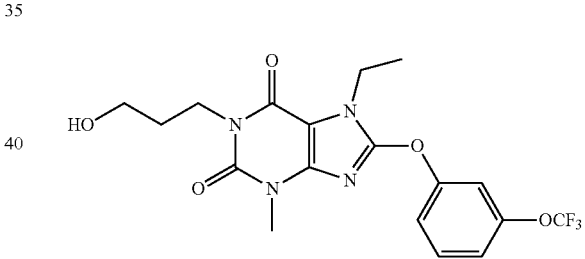

White solid, 40 mg, 54.9% yield: ¹H-NMR (DMSO-d₆) δ 7.64-7.60 (t, 1H), 7.55 (s, 1H), 7.47-7.45 (dd, 1H), 7.34-7.32 (d, 1H), 4.25-4.20 (m, 2H), 3.95-3.91 (t, 2H), 3.46-3.42 (m, 2H), 3.28 (s, 3H), 1.72-1.68 (m, 2H), 1.39-1.35 (t, 3H). LCMS retention time 2.525 min; LCMS MH+ 429.

Example 45k 1-(3-hydroxypropyl)-3,7-dimethyl-8-(3-(trifluoromethoxy)phenoxy)-1H-purine-2,6(3H,7H)-dione

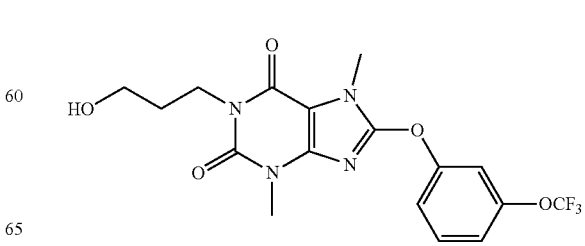

White solid, 40 mg, 55.1% yield: $^1$H-NMR (DMSO-$d_6$) δ 7.64-7.60 (t, 1H), 7.54 (s, 1H), 7.47-7.45 (dd, 1H), 7.32-7.31 (dd, 1H), 4.49-4.46 (t, 1H), 3.94-3.90 (t, 2H), 3.78 (s, 3H), 3.46-3.42 (m, 2H), 3.28 (s, 3H), 11.73-1.66 (m, 2H). LCMS retention time 2.363 min; LCMS MH$^+$ 415.

Example 45l 1-(3-hydroxypropyl)-3-methyl-7-((2-methylpyrimidin-5-yl)methyl)-8-(3-(trifluoromethoxy)phenoxy)-1H-purine-2,6(3H,7H)-dione

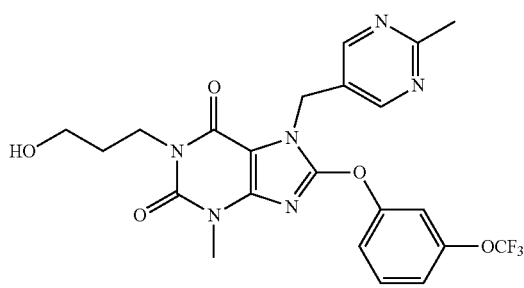 [SMILES: Cc1ncc(Cn2c(Oc3cccc(OC(F)(F)F)c3)nc3c2c(=O)n(CCCO)c(=O)n3C)cn1]

Light yellow solid, 18 mg, 20.9% yield: $^1$H-NMR (DMSO-$d_6$) δ 8.76 (s, 2H), 7.64-7.58 (m, 2H), 7.50-7.48 (m, 1H), 7.35-7.32 (dd, 1H), 5.45 (s, 2H), 3.94-3.91 (t, 2H), 3.46-3.42 (m, 2H), 3.29 (s, 3H), 2.96 (s, 3H), 1.71-1.68 (m, 2H). LCMS retention time 2.226 min; LCMS MH$^+$ 507.

Example 45m 1-(3-hydroxypropyl)-3-methyl-7-((5-methyloxazol-2-yl)methyl)-8-(3-(trifluoromethoxy)phenoxy)-1H-purine-2,6(3H,7H)-dione

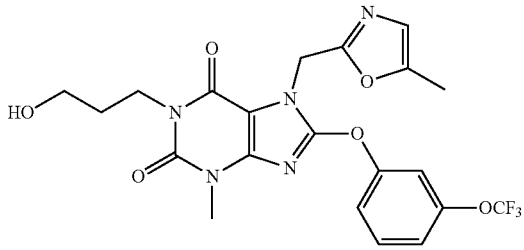 [SMILES: Cc1cnc(Cn2c(Oc3cccc(OC(F)(F)F)c3)nc3c2c(=O)n(CCCO)c(=O)n3C)o1]

Light yellow solid, 15 mg, 20.2% yield: $^1$H-NMR (DMSO-$d_6$) δ 7.64-7.60 (t, 1H), 7.45-7.40 (m, 2H), 7.34-7.32 (d, 1H), 6.78 (s, 1H), 5.59 (s, 2H), 4.50 (bs, 1H), 3.91-3.88 (t, 2H), 3.48 (s, 2H), 3.31 (s, 3H), 2.25 (s, 3H), 1.71-1.64 (m, 2H). LCMS retention time 2.358 min; LCMS MH$^+$ 496.

Example 46 7-(4-((dimethylamino)methyl)benzyl)-1-(3-hydroxypropyl)-3-methyl-8-(3-(trifluoromethoxy)phenoxy)-1H-purine-2,6(3H,7H)-dione

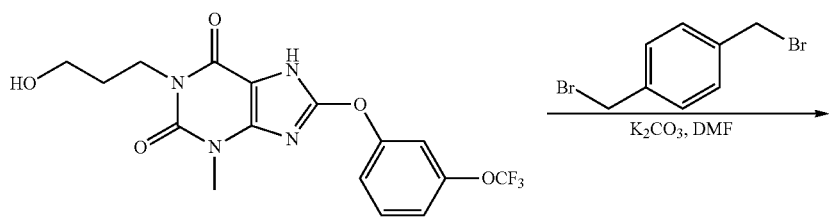

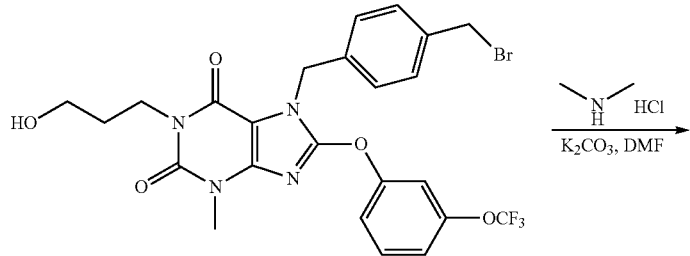

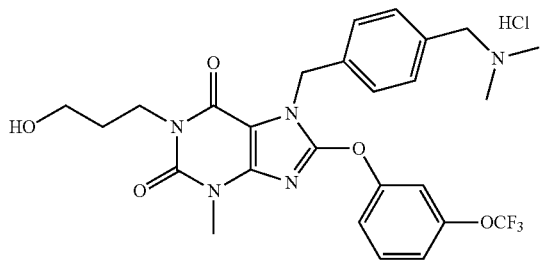

Step 1 7-(4-(bromomethyl)benzyl)-1-(3-hydroxypropyl)-3-methyl-8-(3-(trifluoromethoxy)phenoxy)-1H-purine-2,6(3H,7H)-dione

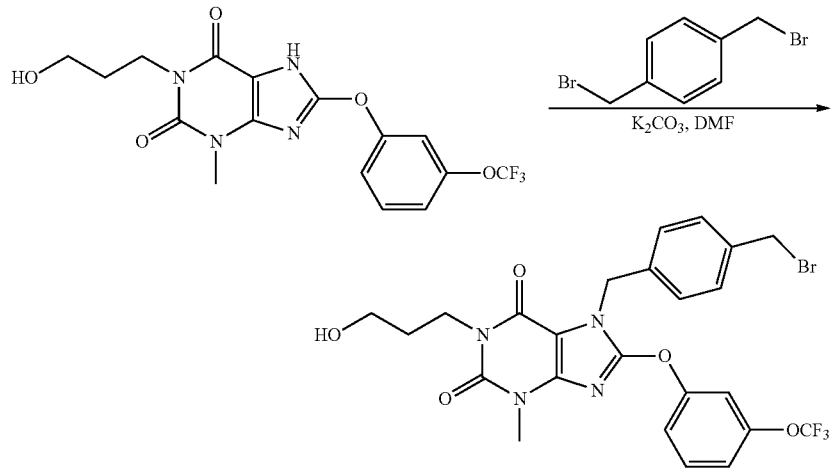

The title compound was prepared using the method of example 44 to give 7-(4-(bromomethyl)benzyl)-1-(3-hydroxypropyl)-3-methyl-8-(3-(trifluoromethoxy)phenoxy)-1H-purine-2,6(3H,7H)-dione (126 mg, 43.3% yield) as white solid. LCMS retention time 1.758 min; LCMS MH+ 583.

Step 2 7-(4-(((dimethylamino)methyl)benzyl)-1-(3-hydroxypropyl)-3-methyl-8-(3-(trifluoromethoxy)phenoxy)-1H-purine-2,6(3H,7H)-dione

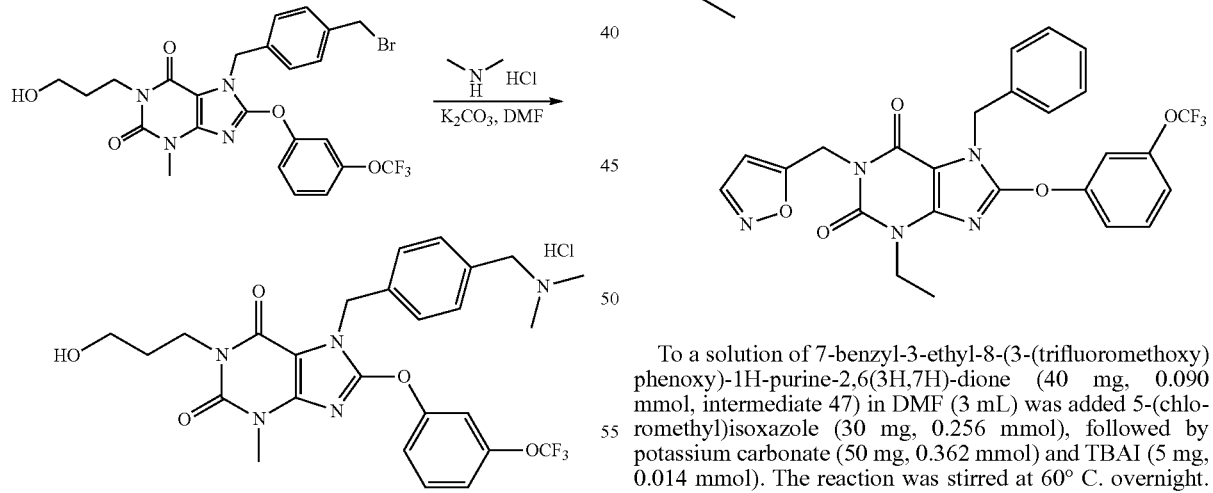

The title compound was prepared using the method of example 25 step 2 and purified via preparative HPLC to give 7-(4-(((dimethylamino)methyl)benzyl)-1-(3-hydroxypropyl)-3-methyl-8-(3-(trifluoromethoxy)phenoxy)-1H-purine-2,6(3H,7H)-dione (15 mg, 35.3% yield) as white solid. $^1$H-NMR (DMSO-$d_6$) δ 10.94 (s, 1H), 7.62-7.57 (m, 3H), 7.50 (s, 1H), 7.46-7.44 (m, 2H), 7.42-7.39 (dd, 1H), 7.33-7.31 (d, 1H), 5.48 (s, 2H), 4.25-4.24 (d, 2H), 3.95-3.91 (t, 2H), 3.45-3.42 (t, 2H), 3.30 (s, 3H), 2.65-2.64 (d, 6H), 1.71-1.67 (m, 2H). LCMS retention time 3.183 min; LCMS MH+ 548.

Example 47 7-benzyl-3-ethyl-1-(isoxazol-5-ylmethyl)-8-(3-(trifluoromethoxy)phenoxy)-1H-purine-2,6(3H,7H)-dione

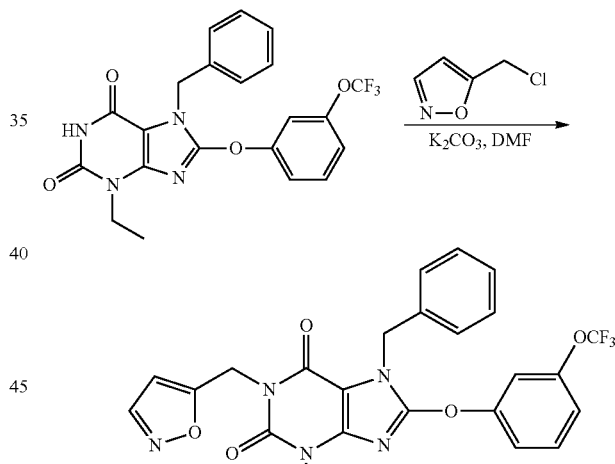

To a solution of 7-benzyl-3-ethyl-8-(3-(trifluoromethoxy)phenoxy)-1H-purine-2,6(3H,7H)-dione (40 mg, 0.090 mmol, intermediate 47) in DMF (3 mL) was added 5-(chloromethyl)isoxazole (30 mg, 0.256 mmol), followed by potassium carbonate (50 mg, 0.362 mmol) and TBAI (5 mg, 0.014 mmol). The reaction was stirred at 60° C. overnight. The mixture was cooled and partitioned between ethyl acetate and water. The organic phase was washed with brine, dried over sodium sulfate, and concentrated to give a crude product, which was purified by preparative HPLC to give 7-benzyl-3-ethyl-1-(isoxazol-5-ylmethyl)-8-(3-(trifluoromethoxy)phenoxy)-1H-purine-2,6(3H,7H)-dione (5.9 mg, 12.6% yield) as white solid. $^1$H-NMR (CD$_3$OD) δ 8.33-8.32 (d, 1H), 7.57-7.53 (t, 1H), 7.47-7.45 (d, 2H), 7.38-7.31 (m, 5H), 7.25-7.23 (d, 1H), 6.34-6.33 (dd, 1H), 5.52 (s, 2H), 5.36 (s, 2H), 4.06-4.01 (q, 2H), 1.27-1.24 (t, 3H). LCMS retention time 3.269 min; LCMS MH+ 528.

Example 48 7-(4-chloro-3-methoxybenzyl)-1-(3-hydroxypropyl)-3-methyl-8-(3-(trifluoromethoxy)phenoxy)-1H-purine-2,6(3H,7H)-dione

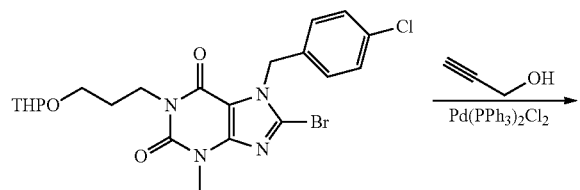

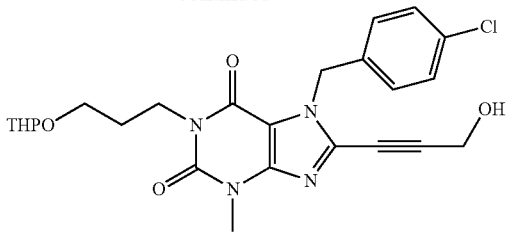

To a solution of 8-bromo-7-(4-chlorobenzyl)-3-methyl-1-(3-(tetrahydro-2H-pyran-2-yloxy)propyl)-1H-purine-2,6(3H,7H)-dione (300 mg, 0.588 mmol, intermediate 14) in anhydrous DMF (12 mL) was added prop-2-yn-1-ol (0.15 ml, 2.545 mmol), bis(triphenylphosphine)palladium(II) chloride (10 mg, 0.043 mmol), copper iodide (10 mg, 0.053 mmol) (45 mg, 0.402 mmol) and TEA (3 mL, 21.6 mmol). Then the mixture was degassed and refilled with nitrogen 3 times. The reaction was stirred at 85° C. overnight under nitrogen. The mixture was cooled, filtered and the filter cake was washed with ethyl acetate. The filtrate was concentrated to give a crude product, which was purified by silica gel chromatography eluting with DCM/ethyl acetate (3:1 to 1:1) to give 7-(4-chlorobenzyl)-8-(3-hydroxyprop-1-ynyl)-3-methyl-1-(3-(tetrahydro-2H-pyran-2-yloxy)propyl)-1H-purine-2,6(3H,7H)-dione (170 mg, 59.5% yield) as a light yellow solid. LCMS retention time 1.523 min; LCMS MH+ 487.

Step 2 7-(4-chlorobenzyl)-8-(3-hydroxypropyl)-3-methyl-1-(3-(tetrahydro-2H-pyran-2-yloxy)propyl)-1H-purine-2,6(3H,7H)-dione

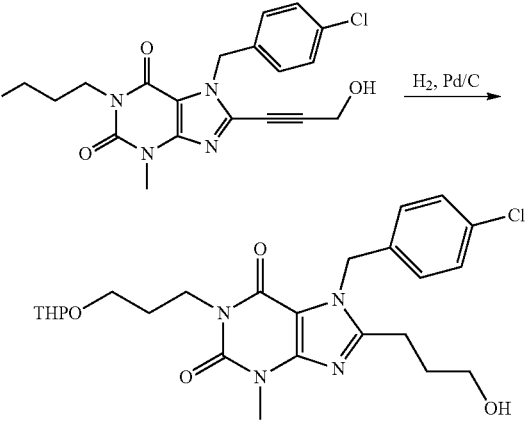

A solution of 7-(4-chlorobenzyl)-8-(3-hydroxyprop-1-ynyl)-3-methyl-1-(3-(tetrahydro-2H-pyran-2-yloxy)propyl)-1H-purine-2,6(3H,7H)-dione (120 mg, 0.247 mmol) in methanol (15 mL) was degassed and refilled with nitrogen for 3 times; then 10% Pd/C (30 mg) was added. The mixture was degassed and refilled with hydrogen 3 times and stirred under 45 psi of hydrogen at room temperature for 20 min. The mixture was filtered and the filter cake was washed with methanol. The filtrate was concentrated to give 7-(4-chlorobenzyl)-8-(3-hydroxypropyl)-3-methyl-1-(3-(tetrahydro-2H-pyran-2-yloxy)propyl)-1H-purine-2,6(3H,7H)-dione (100 mg, 82.6% yield) as a grey solid. LCMS retention time 1.447 min; LCMS MH+ 491.

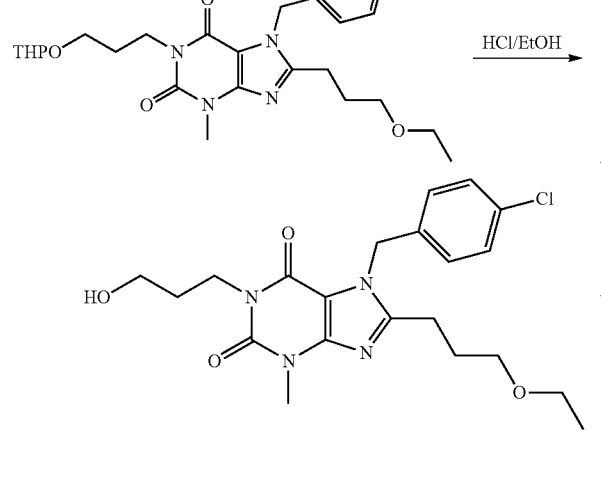

Step 1 7-(4-chlorobenzyl)-8-(3-hydroxyprop-1-ynyl)-3-methyl-1-(3-(tetrahydro-2H-pyran-2-yloxy)propyl)-1H-purine-2,6(3H,7H)-dione

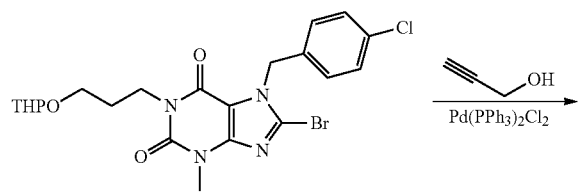

Step 3 7-(4-chlorobenzyl)-8-(3-ethoxypropyl)-3-methyl-1-(3-(tetrahydro-2H-pyran-2-yloxy)propyl)-1H-purine-2,6(3H,7H)-dione

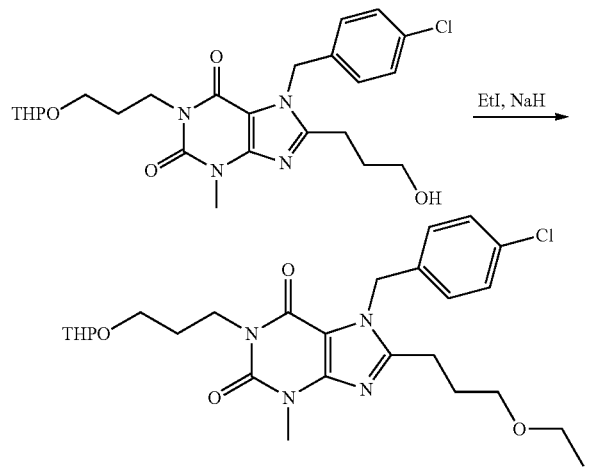

To a solution of 7-(4-chlorobenzyl)-8-(3-hydroxypropyl)-3-methyl-1-(3-(tetrahydro-2H-pyran-2-yloxy)propyl)-1H-purine-2,6(3H,7H)-dione (100 mg, 0.204 mmol) in DMF (3 mL) was added sodium hydride (24.5 mg, 0.612 mmol, 60% dispersion in mineral oil) at 0° C. The mixture was stirred at room temperature for 30 min. Iodoethane (63.6 mg, 0.408 mmol) was added to the reaction and it was stirred at room temperature for 16 h. The reaction was partitioned between ethyl acetate and brine. The organic phase was dried and concentrated to give a crude product, which was purified by silica gel chromatography eluting with petroleum ether/ethyl acetate (2:1 to 1:1) to give 7-(4-chlorobenzyl)-8-(3-ethoxypropyl)-3-methyl-1-(3-(tetrahydro-2H-pyran-2-yloxy)propyl)-1H-purine-2,6(3H,7H)-dione (96 mg, 90.6% yield) as a yellow solid. LCMS retention time 1.870 min; LCMS MH+ 519.

Step 4 7-(4-chloro-3-methoxybenzyl)-1-(3-hydroxypropyl)-3-methyl-8-(3-(trifluoromethoxy)phenoxy)-1H-purine-2,6(3H,7H)-dione

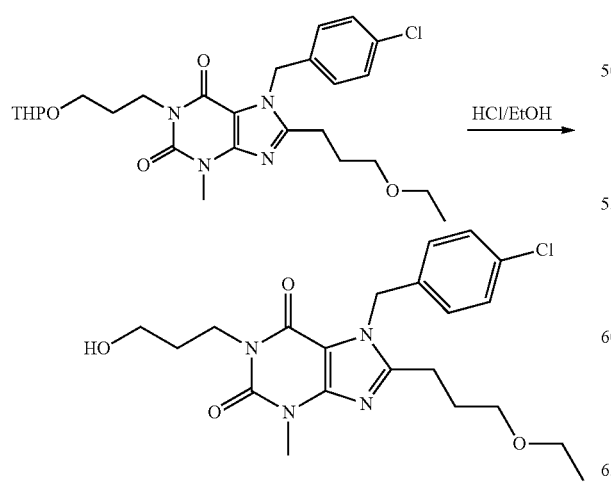

The title compound was prepared as example 14, step 3 to give 7-(4-chloro-3-methoxybenzyl)-1-(3-hydroxypropyl)-3-methyl-8-(3-(trifluoromethoxy)phenoxy)-1H-purine-2,6(3H,7H)-dione (51 mg, 56.5% yield) as a white solid. $^1$H-NMR (CD$_3$OD) δ 7.38-7.35 (d, 2H), 7.24-7.22 (d, 2H), 5.62 (s, 2H), 4.12-4.18 (t, 2H), 3.62-3.59 (t, 2H), 3.57 (s, 3H), 3.46-3.43 (m, 4H), 2.86-2.82 (t, 2H), 1.98-1.84 (m, 4H), 1.18-1.14 (t, 3H). LCMS retention time 2.384 min; LCMS MH+ 435.

Example 49 7-(4-chlorobenzyl)-1,8-bis(3-hydroxypropyl)-3-methyl-1H-purine-2,6(3H,7H)-dione

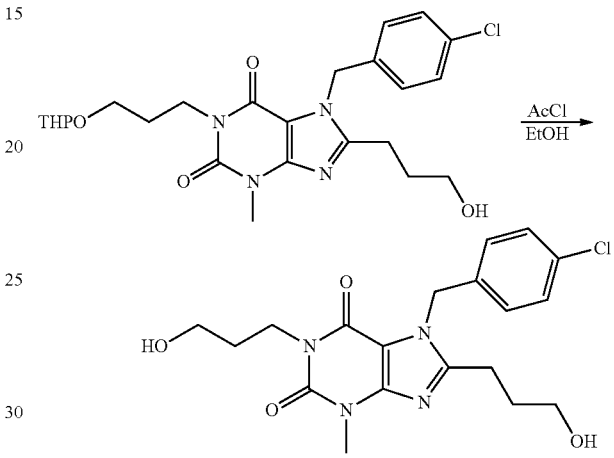

To a solution of 7-(4-chlorobenzyl)-8-(3-hydroxypropyl)-3-methyl-1-(3-(tetrahydro-2H-pyran-2-yloxy)propyl)-1H-purine-2,6(3H,7H)-dione (30 mg, 0.061 mmol, example 48, step 3) in ethyl alcohol (20 mL) was added acetyl chloride (0.2 mL, 2.80 mmol). The reaction was stirred at 0° C. for 10 min. The mixture was concentrated to give a crude product, which was purified by preparative HPLC to give 7-(4-chlorobenzyl)-1,8-bis(3-hydroxypropyl)-3-methyl-1H-purine-2,6(3H,7H)-dione (15 mg, 60.6% yield) as a white solid. $^1$H-NMR (CD$_3$OD) δ 7.37-7.35 (d, 2H), 7.21-7.22 (d, 2H), 5.62 (s, 2H), 4.11-4.08 (t, 2H), 3.62-3.59 (t, 4H), 3.56 (s, 3H), 2.87-2.83 (t, 2H), 1.95-1.83 (m, 4H). LCMS retention time 1.801 min; LCMS MH+ 407.

Example 50 8-(cyclopentyloxy)-1-(3-hydroxypropyl)-3-methyl-7-((4-methylthiazol-2-yl)methyl)-1H-purine-2,6(3H,7H)-dione

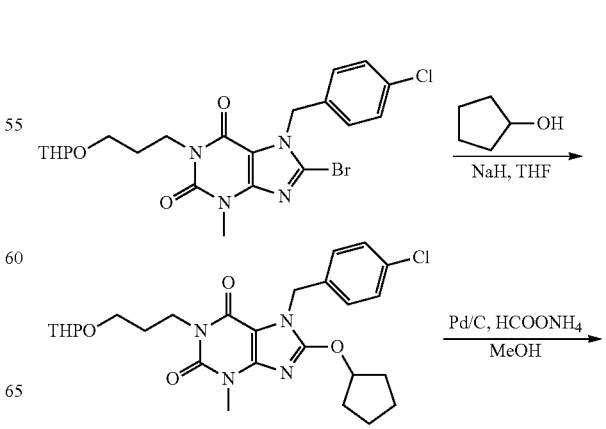

Step 1 7-(4-chlorobenzyl)-8-(cyclopentyloxy)-3-methyl-1-(3-(tetrahydro-2H-pyran-2-yloxy)propyl)-1H-purine-2,6(3H,7H)-dione (GG-000317-120)

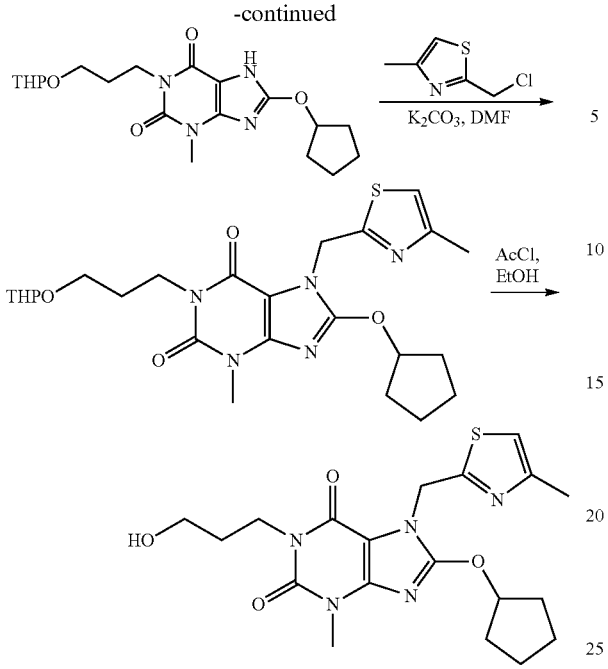

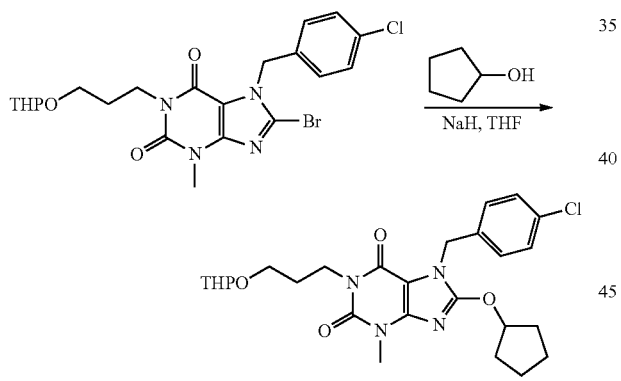

To a solution of cyclopentanol (67 mg, 0.78 mmol) in THF (5 mL) was added sodium hydride (39 mg, 0.98 mmol) at 0° C. After stirring at 0° C. for 30 min, 8-bromo-7-(4-chlorobenzyl)-3-methyl-1-(3-(tetrahydro-2H-pyran-2-yloxy)propyl)-1H-purine-2,6(3H,7H)-dione (0.2 g, 0.39 mmol, intermediate 14) was added. The mixture was stirred at room temperature for 16 h; then aqueous ammonium chloride solution (2 mL) was added at 0° C. The reaction mixture was partitioned between ethyl acetate and water. The combined organic layer was dried over sodium sulfate, filtered and concentrated to give a crude solid product. This material was slurried in ice cold ethanol, collected by filtration, and dried under vacuum to give 7-(4-chlorobenzyl)-8-(cyclopentyloxy)-3-methyl-1-(3-(tetrahydro-2H-pyran-2-yloxy)propyl)-1H-purine-2,6(3H,7H)-dione (180 mg, 89.5% yield) as white solid. LCMS retention time 2.085 min; LCMS MH$^+$-THP 433.

Step 2 8-(cyclopentyloxy)-3-methyl-1-(3-(tetrahydro-2H-pyran-2-yloxy)propyl)-1H-purine-2,6(3H,7H)-dione

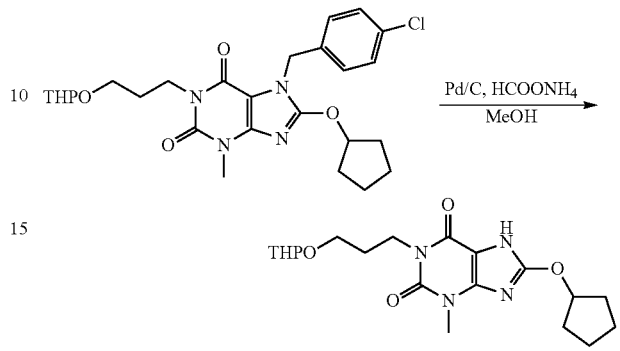

To a solution of 7-(4-chlorobenzyl)-8-(cyclopentyloxy)-3-methyl-1-(3-(tetrahydro-2H-pyran-2-yloxy)propyl)-1H-purine-2,6(3H,7H)-dione (180 mg, 0.35 mmol) in methanol (10 mL) was added ammonium formate (220 mg, 3.5 mmol) and 5% Pd/C (20 mg). The reaction was refluxed under nitrogen atmosphere overnight. The mixture was cooled and filtered. The filtrate was concentrated to give 8-(cyclopentyloxy)-3-methyl-1-(3-(tetrahydro-2H-pyran-2-yloxy)propyl)-1H-purine-2,6(3H,7H)-dione (120 mg, 87.6% yield) as white solid. LCMS retention time 1.345 min; LCMS MH$^+$-THP 309.

Step 3 8-(cyclopentyloxy)-3-methyl-7-((4-methylthiazol-2-yl)methyl)-1-(3-(tetrahydro-2H-pyran-2-yloxy)propyl)-1H-purine-2,6(3H,7H)-dione

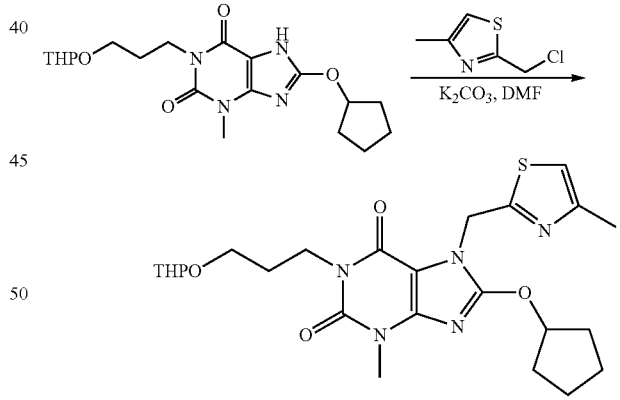

To a solution of 8-(cyclopentyloxy)-3-methyl-1-(3-(tetrahydro-2H-pyran-2-yloxy)propyl)-1H-purine-2,6(3H,7H)-dione (0.12 g, 0.31 mmol) in DMF (5 mL) was added 2-(chloromethyl)-4-methylthiazole (91 mg, 0.62 mmol, intermediate 54), potassium carbonate (85 mg, 0.62 mmol), and TBAI (2 mg, 0.02 mmol). The reaction was heated at 50° C. overnight. The mixture was cooled and partitioned between ethyl acetate and water. The combined organic layer was dried over sodium sulfate, filtered and concentrated to give a crude product which was used without purification. LCMS retention time 1.704 min; LCMS MH$^+$-THP 470.

Step 4 8-(cyclopentyloxy)-1-(3-hydroxypropyl)-3-methyl-7-((4-methylthiazol-2-yl)methyl)-1H-purine-2,6(3H,7H)-dione

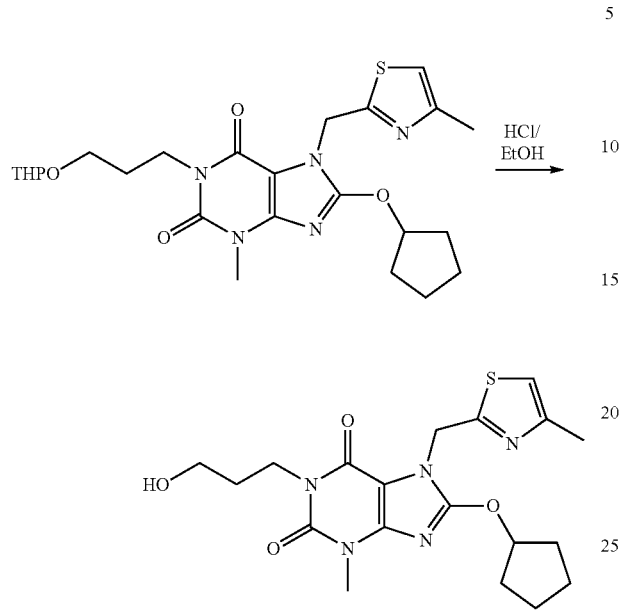

The title compound was prepared using the method of example 48, step 2 to give 8-(cyclopentyloxy)-1-(3-hydroxypropyl)-3-methyl-7-((4-methylthiazol-2-yl)methyl)-1H-purine-2,6(3H,7H)-dione (60 mg, 60.4% yield) as a white solid. $^1$H-NMR (CDCl$_3$) δ 6.84 (d. 1H), 5.55 (s, 2H), 5.46-5.50 (m, 1H), 4.19 (t, 2H), 3.69 (s, 1H), 3.56 (s, 3H), 3.52 (s, 2H), 2.42 (d, 3H), 1.87-1.97 (m, 6H), 1.62-1.79 (m, 4H). LCMS retention time 2.163 min; LCMS MH$^+$ 420.

The following examples 51a through 51j were prepared following the method of example 50.

Example 51a 7-ethyl-1-(3-hydroxypropyl)-8-isopropoxy-3-methyl-1H-purine-2,6(3H,7H)-dione

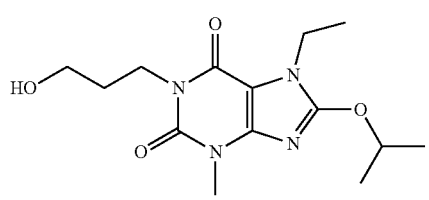 [SMILES: CCn1c(OC(C)C)nc2c1c(=O)n(CCCO)c(=O)n2C]

White solid, 50 mg, 58.8% yield: $^1$H-NMR (DMSO-d$_6$) δ 5.15-5.20 (m, 1H), 4.46 (t, 1H), 4.02 (q, 2H), 3.90 (t, 2H), 3.42 (q, 2H), 3.34 (s, 3H), 1.66-1.70 (m, 2H), 1.38 (d, 6H), 1.25 (t, 3H). LCMS retention time 1.946 min; LCMS MH$^+$ 311.

Example 51b 1-(3-hydroxypropyl)-8-isopropoxy-3-methyl-7-propyl-1H-purine-2,6(3H,7H)-dione

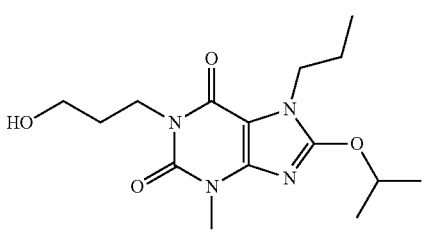 [SMILES: CCCn1c(OC(C)C)nc2c1c(=O)n(CCCO)c(=O)n2C]

White solid, 39 mg, 44.3% yield: $^1$H-NMR (DMSO-d$_6$) δ 5.15-5.21 (m, 1H), 4.46 (t, 1H), 3.95 (t, 2H), 3.90 (t, 2H), 3.41 (q, 2H), 3.37 (s, 3H), 1.64-1.71 (m, 4H), 1.37 (d, 6H), 0.81 (t, 3H). LCMS retention time 2.149 min; LCMS MH$^+$ 325.

Example 51c 7-benzyl-1-(3-hydroxypropyl)-8-isopropoxy-3-methyl-1H-purine-2,6(3H,7H)-dione

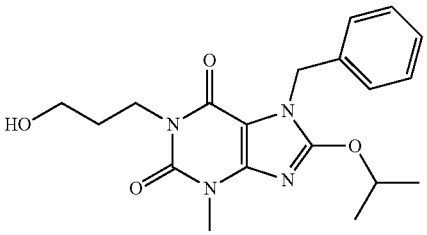 [SMILES: CC(C)Oc1nc2c(c(=O)n(CCCO)c(=O)n2C)n1Cc1ccccc1]

White solid, 26 mg, 31.7% yield: $^1$H-NMR (CDCl$_3$) δ 7.40-7.42 (dd, 2H), 7.28-7.36 (m, 3H), 5.27 (s, 2H), 4.17-4.20 (t, 2H), 3.77 (m, 1H), 3.51 (m, 5H), 1.88-1.92 (m, 2H), 1.43-4.44 (d, 6H). LCMS retention time 2.336 min; LCMS MH$^+$ 373.

Example 51d 1-(3-hydroxypropyl)-8-isopropoxy-3-methyl-7-((6-methylpyridin-3-yl)methyl)-1H-purine-2,6(3H,7H)-dione

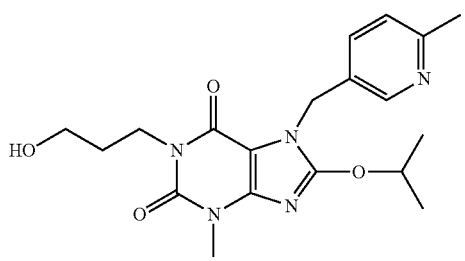 [SMILES: Cc1ccc(Cn2c(OC(C)C)nc3c2c(=O)n(CCCO)c(=O)n3C)cn1]

White solid, 50 mg, 30.4% yield: $^1$H-NMR (DMSO-d$_6$) δ 8.47 (s, 1H), 7.78-7.76 (dd, 1H), 7.31-7.29 (d, 1H), 5.32 (s, 3H), 4.11-4.08 (t, 2H), 3.62-3.59 (t, 2H), 3.50 (s, 3H), 2.52 (s, 3H), 1.88-1.85 (m, 2H), 1.45-1.44 (d, 6H). LCMS retention time 1.581 min; LCMS MH$^+$ 388.

Example 51e 8-ethoxy-1-(3-hydroxypropyl)-3-methyl-7-((6-methylpyridin-3-yl)methyl)-1H-purine-2,6(3H,7H)-dione

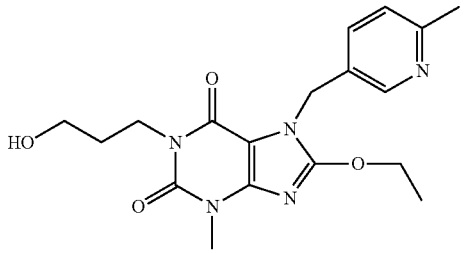 [SMILES: CCOc1nc2c(c(=O)n(CCCO)c(=O)n2C)n1Cc1ccc(C)nc1]

White solid, 17 mg, 28.7% yield: $^1$H-NMR (DMSO-d$_6$) δ 8.47 (s, 1H), 7.75-7.78 (dd, 1H), 7.28-7.30 (d, 1H), 5.32 (s, 3H), 4.58-4.63 (q, 2H), 4.07-4.10 (t, 2H), 3.58-3.61 (t, 2H), 3.49 (s, 3H), 2.52 (s, 3H), 1.84-1.88 (q, 2H), 1.45-1.48 (t, 3H). LCMS retention time 1.371 min; LCMS MH$^+$ 374.

Example 51f 8-ethoxy-1-(3-hydroxypropyl)-3-methyl-7-((5-methyloxazol-2-yl)methyl)-1H-purine-2,6(3H,7H)-dione

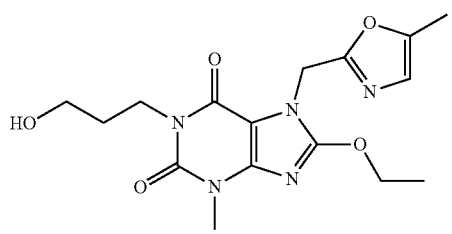 [SMILES: CCOc1nc2c(c(=O)n(CCCO)c(=O)n2C)n1Cc1ncc(C)o1]

White solid, 19 mg, 30.6% yield: $^1$H-NMR (DMSO-d$_6$) δ 6.73 (s, 1H), 5.42 (s, 2H), 4.57-4.62 (q, 2H), 4.04-4.07 (t, 2H), 3.56-3.59 (t, 2H), 3.53 (s, 3H), 2.31 (s, 3H), 1.82-1.86 (q, 2H), 1.40-1.44 (t, 3H). LCMS retention time 1.516 min; LCMS MH$^+$ 364.

Example 51g 7-((5-chloropyridin-2-yl)methyl)-8-ethoxy-1-(3-hydroxypropyl)-3-methyl-1H-purine-2,6(3H,7H)-dione

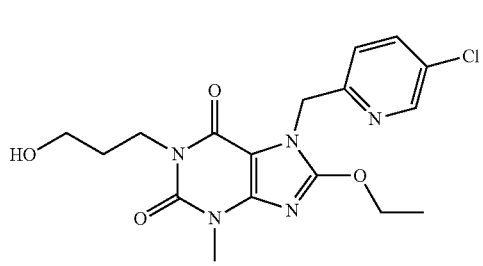

White solid, 13 mg, 31.2% yield: $^1$H-NMR (CDCl$_3$) δ 8.49 (s, 1H), 7.64-7.66 (dd, 1H), 7.20-7.22 (d, 1H), 5.40 (s, 2H), 4.55-4.60 (q, 2H), 4.14-4.16 (t, 2H), 3.59-3.61 (t, 1H), 3.56 (s, 3H), 3.46-3.49 (t, 3H), 1.86-1.88 (m, 2H), 1.40-1.42 (t, 2H). LCMS retention time 1.896 min; LCMS MH$^+$ 394.

Example 51h 8-(cyclopentylmethoxy)-7-ethyl-1-(3-hydroxypropyl)-3-methyl-1H-purine-2,6(3H,7H)-dione

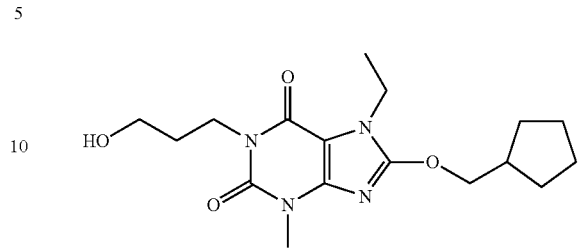

Light yellow solid, 11 mg, 20.7% yield: $^1$H-NMR (DMSO-d$_6$) δ 4.45-4.35 (t, 1H), 4.35-4.33 (d, 2H), 4.07-4.02 (m, 2H), 3.92-3.88 (t, 2H), 3.45-3.40 (q, 2H), 3.30 (s, 3H), 2.39-2.32 (m, 1H), 1.80-1.52 (m, 8H), 1.37-1.24 (m, 5H). LCMS retention time 2.485 min; LCMS MH$^+$ 351.

Example 51i 8-(cyclopentylmethoxy)-1-(3-hydroxypropyl)-3-methyl-7-propyl-1H-purine-2,6(3H,7H)-dione

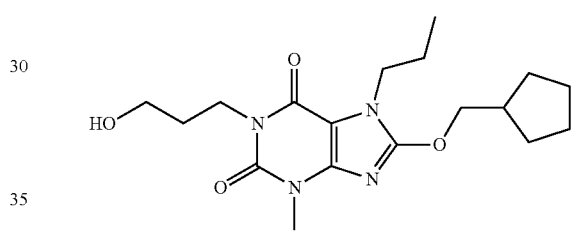

White solid, 16 mg, 31.5% yield: $^1$H-NMR (DMSO-d$_6$) δ 4.45-4.34 (t, 1H), 4.35-4.33 (d, 2H), 3.99-3.96 (t, 2H), 3.91-3.88 (t, 2H), 3.44-3.40 (m, 2H), 3.37 (s, 3H), 2.37-2.34 (m, 1H), 1.78-1.52 (m, 8H), 1.35-1.31 (m, 2H), 0.84-0.80 (t, 3H). LCMS retention time 2.670 min; LCMS MH$^+$ 365.

Example 51j 8-(cyclopentylmethoxy)-1-(3-hydroxypropyl)-3-methyl-7-((6-methylpyridin-3-yl)methyl)-1H-purine-2,6(3H,7H)-dione

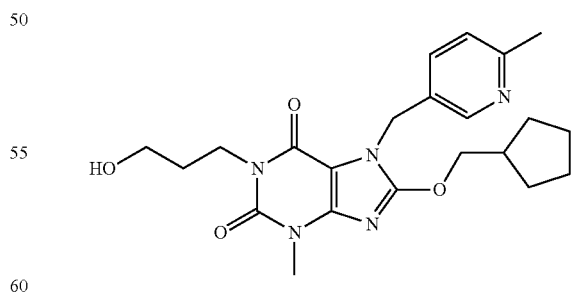

White solid, 25 mg, 49.9% yield: $^1$H-NMR (DMSO-d$_6$) δ 8.43 (s, 1H), 7.61-7.58 (dd, 1H), 7.24-7.22 (d, 1H), 5.22 (s, 2H), 4.47-4.44 (t, 1H), 4.35-4.34 (d, 2H), 3.93-3.89 (t, 2H), 3.45-3.38 (m, 2H), 3.35 (s, 3H), 2.33 (s, 3H), 2.13-2.11 (m, 1H), 1.70-1.51 (m, 8H), 1.28-1.25 (m, 2H). LCMS retention time 1.761 min; LCMS MH$^+$ 428.

Example 52 7-(4-chlorobenzyl)-1-(3-hydroxypropyl)-3-methyl-8-(6-methylpyridin-3-yloxy)-1H-purine-2,6(3H,7H)-dione hydrochloride

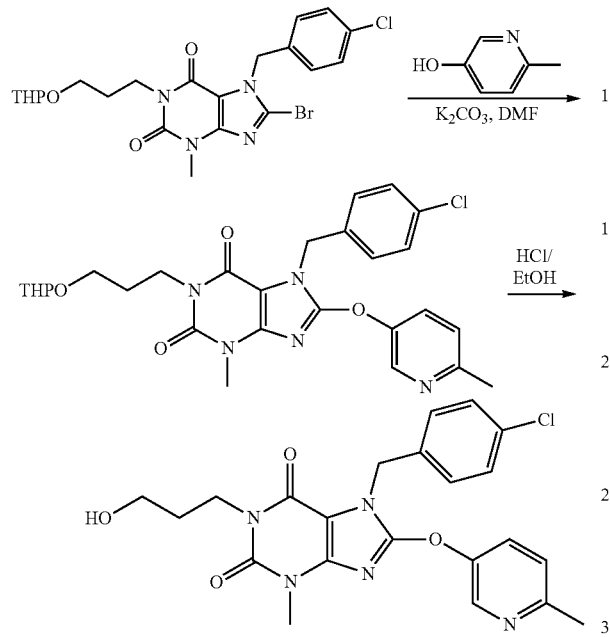

Step 1 7-(4-chlorobenzyl)-3-methyl-8-(6-methylpyridin-3-yloxy)-1-(3-(tetrahydro-2H-pyran-2-yloxy)propyl)-1H-purine-2,6(3H,7H)-dione

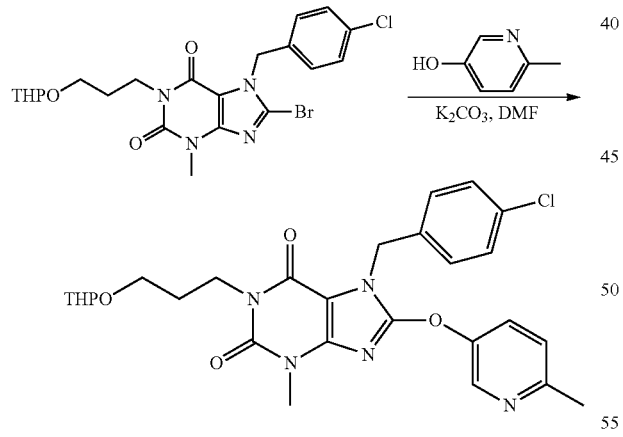

To a solution of 8-bromo-7-(4-chlorobenzyl)-3-methyl-1-(3-(tetrahydro-2H-pyran-2-yloxy)propyl)-1H-purine-2,6(3H,7H)-dione (100 mg, 0.195 mmol, intermediate 14) in DMF (5 mL) was added 6-methylpyridin-3-ol (24 mg, 0.22 mmol) followed by potassium carbonate (76 mg, 0.55 mmol) and the mixture was stirred at 85° C. for 3 h. The mixture was cooled and partitioned between ethyl acetate and brine. The layers were separated and the organic layer was washed with saturated aqueous ammonium chloride, dried and concentrated to give 7-(4-chlorobenzyl)-3-methyl-8-(6-methylpyridin-3-yloxy)-1-(3-(tetrahydro-2H-pyran-2-yloxy)propyl)-1H-purine-2,6(3H,7H)-dione (79 mg, 75% yield) as yellow solid. LCMS retention time 2.297 min; LCMS MH$^+$-THP 456.

Step 2 7-(4-chlorobenzyl)-1-(3-hydroxypropyl)-3-methyl-8-(6-methylpyridin-3-yloxy)-1H-purine-2,6(3H,7H)-dione

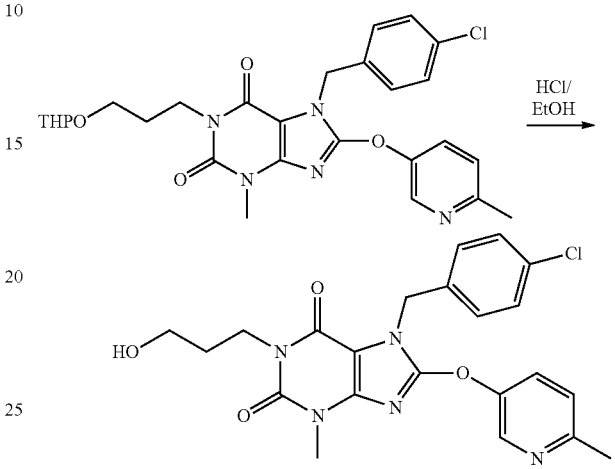

A solution of 7-(4-chlorobenzyl)-3-methyl-8-(6-methylpyridin-3-yloxy)-1-(3-(tetrahydro-2H-pyran-2-yloxy)propyl)-1H-purine-2,6(3H,7H)-dione (79 mg, 0.146 mmol) in 1N ethanolic HCl (3 mL) was stirred at room temperature for 2 h. The mixture was concentrated to dryness to give a crude product, which was purified via preparative HPLC to give 7-(4-chlorobenzyl)-1-(3-hydroxypropyl)-3-methyl-8-(6-methylpyridin-3-yloxy)-1H-purine-2,6(3H,7H)-dione (35 mg, 52.6% yield) as white solid. $^1$H-NMR (DMSO-d$_6$) δ 8.69 (s, 1H), 8.03-8.01 (d, 1H), 7.59-7.57 (d, 1H), 7.45 (s, 4H), 5.45 (s, 2H), 4.06-3.98 (m, 2H), 3.45-3.42 (t, 2H), 3.28 (s, 3H), 2.59 (s, 3H), 1.71-1.67 (t, 2H). LCMS retention time 2.207 min; LCMS MH$^+$ 456.

The following examples 53a and 53b were prepared using the method of example 52.

Example 53a 7-(4-chlorobenzyl)-1-(3-hydroxypropyl)-3-methyl-8-(2-methylpyridin-4-yloxy)-1H-purine-2,6(3H,7H)-dione hydrochloride

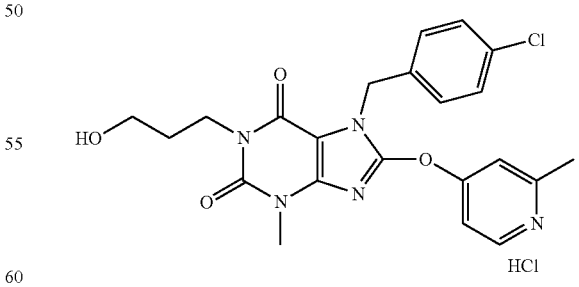

White solid, isolated as the HCl salt, 30 mg, 36.6% yield: $^1$H-NMR (DMSO-d$_6$) δ 8.48-8.46 (d, 1H), 8.17 (s, 1H), 7.43-7.33 (m, 4H), 7.26-7.22 (m, 2H), 5.42 (s, 2H), 4.52 (s, 1H), 3.95-3.92 (t, 2H), 3.44-3.42 (m, 2H), 3.37 (s, 3H), 2.47 (s, 3H), 1.72-1.69 (t, 2H). LCMS retention time 1.716 min; LCMS MH$^+$ 456.

Example 53b 7-(4-chlorobenzyl)-1-(3-hydroxypropyl)-3-methyl-8-(5-methylpyridin-3-yloxy)-1H-purine-2,6(3H,7H)-dione

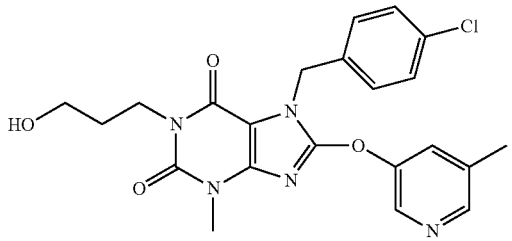 [SMILES: Cc1cncc(Oc2nc3c(c(=O)n(CCCO)c(=O)n3C)n2Cc2ccc(Cl)cc2)c1]

White solid, 40 mg, 48.8% yield: $^1$H-NMR (DMSO-d$_6$) δ 8.45-8.44 (d, 1H), 8.36 (s, 1H), 7.65 (s, 1H), 7.46-7.41 (m, 4H), 5.44 (s, 2H), 4.50-4.47 (t, 1H), 3.94-3.91 (t, 2H), 3.46-3.40 (m, 2H), 3.28 (s, 3H), 2.34 (s, 3H), 1.73-1.66 (m, 2H). LCMS retention time 2.259 min; LCMS MH$^+$ 456.

Example 54 7-butyl-1-(3-hydroxypropyl)-3-methyl-8-(5-methylpyridin-3-yloxy)-1H-purine-2,6(3H,7H)-dione

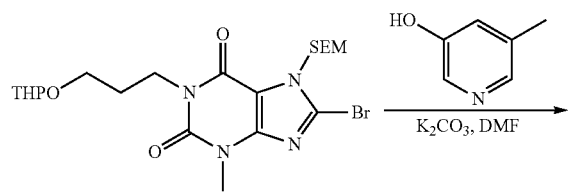

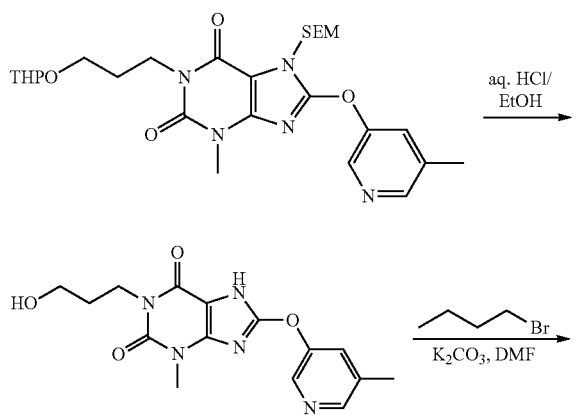

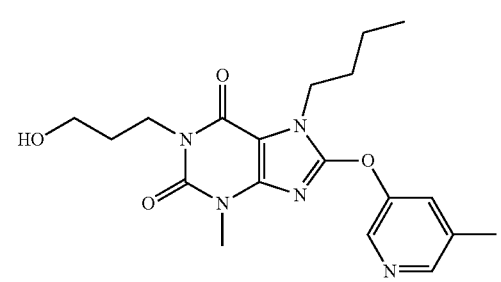

Step 1 3-methyl-8-(5-methylpyridin-3-yloxy)-1-(3-(tetrahydro-2H-pyran-2-yloxy)propyl)-7-((2-(trimethylsilyl)ethoxy)methyl)-1H-purine-2,6(3H,7H)-dione

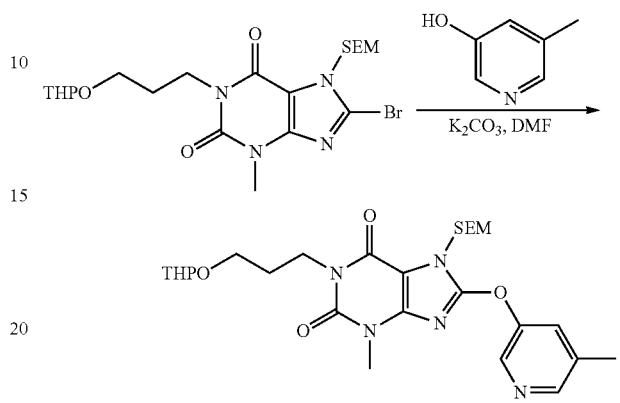

The title compound was prepared using the method of example 52, step 1 from intermediate 16, step 1 to give 3-methyl-8-(5-methylpyridin-3-yloxy)-1-(3-(tetrahydro-2H-pyran-2-yloxy)propyl)-7-((2-(trimethylsilyl)ethoxy)methyl)-1H-purine-2,6(3H,7H)-dione (300 mg, 97.6% yield) as yellow oil. LCMS retention time 1.838 min; LCMS M-THP+H 462.

Step 2 7-(4-chlorobenzyl)-1-(3-hydroxybutyl)-3-methyl-8-(6-methylpyridin-3-yloxy)-1H-purine-2,6(3H,7H)-dione

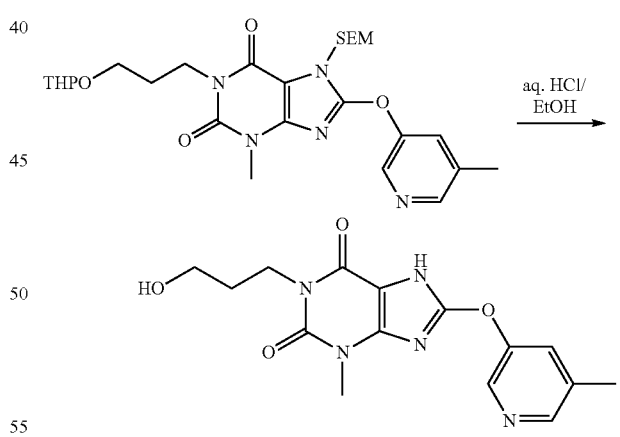

To a solution of 3-methyl-8-(5-methylpyridin-3-yloxy)-1-(3-(tetrahydro-2H-pyran-2-yloxy)propyl)-7-((2-(trimethylsilyl)ethoxy)methyl)-1H-purine-2,6(3H,7H)-dione (300 mg, 0.554 mmol) in ethyl alcohol (10 mL) was added concentrated HCl (3 mL) and the mixture was stirred for 6 h at reflux. The mixture was cooled, concentrated and filtered to give 7-(4-chlorobenzyl)-1-(3-hydroxybutyl)-3-methyl-8-(6-methylpyridin-3-yloxy)-1H-purine-2,6(3H,7H)-dione (159 mg, 86.6% yield) as yellow solid. LCMS retention time 0.356 min; LCMS MH$^+$ 332.

Step 3 7-butyl-1-(3-hydroxypropyl)-3-methyl-8-(5-methylpyridin-3-yloxy)-1H-purine-2,6(3H,7H)-dione

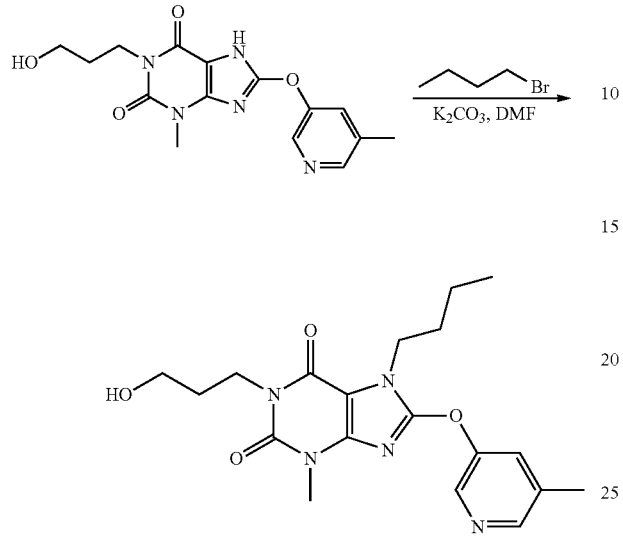

The title compound was prepared using the method of example 44, step 3 to give 7-butyl-1-(3-hydroxypropyl)-3-methyl-8-(5-methylpyridin-3-yloxy)-1H-purine-2,6(3H,7H)-dione (30 mg, 42.8% yield) as white solid. $^1$H-NMR (DMSO-d$_6$)=8.48-8.47 (d, 1H), 8.37-8.36 (d, 1H), 7.71 (s, 1H), 4.51-4.48 (t, 1H), 4.22-4.19 (t, 2H), 3.94-3.91 (t, 2H), 3.46-3.43 (t, 2H), 3.28 (s, 3H), 2.36 (s, 3H), 1.81-1.66 (m, 4H), 1.35-1.30 (m, 2H), 0.93-0.89 (t, 3H). LCMS retention time 1.854 min; LCMS MH$^+$ 388.

Example 55 8-(3-fluorophenoxy)-1-(3-hydroxypropyl)-3-methyl-7-((5-methylthiazol-2-yl)methyl)-1H-purine-2,6(3H,7H)-dione

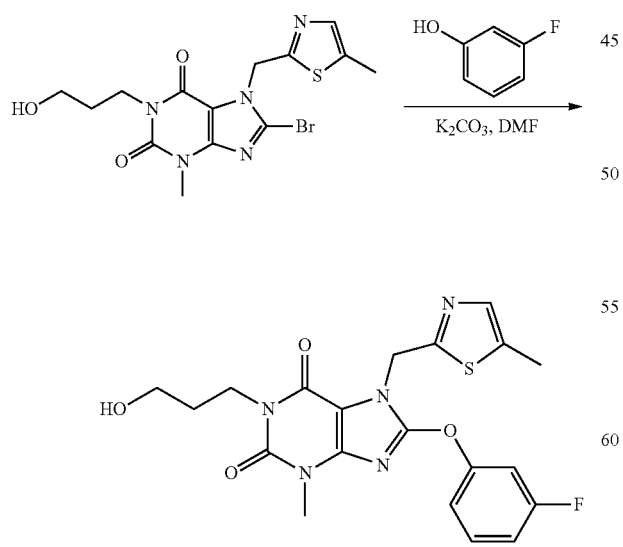

To a solution of 8-bromo-1-(3-hydroxypropyl)-3-methyl-7-((5-methylthiazol-2-yl)methyl)-1H-purine-2,6(3H,7H)-dione (50 mg, 0.12 mmol, intermediate 16) in DMF (3 mL) was added 3-fluorophenol (23 mg, 0.17 mmol) and potassium carbonate (75 g, 0.24 mmol). The mixture was stirred at 80° C. for 12 h. The mixture was cooled and partitioned between ethyl acetate and water. The organic phase was washed with brine, dried over sodium sulfate, filtered and concentrated to give a crude product which was purified by preparative HPLC to give 8-(3-fluorophenoxy)-1-(3-hydroxypropyl)-3-methyl-7-((5-methylthiazol-2-yl)methyl)-1H-purine-2,6(3H,7H)-dione (11 mg, 20.75% yield) as white solid. $^1$H-NMR (CD$_3$OD) δ 7.42-7.48 (m, 2H), 7.18-7.22 (m, 2H), 7.06-7.10 (m, 1H), 5.76 (s, 2H), 4.10 (t, 2H), 3.61 (t, 2H), 3.45 (s, 3H), 2.47 (d, 3H), 1.85-1.90 (m, 2H). LCMS retention time 1.273 min; LCMS MH$^+$ 446.

The following examples 56a through 56i were prepared using the method of example 55.

Example 56a 8-(3-chlorophenoxy)-1-(3-hydroxypropyl)-3-methyl-7-((5-methylthiazol-2-yl)methyl)-1H-purine-2,6(3H,7H)-dione

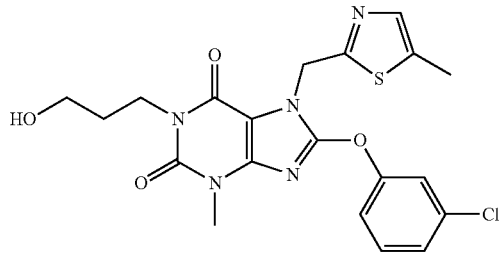 [SMILES: Cc1cnc(Cn2c(Oc3cccc(Cl)c3)nc3c2c(=O)n(CCCO)c(=O)n3C)s1]

White solid, 17 mg, 30.9% yield: $^1$H-NMR (CD$_3$OD) δ 7.42-7.47 (m, 3H), 7.30-7.35 (m, 2H), 5.76 (s, 2H), 4.10 (t, 2H), 3.61 (t, 2H), 3.44 (s, 3H), 2.48 (d, 3H), 1.85-1.90 (m, 2H). LCMS retention time 2.246 min; LCMS MH$^+$ 462.

Example 56b 1-(3-hydroxypropyl)-3-methyl-7-((5-methylthiazol-2-yl)methyl)-8-(m-tolyloxy)-1H-purine-2,6(3H,7H)-dione

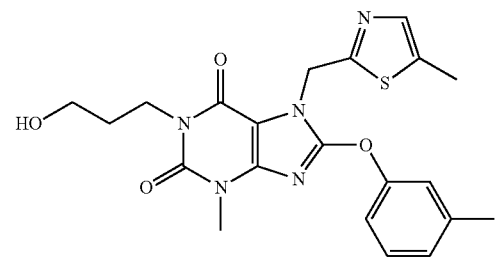 [SMILES: Cc1cccc(Oc2nc3c(c(=O)n(CCCO)c(=O)n3C)n2Cc2ncc(C)s2)c1]

White solid, 25 mg, 47.1% yield: $^1$H-NMR (CD$_3$OD) δ 7.42 (d, 1H), 7.29-7.34 (m, 1H), 7.09-7.13 (m, 3H), 5.75 (s, 2H), 4.10 (t, 2H), 3.61 (t, 2H), 3.43 (s, 3H), 2.48 (d, 3H), 2.38 (s, 3H), 1.84-1.91 (m, 2H). LCMS retention time 2.199 min; LCMS MH$^+$ 442.

Example 56c 1-(3-hydroxypropyl)-8-(3-methoxyphenoxy)-3-methyl-7-((5-methylthiazol-2-yl)methyl)-1H-purine-2,6(3H,7H)-dione

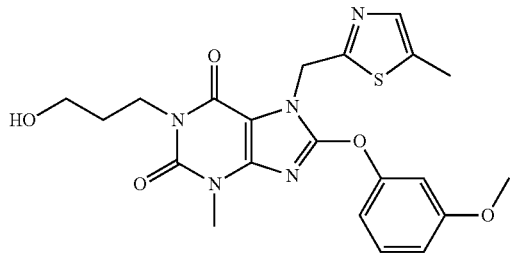 [SMILES: COc1cccc(Oc2nc3c(c(=O)n(CCCO)c(=O)n3C)n2Cc2ncc(C)s2)c1]

White solid, 18 mg, 47.1% yield: $^1$H-NMR (CD$_3$OD) δ 7.41 (d, 1H), 7.33 (t, 1H), 6.85-6.91 (m, 3H), 5.74 (s, 2H), 4.09 (t, 2H), 3.81 (s, 3H), 3.61 (t, 2H), 3.43 (s, 3H), 2.47 (d, 3H), 1.84-1.90 (m, 2H). LCMS retention time 2.092 min; LCMS MH$^+$ 458.

Example 56d 1-(3-hydroxypropyl)-3-methyl-7-((5-methylthiazol-2-yl)methyl)-8-(3-(trifluoromethyl)phenoxy)-1H-purine-2,6(3H,7H)-dione

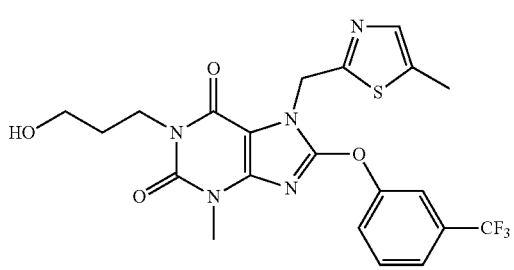 [SMILES: Cc1cnc(Cn2c(Oc3cccc(C(F)(F)F)c3)nc3c2c(=O)n(CCCO)c(=O)n3C)s1]

White solid, 45 mg, 47.1% yield: $^1$H-NMR (CD$_3$OD) δ 7.64-7.71 (m, 4H), 7.41 (d, 1H), 5.78 (s, 2H), 4.10 (t, 2H), 3.61 (t, 2H), 3.45 (s, 3H), 2.47 (d, 3H), 1.85-1.91 (m, 2H). LCMS retention time 2.349 min; LCMS MH$^+$ 496.

Example 56e 8-(4-fluorophenoxy)-1-(3-hydroxypropyl)-3-methyl-7-((5-methylthiazol-2-yl)methyl)-1H-purine-2,6(3H,7H)-dione

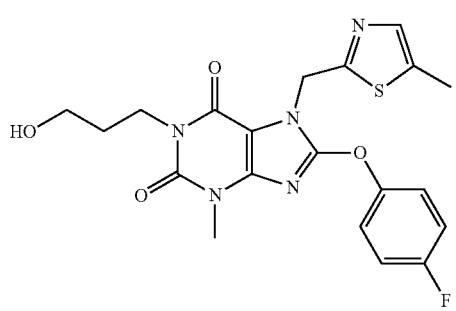 [SMILES: Cc1cnc(Cn2c(Oc3ccc(F)cc3)nc3c2c(=O)n(CCCO)c(=O)n3C)s1]

White solid, 23 mg, 43.4% yield: $^1$H-NMR (CD$_3$OD) δ 7.42 (d, 1H), 7.35-7.39 (m, 2H), 7.17-7.22 (m, 2H), 5.76 (s, 2H), 4.10 (t, 2H), 3.61 (t, 2H), 3.45 (s, 3H), 2.48 (d, 3H), 1.85-1.90 (m, 2H). LCMS retention time 2.108 min; LCMS MH$^+$ 446.

Example 56f 1-(3-hydroxypropyl)-3-methyl-7-((5-methylthiazol-2-yl)methyl)-8-(4-(trifluoromethyl)phenoxy)-1H-purine-2,6(3H,7H)-dione

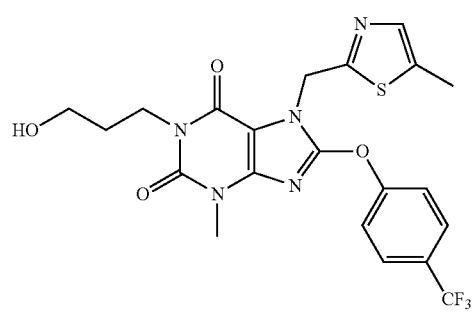 [SMILES: Cc1cnc(Cn2c(Oc3ccc(C(F)(F)F)cc3)nc3c2c(=O)n(CCCO)c(=O)n3C)s1]

White solid, 20 mg, 40.4% yield: $^1$H-NMR (CD$_3$OD) δ 7.78 (d, 2H), 7.57 (d, 2H), 7.41 (d, 1H), 5.78 (s, 2H), 4.10 (t, 2H), 3.61 (t, 2H), 3.45 (s, 3H), 2.48 (d, 3H), 1.85-1.90 (m, 2H). LCMS retention time 2.386 min; LCMS MH$^+$ 496.

Example 56g 1-(3-hydroxypropyl)-3-methyl-7-((5-methylthiazol-2-yl)methyl)-8-(4-(trifluoromethoxy)phenoxy)-1H-purine-2,6(3H,7H)-dione

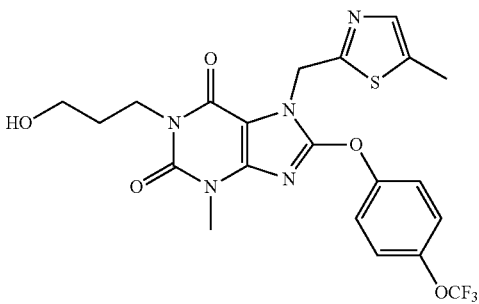 [SMILES: Cc1cnc(Cn2c(Oc3ccc(OC(F)(F)F)cc3)nc3c2c(=O)n(CCCO)c(=O)n3C)s1]

White solid, 19 mg, 31.1% yield: $^1$H-NMR (CD$_3$OD) δ 7.46-7.49 (m, 2H), 7.38-7.42 (m, 3H), 5.77 (s, 2H), 4.10 (t, 2H), 3.61 (t, 2H), 3.44 (s, 3H), 2.47 (s, 3H), 1.85-1.90 (m, 2H). LCMS retention time 2.432 min; LCMS MH$^+$ 512.

Example 56h 8-(4-chlorophenoxy)-1-(3-hydroxypropyl)-3-methyl-7-((5-methylthiazol-2-yl)methyl)-1H-purine-2,6(3H,7H)-dione

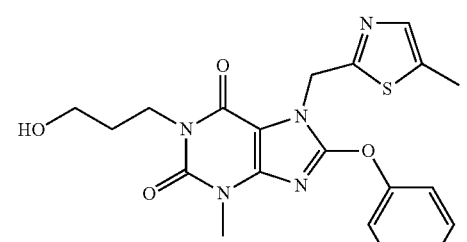

White solid, 15 mg, 31.1% yield: $^1$H-NMR (CD$_3$OD) δ 7.42-7.48 (m, 3H), 7.35-7.38 (m, 2H), 5.76 (s, 2H), 4.10 (t, 2H), 3.61 (t, 2H), 3.43 (s, 3H), 2.48 (d, 3H), 1.85-1.91 (m, 2H). LCMS retention time 2.273 min; LCMS MH+ 462.

Example 56i 1-(3-hydroxypropyl)-8-(4-methoxy-phenoxy)-3-methyl-7-((5-methylthiazol-2-yl)methyl)-1H-purine-2,6(3H,7H)-dione

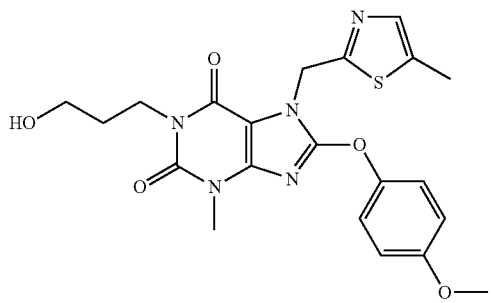 [SMILES: COc1ccc(Oc2nc3c(c(=O)n(CCCO)c(=O)n3C)n2Cc2ncc(C)s2)cc1]

White solid, 13 mg, 31.1% yield: $^1$H-NMR (CD$_3$OD) δ 7.42 (d, 1H), 7.23 (dd, 2H), 6.98 (dd, 2H), 5.74 (s, 2H), 4.09 (t, 2H), 3.82 (s, 3H), 3.60 (t, 2H), 3.42 (s, 3H), 2.48 (d, 3H), 1.85-1.90 (m, 2H). LCMS retention time 2.104 min; LCMS MH+ 458.

Example 57 8-ethoxy-1-(3-hydroxypropyl)-3-methyl-7-((5-methylthiazol-2-yl)methyl)-1H-purine-2,6(3H,7H)-dione

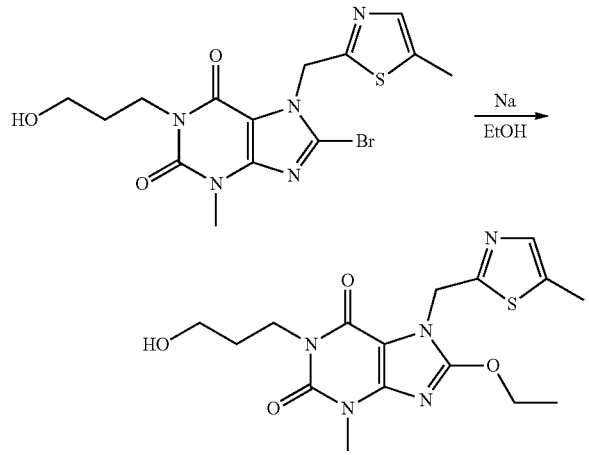

To a solution of 8-bromo-1-(3-hydroxypropyl)-3-methyl-7-((5-methylthiazol-2-yl)methyl)-1H-purine-2,6(3H,7H)-dione (50 mg, 0.12 mmol, intermediate 16) in ethanol (2 mL) was added sodium (10 mg, 0.4 mmol). The mixture was stirred at room temperature for 2 h. The reaction was concentrated and the residue was purified by preparative HPLC to give 8-ethoxy-1-(3-hydroxypropyl)-3-methyl-7-((5-methylthiazol-2-yl)methyl)-1H-purine-2,6(3H,7H)-dione (27 mg, 59.3%) as white solid. $^1$H-NMR (CD$_3$OD) δ 7.38 (d, 1H), 5.55 (s, 2H), 4.60 (q, 2H), 4.09 (t, 2H), 3.59 (t, 2H), 3.52 (s, 3H), 2.45 (d, 3H), 1.83-1.88 (m, 2H), 1.43 (d, 3H). LCMS retention time 1.680 min; LCMS MH+ 380.

Example 58 7-ethyl-1-(3-hydroxypropyl)-3-methyl-8-((5-methylthiazol-2-yl)methoxy)-1H-purine-2,6(3H,7H)-dione

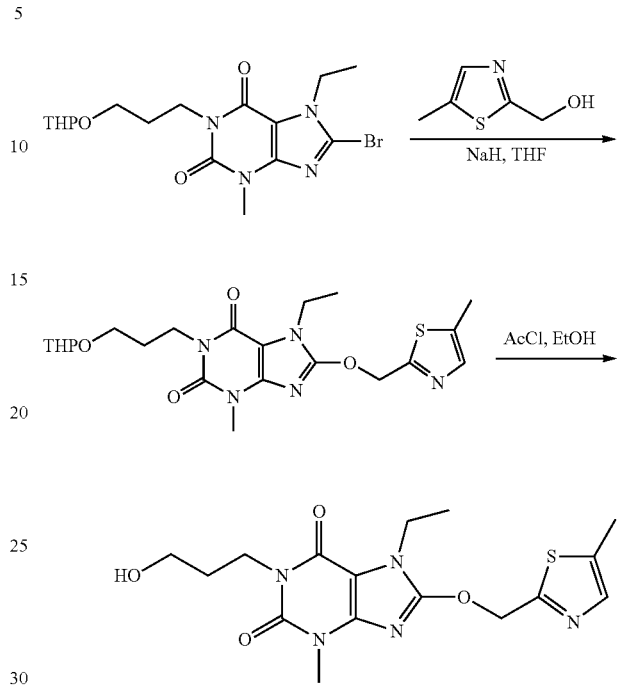

The title compound was prepared using the 2 step method of example 36 from intermediate 6. The product was purified via preparative HPLC to give 7-ethyl-1-(3-hydroxypropyl)-3-methyl-8-((5-methylthiazol-2-yl)methoxy)-1H-purine-2,6(3H,7H)-dione (5 mg, 6.9% yield) as white solid. $^1$H-NMR (DMSO-d$_6$) δ 7.53 (s, 1H), 5.76 (s, 2H), 4.18 (q, 2H), 4.10 (t, 2H), 3.61 (t, 2H), 3.54 (s, 3H), 2.52 (s, 3H), 1.80-1.90 (m, 2H), 1.36 (t, 3H). LCMS retention time 1.760 min; LCMS MH+ 380.

Example 59 7-benzyl-1-(3-hydroxypropyl)-8-(3-(trifluoromethoxy)phenoxy)-1H-purine-2,6(3H,7H)-dione

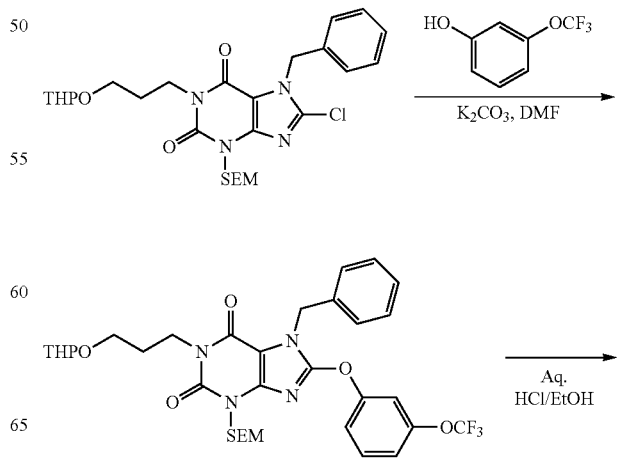

-continued

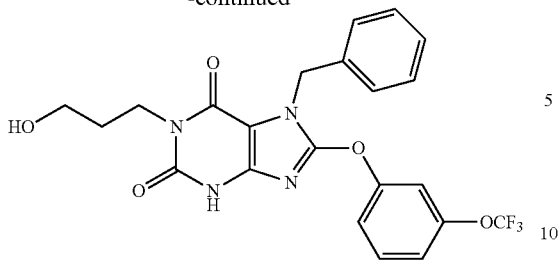

Step 1 7-benzyl-1-(3-(tetrahydro-2H-pyran-2-yloxy)propyl)-8-(3-(trifluoromethoxy)phenoxy)-3-((2-(trimethylsilyl)ethoxy)methyl)-1H-purine-2,6(3H,7H)-dione

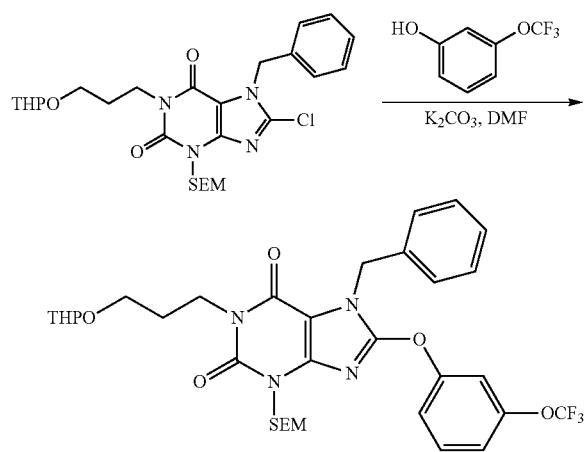

To a solution of 7-benzyl-8-chloro-1-(3-(tetrahydro-2H-pyran-2-yloxy)propyl)-3-((2-(trimethylsilyl)ethoxy)methyl)-1H-purine-2,6(3H,7H)-dione (4.7 g, 8.58 mmol, intermediate 18) in DMF (15 mL) was added 3-(trifluoromethoxy)phenol (1.83 g, 10.28 mmol) and potassium carbonate (2.4 g, 17.39 mmol). The mixture was stirred at 80° C. overnight. The mixture was diluted with ethyl acetate and water, and the phases were separated. The organic phase was washed with brine, dried over sodium sulfate, filtered and concentrated to give 7-benzyl-1-(3-(tetrahydro-2H-pyran-2-yloxy)propyl)-8-(3-(trifluoromethoxy)phenoxy)-3-((2-(trimethylsilyl)ethoxy)methyl)-1H-purine-2,6(3H,7H)-dione (5.3 g, 89.3% yield) as yellow oil. LCMS retention time 3.974 min; LCMS M+Na 713.

Step 2 7-benzyl-1-(3-hydroxypropyl)-8-(3-(trifluoromethoxy)phenoxy)-1H-purine-2,6(3H,7H)-dione

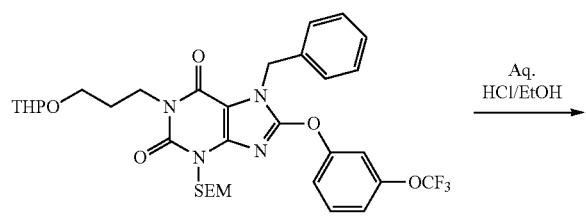

-continued

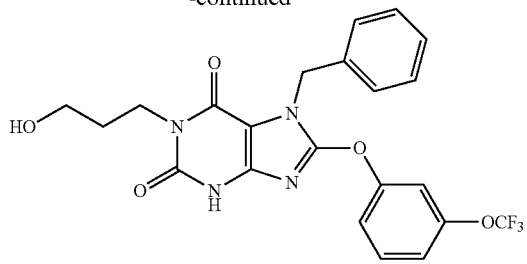

To a solution of 7-benzyl-1-(3-(tetrahydro-2H-pyran-2-yloxy)propyl)-8-(3-(trifluoromethoxy)phenoxy)-3-((2-(trimethylsilyl)ethoxy)methyl)-1H-purine-2,6(3H,7H)-dione (5.3 g, 7.68 mmol) in ethyl alcohol (20 mL) was added concentrated HCl (5 mL). The reaction was stirred at 80° C. overnight. The reaction was concentrated and the residue was neutralized with saturated sodium bicarbonate. This aqueous phase was extracted with ethyl acetate and the phases were separated. The organic phase was washed with brine, dried over sodium sulfate, filtered and concentrated to give 7-benzyl-1-(3-hydroxypropyl)-8-(3-(trifluoromethoxy)phenoxy)-1H-purine-2,6(3H,7H)-dione (4.5 g, 100% yield) as white solid. $^1$H-NMR (DMSO-$d_6$) δ 11.93 (s, 1H), 7.62-7.57 (t, 1H), 7.44-7.32 (m, 8H), 5.42 (s, 2H), 4.49-4.46 (t, 1H), 3.89-3.86 (t, 2H), 3.46-3.41 (m, 2H), 1.72-1.65 (m, 2H). LCMS retention time 2.560 min; LCMS MH$^+$ 477.

Example 60 7-benzyl-3-ethyl-1-(3-hydroxypropyl)-8-(3-(trifluoromethoxy)phenoxy)-1H-purine-2,6(3H,7H)-dione

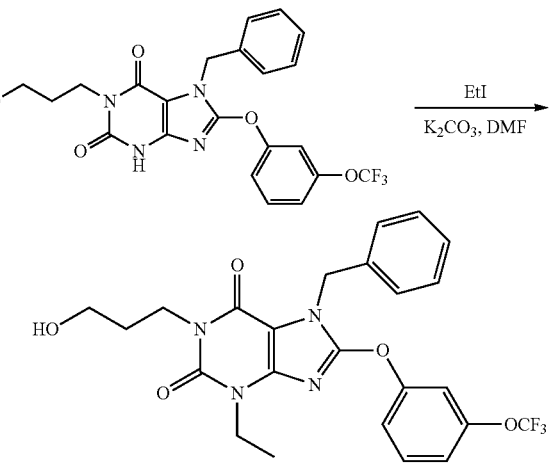

To a solution of 7-benzyl-1-(3-hydroxypropyl)-8-(3-(trifluoromethoxy)phenoxy)-1H-purine-2,6(3H,7H)-dione (1.2 g, 2.52 mmol, example 59) in DMF (5 mL) was added iodoethane (0.7 g, 4.49 mmol), followed by potassium carbonate (0.7 g, 5.07 mmol). The reaction was stirred at 80° C. for 2 h; then it was cooled and partitioned between ethyl acetate and water. The phases were separated and the organic phase was washed with brine. The organic layer was dried over sodium sulfate, filtered and concentrated to give 7-benzyl-3-ethyl-1-(3-hydroxypropyl)-8-(3-(trifluoromethoxy)phenoxy)-1H-purine-2,6(3H,7H)-dione (0.62 g, 49.2% yield) as yellow solid. $^1$H-NMR (DMSO-$d_6$) δ 7.62-7.57 (t, 1H), 7.50 (s, 1H), 7.42-7.31 (m, 7H), 5.44 (s, 2H), 4.51-4.48 (t, 1H), 3.95-3.85 (m, 4H), 3.47-3.42 (q, 2H), 1.73-1.67 (m, 2H), 1.16-1.13 (t, 3H). LCMS retention time 2.974 min; LCMS MH$^+$ 505.

Example 61 3-ethyl-1-(3-hydroxypropyl)-7-((6-methylpyridin-3-yl)methyl)-8-(3-(trifluoromethoxy)phenoxy)-1H-purine-2,6(3H,7H)-dione

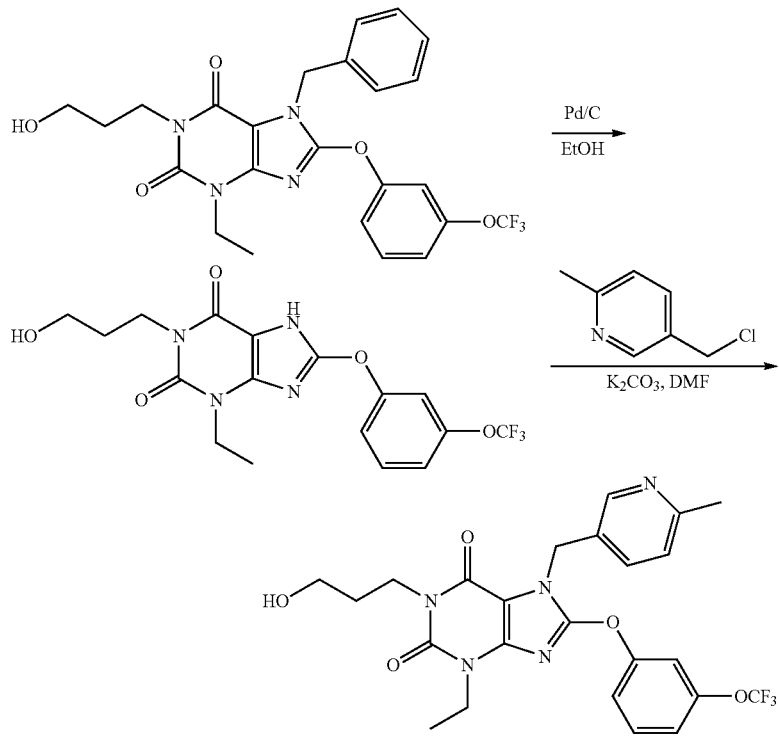

Step 1 3-ethyl-1-(3-hydroxypropyl)-8-(3-(trifluoromethoxy)phenoxy)-1H-purine-2,6(3H,7H)-dione

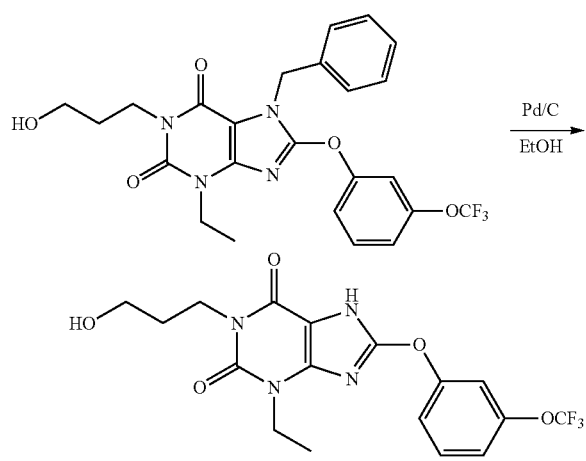

7-benzyl-3-ethyl-1-(3-hydroxypropyl)-8-(3-(trifluoromethoxy)phenoxy)-1H-purine-2,6(3H,7H)-dione (0.62 g, 1.23 mmol, example 60) was dissolved in ethanol (20 mL); then the mixture was degassed and refilled with nitrogen three times. Ammonium formate (0.5 g, 7.94 mmol) and 10% Pd/C (30 mg) were added. The mixture was again degassed and refilled with nitrogen three times; then it was stirred at 80° C. overnight. The reaction was cooled and filtered. The filter cake was washed with methanol. The filtrate was concentrated to give 3-ethyl-1-(3-hydroxypropyl)-8-(3-(trifluoromethoxy)phenoxy)-1H-purine-2,6(3H,7H)-dione (0.6 g, 100% yield) as white solid. $^1$H-NMR (DMSO-$d_6$) δ 7.61-7.57 (t, 1H), 7.50 (s, 1H), 7.40-7.38 (dd, 1H), 7.31-7.29 (d, 1H), 4.50 (s, 1H), 3.95-3.85 (m, 4H), 3.44-3.43 (m, 2H), 1.73-1.66 (t, 2H), 1.17-1.13 (t, 3H). LCMS retention time 1.350 min; LCMS MH$^+$ 415.

Step 2 3-ethyl-1-(3-hydroxypropyl)-7-((6-methylpyridin-3-yl)methyl)-8-(3-(trifluoromethoxy)phenoxy)-1H-purine-2,6(3H,7H)-dione

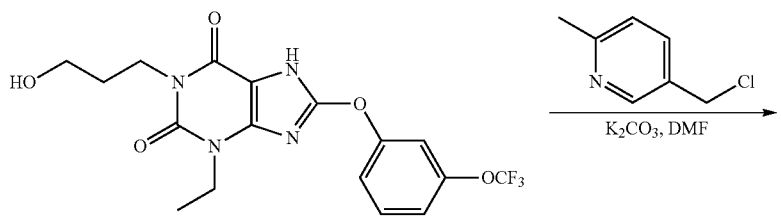

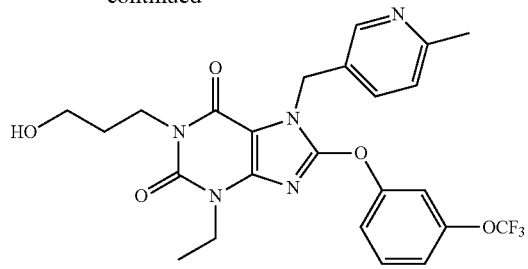

To a solution of 3-ethyl-1-(3-hydroxypropyl)-8-(3-(trifluoromethoxy)phenoxy)-1H-purine-2,6(3H,7H)-dione (110 mg, 0.22 mmol) in DMF (3 mL) was added 5-(chloromethyl)-2-methylpyridine (50 mg, 0.4 mmol), potassium carbonate (91 mg, 0.66 mmol), and TBAI (2 mg, 0.02 mmol). The reaction was heated at 50° C. overnight. The mixture was cooled and partitioned between ethyl acetate and water. The combined organic layer was dried over sodium sulfate, filtered and concentrated to give a crude product, which was purified by preparative HPLC to give 3-ethyl-1-(3-hydroxypropyl)-7-((6-methylpyridin-3-yl)methyl)-8-(3-(trifluoromethoxy)phenoxy)-1H-purine-2,6(3H,7H)-dione (30 mg, 44.8% yield) as a white solid. $^1$H-NMR (DMSO-d$_6$) δ 8.53 (d, 1H), 7.71 (dd, 1H), 7.55-7.63 (m, 2H), 7.50 (dd, 1H), 7.32 (d, 1H), 7.25 (d, 1H), 5.43 (s, 2H), 4.48 (t, 1H), 3.85-3.96 (m, 4H), 3.44 (q, 2H), 2.44 (s, 3H), 1.68-1.73 (m, 2H), 1.14 (t, 3H). LCMS retention time 2.097 min; LCMS MH$^+$ 520.

The following examples 62a through 62d were prepared using the method of example 61.

Example 62a 7-((5-chloropyridin-2-yl)methyl)-3-ethyl-1-(3-hydroxypropyl)-8-(3-(trifluoromethoxy)phenoxy)-1H-purine-2,6(3H,7H)-dione

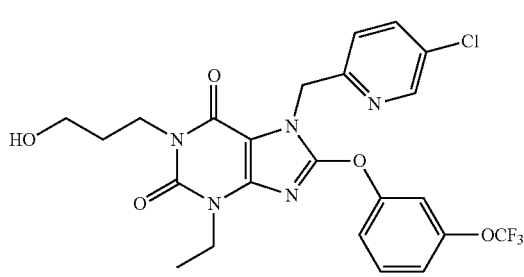 [SMILES: CCn1c(=O)n(CCCO)c(=O)c2c1nc(Oc1cccc(OC(F)(F)F)c1)n2Cc1ccc(Cl)cn1]

White solid, 30 mg, 28.1% yield: $^1$H-NMR (DMSO-d$_6$) δ 8.47 (s, 1H), 7.84-7.87 (dd, 1H), 7.53-7.57 (t, 1H), 7.46-7.48 (d, 1H), 7.34-7.39 (m, 2H), 7.22-7.24 (d, 1H), 5.63 (s, 2H), 4.03-4.08 (m, 4H), 3.56-3.59 (t, 2H), 1.82-1.85 (q, 2H), 1.26-1.29 (t, 3H). LCMS retention time 2.701 min; LCMS MH$^+$ 540.

Example 62b 7-(4-chlorobenzyl)-3-ethyl-1-(3-hydroxypropyl)-8-(3-(trifluoromethoxy)phenoxy)-1H-purine-2,6(3H,7H)-dione

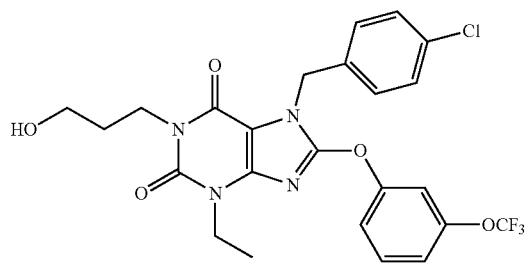 [SMILES: CCn1c(=O)n(CCCO)c(=O)c2c1nc(Oc1cccc(OC(F)(F)F)c1)n2Cc1ccc(Cl)cc1]

White solid, 15 mg, 20.1% yield: $^1$H-NMR (DMSO-d$_6$) δ 7.60-7.56 (t, 1H), 7.49 (s, 1H), 7.43-7.39 (m, 5H), 7.30-7.28 (d, 1H), 5.40 (s, 2H), 4.49 (bs, 1H), 3.92-3.82 (m, 4H), 3.43-3.36 (m, 2H), 1.71-1.64 (m, 2H), 1.14-1.10 (t, 3H). LCMS retention time 1.906 min; LCMS MH$^+$ 539.

Example 62c 3,7-diethyl-1-(3-hydroxypropyl)-8-(3-(trifluoromethoxy)phenoxy)-1H-purine-2,6(3H,7H)-dione

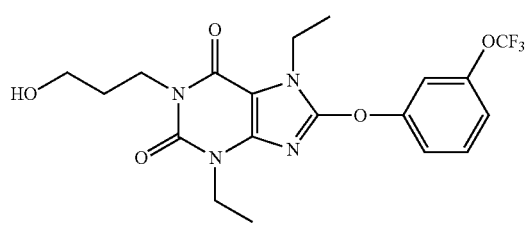 [SMILES: CCn1c(Oc2cccc(OC(F)(F)F)c2)nc2c1c(=O)n(CCCO)c(=O)n2CC]

White solid, 15 mg, 20.1% yield: $^1$H-NMR (DMSO-d$_6$) δ 7.64-7.57 (m, 2H), 7.47-7.45 (dd, 1H), 7.34-7.32 (d, 1H), 4.49-4.47 (t, 1H), 4.25-4.20 (q, 2H), 3.96-3.85 (m, 4H), 3.47-3.38 (m, 2H), 1.74-1.67 (m, 2H), 1.39-1.36 (t, 3H), 1.16-1.13 (t, 3H). LCMS retention time 2.667 min; LCMS MH$^+$ 443.

503
Example 62d 3-ethyl-1-(3-hydroxypropyl)-7-methyl-8-(3-(trifluoromethoxy)phenoxy)-1H-purine-2,6(3H,7H)-dione
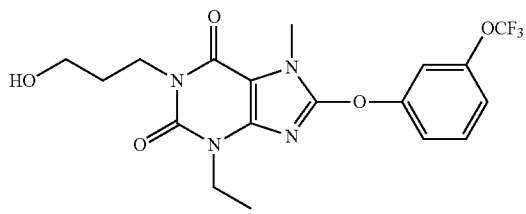 [SMILES: CCn1c(=O)n(CCCO)c(=O)c2c1nc(Oc1cccc(OC(F)(F)F)c1)n2C]
504
White solid, 15 mg, 14.2% yield: $^1$H-NMR (DMSO-$d_6$) δ 7.64-7.59 (t, 1H), 7.56 (s, 1H), 7.47-7.44 (dd, 1H), 7.33-7.31 (d, 1H), 4.50-4.48 (t, 1H), 3.95-3.84 (m, 4H), 3.46-3.42 (m, 2H), 1.73-1.66 (m, 2H), 1.15-1.12 (t, 3H). LCMS retention time 2.504 min; LCMS MH$^+$ 429.
Example 63 1-(3-hydroxypropyl)-7-((6-methylpyridin-3-yl)methyl)-3-propyl-8-(3-(trifluoromethoxy)phenoxy)-1H-purine-2,6(3H,7H)-dione
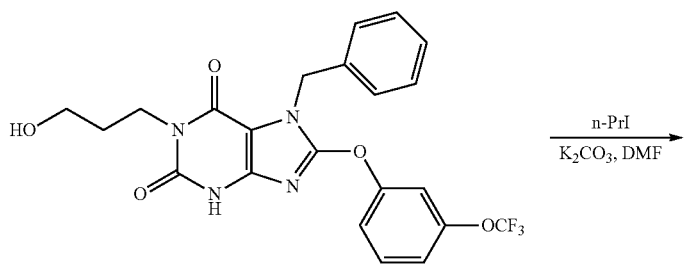
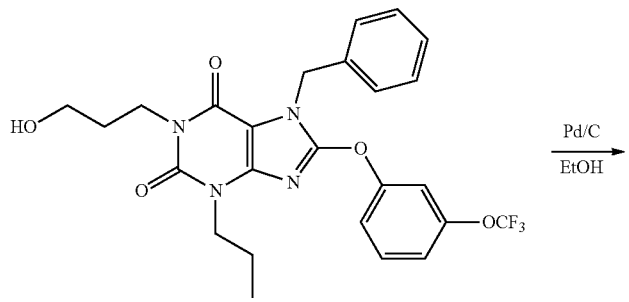
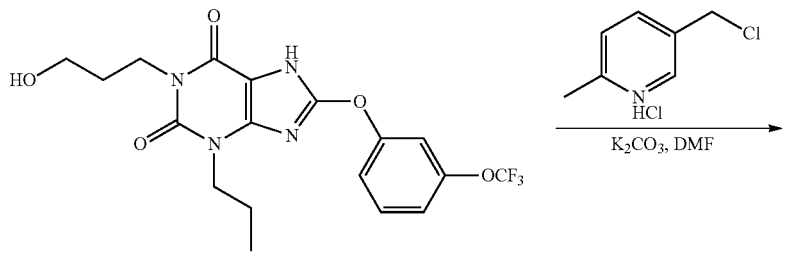
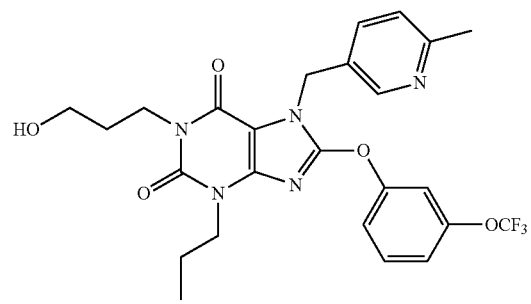

Step 1 1-(3-hydroxypropyl)-3-propyl-8-(3-(trifluoromethoxy)phenoxy)-1H-purine-2,6(3H,7H)-dione

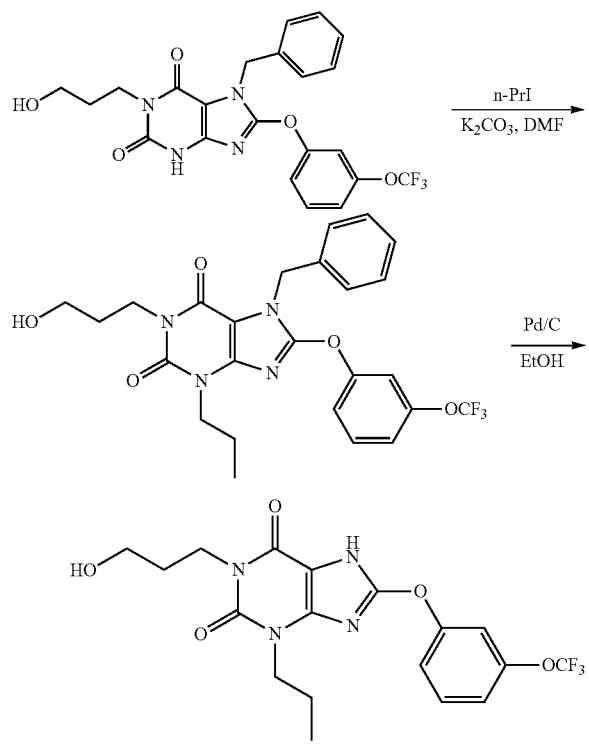

The title compound was prepared using the methods of examples 60 and 61, step 1 from the product of example 59. White solid, 180 mg, 70.1% yield: LCMS retention time 1.452 min; LCMS MH+ 429.

Step 2 1-(3-hydroxypropyl)-7-((6-methylpyridin-3-yl)methyl)-3-propyl-8-(3-(trifluoromethoxy)phenoxy)-1H-purine-2,6(3H,7H)-dione

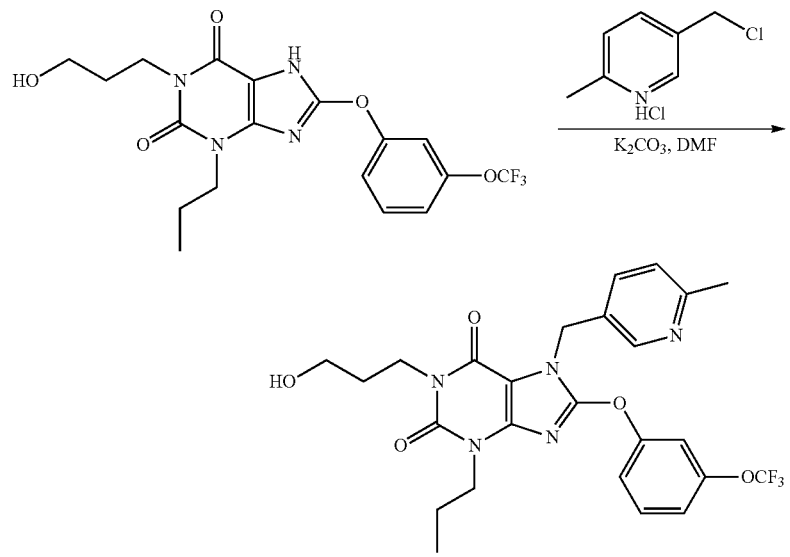

The title compound was prepared using the method of example 61, step 2. The product was purified via preparative HPLC to give 1-(3-hydroxypropyl)-7-((6-methylpyridin-3-yl)methyl)-3-propyl-8-(3-(trifluoromethoxy)phenoxy)-1H-purine-2,6(3H,7H)-dione (7.1 mg, 15.1% yield) as white solid. $^1$H-NMR (DMSO-$d_6$) δ 8.53-8.52 (d, 1H), 7.72-7.68 (dd, 1H), 7.63-7.56 (m, 2H), 7.45-7.42 (dd, 1H), 7.33-7.31 (dd, 1H), 7.26-7.24 (d, 1H), 5.42 (s, 2H), 4.50-4.47 (t, 1H), 3.95-3.91 (t, 2H), 3.82-3.78 (t, 2H), 3.46-3.42 (q, 2H), 2.44 (s, 3H), 1.73-1.58 (m, 4H), 0.82-0.78 (t, 3H). LCMS retention time 2.276 min; LCMS MH+ 534.

Example 64 7-(4-chlorobenzyl)-8-(3-((dimethylamino)methyl)phenoxy)-1-(3-hydroxypropyl)-3-propyl-1H-purine-2,6(3H,7H)-dione

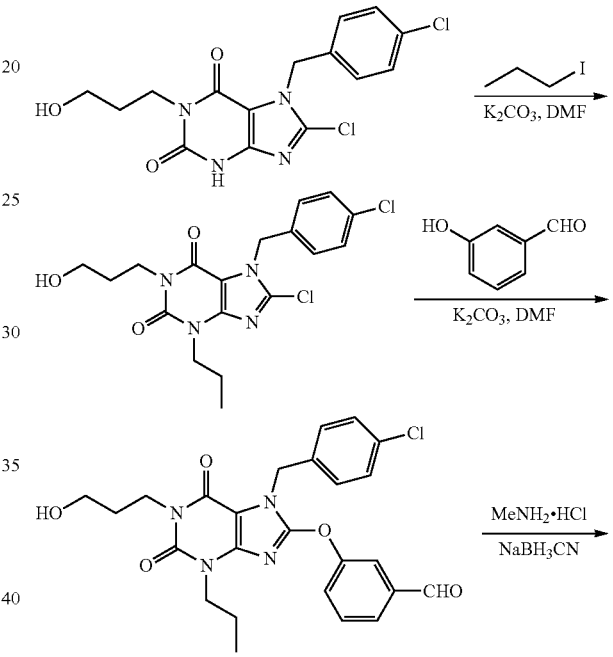

507
-continued

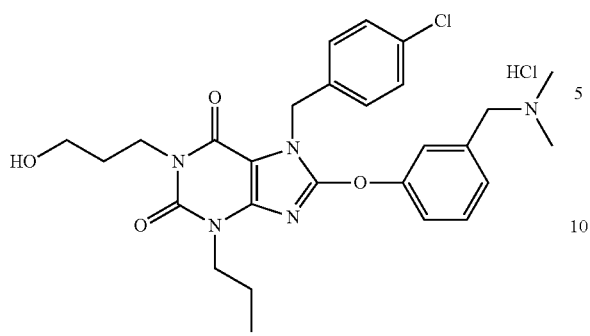

Step 1 8-chloro-7-(4-chlorobenzyl)-1-(3-hydroxypropyl)-3-propyl-1H-purine-2,6(3H,7H)-dione

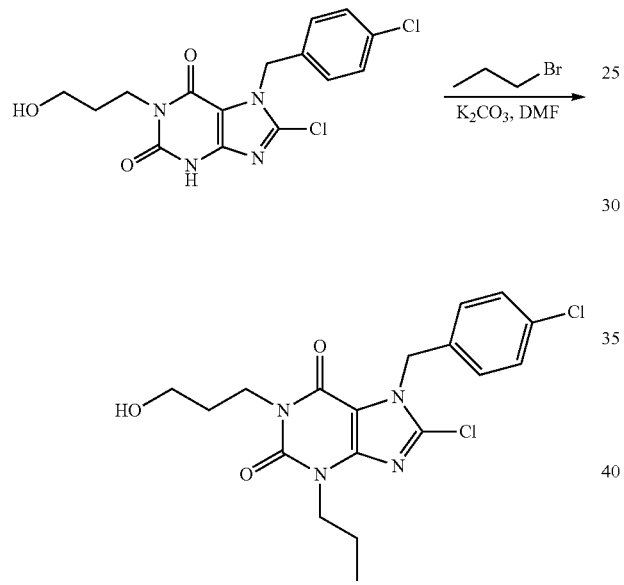

The title compound was prepared using the method of example 60. White solid, 160 mg, 72.3% yield: LCMS retention time 1.574 min; LCMS MH+ 411.

Step 3 3-(7-(4-chlorobenzyl)-1-(3-hydroxypropyl)-2,6-dioxo-3-propyl-2,3,6,7-tetrahydro-1H-purin-8-yloxy)benzaldehyde

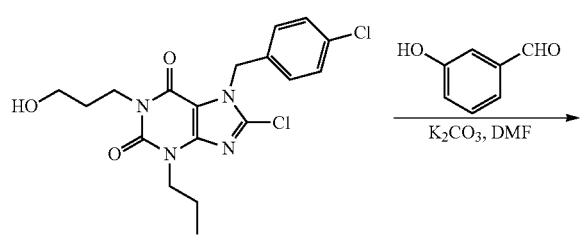

508
-continued

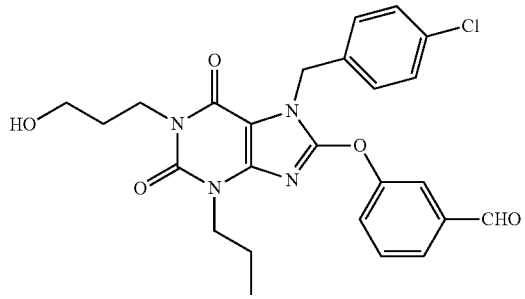

The title compound was prepared using the method of example 59, step 1. Yellow oil, 190 mg, 70.9% yield: LCMS retention time 1.663 min; LCMS MH+ 497.

Step 4 7-(4-chlorobenzyl)-8-(3-((dimethylamino)methyl)phenoxy)-1-(3-hydroxypropyl)-3-propyl-1H-purine-2,6(3H,7H)-dione hydrochloride

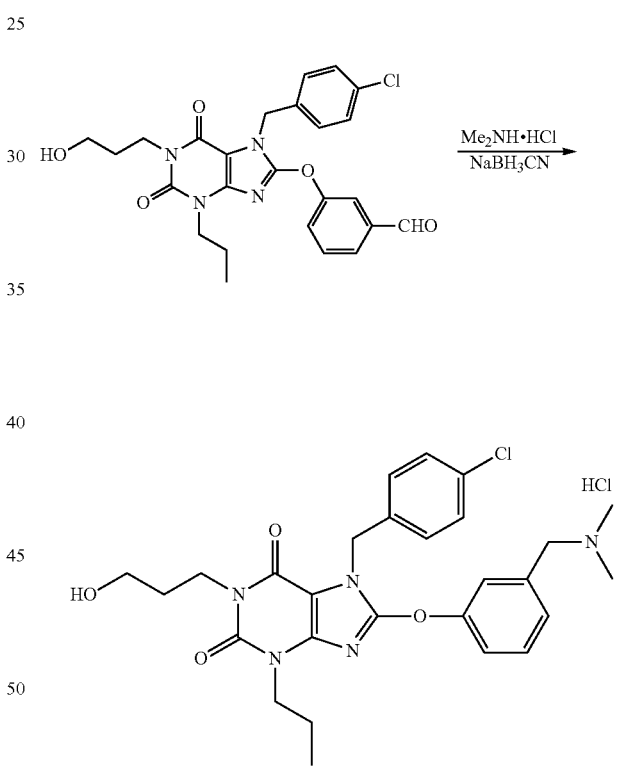

The title product was prepared using the method of example 39, step 2 and the crude product was purified by preparative HPLC. White solid, 15 mg, 14.3%: $^1$H-NMR (DMSO-$d_6$) δ 11.04 (bs, 1H), 7.60 (bs, 1H), 7.57-7.49 (m, 2H), 7.46-7.41 (m, 5H), 5.43 (s, 2H), 4.29-4.28 (d, 2H), 3.95-3.91 (t, 2H), 3.81-3.77 (t, 2H), 3.45-3.42 (t, 2H), 2.68-2.67 (d, 6H), 1.72-1.66 (m, 2H), 1.63-1.54 (m, 2H), 0.81-0.77 (t, 3H). LCMS retention time 1.755 min; LCMS MH+ 526.

Example 65 7-(4-chlorobenzyl)-8-(3-((dimethylamino)methyl)phenoxy)-3-ethyl-1-(3-hydroxypropyl)-1H-purine-2,6(3H,7H)-dione hydrochloride

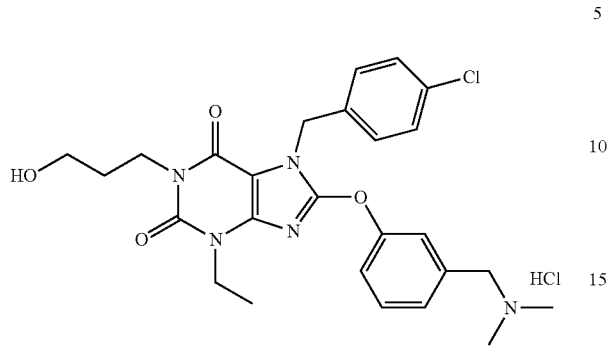

The title compound was prepared using the method of example 64. White solid, 13 mg, 14.5% yield: $^1$H-NMR (DMSO-$d_6$) δ 11.15 (s, 1H), 7.63 (s, 1H), 7.58-7.50 (m, 2H), 7.47-7.42 (m, 5H), 5.43 (s, 2H), 4.31-4.29 (d, 2H), 3.95-3.91 (t, 2H), 3.89-3.83 (m, 2H), 3.46-3.42 (t, 2H), 2.69-2.67 (d, 6H), 1.73-1.66 (m, 2H), 1.15-1.11 (t, 3H). LCMS retention time 1.668 min; LCMS MH$^+$ 512.

Example 66 7-(4-chlorobenzyl)-8-ethoxy-3-ethyl-1-(3-hydroxypropyl)-1H-purine-2,6(3H,7H)-dione

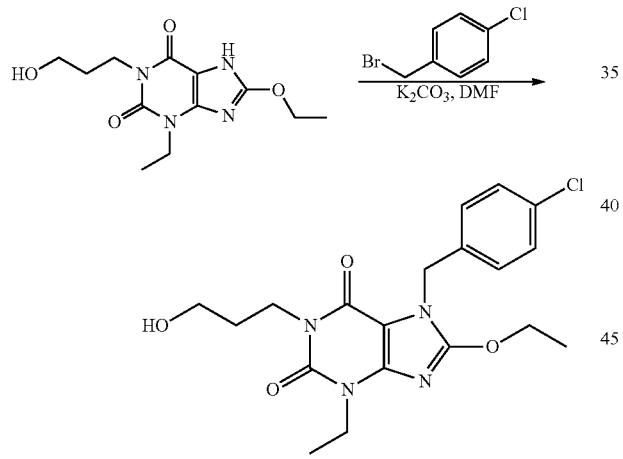

To a solution of 8-ethoxy-3-ethyl-1-(3-hydroxypropyl)-1H-purine-2,6(3H,7H)-dione (70 mg, 0.248 mmol, intermediate 26) in DMF (3 mL) was added 1-(bromomethyl)-4-chlorobenzene (80 mg, 0.390 mmol), followed by potassium carbonate (60 mg, 0.435 mmol). The mixture was stirred at 60° C. for 4 h, then diluted with ethyl acetate and water, and the phases were separated. The organic phase was washed with brine, dried over sodium sulfate, filtered and concentrated to give a crude product which was purified by preparative HPLC to give 7-(4-chlorobenzyl)-8-ethoxy-3-ethyl-1-(3-hydroxypropyl)-1H-purine-2,6(3H,7H)-dione (15 mg, 14.9% yield) as white solid. $^1$H-NMR (DMSO-$d_6$) δ 7.43-7.41 (d, 2H), 7.34-7.32 (d, 2H), 5.21 (s, 2H), 4.53-4.44 (m, 3H), 3.99-3.88 (m, 4H), 3.45-3.39 (m, 2H), 1.71-1.64 (m, 2H), 1.37-1.33 (t, 3H), 1.23-1.19 (t, 3H). LCMS retention time 2.654 min; LCMS MH$^+$ 407.

Example 67 7-(4-chlorobenzyl)-8-ethoxy-1-(3-hydroxypropyl)-3-propyl-1H-purine-2,6(3H,7H)-dione

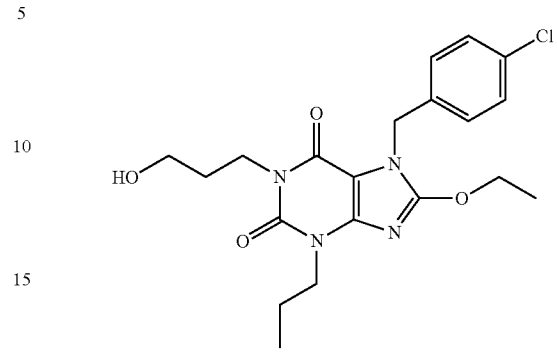

The title compound was prepared using the methods of intermediate 26 and example 66. White solid, 5 mg, 17.0% yield: $^1$H-NMR (DMSO-$d_6$) δ 7.43-7.42 (d, 2H), 7.33-7.31 (d, 2H), 5.21 (s, 2H), 4.52-4.47 (m, 3H), 3.92-3.87 (m, 4H), 3.44-3.41 (m, 2H), 1.72-1.63 (m, 4H), 1.36-1.33 (t, 3H), 0.88-0.84 (t, 3H). LCMS retention time 2.837 min; LCMS MH$^+$ 421.

Example 68 7-(4-chlorobenzyl)-8-(2-ethoxyethoxy)-1-(3-hydroxypropyl)-3-methyl-1H-purine-2,6(3H,7H)-dione

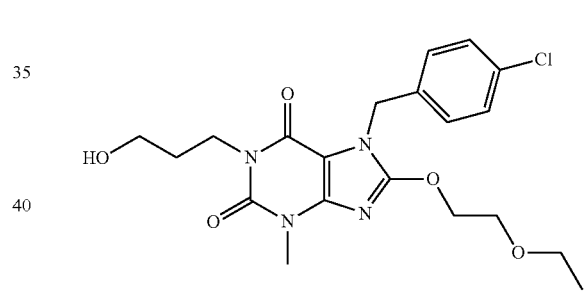

The title compound was prepared using the two-step method of example 36. White solid, 33 mg, 26.2% yield: $^1$H-NMR (DMSO-$d_6$) δ 7.34-7.41 (m, 4H), 5.21 (s, 2H), 4.58 (t, 2H), 4.47 (t, 1 H), 3.90 (t, 2H), 3.69-3.72 (m, 2H), 3.41-3.47 (m, 7H), 1.65-1.70 (m, 2H), 1.08 (t, 3H). LCMS retention time 2.423 min; LCMS MH$^+$ 437.

Example 69 7-(4-chlorobenzyl)-8-(isopropylsulfonyl)-1-(isoxazol-5-ylmethyl)-3-methyl-1H-purine-2,6(3H,7H)-dione

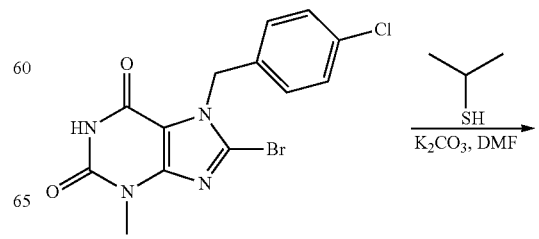

511
-continued

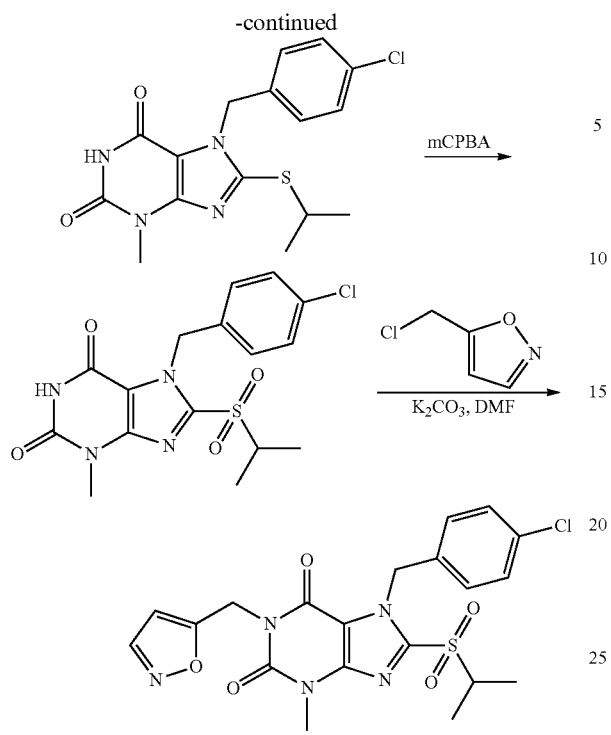

Step 1 7-(4-chlorobenzyl)-8-(isopropylthio)-3-methyl-1H-purine-2,6(3H,7H)-dione

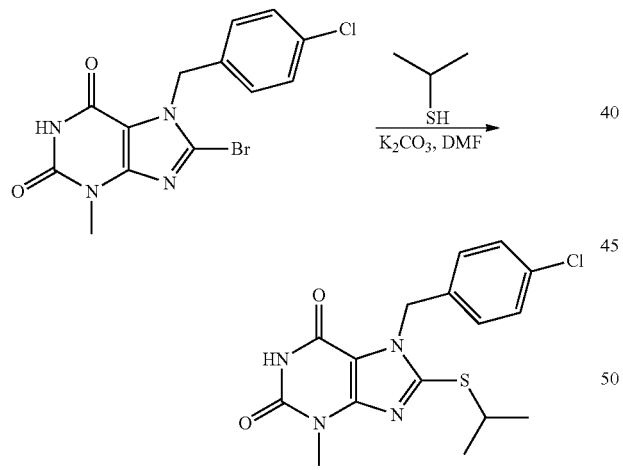

To a solution of 8-bromo-7-(4-chlorobenzyl)-3-methyl-1H-purine-2,6(3H,7H)-dione (0.2 g, 0.54 mmol, intermediate 8) in DMF (5 mL) was added propane-2-thiol (0.2 g, 2.7 mmol) and potassium carbonate (0.38 g, 2.7 mmol). The reaction was heated at 80° C. overnight. The mixture was cooled and partitioned between ethyl acetate and water. The organic phase was dried over sodium sulfate, filtered and concentrated to give a crude product (0.2 g) which was used without purification. LCMS retention time 1.015 min; LCMS MH+ 365.

512

Step 2 7-(4-chlorobenzyl)-8-(isopropylsulfonyl)-3-methyl-1H-purine-2,6(3H,7H)-dione

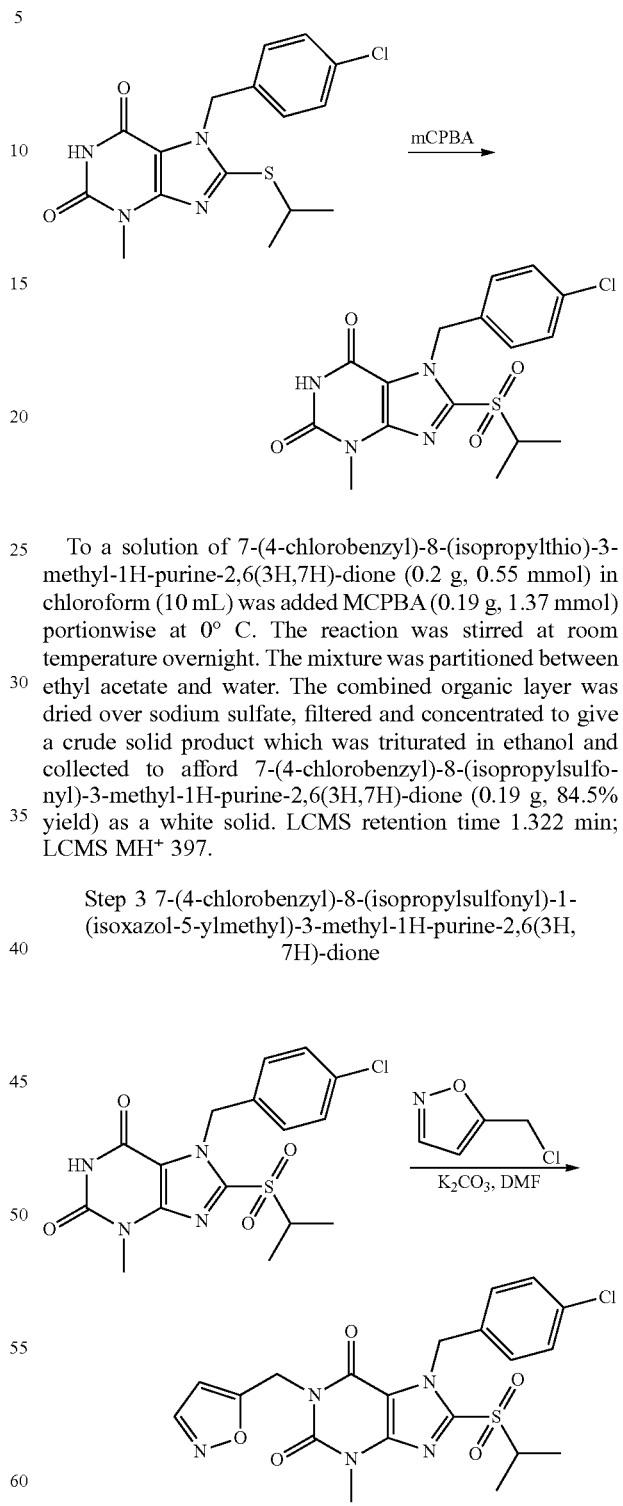

To a solution of 7-(4-chlorobenzyl)-8-(isopropylthio)-3-methyl-1H-purine-2,6(3H,7H)-dione (0.2 g, 0.55 mmol) in chloroform (10 mL) was added MCPBA (0.19 g, 1.37 mmol) portionwise at 0° C. The reaction was stirred at room temperature overnight. The mixture was partitioned between ethyl acetate and water. The combined organic layer was dried over sodium sulfate, filtered and concentrated to give a crude solid product which was triturated in ethanol and collected to afford 7-(4-chlorobenzyl)-8-(isopropylsulfonyl)-3-methyl-1H-purine-2,6(3H,7H)-dione (0.19 g, 84.5% yield) as a white solid. LCMS retention time 1.322 min; LCMS MH+ 397.

Step 3 7-(4-chlorobenzyl)-8-(isopropylsulfonyl)-1-(isoxazol-5-ylmethyl)-3-methyl-1H-purine-2,6(3H,7H)-dione To a solution of 7-(4-chlorobenzyl)-8-(isopropylsulfonyl)-3-methyl-1H-purine-2,6(3H,7H)-dione (80 mg, 0.20 mmol) in DMF (5 mL) was added 5-(chloromethyl)isoxazole (55 mg, 0.5 mmol, intermediate 41), potassium carbonate (58 mg, 0.42 mmol), and TBAI (2 mg, 0.02 mmol).

The reaction was heated at 50° C. overnight. The mixture was cooled and partitioned between ethyl acetate and water. The combined organic layer was dried over sodium sulfate, filtered and concentrated to give a crude product which was purified by preparative HPLC to give 7-(4-chlorobenzyl)-8-(isopropylsulfonyl)-1-(isoxazol-5-ylmethyl)-3-methyl-1H-purine-2,6(3H,7H)-dione (39 mg, 40.6% yield) as a white solid. $^1$H-NMR (CD$_3$OD) δ 8.49 (d, 1H), 7.41 (dd, 2H), 7.28 (d, 2H), 6.43 (d, 1H), 5.87 (s, 2H), 5.21 (s, 2H), 3.60-3.73 (m, 1H), 3.47 (s, 3H), 1.25 (d, 6H). LCMS retention time 2.772 min; LCMS MH$^+$ 478

Example 70 7-(4-chlorobenzyl)-1-(3-hydroxypropyl)-3-methyl-8-(methylsulfonyl)-1H-purine-2,6(3H,7H)-dione

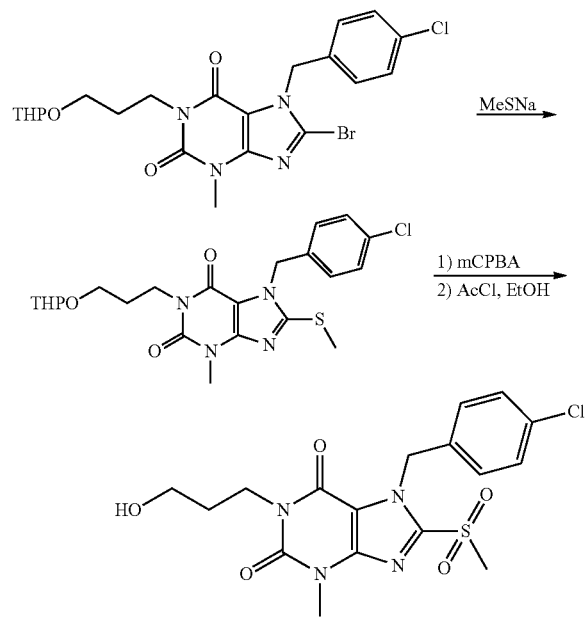

Step 1 7-(4-chlorobenzyl)-3-methyl-8-(methylthio)-1-(3-(tetrahydro-2H-pyran-2-yloxy)propyl)-1H-purine-2,6(3H,7H)-dione

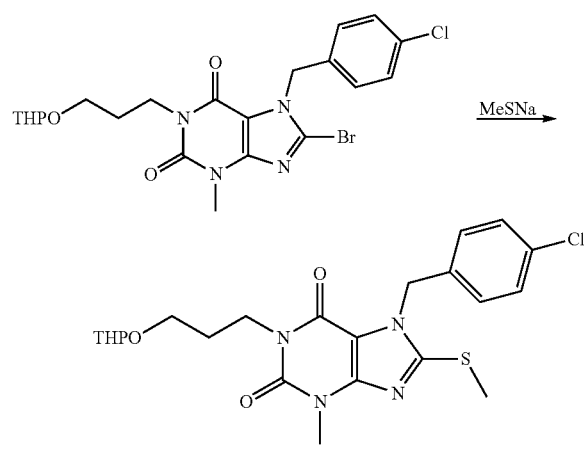

8-bromo-7-(4-chlorobenzyl)-3-methyl-1-(3-(tetrahydro-2H-pyran-2-yloxy)propyl)-1H-purine-2,6(3H,7H)-dione (0.15 g, 0.35 mmol, intermediate 14) was dissolved in sodium thiomethoxide (5 mL). The reaction was heated at 80° C. overnight. The mixture was cooled and partitioned between ethyl acetate and water. The combined organic layer was dried over sodium sulfate, filtered and concentrated to give a crude product which was used without purification. LCMS retention time 1.875 min; LCMS MH$^+$-THP 395.

Step 2 7-(4-chlorobenzyl)-1-(3-hydroxypropyl)-3-methyl-8-(methylsulfonyl)-1H-purine-2,6(3H,7H)-dione

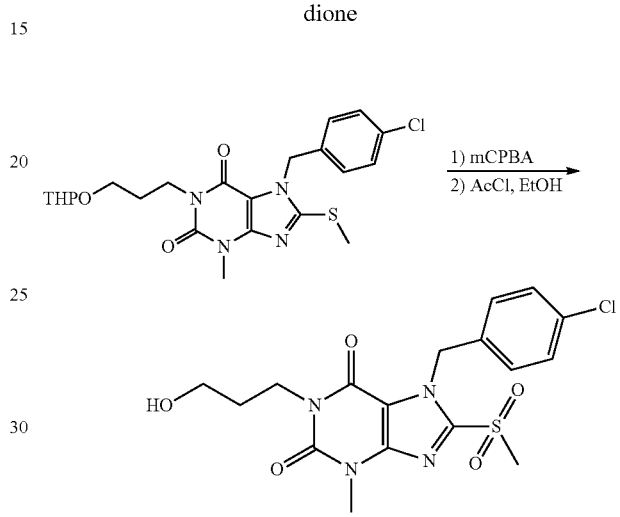

To a solution of 7-(4-chlorobenzyl)-3-methyl-8-(methylthio)-1-(3-(tetrahydro-2H-pyran-2-yloxy)propyl)-1H-purine-2,6(3H,7H)-dione (0.14 g, 0.35 mmol) in chloroform (10 mL) was added MCPBA (0.15 g, 0.87 mmol) portionwise at 0° C. The reaction was stirred at room temperature overnight. The mixture was partitioned between ethyl acetate and water. The combined organic layer was dried over sodium sulfate, filtered and concentrated to give a yellow oil. This oil was dissolved in ethanol (5 mL); then acetyl chloride (0.2 mL) was added dropwise at 0° C. The reaction was stirred at this temperature for 1 h. The mixture was concentrated to give a crude product which was purified by preparative HPLC to give 7-(4-chlorobenzyl)-1-(3-hydroxypropyl)-3-methyl-8-(methylsulfonyl)-1H-purine-2,6(3H,7H)-dione (15 mg, 10.0% yield) as a white solid. $^1$H-NMR (CD$_3$OD) δ 7.34-7.42 (m, 4H), 5.97 (s, 2H), 4.11 (t, 2H), 3.61 (t, 2H), 3.57 (s, 3H), 3.38 (s, 3H), 1.84-1.89 (m, 2H). LCMS retention time 2.052 min; LCMS MH$^+$ 427

Example 71 7-(4-chlorobenzyl)-8-(ethylsulfonyl)-1-(3-hydroxypropyl)-3-methyl-1H-purine-2,6(3H,7H)-dione

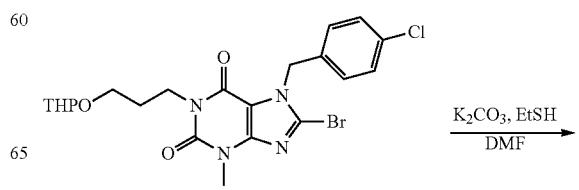

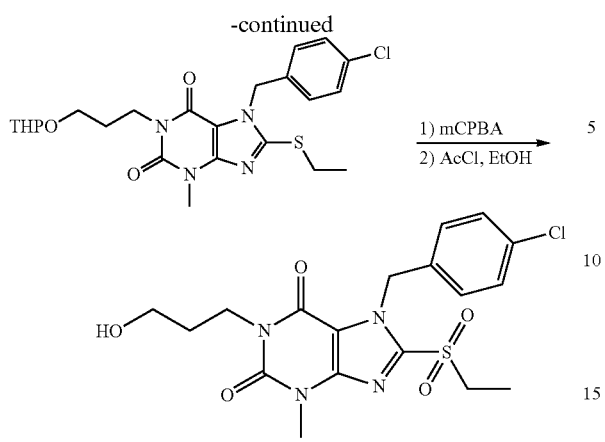

Step 1 7-(4-chlorobenzyl)-8-(ethylthio)-3-methyl-1-(3-(tetrahydro-2H-pyran-2-yloxy)propyl)-1H-purine-2,6(3H,7H)-dione

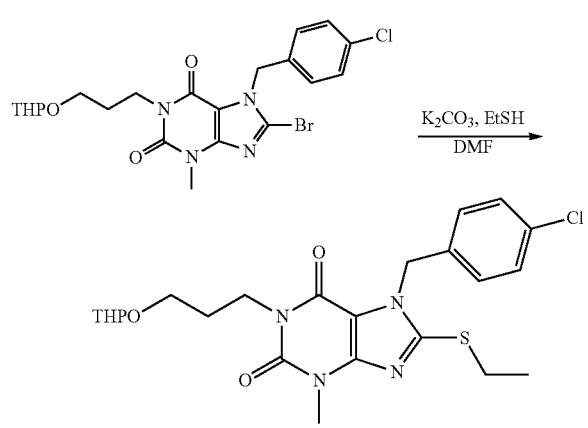

To a solution of 8-bromo-7-(4-chlorobenzyl)-3-methyl-1-(3-(tetrahydro-2H-pyran-2-yloxy)propyl)-1H-purine-2,6(3H,7H)-dione (0.15 g, 0.29 mmol, intermediate 14) in DMF (10 mL) was added ethanethiol (27 mg, 0.44 mmol) and potassium carbonate (81 mg, 0.58 mmol). The reaction was heated at 80° C. overnight. The mixture was cooled and partitioned between ethyl acetate and water. The combined organic layer was dried over sodium sulfate, filtered and concentrated to give a crude product which was used without purification. LCMS retention time 1.912 min; LCMS MH$^+$-THP 409.

Step 2 7-(4-chlorobenzyl)-8-(ethylsulfonyl)-1-(3-hydroxypropyl)-3-methyl-1H-purine-2,6(3H,7H)-dione

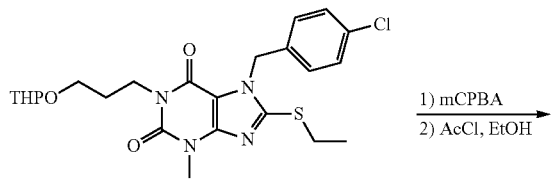

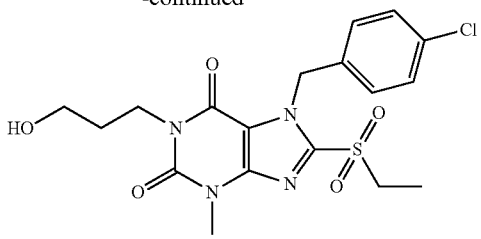

The title compound was prepared using the method of example 70, step 2 and purified by preparative HPLC to give 7-(4-chlorobenzyl)-8-(ethylsulfonyl)-1-(3-hydroxypropyl)-3-methyl-1H-purine-2,6(3H,7H)-dione (26 mg, 20.5% yield) as a white solid. $^1$H-NMR (CD$_3$OD) δ=7.34-7.41 (m, 4H), 5.98 (s, 2H), 4.11 (t, 1H), 3.62 (t, 2H), 3.57 (s, 3H), 3.47-3.53 (m, 2H), 1.85-1.90 (m, 2H), 1.31 (t, 3H). LCMS retention time 2.192 min; LCMS MH$^+$ 441.

Example 72 7-(4-chlorobenzyl)-1-(3-hydroxypropyl)-8-(isopropylsulfonyl)-3-methyl-1H-purine-2,6(3H,7H)-dione

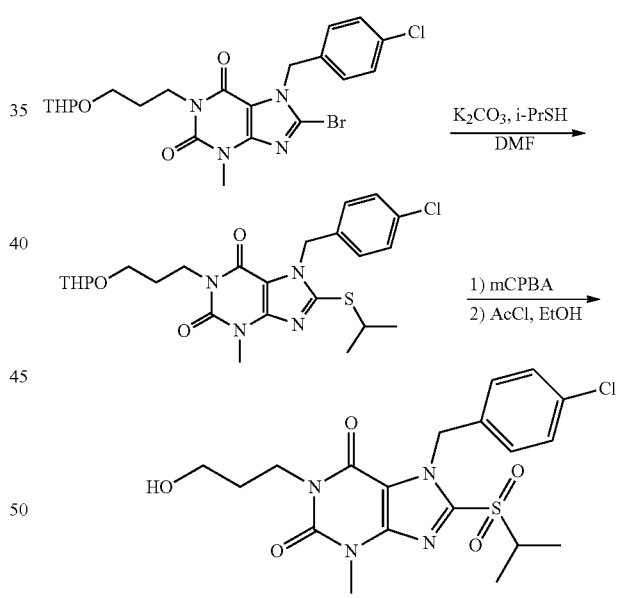

The title compound was prepared using the method of example 71 and purified by preparative HPLC to give 7-(4-chlorobenzyl)-8-(ethylsulfonyl)-1-(3-hydroxypropyl)-3-methyl-1H-purine-2,6(3H,7H)-dione (26 mg, 20.5% yield) as white solid. $^1$H-NMR (CDCl$_3$) δ 7.43-7.45 (d, 2H), 7.31-7.34 (d, 2H), 5.97 (s, 2H), 4.19-4.22 (t, 2H), 3.73-3.76 (m, 1H), 3.59 (s, 3H), 3.54-3.59 (m, 2H), 3.04-3.06 (t, 1H), 1.90-1.93 (m, 2H), 1.38-1.40 (d, 6H). LCMS retention time 2.311 min; LCMS MH$^+$ 455.

Example 73 7-(4-chlorobenzyl)-1-(3-hydroxypropyl)-3-methyl-8-(3-(trifluoromethoxy)phenylthio)-1H-purine-2,6(3H,7H)-dione

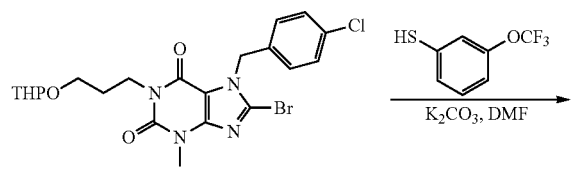

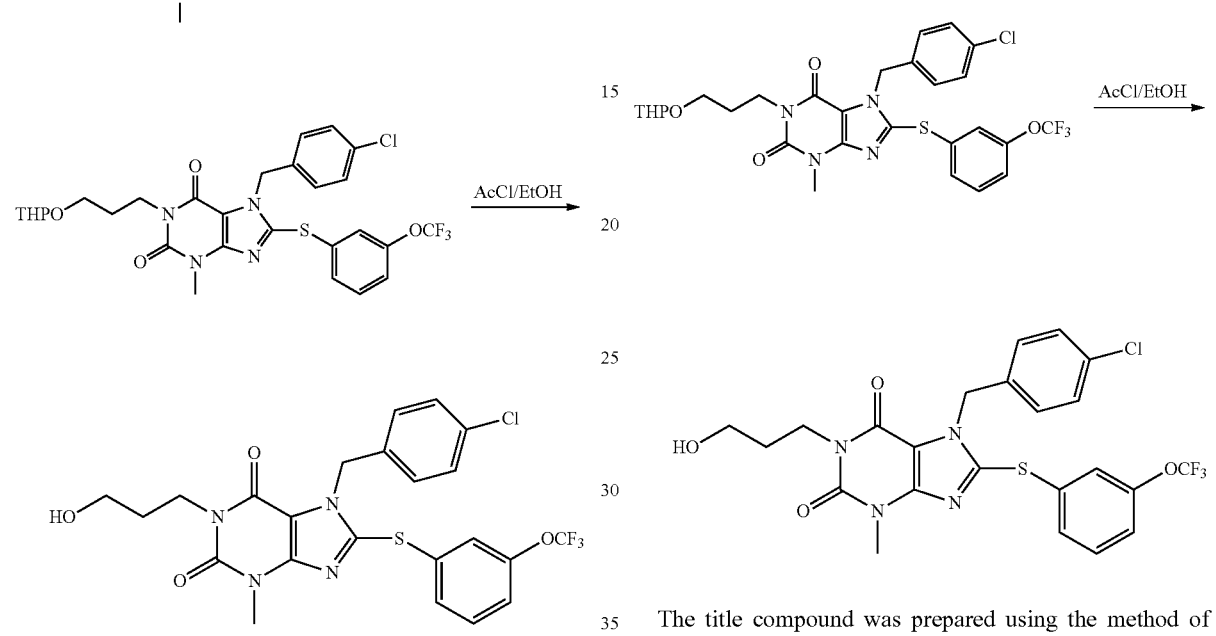

Step 1 7-(4-chlorobenzyl)-3-methyl-1-(3-(tetrahydro-2H-pyran-2-yloxy)propyl)-8-(3-(trifluoromethoxy)phenylthio)-1H-purine-2,6(3H,7H)-dione

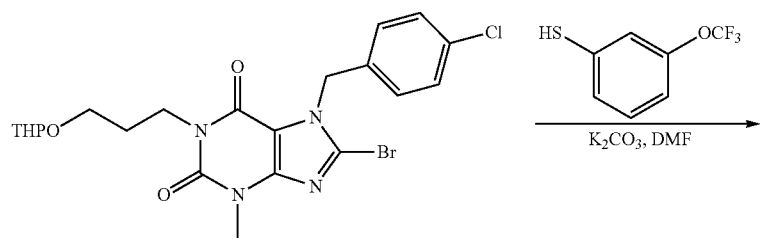

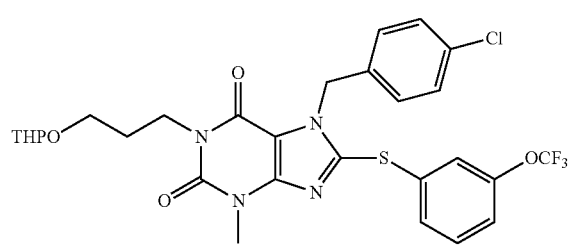

The title compound was prepared using the method of example 71, step 1 and using 3-(trifluoromethoxy)benzenethiol. Yellow oil, 100 mg, 81.9% yield. LCMS retention time 2.098 min; LCMS MH$^+$-THP 541

Step 2 7-(4-chlorobenzyl)-1-(3-hydroxypropyl)-3-methyl-8-(3-(trifluoromethoxy)phenylthio)-1H-purine-2,6(3H,7H)-dione The title compound was prepared using the method of example 37, step 2. Light yellow solid, 20 mg, 23.1% yield: $^1$H-NMR (DMSO-d$_6$) δ 7.47-7.42 (t, 1H), 7.33-7.30 (m, 5H), 7.24-7.22 (d, 2H), 5.63 (s, 2H), 4.49-4.46 (t, 1H), 3.95-3.92 (t, 2H), 3.47-3.42 (m, 2H), 3.39 (s, 3H), 1.72-1.69 (m, 2H). LCMS retention time 2.950 min; LCMS MH$^+$ 541

Example 74 8-(butylsulfonyl)-7-(4-chlorobenzyl)-1-(3-hydroxypropyl)-3-methyl-1H-purine-2,6(3H,7H)-dione

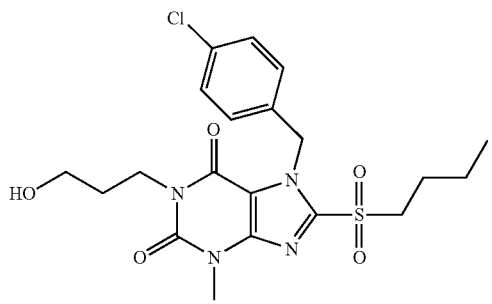 [SMILES: CCCCS(=O)(=O)c1nc2c(c(=O)n(CCCO)c(=O)n2C)n1Cc1ccc(Cl)cc1]

The title compound was prepared using the method of example 71. Light yellow oil, 30 mg, 39.3% yield: $^1$H-NMR (CD$_3$OD) δ 7.40-7.35 (m, 4H), 5.99 (s, 2H), 4.14-4.10 (t, 2H), 3.64-3.61 (t, 2H), 3.57 (s, 3H), 3.44-3.40 (m, 2H), 1.90-1.86 (m, 2H), 1.69-1.65 (m, 2H), 1.44-1.38 (m, 2H), 0.92-0.89 (t, 3H). LCMS retention time 1.671 min; LCMS MH$^+$ 469

Example 75 7-(4-chlorobenzyl)-1-(3-hydroxypropyl)-3-methyl-8-(propylsulfonyl)-1H-purine-2,6(3H,7H)-dione

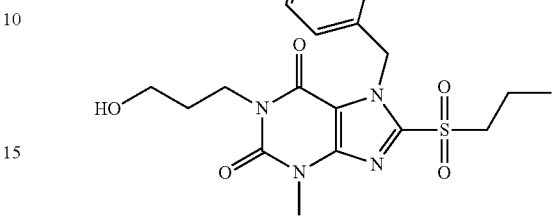

The title compound was prepared using the method of example 71. Light brown solid, 30 mg, 39.5% yield: $^1$H-NMR (CD$_3$OD) δ 7.40-7.34 (m, 4H), 5.99 (s, 2H), 4.13-4.09 (t, 2H), 3.63-3.60 (t, 2H), 3.57 (s, 3H), 3.43-3.39 (t, 2H), 1.89-1.85 (m, 2H), 1.80-1.75 (m, 2H), 1.04-0.99 (t, 3H). LCMS retention time 2.353 min; LCMS MH$^+$ 455

Example 76 7-(4-chlorobenzyl)-1-(3-hydroxypropyl)-3-methyl-8-(propylsulfonyl)-1H-purine-2,6(3H,7H)-dione

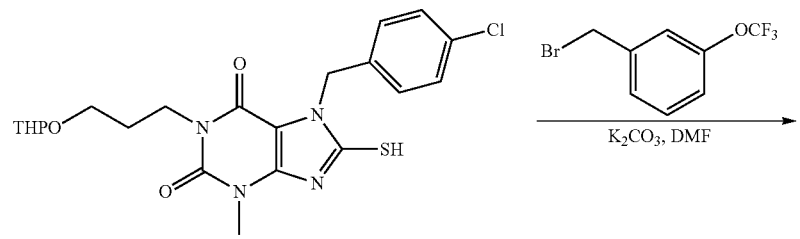

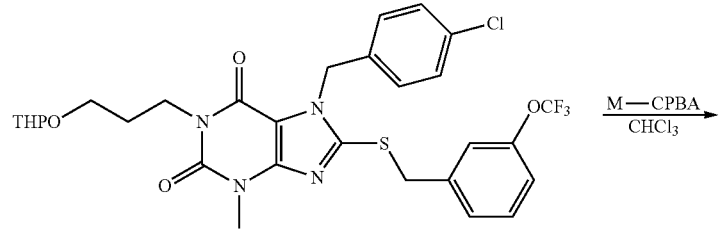

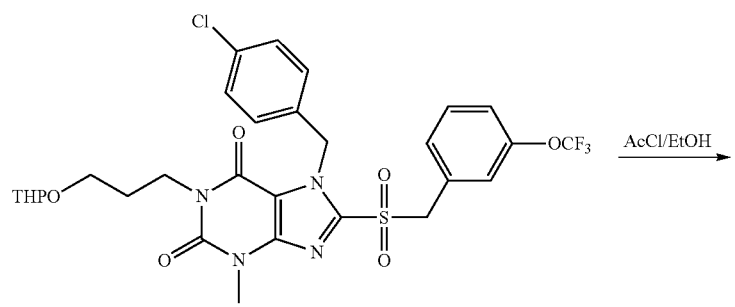

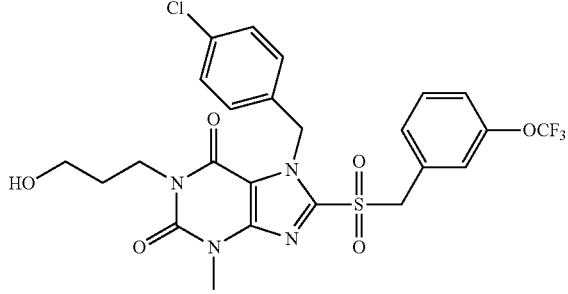

Step 1 7-(4-chlorobenzyl)-3-methyl-1-(3-(tetrahydro-2H-pyran-2-yloxy)propyl)-8-(3-(trifluoromethoxy)benzylthio)-1H-purine-2,6(3H,7H)-dione

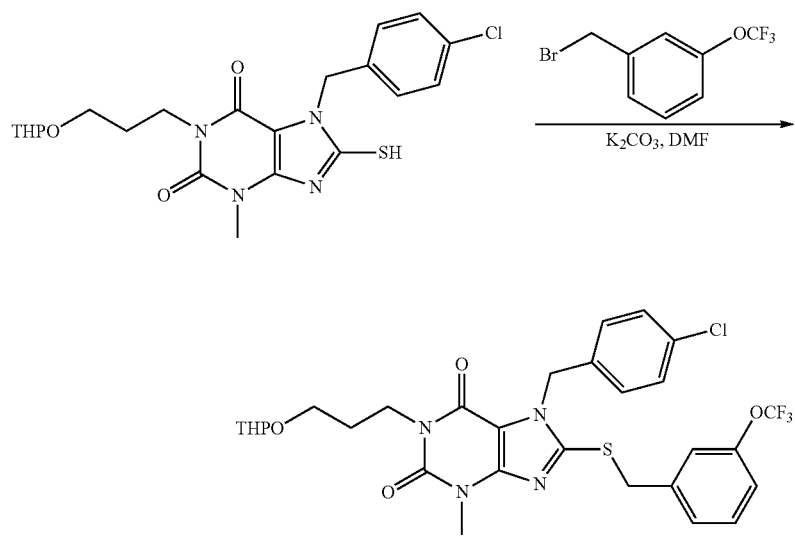

To a solution of 7-(4-chlorobenzyl)-8-mercapto-3-methyl-1-(3-(tetrahydro-2H-pyran-2-yloxy)propyl)-1H-purine-2,6(3H,7H)-dione (100 mg, 0.216 mmol) in DMF (5 mL) was added 1-(bromomethyl)-3-(trifluoromethoxy)benzene (66 mg, 0.259 mmol), followed by potassium carbonate (89 mg, 0.645 mmol). The reaction was stirred at 80° C. for 2 h. The mixture was cooled, diluted with ethyl acetate and water, and the phases were separated. The organic phase was washed with brine, dried over sodium sulfate, filtered and concentrated to give 7-(4-chlorobenzyl)-3-methyl-1-(3-(tetrahydro-2H-pyran-2-yloxy)propyl)-8-(3-(trifluoromethoxy)benzylthio)-1H-purine-2,6(3H,7H)-dione (120 mg, 87.3%) as light yellow oil. LCMS retention time 2.106 min; LCMS MH$^+$-THP 555.

Step 2 7-(4-chlorobenzyl)-1-(3-hydroxypropyl)-3-methyl-8-(propylsulfonyl)-1H-purine-2,6(3H,7H)-dione

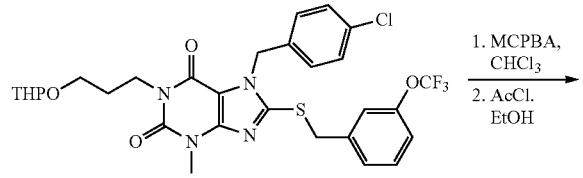

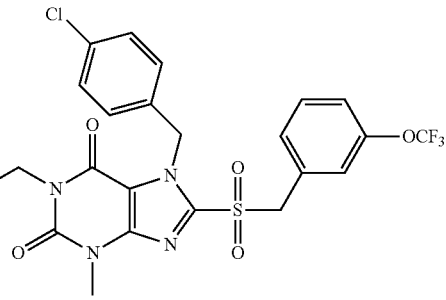

The title compound was prepared using the method of example 70, step 2. White solid, 14.3% yield: $^1$H-NMR (CD$_3$OD) δ 7.47-7.43 (t, 1H), 7.32-7.30 (d, 2H), 7.27-7.23 (d, 2H), 7.18-7.16 (d, 3H), 5.64 (s, 2H), 4.91 (s, 2H), 4.10-4.07 (t, 2H), 3.62-3.59 (s, 5H), 1.88-1.81 (m, 2H). LCMS retention time 2.922 min; LCMS MH$^+$ 587.

Example 77 7-(4-chlorobenzyl)-1-(3-hydroxypropyl)-3-methyl-8-(3-(trifluoromethoxy)benzylsulfinyl)-1H-purine-2,6(3H,7H)-dione To a solution of 7-(4-chlorobenzyl)-3-methyl-1-(3-(tetrahydro-2H-pyran-2-yloxy)propyl)-8-(3-(trifluoromethoxy)benzylthio)-1H-purine-2,6(3H,7H)-dione (60 mg, 0.108

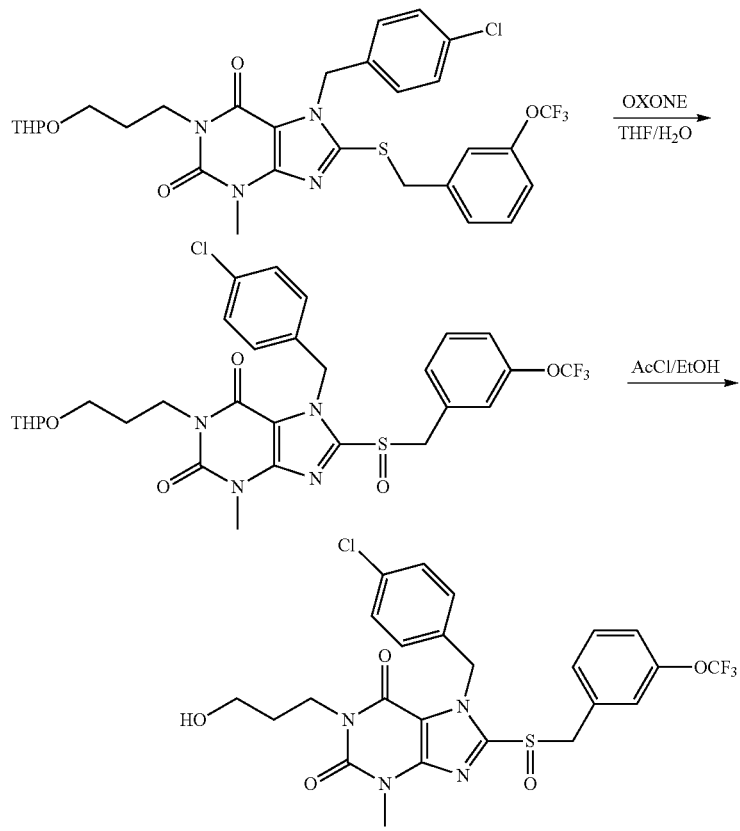

Step 1 7-(4-chlorobenzyl)-3-methyl-1-(3-(tetrahydro-2H-pyran-2-yloxy)propyl)-8-(3-(trifluoromethoxy)benzylsulfinyl)-1H-purine-2,6(3H,7H)-dione mmol, example 129, step 2) in THF (4 mL) and water (2 mL) was added Oxone (73 mg, 0.119 mmol) at 0° C. The resulting mixture was stirred at room temperature for 16 h. The mixture was quenched with aqueous sodium thiosulfate,

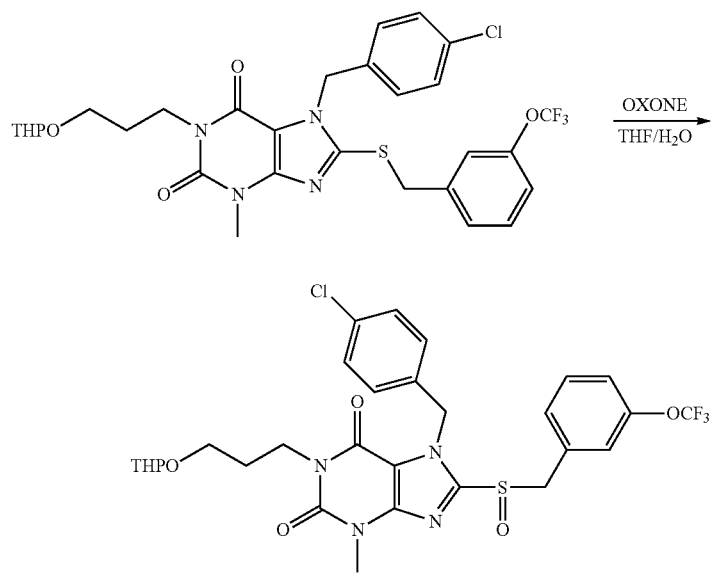

partitioned between DCM and water, and the phases were separated. The organic phase was washed with brine, dried over sodium sulfate, filtered and concentrated to give crude product. This crude material was purified by silica gel chromatography eluting with petroleum/ethyl acetate (1:0 to 1:1) to give 7-(4-chlorobenzyl)-3-methyl-1-(3-(tetrahydro-2H-pyran-2-yloxy)propyl)-8-(3-(trifluoromethoxy)benzyl-sulfinyl)-1H-purine-2,6(3H,7H)-dione (60 mg, 97.6%) as yellow oil. LCMS retention time 1.499 min; LCMS MH$^+$-THP 571.

Step 2 7-(4-chlorobenzyl)-1-(3-hydroxypropyl)-3-methyl-8-(3-(trifluoromethoxy)benzyl sulfinyl)-1H-purine-2,6(3H,7H)-dione

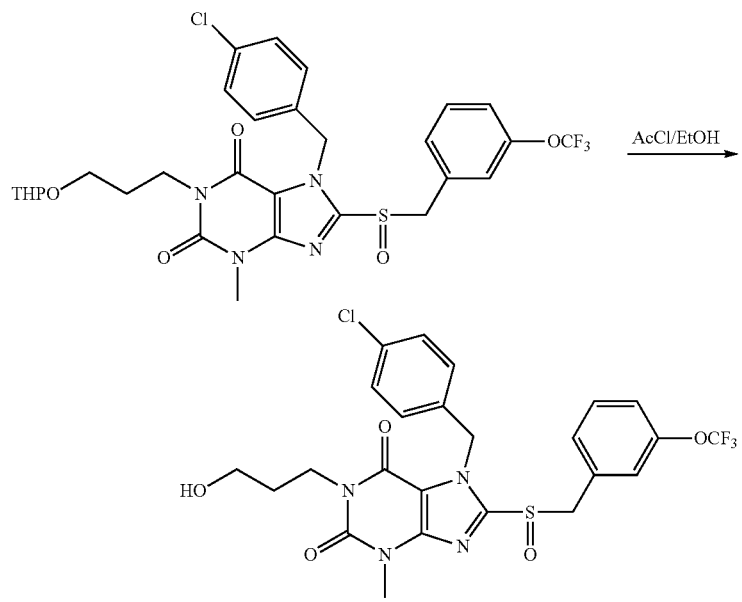

The title compound was prepared using the method of example 37, step 2. White solid, 30 mg, 57.4% yield: $^1$H-NMR (CD$_3$OD) δ 7.43-7.39 (t, 1H), 7.27-7.23 (m, 4H), 7.17-7.12 (m, 3H), 5.59 (s, 2H), 4.89-4.74 (m, 2H), 4.12-4.08 (t, 2H), 3.62-3.59 (m, 5H), 1.88-1.84 (m, 2H). LCMS retention time 2552 min; LCMS MH$^+$ 571.

Example 78 7-(4-chlorobenzyl)-1-(3-hydroxypropyl)-N-isopropyl-3-methyl-2,6-dioxo-2,3,6,7-tetrahydro-1H-purine-8-sulfonamide

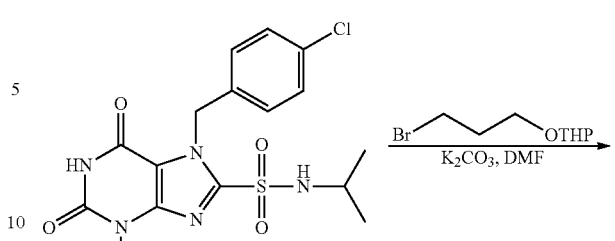

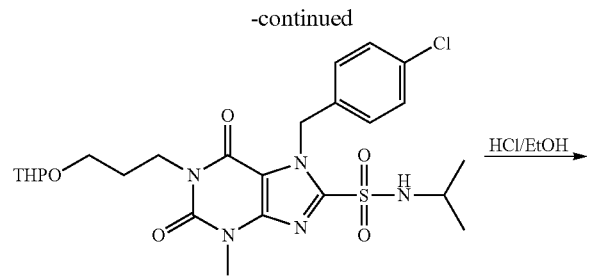

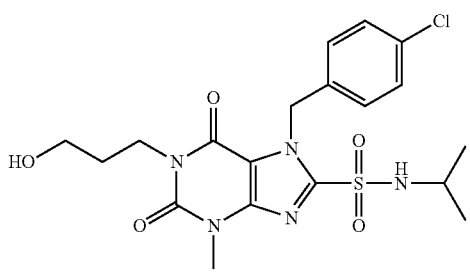

Step 1 7-(4-chlorobenzyl)-N-isopropyl-3-methyl-2,6-dioxo-2,3,6,7-tetrahydro-1H-purine-8-sulfonamide

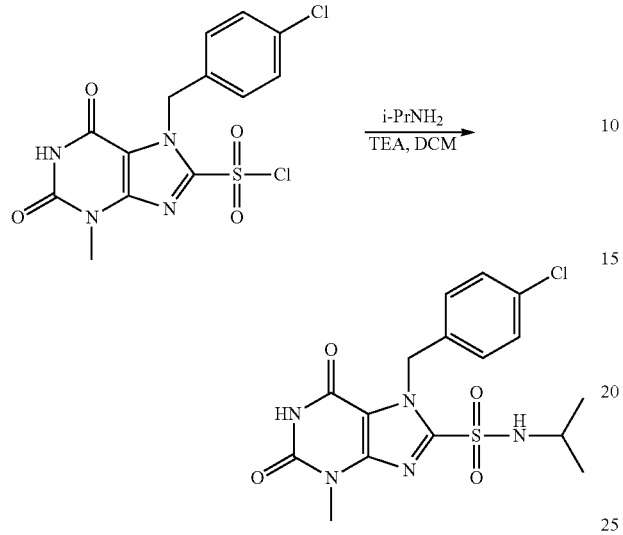

To a solution of 7-(4-chlorobenzyl)-3-methyl-2,6-dioxo-2,3,6,7-tetrahydro-1H-purine-8-sulfonyl chloride (115 mg, 0.295 mmol, intermediate 64) in DCM (5 mL) was added isopropylamine (17.4 mg, 0.59 mmol) followed by TEA (60 mg, 0.59 mmol) at 0° C. and the mixture was stirred at room temperature for 1 h. The mixture was diluted with DCM and washed brine. The organic phase was dried and concentrated to give a crude product, which was purified by silica gel chromatography eluting with DCM/methanol (50:1) to give 7-(4-chlorobenzyl)-N-isopropyl-3-methyl-2,6-dioxo-2,3,6,7-tetrahydro-1H-purine-8-sulfonamide (59 mg, 48.6% yield) as yellow syrup. LCMS retention time 1.436 min; LCMS MH+ 412.

Step 2 7-(4-chlorobenzyl)-N-isopropyl-3-methyl-2,6-dioxo-1-(3-(tetrahydro-2H-pyran-2-yloxy)propyl)-2,3,6,7-tetrahydro-1H-purine-8-sulfonamide

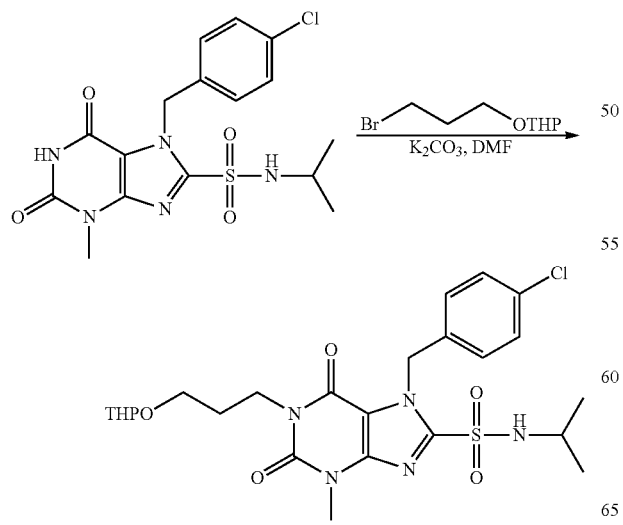

To a solution of 7-(4-chlorobenzyl)-N-isopropyl-3-methyl-2,6-dioxo-2,3,6,7-tetrahydro-1H-purine-8-sulfonamide (59 mg, 0.143 mmol) in DMF (3 mL) was added 2-(3-bromopropoxy)tetrahydro-2H-pyran (32 mg, 0.143 mmol) followed by potassium carbonate (30 mg, 0.214 mmol) and the mixture was stirred at 60° C. for 4 h. The reaction was diluted with ethyl acetate and washed with brine and saturated aqueous ammonium chloride. The organic phase was dried and concentrated to give 7-(4-chlorobenzyl)-N-isopropyl-3-methyl-2,6-dioxo-1-(3-(tetrahydro-2H-pyran-2-yloxy)propyl)-2,3,6,7-tetrahydro-1H-purine-8-sulfonamide (61 mg, 77% yield) as yellow solid. LCMS retention time 1.805 min; LCMS MH+-THP 470.

Step 3 7-(4-chlorobenzyl)-N-isopropyl-3-methyl-2,6-dioxo-1-(3-(tetrahydro-2H-pyran-2-yloxy)propyl)-2,3,6,7-tetrahydro-1H-purine-8-sulfonamide A solution of 7-(4-chlorobenzyl)-N-isopropyl-3-methyl-2,6-dioxo-1-(3-(tetrahydro-2H-pyran-2-yloxy)propyl)-2,3,6,7-tetrahydro-1H-purine-8-sulfonamide (61 mg, 0.11 mmol) in 1 mM ethanolic HCl (1 mL, 1 mmol/L) was stirred at room temperature for 30 min. The mixture was concentrated and purified by preparative HPLC to give 7-(4-chlorobenzyl)-1-(3-hydroxypropyl)-N-isopropyl-3-methyl-2,6-dioxo-2,3,6,7-tetrahydro-1H-purine-8-sulfonamide (17.9 mg, 34.6% yield) as white solid. $^1$H-NMR (CD$_3$OD) δ 7.31-7.38 (m, 4H), 5.89 (s, 2H), 4.06-4.10 (t, 2H), 3.58-3.63 (m, 3H), 3.56 (s, 3H), 1.83-1.87 (m, 2H), 1.19-1.21 (d, 6H). LCMS retention time 2.315 min; LCMS MH+ 470.

Example 79 7-(4-chlorobenzyl)-N-cyclopropyl-N,1-bis(3-hydroxypropyl)-3-methyl-2,6-dioxo-2,3,6,7-tetrahydro-1H-purine-8-sulfonamide

Example 80 N-(7-(4-chlorobenzyl)-1-(3-hydroxypropyl)-3-methyl-2,6-dioxo-2,3,6,7-tetrahydro-1H-purin-8-yl)propane-2-sulfonamide

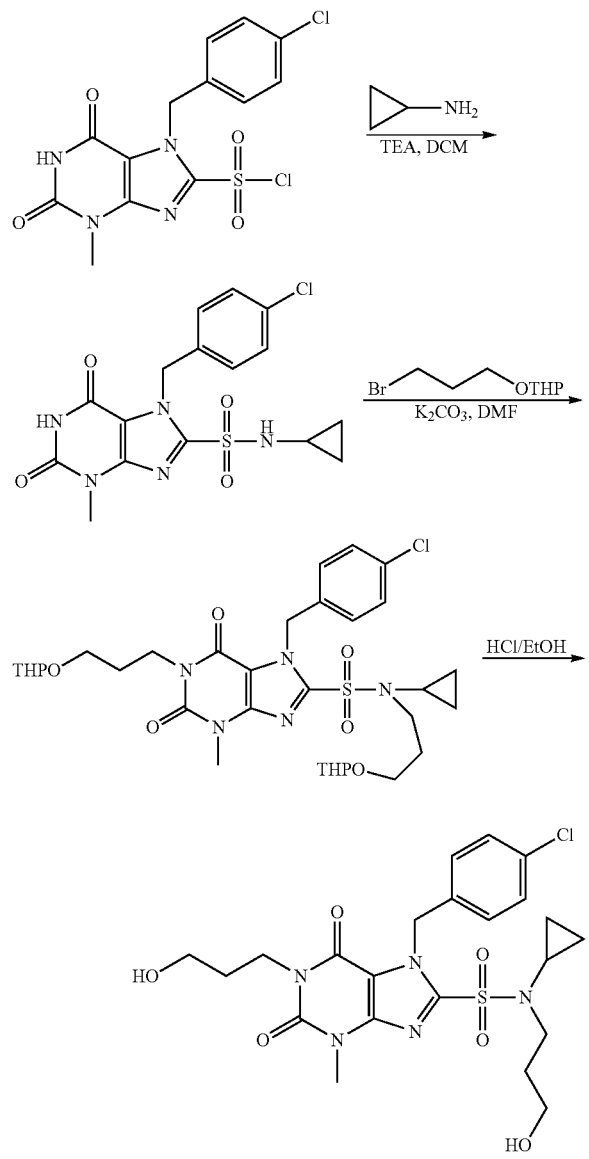

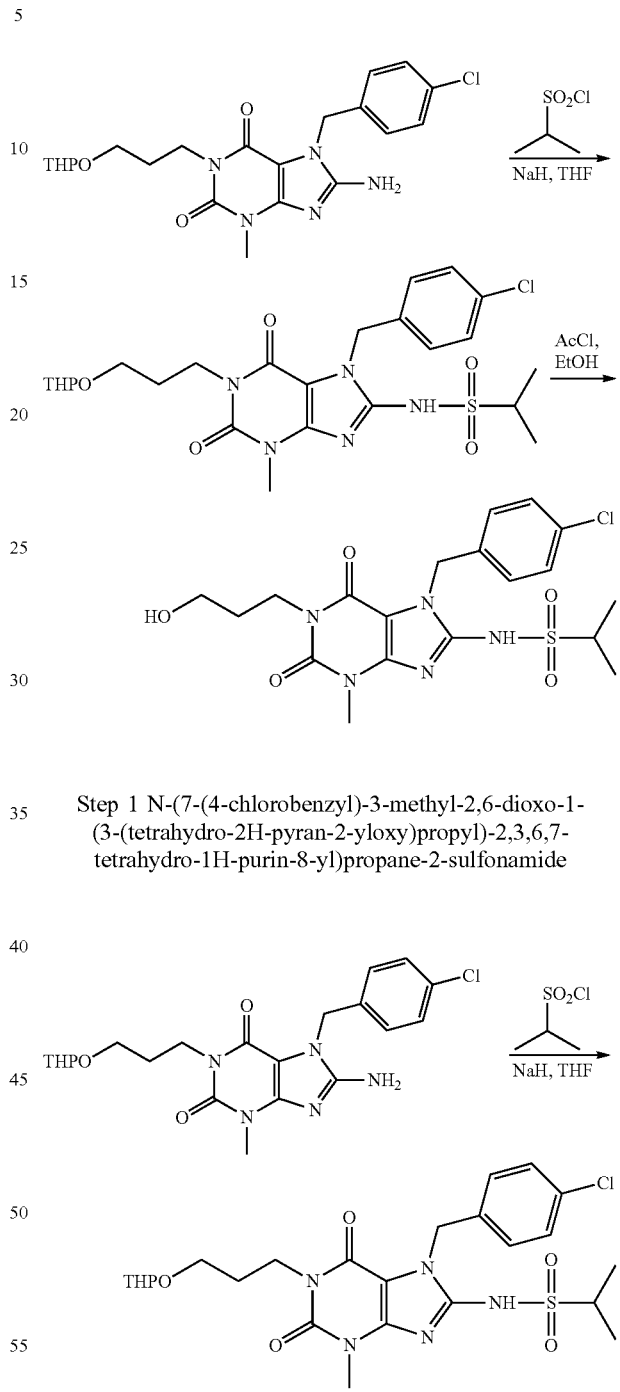

The title compound was prepared using the method of example 78 except in step 2, 2 equivalent of 2-(3-bromopropoxy)tetrahydro-2H-pyran was added. The final product was purified via preparative HPLC to give 7-(4-chlorobenzyl)-N-cyclopropyl-N,1-bis(3-hydroxypropyl)-3-methyl-2,6-dioxo-2,3,6,7-tetrahydro-1H-purine-8-sulfonamide (21 mg, 38.9% yield) as white solid. $^1$H-NMR (CD$_3$OD) δ 7.32-7.39 (m, 4H), 5.92 (s, 2H), 4.07-4.11 (t, 2H), 3.57-3.62 (m, 6H), 3.53 (s, 3H), 2.71-2.75 (m, 1H), 1.84-1.95 (m, 4H), 0.91-0.94 (m, 2H), 0.75-0.078 (m, 2H). LCMS retention time 2.238 min; LCMS MH$^+$ 526.

Step 1 N-(7-(4-chlorobenzyl)-3-methyl-2,6-dioxo-1-(3-(tetrahydro-2H-pyran-2-yloxy)propyl)-2,3,6,7-tetrahydro-1H-purin-8-yl)propane-2-sulfonamide To a solution of 8-amino-7-(4-chlorobenzyl)-3-methyl-1-(3-(tetrahydro-2H-pyran-2-yloxy)propyl)-1H-purine-2,6 (3H,7H)-dione (95 mg, 0.21 mmol, intermediate 53) in THF (5 mL) was added sodium hydride (10 mg, 0.23 mmol) at 0° C. The reaction was stirred at room temperature for 1 h; then Isopropylsulphonyl chloride (29 mg, 0.21 mmol) was added dropwise at 0° C. The mixture was stirred at room temperature 1 h. The reaction was quenched with aqueous ammonium chloride (2 mL) at 0° C. and then was partitioned between ethyl acetate and water. The combined organic layer was dried over sodium sulfate, filtered and concentrated to give the product as a yellow syrup (60 mg) which was used without purification. LCMS retention time 1.519 min; LCMS MH+-THP 470.

Step 2 N-(7-(4-chlorobenzyl)-1-(3-hydroxypropyl)-3-methyl-2,6-dioxo-2,3,6,7-tetrahydro-1H-purin-8-yl)propane-2-sulfonamide

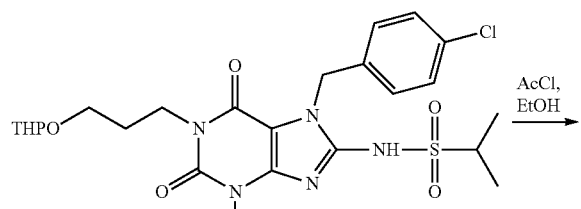

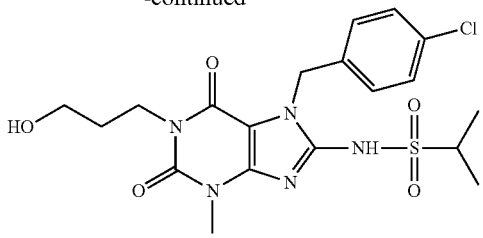

The title compound was prepared using the method of example 37, step 2 and purified by preparative HPLC. White solid, 19 mg, 37.2% yield: $^1$H-NMR (CD$_3$OD) δ 7.44 (d, 2H), 7.31-7.33 (m, 2H), 5.37 (s, 2H), 4.19 (t, 2H), 3.56 (s, 2H), 3.52 (s, 3H), 3.39 (brs, 1). 3.10 (brs, 1H), 1.88-1.94 (m, 2H), 1.40 (d, 6H). LCMS retention time 1.942 min; LCMS MH$^+$ 470

Example 81 7-(4-chlorobenzyl)-1-(3-hydroxypropyl)-3-methyl-8-(3-(trifluoromethoxy)phenylamino)-1H-purine-2,6(3H,7H)-dione

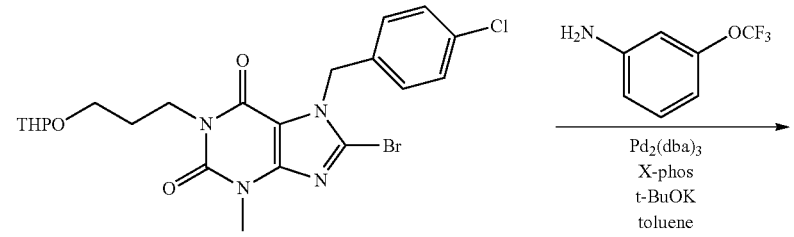

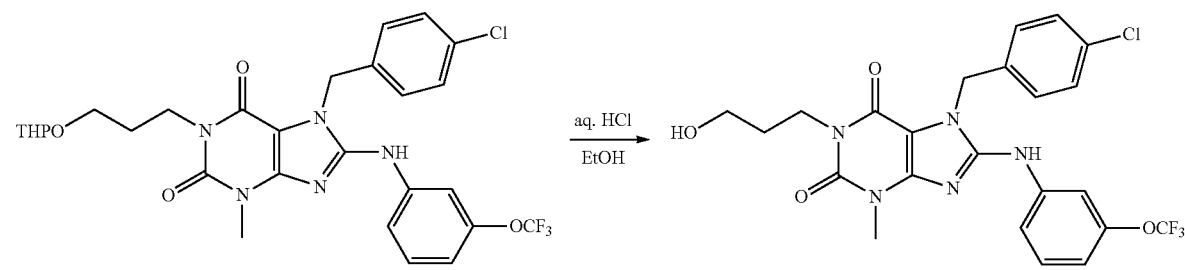

Step 1 7-(4-chlorobenzyl)-3-methyl-1-(3-(tetrahydro-2H-pyran-2-yloxy)propyl)-8-(3-(trifluoromethoxy)phenylamino)-1H-purine-2,6(3H,7H)-dione (WYS-000356-026)

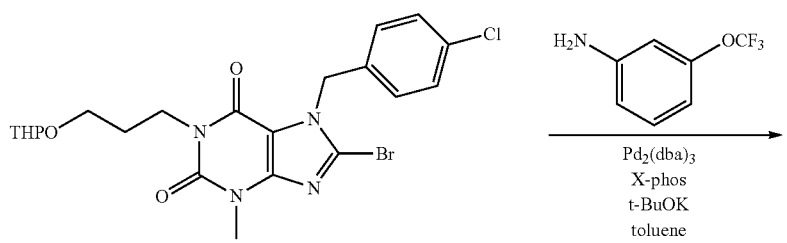

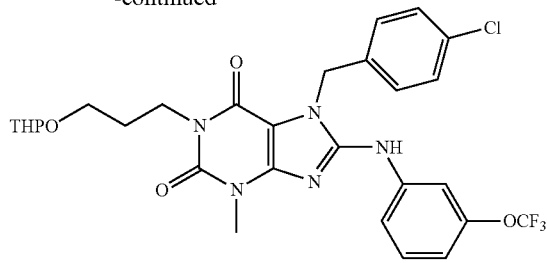

To a solution of 8-bromo-7-(4-chlorobenzyl)-3-methyl-1-(3-(tetrahydro-2H-pyran-2-yloxy)propyl)-1H-purine-2,6(3H,7H)-dione (100 mg, 0.196 mmol, Intermediate 14) in toluene (30 mL) was added 3-(trifluoromethoxy)aniline (45 mg, 0.254 mmol), tris(dibenzylideneacetone)dipalladium(0) (10 mg, 0.011 mmol), X-phos (10 mg, 0.021 mmol) and potassium tert-butanolate (45 mg, 0.402 mmol). The mixture was degassed and refilled with nitrogen 3 times. The reaction was stirred at 100° C. overnight under nitrogen. The mixture was filtered and the filter cake was washed with ethyl acetate. The filtrate was concentrated to give a crude product which was purified by silica gel chromatography eluting with petroleum/ethyl acetate (3:1 to 3:2). The product was collected, concentrated, and dried in vacuo to give 7-(4-chlorobenzyl)-3-methyl-1-(3-(tetrahydro-2H-pyran-2-yloxy)propyl)-8-(3-(trifluoromethoxy)phenylamino)-1H-purine-2,6(3H,7H)-dione (70 mg, 57.6%) as a yellow solid. LCMS MH$^+$-THP 524.

Step 2 7-(4-chlorobenzyl)-1-(3-hydroxypropyl)-3-methyl-8-(3-(trifluoromethoxy)phenylamino)-1H-purine-2,6(3H,7H)-dione

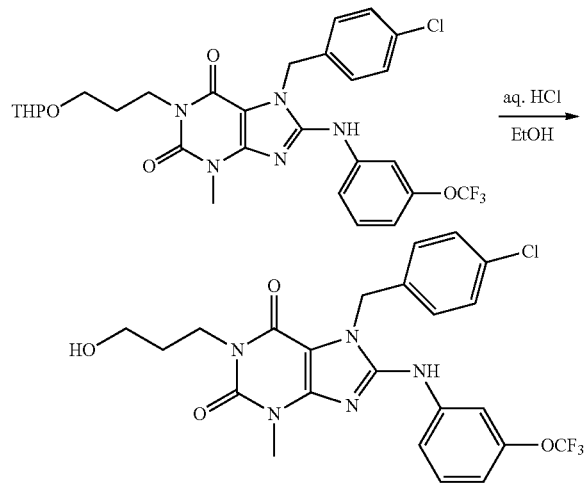

The title compound was prepared as example 36, step 2 but with aqueous ethanolic HCl. White solid, 13 mg, 12.4% yield: $^1$H-NMR (DMSO-d$_6$) δ 9.63 (s, 1H), 7.91 (s, 1H), 7.63-7.61 (d, 1H), 7.45-7.38 (m, 3H), 7.24-7.22 (d, 2H), 6.97-6.94 (d, 1H), 5.57 (s, 2H), 4.44-4.42 (t, 1H), 3.89-3.86 (t, 2H), 3.42-3.38 (m, 4H), 3.31 (s, 3H), 1.69-1.61 (m, 2H). LCMS retention time 2.853 min; LCMS MH$^+$ 524.

Example 82 7-(4-chlorobenzyl)-1-((1-(hydroxymethyl)cyclopropyl)methyl)-3-methyl-8-(3-(trifluoromethoxy)phenoxy)-1H-purine-2,6(3H,7H)-dione

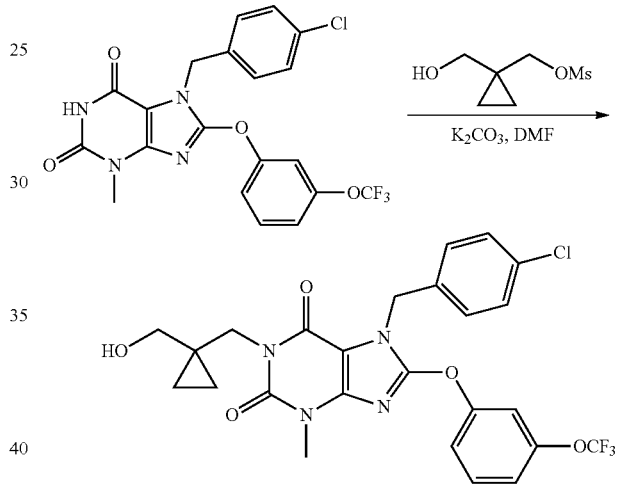

To a solution of 7-(4-chlorobenzyl)-3-methyl-8-(3-(trifluoromethoxy)phenoxy)-1H-purine-2,6(3H,7H)-dione (80 mg, 0.17 mmol, intermediate 9) in DMF (5 mL) was added (1-(hydroxymethyl)cyclopropyl)methyl methanesulfonate (0.1 g, 0.5 mmol, intermediate 42), potassium carbonate (47 mg, 0.34 mmol) and TBAI (2 mg, 0.02 mmol). The reaction was stirred at 50° C. for 8 h. The mixture was cooled and partitioned between ethyl acetate and water. The combined organic layer was dried over sodium sulfate, filtered and concentrated to give a crude product which was purified by preparative HPLC to give 7-(4-chlorobenzyl)-1-((1-(hydroxymethyl)cyclopropyl)methyl)-3-methyl-8-(3(trifluoromethoxy)phenoxy)-1H-purine-2,6(3H,7H)-dione (36 mg, 39.9% yield) as a white solid. $^1$H-NMR (CD$_3$OD) δ 7.39 (t, 1H), 7.01 (dd, 1H), 6.88-6.90 (m, 2H), 4.87-4.88 (m, 2H), 4.44-4.46 (m, 2H), 4.08-4.16 (m, 4H), 3.61 (t, 2H), 3.51 (s, 3H), 1.80-1.90 (m, 2H), 1.32 (t, 3H). LCMS retention time 3.099 min; LCMS MH$^+$ 533.

The following examples 83a and 83d were prepared using the method of example 82.

Example 83a 7-(4-chlorobenzyl)-1-(2-(1-hydroxycyclopentyl)ethyl)-3-methyl-8-(3-(trifluoromethoxy)phenoxy)-1H-purine-2,6(3H,7H)-dione

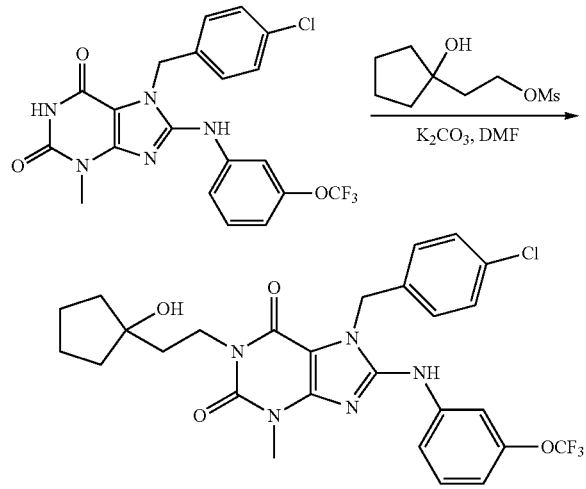

The title compound was prepared from Intermediates 9 and 43. White solid, 18 mg, 17.9% yield: $^1$H-NMR (CD$_3$OD) δ 7.54 (t, 1H), 7.44 (dd, 2H), 7.32-7.36 (m, 4H), 7.22-7.25 (m, 1H), 5.48 (s, 2H), 4.14-4.18 (m, 2H), 3.51 (s, 3H), 1.88-1.92 (m, 2H), 1.62-1.82 (m, 8H). LCMS retention time 3.304 min; LCMS MH$^+$ 561

Example 83b 7-(4-chlorobenzyl)-1-(2-(1-hydroxycyclobutyl)ethyl)-3-methyl-8-(3-(trifluoromethoxy)phenoxy)-1H-purine-2,6(3H,7H)-dione

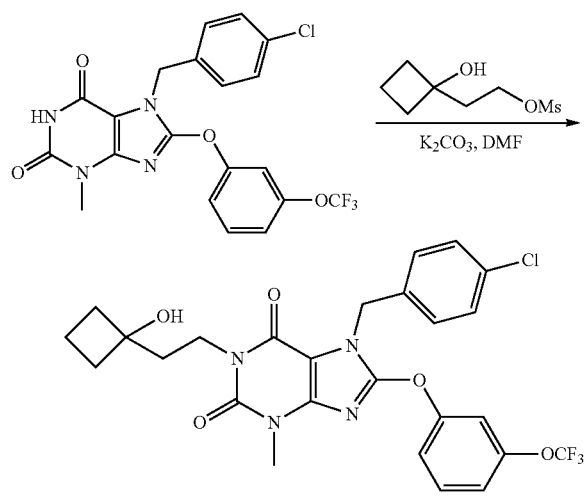

The title compound was prepared from intermediates 9 and 44. White solid, 20 mg, 17.9% yield: $^1$H-NMR (CD$_3$OD) δ 7.55 (t, 1H), 7.54 (d, 2H), 7.32-7.38 (m, 4H), 7.23-7.26 (m, 1H), 5.51 (s, 2H), 4.11-4.15 (m, 2H), 3.50 (s, 3H), 2.05-2.17 (m, 4H), 1.93-1.97 (m, 2H), 1.76-1.80 (m, 1H) 1.59-1.63 (m, 1H). LCMS retention time 3.111 min; LCMS MH$^+$ 547

Example 83c 7-(4-chlorobenzyl)-1-(3-hydroxy-3-methylbutyl)-3-methyl-8-(3-(trifluoromethoxy)phenoxy)-1H-purine-2,6(3H,7H)-dione

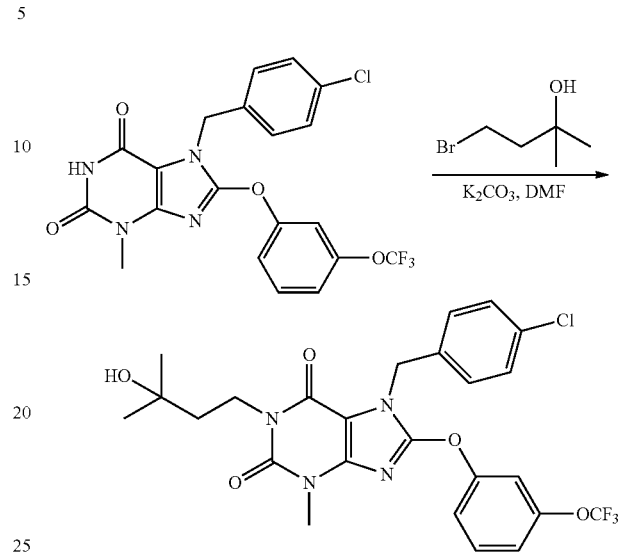

The title compound was prepared from intermediates 9 and 45. White solid, 23 mg, 39.6% yield: $^1$H-NMR (CD$_3$OD) δ 7.55 (t, 1H), 7.44 (d, 2H), 7.32-7.38 (m, 4H), 7.24 (d, 1H), 5.50 (s, 2H), 4.11-4.15 (m, 2H), 3.42 (s, 3H), 1.78-1.82 (m, 2H), 1.29 (s, 6H). LCMS retention time 3.235 min; LCMS MH$^+$ 535

Example 83d 7-(4-chlorobenzyl)-1-(2-(1-hydroxycyclopropyl)ethyl)-3-methyl-8-(3-(trifluoromethoxy)phenoxy)-1H-purine-2,6(3H,7H)-dione

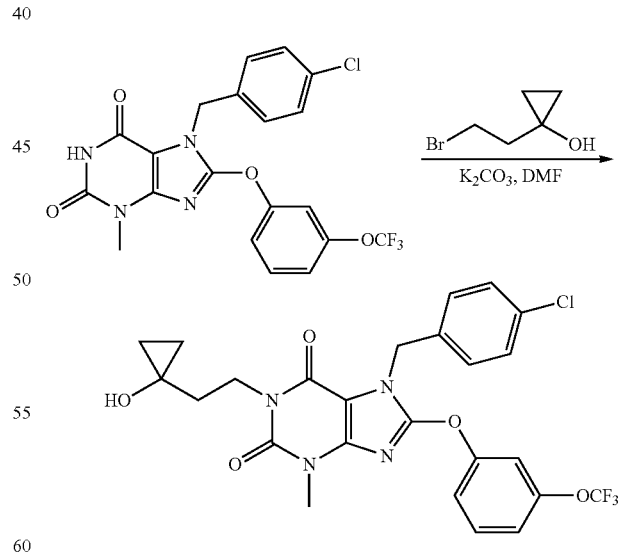

The title compound was prepared from intermediates 9 and 46. White solid, 39 mg, 33.9% yield: $^1$H-NMR (CD$_3$OD) δ 7.55 (t, 1H), 7.44 (d, 2H), 7.34-7.36 (m, 4H), 7.25 (d, 1H), 5.49 (s, 2H), 4.26 (t, 2H), 3.42 (s, 3H), 1.84 (t, 2H), 0.62 (t, 2H), 0.38 (t, 2H). LCMS retention time 3.301 min; LCMS MH$^+$ 551

Example 84 7-(4-chlorobenzyl)-8-(2-(cyclohexyloxy)ethoxy)-1-(3-hydroxypropyl)-3-methyl-1H-purine-2,6(3H,7H)-dione temperature for 30 min. Then a solution of 8-bromo-7-(4-chlorobenzyl)-3-methyl-1-(3-(tetrahydro-2H-pyran-2-yloxy)propyl)-1H-purine-2,6(3H,7H)-dione (150 mg, 0.293

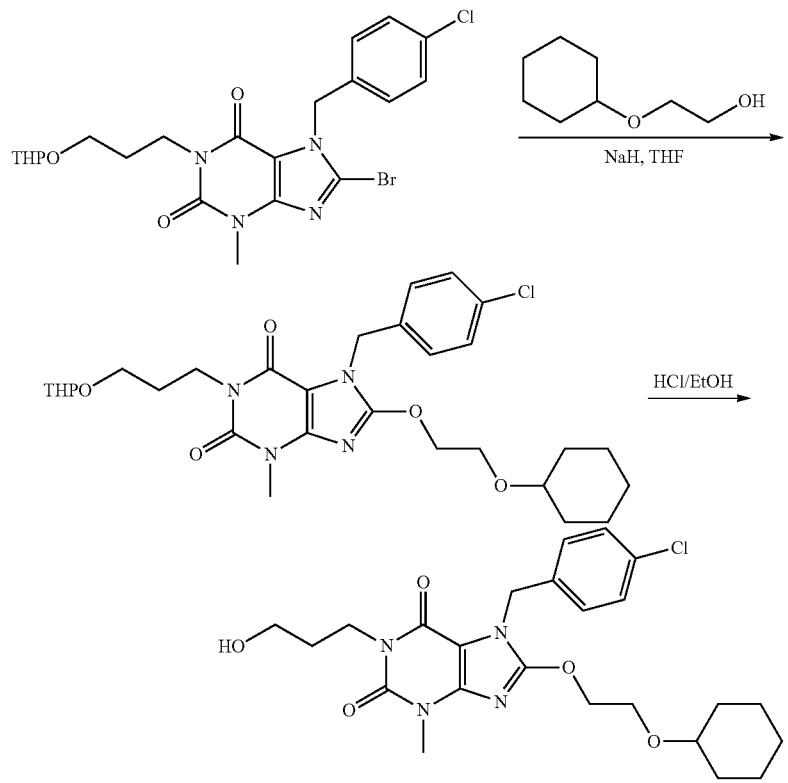

Step 1 7-(4-chlorobenzyl)-8-(2-(cyclohexyloxy)ethoxy)-3-methyl-1-(3-(tetrahydro-2H-pyran-2-yloxy)propyl)-1H-purine-2,6(3H,7H)-dione mmol, intermediate 14) in THF (1 mL) was added and the resulting mixture was stirred at reflux for 1 h. The reaction was cooled and quenched with ice-water. The mixture was

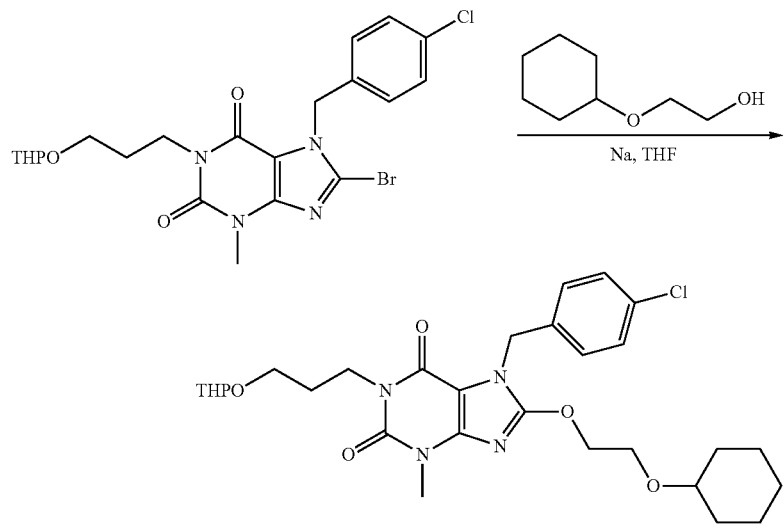

To a solution of 2-(cyclohexyloxy)ethanol (63.4 mg, 0.439 mmol, intermediate 38) in THF (5 mL) was added sodium hydride (23.4 mg, 0.586 mmol, 60% dispersion in mineral oil) at 0° C., and the mixture was stirred at room extracted with ethyl acetate. The organic phase was dried and concentrated to give 7-(4-chlorobenzyl)-8-(2-(cyclohexyloxy)ethoxy)-3-methyl-1-(3-(tetrahydro-2H-pyran-2-yloxy)propyl)-1H-purine-2,6(3H,7H)-dione (123 mg, 73% yield) as a yellow solid. LCMS retention time 2.064 min; LCMS MH⁺-THP 491.

Step 2 7-(4-chlorobenzyl)-8-(2-(cyclohexyloxy)ethoxy)-1-(3-hydroxypropyl)-3-methyl-1H-purine-2,6(3H,7H)-dione

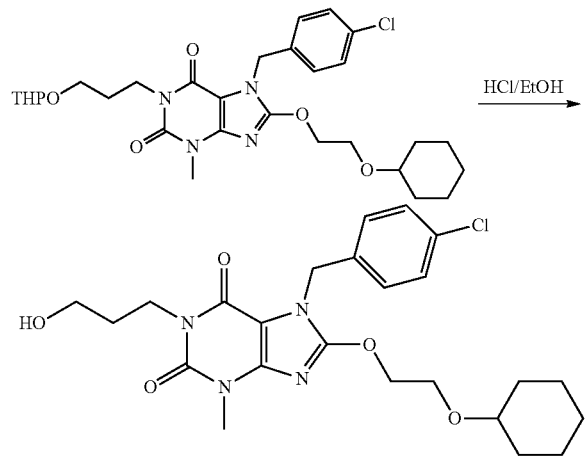

A solution of 7-(4-chlorobenzyl)-8-(2-(cyclohexyloxy)ethoxy)-3-methyl-1-(3-(tetrahydro-2H-pyran-2-yloxy)propyl)-1H-purine-2,6(3H,7H)-dione (123 mg, 0.214 mmol) in 1 mM ethanolic HCl (2 mL) was stirred at room temperature for 30 min. The reaction was concentrated to dryness to give a crude product, which was purified by preparative HPLC to give 7-(4-chlorobenzyl)-8-(2-(cyclohexyloxy)ethoxy)-1-(3-hydroxypropyl)-3-methyl-1H-purine-2,6(3H,7H)-dione (64 mg, 60.9% yield) as a white solid. $^1$H-NMR (CDCl$_3$) δ 7.41-7.44 (d, 2H), 7.28-7.31 (d, 2H), 5.26 (s, 2H), 4.63-4.65 (m, 2H), 4.17-4.20 (t, 2H), 3.81-3.84 (m, 2H), 3.68-3.70 (br, 1H), 3.21 (m, 5H), 3.30-3.34 (m, 1H), 1.87-1.93 (m, 4H), 1.75-1.77 (t, 2H), 1.55-1.58 (m, 1H), 1.23-1.36 (m, 5H). LCMS retention time 2.893 min; LCMS MH⁺ 491.

Example 85 7-(4-chlorobenzyl)-1-(3-hydroxypropyl)-3-methyl-8-(2-propoxyethoxy)-1H-purine-2,6(3H,7H)-dione

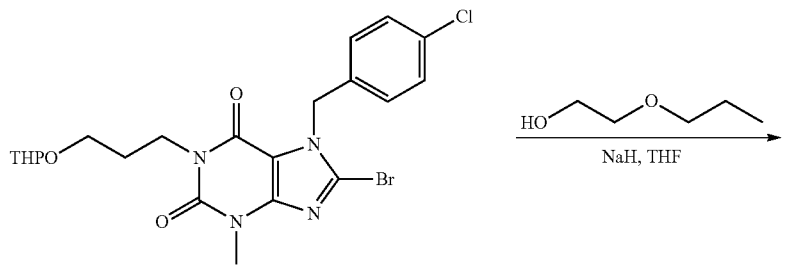

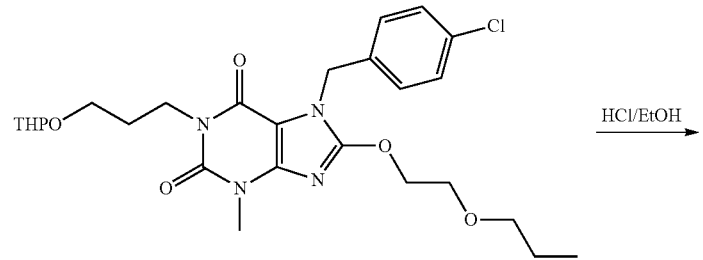

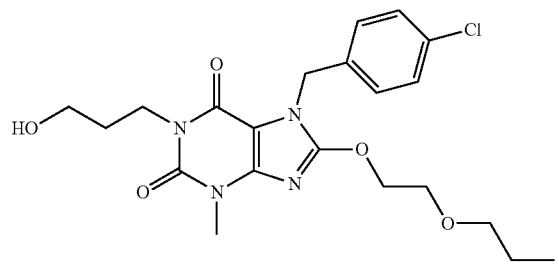

The title compound was prepared using the method of example 84 and purified by preparative HPLC to give 7-(4-chlorobenzyl)-1-(3-hydroxypropyl)-3-methyl-8-(2-propoxyethoxy)-1H-purine-2,6(3H,7H)-dione (39 mg, 38.7% yield) as a white solid. ¹H-NMR (CD₃OD) δ 7.39-7.42 (d, 2H), 7.31-7.33 (d, 2H), 5.29 (s, 2H), 4.63-4.65 (m, 2H), 4.06-4.10 (t, 2H), 3.80-3.83 (m, 2H), 3.58-3.61 (t, 2H), 3.49 (s, 3H), 3.44-3.47 (t, 2H), 1.84-1.87 (t, 2H), 1.55-1.60 (m, 2H), 0.90-0.94 (t, 3H). LCMS retention time 2.561 min; LCMS MH⁺ 451.

Example 86 7-(4-chlorobenzyl)-1-(3-hydroxypropyl)-3-methyl-8-(6-methylpyridin-3-yloxy)-1H-purine-2,6(3H,7H)-dione hydrochloride

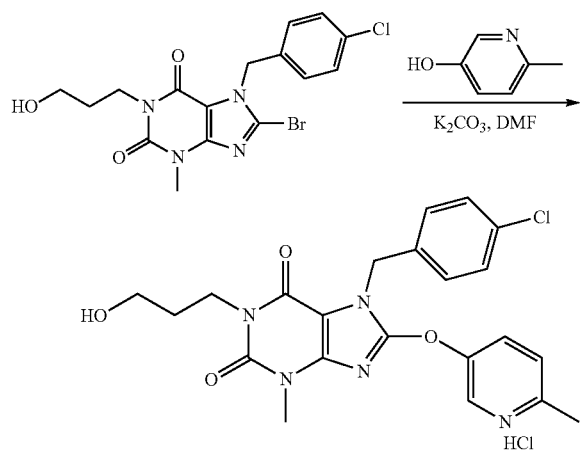

The title compound was prepared from intermediate 63 using the method of example 55 except with 6-methylpyridin-3-ol to give 35 mg (44.1% yield) as white solid. ¹H-NMR (DMSO-d₆) δ 8.69 (s, 1H), 8.03-8.01 (d, 1H), 7.59-7.57 (d, 1H), 7.45 (s, 4H), 5.45 (s, 2H), 4.06-3.98 (m, 2H), 3.45-3.42 (t, 2H), 3.28 (s, 3H), 2.59 (s, 3H), 1.71-1.67 (t, 2H). LCMS retention time 2.207 min; LCMS MH⁺ 456.

Example 87 7-(4-chlorobenzyl)-1-(3-hydroxypropyl)-3-methyl-8-(2-methylpyridin-4-yloxy)-1H-purine-2,6(3H,7H)-dione hydrochloride

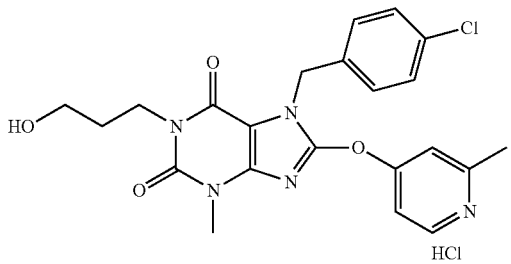 [SMILES: Cc1cc(Oc2nc3c(c(=O)n(CCCO)c(=O)n3C)n2Cc2ccc(Cl)cc2)ccn1 ; Cl]

The title compound was prepared using the method of example 55. White solid, 30 mg, 36.6% yield: ¹H-NMR (DMSO-d₆) δ 8.48-8.46 (d, 1H), 8.17 (s, 1H), 7.43-7.33 (m, 4H), 7.26-7.22 (m, 2H), 5.42 (s, 2H), 4.52 (s, 1H), 3.95-3.92 (t, 2H), 3.44-3.42 (m, 2H), 3.37 (s, 3H), 2.47 (s, 3H), 1.72-1.69 (t, 2H). LCMS retention time 1.716 min; LCMS MH⁺ 456.

Example 88 7-(4-chlorobenzyl)-1-(3-hydroxypropyl)-3-methyl-8-(5-methylpyridin-3-yloxy)-1H-purine-2,6(3H,7H)-dione

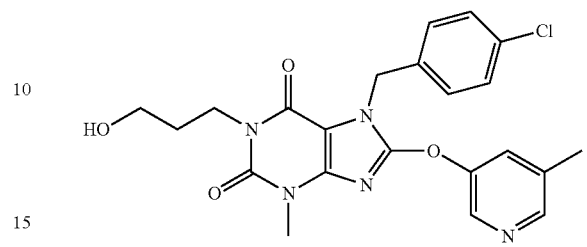

The title compound was prepared using the method of example 55. White solid, 40 mg, 48.8% yield: ¹H-NMR (DMSO-d₆) δ 8.45-8.44 (d, 1H), 8.36 (s, 1H), 7.65 (s, 1H), 7.46-7.41 (m, 4H), 5.44 (s, 2H), 4.50-4.47 (t, 1H), 3.94-3.91 (t, 2H), 3.46-3.40 (m, 2H), 3.28 (s, 3H), 2.34 (s, 3H), 1.73-1.66 (m, 2H). LCMS retention time 2.259 min; LCMS MH⁺ 456

Example 89 7-butyl-1-(3-hydroxypropyl)-3-methyl-8-(5-methylpyridin-3-yloxy)-1H-purine-2,6(3H,7H)-dione

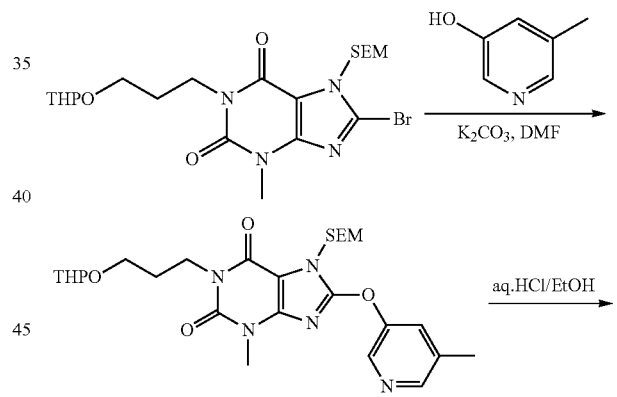

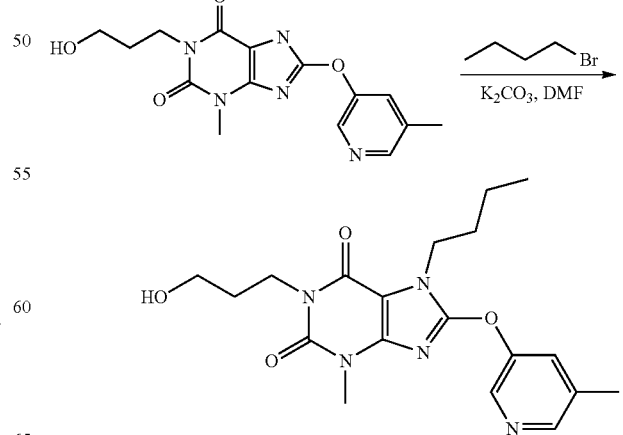

543

Step 1 3-methyl-8-(5-methylpyridin-3-yloxy)-1-(3-(tetrahydro-2H-pyran-2-yloxy)propyl)-7-((2-(trimethylsilyl)ethoxy)methyl)-1H-purine-2,6(3H,7H)-dione

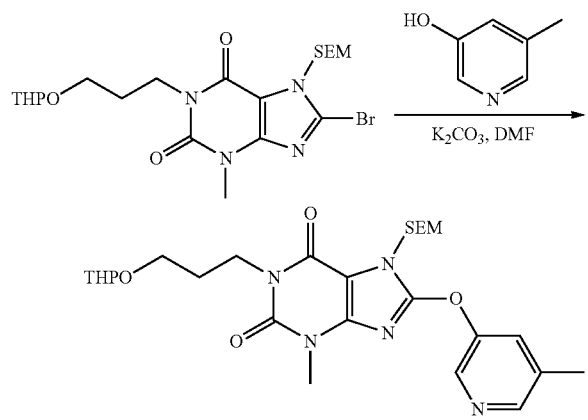

The title compound was prepared using the method of example 52, step 1. Yellow oil, 300 mg, 97.6% yield: LCMS retention time 1.838 min; LCMS MH+-THP 462

Step 2 7-(4-chlorobenzyl)-1-(3-hydroxybutyl)-3-methyl-8-(6-methylpyridin-3-yloxy)-1H-purine-2,6(3H,7H)-dione

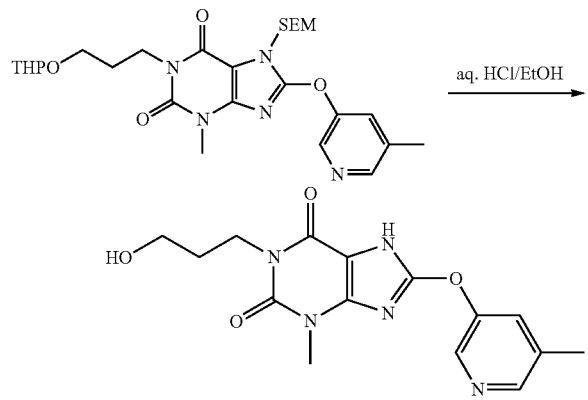

544

To a solution of 3-methyl-8-(5-methylpyridin-3-yloxy)-1-(3-(tetrahydro-2H-pyran-2-yloxy)propyl)-7-((2-(trimethylsilyl)ethoxy)methyl)-1H-purine-2,6(3H,7H)-dione (300 mg, 0.554 mmol) in ethyl alcohol (10 ml) was added concentrated HCl (3 ml). The reaction was stirred for 6 h at 90° C. The reaction was cooled and concentrated to give 7-(4-chlorobenzyl)-1-(3-hydroxybutyl)-3-methyl-8-(6-methylpyridin-3-yloxy)-1H-purine-2,6(3H,7H)-dione (180 mg, 98.9%) as yellow oil. LCMS retention time 0.356 min; LCMS MH+ 332.

Step 3 7-butyl-1-(3-hydroxypropyl)-3-methyl-8-(5-methylpyridin-3-yloxy)-1H-purine-2,6(3H,7H)-dione

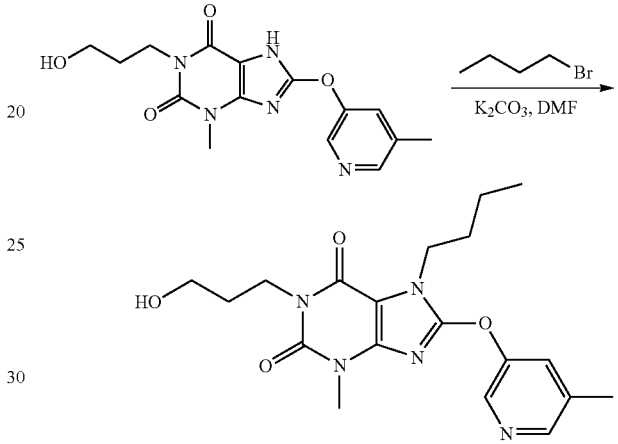

The title compound was prepared using the method of example 61, step 2. White solid, 30 mg, 42.8% yield: $^{1}$H-NMR (DMSO-$d_6$) δ 8.48-8.47 (d, 1H), 8.37-8.36 (d, 1H), 7.71 (s, 1H), 4.51-4.48 (t, 1H), 4.22-4.19 (t, 2H), 3.94-3.91 (t, 2H), 3.46-3.43 (t, 2H), 3.28 (s, 3H), 2.36 (s, 3H), 1.81-1.66 (m, 4H), 1.35-1.30 (m, 2H), 0.93-0.89 (t, 3H). LCMS retention time 1.854 min; LCMS MH+ 388.

Example 90 7-(4-chlorobenzyl)-8-(2-isopropoxyethoxy)-3-methyl-1-(3-(tetrahydro-2H-pyran-2-yloxy)propyl)-1H-purine-2,6(3H,7H)-dione

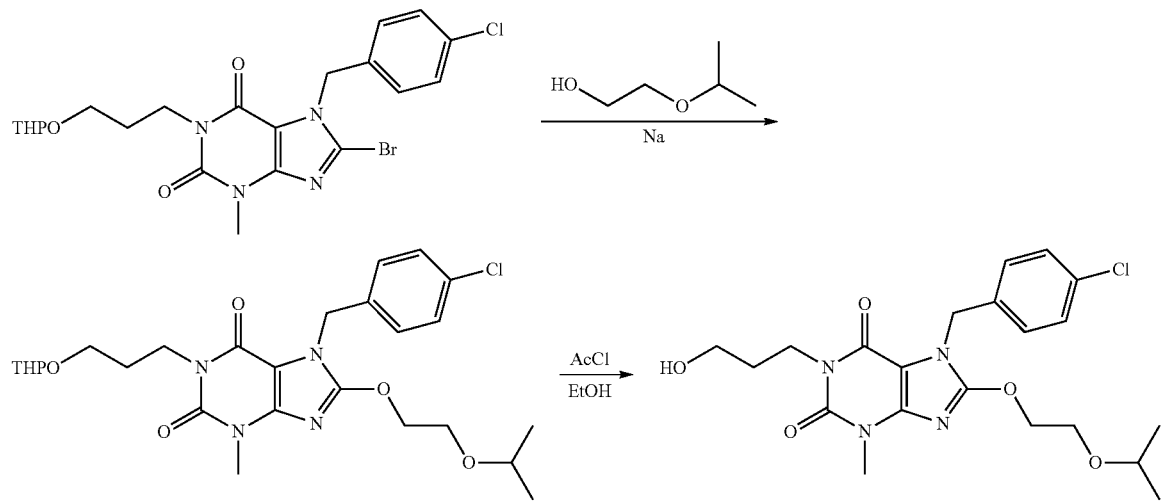

Step 1 7-(4-chlorobenzyl)-8-(2-isopropoxyethoxy)-3-methyl-1-(3-(tetrahydro-2H-pyran-2-yloxy)propyl)-1H-purine-2,6(3H,7H)-dione

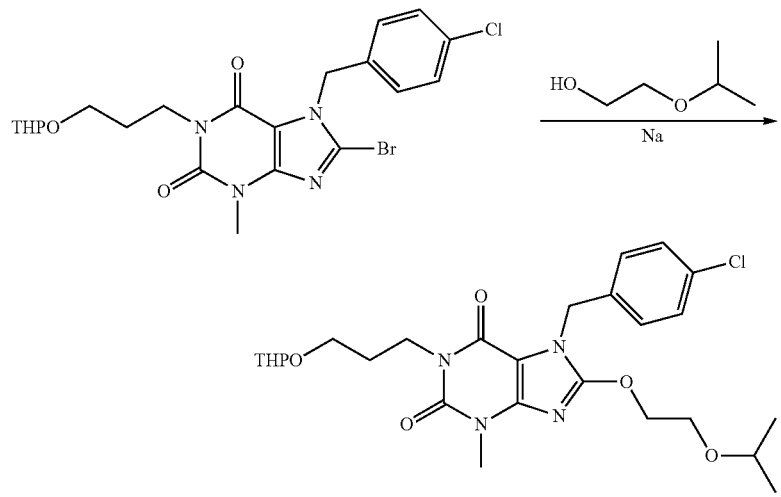

The title compound was prepared using the method of example 50, step 1. Yellow oil, 100 mg, 95.2%. LCMS retention time 1.864 min; LCMS MH⁺-THP 451

Step 2 7-(4-chlorobenzyl)-8-(2-isopropoxyethoxy)-3-methyl-1-(3-(tetrahydro-2H-pyran-2-yloxy)propyl)-1H-purine-2,6(3H,7H)-dione

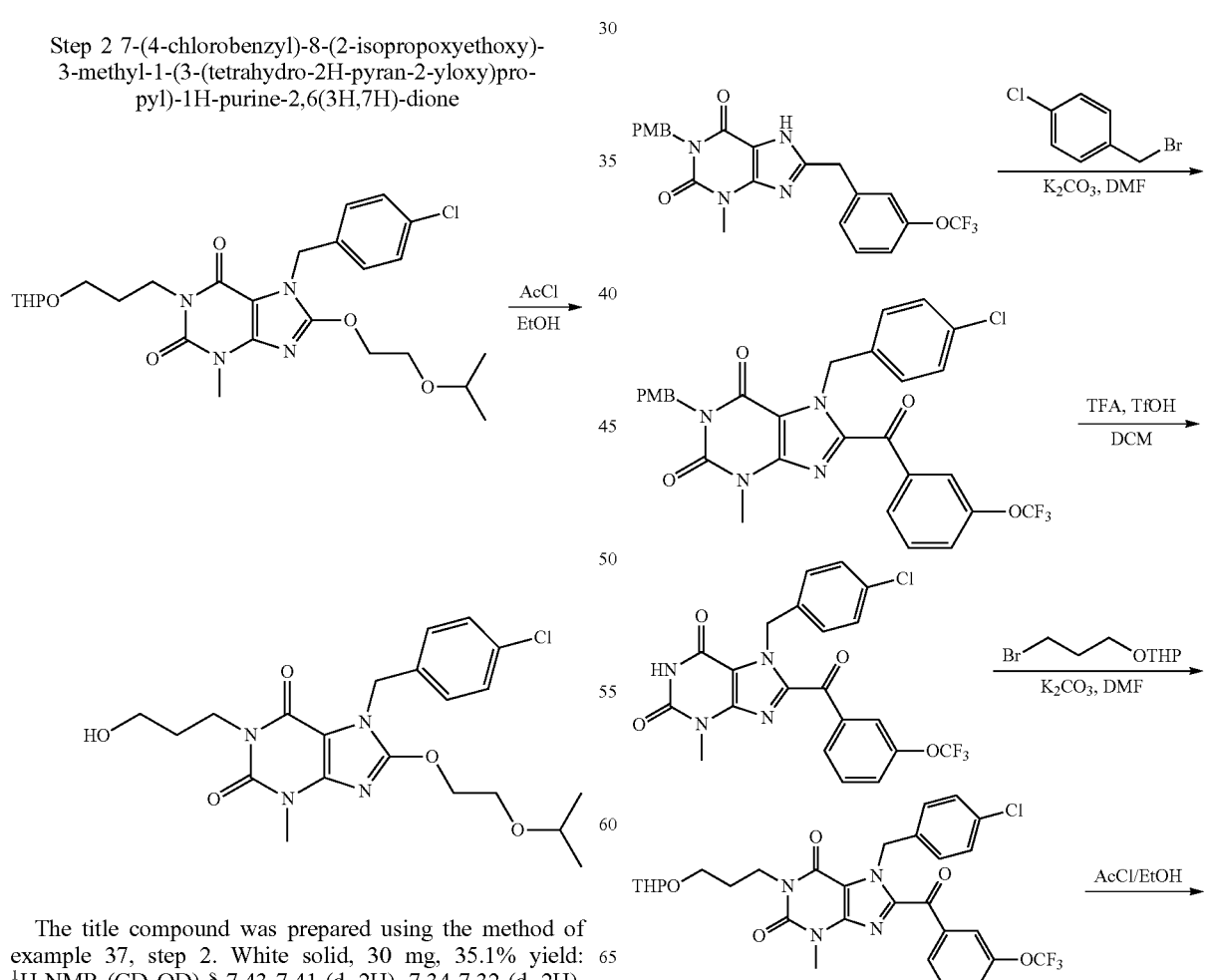

The title compound was prepared using the method of example 37, step 2. White solid, 30 mg, 35.1% yield: ¹H-NMR (CD₃OD) δ 7.43-7.41 (d, 2H), 7.34-7.32 (d, 2H), 5.30 (s, 2H), 4.66-4.64 (m, 2H), 4.11-4.07 (t, 2H), 3.83-3.81 (m, 2H), 3.68-3.58 (m, 3H), 3.50 (s, 3H), 1.88-1.85 (m, 2H), 1.17-1.56 (d, 6H). LCMS retention time 2.464 min; LCMS MH⁺ 451

Example 91 7-(4-chlorobenzyl)-1-(3-hydroxypropyl)-3-methyl-8-(3-(trifluoromethoxy)benzoyl)-1H-purine-2,6(3H,7H)-dione -continued

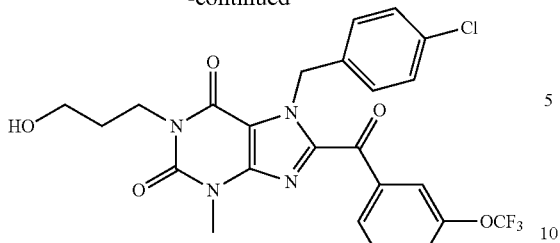

Step 1 7-(4-chlorobenzyl)-1-(4-methoxybenzyl)-3-methyl-8-(3-(trifluoromethoxy)benzoyl)-1H-purine-2,6(3H,7H)-dione

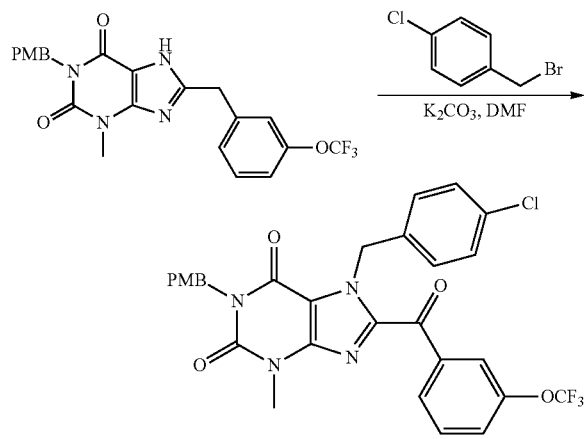

The title compound was prepared using the method of intermediate 16, step 3. White solid, 15 mg, 21.5% yield. LCMS retention time 2.159 min; LCMS MH+ 599.

Step 2 7-(4-chlorobenzyl)-3-methyl-8-(3-(trifluoromethoxy)benzoyl)-1H-purine-2,6(3H,7H)-dione

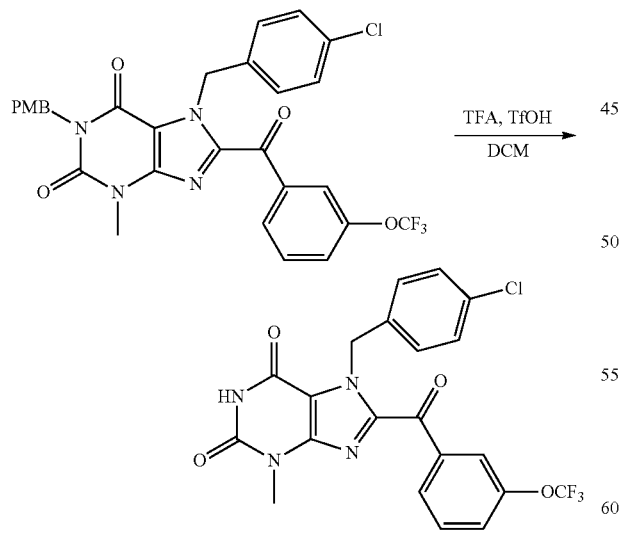

To a solution of 7-(4-chlorobenzyl)-1-(4-methoxybenzyl)-3-methyl-8-(3-(trifluoromethoxy)benzoyl)-1H-purine-2,6(3H,7H)-dione (15 mg, 0.025 mmol) in DCM (1 ml) was added TFA (1 ml) dropwise followed by trifluoromethanesulfonic acid (0.25 ml), both at 0° C. The reaction was stirred at 0° C. for 10 min, then stirred at room temperature for 16 h. The reaction was quenched with aqueous saturated sodium bicarbonate and extracted with DCM. The organic phase was washed with water dried over sodium sulfate, filtered and concentrated to give 7-(4-chlorobenzyl)-3-methyl-8-(3-(trifluoromethoxy)benzoyl)-1H-purine-2,6(3H,7H)-dione (10 mg, 83.7%) as yellow oil. LCMS retention time 1.821 min; LCMS MH+ 479.

Step 3 7-(4-chlorobenzyl)-3-methyl-1-(3-(tetrahydro-2H-pyran-2-yloxy)propyl)-8-(3-(trifluoromethoxy)benzoyl)-1H-purine-2,6(3H,7H)-dione

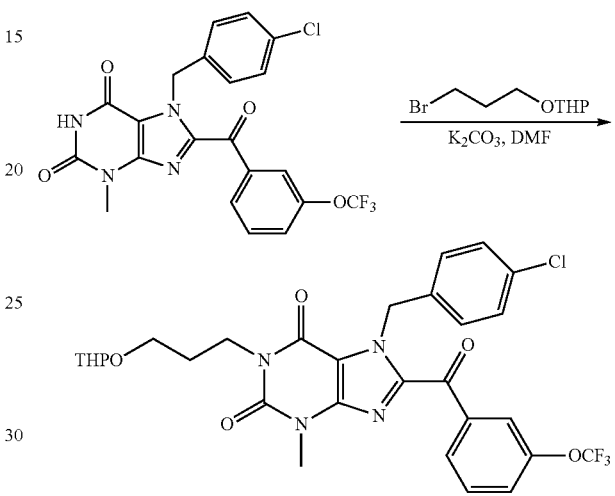

The title compound was prepared using the method of intermediate 14. Yellow oil, 10 mg, 76.8% yield: LCMS retention time 2.176 min; LCMS MH+-THP 537.

Step 4 7-(4-chlorobenzyl)-1-(3-hydroxypropyl)-3-methyl-8-(3-(trifluoromethoxy)benzoyl)-1H-purine-2,6(3H,7H)-dione

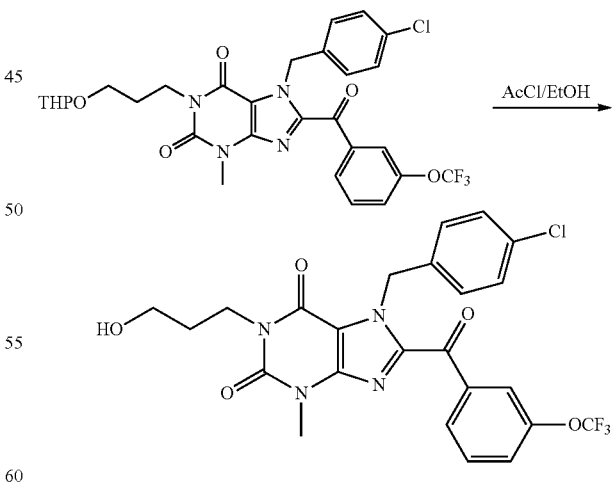

The title compound was prepared using the method of example 37, step 2. Light yellow solid, 8 mg, 92.6% yield: $^1$H-NMR (DMSO-$d_6$) δ 8.20-8.16 (m, 2H), 7.74-7.72 (m, 2H), 7.40-7.37 (d, 2H), 7.30-7.28 (d, 2H), 5.93 (s, 2H), 4.51 (s, 1H), 3.97-3.93 (t, 2H), 3.47-3.39 (m, 5H), 1.73-1.69 (m, 2H). LCMS retention time 2.996 min; LCMS MH+ 537

Example 92 7-(4-chlorobenzyl)-8-(hydroxy(3-(trifluoromethoxy)phenyl)methyl)-1-(3-hydroxypropyl)-3-methyl-1H-purine-2,6(3H,7H)-dione

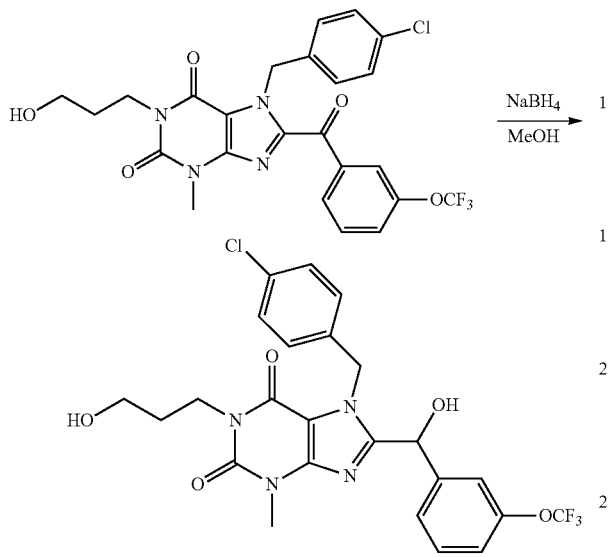

To a solution of 7-(4-chlorobenzyl)-1-(3-hydroxypropyl)-3-methyl-8-(3-(trifluoromethoxy)benzoyl)-1H-purine-2,6(3H,7H)-dione (50 mg, 0.081 mmol, example 91) in methanol (3 mL) was added sodium borohydride (10 mg, 0.263 mmol) at 0° C. under nitrogen. The reaction was stirred at 0° C. for 2 h. The reaction was quenched and partitioned with ethyl acetate and water. The organic phase was washed with brine, dried over sodium sulfate, filtered and concentrated to give a crude product, which was purified by preparative HPLC to give 7-(4-chlorobenzyl)-8-(hydroxy(3-(trifluoromethoxy)phenyl)methyl)-1-(3-hydroxypropyl)-3-methyl-1H-purine-2,6(3H,7H)-dione (10 mg, 22.9%) as white solid. $^1$H-NMR (CDCl$_3$) δ 7.36-7.31 (t, 1H), 7.23-7.14 (m, 5H), 6.94-6.92 (d, 2H), 5.87-5.85 (d, 1H), 5.60-5.56 (d, 1H), 5.39-5.35 (d, 1H), 4.20-4.17 (t, 2H), 3.65-3.63 (s, 4H), 3.54-3.51 (m, 2H), 3.31 (s, 1H), 1.91-1.88 (t, 2H). LCMS retention time 2.605 min; LCMS MH$^+$ 539.

Example 93 7-(4-chlorobenzyl)-1-(3-hydroxypropyl)-3-methyl-8-(3-(3-(trifluoromethoxy)phenoxy)propyl)-1H-purine-2,6(3H,7H)-dione

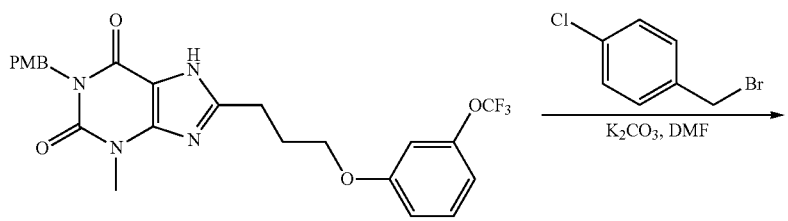

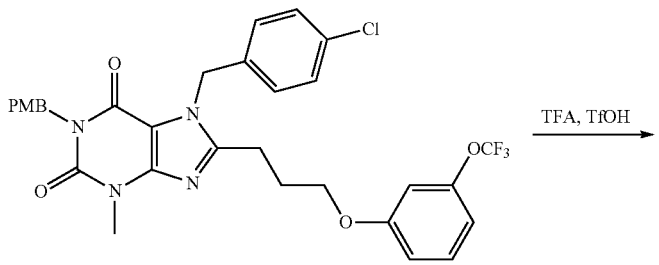

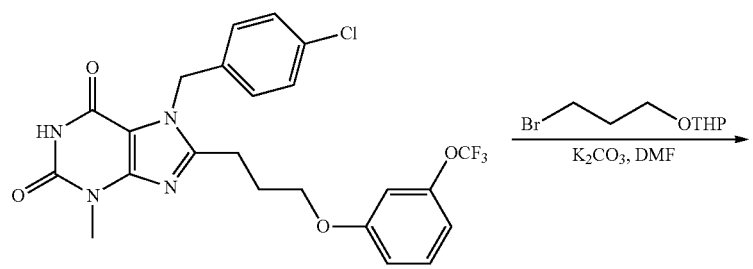

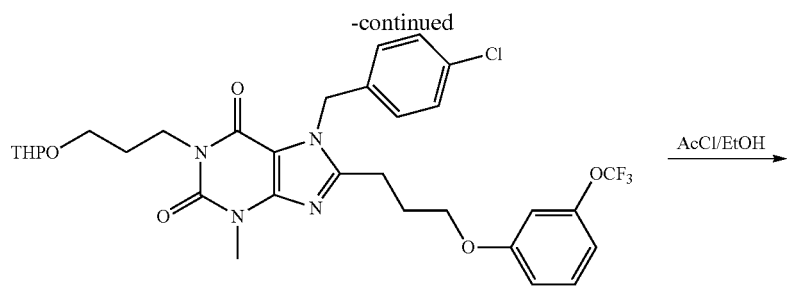

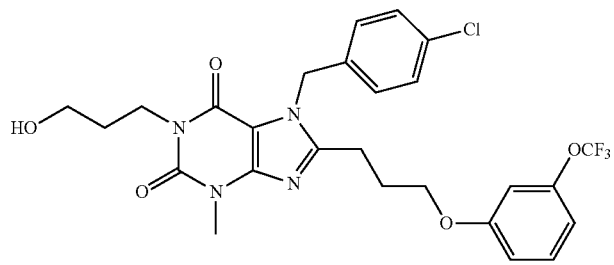

Step 1 7-(4-chlorobenzyl)-1-(4-methoxybenzyl)-3-methyl-8-(3-(3-(trifluoromethoxy)phenoxy)propyl)-1H-purine-2,6(3H,7H)-dione

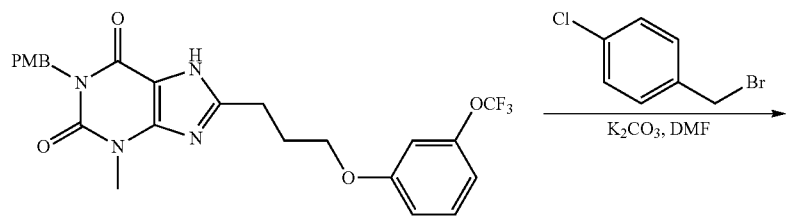

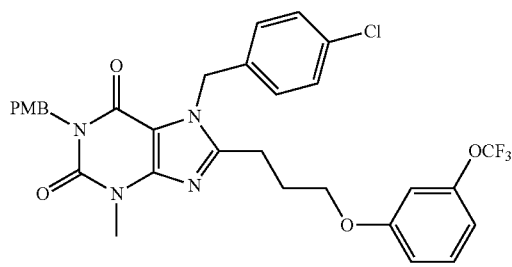

To a solution of 1-(4-methoxybenzyl)-3-methyl-8-(3-(3-(trifluoromethoxy)phenoxy)propyl)-1H-purine-2,6(3H,7H)-dione (130 mg, 0.261 mmol, intermediate 60) in DMF (3 mL) was added 1-(bromomethyl)-4-chlorobenzene (70 mg, 0.345 mmol), followed by potassium carbonate (107 mg, 0.775 mmol) and TBAI (5 mg, 0.014 mmol). The mixture was stirred at 60° C. overnight. The reaction was cooled and partitioned between ethyl acetate and water. The combined organic phase was washed with brine, dried over sodium sulfate, and concentrated to give the crude product 7-(4-chlorobenzyl)-1-(4-methoxybenzyl)-3-methyl-8-(3-(3-(trifluoromethoxy)phenoxy)propyl)-1H-purine-2,6(3H,7H)-dione (150 mg, 92.5% yield) as a yellow oil. LCMS retention time 2.075 min; LCMS MH+ 629.

Step 2 7-(4-chlorobenzyl)-3-methyl-8-(3-(3-(trifluoromethoxy)phenoxy)propyl)-1H-purine-2,6(3H,7H)-dione

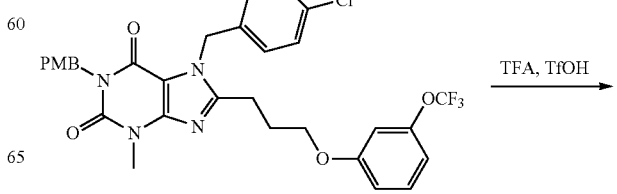

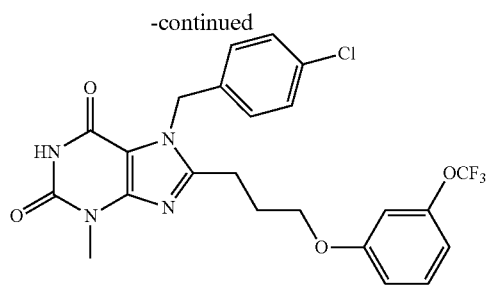

To a solution of 7-(4-chlorobenzyl)-1-(4-methoxybenzyl)-3-methyl-8-(3-(3-(trifluoromethoxy)phenoxy)propyl)-1H-purine-2,6(3H,7H)-dione (105 mg, 0.167 mmol) in DCM (4 mL) was added TFA (1 mL) dropwise followed by trifluoromethanesulfonic acid (0.25 mL) at 0° C. The reaction was stirred at 0° C. for 10 min, then at room temperature for 16 h. The reaction was quenched with saturated sodium bicarbonate and extracted with DCM. The organic phase was washed with water, dried over sodium sulfate, and concentrated to give 7-(4-chlorobenzyl)-3-methyl-8-(3-(3-(trifluoromethoxy)phenoxy)propyl)-1H-purine-2,6(3H,7H)-dione (66 mg, 77.6% yield) as a yellow oil. LCMS retention time 2.868 min; LCMS MH$^+$ 509.

Step 3 7-(4-chlorobenzyl)-3-methyl-1-(3-(tetrahydro-2H-pyran-2-yloxy)propyl)-8-(3-(3-(trifluoromethoxy)phenoxy)propyl)-1H-purine-2,6(3H,7H)-dione

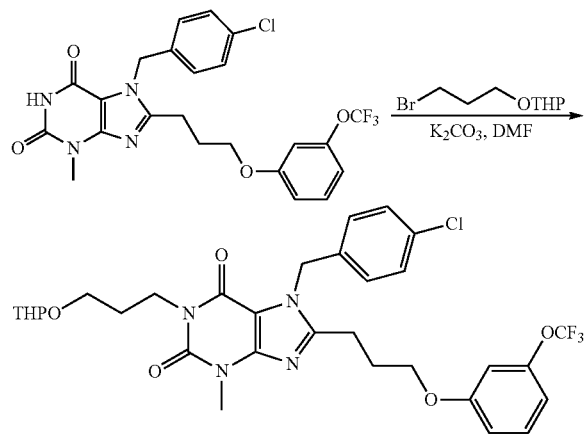

The title compound was prepared using the method of intermediate 14 and purified by silica gel chromatography eluting with petroleum/ethyl acetate (10:1 to 2:1) to give 7-(4-chlorobenzyl)-3-methyl-1-(3-(tetrahydro-2H-pyran-2-yloxy)propyl)-8-(3-(3-(trifluoromethoxy)phenoxy)propyl)-1H-purine-2,6(3H,7H)-dione (39 mg, 38.5% yield) as yellow oil. LCMS retention time 2.048 min; LCMS MH$^+$-THP 567.

Step 4 7-(4-chlorobenzyl)-1-(3-hydroxypropyl)-3-methyl-8-(3-(3-(trifluoromethoxy)phenoxy)propyl)-1H-purine-2,6(3H,7H)-dione

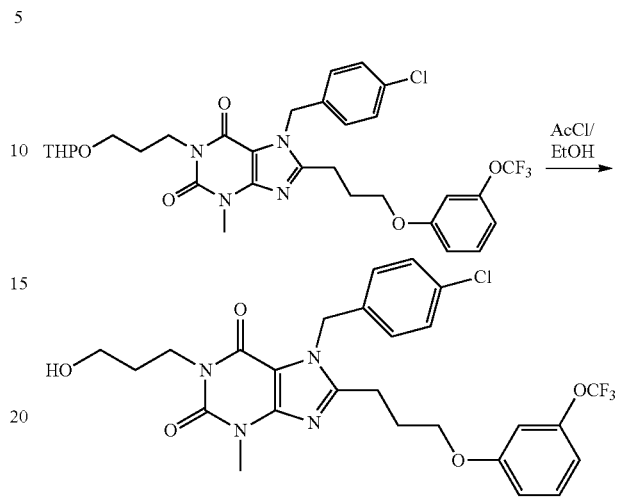

The title compound was prepared as example 37, step 2 and purified via preparative HPLC to give 7-(4-chlorobenzyl)-1-(3-hydroxypropyl)-3-methyl-8-(3-(3-(trifluoromethoxy)phenoxy)propyl)-1H-purine-2,6(3H,7H)-dione (17 mg, 38.3% yield) as white solid. $^1$H-NMR (DMSO-d$_6$) δ 7.41-7.36 (m, 3H), 7.23-7.21 (d, 2H), 6.93-6.90 (dd, 2H), 6.84 (s, 1H), 5.56 (s, 2H), 4.48-4.46 (t, 1H), 4.05-4.02 (t, 2H), 3.93-3.89 (t, 2H), 3.45-3.33 (m, 5H), 2.89-2.85 (t, 2H), 2.09-2.06 (t, 2H), 1.70-1.66 (t, 2H). LCMS retention time 2.925 min; LCMS MH$^+$ 567.

Example 94 7-(4-chlorobenzyl)-8-ethyl-1-(3-hydroxypropyl)-3-methyl-1H-purine-2,6(3H,7H)-dione

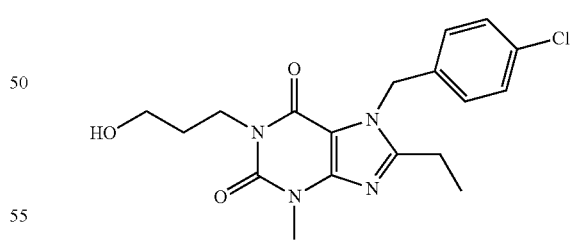

The title compound was prepared using the method of intermediate 48 and example 91 and using propionic acid. White solid, 15 mg, 22.8% yield: $^1$H-NMR (CD$_3$OD) δ 7.35-7.33 (d, 2H), 7.20-7.18 (d, 2H), 5.58 (s, 2H), 4.09-4.06 (t, 2H), 3.59-3.55 (m, 5H), 2.78-2.73 (q, 2H), 1.88-1.81 (m, 2H), 1.23-1.19 (t, 3H). LCMS retention time 2.207 min; LCMS MH$^+$ 377.

Example 95 7-(4-chlorobenzyl)-1-(3-hydroxypropyl)-3-methyl-8-propyl-1H-purine-2,6(3H,7H)-dione

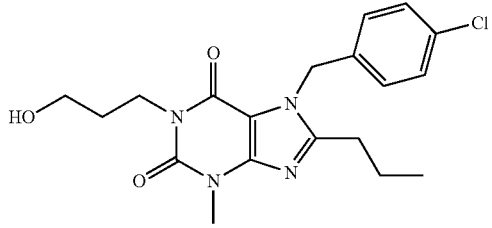 [SMILES: CCCc1nc2c(c(=O)n(CCCO)c(=O)n2C)n1Cc1ccc(Cl)cc1]

The title compound was prepared using the methods of intermediate 48 and example 91 and using butyric acid. White solid, 10 mg, 30.4% yield: $^1$H-NMR (CD$_3$OD) δ 7.33-7.31 (d, 2H), 7.20-7.17 (d, 2H), 5.58 (s, 2H), 4.07-4.04 (t, 2H), 3.59-3.56 (t, 2H), 3.53 (s, 3H), 2.72-2.69 (t, 2H), 1.87-1.80 (m, 2H), 1.70-1.61 (m, 2H), 0.93-0.90 (t, 3H). LCMS retention time 2.379 min; LCMS MH$^+$ 391.

Example 96 7-(4-chlorobenzyl)-1-(3-hydroxypropyl)-3-methyl-8-(2-(5-methylthiazol-2-yl)ethyl)-3,4,5,7-tetrahydro-1H-purine-2,6-dione

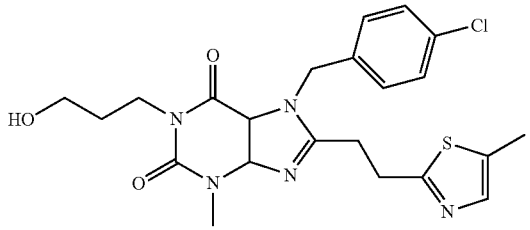 [SMILES: Cc1cnc(CCC2=NC3C(C(=O)N(CCCO)C(=O)N3C)N2Cc2ccc(Cl)cc2)s1]

The title compound was prepared using the methods of intermediate 48 and example 91 and using intermediate 49. White solid, 15 mg, 45.4% yield: $^1$H-NMR (CD$_3$OD) δ=7.32 (d, 2H), 7.28 (d, 1H), 7.18 (d, 1H), 5.58 (s, 2H), 4.10 (t, 2H), 3.60 (t, 2H), 3.57 (s, 3H), 3.41 (t, 2H), 3.20 (t, 2H), 2.40 (d, 3H), 1.85-1.89 (m, 2H). LCMS retention time 2.334 min; LCMS MH$^+$ 474.

Example 97 7-(4-chlorobenzyl)-1-(3-hydroxybutyl)-3-methyl-8-(6-methylpyridin-3-yloxy)-1H-purine-2,6(3H,7H)-dione

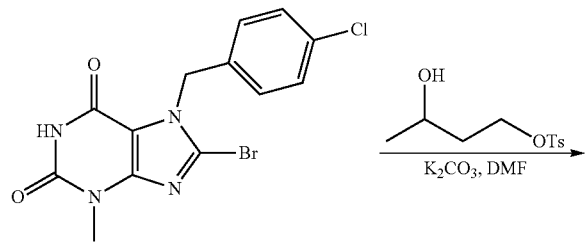

Step 1 8-bromo-7-(4-chlorobenzyl)-1-(3-hydroxybutyl)-3-methyl-1H-purine-2,6(3H,7H)-dione

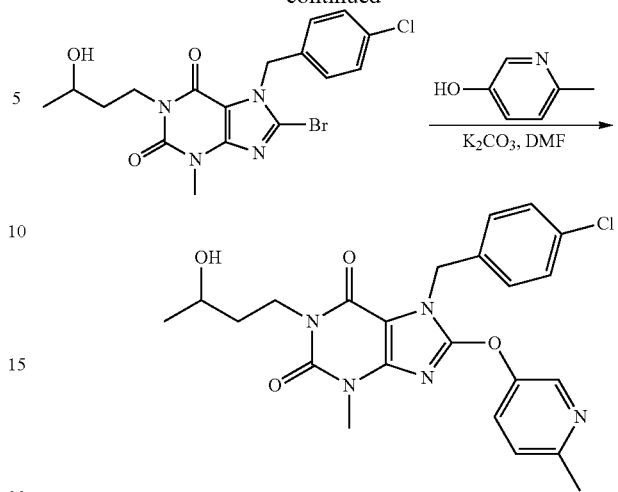

The title compound was prepared using the method of example 7k from intermediates 8 and 33. White solid, 275 mg, 57.5% yield. LCMS retention time 1.465 min; LCMS MH$^+$ 441

Step 2 7-(4-chlorobenzyl)-1-(3-hydroxybutyl)-3-methyl-8-(6-methylpyridin-3-yloxy)-1H-purine-2,6(3H,7H)-dione

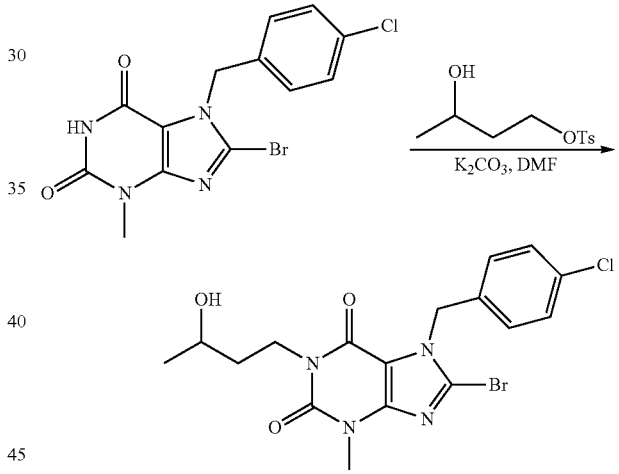

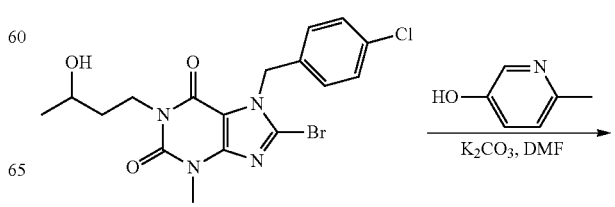

557
-continued

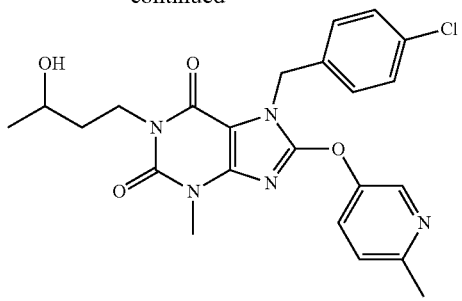

The title compound was prepared using the method of example 86. White solid, 35 mg, 43.9% yield: $^1$H-NMR (DMSO-d$_6$) δ 8.46-8.45 (d, 1H), 7.78-7.75 (dd, 1H), 7.47-7.45 (d, 2H), 7.42-7.37 (m, 3H), 5.52 (s, 2H), 4.17-4.05 (m, 2H), 3.82-3.77 (m, 1H), 3.40 (s, 3H), 2.58 (s, 3H), 1.79-1.73 (m, 2H), 1.23-1.21 (d, 3H). LCMS retention time 2.390 min; LCMS MH$^+$ 470

Example 98 1-(3-hydroxybutyl)-3-methyl-7-((5-methylpyridin-2-yl)methyl)-8-(3-(trifluoromethoxy)benzyl)-1H-purine-2,6(3H,7H)-dione

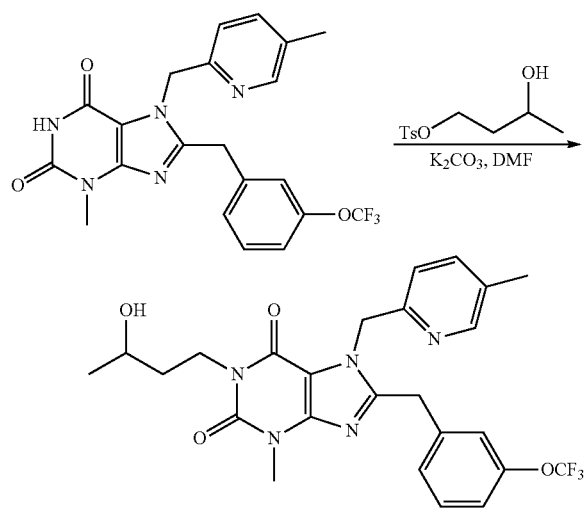

To a solution of 3-methyl-7-((5-methylpyridin-2-yl)methyl)-8-(3-(trifluoromethoxy)benzyl)-1H-purine-2,6(3H, 7H)-dione (30 mg, 0.067 mmol, intermediate 51) in DMF (3 mL) was added 3-hydroxybutyl-4-methylbenzenesulfonate (24.68 mg, 0.10 mmol), followed by potassium carbonate (27.93 mg, 0.20 mmol). The reaction was stirred at 70° C. for 4 h. The mixture was partitioned between ethyl acetate and water. The organic phase was washed with brine, dried over sodium sulfate, filtered and concentrated to give crude product, which was purified by preparative HPLC to give 1-(3-hydroxybutyl)-3-methyl-7-((5-methylpyridin-2-yl)methyl)-8-(3-(trifluoromethoxy)benzyl)-1H-purine-2,6(3H, 7H)-dione (9 mg, 25.8%) as white solid. $^1$H-NMR (CD$_3$OD) δ 8.216 (s, 1H), 7.491-7.467 (d, 1H), 7.312-7.272 (m, 1H), 7.154-6.995 (m, 4H), 5.688 (s, 2H), 4.305 (s, 2H), 4.143-4.011 (m, 2H), 3.772-3.440 (m, 1H), 3.585 (s, 3H), 2.283 (s, 3H), 1.761-1.703 (m, 2H), 1.194-1.179 (d, 3H). LCMS retention time 2.569 min; LCMS MH$^+$ 518.

558
Example 99 1-(2-(1-hydroxycyclopropyl)ethyl)-3-methyl-7-((5-methylpyridin-2-yl)methyl)-8-(3-(trifluoromethoxy)benzyl)-1H-purine-2,6(3H,7H)-dione

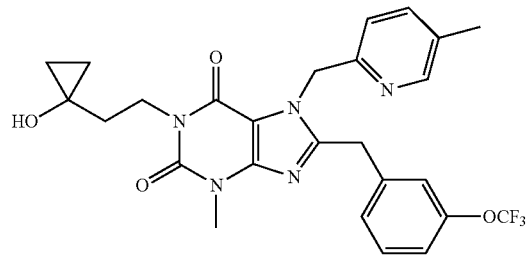 [SMILES: Cc1ccc(Cn2c(Cc3cccc(OC(F)(F)F)c3)nc3c2c(=O)n(CCC2(O)CC2)c(=O)n3C)nc1]

The title compound was prepared using the method of example 98 and using 1-(2-bromoethyl)cyclopropanol, intermediate 46). White solid, 8.7 mg, 24.4%: $^1$H-NMR (CD$_3$OD) δ 8.220 (s, 1H), 7.487-7.463 (d, 1H), 7.319-7.279 (m, 1H), 7.169-6.984 (m, 4H), 5.690 (s, 2H), 4.315 (s, 2H), 4.256-4.221 (m, 2H), 3.589 (s, 3H), 2.282 (s, 3H), 1.834-1.799 (m, 2H), 0.585-0.569 (m, 2H), 0.386-0.356 (m, 2H). LCMS retention time 2.717 min; LCMS MH$^+$ 530.

Example 100 1-(3-hydroxybutyl)-3-methyl-7-((5-methylpyridin-2-yl)methyl)-8-(3-(trifluoromethoxy)phenoxy)-1H-purine-2,6(3H,7H)-dione

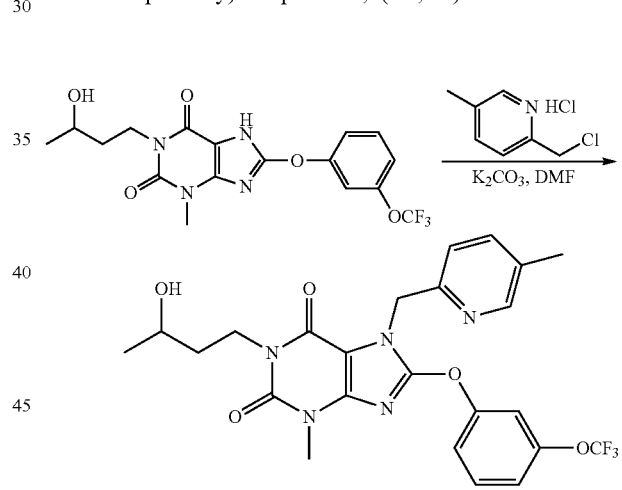

To a solution of 1-(3-hydroxybutyl)-3-methyl-8-(3-(trifluoromethoxy)phenoxy)-1H-purine-2,6(3H,7H)-dione (50 mg, 0.121 mmol, intermediate 57) in DMF (3 mL) was added 2-(chloromethyl)-5-methylpyridine hydrochloride (30 mg, 0.182 mmol, intermediate 50), followed by potassium carbonate (50 mg, 0.363 mmol) and TBAI (10 mg, 0.027 mmol). The reaction was stirred at 65° C. overnight. The reaction was cooled and partitioned between ethyl acetate and water. The organic phase was washed with brine, dried over sodium sulfate, filtered and concentrated to give a crude product, which was purified by preparative HPLC to give 1-(3-hydroxybutyl)-3-methyl-7-((5-methylpyridin-2-yl)methyl)-8-(3-(trifluoromethoxy)phenoxy)-1H-purine-2,6 (3H,7H)-dione (20 mg, 31.9% yield) as white solid. $^1$H-NMR (CD$_3$OD) δ 8.319 (s, 1H), 7.663-7.640 (d, 1H), 7.553-7.510 (t, 1H), 7.348-7.316 (m, 3H), 7.233-7.208 (m, 1H), 5.609 (s, 2H), 4.112-4.004 (m, 2H), 3.763-3.731 (m, 1H), 3.457 (s, 3H), 2.339 (s, 3H), 1.758-1.698 (m, 2H), 1.197-1.182 (d, 2H). LCMS retention time 2.714 min; LCMS MH+ 520.

Example 101 1-(2-(1-hydroxycyclopropyl)ethyl)-3-methyl-7-((5-methylpyridin-2-yl)methyl)-8-(3-(trifluoromethoxy)phenoxy)-1H-purine-2,6(3H,7H)-dione

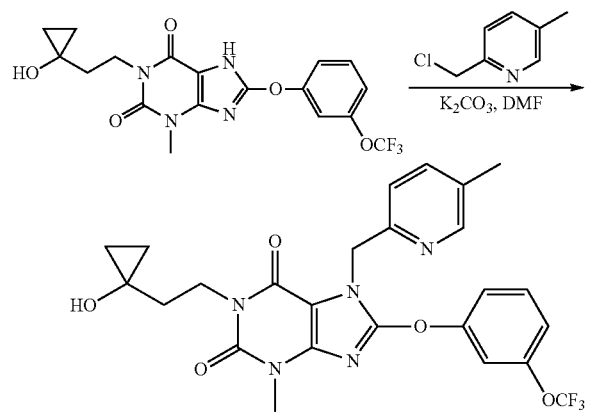

To a solution of 1-(2-(1-hydroxycyclopropyl)ethyl)-3-methyl-8-(3-(trifluoromethoxy)phenoxy)-1H-purine-2,6(3H,7H)-dione (50 mg, 0.117 mmol, intermediate 58) in DMF (3 mL) was added 2-(chloromethyl)-5-methylpyridine hydrochloride (24.9 mg, 0.176 mmol, intermediate 50), followed by potassium carbonate (48.6 mg, 0.351 mmol) and TBAI (10 mg, 0.027 mmol). The reaction was stirred at 65° C. overnight. The reaction was cooled and partitioned between ethyl acetate and water. The organic phase was washed with brine, dried over sodium sulfate, filtered and concentrated to give crude product, which was purified by preparative HPLC to give 1-(2-(1-hydroxycyclopropyl)ethyl)-3-methyl-7-((5-methylpyridin-2-yl)methyl)-8-(3-(trifluoromethoxy)phenoxy)-1H-purine-2,6(3H,7H)-dione (21 mg, 33.7% yield) as white solid. 1H-NMR (CD3OD) δ 8.320-8.315 (d, 1H), 7.662-7.636 (d, 1H), 7.561-7.517 (t, 1H), 7.363-7.315 (m, 3H), 7.240-7.215 (m, 1H), 5.608 (s, 2H), 4.247-4.212 (t, 2H), 3.462 (s, 3H), 2.338 (s, 3H), 1.829-1.793 (t, 2H), 0.582-0.554 (m, 2H), 0.370-0.340 (m, 2H). LCMS retention time 2.869 min; LCMS MH+ 532.

Example 102 1-(2-(1-hydroxycyclopropyl)ethyl)-3-methyl-7-(pyridin-2-ylmethyl)-8-(3-(trifluoromethoxy)phenoxy)-1H-purine-2,6(3H,7H)-dione

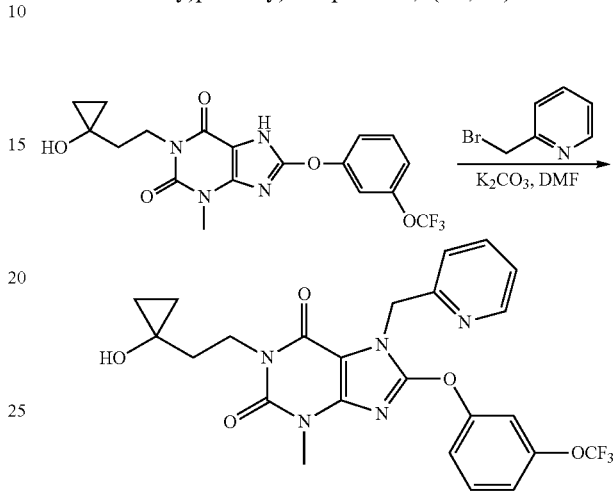

The title compound was prepared using the method of example 101. White solid, 20 mg, 32.9% yield: 1H-NMR (CD3OD) δ 8.488-8.475 (d, 1H), 7.831-7.627 (t, 1H), 7.562-7.521 (t, 1H), 7.446-7.427 (d, 1H), 7.375-7.341 (m, 3H), 7.240-7.220 (d, 1H), 5.656 (s, 2H), 4.242-4.207 (t, 2H), 3.465 (s, 3H), 1.823-1.788 (t, 2H), 0.562-0.546 (m, 2H), 0.364-0.335 (m, 2H). LCMS retention time 2.759 min; LCMS MH+ 518.

Example 103 7-((5-chloropyridin-2-yl)methyl)-1-(2-(1-hydroxycyclopropyl)ethyl)-3-methyl-8-(3-(trifluoromethoxy)phenoxy)-1H-purine-2,6(3H,7H)-dione

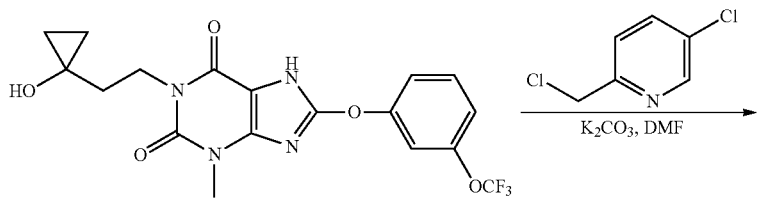

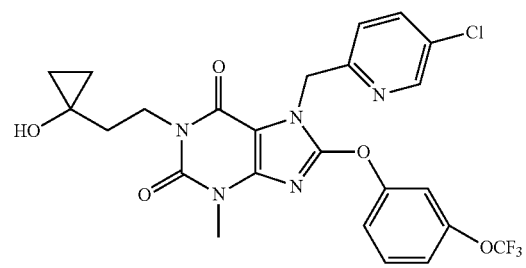

The title compound was prepared using the method of example 101. White solid, 30 mg, 49.4% yield: $^1$H-NMR (CD$_3$OD) δ 8.469-8.464 (d, 1H), 7.868-7.841 (d, 1H), 7.557-7.535 (t, 1H), 7.484-7.463 (d, 1H), 7.385-7.370 (m, 2H), 7.252-7.231 (d, 1H), 5.638 (s, 2H), 4.237-4.201 (t, 2H), 3.460 (s, 3H), 1.820-1.784 (t, 2H), 0.563-0.548 (m, 2H), 0.366-0.337 (m, 2H). LCMS retention time 3.058 min; LCMS MH$^+$ 552.

Example 104 7-(4-chlorobenzyl)-1-(2-(1-hydroxycyclopropyl)ethyl)-3-methyl-8-((6-methylpyridin-3-yl)oxy)-1H-purine-2,6(3H,7H)-dione

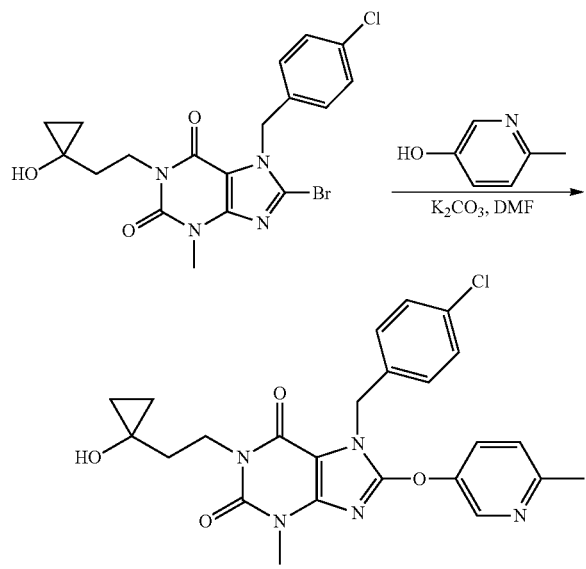

To a solution of 8-bromo-7-(4-chlorobenzyl)-1-(2-(1-hydroxycyclopropyl)ethyl)-3-methyl-1H-purine-2,6(3H,7H)-dione (128 mg, 0.282 mmol, intermediate 56) in DMF (5 mL) was added 6-methylpyridin-3-ol (37 mg, 0.338 mmol), followed by potassium carbonate (58 mg, 0.423 mmol). The reaction was stirred at 80° C. for 2 h. The reaction was partitioned between ethyl acetate and water. The organic phase was washed with brine, dried over sodium sulfate, filtered and concentrated to give a crude product, which was purified by preparative HPLC to give 7-(4-chlorobenzyl)-1-(2-(1-hydroxycyclopropyl)ethyl)-3-methyl-8-((6-methylpyridin-3-yl)oxy)-1H-purine-2,6(3H,7H)-dione (110 mg, 80.9% yield) as white solid. $^1$H-NMR (CD$_3$OD) δ 8.457-8.451 (d, 1H), 7.776-7.748 (d, 1H), 7.470-7.374 (m, 5H), 5.519 (s, 2H), 4.291-4.256 (t, 2H), 3.411 (s, 3H), 2.584 (s, 3H), 1.867-1.832 (t, 2H), 0.618-0.610 (m, 2H), 0.403-0.387 (m, 2H). LCMS retention time 2.619 min; LCMS MH$^+$ 482.

Example 105 7-(4-chlorobenzyl)-3-methyl-1-(4,4,4-trifluorobutyl)-8-(3-(trifluoromethoxy)phenoxy)-1H-purine-2,6(3H,7H)-dione

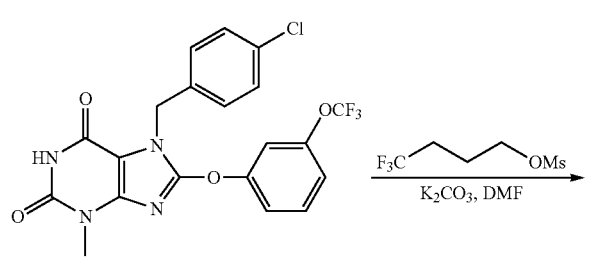

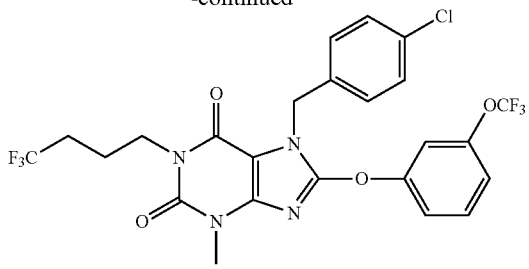

To a solution of 7-(4-chlorobenzyl)-3-methyl-8-(3-(trifluoromethoxy)phenoxy)-1H-purine-2,6(3H,7H)-dione (80 mg, 0.171 mmol, intermediate 9) in DMF (2 mL) was added 4,4,4-trifluorobutyl methanesulfonate (50 mg, 0.239 mmol, intermediate 52), followed by potassium carbonate (71 mg, 0.518 mmol). The reaction was stirred at 50° C. overnight. The mixture was cooled and partitioned between ethyl acetate and water. The organic phase was washed with brine, dried over sodium sulfate, filtered and concentrated to give a crude product, which was purified by preparative HPLC to give 1-(3-hydroxybutyl)-3-methyl-7-((5-methylpyridin-2-yl)methyl)-8-(3-(trifluoromethoxy)phenoxy)-1H-purine-2,6 (3H,7H)-dione (20 mg, 31.9% yield) as white solid. $^1$H-NMR (CD$_3$OD) δ 7.571-7.529 (t, 1H), 7.458-7.431 (m, 2H), 7.377-7.255 (m, 4H), 7.237-7.231 (m, 1H), 5.496 (s, 2H), 4.098-4.063 (t, 2H), 3.423 (s, 3H), 2.288-2.219 (m, 2H), 1.958-1.901 (m, 2H). LCMS retention time 3.653 min; LCMS MH$^+$ 577.

Example 106 7-(4-chlorobenzyl)-1-(3-hydroxybutyl)-3-methyl-8-(propylsulfonyl)-1H-purine-2,6(3H,7H)-dione

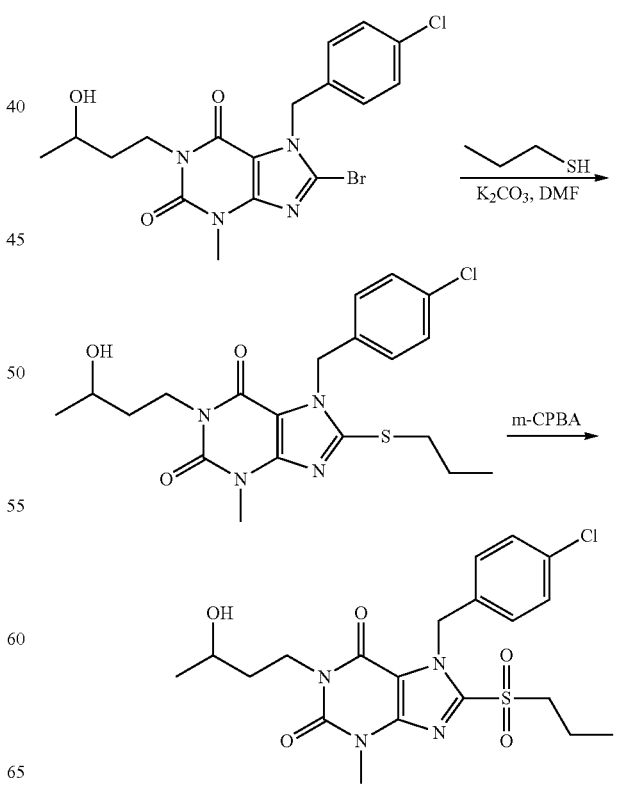

Step 1 7-(4-chlorobenzyl)-1-(3-hydroxybutyl)-3-methyl-8-(propylthio)-1H-purine-2,6(3H,7H)-dione

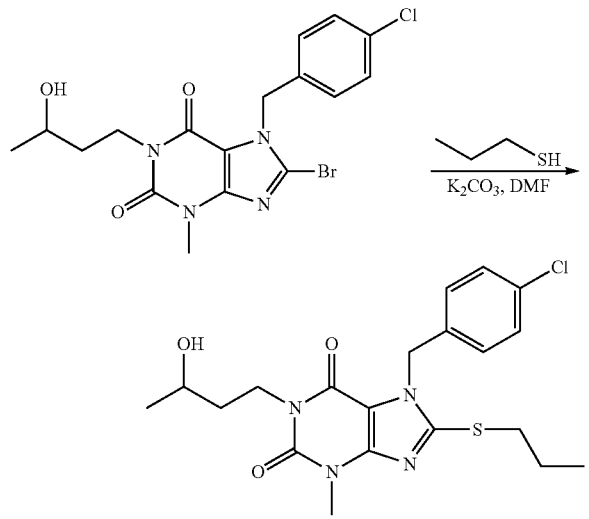

To a solution of 8-bromo-7-(4-chlorobenzyl)-1-(3-hydroxybutyl)-3-methyl-1H-purine-2,6(3H,7H)-dione (100 mg, 0.23 mmol, example 97, step 1) in DMF (5 mL) was added propane-1-thiol (20.7 mg, 0.27 mmol) followed by potassium carbonate (93.9 mg, 0.68 mmol). The reaction was stirred at 60° C. for 3 h. The reaction was partitioned between ethyl acetate and water. The organic phase was washed with brine, dried over sodium sulfate, filtered and concentrated to give crude product (80 mg, 80.9% yield) as yellow oil. LCMS MH+ 437.

Step 2 7-(4-chlorobenzyl)-1-(3-hydroxybutyl)-3-methyl-8-(propylsulfonyl)-1H-purine-2,6(3H,7H)-dione

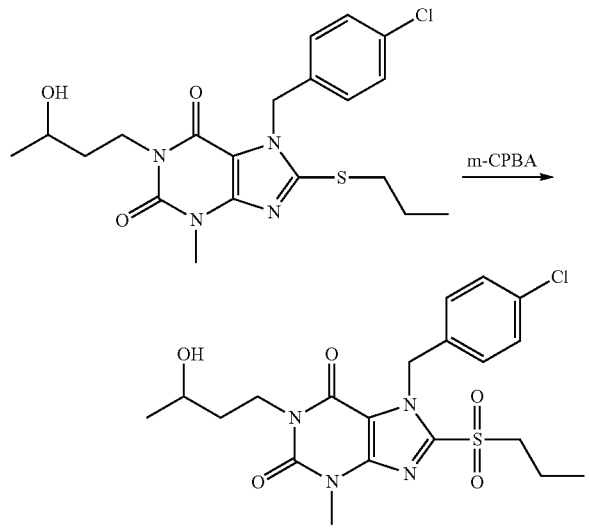

To a solution of 7-(4-chlorobenzyl)-1-(3-hydroxybutyl)-3-methyl-8-(propylthio)-1H-purine-2,6(3H,7H)-dione (80 mg, 0.18 mmol) in CHCl$_3$ (10 mL) was added MCPBA (126 mg, 0.73 mmol). The reaction was stirred at room temperature overnight. The reaction was quenched with aqueous Na$_2$S$_2$O$_3$ and NaHCO$_3$ and extracted with DCM. The phases were separated. The organic phase was washed with aqueous NaHCO$_3$ and brine; then it was dried over sodium sulfate, filtered and concentrated to give a crude product, which was purified by preparative HPLC to give 7-(4-chlorobenzyl)-1-(3-hydroxybutyl)-3-methyl-8-(propylsulfonyl)-1H-purine-2,6(3H,7H)-dione (30 mg, 34.9%) as white solid. $^1$H-NMR (DMSO-d$_6$) δ 7.429-7.408 (d, 2H), 7.278-7.257 (d, 2H), 5.870 (s, 2H), 4.511-4.500 (d, 1H), 4.044-3.973 (m, 1H), 3.874-3.805 (m, 1H), 3.675-3.619 (m, 1H), 3.499-3.459 (m, 2H), 3.446 (s, 3H), 1.691-1.540 (m, 4H), 1.081-1.065 (m, 3H), 0.934-0.897 (m, 3H). LCMS retention time 2.599 min; LCMS MH+ 469.

Example 107 7-(4-chlorobenzyl)-1-(2-(1-hydroxycyclopropyl)ethyl)-3-methyl-8-(propylsulfonyl)-1H-purine-2,6(3H,7H)-dione

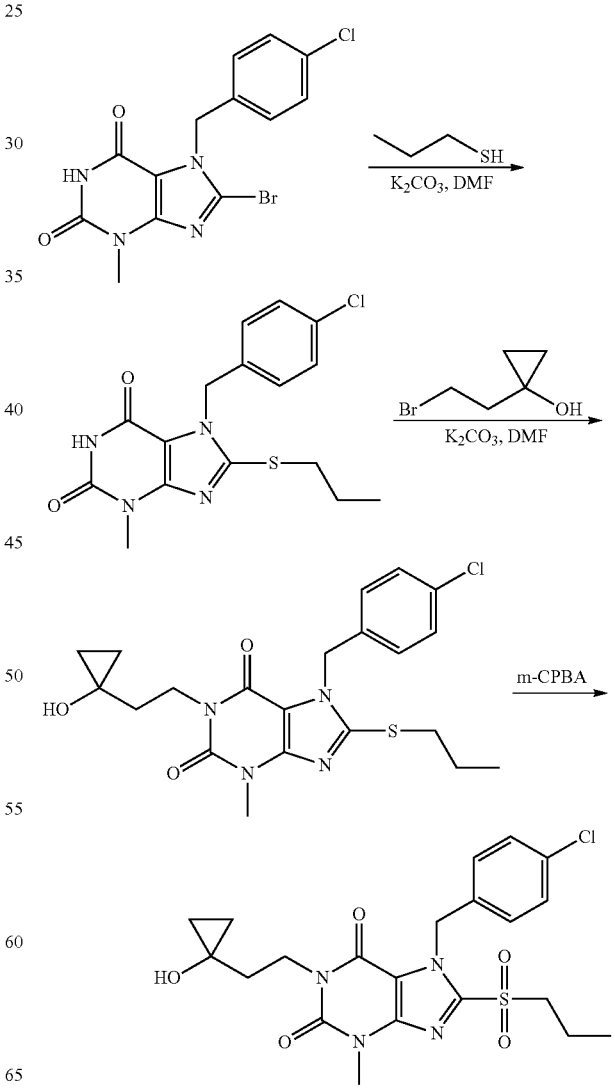

Step 1 7-(4-chlorobenzyl)-3-methyl-8-(propylthio)-1H-purine-2,6(3H,7H)-dione

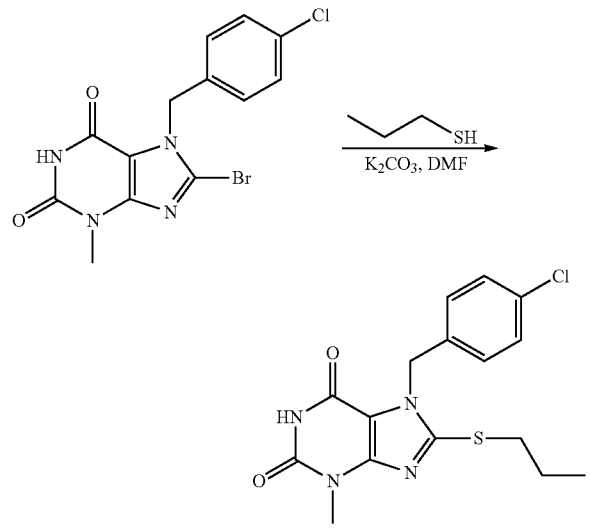

To a solution of 8-bromo-7-(4-chlorobenzyl)-3-methyl-1H-purine-2,6(3H,7H)-dione (100 mg, 0.27 mmol, intermediate 8) in DMF (5 mL) was added propane-1-thiol (24.7 mg, 0.32 mmol) followed by potassium carbonate (112.2 mg, 0.81 mmol). The reaction was stirred at 60° C. for 4 h. The reaction was cooled and partitioned between ethyl acetate and water. The organic phase was washed with brine, dried over sodium sulfate, filtered and concentrated to give a crude white solid product (124 mg, 99.9% yield). LCMS MH+ 365.

Step 2 7-(4-chlorobenzyl)-1-(2-(1-hydroxycyclopropyl)ethyl)-3-methyl-8-(propylthio)-1H-purine-2,6(3H,7H)-dione

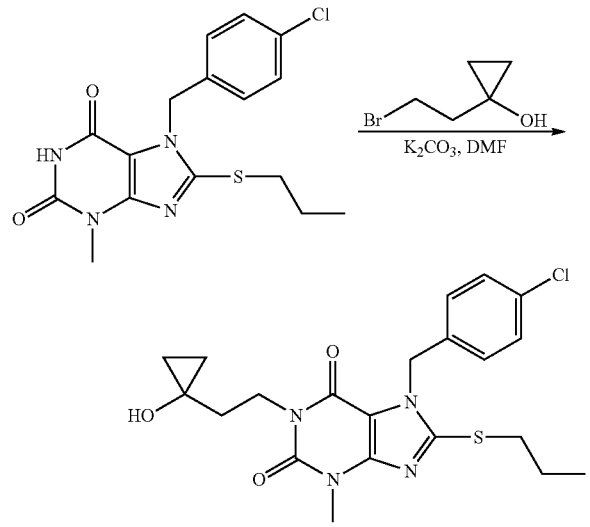

To a solution of 7-(4-chlorobenzyl)-3-methyl-8-(propylthio)-1H-purine-2,6(3H,7H)-dione (124 mg, 0.34 mmol) in DMF (7 mL) was added 1-(2-bromoethyl)cyclopropanol (67.3 mg, 0.41 mmol, intermediate 46), followed by potassium carbonate (141 mg, 1.02 mmol). The reaction was stirred at 70° C. for 5 h. The reaction was cooled and partitioned between ethyl acetate and water. The organic phase was washed with brine, dried over sodium sulfate, filtered and concentrated to give a crude yellow oil product (100 mg, 66.9% yield). LCMS MH+ 449.

Step 3 7-(4-chlorobenzyl)-1-(2-(1-hydroxycyclopropyl)ethyl)-3-methyl-8-(propylsulfonyl)-1H-purine-2,6(3H,7H)-dione

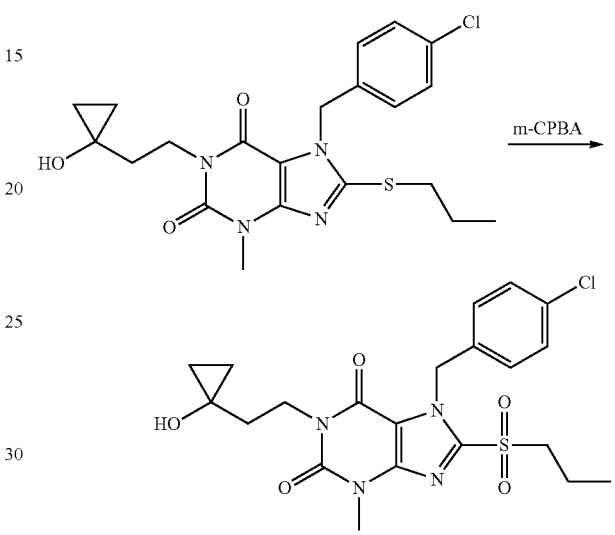

To a solution of 7-(4-chlorobenzyl)-1-(2-(1-hydroxycyclopropyl)ethyl)-3-methyl-8-(propylthio)-1H-purine-2,6(3H,7H)-dione (100 mg, 0.22 mmol) in CHCl$_3$ (7 mL) was added MCPBA (153 mg, 0.89 mmol) in portions. The mixture was stirred at room temperature for 3 h. The reaction was quenched with aqueous Na$_2$S$_2$O$_3$ and extracted with DCM. The phases were separated. The organic phase was washed with brine, dried over sodium sulfate, filtered and concentrated to give a crude product, which was purified by preparative HPLC to give 7-(4-chlorobenzyl)-1-(2-(1-hydroxycyclopropyl)ethyl)-3-methyl-8-(propylsulfonyl)-1H-purine-2,6(3H,7H)-dione (20 mg, 18.7%) as white solid. $^1$H-NMR (CD$_3$OD) δ 7.392-7.336 (m, 4H), 5.982 (s, 2H), 4.285-4.248 (t, 2H), 3.567 (s, 3H), 3.445-3.406 (m, 2H), 1.855-1.756 (m, 4H), 1.042-1.005 (m, 3H), 0.633-0.604 (m, 2H), 0.433-0.403 (m, 2H). LCMS retention time 2.734 min; LCMS MH+ 481.

Example 108 8-(3-chloro-5-(trifluoromethoxy)phenoxy)-7-(4-chlorobenzyl)-1-(3-hydroxypropyl)-3-methyl-1H-purine-2,6(3H,7H)-dione

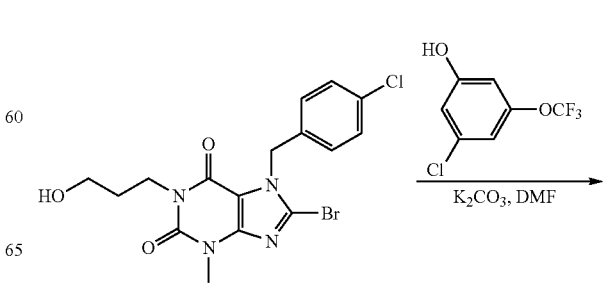

-continued

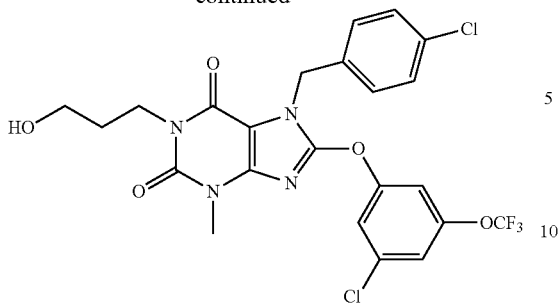

To a solution of the 8-bromo-7-(4-chlorobenzyl)-1-(3-hydroxypropyl)-3-methyl-1H-purine-2,6(3H,7H)-dione (50 mg, 0.116 mmol, intermediate 63) in DMF (2 mL) was added 3-chloro-5-(trifluoromethoxy)phenol (29.82 mg, 0.140 mmol) followed by potassium carbonate (24.24 mg, 0.175 mmol). The reaction was stirred at 85° C. for 2 h. The reaction was cooled and partitioned between ethyl acetate and water. The organic phase was washed with brine, dried over sodium sulfate, filtered and concentrated to give crude product, which was purified by preparative HPLC to give 8-(3-chloro-5-(trifluoromethoxy)phenoxy)-7-(4-chlorobenzyl)-1-(3-hydroxypropyl)-3-methyl-1H-purine-2,6(3H,7H)-dione (35 mg, 53.5% yield) as white solid. $^1$H-NMR (CD$_3$OD) δ 7.458-7.435 (m, 3H), 7.381-7.365 (m, 3H), 7.361 (s, 1H), 5.507 (s, 2H), 4.138-4.102 (t, 2H), 3.640-3.608 (t, 2H), 3.448 (s, 3H), 1.905-1.871 (m, 2H). LCMS retention time 3.325 min; LCMS MH$^+$ 559.

Example 109 7-(4-chlorobenzyl)-8-(2-fluoro-5-(trifluoromethoxy)phenoxy)-1-(3-hydroxypropyl)-3-methyl-1H-purine-2,6(3H,7H)-dione

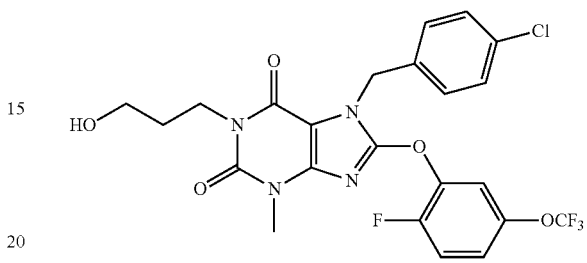

The title compound was prepared using the method of example 108. White solid, 30 mg, 47.27% yield: $^1$H-NMR (CD$_3$OD) δ 7.588-7.566 (m, 1H), 7.491-7.425 (m, 3H), 7.392-7.371 (d, 2H), 7.347-7.310 (m, 1H), 5.520 (s, 2H), 4.127-4.091 (t, 2H), 3.633-3.602 (t, 2H), 3.390 (s, 3H), 1.914-1.847 (m, 2H). LCMS retention time 3.099 min; LCMS MH$^+$ 543.

Example 110 1-(2-hydroxyethyl)-3-methyl-7-((6-methylpyridin-3-yl)methyl)-8-(2-(3-(trifluoromethoxy)phenoxy)ethoxy)-1H-purine-2,6(3H,7H)-dione

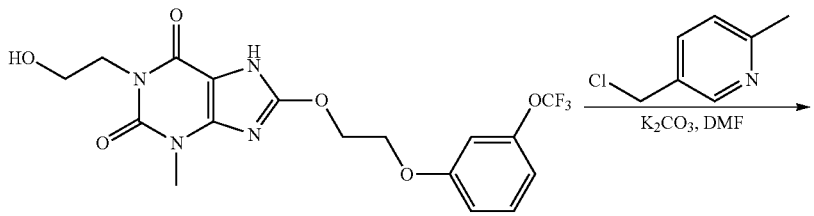

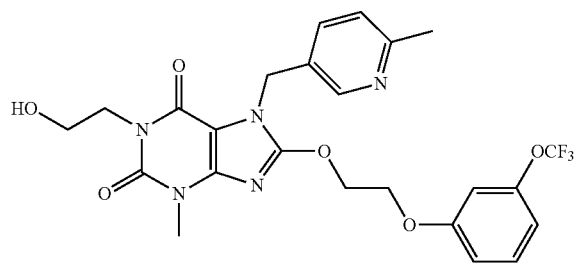

The title compound was prepared using the method of example 42 and purified by preparative HPLC to give 1-(2-hydroxyethyl)-3,7-dimethyl-8-(2-(3-(trifluoromethoxy)phenoxy)ethoxy)-1H-purine-2,6(3H,7H)-dione (13.1 mg, 29.9% yield) as white solid. $^1$H-NMR (DMSO-d$_6$) δ 8.45 (s, 2H), 7.57-7.59 (d, 1H), 7.41-7.45 (t, 1H), 7.09-7.11 (d, 1H), 6.97-7.04 (m, 3H), 5.20 (s, 2H), 4.79-4.81 (m, 4H), 4.73-4.75 (t, 1H), 4.41-4.43 (t, 2H), 3.92-3.96 (t, 2H), 3.49-3.51 (m, 2H), 3.47 (s, 3H), 2.39 (s, 3H). LCMS retention time 2.003 min; LCMS MH$^+$ 536.

Example 111 7-(4-chlorobenzyl)-1-(3-hydroxypropyl)-3-methyl-8-(3-(trifluoromethoxy)phenyl)-1H-purine-2,6(3H,7H)-dione

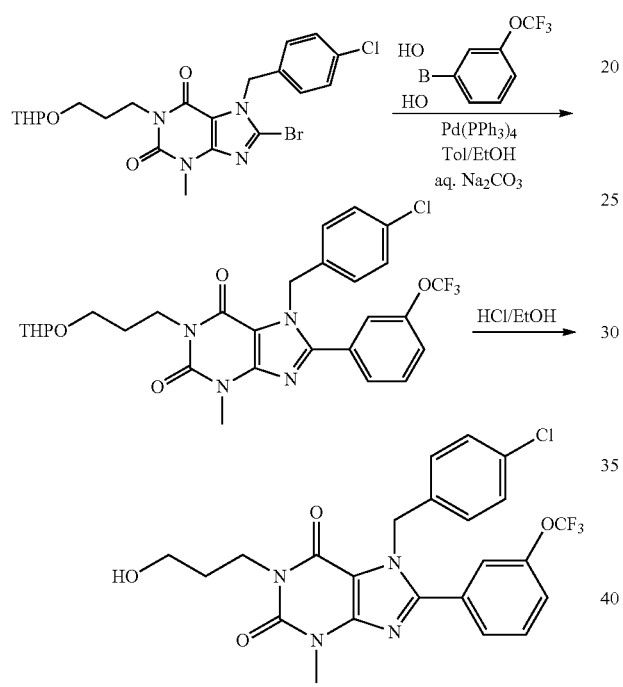

To a solution of 8-bromo-7-(4-chlorobenzyl)-3-methyl-1-(3-(tetrahydro-2H-pyran-2-yloxy)propyl)-1H-purine-2,6(3H,7H)-dione (100 mg, 0.195 mmol, intermediate 14) in toluene and ethanol (6 mL/2 mL) was added 3-(trifluoromethoxy)phenylboronic acid (60.2 mg, 0.293 mmol) followed by 1 mM aqueous sodium carbonate (1 mL). The mixture was degassed and refilled with a nitrogen atmosphere 3 times. Tetrakis(triphenylphosphine)palladium (12 mg, 0.01 mmol) was added and the reaction was stirred at 100° C. for 16 h. The reaction was cooled and partitioned between ethyl acetate and brine The organic phase was dried and concentrated to give a crude product (110 mg). This crude product was dissolved in 1 mM ethanolic HCl (2 mL) and the mixture was stirred at room temperature for 30 min. The mixture was concentrated and purified by preparative HPLC to give 7-(4-chlorobenzyl)-1-(3-hydroxypropyl)-3-methyl-8-(3-(trifluoromethoxy)phenyl)-1H-purine-2,6(3H,7H)-dione (49 mg, 49.4% yield) as a white solid. $^1$H-NMR (CD$_3$OD) δ 7.62-7.64 (t, 1H), 7.55 (s, 1H), 7.51-7.53 (m, 1H), 7.29-7.31 (d, 2H), 7.22-7.24 (d, 2H), 5.71 (s, 2H), 4.11-4.14 (t, 2H), 3.63 (s, 3H), 3.61-3.63 (t, 2H), 1.87-1.90 (m, 2H). LCMS retention time 2.746 min; LCMS MH$^+$ 509.

Example 112 7-(4-chlorobenzyl)-8-(2-fluoro-5-(trifluoromethoxy)benzyl)-1-(3-hydroxypropyl)-3-methyl-1H-purine-2,6(3H,7H)-dione

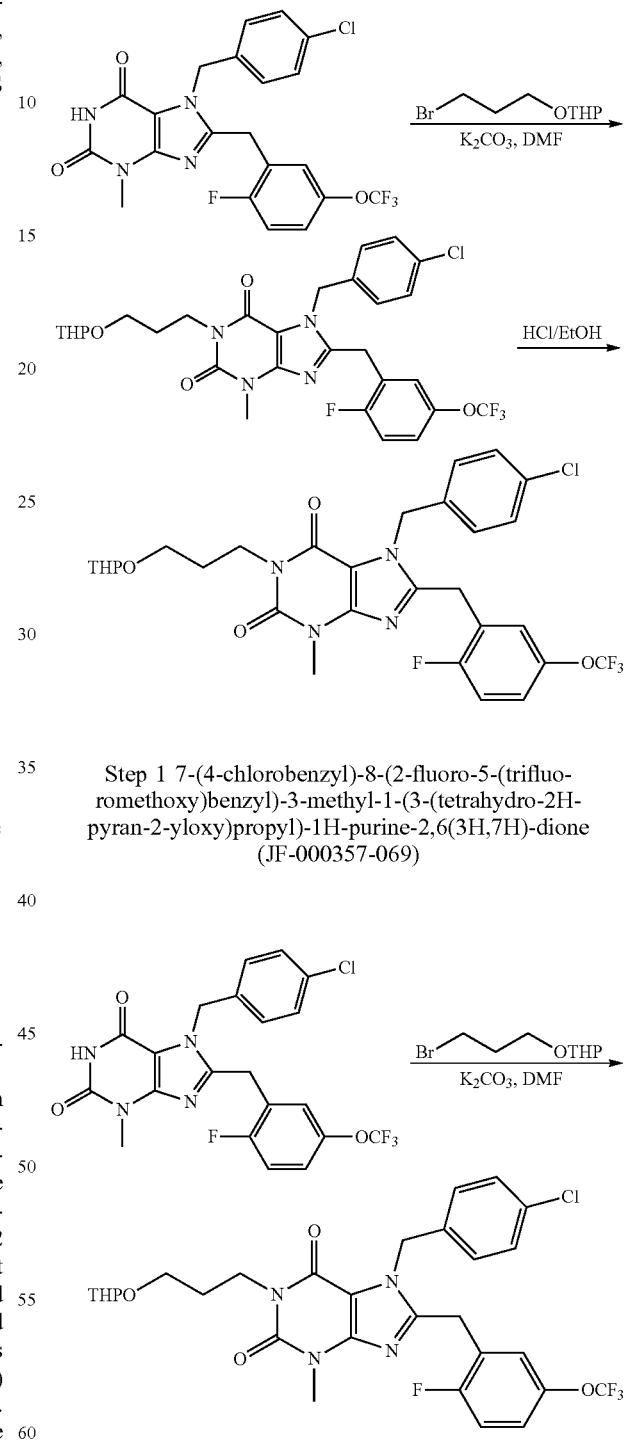

Step 1 7-(4-chlorobenzyl)-8-(2-fluoro-5-(trifluoromethoxy)benzyl)-3-methyl-1-(3-(tetrahydro-2H-pyran-2-yloxy)propyl)-1H-purine-2,6(3H,7H)-dione (JF-000357-069)

The title compound was prepared from intermediate 39 using the method of intermediate 14 to give 7-(4-chlorobenzyl)-8-(2-fluoro-5-(trifluoromethoxy)benzyl)-3-methyl-1-(3-(tetrahydro-2H-pyran-2-yloxy)propyl)-1H-purine-2,6(3H,7H)-dione (43.1 mg, 85.1% yield) as a yellow solid. LCMS retention time 2.046, LCMS MH$^+$-THP 541.

Step 2 7-(4-chlorobenzyl)-8-(2-fluoro-5-(trifluoromethoxy)benzyl)-1-(3-hydroxypropyl)-3-methyl-1H-purine-2,6(3H,7H)-dione

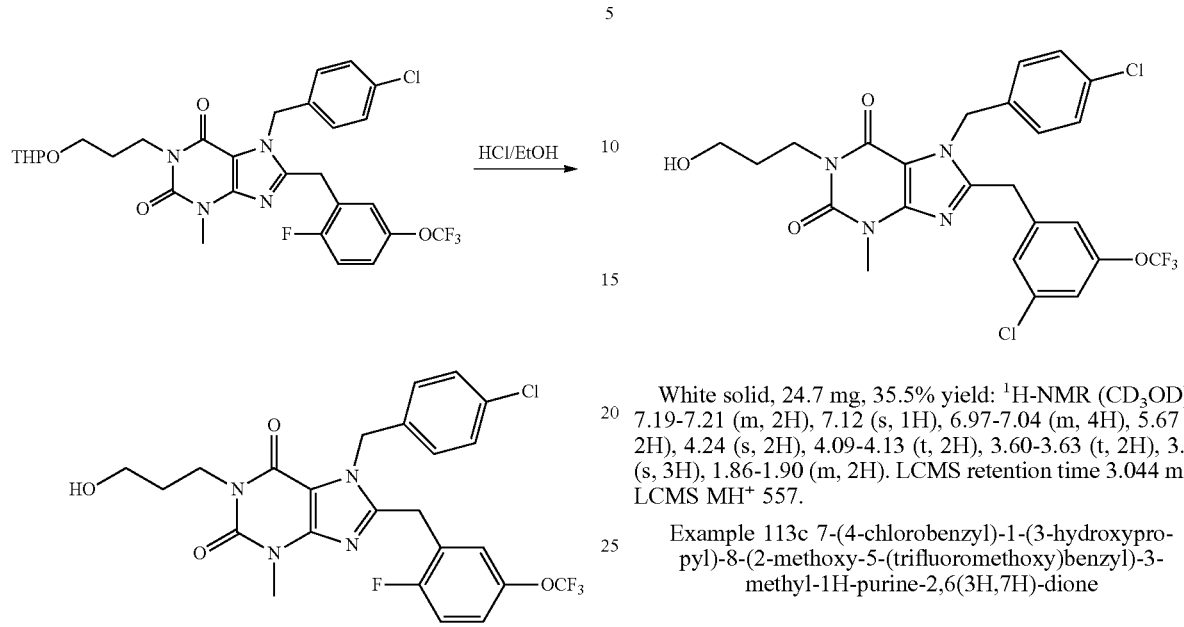

The title compound was prepared using the hydrolysis method of example 111 to give 7-(4-chlorobenzyl)-8-(2-fluoro-5-(trifluoromethoxy)benzyl)-1-(3-hydroxypropyl)-3-methyl-1H-purine-2,6(3H,7H)-dione (17 mg, 38.8% yield) as a white solid. $^1$H-NMR (CD$_3$OD) δ 7.22-7.25 (m, 2H), 7.08-7.17 (m, 4H), 7.01-7.02 (d, 1H), 5.67 (s, 2H), 4.22 (s, 2H), 4.08-4.11 (t, 2H), 3.59-3.62 (t, 2H), 3.54 (s, 3H), 1.85-1.89 (s, 2H). LCMS retention time 2.862 min; LCMS MH$^+$ 541.

The following examples 113a to 113c were prepared using the methods of intermediate 39 and example 112.

Example 113a 8-(4-chloro-3-(trifluoromethoxy)benzyl)-7-(4-chlorobenzyl)-1-(3-hydroxypropyl)-3-methyl-1H-purine-2,6(3H,7H)-dione

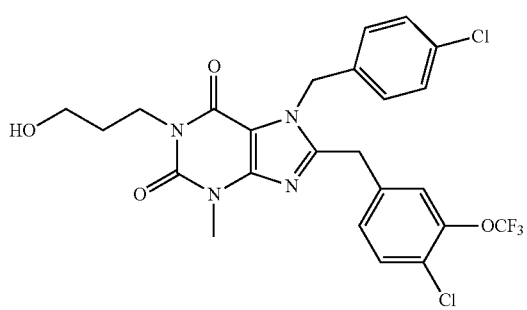 [SMILES: Cn1c(=O)n(CCCO)c(=O)c2c1nc(Cc1ccc(Cl)c(OC(F)(F)F)c1)n2Cc1ccc(Cl)cc1]

White solid, 10.7 mg, 35.2% yield: $^1$H-NMR (CD$_3$OD) δ 7.35-7.37 (d, 1H), 7.19-7.23 (m, 3H), 7.02-7.04 (m, 3H), 5.65 (s, 2H), 4.24 (s, 2H), 4.09-4.12 (t, 2H), 3.58-3.62 (t, 2H), 3.59 (s, 3H), 1.86-1.89 (m, 2H). LCMS retention time 3.033 min; LCMS MH$^+$ 557.

Example 113b 8-(3-chloro-5-(trifluoromethoxy)benzyl)-7-(4-chlorobenzyl)-1-(3-hydroxypropyl)-3-methyl-1H-purine-2,6(3H,7H)-dione

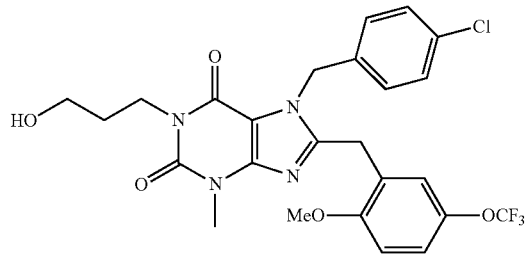

White solid, 24.7 mg, 35.5% yield: $^1$H-NMR (CD$_3$OD) δ 7.19-7.21 (m, 2H), 7.12 (s, 1H), 6.97-7.04 (m, 4H), 5.67 (s, 2H), 4.24 (s, 2H), 4.09-4.13 (t, 2H), 3.60-3.63 (t, 2H), 3.59 (s, 3H), 1.86-1.90 (m, 2H). LCMS retention time 3.044 min; LCMS MH$^+$ 557.

Example 113c 7-(4-chlorobenzyl)-1-(3-hydroxypropyl)-8-(2-methoxy-5-(trifluoromethoxy)benzyl)-3-methyl-1H-purine-2,6(3H,7H)-dione White solid, 36.5 mg, 60.1% yield: $^1$H-NMR (CD$_3$OD) δ 7.22-7.24 (m, 2H), 7.10-7.13 (d, 1H), 7.04-7.06 (d, 2H), 6.90-6.98 (m, 2H), 5.64 (s, 2H), 4.15 (s, 2H), 4.07-4.11 (t, 2H), 3.78 (s, 3H), 3.58-3.61 (t, 2H), 3.55 (s, 3H), 1.85-1.88 (m, 2H). LCMS retention time 2.914 min; LCMS MH$^+$ 553.

Example 114 1-(3-hydroxybutyl)-3-methyl-7-(pyridin-2-ylmethyl)-8-(3-(trifluoromethoxy)benzyl)-1H-purine-2,6(3H,7H)-dione

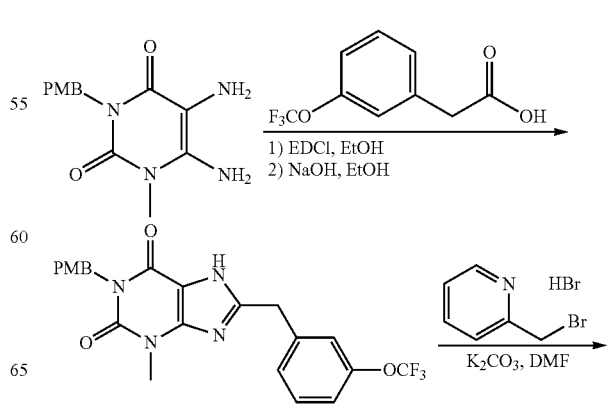

573

-continued

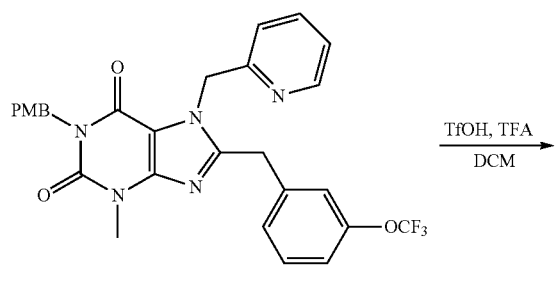

Step 1 1-(4-methoxybenzyl)-3-methyl-8-(3-(trifluoromethoxy)benzyl)-1H-purine-2,6(3H,7H)-dione

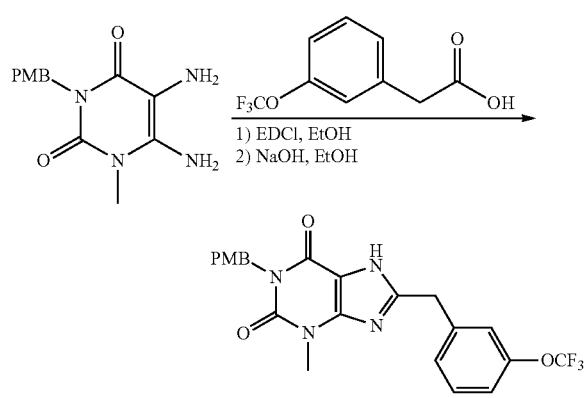

The title compound was prepared using the method of intermediate 39 and purified by trituration with ethanol to give 1-(4-methoxybenzyl)-3-methyl-8-(3-(trifluoromethoxy)benzyl)-1H-purine-2,6(3H,7H)-dione (136 mg, 81.6% yield) as white solid. LCMS retention time 1.638 min; LCMS MH+ 461.

574

Step 2 1-(4-methoxybenzyl)-3-methyl-7-(pyridin-2-ylmethyl)-8-(3-(trifluoromethoxy)benzyl)-1H-purine-2,6(3H,7H)-dione

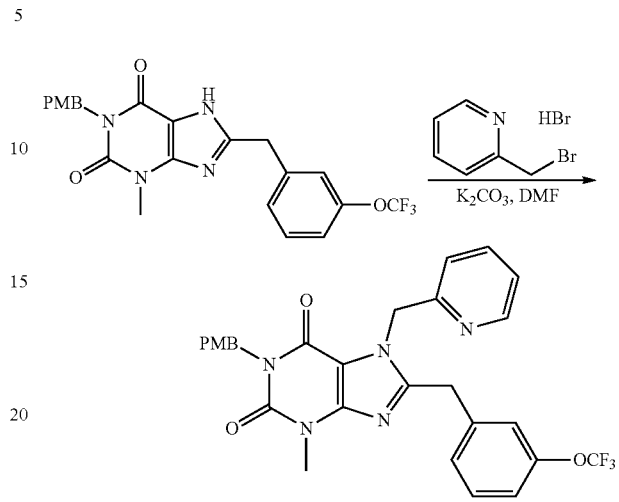

To a solution of 1-(4-methoxybenzyl)-3-methyl-8-(3-(trifluoromethoxy)benzyl)-1H-purine-2,6(3H,7H)-dione (136 mg, 0.295 mmol) in DMF (2 mL) was added 2-(bromomethyl)pyridine hydrobromide (112 mg, 0.442 mmol) followed by potassium carbonate (102 mg, 0.738 mmol). The reaction was stirred at 65° C. for 2 h. The mixture partitioned between ethyl acetate and brine. The organic layer was dried and concentrated to give a crude product, which was purified by silica gel chromatography eluting with DCM/methanol (45:1) to give 1-(4-methoxybenzyl)-3-methyl-7-(pyridin-2-ylmethyl)-8-(3-(trifluoromethoxy)benzyl)-1H-purine-2,6 (3H,7H)-dione (96 mg, 59% yield) as a white solid. LCMS retention time 1.791 min; LCMS MH+ 552.

Step 3 3-methyl-7-(pyridin-2-ylmethyl)-8-(3-(trifluoromethoxy)benzyl)-1H-purine-2,6(3H,7H)-dione The title compound was prepared using the method of intermediate 39, step 3 to give 3-methyl-7-(pyridin-2-ylmethyl)-8-(3-(trifluoromethoxy)benzyl)-1H-purine-2,6(3H, 7H)-dione (61 mg, 81.2% yield) as a light yellow solid. LCMS retention time 1.276 min; LCMS MH+ 432.

Step 4 1-(3-hydroxybutyl)-3-methyl-7-(pyridin-2-ylmethyl)-8-(3-(trifluoromethoxy)benzyl)-1H-purine-2,6(3H,7H)-dione

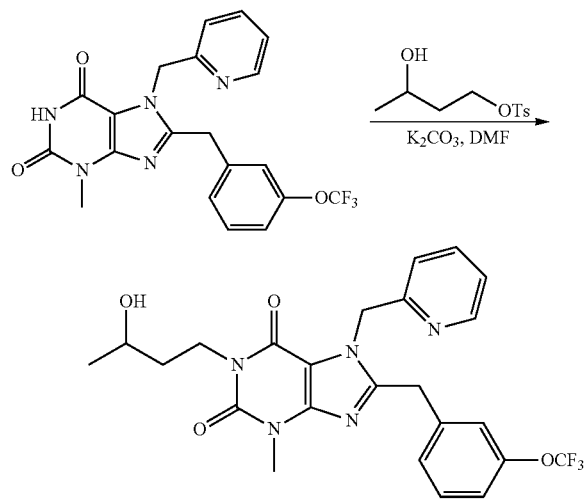

To a solution of 3-methyl-7-(pyridin-2-ylmethyl)-8-(3-(trifluoromethoxy)benzyl)-1H-purine-2,6(3H,7H)-dione (30 mg, 0.07 mmol) in DMF (1 mL) was added 3-hydroxybutyl 4-methylbenzenesulfonate (25.6 mg, 0.105 mmol, intermediate 33) followed by potassium carbonate (14.5 mg, 0.105 mmol) and a catalytic amount of TBAI. The reaction was stirred at 60° C. for 2 h. The reaction was partitioned between ethyl acetate and brine. The organic phase was dried and concentrated to give crude product, which was purified by preparative HPLC to give 1-(3-hydroxybutyl)-3-methyl-7-(pyridin-2-ylmethyl)-8-(3-(trifluoromethoxy)benzyl)-1H-purine-2,6(3H,7H)-dione (11.2 mg, 32% yield) as white solid. $^1$H-NMR (CD$_3$OD) δ 8.38-8.39 (d, 1H), 7.65-7.69 (t, 1H), 7.23-7.31 (m, 2H), 7.07-7.17 (m, 2H), 5.72 (s, 2H), 4.32 (s, 2H), 4.01-4.11 (m, 2H), 3.75-3.77 (m, 1H), 3.58 (s, 3H), 1.71-1.75 (m, 2H), 1.17-1.19 (d, 3H). LCMS retention time 2.480 min; LCMS MH+ 504.

Example 115 1-(3-hydroxybutyl)-3-methyl-7-(pyridin-2-ylmethyl)-8-(3-(trifluoromethoxy)benzyl)-1H-purine-2,6(3H,7H)-dione

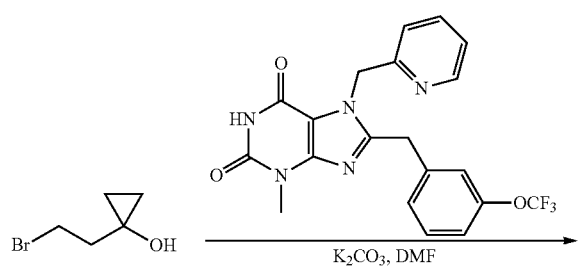

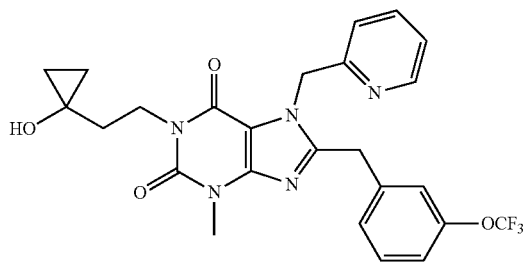

The title compound was prepared using the method of example 114, step 4 and purified by preparative HPLC to give 1-(2-(1-hydroxycyclopropyl)ethyl)-3-methyl-7-(pyridin-2-ylmethyl)-8-(3-(trifluoromethoxy)benzyl)-1H-purine-2,6(3H,7H)-dione (14.1 mg, 33.8%) as white solid. $^1$H-NMR (CD$_3$OD) δ 8.39-8.40 (d, 1H), 7.65-7.69 (t, 1H), 7.28-7.32 (t, 1H), 7.23-7.25 (m, 1H), 7.16-7.19 (d, 1H), 7.08-7.12 (m, 3H), 5.72 (s, 2H), 4.33 (s, 2H), 4.21-4.24 (t, 2H), 3.59 (s, 3H), 1.79-1.82 (t, 2H), 0.55-0.58 (t, 2H), 0.34-0.37 (t, 2H). LCMS retention time 2.609 min; LCMS MH+ 516.

Example 116 7-(4-chlorobenzyl)-1-((2-hydroxycyclopentyl)methyl)-3-methyl-8-(3-(trifluoromethoxy)phenoxy)-1H-purine-2,6(3H,7H)-dione

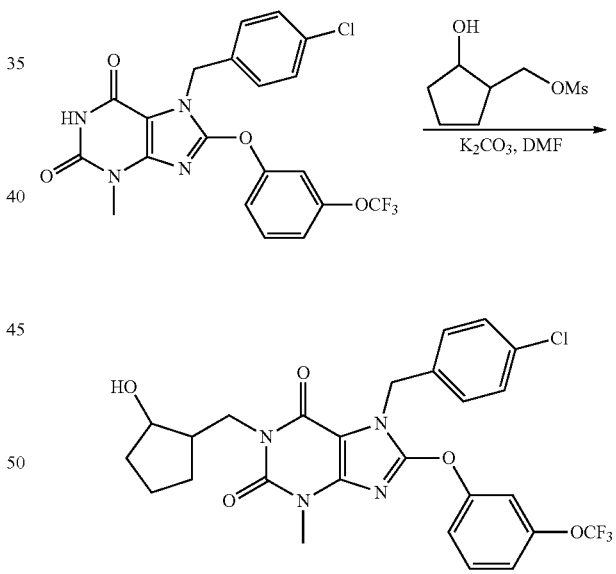

The title compound was prepared from intermediates 9 and 72 using the method of example 82 and purified by preparative HPLC to give 7-(4-chlorobenzyl)-1-((2-hydroxycyclopentyl)methyl)-3-methyl-8-(3-(trifluoromethoxy)phenoxy)-1H-purine-2,6(3H,7H)-dione (20 mg, 33.1% yield) as white solid. $^1$H-NMR (DMSO-d$_6$) δ 7.62-7.58 (t, 1H), 7.48 (s, 1H), 7.44-7.42 (m, 5H), 7.33-7.31 (dd, 1H), 5.44 (s, 2H), 4.43-4.42 (d, 1H), 3.92-3.87 (m, 1H), 3.81-3.71 (m, 2H), 3.29 (s, 3H), 2.21-2.16 (m, 1H), 1.85-1.19 (m, 6H). LCMS retention time 3.307 min; LCMS MH+ 565.

Example 117 7-(4-chlorobenzyl)-1-(3-hydroxycyclobutyl)-3-methyl-8-(3-(trifluoromethoxy)phenoxy)-1H-purine-2,6(3H,7H)-dione

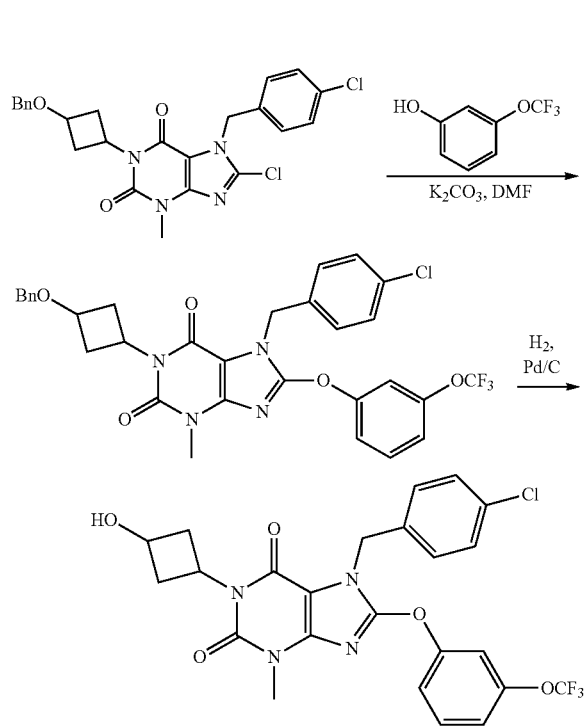

Step 1 1-(3-(benzyloxy)cyclobutyl)-7-(4-chlorobenzyl)-3-methyl-8-(3-(trifluoromethoxy)phenoxy)-1H-purine-2,6(3H,7H)-dione The title compound was prepared using the method of example 52, step 1 and purified by silica gel chromatography eluting with DCM/methanol (60:1) to give 1-(3-(benzyloxy)cyclobutyl)-7-(4-chlorobenzyl)-3-methyl-8-(3-(trifluoromethoxy)phenoxy)-1H-purine-2,6(3H,7H)-dione (110 mg, 50.1% yield) as white solid. LCMS retention time 2.378 min; LCMS MH+ 627.

Step 2 7-(4-chlorobenzyl)-1-(3-hydroxycyclobutyl)-3-methyl-8-(3-(trifluoromethoxy)phenoxy)-1H-purine-2,6(3H,7H)-dione

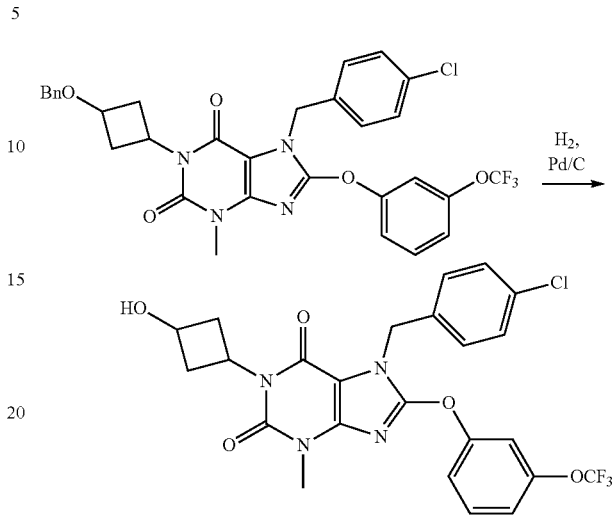

To a solution of 1-(3-(benzyloxy)cyclobutyl)-7-(4-chlorobenzyl)-3-methyl-8-(3-(trifluoromethoxy)phenoxy)-1H-purine-2,6(3H,7H)-dione (110 mg, 0.175 mmol) in methanol was added 5% Pd/C (15 mg). The mixture was hydrogenated at 45 psi for 30 min. The reaction was filtered and concentrated to give a crude product which was purified via preparative HPLC to give 7-(4-chlorobenzyl)-1-(3-hydroxycyclobutyl)-3-methyl-8-(3-(trifluoromethoxy)phenoxy)-1H-purine-2,6(3H,7H)-dione (11 mg, 17.7% yield) as white solid. $^1$H-NMR (DMSO-$d_6$) δ 7.53-7.57 (t, 1H), 7.43-7.45 (d, 2H), 7.36-7.38 (d, 2H), 7.31-7.33 (m, 1H), 7.23-7.25 (d, 1H), 5.79-5.84 (m, 0.65H), 5.50 (s, 2H), 4.83-4.85 (m, 0.35H), 4.64-4.66 (m, 0.65H), 4.00-4.02 (m, 0.35H), 3.40 (s, 3H), 3.16-3.19 (m, 1.3H), 2.88-2.91 (m, 0.7H), 2.66-2.70 (m, 0.7H), 2.25-2.30 (m, 1.3H). LCMS retention time 3.131 min; LCMS MH+ 537.

Example 118 7-(4-chlorobenzyl)-1-(3-hydroxycyclobutyl)-3-methyl-8-(3-(trifluoromethoxy)phenoxy)-1H-purine-2,6(3H,7H)-dione

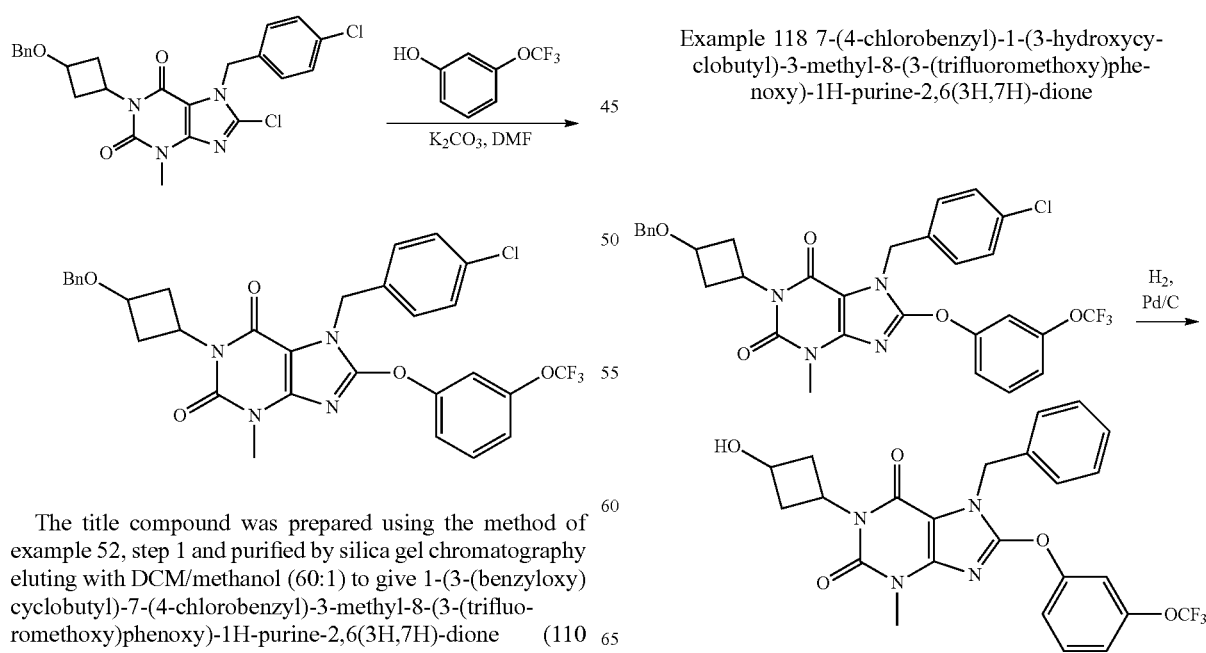

The title compound was prepared from the product of example 117 using the method of example 117, step 2, but with a longer hydrogenation time. The product was purified by preparative HPLC to give 7-benzyl-1-(3-hydroxycyclobutyl)-3-methyl-8-(3-(trifluoromethoxy)phenoxy)-1H-purine-2,6(3H,7H)-dione (46 mg, 52.3% yield) as white solid. $^1$H-NMR (DMSO-d$_6$) δ 7.54-7.58 (t, 1H), 7.42-7.44 (d, 2H), 7.23-7.37 (m, 5H), 7.22-7.24 (d, 1H), 5.80-5.84 (m, 0.6H), 5.50 (s, 2H), 4.77-4.82 (m, 0.4H), 4.62-4.66 (m, 0.6H), 4.00-4.04 (m, 0.4H), 3.39 (s, 3H), 3.16-3.23 (m, 1.2H), 2.83-2.91 (m, 0.8H), 2.68-2.73 (m, 0.8H), 2.25-2.31 (m, 1.2H). LCMS retention time 2.961 min; LCMS MH$^+$ 503.

Example 119 7-(4-chlorobenzyl)-1-(3-hydroxycyclobutyl)-3-methyl-8-(3-(trifluoromethoxy)phenoxy)-1H-purine-2,6(3H,7H)-dione

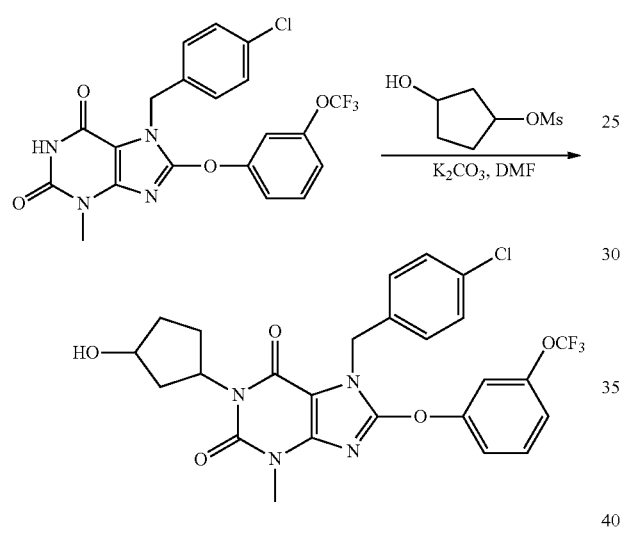

The title compound was prepared using the method of example 82 with intermediates 9 and 74 and purified via preparative HPLC to give 7-(4-chlorobenzyl)-1-(3-hydroxycyclopentyl)-3-methyl-8-(3-(trifluoromethoxy)phenoxy)-1H-purine-2,6(3H,7H)-dione (29 mg, 24.6% yield) as white solid. $^1$H-NMR (DMSO-d$_6$) δ 7.53-7.57 (t, 1H), 7.43-7.45 (d, 2H), 7.32-7.38 (m, 6H), 7.24-7.26 (dd, 1H), 5.52-5.56 (m, 1H), 5.50 (s, 2H), 4.21-4.24 (m, 0.4H), 3.42 (s, 3H), 2.33-2.38 (m, 1H), 2.22-2.27 (m, 1H), 2.13-2.16 (m, 1H), 1.89-1.99 (m, 2H), 1.77-1.80 (m, 1H). LCMS retention time 3.168 LCMS MH$^+$ 551.

Example 120 7-(4-chlorobenzyl)-1-(3-(hydroxymethyl)cyclobutyl)-3-methyl-8-(3-(trifluoromethoxy)phenoxy)-1H-purine-2,6(3H,7H)-dione

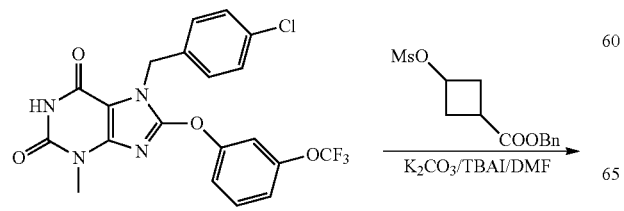

Step 1 benzyl 3-(7-(4-chlorobenzyl)-3-methyl-2,6-dioxo-8-(3-(trifluoromethoxy)phenoxy)-2,3,6,7-tetrahydro-1H-purin-1-yl)cyclobutanecarboxylate

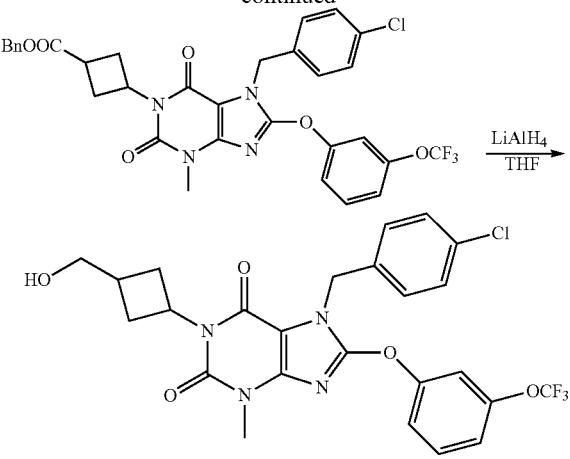

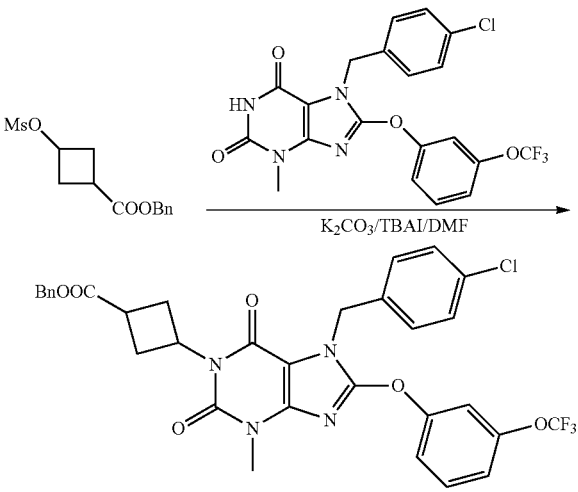

The title compound was prepared using the method of example 82 with intermediates 9 and 75 to give 3-(7-(4-chlorobenzyl)-3-methyl-2,6-dioxo-8-(3-(trifluoromethoxy)phenoxy)-2,3,6,7-tetrahydro-1H-purin-1-yl)cyclobutanecarboxylate (59 mg, 26.1% yield) as a yellow solid. LCMS retention time 1.981 min; LCMS MH$^+$ 655.

Step 2 7-(4-chlorobenzyl)-1-(3-(hydroxymethyl)cyclobutyl)-3-methyl-8-(3-(trifluoromethoxy)phenoxy)-1H-purine-2,6(3H,7H)-dione

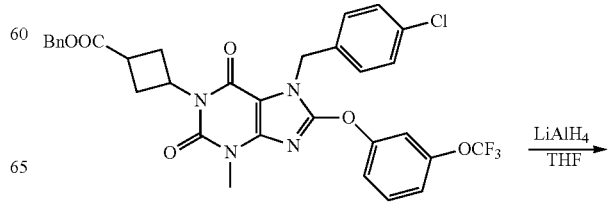

-continued

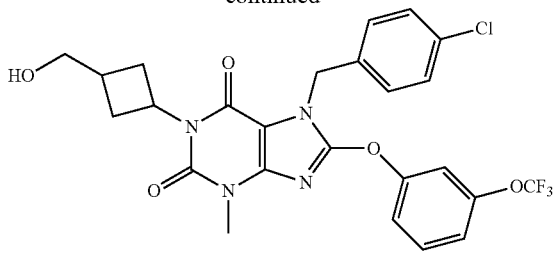

To a solution of 3-(7-(4-chlorobenzyl)-3-methyl-2,6-dioxo-8-(3-(trifluoromethoxy)phenoxy)-2,3,6,7-tetrahydro-1H-purin-1-yl)cyclobutanecarboxylate (59 mg, 0.09 mmol) in THF (3 mL) was added LAH (6.8 mg, 0.18 mmol) in one portion and the mixture was stirred at room temperature for 2 h. The reaction was carefully quenched with ethyl acetate and filtered. The filtrate was concentrated to dryness to give a crude product which was purified via preparative HPLC to give 7-(4-chlorobenzyl)-1-(3-(hydroxymethyl)cyclobutyl)-3-methyl-8-(3-(trifluoromethoxy)phenoxy)-1H-purine-2,6(3H,7H)-dione (17 mg, 34.3% yield) as white solid. $^1$H-NMR (CDCl$_3$) δ 7.40-7.48 (m, 3H), 7.33-7.35 (m, 2H), 7.21-7.26 (m, 2H), 7.15-7.17 (d, 1H), 5.52-5.63 (m, 1H), 5.44 (s, 2H), 3.73-3.80 (m, 2H), 3.11-3.17 (q, 1H), 2.96-2.98 (m, 1H), 2.60-2.64 (m, 1H), 2.34-2.38 (m, 1H), 2.08-2.14 (m, 1H). LCMS retention time 3.054; LCMS MH$^+$ 551.

Example 121 1-(3-hydroxybutyl)-3-methyl-7-(pyridin-2-ylmethyl)-8-(3-(trifluoromethoxy)phenoxy)-1H-purine-2,6(3H,7H)-dione

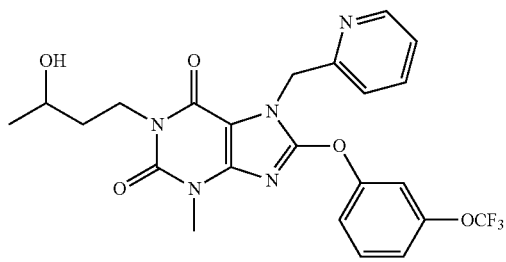 [SMILES: CC(O)CCn1c(=O)c2c(nc(Oc3cccc(OC(F)(F)F)c3)n2Cc2ccccn2)n(C)c1=O]

The title compound was prepared from intermediate 57 using the method of example 100 and purified by preparative HPLC to give 1-(3-hydroxybutyl)-3-methyl-7-(pyridin-2-ylmethyl)-8-(3-(trifluoromethoxy)phenoxy)-1H-purine-2,6(3H,7H)-dione (40 mg, 21.9% yield) as a white solid. $^1$H-NMR (CD$_3$OD) δ 8.49-8.48 (d, 1H), 7.88-7.81 (t, 1H), 7.53-7.51 (t, 1H), 7.45-7.43 (d, 1H), 7.36-7.33 (m, 3H), 7.23-7.19 (d, 1H), 5.66 (s, 2H), 4.14-3.98 (m, 2H), 3.78-3.71 (m, 1H), 3.46 (s, 3H), 1.75-1.71 (m, 2H), 1.19-1.18 (d, 3H). LCMS retention time 2.575 min; LCMS MH$^+$ 506.

Example 122 7-((5-chloropyridin-2-yl)methyl)-1-(3-hydroxybutyl)-3-methyl-8-(3-(trifluoromethoxy)phenoxy)-1H-purine-2,6(3H,7H)-dione

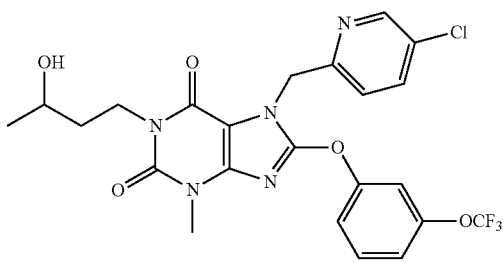 [SMILES: CC(O)CCn1c(=O)c2c(nc(Oc3cccc(OC(F)(F)F)c3)n2Cc2ccc(Cl)cn2)n(C)c1=O]

The title compound was prepared from intermediate 57 using the method of example 100 and purified by preparative HPLC to give 7-((5-chloropyridin-2-yl)methyl)-1-(3-hydroxybutyl)-3-methyl-8-(3-(trifluoromethoxy)phenoxy)-1H-purine-2,6(3H,7H)-dione (40 mg, 21.9% yield) as a white solid. $^1$H-NMR (CD$_3$OD) δ 8.47-8.46 (d, 1H), 7.87-7.84 (d, 1H), 7.57-7.46 (t, 1H), 7.37-7.36 (d, 1H), 7.25-7.22 (m, 2H), 7.14-7.12 (d, 1H), 5.64 (s, 2H), 4.13-3.97 (m, 2H), 3.78-3.72 (m, 1H), 3.45 (s, 3H), 1.75-1.69 (m, 2H), 1.19-1.18 (d, 3H). LCMS retention time 2.944 min; LCMS MH$^+$ 540.

Example 123 7-((5-fluoropyridin-2-yl)methyl)-1-(3-hydroxybutyl)-3-methyl-8-(3-(trifluoromethoxy)phenoxy)-1H-purine-2,6(3H,7H)-dione

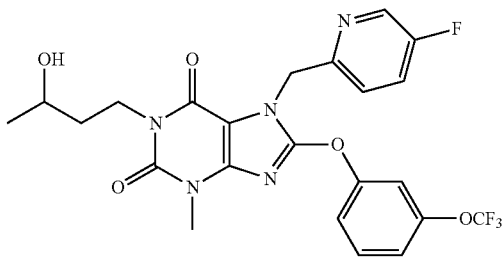 [SMILES: CC(O)CCn1c(=O)c2c(nc(Oc3cccc(OC(F)(F)F)c3)n2Cc2ccc(F)cn2)n(C)c1=O]

The title compound was prepared from intermediate 57 using the method of example 100 and purified by preparative HPLC to give 7-((5-fluoropyridin-2-yl)methyl)-1-(3-hydroxybutyl)-3-methyl-8-(3-(trifluoromethoxy)phenoxy)-1H-purine-2,6(3H,7H)-dione (40 mg, 21.1% yield) as a white solid. $^1$H-NMR (CD$_3$OD) δ 8.38-8.37 (d, 1H), 7.66-7.51 (m, 3H), 7.37-7.35 (m, 2H), 7.24-7.22 (d, 1H), 5.64 (s, 2H), 4.12-3.97 (m, 2H), 3.77-3.72 (m, 1H), 3.45 (s, 3H), 1.75-1.68 (m, 2H), 1.19-1.18 (d, 3H). LCMS retention time 2.733 min; LCMS MH$^+$ 524.

Example 124 7-((5-fluoropyridin-2-yl)methyl)-1-(2-(1-hydroxycyclopropyl)ethyl)-3-methyl-8-(3-(trifluoromethoxy)phenoxy)-1H-purine-2,6(3H,7H)-dione

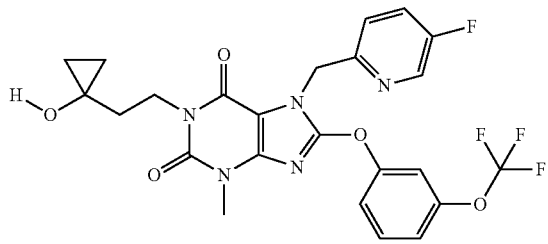 [SMILES: Cn1c(=O)n(CCC2(O)CC2)c(=O)c2c1nc(Oc1cccc(OC(F)(F)F)c1)n2Cc1ccc(F)cn1]

The title compound was prepared from intermediate 58 using the method of example 100 and purified by preparative HPLC to give 7-((5-fluoropyridin-2-yl)methyl)-1-(2-(1-hydroxycyclopropyl)ethyl)-3-methyl-8-(3-(trifluoromethoxy)phenoxy)-1H-purine-2,6(3H,7H)-dione (25 mg, 33.7% yield) as white solid. $^1$H-NMR (CD$_3$OD) δ 8.49 (d, 1H), 7.51-7.65 (m, 3H), 7.36-7.39 (m, 2H), 7.24 (dd, 1H), 5.64 (s, 2H), 4.22 (t, 2H), 3.44 (s, 3H), 1.81 (t, 2H), 0.56 (t, 2H), 0.35 (t, 2H). LCMS retention time 2.894 min; LCMS MH$^+$ 536.

Example 125 7-(4-chlorobenzyl)-3-ethyl-1-(3-hydroxypropyl)-8-((5-methylpyridin-3-yl)oxy)-1H-purine-2,6(3H,7H)-dione

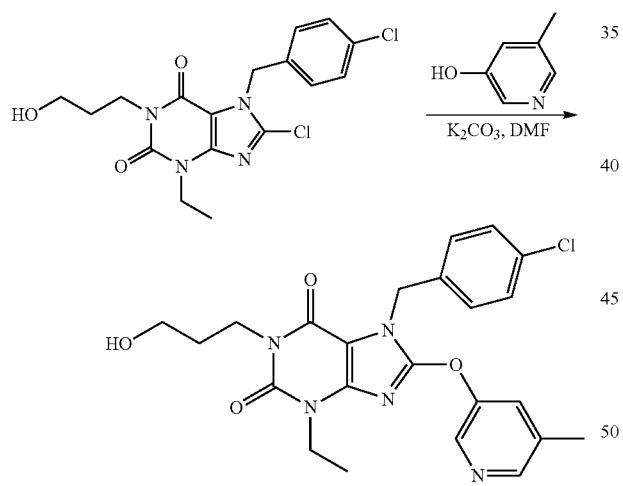

To a solution of 8-chloro-7-(4-chlorobenzyl)-3-ethyl-1-(3-hydroxypropyl)-1H-purine-2,6(3H,7H)-dione (30 mg, 0.08 mmol, intermediate 78) in DMF (2 mL) was added 5-methylpyridin-3-ol (12.36 mg, 0.12 mmol), followed by potassium carbonate (15.66 mg, 0.11 mmol). The reaction was stirred at 80° C. for 3 h. The reaction was cooled and partitioned between ethyl acetate and water. The organic phase was washed with brine, dried over sodium sulfate, and concentrated to give a crude product, which was purified by preparative HPLC to give 7-(4-chlorobenzyl)-3-ethyl-1-(3-hydroxypropyl)-8-((5-methylpyridin-3-yl)oxy)-1H-purine-2,6(3H,7H)-dione (8 mg, 22.5%) as white solid. $^1$H-NMR (CD$_3$OD) δ 8.35-8.42 (d, 2H), 7.68 (s, 1H), 7.38-7.48 (m, 4H), 5.52 (s, 2H), 4.01-4.14 (m, 4H), 3.61-3.64 (m, 2H), 2.43 (s, 3H), 1.87-1.90 (m, 2H), 1.22-1.26 (m, 3H). LCMS retention time 2.511 min; LCMS MH$^+$ 470.

Example 126 7-(4-chlorobenzyl)-3-ethyl-1-(3-hydroxypropyl)-8-(propylsulfonyl)-1H-purine-2,6(3H,7H)-dione

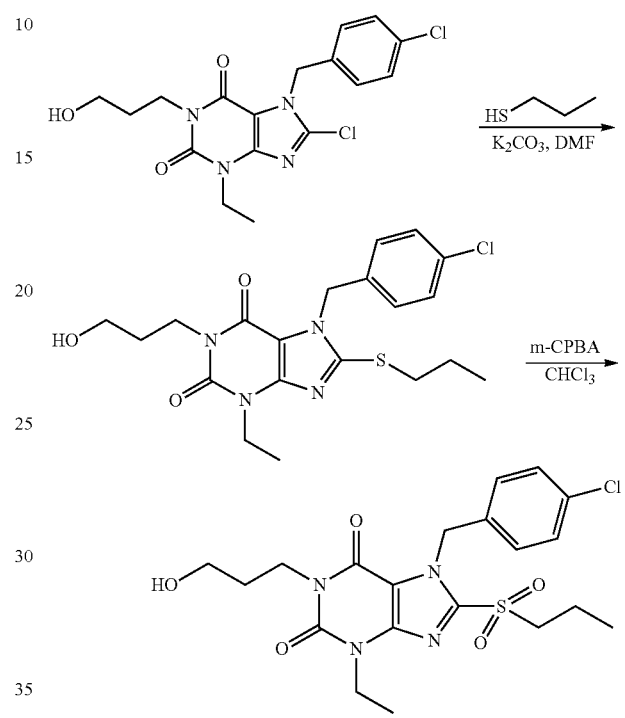

The title compound was prepared using the method of example 106 and purified by preparative HPLC to give 7-(4-chlorobenzyl)-3-ethyl-1-(3-hydroxypropyl)-8-(propylsulfonyl)-1H-purine-2,6(3H,7H)-dione (7 mg, 16.3%) as white solid. $^1$H-NMR (CD$_3$OD) δ 7.35-7.41 (m, 4H), 5.98 (s, 2H), 4.10-4.18 (m, 4H), 3.60-3.64 (m, 2H), 3.40-3.44 (m, 2H), 1.77-1.89 (m, 4H), 1.32-1.36 (m, 3H), 1.00-1.04 (m, 3H). LCMS retention time 2.521 min; LCMS MH$^+$ 469.

Example 127 8-(4-chloro-3-(trifluoromethoxy)phenoxy)-7-(4-chlorobenzyl)-1-(3-hydroxypropyl)-3-methyl-1H-purine-2,6(3H,7H)-dione

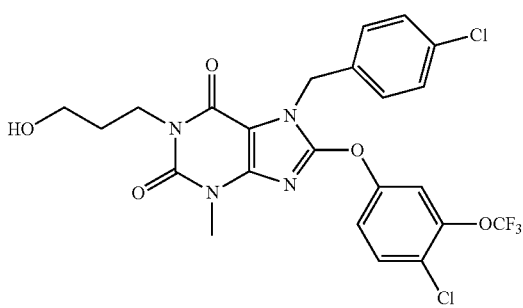

The title compound was prepared from intermediate 63 using the method of example 108 and purified by preparative HPLC to give 8-(4-chloro-3-(trifluoromethoxy)phenoxy)-7-(4-chlorobenzyl)-1-(3-hydroxypropyl)-3-methyl-1H-purine-2,6(3H,7H)-dione (39.4 mg, 30.1% yield) as white solid. $^1$H-NMR (CD$_3$OD) δ 7.66-7.68 (d, 2H), 7.58 (s, 1H), 7.44-7.46 (d, 2H), 7.36-7.40 (m, 2H), 5.51 (s, 2H), 4.10-4.13 (t, 2H), 3.60-3.63 (t, 2H), 3.43 (s, 3H), 1.87-1.90 (m, 2H). LCMS retention time 3.268 min; LCMS MH$^+$ 559.

Example 128 7-(4-chlorobenzyl)-8-(4-fluoro-3-(trifluoromethoxy)phenoxy)-1-(3-hydroxypropyl)-3-methyl-1H-purine-2,6(3H,7H)-dione

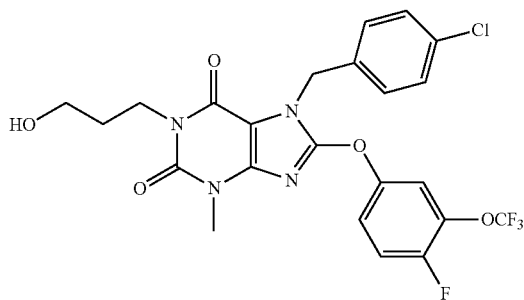 [SMILES: Cn1c(=O)n(CCCO)c(=O)c2c1nc(Oc1ccc(Cl)c(OC(F)(F)F)c1)n2Cc1ccc(Cl)cc1]

The title compound was prepared from intermediate 63 using the method of example 108 and purified by preparative HPLC to give 7-(4-chlorobenzyl)-8-(4-fluoro-3-(trifluoromethoxy)phenoxy)-1-(3-hydroxypropyl)-3-methyl-1H-purine-2,6(3H,7H)-dione (52.9 mg, 55.6% yield) as white solid. $^1$H-NMR (CD$_3$OD) δ=7.55-7.56 (m, 1H), 7.44-7.46 (d, 2H), 7.39-7.42 (m, 1H), 7.37-7.39 (d, 2H), 5.50 (s, 2H), 4.13-4.09 (t, 2H), 3.60-3.63 (t, 2H), 3.42 (s, 3H), 1.86-1.90 (m, 2H). LCMS retention time 3.114 min; LCMS MH$^+$ 543.

Example 129 7-(4-chlorobenzyl)-1-(3-hydroxypropyl)-8-(2-methoxy-5-(trifluoromethoxy)phenoxy)-3-methyl-1H-purine-2,6(3H,7H)-dione

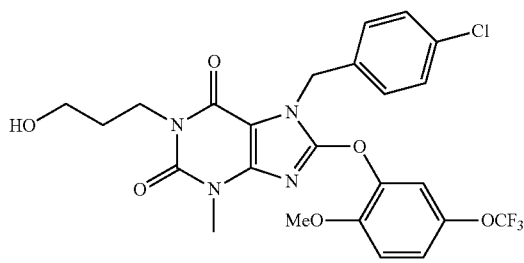 [SMILES: COc1ccc(OC(F)(F)F)cc1Oc1nc2c(c(=O)n(CCCO)c(=O)n2C)n1Cc1ccc(Cl)cc1]

The title compound was prepared from intermediate 63 using the method of example 108 and purified by preparative HPLC to give 7-(4-chlorobenzyl)-1-(3-hydroxypropyl)-8-(2-methoxy-5-(trifluoromethoxy)phenoxy)-3-methyl-1H-purine-2,6(3H,7H)-dione (56.5 mg, 43.5% yield) as white solid. $^1$H-NMR (CD$_3$OD) δ 7.50-7.52 (d, 2H), 7.38-7.40 (d, 2H), 7.37 (s, 1H), 7.21-7.26 (m, 2H), 5.49 (s, 2H), 4.08-4.11 (t, 2H), 3.75 (s, 3H), 3.59-3.62 (t, 2H), 3.36 (s, 3H), 1.85-1.89 (m, 2H). LCMS retention time 3.066 min; LCMS MH$^+$ 555.

Example 130 7-benzyl-3-methyl-8-(3-(trifluoromethoxy)phenoxy)-1-(3,3,3-trifluoropropyl)-1H-purine-2,6(3H,7H)-dione

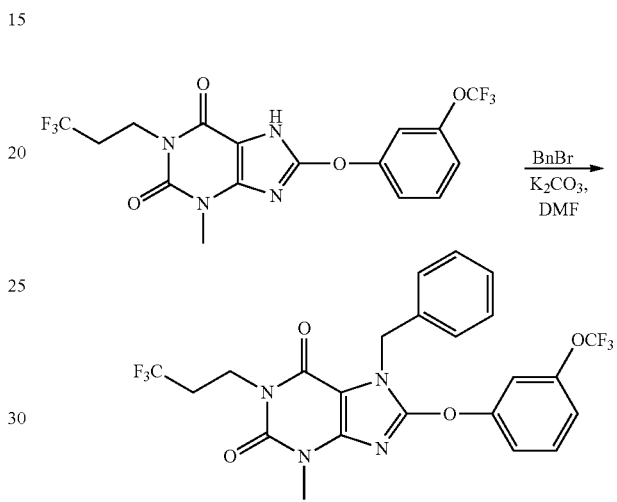

The title compound was prepared from intermediate 80 using the method example 100 and purified via preparative HPLC to give 7-benzyl-3-methyl-8-(3-(trifluoromethoxy)phenoxy)-1-(3,3,3-trifluoropropyl)-1H-purine-2,6(3H,7H)-dione (35.6 mg, 59.1% yield) as white solid. $^1$H-NMR (CD$_3$OD) δ 7.52-7.56 (t, 1H), 7.44-7.46 (d, 2H), 7.29-7.38 (m, 5H), 7.22-7.24 (d, 1H), 5.52 (s, 2H), 4.27-4.30 (t, 2H), 3.42 (s, 3H), 2.54-2.60 (m, 2H). LCMS retention time 3.382 min; LCMS MH$^+$ 529.

Example 131 7-((5-chloropyridin-2-yl)methyl)-3-methyl-8-(3-(trifluoromethoxy)phenoxy)-1-(3,3,3-trifluoropropyl)-1H-purine-2,6(3H,7H)-dione

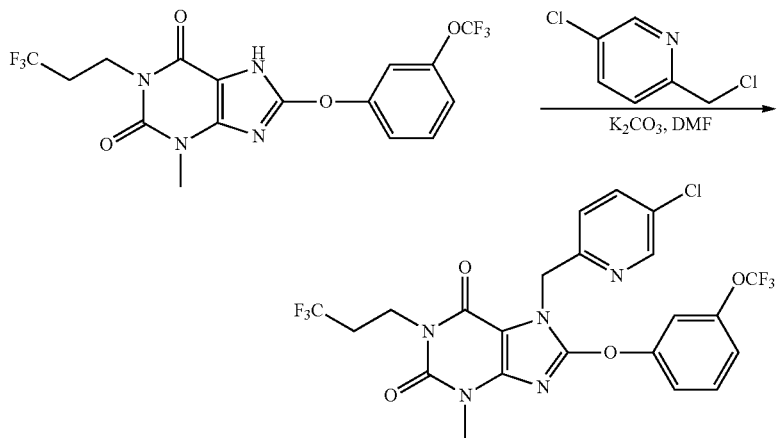

The title compound was prepared using the method of example 100 and purified via preparative HPLC to give 7-benzyl-3-methyl-8-(3-(trifluoromethoxy)phenoxy)-1-(3,3,3-trifluoropropyl)-1H-purine-2,6(3H,7H)-dione (18.7 mg, 29.1% yield) as white solid. $^1$H-NMR (CD$_3$OD) δ 8.52 (s, 1H), 8.46 (s, 1H), 7.84-7.87 (dd, 1H), 7.53-7.57 (t, 1H), 7.47-7.49 (d, 1H), 7.36-7.37 (m, 1H), 7.22-7.24 (d, 1H), 5.63 (s, 2H), 4.19-4.23 (t, 2H), 3.45 (s, 3H), 2.50-2.55 (m, 2H). LCMS retention time 3.369 min; LCMS MH$^+$ 564.

Example 132 7-(4-fluorobenzyl)-8-(2-fluorophenoxy)-1-(3-hydroxypropyl)-3-methyl-1H-purine-2,6(3H,7H)-dione

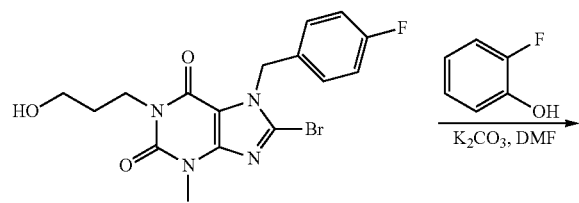

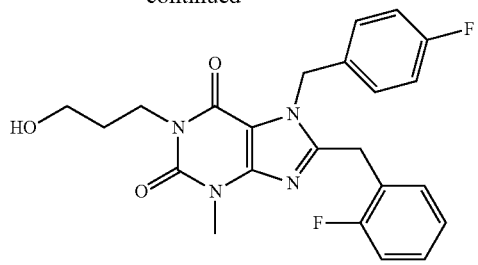

To a solution of 8-bromo-7-(4-fluorobenzyl)-1-(3-hydroxypropyl)-3-methyl-1H-purine-2,6(3H,7H)-dione (50 mg, 0.121 mmol, intermediate 62) in DMF (1 mL) was added 2-fluorophenol (16.4 mg, 0.146 mmol) followed by potassium carbonate (25.2 mg, 0.182 mmol). The reaction was stirred at 80° C. for 4 h. The mixture was partitioned between ethyl acetate and brine. The organic phase was washed with saturated aqueous ammonium chloride, dried and concentrated to give crude product, which was purified by preparative HPLC to give 7-(4-fluorobenzyl)-8-(2-fluorophenoxy)-1-(3-hydroxypropyl)-3-methyl-1H-purine-2,6(3H,7H)-dione (19.8 mg, 36.9% yield) as white solid. $^1$H-NMR (CD$_3$OD) δ 7.52-7.56 (m, 2H), 7.43-7.45 (t, 1H), 7.2-7.38 (m, 3H), 7.08-7.13 (t, 1H), 5.51 (s, 2H), 4.09-4.13 (t, 2H), 3.60-3.63 (t, 2H), 3.37 (s, 3H), 1.86-1.90 (m, 2H). LCMS retention time 2.604; LCMS MH$^+$ 443.

The compounds in Table 2 were prepared using the method of example 132.

TABLE 1

| Example | Structure | Chemical Name | LCMS retention time, min | LCMS M + 1 |
|---|---|---|---|---|
| 133 | 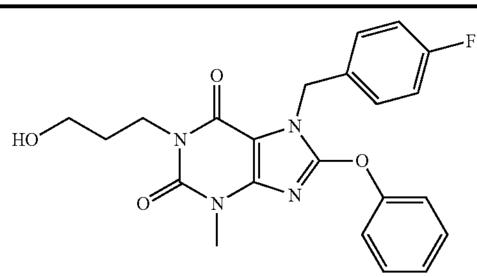 | 7-(4-fluorobenzyl)-1-(3-hydroxypropyl)-3-methyl-8-phenoxy-1H-purine-2,6(3H,7H)-dione | 2.576 | 425 |
| 134 | 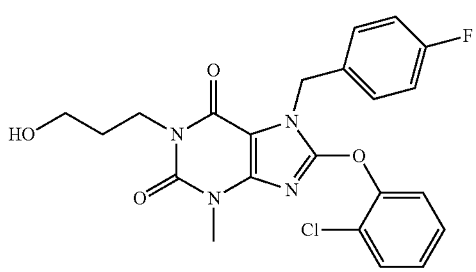 [SMILES: Cn1c(=O)n(CCCO)c(=O)c2c1nc(Oc1ccccc1Cl)n2Cc1ccc(F)cc1] | 8-(2-chlorophenoxy)-7-(4-fluorobenzyl)-1-(3-hydroxypropyl)-3-methyl-1H-purine-2,6(3H,7H)-dione | 2.708 | 459 |
| 135 | 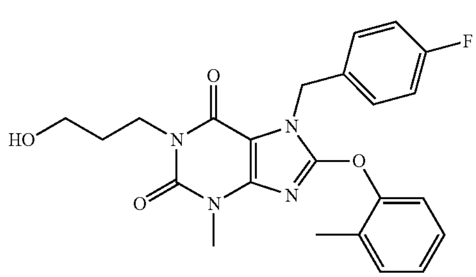 [SMILES: Cc1ccccc1Oc1nc2c(c(=O)n(CCCO)c(=O)n2C)n1Cc1ccc(F)cc1] | 7-(4-fluorobenzyl)-1-(3-hydroxypropyl)-3-methyl-8-(o-tolyloxy)-1H-purine-2,6(3H,7H)-dione | 2.684 | 439 |

TABLE 1-continued

| Example | Structure | Chemical Name | LCMS retention time, min | LCMS M + 1 |
|---|---|---|---|---|
| 136 | 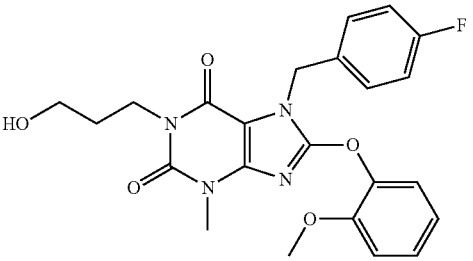 [SMILES: COc1ccccc1Oc1nc2c(c(=O)n(CCCO)c(=O)n2C)n1Cc1ccc(F)cc1] | 7-(4-fluorobenzyl)-1-(3-hydroxypropyl)-8-(2-methoxyphenoxy)-3-methyl-1H-purine-2,6(3H,7H)-dione | 2.555 | 455 |
| 137 | 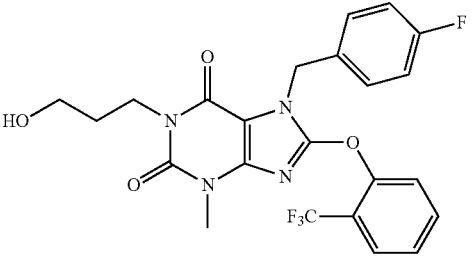 [SMILES: Cn1c(=O)n(CCCO)c(=O)c2c1nc(Oc1ccccc1C(F)(F)F)n2Cc1ccc(F)cc1] | 7-(4-fluorobenzyl)-1-(3-hydroxypropyl)-3-methyl-8-(2-(trifluoromethyl)phenoxy)-1H-purine-2,6(3H,7H)-dione | 2.782 | 493 |
| 138 | 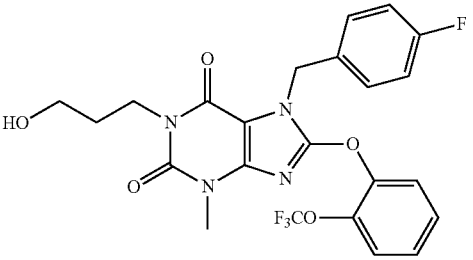 [SMILES: Cn1c(=O)n(CCCO)c(=O)c2c1nc(Oc1ccccc1OC(F)(F)F)n2Cc1ccc(F)cc1] | 7-(4-fluorobenzyl)-1-(3-hydroxypropyl)-3-methyl-8-(trifluoromethoxy)phenoxy)-1H-purine-2,6(3H,7H)-dione | 2.828 | 509 |
| 139 | 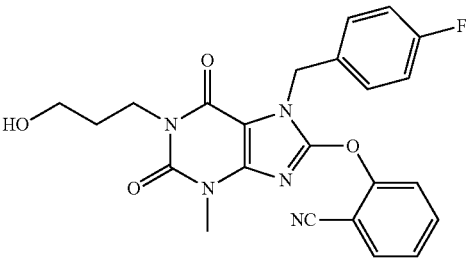 [SMILES: Cn1c(=O)n(CCCO)c(=O)c2c1nc(Oc1ccccc1C#N)n2Cc1ccc(F)cc1] | 2-((7-(4-fluorobenzyl)-1-(3-hydroxypropyl)-3-methyl-2,6-dioxo-2,3,6,7-tetrahydro-1H-purin-8-yl)oxy)benzonitrile | 2.444 | 450 |
| 140 | 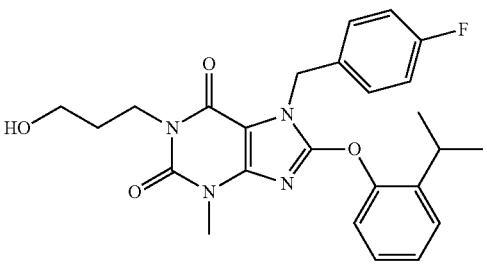 [SMILES: CC(C)c1ccccc1Oc1nc2c(c(=O)n(CCCO)c(=O)n2C)n1Cc1ccc(F)cc1] | 7-(4-fluorobenzyl)-1-(3-hydroxypropyl)-8-(2-isopropylphenoxy)-3-methyl-1H-purine-2,6(3H,7H)-dione | 2.960 | 467 |

TABLE 1-continued

| Example | Structure | Chemical Name | LCMS retention time, min | LCMS M + 1 |
|---|---|---|---|---|
| 141 | 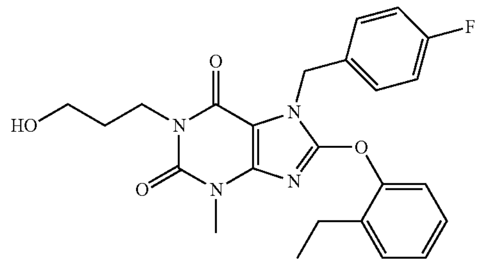 [SMILES: CCc1ccccc1Oc1nc2c(c(=O)n(CCCO)c(=O)n2C)n1Cc1ccc(F)cc1] | 8-(2-ethylphenoxy)-7-(4-fluorobenzyl)-1-(3-hydroxypropyl)-3-methyl-1H-purine-2,6(3H,7H)-dione | 2.810 | 453 |
| 142 | 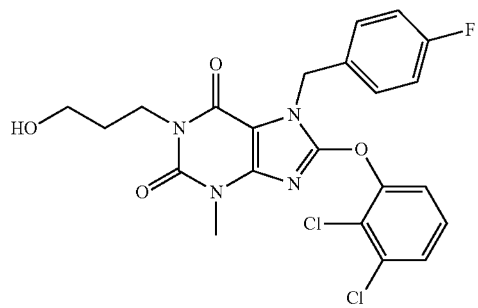 [SMILES: Cn1c(=O)n(CCCO)c(=O)c2c1nc(Oc1cccc(Cl)c1Cl)n2Cc1ccc(F)cc1] | 8-(2,3-dichlorophenoxy)-7-(4-fluorobenzyl)-1-(3-hydroxypropyl)-3-methyl-1H-purine-2,6(3H,7H)-dione | 2.928 | 473 |
| 143 | 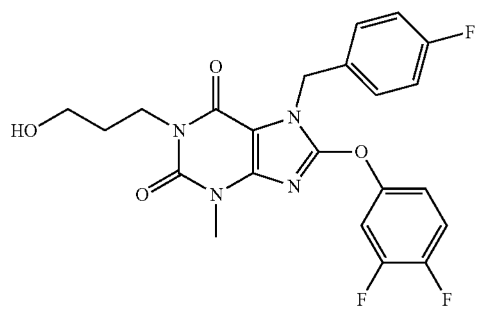 [SMILES: Cn1c(=O)n(CCCO)c(=O)c2c1nc(Oc1ccc(F)c(F)c1)n2Cc1ccc(F)cc1] | 8-(3,4-difluorophenoxy)-7-(4-fluorobenzyl)-1-(3-hydroxypropyl)-3-methyl-1H-purine-2,6(3H,7H)-dione | 2.689 | 461 |
| 144 | 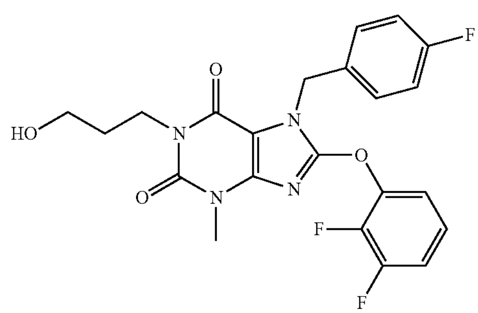 [SMILES: Cn1c(=O)n(CCCO)c(=O)c2c1nc(Oc1cccc(F)c1F)n2Cc1ccc(F)cc1] | 8-(2,3-difluorophenoxy)-7-(4-fluorobenzyl)-1-(3-hydroxypropyl)-3-methyl-1H-purine-2,6(3H,7H)-dione | 2.671 | 461 |
| 145 | 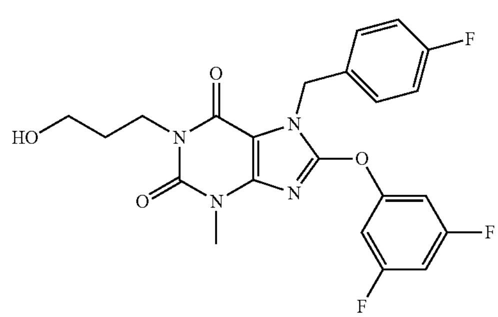 [SMILES: Cn1c(=O)n(CCCO)c(=O)c2c1nc(Oc1cc(F)cc(F)c1)n2Cc1ccc(F)cc1] | 8-(3,5-difluorophenoxy)-7-(4-fluorobenzyl)-1-(3-hydroxypropyl)-3-methyl-1H-purine-2,6(3H,7H)-dione | 2.727 | 461 |

TABLE 1-continued

| Example | Chemical Name | LCMS retention time, min | LCMS M + 1 |
|---|---|---|---|
| 146 | 8-(3-chlorophenoxy)-7-(4-fluorobenzyl)-1-(3-hydroxypropyl)-3-methyl-1H-purine-2,6(3H,7H)-dione | 2.796 | 459 |
| 147 | 7-(4-fluorobenzyl)-8-(3-fluorophenoxy)-1-(3-hydroxypropyl)-3-methyl-1H-purine-2,6(3H,7H)-dione | 2.652 | 443 |
| 148 | 7-(4-fluorobenzyl)-1-(3-hydroxypropyl)-3-methyl-8-(m-tolyloxy)-1H-purine-2,6(3H,7H)-dione | 2.756 | 439 |
| 149 | 7-(4-fluorobenzyl)-1-(3-hydroxypropyl)-8-(3-methoxyphenoxy)-3-methyl-1H-purine-2,6(3H,7H)-dione | 2.625 | 455 |
| 150 | 7-(4-fluorobenzyl)-1-(3-hydroxypropyl)-3-methyl-8-(3-(trifluoromethyl)phenoxy)-1H-purine-2,6(3H,7H)-dione | 2.870 | 493 |

TABLE 1-continued

| Example | Structure | Chemical Name | LCMS retention time, min | LCMS M + 1 |
|---|---|---|---|---|
| 151 | 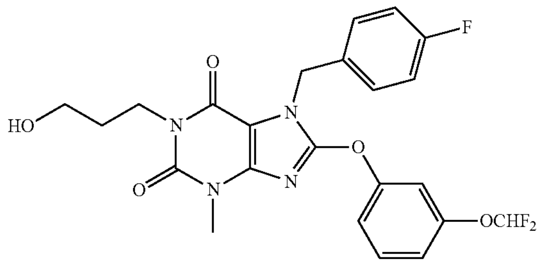 [SMILES: Cn1c(=O)n(CCCO)c(=O)c2c1nc(Oc1cccc(OC(F)F)c1)n2Cc1ccc(F)cc1] | 8-(3-(difluoromethoxy)phenoxy)-7-(4-fluorobenzyl)-1-(3-hydroxypropyl)-3-methyl-1H-purine-2,6(3H,7H)-dione | 2.697 | 491 |
| 152 | 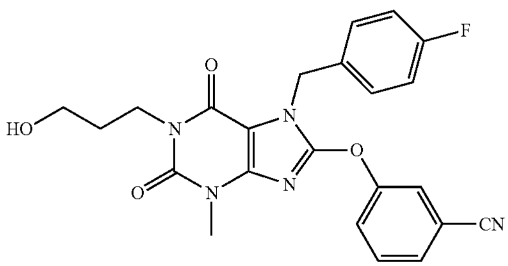 [SMILES: Cn1c(=O)n(CCCO)c(=O)c2c1nc(Oc1cccc(C#N)c1)n2Cc1ccc(F)cc1] | 3-((7-(4-fluorobenzyl)-1-(3-hydroxypropyl)-3-methyl-2,6-dioxo-2,3,6,7-tetrahydro-1H-purin-8-yl)oxy)benzonitrile | 2.464 | 450 |
| 153 | 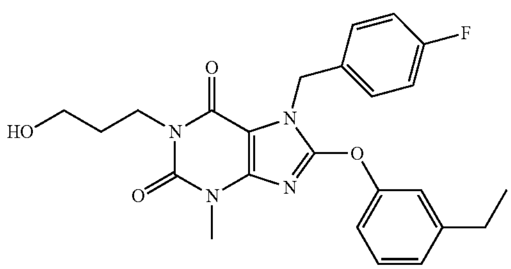 [SMILES: CCc1cccc(Oc2nc3c(c(=O)n(CCCO)c(=O)n3C)n2Cc2ccc(F)cc2)c1] | 8-(3-ethylphenoxy)-7-(4-fluorobenzyl)-1-(3-hydroxypropyl)-3-methyl-1H-purine-2,6(3H,7H)-dione | 2.893 | 453 |
| 154 | 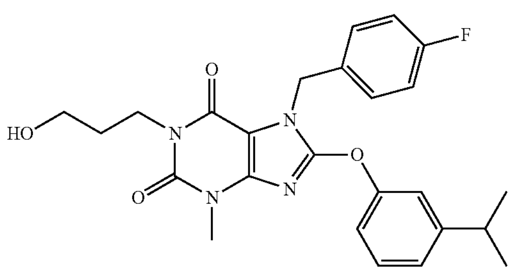 [SMILES: CC(C)c1cccc(Oc2nc3c(c(=O)n(CCCO)c(=O)n3C)n2Cc2ccc(F)cc2)c1] | 7-(4-fluorobenzyl)-1-(3-hydroxypropyl)-8-(3-isopropylphenoxy)-3-methyl-1H-purine-2,6(3H,7H)-dione | 3.025 | 467 |
| 155 | 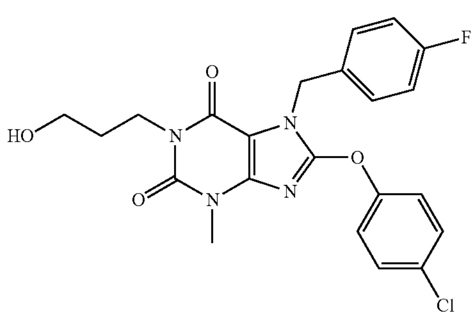 | 8-(4-chlorophenoxy)-7-(4-fluorobenzyl)-1-(3-hydroxypropyl)-3-methyl-1H-purine-2,6(3H,7H)-dione | 2.809 | 459 |

TABLE 1-continued

| Example | Structure | Chemical Name | LCMS retention time, min | LCMS M + 1 |
|---|---|---|---|---|
| 156 | 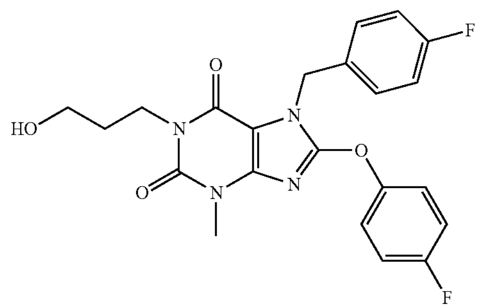 [SMILES: Cn1c(=O)n(CCCO)c(=O)c2c1nc(Oc1ccc(F)cc1)n2Cc1ccc(F)cc1] | 7-(4-fluorobenzyl)-8-(4-fluorophenoxy)-1-(3-hydroxypropyl)-3-methyl-1H-purine-2,6(3H,7H)-dione | 2.619 | 443 |
| 157 | 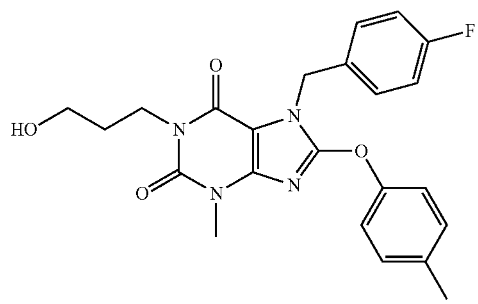 [SMILES: Cc1ccc(Oc2nc3c(c(=O)n(CCCO)c(=O)n3C)n2Cc2ccc(F)cc2)cc1] | 7-(4-fluorobenzyl)-1-(3-hydroxypropyl)-3-methyl-8-(p-tolyloxy)-1H-purine-2,6(3H,7H)-dione | 2.766 | 439 |
| 158 | 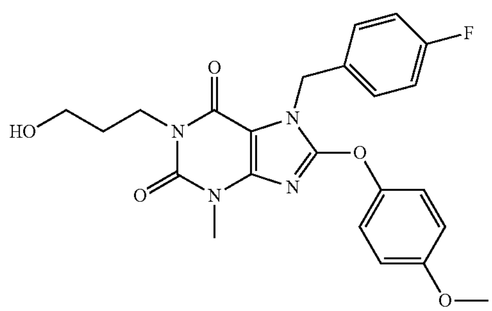 [SMILES: COc1ccc(Oc2nc3c(c(=O)n(CCCO)c(=O)n3C)n2Cc2ccc(F)cc2)cc1] | 7-(4-fluorobenzyl)-1-(3-hydroxypropyl)-8-(4-methoxyphenoxy)-3-methyl-1H-purine-2,6(3H,7H)-dione | 2.572 | 455 |
| 159 | 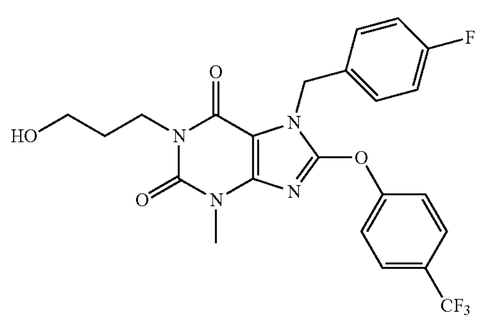 [SMILES: Cn1c(=O)n(CCCO)c(=O)c2c1nc(Oc1ccc(C(F)(F)F)cc1)n2Cc1ccc(F)cc1] | 7-(4-fluorobenzyl)-1-(3-hydroxypropyl)-3-methyl-8-(4-(trifluoromethyl)phenoxy)-1H-purine-2,6(3H,7H)-dione | 2.889 | 493 |
| 160 | 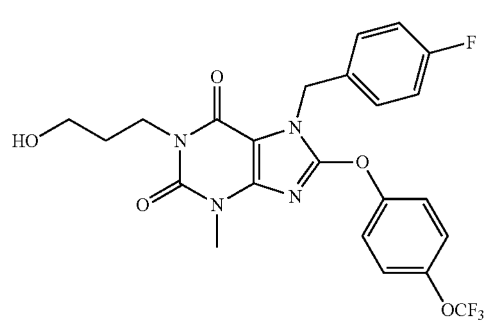 [SMILES: Cn1c(=O)n(CCCO)c(=O)c2c1nc(Oc1ccc(OC(F)(F)F)cc1)n2Cc1ccc(F)cc1] | 7-(4-fluorobenzyl)-1-(3-hydroxypropyl)-3-methyl-8-(4-(trifluoromethoxy)phenoxy)-1H-purine-2,6(3H,7H)-dione | 2.957 | 509 |

TABLE 1-continued

| Example | Structure | Chemical Name | LCMS retention time, min | LCMS M + 1 |
|---|---|---|---|---|
| 161 | 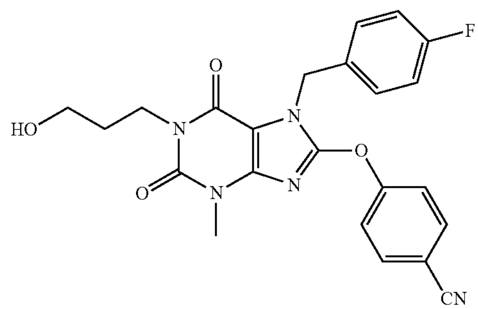 | 4-((7-(4-fluorobenzyl)-1-(3-hydroxypropyl)-3-methyl-2,6-dioxo-2,3,6,7-tetrahydro-1H-purin-8-yl)oxy)benzonitrile | 2.431 | 450 |
| 162 | 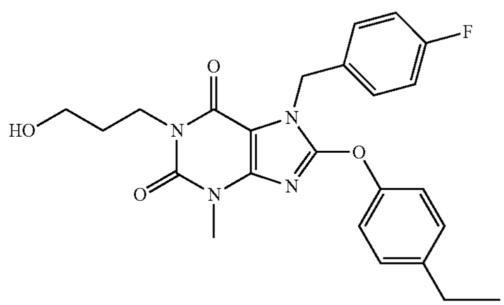 [SMILES: CCc1ccc(Oc2nc3c(c(=O)n(CCCO)c(=O)n3C)n2Cc2ccc(F)cc2)cc1] | 8-(4-ethylphenoxy)-7-(4-fluorobenzyl)-1-(3-hydroxypropyl)-3-methyl-1H-purine-2,6(3H,7H)-dione | 2.936 | 453 |
| 163 | 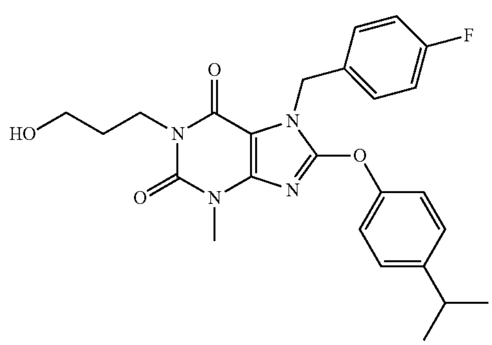 [SMILES: CC(C)c1ccc(Oc2nc3c(c(=O)n(CCCO)c(=O)n3C)n2Cc2ccc(F)cc2)cc1] | 7-(4-fluorobenzyl)-1-(3-hydroxypropyl)-8-(4-isopropylphenoxy)-3-methyl-1H-purine-2,6(3H,7H)-dione | 3.096 | 467 |
| 164 | 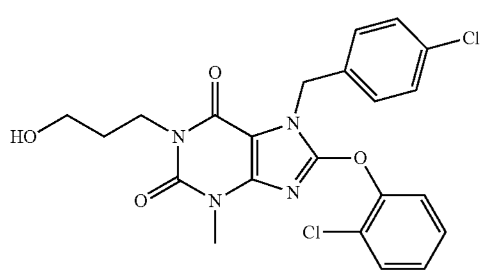 [SMILES: Cn1c(=O)n(CCCO)c(=O)c2c1nc(Oc1ccccc1Cl)n2Cc1ccc(Cl)cc1] | 7-(4-chlorobenzyl)-8-(2-chlorophenoxy)-1-(3-hydroxypropyl)-3-methyl-1H-purine-2,6(3H,7H)-dione | 3.692 | 475 |
| 165 | 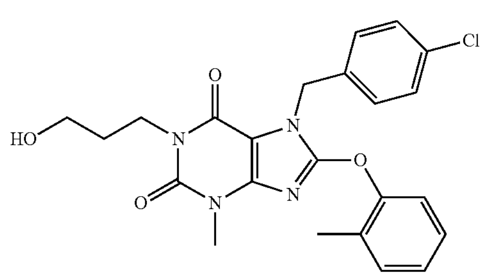 [SMILES: Cc1ccccc1Oc1nc2c(c(=O)n(CCCO)c(=O)n2C)n1Cc1ccc(Cl)cc1] | 7-(4-chlorobenzyl)-1-(3-hydroxypropyl)-3-methyl-8-(o-tolyloxy)-1H-purine-2,6(3H,7H)-dione | 2.871 | 455 |

TABLE 1-continued

| Example | Structure | Chemical Name | LCMS retention time, min | LCMS M + 1 |
|---|---|---|---|---|
| 166 | 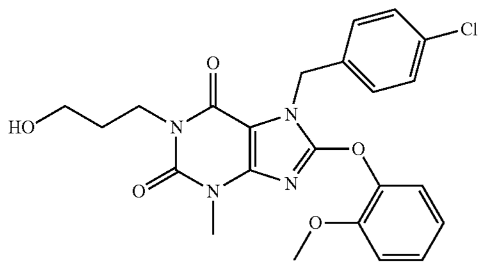 [SMILES: COc1ccccc1Oc1nc2c(c(=O)n(CCCO)c(=O)n2C)n1Cc1ccc(Cl)cc1] | 7-(4-chlorobenzyl)-1-(3-hydroxypropyl)-8-(2-methoxyphenoxy)-3-methyl-1H-purine-2,6(3H,7H)-dione | 3.535 | 471 |
| 167 | 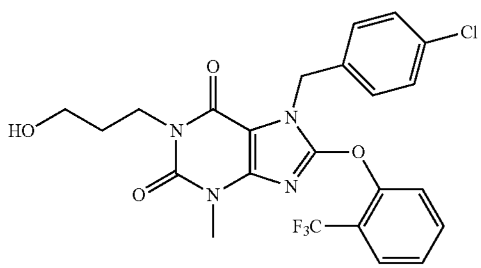 [SMILES: Cn1c(=O)n(CCCO)c(=O)c2c1nc(Oc1ccccc1C(F)(F)F)n2Cc1ccc(Cl)cc1] | 7-(4-chlorobenzyl)-1-(3-hydroxypropyl)-3-methyl-8-(2-(trifluoromethyl)phenoxy)-1H-purine-2,6(3H,7H)-dione | 3.695 | 509 |
| 168 | 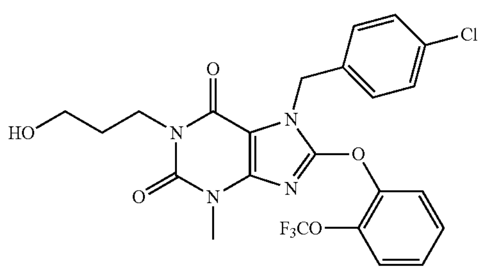 [SMILES: Cn1c(=O)n(CCCO)c(=O)c2c1nc(Oc1ccccc1OC(F)(F)F)n2Cc1ccc(Cl)cc1] | 7-(4-chlorobenzyl)-1-(3-hydroxypropyl)-3-methyl-8-(2-(trifluoromethoxy)phenoxy)-1H-purine-2,6(3H,7H)-dione | 3.003 | 525 |
| 169 | 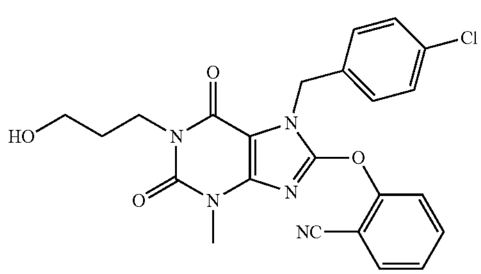 [SMILES: Cn1c(=O)n(CCCO)c(=O)c2c1nc(Oc1ccccc1C#N)n2Cc1ccc(Cl)cc1] | 2-((7-(4-chlorobenzyl)-1-(3-hydroxypropyl)-3-methyl-2,6-dioxo-2,3,6,7-tetrahydro-1H-purin-8-yl)oxy)benzonitrile | 2.601 | 466 |
| 170 | 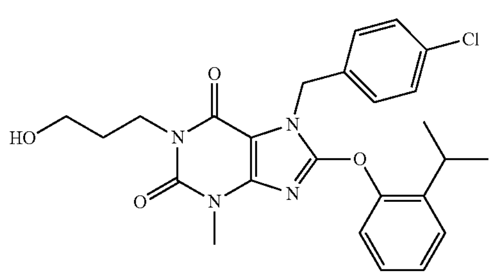 [SMILES: CC(C)c1ccccc1Oc1nc2c(c(=O)n(CCCO)c(=O)n2C)n1Cc1ccc(Cl)cc1] | 7-(4-chlorobenzyl)-1-(3-hydroxypropyl)-8-(2-isopropylphenoxy)-3-methyl-1H-purine-2,6(3H,7H)-dione | 3.100 | 483 |

TABLE 1-continued

| Example | Structure | Chemical Name | LCMS retention time, min | LCMS M + 1 |
|---|---|---|---|---|
| 171 | 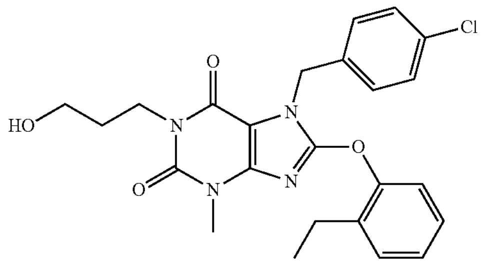 [SMILES: CCc1ccccc1Oc1nc2c(c(=O)n(CCCO)c(=O)n2C)n1Cc1ccc(Cl)cc1] | 7-(4-chlorobenzyl)-8-(2-ethylphenoxy)-1-(3-hydroxypropyl)-3-methyl-1H-purine-2,6(3H,7H)-dione | 3.035 | 469 |
| 172 | 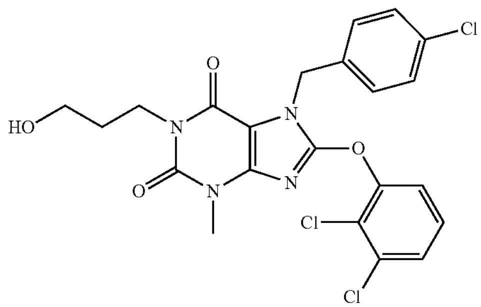 [SMILES: Cn1c(=O)n(CCCO)c(=O)c2c1nc(Oc1cccc(Cl)c1Cl)n2Cc1ccc(Cl)cc1] | 7-(4-chlorobenzyl)-8-(2,3-dichlorophenoxy)-1-(3-hydroxypropyl)-3-methyl-1H-purine-2,6(3H,7H)-dione | 3.086 | 510 |
| 173 | 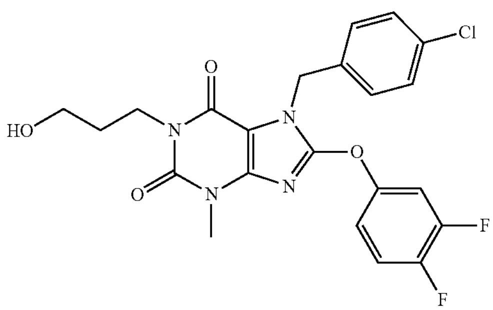 [SMILES: Cn1c(=O)n(CCCO)c(=O)c2c1nc(Oc1ccc(F)c(F)c1)n2Cc1ccc(Cl)cc1] | 7-(4-chlorobenzyl)-8-(3,4-difluorophenoxy)-1-(3-hydroxypropyl)-3-methyl-1H-purine-2,6(3H,7H)-dione | 3.636 | 477 |
| 174 | 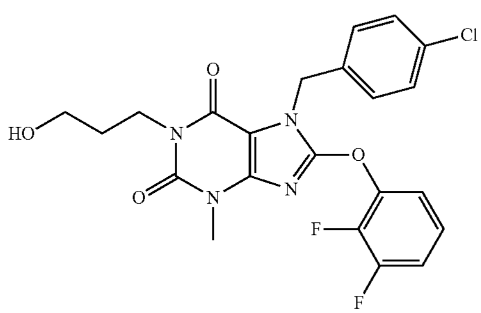 [SMILES: Cn1c(=O)n(CCCO)c(=O)c2c1nc(Oc1cccc(F)c1F)n2Cc1ccc(Cl)cc1] | 7-(4-chlorobenzyl)-8-(2,3-difluorophenoxy)-1-(3-hydroxypropyl)-3-methyl-1H-purine-2,6(3H,7H)-dione | 3.640 | 477 |
| 175 | 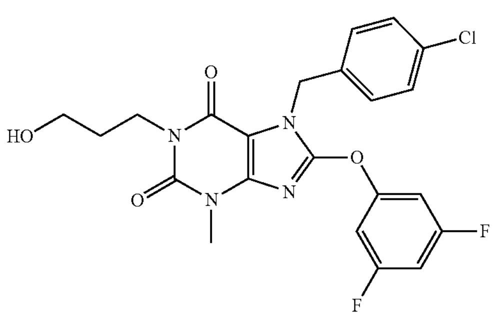 [SMILES: Cn1c(=O)n(CCCO)c(=O)c2c1nc(Oc1cc(F)cc(F)c1)n2Cc1ccc(Cl)cc1] | 7-(4-chlorobenzyl)-8-(3,5-difluorophenoxy)-1-(3-hydroxypropyl)-3-methyl-1H-purine-2,6(3H,7H)-dione | 3.673 | 477 |

TABLE 1-continued

| Example | Structure | Chemical Name | LCMS retention time, min | LCMS M + 1 |
|---|---|---|---|---|
| 176 | 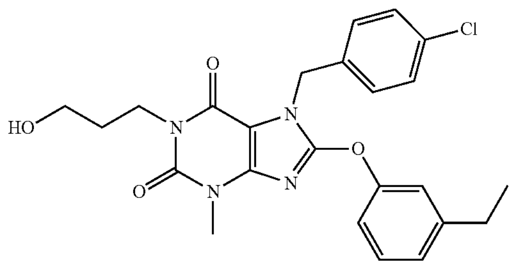 [SMILES: CCc1cccc(Oc2nc3c(c(=O)n(CCCO)c(=O)n3C)n2Cc2ccc(Cl)cc2)c1] | 7-(4-chlorobenzyl)-8-(3-ethylphenoxy)-1-(3-hydroxypropyl)-3-methyl-1H-purine-2,6(3H,7H)-dione | 3.822 | 469 |
| 177 | 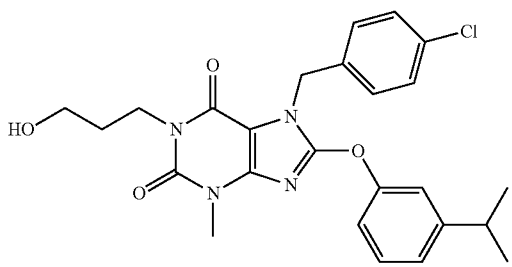 [SMILES: CC(C)c1cccc(Oc2nc3c(c(=O)n(CCCO)c(=O)n3C)n2Cc2ccc(Cl)cc2)c1] | 7-(4-chlorobenzyl)-1-(3-hydroxypropyl)-8-(3-isopropylphenoxy)-3-methyl-1H-purine-2,6(3H,7H)-dione | 3.218 | 483 |
| 178 | 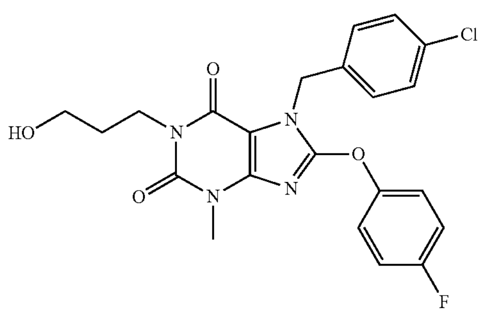 [SMILES: Cn1c(=O)n(CCCO)c(=O)c2c1nc(Oc1ccc(F)cc1)n2Cc1ccc(Cl)cc1] | 7-(4-chlorobenzyl)-8-(4-fluorophenoxy)-1-(3-hydroxypropyl)-3-methyl-1H-purine-2,6(3H,7H)-dione | 3.569 | 459 |
| 179 | 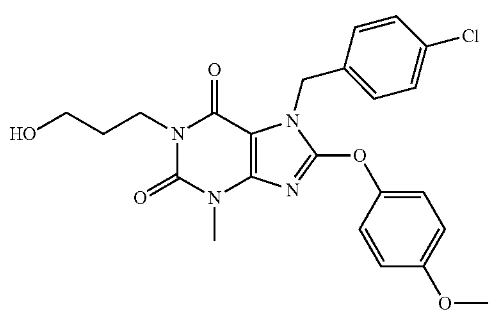 [SMILES: COc1ccc(Oc2nc3c(c(=O)n(CCCO)c(=O)n3C)n2Cc2ccc(Cl)cc2)cc1] | 7-(4-chlorobenzyl)-1-(3-hydroxypropyl)-8-(4-methoxyphenoxy)-3-methyl-1H-purine-2,6(3H,7H)-dione | 3.587 | 471 |
| 180 | 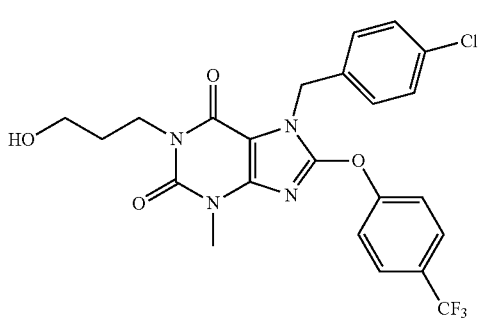 [SMILES: Cn1c(=O)n(CCCO)c(=O)c2c1nc(Oc1ccc(C(F)(F)F)cc1)n2Cc1ccc(Cl)cc1] | 7-(4-chlorobenzyl)-1-(3-hydroxypropyl)-3-methyl-8-(4-(trifluoromethyl)phenoxy)-1H-purine-2,6(3H,7H)-dione | 3.044 | 509 |

TABLE 1-continued

| Example | Structure | Chemical Name | LCMS retention time, min | LCMS M + 1 |
|---|---|---|---|---|
| 181 | 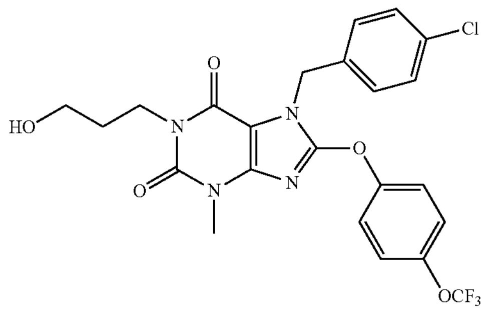 [SMILES: Cn1c(=O)n(CCCO)c(=O)c2c1nc(Oc1ccc(OC(F)(F)F)cc1)n2Cc1ccc(Cl)cc1] | 7-(4-chlorobenzyl)-1-(3-hydroxypropyl)-3-methyl-8-(4-(trifluoromethoxy)phenoxy)-1H-purine-2,6(3H,7H)-dione | 3.099 | 525 |
| 182 | 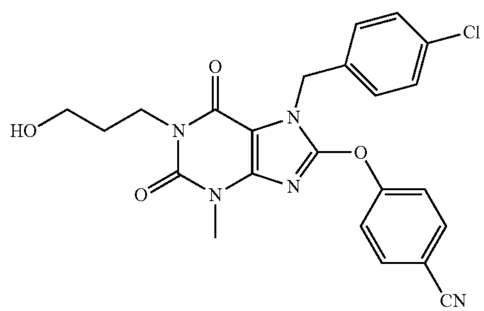 [SMILES: Cn1c(=O)n(CCCO)c(=O)c2c1nc(Oc1ccc(C#N)cc1)n2Cc1ccc(Cl)cc1] | 4-((7-(4-chlorobenzyl)-1-(3-hydroxypropyl)-3-methyl-2,6-dioxo-2,3,6,7-tetrahydro-1H-purin-8-yl)oxy)benzonitrile | 3.327 | 466 |
| 183 | 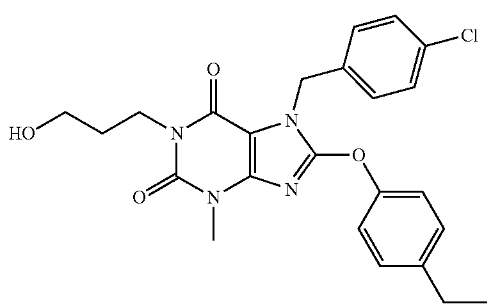 [SMILES: CCc1ccc(Oc2nc3c(c(=O)n(CCCO)c(=O)n3C)n2Cc2ccc(Cl)cc2)cc1] | 7-(4-chlorobenzyl)-8-(4-ethylphenoxy)-1-(3-hydroxypropyl)-3-methyl-1H-purine-2,6(3H,7H)-dione | 3.098 | 469 |
| 184 | 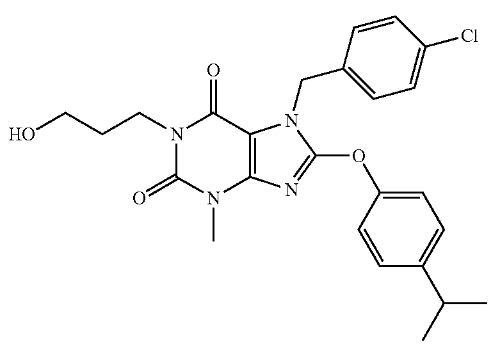 [SMILES: CC(C)c1ccc(Oc2nc3c(c(=O)n(CCCO)c(=O)n3C)n2Cc2ccc(Cl)cc2)cc1] | 7-(4-chlorobenzyl)-1-(3-hydroxypropyl)-8-(4-isopropylphenoxy)-3-methyl-1H-purine-2,6(3H,7H)-dione | 3.239 | 483 |
| 185 | 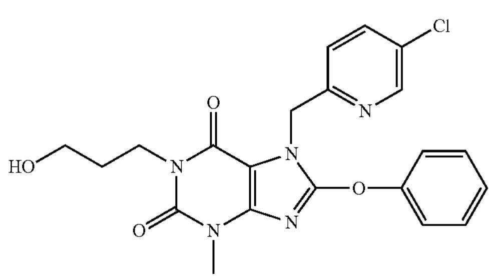 [SMILES: Cn1c(=O)n(CCCO)c(=O)c2c1nc(Oc1ccccc1)n2Cc1ccc(Cl)cn1] | 7-((5-chloropyridin-2-yl)methyl)-1-(3-hydroxypropyl)-3-methyl-8-phenoxy-1H-purine-2,6(3H,7H)-dione | 2.418 | 442 |

TABLE 1-continued

| Example | Chemical Name | LCMS retention time, min | LCMS M + 1 |
|---|---|---|---|
| 186 | 8-(2-chlorophenoxy)-7-((5-chloropyridin-2-yl)methyl)-1-(3-hydroxypropyl)-3-methyl-1H-purine-2,6(3H,7H)-dione | 2.548 | 476 |
| 187 | 7-((5-chloropyridin-2-yl)methyl)-8-(2-fluorophenoxy)-1-(3-hydroxypropyl)-3-methyl-1H-purine-2,6(3H,7H)-dione | 2.409 | 460 |
| 188 | 7-((5-chloropyridin-2-yl)methyl)-1-(3-hydroxypropyl)-3-methyl-8-(o-tolyloxy)-1H-purine-2,6(3H,7H)-dione | 2.566 | 456 |
| 189 | 7-((5-chloropyridin-2-yl)methyl)-1-(3-hydroxypropyl)-8-(2-methoxyphenoxy)-3-methyl-1H-purine-2,6(3H,7H)-dione | 2.346 | 472 |
| 190 | 7-((5-chloropyridin-2-yl)methyl)-1-(3-hydroxypropyl)-3-methyl-8-(2-(trifluoromethyl)phenoxy)-1H-purine-2,6(3H,7H)-dione | 1.586 | 510 |

TABLE 1-continued

| Example | Structure | Chemical Name | LCMS retention time, min | LCMS M + 1 |
|---|---|---|---|---|
| 191 | 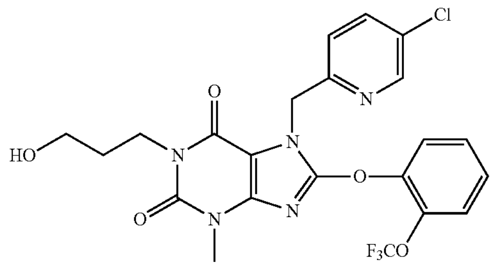 [SMILES: Cn1c(=O)n(CCCO)c(=O)c2c1nc(Oc1ccccc1OC(F)(F)F)n2Cc1ccc(Cl)cn1] | 7-((5-chloropyridin-2-yl)methyl)-1-(3-hydroxypropyl)-3-methyl-8-(2-(trifluoromethoxy)phenoxy)-1H-purine-2,6(3H,7H)-dione | 1.611 | 526 |
| 192 | 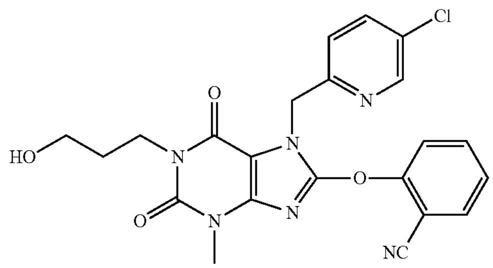 [SMILES: Cn1c(=O)n(CCCO)c(=O)c2c1nc(Oc1ccccc1C#N)n2Cc1ccc(Cl)cn1] | 2-((7-((5-chloropyridin-2-yl)methyl)-1-(3-hydroxypropyl)-3-methyl-2,6-dioxo-2,3,6,7-tetrahydro-1H-purin-8-yl)oxy)benzonitrile | 2.273 | 467 |
| 193 | 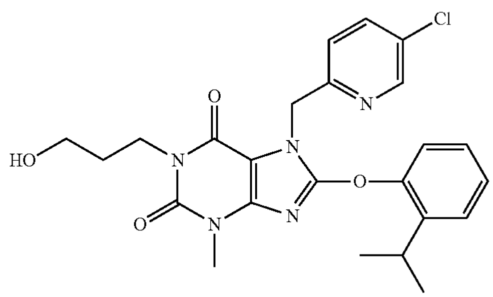 [SMILES: CC(C)c1ccccc1Oc1nc2c(c(=O)n(CCCO)c(=O)n2C)n1Cc1ccc(Cl)cn1] | 7-((5-chloropyridin-2-yl)methyl)-1-(3-hydroxypropyl)-8-(2-isopropylphenoxy)-3-methyl-1H-purine-2,6(3H,7H)-dione | 2.810 | 484 |
| 194 | 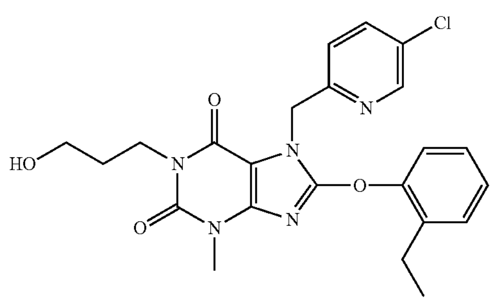 [SMILES: CCc1ccccc1Oc1nc2c(c(=O)n(CCCO)c(=O)n2C)n1Cc1ccc(Cl)cn1] | 7-((5-chloropyridin-2-yl)methyl)-8-(2-ethylphenoxy)-1-(3-hydroxypropyl)-3-methyl-1H-purine-2,6(3H,7H)-dione | 2.682 | 470 |
| 195 | 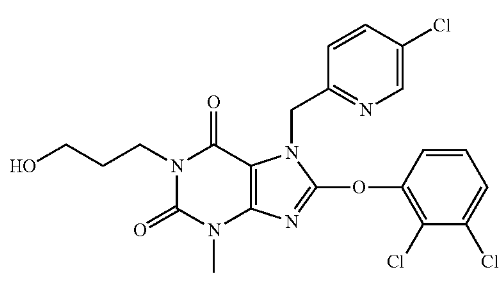 [SMILES: Cn1c(=O)n(CCCO)c(=O)c2c1nc(Oc1cccc(Cl)c1Cl)n2Cc1ccc(Cl)cn1] | 7-((5-chloropyridin-2-yl)methyl)-8-(2,3-dichlorophenoxy)-1-(3-hydroxypropyl)-3-methyl-1H-purine-2,6(3H,7H)-dione | 2.760 | 510 |

TABLE 1-continued

| Example | Structure | Chemical Name | LCMS retention time, min | LCMS M + 1 |
|---|---|---|---|---|
| 196 | 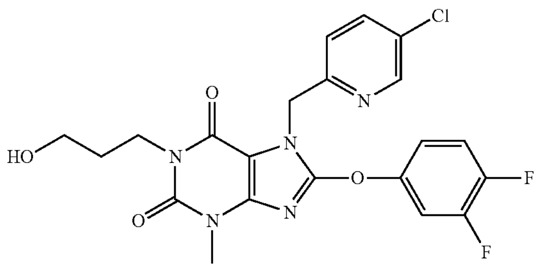 [SMILES: Cn1c(=O)n(CCCO)c(=O)c2c1nc(Oc1ccc(F)c(F)c1)n2Cc1ccc(Cl)cn1] | 7-((5-chloropyridin-2-yl)methyl)-8-(3,4-difluorophenoxy)-1-(3-hydroxypropyl)-3-methyl-1H-purine-2,6(3H,7H)-dione | 1.535 | 478 |
| 197 | 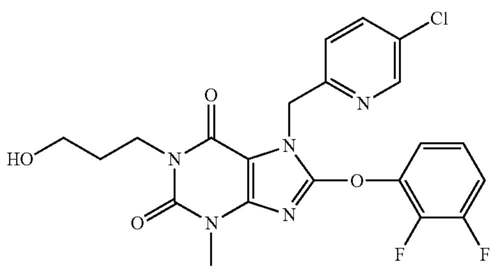 [SMILES: Cn1c(=O)n(CCCO)c(=O)c2c1nc(Oc1cccc(F)c1F)n2Cc1ccc(Cl)cn1] | 7-((5-chloropyridin-2-yl)methyl)-8-(2,3-difluorophenoxy)-1-(3-hydroxypropyl)-3-methyl-1H-purine-2,6(3H,7H)-dione | 1.507 | 478 |
| 198 | 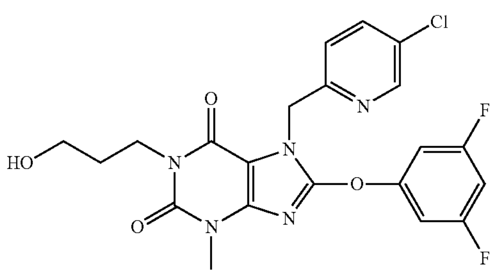 [SMILES: Cn1c(=O)n(CCCO)c(=O)c2c1nc(Oc1cc(F)cc(F)c1)n2Cc1ccc(Cl)cn1] | 7-((5-chloropyridin-2-yl)methyl)-8-(3,5-difluorophenoxy)-1-(3-hydroxypropyl)-3-methyl-1H-purine-2,6(3H,7H)-dione | 1.560 | 478 |
| 199 | 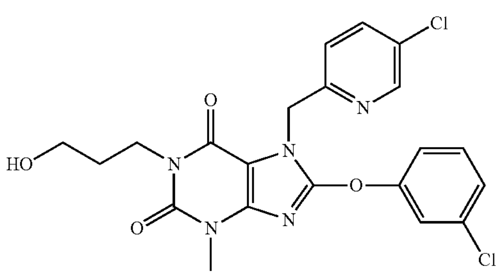 [SMILES: Cn1c(=O)n(CCCO)c(=O)c2c1nc(Oc1cccc(Cl)c1)n2Cc1ccc(Cl)cn1] | 8-(3-chlorophenoxy)-7-((5-chloropyridin-2-yl)methyl)-1-(3-hydroxypropyl)-3-methyl-1H-purine-2,6(3H,7H)-dione | 2.648 | 476 |
| 200 | 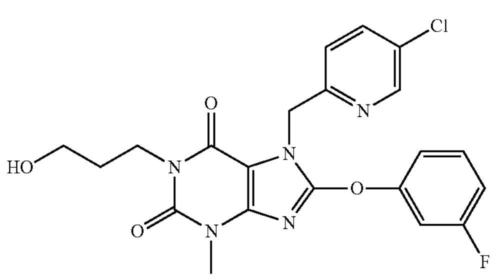 [SMILES: Cn1c(=O)n(CCCO)c(=O)c2c1nc(Oc1cccc(F)c1)n2Cc1ccc(Cl)cn1] | 7-((5-chloropyridin-2-yl)methyl)-8-(3-fluorophenoxy)-1-(3-hydroxypropyl)-3-methyl-1H-purine-2,6(3H,7H)-dione | 2.476 | 460 |

TABLE 1-continued

| Example | Structure | Chemical Name | LCMS retention time, min | LCMS M + 1 |
|---|---|---|---|---|
| 201 | 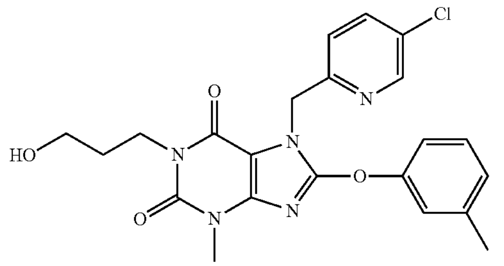 | 7-((5-chloropyridin-2-yl)methyl)-1-(3-hydroxypropyl)-3-methyl-8-(m-tolyloxy)-1H-purine-2,6(3H,7H)-dione | 2.584 | 456 |
| 202 | 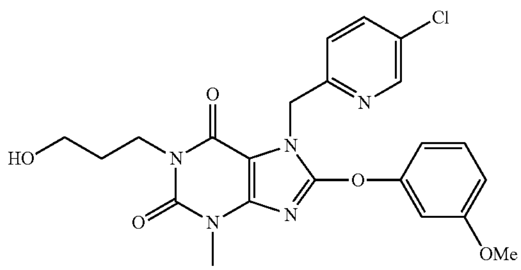 [SMILES: COc1cccc(Oc2nc3c(c(=O)n(CCCO)c(=O)n3C)n2Cc2ccc(Cl)cn2)c1] | 7-((5-chloropyridin-2-yl)methyl)-1-(3-hydroxypropyl)-8-(3-methoxyphenoxy)-3-methyl-1H-purine-2,6(3H,7H)-dione | 2.432 | 472 |
| 203 | 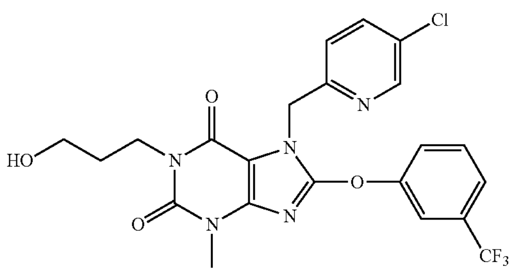 [SMILES: Cn1c(=O)n(CCCO)c(=O)c2c1nc(Oc1cccc(C(F)(F)F)c1)n2Cc1ccc(Cl)cn1] | 7-((5-chloropyridin-2-yl)methyl)-1-(3-hydroxypropylmethyl)phenoxy)-1H-purine-2,6(3H,7H)-dione | 2.735 | 510 |
| 204 | 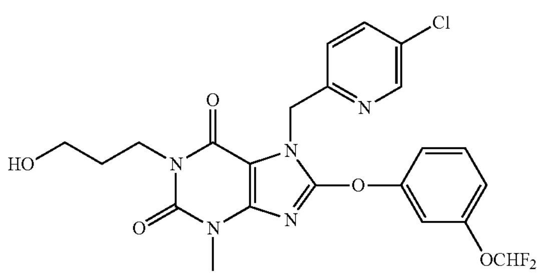 [SMILES: Cn1c(=O)n(CCCO)c(=O)c2c1nc(Oc1cccc(OC(F)F)c1)n2Cc1ccc(Cl)cn1] | 7-((5-chloropyridin-2-yl)methyl)-8-(3-(difluoromethoxy)phenoxy)-1-(3-hydroxypropyl)-3-methyl-1H-purine-2,6(3H,7H)-dione | 1.528 | 508 |
| 205 | 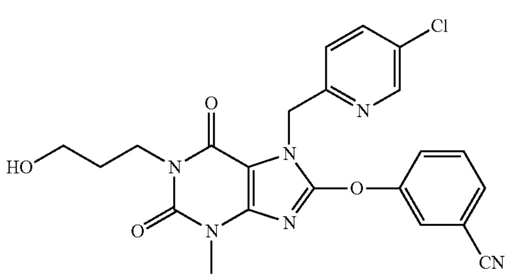 [SMILES: Cn1c(=O)n(CCCO)c(=O)c2c1nc(Oc1cccc(C#N)c1)n2Cc1ccc(Cl)cn1] | 3-((7-((5-chloropyridin-2-yl)methyl)-1-(3-hydroxypropyl)-3-methyl-2,6-dioxo-2,3,6,7-tetrahydro-1H-purin-8-yl)oxy)benzonitrile | 2.296 | 467 |

TABLE 1-continued

| Example | Structure | Chemical Name | LCMS retention time, min | LCMS M + 1 |
|---|---|---|---|---|
| 206 | 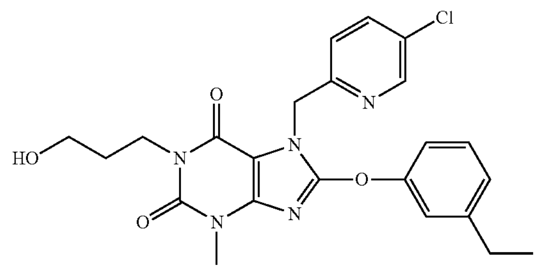 [SMILES: CCc1cccc(Oc2nc3c(c(=O)n(CCCO)c(=O)n3C)n2Cc2ccc(Cl)cn2)c1] | 7-((5-chloropyridin-2-yl)methyl)-8-(3-ethylphenoxy)-1-(3-hydroxypropyl)-3-methyl-1H-purine-2,6(3H,7H)-dione | 2.748 | 470 |
| 207 | 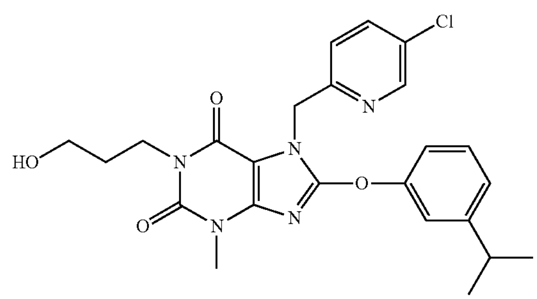 [SMILES: CC(C)c1cccc(Oc2nc3c(c(=O)n(CCCO)c(=O)n3C)n2Cc2ccc(Cl)cn2)c1] | 7-((5-chloropyridin-2-yl)methyl)-1-(3-hydroxypropyl)-8-(3-isopropylphenoxy)-3-methyl-1H-purine-2,6(3H,7H)-dione | 1.753 | 484 |
| 208 | 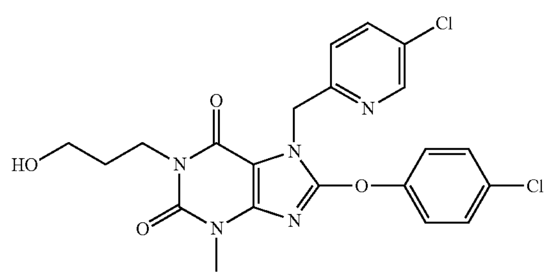 | 8-(4-chlorophenoxy)-7-((5-chloropyridin-2-yl)methyl)-1-(3-hydroxypropyl)-3-methyl-1H-purine-2,6(3H,7H)-dione | 2.676 | 476 |
| 209 | 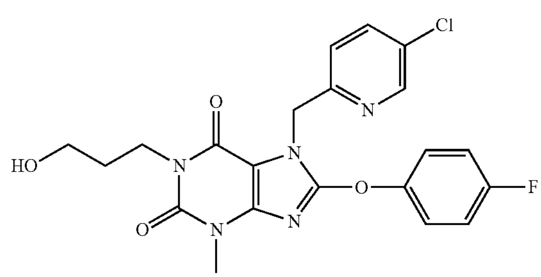 [SMILES: Cn1c(=O)n(CCCO)c(=O)c2c1nc(Oc1ccc(F)cc1)n2Cc1ccc(Cl)cn1] | 7-((5-chloropyridin-2-yl)methyl)-8-(4-fluorophenoxy)-1-(3-hydroxypropyl)-3-methyl-1H-purine-2,6(3H,7H)-dione | 2.477 | 460 |
| 210 | 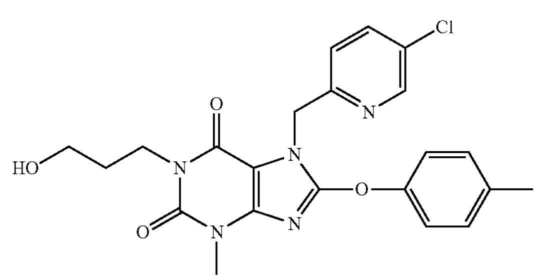 [SMILES: Cc1ccc(Oc2nc3c(c(=O)n(CCCO)c(=O)n3C)n2Cc2ccc(Cl)cn2)cc1] | 7-((5-chloropyridin-2-yl)methyl)-1-(3-hydroxypropyl)-3-methyl-8-(p-tolyloxy)-1H-purine-2,6(3H,7H)-dione | 2.598 | 456 |

TABLE 1-continued

| Example | Structure | Chemical Name | LCMS retention time, min | LCMS M + 1 |
|---|---|---|---|---|
| 211 | 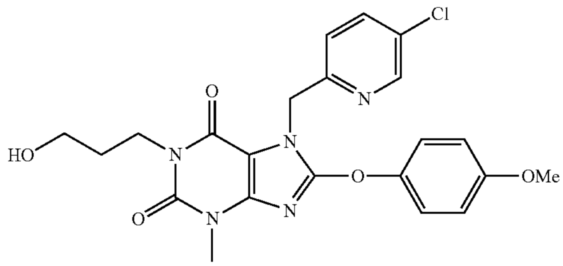 [SMILES: COc1ccc(Oc2nc3c(c(=O)n(CCCO)c(=O)n3C)n2Cc2ccc(Cl)cn2)cc1] | 7-((5-chloropyridin-2-yl)methyl)-1-(3-hydroxypropyl)-8-(4-methoxyphenoxy)-3-methyl-1H-purine-2,6(3H,7H)-dione | 2.433 | 472 |
| 212 | 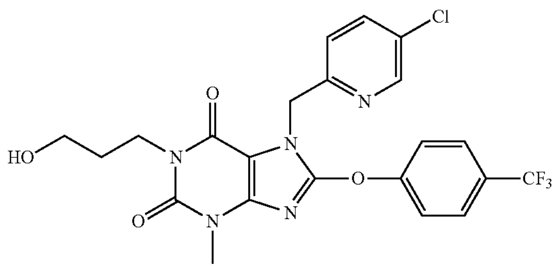 [SMILES: Cn1c(=O)n(CCCO)c(=O)c2c1nc(Oc1ccc(C(F)(F)F)cc1)n2Cc1ccc(Cl)cn1] | 7-((5-chloropyridin-2-yl)methyl)-1-(3-hydroxypropyl)-3-methyl-8-(4-(trifluoromethyl)phenoxy)-1H-purine-2,6(3H,7H)-dione | 2.746 | 510 |
| 213 | 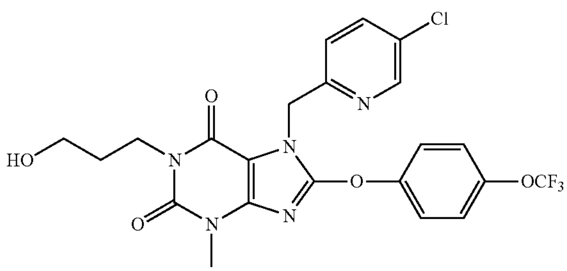 [SMILES: Cn1c(=O)n(CCCO)c(=O)c2c1nc(Oc1ccc(OC(F)(F)F)cc1)n2Cc1ccc(Cl)cn1] | 7-((5-chloropyridin-2-yl)methyl)-1-(3-hydroxypropyl)-3-methyl-8-(4-(trifluoromethoxy)phenoxy)-1H-purine-2,6(3H,7H)-dione | 2.802 | 526 |
| 214 | 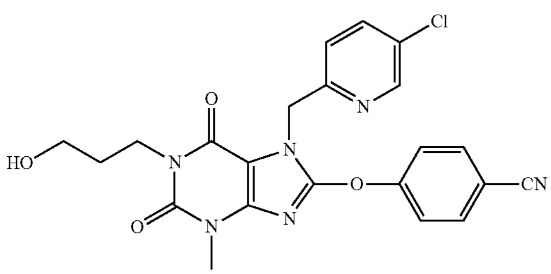 [SMILES: Cn1c(=O)n(CCCO)c(=O)c2c1nc(Oc1ccc(C#N)cc1)n2Cc1ccc(Cl)cn1] | 4-((7-((5-chloropyridin-2-yl)methyl)-1-(3-hydroxypropyl)-3-methyl-2,6-dioxo-2,3,6,7-tetrahydro-1H-purin-8-yl)oxy)benzonitrile | 2.270 | 467 |
| 215 | 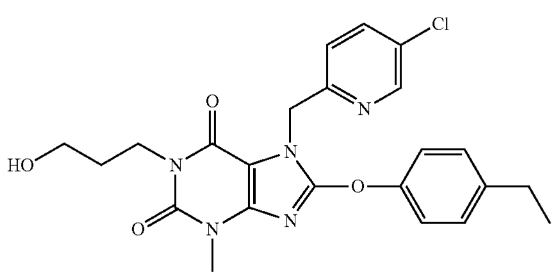 [SMILES: CCc1ccc(Oc2nc3c(c(=O)n(CCCO)c(=O)n3C)n2Cc2ccc(Cl)cn2)cc1] | 7-((5-chloropyridin-2-yl)methyl)-8-(4-ethylphenoxy)-1-(3-hydroxypropyl)-3-methyl-1H-purine-2,6(3H,7H)-dione | 1.667 | 470 |

TABLE 1-continued

| Example | Structure | Chemical Name | LCMS retention time, min | LCMS M + 1 |
|---|---|---|---|---|
| 216 | 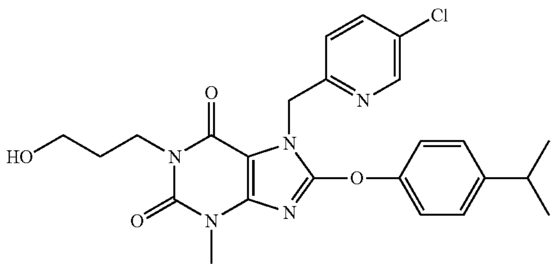 | 7-((5-chloropyridin-2-yl)methyl)-1-(3-hydroxypropyl)-8-(4-isopropylphenoxy)-3-methyl-1H-purine-2,6(3H,7H)-dione | 2.944 | 484 |
| 217 | 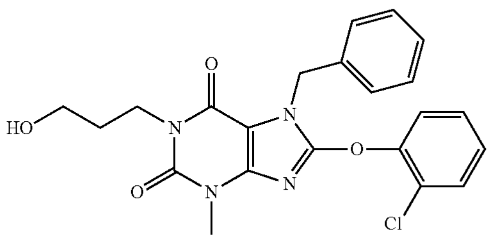 [SMILES: Cn1c(=O)n(CCCO)c(=O)c2c1nc(Oc1ccccc1Cl)n2Cc1ccccc1] | 7-benzyl-8-(2-chlorophenoxy)-1-(3-hydroxypropyl)-3-methyl-1H-purine-2,6(3H,7H)-dione | 2.672 | 441 |
| 218 | 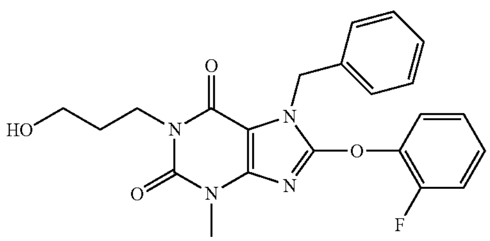 [SMILES: Cn1c(=O)n(CCCO)c(=O)c2c1nc(Oc1ccccc1F)n2Cc1ccccc1] | 7-benzyl-8-(2-fluorophenoxy)-1-(3-hydroxypropyl)-3-methyl-1H-purine-2,6(3H,7H)-dione | 3.381 | 425 |
| 219 | 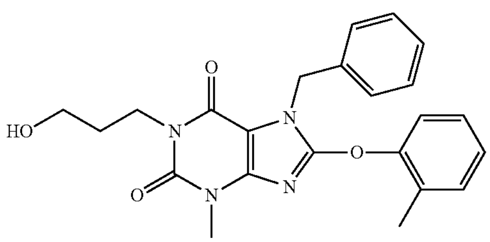 [SMILES: Cc1ccccc1Oc1nc2c(c(=O)n(CCCO)c(=O)n2C)n1Cc1ccccc1] | 7-benzyl-1-(3-hydroxypropyl)-3-methyl-8-(o-tolyloxy)-1H-purine-2,6(3H,7H)-dione | 2.664 | 421 |
| 220 | 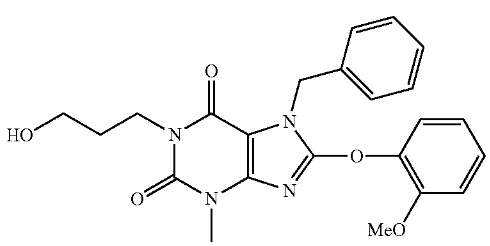 [SMILES: COc1ccccc1Oc1nc2c(c(=O)n(CCCO)c(=O)n2C)n1Cc1ccccc1] | 7-benzyl-1-(3-hydroxypropyl)-8-(2-methoxyphenoxy)-3-methyl-1H-purine-2,6(3H,7H)-dione | 3.349 | 437 |
| 221 | 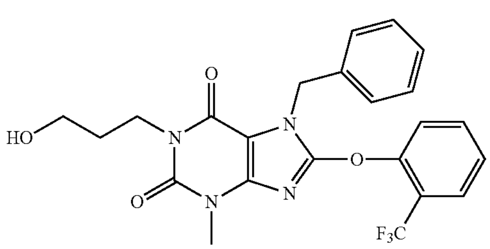 [SMILES: Cn1c(=O)n(CCCO)c(=O)c2c1nc(Oc1ccccc1C(F)(F)F)n2Cc1ccccc1] | 7-benzyl-1-(3-hydroxypropyl)-3-methyl-8-(2-(trifluoromethyl)phenoxy)-1H-purine-2,6(3H,7H)-dione | 3.519 | 475 |

TABLE 1-continued

| Example | Structure | Chemical Name | LCMS retention time, min | LCMS M + 1 |
|---|---|---|---|---|
| 222 | 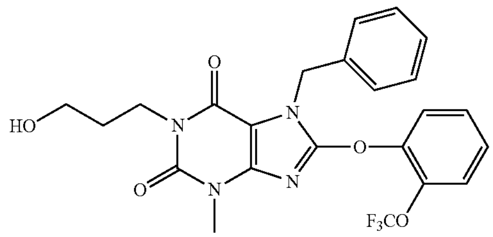 [SMILES: Cn1c(=O)n(CCCO)c(=O)c2c1nc(Oc1ccccc1OC(F)(F)F)n2Cc1ccccc1] | 7-benzyl-1-(3-hydroxypropyl)-3-methyl-8-(2-(trifluoromethoxy)phenoxy)-1H-purine-2,6(3H,7H)-dione | 2.801 | 491 |
| 223 | 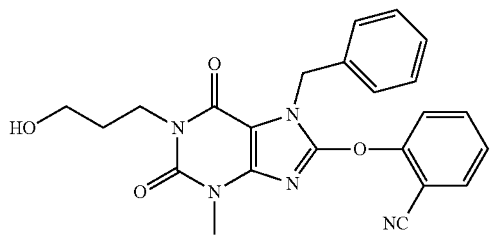 [SMILES: Cn1c(=O)n(CCCO)c(=O)c2c1nc(Oc1ccccc1C#N)n2Cc1ccccc1] | 2-((7-benzyl-1-(3-hydroxypropyl)-3-methyl-2,6-dioxo-2,3,6,7-tetrahydro-1H-purin-8-yl)oxy)benzonitrile | 3.122 | 432 |
| 224 | 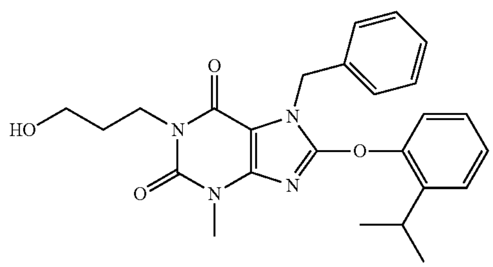 [SMILES: CC(C)c1ccccc1Oc1nc2c(c(=O)n(CCCO)c(=O)n2C)n1Cc1ccccc1] | 7-benzyl-1-(3-hydroxypropyl)-8-(2-isopropylphenoxy)-3-methyl-1H-purine-2,6(3H,7H)-dione | 3.685 | 449 |
| 225 | 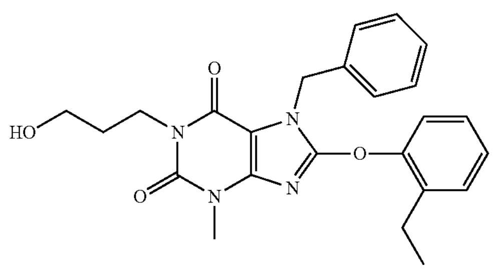 [SMILES: CCc1ccccc1Oc1nc2c(c(=O)n(CCCO)c(=O)n2C)n1Cc1ccccc1] | 7-benzyl-8-(2-ethylphenoxy)-1-(3-hydroxypropyl)-3-methyl-1H-purine-2,6(3H,7H)-dione | 2.807 | 435 |
| 226 | 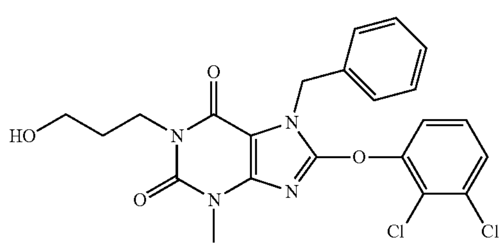 [SMILES: Cn1c(=O)n(CCCO)c(=O)c2c1nc(Oc1cccc(Cl)c1Cl)n2Cc1ccccc1] | 7-benzyl-8-(2,3-dichlorophenoxy)-1-(3-hydroxypropyl)-3-methyl-1H-purine-2,6(3H,7H)-dione | 2.884 | 475 |
| 227 | 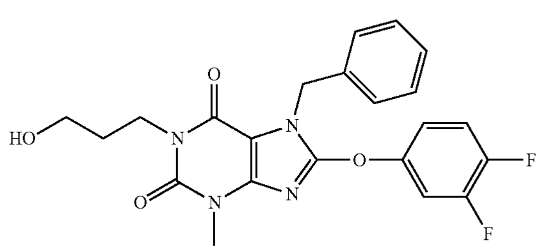 [SMILES: Cn1c(=O)n(CCCO)c(=O)c2c1nc(Oc1ccc(F)c(F)c1)n2Cc1ccccc1] | 7-benzyl-8-(3,4-difluorophenoxy)-1-(3-hydroxypropyl)-3-methyl-1H-purine-2,6(3H,7H)-dione | 3.451 | 443 |

TABLE 1-continued

| Example | Structure | Chemical Name | LCMS retention time, min | LCMS M + 1 |
|---|---|---|---|---|
| 228 | 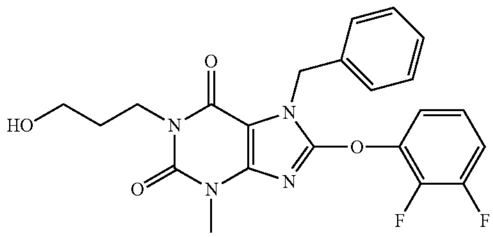 [SMILES: Cn1c(=O)n(CCCO)c(=O)c2c1nc(Oc1cccc(F)c1F)n2Cc1ccccc1] | 7-benzyl-8-(2,3-difluorophenoxy)-1-(3-hydroxypropyl)-3-methyl-1H-purine-2,6(3H,7H)-dione | 3.449 | 443 |
| 229 | 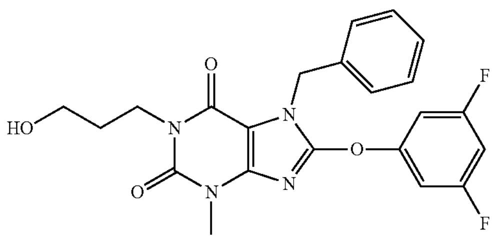 [SMILES: Cn1c(=O)n(CCCO)c(=O)c2c1nc(Oc1cc(F)cc(F)c1)n2Cc1ccccc1] | 7-benzyl-8-(3,5-difluorophenoxy)-1-(3-hydroxypropyl)-3-methyl-1H-purine-2,6(3H,7H)-dione | 3.505 | 443 |
| 230 | 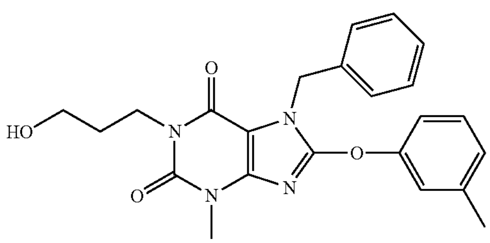 [SMILES: Cc1cccc(Oc2nc3c(c(=O)n(CCCO)c(=O)n3C)n2Cc2ccccc2)c1] | 7-benzyl-1-(3-hydroxypropyl)-3-methyl-8-(m-tolyloxy)-1H-purine-2,6(3H,7H)-dione | 3.541 | 421 |
| 231 | 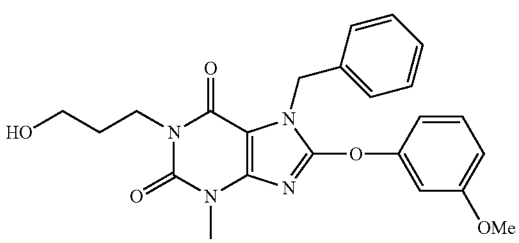 [SMILES: COc1cccc(Oc2nc3c(c(=O)n(CCCO)c(=O)n3C)n2Cc2ccccc2)c1] | 7-benzyl-1-(3-hydroxypropyl)-8-(3 methoxyphenoxy)-3-methyl-1H-purine-2,6(3H,7H)-dione | 3.399 | 437 |
| 232 | 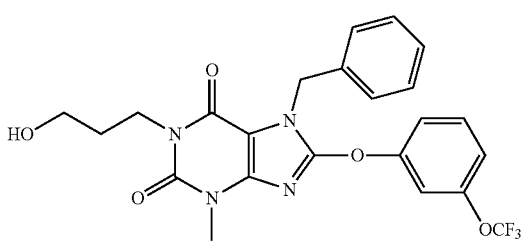 [SMILES: Cn1c(=O)n(CCCO)c(=O)c2c1nc(Oc1cccc(OC(F)(F)F)c1)n2Cc1ccccc1] | 7-benzyl-1-(3-hydroxypropyl)-3-methyl-8-(3-(trifluoromethoxy)phenoxy)-1H-purine-2,6(3H,7H)-dione | 2.603 | 491 |
| 233 | 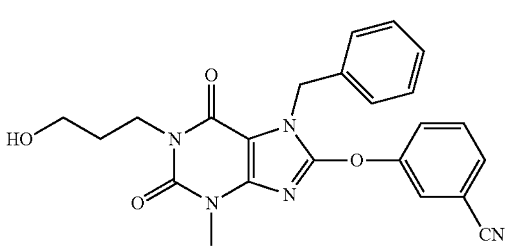 [SMILES: Cn1c(=O)n(CCCO)c(=O)c2c1nc(Oc1cccc(C#N)c1)n2Cc1ccccc1] | 3-((7-benzyl-1-(3-hydroxypropyl)-3-methyl-2,6-dioxo-2,3,6,7-tetrahydro-1H-purin-8-yl)oxy)benzonitrile | 3.160 | 432 |

TABLE 1-continued

| Example | Structure | Chemical Name | LCMS retention time, min | LCMS M + 1 |
|---|---|---|---|---|
| 234 | 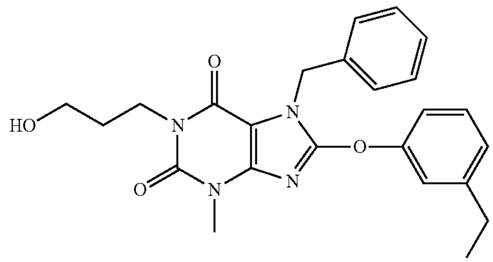 [SMILES: CCc1cccc(Oc2nc3c(c(=O)n(CCCO)c(=O)n3C)n2Cc2ccccc2)c1] | 7-benzyl-8-(3-ethylphenoxy)-1-(3-hydroxypropyl)-3-methyl-1H-purine-2,6(3H,7H)-dione | 3.669 | 435 |
| 235 | 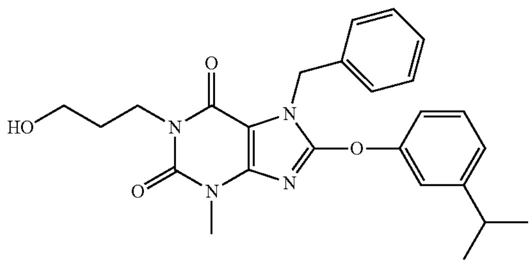 [SMILES: CC(C)c1cccc(Oc2nc3c(c(=O)n(CCCO)c(=O)n3C)n2Cc2ccccc2)c1] | 7-benzyl-1-(3-hydroxypropyl)-8-(3-isopropylphenoxy)-3-methyl-1H-purine-2,6(3H,7H)-dione | 3.015 | 449 |
| 236 | 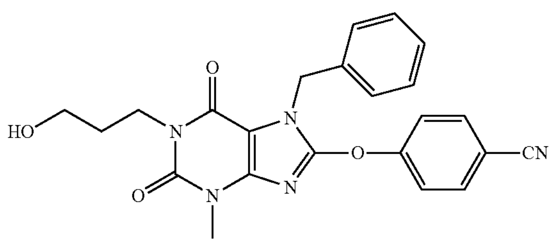 [SMILES: Cn1c(=O)n(CCCO)c(=O)c2c1nc(Oc1ccc(C#N)cc1)n2Cc1ccccc1] | 4-((7-benzyl-1-(3-hydroxypropyl)-3-methyl-2,6-dioxo-2,3,6,7-tetrahydro-1H-purin-8-yl)oxy)benzonitrile | 3.140 | 432 |
| 237 | 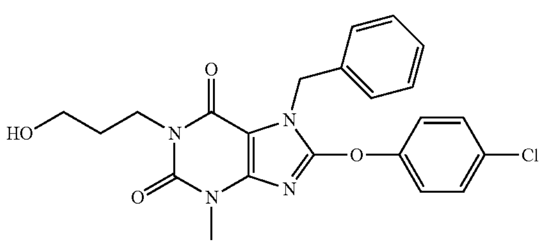 [SMILES: Cn1c(=O)n(CCCO)c(=O)c2c1nc(Oc1ccc(Cl)cc1)n2Cc1ccccc1] | 7-benzyl-8-(4-chlorophenoxy)-1-(3-hydroxypropyl)-3-methyl-1H-purine-2,6(3H,7H)-dione | 3.578 | 441 |
| 238 | 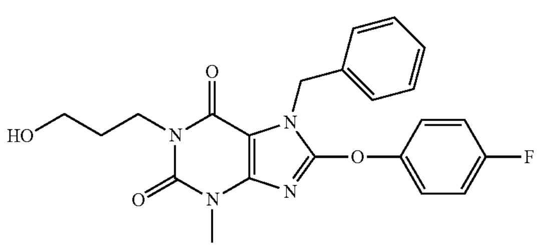 [SMILES: Cn1c(=O)n(CCCO)c(=O)c2c1nc(Oc1ccc(F)cc1)n2Cc1ccccc1] | 7-benzyl-8-(4-fluorophenoxy)-1-(3-hydroxypropyl)-3-methyl-1H-purine-2,6(3H,7H)-dione | 3.392 | 425 |
| 239 | 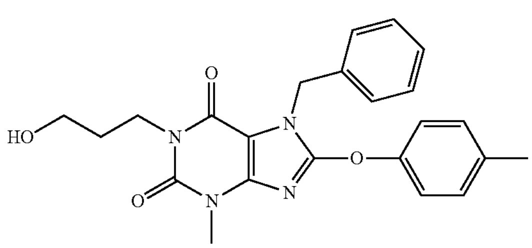 [SMILES: Cc1ccc(Oc2nc3c(c(=O)n(CCCO)c(=O)n3C)n2Cc2ccccc2)cc1] | 7-benzyl-1-(3-hydroxypropyl)-3-methyl-8-(p-tolyloxy)-1H-purine-2,6(3H,7H)-dione | 3.558 | 421 |

TABLE 1-continued

| Example | Structure | Chemical Name | LCMS retention time, min | LCMS M + 1 |
|---|---|---|---|---|
| 240 | 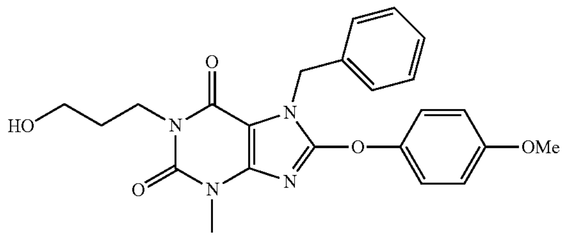 [SMILES: COc1ccc(Oc2nc3c(c(=O)n(CCCO)c(=O)n3C)n2Cc2ccccc2)cc1] | 7-benzyl-1-(3-hydroxypropyl)-8-(4-methoxyphenoxy)-3-methyl-1H-purine-2,6(3H,7H)-dione | 3.389 | 437 |
| 241 | 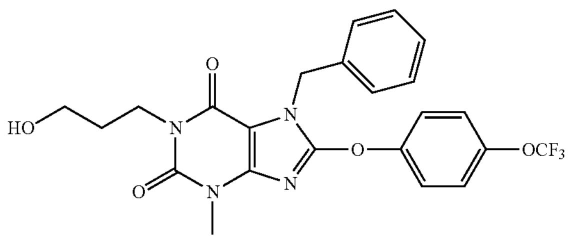 [SMILES: Cn1c(=O)n(CCCO)c(=O)c2c1nc(Oc1ccc(OC(F)(F)F)cc1)n2Cc1ccccc1] | 7-benzyl-1-(3-hydroxypropyl)-3-methyl-8-(4-(trifluoromethoxy)phenoxy)-1H-purine-2,6(3H,7H)-dione | 3.640 | 491 |
| 242 | 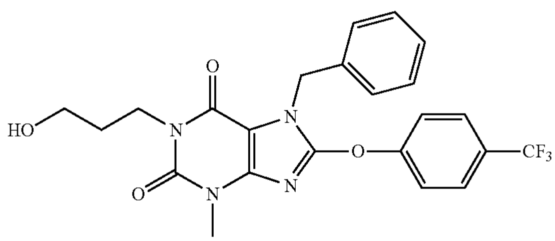 [SMILES: Cn1c(=O)n(CCCO)c(=O)c2c1nc(Oc1ccc(C(F)(F)F)cc1)n2Cc1ccccc1] | 7-benzyl-1-(3-hydroxypropyl)-3-methyl-8-(4-(trifluoromethyl)phenoxy)-1H-purine-2,6(3H,7H)-dione | 3.588 | 475 |
| 243 | 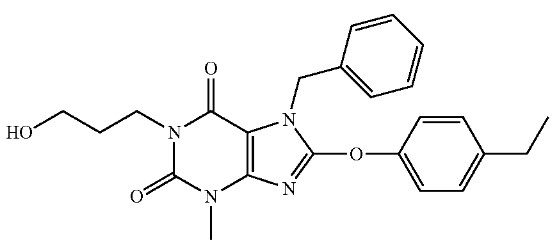 [SMILES: CCc1ccc(Oc2nc3c(c(=O)n(CCCO)c(=O)n3C)n2Cc2ccccc2)cc1] | 7-benzyl-8-(4-ethylphenoxy)-1-(3-hydroxypropyl)-3-methyl-1H-purine-2,6(3H,7H)-dione | 2.912 | 435 |
| 244 | 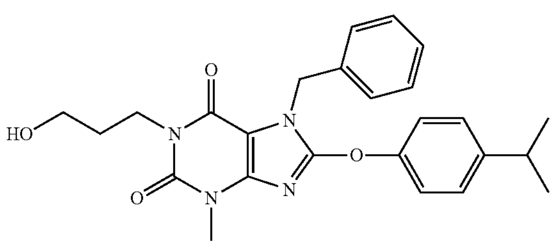 [SMILES: CC(C)c1ccc(Oc2nc3c(c(=O)n(CCCO)c(=O)n3C)n2Cc2ccccc2)cc1] | 7-benzyl-1-(3-hydroxypropyl)-8-(4-isopropylphenoxy)-3-methyl-1H-purine-2,6(3H,7H)-dione | 3.054 | 449 |
| 245 | 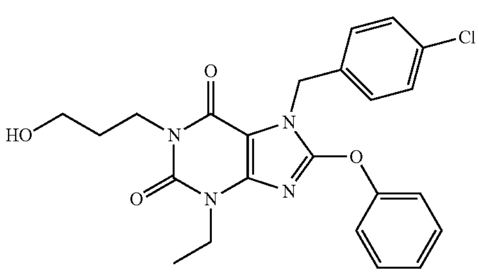 [SMILES: CCn1c(=O)n(CCCO)c(=O)c2c1nc(Oc1ccccc1)n2Cc1ccc(Cl)cc1] | 7-(4-chlorobenzyl)-3-ethyl-1-(3-hydroxypropyl)-8-phenoxy-1H-purine-2,6(3H,7H)-dione | 2.936 | 455 |

TABLE 1-continued

| Example | Structure | Chemical Name | LCMS retention time, min | LCMS M + 1 |
|---|---|---|---|---|
| 246 | 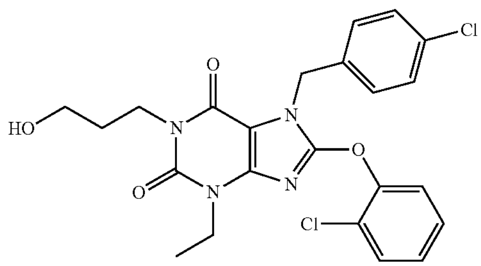 [SMILES: CCn1c(=O)n(CCCO)c(=O)c2c1nc(Oc1ccccc1Cl)n2Cc1ccc(Cl)cc1] | 7-(4-chlorobenzyl)-8-(2-chlorophenoxy)-3-ethyl-1-(3-hydroxypropyl)-1H-purine-2,6(3H,7H)-dione | 3.034 | 489 |
| 247 | 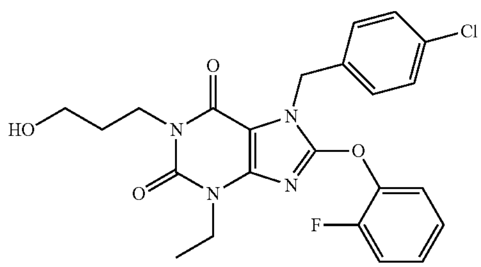 [SMILES: CCn1c(=O)n(CCCO)c(=O)c2c1nc(Oc1ccccc1F)n2Cc1ccc(Cl)cc1] | 7-(4-chlorobenzyl)-3-ethyl-8-(2-fluorophenoxy)-1-(3-hydroxypropyl)-1H-purine-2,6(3H,7H)-dione | 2.835 | 473 |
| 248 | 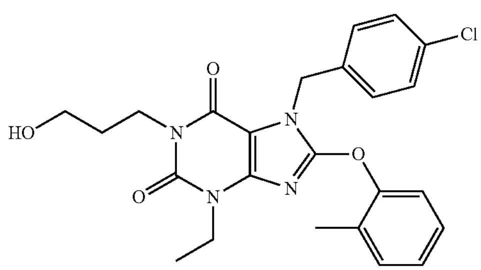 [SMILES: CCn1c(=O)n(CCCO)c(=O)c2c1nc(Oc1ccccc1C)n2Cc1ccc(Cl)cc1] | 7-(4-chlorobenzyl)-3-ethyl-1-(3-hydroxypropyl)-8-(o-tolyloxy)-1H-purine-2,6(3H,7H)-dione | 2.021 | 469 |
| 249 | 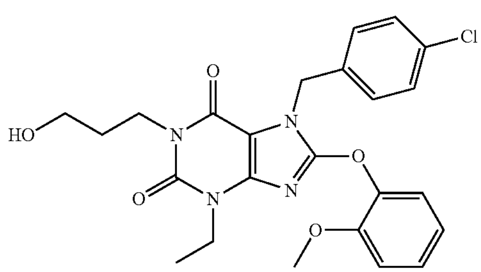 [SMILES: CCn1c(=O)n(CCCO)c(=O)c2c1nc(Oc1ccccc1OC)n2Cc1ccc(Cl)cc1] | 7-(4-chlorobenzyl)-3-ethyl-1-(3-hydroxypropyl)-8-(2-methoxyphenoxy)-1H-purine-2,6(3H,7H)-dione | 2.884 | 485 |
| 250 | 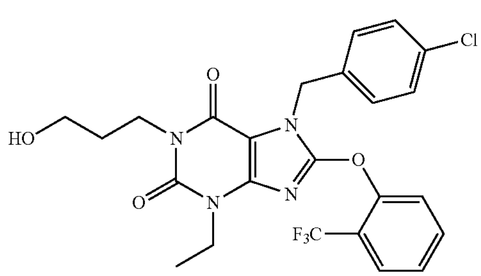 [SMILES: CCn1c(=O)n(CCCO)c(=O)c2c1nc(Oc1ccccc1C(F)(F)F)n2Cc1ccc(Cl)cc1] | 7-(4-chlorobenzyl)-3-ethyl-1-(3-hydroxypropyl)-8-(2-(trifluoromethyl)phenoxy)-1H-purine-2,6(3H,7H)-dione | 3.063 | 523 |

TABLE 1-continued

| Example | Structure | Chemical Name | LCMS retention time, min | LCMS M + 1 |
| --- | --- | --- | --- | --- |
| 251 | 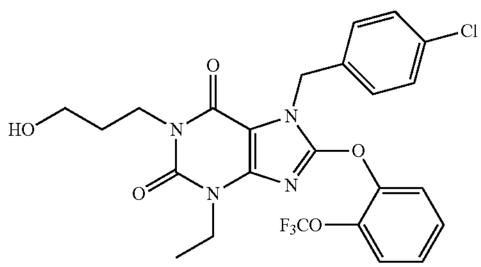 [SMILES: CCn1c(=O)n(CCCO)c(=O)c2c1nc(Oc1ccccc1OC(F)(F)F)n2Cc1ccc(Cl)cc1] | 7-(4-chlorobenzyl)-3-ethyl-1-(3-hydroxypropyl)-8-(2-(trifluoromethoxy)phenoxy)-1H-purine-2,6(3H,7H)-dione | 3.120 | 539 |
| 252 | 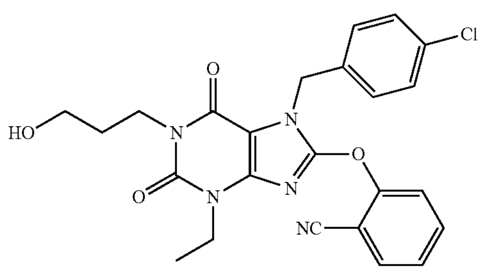 [SMILES: CCn1c(=O)n(CCCO)c(=O)c2c1nc(Oc1ccccc1C#N)n2Cc1ccc(Cl)cc1] | 2-((7-(4-chlorobenzyl)-3-ethyl-1-(3-hydroxypropyl)-2,6-dioxo-2,3,6,7-tertrahydro-1H-purin-8-yl)oxy)benzonitrile | 3.673 | 480 |
| 253 | 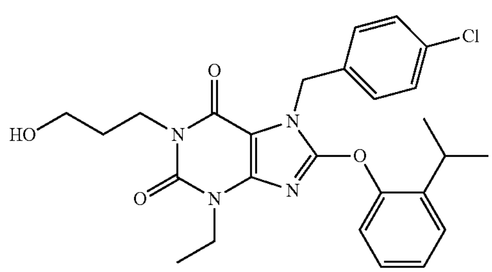 [SMILES: CCn1c(=O)n(CCCO)c(=O)c2c1nc(Oc1ccccc1C(C)C)n2Cc1ccc(Cl)cc1] | 7-(4-chlorobenzyl)-3-ethyl-1-(3-hydroxypropyl)-8-(2-isopropylphenoxy)-1H-purine-2,6(3H,7H)-dione | 3.252 | 497 |
| 254 | 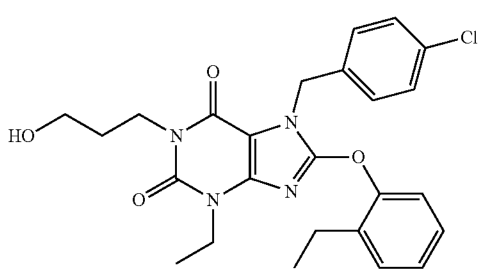 [SMILES: CCc1ccccc1Oc1nc2c(c(=O)n(CCCO)c(=O)n2CC)n1Cc1ccc(Cl)cc1] | 7-(4-chlorobenzyl)-3-ethyl-8-(2-ethylphenoxy)-1-(3-hydroxypropyl)-1H-purine-2,6(3H,7H)-dione | 3.144 | 483 |
| 255 | 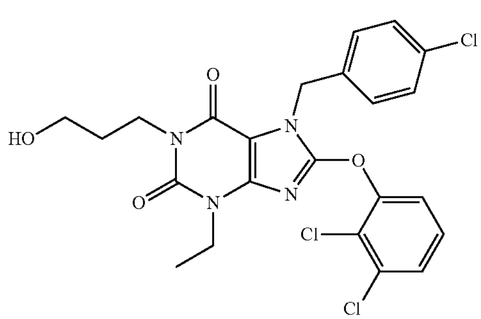 [SMILES: CCn1c(=O)n(CCCO)c(=O)c2c1nc(Oc1cccc(Cl)c1Cl)n2Cc1ccc(Cl)cc1] | 7-(4-chlorobenzyl)-8-(2,3-dichlorophenoxy)-3-ethyl-1-(3-hydroxypropyl)-1H-purine-2,6(3H,7H)-dione | 3.249 | 525 |

TABLE 1-continued

| Example | Chemical Name | LCMS retention time, min | LCMS M + 1 |
|---|---|---|---|
| 256 | 7-(4-chlorobenzyl)-8-(3,4-difluorophenoxy)-3-ethyl-1-(3-hydroxypropyl)-1H-purine-2,6(3H,7H)-dione | 3.047 | 491 |
| 257 | 7-(4-chlorobenzyl)-8-(2,3-difluorophenoxy)-3-ethyl-1-(3-hydroxypropyl)-1H-purine-2,6(3H,7H)-dione | 2.898 | 491 |
| 258 | 7-(4-chlorobenzyl)-8-(3,5-difluorophenoxy)-3-ethyl-1-(3-hydroxypropyl)-1H-purine-2,6(3H,7H)-dione | 3.051 | 491 |
| 259 | 7-(4-chlorobenzyl)-8-(3-chlorophenoxy)-3-ethyl-1-(3-hydroxypropyl)-1H-purine-2,6(3H,7H)-dione | 3.148 | 489 |
| 260 | 7-(4-chlorobenzyl)-3-ethyl-8-(3-fluorophenoxy)-1-(3-hydroxypropyl)-1H-purine-2,6(3H,7H)-dione | 3.901 | 473 |

TABLE 1-continued

| Example | Structure | Chemical Name | LCMS retention time, min | LCMS M + 1 |
|---|---|---|---|---|
| 261 | 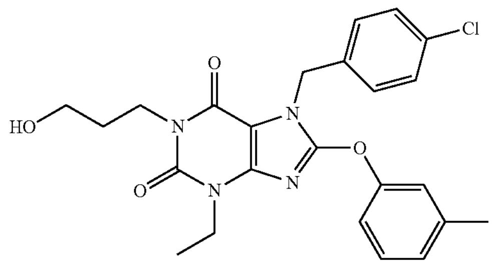 [SMILES: CCn1c(=O)n(CCCO)c(=O)c2c1nc(Oc1cccc(C)c1)n2Cc1ccc(Cl)cc1] | 7-(4-chlorobenzyl)-3-ethyl-1-(3-hydroxypropyl)-8-(m-tolyloxy)-1H-purine-2,6(3H,7H)-dione | 3.001 | 469 |
| 262 | 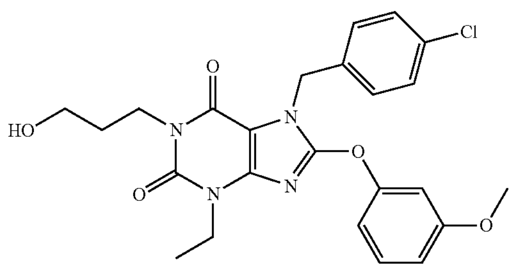 [SMILES: CCn1c(=O)n(CCCO)c(=O)c2c1nc(Oc1cccc(OC)c1)n2Cc1ccc(Cl)cc1] | 7-(4-chlorobenzyl)-3-ethyl-1-(3-hydroxypropyl)-8-(3-methoxyphenoxy)-1H-purine-2,6(3H,7H)-dione | 2.904 | 485 |
| 263 | 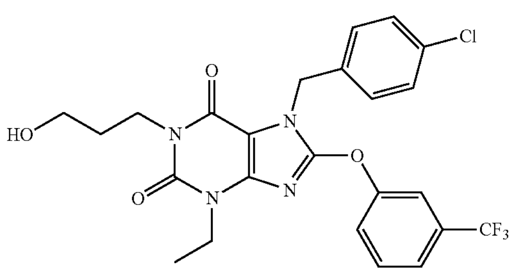 [SMILES: CCn1c(=O)n(CCCO)c(=O)c2c1nc(Oc1cccc(C(F)(F)F)c1)n2Cc1ccc(Cl)cc1] | 7-(4-chlorobenzyl)-3-ethyl-1-(3-hydroxypropyl)-8-(3-(trifluoromethyl)phenoxy)-1H-purine-2,6(3H,7H)-dione | 3.138 | 523 |
| 264 | 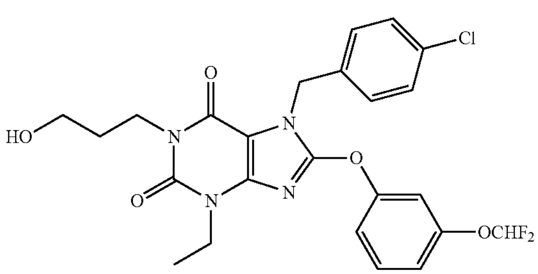 [SMILES: CCn1c(=O)n(CCCO)c(=O)c2c1nc(Oc1cccc(OC(F)F)c1)n2Cc1ccc(Cl)cc1] | 7-(4-chlorobenzyl)-8-(3-(difluoromethoxy)phenoxy)-3-ethyl-1-(3-hydroxypropyl)-1H-purine-2,6(3H,7H)-dione | 2.976 | 521 |
| 265 | 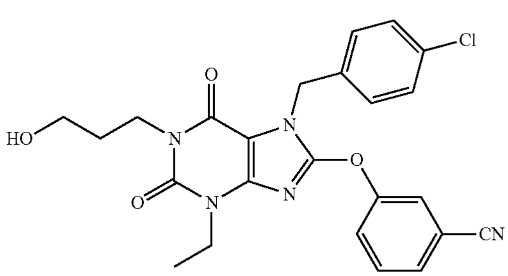 [SMILES: CCn1c(=O)n(CCCO)c(=O)c2c1nc(Oc1cccc(C#N)c1)n2Cc1ccc(Cl)cc1] | 3-((7-(4-chlorobenzyl)-3-ethyl-1-(3-hydroxypropyl)-2,6-dioxo-2,3,6,7-tetrahydro-1H-purin-8-yl)oxy)benzonitrile | 2.690 | 480 |

TABLE 1-continued

| Example | Structure | Chemical Name | LCMS retention time, min | LCMS M + 1 |
|---|---|---|---|---|
| 266 | 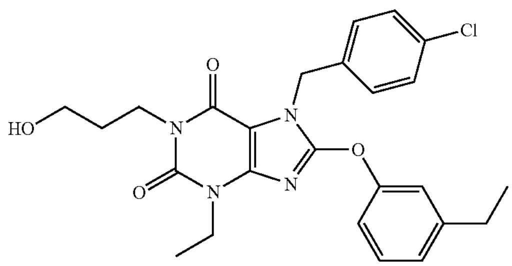 [SMILES: CCc1cccc(Oc2nc3c(c(=O)n(CCCO)c(=O)n3CC)n2Cc2ccc(Cl)cc2)c1] | 7-(4-chlorobenzyl)-3-ethyl-8-(3-ethylphenoxy)-1-(3-hydroxypropyl)-1H-purine-2,6(3H,7H)-dione | 2.221 | 483 |
| 267 | 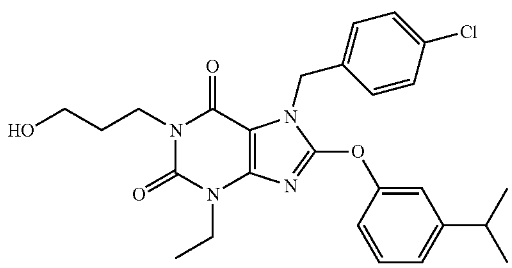 [SMILES: CCn1c(=O)n(CCCO)c(=O)c2c1nc(Oc1cccc(C(C)C)c1)n2Cc1ccc(Cl)cc1] | 7-(4-chlorobenzyl)-3-ethyl-1-(3-hydroxypropyl)-8-(3-isopropylphenoxy)-1H-purine-2,6(3H,7H)-dione | 3.361 | 497 |
| 268 | 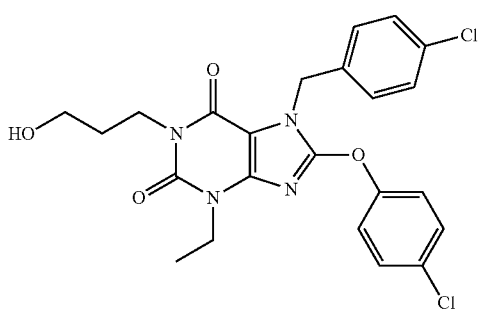 | 7-(4-chlorobenzyl)-8-(4-chlorophenoxy)-3-ethyl-1-(3-hydroxypropyl)-1H-purine-2,6(3H,7H)-dione | 3.153 | 489 |
| 269 | 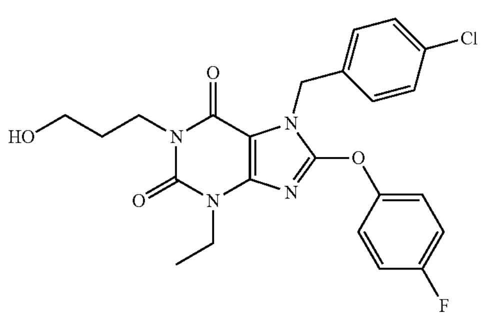 [SMILES: CCn1c(=O)n(CCCO)c(=O)c2c1nc(Oc1ccc(F)cc1)n2Cc1ccc(Cl)cc1] | 7-(4-chlorobenzyl)-3-ethyl-8-(4-fluorophenoxy)-1-(3-hydroxypropyl)-1H-purine-2,6(3H,7H)-dione | 2.952 | 473 |
| 270 | 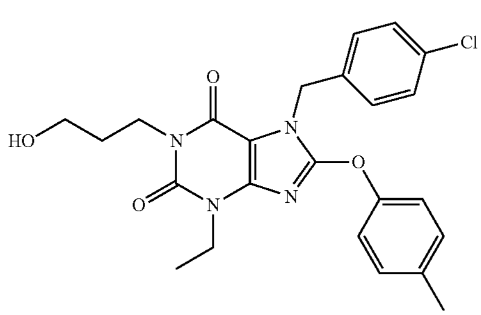 [SMILES: CCn1c(=O)n(CCCO)c(=O)c2c1nc(Oc1ccc(C)cc1)n2Cc1ccc(Cl)cc1] | 7-(4-chlorobenzyl)-3-ethyl-1-(3-hydroxypropyl)-8-(p-tolyloxy)-1H-purine-2,6(3H,7H)-dione | 3.082 | 469 |

TABLE 1-continued

| Example | Structure | Chemical Name | LCMS retention time, min | LCMS M + 1 |
|---|---|---|---|---|
| 271 | 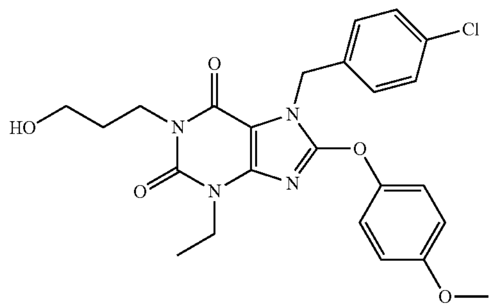 [SMILES: CCn1c(=O)n(CCCO)c(=O)c2c1nc(Oc1ccc(OC)cc1)n2Cc1ccc(Cl)cc1] | 7-(4-chlorobenzyl)-3-ethyl-1-(3-hydroxypropyl)-8-(4-methoxyphenoxy)-1H-purine-2,6(3H,7H)-dione | 2.907 | 485 |
| 272 | 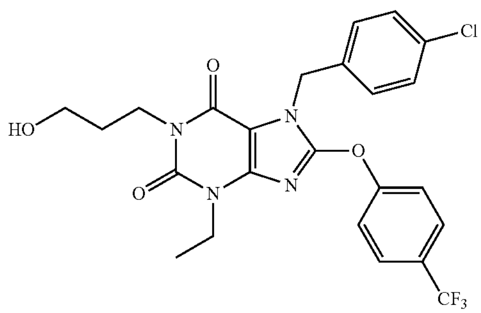 [SMILES: CCn1c(=O)n(CCCO)c(=O)c2c1nc(Oc1ccc(C(F)(F)F)cc1)n2Cc1ccc(Cl)cc1] | 7-(4-chlorobenzyl)-3-ethyl-1-(3-hydroxypropyl)-8-(4-(trifluoromethyl)phenoxy)-1H-purine-2,6(3H,7H)-dione | 3.193 | 523 |
| 273 | 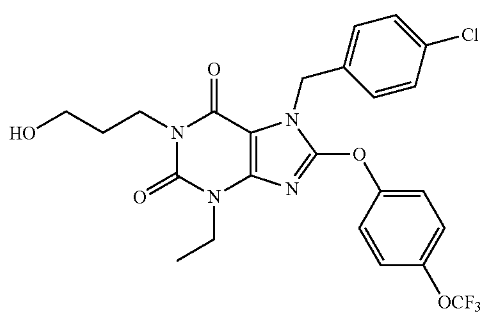 [SMILES: CCn1c(=O)n(CCCO)c(=O)c2c1nc(Oc1ccc(OC(F)(F)F)cc1)n2Cc1ccc(Cl)cc1] | 7-(4-chlorobenzyl)-3-ethyl-1-(3-hydroxypropyl)-8-(4-(trifluoromethoxy)phenoxy)-1H-purine-2,6(3H,7H)-dione | 3.169 | 539 |
| 274 | 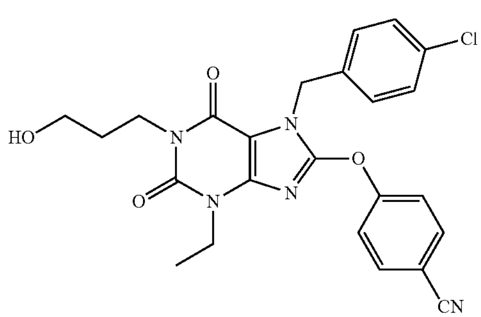 [SMILES: CCn1c(=O)n(CCCO)c(=O)c2c1nc(Oc1ccc(C#N)cc1)n2Cc1ccc(Cl)cc1] | 4-((7-(4-chlorobenzyl)-3-ethyl-1-(3-hydroxypropyl)-2,6-dioxo-2,3,6,7-tetrahydro-1H-purin-8-yl)oxy)benzonitrile | 2.713 | 480 |
| 275 | 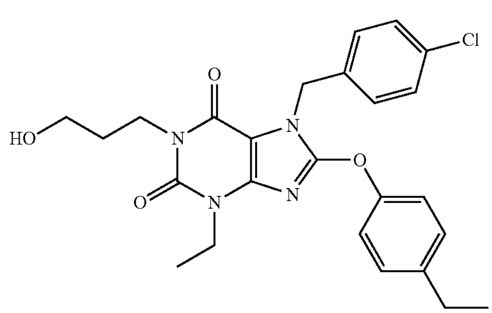 [SMILES: CCc1ccc(Oc2nc3c(c(=O)n(CCCO)c(=O)n3CC)n2Cc2ccc(Cl)cc2)cc1] | 7-(4-chlorobenzyl)-3-ethyl-8-(4-ethylphenoxy)-1-(3-hydroxypropyl)-1H-purine-2,6(3H,7H)-dione | 3.267 | 483 |

TABLE 1-continued

| Example | Structure | Chemical Name | LCMS retention time, min | LCMS M + 1 |
|---|---|---|---|---|
| 276 | 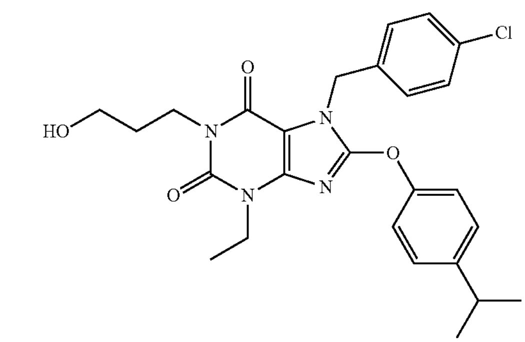 [SMILES: CCn1c(=O)n(CCCO)c(=O)c2c1nc(Oc1ccc(C(C)C)cc1)n2Cc1ccc(Cl)cc1] | 7-(4-chlorobenzyl)-3-ethyl-1-(3-hydroxypropyl)-8-(4-isopropylphenoxy)-1H-purine-2,6(3H,7H)-dione | 3.408 | 497 |

Example 277 7-(4-fluorobenzyl)-1-(3-hydroxypropyl)-3-methyl-8-p-tolyl-1H-purine-2,6(3H,7H)-dione

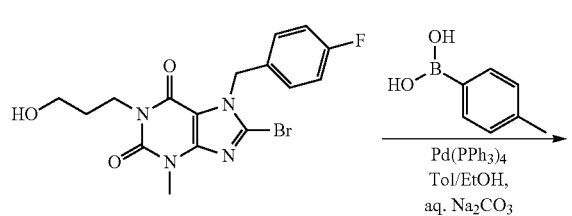

To a solution of 8-bromo-7-(4-fluorobenzyl)-1-(3-hydroxypropyl)-3-methyl-1H-purine-2,6(3H,7H)-dione (50 mg, 0.121 mmol, intermediate 62) in toluene (2 mL) and ethanol (0.5 mL) was added p-tolylboronic acid (19.7 mg, 0.145 mmol) followed by aqueous sodium carbonate solution (0.5 mL), and the mixture was degassed under nitrogen atmosphere three times. Tetrakis(triphenylphosphine)platinum (7.5 mg, 0.006 mmol) was added to the reaction under nitrogen and the resulting mixture was stirred at 100° C. for 16 h. The mixture was partitioned between ethyl acetate and brine. The organic phase was dried and concentrated to give crude product, which was purified via preparative HPLC to give 7-(4-fluorobenzyl)-1-(3-hydroxypropyl)-3-methyl-8-p-tolyl-1H-purine-2,6(3H,7H)-dione (20.9 mg, 40.9% yield) as white solid. $^1$H-NMR (CD$_3$OD) δ 7.51-7.53 (d, 2H), 7.34-7.36 (d, 2H), 6.97-7.07 (m, 4H), 5.66 (s, 2H), 4.09-4.12 (t, 2H), 3.59-3.62 (t, 2H), 3.59 (s, 3H), 2.44 (s, 3H), 1.85-1.89 (m, 2H). LCMS retention time 2.306; LCMS MH$^+$ 423.

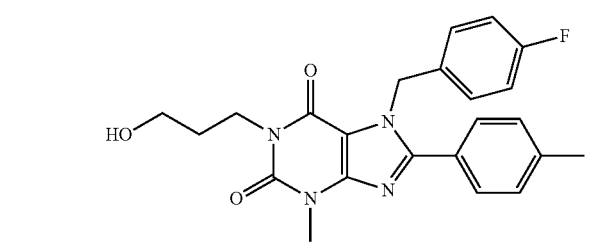

The examples in Table 3 were prepared using the method of example 277.

TABLE 2

| Example | Structure | Chemical Name | LCMS retention time, min | LCMS M + 1 |
|---|---|---|---|---|
| 278 | 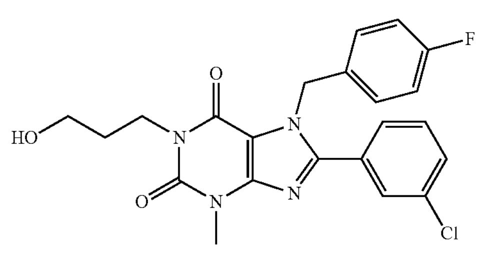 [SMILES: Cn1c(=O)n(CCCO)c(=O)c2c1nc(-c1cccc(Cl)c1)n2Cc1ccc(F)cc1] | 8-(3-chlorophenyl)-7-(4-fluorobenzyl)-1-(3-hydroxypropyl)-3-methyl-1H-purine-2,6(3H,7H)-dione | 2.644 | 443 |

TABLE 2-continued

| Example | Structure | Chemical Name | LCMS retention time, min | LCMS M + 1 |
|---|---|---|---|---|
| 279 | 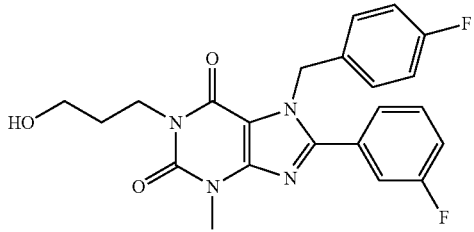 | 7-(4-fluorobenzyl)-8-(3-fluorophenyl)-1-(3-hydroxypropyl)-3-methyl-1H-purine-2,6(3H,7H)-dione | 2.425 | 427 |
| 280 | 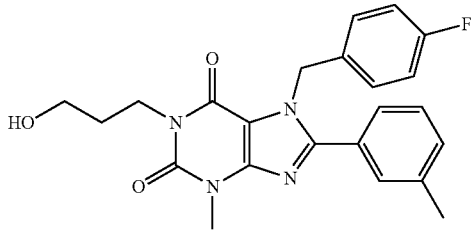 [SMILES: Cc1cccc(-c2nc3c(c(=O)n(CCCO)c(=O)n3C)n2Cc2ccc(F)cc2)c1] | 7-(4-fluorobenzyl)-1-(3-hydroxypropyl)-3-methyl-8-m-tolyl-1H-purine-2,6(3H,7H)-dione | 2.577 | 423 |
| 281 | 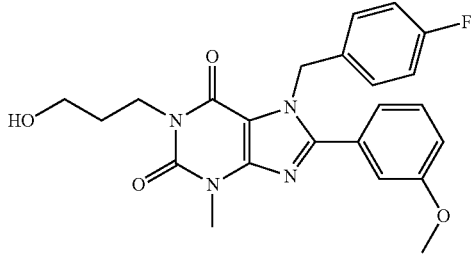 [SMILES: COc1cccc(-c2nc3c(c(=O)n(CCCO)c(=O)n3C)n2Cc2ccc(F)cc2)c1] | 7-(4-fluorobenzyl)-1-(3-hydroxypropyl)-8-(3-methoxyphenyl)-3-methyl-1H-purine-2,6(3H,7H)-dione | 2.388 | 439 |
| 282 | 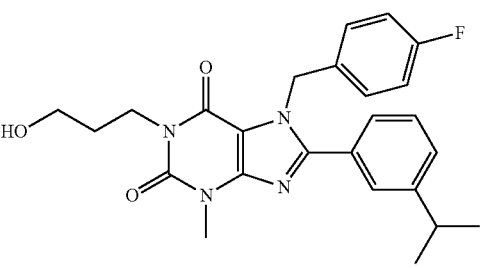 [SMILES: CC(C)c1cccc(-c2nc3c(c(=O)n(CCCO)c(=O)n3C)n2Cc2ccc(F)cc2)c1] | 7-(4-fluorobenzyl)-1-(3-hydroxypropyl)-8-(3-isopropylphenyl)-3-methyl-1H-purine-2,6(3H,7H)-dione | 2.868 | 451 |
| 283 | 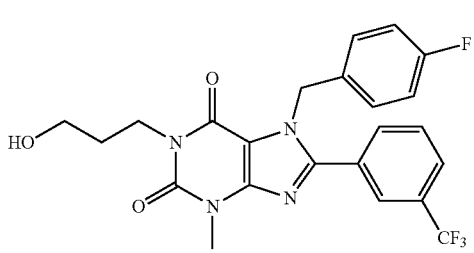 | 7-(4-fluorobenzyl)-1-(3-hydroxypropyl)-3-methyl-8-(3-(trifluoromethyl)phenyl)-1H-purine-2,6(3H,7H)-dione | 2.664 | 477 |
| 284 | 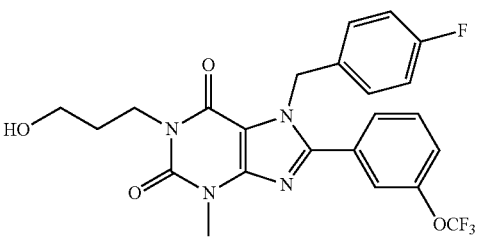 [SMILES: Cn1c(=O)n(CCCO)c(=O)c2c1nc(-c1cccc(OC(F)(F)F)c1)n2Cc1ccc(F)cc1] | 7-(4-fluorobenzyl)-1-(3-hydroxypropyl)-3-methyl-8-(3-(trifluoromethoxy)phenyl)-1H-purine-2,6(3H,7H)-dione | 2.782 | 493 |

TABLE 2-continued

| Example | Structure | Chemical Name | LCMS retention time, min | LCMS M + 1 |
|---|---|---|---|---|
| 285 | 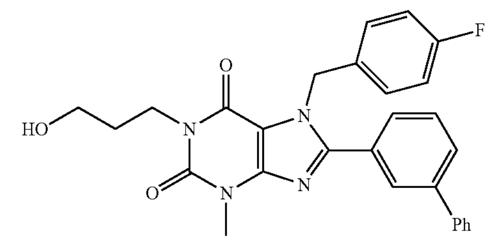 | 8-(biphenyl-3-yl)-7-(4-fluorobenzyl)-1-(3-hydroxypropyl)-3-methyl-1H-purine-2,6(3H,7H)-dione | 2.572 | 485 |
| 286 | 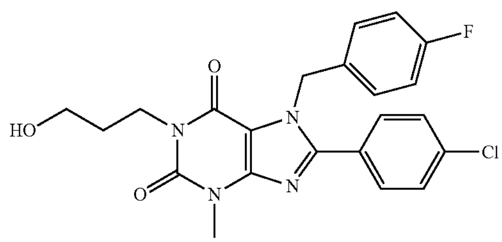 [SMILES: Cn1c(=O)n(CCCO)c(=O)c2c1nc(-c1ccc(Cl)cc1)n2Cc1ccc(F)cc1] | 8-(4-chlorophenyl)-7-(4-fluorobenzyl)-1-(3-hydroxypropyl)-3-methyl-1H-purine-2,6(3H,7H)-dione | 2.613 | 443 |
| 287 | 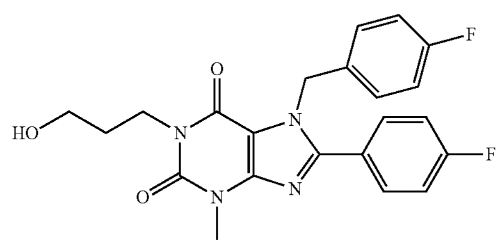 [SMILES: Cn1c(=O)n(CCCO)c(=O)c2c1nc(-c1ccc(F)cc1)n2Cc1ccc(F)cc1] | 7-(4-fluorobenzyl)-8-(4-fluorophenyl)-1-(3-hydroxypropyl)-3-methyl-1H-purine-2,6(3H,7H)-dione | 2.401 | 427 |
| 288 | 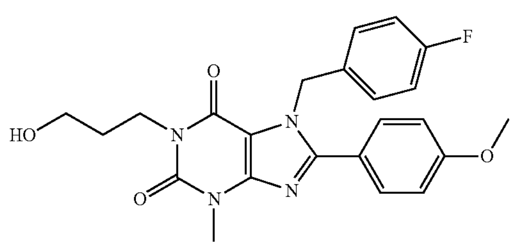 [SMILES: COc1ccc(-c2nc3c(c(=O)n(CCCO)c(=O)n3C)n2Cc2ccc(F)cc2)cc1] | 7-(4-fluorobenzyl)-1-(3-hydroxypropyl)-8-(4-methoxyphenyl)-3-methyl-1H-purine-2,6(3H,7H)-dione | 2.367 | 439 |
| 289 | 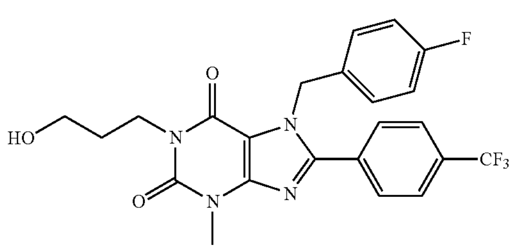 [SMILES: Cn1c(=O)n(CCCO)c(=O)c2c1nc(-c1ccc(C(F)(F)F)cc1)n2Cc1ccc(F)cc1] | 7-(4-fluorobenzyl)-1-(3-hydroxypropyl)-3-methyl-8-(4-(trifluoromethyl)phenyl)-1H-purine-2,6(3H,7H)-dione | 2.453 | 477 |
| 290 | 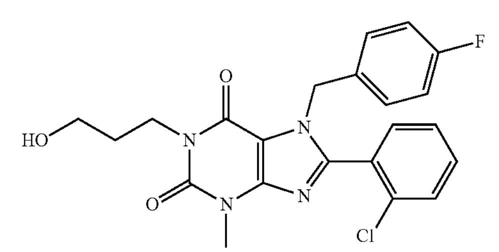 [SMILES: Cn1c(=O)n(CCCO)c(=O)c2c1nc(-c1ccccc1Cl)n2Cc1ccc(F)cc1] | 8-(2-chlorophenyl)-7-(4-fluorobenzyl)-1-(3-hydroxypropyl)-3-methyl-1H-purine-2,6(3H,7H)-dione | 2.219 | 443 |

TABLE 2-continued

| Example | Structure | Chemical Name | LCMS retention time, min | LCMS M + 1 |
|---|---|---|---|---|
| 291 | 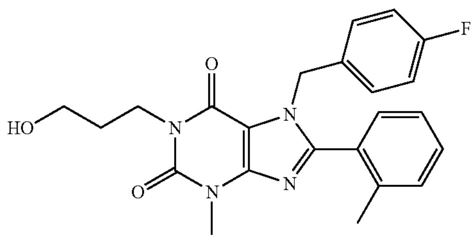 [SMILES: Cc1ccccc1-c1nc2c(c(=O)n(CCCO)c(=O)n2C)n1Cc1ccc(F)cc1] | 7-(4-fluorobenzyl)-1-(3-hydroxypropyl)-3-methyl-8-(o-tolyl)-1H-purine-2,6(3H,7H)-dione | 2.432 | 423 |
| 292 | 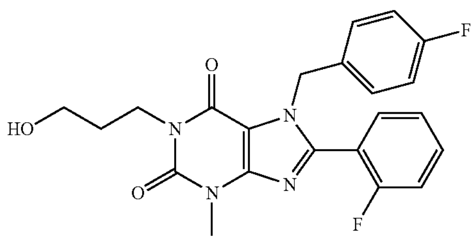 [SMILES: Cn1c(=O)n(CCCO)c(=O)c2c1nc(-c1ccccc1F)n2Cc1ccc(F)cc1] | 7-(4-fluorobenzyl)-8-(2-fluorophenyl)-1-(3-hydroxypropyl)-3-methyl-1H-purine-2,6(3H,7H)-dione | 2.307 | 427 |
| 293 | 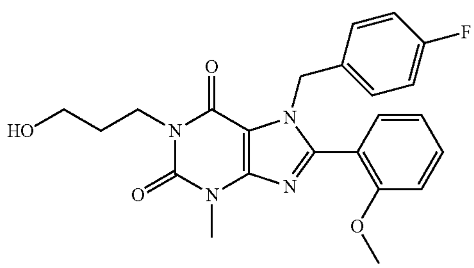 [SMILES: COc1ccccc1-c1nc2c(c(=O)n(CCCO)c(=O)n2C)n1Cc1ccc(F)cc1] | 7-(4-fluorobenzyl)-1-(3-hydroxypropyl)-8-(2-methoxyphenyl)-3-methyl-1H-purine-2,6(3H,7H)-dione | 2.303 | 439 |
| 294 | 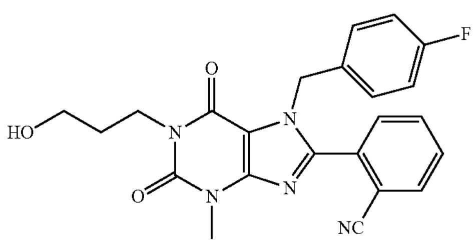 [SMILES: Cn1c(=O)n(CCCO)c(=O)c2c1nc(-c1ccccc1C#N)n2Cc1ccc(F)cc1] | 2-(7-(4-fluorobenzyl)-1-(3-hydroxypropyl)-3-methyl-2,6-dioxo-2,3,6,7-tetrahydro-1H-purin-8-yl)benzonitrile | 2.204 | 434 |
| 295 | 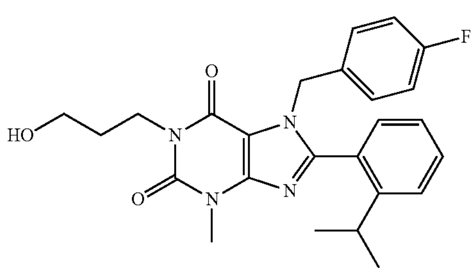 [SMILES: CC(C)c1ccccc1-c1nc2c(c(=O)n(CCCO)c(=O)n2C)n1Cc1ccc(F)cc1] | 7-(4-fluorobenzyl)-1-(3-hydroxypropyl)-8-(2-isopropylphenyl)-3-methyl-1H-purine-2,6(3H,7H)-dione | 2.507 | 451 |
| 296 | 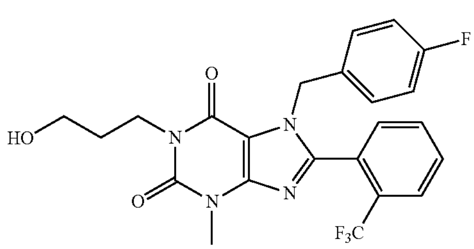 [SMILES: Cn1c(=O)n(CCCO)c(=O)c2c1nc(-c1ccccc1C(F)(F)F)n2Cc1ccc(F)cc1] | 7-(4-fluorobenzyl)-1-(3-hydroxypropyl)-3-methyl-8-(2-(trifluoromethyl)phenyl)-1H-purine-2,6(3H,7H)-dione | 2.461 | 477 |

TABLE 2-continued

| Example | Structure | Chemical Name | LCMS retention time, min | LCMS M + 1 |
|---|---|---|---|---|
| 297 | 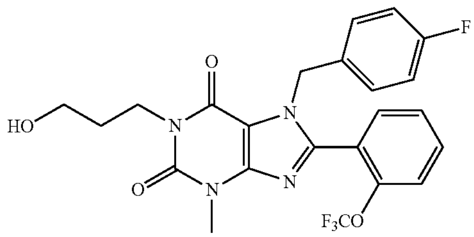 [SMILES: Cn1c(=O)n(CCCO)c(=O)c2c1nc(-c1ccccc1OC(F)(F)F)n2Cc1ccc(F)cc1] | 7-(4-fluorobenzyl)-1-(3-hydroxypropyl)-3-methyl-8-(2-(trifluoromethoxy)phenyl)-1H-purine-2,6(3H,7H)-dione | 2.341 | 493 |
| 298 | 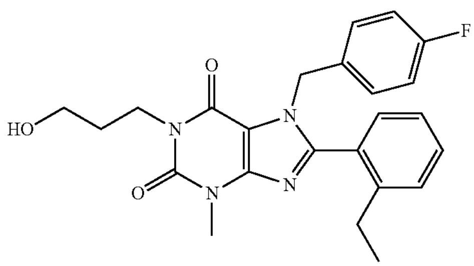 [SMILES: CCc1ccccc1-c1nc2c(c(=O)n(CCCO)c(=O)n2C)n1Cc1ccc(F)cc1] | 8-(2-ethylphenyl)-7-(4-fluorobenzyl)-1-(3-hydroxypropyl)-3-methyl-1H-purine-2,6(3H,7H)-dione | 2.602 | 437 |
| 299 | 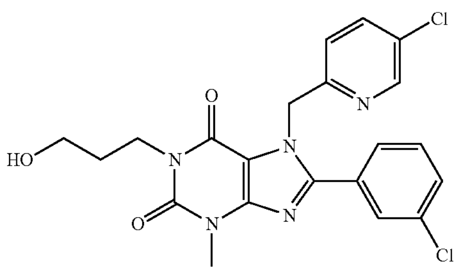 [SMILES: Cn1c(=O)n(CCCO)c(=O)c2c1nc(-c1cccc(Cl)c1)n2Cc1ccc(Cl)cn1] | 8-(3-chlorophenyl)-7-((5-chloropyridin-2-yl)methyl)-1-(3-hydroxypropyl)-3-methyl-1H-purine-2,6(3H,7H)-dione | 2.533 | 461 |
| 300 | 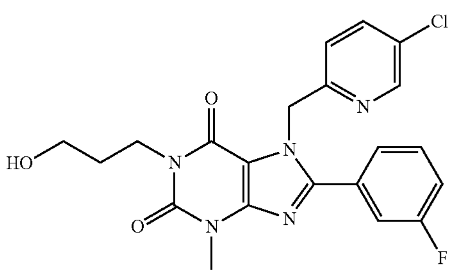 | 7-((5-chloropyridin-2-yl)methyl)-8-(3-fluorophenyl)-1-(3-hydroxypropyl)-3-methyl-1H-purine-2,6(3H,7H)-dione | 2.313 | 444 |
| 301 | 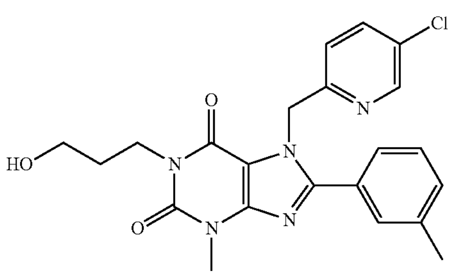 [SMILES: Cc1cccc(-c2nc3c(c(=O)n(CCCO)c(=O)n3C)n2Cc2ccc(Cl)cn2)c1] | 7-((5-chloropyridin-2-yl)methyl)-1-(3-hydroxypropyl)-3-methyl-8-(m-tolyl)-1H-purine-2,6(3H,7H)-dione | 2.432 | 440 |

TABLE 2-continued

| Example | Structure | Chemical Name | LCMS retention time, min | LCMS M + 1 |
|---|---|---|---|---|
| 302 | 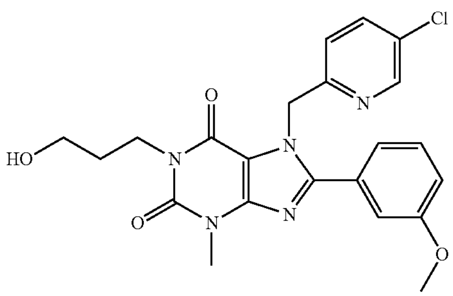 [SMILES: COc1cccc(-c2nc3c(c(=O)n(CCCO)c(=O)n3C)n2Cc2ccc(Cl)cn2)c1] | 7-((5-chloropyridin-2-yl)methyl)-1-(3-hydroxypropyl)-8-(3-methoxyphenyl)-3-methyl-1H-purine-2,6(3H,7H)-dione | 2.276 | 456 |
| 303 | 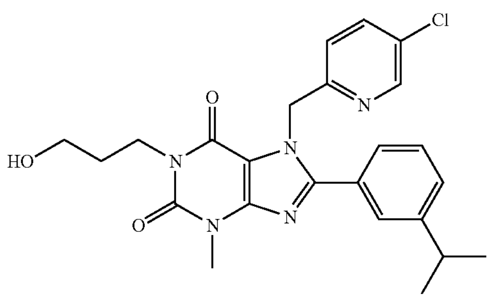 [SMILES: CC(C)c1cccc(-c2nc3c(c(=O)n(CCCO)c(=O)n3C)n2Cc2ccc(Cl)cn2)c1] | 7-((5-chloropyridin-2-yl)methyl)-1-(3-hydroxypropyl)-8-(3-isopropylphenyl)-3-methyl-1H-purine-2,6(3H,7H)-dione | 2.791 | 468 |
| 304 | 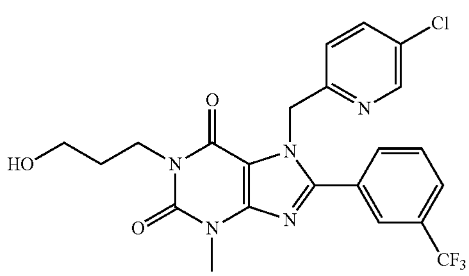 [SMILES: Cn1c(=O)n(CCCO)c(=O)c2c1nc(-c1cccc(C(F)(F)F)c1)n2Cc1ccc(Cl)cn1] | 7-((5-chloropyridin-2-yl)methyl)-1-(3-hydroxypropyl)-3-methyl-8-(3-(trifluoromethyl)phenyl)-1H-purine-2,6(3H,7H)-dione | 2.614 | 494 |
| 305 | 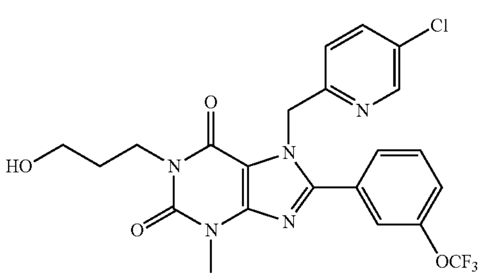 [SMILES: Cn1c(=O)n(CCCO)c(=O)c2c1nc(-c1cccc(OC(F)(F)F)c1)n2Cc1ccc(Cl)cn1] | 7-((5-chloropyridin-2-yl)methyl)-1-(3-hydroxypropyl)-3-methyl-8-(3-(trifluoromethoxy)phenyl)-1H-purine-2,6(3H,7H)-dione | 2.735 | 510 |
| 306 | 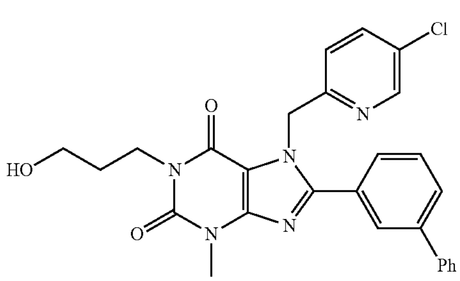 [SMILES: Cn1c(=O)n(CCCO)c(=O)c2c1nc(-c1cccc(-c3ccccc3)c1)n2Cc1ccc(Cl)cn1] | 8-([1,1'-biphenyl]-3-yl)-7-((5-chloropyridin-2-yl)methyl)-1-(3-hydroxypropyl)-3-methyl-1H-purine-2,6(3H,7H)-dione | 2.750 | 502 |

TABLE 2-continued

| Example | Structure | Chemical Name | LCMS retention time, min | LCMS M + 1 |
|---|---|---|---|---|
| 307 | 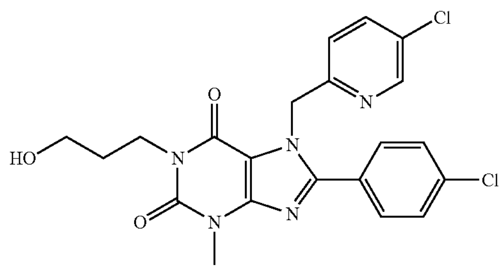 [SMILES: Cn1c(=O)n(CCCO)c(=O)c2c1nc(-c1ccc(Cl)cc1)n2Cc1ccc(Cl)cn1] | 8-(4-chlorophenyl)-7-((5-chloropyridin-2-yl)methyl)-1-(3-hydroxypropyl)-3-methyl-1H-purine-2,6(3H,7H)-dione | 2.501 | 461 |
| 308 | 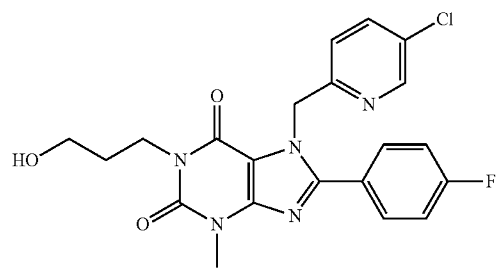 [SMILES: Cn1c(=O)n(CCCO)c(=O)c2c1nc(-c1ccc(F)cc1)n2Cc1ccc(Cl)cn1] | 7-((5-chloropyridin-2-yl)methyl)-8-(4-fluorophenyl)-1-(3-hydroxypropyl)-3-methyl-1H-purine-2,6(3H,7H)-dione | 2.281 | 444 |
| 309 | 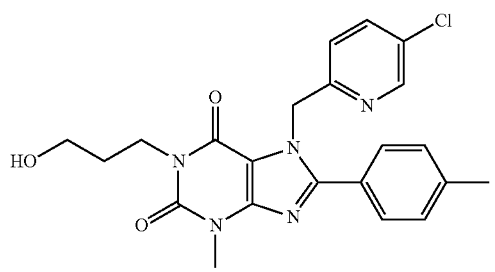 [SMILES: Cc1ccc(-c2nc3c(c(=O)n(CCCO)c(=O)n3C)n2Cc2ccc(Cl)cn2)cc1] | 7-((5-chloropyridin-2-yl)methyl)-1-(3-hydroxypropyl)-3-methyl-8-(p-tolyl)-1H-purine-2,6(3H,7H)-dione | 2.413 | 440 |
| 310 | 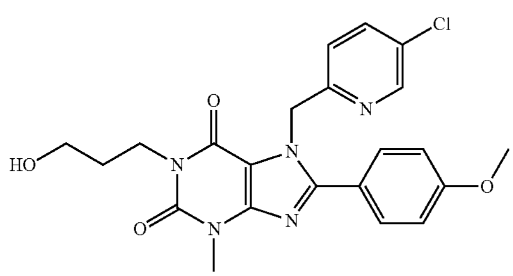 [SMILES: COc1ccc(-c2nc3c(c(=O)n(CCCO)c(=O)n3C)n2Cc2ccc(Cl)cn2)cc1] | 7-((5-chloropyridin-2-yl)methyl)-1-(3-hydroxypropyl)-8-(4-methoxyphenyl)-3-methyl-1H-purine-2,6(3H,7H)-dione | 2.360 | 456 |
| 311 | 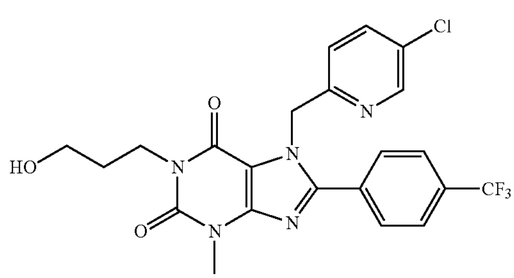 [SMILES: Cn1c(=O)n(CCCO)c(=O)c2c1nc(-c1ccc(C(F)(F)F)cc1)n2Cc1ccc(Cl)cn1] | 7-((5-chloropyridin-2-yl)methyl)-1-(3-hydroxypropyl)-3-methyl-8-(4-(trifluoromethyl)phenyl)-1H-purine-2,6(3H,7H)-dione | 2.666 | 494 |

TABLE 2-continued

| Example | Structure | Chemical Name | LCMS retention time, min | LCMS M + 1 |
|---|---|---|---|---|
| 312 | 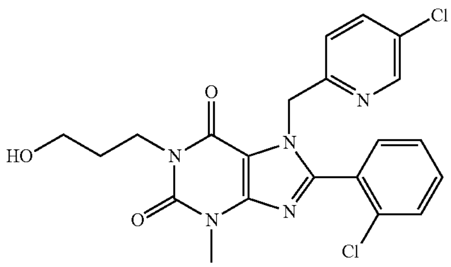 [SMILES: Cn1c(=O)n(CCCO)c(=O)c2c1nc(-c1ccccc1Cl)n2Cc1ccc(Cl)cn1] | 8-(2-chlorophenyl)-7-((5-chloropyridin-2-yl)methyl)-1-(3-hydroxypropyl)-3-methyl-1H-purine-2,6(3H,7H)-dione | 2.100 | 461 |
| 313 | 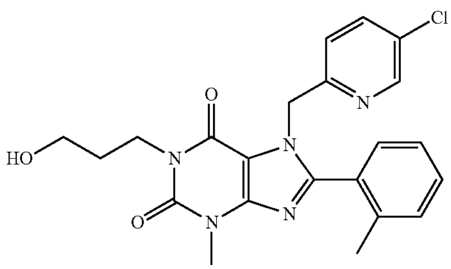 [SMILES: Cc1ccccc1-c1nc2c(c(=O)n(CCCO)c(=O)n2C)n1Cc1ccc(Cl)cn1] | 7-((5-chloropyridin-2-yl)methyl)-1-(3-hydroxypropyl)-3-methyl-8-(o-tolyl)-1H-purine-2,6(3H,7H)-dione | 2.306 | 440 |
| 314 | 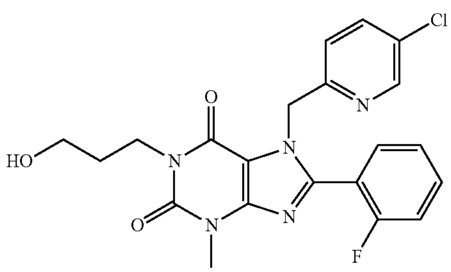 [SMILES: Cn1c(=O)n(CCCO)c(=O)c2c1nc(-c1ccccc1F)n2Cc1ccc(Cl)cn1] | 7-((5-chloropyridin-2-yl)methyl)-8-(2-fluorophenyl)-1-(3-hydroxypropyl)-3-methyl-1H-purine-2,6(3H,7H)-dione | 2.175 | 444 |
| 315 | 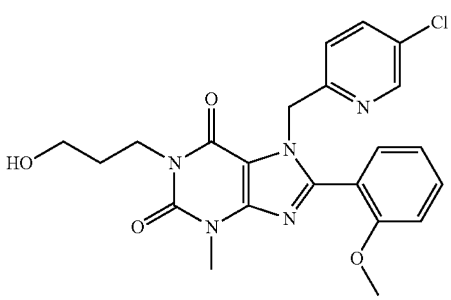 [SMILES: COc1ccccc1-c1nc2c(c(=O)n(CCCO)c(=O)n2C)n1Cc1ccc(Cl)cn1] | 7-((5-chloropyridin-2-yl)methyl)-1-(3-hydroxypropyl)-8-(2-methoxyphenyl)-3-methyl-1H-purine-2,6(3H,7H)-dione | 2.252 | 456 |
| 316 | 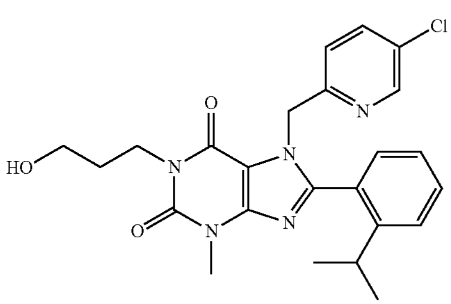 [SMILES: CC(C)c1ccccc1-c1nc2c(c(=O)n(CCCO)c(=O)n2C)n1Cc1ccc(Cl)cn1] | 7-((5-chloropyridin-2-yl)methyl)-1-(3-hydroxypropyl)-8-(2-isopropylphenyl)-3-methyl-1H-purine-2,6(3H,7H)-dione | 2.668 | 468 |

TABLE 2-continued

| Example | Structure | Chemical Name | LCMS retention time, min | LCMS M + 1 |
|---------|-----------|---------------|--------------------------|------------|
| 317 | 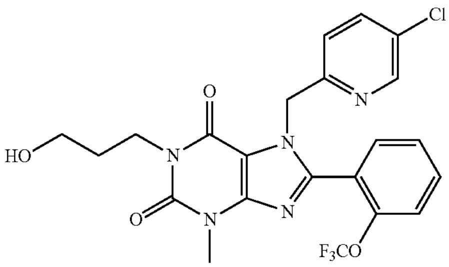 [SMILES: Cn1c(=O)n(CCCO)c(=O)c2c1nc(-c1ccccc1OC(F)(F)F)n2Cc1ccc(Cl)cn1] | 7-((5-chloropyridin-2-yl)methyl)-1-(3-hydroxypropyl)-3-methyl-8-(2-(trifluoromethoxy)phenyl)-1H-purine-2,6(3H,7H)-dione | 2.464 | 510 |
| 318 | 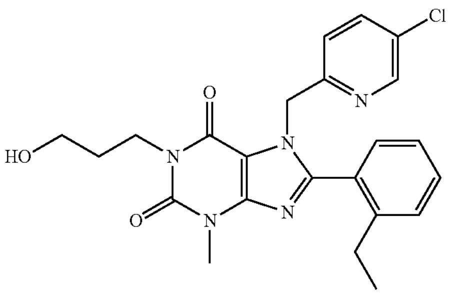 [SMILES: CCc1ccccc1-c1nc2c(c(=O)n(CCCO)c(=O)n2C)n1Cc1ccc(Cl)cn1] | 7-((5-chloropyridin-2-yl)methyl)-8-(2-ethylphenyl)-1-(3-hydroxypropyl)-3-methyl-1H-purine-2,6(3H,7H)-dione | 2.577 | 454 |

Example 319 7-((5-fluoropyridin-3-yl)methyl)-1-(3-hydroxypropyl)-3-methyl-8-(3-(trifluoromethoxy)phenoxy)-1H-purine-2,6(3H,7H)-dione

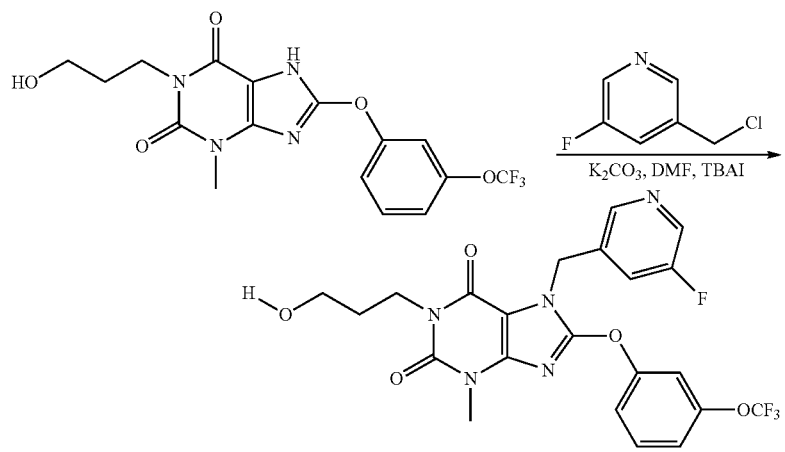

To a solution of 1-(3-hydroxypropyl)-3-methyl-8-(3-(trifluoromethoxy)phenoxy)-1H-purine-2,6(3H,7H)-dione (60 mg, 0.15 mmol, intermediate 15) in DMF (5 mL) was added 3-(chloromethyl)-5-fluoropyridine (80 mg, 0.55 mmol), potassium carbonate (0.55 g, 0.6 mmol), and TBAI (2 mg, 0.02 mmol). The reaction was heated at 60° C. for 2 h. The mixture was cooled and partitioned between ethyl acetate and water. The organic phase was dried over sodium sulfate, and concentrated. The residue was purified by preparative HPLC to give 7-((5-fluoropyridin-3-yl)methyl)-1-(3-hydroxypropyl)-3-methyl-8-(3-(trifluoromethoxy)phenoxy)-1H-purine-2,6(3H,7H)-dione (35 mg, 46% yield) as white solid. LCMS retention time 2.577 min; LCMS MH+ 510.

Example 320 1-(3-hydroxypropyl)-3-methyl-7-((6-methylpyridin-2-yl)methyl)-8-(3-(trifluoromethoxy)phenoxy)-1H-purine-2,6(3H,7H)-dione

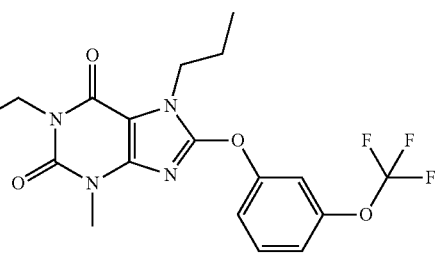

The title compound was prepared using the method of example 319 and purified via preparative HPLC to give 1-(3-hydroxypropyl)-3-methyl-7-((6-methylpyridin-2-yl)methyl)-8-(3-(trifluoromethoxy)phenoxy)-1H-purine-2,6(3H,7H)-dione (20 mg, 36.2% yield) as white solid. $^1$H-NMR (CD$_3$OD) δ 7.60-7.56 (t, 1H), 7.42-7.40 (m, 2H), 7.27-7.25 (d, 1H), 4.30-4.26 (t, 2H), 4.13-4.10 (t, 2H), 3.64-3.61 (t, 2H), 3.44 (s, 3H), 1.94-1.87 (m, 4H), 1.02-0.980 (t, 3H). LCMS retention time 2.803 min; LCMS MH$^+$ 443.

The examples in Table 3 were prepared using the methods of example 319.

TABLE 3

| Example | Structure | Chemical Name | LCMS retention time, min | LCMS M + 1 |
|---|---|---|---|---|
| 321 | 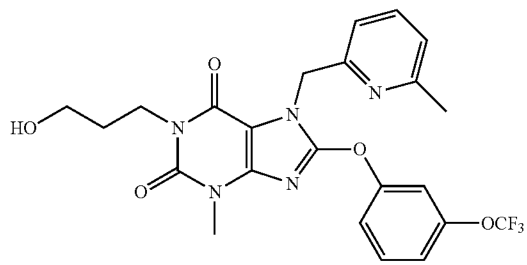 [SMILES: Cc1cccc(Cn2c(Oc3cccc(OC(F)(F)F)c3)nc3c2c(=O)n(CCCO)c(=O)n3C)n1] | 1-(3-hydroxypropyl)-3-methyl-7-((6-methylpyridin-2-yl)methyl)-8-(3-(trifluoromethoxy)phenoxy)-1H-purine-2,6(3H,7H)-dione | 2.525 | 506 |
| 322 | 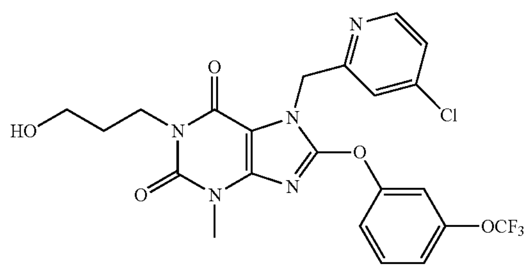 [SMILES: Cn1c(=O)n(CCCO)c(=O)c2c1nc(Oc1cccc(OC(F)(F)F)c1)n2Cc1cc(Cl)ccn1] | 7-((4-chloropyridin-2-yl)methyl)-1-(3-hydroxypropyl)-3-methyl-8-(3-(trifluoromethoxy)phenoxy)-1H-purine-2,6(3H,7H)-dione | 2.785 | 526 |
| 323 | 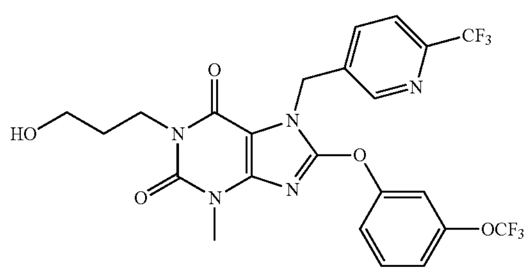 [SMILES: Cn1c(=O)n(CCCO)c(=O)c2c1nc(Oc1cccc(OC(F)(F)F)c1)n2Cc1ccc(C(F)(F)F)nc1] | 1-(3-hydroxypropyl)-3-methyl-8-(3-(trifluoromethoxy)phenoxy)-7-((6-(trifluoromethyl)pyridin-3-yl)methyl)-1H-purine-2,6(3H,7H)-dione | 2.845 | 560 |
| 324 | 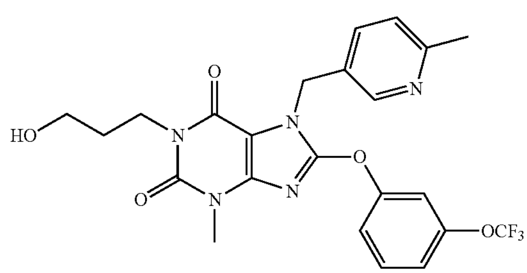 [SMILES: Cc1ccc(Cn2c(Oc3cccc(OC(F)(F)F)c3)nc3c2c(=O)n(CCCO)c(=O)n3C)cn1] | 1-(3-hydroxypropyl)-3-methyl-7-((6-methylpyridin-3-yl)methyl)-8-(3-(trifluoromethoxy)phenoxy)-1H-purine-2,6(3H,7H)-dione | 2.525 | 506 |
| 325 | 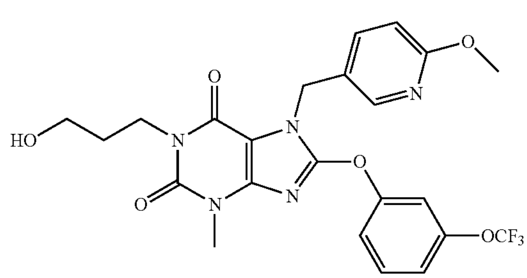 [SMILES: COc1ccc(Cn2c(Oc3cccc(OC(F)(F)F)c3)nc3c2c(=O)n(CCCO)c(=O)n3C)cn1] | 1-(3-hydroxypropyl)-7-((6-methoxypyridin-3-yl)methyl)-3-methyl-8-(3-(trifluoromethoxy)phenoxy)-1H-purine-2,6(3H,7H)-dione | 2.775 | 522 |

TABLE 3-continued

| Example | Structure | Chemical Name | LCMS retention time, min | LCMS M + 1 |
|---|---|---|---|---|
| 326 | 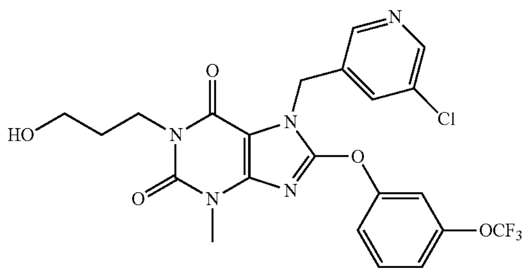 [SMILES: Cn1c(=O)n(CCCO)c(=O)c2c1nc(Oc1cccc(OC(F)(F)F)c1)n2Cc1cncc(Cl)c1] | 7-((5-chloropyridin-3-yl)methyl)-1-(3-hydroxypropyl)-3-methyl-8-(3-(trifluoromethoxy)phenoxy)-1H-purine-2,6(3H,7H)-dione | 2.715 | 526 |
| 327 | 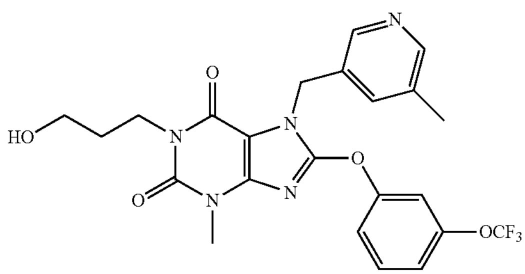 [SMILES: Cc1cncc(Cn2c(Oc3cccc(OC(F)(F)F)c3)nc3c2c(=O)n(CCCO)c(=O)n3C)c1] | 1-(3-hydroxypropyl)-3-methyl-7-((5-methylpyridin-3-yl)methyl)-8-(3-(trifluoromethoxy)phenoxy)-1H-purine-2,6(3H,7H)-dione | 2.234 | 506 |
| 328 | 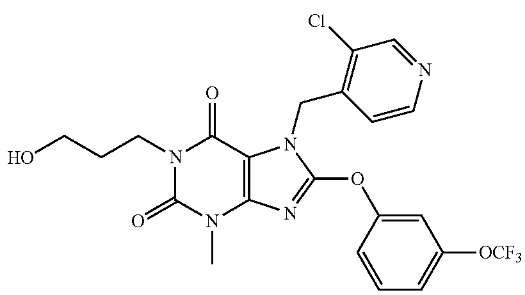 | 7-((3-chloropyridin-4-yl)methyl)-1-(3-hydroxypropyl)-3-methyl-8-(3-(trifluoromethoxy)phenoxy)-1H-purine-2,6(3H,7H)-dione | 2.692 | 526 |
| 329 | 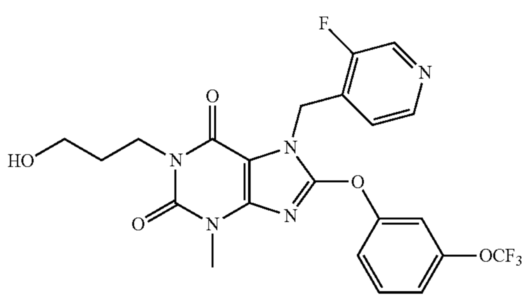 [SMILES: Cn1c(=O)n(CCCO)c(=O)c2c1nc(Oc1cccc(OC(F)(F)F)c1)n2Cc1ccncc1F] | 7-((3-fluoropyridin-4-yl)methyl)-1-(3-hydroxypropyl)-3-methyl-8-(3-(trifluoromethoxy)phenoxy)-1H-purine-2,6(3H,7H)-dione | 2.568 | 510 |
| 330 | 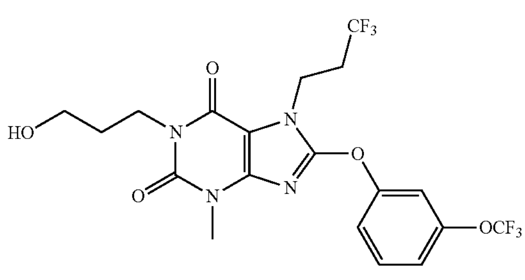 [SMILES: Cn1c(=O)n(CCCO)c(=O)c2c1nc(Oc1cccc(OC(F)(F)F)c1)n2CCC(F)(F)F] | 1-(3-hydroxypropyl)-3-methyl-8-(3-(trifluoromethoxy)phenoxy)-7-(3,3,3-trifluoropropyl)-1H-purine-2,6(3H,7H)-dione | 2.803 | 497 |

TABLE 3-continued

| Example | Structure | Chemical Name | LCMS retention time, min | LCMS M + 1 |
| --- | --- | --- | --- | --- |
| 331 | 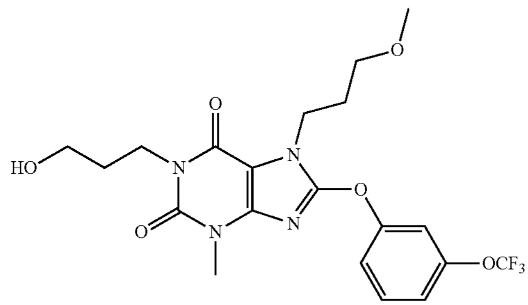 [SMILES: COCCCn1c(Oc2cccc(OC(F)(F)F)c2)nc2c1c(=O)n(CCCO)c(=O)n2C] | 1-(3-hydroxypropyl)-7-(3-methoxypropyl)-3-methyl-8-(3-(trifluoromethoxy)phenoxy)-1H-purine-2,6(3H,7H)-dione | 2.627 | 473 |
| 332 | 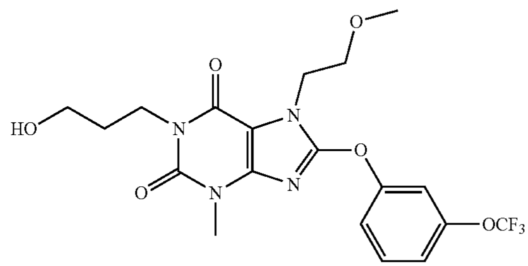 [SMILES: COCCn1c(Oc2cccc(OC(F)(F)F)c2)nc2c1c(=O)n(CCCO)c(=O)n2C] | 1-(3-hydroxypropyl)-7-(2-methoxyethyl)-3-methyl-8-(3-(trifluoromethoxy)phenoxy)-1H-purine-2,6(3H,7H)-dione | 2.632 | 459 |
| 333 | 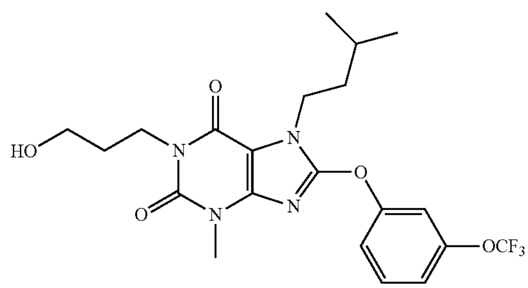 [SMILES: CC(C)CCn1c(Oc2cccc(OC(F)(F)F)c2)nc2c1c(=O)n(CCCO)c(=O)n2C] | 1-(3-hydroxypropyl)-7-isopentyl-3-methyl-8-(3-(trifluoromethoxy)phenoxy)-1H-purine-2,6(3H,7H)-dione | 1.861 | 471 |
| 334 | 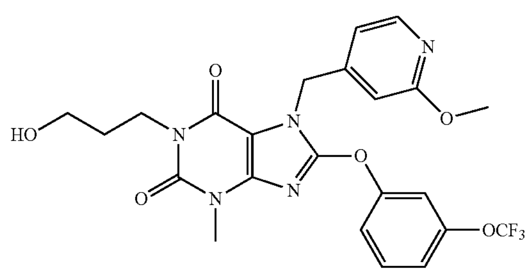 [SMILES: COc1cc(Cn2c(Oc3cccc(OC(F)(F)F)c3)nc3c2c(=O)n(CCCO)c(=O)n3C)ccn1] | 7-((4-chloropyridin-3-yl)methyl)-1-(3-hydroxypropyl)-3-methyl-8-(3-(trifluoromethoxy)phenoxy)-1H-purine-2,6(3H,7H)-dione | 2.744 | 522 |

Example 335 7-(4-chlorobenzyl)-3-ethyl-1-(3-hydroxypropyl)-8-propoxy-1H-purine-2,6(3H,7H)-dione

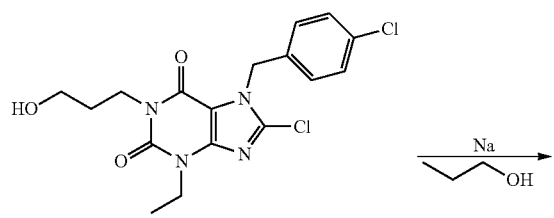

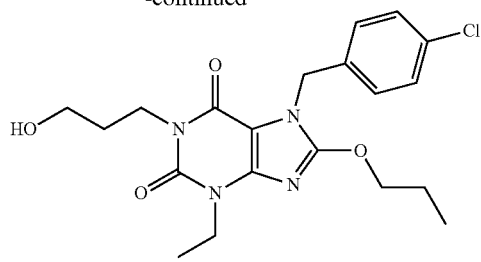

To a solution of 8-chloro-3-ethyl-7-(4-fluorobenzyl)-1-(3-hydroxypropyl)-1H-purine-2,6(3H,7H)-dione (50 mg, 0.117 mmol, intermediate 78) in propanol (5 mL) was added sodium (10 mg, 0.43 mmol). The reaction was stirred at room temperature for 1 h. The reaction was partitioned between ethyl acetate and brine. The organic phase was dried and concentrated to give a crude product, which was purified via preparative HPLC to give 7-(4-chlorobenzyl)-3-ethyl-1-(3-hydroxypropyl)-8-propoxy-1H-purine-2,6(3H,7H)-dione (11.6 mg, 24.4% yield) as white solid. $^1$H-NMR (CD$_3$OD) δ 7.24-7.29 (s, 4H), 5.21 (s, 2H), 4.39-4.42 (t, 2H), 3.98-4.05 (m, 4H), 3.49-3.53 (m, 2H), 1.73-1.81 (m, 4H), 1.20-1.23 (m, 3H), 0.90-0.94 (m, 3H). LCMS retention time 2.881; LCMS MH$^+$ 421.

The examples in Table 4 were prepared using the method of example 335.

TABLE 4

| Example | Structure | Chemical Name | LCMS retention time | LCMS M + 1 |
|---|---|---|---|---|
| 336 | 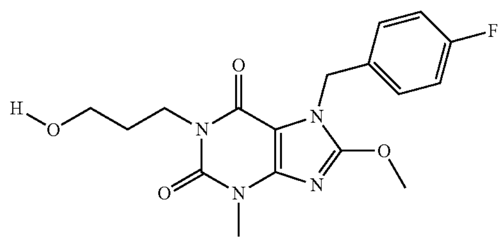 [SMILES: COc1nc2c(c(=O)n(CCCO)c(=O)n2C)n1Cc1ccc(F)cc1] | 7-(4-fluorobenzyl)-1-(3-hydroxypropyl)-8-methoxy-3-methyl-1H-purine-2,6(3H,7H)-dione | 2.156 | 363 |
| 337 | 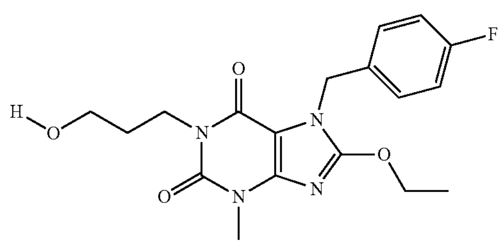 [SMILES: CCOc1nc2c(c(=O)n(CCCO)c(=O)n2C)n1Cc1ccc(F)cc1] | 8-ethoxy-7-(4-fluorobenzyl)-1-(3-hydroxypropyl)-3-methyl-1H-purine-2,6(3H,7H)-dione | 2.366 | 377 |
| 338 | 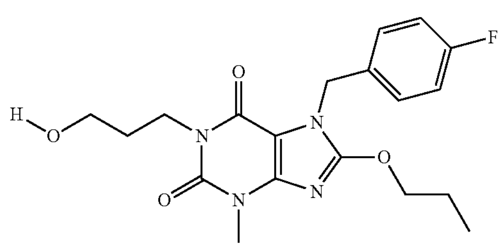 [SMILES: CCCOc1nc2c(c(=O)n(CCCO)c(=O)n2C)n1Cc1ccc(F)cc1] | 7-(4-fluorobenzyl)-1-(3-hydroxypropyl)-3-methyl-8-propoxy-1H-purine-2,6(3H,7H)-dione | 2.528 | 391 |
| 339 | 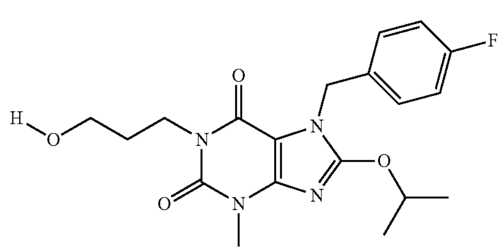 [SMILES: CC(C)Oc1nc2c(c(=O)n(CCCO)c(=O)n2C)n1Cc1ccc(F)cc1] | 7-(4-fluorobenzyl)-1-(3-hydroxypropyl)-8-isopropoxy-3-methyl-1H-purine-2,6(3H,7H)-dione | 2.570 | 391 |
| 340 | 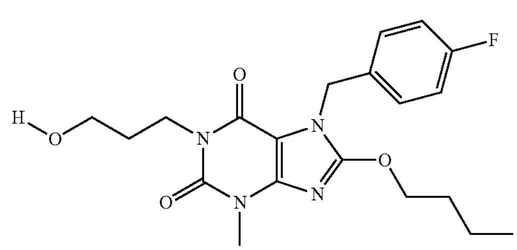 [SMILES: CCCCOc1nc2c(c(=O)n(CCCO)c(=O)n2C)n1Cc1ccc(F)cc1] | 8-butoxy-7-(4-fluorobenzyl)-1-(3-hydroxypropyl)-3-methyl-1H-purine-2,6(3H,7H)-dione | 2.804 | 405 |

TABLE 4-continued

| Example | Structure | Chemical Name | LCMS retention time | LCMS M + 1 |
|---|---|---|---|---|
| 341 | 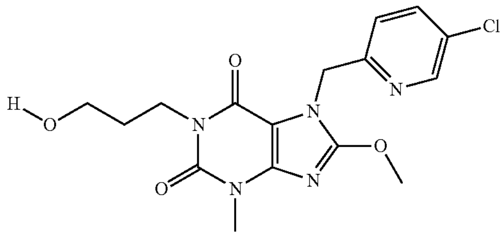 [SMILES: COc1nc2c(c(=O)n(CCCO)c(=O)n2C)n1Cc1ccc(Cl)cn1] | 7-((5-chloropyridin-2-yl)methyl)-1-(3-hydroxypropyl)-8-methoxy-3-methyl-1H-purine-2,6(3H,7H)-dione | 1.937 | 380 |
| 342 | 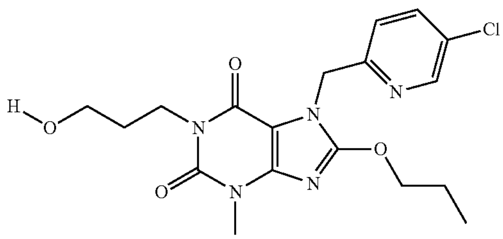 [SMILES: CCCOc1nc2c(c(=O)n(CCCO)c(=O)n2C)n1Cc1ccc(Cl)cn1] | 7-((5-chloropyridin-2-yl)methyl)-1-(3-hydroxypropyl)-3-methyl-8-propoxy-1H-purine-2,6(3H,7H)-dione | 2.319 | 408 |
| 343 | 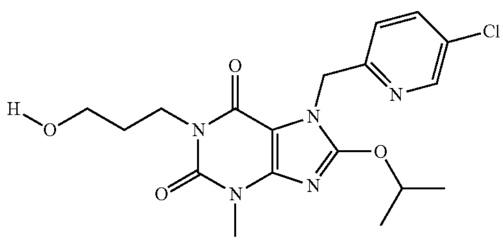 [SMILES: CC(C)Oc1nc2c(c(=O)n(CCCO)c(=O)n2C)n1Cc1ccc(Cl)cn1] | 7-((5-chloropyridin-2-yl)methyl)-1-(3-hydroxypropyl)-8-isopropoxy-3-methyl-1H-purine-2,6(3H,7H)-dione | 2.357 | 408 |
| 344 | 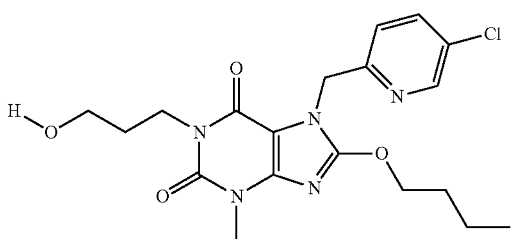 [SMILES: CCCCOc1nc2c(c(=O)n(CCCO)c(=O)n2C)n1Cc1ccc(Cl)cn1] | 8-butoxy-7-((5-chloropyridin-2-yl)methyl)-1-(3-hydroxypropyl)-3-methyl-1H-purine-2,6(3H,7H)-dione | 2.588 | 422 |
| 345 | 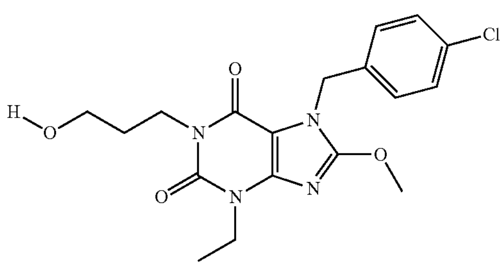 [SMILES: CCn1c(=O)n(CCCO)c(=O)c2c1nc(OC)n2Cc1ccc(Cl)cc1] | 7-(4-chlorobenzyl)-3-ethyl-1-(3-hydroxypropyl)-8-methoxy-1H-purine-2,6(3H,7H)-dione | 2.537 | 393 |
| 346 | 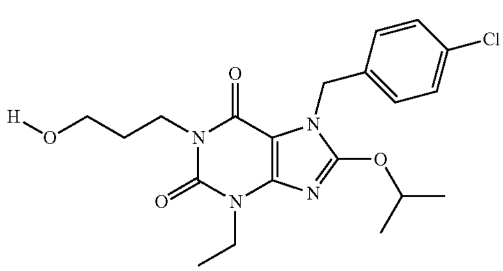 [SMILES: CCn1c(=O)n(CCCO)c(=O)c2c1nc(OC(C)C)n2Cc1ccc(Cl)cc1] | 7-(4-chlorobenzyl)-3-ethyl-1-(3-hydroxypropyl)-8-isopropoxy-1H-purine 2,6(3H,7H)-dione | 2.932 | 421 |

TABLE 4-continued

| Example | Structure | Chemical Name | LCMS retention time | LCMS M + 1 |
|---|---|---|---|---|
| 347 | 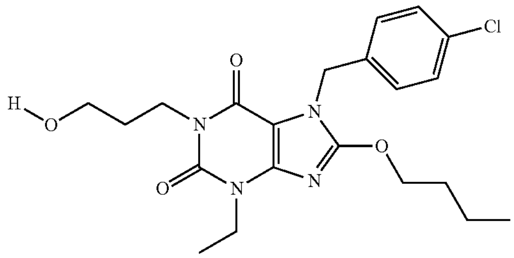 [SMILES: CCCCOc1nc2c(c(=O)n(CCCO)c(=O)n2CC)n1Cc1ccc(Cl)cc1] | 8-butoxy-7-(4-chlorobenzyl)-3-ethyl-1-(3-hydroxypropyl)-1H-purine-2,6(3H,7H)-dione | 3.171 | 435 |

Example 348 7-(4-Chlorobenzyl)-3-methyl-1-(2-oxopropyl)-8-(3-(trifluoromethoxy)phenoxy)-1H-purine-2,6(3H,7H)-dione

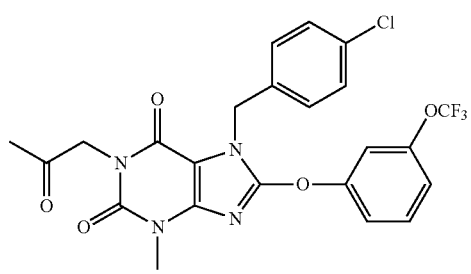

7-(4-Chlorobenzyl)-3-methyl-8-(3-(trifluoromethoxy)phenoxy)-1H-purine-2,6(3H,7H)-dione (0.25 g, 0.54 mmol, intermediate 9), potassium carbonate (0.11 g, 0.80 mmol), TBAI (0.10 g) and 1-chloropropan-2-one (0.040 mL, 0.59 mmol) were combined in DMF (3 mL) and heated at 50° C. for 1.5 h. The reaction was cooled to room temperature, diluted with water (100 mL) and extracted with ethyl acetate (3×75 mL). The combined organic extracts were washed with 1N lithium chloride (2×75 mL) dried with magnesium sulfate, filtered and evaporated under reduced pressure to an off-white solid. The solid was purified using a 25 g silica gel flash column eluted with 1% methanol/DCM to give 7-(4-chlorobenzyl)-3-methyl-1-(2-oxopropyl)-8-(3-(trifluoromethoxy)phenoxy)-1H-purine-2,6(3H,7H)-dione (0.22 g, 79% yield) as a white solid. LCMS retention time 4.433 minutes and 99% purity, LCMS MH+ 523. $^1$H NMR (DMSO-d$_6$) δ 7.60 (t, 1H, J=8 Hz), 7.50-7.53 (m, 1H), 7.38-7.47 (m, 5H), 7.32 (d, 1H, J=8 Hz), 5.40 (s, 2H), 4.73 (s, 2H) 3.28 (s, 3H), 2.19 (s, 3H).

Example 349 7-(4-Chlorobenzyl)-3-methyl-1-((3-methylisoxazol-5-yl)methyl)-8-(3-(trifluoromethoxy)phenoxy)-1H-purine-2,6(3H,7H)-dione

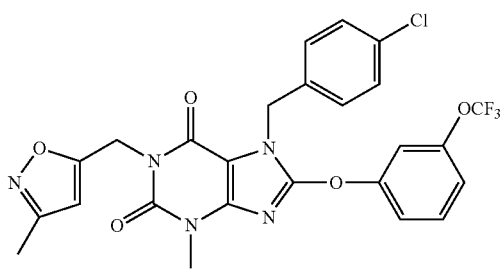 [SMILES: Cc1cc(Cn2c(=O)c3c(nc(Oc4cccc(OC(F)(F)F)c4)n3Cc3ccc(Cl)cc3)n(C)c2=O)on1]

The title compound was prepared using the method of example 348. White solid. LCMS retention time=4.601 minutes and 99% purity, LCMS MH+ 562. $^1$H NMR (DMSO-d$_6$) δ (DMSO-d$_6$) δ 7.60 (t, 1H, J=8 Hz), 7.47-7.51 (m, 1H), 7.40-7.45 (m, 5H), 7.32 (d, 1H, J=8 Hz), 6.20 (s, 1H), 5.43 (s, 2H), 5.13 (s, 2H), 3.30 (s, 3H), 2.17 (s, 3H).

Example 350 Ethyl-2(7-(4-chlorobenzyl)-3-methyl-2,6-dioxo-8-(3-(trifluoromethoxy)phenoxy)-2,3,6,7-tetrahydro-1H-purin-1-yl)acetate

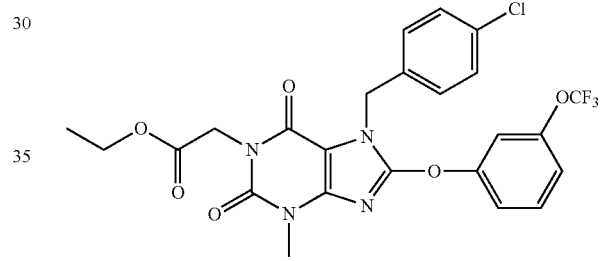

The title compound was prepared using the method of example 348. White solid. LCMS retention time=4.697 minutes and 99% purity, LCMS MH+ 553. $^1$H NMR (DMSO-d$_6$) δ 7.58 (t, 1H, J=8 Hz), 7.51-7.54 (m, 1H), 7.38-7.47 (m, 5H), 7.32 (d, 1H, J=12 Hz), 5.41 (s, 2H), 4.60 (s, 2H), 4.12 (dd, 2H, J=8 Hz and 16 Hz), 3.30 (s, 3H). 1.18 (t, 3H, J=8 Hz).

Example 351 7-(4-Chlorobenzyl)-1-(2-hydroxypropyl)-3-methyl-8-(3-(trifluoromethoxy)phenoxy)-1H-purine-2,6(3H,7H)-dione

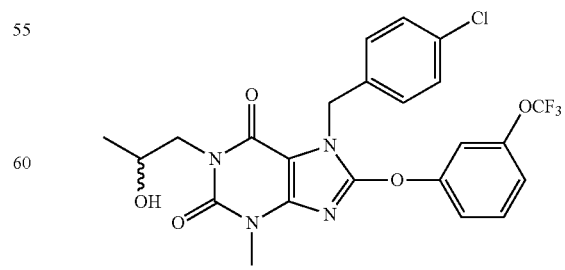

7-(4-Chlorobenzyl)-3-methyl-1-(2-oxopropyl)-8-(3-(trifluoromethoxy)phenoxy)-1H-purine-2,6(3H,7H)-dione (0.18 g, 0.35 mmol, example 348) was dissolved in methanol (3 mL) and cooled to 0° C. Then sodium borohydride (0.040 g, 1.05 mmol) was added portion wise over 20 minutes. The reaction was stirred in the cold for 2 h. The reaction solvent was removed under reduced pressure, then diluted with water (100 mL) and extracted with ethyl acetate (3×75 mL). The combined extracts were dried with magnesium sulfate, filtered and evaporated under reduced pressure to a light golden solid. Solid was purified using a 12 g silica gel flash column eluted with 1% methanol/DCM to give 7-(4-chlorobenzyl)-1-(2-hydroxypropyl)-3-methyl-8-(3-(trifluoromethoxy)phenoxy)-1H-purine-2,6(3H,7H)-dione (0.15 g, 79% yield) as a white solid. LCMS retention time=4.280 minutes and 97% purity, LCMS MH+ 525. 1H NMR (DMSO-d6) δ 7.59 (t, 1H, J=8 Hz), 7.46-7.48 (m, 1H), 7.38-7.43 (m, 5H), 7.31 (d, 1H, J=8 Hz), 5.43 (s, 2H), 4.65 (d, 1H, J=8 Hz), 3.90-3.95 (m, 2H), 3.68-3.74 (m, 1H), 3.28 (s, 3H), 1.02 (d, 3H, J=8 Hz).

Example 352 (S*)-1-(7-(4-chlorobenzyl)-3-methyl-2,6-dioxo-8-(3-trifluoromethoxy)phenoxy)-2,3,6,7-tetrahydro-1H-purin-1-yl)propan-2yl acetate

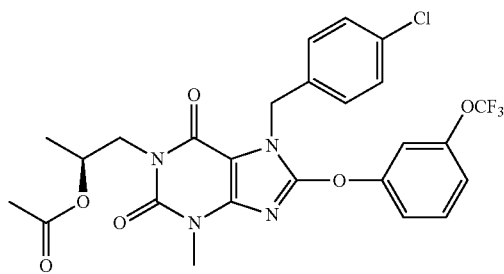 [SMILES: CC(=O)O[C@@H](C)Cn1c(=O)c2c(nc(Oc3cccc(OC(F)(F)F)c3)n2Cc2ccc(Cl)cc2)n(C)c1=O]

and (R*)-7-(4-chlorobenzyl)-1-(2-hydroxypropyl)-3-methyl-8-(3-(trifluoromethoxy)phenoxy)-2,6(3H,7H)-dione

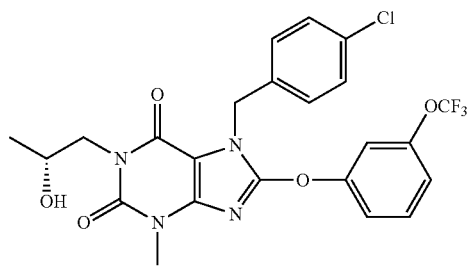 [SMILES: C[C@@H](O)Cn1c(=O)c2c(nc(Oc3cccc(OC(F)(F)F)c3)n2Cc2ccc(Cl)cc2)n(C)c1=O]

7-(4-Chlorobenzyl)-1-(2-hydroxypropyl)-3-methyl-8-(3-(trifluoromethoxy)phenoxy)-1H-purine-2,6(3H,7H)-dione (0.25 g, 0.48 mmol, example 351), vinyl acetate (0.15 mL, 1.67 mmol) and candida antartica acrylic resin ("Novozym") (0.14 g) were combined in ethyl acetate (5 mL) and stirred at room temperature for 24 h. The reaction was filtered and the filtrate was evaporated under reduced pressure to a clear oil. The oil was purified using a 25 g silica gel flash column eluted with a gradient of 20% to 30% ethyl acetate/hexanes to yield both (S*)-1-(7-(4-chlorobenzyl)-3-methyl-2,6-dioxo-8-(3-trifluoromethoxy)phenoxy)-2,3,6,7-tetrahydro-1H-purin-1-yl)propan-2yl acetate (0.12 g, 91% yield). LCMS retention time=4.448 minutes and 94% purity, LCMS MH+ 567. 1H NMR (DMSO-d6) δ 7.60 (t, 1H, J=8 Hz), 7.48-7.54 (m, 1H), 7.38-7.45 (m, 5H), 7.32 (d, 1H, J=8 Hz), 5.42 (s, 2H), 5.10-5.19 (m, 1H), 4.13-4.22 (m, 1H), 3.85 (dd, 1H, J=4 Hz and 12 Hz), 3.27 (s, 3H), 1.79 (s, 3H), 1.17 (d, 3H, J=4 Hz) and (R*)-7-(4-chlorobenzyl)-1-(2-hydroxypropyl)-3-methyl-8-(3-(trifluoromethoxy)phenoxy)-2,6(3H,7H)-dione (0.11 g, 88% yield) as a clear oil. LCMS retention time=4.019 minutes and 95% purity, LCMS MH+=525. 1H NMR (DMSO-d6) δ 7.59 (t, 1H, J=8 Hz), 7.45-7.48 (m, 1H), 7.39-7.44 (m, 5H), 7.31 (d, 1H, J=8 Hz), 5.43 (s, 2H), 4.65 (d, 1H, J=4 Hz), 3.89-4.00 (m, 2H), 3.67-3.74 (m, 1H), 3.28 (s, 3H), 1.02 (d, 3H, J=8 Hz).

Example 353 2-(7-(4-Chlorobenzyl)-3-methyl-3-methyl-2,6-dioxo-8-(3-(trifluoromethoxy)phenoxy)-2,3,6,7-tetrahydro-1H-purin-1-yl)-N-methylacetamide

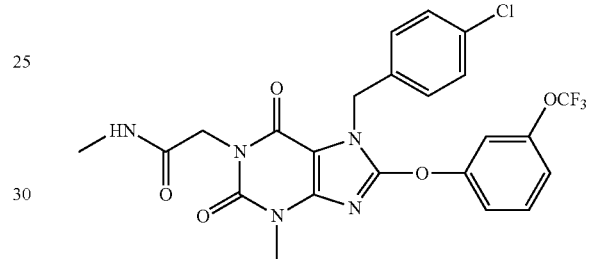

The title compound was prepared using the method of example 348 but with heating at 50° C. for 15 h. White solid: 0.18 g, 63% yield: LCMS retention time=4.084 minutes and 99% purity, LCMS MH+ 538. 1H NMR (DMSO-d6) δ 7.92-7.98 (m, NH), 7.60 (t, 1H, J=8 Hz), 7.47-7.51 (m, 1H), 7.38-7.45 (m, 5H), 7.29-7.34 (d, 1H, J=8 Hz), 5.42 (s, 2H), 4.41 (s, 2H), 3.28 (s, 3H), 2.57 (d, 3H, J=4 Hz).

Example 354 7-(4-Chlorobenzyl)-3-methyl-1-(thiazol-5-ylmethyl)-8-(3-(trifluoromethoxy)phenoxy)-1H-purine-2,6(3H,7H)-dione

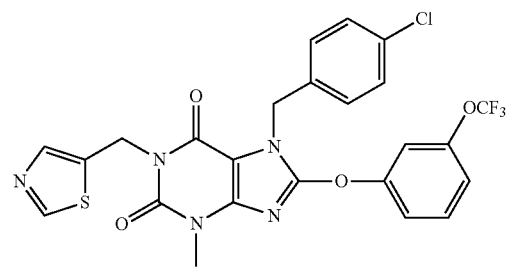 [SMILES: Cn1c(=O)n(Cc2cncs2)c(=O)c2c1nc(Oc1cccc(OC(F)(F)F)c1)n2Cc1ccc(Cl)cc1]

The title compound was prepared using the method of example 348 but with heating at 50° C. for 3 h. White solid, 0.088 g, 29% yield: LCMS retention time=4.552 minutes and 99% purity, LCMS MH+ 564. 1H NMR (DMSO-d6) δ 8.97 (s, 1H), 7.85 (s, 1H), 7.58 (t, 1H, J=8 Hz), 7.46-7.48 (m, 1H), 7.39-7.43 (m, 5H), 7.30 (d, 1H, J=12 Hz), 5.43 (s, 2H), 5.24 (s, 2H), 3.29 (s, 3H).

Example 355 7-(4-Chlorobenzyl)-1-(2-hydroxy-2-methylpentyl)-3-methyl-8-(3-(trifluoromethoxy)phenoxy)-1H-purine-2,6(3H,7H)-dione

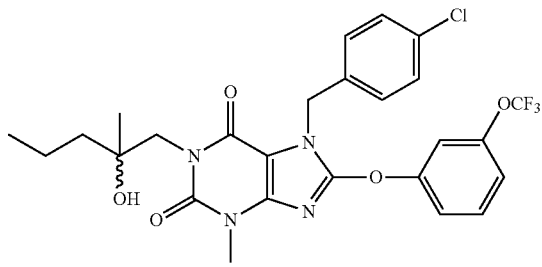 [SMILES: CCCC(C)(O)Cn1c(=O)c2c(nc(Oc3cccc(OC(F)(F)F)c3)n2Cc2ccc(Cl)cc2)n(C)c1=O]

7-(4-Chlorobenzyl)-3-methyl-1-(2-oxopropyl)-8-(3-(trifluoromethoxy)phenoxy)-1H-purine-2,6(3H,7H)-dione (0.25 g, 0.48 mmol, example 348) was dissolved in THF (6 mL), cooled to 0° C. and 2.0 M propyl magnesium bromide in THF (0.36 mL, 0.72 mmol) was added drop wise. The reaction was stirred in the cold for 15 min then warmed to room temperature and stirred 1 h. The reaction was diluted with water (100 mL) and extracted with ethyl acetate (3×75 mL). The combined extracts were dried with magnesium sulfate, filtered and evaporated under reduced pressure to a golden oil. The oil was purified using a 25 g silica gel flash column eluted with 20% ethyl acetate/hexanes to give 7-(4-chlorobenzyl)-1-(2-hydroxy-2-methylpentyl)-3-methyl-8-(3-(trifluoromethoxy)phenoxy)-1H-purine-2,6(3H,7H)-dione (0.88 g, 32% yield) as a clear oil. LCMS retention time=4.792 minutes and 98% purity, LCMS MH+=567. $^1$H NMR (DMSO-$d_6$) δ 7.59 (t, 1H, J=8 Hz), 7.47-7.50 (m, 1H), 7.38-7.44 (m, 5H), 7.31 (d, 1H, J=8 Hz), 5.42 (s, 2H), 4.23 (s, 1H) 3.92-4.02 (dd, 2H, J=4 Hz and 16 Hz), 3.29 (s, 3H), 1.30-1.41 (m, 4H), 0.99 (s, 3H), 0.80 (t, 3H, J=8 Hz).

Example 356 7-(4-Chlorobenzyl)-1-(3-hydroxypropyl)-3-methyl-8-(3-trifluoromethoxy)phenoxy)-1H-purine-2,6(3H,7H)-dione

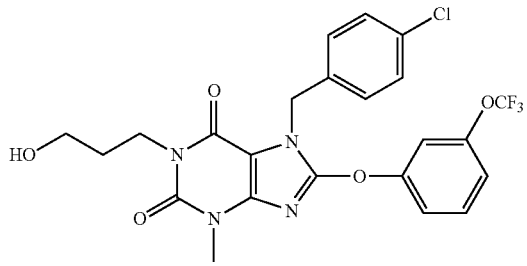

Step 1 7-(4-chlorobenzyl)-3-methyl-8-(3-(trifluoromethoxy)phenoxy)-1H-2,6(3H,7H)-dione (3.73 g, 7.99 mmol, intermediate 9) and potassium carbonate (1.66 g, 11.99 mmol) were combined in DMF (56 mL) and (3-bromopropoxy)(tert-butyl)dimethylsilane (2.43 g, 9.59 mmol) was added. The reaction was heated at 100° C. After heating for 3 h the reaction was cooled, diluted with water (200 mL) and extracted with ethyl acetate (3×200 ml). The combined extracts were washed with 1N lithium chloride (2×100 mL), dried with magnesium sulfate and evaporated under reduced pressure to provide 1-(3-((tert-butyldimethylsilyl)oxy)propyl)-7-(4-chlorobenzyl)-3-methyl-8-(3-trifluoromethoxy)phenoxy)-1H-purine-2,6(3H,7H)-dione (5.7 g crude) as a light golden oil. LCMS retention time=5.646 and 98% purity, LCMS MH+ 639.

Step 2 1-(3-(((tert-Butyldimethylsilyl)oxy)propyl)-7-(4-chlorobenzyl)-3-methyl-8-(3-(trifluoromethoxy)phenoxy)-1H-purine-2,6(3H,7H)-dione (5.7 g crude, 7.99 mmol) was dissolved in ethanol (40 mL) and 6N aqueous HCl (4 mL) was added. The clear solution was stirred at room temperature. After 1 h the reaction was evaporated under reduce pressure, diluted with water (200 mL) and extracted with ethyl acetate (3×100 mL). The combined extracts were dried with magnesium sulfate, filtered and evaporated under reduced pressure to a clear oil. The oil was purified using an 80 g silica gel flash column eluted with 1:1 ethyl acetate/hexanes to provide 7-(4-chlorobenzyl)-1-(3-hydroxypropyl)-3-methyl-8-(3-trifluoromethoxy)phenoxy)-1H-purine-2,6(3H,7H)-dione (3.8 g, 90.9% yield) as a white crystalline solid. LCMS retention time=3.955 and 100% purity, LCMS MH+ 525. $^1$HNMR (DMSO-$d_6$) δ 7.59 (t, 1H, J=2 Hz), 7.47 (s, 1H), 7.41 (s, 4H), 7.41 (m, 1H), 7.31 (d, 1H, J=2 Hz), 5.42 (s, 2H), 4.44 (t, OH, J=1 Hz), 3.92 (t, 2H, J=1 Hz), 3.41 (m, 2H), 3.28 (s, 3H), 1.68 (m, 2H).

Example 357 1-(3-Aminopropyl)-7-(4-chlorobenzyl)-3-methyl-8-(3-(trifluoromethoxy)phenoxy)-1H-purine-2,6(3H,7H)-dione hydrochloride

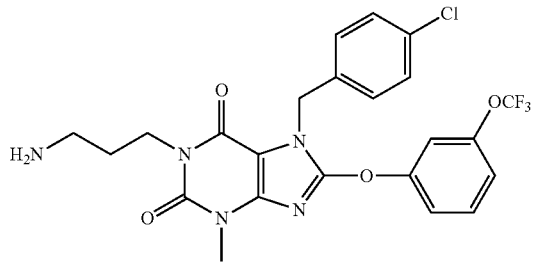 [SMILES: Cn1c(=O)n(CCCN)c(=O)c2c1nc(Oc1cccc(OC(F)(F)F)c1)n2Cc1ccc(Cl)cc1]

Step 1 7-(4-Chlorobenzyl)-3-methyl-8-(3-(trifluoromethoxy)phenoxy)-1H-purine-2,6(3H,7H)-dione (1.0 g, 2.14 mmol, intermediate 9), 2-(3-bromopropyl)isoindoline-1,3-dione (0.63 g, 2.36 mmol), potassium carbonate (0.44 g, 3.21 mmol) and TBAI (0.040 g) were combined in DMF (20 mL) and heated at 100° C. for 3 h. The reaction was cooled to room temperature, diluted with water (200 mL) and extracted with ethyl acetate (3×100 mL). The combined organic extracts were washed with 1N lithium chloride (2×100 mL), dried with magnesium sulfate, filtered and the solvent removed under reduced pressure to give a clear oil. The oil was purified using an 80 g silica gel flash column eluted with a gradient of 25% to 50% ethyl acetate/hexanes to give 7-(4-chlorobenzyl)-1-(3-(1,3-dioxoisoindolin-2-yl)propyl)-3-methyl-8-(3-(trifluoromethoxy)phenoxy)-1H-purine-2,6(3H,7H)-dione (1.4 g, 100% yield) as a white solid. LCMS retention time=4.660 minutes and 100% purity, LCMS MH+ 654. $^1$H NMR (CDCl$_3$) δ 7.78-7.83 (m, 2H), 7.65-7.70 (m, 2H), 7.41 (t, 1H, J=8 Hz), 7.32 (dd, 4H, J=12 Hz and 28 Hz), 7.10-7.23 (m, 4H), 5.35 (s, 2H), 4.05-4.14 (m, 2H), 3.76 (t, 2H, J=8 Hz), 3.38 (s, 3H), 2.01-2.11 (m, 2H).

Step 2 7-(4-Chlorobenzyl)-1-(3-(1,3-dioxoisoindolin-2-yl)propyl)-3-methyl-8-(3-(trifluoromethoxy)phenoxy)-1H- purine-2,6(3H,7H)-dione (1.4 g, 2.14 mmol) was slurried in ethanol (20 mL) and hydrazine hydrate (0.42 mL, 8.56 mmol) was added and the reaction was heated at reflux. The reaction at reflux changed to a clear solution then after 30 min setup as a white mass. The reaction was cooled to room temperature, diluted with water (100 mL) and extracted with DCM (3×75 mL). The combined organic extracts were dried with magnesium sulfate, filtered and the solvent removed under reduced pressure to give an oil. The oil was purified using a 40 g silica gel flash column eluted with 10% methanol/DCM to give a light tan solid. Solid was dissolved in DCM (5 mL) and excess 1N HCl/diethyl ether was added. The solvent was removed under reduced pressure to give 1-(3-aminopropyl)-7-(4-chlorobenzyl)-3-methyl-8-(3-(trifluoromethoxy)phenoxy)-1H-purine-2,6(3H,7H)-dione hydrochloride (0.87 g, 49% yield) as a tan solid. LCMS retention time=2.802 minutes and 97% purity, LCMS MH+ 524. $^1$H NMR (DMSO-$d_6$) δ 7.91-8.11 (brd s, NH$_2$ and HCl), 7.60 (t, 1H, J=8 Hz), 7.38-7.48 (m, 6H), 7.31 (d, 1H, J=12 Hz), 5.43 (s, 2H), 3.93 (t, 2H, J=8 Hz), 3.29 (s, 3H), 2.73-2.85 (m, 2H), 1.83-1.94 (m, 2H).

Example 358 1-(2-Aminoethyl)-7-(4-chlorobenzyl)-3-methyl-8-(3-(trifluoromethoxy)phenoxy)-1H-purine-2,6(3H,7H)-dione hydrochloride

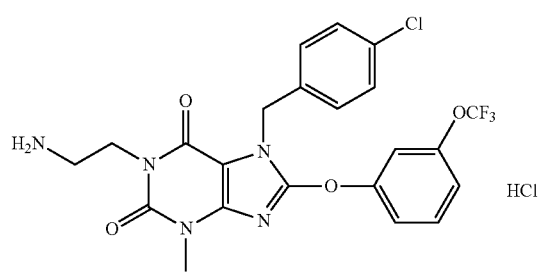 [SMILES: Cn1c(=O)n(CCN)c(=O)c2c1nc(Oc1cccc(OC(F)(F)F)c1)n2Cc1ccc(Cl)cc1 ; Cl]

The title compound was prepared using the method of example 357. White solid, 0.062 g, 33% yield: LCMS retention time=2.802 minutes and 99% purity, LCMS MH+ 510. $^1$H NMR (DMSO-$d_6$) δ 7.82-7.99 (brd s, NH$_2$ and HCl), 7.62 (t, 1H, J=8 Hz), 7.38-7.48 (m, 6H), 7.31 (d, 1H, J=12 Hz), 5.43 (s, 2H), 4.11 (m, 2H) 3.29 (s, 3H), 2.99-2.15 (m, 2H).

Example 359 N-(3-(7-(4-chlorobenzyl)-3-methyl-2,6-dioxo-8-(3-(trifluoromethoxy)phenoxy)-2,3,6,7-tetrahydro-1H-purin-1-yl)propyl)acetamide Notebook: C5-0249-047

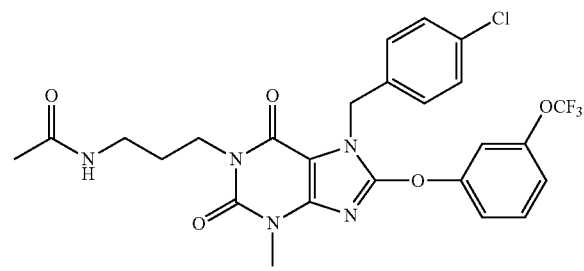 [SMILES: CC(=O)NCCCn1c(=O)c2c(nc(Oc3cccc(OC(F)(F)F)c3)n2Cc2ccc(Cl)cc2)n(C)c1=O]

1-(3-Aminopropyl)-7-(4-chlorobenzyl)-3-methyl-8-(3-(trifluoromethoxy)phenoxy)-1H-purine-2,6(3H,7H)-dione (0.10 g, 0.19 mmol, example 357) and TEA (0.80 mL, 0.57 mmol) were combined in THF (1 mL). Acetyl chloride (0.28 mL, 0.42 mmol) was added and the reaction was stirred at room temperature for 4 h. The reaction was diluted with water (100 mL) and extracted with ethyl acetate (3×75 mL). The combined extracts were dried with magnesium sulfate, filtered and evaporated under reduced pressure to an oil. The oil was purified using a 2000 micron preparative TLC plate eluted with 5% methanol/DCM. Target band was scraped off plate and eluted off silica gel with eluent to give N-(3-(7-(4-chlorobenzyl)-3-methyl-2,6-dioxo-8-(3-(trifluoromethoxy)phenoxy)-2,3,6,7-tetrahydro-1H-purin-1-yl)propyl)acetamide (0.053 g, 49% yield) as a light tan solid. LCMS retention time=3.789 minutes and 99% purity, LCMS MH+ 566. $^1$H NMR (DMSO-$d_6$) δ 7.78-7.82 (m, 1H), 7.59 (t, 1H, J=8 Hz), 7.44-7.48 (m, 1H), 7.38-7.42 (m, 5H), 7.31 (d, 1H, J=8 Hz), 5.42 (s, 2H), 3.87 (t, 2H, J=8 Hz), 3.28 (s, 3H), 2.04 (dd, 2H, J=4 Hz and 12 Hz), 1.78 (s, 3H), 1.61-1.70 (m, 2H).

Example 360 N-(3-(7-(4-chlorobenzyl)-3-methyl-2,6-dioxo-8-(3-(trifluoromethoxy)phenoxy)-2,3,6,7-tetrahydro-1H-purin-1-yl)propyl)methanesulfonamide

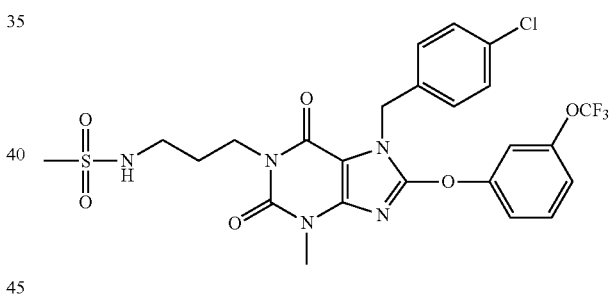

1-(3-Aminopropyl)-7-(4-chlorobenzyl)-3-methyl-8-(3-(trifluoromethoxy)phenoxy)-1H-purine-2,6(3H,7H)-dione (0.10 g, 0.19 mmol, example 357) and TEA (0.80 mL, 0.57 mmol) were combined in THF (1 mL). Methanesulfonyl chloride (0.30 mL, 0.38 mmol) was added and the reaction was stirred at room temperature for 3 h. The reaction was diluted with water (100 mL) and extracted with ethyl acetate (3×75 mL). The combined extracts were dried with magnesium sulfate, filtered and evaporated under reduced pressure to an oil. The oil was purified using a 2000 micron preparative TLC plate eluted with 5% methanol/DCM. Target band was scraped off plate and eluted off silica gel with eluent to give N-(3-(7-(4-chlorobenzyl)-3-methyl-2,6-dioxo-8-(3-(trifluoromethoxy)phenoxy)-2,3,6,7-tetrahydro-1H-purin-1-yl)propyl)methanesulfonamide (0.045 g, 39% yield) as a tan solid. LCMS retention time=4.048 minutes and 99% purity, LCMS MH+ 602. $^1$H NMR (DMSO-$d_6$) δ 7.59 (t, 1H, J=8 Hz), 7.45-7.48 (m, 1H), 7.39-7.43 (m, 5H), 7.31 (d, 1H, J=8 Hz), 6.96 (t, 1H), 5.43 (s, 2H), 3.91 (t, 2H, J=8 Hz), 3.29 (s, 3H), 2.96 (dd, 2H, J=4 Hz and 12 Hz), 2.87 (s, 3H), 1.69-1.79 (m, 2H).

Example 361 2-(7-(4-Chlorobenzyl)-3-methyl-2,6-dioxo-8-(3-(trifluoromethoxy)phenoxy)-2,3,6,7-tetrahydro-1H-purin-1-yl)acetic acid

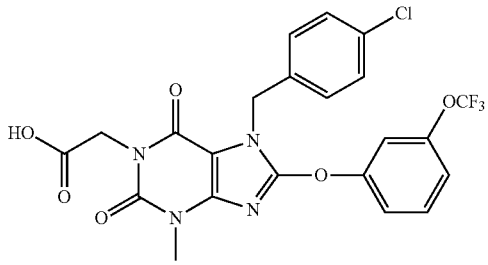 [SMILES: Cn1c(=O)n(CC(=O)O)c(=O)c2c1nc(Oc1cccc(OC(F)(F)F)c1)n2Cc1ccc(Cl)cc1]

Step 1 7-(4-Chlorobenzyl)-3-methyl-8-(3-(trifluoromethoxy)phenoxy)-1H-purine-2,6(3H,7H)-dione (1.0 g, 2.14 mmol, intermediate 9), tert-butyl 2-bromoacetate (0.34 mL, 2.36 mmol), and potassium carbonate (0.45 g, 3.21 mmol) were combined in DMF (20 mL) and heated at 50° C. for 2 h. The reaction was cooled to room temperature diluted with water (200 mL) and extracted with ethyl acetate (3×100 mL). The combined extracts were washed with 1N lithium chloride (2×100 mL), dried with magnesium sulfate, filtered and evaporated under reduced pressure to give tert-butyl-2-(7-(4-chlorobenzyl)-3-methyl-2,6-dioxo-8-(3-(trifluoromethoxy)phenoxy)-2,3,6,7-tetrahydro-1H-purin-1-yl)acetate (1.24 g, 100% yield) as a clear oil. LCMS retention time=4.817 minutes and 97% purity, LCMS MH+ 581.

Step 2 tert-Butyl-2-(7-(4-chlorobenzyl)-3-methyl-2,6-dioxo-8-(3-(trifluoromethoxy)phenoxy)-2,3,6,7-tetrahydro-1H-purin-1-yl)acetate (0.20 g, 0.34 mmol) was dissolved in DCM (4 mL) and TFA (0.26 ml, 3.4 mmol) was added. The reaction was stirred at room temperature for 15 h then evaporated under reduced pressure to give 2-(7-(4-chlorobenzyl)-3-methyl-2,6-dioxo-8-(3-(trifluoromethoxy)phenoxy)-2,3,6,7-tetrahydro-1H-purin-1-yl)acetic acid (0.18 g, 100% yield). LCMS retention time=3.915 minutes and 97% purity, LCMS MH+ 525. $^1$H NMR (DMSO-$d_6$) δ 7.59 (t, 1H, J=8 Hz), 7.50-7.54 (m, 1H), 7.45 (d, 1H, J=8 Hz), 7.41 (s, 4H), 7.31 (d, 1H, J=8 Hz), 5.41 (s, 2H), 4.52 (s, 2H), 3.30 (s, 3H)

Example 362 2-(7-(4-Chlorobenzyl)-3-methyl-2,6-dioxo-8-(3-(trifluoromethoxy)phenoxy)-2,3,6,7-tetrahydro-1H-purin-1-yl)-N-propylacetamide

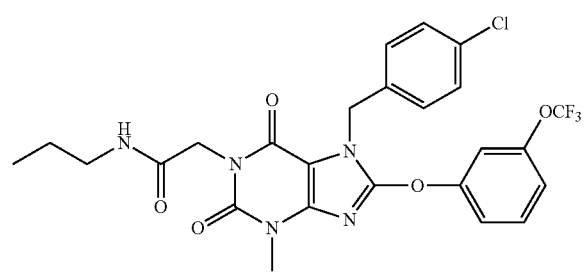 [SMILES: CCCNC(=O)Cn1c(=O)c2c(nc(Oc3cccc(OC(F)(F)F)c3)n2Cc2ccc(Cl)cc2)n(C)c1=O]

2-(7-(4-Chlorobenzyl)-3-methyl-2,6-dioxo-8-(3-(trifluoromethoxy)phenoxy)-2,3,6,7-tetrahydro-1H-purin-1-yl)acetic acid (0.25 g, 0.48 mmol, Example 361) and CDI (0.93 g, 0.57 mmol) were combined in DMF (4 mL) and stirred at room temperature for 20 min. Propan-1-amine was added and the reaction was stirred at room temperature for 3 h. The reaction was diluted with water (100 mL) and extracted with ethyl acetate (3×75 mL). The combined extracts were washed with 1N lithium chloride (2×75 mL), dried with magnesium sulfate, filtered and evaporated under reduced pressure to a white solid. Solid was purified using a 25 g silica gel flash column eluted with 1% methanol/DCM to give 2-(7-(4-chlorobenzyl)-3-methyl-2,6-dioxo-8-(3-(trifluoromethoxy)phenoxy)-2,3,6,7-tetrahydro-1H-purin-1-yl)-N-propylacetamide (0.13 g, 47% yield) as a white solid. LCMS retention time=4.070 min and 99% purity, LCMS MH+ 566. $^1$H NMR (DMSO-$d_6$) δ 7.99 (t, NH), 7.60 (t, 1H, J=8 Hz), 7.48-7.52 (m, 1H), 7.39-7.46 (m, 5H), 7.32 (d, 1H, J=8 Hz), 5.42 (s, 2H), 4.42 (s, 2H), 3.31 (s, 3H), 3.00 (dd, 2H, J=8 Hz and 16 Hz), 1.34-1.45 (m, 2H), 0.83 (t, 3H, J=8 Hz).

Example 363 7-(4-Chlorobenzyl)-3-methyl-1-(2-oxobutyl)-8-(3-(trifluoromethoxy)phenoxy)-1H-purine-2,6(3H,7H)-dione

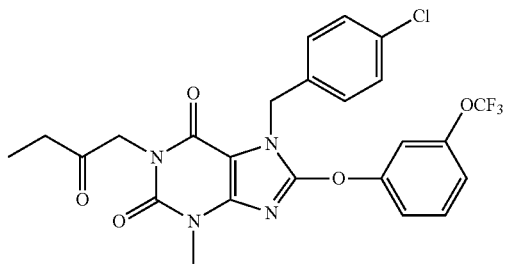 [SMILES: CCC(=O)Cn1c(=O)c2c(nc(Oc3cccc(OC(F)(F)F)c3)n2Cc2ccc(Cl)cc2)n(C)c1=O]

The title compound was prepared using the method of example 348. White solid, 0.49 g, 85% yield: LCMS retention time=4.408 min and 99% purity, LCMS MH+ 537. $^1$H NMR (DMSO-$d_6$) δ 7.60 (t, 1H, J=8 Hz), 7.51-7.54 (m, 1H), 7.37-7.47 (m, 5H), 7.30-7.33 (m, 1H), 5.40 (s, 2H), 4.72 (s, 2H), 3.28 (s, 3H), 2.55 (dd, 2H, J=8 Hz and 16 Hz), 0.96 (t, 3H, J=8 Hz).

Example 364 7-(4-Chlorobenzyl)-8-ethoxy-1-(3-hydroxypropyl)-3-methyl-1H-purine-2,6(3H,7H)-dione

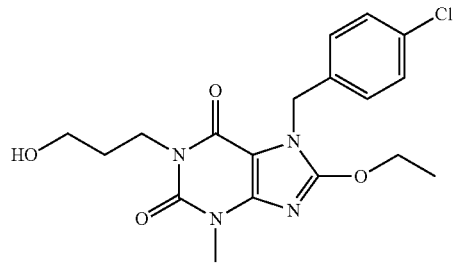 [SMILES: CCOc1nc2c(c(=O)n(CCCO)c(=O)n2C)n1Cc1ccc(Cl)cc1]

Step 1 Sodium (0.35 g, 15.03 mmol) was dissolved in ethanol (30 mL) and 8-bromo-7-(4-chlorobenzyl)-3-methyl-1H-purine-2,6(3H,7H)-dione (1.63 g, 3.01 mmol, intermediate 77) was added and the reaction was stirred at room temperature for 24 h. The reaction was evaporated to dryness under reduced pressure, diluted with water (100 mL) and extracted with ethyl acetate (3×75 mL). The combined extracts were dried with magnesium sulfate, filtered and the solvent was removed under reduced pressure to give 1-(3-((tert-butyldimethylsilyl)oxy)propyl)-7-(4-chlorobenzyl)-8-ethoxy-3-methyl-1H-purine-2,6(3H,7H)-dione (1.5 g, 100% yield) as a light golden oil. LCMS retention time=5.317 min and 95% purity, LCMS MH+ 507.

Step 2 7-(4-Chlorobenzyl)-8-ethoxy-1-(3-hydroxypropyl)-3-methyl-1H-purine-2,6(3H,7H)-dione (1.5 g, 3.01 mmol) was dissolved in ethanol (20 mL) and 6N aqueous HCl (4 mL) was added. The clear solution was stirred at room temperature for 1 h. The reaction was diluted with water (150 mL) and extracted with DCM (3×100 mL). The combined extracts were dried with magnesium sulfate, filtered and the solvent was removed under reduced pressure to an off-white solid. The solid was purified using an 80 g silica gel flash column eluted with 2% methanol/DCM which gave 7-(4-chlorobenzyl)-8-ethoxy-1-(3-hydroxypropyl)-3-methyl-1H-purine-2,6(3H,7H)-dione (1.0 g, 84% yield) as a white solid. LCMS retention time=3.173 min and 98% purity, LCMS MH+ 393. $^1$H NMR (DMSO-$d_6$) δ 7.35 (dd, 4H, J=4 Hz and 12 Hz), 5.20 (s, 2H), 4.47 (dd, 2H, J=8 Hz and 16 Hz), 4.43 (t, 1H, J=4 Hz)), 3.88 (t, 2H, J=8 Hz), 3.40 (dd, 2H, J=4 Hz and 12 Hz), 3.36 (s, 3H), 1.62-1.71 (m, 2H), 1.33 (t, 3H, J=8 Hz).

Example 365 7-(4-Chlorobenzyl)-1-(2-hydroxybutyl)-3-methyl-8-(3-(trifluoromethoxy)phenoxy)-1H-purine-2,6(3H,7H)-dione

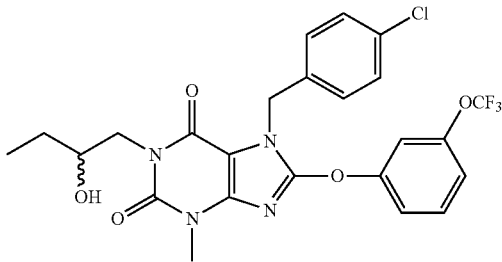 [SMILES: CCC(O)Cn1c(=O)c2c(nc(Oc3cccc(OC(F)(F)F)c3)n2Cc2ccc(Cl)cc2)n(C)c1=O]

7-(4-Chlorobenzyl)-3-methyl-1-(2-oxobutyl)-8-(3-(trifluoromethoxy)phenoxy)-1H-purine-2,6(3H,7H)-dione (0.44 g, 0.82 mmol, example 363) was dissolved in methanol (8 mL) and DCM (1 mL), then cooled to 0° C. Sodium borohydride (0.93 g, 2.46 mmol) was added portion wise over 20 min and reaction was stirred in the cold for 2 h. The reaction solvent was removed under reduced pressure then the mixture was diluted with water (100 mL) and extracted with ethyl acetate (3×75 mL). The combined organic extracts were dried with magnesium sulfate, filtered and the solvent removed under reduced pressure to give a clear oil. The oil was purified using an 40 g silica gel flash column eluted with 1% methanol/DCM to give 7-(4-chlorobenzyl)-1-(2-hydroxybutyl)-3-methyl-8-(3-(trifluoromethoxy)phenoxy)-1H-purine-2,6(3H,7H)-dione (0.32 g, 73% yield) as a white solid. LCMS retention time=4.265 min and 97% purity, LCMS MH+ 539. $^1$H NMR (DMSO-$d_6$) δ 7.59 (t, 1H, J=8 Hz), 7.45-7.48 (m, 1H), 7.38-7.45 (m, 5H), 7.30 (d, 1H, J=12 Hz), 5.43 (s, 2H), 4.56 (d, 1H, J=4 Hz), 3.92-4.00 (m, 1H), 3.65-3.76 (m, 2H), 3.28 (s, 3H), 1.23-1.41 (m, 2H).

Example 366 7-(4-Chlorobenzyl)-1-(3-hydroxypropyl)-3-methyl-8-(propylamino)-1H-purine-2,6(3H,7H)-dione hydrochloride

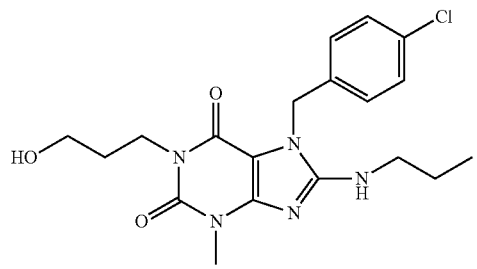 [SMILES: CCCNc1nc2c(c(=O)n(CCCO)c(=O)n2C)n1Cc1ccc(Cl)cc1]

Step 1 8-Bromo-1-(3-((tert-butyldimethylsilyl)oxy)propyl)-7-(4-chlorobenzyl)-3-methyl-1H-purine-2,6(3H,7H)-dione (0.25 g, 0.46 mmol, intermediate 77) and propan-1-amine (1.44 mL, 9.2 mmol) were combined in ethanol (5 mL) and heated at reflux for 24 h. The reaction was cooled to room temperature, diluted with water (75 mL) and extracted with ethyl acetate (3×75 mL). The combined organic extracts were dried with magnesium sulfate, filtered and the solvent evaporated under reduced pressure to yield a light golden oil. The oil was purified using a 25 g silica gel column eluted with 20% ethyl acetate/hexanes to give 1-(3-((tert-butyldimethylsilyl)oxy)propyl-7-(4-chlorobenzyl)-3-methyl-8-(propylamino)-1H-purine-2,6(3H,7H)-dione (0.15 g, 63% yield) as a white solid. LCMS retention time=5.013 min and 97% purity, LCMS MH+ 520.

Step 2 1-(3-((tert-Butyldimethylsilyl)oxy)propyl-7-(4-chlorobenzyl)-3-methyl-8-(propylamino)-1H-purine-2,6(3H,7H)-dione (0.15 g, 0.29 mmol) was dissolved in ethanol (3 mL) and 6N aqueous HCl (0.5 mL) was added. The clear solution was stirred at room temperature for 1 h. The reaction solvent was removed under reduced pressure to give 7-(4-chlorobenzyl)-1-(3-hydroxypropyl)-3-methyl-8-(propylamino)-1H-purine-2,6(3H,7H)-dione hydrochloride (0.13 g, 100% yield) as a white foam. LCMS retention time=3.021 min and 99% purity, LCMS MH+ 406. $^1$H NMR (DMSO-$d_6$) δ 7.31 (dd, 4H, J=8 Hz and 42 Hz), 6.15-6.48 (brd s, NH$_2$ and HCl), 5.30 (s, 2H), 3.84 (t, 2H, J=8 Hz), 3.38 (t, 2H, J=8 Hz), 3.34 (s, 3H), 3.26 (t, 2H, J=8 Hz), 1.59-1.68 (m, 2H), 1.46-1.57 (m, 2H), 0.81 (s, 3H, J=8 Hz).

Example 367 7-(4-Chlorobenzyl)-1-(3-hydroxypropyl)-3-methyl-8-propoxy-1H-purine-2,6(3H,7H)-dione

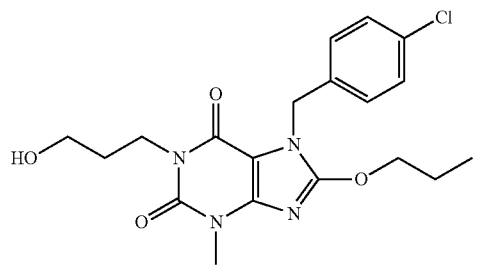 [SMILES: CCCOc1nc2c(c(=O)n(CCCO)c(=O)n2C)n1Cc1ccc(Cl)cc1]

The title compound was prepared using the method of example 364. White solid, 0.14 g, 78% yield: LCMS retention time=2.914 min and 98% purity, LCMS MH+ 379. $^1$H NMR (DMSO-$d_6$) δ 7.35 (dd, 4H, J=12 Hz and 40 Hz), 5.21 (s, 2H), 4.36-4.44 (m, 3H), 3.89 (t, 2H, J=4 Hz), 3.41 (dd, 2H, J=4 Hz and 12 Hz), 3.35 (s, 3H), 1.62-1.78 (m, 4H), 0.88 (t, 3H, J=8 Hz).

Example 368 7-(4-Chlorobenzyl)-1-(3-hydroxypropyl)-8-methoxy-3-methyl-1H-purine-2,6(3H,7H)-dione

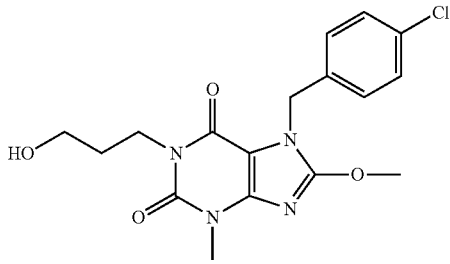 [SMILES: COc1nc2c(c(=O)n(CCCO)c(=O)n2C)n1Cc1ccc(Cl)cc1]

The title compound was prepared using the method of example 364. White solid, 0.14 g, 78%: LCMS retention time=2.914 min and 98% purity, LCMS MH⁺ 379. $^1$H NMR (DMSO-d$_6$) δ 7.34 (dd, 4H, J=8 Hz and 48 Hz), 5.21 (s, 2H), 4.42 (t, 1H, J=4 Hz), 4.08 (s, 3H), 3.88 (t, 2H, J=8 Hz)), 3.38-3.43 (m, 2H), 3.37 (s, 3H), 1.62-1.70 (m, 2H).

Example 369 8-Butoxy-7-(4-chlorobenzyl)-1-(3-hydroxypropyl)-3-methyl-1H-purine-2,6(3H,7H)-dione

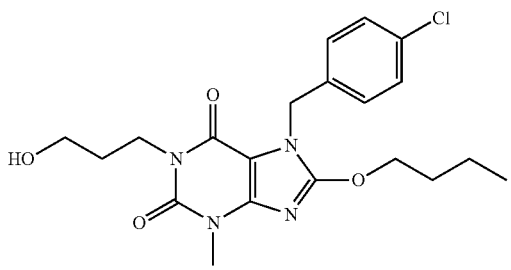 [SMILES: CCCCOc1nc2c(c(=O)n(CCCO)c(=O)n2C)n1Cc1ccc(Cl)cc1]

The title compound was prepared using the method of example 364. White solid, 0.15 g, 77% yield: LCMS retention time=3.690 min and 97% purity, LCMS MH⁺ 421. $^1$H NMR (DMSO-d$_6$) δ 7.34 (dd, 4H, J=4 Hz and 12 Hz), 5.21 (s, 2H), 4.43 (m, 3H), 3.89 (t, 1H, J=8 Hz)), 3.41 (dd, 2H, J=4 Hz and 12 Hz), 1.62-1.72 (m, 2H), 1.25-1.36 (m, 2H), 0.86 (t, 3H, J=8 Hz).

Example 370 7-(4-Chlorobenzyl)-1-(3-hydroxypropyl)-8-isopropoxy-3-methyl-1H-purine-2,6(3H,7H)-dione

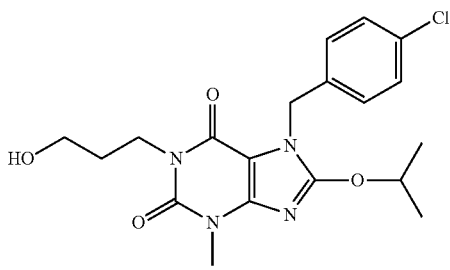 [SMILES: CC(C)Oc1nc2c(c(=O)n(CCCO)c(=O)n2C)n1Cc1ccc(Cl)cc1]

The title compound was prepared using the method of example 364. White solid, 0.056 g, 30% yield: LCMS retention time=3.355 min and 94% purity, LCMS MH⁺ 407. $^1$H NMR (DMSO-d$_6$) δ 7.36 (dd, 4H, J=8 Hz and 48 Hz), 5.19 (s, 2H), 5.12-5.18 (m, 1H), 4.44 (t, 1H, J=4 Hz), 3.80 (t, 2H, J=8 Hz), 3.38-3.45 (m, 2H), 3.37 (s, 3H), 1.63-1.72 (m, 2H), 1.34 (d, 6H, J=8 Hz).

Example 371 7-(4-Chlorobenzyl)-1-(3-hydroxypropyl)-3-methyl-8-(2-morpholinoethoxy)-1H-purine-2,6(3H,7H)-dione hydrochloride

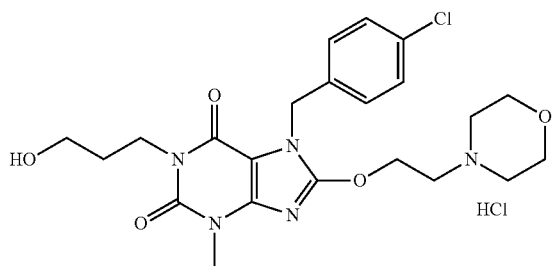 [SMILES: Cn1c(=O)n(CCCO)c(=O)c2c1nc(OCCN1CCOCC1)n2Cc1ccc(Cl)cc1 ; Cl]

Step 1 Sodium (0.053 g, 2.31 mmol) was dissolved in 2-morpholinoethanol (5 mL) and 8-bromo-1-(3-((tert-butyldimethylsilyl)oxy)propyl)-7-(4-chlorobenzyl)-3-methyl-1H-purine-2,6(3H,7H)-dione (0.25 g, 0.46 mmol, intermediate 77) was added. The reaction was stirred at room temperature for 24 h. The reaction was diluted with water (75 mL) and extracted with ethyl acetate (3×75 mL). The combined extracts were dried with magnesium sulfate, filtered and the solvent was removed under reduced pressure to give 1-(3-((tert-butyldimethylsilyl)oxy)propyl)-7-(4-chlorobenzyl)-3-methyl-8-(2-morpholinoethoxy)-1H-purine-2,6(3H,7H)-dione (0.27 g, 100% yield) as a clear oil. LCMS retention time=2.990 min and 96% purity, LCMS MH⁺ 592.

Step 2 1-(3-((tert-Butyldimethylsilyl)oxy)propyl)-7-(4-chlorobenzyl)-3-methyl-8-(2-morpholinoethoxy)-1H-purine-2,6(3H,7H)-dione (0.27 g, 0.46 mmol) was dissolved in ethanol (5 mL) and 6N aqueous HCl (1 mL) and stirred at room temperature for 1 h. The reaction was evaporated and azeotroped with methanol (3×10 mL). The solid residue was triturated with methanol (5 mL) and filtered. The white solid was washed with diethyl ether (2×10 mL) and high vacuum dried to give 7-(4-chlorobenzyl)-1-(3-hydroxypropyl)-3-methyl-8-(2-morpholinoethoxy)-1H-purine-2,6(3H,7H)-dione hydrochloride (0.14, 57% yield) as a white solid. LCMS retention time=1.908 min and 95% purity, LCMS MH⁺ 478. $^1$H NMR (DMSO-d$_6$) δ 11.54 (s, HCl), 7.38 (dd, 4H, J=12 and 28 Hz), 5.33 (2, 2H), 4.82-4.89 (m, 2H), 3.75-3.95 (m, 2H), 3.58-3.64 (m, 2H), 3.33-3.44 (m, 5H), 3.06 (m, 2H), 1.62-1.72 (m, 2H).

Example 372 7-(4-Chlorobenzyl)-8-(2-(dimethylamino)ethoxy)-1-(3-hydroxypropyl)-3-methyl-1H-purine-2,6(3H,7H)-dione hydrochloride

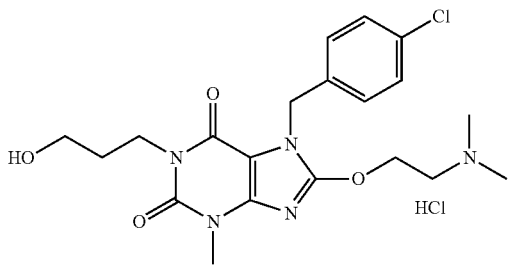 [SMILES: CN(C)CCOc1nc2c(c(=O)n(CCCO)c(=O)n2C)n1Cc1ccc(Cl)cc1 ; Cl]

The title compound was prepared using the method of example 371. White solid, 0.153 g, 95% yield: LCMS retention time=1.837 min and 94% purity, LCMS MH+ 436. $^1$H NMR (DMSO-$d_6$) δ 10.70 (s, HCl), 7.37-7.42 (m, 4H), 5.35 (s, 2H), 4.77-4.83 (m, 2H), 3.87-3.93 (m, 3H), 3.52-3.60 (m, 2H), 3.40-3.44 (t, 2H, J=8 Hz), 3.39 (s, 3H), 2.50 (s, 6H), 1.62-1.72 (m, 2H).

Example 373 7-(4-chlorobenzyl)-8-(cyclopentyloxy)-1-(3-hydroxypropyl)-3-methyl-1H-purine-2,6(3H,7H)-dione

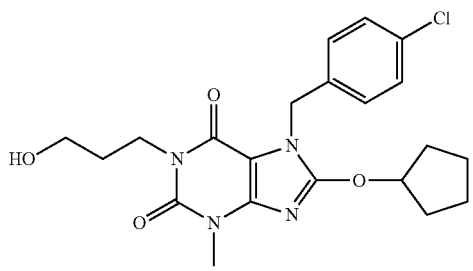 [SMILES: Cn1c(=O)n(CCCO)c(=O)c2c1nc(OC1CCCC1)n2Cc1ccc(Cl)cc1]

Step 1 Cyclopentanol (0.21 mL, 2.31 mmol) was dissolved in THF (5 mL) and sodium hydride (60% in oil, 0.092 g, 2.31 mmol) was added. The reaction was stirred for 1 h. 8-Bromo-1-(3-((tert-butyldimethylsilyl)oxy)propyl)-7-(4-chlorobenzyl)-3-methyl-1H-purine-2,6(3H,7H)-dione (0.25 g, 0.46 mmol, intermediate 77) was added and the reaction was stirred at room temperature for 15 h. The reaction was diluted with water (100 mL) and extracted with ethyl acetate (3×75 mL). The combined extracts were dried with magnesium sulfate, filtered and the solvent was removed under reduced pressure to give 1-(3-((tert-butyldimethylsilyl)oxy)propyl)-7-(4-chlorobenzyl)-8-(cyclopentyloxy)-3-methyl-1H-purine-2,6(3H,7H)-dione (0.25 g, 100% yield) as a golden oil. LCMS retention time=5.843 min and 71% purity, LCMS MH+ 547.

Step 2 1-(3-((tert-Butyldimethylsilyl)oxy)propyl)-7-(4-chlorobenzyl)-8-(cyclopentyloxy)-3-methyl-1H-purine-2,6(3H,7H)-dione (0.25 g, 0.46 mmol) was dissolved in ethanol (5 mL) and 6N aqueous HCl (1 mL) was added. The clear solution was stirred at room temperature for 1 h. The reaction was diluted with water (100 mL) and extracted with ethyl acetate (3×100 mL). The combined extracts were dried with magnesium sulfate, filtered and the solvent was removed under reduced pressure to a golden oil. The oil was purified using a 2000 micron preparative TLC plate eluted with ethyl acetate. Target band was scraped off plate, eluted off silica gel with ethyl acetate and evaporated under reduced pressure to give 7-(4-chlorobenzyl)-8-(cyclopentyloxy)-1-(3-hydroxypropyl)-3-methyl-1H-purine-2,6(3H, 7H)-dione (0.028 g, 14% yield) as a white solid. LCMS retention time=3.656 min and 98% purity, LCMS MH+ 433. $^1$H NMR (DMSO-$d_6$) δ 7.34 (dd, 4H, J=12 and 48 Hz), 5.34-5.40 (m, 1H), 5.18 (s, 2H), 4.42 (t, 1H, J=4 Hz), 3.89 (t, 2H, J=8 Hz), 3.38-3.45 (m, 2H), 3.36 (s, 3H), 1.55-1.93 (m, 8H).

Example 374 7-(4-Chlorobenzyl)-8-(cyclohexyloxy)-1-(3-hydroxypropyl)-3-methyl-1H-purine-2,6(3H,7H)-dione

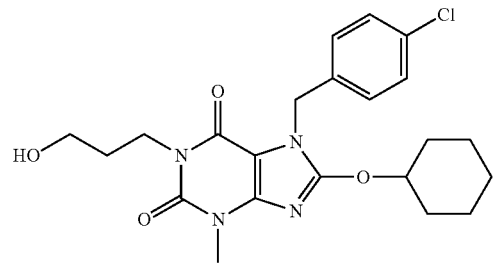 [SMILES: Cn1c(=O)n(CCCO)c(=O)c2c1nc(OC1CCCCC1)n2Cc1ccc(Cl)cc1]

The title compound was prepared using the method of example 373. White solid, 0.86 g, 42% yield: LCMS retention time=3.929 min and 97% purity, LCMS MH+ 447. $^1$H NMR (DMSO-$d_6$) δ 7.35 (dd, 4H, J=12 Hz and 36 Hz), 5.20 (s, 2H), 4.92-4.99 (m, 1H), 4.42 (t, 1H, J=4 Hz), 3.99 (t, 2H, J=8 Hz), 3.38-3.44 (m, 2H), 3.35 (s, 3H), 1.83-1.94 (m, 2H), 1.50-1.72 (m, 6H), 1.20-1.45 (m, 4H).

Example 375 7-(4-Chlorobenzyl)-1-(3-hydroxypropyl)-3-methyl-8-(pentyloxy)-1H-purine-2,6(3H,7H)-dione

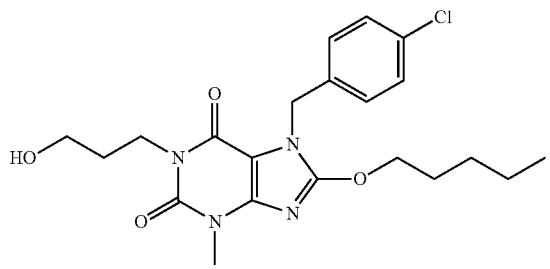 [SMILES: CCCCCOc1nc2c(c(=O)n(CCCO)c(=O)n2C)n1Cc1ccc(Cl)cc1]

The title compound was prepared using the method of example 373. White solid, 0.13 g, 63% yield: LCMS retention time=3.886 min and 98% purity, LCMS MH+ 435. $^1$H NMR (DMSO-$d_6$) δ 7.34 (dd, 4H, J=8 Hz and 44 Hz), 5.21 (s, 2H), 4.36-4.49 (m, 3H), 3.99 (t, 3H, J=8 Hz), 3.37-3.45 (m, 2H), 3.35 (s, 3H), 1.62-1.72 (m, 4H), 1.16-1.30 (m, 4H), 0.82 (t, 3H, J=8 Hz).

Example 376 7-(4-Chlorobenzyl)-8-(cyclopentylmethoxy)-1-(3-hydroxypropyl)-3-methyl-1H-purine-2,6(3H,7H)-dione using the method of example 373. White solid, 0.13 g, 63% yield: LCMS retention time=3.970 min and 95% purity, LCMS MH⁺ 447 and. ¹H NMR (DMSO-d₆) δ 7.34 (dd, 4H, J=8 Hz and 44 Hz), 5.21 (s, 2H), 4.42 (brd s, 1H), 4.31 (d, 2H, J=4 Hz), 3.89 (t, 3H, J=8 Hz), 3.41 (t, 2H, J=8 Hz), 3.35 (s, 3H), 2.23-2.35 (m, 2H), 1.62-1.72 (m, 4H), 1.44-1.59 (m, 4H), 1.16-1.28 (m, 2H).

Example 377 7-(4-Chlorobenzyl)-1-(3-hydroxypropyl)-3-methyl-8-((6-methylpyridin-3-yl)methoxy)-1H-purine-2,6(3H,7H)-dione

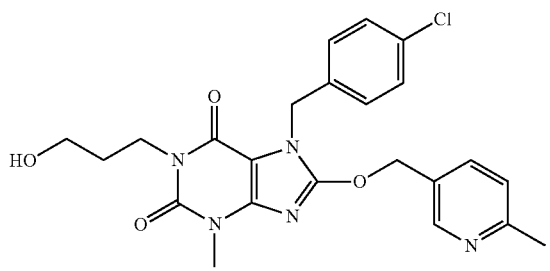 [SMILES: Cc1ccc(COc2nc3c(c(=O)n(CCCO)c(=O)n3C)n2Cc2ccc(Cl)cc2)cn1]

The title compound was prepared using the method of example 373. White solid, 0.0.87 g, 44% yield: LCMS retention time=2.255 min and 97% purity, LCMS MH⁺ 470. ¹H NMR (DMSO-d₆) δ 7.34 (dd, 4H, J=8 Hz and 44 Hz), 5.21 (s, 2H), 4.36-4.49 (m, 3H), 3.99 (t, 3H, J=8 Hz), 3.37-3.45 (m, 2H), 3.35 (s, 3H), 1.62-1.72 (m, 4H), 1.16-1.30 (m, 4H), 0.82 (t, 3H, J=8 Hz).

Example 378 Ethyl 2-(7-(4-chlorobenzyl)-1-(3-hydroxypropyl)-3-methyl-2,6-dioxo-2,3,6,7-tetrahydro-1H-purin-8-yl)acetate

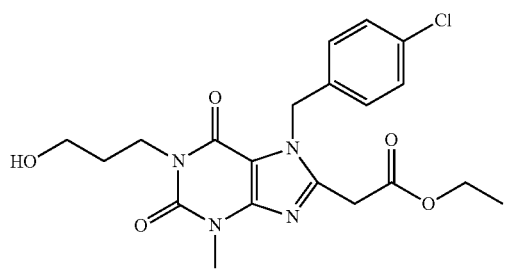 [SMILES: CCOC(=O)Cc1nc2c(c(=O)n(CCCO)c(=O)n2C)n1Cc1ccc(Cl)cc1]

Step 1 Diethyl malonate (0.35 mL, 2.31 mmol) was dissolved in DMF (5 mL) and sodium hydride (60% in oil, 0.74 g, 1.85 mmol) was added portion wise. The mixture was stirred for 15 min and 8-bromo-1-(3-((tert-butyldimethylsilyl)oxy)propyl)-7-(4-chlorobenzyl)-3-methyl-1H-purine-2,6(3H,7H)-dione (0.50 g, 0.92 mmol, intermediate 77) was added. The reaction was heated at 100° C. for 15 h. The reaction was cooled, diluted with water (100 mL) and extracted with ethyl acetate (3×75 mL). The combined extracts were washed with 1N lithium chloride (2×100 mL), dried with magnesium sulfate, filtered and the solvent was removed under reduced pressure to a golden oil. The oil was purified using a 25 g silica gel flash column eluted with 20% ethyl acetate/hexanes to give diethyl-2-(1-(3-((tert-butyldimethylsilyl)oxy)propyl)-7-(4-chlorobenzyl)-3-methyl-2,6-dioxo-2,3,6,7-tetrahydro-1H-purin-8-yl)malonate (0.23 g, 40% yield) as a clear oil. LCMS retention time=5.015 min and 95% purity, LCMS MH⁺ 621. ¹H NMR (DMSO-d₆) δ 7.27 (dd, 4H, J=8 Hz and 72 Hz), 5.62 (d, 2H, J=12 Hz), 5.54 (s, 2H), 5.61 (s, 1H), 3.90-4.03 (m, 6H), 3.62 (t, 2H, J=8 Hz), 3.37 (s, 3H), 1.70-1.78 (m, 2H), 1.08 (t, 6H, J=8 Hz), 0.80 (s, 9H).

Step 2 Diethyl-2-(1-(3-((tert-butyldimethylsilyl)oxy)propyl)-7-(4-chlorobenzyl)-3-methyl-2,6-dioxo-2,3,6,7-tetrahydro-1H-purin-8-yl)-2-(3-(trifluoromethyl)phenyl)malonate (0.23 g, 0.36 mmol) was slurried in 18% aqueous HCl (3 mL) and heated at reflux for 3 h, yielding a clear solution. The solvent was removed under reduced pressure and the residue was high vacuum dried for 15 h to give 2-(7-(4-chlorobenzyl)-1-(3-hydroxypropyl)-3-methyl-2,6-dioxo-2,3,6,7-tetrahydro-1H-purin-8-yl)acetic acid (0.14 g, 100% yield) as a tan solid. LCMS retention time=2.318 min and 70% purity, LCMS MH⁺ 407.

Step 3 Crude 2-(7-(4-chlorobenzyl)-1-(3-hydroxypropyl)-3-methyl-2,6-dioxo-2,3,6,7-tetrahydro-1H-purin-8-yl)acetic acid (0.14 g, 0.36 mmol) was dissolved in ethanol (5 mL) and concentrated sulfuric acid (1 drop). The reaction was heated at reflux for 1 h. The reaction was cooled, evaporated under reduced pressure to remove the ethanol then diluted with water (50 mL) and extracted with ethyl acetate (3×40 mL). The combined extracts were dried with magnesium sulfate, filtered and the solvent was removed under reduced pressure to a light golden oil. The oil was purified using a 12 g silica gel flash column and eluted with 20% ethyl acetate/hexanes to give ethyl 2-(7-(4-chlorobenzyl)-1-(3-hydroxypropyl)-3-methyl-2,6-dioxo-2,3,6,7-tetrahydro-1H-purin-8-yl)acetate (0.062, 40% yield) as a light tan solid. LCMS retention time=2.804 min and 99% purity, LCMS MH⁺ 435. ¹H NMR (CDCl₃) δ 7.21 (dd, 4H, J=8 Hz and 84 Hz), 5.57 (s, 2H), 4.11-4.23 (m, 4H), 3.77 (s, 2H), 3.59 (s, 3H), 3.50-3.56 (m, 2H), 3.32-3.39 (m, 1H), 1.86-1.94 (m, 2H), 1.25 (t, 3H, J=8 Hz).

Example 379 7-(4-Chlorobenzyl)-1-(3-hydroxypropyl)-3-methyl-8-(3-(trifluoromethoxy)benzyl)-1H-purine-2,6(3H, 7H)-dione

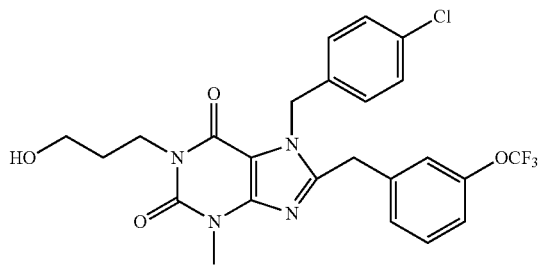 [SMILES: Cn1c(=O)n(CCCO)c(=O)c2c1nc(Cc1cccc(OC(F)(F)F)c1)n2Cc1ccc(Cl)cc1]

Step 1 Sodium hydride (60% in oil, 0.15 g, 3.69 mmol) was added portion wise to ethyl-2-(3-(trifluoromethoxy)phenyl)acetate (1.03 g, 4.15 mmol) in DMF (5 mL) and the dark golden solution was stirred at room temperature for 20 min. 8-Bromo-1-(3-((tert-butyldimethylsilyl)oxy)propyl)-7-(4-chlorobenzyl)-3-methyl-1H-purine-2,6(3H,7H)-dione (0.50 g, 0.92 mmol, intermediate 77) was added and the reaction was heated at 100° C. for 2 h. The reaction was cooled, diluted with water (100 mL) and extracted with ethyl acetate (3×100 mL). The combined extracts were washed with 1N lithium chloride (2×100 mL), dried with magnesium sulfate, filtered and the solvent was removed under reduced pressure to a golden oil. The oil was purified using a 40 g silica gel flash column eluted with 10% ethyl acetate/hexanes to give ethyl-2-(1-(3-((tert-butyldimethylsilyl)oxy)propyl)-7-(4-chlorobenzyl)-3-methyl-2,6-dioxo-2,3,6,7-tetrahydro-1H-purin-8-yl)-2-(3-trifluoromethoxy)phenyl)acetate (0.54 g, 82% yield) as a light golden oil. LCMS retention time=5.407 min and 99% purity, LCMS MH+ 709.

Step 2 Ethyl-2-(1-(3-((tert-butyldimethylsilyl)oxy)propyl)-7-(4-chlorobenzyl)-3-methyl-2,6-dioxo-2,3,6,7-tetrahydro-1H-purin-8-yl)-2-(3-trifluoromethoxy)phenyl)acetate was slurried in 6N HCl (6 mL) and heated at reflux for 1 h. The reaction solution was cooled, diluted with water (50 mL) and extracted with DCM (3×50 mL). The combined extracts were dried with magnesium sulfate, filtered and the solvent was removed under reduced pressure to a light golden oil. The oil was purified using a 12 g silica gel flash column eluted with a gradient of 20% ethyl acetate/hexanes to 100% ethyl acetate to give 7-(4-chlorobenzyl)-1-(3-hydroxypropyl)-3-methyl-8-(3-(trifluoromethoxy)benzyl)-1H-purine-2,6(3H,7H)-dione (0.088 g, 60% yield) as a clear oil. LCMS retention time=3.623 min and 98% purity, LCMS MH+ 523. $^1$H NMR (DMSO-$d_6$) δ 7.33 (t, 1H, J=8 Hz), 7.25-7.29 (m, 2H), 7.05-7.18 (m, 5H), 5.61 (s, 2H), 4.41 (t, 1H, J=4 Hz), 4.24 (s, 2H), 3.89 (t, 2H, J=12 Hz), 3.40 (s, 3H), 3.38-3.43 (m, 2H), 1.62-1.72 (m, 2H).

Example 380 Ethyl-2-(7-(4-chlorobenzyl)-1-(3-hydroxypropyl)-3-methyl-2,6-dioxo-2,3,6,7-tetrahydro-1H-purin-8-yl)-2-(3-trifluoromethoxy)phenyl)propanoate

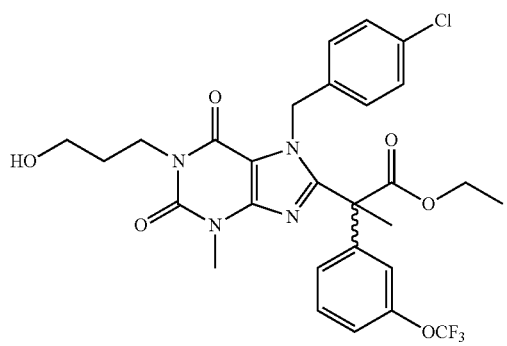 [SMILES: CCOC(=O)C(C)(c1cccc(OC(F)(F)F)c1)c1nc2c(c(=O)n(CCCO)c(=O)n2C)n1Cc1ccc(Cl)cc1]

Sodium (0.025 g, 1.07 mmol) was dissolved in ethanol (3 mL) and ethyl-2-(1-(3-((tert-butyldimethylsilyl)oxy)propyl)-7-(4-chlorobenzyl)-3-methyl-2,6-dioxo-2,3,6,7-tetrahydro-1H-purin-8-yl)-2-(3-trifluoromethoxy)phenyl)acetate (0.33 g, 0.47 mmol, example 379, step 1) was added. The reaction was stirred for 10 min and methyl iodide (0.29 mL, 4.7 mmol) and the reaction was heated at reflux for 1 h. The reaction was cooled, evaporated under reduced pressure, diluted with water (50 mL) and extracted with ethyl acetate (3×50 mL). The combined extracts were dried with magnesium sulfate, filtered and the solvent was removed under reduced pressure to a golden oil. The oil was purified using a 25 g silica gel flash column eluted with 20% ethyl acetate/hexanes to give ethyl-2-(7-(4-chlorobenzyl)-1-(3-hydroxypropyl)-3-methyl-2,6-dioxo-2,3,6,7-tetrahydro-1H-purin-8-yl)-2-(3-trifluoromethoxy)phenyl)propanoate (0.17 g, 67% yield) as a white foam. LCMS retention time=3.263 min and 99% purity, LCMS MH+ 609. $^1$H NMR (CDCl$_3$) δ 7.06-7.24 (m, 5H), 6.73 (d, 2H, J=8 Hz), 5.14 (s, 2H), 4.39 (t, 1H, J=8 Hz), 3.95-4.05 (m, 2H), 3.81-3.89 (m, 2H), 3.35-3.42 (m, 2H), 1.95 (s, 3H), 1.59-1.67 (m, 2H), 1.09 (t, 3H, J=8 Hz).

Example 381 7-(4-Chlorobenzyl)-1-(3-hydroxypropyl)-3-methyl-8-(3-(trifluoromethyl)benzyl)-1H-purine-2,6(3H,7H)-dione

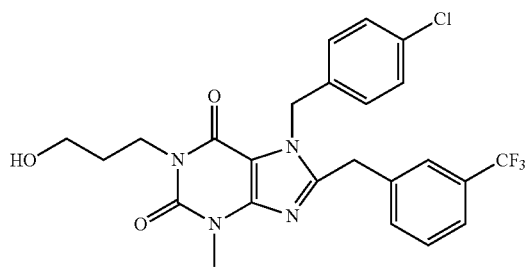 [SMILES: Cn1c(=O)n(CCCO)c(=O)c2c1nc(Cc1cccc(C(F)(F)F)c1)n2Cc1ccc(Cl)cc1]

Step 1 Ethyl-2-(1-(3-((tert-butyldimethylsilyl)oxy)propyl)-7-(4-chlorobenzyl)-3-methyl-2,6-dioxo-2,3,6,7-tetrahydro-1H-purin-8-yl)-2-(3-trifluoromethyl)phenyl)acetate was prepared from intermediate 77 and ethyl 3-trifluoromethylphenylacetate using the method of example 378, step 1. (0.45 g, 70% yield) as a yellow foam. LCMS retention time=5.334 min and 87% purity, LCMS MH+ 693.

Step 2 7-(4-Chlorobenzyl)-1-(3-hydroxypropyl)-3-methyl-8-(3-(trifluoromethyl)benzyl)-1H-purine-2,6(3H,7H)-dione was prepared using the method of example 379, step 2. Clear oil, 0.032 g, 44% yield: LCMS retention time=3.523 min and 99% pure, LCMS MH+ 507. $^1$H NMR (DMSO-$d_6$) δ 7.65-7.75 (m, 1H), 7.47-7.52 (m, 1H), 7.43 (d, 1H, J=4 Hz), 7.38 (s, 1H), 7.17 (dd, 4H, J=8 Hz and 68 Hz), 5.53 (s, 2H), 4.29 (s, 2H), 4.11-4.15 (m, 1H), 3.90 (t, 1H, J=4 Hz), 3.40 (s, 3H), 3.37-3.45 (m, 2H), 1.60-1.71 (m, 2H).

Example 382 Ethyl 2-(7-(4-chlorobenzyl)-1-(3-hydroxypropyl)-3-methyl-2,6-dioxo-2,3,6,7-tetrahydro-1H-purin-8-yl)-2-(3-(trifluoromethyl)phenyl)acetate

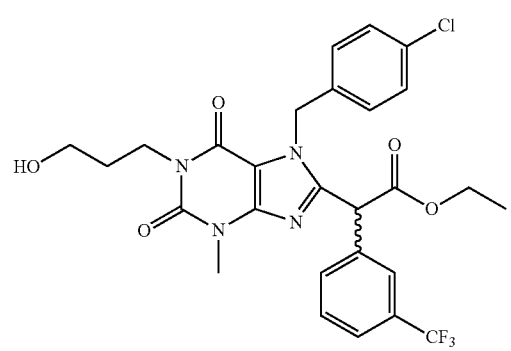 [SMILES: CCOC(=O)C(c1cccc(C(F)(F)F)c1)c1nc2c(c(=O)n(CCCO)c(=O)n2C)n1Cc1ccc(Cl)cc1]

Ethyl-2-(1-(3-((tert-butyldimethylsilyl)oxy)propyl)-7-(4-chlorobenzyl)-3-methyl-2,6-dioxo-2,3,6,7-tetrahydro-1H-purin-8-yl)-2-(3-trifluoromethyl)phenyl)acetate (0.050 g, 0.72 mmol, example 381, step 1) was dissolved in ethanol (3 mL) and 6N aqueous HCl (0.3 mL) was added. The clear solution was stirred at room temperature for 1 h. The reaction solvent was removed under reduced pressure, added DCM (3 mL) and directly spotted on a 2000 micron preparative TLC plate which was eluted with 50% ethyl acetate/hexanes. Target band was scraped off plate, eluted off silica gel with ethyl acetate and the solvent removed under reduced pressure to give ethyl 2-(7-(4-chlorobenzyl)-1-(3- hydroxypropyl)-3-methyl-2,6-dioxo-2,3,6,7-tetrahydro-1H-purin-8-yl)-2-(3-(trifluoromethyl)phenyl)acetate (0.025 g, 50% yield) as a white foam. LCMS retention time=3.731 min and 96% purity, LCMS MH+ 579. $^1$H NMR (DMSO-d$_6$) δ 7.55-7.65 (m, 3H), 7.48 (t, 1H, J=8 Hz), 7.12 (dd, 4H, J=8 Hz and 72 Hz), 5.69 (dd, 2H, J=16 Hz and 32 Hz), 4.40 (brd s, 1H), 4.05 (dd, 2H, J=8 Hz and 16 Hz), 3.88 (t, 2H, J=8 Hz), 3.41 (s, 3H), 1.61-1.69 (m, 2H).

Example 383 Ethyl 2-(7-(4-chlorobenzyl)-1-(3-hydroxypropyl)-3-methyl-2,6-dioxo-2,3,6,7-tetrahydro-1H-purin-8-yl)-2-(3-(trifluoromethyl)phenyl)propanoate

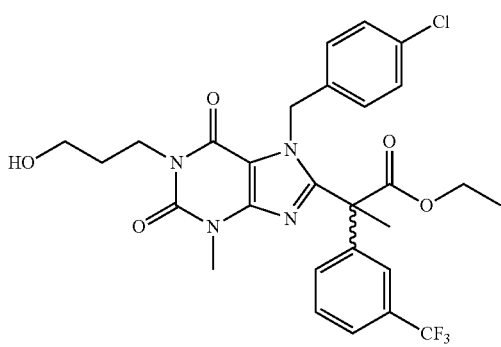 [SMILES: CCOC(=O)C(C)(c1cccc(C(F)(F)F)c1)c1nc2c(c(=O)n(CCCO)c(=O)n2C)n1Cc1ccc(Cl)cc1]

Ethyl 2-(7-(4-chlorobenzyl)-1-(3-hydroxypropyl)-3-methyl-2,6-dioxo-2,3,6,7-tetrahydro-1H-purin-8-yl)-2-(3-(trifluoromethyl)phenyl)propanoate was prepared from example 381, step 1 using the method of example 380. Pale yellow foam, 0.13 g, 61% yield: LCMS retention time=3.999 min and 96% purity, LCMS MH+ 593. $^1$H NMR (DMSO-d$_6$) δ 7.51 (s, 2H), 7.40 (t, 1H, J=8 Hz), 7.32 (d, 1H, J=8 Hz), 6.90 (dd, 4H, J=8 Hz and 92 Hz), 5.15 (s, 2H), 4.39 (t, 1H), 3.98-4.07 (m, 2H), 3.84-3.95 (m, 3H), 3.48 (s, 3H), 3.35-3.42 (m, 2H), 3.61 (s, 3H), 1.59-1.78 (m, 2H), 1.12 (t, 3H, J=8 Hz).

Example 384 2-(7-(4-Chlorobenzyl)-1-(3-hydroxypropyl)-3-methyl-2,6-dioxo-2,3,6,7-tetrahydro-1H-purin-8-yl)-2-(3-(trifluoromethoxy)phenyl)acetonitrile

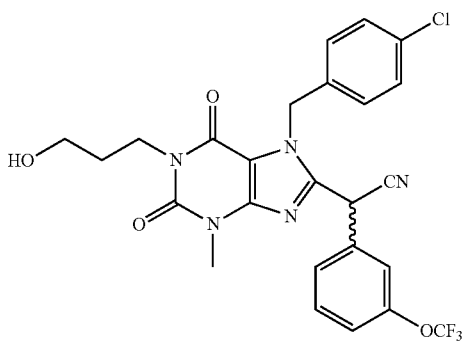 [SMILES: Cn1c(=O)n(CCCO)c(=O)c2c1nc(C(C#N)c1cccc(OC(F)(F)F)c1)n2Cc1ccc(Cl)cc1]

Step 1 Sodium hydride (60% in oil, 0.15 g, 3.69 mmol) was added portion wise to 2-(3-(trifluoromethoxy)phenyl) acetonitrile (0.84 g, 4.15 mmol) and stirred at room temperature over 15 min. 8-Bromo-1-(3-((tert-butyldimethylsilyl)oxy)propyl)-7-(4-chlorobenzyl)-3-methyl-1H-purine-2,6(3H,7H)-dione (0.50 g, 0.92 mmol, intermediate 77) was added and the reaction was stirred at room temperature for 1 h. The reaction was diluted with water (100 mL) and extracted with ethyl acetate (3×100 mL). The combined extracts were washed with 1N lithium chloride (2×75 mL), dried with magnesium sulfate, filtered and the solvent was removed under reduced pressure to a golden oil. The oil was purified using a 25 g silica gel flash column eluted with 10% ethyl acetate/hexanes to give 2-(1-(3-((tert-butyldimethylsilyl)oxy)propyl)-7-(4-chlorobenzyl)-3-methyl-2,6-dioxo-2,3,6,7-tetrahydro-1H-purin-8-yl)-2-(3-trifluoromethoxy)phenyl)acetonitrile (0.58 g, 95% yield) as a pale yellow foam. LCMS retention time=5.265 min and 90% purity, LCMS MH+ 662.

Step 2 2-(1-(3-(((tert-Butyldimethylsilyl)oxy)propyl)-7-(4-chlorobenzyl)-3-methyl-2,6-dioxo-2,3,6,7-tetrahydro-1H-purin-8-yl)-2-(3-trifluoromethoxy)phenyl)acetonitrile (0.20 g, 0.30 mmol) was dissolved in ethanol (5 mL) and 6 N aqueous HCl (1 mL) was added. The clear solution was stirred at room temperature for 1 h. The reaction was diluted with water (50 mL) and extracted with DCM (3×50 ml). The combined extracts were dried with magnesium sulfate, filtered and the solvent was removed under reduced pressure to yield a golden oil. The oil was purified using a 25 g silica gel flash column eluted with a gradient of 20% to 50% ethyl acetate/hexanes to give 2-(7-(4-chlorobenzyl)-1-(3-hydroxypropyl)-3-methyl-2,6-dioxo-2,3,6,7-tetrahydro-1H-purin-8-yl)-2-(3-(trifluoromethoxy)phenyl)acetonitrile (0.082 g, 50% yield) as a white foam. LCMS retention time=3.709 min and 97% purity, LCMS MH+ 548. $^1$H NMR (CDCl$_3$) δ 7.34 (t, 1H, J=8 Hz), 7.05-7.25 (m, 5H), 6.88 (d, 2H, J=8 Hz), 5.54 (dd, 2H, J=12 Hz and 80 Hz), 4.18 (t, 2H, J=8 Hz), 3.64 (s, 3H), 3.50-3.58 (m, 2H), 3.13 (t, 1H, J=8 Hz), 1.85-1.93 (m, 2H).

Example 385 7-(4-Chlorobenzyl)-1-(3-hydroxypropyl)-3-methyl-8-(1-(3-trifluoromethoxy)phenyl) ethyl-1H-purine-2,6(3H,7H)-dione

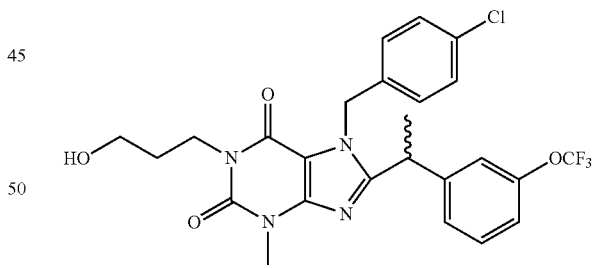

Ethyl-2-(7-(4-chlorobenzyl)-1-(3-hydroxypropyl)-3-methyl-2,6-dioxo-2,3,6,7-tetrahydro-1H-purin-8-yl)-2-(3-trifluoromethoxy)phenyl)propanoate (0.14 g, 0.23 mmol, example 380) was slurried in 6N HCl (6 mL) and heated at reflux for 15 h. The clear solution was cooled, diluted with water (75 mL) and extracted with DCM (3×50 mL). The combined extracts were dried with magnesium sulfate, filtered and the solvent was removed under reduced pressure to a clear oil. The oil was purified using a 2000 micron preparative TLC plate eluted with 50% ethyl acetate/hexanes. Target band was collected and extracted with ethyl acetate. The extracts were evaporated under reduced pressure to give 7-(4-chlorobenzyl)-1-(3-hydroxypropyl)-3- methyl-8-(1-(3-trifluoromethoxy)phenyl)ethyl-1H-purine-2,6(3H,7H)-dione (0.026 g, 22% yield) as a white foam. LCMS retention time=4.029 min and 96% purity, LCMS MH+ 537. ¹H NMR (CDCl₃) δ 7.20-7.30 (m, 3H), 7.09 (d, 1H, J=8 Hz), 7.00-7.05 (m, 2H), 6.91 (d, 2H, J=12 Hz), 5.38 (dd, 2H, J=16 Hz and 100 Hz), 4.18 (t, 2H, J=8 Hz), 4.00-4.09 (m, 1H), 3.67 (s, 3H), 3.48-3.53 (m, 2H), 3.39 (t, 1H, J=4 Hz), 1.85-1.93 (m, 2H), 1.66 (d, 3H, J=8 Hz).

Example 386 7-(4-Chlorobenzyl)-8-(2-hydroxy-1-(3-(trifluoromethoxy)phenyl)ethyl)-1-(3-hydroxypropyl)-3-methyl-1H-purine-2,6(3H,7H)-dione

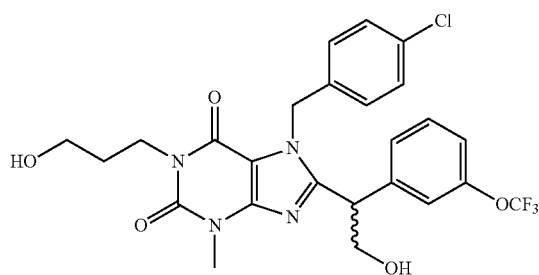 [SMILES: Cn1c(=O)n(CCCO)c(=O)c2c1nc(C(CO)c1cccc(OC(F)(F)F)c1)n2Cc1ccc(Cl)cc1]

Ethyl 2-)1-(3-((tert-butyldimethylsilyl)oxy)propyl)-7-(4-chlorobenzyl)-3-methyl-2,6-dioxo-2,3,6,7-tetrahydro-1H-purin-8-yl)-2-(3-trifluoromethoxy)phenyl)acetate (0.25 g, 0.352 mmol, example 379, step 1) was dissolved in THF (4 mL) and sodium borohydride (0.080 g, 2.11 mmol) was added. The reaction was refluxed for 15 min then methanol (2 mL) was added dropwise through condenser. After refluxing another 15 min the reaction was cooled and acidified with 6N HCl until pH 1 was achieved. The mixture was stirred at room temperature for 1 h. The reaction was diluted with water (100 mL) and extracted with DCM (3×75 ml). The combined extracts were dried with magnesium sulfate, filtered and the solvent was removed under reduced pressure to yield an oil. The oil was purified using a 25 g silica gel column eluted with a gradient of 5% to 10% methanol/DCM to give 7-(4-chlorobenzyl)-8-(2-hydroxy-1-(3-(trifluoromethoxy)phenyl)ethyl)-1-(3-hydroxypropyl)-3-methyl-1H-purine-2,6(3H,7H)-dione (0.030 g, 13% yield) as a white foam. LCMS retention time=2.665 min and 98% purity, LCMS MH+ 553. ¹H NMR (CDCl₃) δ 7.25-7.30 (m, 2H), 7.03 (dd, 4H, J=8 Hz and 91 Hz), 7.11 (d, 1H, J=8 Hz), 6.99-7.02 (m, 1H), 5.26-5.57 (dd, 2H, J=16 Hz and 91 Hz), 5.30 (s, 1H), 4.17 (t, 2H, J=8 Hz), 4.04-4.10 (m, OH), 3.67 (s, 3H), 3.46-3.50 (m, 3H), 3.20-3.27 (m, 1H), 1.85-1.93 (m, 2H).

Example 387 7-(4-Chlorobenzyl)-8-(1-hydroxyethyl)-1-(3-hydroxypropyl)-3-methyl-1H-purine-2,6(3H,7H)-dione

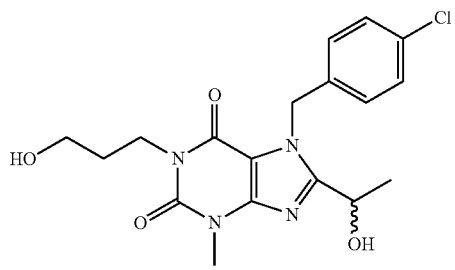 [SMILES: CC(O)c1nc2c(c(=O)n(CCCO)c(=O)n2C)n1Cc1ccc(Cl)cc1]

Step 1 8-Bromo-1-(3-((tert-butyldimethylsilyl)oxy)propyl)-7-(4-chlorobenzyl)-3-methyl-1H-purine-2,6(3H,7H)-dione (0.25 g, 0.46 mmol, intermediate 77) was dissolved in THF (5 mL) and cooled to −78° C. To the clear solution was added 2.5 M n-butyllithium in hexanes (0.20 mL, 0.51 mmol) dropwise. The reaction was stirred in the cold for 5 min and acetaldehyde (0.13 mL, 2.31 mmol) was added. The reaction was warmed to room temperature and stirred for 1 h. The reaction was diluted with water (100 mL) and extracted with ethyl acetate (3×75 mL). The combined extracts were dried with magnesium sulfate, filtered and the solvent was removed under reduced pressure to leave a golden oil. The oil was purified using two 1000 microns preparative TLC plates eluted with 50% ethyl acetate/hexanes. Target band was extracted with ethyl acetate and the solvent was removed under reduced pressure to give 1-(3-((tert-butyldimethylsilyl)oxy)propyl)-7-(4-chlorobenzyl)-8-(1-hydroxyethyl)-3-methyl-1H-purine-2,6(3H,7H)-dione (0.052 g, 30% yield) as a clear oil. LCMS retention time=4.490 min and 97% purity, LCMS MH+ 507.

Step 2 1-(3-((tert-butyldimethylsilyl)oxy)propyl)-7-(4-chlorobenzyl)-8-(1-hydroxyethyl)-3-methyl-1H-purine-2,6(3H,7H)-dione (0.052 g, 0.10 mmoL) was dissolved in ethanol (2 mL) and 6N aqueous HCl (0.5 mL) was added. The clear solution was stirred at room temperature for 1 h. The reaction was diluted with water (25 mL) and extracted with DCM (3×25 mL). The combined organic extracts were dried with magnesium sulfate, filtered and the solvent removed under reduced pressure to a golden oil. The oil was purified using a 2000 micron preparative TLC plate eluted with 50% ethyl acetate/hexanes. Target band was extracted with ethyl acetate and the solvent was removed under reduced pressure to give 7-(4-chlorobenzyl)-8-(1-hydroxyethyl)-1-(3-hydroxypropyl)-3-methyl-1H-purine-2,6(3H,7H)-dione (0.012 g, 29% yield) as a clear oil. LCMS retention time=2.429 min and 96% purity, LCMS MH+ 393. ¹H NMR (CDCl₃) δ 7.25 (dd, 4H, J=8 Hz and 64 Hz), 5.65 (dd, J=12 Hz and 40 Hz), 4.91-4.97 (m, 1H), 4.19 (t, 2H, J=4 Hz), 3.61 (s, 3H), 3.51-3.55 (m, 2H), 2.52 (d, 1H, J=4 Hz), 1.87-1.93 (m, 2H), 1.57 (d, 3H, J=4 Hz).

Example 388 7-(4-Chlorobenzyl)-8-(1-hydroxy-2-methylpropyl)-1-(3-hydroxypropyl)-3-methyl-1H-purine-2,6(3H,7H)-dione

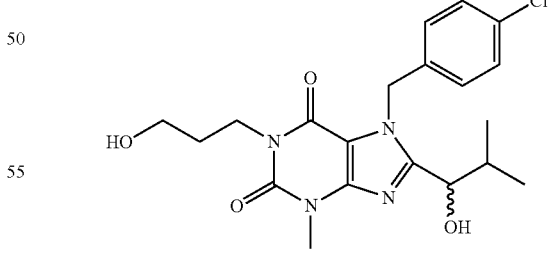

Step 1 8-Bromo-1-(3-((tert-butyldimethylsilyl)oxy)propyl-7-(4-chlorobenzyl)-3-methyl-1H-purine-2,6(3H,7H)-dione (0.50 g, 0.923 mmol, intermediate 77) was dissolved in THF (5 mL) and cooled to −78° C. To the clear solution was slowly added drop wise 2.5 M n-butyllithium in THF (0.35 mL, 0.877 mmol) followed by the immediate addition of isobutyraldehyde (0.42 mL, 4.61 mmol). The reaction was warmed to room temperature and stirred for 1 h. The reaction was diluted with water (75 mL) and extracted with ethyl acetate (3×75 mL). The combined extracts were dried with magnesium sulfate, filtered and the solvent was removed under reduced pressure to yield an oil. The oil was purified using a 25 g silica column eluted with a gradient of 10% to 30% ethyl acetate/hexanes yielding 1-(3-((tert-butyldimethylsilyl)oxy)propyl)-7-(4-chlorobenzyl)-8-(1-hydroxy-2-methylpropyl)-3-methyl-1H-purine-2,6(3H,7H)-dione (0.20 g, 40% yield) as a light golden oil. LCMS retention time=4.923 min and 98% purity, LCMS MH+ 535.

Step 2 1-(3-((tert-Butyldimethylsilyl)oxy)propyl)-7-(4-chlorobenzyl)-8-(1-hydroxy-2-methylpropyl)-3-methyl-1H-purine-2,6(3H,7H)-dione (0.19 g, 0.355 mmol) was dissolved in ethanol (5 mL) and 6 N HCl (0.5 mL) was added. The clear solution was stirred at room temperature for 1 h. The reaction was diluted with water (75 mL) and extracted with DCM (3×50 ml). The combined extracts were dried with magnesium sulfate, filtered and the solvent was removed under reduced pressure to yield a white solid. Solid was slurried in diethyl ether (4 mL) and collected to give 7-(4-chlorobenzyl)-8-(1-hydroxy-2-methylpropyl)-1-(3-hydroxypropyl)-3-methyl-1H-purine-2,6(3H,7H)-dione (0.085 g, 56% yield) as a white solid. LCMS retention time=3.263 min and 94% purity, LCMS MH+ 421. $^1$H NMR (CDCl$_3$) δ 7.23 (dd, 4H, J=8 Hz and 68 Hz), 5.59 (dd, 2H, J=16 Hz and 40 Hz), 4.43 (t, 1H, J=8 Hz). 4.17 (t, 2H, J=8 Hz), 3.59 (s, 3H), 3.48-3.54 (m, 2H), 3.35-3.40 (m, 1H), 2.48 (d, 1H, J=8 Hz), 2.08-2.16 (m, 1H), 1.85-1.92 (m, 2H), 1.03 (d, 3H, J=8 Hz), 0.82 (d, 3H, J=8 Hz).

Example 389 7-(4-Chlorobenzyl)-8-(3-chlorophenoxy)-1-(3-hydroxypropyl)-3-methyl-1H-purine-2,6(3H,7H)-dione

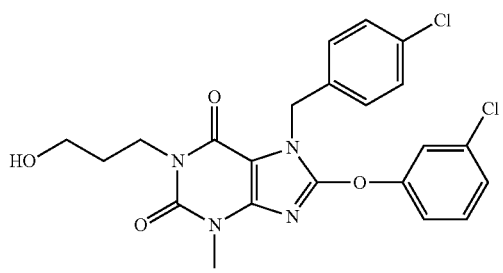 [SMILES: Cn1c(=O)n(CCCO)c(=O)c2c1nc(Oc1cccc(Cl)c1)n2Cc1ccc(Cl)cc1]

Step 1 8-Bromo-1-(3-((tert-butyldimethylsilyl)oxy)propyl)-7-(4-chlorobenzyl)-3-methyl-1H-purine-2,6(3H,7H)-dione (0.50 g, 0.92 mmol, intermediate 77), potassium carbonate (0.255 g, 1.85 mmol) and 3-chlorophenol (0.104 mL, 0.97 mmol) were combined in DMF (5 mL) and heated at 90° C. for 3 h. The reaction was cooled to room temperature, diluted with water (100 mL) and extracted with ethyl acetate (3×75 mL). The combined organic extracts were washed with 1N lithium chloride (2×100 mL), dried with magnesium sulfate, and concentrated under reduced pressure to yield a light golden oil (0.65 g). The oil was purified using a 24 g silica gel column eluted with a gradient of 10% to 20% ethyl acetate/hexanes to yield 1-(3-(((tert-butyldimethylsilyl)oxy)propyl)-7-(4-chlorobenzyl)-8-(3-chlorophenoxy)-3-methyl-1H-purine-2,6(3H,7H)-dione as an off-white solid (0.413 g, 76% yield). LCMS retention time=5.598 min and 98% purity, LCMS MH+ 589.

Step 2 1-(3-(((tert-Butyldimethylsilyl)oxy)propyl)-7-(4-chlorobenzyl)-8-(3-chlorophenoxy)-3-methyl-1H-purine-2,6(3H,7H)-dione (0.413 g, 0.70 mmol) was dissolved in ethanol (8 mL) and 6N HCl (1 mL) was added. The clear solution was stirred at room temperature for 1 h. The reaction was diluted with water (75 mL) and extracted with DCM (3×75 mL). The combined organic extracts were dried with magnesium sulfate, and concentrated under reduced pressure to leave an off-white solid. The solid was slurried in diethyl ether (3 mL) and filtered to yield 7-(4-chlorobenzyl)-8-(3-chlorophenoxy)-1-(3-hydroxypropyl)-3-methyl-1H-purine-2,6(3H,7H)-dione (0.30 g, 90% yield) as an off-white solid. LCMS retention time=3.810 min and 99% purity, LCMS MH+ 475. $^1$H NMR (DMSO-d$_6$) δ 7.15-7.41 (m, 8H), 5.41 (s, 2H), 4.20 (t, 2H, J=8 Hz), 3.49-3.51 (m, 2H), 3.45 (s, 3H), 1.87-1.93 (m, 2H).

The following examples 390a through 390r were prepared using the two step method of example 389

Example 390a 7-(4-Chlorobenzyl)-8-(3,4-dichlorophenoxy)1-(3-hydroxypropyl)-3-methyl-1H-purine-2,6(3H,7H)-dione

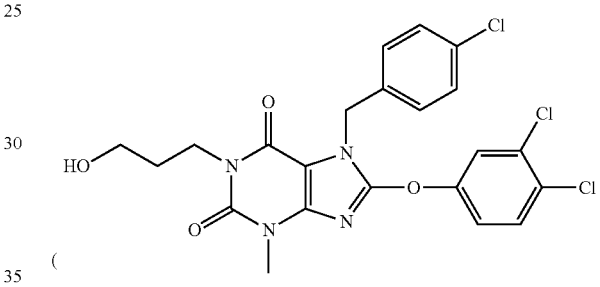

(

White solid, 0.34 g, 92% yield: LCMS retention time=4.080 min and 99% purity, LCMS MH+=509. $^1$H NMR (CDCl$_3$) δ 7.50 (d, 1H, J=12 Hz), 7.31-7.44 (m, 5H), 7.15 (dd, 2H, J=4 Hz and 8 Hz), 5.41 (s, 2H), 3.48-3.51 (m, 2H), 3.45 (s, 3H), 1.87-1.95 (m, 2H).

Example 390b 7-(4-Chlorobenzyl)-1-(3-hydroxypropyl)-3-methyl-8-(m-tolyloxy)-1H-purine-2,6(3H,7H)-dione

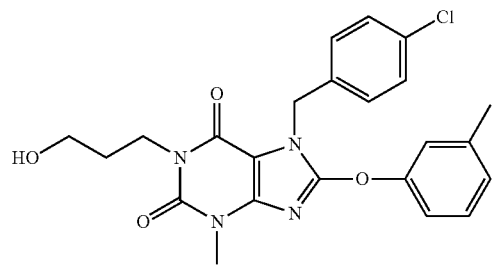 [SMILES: Cc1cccc(Oc2nc3c(c(=O)n(CCCO)c(=O)n3C)n2Cc2ccc(Cl)cc2)c1]

White solid, 0.29 g, 76% yield: LCMS retention time=3.724 min and 96% purity, LCMS MH+=455. $^1$H NMR (CDCl$_3$) δ (CDCl$_3$) δ 7.27-7.45 (m, 5H), 7.01-7.13 (m, 3H), 5.41 (s, 2H), 4.20 (t, 2H, J=8 Hz), 3.49-3.57 (m, 2H), 3.44 (s, 3H), 2.39 (s, 3H), 1.86-1.94 (m, 2H).

Example 390c 7-(4-Chlorobenzyl)-1-(3-hydroxypropyl)-8-(3-methoxyphenoxy)-3-methyl-1H-purine-2,6(3H,7H)-dione

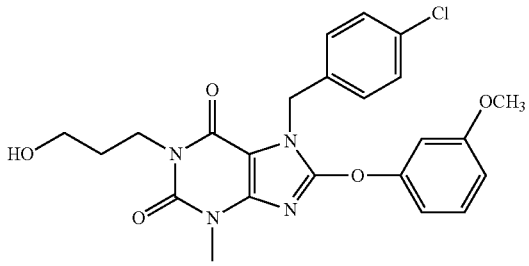 [SMILES: COc1cccc(Oc2nc3c(c(=O)n(CCCO)c(=O)n3C)n2Cc2ccc(Cl)cc2)c1]

White solid, 0.14 g, 41% yield: LCMS retention time=3.550 min and 97% purity, LCMS MH+=471. $^1$H NMR (CDCl$_3$) δ (CDCl$_3$) δ 7.29-7.44 (m, 5H), 6.79-6.86 (m, 3H), 5.41 (s, 2H), 4.20 (t, 2H, J=8 Hz), 3.82 (s, 3H), 3.50-3.55 (m, 2H), 3.44 (s, 3H), 1.87-1.94 (m, 2H).

Example 390d 7-(4-Chlorobenzyl)-8-(3-fluorophenoxy)-1-(3-hydroxypropyl)-3-methyl-1H-purine-2,6(3H,7H)-dione

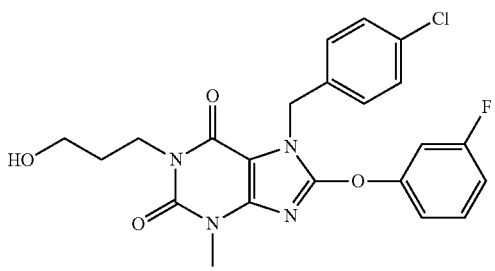

White solid, 0.23 g, 74% yield: LCMS retention time=3.584 min and 99% purity, LCMS MH+=459. $^1$H NMR (CDCl$_3$) δ (CDCl$_3$) δ 7.30-7.43 (m, 5H), 6.98-7.10 (m, 3H), 5.42 (s, 2H), 4.20 (t, 2H, J=8 Hz), 3.49-3.55 (m, 2H), 3.45 (s, 3H), 1.88-1.93 (m, 2H).

Example 390e 7-(4-Chlorobenzyl)-8-(4-chlorophenoxy)-1-(3-hydroxypropyl)-3-methyl-1H-purine-2,6(3H,7H)-dione

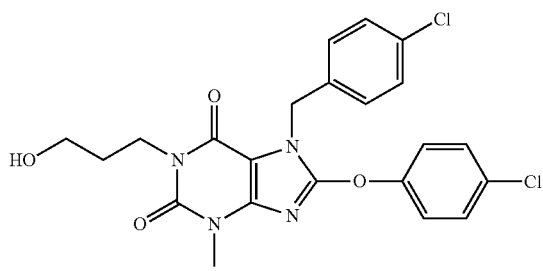

White solid, 0.28 g, 76% yield: LCMS retention time=3.814 min and 99% purity, LCMS MH+=475. $^1$H NMR (CDCl$_3$) δ 7.37-7.43 (m, 5H), 7.30-7.35 (m, 2H), 7.19-7.23 (m, 2H), 5.41 (s, 2H), 4.20 (t, 2H, J=8 Hz), 3.47-3.56 (m, 2H), 3.43 (s, 3H), 1.86-1.94 (m, 2H).

Example 390f 7-(4-Chlorobenzyl)-1-(3-hydroxypropyl)-3-methyl-8-(p-tolyloxy)-1H-purine-2,6(3H,7H)-dione

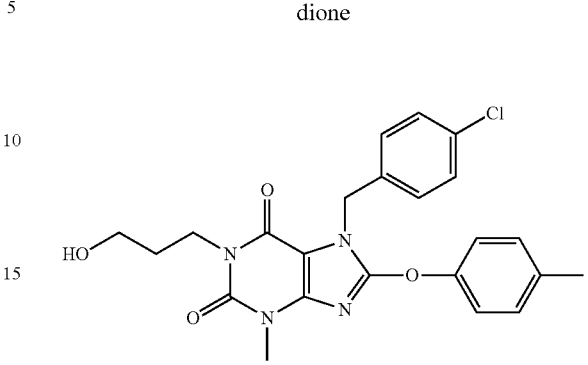

White solid, 0.14 g, 41% yield: LCMS retention time=3.732 min and 99% purity, LCMS MH+=455. $^1$H NMR (CDCl$_3$) δ (CDCl$_3$) δ 7.46 (dd, 4H, J=8 Hz and J=44 Hz), 7.24 (dd, 4H, J=8 Hz and J=36 Hz), 5.41 (s, 2H), 4.19 (t, 2H, J=8 Hz), 3.50-3.59 (m, 2H), 3.42 (s, 3H), 2.38 (s, 3H), 1.88-1.92 (m, 2H).

Example 390g 7-Benzyl-8-(3-chlorophenoxy)-1-(3-hydroxypropyl)-3-methyl-1H-purine-2,6(3H,7H)-dione

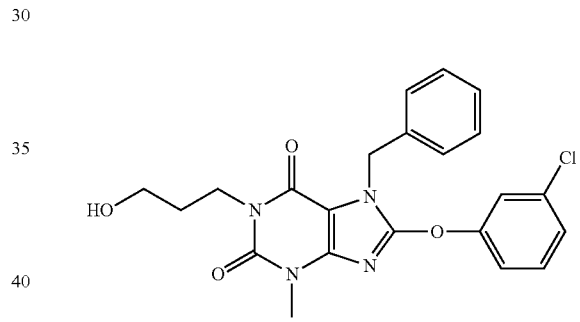

The title compound was prepared from intermediate 83 using the method of example 389. White solid, 0.11 g, 61% yield: LCMS retention time=3.503 min and 98% purity, LCMS MH+=441. $^1$H NMR (CDCl$_3$) δ 7.42-7.47 (m, 1H), 7.31-7.38 (m, 5H), 7.24-7.30 (m, 2H), 7.14-7.18 (m, 1H), 5.45 (s, 2H), 4.20 (t, 2H, J=8 Hz), 3.50-3.56 (m, 2H), 3.45 (s, 3H), 1.85-1.95 (m, 2H).

Example 390h 7-Benzyl-8-(3-fluorophenoxy)-1-(3-hydroxypropyl)-3-methyl-1H-purine-2,6(3H,7H)-dione

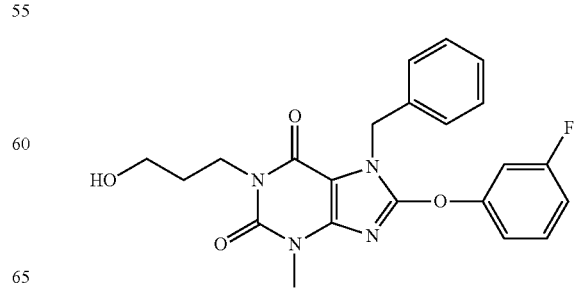

The title compound was prepared from intermediate 83 using the method of example 389. White solid, 0.17 g, 88% yield: LCMS retention time=3.282 min and 98% purity, LCMS MH+=425. $^1$H NMR (CDCl$_3$) δ 7.43-7.47 (m, 2H), 7.30-7.41 (m, 4H), 7.04-7.08 (m, 2H), 6.96-7.02 (m, 1H), 5.45 (s, 2H), 4.20 (t, 2H, J=8 Hz), 3.50-3.55 (m, 2H), 3.45 (s, 3H), 1.87-1.94 (m, 2H).

Example 390i 7-Benzyl-8-(4-chloro-3-fluorophenoxy)-1-(3-hydroxypropyl)-3-methyl-1H-purine-2,6(3H,7H)-dione

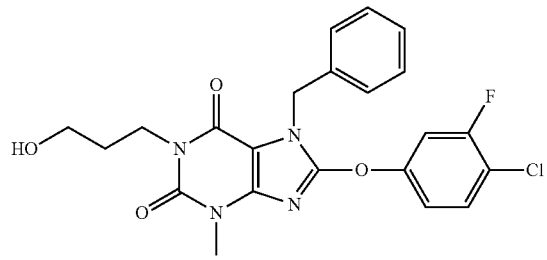 [SMILES: Cn1c(=O)n(CCCO)c(=O)c2c1nc(Oc1ccc(Cl)c(F)c1)n2Cc1ccccc1]

The title compound was prepared from intermediate 83 using the method of example 389. White solid, 0.25 g, 56% yield: LCMS retention time=3.860 min and 99% purity, LCMS MH+=459. $^1$H NMR (CDCl$_3$) δ 7.15-7.48 (m, 8H), 5.46 (s, 2H), 4.20 (t, 2H, J=8 HZ), 3.50-3.61 (m, 3H), 3.43 (s, 3H), 1.87-1.94 (m, 2H).

Example 390j 7-Benzyl-1-(3-hydroxypropyl)-3-methyl-8-phenoxy-1H-purine-2,6(3H,7H)-dione

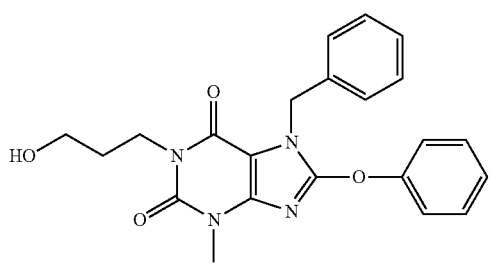 [SMILES: Cn1c(=O)n(CCCO)c(=O)c2c1nc(Oc1ccccc1)n2Cc1ccccc1]

The title compound was prepared from intermediate 83 using the method of example 389. White solid, 0.18 g, 46% yield: LCMS retention time=3.435 min and 99% purity, LCMS MH+=407. $^1$H NMR (CDCl$_3$) δ 7.15-7.48 (m, 10H), 5.46 (s, 2H), 4.20 (t, 2H, J=8 Hz), 3.50-3.61 (m, 3H), 3.43 (s, 3H), 1.87-1.94 (m, 2H).

Example 390k 7-Benzyl-8-(3-difluoromethoxy)phenoxy)-1-(3-hydroxypropyl)-3-methyl-1H-purine-2,6(3H,7H)-dione

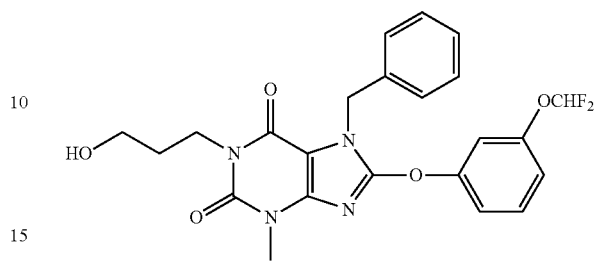

The title compound was prepared from intermediate 83 using the method of example 389. White solid, 0.18 g, 39% yield: LCMS retention time=3.581 min and 97% purity, LCMS MH+=473. $^1$H NMR (CDCl$_3$) δ 7.31-7.47 (m, 6H), 7.10-7.14 (m, 2H), 7.02-7.06 (m, 2H), 6.34-6.72 (t, 1H, J=18 Hz), 5.46 (s, 2H), 4.20 (t, 2H, J=2 Hz). 3.51-3.55 (m, 2H), 3.45 (s, 3H), 1.87-1.94 (m, 2H)

Example 390l 7-(4-Chlorobenzyl)-8-(3-difluoromethoxy)phenoxy)-1-(3-hydroxypropyl)-3-methyl-1H-purine-2,6(3H,7H)-dione

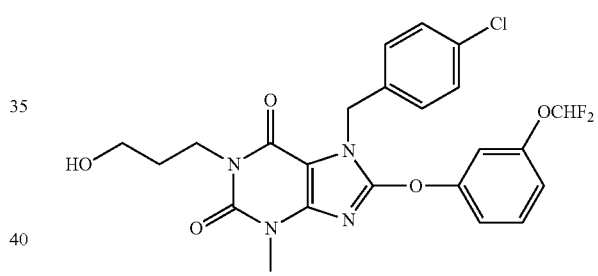

White solid, 0.14 g, 27% yield: LCMS retention time=3.820 min and 99% purity, LCMS MH+ 507. $^1$H NMR (CDCl$_3$) δ 7.44 (s, 1H), 7.36 (dd, 4H, J=12 Hz and 32 Hz), 7.11-7.14 (m, 2H), 7.04-7.07 (m, 1H), 6.54 (t, 1H, J=72 Hz), 5.42 (s, 2H), 4.20 (t, 2H, J=2 Hz), 3.48-3.56 (m, 2H), 3.45 (s, 3H), 1.87-1.94 (m, 2H).

Example 390m 7-(4-Chlorobenzyl)-1-(3-hydroxypropyl)-3-methyl-8-phenoxy-1H-purine-2,6(3H,7H)-dione

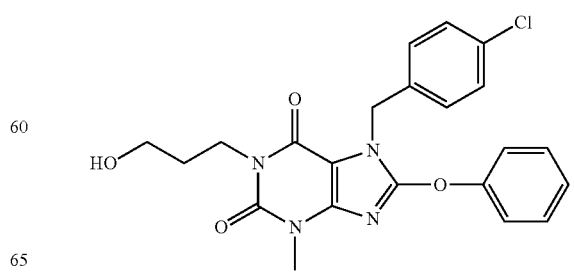

White solid, 0.24 g, 59% yield: LCMS retention time=3.471 min and 99% purity, LCMS MH+=441. $^1$H NMR (CDCl$_3$) δ 7.41-7.45 (m, 4H), 7.24-7.33 (m, 4H), 5.42 (s, 3H), 4.20 (t, 2H, J=8 Hz), 3.51-3.54 (m, 2H), 3.43 (s, 3H), 1.87-1.94 (m, 2H).

Example 390n 3-((7-Benzyl-1-(3-hydroxypropyl)-3-methyl-2,6-dioxo-2,3,6,7-tetrahydro-1H-purin-8-yl)oxy)benzonitrile

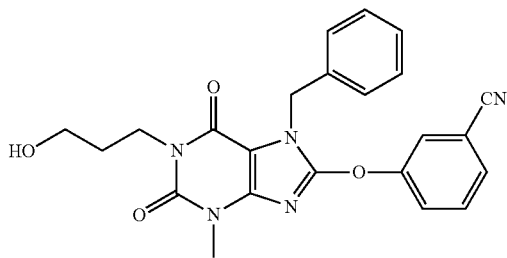

The title compound was prepared from intermediate 83 using the method of example 389. White solid, 0.32 g, 74% yield: LCMS retention time=3.292 min and 99% purity, LCMS MH+=466. $^1$H NMR (CDCl$_3$) δ 7.52-7.65 (m, 4H), 7.36 (dd, 4H, J=8 Hz and 24 Hz), 5.43 (s, 2H), 4.20 (t, 2H, J=8 Hz), 3.51-3.56 (m, 2H), 3.45 (s, 3H), 1.88-1.93 (m, 2H).

Example 390o 3-((7-Benzyl-1-(3-hydroxypropyl)-3-methyl-2,6-dioxo-2,3,6,7-tetrahydro-1H-purin-8-yl)oxy)benzonitrile

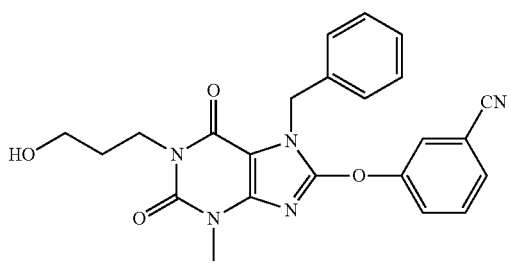 [SMILES: Cn1c(=O)n(CCCO)c(=O)c2c1nc(Oc1cccc(C(F)(F)F)c1)n2Cc1ccccc1]

The title compound was prepared from intermediate 83 using the method of example 389. White solid, 0.24 g, 74%: LCMS retention time=3.581 min and 99% purity, LCMS MH+=432. $^1$H NMR (CDCl$_3$) δ 7.54 (s, 3H), 7.46 (d, 3H, J=8 Hz), 7.30-7.40 (m, 3H), 5.48 (s, 2H), 4.21 (t, 2H, J=8 Hz), 3.50-3.56 (m, 2H), 3.45 (s, 3H), 1.88-1.96 (m, 2H)

Example 390p 7-(4-Chlorobenzyl)-1-(3-hydroxypropyl)-8-(4-isopropylphenoxy)-3-methyl-1H-purine-2,6(3H,7H)-dione

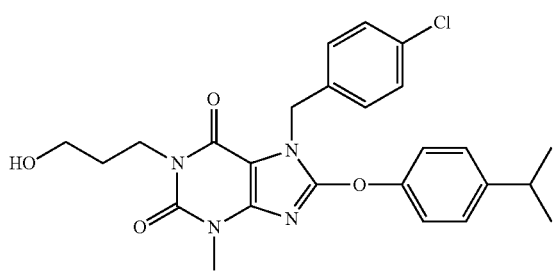

White solid, 0.33 g, 88% yield: LCMS retention time=4.160 min and 99% purity, LCMS MH+=483. $^1$H NMR (CDCl$_3$) δ 7.38 (dd, 4H, J=8 Hz and 44 Hz), 7.22 (dd, 4H, J=8 Hz and 40 Hz), 5.41 (s, 2H), 4.20 (t, 2H, J=8 Hz), 3.50-3.59 (m, 2H), 3.45 (s, 3H), 2.91-2.98 (m, 2H), 1.85-1.95 (m, 2H), 1.28 (d, 2H, J=2 Hz).

Example 390q 7-Benzyl-1-(3-hydroxypropyl)-8-(4-isopropylphenoxy)-3-methyl-1H-purine-2,6(3H,7H)-dione

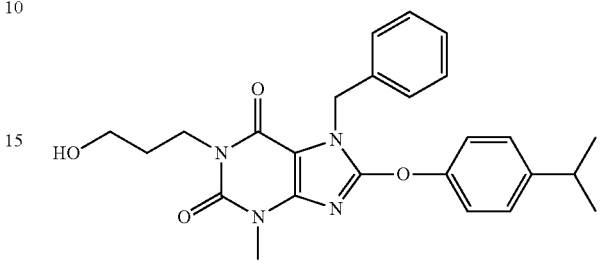

The title compound was prepared from intermediate 83 using the method of example 389. White solid, 0.33 g, 91% yield: LCMS retention time=3.894 min and 99% purity, LCMS MH+=449. $^1$H NMR (CDCl$_3$) δ 7.48 (d, 2H, J=8 Hz), 7.31-7.37 (m, 3H), 7.21 (dd, 4H, J=8 Hz and 32 Hz), 5.45 (s, 2H), 4.20 (t, 2H, J=8 Hz), 3.62 (brd s, 1H), 3.50-3.56 (m, 2H), 3.44 (s, 3H), 2.90-2.93 (m, 1H), 1.91 (m, 2H), 1.27 (d, 6H, J=2 Hz).

Example 390r 7-Benzyl-1-(3-hydroxypropyl)-3-methyl-8-(3-(trifluoromethyl)phenoxy)-1H-purine-2,6(3H,7H)-dione

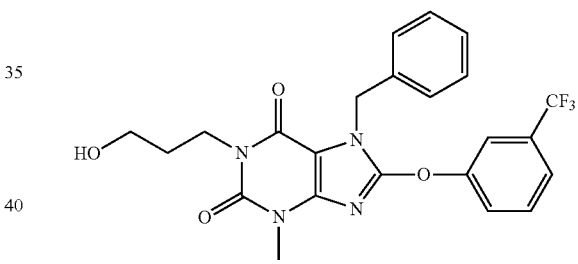

The title compound was prepared from intermediate 83 using the method of example 389. White solid, 0.20 g, 79% yield: LCMS retention time=3.600 min and 99% purity, LCMS MH+=475. $^1$H NMR (CDCl$_3$) δ 7.34-7.59 (m, 8H), 5.48 (s, 2H), 4.21 (t, 2H, J=8 Hz), 3.49-3.55 (m, 2H), 3.45 (s, 3H), 1.88-1.95 (m, 2H)

Example 391 7-Benzyl-8-(4-fluoro-3-(trifluoromethyl)phenoxy)-1-(3-hydroxypropyl)-3-methyl-1H-purine-2,6(3H,7H)-dione

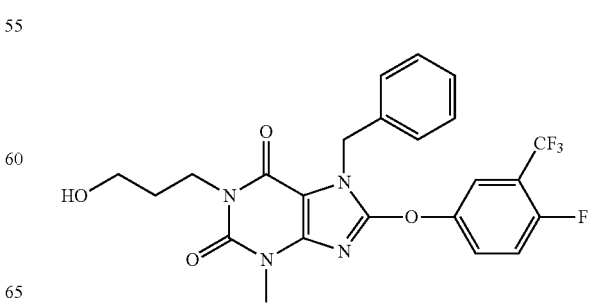

Step 1 7-Benzyl-8-bromo-1-(3-((tert-butyldimethylsilyl) oxy)propyl)-3-methyl-1H-purine-2,6(3H,7H)-dione (0.50 g, 0.985 mmol, intermediate 83), potassium carbonate (0.272 g, 1.97 mmol) and 4-fluoro-3-(trifluoromethyl)phenol (0.19 g, 1.03 mmol) were combined in DMF (5 mL). The reaction was heated at 90° C. After 6 h the reaction was cooled, diluted with water (100 mL) and extracted with ethyl acetate (3×75 mL). The combined extracts were dried with magnesium sulfate, filtered and the solvent was removed under reduced pressure to yield a white solid. This solid was purified using a 25 g silica column eluted with 20% ethyl acetate/hexanes to give 7-benzyl-1-(3-((tert-butyldimethylsilyl)oxy)propyl)-8-(4-fluoro-3-(trifluoromethyl)phenoxy)-3-methyl-1H-purine-2,6(3H,7H)-dione (0.54 g, 90% yield) as a white solid. LCMS retention time=5.342 min and 97% purity, LCMS MH$^+$=607.

Step 2 7-Benzyl-1-(3-((tert-butyldimethylsilyl)oxy)propyl)-8-(4-fluoro-3-(trifluoromethyl)phenoxy)-3-methyl-1H-purine-2,6(3H,7H)-dione (0.44 g, 0.686 mmol) was dissolved in ethanol (15 mL) and DCM (1 mL) then 6 N aqueous HCl (2.0 mL) were added. The clear solution was stirred at room temperature. After 1 h reaction was diluted with water (100 mL) and extracted with DCM (3×75 ml). The combined extracts were dried with magnesium sulfate, filtered and the solvent was removed under reduced pressure to yield a white solid. Solid was slurried in diethyl ether (6 mL) and filtered to give 7-benzyl-8-(4-fluoro-3-(trifluoromethyl)phenoxy)-1-(3-hydroxypropyl)-3-methyl-1H-purine-2,6(3H,7H)-dione (0.35 g, 79% yield) as a white solid. LCMS retention time=3.641 min and 99% purity, LCMS MH$^+$=493. $^1$H NMR (CDCl$_3$) δ 7.23-7.52 (m, 8H), 5.47 (s, 2H), 4.20 (t, 2H, J=8 Hz), 3.47-3.54 (m, 2H), 3.43 (s, 3H), 1.88-1.92 (m, 2H).

Example 392 7-(4-Chlorobenzyl)-8-(4-fluoro-3-(trifluoromethyl)phenoxy)-1-(3-hydroxypropyl)-3-methyl-1H-purine-2,6(3H,7H)-dione

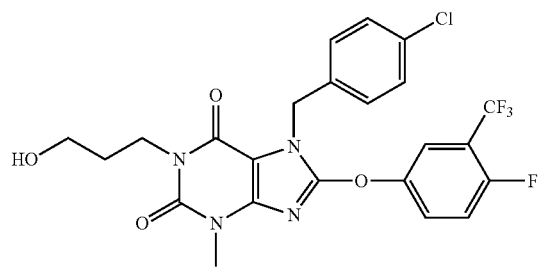 [SMILES: Cn1c(=O)n(CCCO)c(=O)c2c1nc(Oc1ccc(F)c(C(F)(F)F)c1)n2Cc1ccc(Cl)cc1]

The title compound was prepared using the two step method of example 391. White solid, 0.33 g, 95% yield: LCMS retention time=3.870 min and 99% purity, LCMS MH$^+$=527. $^1$H NMR (CDCl$_3$) δ 7.25-7.56 (m, 7H), 5.43 (s, 2H), 4.20 (t, 2H, J=8 Hz), 3.55-3.51 (m, 2H), 3.45 (t, 2H, J=8 Hz), 3.43 (s, 3H), 1.89-1.92 (m, 2H).

Example 393 8-(4-Chloro-3-fluorophenoxy)-7-(4-chlorobenzyl)-1-(3-hydroxypropyl)-3-methyl-1H-purine-2,6(3H,7H)-dione

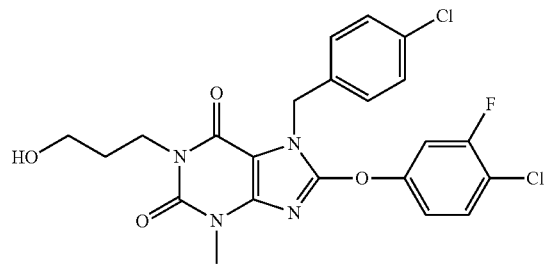

The title compound was prepared using the two step method of example 391 except the crude product was purified by slurrying in ether and filtration. White solid, 0.33 g, 95% yield: LCMS retention time=3.840 min and 99% purity, LCMS MH$^+$=493. $^1$H NMR (CDCl$_3$) δ 7.45 (t, 1H, J=2 Hz), 7.36 (dd, 4H, J=8 Hz and 24 Hz), 7.20 (dd, 1H, J=4 Hz and 12 Hz), 7.04 (d, 1H, J=8 Hz), 5.41 (s, 2H), 4.20 (t, 2H, J=8 Hz), 3.51-3.55 (m, 2H), 3.43-3.47 (m, 5H), 1.89-1.92 (m, 2H)

Example 394 3-(7-(4-chlorobenzyl)-3-methyl-2,6-dioxo-8-(3-(trifluoromethoxy)phenoxy)-2,3,6,7-tetrahydro-1H-purin-1-yl)propanol

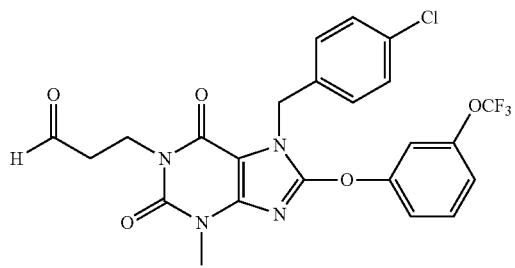 [SMILES: Cn1c(=O)n(CCC=O)c(=O)c2c1nc(Oc1cccc(OC(F)(F)F)c1)n2Cc1ccc(Cl)cc1]

7-(4-Chlorobenzyl)-1-(3-hydroxypropyl)-3-methyl-8-(3-(trifluoromethoxy)phenoxy)-1H-purine-2,6(3H,7H)-dione (2.0 g, 3.81 mmol, example 356) and pyridinium chlorochromate (1.64 g, 7.62 mmol) were dissolved in DCM (40 mL). The orange solution was stirred at room temperature for 15 h. Solvent was decanted away from salts, absorbed onto silica gel and purified using a 40 g silica gel flash column eluted with 40% ethyl acetate/hexanes to give 3-(7-(4-chlorobenzyl)-3-methyl-2,6-dioxo-8-(3-(trifluoromethoxy)phenoxy)-2,3,6,7-tetrahydro-1H-purin-1-yl)propanol (1.25 g, 63% yield) as a white solid. $^1$H NMR (CDCl$_3$) δ 9.84 (s, 1H), 7.12-7.47 (m, 8H), 5.40 (s, 2H), 4.38 (t, 2H, J=8 Hz), 3.45 (s, 3H), 2.75-2.83 (m, 2H).

Example 395 7-Benzyl-8-ethoxy-1-(3-hydroxypropyl)-3-methyl-1H-purine-2,6(3H,7H)-dione

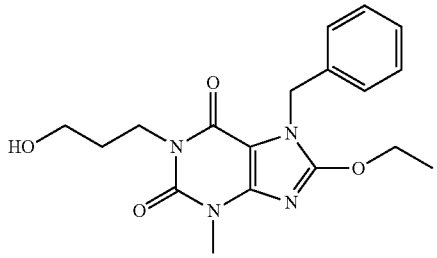 [SMILES: CCOc1nc2c(c(=O)n(CCCO)c(=O)n2C)n1Cc1ccccc1]

Step 1 Sodium metal (0.11 g, 4.93 mmol) was dissolved in ethanol (10 mL) and 7-benzyl-8-bromo-1-(3-((tert-butyldimethylsilyl)oxy)propyl)-3-methyl-1H-purine-2,6(3H,7H)-dione (0.50 g, 0.985 mmol, intermediate 83) was added. The clear solution was stirred at room temperature 15 h. The reaction was diluted with water (100 mL) and extracted with ethyl acetate (3×75 mL). The combined extracts were dried with magnesium sulfate, filtered and the solvent was removed under reduced pressure to give 7-benzyl-1-(3-((tert-butyldimethylsilyl)oxy)propyl)-3-ethoxy-3-methyl-1H-purine-2,6(3H,7H)-dione (0.47 g, 100% yield) as a white solid. LCMS retention time=5.074 min and 97% purity, LCMS MH$^+$=473.

Step 2 7-Benzyl-1-(3-((tert-butyldimethylsilyl)oxy)propyl)-3-ethoxy-3-methyl-1H-purine-2,6(3H,7H)-dione (0.47 g, 0.985 mmol) was dissolved in ethanol (8 mL) and 6 N HCl (2.0 mL) was added. The clear solution was stirred at room temperature. After 1 h the reaction was diluted with water (75 mL) and extracted with DCM (3×50 ml). The combined extracts were dried with magnesium sulfate, filtered and the solvent was removed under reduced pressure to yield a white solid. Solid was slurried in hexanes (5 mL) and filtered to give 7-benzyl-8-ethoxy-1-(3-hydroxypropyl)-3-methyl-1H-purine-2,6(3H,7H)-dione (0.26 g, 73% yield) as a white solid. LCMS retention time=2.848 min and 97% purity, LCMS MH$^+$=359. $^1$H NMR (CDCl$_3$) δ 7.26-7.40 (m, 5H), 5.26 (s, 2H), 4.53-4.59 (m, 2H), 4.17 (t, 2H, J=8 Hz), 3.49-3.51 (m, 5H), 1.85-1.91 (m, 2H), 1.45 (t, 3H, J=8 Hz).

Example 396 7-Benzyl-1-(3-hydroxypropyl)-3-methyl-8-propoxy-1H-purine-2,6(3H,7H)-dione

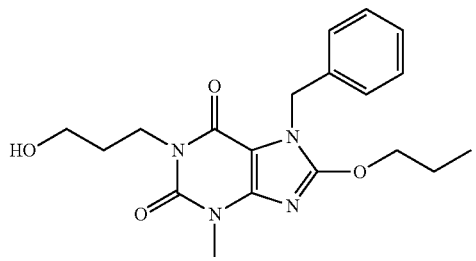 [SMILES: CCCOc1nc2c(c(=O)n(CCCO)c(=O)n2C)n1Cc1ccccc1]

The title product was prepared using the two step method of example 395. White solid, 0.32 g, 87% yield: LCMS retention time=3.119 min and 99% purity, LCMS MH$^+$=373.

Example 397 tert-Butyl 3-(7-(4-chlorobenzyl)-3-methyl-2,6-dioxo-8-(3-(trifluoromethoxy)phenoxy)-2,3,6,7-tetrahydro-1H-purin-1-yl)propanoate

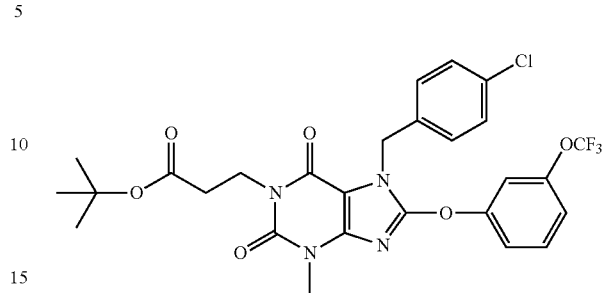

7-(4-Chlorobenzyl)-3-methyl-8-(3-(trifluoromethoxy)-1H-purine-2,6(3H,7H)-dione (0.50 g, 1.07 mmol, intermediate 9), tert-butyl 3-bromopropanoate (0.22 mL, 1.29 mmol) and potassium carbonate (0.22 g, 1.61 mmol) were combined in DMF (5 mL) and heated at 100° C. for 24 h. The reaction was cooled, diluted with water (100 mL) and extracted with ethyl acetate (3×75 mL). The combined extracts were washed with 1N lithium chloride (2×50 mL), dried with magnesium sulfate, filtered and the solvent was removed under reduced pressure to leave a white solid. This solid was purified using a 25 g silica gel flash column eluted with 10% ethyl acetate/hexanes to give tert-butyl 3-(7-(4-chlorobenzyl)-3-methyl-2,6-dioxo-8-(3-(trifluoromethoxy)phenoxy)-2,3,6,7-tetrahydro-1H-purin-1-yl)propanoate (0.26 g, 41% yield) as a white solid. LCMS retention time=4.841 min and 99% purity, LCMS MH$^+$=595. $^1$H NMR (CDCl$_3$) δ 7.12-7.46 (m, 8H), 5.41 (s, 2H), 4.29 (t, 2H, J=8 Hz), 3.53 (s, 3H), 2.61 (t, 2H, J=8 Hz), 1.43 (s, 9H).

Example 398 3-(7-(4-Chlorobenzyl)-3-methyl-2,6-dioxo-8-(3-(trifluoromethoxy)phenoxy)-2,3,6,7-tetrahydro-1H-purin-1-yl)propanoic acid

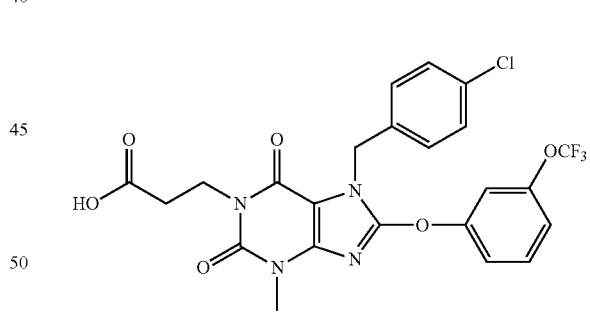

tert-Butyl 3-(7-(4-chlorobenzyl)-3-methyl-2,6-dioxo-8-(3-(trifluoromethoxy)phenoxy)-2,3,6,7-tetrahydro-1H-purin-1-yl)propanoate (0.23 g, 0.383 mmol, Example 397) was dissolved in DCM (4 mL) and TFA (0.57 mL, 7.66 mmol) was added. The reaction was stirred at room temperature for 1 h; then the solvent was removed under reduced pressure to leave a golden oil (0.21 g). The oil was purified using a 12 g silica gel column eluted with 5% methanol/DCM to give 3-(7-(4-chlorobenzyl)-3-methyl-2,6-dioxo-8-(3-(trifluoromethoxy)phenoxy)-2,3,6,7-tetrahydro-1H-purin-1-yl)propanoic acid (0.13 g, 63% yield) as an white solid. LCMS retention time=3.903 min and 99% purity, LCMS MH$^+$=539. $^1$H NMR (CDCl$_3$) δ 7.14-7.47 (m, 8H), 5.41 (s, 2H), 4.35 (t, 2H, J=8 HZ), 3.44 (s, 3H), 2.77 (t, 2H, J=8 HZ).

Example 399 8-(3-Chlorophenoxy)-1-(3-hydroxypropyl)-7-isopentyl-3-methyl-1H-purine-2,6(3H,7H)-dione

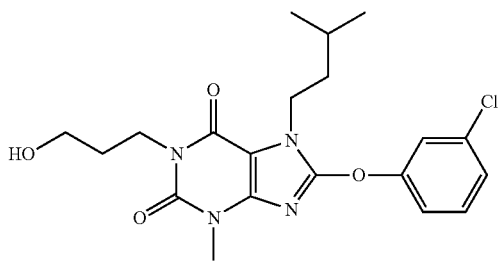 [SMILES: CC(C)CCn1c(Oc2cccc(Cl)c2)nc2c1c(=O)n(CCCO)c(=O)n2C]

Step 1 8-Bromo-1-(3-((tert-butyldimethylsilyl)oxy)propyl)-7-isopentyl-3-methyl-1H-purine-2,6(3H,7H)-dione (0.50 g, 1.03 mmol, intermediate 82), 3-chlorophenol (0.14 g, 1.08 mmol), potassium carbonate (0.29 g, 2.06 mmol) were combined in DMF (5 mL) and heated at 90° C. for 15 h. The reaction was cooled, diluted with water (100 mL) and extracted with ethyl acetate (3×75 mL). The combined extracts were washed with 1 N LiCl (2×75 mL), dried with magnesium sulfate, filtered and evaporated under reduced pressure to give 1-(3-((tert-butyldimethylsilyl)oxy)propyl-8-(3-chlorophenoxy)-7-isopentyl-3-methyl-1H-purine-2,6(3H,7H)-dione (0.55 g, 100% yield) as a yellow oil. LCMS retention time=6.238 min and 85% purity, LCMS MH+=535.

Step 2 1-(3-((tert-Butyldimethylsilyl)oxy)propyl-8-(3-chlorophenoxy)-7-isopentyl-3-methyl-1H-purine-2,6(3H,7H)-dione (0.55 g, 1.03 mmol) was dissolved in ethanol (10 mL) and 6N HCl (2 mL) was added and the reaction was stirred at room temperature for 1 h. The reaction was diluted with water (100 mL) and extracted with DCM (3×75 mL). The combined extracted were dried with magnesium sulfate, filtered and evaporated under reduced pressure to leave a golden oil. The oil was purified using a 24 g silica gel flash column eluted with 50% ethyl acetate/hexanes to give 8-(3-chlorophenoxy)-1-(3-hydroxypropyl)-7-isopentyl-3-methyl-1H-purine-2,6(3H,7H)-dione (0.21 g, 49% yield) as a white solid. LCMS retention time=3.859 min and 98% purity, LCMS MH+=421. ¹H NMR (CDCl₃) δ 7.35-7.38 (m, 2H), 7.24-7.28 (m, 1H), 7.18-7.25 (m, 1H), 4.27 (t, 2H, J=8 Hz), 4.20 (t, 2H, J=8 Hz), 3.52-3.58 (m, 3H), 3.47 (s, 3H), 1.86-1.94 (m, 2H), 1.70-1.78 (m, 2H), 1.59-1.69 (m, 1H), 0.98 (d, 6H, J=8 Hz).

Example 400 1-(3-Hydroxypropyl)-7-isopentyl-8-isopropoxy-3-methyl-1H-purine-2,6(3H,7H)-dione

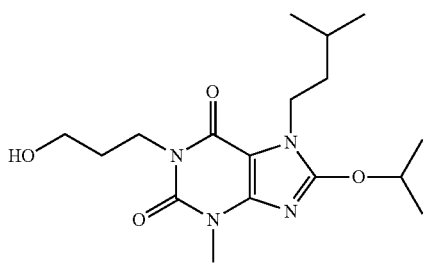 [SMILES: CC(C)CCn1c(OC(C)C)nc2c1c(=O)n(CCCO)c(=O)n2C]

Sodium (0.12 g, 5.15 mmol) was dissolved in isopropanol (8 mL) and 8-bromo-1-(3-((tert-butyldimethylsilyl)oxy)propyl-7-isopentyl-3-methyl-1H-purine-2,6(3H,7H)-dione (0.50 g, 1.03 mmol, intermediate 82) was added. The reaction was stirred at room temperature for 15 h. The reaction was treated with 6N HCl to achieve pH=1, and stirred at room temperature for 1 h. The reaction was diluted with water (100 mL) and extracted with DCM (3×75 mL). The combined extracts were dried with magnesium sulfate, filtered and evaporated under reduced pressure to leave a golden oil. The oil was purified using two 2000 micron preparative TLC plate eluted with 50% ethyl acetate/hexanes to give 1-(3-hydroxypropyl)-7-isopentyl-8-isopropoxy3-methyl-1H-purine-2,6(3H,7H)-dione (0.27 g, 75 yield) as a white solid. LCMS retention time=3.325 min and 97% purity, LCMS MH+=353. ¹H NMR (CDCl₃) δ 5.20-5.30 (m, 1H), 4.17 (t, 2H, J=8 Hz), 4.07 (t, 2H, J=8 Hz), 3.73 (t, 1H, J=8 Hz), 3.45-3.54 (m, 5H), 1.85-1.93 (m, 2H), 1.58-1.66 (m, 2H), 1.48-1.57 (m, 1H), 1.42 (d, 6H, J=8 Hz), 0.94 (d, 6H, J=8 Hz).

Example 401 8-Ethoxy-1-(3-hydroxypropyl)-7-isopentyl-3-methyl-1H-purine-2,6(3H,7H)-dione

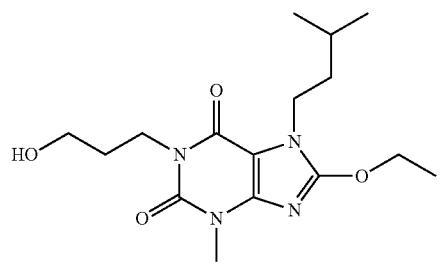 [SMILES: CCOc1nc2c(c(=O)n(CCCO)c(=O)n2C)n1CCC(C)C]

The title compound was prepared using the method of example 400 as a white solid. LCMS retention time=3.050 min and 96% purity, LCMS MH+ 339. ¹H NMR (CDCl₃) δ 4.53 (dd, 2H, J=8 Hz and 16 Hz), 4.17 (t, 2H, J=8 Hz), 4.08 (t, 2H, J=8 Hz), 3.71 (t, 1H, J=4 Hz), 3.47-3.53 (m, 5H), 1.84-1.92 (m, 2H), 1.60-1.67 (m, 2H), 1.49-1.58 (m, 1H), 1.45 (t, 2H, J=4 Hz), 0.94 (d, 6H, J=4 Hz).

Example 402 1-(3-Hydroxypropyl)-7-isopentyl-3-methyl-8-propoxy-1H-purine-2,6(3H,7H)-dione

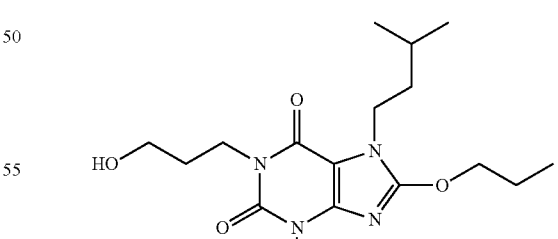

The title compound was prepared using the method of example 400 as a white solid. LCMS retention time=3.383 min and 95% purity, LCMS MH+=352. ¹H NMR (CDCl₃) δ 4.42 (t, 2H, J=8 Hz), 4.17 (t, 2H, J=8 Hz), 4.09 (t, 2H, J=8 Hz), 3.70 (t, 1H, J=4 Hz), 3.45-3.56 (m, 5H), 1.78-1.94 (m, 4H), 1.51-1.72 (m, 3H), 1.04 (t, 3H, J=8 Hz), 0.94 (d, 6H, J=8 Hz).

Example 403 8-Butoxy 1-(3-hydroxypropyl)-7-isopentyl-3-methyl-1H-purine-2,6(3H,7H)-dione

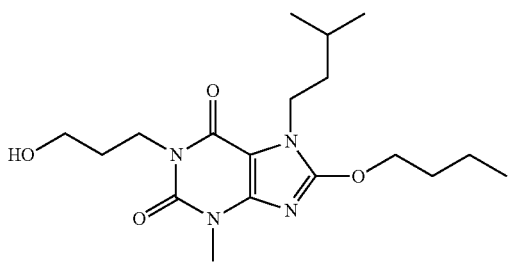 [SMILES: CCCCOc1nc2c(c(=O)n(CCCO)c(=O)n2C)n1CCC(C)C]

The title compound was prepared using the method of example 400 as a white solid. LCMS retention time=3.681 min and 99% purity, LCMS MH$^+$=367. $^1$H NMR (CDCl$_3$) δ 4.47 (t, 2H, J=8 Hz), 4.16 (t, 2H, J=8 Hz), 4.08 (t, 2H, J=8 Hz), 3.70 (t, 1H, J=8 Hz), 3.45-3.59 (m, 5H), 1.73-1.93 (m, 4H), 0.99 (t, 3H, J=8 Hz), 0.94 (d, 6H, J=8 Hz).

Example 404 7-Benzyl-8-(3,4-dichlorophenyl)-1-(3-hydroxypropyl)-3-methyl-1H-purine-2,6(3H,7H)-dione

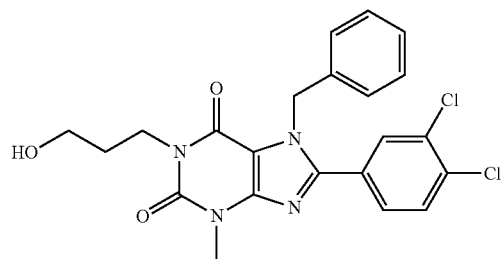 [SMILES: Cn1c(=O)n(CCCO)c(=O)c2c1nc(-c1ccc(Cl)c(Cl)c1)n2Cc1ccccc1]

Step 1 7-Benzyl-8-bromo-1-(3-((tert-butyldimethylsilyl)oxy)propyl)-3-methyl-1H-purine-2,6(3H,7H)-dione (0.50 g, 0.985 mmol, intermediate 83), potassium carbonate (0.326 g, 2.36 mmol), tetrakis(triphenylphosphine) palladium(0) (0.032 g, 0.028 mmol) and 3,4-dichlorophenyl boronic acid (0.206 g, 1.08 mmol) were combined in ethanol (12.0 mL), toluene (2.0 mL) and water (2.0 mL) in a sealed vial. The reaction was heated at 85° C. for 18 h. The reaction was cooled and filtered through Celite. The filtrate was diluted with water (100 mL) and extracted with ethyl acetate (3×75 mL). The combined extracts were dried with magnesium sulfate, filtered and the solvent was removed under reduced pressure to yield a golden solid. The solid was purified using a 25 g silica gel CombiFlash column eluted with 20% ethyl acetate/hexanes to give 7-benzyl-1-(3-((tert-butyldimethylsilyl)oxy)propyl)-8-(3,4-dichlorophenyl)-3-methyl-1H-purine-2,6(3H,7H)-dione (0.49 g, 86% yield) as a golden oil. LCMS retention time=5.489 min and 97% purity, LCMS MH$^+$=573.

Step 2 7-Benzyl-1-(3-((tert-butyldimethylsilyl)oxy)propyl)-8-(3,4-dichlorophenyl)-3-methyl-1H-purine-2,6(3H, 7H)-dione (0.49 g, 0.854 mmol) was dissolved in ethanol (15 mL) and 6 N HCl (2.0 mL) was added. The clear solution was stirred at room temperature for 1 h. The reaction was diluted with water (100 mL) and extracted with DCM (3×75 ml). The combined extracts were dried with magnesium sulfate, filtered and the solvent was removed under reduced pressure to give a white solid. The solid was slurried in diethyl ether (5 mL) and filtered to give 7-benzyl-8-(3,4-dichlorophenyl)-1-(3-hydroxypropyl)-3-methyl-1H-purine-2,6(3H,7H)-dione (0.28 g, 71% yield) as a white solid. LCMS retention time=3.567 min and 96% purity, LCMS MH$^+$=459. $^1$H NMR (CDCl$_3$) δ 7.71 (s, 1H), 7.53 (d, 1H, J=8 Hz), 7.38-7.41 (d, 1H, J=4 Hz), 7.26-7.29 (m, 3H), 7.04 (d, 2H), 5.64 (s, 2H), 4.20 (t, 2H, J=8 Hz), 3.65 (s, 3H), 3.47-3.54 (m, 2H), 3.30 (t, 2H, J=8 Hz).

Example 405 8-(3-Chlorophenyl)-1-(3-hydroxypropyl)-7-isopentyl-3-methyl-1H-purine-2,6(3H,7H)-dione

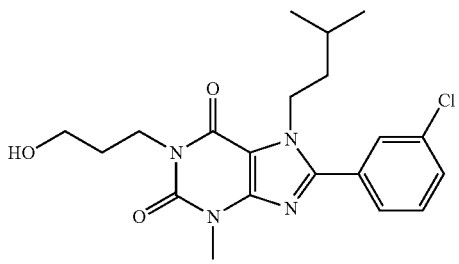 [SMILES: CC(C)CCn1c(-c2cccc(Cl)c2)nc2c1c(=O)n(CCCO)c(=O)n2C]

The title compound was prepared from intermediate 82 using the method of example 404. Golden yellow solid, 0.31 g, 74% yield: LCMS retention time=3.516 min and 85% purity, LCMS MH$^+$=405. $^1$H NMR (CDCl$_3$) δ 7.65-7.70 (m, 1H), 7.45-7.54 (m, 3H), 4.33-4.39 (m, 2H), 4.23 (t, 2H, J=4 Hz), 3.63 (s, 3H), 3.52-3.58 (m, 2H), 3.43-3.48 (m, 2H), 1.89-1.96 (m, 2H), 1.69-1.76 (m, 2H), 1.53-1.64 (m, 2H), 0.89 (d, 6H, J=4 Hz).

Example 406 1-(3-Hydroxypropyl)-7-isopentyl-3-methyl-8-(3-(trifluoromethyl)phenyl)-1H-purine-2,6(3H,7H)-dione

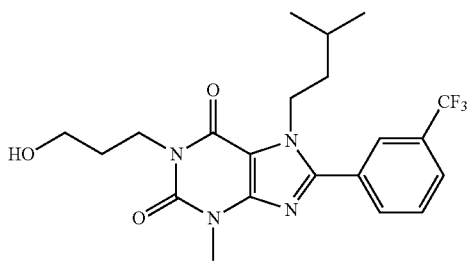 [SMILES: CC(C)CCn1c(-c2cccc(C(F)(F)F)c2)nc2c1c(=O)n(CCCO)c(=O)n2C]

The title compound was prepared from intermediate 82 using the method of example 404. White solid, 0.089 g, 40% yield: LCMS retention time=3.598 min and 97% purity, LCMS MH$^+$=438.

Example 407 1-(3-hydroxypropyl)-7-isopentyl-8-(2-isopropylphenyl)-3-methyl-1H-purine-2,6(3H,7H)-dione

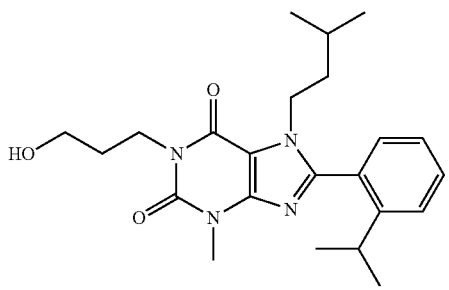 [SMILES: CC(C)CCn1c(-c2ccccc2C(C)C)nc2c1c(=O)n(CCCO)c(=O)n2C]

The title compound was prepared from intermediate 82 using the method of example 404. White solid, 0.089 g, 40% yield: LCMS retention time=3.749 min and 99% purity, LCMS MH$^+$=413.

Example 408 8-(3-Fluorophenoxy)-1-(3-hydroxypropyl)-7-isopentyl-3-methyl-1H-purine-2,6(3H,7H)-dione

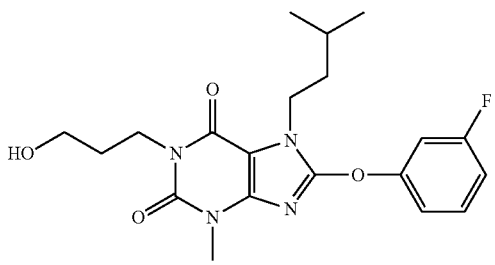

8-Bromo-1-(3-((tert-butyldimethylsilyl)oxy)propyl-7-isopentyl-3-methyl-1H-purine-2,6(3H,7H)-dione (0.50 g, 1.03 mmol, intermediate 82), 3-fluorophenol (0.098 mL, 1.08 mmol) and potassium carbonate (0.29 g, 2.06 mmol) were combined in DMF (8 mL) and heated at 90° C. for 15 h. The reaction was cooled to room temperature and acidified with 6N HCl to pH=1. The reaction was stirred for 1 h then diluted with water (100 mL) and extracted with ethyl acetate (3×75 mL). The combined extracts were washed with 1N LiCl (2×100 mL), dried with magnesium sulfate, filtered and the solvent was removed under reduced pressure to yield a golden oil. The oil was purified using a 24 g silica gel flash column eluted with a gradient of 20% ethyl acetate/hexanes to 100% ethyl acetate to give 8-(3-fluorophenoxy)-1-(3-hydroxypropyl)-7-isopentyl-3-methyl-1H-purine-2,6(3H,7H)-dione (0.20 g, 48% yield) as a white solid. LCMS retention time=3.524 min and 96% purity, LCMS MH$^+$=405.

Example 409 1-(3-Hydroxypropyl)-7-isopentyl-3-methyl-8-(3-(trifluoromethyl)phenoxy)-1H-purine-2,6(3H,7H)-dione

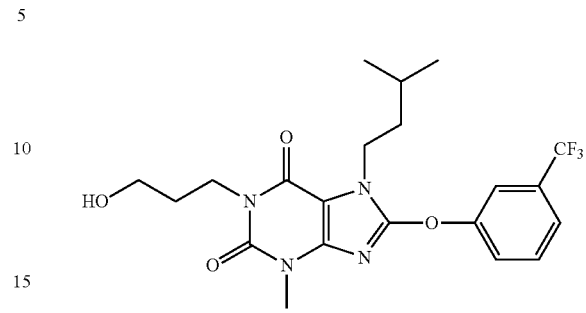

The title compound was prepared using the method of example 408. White solid, 0.26 g, 55% yield: LCMS retention time=3.838 min and 99% purity, LCMS MH$^+$=455.

The following examples 410a through 410w were prepared using the method of example 404.

Example 410a 7-Benzyl-8-(4-chloro-3-(trifluoromethyl)phenyl)-1-(3-hydroxypropyl)-3-methyl-1H-purine-2,6(3H,7H)-dione

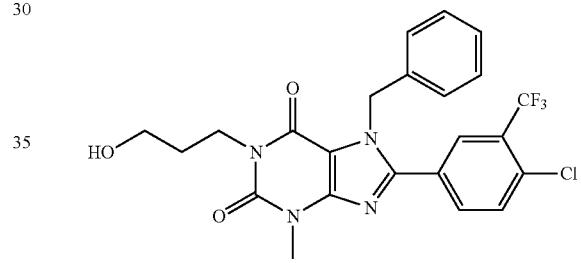

White solid, LCMS retention time=3.625 min and 97% purity, LCMS MH$^+$=493. $^1$H NMR (CDCl$_3$) δ 7.91 (s, 1H), 7.63 (d, 2H, J=8 Hz), 7.59 (d, 2H, J=8 Hz), 7.30-7.35 (m, 2H), 7.01 (d, 2H, J=8 Hz), 5.55 (s, 2H), 4.21 (t, 2H, J=8 Hz), 3.66 (s, 3H), 3.47-3.55 (m, 2H), 3.28 (t, 2H, J=8 Hz), 1.89-1.93 (m, 2H).

Example 410b 7-Benzyl-8-(3-fluorophenyl)-1-(3-hydroxypropyl)-3-methyl-1H-purine-2,6(3H,7H)-dione

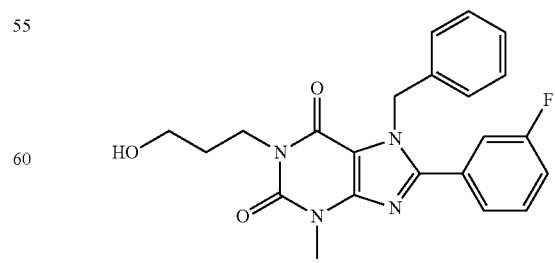

White solid, 0.051 g, 80% yield: LCMS retention time=3.004 min and 99% purity, LCMS MH$^+$=409.

Example 410c 7-Benzyl-1-(3-hydroxypropyl)-3-methyl-8-(m-tolyl)-1H-purine-2,6(3H,7H)-dione

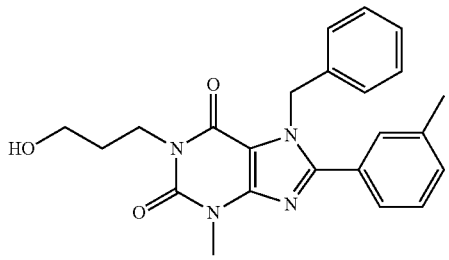 [SMILES: Cc1cccc(-c2nc3c(c(=O)n(CCCO)c(=O)n3C)n2Cc2ccccc2)c1]

White solid, 0.054 g, 85% yield: LCMS retention time=3.133 min and 99% purity, LCMS MH$^+$=405.

Example 410d 7-benzyl-1-(3-hydroxypropyl)-8-(3-methoxyphenyl)-3-methyl-1H-purine-2,6(3H,7H)-dione

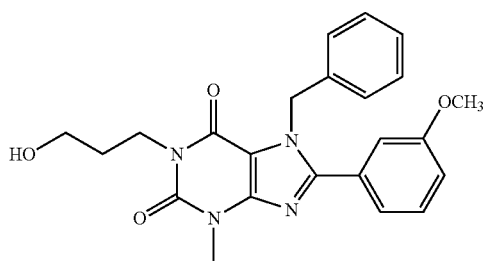

White solid, 0.051 g, 84% yield: LCMS retention time=2.950 min and 99% purity, LCMS MH$^+$=421.

Example 410e 7-Benzyl-1-(3-hydroxypropyl)-3-methyl-8-(3-(trifluoromethoxy)phenyl)-1H-purine-2,6(3H,7H)-dione

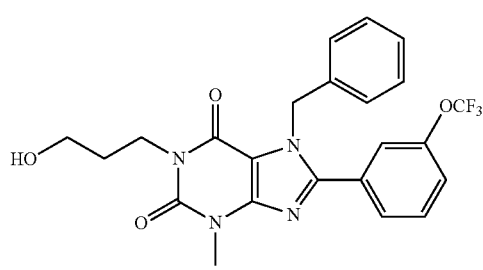 [SMILES: COc1cccc(-c2nc3c(c(=O)n(CCCO)c(=O)n3C)n2Cc2ccccc2)c1]

White solid, 0.052 g, 80% yield: LCMS retention time=3.312 min and 99% purity, LCMS MH$^+$=459.

Example 410f 7-Benzyl-8-(4-chlorophenyl)-1-(3-hydroxypropyl)-3-methyl-1H-purine-2,6(3H,7H)-dione

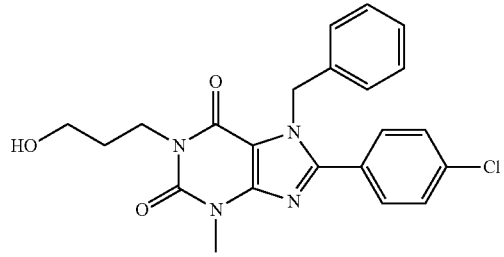 [SMILES: Cn1c(=O)n(CCCO)c(=O)c2c1nc(-c1ccc(Cl)cc1)n2Cc1ccccc1]

White solid, 0.050 g, 91% yield: LCMS retention time=3.227 min and 98% purity, LCMS MH$^+$=425.

Example 410g 7-Benzyl-8-(4-fluorophenyl)-1-(3-hydroxypropyl)-3-methyl-1H-purine-2,6(3H,7H)-dione

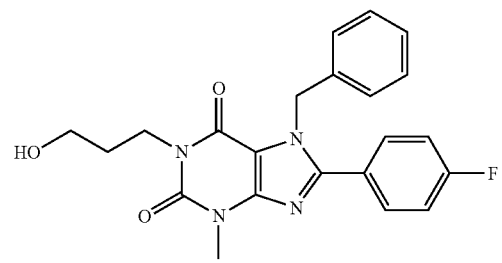 [SMILES: Cn1c(=O)n(CCCO)c(=O)c2c1nc(-c1ccc(F)cc1)n2Cc1ccccc1]

White solid, 0.052 g, 60% yield: LCMS retention time=2.977 min and 99% purity, LCMS MH$^+$=409.

Example 410h 7-Benzyl-1-(3-hydroxypropyl)-3-methyl-8-(p-tolyl)-1H-purine-2,6(3H,7H)-dione

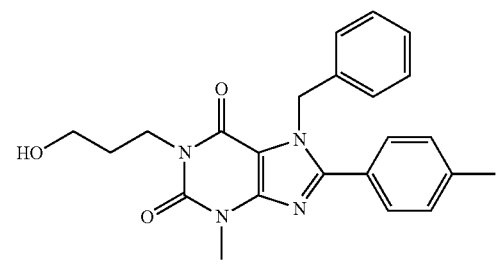 [SMILES: Cc1ccc(-c2nc3c(c(=O)n(CCCO)c(=O)n3C)n2Cc2ccccc2)cc1]

Clear oil, 0.028 g, 55% yield: LCMS retention time=3.122 min and 98% purity, LCMS MH$^+$=405.

Example 410i 7-Benzyl-1-(3-hydroxypropyl)-8-(4-methoxyphenyl)-3-methyl-1H-purine-2,6(3H,7H)-dione

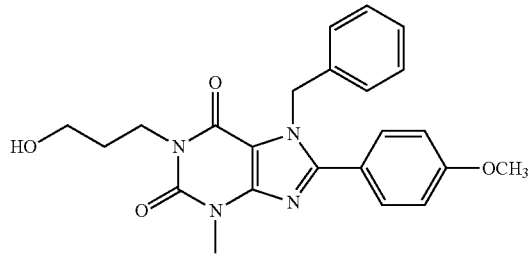 [SMILES: COc1ccc(-c2nc3c(c(=O)n(CCCO)c(=O)n3C)n2Cc2ccccc2)cc1]

White solid, 0.049 g, 91% yield: LCMS retention time=2.944 min and 96% purity, LCMS MH+=421.

Example 410j 7-Benzyl-1-(3-hydroxypropyl)-3-methyl-8-(4-(trifluoromethyl)phenyl)-1H-purine-2,6(3H,7H)-dione

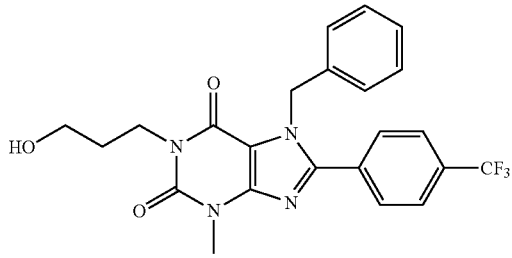 [SMILES: Cn1c(=O)n(CCCO)c(=O)c2c1nc(-c1ccc(C(F)(F)F)cc1)n2Cc1ccccc1]

White solid, 0.052 g, 76% yield: LCMS retention time=3.348 min and 99% purity, LCMS MH+=459.

Example 410k 7-Benzyl-8-(2-chlorophenyl)-1-(3-hydroxypropyl)-3-methyl-1H-purine-2,6(3H,7H)-dione

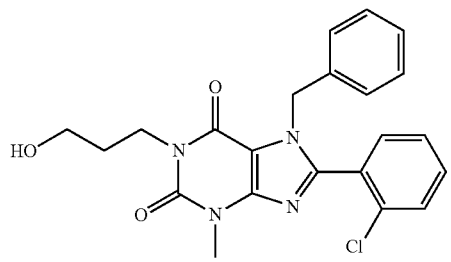 [SMILES: Cc1ccccc1-c1nc2c(c(=O)n(CCCO)c(=O)n2C)n1Cc1ccccc1]

Clear oil, 0.057 g, 93% yield: LCMS retention time=2.979 min and 99% purity, LCMS MH+=425.

Example 410l 7-Benzyl-8-(2-fluorophenyl)-1-(3-hydroxypropyl)-3-methyl-1H-purine-2,6(3H,7H)-dione

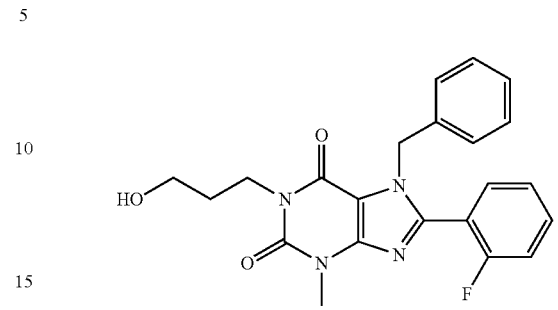

Golden oil, 0.030 g, 91% yield: LCMS retention time=2.858 min and 99% purity, LCMS MH+=409.

Example 410m 7-Benzyl-1-(3-hydroxypropyl)-3-methyl-8-(o-tolyl)-1H-purine-2,6(3H,7H)-dione

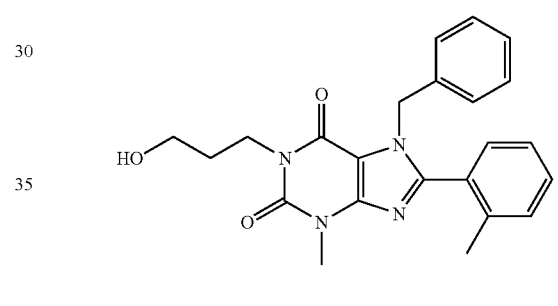

White solid, 0.027 g, 77% yield: LCMS retention time=2.995 min and 98% purity, LCMS MH+=405.

Example 410n 7-Benzyl-1-(3-hydroxypropyl)-8-(2-methoxyphenyl)-3-methyl-1H-purine-2,6(3H,7H)-dione

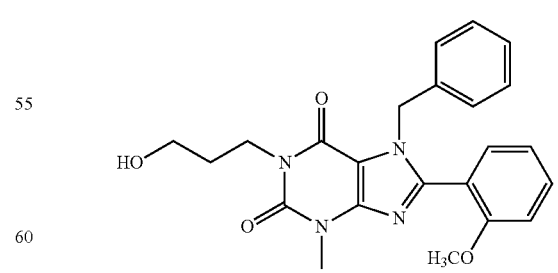

White solid, 0.061 g, 86% yield: LCMS retention time=2.831 min and 98% purity, LCMS MH+=421.

Example 410o 7-Benzyl-1-(3-hydroxypropyl)-3-methyl-8-(2-(trifluoromethyl)phenyl)-1H-purine-2,6 (3H,7H)-dione

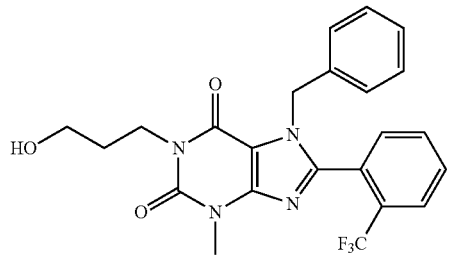 [SMILES: Cn1c(=O)n(CCCO)c(=O)c2c1nc(-c1ccccc1C(F)(F)F)n2Cc1ccccc1]

White solid, 0.017 g, 57% yield: LCMS retention time=3.055 min and 97% purity, LCMS MH+=459.

Example 410p 7-Benzyl-1-(3-hydroxypropyl)-8-(4-(isopropylsulfonyl)phenyl)-3-methyl-1H-purine-2,6 (3H,7H)-dione

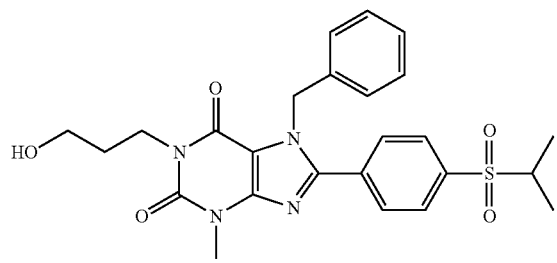 [SMILES: CC(C)S(=O)(=O)c1ccc(-c2nc3c(c(=O)n(CCCO)c(=O)n3C)n2Cc2ccccc2)cc1]

Colorless oil, 0.057 g, 88% yield: LCMS retention time=2.886 min and 98% purity, LCMS MH+=498.

Example 410q 7-Benzyl-1-(3-hydroxypropyl)-8-(2-isopropylphenyl)-3-methyl-1H-purine-2,6(3H,7H)-dione

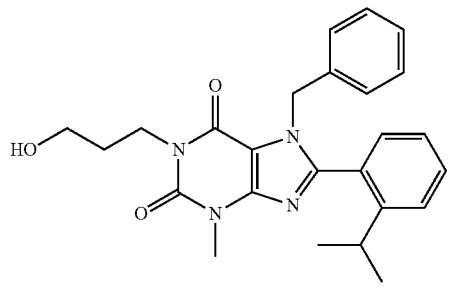 [SMILES: CC(C)c1ccccc1-c1nc2c(c(=O)n(CCCO)c(=O)n2C)n1Cc1ccccc1]

Colorless oil, 0.038 g, 79% yield LCMS retention time=3.520 min, LCMS MH+=433 and 99% pure.

Example 410r 7-Benzyl-1-(3-hydroxypropyl)-8-(3-isopropylphenyl)-3-methyl-1H-purine-2,6(3H,7H)-dione

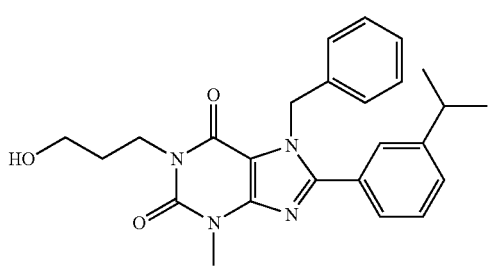 [SMILES: CC(C)c1cccc(-c2nc3c(c(=O)n(CCCO)c(=O)n3C)n2Cc2ccccc2)c1]

Colorless oil, 0.026 g, 81% yield: LCMS retention time=3.609 min and 98% purity, LCMS MH+=433.

Example 410s 8-([1,1'-Biphenyl]-3-yl)-7-benzyl-1-(3-hydroxypropyl)-3-methyl-1H-purine-2,6(3H,7H)-dione

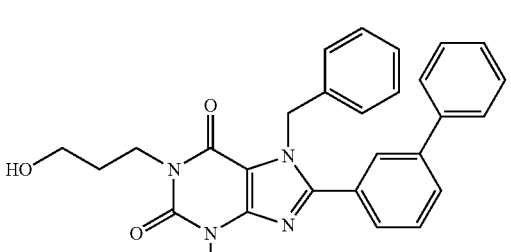

Colorless oil, 0.045 g, 80% yield: LCMS retention time=3.609 min, LCMS MH+=467 and 99% pure.

Example 410t 7-Benzyl-1-(3-hydroxypropyl)-3-methyl-8-(2-(trifluoromethoxy)phenyl)-1H-purine-2,6(3H,7H)-dione

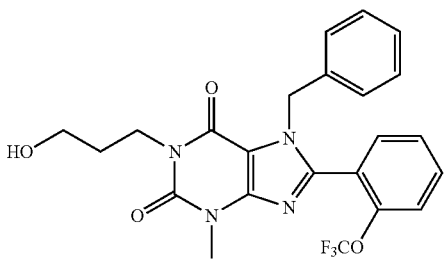 [SMILES: Cn1c(=O)n(CCCO)c(=O)c2c1nc(-c1ccccc1OC(F)(F)F)n2Cc1ccccc1]

Colorless oil, 0.048 g, 83% yield: LCMS retention time=3.231 min and 99% purity, LCMS MH+=475.

Example 410u 7-Benzyl-8-(3-(difluoromethoxy)phenyl)-1-(3-hydroxypropyl)-3-methyl-1H-purine-2,6(3H,7H)-dione

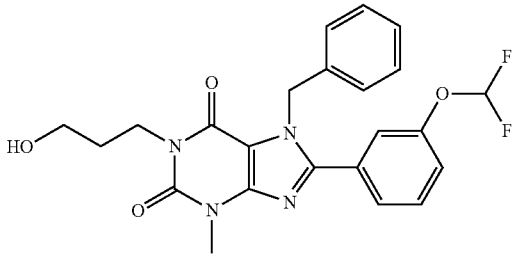 [SMILES: Cn1c(=O)n(CCCO)c(=O)c2c1nc(-c1cccc(OC(F)F)c1)n2Cc1ccccc1]

Colorless oil, 0.048 g, 83%: LCMS retention time=3.150 min and 99% purity, LCMS MH$^+$=457.

Example 410v 7-Benzyl-8-(4-(difluoromethoxy)phenyl)-1-(3-hydroxypropyl)-3-methyl-1H-purine-2,6(3H,7H)-dione

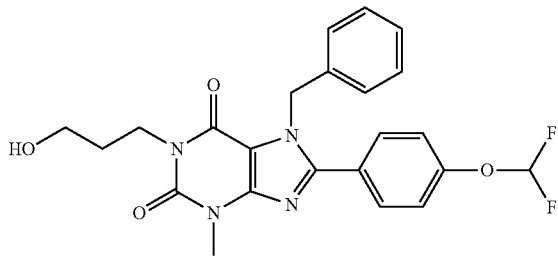 [SMILES: Cn1c(=O)n(CCCO)c(=O)c2c1nc(-c1ccc(OC(F)F)cc1)n2Cc1ccccc1]

Colorless oil, 0.050 g, 78% yield: LCMS retention time=3.161 min and 99% purity, LCMS MH$^+$=457.

Example 410w 7-Benzyl-8-(4-(difluoromethyl)phenyl)-1-(3-hydroxypropyl)-3-methyl-1H-purine-2,6(3H,7H)-dione

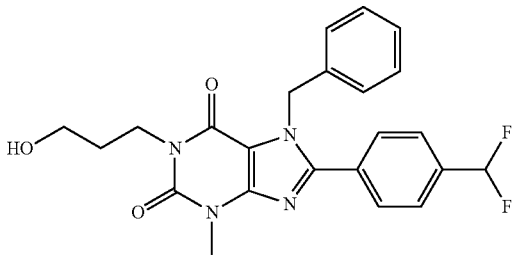 [SMILES: Cn1c(=O)n(CCCO)c(=O)c2c1nc(-c1ccc(C(F)F)cc1)n2Cc1ccccc1]

Colorless oil, 0.048 g, 75% yield: LCMS retention time=3.098 min and 99% purity, LCMS MH$^+$=441.

Example 433 1-(5-Hydroxyhexyl)-3,7-dimethyl-1H-purine-2,6(3H,7H)-dione

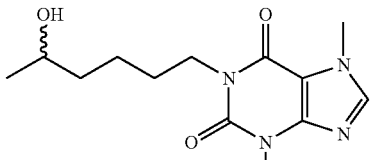

Pentoxifylline (1.0 g, 3.59 mmol) was dissolved in methanol (20 mL) and DCM (3 mL) then cooled to 0° C. To the reaction was added sodium borohydride (0.41 g, 10.8 mmol) portionwise over 30 min. The reaction was stirred in the cold for 2 h; then it was evaporated to dryness under reduced pressure, diluted with water (100 mL) and extracted with ethyl acetate (3×75 mL). The combined extracts were dried with magnesium sulfate, filtered and the solvent was removed under reduced pressure to give 1-(5-hydroxyhexyl)-3,7-dimethyl-1H-purine-2,6(3H,7H)-dione (0.72 g, 71% yield) as a white solid. LCMS retention time=1.849 min and 98% purity, LCMS MH$^+$ 281. $^1$H NMR (DMSO-d$_6$) δ 8.00 (s, 1H), 4.31 (d, 1H, J=4 Hz), 3.88 (s, 3H), 3.84 (t, 2H, J=8 Hz), 3.51-3.59 (m, 1H), 1.45-1.56 (m, 2H), 1.25-1.37 (m, 4H), 1.02 (d, 3H, J=4 Hz).

INCORPORATION BY REFERENCE

All publications and patents mentioned herein, are hereby incorporated by reference in their entirety as if each individual publication or patent was specifically and individually indicated to be incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method of therapeutically treating depression in a subject in need thereof, the method comprising administering to the subject an effective amount of a compound or a pharmaceutically acceptable salt thereof, wherein the compound is selected from the group consisting of:
   7-(4-chlorobenzyl)-1-(3-hydroxypropyl)-3-methyl-8-(3-(trifluoromethoxy)phenoxy)-1H-purine-2,6(3H,7H)-dione;
   7-(4-chlorobenzyl)-1-(4-hydroxybutyl)-3-methyl-8-(3-(trifluoromethoxy)phenoxy)-1H-purine-2,6(3H,7H)-dione;
   1-(3-hydroxypropyl)-3-methyl-7-((6-methylpyridin-3-yl)methyl)-8-(3-(trifluoromethoxy)phenoxy)-1H-purine-2,6(3H,7H)-dione; and
   7-(4-Chlorobenzyl)-8-(3-chlorophenoxy)-1-(3-hydroxypropyl)-3-methyl-1H-purine-2,6(3H,7H)-dione.

2. The method of claim 1, wherein the depression is selected from the group consisting of major depression, psychiatric depression, dysthymia, and postpartum depression.

* * * * *